US008865734B2

(12) United States Patent
No et al.

(10) Patent No.: US 8,865,734 B2
(45) Date of Patent: Oct. 21, 2014

(54) ANTI-INFECTIVE COMPOUNDS

(75) Inventors: Zaesung No, Gyeonggido (KR);
Jaeseung Kim, Seoul (KR); Priscille Brodin, Paris (FR); Min Jung Seo, Gyeonggi-do (KR); Young Mi Kim, Gyeonggi-do (KR); Jonathan Cechetto, Seoul (KR); Heekyoung Jeon, Gyeonggi-do (KR); Auguste Genovesio, Paris (FR); Saeyeon Lee, Gyeonggi-do (KR); Sunhee Kang, Gyeonggi-do (KR); Fanny Anne Ewann, Haramont (FR); Ji Youn Nam, CheongJu (KR); Thierry Christophe, Pontarlier (FR); Denis Philippe Cedric Fenistein, Amsterdam (NL); Jamung Heo, Chungcheongnam-do (KR); Jang Jiyeon, Seoul (KR)

(73) Assignees: Institut Pasteur Korea, Gyeonggi-Do (KR); Institut National de la Sante et de la Rech, Paris (FR)

( * ) Notice: Subject to any disclaimer, the term of this patent is extended or adjusted under 35 U.S.C. 154(b) by 0 days.

(21) Appl. No.: 13/634,165

(22) PCT Filed: Mar. 18, 2011

(86) PCT No.: PCT/EP2011/001345
§ 371 (c)(1),
(2), (4) Date: Nov. 26, 2012

(87) PCT Pub. No.: WO2011/113606
PCT Pub. Date: Sep. 22, 2011

(65) Prior Publication Data
US 2013/0065884 A1    Mar. 14, 2013

Related U.S. Application Data

(60) Provisional application No. 61/315,113, filed on Mar. 18, 2010, provisional application No. 61/440,937, filed on Feb. 9, 2011.

(51) Int. Cl.
*C07D 401/04* (2006.01)
*A61K 31/437* (2006.01)

(52) U.S. Cl.
CPC ............ *C07D 401/04* (2013.01); *A61K 31/437* (2013.01)
USPC .......................................... 514/300; 546/121

(58) Field of Classification Search
CPC .................... C07D 401/04; A61K 31/437
USPC ................... 514/300; 546/121; 544/106, 362
See application file for complete search history.

(56) References Cited

U.S. PATENT DOCUMENTS 3,105,834 A * 10/1963 Wei ............................... 544/281
3,133,076 A *  5/1964 Ferrari .......................... 430/570
3,234,218 A *  2/1966 Eichenberger et al. ........ 548/193
6,080,767 A *  6/2000 Klein et al. .................... 514/357

FOREIGN PATENT DOCUMENTS

| WO | WO 01/92257 A1    | 12/2001 |
| WO | 2007034278        | * 3/2007 |
| WO | 2007034282        | * 3/2007 |
| WO | WO 2007/027999 A2 | 3/2007  |
| WO | WO 2008/082490 A2 | 7/2008  |
| WO | WO 2008/154271 A1 | 12/2008 |
| WO | WO 2009/015208 A1 | 1/2009  |
| WO | WO 2011/050245 A1 | 4/2011  |
| WO | WO 2011/057145 A2 | 5/2011  |

OTHER PUBLICATIONS

Bristow et al., J. Ckem. Soc. (1954) 616-29.*
Paudler et al., Journal of Organic Chemistry (1968), 33(4), 1638-9.*
Boehme et al., Archiv der Pharmazie (Weinheim, Germany) (1976), 309(12), 959-65.*
Saldabols et al., Khimiko-Farmatsevticheskii Zhurnal (1977), 11(6), 64-70.*
Gueiffier et al., Journal of Medicinal Chemistry (1996), 39(14), 2856-2859.*
Chavignon et al., Heterocycles (1995), 41(9), 2019-26.*
Royer et al., Bulletin de la Societe Chimique de France (1961) 933-8.*
Takizawa et al., Inorganic Chemistry (2007), 46(10), 4308-4319.*
Kawamoto et al., "Efficient syntheses of a novel 5-thia-1-azacycl[3.3.2]azine ring system and 3H-1, 4-diazacycl[3.3.2]azine derivatives," 2000, *Tetrahedron Letters,* vol. 41, No. 18, p. 3447-3451.
Database Reaxys [Online], Database accession No. 8503486.
Database Reaxys [Online], Database accession No. 84996050.
Database Registry [Online], Chemical Abstracts 2010, retrieved from STN; Database accession No. 1235377-77-1.
Database Caplus [Online] Chemical Abstract Service, "Interaction of bromomalonic acid N,N'dibenzylamide with bifunctional amines—A pathway to the new pharmacologically active substances," STN Accession No. 2004:36264, 2003, XP002638964, *Medichna Khimiya,* vol. 5, No. 3, 2003, pp. 95-99.
Database Registry [Online] Chemical Abstract Service, STN Database Accession No. 1181391-06-9, Sep. 9, 2009, XP002638965.
Database Registry [Online] Chemical Abstract Service, STN Database Accession No. 1181334-07-5, Sep. 8, 2009, XP002638966.
Database Registry [Online] Chemical Abstract Service, STN Database Accession No. 1181286-95-2, Sep. 8, 2009, XP002638967.
Database Registry [Online] Chemical Abstract Service, STN Database Accession No. 1181266-00-1, Sep. 8, 2009, XP002638968.
Database Registry [Online] Chemical Abstract Service, STN Database Accession No. 1147732-93-1, May 20, 2009, XP002638969.
Database Registry [Online] Chemical Abstract Service, STN Database Accession No. 570361-25-0, Aug. 21, 2003, XP002638970.

(Continued)

*Primary Examiner* — Niloofar Rahmani
(74) *Attorney, Agent, or Firm* — Saliwanchik, Lloyd & Eisenschenk

(57) ABSTRACT

The present invention relates to small molecule compounds and their use in the treatment of bacterial infections, in particular Tuberculosis.

21 Claims, 3 Drawing Sheets

(56) References Cited

OTHER PUBLICATIONS

Database Registry [Online] Chemical Abstract Service, STN Database Accession No. 570361-12-5, Aug. 21, 2003, XP002638971.
Database Registry [Online] Chemical Abstract Service, STN Database Accession No. 352024-12-5, Aug. 20, 2001, XP002638972.
Database Registry [Online] Chemical Abstract Service, STN Database Accession No. 332057-26-8, Apr. 23, 2001, XP002638973.

Kaplancikli, Zafer et al., "Synthesis and antituberculosis activity of new hydrazine derivatives", *Arch. Pharm. Chem. Life Sci.*, Nov. 1, 2008, vol. 341, No. 11, pp. 721-724.
Qiao, Lixin et al., "Structure-activity relationship study if EphB3 receptor tyrosine kinase inhibitors" *Bioorganic & Medicinal Chemistry Letters,* Nov. 1, 2009, vol. 19, No. 21, pp. 6122-6126.

\* cited by examiner

ANTI-INFECTIVE COMPOUNDS

CROSS REFERENCE TO A RELATED APPLICATION

This application is a National Stage Application of International Application Number PCT/EP2011/001345, filed Mar. 18, 2011; which claims the benefit of U.S. Provisional Application No. 61/315,113, filed Mar. 18, 2010 and U.S. Provisional Application No. 61/440,937, filed Feb. 9, 2011; all of which are incorporated herein by reference in their entirety.

The present invention relates to small molecule compounds and their use in the treatment of bacterial infections, in particular Tuberculosis.

BACKGROUND OF THE INVENTION

Tuberculosis (TB) as a disease continues to result in millions of deaths each year. Inadequate use of chemotherapy has led to an increasing number of drug resistant cases. This situation is likely to worsen with the emergence of extremely resistant strains to all currently known drugs (Van Rie and Enarson, 2006). The internationally recommended TB control strategy, also referred to as directly observed short-course chemotherapy (DOTS), relies on a combination of five anti-bacterial agents to be taken for a protracted period of more than six months (http://www.who.int/tb/dots/en/). With the use of a mathematical model, taking into consideration treatment duration and TB dynamics, benefits of reduced treatment length were predicted to be substantial and likely to greatly contribute to a reduced global TB burden (Salomon et al., 2006).

Current chemotherapy consists of compounds that directly target *Mycobacterium tuberculosis bacillus*, either by neutralizing general information pathways and critical processes such as RNA polymerization and protein synthesis inhibition or by interfering with mycobacterial specific cell envelope synthesis. The most widely used dedicated anti-tubercular drugs isoniazid, ethionamide and pyrazinamide are pro-drugs that first require activation. As active forms, they demonstrate inhibitory activity on a wide range of mycobacterial targets, which have not yet been fully characterized. As for other chronic infectious diseases like human immunodeficiency virus, a multi-therapy approach, including drugs that target a wide range of critical features of *M. tuberculosis*, proved to be the most successful strategy to date. It is, thus, likely that a combination of current drug inhibitors, having different mechanisms of action against *M. tuberculosis*, will be the solution for the control of the disease.

The most challenging approaches for discovering new anti-TB drugs rely on screening for active compounds that target critical features essential for the survival of the *bacillus*. Although there is still a lack of understanding of the biological mechanisms behind tubercle *bacillus* persistence, i.e. the location and state of latent bacteria, in humans, *M. tuberculosis* is thought to reside in primary granulomas under hypoxic conditions (Lenaerts et al., 2007) as well as to hide within various types of cells (Houben et al., 2006; Neyrolles et al., 2006). The *bacillus* mainly localizes inside phagocytic cells, such as macrophages and dendritic cells, and it has clearly been established that the tubercle *bacillus* adopts a different phenotype in the host macrophage's phagosome compared to growth in extracellular conditions (Rohde et al., 2007; Schnappinger et al., 2003). Upon infection, an inflammatory response is induced, thereby initiating recruitment of T lymphocytes that release interleukins and cytokines, which in turn activate the infected macrophages to enable the destruction of the pathogen. Upon the appropriate trigger, the host macrophage is, thus, able to eliminate the invading *bacillus*. This is further supported by the fact that of the people that inhale *M. tuberculosis*, more than 95% percent do not develop the disease, suggesting that the human host response is sufficient in most cases to thwart *M. tuberculosis* induced pathogenesis. This gives rise to the hypothesis that small molecular compounds could mimic the immune cell response signals and induce the host cells to clear the mycobacteria.

Accordingly, a phenotypic cell-based assay, suitable for high throughput screening, which allows for the search of compounds that would prevent *M. tuberculosis* multiplication inside the host macrophage was utilized (WO2010003533A2), overcoming many of the numerous and burdensome steps involved in previous methodologies (Arain et al., 1996).

It was an object of the present invention to identify compounds effective against bacterial infections, in particular compounds that would prevent *M. tuberculosis* multiplication inside the host macrophage.

DESCRIPTION OF THE INVENTION

In one aspect, the present invention relates to compounds having the general formula Ia:

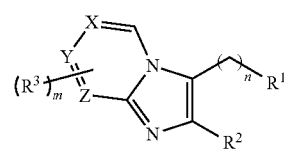

Ia wherein
m is 0, 1, 2, 3 or 4;
n is 0, 1, 2, or 3;
X, Y and Z are CH, N or N-oxide;
$R^1$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, —C(O)OR$^4$, —C(O)R$^4$, —C(O)N(R$^4$)$_2$, —CN, —NO$_2$, —NH$_2$, —N(R$^4$)$_2$, —OR$^4$HetA, —OR$^4$N(R$^4$)$_2$, —C(O)N(R$^4$)R$^4$HetA, —C(O)N(R$^4$)HetA, —C(O)HetA, —C(O)N(R$^4$)R$^4$S(O)$_2$R$_4$; —S(O)$_2$N(R$^4$)$_2$, —S(O)$_2$R$^4$, —N(R$^4$)C(O)R$^4$SR$^4$, —N(R$^4$)R$^4$S(O)$_2$R$^4$, or —N(R$^4$)S(O)$_2$R$^4$, —C(S)R$^4$, aryl, e.g. phenyl, benzyl, heteroaryl, and heterocyclyl, any of which is optionally substituted;
$R^2$ is, at each occurrence, independently, selected from the group consisting of hydrogen, halogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —OH, —OR$^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, —CN, —NO$_2$, —NH$_2$, —N(R$^5$)$_2$, —C(O)R$^5$, —C(O)OR$^5$, —C(O)N(R$^5$)$_2$, —SR$^5$, —S(O)R$^5$, —S(O)$_2$R$^5$, —S(O)$_2$N(R$^5$)$_2$, aryl, e.g. phenyl, benzyl, heteroaryl, and heterocyclyl, any of which is optionally substituted;
$R^3$ is, at each occurrence, independently selected from the group consisting of hydrogen, halogen, $C_1$-$C_{10}$ alkyl, $C_3$-$C_{10}$ cycloalkyl, $C_1$-$C_3$ haloalkyl, hydroxyl, —OR$^6$, —CN, —NO$_2$, —NH$_2$, —N(R$^6$)C(O)R$^6$, —C(O)R$^6$, —C(O)OR$^6$, —C(O)N(R$^6$)$_2$, —S(O)R$^6$, —S(O)$_2$R$^6$, —S(O)$_2$N(R$^6$)$_2$, aryl, e.g. phenyl, benzyl, heteroaryl, heterocyclyl, any of which is optionally substituted, or two groups of $R^3$ are connected to each other to make five or six membered cyclic and heterocyclic rings, any of which is optionally substituted;

$R^4$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —C(O)$R^7$, —$R^7(R^7)$C(O)$R^7$, —C(O)O$R^7$, —$R^7(R^7)$C(O)O$R^7$, —C(O)N($R^7)_2$, —$R^7(R^7)$C(O)N($R^7)_2$, —S(O)$R^7$, —S(O)$_2R^7$, —S(O)$_2$N($R^7)_2$, aryl, e.g. phenyl, benzyl, heteroaryl, and heterocyclyl, any of which is optionally substituted; and $R^5$, $R^6$ and $R^7$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, e.g. phenyl, benzyl, heteroaryl, and heterocyclyl, any of which is optionally substituted.

The term "optionally substituted" as used herein is meant to indicate that a hydrogen atom attached to a member atom within a group, or several such hydrogen atoms, is replaced by a group, such as halogen including fluorine, $C_1$-$C_{10}$ alkyl, $C_1$-$C_3$ haloalkyl, $C_3$-$C_7$ cycloalkyl, oxo, —OH, —O$R^8$, —OC(O)$R^8$, —CN, NO$_2$, —N($R^8)_2$, —N($R^8$)C(O)$R^8$, —$R^8$N($R^8$)C(O)$R^8$, —C(O)$R^8$, —$R^8$C(O)$R^8$, —C(O)O$R^8$, —$R^8$C(O)O$R^8$, —C(O)N($R^8)_2$, —$R^8$C(O)N($R^8)_2$, —S(O)$R^8$, —S(O)$_2R^8$, —S(O)$_2$N($R^8)_2$, phenyl, benzyl, aryl, heteroaryl or heterocyclyl, any of which itself is "optionally substituted"; i.e. one or several of the hydrogen atoms may be replaced by one of the aforementioned groups.

$R^8$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, —O$R^9$, —C(O)O$R^9$, —C(O)$R^9$, —C(O)N($R^9)_2$, —CN, —NO$_2$, —NH$_2$, —N($R^9)_2$, —O$R^4$HetA, —O$R^4$N($R^9)_2$, —C(O)N($R^9$)HetA, —C(O)HetA, —C(O)N($R^9$)$R^4$S(O)$_2R^9$; —S(O)$_2$N($R^9)_2$, —S(O)$_2R^9$, —N($R^9$)C(O)$R^4$S$R^9$, —N($R^9$)$R^4$S(O)$_2R^9$, or —N($R^9$)S(O)$_2R^9$, aryl, e.g. phenyl, benzyl, heteroaryl, and heterocyclyl, any of which is optionally substituted.

$R^9$ is, at each occurrence, independently selected from the group consisting of hydrogen, $C_1$-$C_8$ alkyl optionally substituted with at least one hydroxyl or halogen; $C_3$-$C_7$ cycloalkyl, aryl, e.g. phenyl, benzyl, and heterocyclyl, any of which is optionally substituted.

In one embodiment, the present invention also relates to pharmaceutically acceptable salts of the compounds according to the present invention.

The term "alkyl" refers to a monovalent straight or branched chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, ethyl and methyl.

The term "alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or OMe), ethoxy (—OCH$_2$CH$_3$ or —OEt), t-butoxy (—O—C(CH$_3$)$_3$ or —OtBu) and the like.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" refers to a monovalent straight or branched chain aliphatic hydrocarbon radical containing one carbon-carbon triple bond and having a number of carbon atoms in the specified range. Thus, for example, "$C_2$-$C_6$ alkynyl" refers to all of the hexynyl and pentynyl isomers as well as 1-butynyl, 2-butynyl, 3-butynyl, 1-propynyl, 2-propynyl, and ethynyl.

The term "alkylene" refers to a saturated, branched or straight chain or cyclic hydrocarbon radical having two monovalent radical centers derived by the removal of two hydrogen atoms from the same or two different carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

The term "alkenylene" refers to an unsaturated, branched or straight chain or cyclic hydrocarbon radical having two monovalent radical centers derived by the removal of two hydrogen atoms from the same or two different carbon atoms of parent alkene. For example, an alkenylene group can have 1 to 20 carbon atoms, 1 to 10 carbon atoms, or 1 to 6 carbon atoms. Typical alkenylene radicals include, but are not limited to, 1,2-ethenyl (—CH═CH—).

The term "alkynylene" refers to an unsaturated, branched or straight chain or cyclic hydrocarbon radical having two monovalent radical centers derived by the removal of two hydrogen atoms from the same or two different carbon atoms of parent alkyne. For example, an alkynylene group can have 1 to 20 carbon atoms, 1 to 10 carbon atoms or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —CHF$_2$, —CF$_3$, —CH$_2$—CH$_2$—F, —CH$_2$—CF$_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or thioalkyl group (e.g., —SCH$_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), alkyl amine (e.g., —CH$_2$NHCH$_3$, —CH$_2$N(CH$_3$)$_2$, etc.), or thioalkyl ether (e.g., —CH$_2$—S—CH$_3$).

The term "halogen" refers to fluorine, chlorine, bromine, or iodine.

The term "aryl" refers to (i) optionally substituted phenyl, (ii) optionally substituted 9- or 10 membered bicyclic, fused carbocyclic ring systems in which at least one ring is aromatic, and (iii) optionally substituted 11- to 14-membered tricyclic, fused carbocyclic ring systems in which at least one ring is aromatic. Suitable aryls include, for example, phenyl, biphenyl, naphthyl, tetrahydronaphthyl(tetralinyl), indenyl, anthracenyl, and fluorenyl.

The term "phenyl" as used herein is meant to indicate that optionally substituted or non-substituted phenyl group.

The term "benzyl" as used herein is meant to indicate that optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally $S(O)$ or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to $S(O)$ or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

In one embodiment, the compound has the general formula Ib:

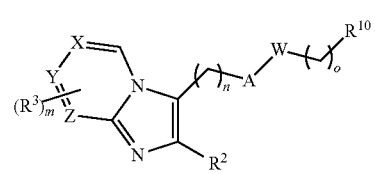

wherein
o is 0, 1, 2, or 3; n is 0, 1, 2 or 3; m is 0, 1, 2, 3 or 4;
A is $NR^{11}$, C=O, C=S, OP(O), P=O, $CH_2$, or a heteroaryl selected from the group consisting of

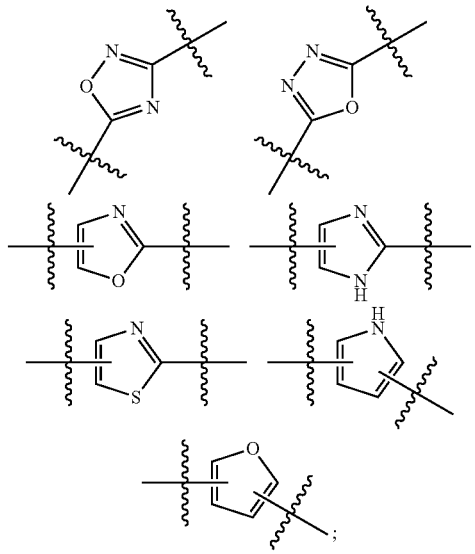

W is C=O, O, S, $CH_2$ or $NR^{11}$;
$R^{10}$ is a moiety selected from the group consisting of

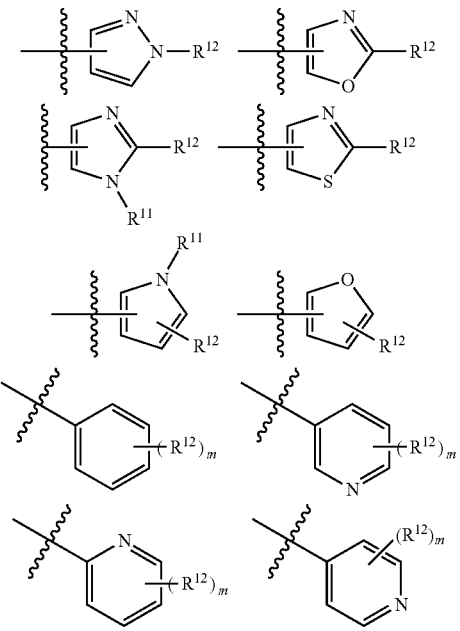

-continued

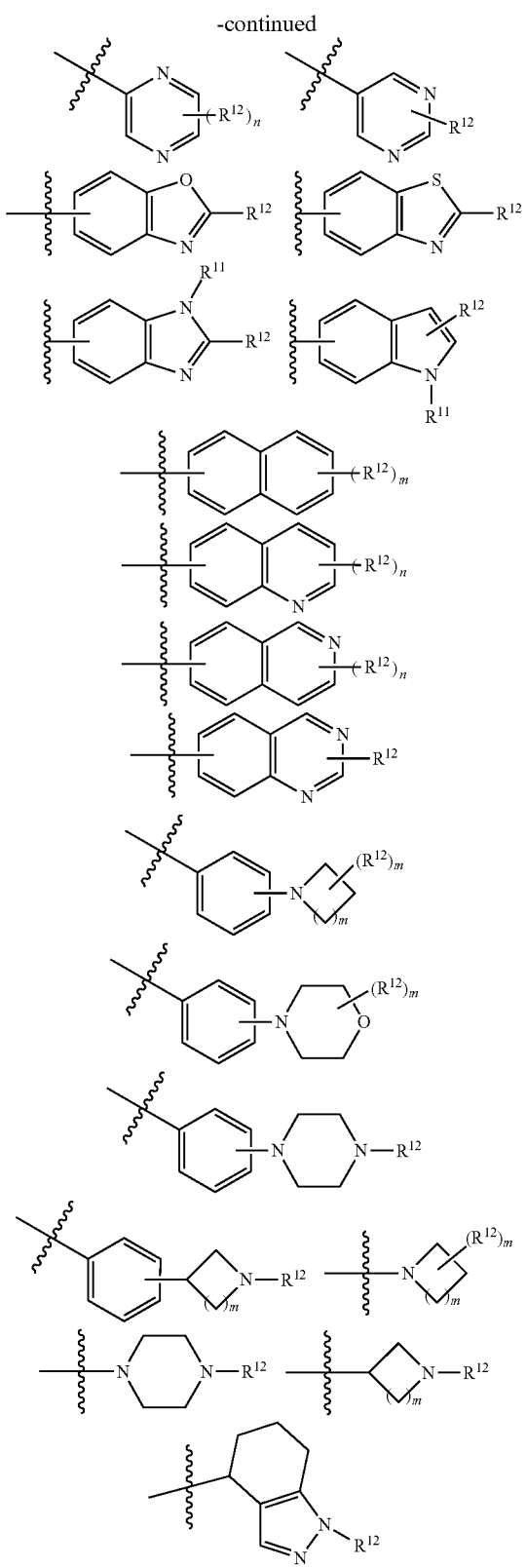

$R^{11}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —OH, —OR$^{13}$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, —NH$_2$, —N(R$^{13}$)$_2$, —C(O)R$^{13}$, —C(O)OR$^{13}$, —C(O)N(R$^{13}$)$_2$, —S(O)R$^{13}$, —S(O)$_2$R$^{13}$, —S(O)$_2$N(R$^{13}$)$_2$, aryl, e.g. phenyl, benzyl, heteroaryl, and heterocyclyl, any of which is optionally substituted;

$R^{12}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, hydroxyl, —OR$^{14}$, —C(O)R$^{14}$, —R$^{14}$(R$^{14}$)C(O)R$^{14}$, —C(O)OR$^{14}$, —R$^{14}$(R$^{14}$)C(O)OR$^{14}$, —CN, —NO$_2$, —NH$_2$, —N(R$^{14}$)$_2$, —C(O)N(R$^{14}$)$_2$, —R$^{14}$(R$^{14}$)C(O)N(R$^{14}$)$_2$, S(O)R$^{14}$, —S(O)$_2$R$^{14}$, —S(O)$_2$N(R$^{14}$)$_2$, aryl, e.g. phenyl, benzyl, heteroaryl, and heterocyclyl, any of which is optionally substituted;

$R^{13}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, e.g. phenyl, benzyl, heteroaryl, and heterocyclyl, any of which is optionally substituted; and $R^{14}$ is, at each occurrence, independently selected from the group consisting of hydrogen, $C_1$-$C_8$ alkyl optionally substituted with at least one hydroxyl or halogen; $C_3$-$C_7$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, e.g. phenyl, benzyl, heteroaryl and heterocyclyl, any of which is optionally substituted.

In another aspect, the present invention relates to compounds having one of the formulae 1-352, as shown in Table 1 and/or Example 2, preferably 15, 16, 31, 32, 44, 45, 47, 49, 54-57, 60-87, 89-103, 106, 107, 110, 111, 113, 116-135, 137-141, 143, 144, 147, 148, 152, 154, 157-159, 161-167, 171-182, 184-193, 196, 198, 199-202, 209-218, 221-227, 231, 248-260, 262-264, 267-269, 271-274, 280-293, 295-315, 317-318, 320-321, 324, and 330 as shown in Table 1, and pharmaceutically acceptable salts thereof. Particularly preferred compounds are compounds having one of the formulae 47, 54, 177 and 185 as shown in Table 1. Their pharmaceutical activity is also shown in FIG. 2.

Preferably, the compounds as defined above have an inhibitory activity on bacterial growth, preferably on the growth of *M. tuberculosis*, inside a host cell, preferably a macrophage, at a concentration between 1-20 µM, preferably less than 1 µM.

In one aspect, the present invention relates to compounds as defined above for use in the treatment of a bacterial infection, e.g. tuberculosis.

In one aspect, the present invention relates to compounds as defined above for use in the treatment of Tuberculosis.

In one aspect, the present invention relates to a pharmaceutical composition comprising a compound as defined above, and a pharmaceutically acceptable carrier.

In one aspect, the present invention relates to a method of treatment of Tuberculosis, comprising the application of a suitable amount of a compound as defined above or of a pharmaceutical composition as defined above to a person in need thereof.

In one embodiment, a "suitable amount", as used herein, is meant to refer to an amount in the range of from 0.01 mg/kg body weight to 1 g/kg body weight.

The objects of the present invention are also solved by a compound that competitively inhibits the specific binding of a compound according to the present invention. Preferably, such specific binding is with respect to a target protein of said compound according to the present invention.

The objects of the present invention are also solved by a method of treatment of a bacterial infection, in particular tuberculosis comprising the application of a suitable amount of a compound which compound is characterized by an ability to competitively inhibit the specific binding of a compound according to the present invention or a pharmaceutical composition according to the present invention, to a target protein, to a person in need thereof.

Pharmaceutical Compositions

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of from 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

FIGURES AND TABLES

Reference is now made to the figures and tables, wherein

Table 1 summarizes imidazopyridine derivatives (general scaffolds Ia and Ib) with their respective inhibitory activities, wherein the numbers in bold print refer to the compounds listed in Example 2;

Table 2 shows anti-bacterial activity for compound 47 and compound 54 on several multi-drug resistant (MDR) strains.

EXAMPLES

The invention is now further described by reference to the following examples which are intended to illustrate, not to limit the scope of the invention.

Example 1

Figure 1:
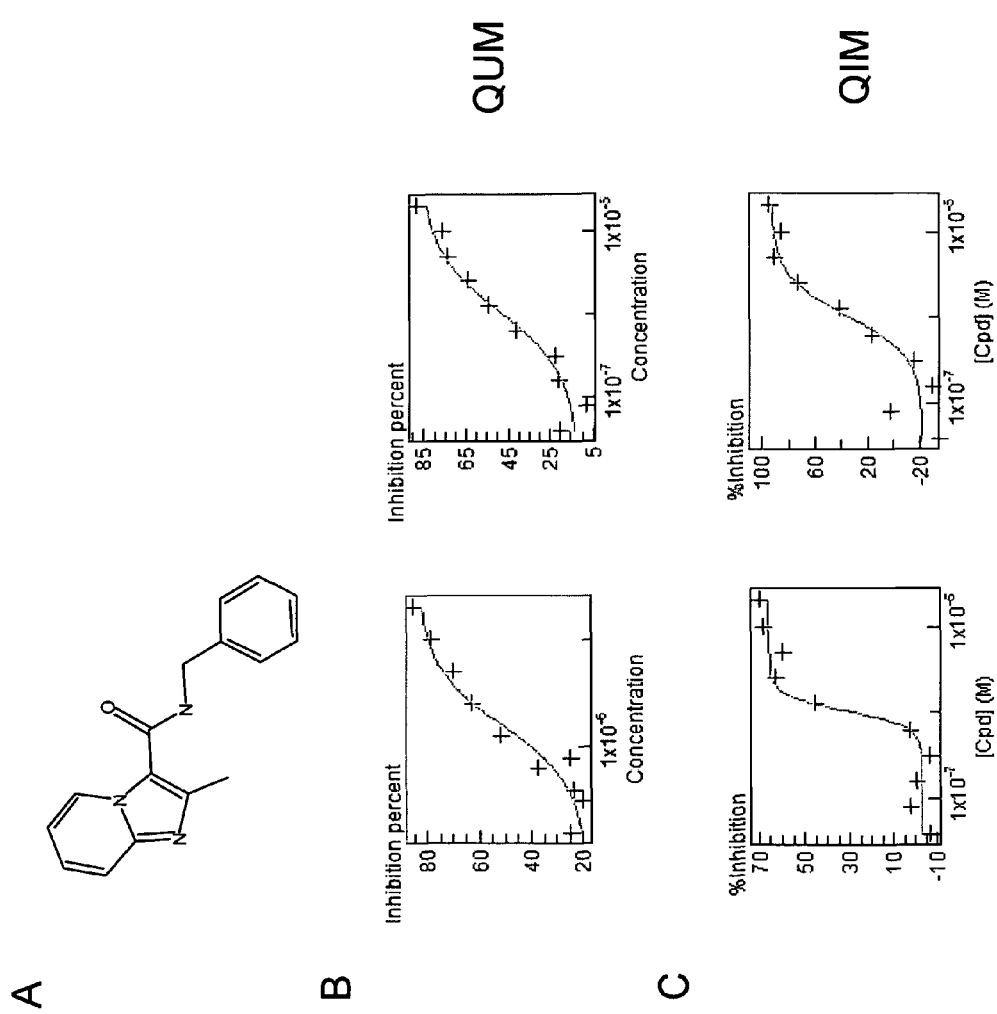
FIG. 1 shows the dose response results on compound 8 (A) from the in vitro growth fluorescence assay (QUM) (B) and the intracellular growth assay (QIM) (C). Each curve represents a separate replicate experiment, [Cpd] refers to compound concentration, (M) refers to molar.

Primary Screening of a Large Library of Small Synthetic Compounds Using the Phenotypic Cell-Based Assay A 120,000 small molecule compound library was screened using a validated phenotypic cell-based assay (WO2010003533A2). Active compounds from the primary screen were confirmed via dose response in the intracellular (QIM) assay and an in vitro (QUM) assay, wherein the abbreviation "QIM" stands for Quantification of Intracellular *Mycobacteria* and the abbreviation "QUM" stands for Quantification of in vitro grown *Mycobacteria*. Compound 8 (FIG. 1A) demonstrated activity in both the QUM and QIM assay (FIGS. 1B and 1C respectively) and is the basis of the imidazopyridine general scaffolds Ia and Ib. Compound 8, from the dose response confirmation experiments demonstrated a minimum inhibitory concentration (MIC) or 5 μM and 2.5 μM in the QUM and QIM assays respectively. The MIC is the minimum concentration of compound required to obtain 80% bacterial growth inhibition. Compound 8 demonstrated potent antibacterial activity and consequently is the focus of the present invention.

Example 2

Derivatization of the Imidazopyridine General Scaffold

The imidazopyridine compounds (scaffolds Ia and Ib; see Table 1) underwent derivatization according to the methods outlined below (Schemes 1-13). Resulting derivatives were examined for inhibitory activity (MIC) using the assays described above (Example 1) and the results are summarized in Table 1.

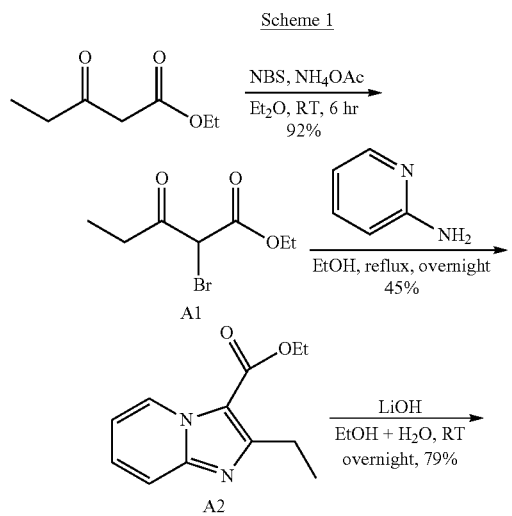

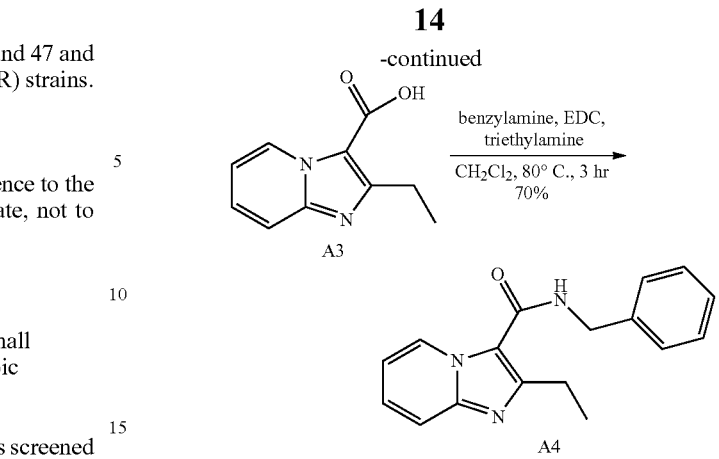

General Procedure for the Synthesis of A1

To a solution of Ethyl propionylacetate (6.9 mmol) in $Et_2O$ (30 mL) was added Ammonium acetate (2.07 mmol) and N-Bromosuccinimide (7.6 mmol). The mixture was stirred at room temperature for 6 hour. After reaction was completed, the reaction mixture was filtered off and washed with $H_2O$ (30 mL). The organic layer was dried over anhydrous $MgSO_4$ and concentrated in vacuo to give A1.

General Procedure for the Synthesis of A2

To a solution of A1 (0.89 mmol) in EtOH (4 mL) was added 2-aminopyridine (0.89 mmol). The mixture was stirred and refluxed for overnight. After cooling, the dark residue was diluted with EtOAc (20 mL) and saturated $NaHCO_3$ solution (30 mL). The organic layer was dried over anhydrous $MgSO_4$ and concentrated in vacuo. The crude product was purified by flash column chromatography to give A2.

Ethyl 2-methylimidazo[1,2-a]pyridine-3-carboxylate (A2)

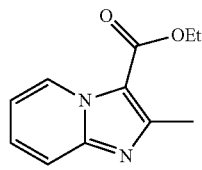

$^1$H NMR (400 MHz, $CDCl_3$) δ 1.28 (t, J=7.2 Hz, 3H), 2.56 (s, 3H), 4.27 (q, J=7.2 Hz, 2H), 6.78 (dd, J=7.2 Hz, 7.2 Hz, 1H), 7.19 (dd, J=6.8 Hz, 6.8 Hz, 1H), 7.42 (dd, J=8.8 Hz, 8.8 Hz, 1H), 9.12 (dd, J=6.8 Hz, 6.8 Hz, 1H); $^{13}$C NMR (100 MHz, $CDCl_3$) δ 14.5, 16.7, 60.3, 112.6, 113.6, 116.9, 127.5, 127.9, 146.9, 152.8, 161.4.

General Procedure for the Synthesis of A3

To a solution of A2 (0.31 mmol) in $H_2O$ (1.0 mL) and EtOH (3.0 mL) was added Lithium hydroxide (0.93 mmol). The mixture was stirred at room temperature for overnight. After reaction was completed, the mixture was evaporated and 1 N HCl (10 ml) was added until pH was 4. The residual pale solid was collected by filtration and washed with $H_2O$ to give A3.

General Procedure for the Synthesis of A4

To a solution of A3 (0.56 mmol) in $CH_2Cl_2$ (3 mL) was added triethylamine (1.7 mmol), benzylamine (0.56 mmol) and 1-ethyl-3-(3-dimethylaminopropyl)carbodiimide (0.84 mmol). The reaction mixture was stirred at room temperature for overnight. After reaction was completed, the reaction mixture was diluted with $CH_2Cl_2$ (10 mL) washed with 1N HCl (10 ml) and saturated NaHCO₃ solution (10 mL). The organic layer was dried over anhydrous MgSO₄ and concentrated in vacuo. The crude product was purified by flash column chromatography to give A4.

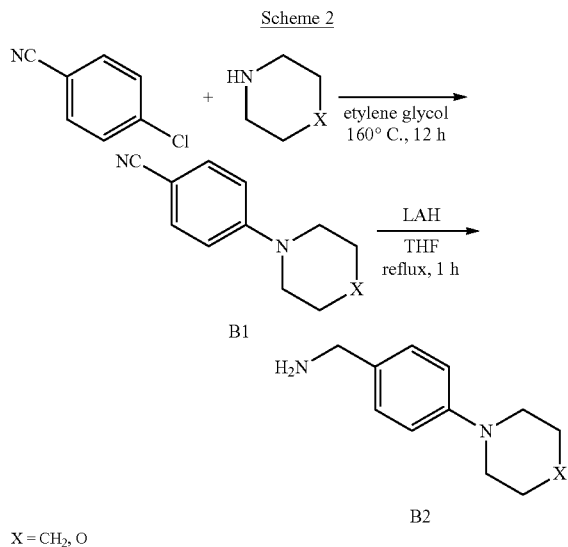

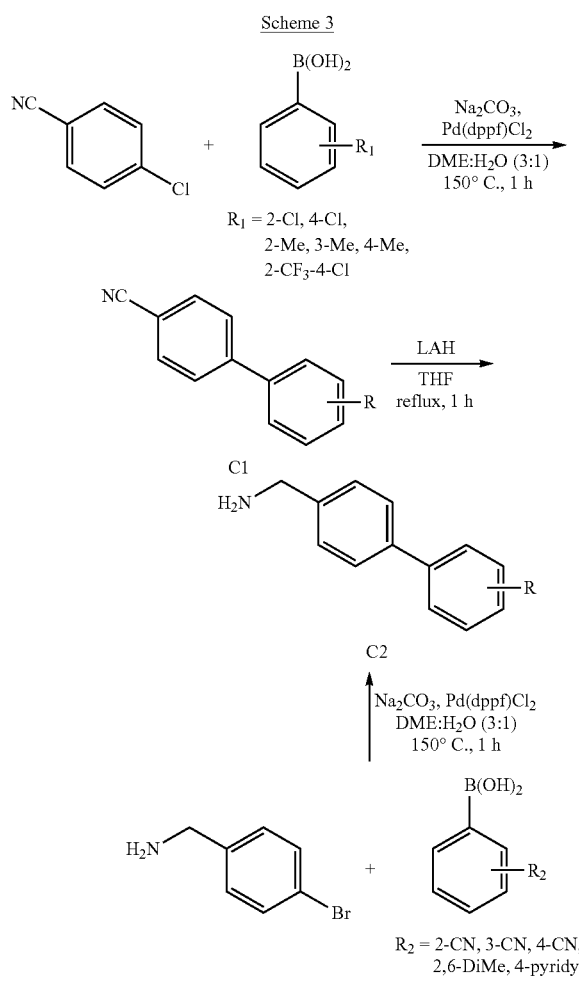

General Procedure of B1

A solution of 4-chlorobenzonitrile (1.0 mmol) in ethylene glycol (2 mL) was added the appropriate amine (5.0 mmol). The reaction mixture was heated to 160° C. for 12 h and then cooled to room temperature, poured into ice water, and extracted three times with EtOAc. The combined organic layers were washed with brine and dried over MgSO₄, filtered and concentrated in vacuo. The residue was purified via flash column chromatography to give B1.

4-(Piperidin-1-yl)benzonitrile

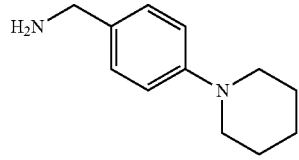 [SMILES: NCc1ccc(N2CCCCC2)cc1]

$^1$H NMR (400 MHz, CDCl₃) δ 1.60-1.68 (m, 5H), 3.30-3.40 (m, 4H), 6.83 (d, J=9.2 Hz 2H), 7.46 (d, J=8.8 Hz, 2H).

General Procedure of B2 and C2

Method I:

A solution of B1 (1.0 mmol) in THF (10 mL) was added LAH at 0° C. The mixture was refluxed for 1 h and then cooled to room temperature. The reaction mixture was quenched by the addition of saturated aq. NaHCO₃ (10 mL) and extracted three times with EtOAc. The combined organic layers were washed with brine and dried over MgSO₄, filtered and concentrated in vacuo. The residue was purified via flash column chromatography to give B2.

(4-(Piperidin-1-yl)phenyl)methanamine $^1$H NMR (400 MHz, CDCl₃) δ 1.55-1.59 (m, 2H), 1.68-1.74 (m, 4H), 3.13 (t, J=5.6 Hz, 4H), 3.77 (s, 2H), 6.92 (d, J=8.4 Hz 2H), 7.19 (d, J=8.8 Hz, 2H).

Method II:

A solution of 4-bromobenzylamine (1.0 mmol) in DME (3 mL) were added the appropriate arylboronic acid (1.0 mmol), 1,1'-bis(diphenylphosphino)ferrocene)-dichloropalladium (II) (0.03 mmol), Na₂CO₃ (aq. 2.0 mmol). The mixture was stirred and heated at reflux under N₂ atmosphere. After 1 h, the mixture was cooled to room temperature, then the mixture was extracted with EtOAc, washed with sat. NaHCO₃ (aq.) brine and dried over MgSO₄ and filtered. After removal of the solvent, the amines were obtained, which were used without purification.

General Procedure of C1

A solution of 4-chlorobenzonitrile (1.0 mmol) in DME (3 mL) were added the appropriate arylboronic acid (1.0 mmol), 1,1'-bis(diphenylphosphino)ferrocene)dichloropalladium (II) (0.03 mmol), Na₂CO₃ (aq. 2.0 mmol). The mixture was stirred and heated at reflux under N₂ atmosphere. After 1 h, the mixture was cooled to room temperature, then filtered and evaporated in vacuo. The residue was extracted with EtOAc, washed with sat. NaHCO₃ (aq.) brine and dried over MgSO₄, filtered and concentrated in vacuo. The residue was purified via flash column chromatography to give C1.

2'-(Trifluoromethyl)biphenyl-4-carbonitrile
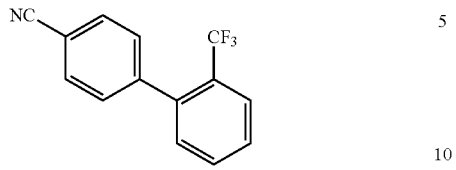
$^1$H NMR (400 MHz, CDCl$_3$) δ 7.30 (d, J=7.0 Hz, 1H), 7.45 (d, J=8.0 Hz, 2H), 7.54 (dd, J=7.6, 7.6 Hz, 1H), 7.61 (dd, J=7.2, 7.6 Hz, 1H), 7.70 (d, J=8.0 Hz, 2H), 7.76 (d, J=7.6 Hz, 1H).
Scheme 4
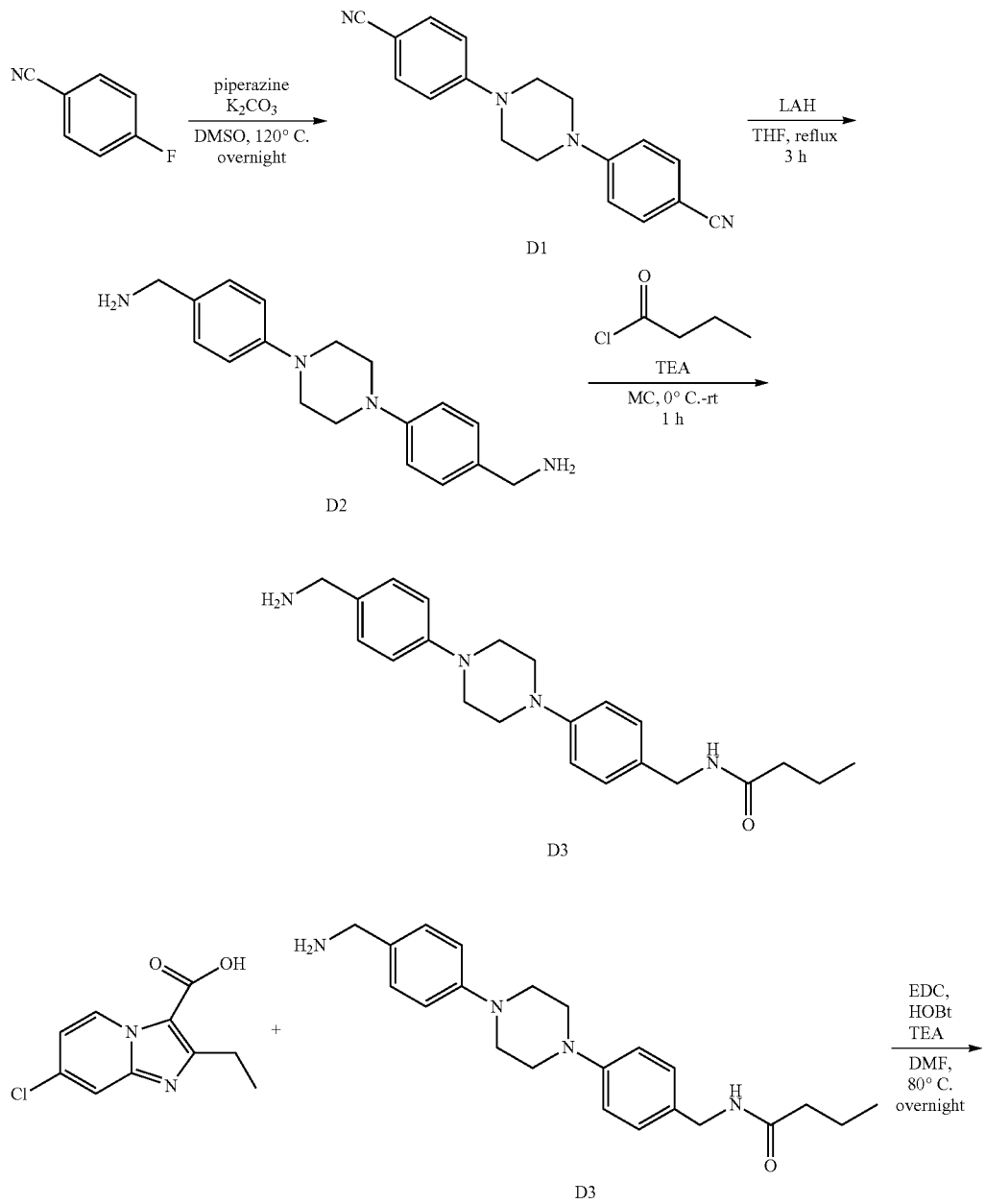

D4

Procedure for the Synthesis of D1

A mixture of 4-fluorobenzonitrile (4.2 g, 35 mmol), piperazine (1.0 g, 12 mmol) and $K_2CO_3$ (4.8 g, 35 mmol) in DMSO (30 mL) was stirred for overnight at 120° C. The reaction mixture was poured to the ice and resulting solid was filtered, washed with methanol and dried in vacuo to give D1 as a white solid; $^1$H NMR (400 MHz, DMSO) δ 3.49 (s, 8H), 7.01 (d, J=9.2 Hz, 4H), 7.57 (d, J=9.2 Hz, 4H); LCMS (electrospray) m/z (M+H)$^+$ 289.

Procedure for the Synthesis of D2

To a stirred solution of D1 (0.30 g, 1.00 mmol) in THF (5 mL) was added LAH (0.24 g, 6.20 mmol) and the resulting mixture was heated to reflux temperature for 3 h. The reaction mixture was quenched with water and the solid was filtered off. The filtrate was extracted with MC (30 mL×2), the organic layer was washed with saturated aqueous $Na_2CO_3$ (20 mL) and concentrated in vacuo to give D2; $^1$H NMR (400 MHz, CDCl$_3$) δ 3.32 (s, 8H), 3.80 (s, 4H), 6.95 (d, J=8.4 Hz, 4H), 7.25 (d, J=8.4 Hz, 4H); LCMS (electrospray) m/z (M)$^+$ 296.

Procedure for the Synthesis of D3

To a stirred solution of D2 (0.70 g, 2.36 mmol) in MC (25 mL) was added butyryl chloride (25 uL, 0.23 mmol) and the resulting mixture was stirred for 30 min under ice bath. After removal of the ice bath, the reaction mixture was stirred for another 30 min. The reaction mixture was diluted with MC (20 mL), washed with saturated aqueous $Na_2CO_3$ (20 mL) and the organic layer was concentrated under reduced pressure. The crude residue was purified by column chromatography (20% MeOH in MC) to give D3; $^1$H NMR (400 MHz, CDCl$_3$) δ 0.41 (t, J=7.2 Hz, 3H), 1.00 (brs, 2H), 1.12-1.21 (m, 2H), 1.63 (t, J=7.2 Hz, 2H), 2.80 (s, 8H), 3.27 (s, 2H), 3.84 (d, J=5.2 Hz, 2H), 5.16 (brs, 1H), 6.38-6.45 (m, 4H), 6.67-6.74 (m, 4H); LCMS (electrospray) m/z (M+H)$^+$ 367.

Procedure for the Synthesis of D4

To a solution of acid (0.012 g, 0.054 mmol) in DMF (1 mL) was added triethylamine (15 uL, 0.11 mmol), D3 (0.020 g, 0.055 mmol), hydroxybenzotriazole (3.7 mg, 0.027 mmol) and 1-ethyl-3-(3-dimethylaminopropyl)carbodiimide (0.016 g, 0.082 mmol) and the reaction mixture was stirred at 80° C. for overnight. The reaction mixture was cooled to −10° C., the resulting solid was filtered, washed with MC and dried in vacuo to give D4;

Scheme 5

E1

Procedure for the Synthesis of E2

A mixture of E1 (0.32 g, 0.86 mmol), an amine (excess) and DIPEA (0.75 mL, 4.32 mmol) in ethylene glycol (4 mL) was heated to 160° C. for 1.5 days. After reaction completion, the reaction mixture was diluted with water (20 mL) and extracted with ethyl acetate (20 mL×3). The organic layer was dried over anhydrous MgSO$_4$ and concentrated in vacuo. The crude residue was purified by flash column chromatography (20% MeOH in MC) and then precipitated with acetonitrile to give E2 as a white solid.

Scheme 6

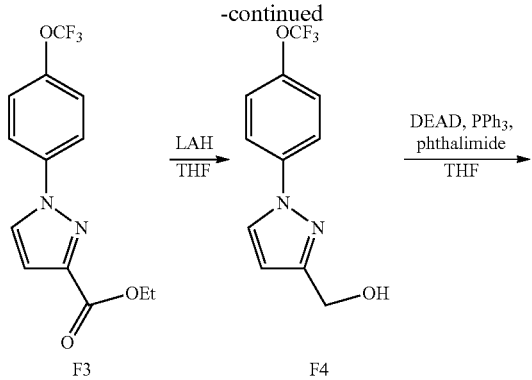

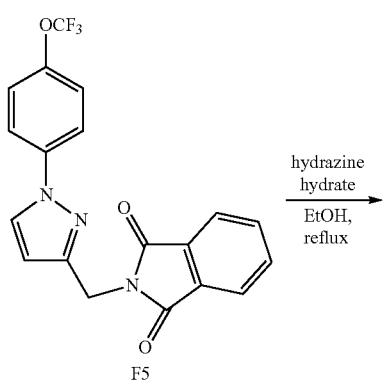

General Procedure for the Synthesis of F1

To an ice-salt-cooled solution of the 4-(trifluoromethoxy) aniline (11.29 mmol) in HBF$_4$ (50%, 22.58 mmol) and water (2 mL) was dropwise added a precooled solution of NaNO$_2$ (12.42 mmol) in water (2 mL). During the addition, the temperature was carefully kept below 5° C. and the resulting mixture was left to stir at 0° C. for 30 min. The diazonium salt (F1) was collected by filtration, washed with Et$_2$O, and extensively dried in vacuo.

General Procedure for the Synthesis of F2

F1 (11.30 mmol) was added to a solution of 2-chloroacetoacetate (11.30 mmol) in pyridine (4 mL) and water (4 mL) at −5° C. The mixture was stirred at −5° C. for 30 min, and the resulting precipitate was filtered and washed with ice cold water. Recrystallization from EtOH/water gave F2.

(E)-Ethyl 2-chloro-2-(2-(4-(trifluoromethoxy)phenyl)hydrazono)acetate (F2)

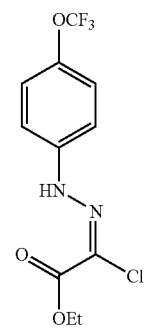 [SMILES: CCOC(=O)/C(Cl)=N\Nc1ccc(OC(F)(F)F)cc1]

$^1$H NMR (400 MHz, CDCl$_3$) δ 1.41 (t, J=7.2 Hz, 3H), 4.39 (q, J=7.2 Hz, 2H), 7.20 (d, J=9.6 Hz, 2H), 7.24 (d, J=9.2 Hz, 2H), 8.32 (brs, 1H)

General Procedure for the Synthesis of F3

A mixture of F2 (9.33 mmol), bicyclo[2.2.1]hepta-2,5-diene (46.67 mmol) and Et$_3$N (28.00 mmol) in toluene (10 mL) was stirred at 70° C. for 1 h. The resulting mixture was cooled and filtered, the filter cake was washed with toluene, and the organic fractions were combined and evaporated. The residue was refluxed in xylenes (10 mL) for 2 h. Column chromatography of the cooled reaction mixture, eluting with hexanes, first gave xylenes, and then further elution with ethyl acetate gave F3.

Ethyl 1-(4-(trifluoromethoxy)phenyl)-1H-pyrazole-3-carboxylate (F3)

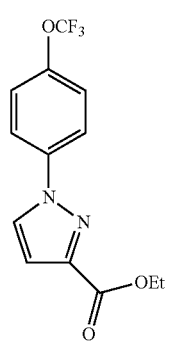 [SMILES: CCOC(=O)c1ccn(-c2ccc(OC(F)(F)F)cc2)n1]

$^1$H NMR (400 MHz, CDCl$_3$) δ 1.42 (t, J=7.2 Hz, 3H), 4.44 (q, J=7.2 Hz, 2H), 7.00 (d, J=2.4 Hz, 1H), 7.33 (d, J=8.8 Hz, 2H), 7.79 (d, J=9.2 Hz, 2H), 7.91 (d, J=2.4 Hz, 1H)

General Procedure for the Synthesis of F4

LiAlH$_4$ (0.67 mmol) was added to a stirred solution of F3 (0.67 mmol) in THF (5 mL) at 0° C., and the mixture was warmed to room temperature for 1 hr, then cooled to 0° C. and quenched with ice. The resulting mixture was diluted with ethyl acetate (10 mL) washed with water (10 mL) and brine (10 mL). The organic layer was dried over anhydrous MgSO$_4$, filtered and concentrated in vacuo. The crude product was purified by flash column chromatography to give F4.

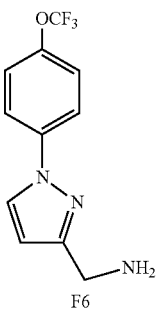

General Procedure for the Synthesis of F5

DEAD (0.84 mmol) was added dropwise to a stirred and cooled (0° C.) solution of phthalimide (0.83 mmol), Ph$_3$P (0.84 mmol) and F4 (0.69 mmol) in dry THF. The cooling bath removed and stirring was continued at room temperature for 4 hr, then water (1 mL) was added the reaction mixture was filtered through a column of silica, eluting with CH$_2$Cl$_2$. The eluate was concentrated in vacuo and the residue was purified by flash column chromatography to give F5.

General Procedure for the Synthesis of F6

To a solution of F5 (0.69 mmol) in EtOH (5 mL) was added hydrazine hydrate (1.38 mmol). The reaction mixture was stirred and refluxed for 4 hr. After cooling, the reaction mixture was evaporated and diluted with EtOAc (10 mL) and saturated NaHCO$_3$ solution (10 mL), then washed with brine (10 mL). The organic layer was dried over anhydrous MgSO$_4$, filtered and concentrated in vacuo. The crude product F6 was used for next step without further purification.

General Procedure for the Synthesis of G2

To a solution of G1 (8.98 mmol) in methanol (20 mL) and water (3 mL) was added (4-(trifluoromethoxy)phenyl)hydrazine hydrochloride (8.98 mmol) and sodium hydroxide (8.98 mmol). The reaction mixture heated at reflux for 2 h and concentrated in vacuo. Then to the residue were added AcOH (20 mL) and water (10 mL), and the reaction mixture was heated to 110° C. for 2 h. On completion of the reaction, the solution was concentrated in vacuo, the residue was diluted with EtOAc (20 mL) and saturated NaHCO$_3$ solution (20 mL), then washed with brine (20 mL). The organic layer was dried over anhydrous MgSO$_4$, filtered and concentrated in vacuo. The residue was purified by flash column chromatography to give G2.

General Procedure for the Synthesis of G3

To a solution of G2 (2.36 mmol) in 2-propanol (5 mL) was added ammonium acetate (23.65 mmol). After complete dissolution, molecular sieves (4 Å, 1.0 g) and NaBH$_3$CN (11.82 mmol) were added and the reaction mixture was stirred and refluxed for overnight. After cooling, the reaction mixture was evaporated and diluted with EtOAc (10 mL) and saturated NaHCO$_3$ solution (10 mL), then washed with brine (10 mL). The organic layer was dried over anhydrous MgSO$_4$, filtered and concentrated in vacuo. The crude product G3 was used for next step without further purification.

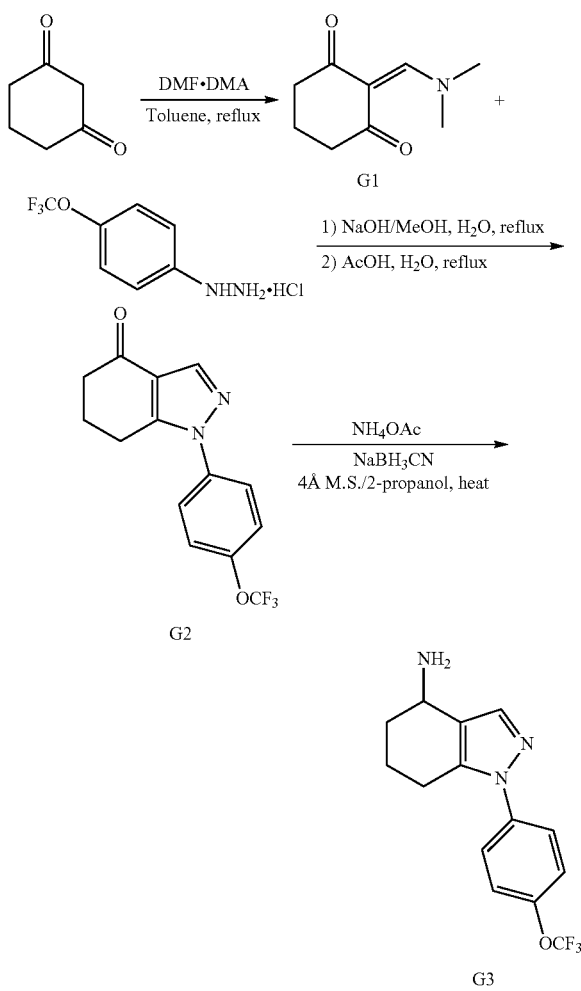

Scheme 7

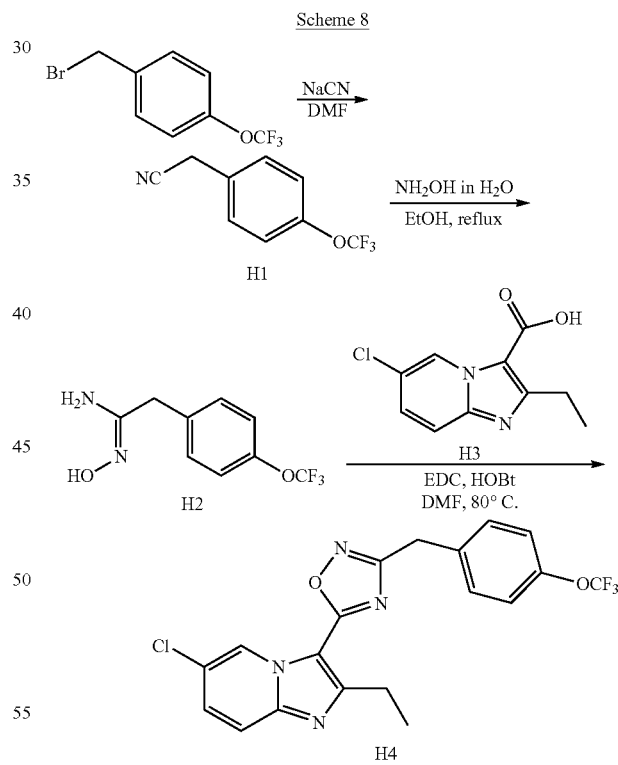

Scheme 8

General Procedure for the Synthesis of G1

To a solution of cyclohexane-1,3-dione (17.84 mmol) in toluene (20 mL) was added DMF.DMA (26.75 mmol). The reaction mixture was stirred and refluxed for overnight. After cooling, the reaction mixture was concentrated in vacuo. The crude product G1 was used for next step without further purification.

General Procedure for the Synthesis of H1

To a solution of 4-trifluoromethoxybenzyl bromide (1.05 g, 4.09 mmol) in 5 mL dry DMF was added sodium cyanide (220 mg, 4.50 mmol). The reaction was stirred for 1 h at room temperature, poured into water and extracted with of ethyl acetate (2×20 mL). The combined layer was dried over anhydrous MgSO$_4$, filtered and concentrated in vacuo. The crude product H1 was used in the next reaction without further purification.

General Procedure for the Synthesis of H2

To a solution of H1 (93 mg, 0.46 mmol) in EtOH was added a solution of hydroxylamine 50 wt % in water (0.12 mL, 1.84 mmol). The reaction mixture was refluxed for overnight. After cooling, the mixture was concentrated in vacuo. The crude product H2 was used in the next reaction without further purification.

General Procedure for the Synthesis of H4

To a solution of H3 (114 mg, 0.506 mmol) in dry DMF were added 1-ethyl-3-(3-dimethylaminopropyl)carbodiimide (97 mg, 0.506 mmol), 1-hydroxybenzotriazole (68 mg, 0.506 mmol). The mixture was stirred for 30 min at room temperature. Then to the reaction mixture was added a solution of C2 (108 mg, 0.46 mmol) in dry DMF. The reaction mixture was stirred at 140° C. for 2 h. After cooling, the reaction mixture was diluted with ethyl acetate (10 mL), washed with saturated NaHCO$_3$ solution (10 mL) and brine (10 mL). The organic layer was dried over anhydrous MgSO$_4$ and concentrated in vacuo. The crude product was purified by flash column chromatography to give H4.

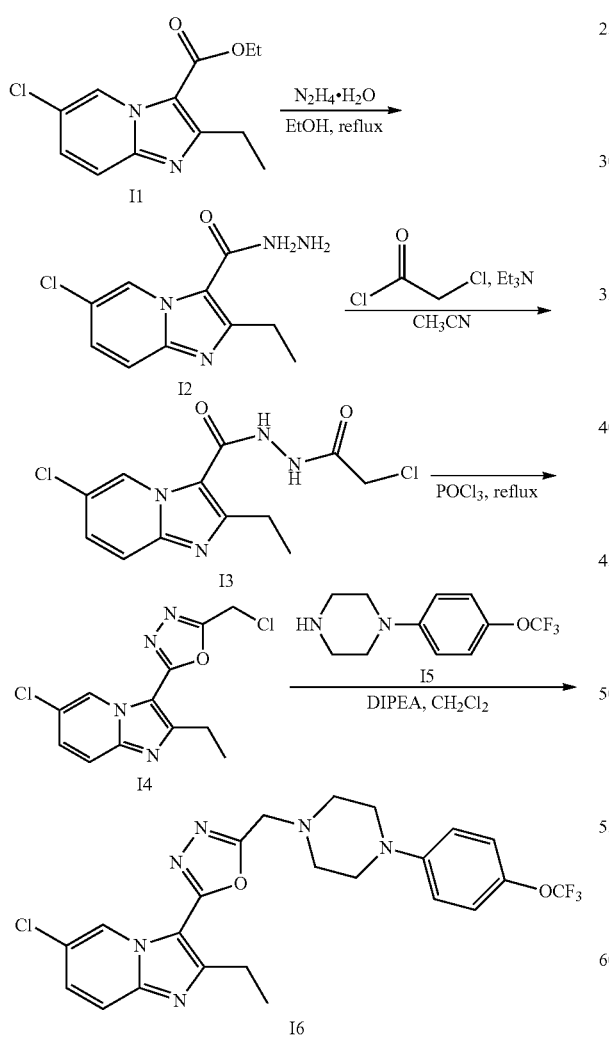

Scheme 9

General Procedure for the Synthesis of I2

To a solution of I1 (253 mg, 1.0 mmol) in EtOH was added hydrazine hydrate (0.75 mL, mmol). The reaction mixture was refluxed for 12 h. After cooling, the resulting precipitate (D2) was filtered, washed with EtOH and dried.

General Procedure for the Synthesis of I3

To a solution of I2 (96 mg, 0.402 mmol) in CH$_2$Cl$_2$ was added Et$_3$N (0.057 mL, 0.406 mmol). The reaction mixture was cooled to 0° C. and to the mixture was added dropwise a solution of chloroacetyl chloride (0.035 mL, 0.442 mmol) in CH$_2$Cl$_2$. The reaction mixture was stirred at 0° C., the reaction temperature was raised to room temperature and the resultant mixture is further stirred for 30 min. To the mixture was added water, the solution was extracted with CH$_2$Cl$_2$, washed with brine. The organic layer was dried over anhydrous MgSO$_4$ and concentrated in vacuo. The crude product (I3) was used in the next reaction without further purification.

General Procedure for the Synthesis of I4

I3 (0.402 mmol) was placed under nitrogen and POCl$_3$ (2 mL) was added. The reaction mixture was refluxed for 2 h. The mixture was cooled to room temperature, poured into water and extracted with ethylacetate (×2). The combined organic layers were washed with brine, dried over anhydrous MgSO$_4$ and concentrated in vacuo. The crude product was purified by flash column chromatography to give I4.

General Procedure for the Synthesis of I6

To a solution of I4 (50 mg, 0.17 mmol) in CH$_2$Cl$_2$ were added I5 (50 mg, 0.20 mmol) and DIPEA (0.035 mL, 0.20 mmol). The reaction mixture was stirred for overnight the mixture was extracted with CH$_2$Cl$_2$ and water, washed with brine. The organic layer was dried over anhydrous MgSO$_4$ and concentrated in vacuo. The crude product was purified by flash column chromatography to give I6.

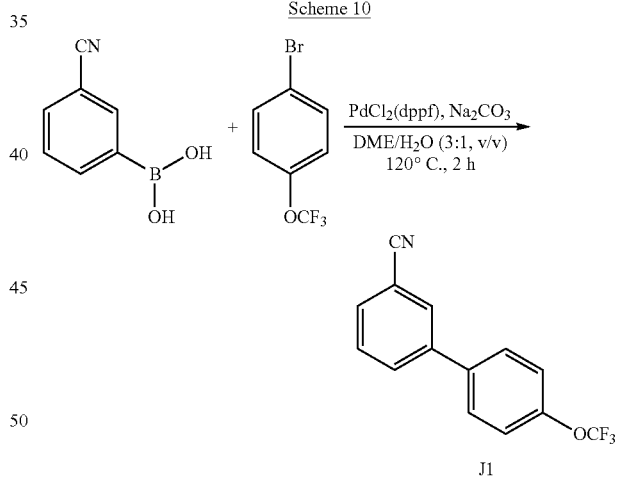

Scheme 10

General Procedure for the Synthesis of J1

To a solution of 1-bromo-4-(trifluoromethoxy)benzene (0.50 g, 2.07 mmol) in DME (6 mL) were added 3-cyanophenyl boronic acid (0.37 g, 2.49 mmol), 1,1'-bis(diphenylphosphino)ferrocene)-dichloropalladium(II) (0.046 g, 0.062 mmol) and Na$_2$CO$_3$ (2 mL of aqueous solution, 0.44 g, 4.14 mmol). The resulting mixture was stirred at 120° C. for 2 h. After removal of organic solvent, the resulting residue was diluted with water (10 mL) and extracted with methylene chloride (10 mL×2). The organic layer was dried over MgSO$_4$ and concentrated in vacuo. The resulting crude residue was purified by flash column chromatography (n-hexane:ethyl acetate=10:1 ratio) to give a J1.

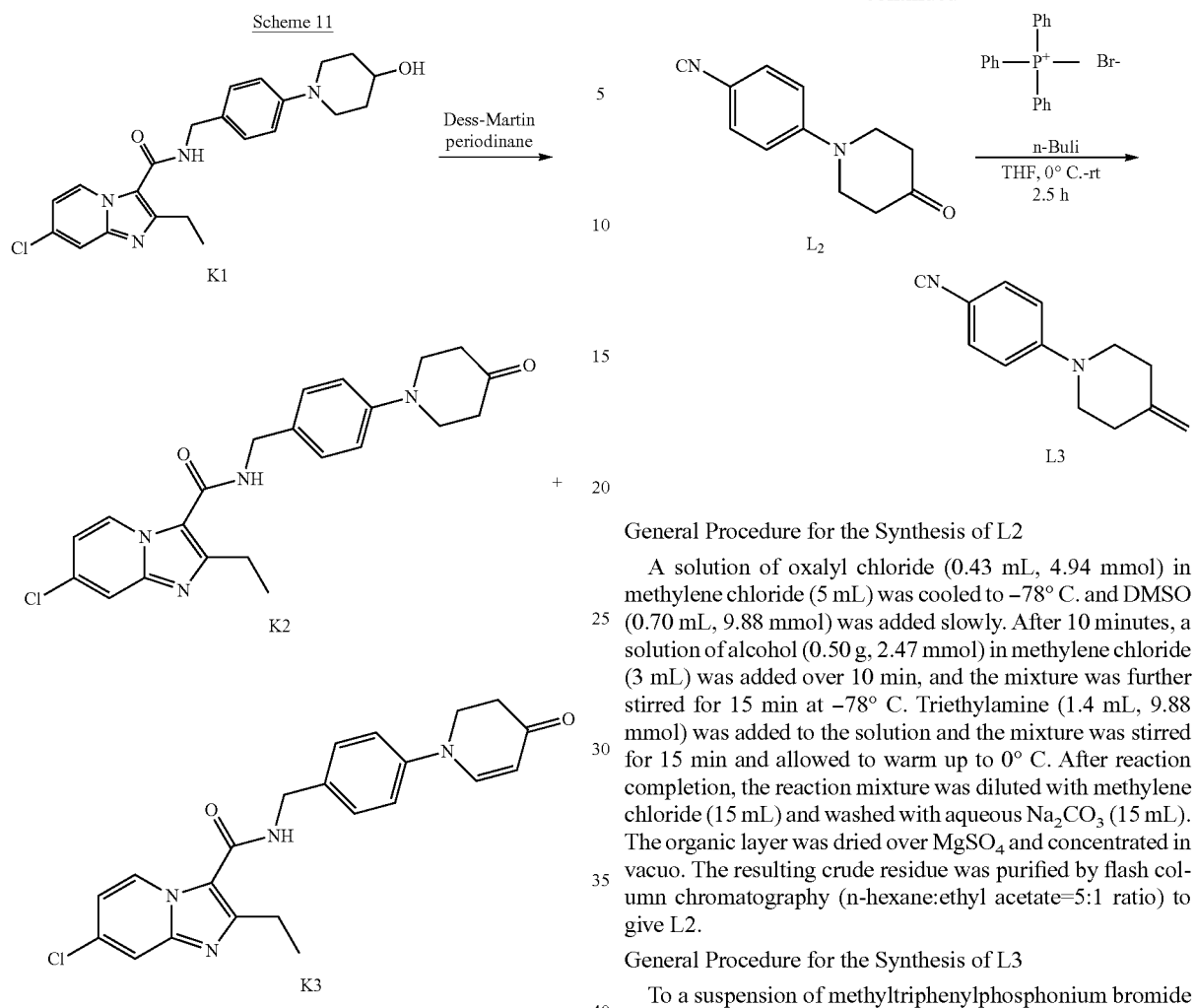

General Procedure for the Synthesis of K2 and K3

To a stirred suspension of K1 (0.050 g, 0.12 mmol) and NaHCO₃ (0.051 g, 0.60 mmol) in methylene chloride (2.0 mL) was added dess-martin periodinane (0.10 g, 0.24 mmol) under ice-bath. After 5-minutes, the reaction temperature was raise to room temperature and the resulting solution was stirred for 2 h. The reaction mixture was diluted with methylene chloride (10 mL) and washed with saturated aqueous NaHCO₃ solution (10 mL) and brine (10 mL). The organic layer was dried over anhydrous MgSO₄ and concentrated in vacuo. The resulting crude residue was purified by flash column chromatography (methylene chloride:methanol=50:1 ratio) to give K2 and K3.

General Procedure for the Synthesis of L2

A solution of oxalyl chloride (0.43 mL, 4.94 mmol) in methylene chloride (5 mL) was cooled to −78° C. and DMSO (0.70 mL, 9.88 mmol) was added slowly. After 10 minutes, a solution of alcohol (0.50 g, 2.47 mmol) in methylene chloride (3 mL) was added over 10 min, and the mixture was further stirred for 15 min at −78° C. Triethylamine (1.4 mL, 9.88 mmol) was added to the solution and the mixture was stirred for 15 min and allowed to warm up to 0° C. After reaction completion, the reaction mixture was diluted with methylene chloride (15 mL) and washed with aqueous Na₂CO₃ (15 mL). The organic layer was dried over MgSO₄ and concentrated in vacuo. The resulting crude residue was purified by flash column chromatography (n-hexane:ethyl acetate=5:1 ratio) to give L2.

General Procedure for the Synthesis of L3

To a suspension of methyltriphenylphosphonium bromide (0.43 g, 1.20 mmol) in THF (5 mL) was added nBuLi (2.5 M in n-hexane, 0.48 mL, 1.20 mmol) under ice-bath and the mixture was stirred for 30 min. A solution of ketone compound in THF (3 mL) was added dropwise and the resulting mixture was allowed to warm up to room temperature over 2 h. After reaction completion, solution was diluted with methylene chloride (10 mL) and washed with aqueous NaHCO₃ (15 mL). The organic layer was dried over MgSO₄ and concentrated in vacuo. The resulting crude residue was purified by flash column chromatography (n-hexane:ethyl acetate=15:1 ratio) to give a target compound L3.

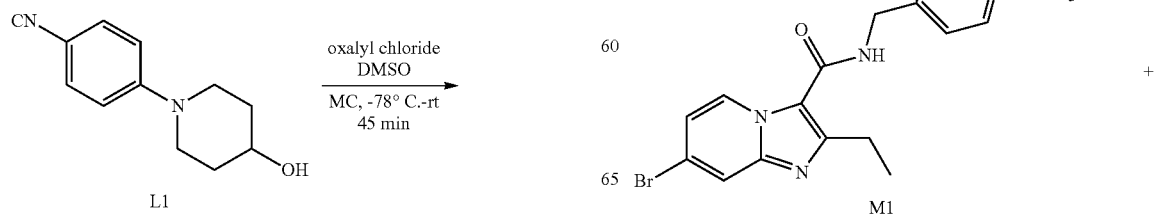

-continued

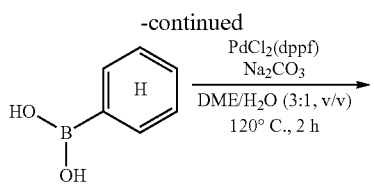

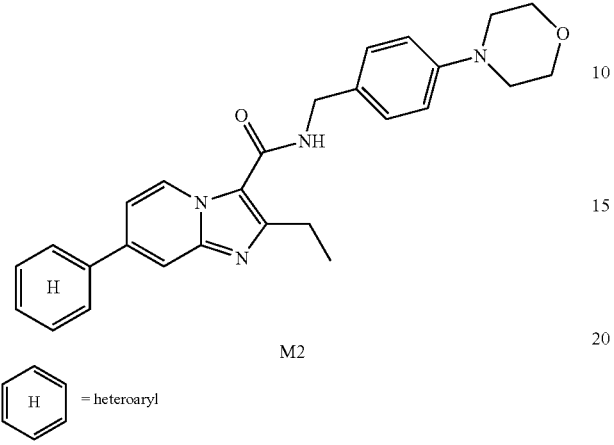

H = heteroaryl

General Procedure for the Synthesis of M2

To a solution of M1 (0.050 g, 0.13 mmol) in DME (2 mL) were added pyridine boronic acid (0.017 g, 0.13 mmol), 1,1'-bis(diphenylphosphino)ferrocene)-dichloropalladium(II) (1.5 mg, 3.38 umol) and $Na_2CO_3$ (0.5 mL of aqueous solution, 0.024 g, 0.22 mmol). The resulting mixture was stirred at 120° C. for 2 h. After removal of organic solvent, the resulting residue was diluted with water (10 mL) and extracted with methylene chloride (10 mL×2). The organic layer was dried over $MgSO_4$ and concentrated in vacuo. The resulting crude residue was purified by flash column chromatography (methylene chloride:methanol=20:1 ratio) to give a target compound M2.

2-Methylimidazo[1,2-a]pyridine-3-carboxylic acid (1)

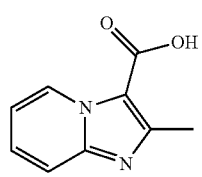

$^1$H NMR (400 MHz, $CD_3OD$) δ 2.84 (s, 3H), 7.04 (dd, J=1.2 Hz, 7.2 Hz, 1H), 7.96 (d, J=8.8 Hz, 1H), 8.07 (dd, J=1.2 Hz, 7.2 Hz, 1H), 9.65 (d, J=7.2 Hz, 1H).

Ethyl 2-methyl-7-phenylimidazo[1,2-a]pyridine-3-carboxylate (2)

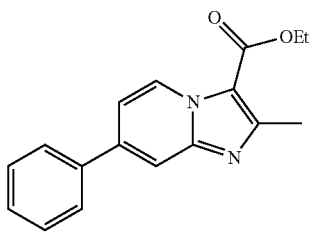 [SMILES: CCOC(=O)c1c(C)nc2cc(-c3ccccc3)ccn12]

$^1$H NMR (400 MHz, $CDCl_3$) δ 1.45 (t, J=7.2 Hz, 3H), 2.73 (s, 3H), 4.44 (q, J=7.2 Hz, 2H), 7.25 (dd, J=1.6 Hz, 7.2 Hz, 1H), 7.42-7.51 (m, 3H), 7.68 (d, J=7.6 Hz, 2H), 7.80 (s, 1H), 9.32 (d, J=7.2 Hz, 1H).

2-Methyl-7-phenylimidazo[1,2-a]pyridine-3-carboxylic acid (3)

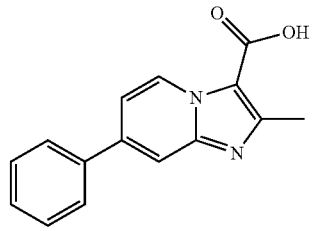 [SMILES: Cc1nc2cc(-c3ccccc3)ccn2c1C(=O)O]

$^1$H NMR (400 MHz, DMSO d-6) δ 2.60 (s, 3H), 7.43-7.52 (m, 5H), 7.83 (s, 1H), 7.85 (s, 1H), 7.94 (s, 1H), 9.26 (d, J=7.6 Hz, 1H)

Ethyl 2-methyl-6-phenylimidazo[1,2-a]pyridine-3-carboxylate (4)

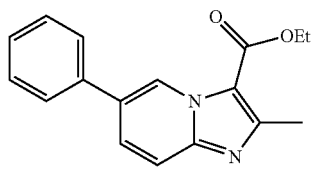 [SMILES: CCOC(=O)c1c(C)nc2ccc(-c3ccccc3)cn12]

$^1$H NMR (400 MHz, $CDCl_3$) δ 1.41 (t, J=7.2 Hz, 3H), 2.70 (s, 3H), 4.40 (q, J=7.2 Hz, 2H), 7.33-7.36 (m, 1H), 7.42 (t, J=7.4 Hz, 2H), 7.56 (d, J=7.2 Hz, 2H), 7.60-7.61 (m, 1H), 9.52 (s, 1H).

2-Methyl-N-(pyridin-4-yl)imidazo[1,2-a]pyridine-3-carboxamide (5)

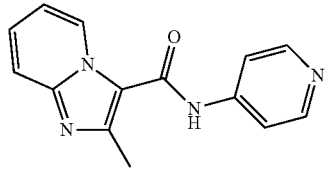 [SMILES: Cc1nc2ccccn2c1C(=O)Nc1ccncc1]

$^1$H NMR (400 MHz, $CDCl_3$+DMSO-$d_6$) δ 2.72 (s, 3H), 6.89 (dd, J=1.2, 7.2 Hz, 1H), 7.28-7.33 (m, 1H), 7.52 (d, J=9.2 Hz, 1H), 7.57 (dd, J=1.6, 4.8 Hz, 2H), 8.43 (dd, J=1.6, 4.8 Hz, 1H), 8.92 (br s, 1H), 9.11 (d, J=6.8 Hz, 1H); LCMS (electrospray) m/z (M+H)$^+$ 253.18

2-Methyl-N-(4-phenoxyphenyl)imidazo[1,2-a]pyridine-3-carboxamide (6)

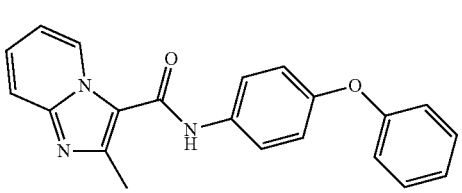 [SMILES: Cc1nc2ccccn2c1C(=O)Nc1ccc(Oc2ccccc2)cc1]

¹H NMR (400 MHz, CDCl₃) δ 2.60 (s, 3H), 6.89 (t, J=8.0 Hz, 3H), 6.96 (d, J=6.8 Hz, 2H), 7.02 (t, J=7.6 Hz, 1H), 7.27 (t, J=7.6 Hz, 2H), 7.38 (t, J=6.8 Hz, 1H), 7.47 (d, J=8.8 Hz, 1H), 7.57 (d, J=6.8 Hz, 2H), 8.89 (d, J=6.8 Hz, 1H).

N-(4-(Benzyloxy)phenyl)-2-methylimidazo[1,2-a]pyridine-3-carboxamide (7)

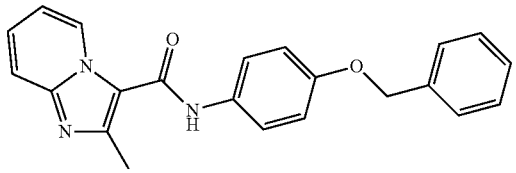 [SMILES: Cc1nc2ccccn2c1C(=O)Nc1ccc(OCc2ccccc2)cc1]

¹H NMR (400 MHz, CDCl₃) δ 2.57 (s, 3H), 4.97 (s, 2H), 6.88-6.91 (m, 3H), 7.19 (t, J=7.2 Hz, 1H), 7.28 (t, J=8.4 Hz, 2H), 7.32 (t, J=6.8 Hz, 3H), 7.43-7.46 (m, 3H), 8.85 (d, J=5.6 Hz, 1H).

N-Benzyl-2-methylimidazo[1,2-a]pyridine-3-carboxamide (8)

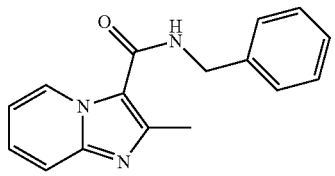 [SMILES: Cc1nc2ccccn2c1C(=O)NCc1ccccc1]

¹H NMR (400 MHz, CDCl₃) δ 2.68 (s, 3H), 4.70 (d, J=5.6 Hz, 2H), 6.13 (brs, 1H), 6.91 (dd, J=1.2 Hz, 7.2 Hz, 1H), 7.29-7.39 (m, 6H), 7.56 (d, J=9.2 Hz, 1H), 9.42 (d, J=7.2 Hz, 1H).

N-(4-Fluorobenzyl)-2-methylimidazo[1,2-a]pyridine-3-carboxamide (9)

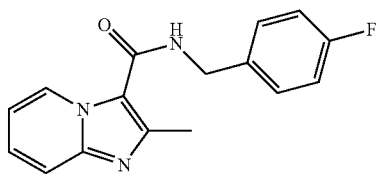 [SMILES: Cc1nc2ccccn2c1C(=O)NCc1ccc(F)cc1]

¹H NMR (400 MHz, CDCl₃) δ 2.67 (s, 3H), 4.66 (d, J=6.0 Hz, 2H), 6.11 (brs, 1H), 6.91 (d, J=6.8 Hz, 1H), 7.02-7.06 (m, 2H), 7.30-7.36 (m, 3H), 7.56 (d, J=8.8 Hz, 1H), 9.41 (d, J=6.8 Hz, 1H).

Methyl 4-((2-me3thylimidazo[1,2-a]pyridine-3-carboxamido)methyl)benzoate (10)

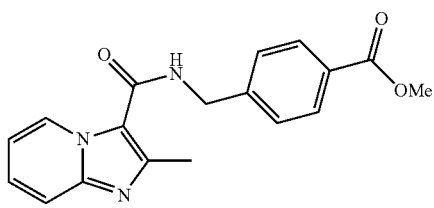 [SMILES: COC(=O)c1ccc(CNC(=O)c2c(C)nc3ccccn23)cc1]

¹H NMR (400 MHz, CDCl₃) δ 2.70 (s, 3H), 3.90 (s, 3H), 4.76 (d, J=6.0 Hz, 2H), 6.24 (brs, 1H), 6.91-6.95 (m, 1H), 7.32-7.36 (m, 1H), 7.44 (d, J=8.4 Hz, 2H), 7.56 (d, J=9.2 Hz, 1H), 8.02 (d, J=8.4 Hz, 2H), 9.41 (d, J=6.8 Hz, 1H).

4-((2-Methylimidazo[1,2-a]pyridine-3-carboxamido)methyl)benzoic acid (11)

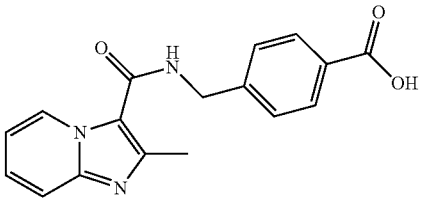 [SMILES: Cc1nc2ccccn2c1C(=O)NCc1ccc(C(=O)O)cc1]

¹H NMR (400 MHz, CD₃OD) δ 2.64 (s, 3H), 4.69 (s, 2H), 7.03 (dd, J=6.8 Hz, 6.8 Hz, 1H), 7.43-7.47 (m, 1H), 7.50 (d, J=8.4 Hz, 2H), 7.53-7.55 (m, 1H), 8.01 (d, J=8.4 Hz, 2H), 9.04 (d, J=7.2 Hz, 1H).

N-(4-Methoxybenzyl)-2-methylimidazo[1,2-a]pyridine-3-carboxamide (12)

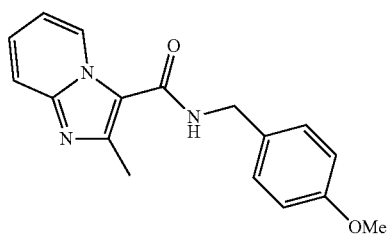 [SMILES: COc1ccc(CNC(=O)c2c(C)nc3ccccn23)cc1]

¹H NMR (400 MHz, CDCl₃) δ 2.67 (s, 3H), 3.810 (s, 3H), 4.63 (d, J=5.2 Hz, 2H), 6.01 (m, 1H), 6.89-6.94 (m, 3H), 7.30-7.35 (m, 3H), 7.56-7.58 (m, 1H), 9.43 (dd, J=0.8, 6.8 Hz, 1H).

2-Methyl-N-(pyridin-3-ylmethyl)imidazo[1,2-a]pyridine-3-carboxamide (13)

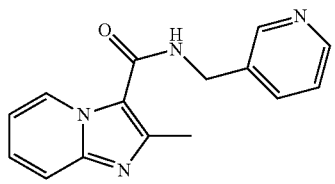 [SMILES: Cc1nc2ccccn2c1C(=O)NCc1cccnc1]

¹H NMR (400 MHz, CDCl₃) δ 2.68 (s, 3H), 4.70 (d, J=6.0 Hz, 2H), 6.30 (brs, 1H), 6.89-6.93 (m, 1H), 7.26-7.35 (m, 2H), 7.55 (d, J=8.8 Hz, 1H), 7.72 (d, J=8.0 Hz, 1H), 8.53 (d, J=3.6 Hz, 1H), 8.62 (s, 1H), 9.38 (d, J=7.2 Hz, 1H).

2-Methyl-N-(pyridin-4-ylmethyl)imidazo[1,2-a]pyridine-3-carboxamide (14)

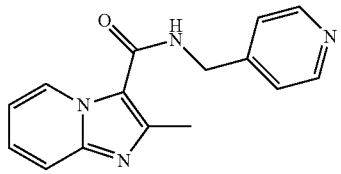 [SMILES: Cc1nc2ccccn2c1C(=O)NCc1ccncc1]

¹H NMR (400 MHz, CDCl₃) δ 2.70 (s, 3H), 4.68 (d, J=6.0 Hz, 2H), 6.41 (brs, 1H), 6.88-6.92 (m, 1H), 7.25 (d, J=4.4 Hz, 2H), 7.30-7.34 (m, 1H), 7.53 (d, J=8.8 Hz, 1H), 8.53 (d, J=4.4 Hz, 2H), 9.35 (d, J=7.2 Hz, 1H); ¹³C NMR (100 MHz, CDCl₃) δ 17.0, 42.4, 113.6, 115.2, 116.7, 122.3, 127.5, 128.3, 145.9, 146.4, 147.7, 150.3, 161.9.

2-Methyl-N-(4-phenoxybenzyl)imidazo[1,2-a]pyridine-3-carboxamide (15)

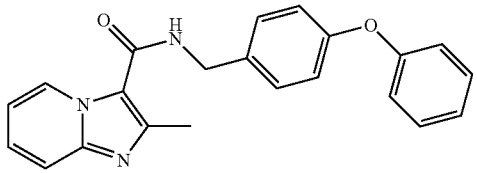 [SMILES: Cc1nc2ccccn2c1C(=O)NCc1ccc(Oc2ccccc2)cc1]

¹H NMR (400 MHz, CDCl₃) δ 2.70 (s, 3H), 4.67 (d, J=5.6 Hz, 2H), 6.14 (brs, 1H), 6.92-6.96 (m, 1H), 6.99-7.08 (m, 4H), 7.12 (dd, J=6.4 Hz, 6.4 Hz, 1H), 7.31-7.37 (m, 5H), 7.59 (d, J=8.8 Hz, 1H), 9.43 (d, J=6.8 Hz, 1H).

N-(Biphenyl-4-ylmethyl)-2-methylimidazo[1,2-a]pyridine-3-carboxamide (16)

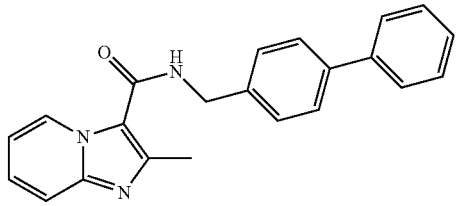 [SMILES: Cc1nc2ccccn2c1C(=O)NCc1ccc(-c2ccccc2)cc1]

¹H NMR (400 MHz, CDCl₃) δ 2.70 (s, 3H), 4.74 (d, J=4.0 Hz, 2H), 6.19 (brs, 1H), 6.91 (dd, J=6.0 Hz, 6.0 Hz, 1H), 7.30-7.36 (m, 2H), 7.41-7.45 (m, 5H), 7.58 (m, 4H), 9.43 (d, J=6.8 Hz, 1H).

N-((1H-Indol-5-yl)methyl)-2-methylimidazo[1,2-a]pyridine-3-carboxamide (17)

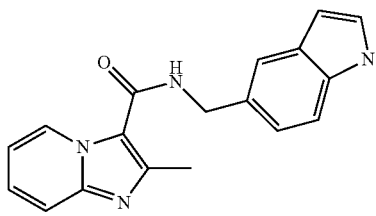 [SMILES: Cc1nc2ccccn2c1C(=O)NCc1ccc2[nH]ccc2c1]

¹H NMR (400 MHz, CDCl₃) δ 2.68 (s, 3H), 4.78 (d, J=5.2 Hz, 2H), 6.18 (brs, 1H), 6.55 (s, 1H), 6.98-7.02 (m, 1H), 7.22-7.24 (m, 2H), 7.40 (s, 1H), 7.42 (s, 1H), 7.66-7.68 (m, 2H), 8.24 (brs, 1H), 9.47 (d, J=7.2 Hz, 1H).

N-(Cyclohexylmethyl)-2-methylimidazo[1,2-a]pyridine-3-carboxamide (18)

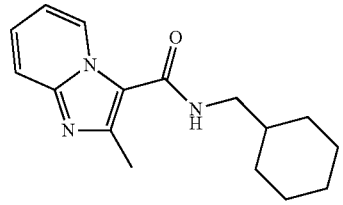 [SMILES: Cc1nc2ccccn2c1C(=O)NCC1CCCCC1]

¹H NMR (400 MHz, CDCl₃) δ 0.94-1.27 (m, 5H), 1.54-1.78 (m, 6H), 2.67 (s, 3H), 3.31 (t, J=6.2 Hz, 2H), 5.91 (m 1H), 6.64 (t, J=6.8 Hz, 1H), 7.24-7.28 (m, 1H), 7.50 (d, J=9.2 Hz, 1H), 9.32 (d, J=6.8 Hz, 1H).

tert-Butyl 4-((2-methylimidazo[1,2-a]pyridine-3-carboxamido)methyl)piperidine-1-carboxylate (19)

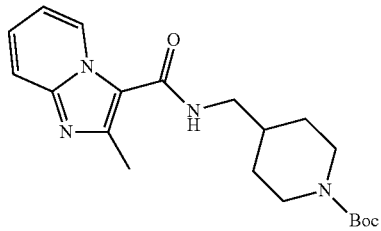 [SMILES: Cc1nc2ccccn2c1C(=O)NCC1CCN(C(=O)OC(C)(C)C)CC1]

¹H NMR (400 MHz, CDCl₃) δ 1.87-1.25 (m, 2H), 1.44 (s, 9H), 1.73-1.82 (m, 3H), 1.97 (m, 2H), 2.70 (s, 3H), 3.40 (m, 2H), 5.92 (t, J=5.6 Hz, 1H), 6.90 (t, J=6.8 Hz, 1H), 7.29-7.33 (m, 1H), 7.55 (d, J=8.8 Hz, 1H), 9.36 (d, J=6.8 Hz, 1H).

2-Methyl-N-(piperidin-4-ylmethyl)imidazo[1,2-a]pyridine-3-carboxamide (20)

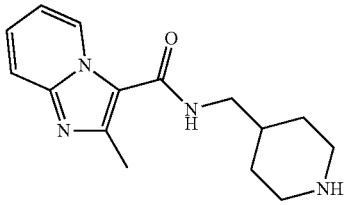 [SMILES: Cc1nc2ccccn2c1C(=O)NCC1CCNCC1]

¹H NMR (400 MHz, CDCl₃) δ 1.20-1.77 (m, 6H), 2.58-2.64 (m, 1H), 2.65 (s, 3H), 3.13 (d, J=11.6 Hz, 2H), 3.34 (t, J=12.0 Hz, 2H), 3.68 (br s, 1H), 6.71 (m, 1H), 6.84 (t, J=6.8 Hz, 1H), 7.26 (t, J=7.6 Hz, 1H), 7.49 (d, J=8.8 Hz, 1H), 9.28 (d, J=6.8 Hz, 1H).

2-Methyl-N-phenethylimidazo[1,2-a]pyridine-3-carboxamide (21)

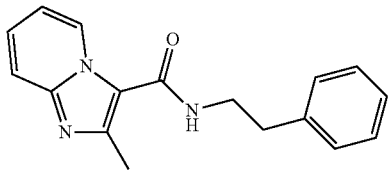 [SMILES: Cc1nc2ccccn2c1C(=O)NCCc1ccccc1]

¹H NMR (400 MHz, CDCl₃) δ 2.28 (s, 3H), 2.82 (t, J=7.2 Hz, 2H), 3.56 (t, J=6.8 Hz, 2H), 6.79 (t, J=6.8 Hz, 1H), 7.06 (t, J=6.8 Hz, 1H), 7.14 (d, J=7.2 Hz, 3H), 7.30 (t, J=7.2 Hz, 2H), 7.33 (d, J=6.8 Hz, 1H), 8.74 (d, J=5.6 Hz, 1H).

N-(4-Methoxyphenethyl)-2-methylimidazo[1,2-a]pyridine-3-carboxamide (22)

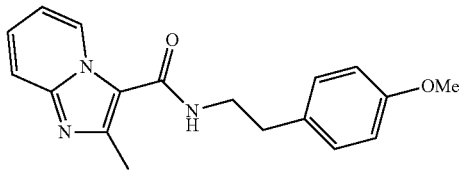 [SMILES: COc1ccc(CCNC(=O)c2c(C)nc3ccccn23)cc1]

¹H NMR (400 MHz, CDCl₃) δ 2.46 (s, 3H), 2.92 (t, J=6.6 Hz, 2H), 3.74 (q, J=6.4 Hz, 2H), 3.80 (s, 3H), 6.87-6.92 (m, 3H), 7.18 (d, J=8.4 Hz, 2H), 7.29-7.33 (m, 1H), 7.55 (d, J=8.8 Hz, 1H), 9.41 (d, J=7.2 Hz, 1H); LCMS (electrospray) m/z (M+H)⁺ 310.25

2-Methyl-N-(2-phenoxyethyl)imidazo[1,2-a]pyridine-3-carboxamide (23)

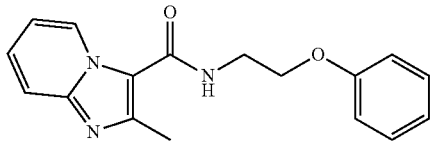 [SMILES: Cc1nc2ccccn2c1C(=O)NCCOc1ccccc1]

¹H NMR (400 MHz, CDCl₃) δ 2.72 (s, 3H), 3.93 (q, J=4.8 Hz, 2H), 4.19 (t, J=5.0 Hz, 2H), 6.33 (m, 1H), 6.90-9.94 (m, 3H), 6.98 (d, J=7.4 Hz, 1H), 7.28-7.34 (m, 3H), 7.57 (d, J=9.2 Hz, 1H), 9.40 (d, J=7.2 Hz, 1H).

N-(2-(Benzyloxy)ethyl)-2-methylimidazo[1,2-a]pyridine-3-carboxamide (24)

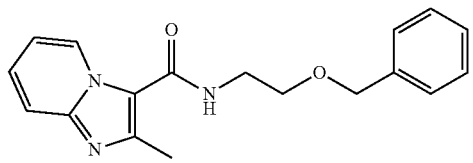 [SMILES: Cc1nc2ccccn2c1C(=O)NCCOCc1ccccc1]

¹H NMR (400 MHz, CDCl₃) δ 2.66 (s, 3H), 3.68-3.75 (m, 4H), 4.57 (s, 2H), 6.90 (dd, J=1.2, 6.8 Hz, 1H), 7.27-7.34 (m, 6H), 7.57 (dd, J=1.2, 9.2 Hz, 1H), 9.37 (dd, J=2.0, 6.8 Hz, 1H).

(S)-Methyl 2-(2-methylimidazo[1,2-a]pyridine-3-carboxamido)-3-phenylpropanoate (25)

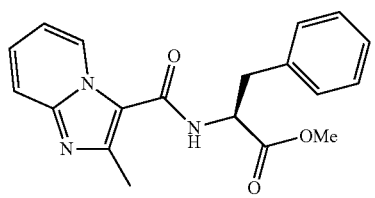 [SMILES: COC(=O)[C@H](Cc1ccccc1)NC(=O)c1c(C)nc2ccccn12]

¹H NMR (400 MHz, CDCl₃) δ 2.50 (s, 3H), 3.25 (dd, J=5.6, 14.0 Hz, 1H), 3.33 (dd, J=5.6, 14.0 Hz, 1H), 5.08-5.13 (m, 1H), 6.23 (d, J=7.2 Hz, 1H), 6.91 (dd, J=1.2, 6.8 Hz, 1H), 7.14-7.16 (m, 2H), 7.27-7.35 (m, 4H), 7.57 (d, J=8.8 Hz, 1H), 9.39 (d, J=7.2 Hz, 1H); LCMS (electrospray) m/z (M+H)⁺ 338.28

N-(2-Methylimidazo[1,2-a]pyridin-3-yl)-2-phenylacetamide (26)

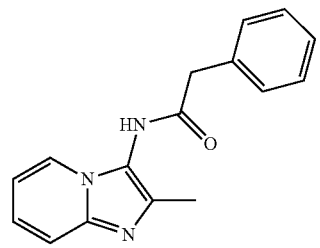

¹H NMR (400 MHz, CD₃OD) δ 2.26 (s, 3H), 3.82 (s, 2H), 7.24-7.31 (m, 2H), 7.36-7.41 (m, 2H), 7.43-7.44 (m, 3H), 7.76 (d, J=6.8 Hz, 1H).

N-Benzyl-8-chloro-2-methylimidazo[1,2-a]pyridine-3-carboxamide (27)

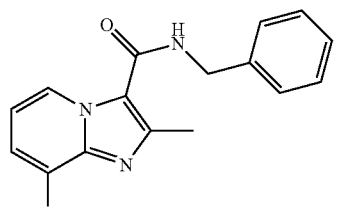

¹H NMR (400 MHz, CDCl₃) δ 2.72 (s, 3H), 4.71 (d, J=6.0 Hz, 2H), 6.14 (brs, 1H), 6.87 (dd, J=7.2, 7.2 Hz, 1H), 7.32 (dd, J=4.4 Hz, 4.4 Hz, 1H), 7.34-7.42 (m, 5H), 9.38 (d, J=7.2

Hz, 1H); $^{13}$C NMR (100 MHz, CDCl$_3$) δ 16.9, 29.9, 43.8, 113.1, 122.4, 126.2, 127.1, 127.9, 128.0, 129.1, 138.1, 141.8, 145.9, 161.3.

N-Benzyl-7-chloro-2-methylimidazo[1,2-a]pyridine-3-carboxamide (28)

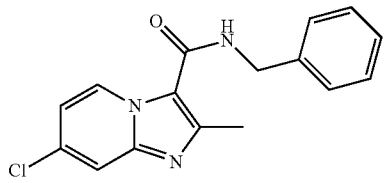 [SMILES: Cc1nc2cc(Cl)ccn2c1C(=O)NCc1ccccc1]

$^1$H NMR (400 MHz, CDCl$_3$) δ 2.66 (s, 3H), 4.69 (d, J=5.6 Hz, 2H), 6.13 (brs, 1H), 6.89-6.91 (m, 1H), 7.29-7.37 (m, 5H), 7.55 (d, J=1.6 Hz, 1H), 9.37 (d, J=7.6 Hz, 1H).

N-Benzyl-6-chloro-2-methylimidazo[1,2-a]pyridine-3-carboxamide (29)

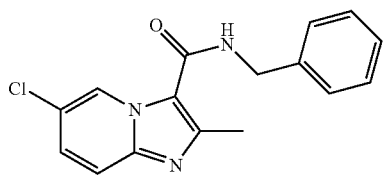 [SMILES: Cc1nc2ccc(Cl)cn2c1C(=O)NCc1ccccc1]

$^1$H NMR (40.0 MHz, CDCl$_3$) δ 2.68 (s, 3H), 4.70 (d, J=5.6 Hz, 2H), 6.16 (brs, 1H), 7.30-7.35 (m, 3H), 7.37-7.38 (m, 3H), 7.53 (d, J=9.2 Hz, 1H), 9.56 (d, J=1.6 Hz, 1H).

N-Benzyl-2,8-dimethylimidazo[1,2-a]pyridine-3-carboxamide (30)

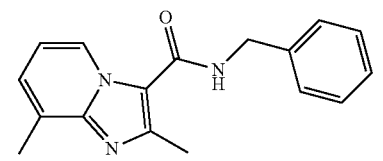 [SMILES: Cc1nc2c(C)cccn2c1C(=O)NCc1ccccc1]

$^1$H NMR (400 MHz, MeOH-d$_4$) δ 2.55 (s, 3H), 2.63 (s, 3H), 4.63 (s, 2H), 6.95 (t, J=6.8 Hz, 1H), 7.25 (d, J=6.8 Hz, 1H), 7.28 (d, J=7.2 Hz, 1H), 7.37 (t, J=7.2 Hz, 2H), 7.42 (d, J=7.6 Hz, 2H), 8.87 (d, J=6.8 Hz, 1H).

N-Benzyl-2,7-dimethylimidazo[1,2-a]pyridine-3-carboxamide (31)

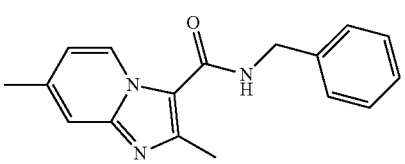 [SMILES: Cc1ccn2c(C(=O)NCc3ccccc3)c(C)nc2c1]

$^1$H NMR (400 MHz, MeOH-d$_4$) δ 2.44 (s, 3H), 2.59 (s, 3H), 4.63 (s, 2H), 6.91 (d, J=7.2 Hz, 1H), 7.28 (t, J=7.2 Hz, 1H), 7.33 (d, J=6.4 Hz, 2H), 7.37 (t, J=7.2 Hz, 1H), 7.42 (d, J=7.6 Hz, 2H), 8.92 (d, J=7.2 Hz, 1H).

N-Benzyl-2,6-dimethylimidazo[1,2-a]pyridine-3-carboxamide (32)

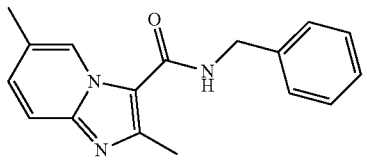 [SMILES: Cc1ccc2nc(C)c(C(=O)NCc3ccccc3)n2c1]

$^1$H NMR (400 MHz, MeOH-d$_4$) δ 2.36 (s, 3H), 2.59 (s, 3H), 4.63 (s, 2H), 7.29 (d, J=7.6 Hz, 1H), 7.31 (d, J=1.6 Hz, 1H), 7.37 (t, J=7.2 Hz, 3H), 7.43 (t, J=4.8 Hz, 2H), 7.46 (s, 1H), 8.83 (s, 1H).

N-Benzyl-2,5-dimethylimidazo[1,2-a]pyridine-3-carboxamide (33)

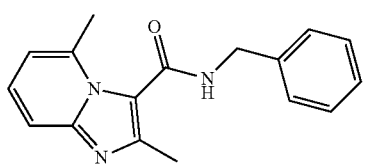 [SMILES: Cc1nc2cccc(C)n2c1C(=O)NCc1ccccc1]

$^1$H NMR (400 MHz, MeOH-d$_t$) δ 2.44 (s, 3H), 2.59 (s, 3H), 4.29 (s, 2H), 6.75 (d, J=7.2 Hz, 1H), 7.21-7.27 (m, 3H), 7.33 (t, J=6.4 Hz, 2H), 7.41 (t, J=8.8 Hz, 1H), 7.49 (s, 1H).

N-Benzyl-6-fluoro-2-methylimidazo[1,2-a]pyridine-3-carboxamide (34)

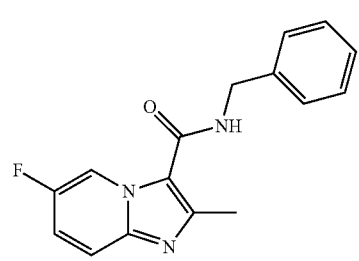 [SMILES: Cc1nc2ccc(F)cn2c1C(=O)NCc1ccccc1]

$^1$H NMR (400 MHz, CD$_3$OD) δ 2.68 (s, 3H), 4.71 (d, J=6.0 Hz, 2H), 7.24-7.39 (m 6H), 7.52-7.56 (m, 1H), 9.48-9.49 (m, 1H); LCMS (electrospray) m/z (M+H)$^+$ 284.27

N-Benzyl-7-cyano-2-methylimidazo[1,2-a]pyridine-3-carboxamide (35)

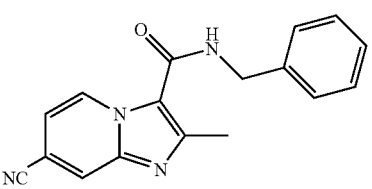

¹H NMR (400 MHz, CDCl₃) δ 1.64 (s, 3H), 4.61 (d, J=6.0 Hz, 2H), 6.39 (brs, 1H), 6.85 (dd, J=1.2 Hz, 5.2 Hz, 1H), 6.89 (s, 1H), 7.29-7.38 (m, 5H), 8.13 (d, J=5.6 Hz, 1H)

N-Benzyl-6-cyano-2-methylimidazo[1,2-a]pyridine-3-carboxamide (36)

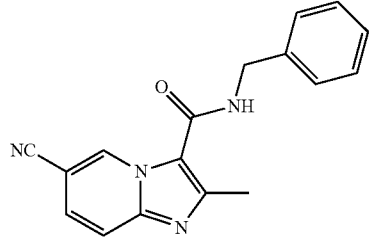 [SMILES: Cc1nc2ccc(C#N)cn2c1C(=O)NCc1ccccc1]

¹H NMR (400 MHz, CD₃OD) δ 2.63 (s, 3H), 4.65 (s, 2H), 7.27 (t, J=7.4 Hz, 1H), 7.35 (t, J=7.6 Hz, 2H), 7.42 (d, J=7.6 Hz, 2H), 7.57 (dd, J=0.8, 9.2 Hz, 1H), 7.85 (dd, J=1.6, 9.2 Hz, 1H), 9.58 (m, 1H).

N-Benzyl-2-methyl-7-phenylimidazo[1,2-a]pyridine-3-carboxamide (37)

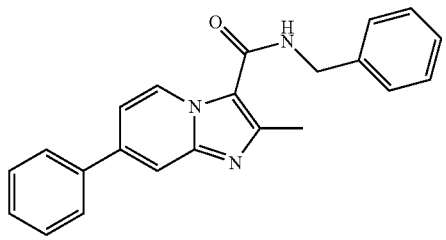 [SMILES: Cc1nc2cc(-c3ccccc3)ccn2c1C(=O)NCc1ccccc1]

¹H NMR (400 MHz, CDCl₃) δ 2.70 (s, 3H), 4.71 (d, J=5.6 Hz, 2H), 6.15 (brs, 1H), 7.22 (dd, J=2.0 Hz, 7.2 Hz, 1H), 7.29-7.33 (m, 1H), 7.36-7.44 (m, 5H), 7.47-7.51 (m, 2H), 7.66 (s, 1H), 7.68 (d, J=1.2 Hz, 1H), 7.78 (s, 1H), 9.47 (d, J=7.2 Hz, 1H).

N-Benzyl-2-methyl-6-phenylimidazo[1,2-a]pyridine-3-carboxamide (38)

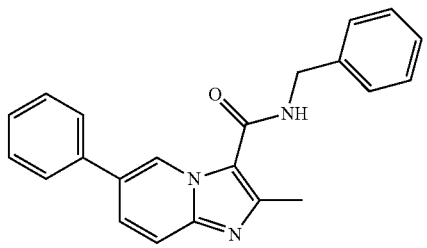 [SMILES: Cc1nc2ccc(-c3ccccc3)cn2c1C(=O)NCc1ccccc1]

¹H NMR (400 MHz, CDCl₃) δ 2.71 (s, 3H), 4.73 (d, J=5.6 Hz, 2H), 6.12 (m, 1H), 7.30-7.34 (m, 1H), 7.36-7.40 (m, 7H), 7.60-7.66 (m, 4H), 9.71 (s, 1H).

N-Benzyl-8-fluoro-2-methylimidazo[1,2-a]pyridine-3-carboxamide (39)

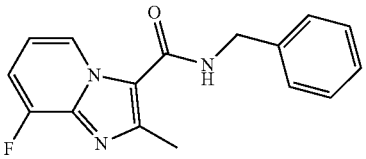 [SMILES: Cc1nc2c(F)cccn2c1C(=O)NCc1ccccc1]

¹H NMR (400 MHz, MeOH-d₄) δ 2.63 (s, 3H), 4.64 (s, 2H), 6.96-7.01 (m, 1H), 7.21 (t, J=6.8 Hz, 1H), 7.25-7.29 (m, 2H), 7.37 (t, J=7.2 Hz, 2H), 7.41 (t, J=7.6 Hz, 2H), 8.84 (d, J=6.8 Hz, 1H).

N-Benzyl-2-methyl-8-(trifluoromethyl)imidazo[1,2-a]pyridine-3-carboxamide (40)

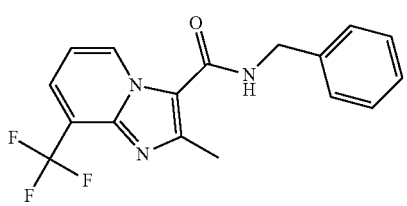 [SMILES: Cc1nc2c(C(F)(F)F)cccn2c1C(=O)NCc1ccccc1]

¹H NMR (400 MHz, MeOH-d₄) δ 2.66 (s, 3H), 4.63 (s, 2H), 7.15 (t, J=6.8 Hz, 1H), 7.25-7.28 (m, 1H), 7.37 (t, J=8.0 Hz, 2H), 7.43 (d, J=7.6 Hz, 2H), 7.82 (d, J=7.2 Hz, 1H), 9.21 (d, J=6.8 Hz, 1H).

N-Benzyl-8-methoxy-2-methylimidazo[1,2-a]pyridine-3-carboxamide (41)

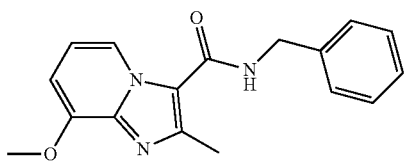 [SMILES: COc1cccn2c(C(=O)NCc3ccccc3)c(C)nc12]

¹H NMR (400 MHz, MeOH-d₄) δ 2.65 (s, 3H), 3.95 (s, 2H), 4.02 (s, 3H), 6.96 (d, J=8.0 Hz, 1H), 7.03 (t, J=6.8 Hz, 1H), 7.23-7.26 (m, 1H), 7.29 (d, J=5.6 Hz, 2H), 7.34 (t, J=6.0 Hz, 2H), 7.39 (t, J=6.4 Hz, 1H), 8.93 (d, J=7.2 Hz, 1H).

N-Benzyl-8-cyano-2-methylimidazo[1,2-a]pyridine-3-carboxamide (42)

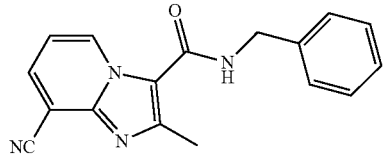 [SMILES: Cc1nc2c(C#N)cccn2c1C(=O)NCc1ccccc1]

¹H NMR (400 MHz, MeOH-d₄) δ 2.67 (s, 3H), 4.65 (s, 2H), 7.17 (t, J=7.2 Hz, 1H), 7.26-7.31 (m, 2H), 7.38 (t, J=7.2 Hz, 2H), 7.44 (d, J=8.0 Hz, 2H), 8.21 (d, J=7.2 Hz, 1H), 9.19 (d, J=6.8 Hz, 1H).

N-Benzyl-8-hydroxy-2-methylimidazo[1,2-a]pyridine-3-carboxamide (43)

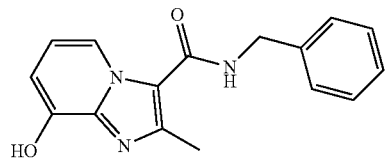

¹H NMR (400 MHz, MeOH-d₄) δ 2.60 (s, 3H), 4.63 (s, 2H), 6.70 (d, J=7.6 Hz, 1H), 6.83 (t, J=6.8 Hz, 1H), 7.28 (t, J=7.2 Hz, 1H), 7.40 (t, J=8.0 Hz, 3H), 7.42 (d, J=7.2 Hz, 2H), 8.53 (d, J=6.0 Hz, 1H).

N-Biphenyl-4-ylmethyl)-6-chloro-2-methylimidazo[1,2-a]pyridine-3-carboxamide (44)

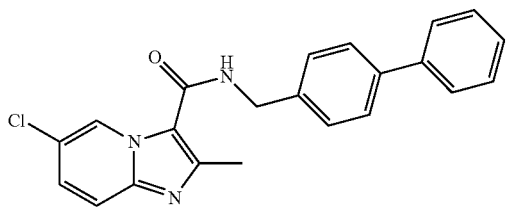 [SMILES: Cc1nc2ccc(Cl)cn2c1C(=O)NCc1ccc(-c2ccccc2)cc1]

¹H NMR (400 MHz, CDCl₃) δ 2.69 (s, 3H), 4.73 (d, J=5.2 Hz, 2H), 6.18 (brs, 1H), 6.92 (d, J=6.4 Hz, 1H), 7.36 (d, J=7.2 Hz, 1H), 7.44-7.45 (m, 4H), 7.57-7.60 (m, 5H), 9.39 (d, J=7.6 Hz, 1H).

N-Biphenyl-4-ylmethyl)-7-chloro-2-methylimidazo[1,2-a]pyridine-3-carboxamide (45)

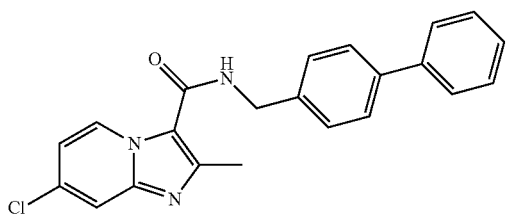 [SMILES: Cc1nc2cc(Cl)ccn2c1C(=O)NCc1ccc(-c2ccccc2)cc1]

¹H NMR (400 MHz, CDCl₃) δ 2.70 (s, 3H), 4.73 (d, J=5.2 Hz, 2H), 6.20 (brs, 1H), 7.29-7.36 (m, 4H), 7.45 (d, J=8.0 Hz, 1H), 7.51 (d, J=9.6 Hz, 1H), 7.57 (m, 5H), 9.56 (s, 1H)

N-Benzyl-2-ethylimidazo[1,2-a]pyridine-3-carboxamide (46)

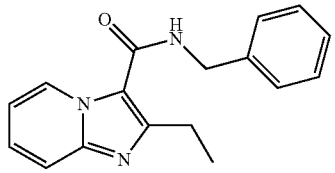 [SMILES: CCc1nc2ccccn2c1C(=O)NCc1ccccc1]

¹H NMR (400 MHz, CDCl₃) δ 1.40 (t, J=7.6 Hz, 3H), 1.63 (s, 3H), 2.99 (q, J=7.6 Hz, 2H), 4.71 (d, J=6.0 Hz, 2H), 6.09 (brs, 1H), 6.92 (dd, J=5.6 Hz, 1H), 7.30-7.38 (m, 6H), 7.60 (d, J=9.2 Hz, 1H), 9.40 (d, J=7.2 Hz, 1H).

N-(Biphenyl-4-ylmethyl)-2-ethylimidazo[1,2-a]pyridine-3-carboxamide (47)

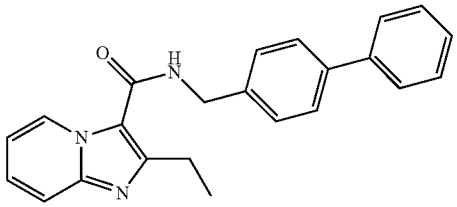

¹H NMR (400 MHz, CDCl₃) δ 1.42 (t, J=7.6 Hz, 3H), 3.02 (q, J=7.6 Hz, 2H), 4.75 (d, J=5.6 Hz, 2H), 6.19 (brs, 1H), 6.92 (dd, J=6.4, 6.4 Hz, 1H), 7.32 (d, J=7.6 Hz, 1H), 7.35 (d, J=7.2 Hz, 1H), 7.45 (d, J=8.0 Hz, 4H), 7.58-7.59 (m, 5H), 9.41 (d, J=6.8 Hz, 1H).

N-Benzyl-2-propylimidazo[1,2-a]pyridine-3-carboxamide (48)

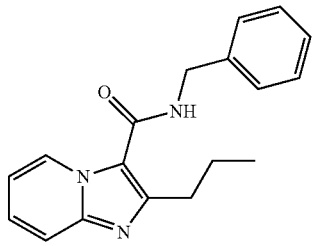 [SMILES: CCCc1nc2ccccn2c1C(=O)NCc1ccccc1]

¹H NMR (400 MHz, CD₃OD) δ 0.93 (t, J=7.4 Hz, 3H), 1.75-1.85 (m, 2H), 2.89 (t, J=7.8 Hz, 2H), 4.67 (d, J=5.6 Hz, 2H), 6.24 (m, 1H), 6.86 (t, J=6.8 Hz, 1H), 7.26-7.36 (m, 6H), 7.54 (d, J=8.8 Hz, 1H), 9.31 (d, J=6.8 Hz, 1H).

N-(Biphenyl-4-ylmethyl)-2-propylimidazo[1,2-a]pyridine-3-carboxamide (49)

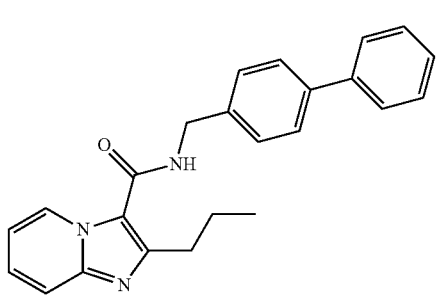 [SMILES: CCCc1nc2ccccn2c1C(=O)NCc1ccc(-c2ccccc2)cc1]

¹H NMR (400 MHz, CDCl₃) δ 0.98 (t, J=7.4 Hz, 3H), 1.80-1.89 (m, 2H), 2.93 (t, J=7.8 Hz, 2H), 4.73 (d, J=5.6 Hz, 2H), 6.29 (t, J=5.2 Hz, 1H), 6.89 (dd, J=1.2, 6.8 Hz, 1H), 7.27-7.37 (m, 2H), 7.42-7.46 (m, 4H), 7.56-7.61 (m, 5H), 9.35 (d, J=6.8 Hz, 1H); LCMS (electrospray) m/z (M+H)⁺ 370.32

N-Benzyl-2-cyclopropylimidazo[1,2-a]pyridine-3-carboxamide (50)

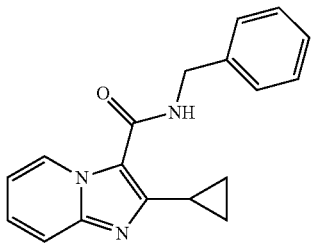 [SMILES: O=C(NCc1ccccc1)c1c(C2CC2)nc2ccccn12]

¹H NMR (400 MHz, CD₃OD) δ 1.00-1.03 (m, 2H), 1.14-1.18 (m, 2H), 2.11-2.15 (m, 1H), 6.91 (dd, J=1.2, 6.8 Hz, 1H), 7.29-7.38 (m, 5H), 7.57 (dd, J=0.8, 8.8 Hz, 1H), 9.49-9.51 (m, 1H); LCMS (electrospray) m/z (M+H)⁺ 292.23

N-Benzyl-2-isopropylimidazo[1,2-a]pyridine-3-carboxamide (51)

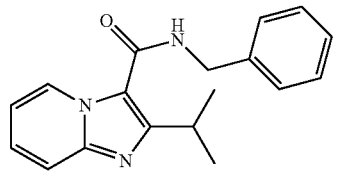 [SMILES: CC(C)c1nc2ccccn2c1C(=O)NCc1ccccc1]

¹H NMR (400 MHz, CDCl₃) δ 1.41 (d, J=6.8 Hz, 6H), 3.36-3.32 (m, 1H), 4.71 (d, J=5.6 Hz, 2H), 6.11 (brs, 1H), 6.88 (dd, J=6.8 Hz, 6.8 Hz, 1H), 7.29 (dd, J=6.8 Hz, 6.8 Hz, 1H), 7.31-7.39 (m, 5H), 7.62 (d, J=9.2 Hz, 1H), 9.31 (d, J=7.2 Hz, 1H).

N-(Biphenyl-4-ylmethyl)-2-isopropylimidazo[1,2-a]pyridine-3-carboxamide (52)

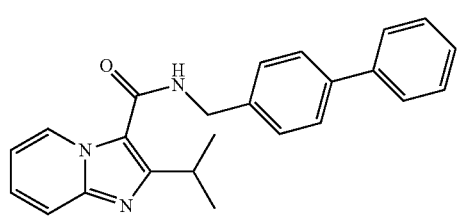 [SMILES: CC(C)c1nc2ccccn2c1C(=O)NCc1ccc(-c2ccccc2)cc1]

¹H NMR (400 MHz, CDCl₃) δ 1.44 (d, J=6.4 Hz, 6H), 3.34-3.41 (m, 1H), 4.76 (d, J=5.6 Hz, 2H), 6.16 (brs, 1H), 6.90 (dd, J=7.2 Hz, 7.2 Hz, 1H), 7.29-7.37 (m, 2H), 7.42-7.47 (m, 4H), 7.60-7.64 (m, 5H), 9.32 (d, J=7.2 Hz, 1H).

N-Benzyl-2-phenylimidazo[1,2-a]pyridine-3-carboxamide (53)

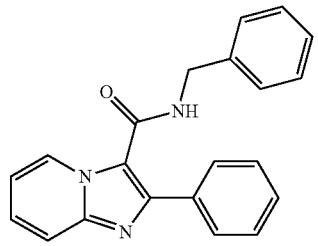 [SMILES: O=C(NCc1ccccc1)c1c(-c2ccccc2)nc2ccccn12]

¹H NMR (400 MHz, CDCl₃) δ 4.50 (d, J=5.6 Hz, 2H), 6.090 (m, 1H), 7.14-7.16 (m, 2H), 7.26-7.32 (m, 4H), 7.36-7.40 (m, 4H), 7.61-7.63 (m, 2H), 7.69 (d, J=9.2 Hz, 1H),

2-Ethyl-N-(4-phenoxybenzyl)imidazo[1,2-a]pyridine-3-carboxamide (54)

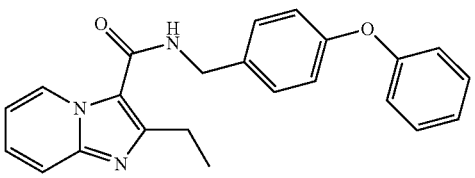

¹H NMR (400 MHz, CDCl₃) δ 1.41 (t, J=7.6 Hz, 3H), 2.99 (q, J=7.6 Hz, 2H), 4.67 (d, J=5.6 Hz, 2H), 6.08 (brs, 1H), 6.89-6.93 (m, 1H), 7.00 (dd, J=2.0 Hz, 8.8 Hz, 4H), 7.08-7.12 (m, 1H), 7.30-7.35 (m, 5H), 7.60 (d, J=9.2 Hz, 1H), 9.39 (d, J=7.2 Hz, 1H).

N-(4-tert-Butylbenzyl)-2-ethylimidazo[1,2-a]pyridine-3-carboxamide (55)

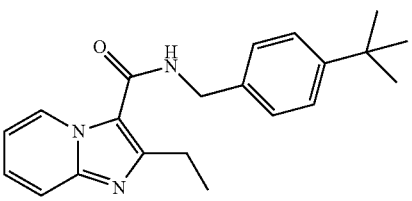 [SMILES: CCc1nc2ccccn2c1C(=O)NCc1ccc(C(C)(C)C)cc1]

¹H NMR (400 MHz, CDCl₃) δ 1.32 (s, 9H), 1.41 (t, J=7.6 Hz, 3H), 2.99 (q, J=7.6 Hz, 2H), 4.68 (d, J=5.6 Hz, 2H), 6.12 (brs, 1H), 6.93 (dd, J=6.8 Hz, 6.8 Hz, 1H), 7.32 (d, J=8.4 Hz, 2H), 7.34-7.36 (m, 1H), 7.40 (d, J=8.4 Hz, 2H), 7.63 (d, J=8.8 Hz, 1H), 9.40 (d, J=7.2 Hz, 1H).

2-Ethyl-N-((1-methyl-1H-indol-5-yl)methyl)imidazo[1,2-a]pyridine-3-carboxamide (56)

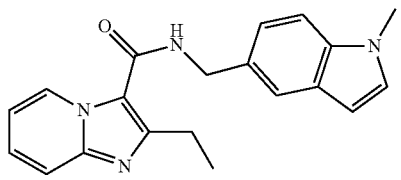 [SMILES: CCc1nc2ccccn2c1C(=O)NCc1ccc2c(ccn2C)c1]

$^1$H NMR (400 MHz, CDCl$_3$) δ 1.37 (t, J=7.6 Hz, 3H), 2.95 (q, J=7.6 Hz, 2H), 3.81 (s, 3H), 4.79 (d, J=5.6 Hz, 2H), 6.08 (brs, 1H), 6.48 (s, 1H), 6.92 (dd, J=6.8 Hz, 6.8 Hz, 1H), 7.08 (s, 1H), 7.25 (s, 1H), 7.26-7.34 (m, 2H), 7.60 (d, J=8.8 Hz, 1H), 7.63 (s, 1H), 9.43 (d, J=7.2 Hz, 1H).

2-Ethyl-N-(4-(trifluoromethoxy)benzyl)imidazo[1,2-a]pyridine-3-carboxamide (57)

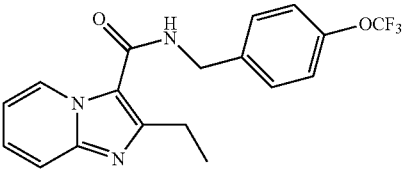 [SMILES: CCc1nc2ccccn2c1C(=O)NCc1ccc(OC(F)(F)F)cc1]

$^1$H NMR (400 MHz, CDCl$_3$) δ 1.41 (t, J=7.6 Hz, 3H), 3.00 (q, J=7.6 Hz, 2H), 4.69 (d, J=6.0 Hz, 2H), 6.21 (brs, 1H), 6.91 (dd, J=6.8 Hz, 6.8 Hz, 1H), 7.19 (s, 1H), 7.21 (s, 1H), 7.30-7.34 (m, 1H), 7.39 (s, 1H), 7.41 (s, 1H), 7.60 (d, J=9.2 Hz, 1H), 9.37 (d, J=7.2 Hz, 1H); $^{13}$C NMR (100 MHz, CDCl$_3$) δ 13.5, 23.7, 42.9, 113.5, 114.7, 119.3, 121.5, 121.9, 127.3, 128.3, 129.2, 137.3, 146.4, 148.8, 151.1, 161.7.

2-Ethyl-N-((1-methyl-1H-indol-6-yl)methyl)imidazo[1,2-a]pyridine-3-carboxamide (58)

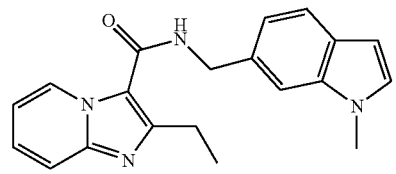 [SMILES: CCc1nc2ccccn2c1C(=O)NCc1ccc2ccn(C)c2c1]

$^1$H NMR (400 MHz, CDCl$_3$) δ 1.37 (t, J=7.6 Hz, 3H), 2.95 (q, J=7.6 Hz, 2H), 3.80 (s, 3H), 4.78 (d, J=5.6 Hz, 2H), 6.09 (brs, 1H), 6.48 (d, J=2.8 Hz, 1H), 6.89-6.93 (m, 1H), 7.08 (d, J=3.2 Hz, 1H), 7.23-7.33 (m, 3H), 7.59 (s, 1H), 7.62 (d, J=5.6 Hz, 1H), 9.41 (d, J=6.8 Hz, 1H).

2-Ethyl-N-(4-(trifluoromethoxy)benzyl)imidazo[1,2-a]pyridine-3-carboxamide (59)

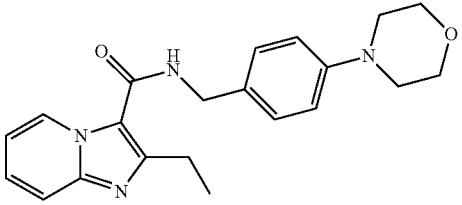 [SMILES: CCc1nc2ccccn2c1C(=O)NCc1ccc(N2CCOCC2)cc1]

$^1$H NMR (400 MHz, CDCl$_3$) δ 1.37 (t, J=7.6 Hz, 3H), 2.96 (q, J=7.6 Hz, 2H), 3.14 (t, J=4.8 Hz, 4H), 3.85 (t, J=4.8 Hz, 4H), 4.61 (d, J=5.6 Hz, 2H), 6.05 (brs, 1H), 6.88-6.92 (m, 3H), 7.27-7.33 (m, 3H), 7.59 (d, J=8.8 Hz, 1H), 9.39 (d, J=7.2 Hz, 1H).

2-Ethyl-N-(4-isopropoxybenzyl)imidazo[1,2-a]pyridine-3-carboxamide (60)

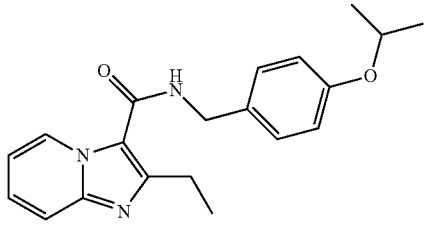 [SMILES: CCc1nc2ccccn2c1C(=O)NCc1ccc(OC(C)C)cc1]

$^1$H NMR (400 MHz, CDCl$_3$) δ 1.32 (d, J=5.6 Hz, 6H), 1.38 (t, J=7.6 Hz, 3H), 2.96 (q, J=7.6 Hz, 2H), 4.52-4.56 (m, 1H), 4.61 (d, J=4.8 Hz, 2H), 6.05 (brs, 1H), 6.86-6.92 (m, 3H), 7.26-7.33 (m, 3H), 7.59 (d, J=8.8 Hz, 1H), 9.38 (d, J=6.4 Hz, 1H).

2-Ethyl-N-(4-isobutoxybenzyl)imidazo[1,2-a]pyridine-3-carboxamide (61)

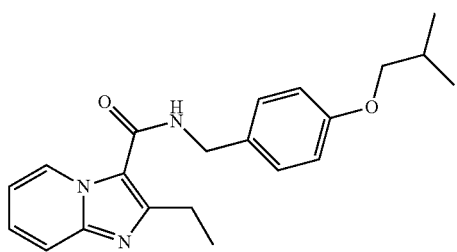 [SMILES: CCc1nc2ccccn2c1C(=O)NCc1ccc(OCC(C)C)cc1]

$^1$H NMR (400 MHz, CDCl$_3$) δ 1.01 (d, J=6.8 Hz, 6H), 1.37 (t, J=7.6 Hz, 3H), 2.05-2.09 (m, 1H), 2.96 (q, J=7.6 Hz, 2H), 3.71 (d, J=6.8 Hz, 2H), 4.62 (d, J=5.2 Hz, 2H), 6.06 (brs, 1H), 6.89 (dd, J=2.4 Hz, 2H), 6.92 (dd, J=1.2 Hz, 6.8 Hz, 1H), 7.27-7.34 (m, 3H), 7.59 (d, J=8.0 Hz, 1H), 9.37 (dd, J=2.4 Hz, 6.8 Hz, 1H); $^{13}$C NMR (100 MHz, CDCl$_3$) δ 13.6, 19.4, 23.5, 28.4, 43.3, 53.1, 74.7, 113.4, 115.0, 116.7, 124.2, 127.2, 128.3, 129.2, 130.0, 146.2, 150.7, 159.0, 161.5.

N-(Biphenyl-4-ylmethyl)-2-ethyl-6-methylimidazo[1,2-a]pyridine-3-carboxamide (62)

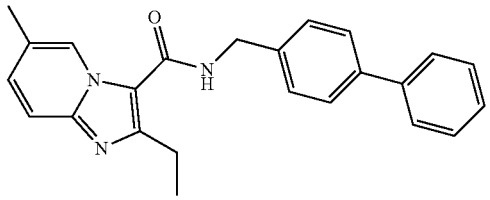 [SMILES: CCc1nc2ccc(C)cn2c1C(=O)NCc1ccc(-c2ccccc2)cc1]

¹H NMR (400 MHz, MeOH-d₄) δ 1.34 (t, J=7.6 Hz, 3H), 2.37 (s, 3H), 3.02 (q, J=7.6 Hz, 2H), 4.68 (s, 2H), 7.31-7.34 (m, 2H), 7.43 (d, J=8.0 Hz, 2H), 7.46 (d, J=4.8 Hz, 1H), 7.51 (d, J=8.8 Hz, 3H), 7.64 (t, J=4.4 Hz, 4H), 8.78 (s, 1H).

2-Ethyl-6-methyl-N-(4-phenoxybenzyl)imidazo[1,2-a]pyridine-3-carboxamide (63)

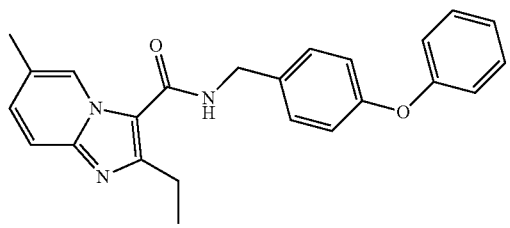 [SMILES: CCc1nc2ccc(C)cn2c1C(=O)NCc1ccc(Oc2ccccc2)cc1]

¹H NMR (400 MHz, MeOH-d₄) δ 1.35 (t, J=8.0 Hz, 3H), 2.37 (s, 3H), 2.99 (q, J=7.2 Hz, 2H), 4.61 (s, 2H), 6.99 (d, J=8.8 Hz, 4H), 7.12 (t, J=7.2 Hz, 1H), 7.31-7.36 (m, 3H), 7.42 (d, J=8.8 Hz, 2H), 7.48 (d, J=9.2 Hz, 1H), 8.76 (s, 1H).

N-(4-tert-Butylbenzyl)-2-ethyl-6-methylimidazo[1,2-a]pyridine-3-carboxamide (64)

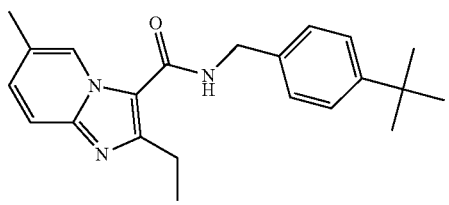 [SMILES: CCc1nc2ccc(C)cn2c1C(=O)NCc1ccc(C(C)(C)C)cc1]

¹H NMR (400 MHz, MeOH-d₄) δ 1.30 (t, J=7.2 Hz, 3H), 1.32 (s, 9H), 2.37 (s, 3H), 2.98 (q, J=8.0 Hz, 2H), 4.59 (s, 2H), 7.30 (d, J=1.6 Hz, 1H), 7.34 (d, J=8.4 Hz, 2H), 7.41 (d, J=6.8 Hz, 2H), 7.47 (d, J=9.2 Hz, 1H), 8.74 (s, 1H).

2-Ethyl-6-methyl-N-(4-(trifluoromethoxy)benzyl)imidazo[1,2-a]pyridine-3-carboxamide (65)

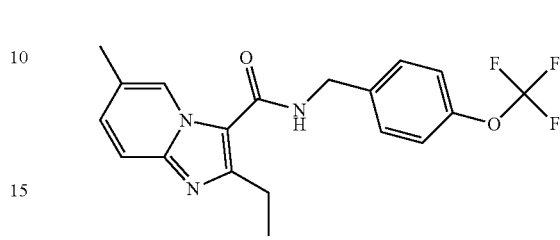

¹H NMR (400 MHz, MeOH-d₄) δ 1.33 (t, J=8.0 Hz, 3H), 2.36 (s, 3H), 3.00 (q, J=7.6 Hz, 2H), 4.65 (s, 2H), 7.28 (d, J=8.0 Hz, 2H), 7.34 (d, J=9.2 Hz, 1H), 7.48 (d, J=9.2 Hz, 1H), 7.52 (d, J=8.4 Hz, 2H), 8.77 (s, 1H).

2-Ethyl-6-methyl-N-((1-methyl-1H-indol-5-yl)methyl)imidazo[1,2-a]pyridine-3-carboxamide (66)

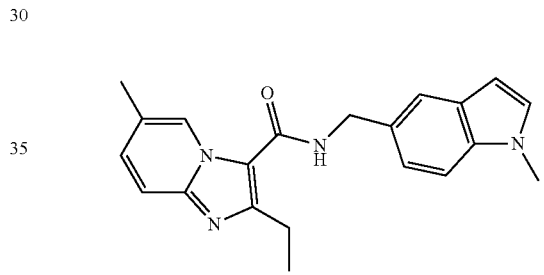

¹H NMR (400 MHz, MeOH-d₄) δ 1.28 (t, J=7.6 Hz, 3H), 2.36 (s, 3H), 2.95 (q, J=7.2 Hz, 2H), 3.80 (s, 3H), 4.71 (s, 2H), 6.42 (d, J=2.8 Hz, 1H), 7.16 (d, J=3.2 Hz, 1H), 7.26 (d, J=8.4 Hz, 1H), 7.32 (d, J=9.2 Hz, 1H), 7.38 (d, J=8.4 Hz, 1H), 7.46 (d, J=9.2 Hz, 2H), 7.59 (s, 1H), 8.73 (s, 1H).

2-Ethyl-6-methyl-N-((1-methyl-1H-indol-6-yl)methyl)imidazo[1,2-a]pyridine-3-carboxamide (67)

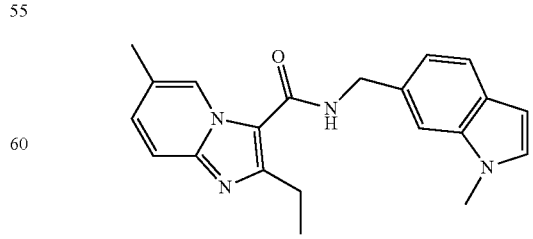

¹H NMR (400 MHz, MeOH-d₄) δ 1.30 (t, J=7.6 Hz, 3H), 2.35 (s, 3H), 3.0 (q, J=7.6 Hz, 2H), 3.80 (s, 3H), 4.75 (s, 2H), 6.41 (d, J=3.2 Hz, 1H), 7.11-7.14 (m, 2H), 7.32 (d, J=9.2 Hz, 1H), 7.46 (d, J=9.2 Hz, 2H), 7.55 (d, J=8.0 Hz, 1H), 8.74 (s, 1H).

2-Ethyl-7-methyl-N-(4-morpholinobenzyl)imidazo[1,2-a]pyridine-3-carboxamide (68)

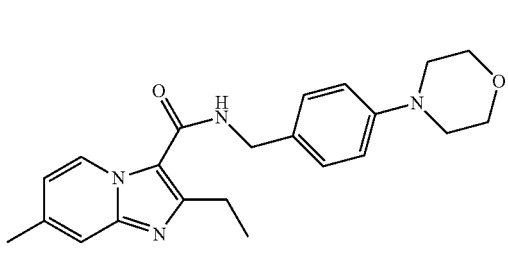 [SMILES: CCc1nc2cc(C)ccn2c1C(=O)NCc1ccc(N2CCOCC2)cc1]

White solid, mp 190° C.; $^1$H NMR (400 MHz, MeOH-d$_4$) δ 1.31 (t, J=7.6 Hz, 3H), 2.43 (s, 3H), 2.98 (q, J=7.6 Hz, 2H), 3.14 (t, J=4.8 Hz, 4H), 3.35 (s, 1H), 3.85 (t, J=4.8 Hz, 4H), 4.53 (s, 2H), 6.90 (d, J=7.2 Hz, 1H), 6.98 (d, J=8.8 Hz, 2H), 7.32 (d, J=8.8 Hz, 3H), 8.83 (d, J=7.2 Hz, 1H).

2-Ethyl-7-methyl-N-(naphthalen-2-ylmethyl)imidazo[1,2-a]pyridine-3-carboxamide (69)

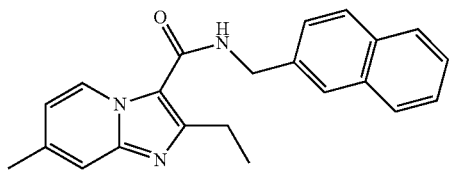 [SMILES: CCc1nc2cc(C)ccn2c1C(=O)NCc1ccc2ccccc2c1]

White solid, mp 192° C.; $^1$H NMR (400 MHz, MeOH-d$_4$) δ 1.33 (t, J=7.6 Hz, 3H), 2.45 (s, 3H), 3.02 (q, J=7.6 Hz, 2H), 4.79 (s, 2H), 6.9 (d, J=7.2 Hz, 1H), 7.33 (s, 1H), 7.45-7.48 (m, 2H), 7.56 (d, J=8.8 Hz, 1H), 7.82-7.88 (m, 4H), 8.87 (d, J=7.2 Hz, 1H).

6-Chloro-N-(4-chlorobenzyl)-2-ethylimidazo[1,2-a]pyridine-3-carboxamide (70)

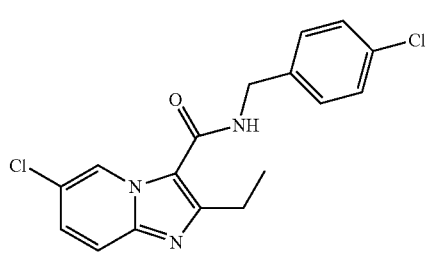 [SMILES: CCc1nc2ccc(Cl)cn2c1C(=O)NCc1ccc(Cl)cc1]

$^1$H NMR (400 MHz, CDCl$_3$) δ 1.41 (t, J=7.6 Hz, 3H), 2.98 (q, J=7.6 Hz, 2H), 4.66 (d, J=5.6 Hz, 2H), 6.14 (m, 1H), 7.29-7.35 (m, 5H), 7.54 (dd, J=0.8, 9.6 Hz, 1H), 9.51 (dd, J=0.8, 2.0 Hz, 1H); LCMS (electrospray) m/z (M+H)$^+$ 348.14

6-Chloro-2-methyl-N-(4-phenoxybenzyl)imidazo[1,2-a]pyridine-3-carboxamide (71)

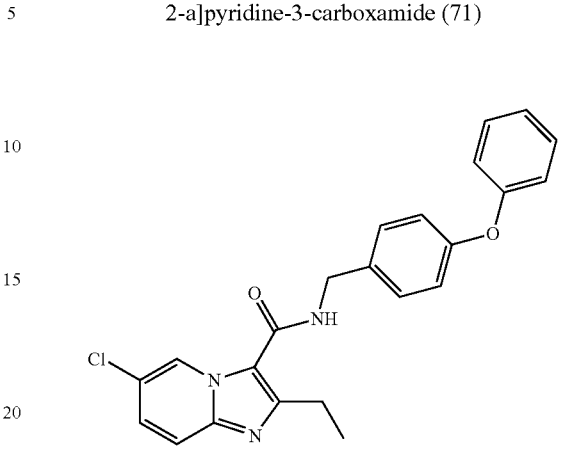

$^1$H NMR (400 MHz, CDCl$_3$) δ 1.41 (t, J=7.6 Hz, 3H), 2.99 (q, J=7.6 Hz, 2H), 4.67 (d, J=5.6 Hz, 2H), 7.01 (d, J=8.4 Hz, 4H), 7.09-7.13 (m, 1H), 7.30 (dd, J=2.0, 9.6 Hz, 1H), 7.32-7.36 (m, 4H), 7.54 (d, J=9.6 Hz, 1H), 9.54 (d, J=2.0 Hz, 1H); LCMS (electrospray) m/z (M+H)$^+$ 406.23

6-Chloro-2-methyl-N-(4-(trifluoromethoxy)benzyl)imidazo[1,2-a]pyridine-3-carboxamide (72)

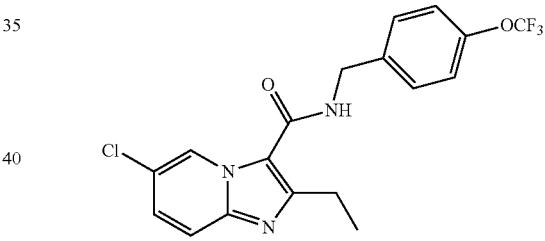

$^1$H NMR (400 MHz, CDCl$_3$) δ 1.43 (t, J=7.6 Hz, 3H), 3.00 (q, J=7.6 Hz, 2H), 4.71 (d, J=6.0 Hz, 2H), 6.15 (m, 1H), 7.23 (d, J=8.4 Hz, 2H), 7.31 (dd, J=2.0, 9.6 Hz, 1H), 7.42 (d, J=8.8 Hz, 2H), 7.55 (d, J=9.6 Hz, 1H), 9.54 (d, J=2.0 Hz, 1H)); LCMS (electrospray) m/z (M+H)$^+$ 398.21

N-(4-tert-Butylbenzyl)-6-chloro-2-methylimidazo[1,2-a]pyridine-3-carboxamide (73)

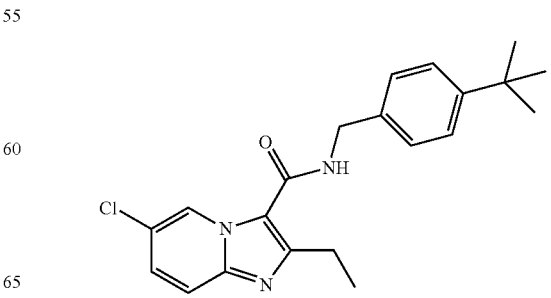

¹H NMR (400 MHz; CDCl₃) δ 1.41 (t, J=7.6 Hz, 3H), 2.98 (q, J=7.6 Hz, 2H), 4.68 (d, J=6.0 Hz, 2H), 6.09 (m, 1H), 7.28-7.31 (m, 1H), 7.32 (d, J=8.0 Hz, 2H), 7.41 (d, J=8.0 Hz, 2H), 7.54 (d, J=9.6 Hz, 1H), 9.54 (d, J=2.0 Hz, 1H); LCMS (electrospray) m/z (M+H)⁺ 370.25

6-Chloro-2-methyl-N-(4-morpholinobenzyl)imidazo[1,2-a]pyridine-3-carboxamide (74)

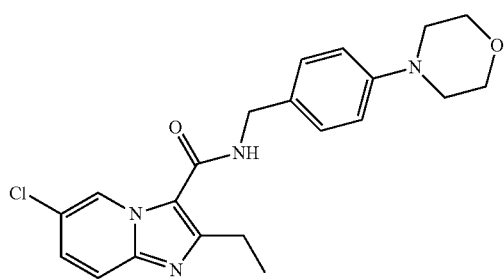 [SMILES: CCc1nc2ccc(Cl)cn2c1C(=O)NCc1ccc(N2CCOCC2)cc1]

¹H NMR (400 MHz, CDCl₃) δ 1.39 (t, J=7.6 Hz, 3H), 2.95 (q, J=7.6 Hz, 2H), 3.16 (t, J=4.8 Hz, 4H), 3.96 (t, J=4.8 Hz, 4H), 4.61 (d, J=5.6 Hz, 2H), 6.92 (d, J=8.8 Hz, 2H), 7.26-7.30 (m, 3H), 7.54 (d, J=9.6 Hz, 1H), 9.52 (d, J=1.2 Hz, 1H); LCMS (electrospray) m/z (M+H)⁺ 399.30

6-Chloro-N-(4-isopropoxybenzyl)-2-methylimidazo[1,2-a]pyridine-3-carboxamide (75)

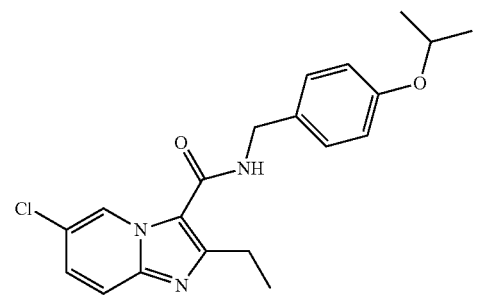 [SMILES: CCc1nc2ccc(Cl)cn2c1C(=O)NCc1ccc(OC(C)C)cc1]

¹H NMR (400 MHz, CDCl₃) δ 1.34 (d, J=6.0 Hz, 6H), 1.39 (t, J=7.6 Hz, 3H), 2.96 (q, J=7.6 Hz, 2H), 4.52-4.58 (m, 1H), 4.62 (d, J=5.6 Hz, 2H), 6.03 (m, 1H), 6.89 (d, J=8.8 Hz, 2H), 7.27-7.31 (m, 3H), 7.54 (d, J=9.6 Hz, 1H), 9.53 (d, J=1.2 Hz, 1H); LCMS (electrospray) m/z (M+H)⁺ 372.22

6-Chloro-N-(4-isobutoxybenzyl)-2-methylimidazo[1,2-a]pyridine-3-carboxamide (76)

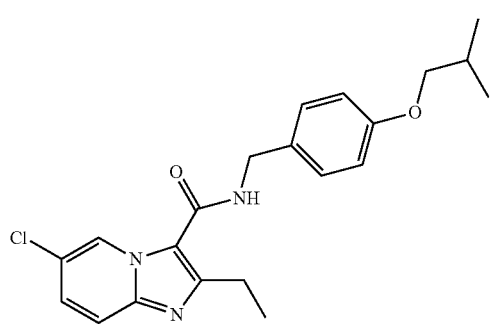 [SMILES: CCc1nc2ccc(Cl)cn2c1C(=O)NCc1ccc(OCC(C)C)cc1]

¹H NMR (400 MHz, CDCl₃) δ 1.00 (d, J=6.8 Hz, 6H), 1.36 (t, J=7.6 Hz, 3H), 2.03-2.09 (m, 1H), 2.93 (q, J=7.6 Hz, 2H), 3.69 (d, J=6.8 Hz, 2H), 4.59 (d, J=5.6 Hz, 2H), 6.13 (t, J=4.8 Hz, 1H), 6.87 (d, J=8.4 Hz, 2H), 7.24-7.27 (m, 3H), 7.49 (d, J=9.6 Hz, 1H), 9.47 (d, J=1.2 Hz, 1H)); LCMS (electrospray) m/z (M+H)⁺ 386.30

6-Chloro-2-methyl-N-((1-methyl-1H-indol-5-yl)methyl)imidazo[1,2-a]pyridine-3-carboxamide (77)

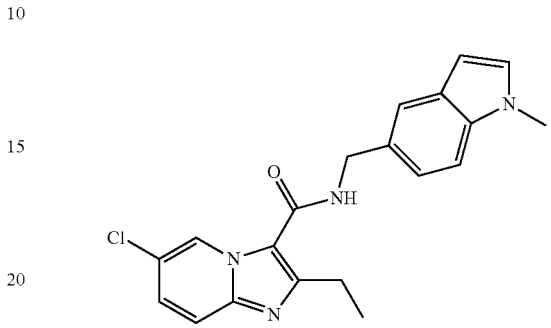

¹H NMR (400 MHz, CDCl₃) δ 1.37 (t, J=7.6 Hz, 3H), 2.94 (q, J=7.6 Hz, 2H), 3.81 (s, 3H), 4.78 (d, J=5.6 Hz, 2H), 6.07 (m, 1H), 6.48 (d, J=3.2 Hz, 1H), 7.09 (d, J=2.8 Hz, 1H), 7.24-7.26 (m, 1H), 7.29 (dd, J=2.0, 9.6 Hz, 1H), 7.34 (d, J=8.4 Hz, 1H), 7.53 (d, J=9.6 Hz, 1H), 7.63 (s, 1H), 9.54 (d, J=1.2 Hz, 1H); LCMS (electrospray) m/z (M+H)⁺ 367.19

6-Chloro-2-methyl-N-((1-methyl-1H-indol-6-yl)methyl)imidazo[1,2-a]pyridine-3-carboxamide (78)

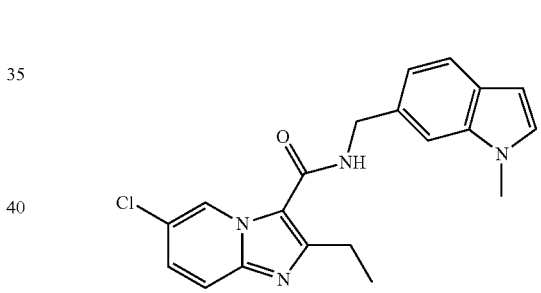

¹H NMR (400 MHz, CDCl₃) δ 1.36 (t, J=7.6 Hz, 3H), 2.95 (q, J=7.6 Hz, 2H), 3.80 (s, 3H), 4.82 (d, J=5.6 Hz, 2H), 6.13 (m, 1H), 6.49 (d, J=3.2 Hz, 1H), 7.08 (d, J=2.8 Hz, 1H), 7.12 (dd, J=1.2, 8.0 Hz, 1H), 7.30 (dd, J=2.0, 9.6 Hz, 1H), 7.34 (s, 1H), 7.55 (d, J=9.6 Hz, 1H), 7.63 (d, J=8.0 Hz, 1H), 9.54 (d, J=1.2 Hz, 1H); LCMS (electrospray) m/z (M+H)⁺ 367.26

6-Chloro-2-ethyl-N-(4-(piperidin-1-yl)benzyl)imidazo[1,2-a]pyridine-3-carboxamide (79)

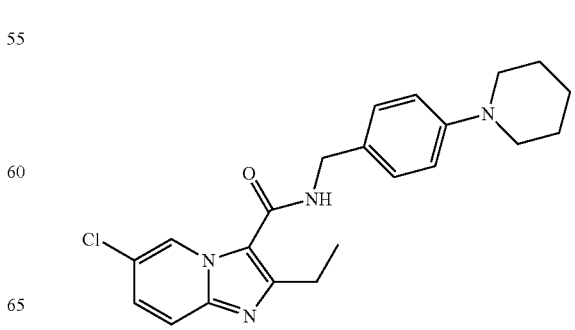

¹H NMR (400 MHz, CDCl₃) δ 1.38 (t, J=7.6 Hz, 3H), 1.54-1.60 (m, 2H), 1.69-1.73 (m, 4H), 2.94 (q, J=7.6 Hz, 2H), 3.16 (t, J=5.14 Hz, 4H), 4.59 (d, J=5.6 Hz, 2H), 6.00 (m, 1H), 6.93 (d, J=8.8 Hz, 2H), 7.25 (d, J=8.0 Hz, 2H), 7.29 (dd, J=2.0, 9.6 Hz, 1H), 7.53 (d, J=9.6 Hz, 1H), 9.52 (d, J=2.0 Hz, 1H); LCMS (electrospray) m/z (M+H)⁺ 397.32

6-Chloro-2-ethyl-N-(naphthalen-2-ylmethyl)imidazo[1,2-a]pyridine-3-carboxamide (80)

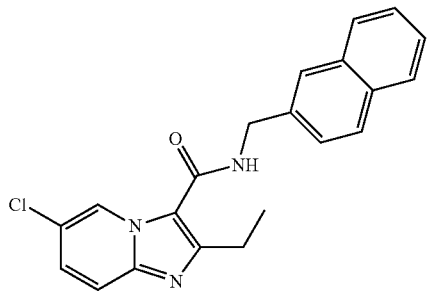 [SMILES: CCc1nc2ccc(Cl)cn2c1C(=O)NCc1ccc2ccccc2c1]

¹H NMR (400 MHz, CDCl₃) δ 1.40 (t, J=7.4 Hz, 3H), 2.98 (q, J=7.6 Hz, 2H), 4.87 (q, J=5.6 Hz, 2H), 6.19 (m, 1H), 7.31 (dd, J=2.0, 9.6 Hz, 1H), 7.47-7.51 (m, 3H), 7.55 (d, J=9.6 Hz, 1H), 7.82-7.85 (m, 3H), 7.87 (d, J=8.4 Hz, 1H), 9.57 (d, J=2.0 Hz, 1H); LCMS (electrospray) m/z (M+H)⁺ 364.20

N-(Biphenyl-4-ylmethyl)-6-chloro-2-methylimidazo[1,2-a]pyridine-3-carboxamide (81)

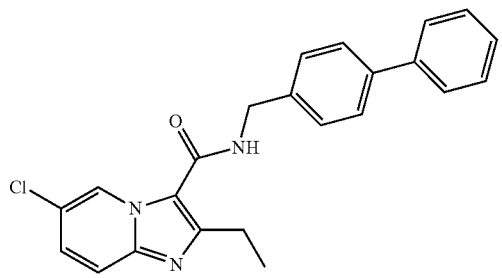 [SMILES: CCc1nc2ccc(Cl)cn2c1C(=O)NCc1ccc(-c2ccccc2)cc1]

¹H NMR (400 MHz, CDCl₃) δ 1.43 (t, J=7.6 Hz, 3H), 3.01 (q, J=7.6 Hz, 2H), 4.75 (d, J=5.6 Hz, 2H), 6.15 (m, 1H), 7.31 (dd, J=2.0, 9.6 Hz, 1H), 7.43-7.47 (m, 4H), 7.55 (d, J=9.2 Hz, 1H), 7.58-7.62 (m, 4H), 9.56 (d, J=2.0 Hz, 1H); LCMS (electrospray) m/z (M+H)⁺ 390.25

6-Chloro-N-((2'-chlorobiphenyl-4-yl)methyl)-2-ethylimidazo[1,2-a]pyridine-3-carboxamide (82)

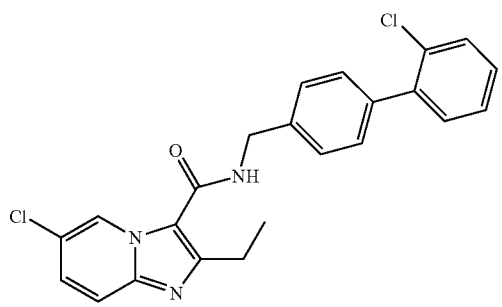 [SMILES: CCc1nc2ccc(Cl)cn2c1C(=O)NCc1ccc(-c2ccccc2Cl)cc1]

¹H NMR (400 MHz, CDCl₃) δ 1.44 (t, J=7.6 Hz, 3H), 3.02 (q, J=7.6 Hz, 2H), 4.77 (d, J=6.0 Hz, 2H), 6.18 (m, 1H), 7.27-7.35 (m, 4H), 7.43-7.48 (m, 5H), 7.56 (d, J=9.6 Hz, 1H), 9.56 (d, J=2.0 Hz, 1H); LCMS (electrospray) m/z (M+H)⁺ 404.26

6-Chloro-N-((4'-chlorobiphenyl-4-yl)methyl)-2-ethylimidazo[1,2-a]pyridine-3-carboxamide (83)

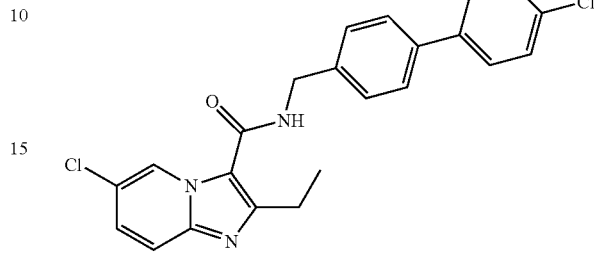

¹H NMR (400 MHz, CDCl₃) δ 1.43 (t, J=7.6 Hz, 3H), 3.01 (q, J=7.6 Hz, 2H), 4.71 (d, J=6.0 Hz, 2H), 6.13 (m, 1H), 7.31 (dd, J=2.0, 9.6 Hz, 1H), 7.41 (d, J=8.8 Hz, 2H), 7.45 (d, J=8.0 Hz, 2H), 7.51 (d, J=8.4 Hz, 2H), 7.54-7.58 (m, 3H), 9.55 (d, J=2.0 Hz, 1H); LCMS (electrospray) m/z (M+H)⁺ 424.26

6-Chloro-2-ethyl-N-((2'-methylbiphenyl-4-yl)methyl)imidazo[1,2-a]pyridine-3-carboxamide (84)

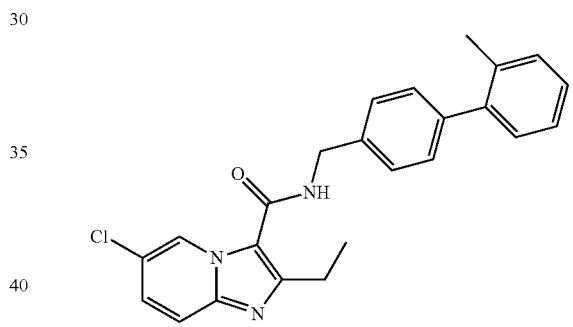

¹H NMR (400 MHz, CDCl₃) δ 1.43 (t, J=7.6 Hz, 3H), 2.27 (s, 3H), 3.02 (q, J=7.6 Hz, 2H), 4.76 (d, J=5.6 Hz, 2H), 6.21 (t, J=5.2 Hz, 1H), 7.20-7.28 (m, 4H), 7.30 (dd, J=2.0, 9.6 Hz, 1H), 7.34 (d, J=8.0 Hz, 2H), 7.42 (d, J=8.0 Hz, 2H), 7.54 (d, J=9.6 Hz, 1H), 9.55 (d, J=2.0 Hz, 1H); LCMS (electrospray) m/z (M+H)⁺ 404.26

6-Chloro-2-ethyl-N-((3'-methylbiphenyl-4-yl)methyl)imidazo[1,2-a]pyridine-3-carboxamide (85)

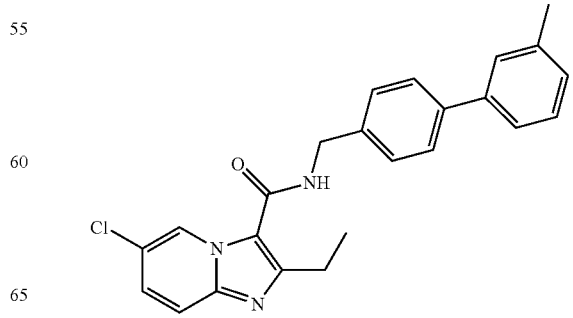

¹H NMR (400 MHz, CDCl₃) δ 1.43 (t, J=7.6 Hz, 3H), 2.42 (s, 3H), 3.00 (q, J=7.6 Hz, 2H), 4.75 (d, J=5.6 Hz, 2H), 6.14 (m, 1H), 7.18 (d, J=7.2 Hz, 1H), 7.31 (dd, J=2.0, 9.6 Hz, 1H), 7.34 (d, J=7.2 Hz, 1H), 7.39 (d, J=8.0 Hz, 2H), 7.44 (d, J=8.4 Hz, 2H), 7.55 (d, J=9.6 Hz, 1H), 7.60 (d, J=8.0 Hz, 2H), 9.56 (d, J=2.0 Hz, 1H); LCMS (electrospray) m/z (M+H)⁺ 404.26

6-Chloro-2-ethyl-N-((4'-methylbiphenyl-4-yl)methyl)imidazo[1,2-a]pyridine-3-carboxamide (86)

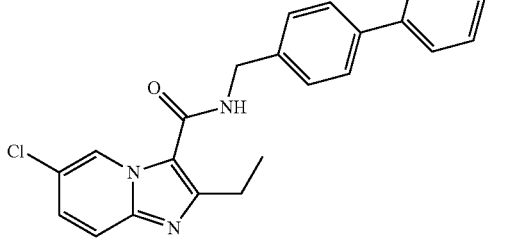

¹H NMR (400 MHz, CDCl₃) δ 1.42 (t, J=7.6 Hz, 3H), 3.00 (q, J=7.6 Hz, 2H), 2.40 (s, 3H), 4.74 (d, J=5.6 Hz, 2H), 6.16 (m, 1H), 7.25 (d, J=7.2 Hz, 2H), 7.30 (dd, J=2.0, 9.6 Hz, 1H), 7.44 (d, J=8.0 Hz, 2H), 7.49 (d, J=8.0 Hz, 2H), 7.54 (d, J=9.6 Hz, 1H), 7.59 (d, J=8.4 Hz, 2H), 9.55 (d, J=2.0 Hz, 1H); LCMS (electrospray) m/z (M+H)⁺ 404.26

7-Chloro-N-(4-chlorobenzyl)-2-ethylimidazo[1,2-a]pyridine-3-carboxamide (87)

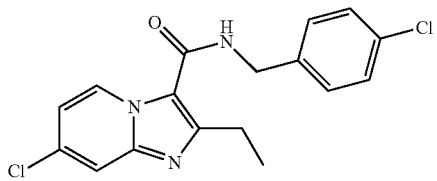 [SMILES: CCc1nc2cc(Cl)ccn2c1C(=O)NCc1ccc(Cl)cc1]

¹H NMR (400 MHz, CDCl₃) δ 1.40 (t, J=7.6 Hz, 3H), 2.96 (q, J=7.6 Hz, 2H), 4.65 (d, J=5.6 Hz, 2H), 6.12 (brs, 1H), 6.90 (dd, J=7.6, 2.4 Hz, 1H), 7.30 (d, J=8.4 Hz, 2H), 7.34 (d, J=8.4 Hz, 2H), 7.58 (d, 1H), 9.34 (d, J=7.6 Hz, 1H); LCMS (electrospray) m/z (M+H)⁺ 348.21

7-Chloro-2-ethyl-N-(4-hydroxybenzyl)imidazo[1,2-a]pyridine-3-carboxamide (88)

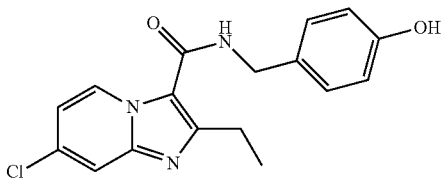 [SMILES: CCc1nc2cc(Cl)ccn2c1C(=O)NCc1ccc(O)cc1]

¹H NMR (400 MHz, MeOH-d₄) δ 1.29 (t, J=7.6 Hz, 3H), 2.96 (q, J=7.6 Hz, 2H), 3.12-3.15 (m, 4H), 4.52 (s, 2H), 6.76 (d, J=8.4 Hz, 2H), 7.06 (dd, J=7.6, 2.0 Hz, 1H), 7.23 (d, J=8.4 Hz, 2H), 7.58 (d, J=1.6 Hz, 1H), 8.91 (d, J=7.6 Hz, 1H); LCMS (electrospray) m/z (M+H)⁺ 330.25

7-Chloro-2-ethyl-N-(4-morpholinobenzyl)imidazo[1,2-a]pyridine-3-carboxamide (89)

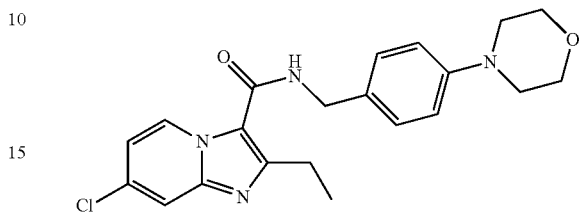

White solid, mp 195° C.; ¹H NMR (400 MHz, MeOH-d₄) δ 1.31 (t, J=7.6 Hz, 3H), 3.00 (q, J=7.6 Hz, 2H), 3.14 (t, J=4.8 Hz, 4H), 3.84 (t, J=4.8 Hz, 4H), 4.54 (s, 2H), 6.97 (d, J=6.8 Hz, 2H), 7.07 (d, J=7.6 Hz, 1H), 7.32 (d, J=8.8 Hz, 2H), 7.59 (s, 1H), 8.93 (d, J=7.2 Hz, 1H).

7-Chloro-2-ethyl-N-(4-(piperidin-1-yl)benzyl)imidazo[1,2-a]pyridine-3-carboxamide (90)

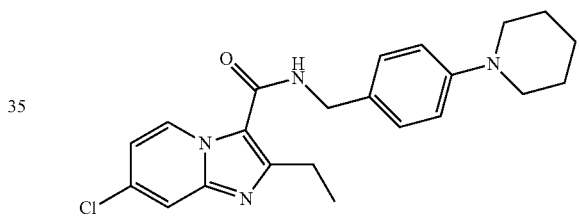

¹H NMR (400 MHz, CDCl₃) δ 1.35 (t, J=7.6 Hz, 3H), 1.55-1.57 (m, 2H), 1.66-1.70 (m, 4H), 2.91 (q, J=7.6 Hz, 2H), 3.12-3.15 (m, 4H), 4.56 (d, J=5.6 Hz, 2H), 6.07 (brs, 1H), 6.86 (dd, J=7.6, 2.0 Hz, 1H), 6.90 (d, J=8.4 Hz, 2H), 7.22 (d, J=8.4 Hz, 2H), 7.54 (d, J=2.0 Hz, 1H), 9.30 (d, J=7.6 Hz, 1H); LCMS (electrospray) m/z (M+H)⁺ 397.32

7-Chloro-2-ethyl-N-(naphthalen-2-ylmethyl)imidazo[1,2-a]pyridine-3-carboxamide (91)

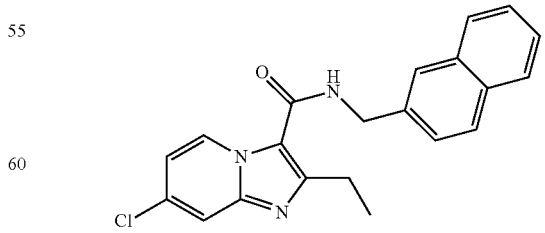

¹H NMR (400 MHz, MeOH-d₄) δ 1.32 (t, J=7.6 Hz, 3H), 3.02 (q, J=7.6 Hz, 2H), 4.79 (s, 2H), 7.06 (dd, J=7.6, 2.0 Hz, 1H), 7.45-7.48 (m, 2H), 7.54 (d, J=8.4 Hz, 1H), 7.59 (d, J=2.0

Hz, 1H), 7.82-7.88 (m, 4H), 8.96 (d, J=7.6 Hz, 1H); LCMS (electrospray) m/z (M+H)+ 364.20

N-(4-tert-Butylbenzyl)-7-chloro-2-ethylimidazo[1,2-a]pyridine-3-carboxamide (92)

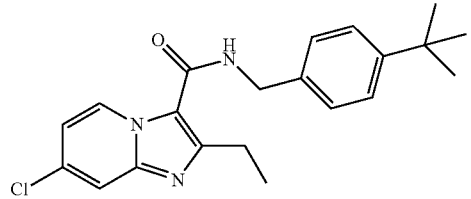 [SMILES: CCc1nc2cc(Cl)ccn2c1C(=O)NCc1ccc(C(C)(C)C)cc1]

¹H NMR (400 MHz, CDCl₃) δ 1.32 (s, 9H), 1.40 (t, J=7.6 Hz, 3H), 2.96 (q, J=7.6 Hz, 2H), 4.67 (d, J=5.6 Hz, 2H), 6.13 (brs, 1H), 6.90 (dd, J=7.2, 2.4 Hz, 1H), 7.31 (d, J=8.0 Hz, 2H), 7.40 (d, J=8.0 Hz, 2H), 7.59 (d, J=1.6 Hz, 1H), 9.36 (d, J=7.2 Hz, 1H); LCMS (electrospray) m/z (M+H)+ 370.25

N-Biphenyl-4-ylmethyl)-7-chloro-2-ethylimidazo[1,2-a]pyridine-3-carboxamide (93)

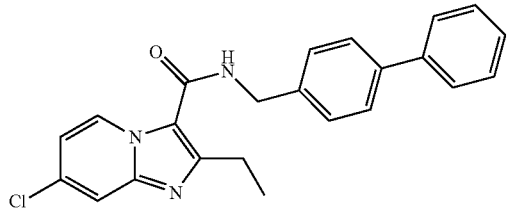 [SMILES: CCc1nc2cc(Cl)ccn2c1C(=O)NCc1ccc(-c2ccccc2)cc1]

¹H NMR (400 MHz, CDCl₃) δ 1.42 (t, J=7.6 Hz, 3H), 3.00 (q, J=7.6 Hz, 2H), 4.74 (d, J=5.6 Hz, 2H), 6.14 (brs, 1H), 6.91 (dd, J=7.6, 2.4 Hz, 1H), 7.35 (m, 1H), 7.42-7.46 (m, 4H), 7.57-7.62 (m, 5H), 9.38 (d, J=7.6 Hz, 1H); ¹³C NMR (100 MHz, CDCl₃) δ 13.4, 23.6, 31.5, 34.7, 43.4, 114.7, 115.8, 126.0, 127.5, 128.6, 133.6, 135.0, 146.2, 150.9, 151.6, 161.3; LCMS (electrospray) m/z (M+H)+ 390.25

7-Chloro-N-((2'-chlorobiphenyl-4-yl)methyl)-2-ethylimidazo[1,2-a]pyridine-3-carboxamide (94)

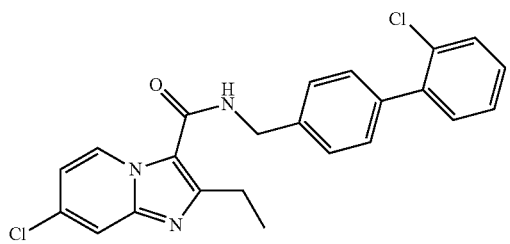

¹H NMR (400 MHz, MeOH-d₄) δ 1.32 (t, J=7.6 Hz, 3H), 3.01 (q, J=7.6 Hz, 2H), 4.68 (s, 2H), 7.03 (dd, J=7.6, 2.0 Hz, 1H), 7.29-7.57 (m, 9H), 8.94 (d, J=7.6 Hz, 1H); LCMS (electrospray) m/z (M+H)+ 424.26

7-Chloro-N-((4'-chlorobiphenyl-4-yl)methyl)-2-ethylimidazo[1,2-a]pyridine-3-carboxamide (95)

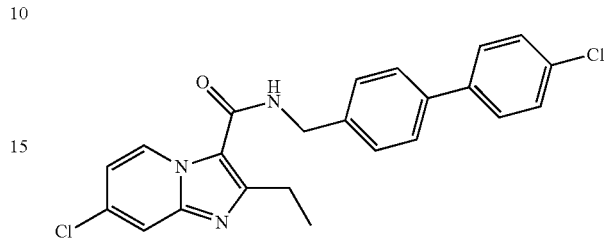

¹H NMR (400 MHz, CDCl₃) δ 1.42 (t, J=7.6 Hz, 3H), 2.99 (q, J=7.6 Hz, 2H), 4.73 (s, 2H), 6.15 (brs, 1H), 6.91 (dd, J=7.6, 2.0 Hz, 1H), 7.40 (d, J=8.4 Hz, 2H), 7.44 (d, J=8.0 Hz, 2H), 7.51 (d, J=8.4 Hz, 2H), 7.56 (d, J=8.0 Hz, 2H), 7.60 (d, J=1.6 Hz, 1H), 9.38 (d, J=7.2 Hz, 1H); LCMS (electrospray) m/z (M+H)+ 424.26

7-Chloro-2-ethyl-N-((2'-methylbiphenyl-4-yl)methyl)imidazo[1,2-a]pyridine-3-carboxamide (96)

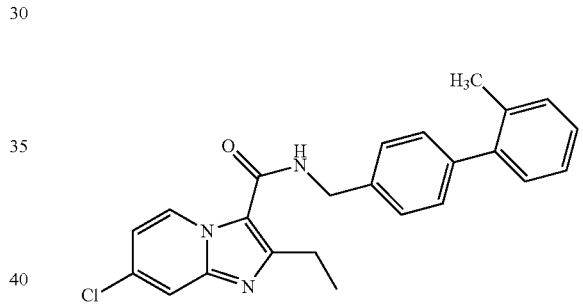

¹H NMR (400 MHz, CDCl₃) δ 1.46 (t, J=7.6 Hz, 3H), 2.31 (s, 3H), 3.05 (q, J=7.6 Hz, 2H), 4.79 (d, J=5.6 Hz, 2H), 6.22 (brs, 1H), 6.95 (dd, J=7.6, 1.6 Hz, 1H), 7.24-7.36 (m, 4H), 7.39 (d, J=7.6 Hz, 2H), 7.45 (d, J=7.6 Hz, 2H), 7.63 (d, 1H), 9.42 (d, J=7.2 Hz, 1H); LCMS (electrospray) m/z (M+H)+ 404.26

7-Chloro-2-ethyl-N-((3'-methylbiphenyl-4-yl)methyl)imidazo[1,2-a]pyridine-3-carboxamide (97)

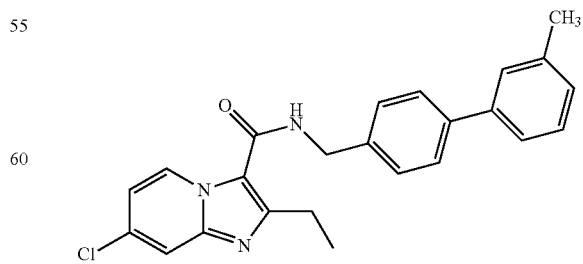

¹H NMR (400 MHz, CDCl₃) δ 1.41 (t, J=7.6 Hz, 3H), 2.42 (s, 3H), 2.99 (q, J=7.6 Hz, 2H), 4.74 (d, J=5.6 Hz, 2H), 6.13

(brs, 1H), 6.91 (dd, J=7.6, 2.0 Hz, 1H), 7.18 (d, J=8.4 Hz, 1H), 7.33-7.40 (m, 3H), 7.43 (d, J=8.4 Hz, 2H), 7.58-7.61 (m, 3H), 9.38 (d, J=7.6 Hz, 1H); LCMS (electrospray) m/z (M+H)+ 404.33

7-Chloro-2-ethyl-N-((4'-methylbiphenyl-4-yl)methyl)imidazo[1,2-a]pyridine-3-carboxamide (98)

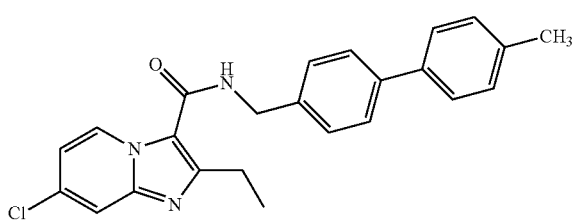 [SMILES: CCc1nc2cc(Cl)ccn2c1C(=O)NCc1ccc(-c2ccc(C)cc2)cc1]

$^1$H NMR (400 MHz, CDCl$_3$) δ 1.41 (t, J=7.6 Hz, 3H), 2.40 (s, 3H), 2.99 (q, J=7.6 Hz, 2H), 4.73 (s, 2H), 6.91 (dd, J=7.6, 2.0 Hz, 1H), 7.25 (d, J=8.4 Hz, 2H), 7.43 (d, J=8.0 Hz, 2H), 7.48 (d, J=8.0 Hz, 2H), 7.58-7.60 (m, 3H), 9.38 (d, J=7.2 Hz, 1H); LCMS (electrospray) m/z (M+H)+ 404.26

N-(Biphenyl-4-ylmethyl)-6-chloro-2-(trifluoromethyl)imidazo[1,2-a]pyridine-3-carboxamide (99)

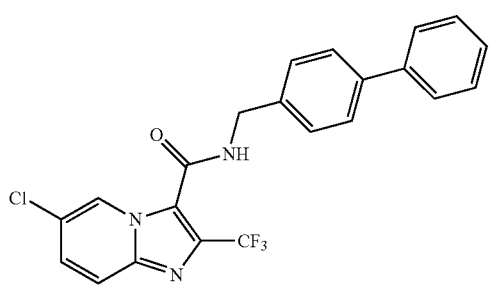 [SMILES: O=C(NCc1ccc(-c2ccccc2)cc1)c1c(C(F)(F)F)nc2ccc(Cl)cn12]

$^1$H NMR (400 MHz, CDCl$_3$) δ 4.74 (d, J=5.6 Hz, 2H), 6.69 (m, 1H), 7.36 (dd, J=7.2, 7.2 Hz, 1H), 7.43-7.47 (m, 5H), 7.56 (dd, J=8.0, 8.4 Hz, 4H), 7.71 (d, J=9.6 Hz, 1H), 9.45 (s, 1H)); LCMS (electrospray) m/z (M+H)+ 430.18

N-(4-tert-Butylbenzyl)-6-chloro-2-(trifluoromethyl)imidazo[1,2-a]pyridine-3-carboxamide (100)

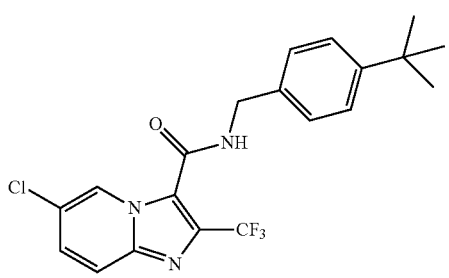 [SMILES: CC(C)(C)c1ccc(CNC(=O)c2c(C(F)(F)F)nc3ccc(Cl)cn23)cc1]

$^1$H NMR (400 MHz, CDCl$_3$) δ 1.32 (s, 9H), 4.67 (d, J=6.0 Hz, 2H), 6.63 (m, 1H), 7.30 (d, J=8.0 Hz, 2H), 7.41 (d, J=8.4 Hz, 2H), 7.41-7.45 (m, 1H), 7.69 (d, J=9.6 Hz, 1H), 9.42 (d, J=1.2 Hz, 1H); LCMS (electrospray) m/z (M+H)+ 410.25

N-(4-Bromobenzyl)-7-chloro-2-ethylimidazo[1,2-a]pyridine-3-carboxamide (101)

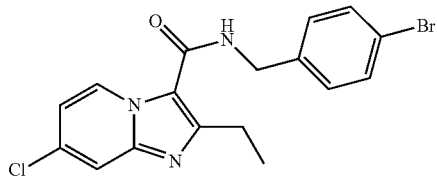 [SMILES: CCc1nc2cc(Cl)ccn2c1C(=O)NCc1ccc(Br)cc1]

$^1$H NMR (400 MHz, CDCl$_3$) δ 1.41 (t, J=7.6 Hz, 3H), 2.97 (q, J=7.6 Hz, 2H), 4.65 (d, J=5.6 Hz, 2H), 6.09 (brs, 1H), 6.91 (dd, J=7.6, 2.0 Hz, 1H), 7.25 (d, J=8.4 Hz, 2H), 7.50 (d, J=8.4 Hz, 2H), 7.60 (d, J=2.0 Hz, 1H), 9.35 (d, J=7.6 Hz, 1H); LCMS (electrospray) m/z (M+H)+ 394.13

7-Chloro-2-ethyl-N-(4-(trifluoromethoxy)benzyl)imidazo[1,2-a]pyridine-3-carboxamide (102)

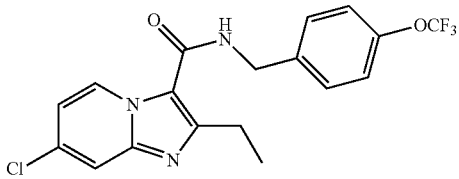 [SMILES: CCc1nc2cc(Cl)ccn2c1C(=O)NCc1ccc(OC(F)(F)F)cc1]

$^1$H NMR (400 MHz, CDCl$_3$) δ 1.41 (t, J=7.6 Hz, 3H), 2.98 (q, J=7.6 Hz, 2H), 4.70 (d, J=5.6 Hz, 2H), 6.09 (brs, 1H), 6.91 (dd, J=7.6, 2.0 Hz, 1H), 7.22 (d, J=8.4 Hz, 2H), 7.40 (d, J=8.4 Hz, 2H), 7.60 (d, J=2.0 Hz, 1H), 9.36 (d, J=7.6 Hz, 1H); LCMS (electrospray) m/z (M+H)+ 398.28

2-Ethyl-6-fluoro-N-(4-(trifluoromethoxy)benzyl)imidazo[1,2-a]pyridine-3-carboxamide (103)

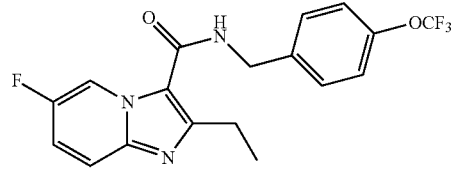 [SMILES: CCc1nc2ccc(F)cn2c1C(=O)NCc1ccc(OC(F)(F)F)cc1]

$^1$H NMR (400 MHz, CDCl$_3$) δ 1.42 (t, J=7.6 Hz, 3H), 3.00 (q, J=7.6 Hz, 2H), 4.71 (d, J=6.0 Hz, 2H), 6.14 (brs, 1H), 6.91 (dd, J=7.6, 2.0 Hz, 1H), 7.20 (d, J=8.0 Hz, 1H), 7.26 (m, 1H), 7.57 (d, J=5.2 Hz, 1H), 7.59 (d, J=5.2 Hz, 1H), 9.45 (dd, J=5.2, 2.4 Hz, 1H); LCMS (electrospray) m/z (M+H)+ 382.15

2-Ethyl-7-methoxy-N-(4-(trifluoromethoxy)benzyl)imidazo[1,2-a]pyridine-3-carboxamide (104)

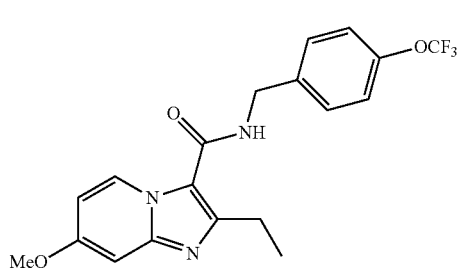 [SMILES: CCc1nc2cc(OC)ccn2c1C(=O)NCc1ccc(OC(F)(F)F)cc1]

$^1$H NMR (400 MHz, CDCl$_3$) δ 1.39 (t, J=7.6 Hz, 3H), 2.95 (q, J=7.6 Hz, 2H), 3.87 (s, 3H), 6.06 (m, 1H), 6.61 (dd, J=2.8, 7.6, 1H), 6.89 (d, J=2.4 Hz, 1H), 7.21 (d, J=8.8 Hz, 2H), 7.41 (d, J=8.4 Hz, 2H), 9.24 (d, J=7.6 Hz, 1H).

2-Ethyl-7-hydroxy-N-(4-(trifluoromethoxy)benzyl)imidazo[1,2-a]pyridine-3-carboxamide (105)

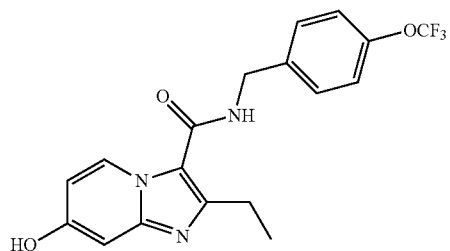 [SMILES: CCc1nc2cc(O)ccn2c1C(=O)NCc1ccc(OC(F)(F)F)cc1]

$^1$H NMR (400 MHz, CDCl$_3$+CD$_3$OD) δ 1.21 (t, J=7.6 Hz, 3H), 2.79 (q, J=7.6 Hz, 2H), 4.51 (q, J=4.0 Hz, 2H), 4.74 (brs, 1H), 6.49 (dd, J=2.4, 7.6, 1H), 6.89 (d, J=2.4 Hz, 1H), 7.21 (d, J=8.0 Hz, 2H), 7.29 (d, J=8.8 Hz, 2H), 8.86 (d, J=7.6 Hz, 1H).

7-Chloro-2-ethyl-N-(4-(propylamino)benzyl)imidazo[1,2-a]pyridine-3-carboxamide (106)

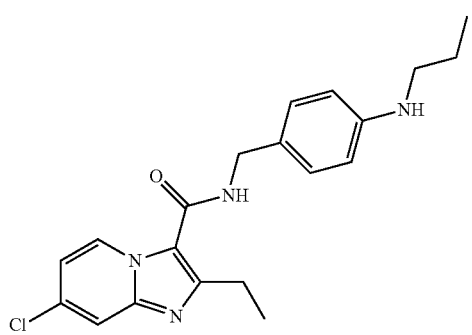 [SMILES: CCCNc1ccc(CNC(=O)c2c(CC)nc3cc(Cl)ccn23)cc1]

$^1$H NMR (400 MHz, CDCl$_3$) δ 1.00 (t, J=7.4 Hz, 3H), 1.37 (t, J=7.6 Hz, 3H), 1.60-1.69 (m, 2H), 2.93 (q, J=8.0 Hz, 2H), 3.08 (t, J=7.2 Hz, 2H), 3.69 (brs, 1H), 4.55 (d, J=5.2 Hz, 2H), 5.96 (m, 1H), 6.60 (d, J=8.4 Hz, 2H), 7.18 (d, J=8.0 Hz, 2H), 7.57 (d, J=1.2 Hz, 1H), 9.35 (d, J=7.6 Hz, 1H).

7-Chloro-2-ethyl-N-(4-(pentylamino)benzyl)imidazo[1,2-a]pyridine-3-carboxamide (107)

$^1$H NMR (400 MHz, CDCl$_3$) δ 0.92 (t, J=7.0 Hz, 3H), 1.25-1.42 (m, 8H), 1.58-1.66 (m, 2H), 2.93 (q, J=7.6 Hz, 2H), 3.10 (t, J=7.2 Hz, 2H), 3.66 (brs, 1H), 4.55 (d, J=5.2 Hz, 2H), 5.95 (m, 1H), 6.60 (d, J=8.4 Hz, 2H), 6.89 (dd, J=2.0, 7.2 Hz, 1H), 7.18 (d, J=8.0 Hz, 2H), 7.58 (d, J=1.2 Hz, 1H), 9.36 (d, J=7.6 Hz, 1H).

6-Chloro-2-ethyl-N-(4-(4-methylpiperazin-1-yl)benzyl)imidazo[1,2-a]pyridine-3-carboxamide (108)

$^1$H NMR (400 MHz, CDCl$_3$) δ 1.39 (t, J=7.6 Hz, 3H), 2.36 (s, 3H), 2.58 (t, J=5.0 Hz, 4H), 2.95 (q, J=7.6 Hz, 2H), 3.22 (t, J=4.8 Hz, 4H), 4.60 (d, J=5.6 Hz, 2H), 6.93 (d, J=8.8 Hz, 2H), 7.26-7.30 (m, 3H), 7.53 (d, J=5.6 Hz, 1H), 9.53 (d, J=1.6 Hz, 1H).

7-Chloro-2-ethyl-N-(4-(4-methylpiperazin-1-yl)benzyl)imidazo[1,2-a]pyridine-3-carboxamide (109)

$^1$H NMR (400 MHz, CDCl$_3$) δ 1.37 (t, J=7.6 Hz, 3H), 2.35 (s, 3H), 2.57-2.59 (m, 4H), 2.94 (q, J=7.6 Hz, 2H), 3.20-3.23 (m, 4H), 4.59 (d, J=5.2 Hz, 2H), 6.00 (brs, 1H), 6.88-6.94 (m, 3H), 7.27 (d, J=8.4 Hz, 2H), 7.58 (d, J=2.0 Hz, 1H), 9.35 (d, J=7.6 Hz, 1H); LCMS (electrospray) m/z (M+H)+ 412.29

7-Chloro-2-ethyl-N-(4-(4-isopropylpiperazin-1-yl) benzyl)imidazo[1,2-a]pyridine-3-carboxamide (110)

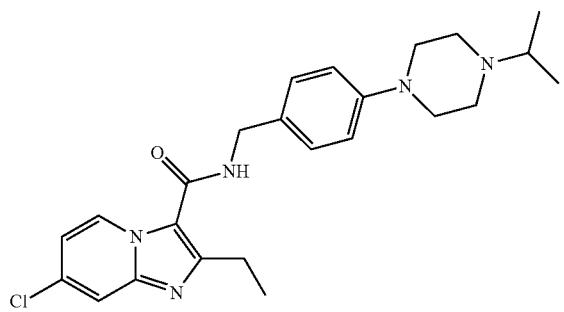 [SMILES: CCc1nc2cc(Cl)ccn2c1C(=O)NCc1ccc(N2CCN(C(C)C)CC2)cc1]

¹H NMR (400 MHz, CDCl₃) δ 1.10 (d, J=6.0 Hz, 6H), 1.38 (t, J=7.6 Hz, 3H), 2.69 (m, 4H), 2.94 (q, J=7.6 Hz, 2H), 3.22 (m, 4H), 4.60 (d, J=5.6 Hz, 2H), 5.99 (m, 1H), 6.90 (dd, J=2.0, 7.6 Hz, 1H), 6.93 (d, J=8.4 Hz, 1H), 7.26-7.38 (m, 5H), 7.58 (d, J=1.6 Hz, 1H), 9.36 (d, J=7.6 Hz, 1H).

7-Chloro-2-ethyl-N-(4-(4-phenylpiperazin-1-yl)benzyl)imidazo[1,2-a]pyridine-3-carboxamide (111)

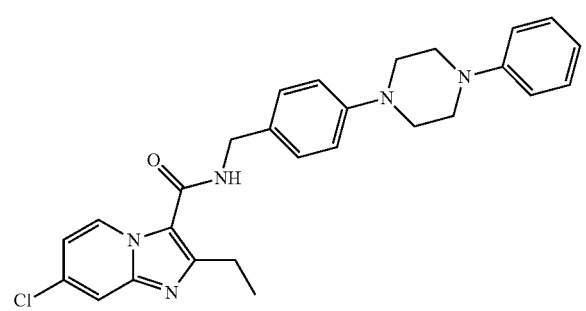 [SMILES: CCc1nc2cc(Cl)ccn2c1C(=O)NCc1ccc(N2CCN(c3ccccc3)CC2)cc1]

¹H NMR (400 MHz, DMSO-d₆) δ 1.29 (t, J=7.6 Hz, 3H), 3.00 (q, J=7.6 Hz, 2H), 3.30 (m, 8H), 4.48 (d, J=6.0 Hz, 2H), 6.84 (t, J=6.0 Hz, 1H), 7.01-7.05 (m, 4H), 7.13 (dd, J=2.4, 7.6 Hz, 1H), 7.26-7.31 (m, 4H), 7.82 (d, J=1.6 Hz, 1H), 8.45 (t, J=6.0 Hz, 1H), 8.99 (d, J=7.6 Hz, 1H).

2-Ethyl-N-(4-(4-(4-fluorophenyl)piperazin-1-yl)benzyl)-6-methoxyimidazo[1,2-a]pyridine-3-carboxamide (112)

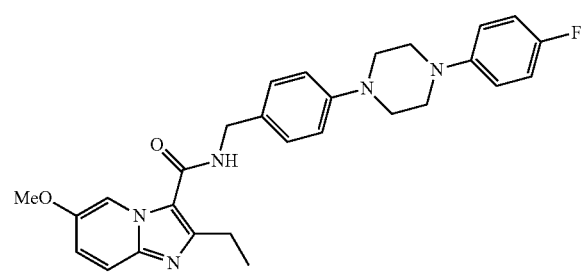 [SMILES: CCc1nc2ccc(OC)cn2c1C(=O)NCc1ccc(N2CCN(c3ccc(F)cc3)CC2)cc1]

White solid; mp=173.8° C.; ¹H NMR (400 MHz, CDCl₃) δ 1.39 (t, J=7.6 Hz, 3H), 2.95 (q, J=7.2 Hz, 2H), 3.24-3.27 (m, 4H), 3.33-3.36 (m, 4H), 3.87 (s, 3H), 4.63 (d, J=5.6 Hz, 2H), 6.03 (t, J=5.0 Hz, 1H), 6.91-7.01 (m, 6H), 7.31 (d, J=8.8 Hz, 2H), 7.48 (d, J=9.6 Hz, 1H), 9.11 (d, J=2.4 Hz, 1H); LCMS (electrospray) m/z (M+H)⁺ 488

6-Chloro-2-ethyl-N-(4-(4-(4-fluorophenyl)piperazin-1-yl)benzyl)imidazo[1,2-a]pyridine-3-carboxamide (113)

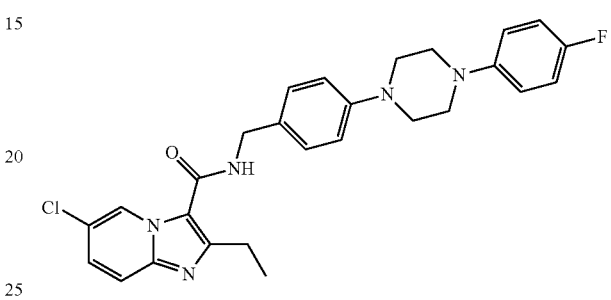

¹H NMR (400 MHz, CDCl₃) δ 1.40 (t, J=7.6 Hz, 3H), 2.96 (q, J=7.6 Hz 2H), 3.25-3.27 (m, 4H), 3.34-3.36 (m, 4H), 4.62 (d, J=5.6 Hz, 2H), 6.02-6.64 (m, 1H), 6.92-6.95 (m, 3H), 6.97-7.01 (m, 3H), 7.29 (dd, J=2.4, 9.6 Hz, 1H), 7.31 (d, J=8.8 Hz, 2H), 7.54 (d, J=9.6 Hz, 2H), 9.54 (d, J=1.2 Hz, 2H); LCMS (electrospray) m/z (M+H)⁺ 492.28

2-Ethyl-N-(4-(4-(4-fluorophenyl)piperazin-1-yl) benzyl)-7-methoxyimidazo[1,2-a]pyridine-3-carboxamide (114)

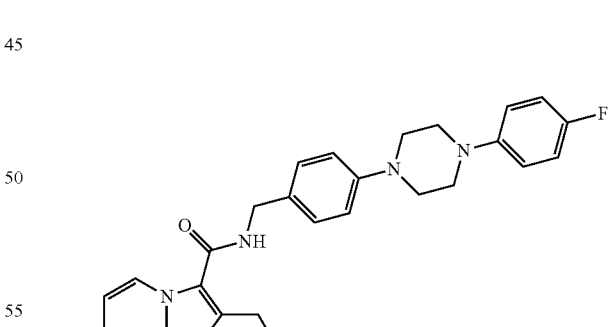

White solid; ¹H NMR (400 MHz, CDCl₃); δ 1.30 (t, J=7.6 Hz, 3H), 2.84 (q, J=7.6 Hz, 2H), 3.18-3.19 (m, 4H), 3.26-3.27 (m, 4H), 3.78 (s, 3H), 4.54 (d, J=5.6 Hz, 2H), 6.15 (brs, 1H), 6.51-6.53 (m, 1H), 6.79 (s, 1H), 6.85-6.95 (m, 6H), 7.24 (d, J=8.0 Hz, 2H), 9.12 (d, J=8.0 Hz, 1H).

2-Ethyl-N-(4-(4-(4-fluorophenyl)piperazin-1-yl)benzyl)-8-methoxyimidazo[1,2-a]pyridine-3-carboxamide (115)

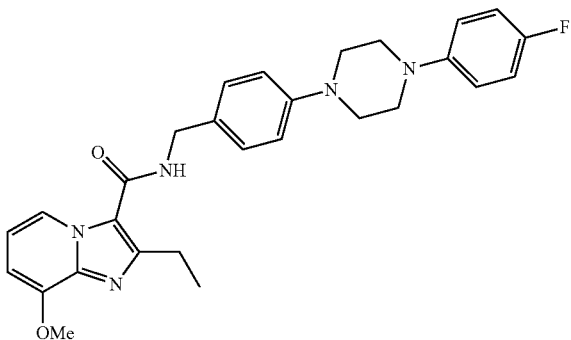 [SMILES: CCc1nc2c(OC)cccn2c1C(=O)NCc1ccc(N2CCN(c3ccc(F)cc3)CC2)cc1]

Pale yellow solid; $^1$H NMR (400 MHz, CDCl$_3$); δ 1.34 (t, J=7.6 Hz, 3H), 2.93 (q, J=7.6 Hz, 2H), 3.22-3.27 (m, 4H), 3.29-3.34 (m, 4H), 3.99 (s, 3H), 4.60 (d, J=5.6 Hz, 2H), 6.08 (brs, 1H), 6.58 (d, J=7.6 Hz, 1H), 6.76 (dd, J=7.2, 7.6 Hz, 1H), 6.89-6.99 (m, 6H), 7.28 (d, J=8.4 Hz, 2H), 8.95 (d, J=7.2 Hz, 1H).

7-Chloro-2-ethyl-N-((4'-fluorobiphenyl-4-yl)methyl)imidazo[1,2-a]pyridine-3-carboxamide (116)

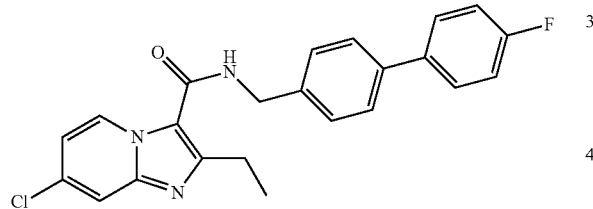

$^1$H NMR (400 MHz, CDCl$_3$) δ 1.42 (t, J=7.6 Hz, 3H), 2.99 (q, J=7.6 Hz, 2H), 4.73 (d, J=5.6 Hz, 2H), 6.14 (brs, 1H), 6.91 (dd, J=7.2, 2.0 Hz, 1H), 7.13 (t, J=8.4 Hz, 2H), 7.44 (d, J=8.4 Hz, 2H), 7.52-7.56 (m, 4H), 7.60 (d, J=2.0 Hz, 1H), 9.38 (d, J=7.2 Hz, 1H); LCMS (electrospray) m/z (M+H)$^+$ 408.21

N-((4'-tert-Butylbiphenyl-4-yl)methyl)-7-chloro-2-ethylimidazo[1,2-a]pyridine-3-carboxamide (117)

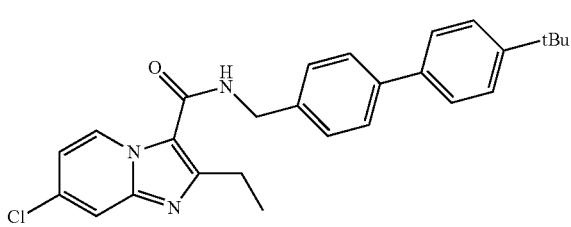 [SMILES: CCc1nc2cc(Cl)ccn2c1C(=O)NCc1ccc(-c2ccc(C(C)(C)C)cc2)cc1]

$^1$H NMR (400 MHz, CDCl$_3$) δ 1.36 (s, 9H), 1.41 (t, J=7.6 Hz, 3H), 2.99 (q, J=7.6 Hz, 2H), 4.73 (d, J=5.6 Hz, 2H), 6.13 (brs, 1H), 6.91 (dd, J=7.2, 2.0 Hz, 1H), 7.43 (d, J=8.0 Hz, 2H), 7.47 (d, J=8.4 Hz, 2H), 7.53 (d, J=8.4 Hz, 2H), 7.59-7.61 (m, 3H), 9.38 (d, J=7.2 Hz, 1H); LCMS (electrospray) m/z (M+H)$^+$ 446.30

7-Chloro-2-ethyl-N-((4'-methoxybiphenyl-4-yl)methyl)imidazo[1,2-a]pyridine-3-carboxamide (118)

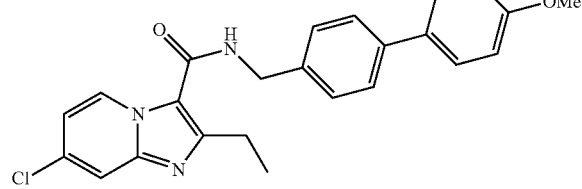

$^1$H NMR (400 MHz, CDCl$_3$) δ 1.41 (t, J=7.6 Hz, 3H), 2.99 (q, J=7.6 Hz, 2H), 3.85 (s, 3H), 4.72 (d, J=6.0 Hz, 2H), 6.12 (brs, 1H), 6.91 (dd, J=7.2, 2.0 Hz, 1H), 6.98 (d, J=8.8 Hz, 2H), 7.42 (d, J=8.0 Hz, 2H), 7.52 (d, J=8.8 Hz, 2H), 7.56 (d, J=8.0 Hz, 2H), 7.59 (d, J=1.6 Hz, 1H), 9.38 (d, J=7.6 Hz, 1H); LCMS (electrospray) m/z (M+H)$^+$ 420.18

7-Chloro-2-ethyl-N-((4'-(trifluoromethoxy)biphenyl-4-yl)methyl)imidazo[1,2-a]pyridine-3-carboxamide (119)

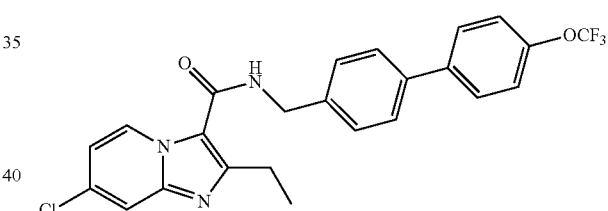

$^1$H NMR (400 MHz, CDCl$_3$) δ 1.42 (t, J=7.6 Hz, 3H), 3.00 (q, J=7.6 Hz, 2H), 4.75 (d, J=6.0 Hz, 2H), 6.15 (brs, 1H), 6.91 (dd, J=7.6, 2.0 Hz, 1H), 7.28 (d, J=8.4 Hz, 2H), 7.46 (d, J=8.4 Hz, 2H), 7.54-7.60 (m, 5H), 9.38 (d, J=7.6 Hz, 1H); LCMS (electrospray) m/z (M+H)$^+$ 474.18

7-Chloro-2-ethyl-N-((4'-(trifluoromethyl)biphenyl-4-yl)methyl)imidazo[1,2-a]pyridine-3-carboxamide (120)

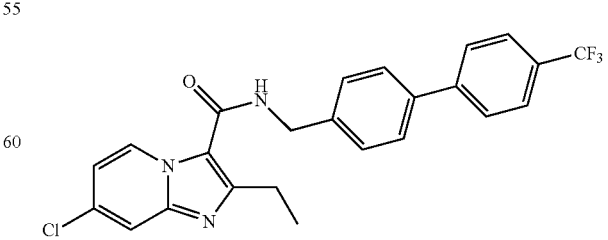

$^1$H NMR (400 MHz, CDCl$_3$) δ 1.42 (t, J=7.6 Hz, 3H), 3.01 (q, J=7.6 Hz, 2H), 4.76 (d, J=6.0 Hz, 2H), 6.16 (brs, 1H), 6.92

(dd, J=7.2, 2.0 Hz, 1H), 7.48 (d, J=8.4 Hz, 2H), 7.60 (m, 3H), 7.70 (m, 3H), 9.38 (d, J=7.2 Hz, 1H); LCMS (electrospray) m/z (M+H)+ 458.20

6-Chloro-N-((4'-cyanobiphenyl-4-yl)methyl)-2-ethylimidazo[1,2-a]pyridine-3-carboxamide (121)

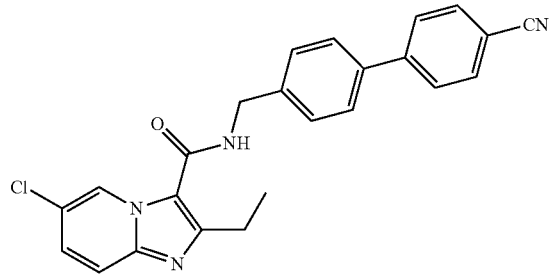 [SMILES: CCc1nc2ccc(Cl)cn2c1C(=O)NCc1ccc(-c2ccc(C#N)cc2)cc1]

¹H NMR (400 MHz, CDCl₃) δ 1.44 (t, J=7.6 Hz, 3H), 3.02 (q, J=7.2 Hz, 2H), 4.77 (d, J=5.6 Hz, 2H), 6.19 (m, 1H), 7.32 (dd, J=2.0, 9.6 Hz, 1H), 7.50 (d, J=8.0 Hz, 2H), 7.56 (d, J=9.6 Hz, 1H), 7.68 (d, J=8.4 Hz, 2H), 7.73 (d, J=8.4 Hz, 2H), 9.55 (d, J=2.0 Hz, 1H).

7-Chloro-N-((4'-cyanobiphenyl-4-yl)methyl)-2-ethylimidazo[1,2-a]pyridine-3-carboxamide (122)

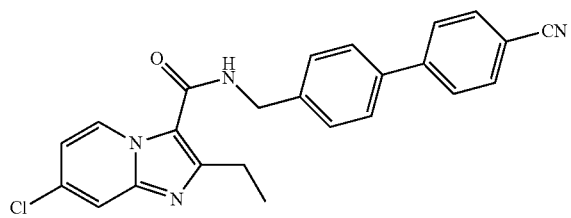 [SMILES: CCc1nc2cc(Cl)ccn2c1C(=O)NCc1ccc(-c2ccc(C#N)cc2)cc1]

¹H NMR (400 MHz, CDCl₃) δ 1.42 (t, J=7.6 Hz, 3H), 3.01 (q, J=7.6 Hz, 2H), 4.76 (d, J=6.0 Hz, 2H), 6.17 (brs, 1H), 6.92 (dd, J=7.6, 2.4 Hz, 1H), 7.49 (d, J=8.0 Hz, 2H), 7.60 (d, J=2.4 Hz, 1H), 7.68 (d, J=8.4 Hz, 2H), 7.73 (d, J=8.4 Hz, 2H), 9.38 (d, J=7.6 Hz, 1H); LCMS (electrospray) m/z (M+H)+ 415.21

6-Chloro-2-ethyl-N-((2'-(trifluoromethyl)biphenyl-4-yl)methyl)imidazo[1,2-a]pyridine-3-carboxamide (123)

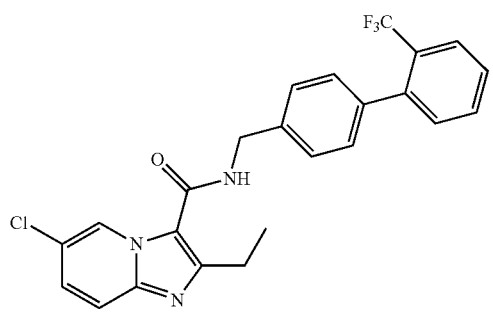

¹H NMR (400 MHz, CDCl₃) δ 1.43 (t, J=7.6 Hz, 3H), 3.02 (q, J=7.2 Hz, 2H), 4.78 (d, J=5.6 Hz, 2H), 6.17 (m, 1H), 7.30-7.35 (m, 4H), 7.42 (d, J=8.0 Hz, 2H), 7.48 (t, J=8.0 Hz, 1H), 7.55 (d, J=8.8 Hz, 2H), 7.75 (d, J=7.6 Hz, 1H), 7.73 (d, J=8.4 Hz, 2H), 9.56 (d, J=1.2 Hz, 1H).

7-Chloro-2-ethyl-N-((2'-trifluoromethyl)biphenyl-4-yl)methyl)imidazo[1,2-a]pyridine-3-carboxamide (124)

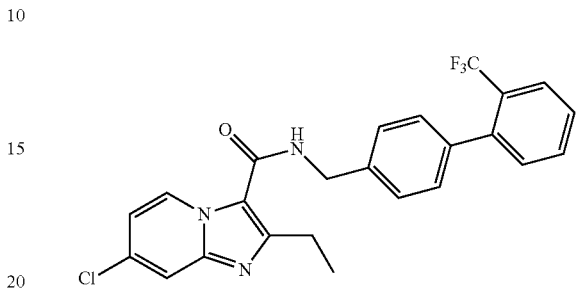

¹H NMR (400 MHz, CDCl₃) δ 1.41 (t, J=7.6 Hz, 3H), 3.01 (q, J=7.6 Hz, 2H), 4.77 (d, J=5.6 Hz, 2H), 6.16 (brs, 1H), 6.92 (dd, J=7.2, 2.4 Hz, 1H), 7.32 (d, J=7.6 Hz, 1H), 7.34 (d, J=8.4 Hz, 2H), 7.41 (d, J=8.4 Hz, 2H), 7.47 (t, J=7.6 Hz, 1H), 7.56 (t, J=7.6 Hz, 1H), 7.60 (d, J=2.4 Hz, 1H), 7.75 (d, J=8.0 Hz, 1H), 9.38 (d, J=7.2 Hz, 1H); LCMS (electrospray) m/z (M+H)+ 458.27

6-Chloro-N-((2'-cyanobiphenyl-4-yl)methyl)-2-ethylimidazo[1,2-a]pyridine-3-carboxamide (125)

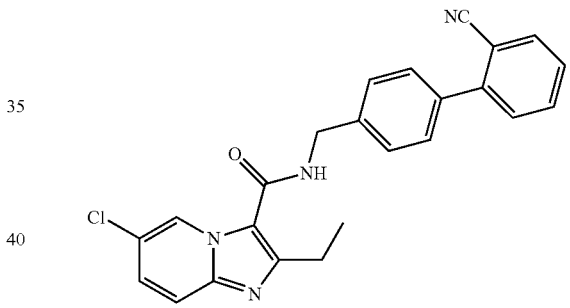

¹H NMR (400 MHz, CDCl₃) δ 1.45 (t, J=7.6 Hz, 3H), 3.03 (q, J=7.6 Hz, 2H), 4.78 (d, J=5.6 Hz, 2H), 6.18-6.20 (m, 1H), 7.32 (dd, J=1.2, 7.6 Hz, 1H), 7.46 (dd, J=7.6, 7.6 Hz, 1H), 7.50-7.55 (m, 3H), 7.57 (d, J=8.4 Hz, 2H), 7.65 (dd, J=7.6, 7.6 Hz, 1H), 7.77 (d, J=7.6 Hz, 1H), 9.56 (d, J=1.2 Hz, 1H).

7-Chloro-N-((2'-cyanobiphenyl-4-yl)methyl)-2-ethylimidazo[1,2-a]pyridine-3-carboxamide (126)

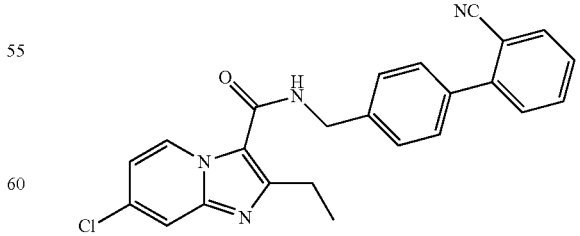

¹H NMR (400 MHz, CDCl₃) δ 1.44 (t, J=7.6 Hz, 3H), 3.02 (q, J=7.6 Hz, 2H), 4.77 (d, J=5.6 Hz, 2H), 6.18 (brs, 1H), 6.92 (dd, J=7.6, 2.0 Hz, 1H), 7.47-7.60 (m, 4H), 7.63-7.65 (m, 4H), 7.77 (d, J=7.6 Hz, 1H), 9.38 (d, J=7.6 Hz, 1H); LCMS (electrospray) m/z (M+H)+ 415.28

6-Chloro-N-((3'-cyanobiphenyl-4-yl)methyl)-2-ethylimidazo[1,2-a]pyridine-3-carboxamide (127)

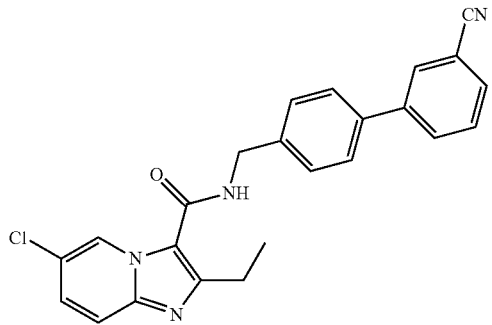 [SMILES: CCc1nc2ccc(Cl)cn2c1C(=O)NCc1ccc(-c2cccc(C#N)c2)cc1]

$^1$H NMR (400 MHz, CDCl$_3$) δ 1.44 (t, J=7.6 Hz, 3H), 3.02 (q, J=7.6 Hz, 2H), 4.77 (d, J=5.6 Hz, 2H), 6.19 (m, 1H), 7.32 (dd, J=2.0, 9.2 Hz, 1H), 7.50 (d, J=8.4 Hz, 2H), 7.55-7.59 (m, 3H), 7.64 (d, J=7.6 Hz, 1H), 7.81 (d, J=8.0 Hz, 1H), 7.86 (s, 1H), 9.56 (d, J=1.6 Hz, 1H).

7-Chloro-N-((3'-cyanobiphenyl-4-yl)methyl)-2-ethylimidazo[1,2-a]pyridine-3-carboxamide (128)

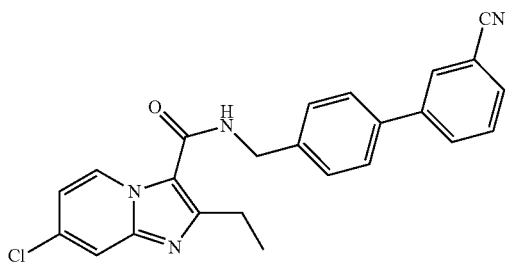 [SMILES: CCc1nc2cc(Cl)ccn2c1C(=O)NCc1ccc(-c2cccc(C#N)c2)cc1]

$^1$H NMR (400 MHz, CDCl$_3$) δ 1.42 (t, J=7.6 Hz, 3H), 3.01 (q, J=7.6 Hz, 2H), 4.76 (d, J=6.0 Hz, 2H), 6.17 (brs, 1H), 6.92 (dd, J=7.2, 2.0 Hz, 1H), 7.49 (d, J=8.4 Hz, 1H), 7.55-7.63 (m, 5H), 7.80 (d, J=8.0 Hz, 1H), 7.85 (d, J=1.6 Hz, 1H), 9.38 (d, J=7.2 Hz, 1H); LCMS (electrospray) m/z (M+H)$^+$ 415.28

6-Chloro-N-((4'-chloro-2'-(trifluoromethyl)biphenyl-4-yl)methyl)-2-ethylimidazo[1,2-a]pyridine-3-carboxamide (129)

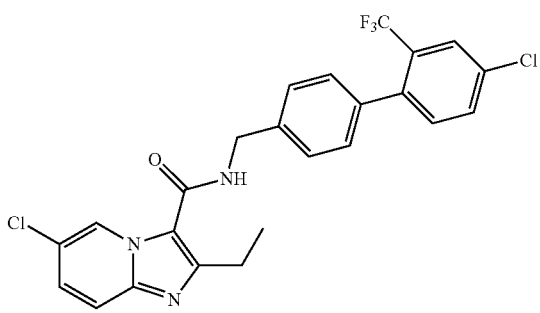 [SMILES: CCc1nc2ccc(Cl)cn2c1C(=O)NCc1ccc(-c2ccc(Cl)cc2C(F)(F)F)cc1]

$^1$H NMR (400 MHz, CDCl$_3$) δ 1.44 (t, J=7.6 Hz, 3H), 3.02 (q, J=7.6 Hz, 2H), 4.77 (d, J=5.6 Hz, 2H), 6.18 (m, 1H), 7.27 (d, J=7.6 Hz, 2H), 7.31 (d, J=7.6 Hz, 2H), 7.42 (d, J=8.0 Hz, 2H), 7.52-7.56 (m, 2H), 7.73 (d, J=2.0 Hz, 1H), 7.86 (s, 1H), 9.55 (d, J=1.2 Hz, 1H).

7-Chloro-N-((4'-chloro-2'-(trifluoromethyl)biphenyl-4-yl)methyl)-2-ethylimidazo[1,2-a]pyridine-3-carboxamide (130)

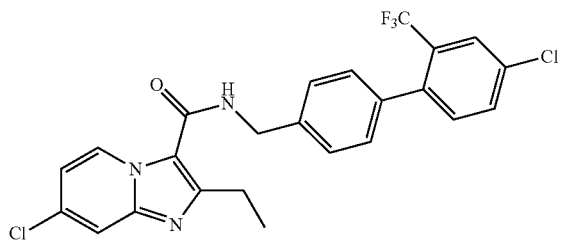 [SMILES: CCc1nc2cc(Cl)ccn2c1C(=O)NCc1ccc(-c2ccc(Cl)cc2C(F)(F)F)cc1]

$^1$H NMR (400 MHz, CDCl$_3$) δ 1.41 (t, J=7.6 Hz, 3H), 3.01 (q, J=7.6 Hz, 2H), 4.76 (d, J=6.0 Hz, 2H), 6.16 (brs, 1H), 6.92 (dd, J=7.2, 2.0 Hz, 1H), 7.28 (d, J=8.0 Hz, 1H), 7.30 (d, J=8.0 Hz, 2H), 7.41 (d, J=8.0 Hz, 2H), 7.53 (dd, J=8.0, 1.6 Hz, 1H), 7.60 (d, J=2.0 Hz, 1H), 7.73 (d, J=2.0 Hz, 1H), 9.38 (d, J=7.6 Hz, 1H); LCMS (electrospray) m/z (M+H)$^+$ 492.21

6-Chloro-N-((4'-cyano-2'-methylbiphenyl-4-yl)methyl)-2-ethylimidazo[1,2-a]pyridine-3-carboxamide (131)

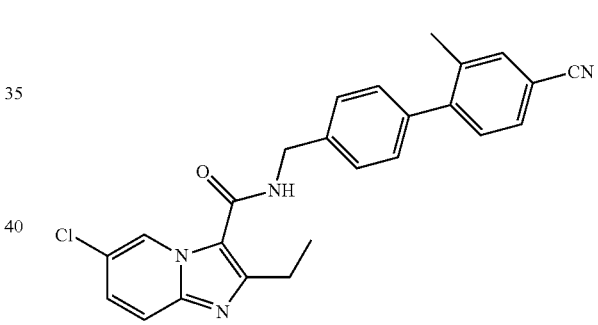

$^1$H NMR (400 MHz, CDCl$_3$) δ 1.44 (t, J=7.6 Hz, 3H), 2.30 (s, 3H), 3.03 (q, J=7.6 Hz, 2H), 4.77 (d, J=5.6 Hz, 2H), 6.21 (t, J=5.2 Hz, 1H), 7.30-7.33 (m, 4H), 7.31 (d, J=7.6 Hz, 2H), 7.46 (d, J=8.0 Hz, 2H), 7.52-7.56 (m, 2H), 7.52-7.57 (m, 3H), 9.56 (d, J=2.0 Hz, 1H).

7-Chloro-N-((4'-cyano-2'-methylbiphenyl-4-yl)methyl)-2-ethylimidazo[1,2-a]pyridine-3-carboxamide (132)

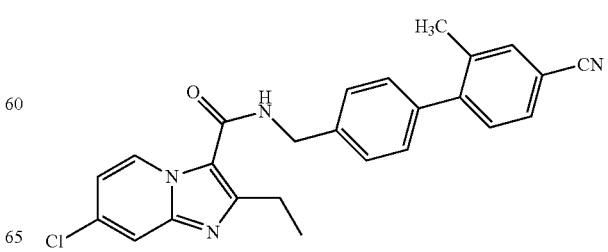

¹H NMR (400 MHz, CDCl₃) δ 1.43 (t, J=7.6 Hz, 3H), 2.29 (s, 3H), 3.02 (q, J=7.6 Hz, 2H), 4.77 (d, J=6.0 Hz, 2H), 6.18 (brs, 1H), 6.92 (dd, J=7.6, 2.0 Hz, 1H), 7.30 (d, J=8.0 Hz, 3H), 7.45 (d, J=8.0 Hz, 2H), 7.52 (d, J=7.6 Hz, 1H), 7.56 (s, 1H), 7.60 (d, J=2.4 Hz, 1H), 9.39 (d, J=7.2 Hz, 1H); LCMS (electrospray) m/z (M+H)⁺ 429.29

7-Chloro-N-((2'-chloro-4'-fluorobiphenyl-4-yl)methyl)-2-ethylimidazo[1,2-a]pyridine-3-carboxamide (133)

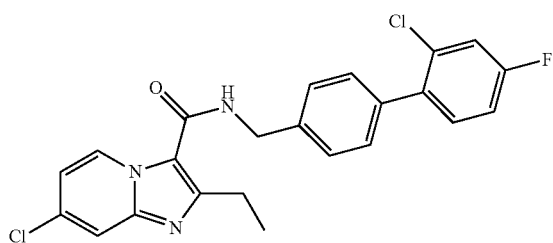 [SMILES: CCc1nc2cc(Cl)ccn2c1C(=O)NCc1ccc(-c2ccc(F)cc2Cl)cc1]

LCMS (electrospray) m/z (M+H)⁺ 442.15

7-Chloro-2-ethyl-N-(4-(pyridin-4-yl)benzyl)imidazo[1,2-a]pyridine-3-carboxamide (134)

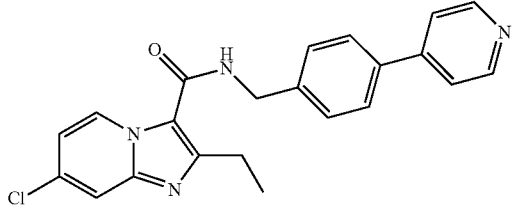 [SMILES: CCc1nc2cc(Cl)ccn2c1C(=O)NCc1ccc(-c2ccncc2)cc1]

¹H NMR (400 MHz, CDCl₃) δ 1.42 (t, J=7.6 Hz, 3H), 3.01 (q, J=7.6 Hz, 2H), 4.76 (d, J=5.6 Hz, 2H), 6.20 (brs, 1H), 6.91 (dd, J=7.6, 2.0 Hz, 1H), 7.26-7.51 (m, 4H), 7.61 (d, J=2.0 Hz, 1H), 7.65 (d, J=8.0 Hz, 2H), 8.65 (brs, 2H), 9.37 (d, J=7.6 Hz, 1H); LCMS (electrospray) m/z (M+H)⁺ 391.20

7-Chloro-2-ethyl-N-(4-(5-methoxypyridin-2-yl)benzyl)imidazo[1,2-a]pyridine-3-carboxamide (135)

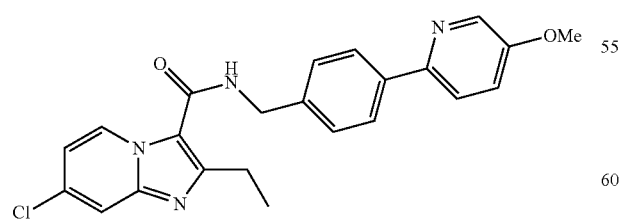

¹H NMR (400 MHz, CDCl₃) δ 1.40 (t, J=7.6 Hz, 3H), 2.97 (q, J=7.6 Hz, 2H), 3.91 (s, 3H), 4.74 (d, J=5.6 Hz, 2H), 6.11 (brs, 1H), 6.91 (dd, J=7.6, 2.0 Hz, 1H), 7.28 (d, J=8.8 Hz, 1H), 7.45 (d, J=8.4 Hz, 2H), 7.60 (d, J=2.0 Hz, 1H), 7.67 (d, J=8.8 Hz, 1H), 7.67 (d, J=8.8 Hz, 1H), 7.94 (d, J=8.4 Hz, 2H), 8.39 (d, J=2.8 Hz, 1H), 9.38 (d, J=7.2 Hz, 1H); LCMS (electrospray) m/z (M+H)⁺ 421.20

N-(4-(1H-Pyrrol-2-yl)benzyl)-7-chloro-2-ethylimidazo[1,2-a]pyridine-3-carboxamide (136)

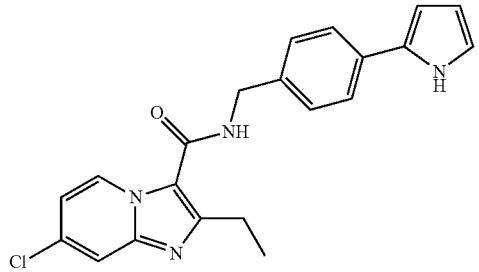

¹H NMR (400 MHz, CDCl₃) δ 1.40 (t, J=7.6 Hz, 3H), 2.69 (m, 4H), 2.97 (q, J=7.6 Hz, 2H), 4.68 (d, J=6.0 Hz, 2H), 6.10 (m, 1H), 6.29-6.32 (m, 1H), 6.53-6.54 (m, 1H), 6.87-6.88 (m, 1H), 6.91 (dd, J=2.0, 7.2 Hz, 1H), 7.37 (d, J=8.0 Hz, 2H), 7.48 (d, J=8.4 Hz, 2H), 7.59 (d, J=2.0 Hz, 1H), 8.51 (brs, 1H), 9.37 (d, J=7.6 Hz, 1H).

7-Chloro-2-ethyl-N-(4-(furan-2-yl)benzyl)imidazo[1,2-a]pyridine-3-carboxamide (137)

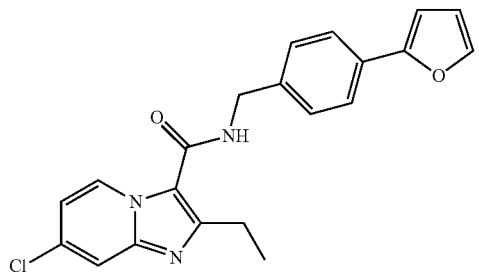 [SMILES: CCc1nc2cc(Cl)ccn2c1C(=O)NCc1ccc(-c2ccco2)cc1]

¹H NMR (400 MHz, CDCl₃) δ 1.40 (t, J=7.6 Hz, 3H), 2.98 (q, J=7.6 Hz, 2H), 4.70 (d, J=5.6 Hz, 2H), 6.47-6.48 (m, 1H), 6.53-6.54 (m, 1H), 6.66 (d, J=3.2, 1H), 6.91 (dd, J=2.0, 7.6 Hz, 1H), 7.40 (d, J=8.4 Hz, 2H), 7.47 (d, J=1.2 Hz, 1H), 7.60 (d, J=1.6 Hz, 1H), 7.68 (d, J=8.0 Hz, 2H), 9.37 (d, J=7.2 Hz, 1H).

N-(4-(1H-Pyrrol-1-yl)benzyl)-7-chloro-2-ethylimidazo[1,2-a]pyridine-3-carboxamide (138)

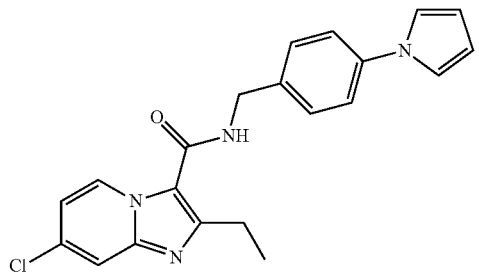 [SMILES: CCc1nc2cc(Cl)ccn2c1C(=O)NCc1ccc(-n2cccc2)cc1]

¹H NMR (400 MHz, CDCl₃) δ 1.41 (t, J=7.6 Hz, 3H), 2.99 (q, J=7.6 Hz, 2H), 4.71 (d, J=6.0 Hz, 2H), 6.12-6.14 (m, 1H), 6.34-6.36 (m, 2H), 6.92 (dd, J=2.0, 7.6 Hz, 1H), 7.08-7.09 (m, 2H), 7.40 (d, J=8.8 Hz, 2H), 7.44 (d, J=8.8 Hz, 21H), 7.60 (d, J=2.0 Hz, 1H), 7.68 (d, J=8.0 Hz, 2H), 9.38 (d, J=7.6 Hz, 1H).

6-Chloro-2-ethyl-N-(4-(4-(4-(trifluoromethoxy)phenoxy)piperidin-1-yl)benzyl)imidazo-[1,2-a]pyridine-3-carboxamide (139)

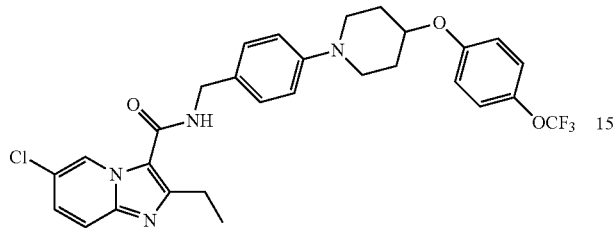

¹H NMR (400 MHz, CDCl₃) δ 1.38 (t, J=7.6 Hz, 3H), 1.90-1.98 (m, 2H), 2.07-2.13 (m, 2H), 2.96 (q, J=7.6 Hz, 2H), 3.10-3.16 (m, 2H), 3.48-3.54 (m, 2H), 4.42-4.48 (m, 1H), 3.22 (t, J=4.8 Hz, 4H), 4.61 (d, J=5.6 Hz, 2H), 6.00-6.20 (m, 1H), 6.91 (d, J=7.2 Hz, 2H), 6.96 (d, J=8.8 Hz, 2H), 7.14 (d, J=8.4 Hz, 1H), 7.26-7.31 (m, 3H), 7.54 (d, J=9.6 Hz, 1H), 9.53 (d, J=1.6 Hz, 1H).

7-Chloro-2-ethyl-N-(4-(4-(4-(trifluoromethoxy)phenoxy)piperidin-1-yl)benzyl)imidazo-[1,2-a]pyridine-3-carboxamide (140)

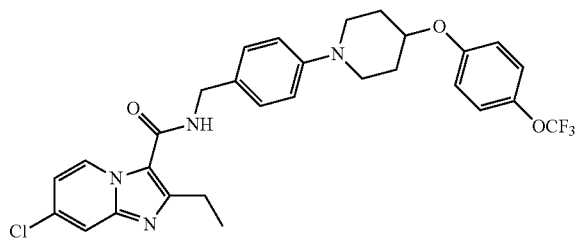 [SMILES: CCc1nc2cc(Cl)ccn2c1C(=O)NCc1ccc(N2CCC(Oc3ccc(OC(F)(F)F)cc3)CC2)cc1]

¹H NMR (400 MHz, CDCl₃) δ 1.38 (t, J=7.6 Hz, 3H), 1.89-1.98 (m, 2H), 2.07-2.13 (m, 2H), 2.95 (q, J=7.6 Hz, 2H), 3.09-3.16 (m, 2H), 3.47-3.53 (m, 2H), 4.42-4.48 (m, 1H), 3.22 (t, J=4.8 Hz, 4H), 4.60 (d, J=5.6 Hz, 2H), 5.99-6.01 (m, 1H), 6.88-6.93 (m, 3H), 6.96 (d, J=8.4 Hz, 2H), 7.14 (d, J=8.8 Hz, 2H), 7.26-7.29 (m, 2H), 7.59 (d, J=2.0 Hz, 1H), 9.36 (d, J=7.6 Hz, 1H).

N-((4'-Chlorobiphenyl-4-yl)methyl)-2-ethylimidazo[1,2-a]pyrazine-3-carboxamide (141)

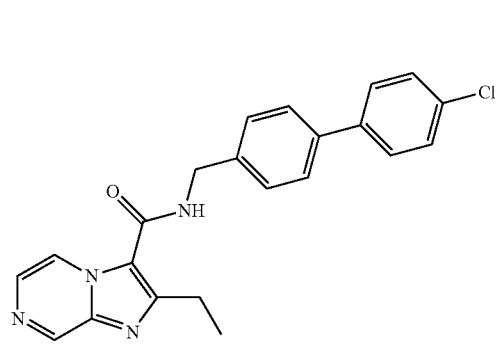 [SMILES: CCc1nc2cnccn2c1C(=O)NCc1ccc(-c2ccc(Cl)cc2)cc1]

¹H NMR (400 MHz, DMSO-d₆) δ 1.46 (t, J=7.6 Hz, 3H), 3.06 (q, J=7.6 Hz, 2H), 4.76 (d, J=5.6 Hz, 2H), 6.23-6.25 (m, 1H), 7.41 (d, J=8.4 Hz, 2H), 7.45 (d, J=8.0 Hz, 2H), 7.51 (d, J=8.4 Hz, 2H), 7.57 (d, J=8.0 Hz, 2H), 8.03 (d, J=4.4 Hz, 1H), 9.11 (s, 1H), 9.28 (d, J=4.8 Hz, 1H).

N-(7-Chloro-2-ethylimidazo[1,2-a]pyridin-3-yl)biphenyl-4-carboxamide (142)

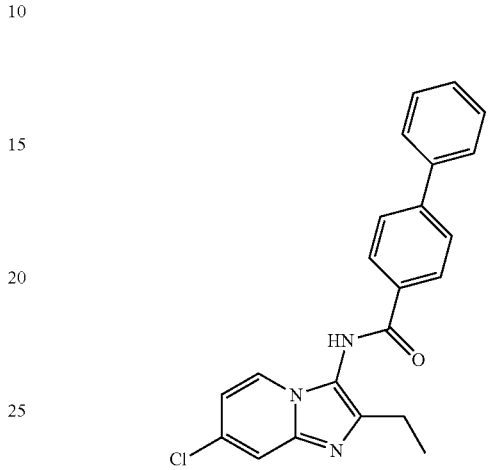

¹H NMR (400 MHz, CDCl₃) δ 1.33 (t, J=7.6 Hz, 3H), 2.75 (q, J=7.2 Hz, 2H), 6.78 (dd, J=1.2, 7.2, 1H), 6.89 (dd, J=1.2, 7.2 Hz, 1H), 7.44 (d, J=8.0 Hz, 2H), 7.48-7.53 (m, 3H), 7.58 (d, J=8.0 Hz, 1H), 7.65 (d, J=7.6 Hz, 2H), 7.72 (d, J=7.6 Hz, 1H), 7.76 (d, J=8.0 Hz, 2H), 8.02 (brs, 1H), 8.07 (d, J=8.0 Hz, 2H).

2-(Biphenyl-4-yl)-N-(7-chloro-2-ethylimidazo[1,2-a]pyridin-3-yl)acetamide (143)

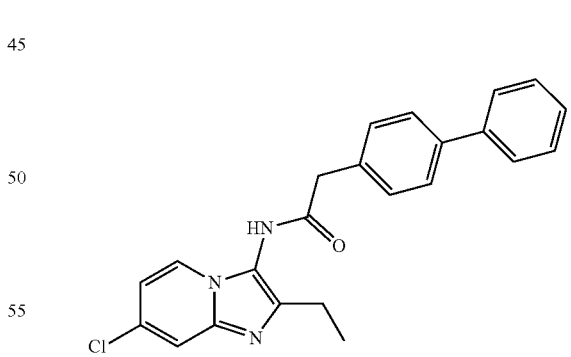

¹H NMR (400 MHz, DMSO-d₆) δ 1.25 (t, J=7.6 Hz, 3H), 2.62 (q, J=7.6 Hz, 2H), 3.89 (s, 2H), 6.74 (dd, J=2.0, 7.2 Hz, 1H), 7.00 (brs, 1H), 7.44-7.53 (m, 5H), 7.61 (d, J=7.2 Hz, 2H), 7.68 (d, J=8.4 Hz, 2H).

N-(4-(4-(4-(Butyramidomethyl)phenyl)piperazin-1-yl)benzyl)-7-chloro-2-ethylimidazo-[1,2-a]pyridine-3-carboxamide (144)

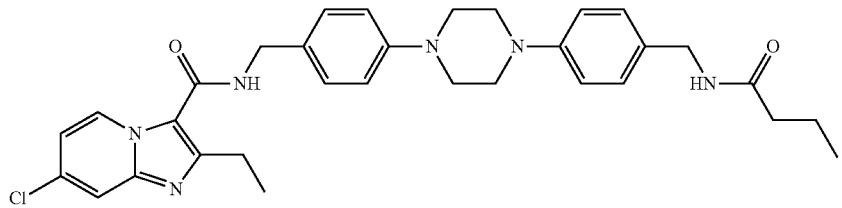 [SMILES: CCCC(=O)NCc1ccc(N2CCN(c3ccc(CNC(=O)c4c(CC)nc5cc(Cl)ccn45)cc3)CC2)cc1]

¹H NMR (400 MHz, CDCl₃) δ 0.93 (t, J=6.4 Hz, 3H), 1.37 (t, J=6.0 Hz, 3H), 1.65-1.71 (m, 2H), 2.15 (t, J=6.4 Hz, 2H), 2.94 (q, J=6.0 Hz, 2H), 3.33 (s, 8H), 4.36 (d, J=4.4 Hz, 2H), 4.61 (d, J=4.0 Hz, 2H), 5.59 (brs, 1H), 6.01 (brs, 1H), 6.88-6.98 (m, 5H), 7.19 (d, J=7.2 Hz, 2H), 7.29 (d, J=7.2 Hz, 2H), 7.58 (s, 1H), 9.35 (d, J=7.2 Hz, 1H); LCMS (electrospray) m/z (M+H)⁺ 573.

N-(4-tert-Butylbenzyl)-2-ethyl-7-(piperazin-1-yl)imidazo[1,2-a]pyridine-3-carboxamide (145)

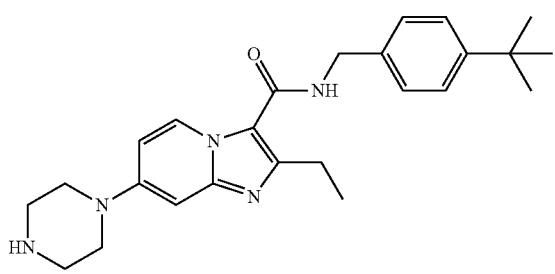 [SMILES: CCc1nc2cc(N3CCNCC3)ccn2c1C(=O)NCc1ccc(C(C)(C)C)cc1]

¹H NMR (400 MHz, DMSO) δ 1.20 (t, J=7.6 Hz, 3H), 1.24 (s, 9H), 2.78-2.80 (m, 4H), 2.86 (q, J=7.6 Hz, 2H), 3.13-3.15 (m, 4H), 4.42 (d, J=6.0 Hz, 2H), 6.66 (d, J=2.0 Hz, 1H), 6.86 (dd, J=8.0, 2.0 Hz, 1H), 7.24 (d, J=8.4 Hz, 2H), 7.32 (d, J=87.4 Hz, 2H), 7.99 (brt, J=6.0 Hz, 1H), 8.75 (d, J=8.0 Hz, 1H); LCMS (electrospray) m/z (M+H)⁺ 420; mp 186.1-186.9° C.

6-Chloro-N-(4-cyanobenzyl)-2-ethylimidazo[1,2-a]pyridine-3-carboxamide (146)

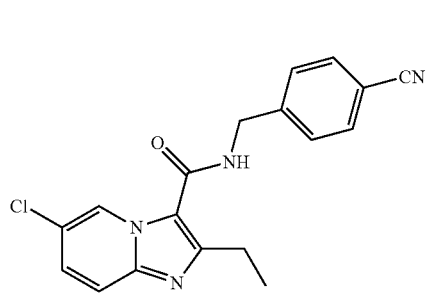 [SMILES: CCc1nc2ccc(Cl)cn2c1C(=O)NCc1ccc(C#N)cc1]

White solid; mp=223-224° C.; ¹H NMR (400 MHz, CDCl₃) δ 1.45 (t, J=7.6 Hz, 3H), 3.02 (q, J=7.2 Hz, 2H), 4.76 (d, J=6.0 Hz, 2H), 6.21-6.23 (m, 1H), 7.33 (dd, J=2.0, 9.6 Hz, 1H), 7.49 (d, J=8.0 Hz, 2H), 7.56 (d, J=9.2 Hz, 1H), 7.67 (d, J=8.0 Hz, 2H), 9.53 (d, J=2.0 Hz, 1H)); LCMS (electrospray) m/z (M+H)⁺ 339.16

6-Chloro-2-ethyl-N-(4-(trifluoromethyl)benzyl)imidazo[1,2-a]pyridine-3-carboxamide (147)

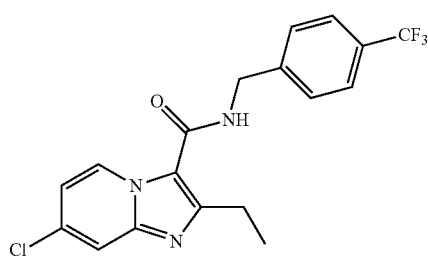 [SMILES: CCc1nc2cc(Cl)ccn2c1C(=O)NCc1ccc(C(F)(F)F)cc1]

White solid; mp=179-180° C.; ¹H NMR (400 MHz, CDCl₃) δ 1.44 (t, J=7.6 Hz, 3H), 3.01 (q, J=7.6 Hz, 2H), 4.77 (d, J=6.0 Hz, 2H), 6.19-6.21 (m, 1H), 7.32 (dd, J=2.0, 9.2 Hz, 1H), 7.50 (d, J=8.4 Hz, 2H), 7.56 (d, J=9.6 Hz, 1H), 7.64 (d, J=8.4 Hz, 2H), 9.54 (d, J=2.0 Hz, 1H)), LCMS (electrospray) m/z (M+H)⁺ 382.15

7-Chloro-2-ethyl-N-(4-(trifluoromethyl)benzyl)imidazo[1,2-a]pyridine-3-carboxamide (148)

White solid; mp=196.2-196.9° C.; ¹H NMR (400 MHz, CDCl₃) δ 1.43 (t, J=7.4 Hz, 3H), 3.00 (q, J=7.6 Hz, 2H), 4.76 (d, J=6.4 Hz, 2H), 6.92 (dd, J=2.0, 7.2 Hz, 1H), 7.49 (d, J=8.4

Hz, 2H), 7.60 (d, J=2.0 Hz, 1H), 7.63 (d, J=8.0 Hz, 2H), 9.36 (d, J=7.6 Hz, 1H); LCMS (electrospray) m/z (M+H)+ 382.15

2-Ethyl-6-nitro-N-(4-(trifluoromethoxy)benzyl)imidazo[1,2-a]pyridine-3-carboxamide (149)

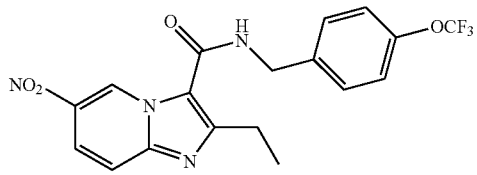 [SMILES: CCc1nc2ccc([N+](=O)[O-])cn2c1C(=O)NCc1ccc(OC(F)(F)F)cc1]

¹H NMR (400 MHz, CDCl₃) δ 1.37 (t, J=7.6 Hz, 3H), 3.49 (q, J=7.6 Hz, 2H), 4.66 (d, J=6.0 Hz, 2H), 7.19 (d, J=7.6 Hz, 2H), 7.41 (d, J=8.4 Hz, 2H), 7.60 (d, J=10.0 Hz, 1H), 7.82 (brs, 1H), 7.99 (dd, J=10.0, 2.0 Hz, 1H), 9.11 (d, J=1.6 Hz, 1H); LCMS (electrospray) m/z (M+H)+ 409.23

2-Ethyl-7-nitro-N-(4-(trifluoromethoxy)benzyl)imidazo[1,2-a]pyridine-3-carboxamide (150)

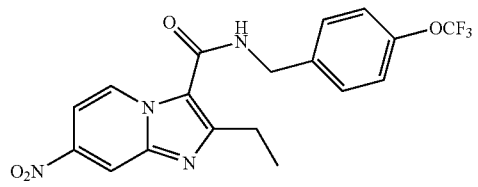

¹H NMR (400 MHz, DMSO-d₆) δ 1.29 (t, J=7.6 Hz, 3H), 3.05 (q, J=7.6 Hz, 2H), 4.57 (d, J=5.6 Hz, 2H), 7.35 (d, J=8.4 Hz, 2H), 7.50 (d, J=8.4 Hz, 2H), 7.76 (dd, J=7.6, 2.4 Hz, 1H), 8.56 (d, J=2.4 Hz, 1H), 8.79 (brs, 1H), 9.06 (d, J=8.0 Hz, 1H); LCMS (electrospray) m/z (M+H)+ 409.35

2-Ethyl-N-(4-(trifluoromethoxy)benzyl)-6-(trifluoromethyl)imidazo[1,2-a]pyridine-3-carboxamide (151)

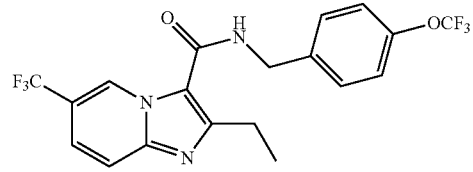 [SMILES: CCc1nc2ccc(C(F)(F)F)cn2c1C(=O)NCc1ccc(OC(F)(F)F)cc1]

¹H NMR (400 MHz, CDCl₃) δ 1.43 (t, J=7.6 Hz, 3H), 3.02 (q, J=7.6 Hz, 2H), 4.71 (d, J=5.6 Hz, 2H), 6.21 (brs, 1H), 7.22 (d, J=8.4 Hz, 2H), 7.41 (d, J=8.4 Hz, 2H), 7.48 (dd, J=9.2, 1.2 Hz, 1H), 7.69 (d, J=9.2 Hz, 1H), 9.84 (d, J=1.2 Hz, 1H); LCMS (electrospray) m/z (M+H)+ 432.42

6-Bromo-2-ethyl-N-(4-(trifluoromethoxy)benzyl)imidazo[1,2-a]pyridine-3-carboxamide (152)

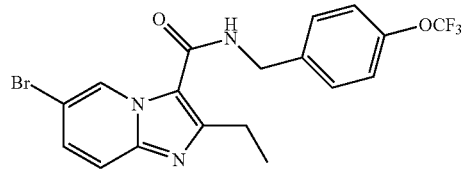 [SMILES: CCc1nc2ccc(Br)cn2c1C(=O)NCc1ccc(OC(F)(F)F)cc1]

¹H NMR (400 MHz, CDCl₃) δ 1.43 (t, J=7.6 Hz, 3H), 2.99 (q, J=7.6 Hz, 2H), 4.71 (d, J=5.6 Hz, 2H), 6.14 (brs, 1H), 7.23 (d, J=8.4 Hz, 2H), 7.39-7.42 (m, 3H), 7.51 (d, J=9.2 Hz, 1H), 9.63 (d, J=2.0 Hz, 1H); LCMS (electrospray) m/z (M+H)+ 444.12

6,7-Dichloro-2-ethyl-N-(4-(trifluoromethoxy)benzyl)imidazo[1,2-a]pyridine-3-carboxamide (153)

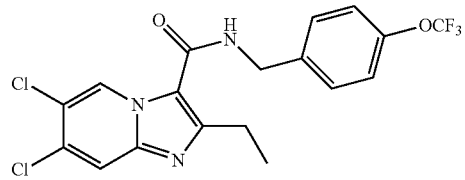 [SMILES: CCc1nc2cc(Cl)c(Cl)cn2c1C(=O)NCc1ccc(OC(F)(F)F)cc1]

¹H NMR (400 MHz, CDCl₃) δ 1.42 (t, J=7.6 Hz, 3H), 2.99 (q, J=7.6 Hz, 2H), 4.70 (d, J=6.0 Hz, 2H), 6.14 (brs, 1H), 7.23 (d, J=8.0 Hz, 2H), 7.41 (d, J=8.8 Hz, 2H), 7.72 (s, 1H), 9.66 (s, 1H); LCMS (electrospray) m/z (M+H)+ 432.15

6-Chloro-2-methyl-N-(4-(trifluoromethoxy)benzyl)imidazo[1,2-a]pyridine-3-carboxamide (154)

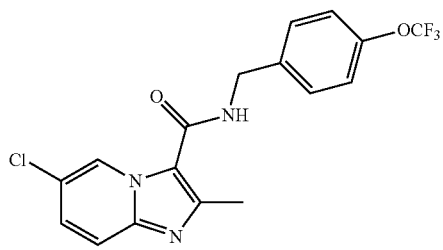 [SMILES: Cc1nc2ccc(Cl)cn2c1C(=O)NCc1ccc(OC(F)(F)F)cc1]

White solid; mp=192-193° C.; ¹H NMR (400 MHz, CDCl₃) δ 2.70 (s, 3H), 4.71 (d, J=6.0 Hz, 2H), 6.12-6.14 (m, 1H), 7.22 (d, J=8.4 Hz, 2H), 7.32 (dd, J=2.0, 9.6 Hz, 1H), 7.42

(d, J=8.8 Hz, 2H), 7.52 (d, J=9.6 Hz, 1H), 9.65 (d, J=2.0 Hz, 1H); LCMS (electrospray) m/z (M+H)+ 384.20

2-Ethyl-N-(4-(trifluoromethoxy)benzyl)imidazo[1,2-a]pyrazine-3-carboxamide (155)

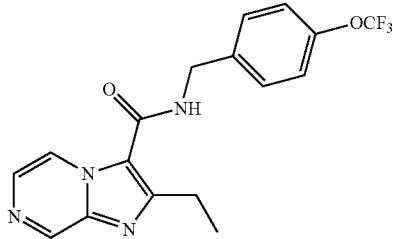 [SMILES: CCc1nc2cnccn2c1C(=O)NCc1ccc(OC(F)(F)F)cc1]

White solid; mp=176-177° C.; $^1$H NMR (400 MHz, CDCl$_3$) δ 1.48 (t, J=7.6 Hz, 3H), 3.04 (q, J=7.6 Hz, 2H), 4.71 (d, J=5.6 Hz, 2H), 6.26-6.27 (m, 1H), 7.22 (d, J=8.0 Hz, 2H), 7.41 (d, J=8.8 Hz, 2H), 8.02 (d, J=4.8 Hz, 1H), 9.10 (d, J=1.2 Hz, 1H), 9.25 (dd, J=1.2, 4.8 Hz, 1H)); LCMS (electrospray) m/z (M+H)+ 365.12

2-Ethyl-3-((4-(trifluoromethoxy)benzyl)carbamoyl)imidazo[1,2-a]pyrazine 7-oxide (156)

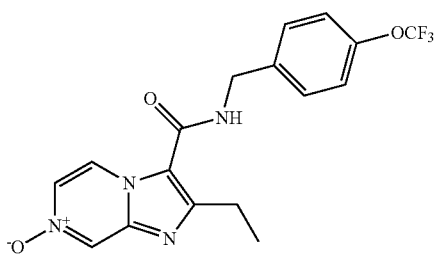

White solid; mp=215-216° C.; $^1$H NMR (400 MHz, CDCl$_3$) δ 1.43 (t, J=7.6 Hz, 3H), 2.99 (q, J=7.6 Hz, 2H), 4.70 (d, J=6.0 Hz, 2H), 6.19-6.20 (m, 1H), 7.23 (d, J=8.0 Hz, 2H), 7.40 (d, J=8.4 Hz, 2H), 7.69 (dd, J=1.6, 5.6 Hz, 1H). 8.57 (d, J=2.0 Hz, 1H), 9.29 (d, J=6.0 Hz, 1H)); LCMS (electrospray) m/z (M+H)+ 381.13

6-Chloro-2-ethyl-N-(4-methoxyphenethyl)imidazo[1,2-a]pyridine-3-carboxamide (157)

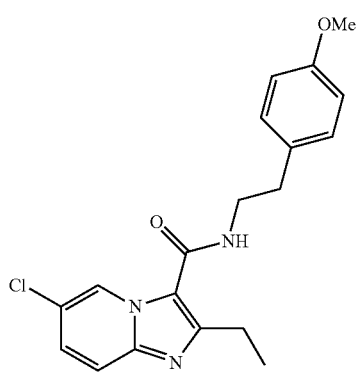 [SMILES: CCc1nc2ccc(Cl)cn2c1C(=O)NCCc1ccc(OC)cc1]

White solid; mp=129-130° C.; $^1$H NMR (400 MHz, CDCl$_3$) δ 1.25 (t, J=7.4 Hz, 3H), 2.72 (q, J=7.6 Hz, 2H), 2.92 (t, J=6.8 Hz, 2H), 3.77 (q, J=5.6 Hz, 2H), 3.80 (s, 3H), 5.73-5.74 (m, 1H), 6.89 (d, J=8.4 Hz, 2H), 7.18 (d, J=8.8 Hz, 2H), 7.28 (d, J=2.0 Hz, 1H), 7.51 (dd, J=0.8, 9.6 Hz, 1H), 9.49 (d, J=2.0 Hz, 1H)); LCMS (electrospray) m/z (M+H)+ 358.21

6-Chloro-N-(4-chlorophenethyl)-2-ethylimidazo[1,2-a]pyridine-3-carboxamide (158)

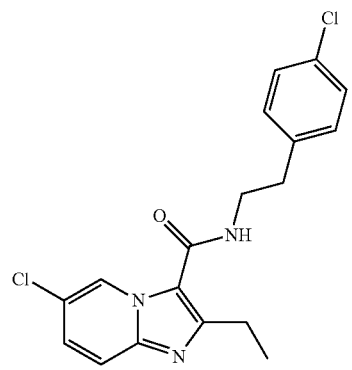 [SMILES: CCc1nc2ccc(Cl)cn2c1C(=O)NCCc1ccc(Cl)cc1]

White solid; mp=158-159° C.; $^1$H NMR (400 MHz, CDCl$_3$) δ 1.28 (t, J=7.4 Hz, 3H), 2.76 (q, J=7.6 Hz, 2H), 2.96 (t, J=6.6 Hz, 2H), 3.78 (q, J=6.0 Hz, 2H), 5.73-5.74 (m, 1H), 7.20 (d, J=8.4 Hz, 2H), 7.29 (d, J=2.0 Hz, 1H), 7.32 (d, J=8.4 Hz, 1H), 7.52 (dd, J=2.0, 9.6 Hz, 1H), 9.48 (d, J=1.6 Hz, 1H)); LCMS (electrospray) m/z (M+H)+ 362.16

N-((4'-(Butyramidomethyl)biphenyl-4-yl)methyl)-7-chloro-2-ethylimidazo[1,2-a]pyridine-3-carboxamide (159)

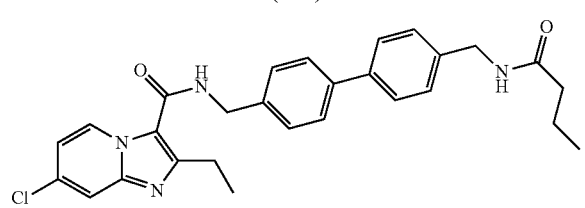

White solid; $^1$H NMR (400 MHz, CDCl$_3$); δ 0.95 (t, J=7.2 Hz, 3H), 1.39 (t, J=7.6 Hz, 3H), 1.64-1.75 (m, 2H), 2.19 (t, J=7.2 Hz, 2H), 2.97 (q, J=7.6 Hz, 2H), 4.48 (d, J=5.6 Hz, 2H), 4.73 (d, J=5.6 Hz, 2H), 5.71 (brs, 1H), 6.12 (brt, J=5.6 Hz, 1H), 6.90 (dd, J=2.0, 7.2 Hz, 1H), 7.34 (d, J=8.0 Hz, 2H), 7.43 (d, J=8.0 Hz, 2H), 7.51-7.60 (m, 5H), 9.37 (d, J=7.2 Hz, 1H); LCMS (electrospray) m/z (M+H)+ 489.

3-(((4'-Chloro-[1,1'-biphenyl]-4-yl)methyl)carbamoyl)-2-ethylimidazo[1,2-a]pyrazine 7-oxide (160)

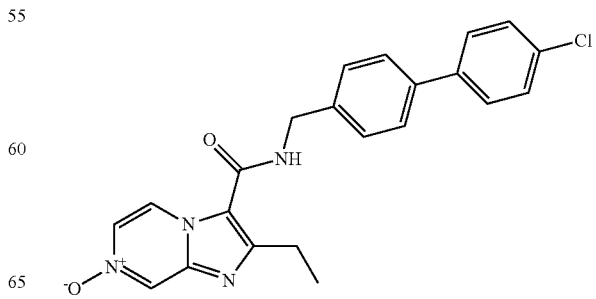

White solid; mp=238° C.; ¹H NMR (400 MHz, CDCl₃) δ 1.43 (t, J=7.6 Hz, 3H), 3.00 (q, J=7.6 Hz, 2H), 4.73 (d, J=6.0 Hz, 2H), 6.21 (t, J=4.8 Hz, 1H), 7.41 (d, J=8.8 Hz, 2H), 7.44 (d, J=8.0 Hz, 2H), 7.51 (d, J=8.4 Hz, 2H), 7.57 (d, J=8.4 Hz, 2H), 7.69 (dd, J=2.0, 6.4 Hz, 1H). 8.56-8.57 (m, 1H), 9.31 (d, J=6.0 Hz, 1H); LCMS (electrospray) m/z (M+H)⁺ 407.12

[1,1'-Biphenyl]-4-ylmethyl 6-chloro-2-ethylimidazo[1,2-a]pyridine-3-carboxylate (161)

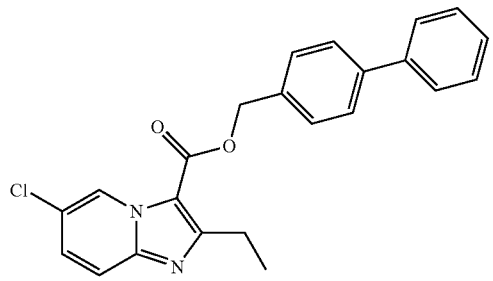 [SMILES: CCc1nc2ccc(Cl)cn2c1C(=O)OCc1ccc(-c2ccccc2)cc1]

White solid; mp=122.3-123.0° C.; ¹H NMR (400 MHz, CDCl₃) δ 1.34 (t, J=7.6 Hz, 3H), 3.13 (q, J=7.6 Hz, 2H), 5.48 (s, 2H), 7.34-7.38 (m, 2H), 7.45 (dd, J=7.2, 8.0 Hz, 2H), 7.54 (d, J=8.4 Hz, 2H), 7.57-7.65 (m, 5H), 9.45 (d, J=2.0 Hz, 1H); LCMS (electrospray) m/z (M+H)⁺ 390.20

6-Chloro-N-(4-(4-(4-chlorophenoxy)piperidin-1-yl)benzyl)-2-ethylimidazo[1,2-a]pyridine-3-carboxamide (162)

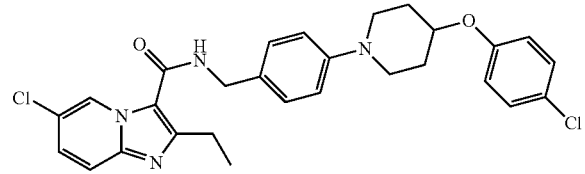 [SMILES: CCc1nc2ccc(Cl)cn2c1C(=O)NCc1ccc(N2CCC(Oc3ccc(Cl)cc3)CC2)cc1]

¹H NMR (400 MHz, CDCl₃) δ 1.39 (t, J=7.6 Hz, 3H), 1.94 (m, 2H), 2.06-2.10 (m, 2H), 2.96 (q, J=7.6 Hz, 2H), 3.09-3.14 (m, 2H), 3.15-3.52 (m, 2H), 4.43 (m, 1H), 4.61 (d, J=5.6 Hz, 2H), 6.01 (brs, 1H), 6.85 (d, J=9.2 Hz, 2H), 6.95 (d, J=8.8 Hz, 2H), 7.20-7.31 (m, 5H), 7.53 (d, J=10.4 Hz, 1H), 9.53 (d, J=1.2 Hz, 1H); LCMS (electrospray) m/z (M+H)⁺ 523.29

7-Chloro-N-(4-(4-(4-chlorophenoxy)piperidin-1-yl)benzyl)-2-ethylimidazo[1,2-a]pyridine-3-carboxamide (163)

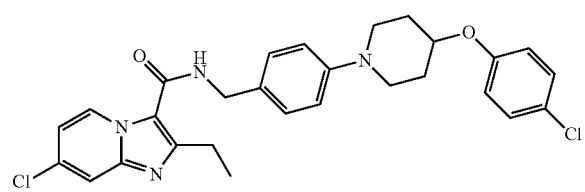 [SMILES: CCc1nc2cc(Cl)ccn2c1C(=O)NCc1ccc(N2CCC(Oc3ccc(Cl)cc3)CC2)cc1]

¹H NMR (400 MHz, CDCl₃) δ 1.21 (t, J=7.2 Hz, 3H), 1.91-1.96 (m, 2H), 2.06-2.11 (m, 2H), 2.96 (q, J=7.6 Hz, 2H), 2.97-3.15 (m, 2H), 3.47-3.52 (m, 2H), 4.43 (m, 1H), 4.60 (d, J=5.6 Hz, 2H), 6.00 (brs, 1H), 6.86 (d, J=8.8 Hz, 2H), 6.90 (dd, J=7.6, 2.4 Hz, 1H), 6.95 (d, J=8.8 Hz, 1H), 7.21-7.28 (m, 4H), 7.58 (d, J=1.6 Hz, 1H), 9.36 (d, J=7.6 Hz, 1H); LCMS (electrospray) m/z (M+H)⁺ 523.29

6-Chloro-2-ethyl-N-(4-(4-(4-(trifluoromethyl)phenoxy)piperidin-1-yl)benzyl) imidazo[1,2-a]pyridine-3-carboxamide (164)

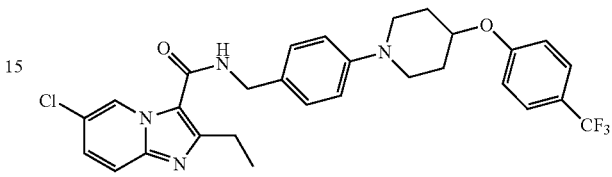

¹H NMR (400 MHz, CDCl₃) δ 1.40 (t, J=7.6 Hz, 3H), 1.94-1.99 (m, 2H), 2.10-2.15 (m, 2H), 2.96 (q, J=7.6 Hz, 2H), 3.12-3.18 (m, 2H), 3.47-3.53 (m, 2H), 4.53-4.57 (m, 1H), 4.61 (d, J=5.2 Hz, 2H), 6.02 (brs, 1H), 6.96 (d, J=8.4 Hz, 2H), 6.98 (d, J=8.4 Hz, 2H), 7.27-7.31 (m, 3H), 7.51-7.55 (m, 3H), 9.53 (d, J=2.0 Hz, 1H); LCMS (electrospray) m/z (M+H)⁺ 557.37

7-Chloro-2-ethyl-N-(4-(4-(4-(trifluoromethyl)phenoxy)piperidin-1-yl)benzyl) imidazo[1,2-a]pyridine-3-carboxamide (165)

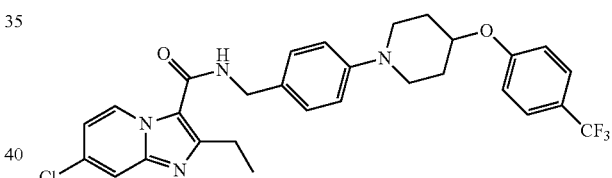

¹H NMR (400 MHz, CDCl₃) δ 1.39 (t, J=7.6 Hz, 3H), 1.94-1.98 (m, 2H), 2.09-2.11 (m, 2H), 2.95 (q, J=7.6 Hz, 2H), 3.12-3.18 (m, 2H), 3.47-3.53 (m, 2H), 4.55 (m, 1H), 4.60 (d, J=5.6 Hz, 2H), 6.00 (brs, 1H), 6.90 (dd, J=7.6, 2.0 Hz, 1H), 6.96 (d, J=8.8 Hz, 2H), 6.98 (d, J=8.4 Hz, 2H), 7.28 (d, J=8.8 Hz, 2H), 7.54 (d, J=8.4 Hz, 2H), 7.58 (d, J=2.0 Hz, 1H), 9.36 (d, J=8.0 Hz, 1H); LCMS (electrospray) m/z (M+H)⁺ 557.37

6-Chloro-2-ethyl-N-(4-(4-(4-fluorophenoxy)piperidin-1-yl)benzyl)imidazo[1,2-a]pyridine-3-carboxamide (166)

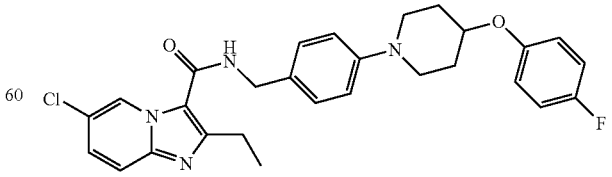

¹H NMR (400 MHz, CDCl₃) δ 1.39 (t, J=7.6 Hz, 3H), 1.91-1.94 (m, 2H), 2.06-2.11 (m, 2H), 2.96 (q, J=7.6 Hz, 2H), 3.08-3.14 (m, 2H), 3.47-3.54 (m, 2H), 4.37-4.39 (m, 1H), 4.61 (d, J=5.6 Hz, 2H), 6.01 (brs, 1H), 6.86-6.89 (m, 2H), 6.95-7.00 (m, 4H), 7.26-7.30 (m, 3H), 7.53 (d, J=8.8 Hz, 1H), 9.53 (d, J=1.6 Hz, 1H); LCMS (electrospray) m/z (M+H)+ 507.31

7-Chloro-2-ethyl-N-(4-(4-(4-fluorophenoxy)piperidin-1-yl)benzyl)imidazo[1,2-a]pyridine-3-carboxamide (167)

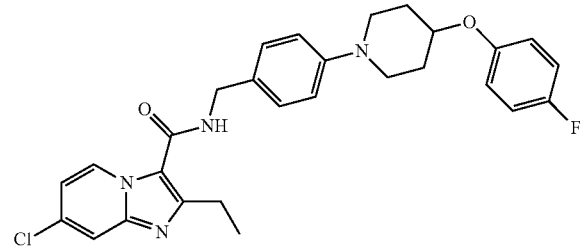 [SMILES: CCc1nc2cc(Cl)ccn2c1C(=O)NCc1ccc(N2CCC(Oc3ccc(F)cc3)CC2)cc1]

White solid; mp=138-139° C.; ¹H NMR (400 MHz, CDCl₃) δ 1.38 (t, J=7.6 Hz, 3H), 1.88-1.96 (m, 2H), 2.05-2.12 (m, 2H), 2.95 (q, J=7.6 Hz, 2H), 3.08-3.14 (m, 2H), 3.48-3.54 (m, 2H), 4.35-4.41 (m, 2H), 4.60 (d, J=5.6 Hz, 2H), 5.99-6.01 (m, 1H), 6.86-6.91 (m, 3H), 6.91-7.00 (m, 4H), 7.27 (d, J=8.4 Hz, 2H), 7.59 (d, J=2.0 Hz, 1H), 9.36 (d, J=7.6 Hz, 1H)); LCMS (electrospray) m/z (M+H)+ 507.31

2-Ethyl-N-(4-(4-(4-(trifluoromethoxy)phenoxy)piperidin-1-yl)benzyl)-6-(trifluoromethyl)imidazo[1,2-a]pyridine-3-carboxamide (168)

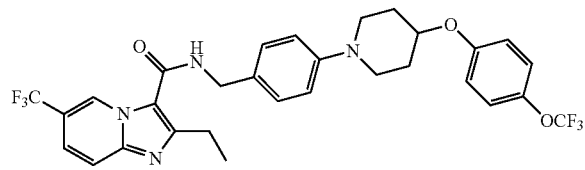 [SMILES: CCc1nc2ccc(C(F)(F)F)cn2c1C(=O)NCc1ccc(N2CCC(Oc3ccc(OC(F)(F)F)cc3)CC2)cc1]

¹H NMR (400 MHz, CDCl₃) δ 1.41 (t, J=7.6 Hz, 3H), 1.90-1.98 (m, 2H), 2.08-2.13 (m, 2H), 2.99 (q, J=7.6 Hz, 2H), 3.10-3.15 (m, 2H), 3.47-3.54 (m, 2H), 4.43-4.46 (m, 1H), 4.62 (d, J=5.6 Hz, 2H), 6.05 (brs, 1H), 6.91 (d, J=8.4 Hz, 2H), 6.96 (d, J=8.4 Hz, 2H), 7.14 (d, J=8.4 Hz, 2H), 7.28 (d, J=8.4 Hz, 2H), 7.46 (dd, J=9.2, 2.0 Hz, 1H), 7.69 (d, J=9.2 Hz, 1H), 9.85 (d, J=2.0 Hz, 1H); LCMS (electrospray) m/z (M+H)+ 607.56

7-Chloro-N-(4-(4-(cyclopentyloxymethyl)piperidin-1-yl)benzyl)-2-ethylimidazo[1,2-a]pyridine-3-carboxamide (169)

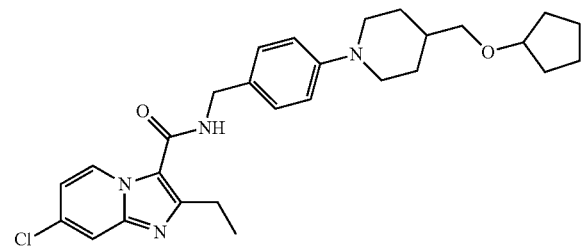 [SMILES: CCc1nc2cc(Cl)ccn2c1C(=O)NCc1ccc(N2CCC(COC3CCCC3)CC2)cc1]

White solid; ¹H NMR (400 MHz, CDCl₃); δ 1.23-1.38 (m, 2H), 1.31 (t, J=7.6 Hz, 3H), 1.47-1.52 (m, 2H), 1.56-1.70 (m, 7H), 1.80-1.83 (m, 2H), 2.64-2.70 (m, 2H), 2.87 (q, J=7.6 Hz, 2H), 3.21 (d, J=6.8 Hz, 2H), 3.63-3.66 (m, 2H), 3.81-3.86 (m, 1H), 4.53 (d, J=5.2 Hz, 2H), 6.07 (brt, J=5.2 Hz, 1H), 6.82 (dd, J=1.6, 7.2 Hz, 1H), 6.88 (d, J=8.4 Hz, 2H), 7.19 (d, J=8.4 Hz, 2H), 7.52 (d, J=1.6 Hz, 1H), 9.26 (d, J=7.2 Hz, 1H); ¹³C NMR (100 MHz, CDCl₃) δ 113.3, 23.4, 23.6, 29.3, 32.3, 36.4, 43.3, 49.6, 73.7, 81.5, 114.5, 115.1, 115.6, 116.7, 128.1, 128.5, 128.7, 128.8, 133.4, 146.0, 151.5, 161.1.

2-Ethyl-7-nitro-N-(4-(4-(4-(trifluoromethoxy)phenoxy)piperidin-1-yl)benzyl) imidazo[1,2-a]pyridine-3-carboxamide (170)

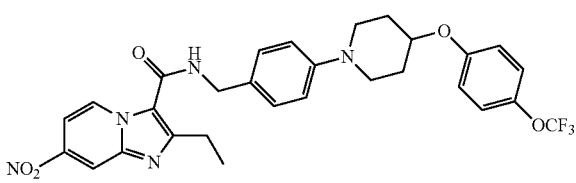 [SMILES: CCc1nc2cc([N+](=O)[O-])ccn2c1C(=O)NCc1ccc(N2CCC(Oc3ccc(OC(F)(F)F)cc3)CC2)cc1]

¹H NMR (400 MHz, CDCl₃) δ 1.43 (t, J=7.6 Hz, 3H), 1.95 (m, 2H), 2.10 (m, 2H), 3.01 (q, J=7.6 Hz, 2H), 3.11-3.16 (m, 2H), 3.49-3.53 (m, 2H), 4.45 (m, 1H), 4.63 (d, J=5.2 Hz, 2H), 6.11 (brs, 1H), 6.91 (d, J=9.2 Hz, 2H), 6.96 (d, J=8.8 Hz, 2H), 7.14 (d, J=8.8 Hz, 2H), 7.28 (d, J=8.8 Hz, 2H), 7.72 (d, J=7.6 Hz, 1H), 8.53 (s, 1H), 9.54 (d, J=7.6 Hz, 1H); LCMS (electrospray) m/z (M+H)+ 584.58

6-Chloro-2-ethyl-N-(4-(4-(4-fluorobenzyl)piperazin-1-yl)benzyl)imidazo[1,2-a]pyridine-3-carboxamide (171)

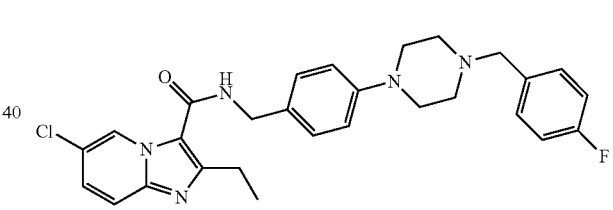

¹H NMR (400 MHz, CDCl₃) δ 1.38 (t, J=7.6 Hz, 3H), 2.59 (m, 4H), 2.95 (q, J=7.6 Hz, 2H), 3.20 (m, 4H), 3.52 (s, 2H), 4.60 (d, J=5.6 Hz, 2H), 6.00 (brs, 1H), 6.91 (d, J=8.4 Hz, 2H), 7.01 (t, J=8.4 Hz, 2H), 7.26-7.32 (m, 5H), 7.53 (d, J=9.6 Hz, 1H), 9.52 (d, J=1.2 Hz, 1H); LCMS (electrospray) m/z (M+H)+ 506.29

7-Chloro-2-ethyl-N-(4-(4-(4-fluorobenzyl)piperazin-1-yl)benzyl)imidazo[1,2-a]pyridine-3-carboxamide (172)

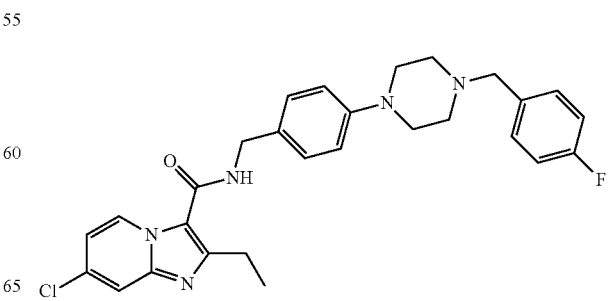

White solid; mp=141-142° C.; ¹H NMR (400 MHz, CDCl₃) δ 1.37 (t, J=7.8 Hz, 3H), 2.59 (t, J=4.8 Hz, 4H), 2.94 (q, J=7.2 Hz, 2H), 3.20 (t, J=5.0 Hz, 4H), 3.53 (s, 2H), 4.59 (d, J=5.2 Hz, 2H), 5.98-6.00 (m, 1H), 6.88-6.92 (m, 3H), 7.01 (dd, J=8.8, 8.8 Hz, 2H), 7.25-7.27 (m, 4H), 7.31 (dd, J=5.6, 8.0 Hz, 2H), 7.58 (d, J=2.0 Hz, 1H), 9.36 (d, J=7.6 Hz, 1H)); LCMS (electrospray) m/z (M+H)⁺ 506.36

6-Chloro-2-ethyl-N-(4-(4-(4-(trifluoromethoxy)benzyl)piperazin-1-yl)benzyl)imidazo[1,2-a]pyridine-3-carboxamide (173)

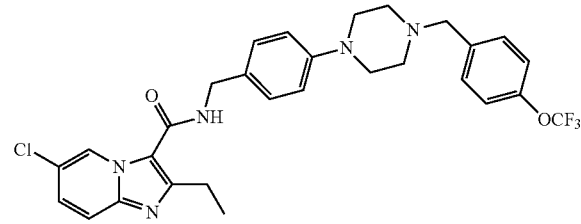 [SMILES: CCc1nc2ccc(Cl)cn2c1C(=O)NCc1ccc(N2CCN(Cc3ccc(OC(F)(F)F)cc3)CC2)cc1]

White solid; mp=138.1-138.7° C.; ¹H NMR (400 MHz, CDCl₃) δ 1.39 (t, J=7.6 Hz, 3H), 2.60 (t, J=5.0 Hz, 4H), 2.95 (q, J=7.6 Hz, 2H), 3.21 (t, J=5.0 Hz, 4H), 3.56 (s, 2H), 4.60 (d, J=5.6 Hz, 2H), 6.00-6.02 (m, 1H), 6.92 (d, J=8.8 Hz, 2H), 7.18 (d, J=8.0 Hz, 2H), 7.26-7.30 (m, 3H), 7.38 (d, J=8.4 Hz, 2H), 7.53 (d, J=9.2 Hz, 1H), 9.53 (d, J=2.0 Hz, 1H); LCMS (electrospray) m/z (M+H)⁺ 572.40

7-Chloro-2-ethyl-N-(4-(4-(4-(trifluoromethoxy)benzyl)piperazin-1-yl)benzyl)imidazo[1,2-a]pyridine-3-carboxamide (174)

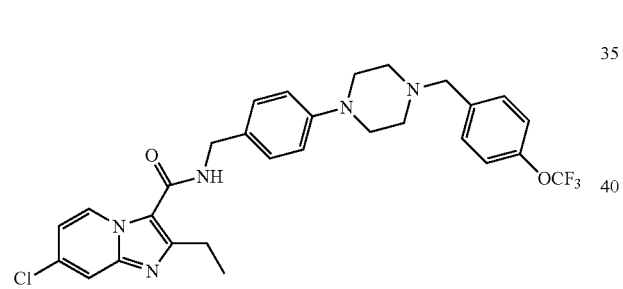

White solid; mp=137.1-137.6° C.; ¹H NMR (400 MHz, CDCl₃) δ 1.37 (t, J=7.6 Hz, 3H), 2.60 (t, J=4.8 Hz, 4H), 2.94 (q, J=7.6 Hz, 2H), 3.21 (t, J=4.8 Hz, 4H), 3.56 (s, 2H), 4.60 (d, J=5.6 Hz, 2H), 5.99-6.00 (m, 1H), 6.88-6.93 (m, 3H), 7.18 (d, J=8.0 Hz, 2H), 7.26 (d, J=8.0 Hz, 2H), 7.38 (d, J=8.4 Hz, 2H), 7.58 (d, J=1.6 Hz, 1H), 9.36 (d, J=7.6 Hz, 1H); LCMS (electrospray) m/z (M+H)⁺ 572.40

6,7-Dichloro-2-ethyl-N-(4-(4-(4-fluorobenzyl)piperazin-1-yl)benzyl)imidazo[1,2-a]pyridine-3-carboxamide (175)

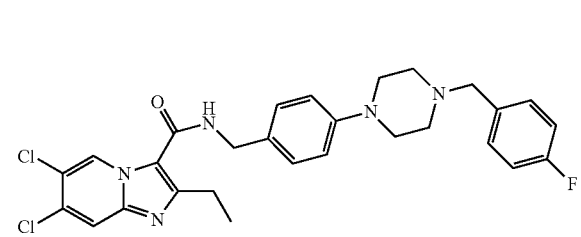 [SMILES: CCc1nc2cc(Cl)c(Cl)cn2c1C(=O)NCc1ccc(N2CCN(Cc3ccc(F)cc3)CC2)cc1]

¹H NMR (400 MHz, DMSO-d₆) δ 1.24 (t, J=7.6 Hz, 3H), 2.50 (m, 4H), 2.95 (q, J=7.6 Hz, 2H), 3.08 (m, 4H), 3.48 (s, 2H), 4.41 (d, J=6.0 Hz, 2H), 6.89 (d, J=8.8 Hz, 2H), 7.14 (dd, J=9.2 Hz, 2H), 7.20 (d, J=8.4 Hz, 2H), 7.33-7.36 (m, 2H), 8.06 (s, 1H), 8.44 (t, 1H), 9.20 (s, 1H); LCMS (electrospray) m/z (M+H)⁺ 540.36

7-Chloro-2-ethyl-N-(4-(4-(4-fluorophenyl)piperazin-1-yl)benzyl)imidazo[1,2-a]pyridine-3-carboxamide (176)

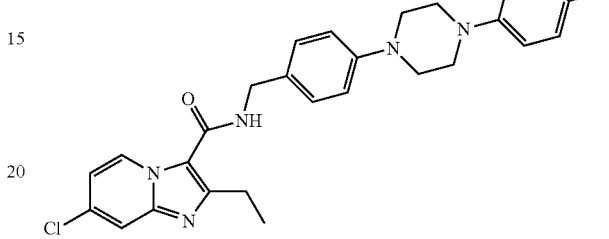

White solid; mp=212-213° C. ¹H NMR (400 MHz, CDCl₃) δ 1.39 (t, J=7.6 Hz, 3H), 2.95 (q, J=7.6 Hz, 2H), 3.26 (t, J=4.8 Hz, 4H), 3.35 (t, J=4.8 Hz, 4H), 4.62 (d, J=5.6 Hz, 2H), −6.01-6.03 (m, 1H), 6.89-7.02 (m, 7H), 7.30 (d, J=8.4 Hz, 2H), 7.59 (d, J=2.0 Hz, 1H), 9.37 (d, J=7.2 Hz, 1H)); LCMS (electrospray) m/z (M+H)⁺ 492.28

7-Chloro-2-ethyl-N-(4-(4-(4-fluorophenyl)piperazin-1-yl)benzyl)imidazo[1,2-a]pyridine-3-carboxamide trihydrochloride (177)

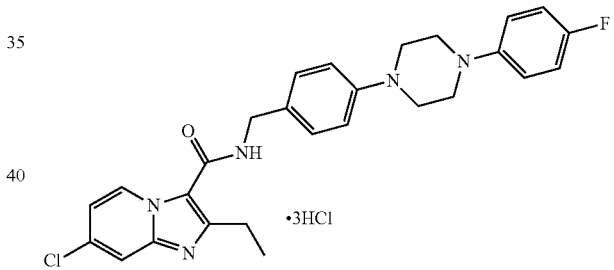

White solid; mp=204.4-206.9° C.; ¹H NMR (400 MHz, DMSO-d₆) δ 1.36 (t, J=7.6 Hz, 3H), 3.14 (q, J=7.6 Hz, 2H), 3.54-3.70 (m, 8H), 4.56 (d, J=6.0 Hz, 2H), 7.26 (dd, J=8.4, 8.8 Hz, 2H), 7.36-7.50 (m, 6H), 7.63 (dd, J=2.4, 7.6 Hz, 1H), 8.15 (d, J=1.6 Hz, 1H), 9.13 (d, J=7.2 Hz, 1H), 9.26 (t, J=5.6 Hz, 1H).

6-Chloro-2-ethyl-N-(4-(4-(4-(trifluoromethoxy)phenyl)piperazin-1-yl)benzyl)imidazo[1,2-a]pyridine-3-carboxamide (178)

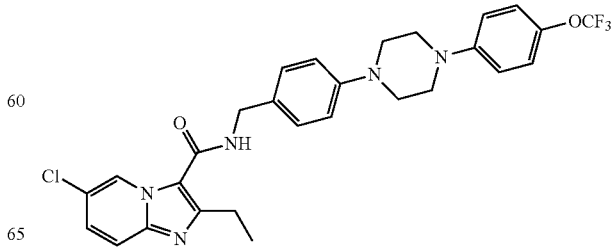

White solid; mp=206.5-207.0° C.; $^1$H NMR (400 MHz, CDCl$_3$) δ 1.40 (t, J=7.6 Hz, 3H), 2.96 (q, J=7.6 Hz, 2H), 3.30-3.40 (m, 8H), 4.63 (d, J=5.2 Hz, 2H), 6.03-6.04 (m, 1H), 6.95 (d, J=9.2 Hz, 2H), 6.98 (d, J=8.4 Hz, 2H), 7.14 (d, J=8.0 Hz, 2H), 7.27-7.32 (m, 3H), 7.54 (d, J=9.6 Hz, 1H), 9.53-9.34 (m, 1H); LCMS (electrospray) m/z (M+H)$^+$ 558.32

7-Chloro-2-ethyl-N-(4-(4-(4-(trifluoromethoxy)phenyl)piperazin-1-yl)benzyl)imidazo[1,2-a]pyridine-3-carboxamide (179)

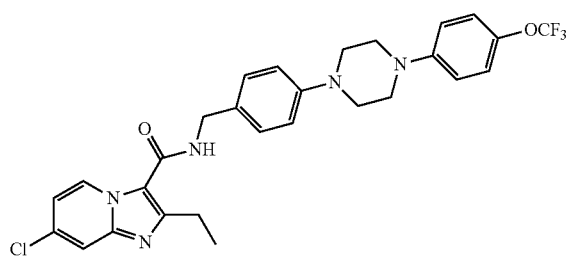 [SMILES: CCc1nc2cc(Cl)ccn2c1C(=O)NCc1ccc(N2CCN(c3ccc(OC(F)(F)F)cc3)CC2)cc1]

White solid; mp=216.3-217.0° C.; $^1$H NMR (400 MHz, CDCl$_3$) δ 1.39 (t, J=7.6 Hz, 3H), 2.95 (q, J=7.6 Hz, 2H), 3.30-3.40 (m, 8H), 4.62 (d, J=5.6 Hz, 2H), 6.01-6.02 (m, 1H), 6.90 (dd, J=2.0, 7.2 Hz, 1H), 6.94 (d, J=9.2 Hz, 2H), 6.98 (d, J=8.8 Hz, 2H), 7.14 (d, J=8.8 Hz, 2H), 7.31 (d, J=8.8 Hz, 2H), 7.59 (d, J=1.6 Hz, 1H), 9.37 (d, J=7.6 Hz, 1H); LCMS (electrospray) m/z (M+H)$^+$ 558.32

6,7-Dichloro-2-ethyl-N-(4-(4-(4-fluorophenyl)piperazin-1-yl)benzyl)imidazo[1,2-a]pyridine-3-carboxamide (180)

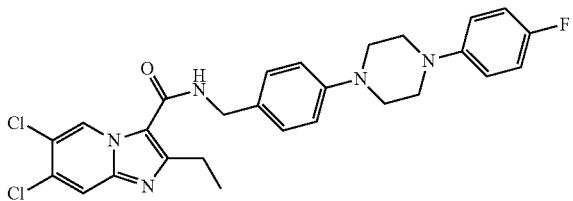 [SMILES: CCc1nc2cc(Cl)c(Cl)cn2c1C(=O)NCc1ccc(N2CCN(c3ccc(F)cc3)CC2)cc1]

$^1$H NMR (400 MHz, CDCl$_3$) δ 1.39 (t, J=7.6 Hz, 3H), 2.95 (q, J=7.6 Hz, 2H), 3.24-3.27 (m, 4H), 3.34-3.36 (m, 4H), 4.62 (d, J=5.6 Hz, 2H), 6.03 (brs, 1H), 6.91-7.02 (m, 6H), 7.30 (d, J=8.8 Hz, 2H), 7.71 (s, 1H), 9.67 (s, 1H); LCMS (electrospray) m/z (M+H)$^+$ 526.35

2-Ethyl-N-(4-(4-(4-(trifluoromethoxy)phenyl)piperazin-1-yl)benzyl)imidazo[1,2-a]pyridine-3-carboxamide (181)

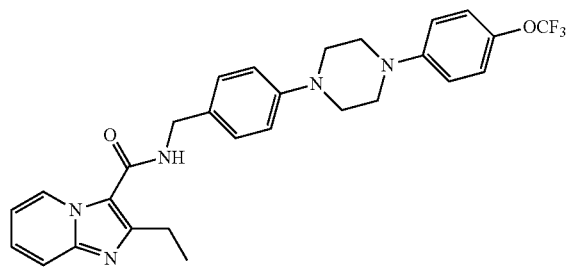 [SMILES: CCc1nc2ccccn2c1C(=O)NCc1ccc(N2CCN(c3ccc(OC(F)(F)F)cc3)CC2)cc1]

White solid; mp=178-179° C.; $^1$H NMR (400 MHz, CDCl$_3$) δ 1.40 (t, J=7.6 Hz, 3H), 2.97 (q, J=7.2 Hz, 2H), 3.31-3.38 (m, 8H), 4.63 (d, J=5.6 Hz, 2H), 6.05 (t, J=5.0 Hz, 1H), 6.89-6.99 (m, 5H), 7.14 (d, J=8.8 Hz, 2H), 7.29-7.32 (m, 3H), 7.60 (d, J=9.2 Hz, 1H), 9.40 (d, J=6.8 Hz, 1H); LCMS (electrospray) m/z (M+H)$^+$ 524.45

6-Chloro-2-ethyl-N-(4-(4-(4-fluorophenyl)piperazin-1-yl)benzyl)-N-methylimidazo[1,2-a]pyridine-3-carboxamide (182)

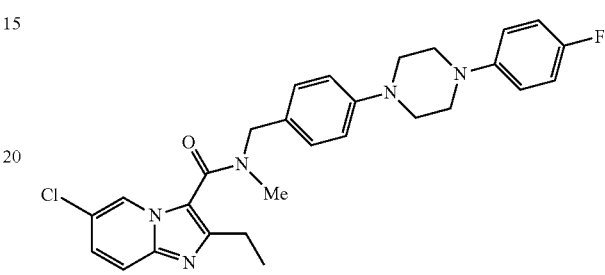

White solid; mp=148-149° C.; $^1$H NMR (400 MHz, CDCl$_3$) δ 1.37 (t, J=7.4 Hz, 3H), 2.78 (q, J=7.6 Hz, 2H), 2.99 (s, 3H), 3.24-3.27 (m, 4H), 3.33-3.36 (m, 4H), 4.66 (s, 2H), 6.92-7.02 (m, 6H), 7.12-7.20 (m, 2H), 7.21 (dd, J=2.0, 9.6 Hz, 1H), 7.52 (d, J=9.6 Hz, 1H), 8.46 (d, J=1.6 Hz, 1H); LCMS (electrospray) m/z (M+H)$^+$ 506.36

7-Chloro-N-(4-(4-((difluoromethoxy)methyl)piperidin-1-yl)benzyl)-2-ethylimidazo[1,2-a]pyridine-3-carboxamide (183)

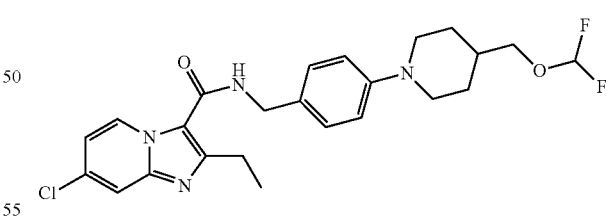

White solid; $^1$H NMR (400 MHz, CDCl$_3$) δ 1.37 (t, J=7.6 Hz, 3H), 1.41-1.48 (m, 2H), 1.70-1.86 (m, 3H), 2.72 (t, J=12.4 Hz, 2H), 2.93 (q, J=7.6 Hz, 2H), 3.69-3.73 (m, 4H), 4.58 (d, J=5.6 Hz, 2H), 6.00 (brs, 1H), 6.20 (t, J=75.2 Hz, due to F2), 6.88 (dd, J=1.6 Hz, 7.6 Hz, 1H), 6.92 (d, J=8.4 Hz, 2H), 7.25 (d, J=8.4 Hz, 2H), 7.56 (d, J=1.6 Hz, 1H), 9.34 (d, J=7.6 Hz, 1H); LCMS (electrospray) m/z (M+H)$^+$ 477.

7-Chloro-2-ethyl-N-((4'-(hexanamidomethyl)biphenyl-4-yl)methyl)imidazo[1,2-a]pyridine-3-carboxamide (184)

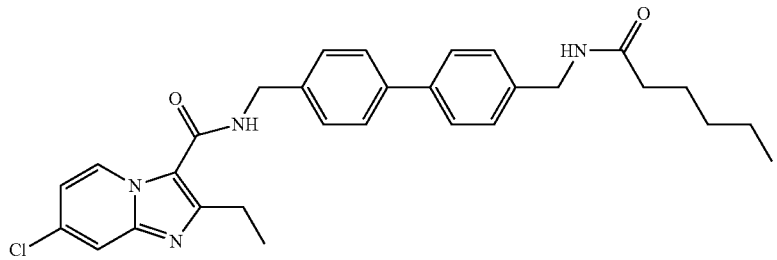 [SMILES: CCCCCC(=O)NCc1ccc(-c2ccc(CNC(=O)c3c(CC)nc4cc(Cl)ccn34)cc2)cc1]

White solid; $^1$H NMR (400 MHz, CDCl$_3$); δ 0.87 (t, J=6.8 Hz, 3H), 1.30-1.35 (m, 4H), 1.40 (t, J=7.6 Hz, 3H), 1.63-1.71 (m, 2H), 2.21 (t, J=7.6 Hz, 2H), 3.03 (q, J=7.6 Hz, 2H), 4.47 (d, J=5.6 Hz, 2H), 4.72 (d, J=6.0 Hz, 2H), 5.74 (brs, 1H), 6.99 (dd, J=2.0, 7.2 Hz, 1H), 7.34 (d, J=8.4 Hz, 2H), 7.45 (d, J=8.4 Hz, 2H), 7.51-7.59 (m, 5H), 7.74 (brs, 1H), 9.32 (d, J=7.2 Hz, 1H); LCMS (electrospray) m/z (M+H)$^+$ 517.

6-Chloro-2-ethyl-N-(4-(4-(trifluoromethoxy)phenoxy)benzyl)imidazo[1,2-a]pyridine-3-carboxamide (185)

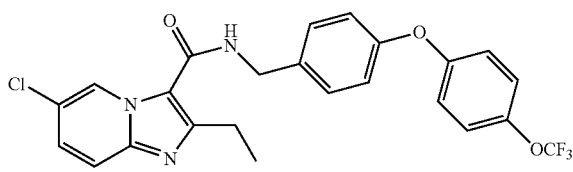 [SMILES: CCc1nc2ccc(Cl)cn2c1C(=O)NCc1ccc(Oc2ccc(OC(F)(F)F)cc2)cc1]

$^1$H NMR (400 MHz, CDCl$_3$) δ 1.42 (t, J=7.6 Hz, 3H), 2.99 (q, J=7.6 Hz, 2H), 4.68 (d, J=6.0 Hz, 2H), 6.11 (brs, 1H), 7.00 (d, J=8.8 Hz, 2H), 7.01 (d, J=8.4 Hz, 2H), 7.18 (d, J=8.8 Hz, 2H), 7.30 (dd, J=9.6, 2.0 Hz, 1H), 7.37 (d, J=8.8 Hz, 2H), 7.54 (d, J=9.2 Hz, 1H), 9.53 (d, J=1.6 Hz, 1H); LCMS (electrospray) m/z (M+H)$^+$ 490.17

7-Chloro-2-ethyl-N-(4-(4-(trifluoromethoxy)phenoxy)benzyl)imidazo[1,2-a]pyridine-3-carboxamide (186)

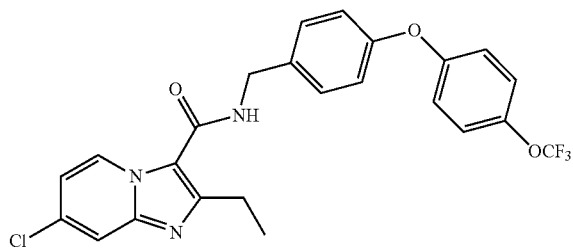 [SMILES: CCc1nc2cc(Cl)ccn2c1C(=O)NCc1ccc(Oc2ccc(OC(F)(F)F)cc2)cc1]

White solid; mp=141-142° C.; $^1$H NMR (400 MHz, CDCl$_3$) δ 1.41 (t, J=7.6 Hz, 3H), 2.98 (q, J=7.6 Hz, 2H), 4.68 (d, J=5.6 Hz, 2H), 6.09-6.11 (m, 1H), 6.91 (dd, J=2.0, 7.6 Hz, 1H), 6.98-7.02 (m, 4H), 7.18 (d, J=8.8 Hz, 2H), 7.37 (d, J=8.4 Hz, 2H), 7.60 (d, J=2.0 Hz, 1H), 9.37 (d, J=7.2 Hz, 1H)); LCMS (electrospray) m/z (M+H)$^+$ 490.24

6-Chloro-2-ethyl-N-(4-(4-fluorophenoxy)benzyl)imidazo[1,2-a]pyridine-3-carboxamide (187)

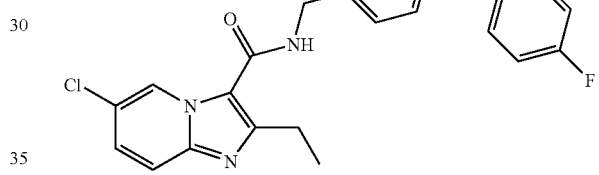

White solid; mp=168-169° C.; $^1$H NMR (400 MHz, CDCl$_3$) δ 1.41 (t, J=7.4 Hz, 3H), 2.99 (q, J=7.6 Hz, 2H), 4.67 (d, J=6.0 Hz, 2H), 6.09-6.11 (m, 1H), 6.96-7.06 (m, 6H), 7.30 (dd, J=2.0, 9.6 Hz, 1H), 7.34 (d, J=8.8 Hz, 2H), 7.54 (d, J=9.6 Hz, 1H), 9.53 (d, J=1.2 Hz, 1H)); LCMS (electrospray) m/z (M+H)$^+$ 424.26

7-Chloro-2-ethyl-N-(4-(4-fluorophenoxy)benzyl)imidazo[1,2-a]pyridine-3-carboxamide (188)

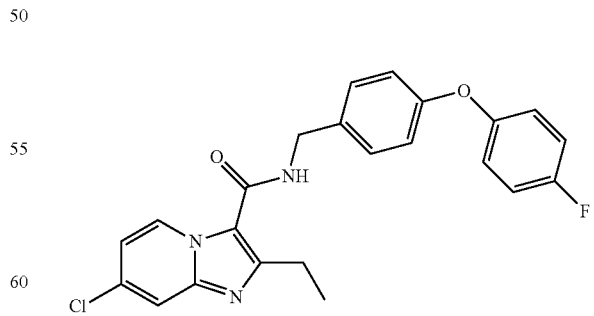

White solid; mp=146-147° C.; $^1$H NMR (400 MHz, CDCl$_3$) δ 1.40 (t, J=7.6 Hz, 3H), 2.97 (q, J=7.6 Hz, 2H), 4.66 (d, J=5.6 Hz, 2H), 6.07-6.09 (m, 1H), 6.91 (dd, J=2.2, 7.4 Hz, 1H), 6.95-7.06 (m, 6H), 7.33 (d, J=8.4 Hz, 2H), 7.59 (d, J=2.2 Hz, 1H), 9.37 (d, J=7.2 Hz, 1H)); LCMS (electrospray) m/z (M+H)+ 424.26

6-Bromo-2-ethyl-N-(4-(4-fluorophenoxy)benzyl)imidazo[1,2-a]pyridine-3-carboxamide (189)

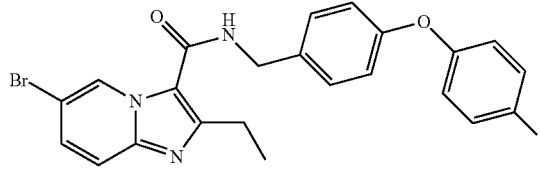

$^1$H NMR (400 MHz, CDCl$_3$) δ 1.41 (t, J=7.6 Hz, 3H), 2.98 (q, J=7.6 Hz, 2H), 4.66 (d, J=5.6 Hz, 2H), 6.09 (brs, 1H), 6.95-7.06 (m, 6H), 7.34 (d, J=8.8 Hz, 2H), 7.40 (dd, J=9.6, 1.6 Hz, 1H), 7.49 (d, J=9.6 Hz, 1H), 9.63 (d, J=1.2 Hz, 1H); LCMS (electrospray) m/z (M+H)+ 470.10

6-Chloro-N-(4-(4-chlorophenoxy)benzyl)-2-ethylimidazo[1,2-a]pyridine-3-carboxamide (190)

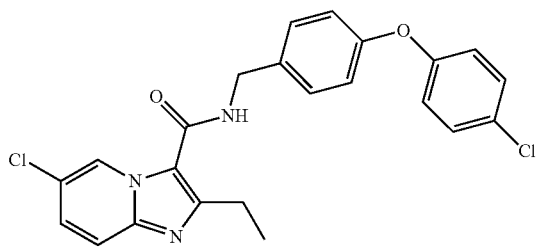 [SMILES: CCc1nc2ccc(Cl)cn2c1C(=O)NCc1ccc(Oc2ccc(Cl)cc2)cc1]

White solid; mp=159-160.7° C.; $^1$H NMR (400 MHz, CDCl$_3$) δ 1.42 (t, J=7.6 Hz, 3H), 2.99 (q, J=7.2 Hz, 2H), 4.68 (d, J=5.6 Hz, 2H), 6.10-6.11 (m, 1H), 6.94 (d, J=9.2 Hz, 2H), 7.00 (d, J=8.8 Hz, 2H), 7.27-7.32 (m, 3H), 7.36 (d, J=8.4 Hz, 2H), 7.55 (d, J=9.6 Hz, 1H), 9.54 (d, J=2.0 Hz, 1H); LCMS (electrospray) m/z (M+H)+ 440.18

7-Chloro-N-(4-(4-chlorophenoxy)benzyl)-2-ethylimidazo[1,2-a]pyridine-3-carboxamide (191)

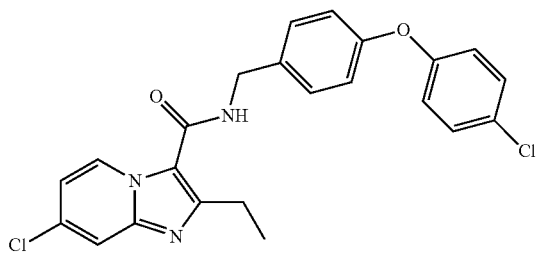 [SMILES: CCc1nc2cc(Cl)ccn2c1C(=O)NCc1ccc(Oc2ccc(Cl)cc2)cc1]

White solid; mp=167.1-167.9° C.; $^1$H NMR (400 MHz, CDCl$_3$) δ 1.41 (t, J=7.6 Hz, 3H), 2.98 (q, J=7.6 Hz, 2H), 4.67 (d, J=5.6 Hz, 2H), 6.08-6.10 (m, 1H), 6.91 (dd, J=2.4, 7.6 Hz, 1H), 6.94 (d, J=8.8 Hz, 2H), 7.00 (d, J=8.8 Hz, 2H), 7.29 (d, J=9.2 Hz, 2H), 7.35 (d, J=8.8 Hz, 2H), 7.60 (d, J=2.0 Hz, 1H), 9.37 (d, J=7.6 Hz, 1H); LCMS (electrospray) m/z (M+H)+ 440.18

2-Ethyl-N-(4-(4-(trifluoromethoxy)phenoxy)benzyl)imidazo[1,2-a]pyridine-3-carboxamide (192)

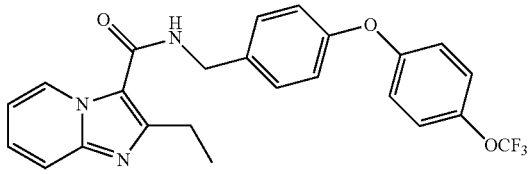 [SMILES: CCc1nc2ccccn2c1C(=O)NCc1ccc(Oc2ccc(OC(F)(F)F)cc2)cc1]

$^1$H NMR (400 MHz, CDCl$_3$) δ 1.42 (t, J=7.6 Hz, 3H), 3.01 (q, J=7.6 Hz, 2H), 4.69 (d, J=6.0 Hz, 2H), 6.12 (brs, 1H), 6.92 (t, J=6.8 Hz, 1H), 7.00 (d, J=9.2 Hz, 2H), 7.01 (d, J=8.8 Hz, 2H), 7.18 (d, J=8.8 Hz, 2H), 7.31-7.36 (m, 1H), 7.37 (d, J=8.8 Hz, 2H), 7.61 (d, J=8.8 Hz, 1H), 9.40 (d, J=6.8 Hz, 1H); LCMS (electrospray) m/z (M+H)+ 456.23

7-Chloro-2-ethyl-N-((6-(4-fluorophenoxy)pyridin-3-yl)methyl)imidazo[1,2-a]pyridine-3-carboxamide (193)

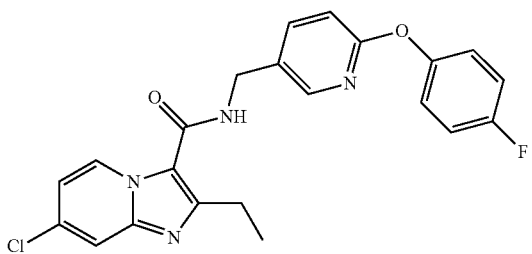 [SMILES: CCc1nc2cc(Cl)ccn2c1C(=O)NCc1ccc(Oc2ccc(F)cc2)nc1]

White solid; mp=167.0-167.6° C.; $^1$H NMR (400 MHz, CDCl$_3$) δ 1.41 (t, J=7.6 Hz, 3H), 2.97 (q, J=7.6 Hz, 2H), 4.64 (d, J=6.0 Hz, 2H), 6.09 (t, J=5.6 Hz, 1H), 6.90-6.93 (m, 2H), 7.06-7.11 (m, 4H), 7.58 (d, J=2.0 Hz, 1H), 7.80 (dd, J=2.8, 8.8 Hz, 1H), 8.20 (d, J=2.0 Hz, 1H), 9.34 (d, J=7.6 Hz, 1H); LCMS (electrospray) m/z (M+H)+ 425.28

6-Chloro-2-ethyl-N-((6-(4-(trifluoromethoxy)phenoxy)pyridin-3-yl)methyl)imidazo[1,2-a]pyridine-3-carboxamide (194)

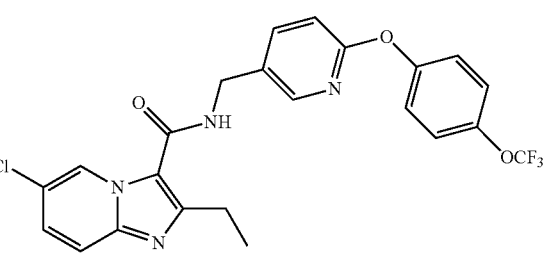

White solid; mp=154-155° C.; $^1$H NMR (400 MHz, CDCl$_3$) δ 1.42 (t, J=7.8 Hz, 3H), 2.98 (q, J=7.6 Hz, 2H), 4.66 (d, J=6.0 Hz, 2H), 6.14 (t, J=5.6 Hz, 1H), 6.96 (d, J=8.4 Hz, 1H), 7.16 (d, J=9.2 Hz, 2H), 7.24 (d, J=9.2 Hz, 2H), 7.32 (dd, J=2.0, 9.6 Hz, 1H), 7.54 (d, J=9.2 Hz, 1H), 7.80 (dd, J=2.4, 8.4 Hz, 1H), 8.20 (d, J=2.4 Hz, 1H), 9.51 (d, J=2.0 Hz, 1H); LCMS (electrospray) m/z (M+H)+ 491.26

7-Chloro-2-ethyl-N-((6-(4-(trifluoromethoxy)phenoxy)pyridin-3-yl)methyl)imidazo[1,2-a]pyridine-3-carboxamide (195)

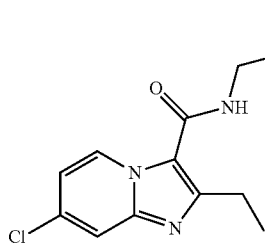

White solid; ¹H NMR (400 MHz, CDCl₃) δ 1.41 (t, J=7.4 Hz, 3H), 2.97 (q, J=7.6 Hz, 2H), 4.66 (d, J=6.0 Hz, 2H), 6.14 (t, J=5.4 Hz, 1H), 6.92 (dd, J=2.0, 7.6 Hz, 1H), 6.96 (d, J=8.8 Hz, 1H), 7.16 (d, J=9.2 Hz, 2H), 7.24 (d, J=9.2 Hz, 2H), 7.60 (d, J=1.6 Hz, 1H), 7.79 (dd, J=2.4, 8.4 Hz, 1H), 8.20 (d, J=2.0 Hz, 1H), 9.35 (d, J=7.6 Hz, 1H).

4-Phenoxybenzyl 6-chloro-2-ethylimidazo[1,2-a]pyridine-3-carboxylate (196)

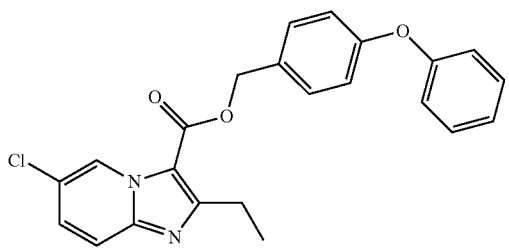 [SMILES: CCc1nc2ccc(Cl)cn2c1C(=O)OCc1ccc(Oc2ccccc2)cc1]

White solid; mp=123.3-123.8° C.; ¹H NMR (400 MHz, CDCl₃) δ 1.31 (t, J=7.4 Hz, 3H), 3.10 (q, J=7.6 Hz, 2H), 4.67 (s, 2H), 7.02 (d, J=8.4 Hz, 4H), 7.12 (dd, J=7.2, 7.6 Hz, 1H), 7.34 (dd, J=7.2, 7.6 Hz, 3H), 7.43 (d, J=8.8 Hz, 2H), 7.58 (d, J=9.6 Hz, 1H), 9.42 (d, J=2.0 Hz, 1H); LCMS (electrospray) m/z (M+H)+ 407.12

6-Chloro-2-ethyl-N-(4-(4-fluorophenoxy)benzyl)-N-methylimidazo[1,2-a]pyridine-3-carboxamide (197)

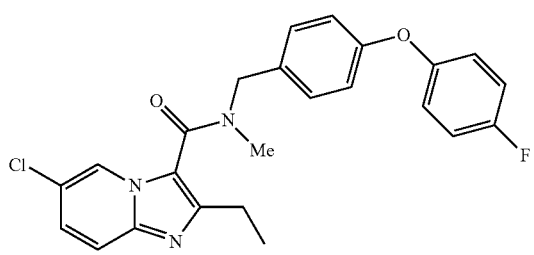 [SMILES: CCc1nc2ccc(Cl)cn2c1C(=O)N(C)Cc1ccc(Oc2ccc(F)cc2)cc1]

White solid; ¹H NMR (400 MHz, CDCl₃) δ 1.37 (t, J=7.4 Hz, 3H), 2.78 (q, J=7.6 Hz, 2H), 3.01 (s, 3H), 4.70 (s, 2H), 6.94-7.06 (m, 6H), 7.21-7.26 (m, 3H), 8.47 (d, J=9.2 Hz, 1H), 8.47 (d, J=1.6 Hz, 1H); LCMS (electrospray) m/z (M+H)+ 438.20

6-Chloro-2-ethyl-N-(4-(4-(trifluoromethoxy)phenylamino)benzyl)imidazo[1,2-a]pyridine-3-carboxamide (198)

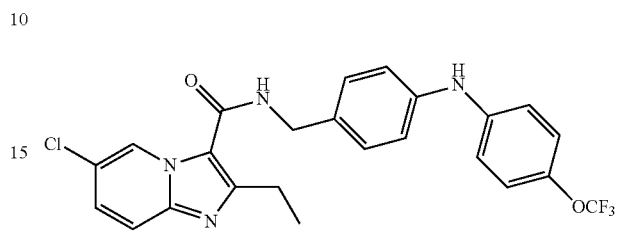

¹H NMR (400 MHz, CDCl₃) δ 1.41 (t, J=7.6 Hz, 3H), 2.98 (q, J=7.6 Hz, 2H), 4.64 (d, J=5.6 Hz, 2H), 5.74 (s, 0.1H), 6.07 (brs, 1H), 7.04 (d, J=7.2 Hz, 2H), 7.06 (d, J=7.2 Hz, 2H), 7.12 (d, J=8.4 Hz, 2H), 7.28-7.32 (m, 3H), 7.54 (d, J=9.2 Hz, 1H), 9.54 (d, J=1.2 Hz, 1H); LCMS (electrospray) m/z (M+H)+ 489.22

7-Chloro-2-ethyl-N-(4-(4-(trifluoromethoxy)phenylamino)benzyl)imidazo[1,2-a]pyridine-3-carboxamide (199)

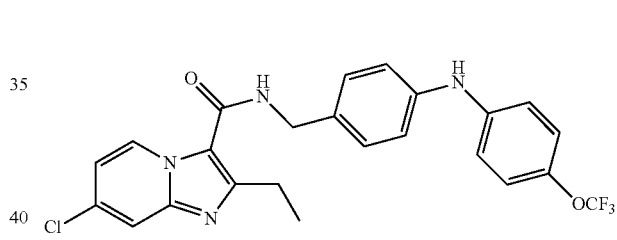

¹H NMR (400 MHz, CDCl₃) δ 1.40 (t, J=7.6 Hz, 3H), 2.98 (q, J=7.6 Hz, 2H), 4.63 (d, J=5.6 Hz, 2H), 5.74 (s, 1H), 6.05 (brs, 1H), 6.91 (dd, J=7.6, 2.0 Hz, 1H), 7.04 (d, J=9.2 Hz, 2H), 7.06 (d, J=8.8 Hz, 2H), 7.12 (d, J=9.2 Hz, 2H), 7.29 (d, J=8.8 Hz, 2H), 7.59 (d, J=1.6 Hz, 1H), 9.36 (d, J=7.6 Hz, 1H); LCMS (electrospray) m/z (M+H)+ 489.22

6-Chloro-2-ethyl-N-(4-(4-(trifluoromethyl)benzyloxy)benzyl)imidazo[1,2-a]pyridine-3-carboxamide (200)

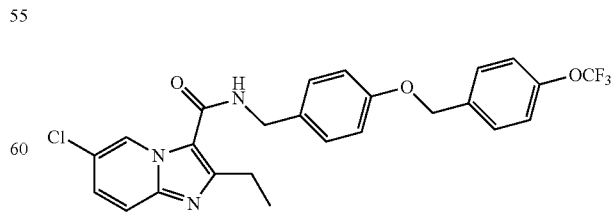

¹H NMR (400 MHz, CDCl₃) δ 1.40 (t, J=7.6 Hz, 3H), 2.96 (q, J=7.6 Hz, 2H), 4.64 (d, J=5.6 Hz, 2H), 5.06 (s, 2H), 6.05 (brs, 1H), 6.97 (d, J=8.4 Hz, 2H), 7.20-7.33 (m, 5H), 7.46 (d, J=8.8 Hz, 2H), 7.54 (d, J=9.2 Hz, 2H), 9.53 (d, J=1.2 Hz, 1H); LCMS (electrospray) m/z (M+H)+ 504.25

7-Chloro-2-ethyl-N-(4-(4-(trifluoromethyl)benzyloxy)benzyl)imidazo[1,2-a]pyridine-3-carboxamide (201)

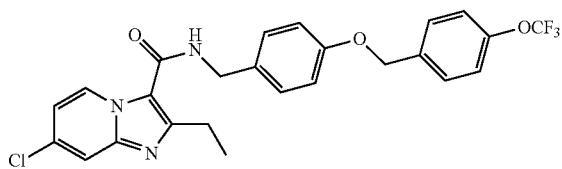 [SMILES: CCc1nc2cc(Cl)ccn2c1C(=O)NCc1ccc(OCc2ccc(OC(F)(F)F)cc2)cc1]

¹H NMR (400 MHz, CDCl₃) δ 1.39 (t, J=7.6 Hz, 3H), 2.95 (q, J=7.6 Hz, 2H), 4.63 (d, J=5.6 Hz, 2H), 5.06 (s, 2H), 6.03 (brs, 1H), 6.90 (dd, J=7.6, 2.0 Hz, 1H), 6.97 (d, J=8.8 Hz, 2H), 7.23 (d, J=8.0 Hz, 2H), 7.28 (d, J=8.8 Hz, 2H), 7.31 (d, J=8.8 Hz, 2H), 7.46 (d, J=8.8 Hz, 2H), 7.59 (d, J=2.0 Hz, 1H), 9.36 (d, J=7.6 Hz, 1H); LCMS (electrospray) m/z (M+H)+ 504.25

6-Chloro-2-ethyl-N-(4-(4-fluorobenzyloxy)benzyl)imidazo[1,2-a]pyridine-3-carboxamide (202)

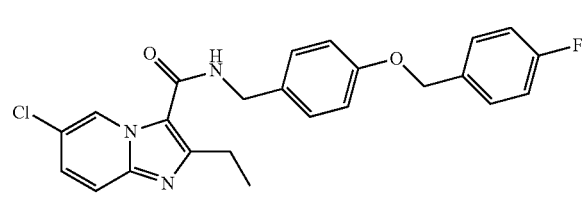 [SMILES: CCc1nc2ccc(Cl)cn2c1C(=O)NCc1ccc(OCc2ccc(F)cc2)cc1]

¹H NMR (400 MHz, CDCl₃) δ 1.40 (t, J=7.6 Hz, 3H), 2.96 (q, J=7.6 Hz, 2H), 4.63 (d, J=5.6 Hz, 2H), 5.03 (s, 2H), 6.04 (brs, 1H), 6.96 (d, J=8.8 Hz, 2H), 7.06 (d, J=8.8 Hz, 1H), 7.08 (d, J=8.4 Hz, 1H), 7.28-7.32 (m, 3H), 7.40 (dd, J=8.8 Hz, 2H), 7.53 (d, J=9.2 Hz, 1H), 9.53 (d, J=1.6 Hz, 1H); LCMS (electrospray) m/z (M+H)+ 438.20

7-Chloro-2-ethyl-N-(4-(4-fluorobenzyloxy)benzyl)imidazo[1,2-a]pyridine-3-carboxamide (203)

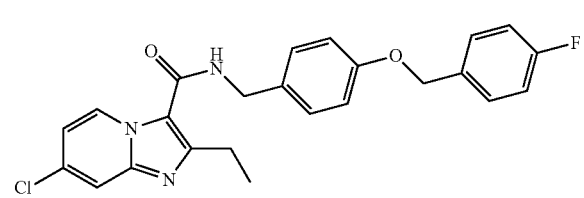 [SMILES: CCc1nc2cc(Cl)ccn2c1C(=O)NCc1ccc(OCc2ccc(F)cc2)cc1]

¹H NMR (400 MHz, CDCl₃) δ 1.38 (t, J=7.6 Hz, 3H), 2.95 (q, J=7.6 Hz, 2H), 4.62 (d, J=5.6 Hz, 2H), 5.03 (s, 2H), 6.02 (brs, 1H), 6.90 (dd, J=7.6, 2.4 Hz, 1H), 6.96 (d, J=8.8 Hz, 2H), 7.07 (dd, J=8.8 Hz, 2H), 7.30 (d, J=8.8 Hz, 2H), 7.40 (dd, J=8.8 Hz, 2H), 7.58 (d, J=1.6 Hz, 1H), 9.36 (d, J=7.6 Hz, 1H); LCMS (electrospray) m/z (M+H)+ 438.20

6-Chloro-2-ethyl-N-((2-(4-(trifluoromethoxy)phenyl)-1H-benzo[d]imidazol-5-yl)methyl) imidazo[1,2-a]pyridine-3-carboxamide (204)

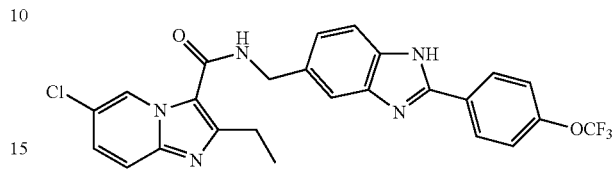

¹H NMR (400 MHz, DMSO-d₆) 1.26 (m, 3H), 2.97-3.03 (m, 2H), 4.65 (t, J=6.4 Hz, 2H), 7.24 (dd, J=18.4, 8.0 Hz, 1H), 7.45 (d, J=9.6, 2.4 Hz, 1H), 7.51-7.56 (m, 3H), 7.65-7.68 (m, 2H), 8.24-8.28 (m, 1H), 8.52-8.56 (m, 1H), 9.09-7.10 (m, 1H), 12.96 (ss, 1H); LCMS (electrospray) m/z (M+H)+ 514.38

7-Chloro-2-ethyl-N-((2-(4-(trifluoromethoxy)phenyl)-1H-benzo[d]imidazol-5-yl)methyl) imidazo[1,2-a]pyridine-3-carboxamide (205)

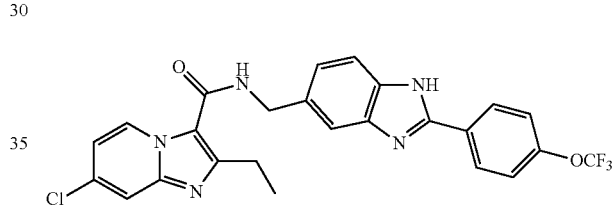

¹H NMR (400 MHz; CDCl₃) δ 1.38 (t, J=7.6 Hz, 3H), 2.97 (q, J=7.6 Hz, 2H), 4.82 (d, J=5.6 Hz, 2H), 6.19 (brs, 1H), 6.90 (dd, J=7.6, 2.0 Hz, 1H), 7.30 (m, 1H), 7.35 (d, J=8.0 Hz, 2H), 7.50-7.52 (m, 1H), 7.59 (d, J=2.0 Hz, 1H), 7.81 (m, 1H), 8.07 (d, J=8.8 Hz, 2H), 9.37 (d, J=7.6 Hz, 1H); LCMS (electrospray) m/z (M+H)+ 514.31

7-Chloro-2-ethyl-N-((2-(morpholinomethyl)-1H-benzo[d]imidazol-5-yl)methyl) imidazo[1,2-a]pyridine-3-carboxamide (206)

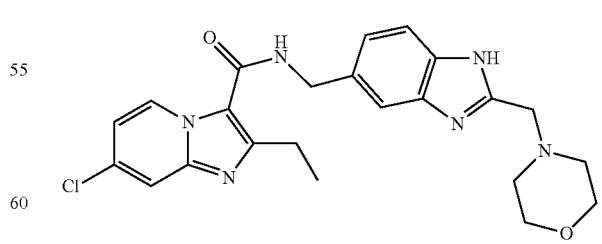

¹H NMR (400 MHz, DMSO-d₆) δ 1.23-1.28 (m, 3H), 2.44 (m, 4H), 2.98 (q, J=7.6 Hz, 2H), 3.59 (m, 4H), 3.69 (s, 2H), 4.61 (M, 2H), 6.19 (brs, 1H), 7.09 (dd, J=9.6, 2.0 Hz, 1H), 7.18 (dd, J=9.6, 7.2 Hz, 1H), 7.41 (m, 1H), 7.51 (m, 1H), 7.79

(d, J=2.0 Hz, 1H), 8.52 (m, 1H), 8.96 (d, J=7.6 Hz, 1H), 9.37 (d, J=7.6 Hz, 1H), 12.27 (m, 1H); LCMS (electrospray) m/z (M+H)⁺ 453.39

6-Chloro-2-ethyl-N-((2-(4-(trifluoromethoxy)phenyl)benzo[d]oxazol-5-yl)methyl)imidazo[1,2-a]pyridine-3-carboxamide (207)


White solid; ¹H NMR (400 MHz, CDCl₃); δ 1.40 (t, J=7.6 Hz, 3H), 2.99 (q, J=7.6 Hz, 2H), 4.82 (d, J=6.0 Hz, 2H), 6.20 (brs, 1H), 7.31 (dd, J=1.6 Hz, 7.6 Hz, 1H), 7.35 (d, J=8.4 Hz, 2H), 7.42 (dd, J=1.6 Hz, 8.4 Hz, 1H), 7.55 (d, J=9.2 Hz, 1H), 7.59 (d, J=8.4 Hz, 1H), 7.77 (s, 1H), 8.29 (d, J=8.8 Hz, 2H), 9.55 (d, J=1.6 Hz, 1H); LCMS (electrospray) m/z (M+H)⁺ 515, 517 (Cl⁻ isotope pattern).

7-Chloro-2-ethyl-N-((2-(4-(trifluoromethoxy)phenyl)benzo[d]oxazol-5-yl)methyl)imidazo[1,2-a]pyridine-3-carboxamide (208)


White solid; ¹H NMR (400 MHz, CDCl₃); δ 1.40 (t, J=7.6 Hz, 3H), 2.98 (q, J=7.6 Hz, 2H), 4.82 (d, J=6.0 Hz, 2H), 6.19 (brs, 1H), 6.92 (dd, J=2.0 Hz, 7.6 Hz, 1H), 7.36 (d, J=8.0 Hz, 2H), 7.41 (dd, J=2.0 Hz, 8.4 Hz, 1H), 7.59 (d, J=8.8 Hz, 2H), 7.77 (s, 1H), 8.28 (d, J=8.8 Hz, 2H), 9.38 (d, J=7.6 Hz, 1H); LCMS (electrospray) (M+H)⁺ 515, 517 (Cl⁻ isotope pattern).

6-Chloro-N-(4-(2,6-dimethylmorpholino)benzyl)-2-ethylimidazo[1,2-a]pyridine-3-carboxamide (209)

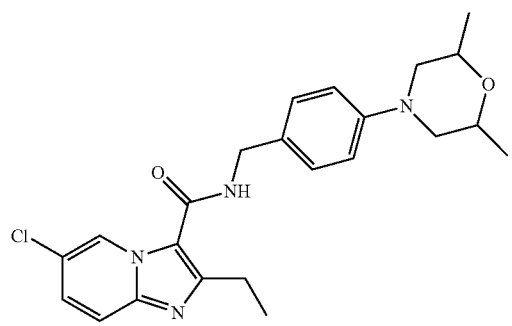 [SMILES: CCc1nc2ccc(Cl)cn2c1C(=O)NCc1ccc(N2CC(C)OC(C)C2)cc1]

White solid; mp=176-177° C.; ¹H NMR (400 MHz, CDCl₃) δ 1.25 (s, 3H),), 1.27 (s, 3H), 1.39 (t, J=7.6 Hz, 3H), 2.42 (t, J=11.2 Hz, 2H), 2.95 (q, J=7.2 Hz, 2H), 3.46 (d, J=10.4 Hz, 2H), 3.78-3.82 (m, 2H), 4.61 (d, J=5.6 Hz, 2H), 6.00-6.02 (m, 1H), 6.91 (d, J=8.8 Hz, 1H), 7.26-7.31 (m, 3H), 7.54 (d, J=9.2 Hz, 1H), 9.53 (d, J=2.2 Hz, 1H); LCMS (electrospray) m/z (M+H)⁺ 427.32

7-Chloro-N-(4-(2,6-dimethylmorpholino)benzyl)-2-ethylimidazo[1,2-a]pyridine-3-carboxamide (210)

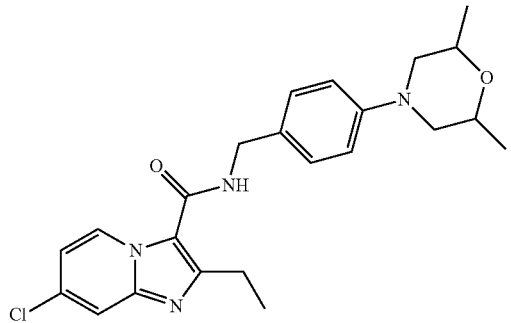 [SMILES: CCc1nc2cc(Cl)ccn2c1C(=O)NCc1ccc(N2CC(C)OC(C)C2)cc1]

White solid; mp=165-166° C.; ¹H NMR (400 MHz, CDCl₃) δ 1.25 (s, 3H), 1.27 (s, 3H), 1.38 (t, J=7.6 Hz, 3H), 2.42 (t, J=11.2 Hz, 2H), 2.94 (q, J=7.6 Hz, 2H), 3.45 (d, J=10.4 Hz, 2H), 3.76-3.84 (m, 2H), 4.60 (d, J=5.6 Hz, 2H), 5.99-6.01 (m, 1H), 6.89-6.92 (m, 3H), 7.28 (d, J=8.4 Hz, 2H), 7.58 (d, J=2.0 Hz, 1H), 9.35 (d, J=7.2 Hz, 1H); LCMS (electrospray) m/z (M+H)⁺ 427.32

6-Chloro-2-ethyl-N-(4-(pyrrolidin-1-yl)benzyl)imidazo[1,2-a]pyridine-3-carboxamide (211)

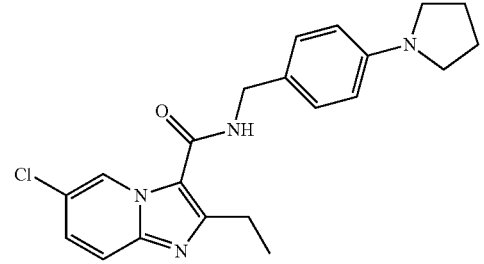 [SMILES: CCc1nc2ccc(Cl)cn2c1C(=O)NCc1ccc(N2CCCC2)cc1]

White solid; mp=222-223° C.; ¹H NMR (400 MHz, CDCl₃) δ 1.38 (t, J=7.4 Hz, 3H), 1.99-2.03 (m, 4H), 2.94 (q, J=7.6 Hz, 2H), 3.29 (t, J=6.6 Hz, 4H), 4.57 (d, J=5.6 Hz, 2H), 5.95-5.97 (m, 1H), 6.56 (d, J=8.4 Hz, 2H), 7.22-7.30 (m, 6H), 7.53 (d, J=9.6 Hz, 1H), 9.53 (d, J=1.6 Hz, 1H); LCMS (electrospray) m/z (M+H)⁺ 383.24

7-Chloro-2-ethyl-N-(4-(pyrrolidin-1-yl)benzyl)imidazo[1,2-a]pyridine-3-carboxamide (212)

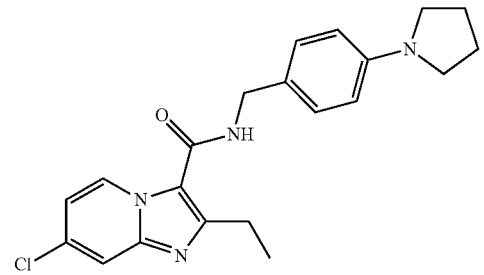 [SMILES: CCc1nc2cc(Cl)ccn2c1C(=O)NCc1ccc(N2CCCC2)cc1]

¹H NMR (400 MHz, CDCl₃) δ 1.35-1.42 (m, 3H), 1.93-1.96 (m, 2H), 1.99-2.02 (m, 2H), 2.90-2.99 (m, 2H), 3.28 (t, J=6.4 Hz, 2H), 3.38 (t, J=6.4 Hz, 2H), 4.57 (d, J=4.8 Hz, 2H), 5.95-6.02 (m, 1H), 6.56 (d, J=8.4 Hz, 2H), 6.85-6.92 (m, 1H), 7.14-7.31 (m, 3H), 7.57-7.59 (m, 1H), 9.36 (d, J=7.6 Hz, 1H)

7-Chloro-N-(4-(5,6-dihydropyridin-1(2H)-yl)benzyl)-2-ethylimidazo[1,2-a]pyridine-3-carboxamide (213)

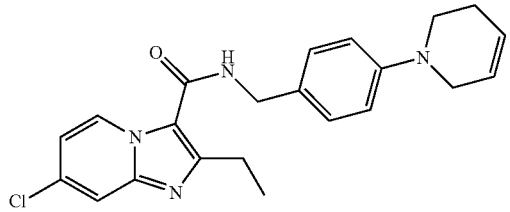 [SMILES: CCc1nc2cc(Cl)ccn2c1C(=O)NCc1ccc(N2CC=CCC2)cc1]

¹H NMR (400 MHz, CDCl₃) δ 1.38 (t, J=7.6 Hz, 3H), 2.29-2.32 (m, 2H), 2.94 (q, J=7.6 Hz, 2H), 3.38 (t, J=5.6 Hz, 2H), 3.68-3.72 (m, 2H), 4.59 (d, J=5.6 Hz, 2H), 5.79-5.82 (m, 1H), 5.88-5.91 (m, 1H), 5.99 (brs, 1H), 6.88-6.93 (m, 3H), 7.27 (d, J=8.0 Hz, 2H), 7.58 (d, J=1.6 Hz, 1H), 9.36 (d, J=7.6 Hz, 1H); LCMS (electrospray) m/z (M+H)⁺ 395.35

6-Chloro-2-ethyl-N-(4-(4-methylpiperidin-1-yl)benzyl)imidazo[1,2-a]pyridine-3-carboxamide (214)

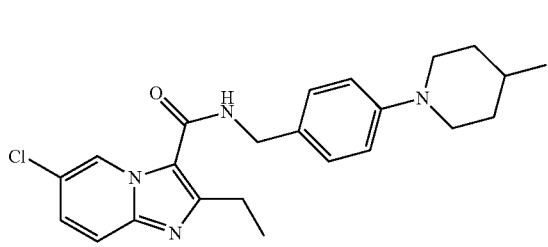 [SMILES: CCc1nc2ccc(Cl)cn2c1C(=O)NCc1ccc(N2CCC(C)CC2)cc1]

¹H NMR (400 MHz, CDCl₃) δ 0.97 (d, J=6.4 Hz, 3H), 1.35 (m, 2H), 1.38 (t, J=7.6 Hz, 3H), 1.53 (m, 1H), 1.72-1.76 (m, 2H), 2.66-2.73 (m, 2H), 2.95 (q, J=7.6 Hz, 2H), 3.64-3.67 (m, 2H), 4.59 (d, J=5.6 Hz, 2H), 5.99 (brs, 1H), 6.93 (d, J=8.4 Hz, 2H), 7.25 (d, J=7.6 Hz, 2H), 7.29 (dd, J=9.6, 2.0 Hz, 1H), 7.53 (d, J=9.6 Hz, 1H), 9.53 (d, J=1.6 Hz, 1H); LCMS (electrospray) m/z (M+H)⁺ 411.40

7-Chloro-2-ethyl-N-(4-(4-methylpiperidin-1-yl)benzyl)imidazo[1,2-a]pyridine-3-carboxamide (215)

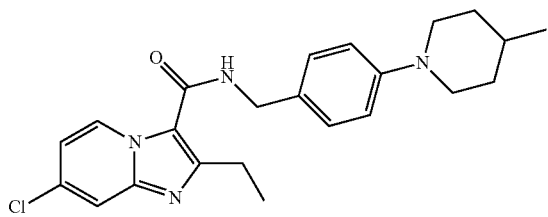 [SMILES: CCc1nc2cc(Cl)ccn2c1C(=O)NCc1ccc(N2CCC(C)CC2)cc1]

¹H NMR (400 MHz, CDCl₃) δ 0.97 (d, J=6.8 Hz, 3H), 1.35 (m, 2H), 1.37 (t, J=7.6 Hz, 3H), 1.51-1.53 (m, 1H), 1.72-1.75 (m, 2H), 2.66-2.73 (m, 2H), 2.94 (q, J=7.6 Hz, 2H), 3.64-3.67 (m, 2H), 4.59 (d, J=5.6 Hz, 2H), 5.98 (brs, 1H), 6.90 (dd, J=7.6, 2.4 Hz, 1H), 6.93 (d, J=8.4 Hz, 2H), 7.25 (d, J=8.4 Hz, 2H), 7.58 (d, J=2.4 Hz, 1H), 9.36 (d, J=7.6 Hz, 1H); LCMS (electrospray) m/z (M+H)⁺ 411.40

6-Chloro-N-(4-(3,5-dimethylpiperidin-1-yl)benzyl)-2-ethylimidazo[1,2-a]pyridine-3-carboxamide (216)

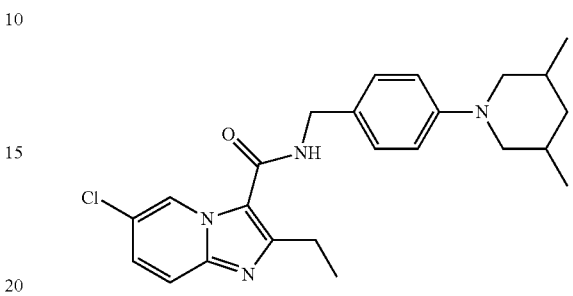

Pale yellow solid; mp=157.2-158.0° C.; ¹H NMR (400 MHz, CDCl₃); δ 0.91 (d, J=6.4 Hz, 6H), 1.35 (t, J=7.6 Hz, 3H), 1.73-1.81 (m, 4H), 2.16 (dd, J=11.6, 11.6 Hz, 2H), 2.90 (q, 7.6 Hz, 2H), 3.58-3.61 (m, 2H), 4.56 (d, J=5.6 Hz, 2H), 6.01 (brs, 1H), 6.90 (d, J=8.8 Hz, 2H), 7.22 (d, J=8.8 Hz, 2H), 7.26 (dd, J=2.0, 9.6 Hz, 1H), 7.49 (d, J=9.6 Hz, 1H), 9.49 (d, J=2.0 Hz, 1H); ¹³C NMR (100 MHz, CDCl₃); δ 13.3, 19.6, 23.6, 30.9, 42.2, 43.4, 57.2, 115.4, 116.6, 117.0, 121.5, 126.3, 127.8, 128.2, 128.9, 144.5, 151.3, 151.4, 161.1; LCMS (electrospray) m/z (M+H)⁺ 425, 427 (Cl⁻ isotope pattern).

7-Chloro-N-(4-(3,5-dimethylpiperidin-1-yl)benzyl)-2-ethylimidazo[1,2-a]pyridine-3-carboxamide (217)

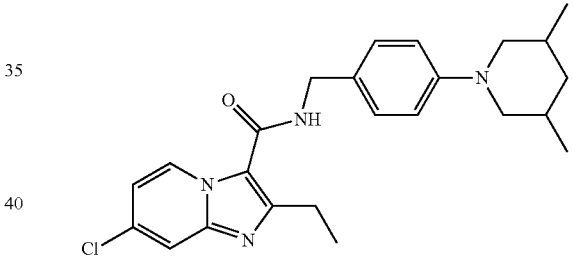

Pale yellow solid; mp=181.5-182.8° C.; ¹H NMR (400 MHz, CDCl₃); δ 0.92 (d, J=6.8 Hz, 6H), 1.35 (t, J=7.6 Hz, 3H), 1.74-1.82 (m, 4H), 2.17 (dd, J=11.6, 11.6 Hz, 2H), 2.90 (q, 7.6 Hz, 2H), 3.59-3.62 (m, 2H), 4.57 (d, J=5.2 Hz, 2H), 6.01 (brs, 1H), 6.87 (dd, J=2.0, 7.6 Hz, 1H), 6.91 (d, J=8.8 Hz, 2H), 7.23 (d, J=8.8 Hz, 2H), 7.57 (d, J=2.0 Hz, 1H), 9.33 (d, J=7.6 Hz, 1H); ¹³C NMR (100 MHz, CDCl₃); δ 13.4, 19.6, 23.6, 30.9, 42.2, 43.4, 57.2, 114.7, 115.1, 115.7, 116.6, 127.8, 128.6, 128.9, 133.6, 146.1, 151.3, 151.6, 161.1; LCMS (electrospray) m/z (M+H)⁺ 425, 427 (Cl⁻ isotope pattern).

7-Chloro-2-ethyl-N-(4-(4-hydroxypiperidin-1-yl)benzyl)imidazo[1,2-a]pyridine-3-carboxamide (218)

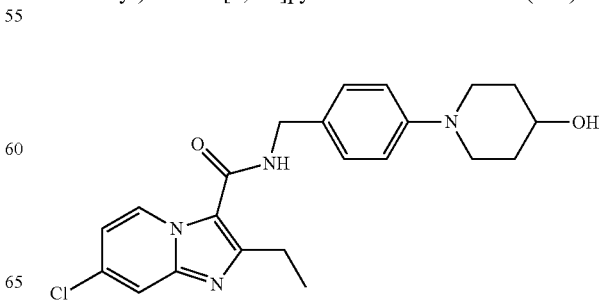

Pale yellow solid; mp=179.1-180.0° C.; ¹H NMR (400 MHz, DMSO-d6); δ 1.22 (t, J=7.2 Hz, 3H), 1.39-1.48 (m, 2H), 1.76-1.81 (m, 2H), 2.76-2.82 (m, 2H), 2.92 (q, J=7.2 Hz, 2H), 3.46-3.51 (m, 2H), 3.57-3.62 (m, 1H), 4.39 (d, J=5.6 Hz, 2H), 4.64 (d, J=4.0 Hz, 1H), 6.88 (d, J=8.4 Hz, 2H), 7.07 (dd, J=2.0, 7.2 Hz, 1H), 7.18 (d, J=8.4 Hz, 2H), 7.77 (d, J=2.0 Hz, 1H), 8.37 (t, J=5.6 Hz, 1H), 8.93 (d, J=7.2 Hz, 1H); LCMS (electrospray) m/z (M+H)⁺ 413, 415 (Cl⁻ isotope pattern).

2-ethyl-6-methyl-N-(4-morpholinobenzyl)imidazo[1,2-a]pyridine-3-carboxamide (219)

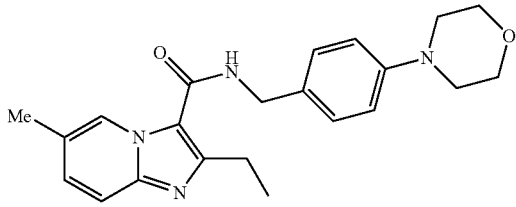 [SMILES: CCc1nc2ccc(C)cn2c1C(=O)NCc1ccc(N2CCOCC2)cc1]

White solid; ¹H NMR (400 MHz, CDCl₃) δ 1.38 (t, J=7.2 Hz, 3H), 2.35 (s, 3H), 2.94 (q, J=7.6 Hz, 2H), 3.15 (t, J=4.8 Hz, 4H), 3.86 (t, J=4 Hz, 4H), 4.61 (d, J=5.2 Hz, 2H), 6.00 (brs, 1H), 6.91 (d, J=8.8 Hz, 2H), 7.16 (dd, J=2.0 Hz, 9.2 Hz, 1H), 7.29 (d, J=8.8 Hz, 2H), 7.49 (d, J=9.2 Hz, 1H), 9.20 (s, 1H); LCMS (electrospray) m/z (M+H)⁺ 379.

1-(4-((6-Chloro-2-ethylimidazo[1,2-a]pyridine-3-carboxamido)methyl)phenyl)piperidine-4-carboxylic acid (220)

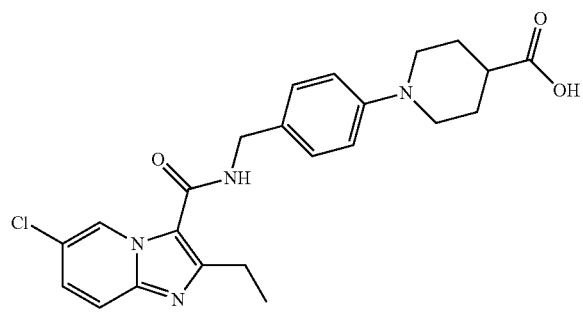 [SMILES: CCc1nc2ccc(Cl)cn2c1C(=O)NCc1ccc(N2CCC(C(=O)O)CC2)cc1]

White solid; ¹H NMR (400 MHz, DMSO-d⁶); δ 1.23 (t, J=7.6 Hz, 3H), 1.57-1.67 (m, 2H), 1.85-1.89 (m, 2H), 2.34-2.41 (m, 1H), 2.68-2.74 (m, 2H), 2.94 (q, J=7.6 Hz, 2H), 3.58-3.61 (m, 2H), 4.41 (d, J=5.6 Hz, 2H), 6.90 (d, J=8.8 Hz, 2H), 7.20 (d, J=8.8 Hz, 2H), 7.43 (dd, J=2.0, 9.6 Hz, 1H), 7.64 (d, J=9.6 Hz, 1H), 8.38 (brt, J=5.6 Hz, 1H), 9.05 (d, J=2.0 Hz, 1H); LCMS (electrospray) m/z 441 (M+H)⁺.

N-(4-(Azepan-1-yl)benzyl)-6-chloro-2-ethylimidazo[1,2-a]pyridine-3-carboxamide (221)

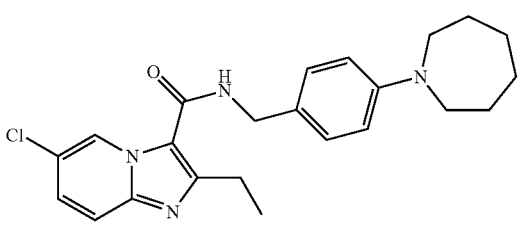 [SMILES: CCc1nc2ccc(Cl)cn2c1C(=O)NCc1ccc(N2CCCCCC2)cc1]

¹H NMR (400 MHz, CDCl₃) δ 1.26 (t, J=7.2 Hz, 3H), 1.38 (m, 4H), 1.53-1.56 (m, 4H), 2.95 (q, J=7.6 Hz, 2H), 3.45 (t, J=5.6 Hz, 4H), 4.56 (d, J=5.6 Hz, 2H), 5.97 (brs, 1H), 6.68 (d, J=8.8 Hz, 2H), 7.21 (d, J=8.8 Hz, 2H), 7.28 (dd, J=9.6, 2.0 Hz, 2H), 7.53 (d, J=9.6 Hz, 1H), 9.53 (d, J=2.4 Hz, 1H); LCMS (electrospray) m/z (M+H)⁺ 411.40

N-(4-(Azepan-1-yl)benzyl)-7-chloro-2-ethylimidazo[1,2-a]pyridine-3-carboxamide (222)

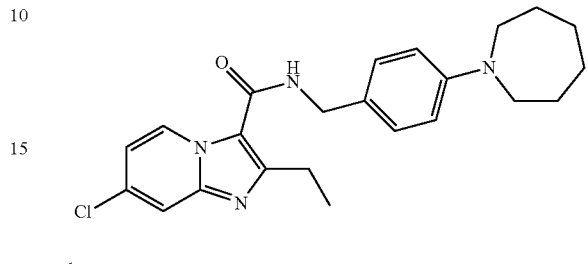

¹H NMR (400 MHz, CDCl₃) δ 1.38 (t, J=7.6 Hz, 3H), 1.52-1.55 (m, 4H), 1.78 (m, 4H), 2.94 (q, J=7.6 Hz, 2H), 3.45 (t, J=6.0 Hz, 4H), 4.56 (d, J=5.2 Hz, 2H), 5.95 (brs, 1H), 6.67 (d, J=8.8 Hz, 2H), 6.89 (dd, J=1.6, 2.4 Hz, 1H), 7.20 (d, J=8.8 Hz, 2H), 7.57 (d, J=2.4 Hz, 1H), 9.36 (d, J=7.6 Hz, 1H); LCMS (electrospray) m/z (M+H)⁺ 411.40

7-Chloro-N-(4-(3a,4-dihydro-1H-isoindol-2(3H,7H,7aH)-yl)benzyl)-2-ethylimidazo[1,2-a]pyridine-3-carboxamide (223)


White solid; ¹H NMR (400 MHz, CDCl₃); δ 1.36 (t, J=7.6 Hz, 3H), 1.96 (dd, J=4.0 Hz, 16.4 Hz, 2H), 2.25-2.31 (m, 2H), 2.45 (dd, J=5.2 Hz, 8.8 Hz, 2H), 2.92 (q, J=7.6 Hz, 2H), 3.11 (dd, J=5.2 Hz, 8.8 Hz, 2H), 3.39 (dd, J=6.4 Hz, 8.8 Hz, 2H), 4.55 (d, J=5.2 Hz, 2H), 5.67 (s, 2H), 5.94 (brs, 1H), 6.51 (d, J=8.8 Hz, 2H), 6.89 (dd, J=2.0, 7.6 Hz, 1H), 7.22 (d, J=8.8 Hz, 2H), 7.57 (d, J=2.0 Hz, 1H), 9.35 (d, J=7.6 Hz, 1H); LCMS (electrospray) m/z (M+H)⁺ 435, 437 (Cl⁻ isotope pattern).

N-(4-(1H-isoindol-2(3H,3aH,4H,5H,6H,7H,7aH)-yl)benzyl)-7-chloro-2-ethylimidazo[1,2-a]pyridine-3-carboxamide (224)

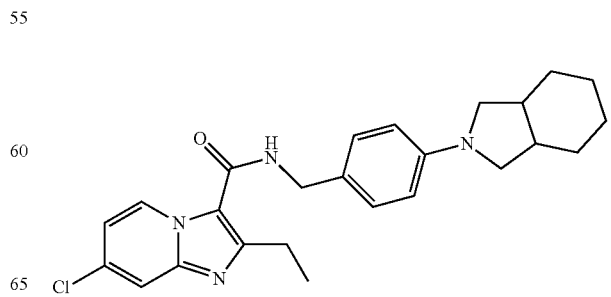

White solid; ¹H NMR (400 MHz, CDCl₃); δ 1.36 (t, J=7.6 Hz, 3H), 1.40-2.03 (m, 8H), 2.29-2.34 (m, 2H), 2.92 (q, J=7.2 Hz, 2H), 3.16 (dd, J=5.2 Hz, 9.2 Hz, 2H), 3.29 (dd, J=6.8 Hz, 8.8 Hz, 2H), 4.55 (d, J=5.2 Hz, 2H), 5.97 (brs, 1H), 6.49 (d, J=8.4 Hz, 2H), 6.88 (dd, J=2.4 Hz, 7.6 Hz, 1H), 7.21 (d, J=8.4 Hz, 2H), 7.56 (d, J=2.4 Hz, 1H), 9.33 (d, J=7.6 Hz, 1H); LCMS (electrospray) m/z (M+H)⁺ 437, 439 (Cl⁻ isotope pattern)

7-Chloro-2-ethyl-N-(4-(4,5,6,7-tetrahydro-2H-isoindol-2-yl)benzyl)imidazo[1,2-a]pyridine-3-carboxamide (225)

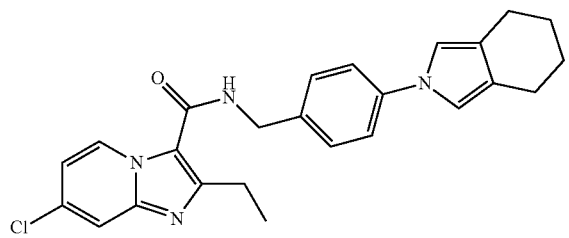 [SMILES: CCc1nc2cc(Cl)ccn2c1C(=O)NCc1ccc(-n2cc3c(c2)CCCC3)cc1]

White solid; ¹H NMR (400 MHz, CDCl₃); δ 1.39 (t, J=7.6 Hz, 3H), 1.74-1.77 (m, 4H), 2.63 (m, 4H), 2.97 (q, J=7.6 Hz, 2H), 4.68 (d, J=6.0 Hz, 2H), 6.14 (brs, 1H), 6.78 (s, 2H), 6.91 (dd, J=2.0 Hz, 7.6 Hz, 1H), 7.32 (d, J=8.4 Hz, 2H), 7.38 (d, J=8.4 Hz, 2H), 7.59 (d, J=2.0 Hz, 1H), 9.36 (d, J=7.2 Hz, 1H); LCMS (electrospray) m/z (M+H)⁺ 433, 435 (Cl⁻ isotope pattern).

6-Chloro-2-ethyl-N-((1-(4-(trifluoromethoxy)benzyl)piperidin-4-yl)methyl)imidazo[1,2-a]pyridine-3-carboxamide (226)

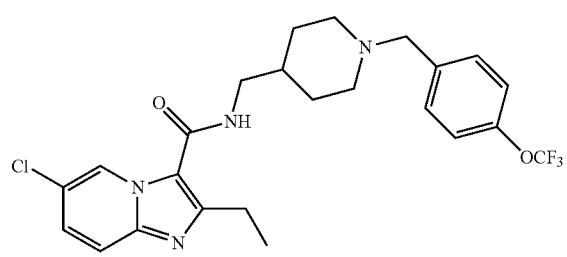 [SMILES: CCc1nc2ccc(Cl)cn2c1C(=O)NCC1CCN(Cc2ccc(OC(F)(F)F)cc2)CC1]

White solid; mp=171-172° C.; ¹H NMR (400 MHz, CDCl₃) δ 1.35-1.41 (m, 2H), 1.44 (t, J=7.6 Hz, 3H), 1.63-1.72 (m, 1H), 1.74-1.77 (m, 2H), 1.99-2.05 (m, 2H), 2.90-2.93 (m, 2H), 3.00 (q, J=7.6 Hz, 2H), 3.41 (t, J=6.2 Hz, 2H), 3.51 (s, 2H), 5.89 (t, J=5.4 Hz, 1H), 7.15 (d, J=8.0 Hz, 2H), 7.28 (dd, J=2.4, 9.6 Hz, 1H), 7.34 (d, J=8.4 Hz, 2H), 7.53 (d, J=9.6 Hz, 1H), 9.49 (d, J=1.6 Hz, 1H)); LCMS (electrospray) m/z (M+H)⁺ 495.34

6-Chloro-2-ethyl-N-((1-(4-fluorobenzyl)piperidin-4-yl)methyl)imidazo[1,2-a]pyridine-3-carboxamide (227)

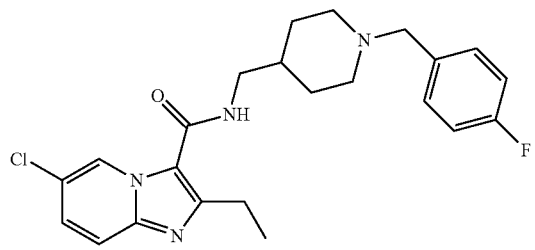 [SMILES: CCc1nc2ccc(Cl)cn2c1C(=O)NCC1CCN(Cc2ccc(F)cc2)CC1]

White solid; mp=176-177° C.; ¹H NMR (400 MHz, CDCl₃) δ 1.33-1.39 (m, 2H), 1.44 (t, J=7.6 Hz, 3H), 1.62-1.70 (m, 1H), 1.72-1.76 (m, 2H), 1.95-2.00 (m, 2H), 2.88-2.91 (m, 2H), 2.99 (q, J=7.6 Hz, 2H), 3.05 (t, J=6.4 Hz, 2H), 3.46 (s, 2H), 5.87-5.89 (m, 1H), 6.99 (dd, J=8.4, 8.8 Hz, 2H), 7.25-7.30 (m, 3H), 7.53 (d, J=9.6 Hz, 1H), 9.48 (d, J=1.6 Hz, 1H)); LCMS (electrospray) m/z (M+H)⁺ 429.29

7-Chloro-2-ethyl-N-((1-(4-(trifluoromethoxy)benzyl)piperidin-4-yl)methyl)imidazo[1,2-a]pyridine-3-carboxamide (228)

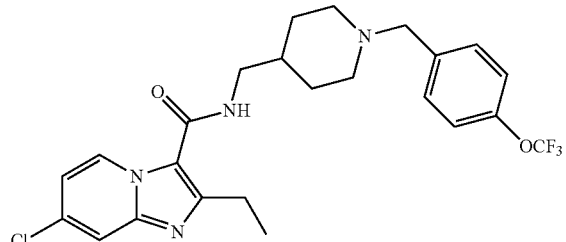

White solid; mp=145-146° C.; ¹H NMR (400 MHz, CDCl₃) δ 1.33-1.39 (m, 2H), 1.44 (t, J=7.6 Hz, 3H), 1.62-1.69 (m, 1H), 1.72-1.76 (m, 2H), 1.96-2.02 (m, 2H), 2.88-2.91 (m, 2H), 2.99 (q, J=7.6 Hz, 2H), 3.41 (t, J=6.4 Hz, 2H), 3.48 (s, 2H), 5.87 (t, J=5.4 Hz, 1H), 6.88 (dd, J=2.0, 7.6 Hz, 1H), 7.15 (d, J=8.0 Hz, 2H), 7.33 (d, J=8.4 Hz, 2H), 7.58 (d, J=2.4 Hz, 1H), 9.31 (d, J=7.2 Hz, 1H)); LCMS (electrospray) m/z (M+H)⁺ 495.20

6-Chloro-2-ethyl-N-(1-(4-(trifluoromethoxy)benzyl)piperidin-4-yl)imidazo[1,2-a]pyridine-3-carboxamide (229)

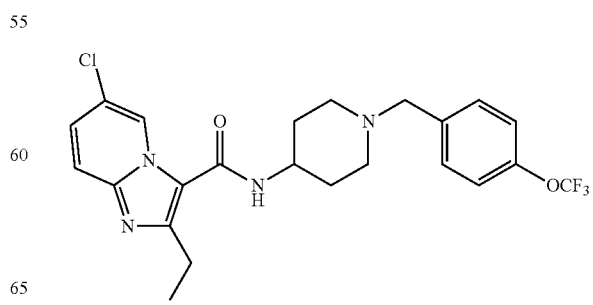

White solid; mp=157-158° C.; ¹H NMR (400 MHz, CDCl₃) δ 1.43 (t, J=7.6 Hz, 3H), 1.56-1.66 (m, 2H), 2.05-2.10 (m, 1H), 2.22-2.27 (m, 2H), 2.81-2.84 (m, 2H), 2.98 (q, J=7.6 Hz, 2H), 3.53 (s, 2H), 4.08-4.11 (m, 1H), 5.69-5.71 (m, 1H), 7.17 (d, J=8.0 Hz, 2H), 7.29 (dd, J=2.0, 9.6 Hz, 1H), 7.36 (d, J=8.4 Hz, 2H), 7.53 (d, J=9.2 Hz, 1H), 9.46 (d, J=1.6 Hz, 1H)); LCMS (electrospray) m/z (M+H)⁺ 481.26

(6-Chloro-2-ethylimidazo[1,2-a]pyridin-3-yl)(4-(4-(trifluoromethoxy)benzyloxy)piperidin-1-yl)methanone (230)

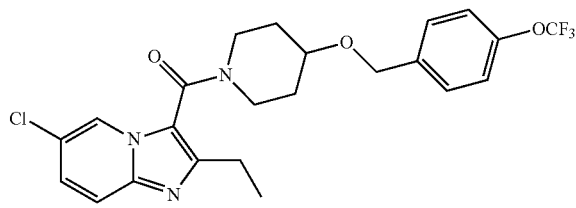 [SMILES: CCc1nc2ccc(Cl)cn2c1C(=O)N1CCC(OCc2ccc(OC(F)(F)F)cc2)CC1]

¹H NMR (400 MHz, CDCl₃) δ 1.38 (t, J=7.2 Hz, 3H), 1.71-1.78 (m, 2H), 1.94 (m, 2H), 2.78 (q, J=7.6 Hz, 2H), 3.51 (m, 2H), 3.74 (m, 1H), 3.89 (m, 2H), 4.58 (s, 2H), 7.19-7.23 (m, 3H), 7.38 (d, J=8.4 Hz, 2H), 7.51 (d, J=9.6 Hz, 1H), 8.48 (s, 1H); LCMS (electrospray) m/z (M+H)⁺ 481.26

6-Chloro-2-ethyl-N-((1-(4-(trifluoromethoxy)phenyl)-1H-pyrazol-3-yl)methyl) imidazo[1,2-a]pyridine-3-carboxamide (231)

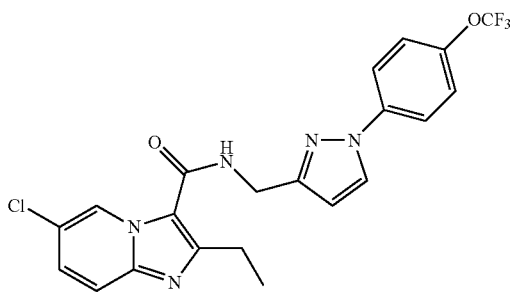 [SMILES: CCc1nc2ccc(Cl)cn2c1C(=O)NCc1ccn(-c2ccc(OC(F)(F)F)cc2)n1]

¹H NMR (400 MHz, CDCl₃) δ 1.48 (t, J=7.6 Hz, 3H), 3.12 (q, J=7.6 Hz, 2H), 4.80 (d, J=-4.8 Hz, 2H), 6.49 (d, J=2.4 Hz, 2H), 6.69 (brs, 1H), 7.29-7.33 (m, 3H), 7.55 (d, J=9.2 Hz, 1H), 7.70 (d, J=9.2 Hz, 2H), 7.90 (d, J=2.4 Hz, 1H), 9.56 (d, J=2.0 Hz, 1H); LCMS (electrospray) m/z (M+H)⁺ 464.19

7-Chloro-2-ethyl-N-((1-(4-(trifluoromethoxy)phenyl)-1H-pyrazol-3-yl)methyl) imidazo[1,2-a]pyridine-3-carboxamide (232)

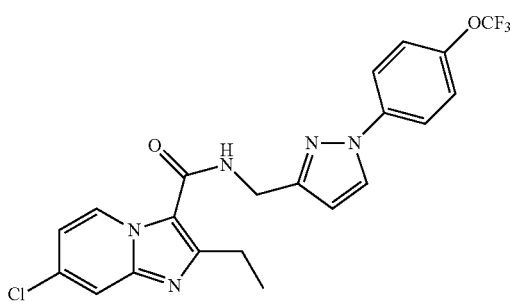 [SMILES: CCc1nc2cc(Cl)ccn2c1C(=O)NCc1ccn(-c2ccc(OC(F)(F)F)cc2)n1]

¹H NMR (400 MHz, CDCl₃) δ 1.47 (t, J=7.6 Hz, 3H), 3.11 (q, J=7.6 Hz, 2H), 4.79 (d, J=5.2 Hz, 2H), 6.48 (d, J=2.4 Hz, 2H), 6.68 (brs, 1H), 6.91 (dd, J=7.6, 2.0 Hz, 1H), 7.32 (d, J=8.4 Hz, 2H), 7.60 (d, J=2.0 Hz, 1H), 7.70 (d, J=6.8 Hz, 2H), 7.90 (d, J=2.0 Hz, 1H), 9.39 (d, J=7.6 Hz, 1H); LCMS (electrospray) m/z (M+H)⁺ 464.19

6-Chloro-2-ethyl-N-4-((1-(4-(trifluoromethyl)phenyl)-1H-pyrazol-3-yl)methyl)imidazo[1,2-a]pyridine-3-carboxamide (233)

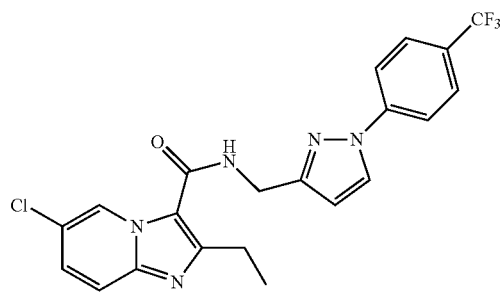 [SMILES: CCc1nc2ccc(Cl)cn2c1C(=O)NCc1ccn(-c2ccc(C(F)(F)F)cc2)n1]

¹H NMR (400 MHz, DMSO-d₆) δ 1.29 (t, J=7.6 Hz, 3H), 3.02 (q, J=7.6 Hz, 2H), 4.62 (d, J=5.6 Hz, 2H), 6.59 (d, J=2.8 Hz, 1H), 7.46 (dd, J=9.2, 1.6 Hz, 1H), 7.67 (d, J=9.2 Hz, 1H), 7.87 (d, J=8.8 Hz, 2H), 8.06 (d, J=8.4 Hz, 2H), 8.55 (t, J=5.6 Hz, 1H), 8.62 (d, J=2.4 Hz, 1H), 9.10 (d, J=2.0 Hz, 2H); LCMS (electrospray) m/z (M+H)⁺ 448.37

7-Chloro-2-ethyl-N-((1-(4-(trifluoromethyl)phenyl)-1H-pyrazol-3-yl)methyl)imidazo[1,2-a]pyridine-3-carboxamide (234)

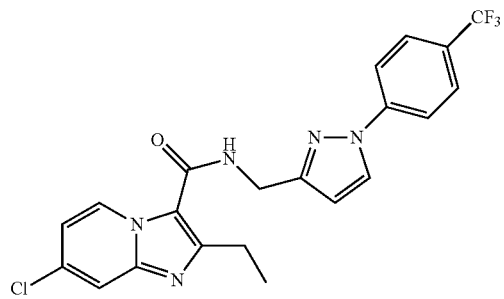 [SMILES: CCc1nc2cc(Cl)ccn2c1C(=O)NCc1ccn(-c2ccc(C(F)(F)F)cc2)n1]

¹H NMR (400 MHz, DMSO-d₆) δ 1.28 (t, J=7.6 Hz, 3H), 3.02 (q, J=7.6 Hz, 2H), 4.61 (d, J=5.6 Hz, 2H), 6.58 (d, J=2.8 Hz, 1H), 7.11 (dd, J=7.6, 2.0 Hz, 1H), 7.80 (d, J=2.0 Hz, 1H), 7.87 (d, J=8.8 Hz, 2H), 8.06 (d, J=8.8 Hz, 2H), 8.52 (t, J=5.6 Hz, 1H), 8.61 (d, J=2.4 Hz, 1H), 8.97 (d, J=7.6 Hz, 1H); LCMS (electrospray) m/z (M+H)⁺ 448.13

6-Chloro-2-ethyl-N-((1-(4-fluorophenyl)-1H-pyrazol-3-yl)methyl)imidazo[1,2-a]pyridine-3-carboxamide (235)

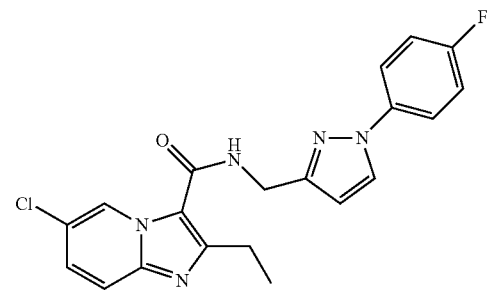 [SMILES: CCc1nc2ccc(Cl)cn2c1C(=O)NCc1ccn(-c2ccc(F)cc2)n1]

¹H NMR (400 MHz, CDCl₃) δ 1.47 (t, J=7.6 Hz, 3H), 3.11 (q, J=7.6 Hz, 2H), 4.79 (d, J=4.8 Hz, 2H), 6.46 (d, J=2.0 Hz, 1H), 6.70 (brs, 1H), 7.16 (dd, J=8.8 Hz, 2H), 7.30 (dd, J=9.2, 2.0 Hz, 1H), 7.55 (d, J=9.6 Hz, 1H), 7.61-7.64 (m, 2H), 7.85 (d, J=2.4 Hz, 1H), 9.56 (d, J=2.0 Hz, 1H); LCMS (electrospray) m/z (M+H)⁺ 398.32

7-Chloro-2-ethyl-N-((1-(4-fluorophenyl)-1H-pyrazol-3-yl)methyl)imidazo[1,2-a]pyridine-3-carboxamide (236)

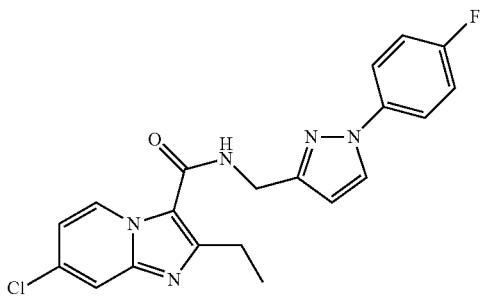 [SMILES: CCc1nc2cc(Cl)ccn2c1C(=O)NCc1ccn(-c2ccc(F)cc2)n1]

¹H NMR (400 MHz, CDCl₃) δ 1.46 (t, J=7.6 Hz, 3H), 3.11 (q, J=7.6 Hz, 2H), 4.78 (d, J=4.8 Hz, 2H), 6.46 (d, J=2.0 Hz, 1H), 6.69 (brs, 1H), 6.91 (dd, J=7.6, 2.4 Hz, 1H), 7.16 (dd, J=8.8 Hz, 2H), 7.59-7.64 (m, 3H), 7.85 (d, J=2.4 Hz, 1H), 9.39 (d, J=7.6 Hz, 1H); LCMS (electrospray) m/z (M+H)⁺ 398.14

6-Chloro-2-ethyl-N-((1-(4-(trifluoromethoxy)phenyl)-4,5,6,7-tetrahydro-1,1-indazol-4-yl)methyl)imidazo[1,2-a]pyridine-3-carboxamide (237)

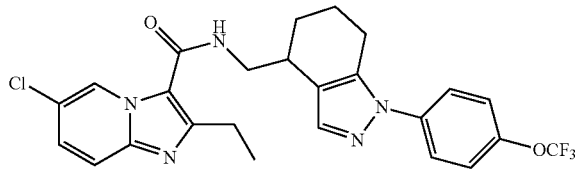 [SMILES: CCc1nc2ccc(Cl)cn2c1C(=O)NCC1CCCc2c1cnn2-c1ccc(OC(F)(F)F)cc1]

¹H NMR (400 MHz, CDCl₃) δ 1.41 (t, J=7.6 Hz, 3H), 1.89-1.98 (m, 3H), 2.27 (m, 1H), 2.77-2.84 (m, 2H), 2.96 (q, J=7.6 Hz, 2H), 5.40 (m, 1H), 5.96 (d, J=8.0 Hz, 1H), 7.29-7.34 (m, 3H), 7.54-7.58 (m, 3H), 7.70 (s, 1H), 9.54 (d, J=1.2 Hz, 1H); LCMS (electrospray) m/z (M+H)⁺ 504.25

6-Chloro-2-ethyl-N-((1-(4-fluorophenyl)-4,5,6,7-tetrahydro-1H-indazol-4-yl)methyl) imidazo[1,2-a]pyridine-3-carboxamide (238)

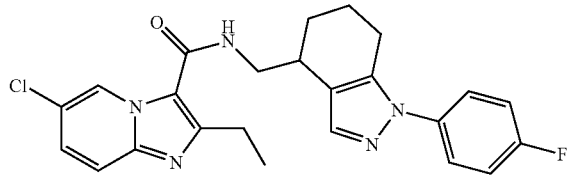 [SMILES: CCc1nc2ccc(Cl)cn2c1C(=O)NCC1CCCc2c1cnn2-c1ccc(F)cc1]

¹H NMR (400 MHz, CDCl₃) δ 1.42 (t, J=7.6 Hz, 3H), 1.88-1.97 (m, 3H), 2.26 (m, 1H), 2.74-2.78 (m, 2H), 2.96 (q, J=7.6 Hz, 2H), 5.40 (m, 1H), 5.96 (d, J=7.6 Hz, 1H), 7.17 (dd, J=8.0, 8.8 Hz, 2H), 7.31 (dd, J=9.2, 2.0 Hz, 1H), 7.48-7.50 (m, 2H), 7.55 (d, J=9.2 Hz, 1H), 7.68 (s, 1H), 9.54 (d, J=2.0 Hz, 1H); LCMS (electrospray) m/z (M+H)⁺ 438.40

6-Chloro-2-ethyl-3-((4-(trifluoromethoxy)phenoxy)methyl)imidazo[1,2-a]pyridine (239)

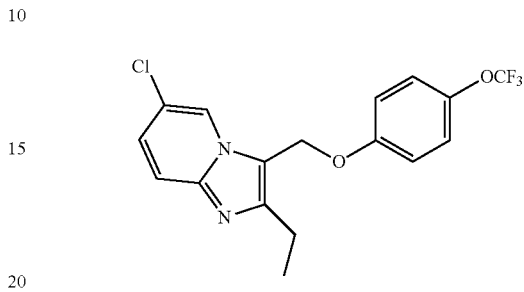

White solid; mp=127-128° C.; ¹H NMR (400 MHz, CDCl₃) δ 1.34 (t, J=7.6 Hz, 3H), 2.82 (q, J=7.6 Hz, 2H), 5.27 (s, 2H), 7.00 (d, J=9.2 Hz, 2H), 7.19 (d, J=9.2 Hz, 2H), 7.53 (dd, J=0.8, 9.2 Hz, 1H), 8.12 (dd, J=0.8, 2.0 Hz, 1H); LCMS (electrospray) m/z (M+H)⁺ 371.07

N-((6-Chloro-2-ethylimidazo[1,2-a]pyridin-3-yl)methyl)-4-(trifluoromethoxy)aniline (240)

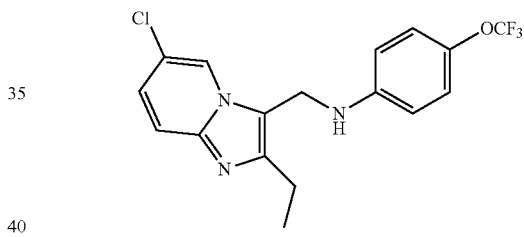

White solid; ¹H NMR (400 MHz, CDCl₃) δ 1.35 (J=7.6 Hz, 3H), 2.82 (q, J=7.2 Hz, 2H), 3.67 (t, J=4.6 Hz, 1H), 4.50 (d, J=5.2 Hz, 2H), 6.72 (d, J=8.8 Hz, 2H), 7.13 (d, J=8.8 Hz, 2H), 7.51 (dd, J=2.0, 9.6 Hz, 1H), 7.51 (d, J=9.6 Hz, 1H), 8.10 (d, J=12 Hz, 1H); LCMS (electrospray) m/z (M+H)⁺ 370.11

N-((6-Chloro-2-ethylimidazo[1,2-a]pyridin-3-yl)methyl)-4-(4-(4-fluorophenyl)piperazin-1-yl)aniline (241)

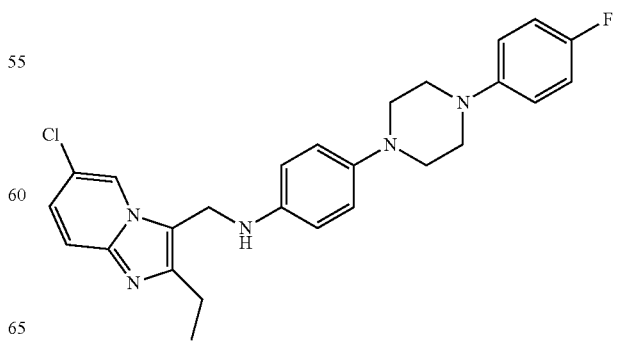

White solid; mp=191-192° C.; ¹H NMR (400 MHz, CDCl₃) δ 1.35 (J=7.6 Hz, 3H), 2.82 (q, J=7.2 Hz, 2H), 3.22-3.24 (m, 4H), 3.26-3.28 (m, 4H), 3.40 (br s, 1H), 4.50 (s, 2H), 6.75 (d, J=8.8 Hz, 2H), 6.92-7.01 (m, 6H), 7.14 (dd, J=1.6, 9.2 Hz, 1H), 7.51 (d, J=9.6 Hz, 1H), 8.18 (d, J=1.2 Hz, 1H); LCMS (electrospray) m/z (M+H)⁺ 464.32

N-((6-Chloro-2-ethylimidazo[1,2-a]pyridin-3-yl)methyl)-4-(4-fluorophenoxy)aniline (242)

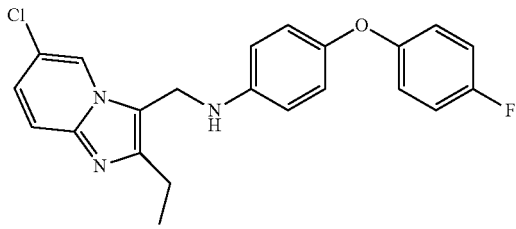 [SMILES: CCc1nc2ccc(Cl)cn2c1CNc1ccc(Oc2ccc(F)cc2)cc1]

White solid; mp=148.6-148.8° C.; ¹H NMR (400 MHz, CDCl₃) δ 1.35 (t, J=7.4 Hz, 3H), 2.82 (q, J=7.6 Hz, 2H), 4.50 (s, 2H), 6.74 (d, J=8.8 Hz, 2H), 6.90-7.01 (m, 6H), 7.15 (dd, J=2.0, 9.6 Hz, 1H), 7.52 (d, J=9.2 Hz, 1H), 8.16 (d, J=1.2 Hz, 1H); LCMS (electrospray) m/z (M+H)⁺ 396.17

5-(6-Chloro-2-ethylimidazo[1,2-a]pyridin-3-yl)-3-(4-(trifluoromethoxy)benzyl)-1,2,4-oxadiazole (243)

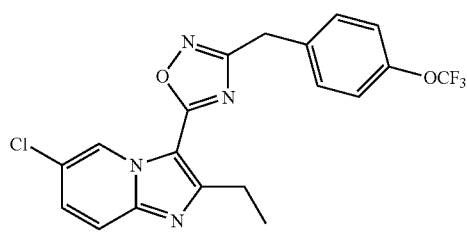 [SMILES: CCc1nc2ccc(Cl)cn2c1-c1nc(Cc2ccc(OC(F)(F)F)cc2)no1]

Pale yellow solid; mp=146.4-146.9° C.; ¹H NMR (400 MHz, CDCl₃) δ 1.42 (t, J=7.6 Hz, 3H), 3.22 (q, 0.1=7.2 Hz, 2H), 4.20 (s, 2H), 7.21 (d, J=8.0 Hz, 2H), 7.40 (dd, J=2.0, 9.6 Hz, 1H), 7.46 (d, J=8.8 Hz, 2H), 7.65 (d, J=9.6 Hz, 1H), 8.47 (d, J=1.2 Hz, 1H); LCMS (electrospray) m/z (M+H)⁺ 423.10

2-(7-Chloro-2-ethylimidazo[1,2-a]pyridin-3-yl)-5-((4-(4-(trifluoromethoxy)phenyl)piperazin-1-yl)methyl)-1,3,4-oxadiazole (244)

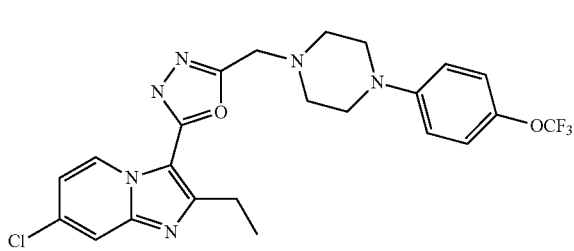

Pale yellow solid; ¹H NMR (400 MHz, CDCl₃) 1.41 (t, J=7.4 Hz, 3H), 2.83 (t, J=4.8 Hz, 4H), 3.16 (q, J=7.6 Hz, 2H), 3.23 (t, J=4.8 Hz, 4H), 4.02 (s, 2H), 6.88 (d, J=9.2 Hz, 2H), 7.05 (dd, J=2.0, 9.6 Hz, 1H), 7.10 (d, J=8.4 Hz, 2H), 7.70 (d, J=1.6 Hz, 1H), 9.42 (d, J=7.6 Hz, 1H); LCMS (electrospray) m/z (M+H)⁺ 507.24

5-(6-Chloro-2-ethylimidazo[1,2-a]pyridin-3-yl)-3-(4-(4-fluorophenoxy)benzyl)-1,2,4-oxadiazole (245)

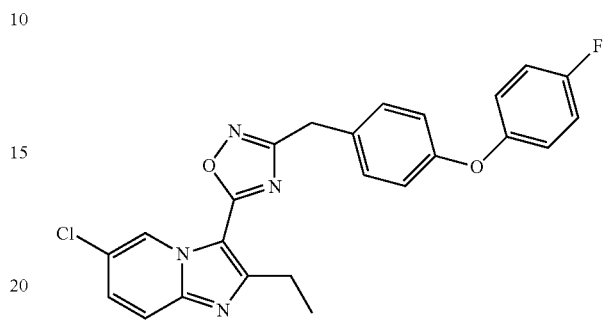

Yellow solid; mp=129.9° C.; ¹H NMR (400 MHz, CDCl₃) δ 1.41 (t, J=7.8 Hz, 3H), 3.22 (q, J=7.2 Hz, 2H), 4.16 (s, 2H), 6.93-7.04 (m, 6H), 7.36-7.39 (m, 3H), 7.63 (d, J=9.6 Hz, 1H), 9.48 (d, J=2.0 Hz, 1H); LCMS (electrospray) m/z (M+H)⁺ 449

6-Chloro-N,2-diethylimidazo[1,2-a]pyridine-3-carboxamide (246)

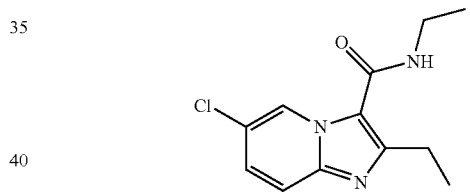

White solid; mp=176.7° C.; ¹H NMR (400 MHz, CDCl₃); δ 1.29 (t, J=7.2 Hz, 3H), 1.43 (t, J=7.6 Hz, 3H), 2.99 (q, J=7.2 Hz, 2H), 3.51-3.57 (m, 2H), 5.79 (brs, 1H), 7.27 (dd, J=2.4 Hz, 9.6 Hz, 1H), 7.51 (d, J=9.6 Hz, 1H), 9.45 (d, J=2.4 Hz, 1H); LCMS (electrospray) m/z (M+H)⁺ 252.

6-Chloro-2-ethyl-N-isobutylimidazo[1,2-a]pyridine-3-carboxamide (247)

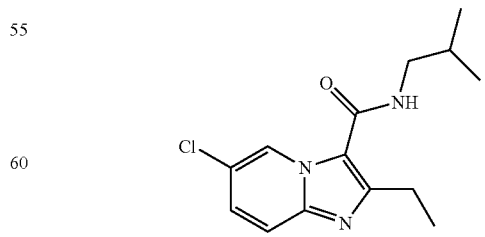

White solid; mp=162.2° C.; ¹H NMR (400 MHz, CDCl₃); δ 1.01 (d, J=6.8 Hz, 6H), 1.45 (t, J=7.6 Hz, 3H), 1.90-1.97 (m, 1H), 3.01 (q, J=7.6 Hz, 2H), 3.34 (t, J=6.8 Hz, 2H), 5.86 (brs, 1H), 7.28 (dd, J=2.0 Hz, 9.6 Hz, 1H), 7.53 (d, J=9.6 Hz, 1H), 9.47 (d, J=2.0 Hz, 1H); LCMS (electrospray) m/z (M+H)+ 280.

7-Chloro-2-ethyl-N-((4'-(trifluoromethoxy)biphenyl-3-yl)methyl)imidazo[1,2-a]pyridine-3-carboxamide (248)

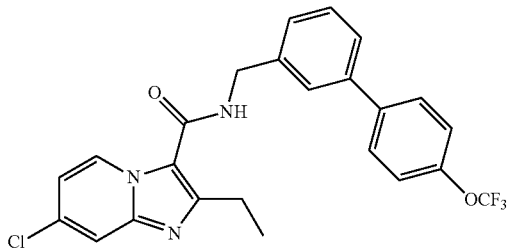 [SMILES: CCc1nc2cc(Cl)ccn2c1C(=O)NCc1cccc(-c2ccc(OC(F)(F)F)cc2)c1]

White solid; mp=192.6° C.; $^1$H NMR (400 MHz, CDCl$_3$); δ 1.37 (t, J=7.2 Hz, 3H), 2.95 (q, J=7.2 Hz, 2H), 4.75 (d, J=6.0 Hz, 2H), 6.19 (brt, J=6.0 Hz, 1H), 6.88 (dd, J=2.0, 7.6 Hz, 1H), 7.26 (d, J=8.8 Hz, 2H), 7.36 (d, J=7.6 Hz, 1H), 7.43 (dd, J=7.2, 7.6 Hz, 1H), 7.48-7.59 (m, 5H), 9.33 (d, J=7.6 Hz, 1H); LCMS (electrospray) m/z 474, 476 (M+H)+ (Cl− isotope pattern).

2-Ethyl-7-methyl-N-(4-(trifluoromethoxy)benzyl)imidazo[1,2-a]pyridine-3-carboxamide (249)

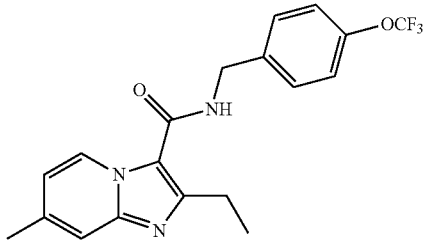 [SMILES: CCc1nc2cc(C)ccn2c1C(=O)NCc1ccc(OC(F)(F)F)cc1]

Pale yellow solid; $^1$H NMR (400 MHz, CDCl$_3$); δ 1.33 (t, J=7.6 Hz, 3H), 2.91 (q, J=7.6 Hz, 2H), 4.64 (d, J=5.2 Hz, 2H), 6.25 (brt, J=5.2 Hz, 1H), 6.69 (dd, J=1.6, 7.2 Hz, 1H), 7.16 (d, J=8.4 Hz, 2H), 7.30 (s, 1H), 7.35 (d, J=8.4 Hz, 2H), 9.19 (d, J=7.2 Hz, 1H).

7-Bromo-2-ethyl-N-(4-(trifluoromethoxy)benzyl)imidazo[1,2-a]pyridine-3-carboxamide (250)

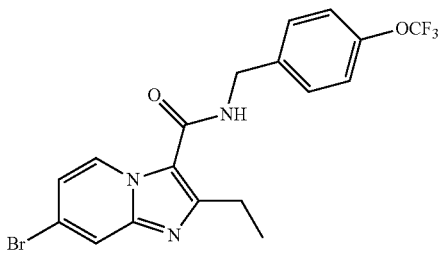 [SMILES: CCc1nc2cc(Br)ccn2c1C(=O)NCc1ccc(OC(F)(F)F)cc1]

White solid; $^1$H NMR (400 MHz, CDCl$_3$); δ 1.37 (t, J=7.6 Hz, 3H), 2.94 (q, J=7.6 Hz, 2H), 4.67 (d, J=5.6 Hz, 2H), 6.18 (brt, J=5.6 Hz, 1H), 6.99 (dd, J=1.6, 7.2 Hz, 1H), 7.19 (d, J=8.4 Hz, 2H), 7.38 (d, J=8.4 Hz, 2H), 7.75 (d, J=1.6 Hz, 1H), 9.25 (d, J=7.2 Hz, 1H).

2-Ethyl-8-fluoro-N-(4-(trifluoromethoxy)benzyl)imidazo[1,2-a]pyridine-3-carboxamide (251)

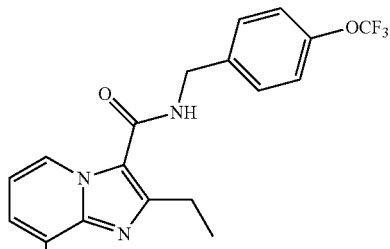

White solid; $^1$H NMR (400 MHz, CDCl$_3$); δ 1.38 (t, J=7.6 Hz, 3H), 2.97 (q, J=7.6 Hz, 2H), 4.68 (d, J=6.0 Hz, 2H), 6.25 (brs, 1H), 6.79-6.84 (m, 1H), 7.00 (dd, J=8.0, 9.6 Hz, 1H), 7.19 (d, J=8.4 Hz, 2H), 7.38 (d, J=8.4 Hz, 2H), 9.16 (d, J=6.8 Hz, 1H).

7-Chloro-2-ethyl-N-((4'-formylbiphenyl-4-yl)methyl)imidazo[1,2-a]pyridine-3-carboxamide (252)

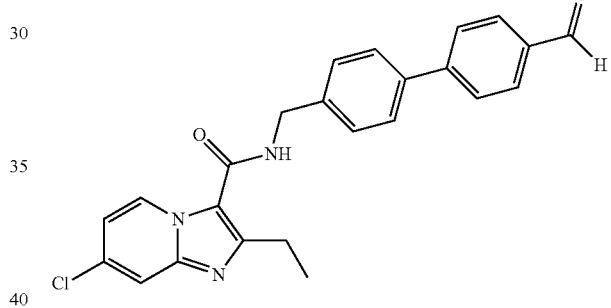

White solid; $^1$H NMR (400 MHz, CDCl$_3$); δ 1.40 (t, J=7.6 Hz, 3H), 2.97 (q, J=7.6 Hz, 2H), 4.75 (d, J=6.0 Hz, 2H), 6.18 (brt, J=6.0 Hz, 1H), 6.89 (dd, J=2.4, 7.6 Hz, 1H), 7.47 (d, J=8.4 Hz, 2H), 7.59 (d, J=2.4 Hz, 1H), 7.63 (d, J=8.0 Hz, 2H), 7.73 (d, J=8.0 Hz, 2H), 7.93 (d, J=8.4 Hz, 2H), 9.36 (d, J=7.6 Hz, 1H), 10.05 (s, 1H); $^{13}$C NMR (100 MHz, CDCl$_3$) δ 13.4, 23.8, 43.4, 114.9, 115.9, 127.8, 128.0, 128.4, 128.7, 130.5, 133.8, 135.5, 138.7, 139.3, 146.3, 146.7, 151.9, 161.4, 192.0 (hidden 1 aromatic carbon).

2-Ethyl-6-fluoro-N-(4-(4-(trifluoromethoxy)phenoxy)benzyl)imidazo[1,2-a]pyridine-3-carboxamide (253)

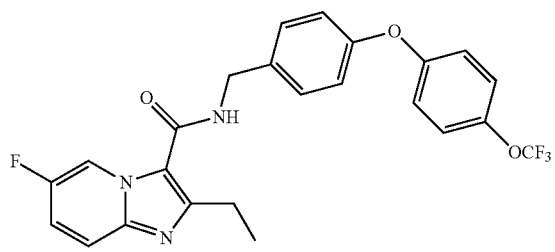 [SMILES: CCc1nc2ccc(F)cn2c1C(=O)NCc1ccc(Oc2ccc(OC(F)(F)F)cc2)cc1]

White solid; mp=133.4° C.; ¹H NMR (400 MHz, CDCl₃) δ 1.42 (t, J=7.6 Hz, 3H), 3.00 (q, J=7.6 Hz, 2H), 4.68 (d, J=5.6 Hz, 2H), 6.12-6.14 (m, 1H), 6.98-7.03 (m, 4H), 7.18 (d, J=8.8 Hz, 2H), 7.23-7.28 (m, 1H), 7.58 (dd, J=5.2, 9.6 Hz, 1H), 9.44-9.46 (m, 1H); LCMS (electrospray) m/z (M+H)⁺ 474.

6-Bromo-2-ethyl-N-(4-(4-(trifluoromethoxy)phenoxy)benzyl)imidazo[1,2-a]pyridine-3-carboxamide (254)

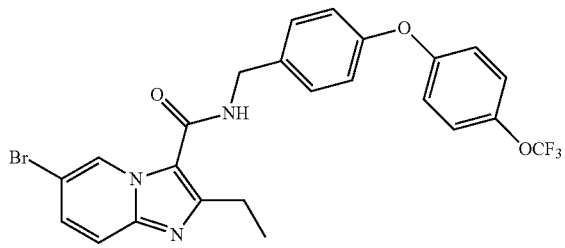

White solid; mp=152.9° C.; ¹H NMR (400 MHz, CDCl₃) δ 1.42 (t, J=7.4 Hz, 3H), 2.99 (q, J=7.6 Hz, 2H), 4.68 (d, J=5.6 Hz, 2H), 6.12-6.14 (m, 1H), 6.98-6.03 (m, 4H), 7.18 (d, J=8.8 Hz, 2H), 7.37 (d, J=8.4 Hz, 1H), 7.40 (dd, J=2.0, 9.6 Hz, 1H), 7.50 (d, J=9.2 Hz, 1H), 9.63 (d, J=1.2 Hz, 1H)); LCMS (electrospray) m/z (M+H)⁺ 534, 536 (Br⁻ isotope pattern).

2-Ethyl-6-methyl-N-(4-(4-(trifluoromethoxy)phenoxy)benzyl)imidazo[1,2-a]pyridine-3-carboxamide (255)

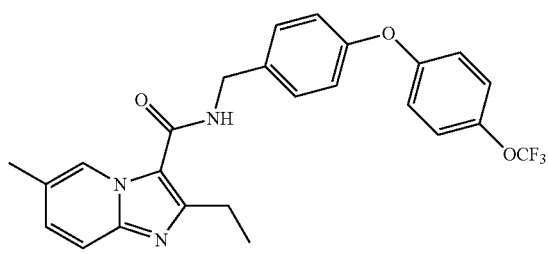 [SMILES: CCc1nc2ccc(C)cn2c1C(=O)NCc1ccc(Oc2ccc(OC(F)(F)F)cc2)cc1]

Pale yellow solid; ¹H NMR (400 MHz, CDCl₃); δ 1.31 (t, J=7.6 Hz, 3H), 2.30 (s, 3H), 2.90 (q, J=7.6 Hz, 2H), 4.62 (d, J=5.6 Hz, 2H), 6.32 (brt, J=5.6 Hz, 1H), 6.93-6.96 (m, 4H), 7.11-7.14 (m, 3H), 7.31 (d, J=8.4 Hz, 2H), 7.42 (d, J=8.4 Hz, 1H), 9.11 (s, 1H); LCMS (electrospray) m/z 470 (M+H)⁺.

2-Ethyl-7-methyl-N-(4-(4-(trifluoromethoxy)phenoxy)benzyl)imidazo[1,2-a]pyridine-3-carboxamide (256)

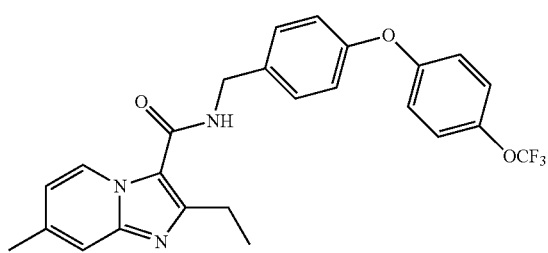 [SMILES: CCc1nc2cc(C)ccn2c1C(=O)NCc1ccc(Oc2ccc(OC(F)(F)F)cc2)cc1]

Pale yellow solid; mp=133.6° C.; ¹H NMR (400 MHz, CDCl₃); δ 1.36 (t, J=7.6 Hz, 3H), 2.39 (s, 3H), 2.93 (q, J=7.6 Hz, 2H), 4.65 (d, J=5.6 Hz, 2H), 6.13 (brt, J=5.6 Hz, 1H), 6.71 (dd, J=1.6; 7.2 Hz, 1H), 6.96-7.00 (m, 4H), 7.15 (d, J=8.4 Hz, 2H), 7.32-7.37 (m, 3H), 9.23 (d, J=7.2 Hz, 1H); LCMS (electrospray) m/z 470 (M+H)⁺.

2-Ethyl-8-fluoro-N-(4-(4-(trifluoromethoxy)phenoxy)benzyl)imidazo[1,2-a]pyridine-3-carboxamide (257)

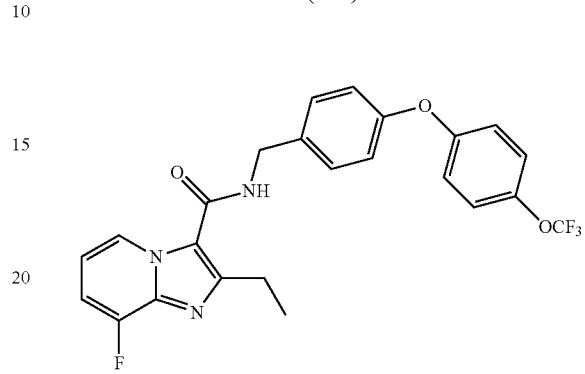

Pale yellow solid; mp=105.6° C.; ¹H NMR (400 MHz, CDCl₃); δ 1.35 (t, J=7.6 Hz, 3H), 2.96 (q, J=7.6 Hz, 2H), 4.65 (d, J=5.6 Hz, 2H), 6.29 (brt, J=5.6 Hz, 1H); 6.77-6.82 (m, 1H), 6.96-7.02 (m, 5H), 7.13-7.17 (m, 2H), 7.32-7.35 (m, 2H), 9.12 (dd, J=0.8, 7.2 Hz, 1H); LCMS (electrospray) m/z 474 (M+H)⁺.

2-Ethyl-6-fluoro-N-(4-(4-(trifluoromethoxy)benzyloxy)benzyl)imidazo[1,2-a]pyridine-3-carboxamide (258)

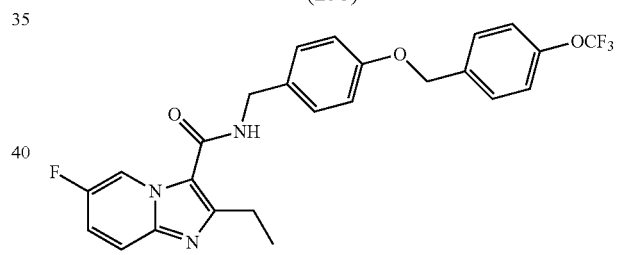

White solid; ¹H NMR (400 MHz, CDCl₃); δ 1.37 (t, J=7.2 Hz, 3H), 2.93 (q, J=7.2 Hz, 2H), 4.62 (d, J=5.6 Hz, 2H), 5.06 (s, 2H), 6.06 (brt, J=5.6 Hz, 1H), 6.95 (d, J=8.8 Hz, 2H), 7.22-7.26 (m, 3H), 7.29 (d, J=8.4 Hz, 2H), 7.45 (d, J=8.8 Hz, 2H), 7.47-7.58 (m, 1H), 9.43-9.45 (m, 1H); LCMS (electrospray) m/z 488 (M+H)⁺.

6-Bromo-2-ethyl-N-(4-(4-(trifluoromethoxy)benzyloxy)benzyl)imidazo[1,2-a]pyridine-3-carboxamide (259)

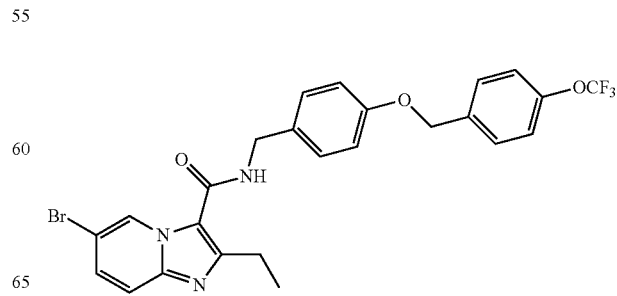

Pale yellow solid; mp=189.7° C.; ¹H NMR (400 MHz, CDCl₃); δ 1.36 (t, J=7.6 Hz, 3H), 2.92 (q, J=7.6 Hz, 2H), 4.62 (d, J=5.6 Hz, 2H), 5.05 (s, 2H), 6.06 (brt, J=5.6 Hz, 1H), 6.95 (d, J=8.4 Hz, 2H), 7.21 (d, J=8.4 Hz, 2H), 7.29 (d, J=8.8 Hz, 2H), 7.36 (dd, J=2.0, 9.2 Hz, 1H), 7.43-7.49 (m, 3H), 9.60 (d, J=2.0 Hz, 1H); LCMS (electrospray) m/z 548, 550 (M+H)⁺ (Br⁻ isotope pattern).

2-Ethyl-N-(4-(4-(trifluoromethoxy)benzyloxy)benzyl)imidazo[1,2-a]pyridine-3-carboxamide (260)

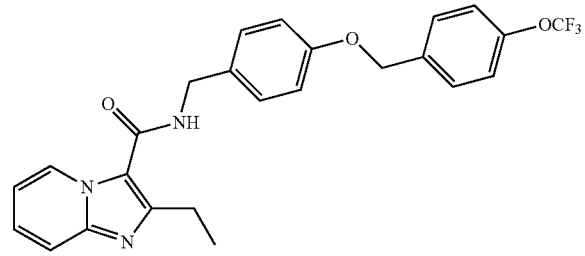 [SMILES: CCc1nc2ccccn2c1C(=O)NCc1ccc(OCc2ccc(OC(F)(F)F)cc2)cc1]

White solid; mp=138.7° C.; ¹H NMR (400 MHz, CDCl₃); δ 1.35 (t, J=7.6 Hz, 3H), 2.91 (q, J=7.6 Hz, 2H), 4.60 (d, J=5.6 Hz, 2H), 5.03 (s, 2H), 6.14 (brt, J=5.6 Hz, 1H), 6.85 (ddd, J=1.2, 7.2, 7.2 Hz, 1H), 6.92 (d, J=8.0 Hz, 2H), 7.20 (d, J=8.0 Hz, 2H), 7.26-7.30 (m, 3H), 7.42 (d, J=8.8 Hz, 2H), 7.55 (d, J=9.2 Hz, 1H), 9.33 (d, J=7.2 Hz, 1H); LCMS (electrospray) m/z 470 (M+H)⁺.

(E)-7-Chloro-2-ethyl-N-(4-((4-(trifluoromethoxy)benzylidene)amino)benzyl)imidazo[1,2-a]pyridine-3-carboxamide (261)

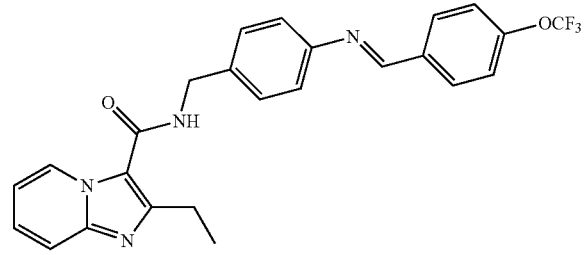 [SMILES: CCc1nc2ccccn2c1C(=O)NCc1ccc(/N=C/c2ccc(OC(F)(F)F)cc2)cc1]

Off-white solid; mp=194° C.; ¹H NMR (400 MHz, CDCl₃) δ 1.42 (t, J=7.4 Hz, 3H), 3.00 (q, J=7.6 Hz, 2H), 4.72 (d, J=5.2 Hz, 2H), 6.14 (t, J=5.2 Hz, 1H), 6.90-6.94 (m, 1H), 7.22 (d, J=8.0 Hz, 2H), 7.30-7.35 (m, 3H), 7.42 (d, J=8.4 Hz, 2H), 7.61 (d, J=8.8 Hz, 1H), 7.94 (d, J=8.8 Hz, 2H), 8.45 (s, 1H), 9.41 (d, J=7.2 Hz, 1H); LCMS (electrospray) m/z (M+H)⁺ 467.

7-Chloro-2-ethyl-N-(4-((4-(trifluoromethoxy)benzyl)amino)benzyl)imidazo[1,2-a]pyridine-3-carboxamide (262)

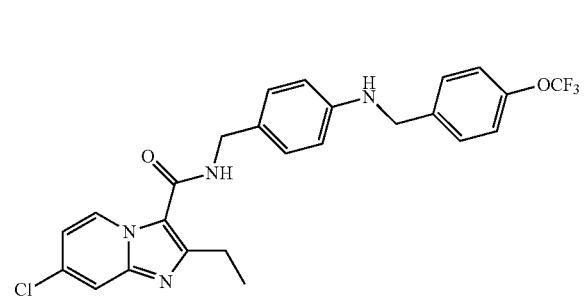 [SMILES: CCc1nc2cc(Cl)ccn2c1C(=O)NCc1ccc(NCc2ccc(OC(F)(F)F)cc2)cc1]

White solid; mp=169.6° C.; ¹H NMR (400 MHz, CDCl₃) δ 1.36 (t, J=7.6 Hz, 3H), 2.05-2.12 (m, 2H), 2.93 (q, J=7.2 Hz, 2H), 4.18 (br s, 1H), 4.55 (d, J=5.2 Hz, 2H), 5.99-6.01 (m, 1H), 6.60 (d, J=8.4 Hz, 2H), 6.87 (d, J=7.6 Hz, 1H), 7.17 (d, J=8.0 Hz, 4H), 7.38 (d, J=8.0 Hz, 2H), 7.56 (s, 1H), 9.33 (d, J=7.2 Hz, 1H); LCMS (electrospray) m/z (M+H)⁺ 503.

2-Ethyl-N-(4-(methyl(4-(trifluoromethoxy)benzyl)amino)benzyl)imidazo[1,2-a]pyridine-3-carboxamide (263)

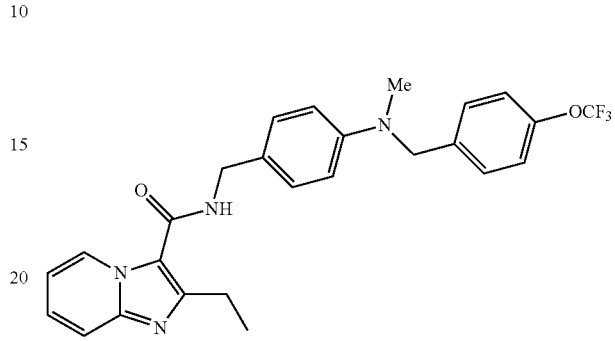

Off-white solid; ¹H NMR (400 MHz, CDCl₃) δ 1.39 (t, J=7.6 Hz, 3H), 2.96 (q, J=7.6 Hz, 2H), 3.03 (s, 3H), 4.53 (s, 2H), 4.59 (d, J=5.6 Hz, 2H), 5.98-5.99 (m, 1H), 6.72 (d, J=8.8 Hz, 2H), 6.89-6.92 (m, 1H), 7.16 (d, J=8.0 Hz, 2H), 7.24 (d, J=8.8 Hz, 1H), 7.29-7.33 (m, 1H), 7.60 (d, J=8.8 Hz, 1H), 9.39 (d, J=6.8 Hz, 1H); LCMS (electrospray) m/z (M+H)⁺ 505.

7-Chloro-2-ethyl-N-(4-(4-fluorophenoxy)benzyl)imidazo[1,2-a]pyridine-3-carboxamide (264)

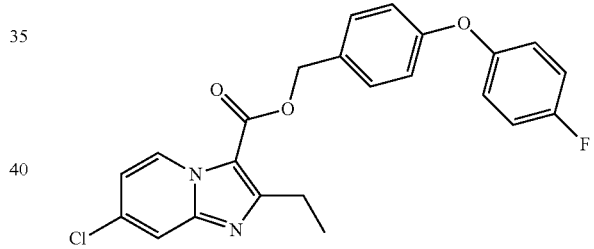

White solid; mp=89.7° C.; ¹H NMR (400 MHz, CDCl₃) δ 1.298 (t, J=7.6 Hz, 3H), 3.07 (q, J=7.6 Hz, 2H), 5.37 (s, 2H), 6.93-7.05 (m, 7H), 7.41 (d, J=8.8 Hz, 2H), 7.62 (d, J=2.0 Hz, 1H), 9.24 (d, J=7.6 Hz, 1H); LCMS (electrospray) m/z (M+H)⁺ 425.

7-Chloro-2-ethyl-N-(4-(hexahydropyrrolo[1,2-a]pyrazin-2(1H)-yl)benzyl)imidazo[1,2-a]pyridine-3-carboxamide (265)

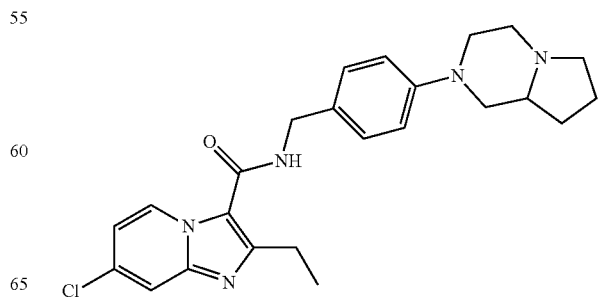

White solid; mp=159.1° C.; ¹H NMR (400 MHz, CDCl₃); δ 1.20 (t, J=7.2 Hz, 3H), 1.85-1.92 (m, 2H), 2.01-2.03 (m, 2H), 2.17-2.21 (m, 2H), 2.39-2.58 (m, 5H), 3.14-3.16 (m, 2H), 3.61 (d, J=11.6 Hz, 1H), 3.75 (d, J=10.0 Hz, 1H), 4.59 (d, J=5.2 Hz, 2H), 6.01 (brs, 1H), 6.88 (dd, J=1.6 Hz, 7.2 Hz, 1H), 6.93 (d, J=8.4 Hz, 2H), 7.25 (d, J=8.4 Hz, 2H), 7.56 (d, J=1.6 Hz, 1H), 9.34 (d, J=7.2 Hz, 1H); LCMS (electrospray) m/z (M+H)⁺ 438.

6-Chloro-2-ethyl-N-(4-(hexahydropyrrolo[1,2-a]pyrazin-2(1H)-yl)benzyl)imidazo[1,2-a]pyridine-3-carboxamide (266)

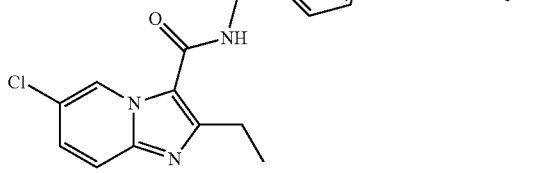

White solid; mp=163.0° C.; ¹H NMR (400 MHz, CDCl₃); δ 1.38 (t, J=7.6 Hz, 3H), 1.47-1.53 (m, 2H), 1.65-1.85 (m, 2H), 2.17 (t, J=8.8 Hz, 2H), 2.34-2.40 (m, 1H), 2.54 (t, J=10.8 Hz, 1H), 2.89-2.97 (m, 3H), 3.13 (m, 2H), 3.61 (d, J=12.4 Hz, 1H), 3.76 (d, J=10.4 Hz, 1H), 4.60 (d, J=5.6 Hz, 2H), 6.01 (brs, 1H), 6.93 (d, J=8.4 Hz, 2H), 7.25-7.29 (m, 3H), 7.52 (d, J=9.6 Hz, 1H), 9.51 (s, 1H); LCMS (electrospray) m/z (M+H)⁺ 438.

6-Chloro-2-ethyl-N-(4-(octahydroisoquinolin-2(1H)-yl)benzyl)imidazo[1,2-a]pyridine-3-carboxamide (267)

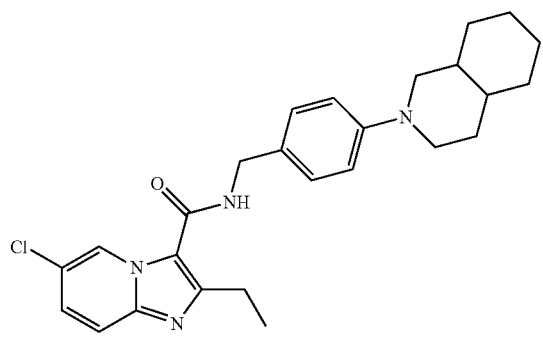 [SMILES: CCc1nc2ccc(Cl)cn2c1C(=O)NCc1ccc(N2CCC3CCCCC3C2)cc1]

White solid; mp=141.7° C.; ¹H NMR (400 MHz, CDCl₃); δ 0.94-1.03 (m, 3H), 1.24-1.42 (m, 4H), 1.34 (t, J=7.2 Hz, 3H), 1.57-1.66 (m, 3H), 1.73-1.74 (m, 2H), 2.30-2.35 (m, 1H), 2.65-2.72 (m, 1H), 2.89 (q, J=7.2 Hz, 2H), 3.48-3.53 (m, 1H), 3.67-3.71 (m, 1H), 4.56 (d, J=5.6 Hz, 2H), 6.03 (brt, J=5.6 Hz, 1H), 6.89 (d, J=8.4 Hz, 2H), 7.21 (d, J=8.4 Hz, 2H) 7.24 (dd, J=2.0, 9.2 Hz, 1H), 7.48 (d, J=9.2 Hz, 1H), 9.48 (d, J=2.0 Hz, 1H); ¹³C NMR (100 MHz, CDCl₃) δ 13.3, 23.5, 26.1, 26.5, 30.5, 32.8, 33.0, 41.6, 41.8, 43.3, 50.3, 56.2, 115.4, 116.5, 116.9, 121.5, 126.3, 127.8, 128.2, 128.8, 144.5, 151.3, 151.5, 161.1; LCMS (electrospray) m/z 451, 453 (M+H)⁺ (Cl⁻ isotope pattern).

7-Chloro-2-ethyl-N-(4-(octahydroisoquinolin-2(1H)-yl)benzyl)imidazo[1,2-a]pyridine-3-carboxamide (268)

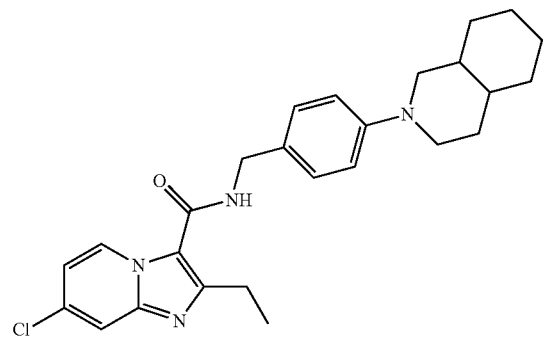 [SMILES: CCc1nc2cc(Cl)ccn2c1C(=O)NCc1ccc(N2CCC3CCCCC3C2)cc1]

White solid; mp=174.2° C.; ¹H NMR (400 MHz, CDCl₃); δ 0.93-1.01 (m, 3H), 1.24-1.40 (m, 4H), 1.30 (t, J=7.6 Hz, 3H), 1.56-1.64 (m, 3H), 1.71-1.72 (m, 2H), 2.27-2.33 (m, 1H), 2.63-2.69 (m, 1H), 2.86 (q, J=7.6 Hz, 2H), 3.48-3.50 (m, 1H), 3.65-3.68 (m, 1H), 4.53 (d, J=5.2 Hz, 2H), 6.10 (brt, J=5.2 Hz, 1H), 6.81 (d, J=7.2 Hz, 1H), 6.87 (d, J=8.0 Hz, 2H), 7.18 (d, J=8.0 Hz, 2H), 7.51 (s, 1H), 9.25 (d, J=7.2 Hz, 1H); ¹³C NMR (100 MHz, CDCl₃) δ 13.3, 23.4, 26.1, 26.4, 30.5, 32.8, 33.0, 41.6, 41.7, 43.3, 50.2, 56.1, 114.5, 115.1, 115.6, 116.4, 127.8, 128.4, 128.7, 133.4, 145.9, 151.4, 151.5, 161.1; LCMS (electrospray) m/z 451, 453 (M+H)⁺ (Cl⁻ isotope pattern).

7-Chloro-2-ethyl-N-(4-(4-oxopiperidin-1-yl)benzyl)imidazo[1,2-a]pyridine-3-carboxamide (269)

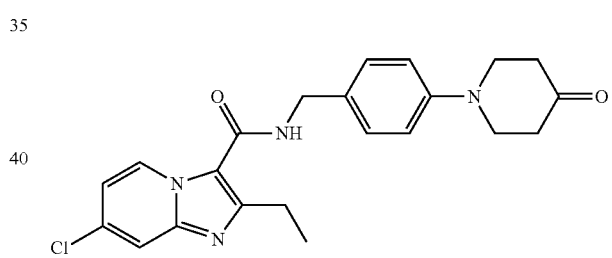

Pale yellow solid; ¹H NMR (400 MHz, CDCl₃); δ 1.37 (t, J=7.2 Hz, 3H), 2.54 (t, J=6.6 Hz, 4H), 2.93 (q, J=7.2 Hz, 2H), 3.60 (t, J=6.0 Hz, 4H), 4.61 (d, J=5.6 Hz, 2H), 6.04 (brt, J=5.6 Hz, 1H), 6.89 (dd, J=2.4, 7.6 Hz, 1H), 6.96 (d, J=8.4 Hz, 2H), 7.29 (d, J=8.4 Hz, 2H), 7.58 (d, J=2.4 Hz, 1H), 9.35 (d, J=7.6 Hz, 1H); LCMS (electrospray) m/z (M+H)⁺ 411, 413 (Cl⁻ isotope pattern).

7-Chloro-2-ethyl-N-(4-(4-oxo-3,4-dihydropyridin-1(2H)-yl)benzyl)imidazo[1,2-a]pyridine-3-carboxamide (270)

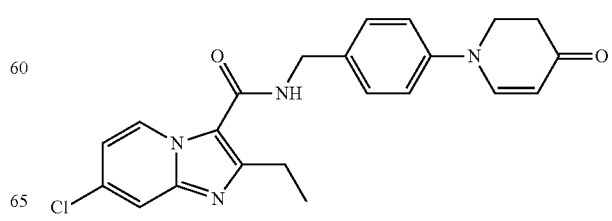

Pale yellow solid; mp=201.3-202.8° C.; ¹H NMR (400 MHz, CDCl₃); δ 1.38 (t, J=7.6 Hz, 3H), 2.64 (t, J=7.6 Hz, 2H), 2.95 (q, J=7.6 Hz, 2H), 3.98 (t, J=7.2 Hz, 2H), 4.66 (d, J=5.6 Hz, 2H), 5.23 (d, J=8.0 Hz, 1H), 6.13 (t, J=5.6 Hz, 1H), 6.89 (dd, J=2.4, 7.6 Hz, 1H), 7.08 (d, J=8.4 Hz, 2H), 7.38 (d, J=8.4 Hz, 2H), 7.41 (d, J=8.0 Hz, 1H), 7.60 (d, J=2.4 Hz, 1H), 9.34 (d, J=7.2 Hz, 1H); LCMS (electrospray) m/z (M+H)⁺ 409, 411 (Cl⁻ isotope pattern).

7-Chloro-2-ethyl-N-(4-(4-methylenepiperidin-1-yl)benzyl)imidazo[1,2-a]pyridine-3-carboxamide (271)

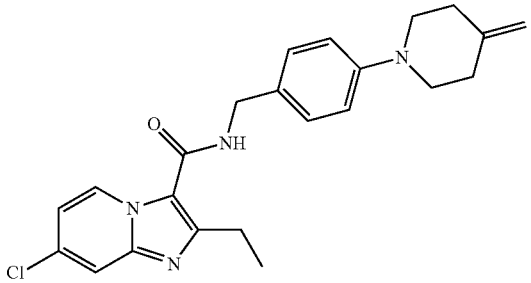 [SMILES: C=C1CCN(c2ccc(CNC(=O)c3c(CC)nc4cc(Cl)ccn34)cc2)CC1]

White solid; mp=168.3° C.; ¹H NMR (400 MHz, CDCl₃); δ 1.33 (t, J=7.2 Hz, 3H), 2.32-2.34 (m, 4H), 2.89 (q, J=7.2 Hz, 2H), 3.23-3.25 (m, 4H), 4.56 (d, J=5.2 Hz, 2H), 4.73 (s, 2H), 6.07 (brs, 1H), 6.84 (d, J=7.2 Hz, 1H), 6.90 (d, J=8.4 Hz, 2H), 7.22 (d, J=8.4 Hz, 2H), 7.54 (s, 1H), 9.29 (d, J=7.2 Hz, 1H); ¹³C NMR (100 MHz, CDCl₃) δ 13.4, 23.5, 34.2, 43.3, 51.2, 108.5, 114.6, 115.1, 115.7, 116.7, 128.3, 128.5, 128.9, 133.5, 145.8, 146.0, 150.8, 151.5, 161.1; LCMS (electrospray) m/z 409, 411 (M+H)⁺ (Cl⁻ isotope pattern).

6-chloro-2-ethyl-N-(4-(2-methylpiperidin-1-yl)benzyl)imidazo[1,2-a]pyridine-3-carboxamide (272)

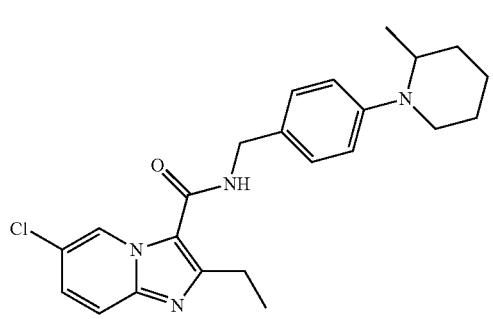 [SMILES: CCc1nc2ccc(Cl)cn2c1C(=O)NCc1ccc(N2CCCCC2C)cc1]

Sticky pale yellow solid; ¹H NMR (400 MHz, CDCl₃); δ 0.99 (d, J=6.4 Hz, 3H), 1.32 (t, J=7.6 Hz, 3H), 1.55-1.70 (m, 4H), 1.81-1.88 (m, 2H), 2.91 (q, J=1.6 Hz, 2H), 2.92-2.98 (m, 1H), 3.21-3.26 (m, 1H), 3.93-3.96 (m, 1H), 4.58 (d, J=5.2 Hz, 2H), 6.01 (brt, J=5.2 Hz, 1H), 6.90 (d, J=8.8 Hz, 2H), 7.22 (d, J=8.8 Hz, 2H), 7.26 (dd, J=2.0, 9.2 Hz, 1H), 7.50 (d, J=9.2 Hz, 1H), 9.50 (d, J=2.0 Hz, 1H); ¹³C NMR (100 MHz, CDCl₃) δ 13.3, 13.7, 19.6, 23.6, 26.2, 31.6, 43.4, 44.6, 51.2, 115.4, 117.0, 117.5, 121.6, 126.3, 127.9, 128.2, 128.8, 144.5, 151.1, 151.4, 161.1; LCMS (electrospray) m/z 411, 413 (M+H)⁺ (Cl⁻ isotope pattern).

7-chloro-2-ethyl-N-(4-(2-methylpiperidin-1-yl)benzyl)imidazo[1,2-a]pyridine-3-carboxamide (273)

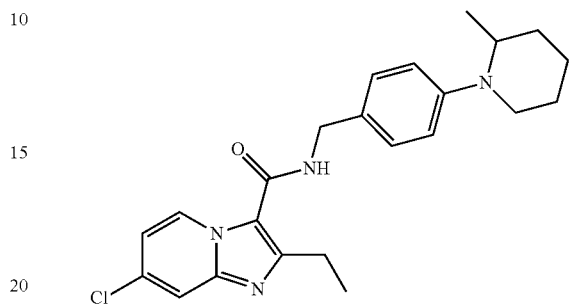

White solid; mp=117.9° C.; ¹H NMR (400 MHz, CDCl₃); δ 1.00 (d, J=6.4 Hz, 3H), 1.35 (t, J=7.6 Hz, 3H), 1.56-1.69 (m, 4H), 1.75-1.90 (m, 2H), 2.92 (q, J=7.6 Hz, 2H), 2.96-2.99 (m, 1H), 3.23-3.28 (m, 1H), 3.95-3.98 (m, 1H), 4.59 (d, J=5.6 Hz, 2H), 6.08 (brt, J=5.6 Hz, 1H), 6.87 (dd, J=2.0, 7.6 Hz, 1H), 6.91 (d, J=8.8 Hz, 2H), 7.23 (d, J=8.8 Hz, 2H), 7.57 (d, J=2.0 Hz, 1H), 9.32 (d, J=7.6 Hz, 1H); ¹³C NMR (100 MHz, CDCl₃) δ 13.4, 13.7, 19.5, 23.5, 26.1, 31.6, 43.3, 44.5, 51.2, 114.6, 115.1, 115.7, 117.4, 127.8, 128.5, 128.8, 133.5, 146.0, 151.0, 151.5, 161.1; LCMS (electrospray) m/z 411, 413 (M+H)⁺ (Cl⁻ isotope pattern).

7-Chloro-N-(4-(4,4-dimethylpiperidin-1-yl)benzyl)-2-ethyl-1,8a-dihydroimidazo[1,2-a]pyridine-3-carboxamide (274)

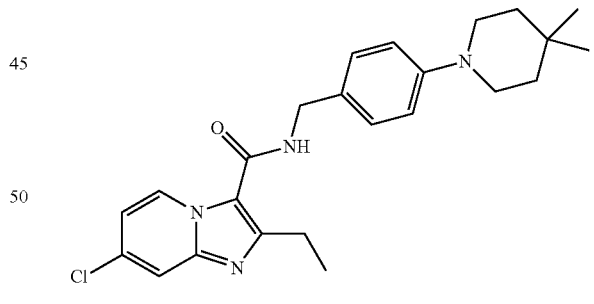

White solid; mp=121.3° C.; ¹H NMR (400 MHz, CDCl₃); δ 0.97 (s, 6H), 1.34 (t, J=7.2 Hz, 3H), 1.49-1.52 (m, 4H), 2.89 (q, J=7.2 Hz, 2H), 3.15-3.17 (m, 4H), 4.57 (d, J=5.2 Hz, 2H), 6.00 (brt, J=5.2 Hz, 1H), 6.86 (dd, J=2.0, 7.6 Hz, 1H), 6.91 (d, J=8.4 Hz, 2H), 7.22 (d, J=8.4 Hz, 2H), 7.56 (d, J=2.0 Hz, 1H), 9.32 (d, J=7.6 Hz, 1H); ¹³C NMR (100 MHz, CDCl₃) δ 13.4, 23.5, 28.0, 29.8, 38.5, 43.4, 45.9, 114.7, 115.7, 116.4, 127.9, 128.6, 128.9, 129.0, 133.6, 146.1, 151.5, 151.6, 161.2; LCMS (electrospray) m/z 425, 427 (M+H)⁺ (Cl⁻ isotope pattern).

6-Chloro-2-ethyl-N-(4-(4-(trifluoromethyl)piperidin-1-yl)benzyl)imidazo[1,2-a]pyridine-3-carboxamide (275)

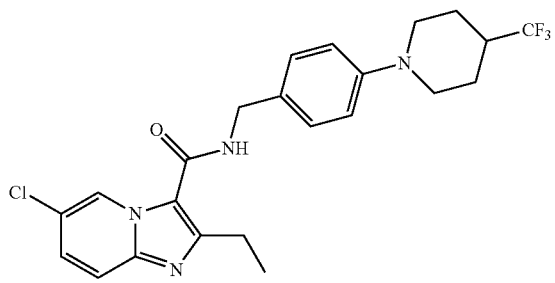 [SMILES: CCc1nc2ccc(Cl)cn2c1C(=O)NCc1ccc(N2CCC(C(F)(F)F)CC2)cc1]

White solid; mp=197.9° C.; $^1$H NMR (400 MHz, CDCl$_3$); δ 1.35 (t, J=7.6 Hz, 3H), 1.68-1.82 (m, 2H), 1.94-1.97 (m, 2H), 2.12-2.18 (m, 1H), 2.66-2.73 (m, 2H), 2.91 (q, J=7.6 Hz, 2H), 3.73-3.77 (m, 2H), 4.58 (d, J=5.6 Hz, 2H), 6.04 (brt, J=5.2 Hz, 1H), 6.91 (d, J=8.8 Hz, 2H), 7.25-7.29 (m, 3H), 7.50 (d, J=9.2 Hz, 1H), 9.50 (d, J=1.2 Hz, 1H); LCMS (electrospray) m/z 465, 467 (M+H)$^+$ (Cl$^-$ isotope pattern).

7-Chloro-2-ethyl-N-(4-(4-(trifluoromethyl)piperidin-1-yl)benzyl)imidazo[1,2-a]pyridine-3-carboxamide (276)

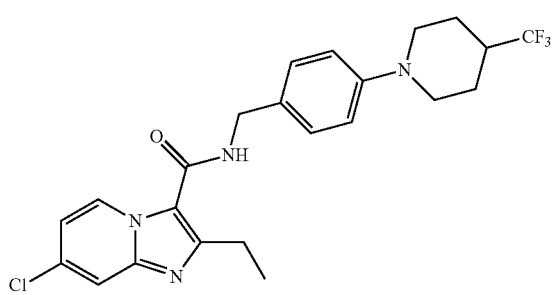 [SMILES: CCc1nc2cc(Cl)ccn2c1C(=O)NCc1ccc(N2CCC(C(F)(F)F)CC2)cc1]

White solid; mp=209.4° C.; $^1$H NMR (400 MHz, CDCl$_3$); δ 1.34 (t, J=7.6 Hz, 3H), 1.68-1.78 (m, 2H), 1.94-1.98 (m, 2H), 2.11-2.20 (m, 1H), 2.66-2.73 (m, 2H), 2.90 (q, J=7.6 Hz, 2H), 3.73-3.77 (m, 2H), 4.58 (d, J=5.2 Hz, 2H), 6.03 (brt, J=5.2 Hz, 1H), 6.86 (dd, J=2.4, 7.6 Hz, 1H), 6.91 (d, J=8.8 Hz, 2H), 7.25 (d, J=8.8 Hz, 2H), 7.56 (d, J=2.4 Hz, 1H), 9.32 (d, J=7.6 Hz, 1H); LCMS (electrospray) m/z 465, 467 (M+H)$^+$ (Cl$^-$ isotope pattern).

6-chloro-N-(4-(4,4-difluoropiperidin-1-yl)benzyl)-2-ethylimidazo[1,2-a]pyridine-3-carboxamide (277)

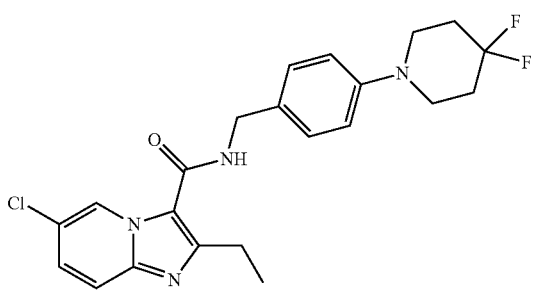 [SMILES: CCc1nc2ccc(Cl)cn2c1C(=O)NCc1ccc(N2CCC(F)(F)CC2)cc1]

White solid; mp=194.2° C.; $^1$H NMR (400 MHz, CDCl$_3$); δ 1.36 (t, J=7.6 Hz, 3H), 1.98-2.13 (m, 4H), 2.92 (q, J=7.6 Hz, 2H), 3.33-3.36 (m, 4H), 4.59 (d, J=5.6 Hz, 2H), 6.04 (brt, J=5.6 Hz, 1H), 6.91-6.95 (m, 2H), 7.25-7.30 (m, 3H), 7.52 (d, J=9.6 Hz, 1H), 9.51 (d, J=2.0 Hz, 1H); LCMS (electrospray) m/z 433, 435 (M+H)$^+$ (Cl$^-$ isotope pattern).

7-Chloro-N-(4-(4,4-difluoropiperidin-1-yl)benzyl)-2-ethylimidazo[1,2-a]pyridine-3-carboxamide (278)

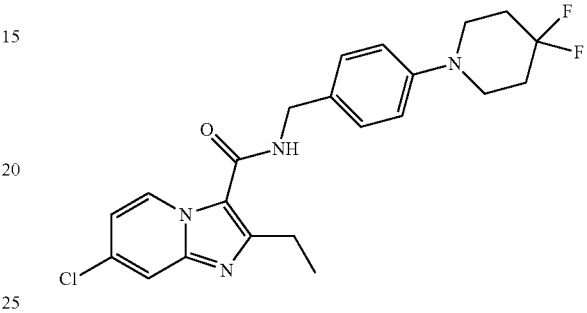

White solid; mp=166.3° C.; $^1$H NMR (400 MHz, CDCl$_3$); δ 1.34 (t, J=7.2 Hz, 3H), 2.03-2.12 (m, 4H), 2.90 (q, J=7.2 Hz, 2H), 3.32-3.35 (m, 4H), 4.58 (d, J=5.2 Hz, 2H), 6.06 (brt, J=5.2 Hz, 1H), 6.86 (dd, J=2.0, 7.6 Hz, 1H), 6.91 (d, J=8.4 Hz, 2H), 7.25 (d, J=8.4 Hz, 2H), 7.55 (d, J=2.0 Hz, 1H), 9.31 (d, J=7.6 Hz, 1H); LCMS (electrospray) m/z 433, 435 (M+H)$^+$ (Cl$^-$ isotope pattern).

6-Chloro-2-ethyl-N-(4-(4-(hydroxymethyl)piperidin-1-yl)benzyl)imidazo[1,2-a]pyridine-3-carboxamide (279)

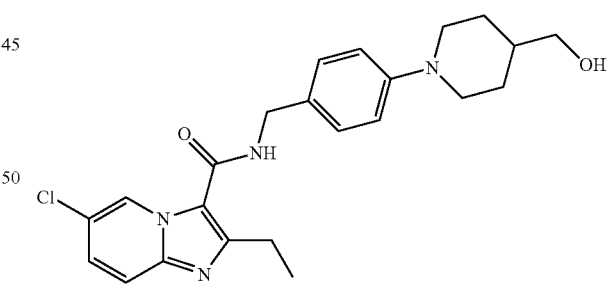

Pale yellow solid; mp=161.1° C.; $^1$H NMR (400 MHz, CDCl$_3$); δ 1.23-1.41 (m, 2H), 1.33 (t, J=7.6 Hz, 3H), 1.59-1.65 (m, 1H), 1.80-1.84 (m, 2H), 2.64-2.71 (m, 2H), 2.89 (q, J=7.6 Hz, 2H), 3.50 (d, J=6.4 Hz, 2H), 3.66-3.69 (m, 2H), 4.55 (d, J=5.2 Hz, 2H), 6.09 (brt, J=5.2 Hz, 1H), 6.89 (d, J=8.4 Hz, 2H), 7.21 (d, J=8.4 Hz, 2H), 7.23 (dd, J=2.0, 9.2 Hz, 1H), 7.47 (d, J=9.2 Hz, 1H), 9.45 (d, J=2.0 Hz, 1H); $^{13}$C NMR (100 MHz, CDCl$_3$) δ 13.3, 23.4, 28.7, 38.6, 43.3, 49.6, 67.6, 115.3, 116.8, 116.9, 121.5, 126.2, 128.2, 128.3, 128.8, 144.4, 151.3, 151.4, 161.1; LCMS (electrospray) m/z 427, 429 (M+H)$^+$ (Cl$^-$ isotope pattern).

123

7-Chloro-2-ethyl-N-(4-(4-(hydroxymethyl)piperidin-1-yl)benzyl)imidazo[1,2-a]pyridine-3-carboxamide (280)

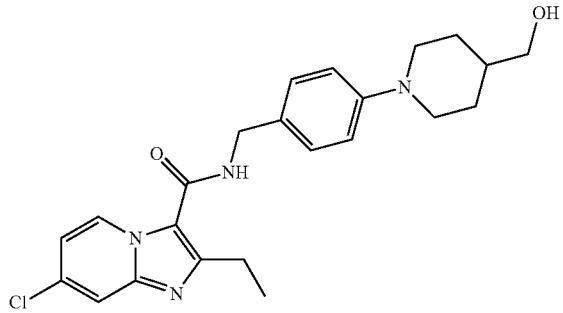 [SMILES: CCc1nc2cc(Cl)ccn2c1C(=O)NCc1ccc(N2CCC(CO)CC2)cc1]

White solid; mp=179.8° C.; $^1$H NMR (400 MHz, CDCl$_3$); δ 1.33 (t, J=7.6 Hz, 3H), 1.35-1.42 (m, 2H), 1.60-1.67 (m, 1H), 1.82-1.85 (m, 2H), 1.98 (brs, 1H), 2.66-2.73 (m, 2H), 2.91 (q, J=7.6 Hz, 2H), 3.52 (d, J=6.4 Hz, 2H), 3.68-3.71 (m, 2H), 4.56 (d, J=5.6 Hz, 2H), 6.04 (brt, J=5.6 Hz, 1H), 6.86 (dd, J=2.0, 7.6 Hz, 1H), 6.91 (d, J=8.8 Hz, 2H), 7.22 (d, J=8.8 Hz, 2H), 7.55 (d, J=2.0 Hz, 1H), 9.30 (d, J=7.6 Hz, 1H); $^{13}$C NMR (100 MHz, CDCl$_3$) δ 13.4, 23.5, 28.7, 38.6, 43.3, 49.7, 67.7, 114.7, 115.1, 115.7, 116.8, 128.3, 128.6, 128.8, 133.6, 146.1, 151.5, 151.6, 161.1; LCMS (electrospray) m/z 427, 429 (M+H)$^+$ (Cl$^-$ isotope pattern).

6-Chloro-2-ethyl-N-(4-(4-(methoxymethyl)piperidin-1-yl)benzyl)imidazo[1,2-a]pyridine-3-carboxamide (281)

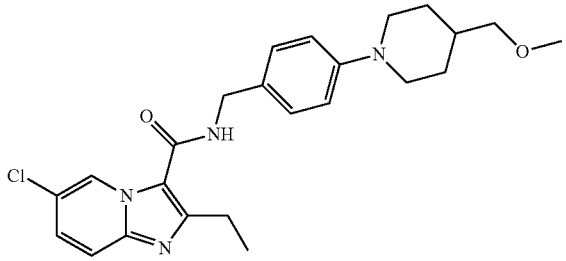 [SMILES: CCc1nc2ccc(Cl)cn2c1C(=O)NCc1ccc(N2CCC(COC)CC2)cc1]

White solid; mp=162.1° C.; $^1$H NMR (400 MHz, CDCl$_3$); δ 1.34-1.57 (m, 2H), 1.36 (t, J=7.6 Hz, 3H), 1.70-1.85 (m, 3H), 2.68-2.74 (m, 2H), 2.88 (q, J=7.6 Hz, 2H), 3.25 (d, J=6.4 Hz, 2H), 3.53 (s, 3H), 3.68-3.71 (m, 2H), 4.58 (d, J=5.6 Hz, 2H), 5.98 (brt, J=5.6 Hz, 1H), 6.92 (d, J=8.4 Hz, 2H), 7.24-7.30 (m, 3H), 7.51 (d, J=10.0 Hz, 1H), 9.52 (d, J=1.6 Hz, 1H); LCMS (electrospray) m/z 441, 443 (M+H)$^+$ (Cl$^-$ isotope pattern).

124

7-Chloro-2-ethyl-N-(4-(4-(methoxymethyl)piperidin-1-yl)benzyl)imidazo[1,2-a]pyridine-3-carboxamide (282)

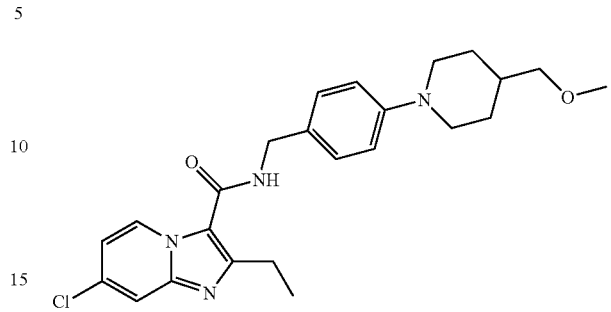

White solid; mp=172.5° C.; $^1$H NMR (400 MHz, CDCl$_3$); δ 1.33-1.43 (m, 2H), 1.35 (t, J=7.6 Hz, 3H), 0.72-1.85 (m, 3H), 2.67-2.74 (m, 2H), 2.90 (q, J=7.6 Hz, 2H), 3.25 (d, J=6.4 Hz, 2H), 3.35 (s, 3H), 3.68-3.71 (m, 2H), 4.58 (d, J=5.2 Hz, 2H), 5.97 (brt, J=5.2 Hz, 1H), 6.88 (dd, J=2.4, 7.6 Hz, 1H), 6.92 (d, J=8.8 Hz, 2H), 7.23 (d, J=8.8 Hz, 2H), 7.57 (d, J=2.4 Hz, 1H), 9.34 (d, J=7.6 Hz, 1H); LCMS (electrospray) m/z 441, 443 (M+H)$^+$ (Cl$^-$ isotope pattern).

7-Chloro-2-ethyl-N-(4-(4-phenylpiperidin-1-yl)benzyl)imidazo[1,2-a]pyridine-3-carboxamide (283)

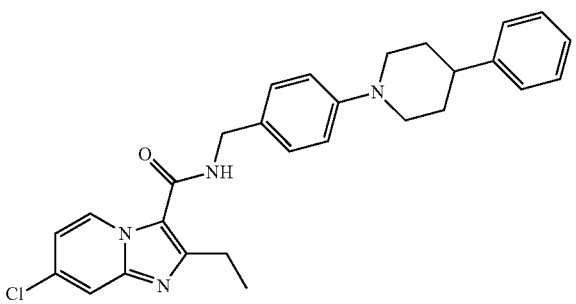

White solid; mp=164.5° C.; $^1$H NMR (400 MHz, CDCl$_3$); δ 1.36 (t, J=7.6 Hz, 3H), 1.87-1.98 (m, 4H), 2.67-2.68 (m, 1H), 2.80-2.85 (m, 2H), 2.91 (q, J=7.6 Hz, 2H), 3.80-3.83 (m, 2H), 4.59 (d, J=5.6 Hz, 2H), 6.01 (brt, J=5.6 Hz, 1H), 6.87 (d, J=7.6 Hz, 1H), 6.97 (d, J=8.4 Hz, 2H), 7.19-7.33 (m, 7H), 7.57 (s, 1H), 9.34 (d, J=7.6 Hz, 1H); $^{13}$C NMR (100 MHz, CDCl$_3$) δ 13.4, 23.6, 33.3, 42.6, 43.4, 50.5, 114.7, 115.1, 115.8, 116.9, 126.5, 127.0, 128.5, 128.6, 128.7, 128.9, 133.6, 146.1, 146.2, 151.5, 151.6, 161.2; LCMS (electrospray) m/z 473, 475 (M+H)$^+$ (Cl$^-$ isotope pattern).

6-Chloro-2-ethyl-N-(4-(4-phenylpiperidin-1-yl)benzyl)imidazo[1,2-a]pyridine-3-carboxamide (284)

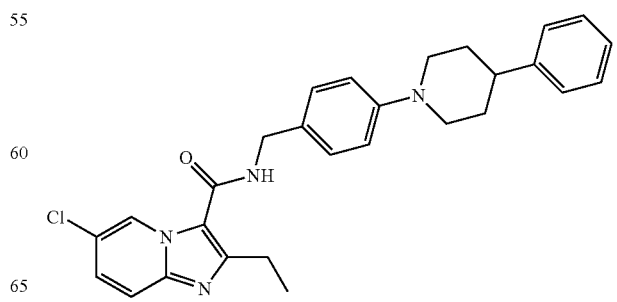

Pale yellow solid; mp=138.2° C.; ¹H NMR (400 MHz, CDCl₃); δ 1.36 (t, J=7.6 Hz, 3H), 1.84-1.97 (m, 4H), 2.62-2.69 (m, 1H), 2.79-2.86 (m, 2H), 2.92 (q, J=7.6 Hz, 2H), 3.80-3.83 (m, 2H), 4.60 (d, J=5.2 Hz, 2H), 6.07 (brt, J=5.2 Hz, 1H), 6.97 (d, J=8.8 Hz, 2H), 7.19-7.33 (m, 8H), 7.50 (d, J=9.6 Hz, 1H), 9.50 (d, J=2.0 Hz, 1H); ¹³C NMR (100 MHz, CDCl₃) δ 13.3, 23.5, 33.3, 42.5, 43.3, 50.5, 115.4, 116.9, 117.0, 121.6, 126.3, 126.4, 126.9, 128.2, 128.4, 128.6, 128.9, 144.4, 146.0, 151.3, 151.4, 161.1; LCMS (electrospray) m/z 473, 475 (M+H)⁺ (Cl⁻ isotope pattern).

2-Ethyl-N-(4-(4-(4-fluorophenyl)piperidin-1-yl)benzyl)imidazo[1,2-a]pyridine-3-carboxamide (285)

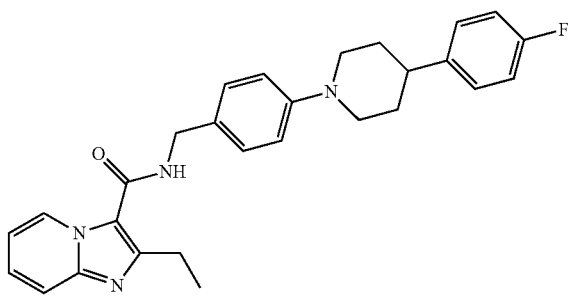

Pale yellow solid; ¹H NMR (400 MHz, CDCl₃); δ 1.37 (t, J=7.6 Hz, 3H), 1.81-1.95 (m, 4H), 2.60-2.67 (m, 1H), 2.77-2.85 (m, 2H), 2.94 (q, J=7.6 Hz, 2H), 3.79-3.82 (m, 2H), 4.61 (d, J=5.6 Hz, 2H), 6.02 (brs, 1H), 6.89 (ddd, J=1.2, 6.8, 6.8 Hz, 1H), 6.96-7.02 (m, 4H), 7.17-7.23 (m, 2H), 7.25-7.33 (m, 3H), 7.8 (d, J=8.8 Hz, 1H), 9.39 (d, J=6.8 Hz, 1H).

6-Chloro-2-ethyl-N-(4-(4-(4-fluorophenyl)piperidin-1-yl)benzyl)imidazo[1,2-a]pyridine-3-carboxamide (286)

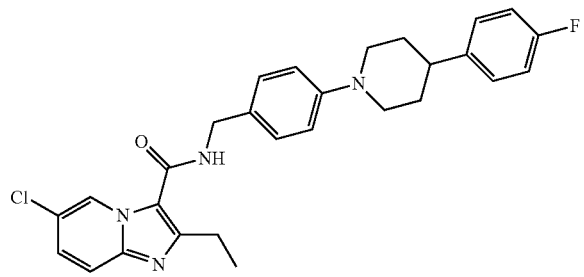 [SMILES: CCc1nc2ccc(Cl)cn2c1C(=O)NCc1ccc(N2CCC(c3ccc(F)cc3)CC2)cc1]

White solid; mp=164.0° C.; ¹H NMR (400 MHz, CDCl₃); δ 1.35 (t, J=7.6 Hz, 3H), 1.76-1.95 (m, 4H), 2.60-2.66 (m, 1H), 2.78-2.85 (m, 2H), 2.92 (q, J=7.6 Hz, 2H), 3.79-3.82 (m, 2H), 4.60 (d, J=5.2 Hz, 2H), 6.03 (brt, J=5.2 Hz, 1H), 6.96-7.01 (m, 4H), 7.17-7.21 (m, 2H), 7.26-7.29 (m, 3H), 7.51 (d, J=9.6 Hz, 1H), 9.52 (d, J=1.6 Hz, 1H); LCMS (electrospray) m/z 491 (M+H)⁺.

7-Chloro-2-ethyl-N-(4-(4-(4-fluorophenyl)piperidin-1-yl)benzyl)imidazo[1,2-a]pyridine-3-carboxamide (287)

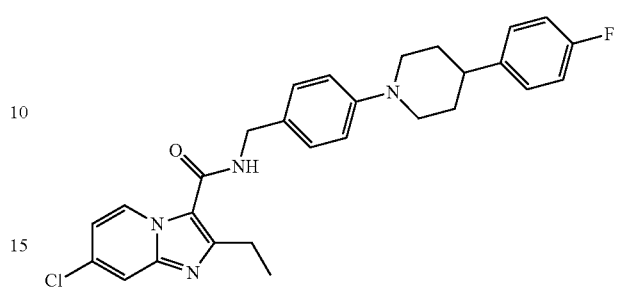

White solid; mp=182.7° C.; ¹H NMR (400 MHz, CDCl₃); δ 1.35 (t, J=7.6 Hz, 3H), 1.79-1.95 (m, 4H), 2.59-2.67 (m, 1H), 2.78-2.85 (m, 2H), 2.91 (q, J=7.6 Hz, 2H), 3.79-3.82 (m, 2H), 4.59 (d, J=5.6 Hz, 2H), 6.03 (brt, J=5.6 Hz, 1H), 6.87 (dd, J=2.4, 7.6 Hz, 1H), 6.96-7.01 (m, 4H), 7.17-7.21 (m, 2H), 7.26 (d, J=8.8 Hz, 2H), 7.57 (d, J=2.4 Hz, 1H), 9.33 (d, J=7.6 Hz, 1H); LCMS (electrospray) m/z 491 (M+H)⁺.

2-Ethyl-N-(4-(4-(4-(trifluoromethoxy)phenyl)piperidin-1-yl)benzyl)imidazo[1,2-a]pyridine-3-carboxamide (288)

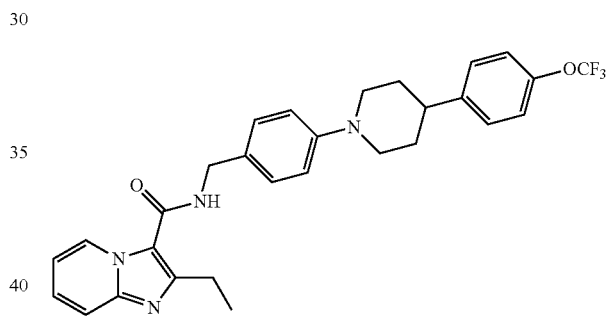

Pale yellow solid; mp=146.0° C.; ¹H NMR (400 MHz, CDCl₃); δ 1.37 (t, J=7.6 Hz, 3H), 1.81-1.96 (m, 4H), 2.63-2.69 (m, 1H), 2.79-2.86 (m, 2H), 2.94 (q, J=7.6 Hz, 2H), 3.80-3.83 (m, 2H), 4.61 (d, J=5.6 Hz, 2H), 6.01 (brt, J=5.6 Hz, 1H), 6.88 (ddd, J=0.8, 6.8, 6.8 Hz, 1H), 6.97 (d, J=8.8 Hz, 2H), 7.14 (d, J=8.4 Hz, 2H), 7.24-7.33 (m, 5H), 7.58 (d, J=8.8 Hz, 1H), 9.39 (d, J=6.8 Hz, 1H).

6-Chloro-2-ethyl-N-(4-(4-(4-(trifluoromethoxy)phenyl)piperidin-1-yl)benzyl)imidazo[1,2-a]pyridine-3-carboxamide (289)

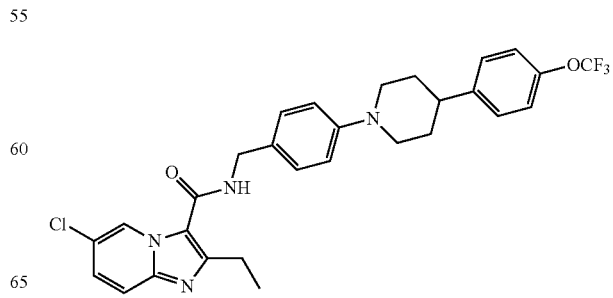

White solid; mp=164.0° C.; $^1$H NMR (400 MHz, CDCl$_3$); δ 1.37 (t, J=7.6 Hz, 3H), 1.81-1.96 (m, 4H), 2.63-2.70 (m, 1H), 2.79-2.86 (m, 2H), 2.92 (q, J=7.6 Hz, 2H), 3.80-3.83 (m, 2H), 4.60 (d, J=5.2 Hz, 2H), 6.04 (brt, J=5.2 Hz, 1H), 6.96 (d, J=8.4 Hz, 2H), 7.14 (d, J=8.4 Hz, 2H), 7.24-7.29 (m, 5H), 7.51 (d, J=9.6 Hz, 1H), 9.51 (d, J=1.6 Hz, 1H).

7-Chloro-2-ethyl-N-(4-(4-(4-(trifluoromethoxy)phenyl)piperidin-1-yl)benzyl)imidazo[1,2-a]pyridine-3-carboxamide (290)

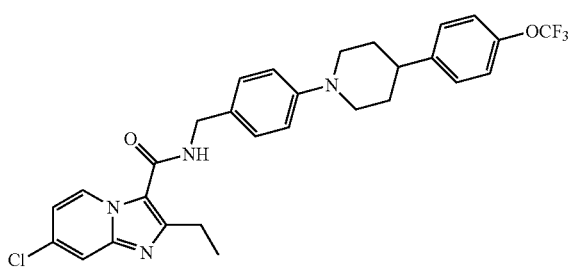 [SMILES: CCc1nc2cc(Cl)ccn2c1C(=O)NCc1ccc(N2CCC(c3ccc(OC(F)(F)F)cc3)CC2)cc1]

White solid; $^1$H NMR (400 MHz, CDCl$_3$); δ 1.36 (t, J=7.6 Hz, 3H), 1.82-1.96 (m, 4H), 2.64-2.70 (m, 1H), 2.79-2.86 (m, 2H), 2.91 (q, J=7.6 Hz, 2H), 3.80-3.83 (m, 2H), 4.59 (d, J=5.36 Hz, 2H), 6.04 (brs, 1H), 6.87 (dd, J=1.6, 7.2 Hz, 1H), 6.97 (d, J=8.4 Hz, 2H), 7.14 (d, J=8.4 Hz, 2H), 7.24-7.28 (m, 4H), 7.57 (d, J=1.6 Hz, 1H), 9.34 (d, J=7.2 Hz, 1H).

6-Chloro-2-ethyl-N-(4-(4-(isopropoxymethyl)piperidin-1-yl)benzyl)imidazo[1,2-a]pyridine-3-carboxamide (291)

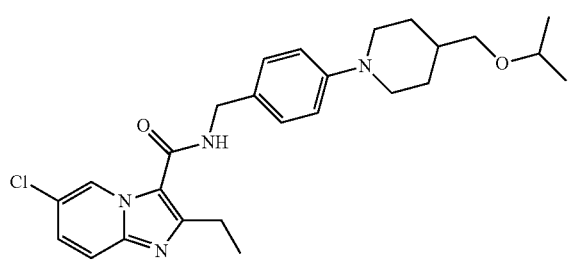 [SMILES: CCc1nc2ccc(Cl)cn2c1C(=O)NCc1ccc(N2CCC(COC(C)C)CC2)cc1]

White solid; $^1$H NMR (400 MHz, CDCl$_3$); δ 1.29 (d, J=6.0 Hz, 6H), 1.46-1.56 (m, 2H), 1.50 (t, J=7.6 Hz, 3H), 1.81-1.89 (m, 1H), 1.99-2.02 (m, 2H), 2.82-2.89 (m, 2H), 3.06 (q, J=7.6 Hz, 2H), 3.43 (d, J=6.4 Hz, 2H), 3.66-3.72 (m, 1H), 3.82-3.85 (m, 2H), 4.73 (d, J=5.6 Hz, 2H), 6.17 (brt, J=5.6 Hz, 1H), 7.06 (d, J=8.4 Hz, 2H), 7.38 (d, J=8.4 Hz, 2H), 7.40 (dd, J=2.0, 9.2 Hz, 1H), 7.65 (d, J=9.2 Hz, 1H), 9.65 (d, J=2.0 Hz, 1H); $^{13}$C NMR (100 MHz, CDCl$_3$) δ 13.3, 22.2, 23.6, 29.4, 36.6, 43.4, 49.7, 71.8, 73.3, 115.4, 116.8, 117.0, 121.5, 126.3, 128.2, 128.8, 144.5, 151.4, 151.6, 161.1 (hidden 1 aromatic carbon).

7-Chloro-2-ethyl-N-(4-(4-(isopropoxymethyl)piperidin-1-yl)benzyl)imidazo[1,2-a]pyridine-3-carboxamide (292)

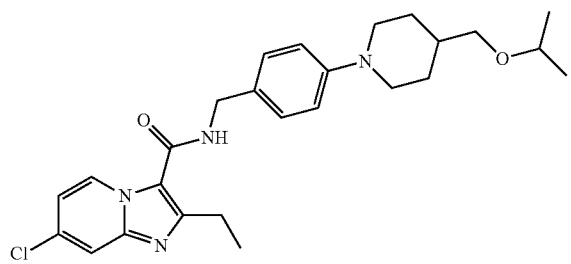 [SMILES: CCc1nc2cc(Cl)ccn2c1C(=O)NCc1ccc(N2CCC(COC(C)C)CC2)cc1]

White solid; $^1$H NMR (400 MHz, CDCl$_3$); δ 1.14 (d, J=6.0 Hz, 6H), 1.31-1.41 (m, 2H), 1.34 (t, J=7.6 Hz, 3H), 1.66-1.73 (m, 1H), 1.84-1.87 (m, 2H), 2.67-2.74 (m, 2H), 2.90 (q, J=7.6 Hz, 2H), 3.27 (d, J=6.8 Hz, 2H), 3.50-3.56 (m, 1H), 3.67-3.70 (m, 2H), 4.57 (d, J=5.6 Hz, 2H), 5.99 (brt, J=5.6 Hz, 1H), 6.86 (dd, J=2.0, 7.2 Hz, 1H), 6.91 (d, J=8.4 Hz, 2H), 7.22 (d, J=8.4 Hz, 2H), 7.56 (d, J=1.6 Hz, 1H), 9.33 (d, J=7.2 Hz, 1H); $^{13}$C NMR (100 MHz, CDCl$_3$) δ 13.4, 22.2, 23.6, 29.4, 36.6, 43.4, 49.7, 71.8, 73.3, 114.7, 115.2, 115.8, 116.8, 128.2, 128.6, 128.8, 133.6, 146.1, 151.6, 151.7, 161.2.

6-Chloro-N-(4-(4-(cyclopentyloxymethyl)piperidin-1-yl)benzyl)-2-ethylimidazo[1,2-a]pyridine-3-carboxamide (293)

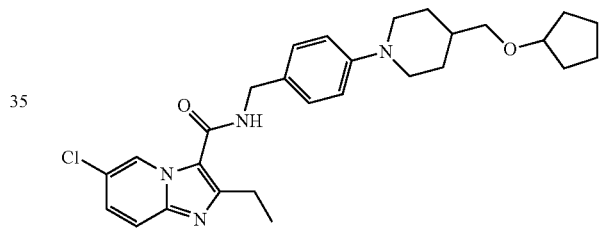

White solid; $^1$H NMR (400 MHz, CDCl$_3$); δ 1.28-1.38 (m, 2H), 1.32 (t, J=7.6 Hz, 3H), 1.46-1.51 (m, 2H), 1.58-1.66 (m, 7H), 1.79-1.83 (m, 2H), 2.63-2.70 (m, 2H), 2.87 (q, J=7.6 Hz, 2H), 3.21 (d, J=6.4 Hz, 2H), 3.63-3.66 (m, 2H), 3.82-3.83 (m, 1H), 4.54 (d, J=5.2 Hz, 2H), 6.08 (brt, J=5.2 Hz, 1H), 6.87 (d, J=8.4 Hz, 2H), 7.19-7.25 (m, 3H), 7.45 (d, J=9.2 Hz, 1H), 9.44 (d, J=1.6 Hz, 1H); $^{13}$C NMR (100 MHz, CDCl$_3$) δ 13.2, 23.4, 23.6, 29.3, 32.3, 36.4, 43.3, 49.6, 73.7, 81.5, 115.3, 116.6, 116.8, 121.4, 126.2, 128.0, 128.1, 128.7, 144.4, 151.3, 151.5, 161.0.

N-(4-(4-Benzylpiperidin-1-yl)benzyl)-7-chloro-2-ethylimidazo[1,2-a]pyridine-3-carboxamide (294)

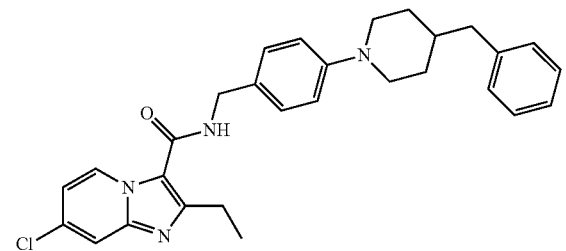 [SMILES: CCc1nc2cc(Cl)ccn2c1C(=O)NCc1ccc(N2CCC(Cc3ccccc3)CC2)cc1]

White solid; mp=63.8° C.; ¹H NMR (400 MHz, CDCl₃); δ 1.33 (t, J=7.6 Hz, 3H), 1.37-1.44 (m, 2H), 1.63-1.70 (m, 1H), 1.72-1.76 (m, 2H), 2.56 (d, J=6.8 Hz, 2H), 2.61-2.67 (m, 2H), 2.89 (q, J=7.6 Hz, 2H), 3.63-3.66 (m, 2H), 4.56 (d, J=5.2 Hz, 2H), 6.08 (brs, 1H), 6.84-6.87 (m, 1H), 6.89 (d, J=8.0 Hz, 2H), 7.14 (d, J=7.2 Hz, 2H), 7.19-7.30 (m, 5H), 7.54 (d, J=1.6 Hz, 1H), 9.29-9.32 (m, 1H); ¹³C NMR (100 MHz, CDCl₃) δ 13.3, 23.5, 32.0, 37.9, 43.2, 43.3, 49.9, 114.6, 115.1, 115.7, 116.7, 126.0, 128.2, 128.3, 128.5, 128.8, 129.2, 133.5, 140.5, 146.0, 151.5, 151.6, 161.1; LCMS (electrospray) m/z 487, 489 (M+H)⁺ (Cl⁻ isotope pattern).

2-Ethyl-N-(4-(4-((4-fluorophenoxy)methyl)piperidin-1-yl)benzyl)imidazo[1,2-a]pyridine-3-carboxamide (295)

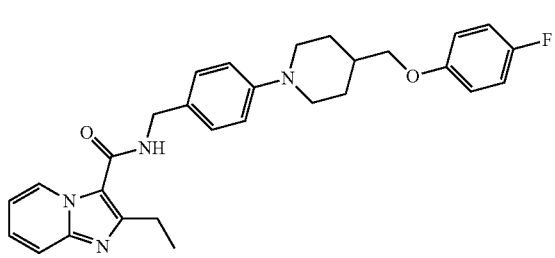 [SMILES: CCc1nc2ccccn2c1C(=O)NCc1ccc(N2CCC(COc3ccc(F)cc3)CC2)cc1]

White solid; mp=144.2° C.; ¹H NMR (400 MHz, CDCl₃); δ 1.39 (t, J=7.2 Hz, 3H), 1.46-1.60 (m, 3H), 1.94-1.96 (m, 2H), 2.73-2.78 (m, 2H), 2.96 (q, J=7.2 Hz, 2H), 3.73 (d, J=12.0 Hz, 2H), 3.80 (d, J=6.0 Hz, 2H), 4.61 (d, J=5.2 Hz, 2H), 5.99 (brs, 1H), 6.82-6.84 (m, 1H), 6.89-6.92 (m, 2H), 6.94-6.98 (m, 4H), 7.25-7.29 (m, 2H), 7.32 (d, J=8.4 Hz, 1H), 7.59 (d, J=8.4 Hz, 1H), 8.40 (d, J=7.2 Hz, 1H); LCMS (electrospray) m/z (M+H)⁺ 487.

6-Chloro-2-ethyl-N-(4-(4-((4-fluorophenoxy)methyl)piperidin-1-yl)benzyl)imidazo[1,2-a]pyridine-3-carboxamide (296)

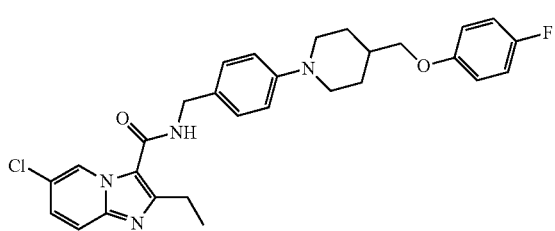 [SMILES: CCc1nc2ccc(Cl)cn2c1C(=O)NCc1ccc(N2CCC(COc3ccc(F)cc3)CC2)cc1]

White solid; mp=171.0° C.; ¹H NMR (400 MHz, CDCl₃); δ 1.38 (t, J=7.6 Hz, 3H), 1.50-1.56 (m, 2H), 1.94-1.96 (m, 3H), 2.72-2.79 (m, 2H), 2.95 (q, J=7.6 Hz, 2H), 3.74 (d, J=12.4 Hz, 2H), 3.80 (d, J=5.6 Hz, 2H), 4.60 (d, J=5.6 Hz, 2H), 6.01 (brs, 1H), 6.81-6.84 (m, 2H), 6.94-6.98 (m, 4H), 7.27-7.29 (m, 3H), 7.53 (d, J=9.6 Hz, 1H), 9.52 (d, J=2.0 Hz, 1H); LCMS (electrospray) m/z (M+H)⁺ 521.

7-Chloro-2-ethyl-N-(4-(4-((4-fluorophenoxy)methyl)piperidin-1-yl)benzyl)imidazo[1,2-a]pyridine-3-carboxamide (297)

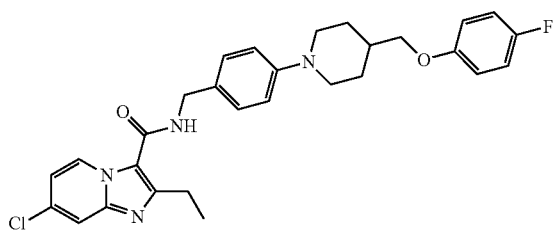 [SMILES: CCc1nc2cc(Cl)ccn2c1C(=O)NCc1ccc(N2CCC(COc3ccc(F)cc3)CC2)cc1]

White solid; mp=186.5° C.; ¹H NMR (400 MHz, CDCl₃); δ 1.37 (t, J=7.6 Hz, 3H), 1.50-1.61 (m, 2H), 1.94-1.96 (m, 3H), 2.76 (t, J=10.8 Hz, 2H), 2.93 (q, J=7.6 Hz, 2H), 3.74 (d, J=12.0 Hz, 2H), 3.80 (d, J=5.6 Hz, 2H), 4.59 (d, J=5.6 Hz, 2H), 6.00 (brs, 1H), 6.80-6.84 (m, 2H), 6.88-6.90 (m, 1H), 6.94-6.98 (m, 4H), 7.25-7.27 (m, 2H), 7.58 (d, J=1.6 Hz, 1H), 9.34 (d, J=8.0 Hz, 1H); LCMS (electrospray) m/z (M+H)⁺ 521.

6-chloro-2-ethyl-N-(4-(4-((4-(trifluoromethoxy)phenoxy)methyl)piperidin-1-yl)benzyl)imidazo[1,2-a]pyridine-3-carboxamide (298)

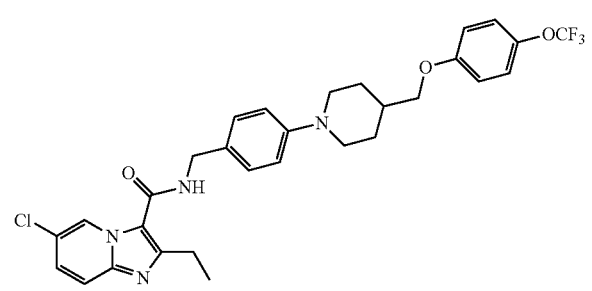 [SMILES: CCc1nc2ccc(Cl)cn2c1C(=O)NCc1ccc(N2CCC(COc3ccc(OC(F)(F)F)cc3)CC2)cc1]

Pale yellow solid; mp=183.6° C.; ¹H NMR (400 MHz, CDCl₃); δ 1.35 (t, J=7.6 Hz, 3H), 1.46-1.57 (m, 2H), 1.93-1.96 (m, 3H), 2.72-2.78 (m, 2H), 2.91 (q, J=7.6 Hz, 2H), 3.71-3.74 (m, 2H), 3.81 (d, J=6.0 Hz, 2H), 4.58 (d, J=5.6 Hz, 2H), 6.05 (brt, J=5.6 Hz, 1H), 6.85 (d, J=8.8 Hz, 2H), 6.93 (d, J=8.8 Hz, 2H), 7.11 (d, J=8.8 Hz, 2H), 7.24-7.28 (m, 3H), 7.50 (d, J=9.6 Hz, 1H), 9.50 (d, J=1.2 Hz, 1H); LCMS (electrospray) m/z 587, 589 (M+H)⁺ (Cl⁻ isotope pattern).

7-Chloro-2-ethyl-N-(4-(4-((4-(trifluoromethoxy)phenoxy)methyl)piperidin-1-yl)benzyl)imidazo[1,2-a]pyridine-3-carboxamide (299)

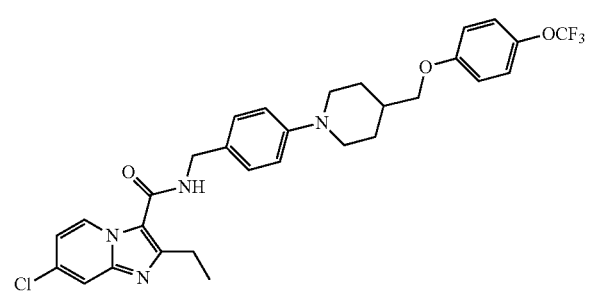 [SMILES: CCc1nc2cc(Cl)ccn2c1C(=O)NCc1ccc(N2CCC(COc3ccc(OC(F)(F)F)cc3)CC2)cc1]

White solid; mp=189.5° C.; ¹H NMR (400 MHz, CDCl₃); δ 1.34 (t, J=7.6 Hz, 3H), 1.46-1.56 (m, 2H), 1.93-2.02 (m, 3H), 2.71-2.78 (m, 2H), 2.90 (q, J=7.6 Hz, 2H), 3.71-3.74 (m, 2H), 3.81 (d, J=6.0 Hz, 2H), 4.57 (d, J=5.2 Hz, 2H), 6.05 (brt, J=5.2 Hz, 1H), 6.84-6.87 (m, 3H), 6.93 (d, J=8.8 Hz, 2H), 7.11 (d, J=8.8 Hz, 2H), 7.24 (d, J=8.8 Hz, 2H), 7.55 (d, J=2.0 Hz, 1H), 9.31 (d, J=7.2 Hz, 1H); LCMS (electrospray) m/z 587, 589 (M+H)⁺ (Cl⁻ isotope pattern).

Ethyl 1-(4-((6-chloro-2-ethylimidazo[1,2-a]pyridine-3-carboxamido)methyl)phenyl)piperidine-4-carboxylate (300)

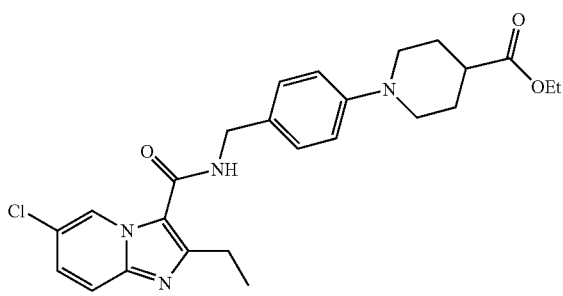 [SMILES: CCOC(=O)C1CCN(c2ccc(CNC(=O)c3c(CC)nc4ccc(Cl)cn34)cc2)CC1]

White solid; ¹H NMR (400 MHz, CDCl₃); δ 1.23 (t, J=7.2 Hz, 3H), 1.35 (t, J=7.2 Hz, 3H), 1.80-1.90 (m, 2H), 1.98-2.02 (m, 2H), 2.38-2.46 (m, 1H), 2.75-2.82 (m, 2H), 2.91 (q, J=7.6 Hz, 2H), 3.61-3.65 (m, 2H), 4.11 (q, J=7.2 Hz, 2H), 4.57 (d, J=5.6 Hz, 2H), 6.03 (brt, J=5.6 Hz, 1H), 6.90 (d, J=8.8 Hz, 2H), 7.23-7.28 (m, 3H), 7.49 (d, J=9.6 Hz, 1H), 9.49 (d, J=1.6 Hz, 1H); ¹³C NMR (100 MHz, CDCl₃) δ 13.3, 14.4, 23.6, 28.1, 41.6, 43.3, 49.2, 60.6, 115.4, 116.9, 117.0, 121.5, 126.3, 128.2, 128.6, 128.9, 144.5, 151.2, 151.4, 161.1, 174.9.

Ethyl 1-(4-((7-chloro-2-ethylimidazo[1,2-a]pyridine-3-carboxamido)methyl)phenyl)piperidine-4-carboxylate (301)

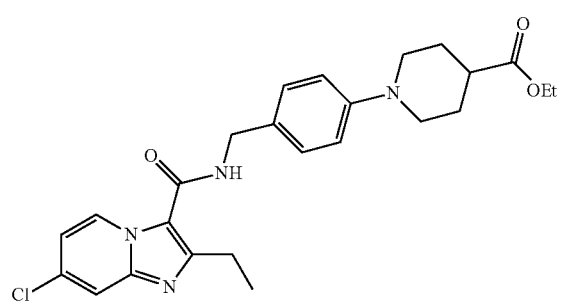 [SMILES: CCOC(=O)C1CCN(c2ccc(CNC(=O)c3c(CC)nc4cc(Cl)ccn34)cc2)CC1]

White solid; ¹H NMR (400 MHz, CDCl₃); δ 1.21 (t, J=7.2 Hz, 3H), 1.31 (t, J=7.2 Hz, 3H), 1.77-1.87 (m, 2H), 1.96-2.00 (m, 2H), 2.36-2.42 (m, 1H), 2.72-2.79 (m, 2H), 2.87 (q, J=7.2 Hz, 2H), 3.58-3.63 (m, 2H), 4.09 (q, J=7.2 Hz, 2H), 4.53 (d, J=5.6 Hz, 2H), 6.12 (brt, J=5.6 Hz, 1H), 6.81 (dd, J=2.0, 7.2 Hz, 1H), 6.87 (d, J=8.8 Hz, 2H), 7.20 (d, J=8.8 Hz, 2H), 7.51 (d, J=2.0, 1H), 9.25 (d, J=7.2 Hz, 1H); ¹³C NMR (100 MHz, CDCl₃) δ 13.3, 14.3, 23.4, 28.0, 41.0, 43.2, 49.1, 60.5, 114.5, 115.1, 115.6, 116.7, 128.4, 128.6, 128.8, 133.4, 146.0, 151.1, 151.5, 161.1, 174.8.

1-(4-((7-Chloro-2-ethylimidazo[1,2-a]pyridine-3-carboxamido)methyl)phenyl)piperidine-4-carboxylic acid (302)

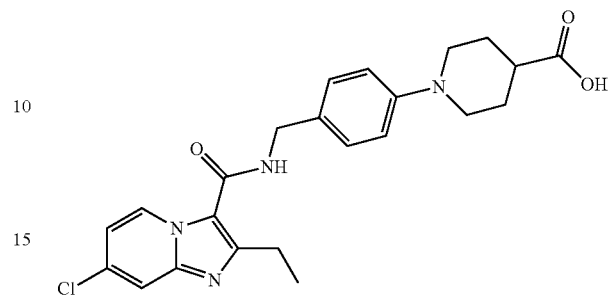

White solid; ¹H NMR (400 MHz, DMSO-d⁶); δ 1.22 (t, J=7.6 Hz, 3H), 1.57-1.66 (m, 2H), 1.84-1.88 (m, 2H), 2.29-2.34 (m, 1H), 2.67-2.73 (m, 2H), 2.92 (q, J=7.6 Hz, 2H), 3.57-3.60 (m, 2H), 4.40 (d, J=5.6 Hz, 2H), 5.75 (s, 1H), 6.89 (d, J=8.4 Hz, 2H), 7.06 (dd, J=1.6, 7.6 Hz, 1H), 7.19 (d, J=8.4 Hz, 2H), 7.77 (d, J=1.6 Hz, 1H), 8.37 (brt, J=5.6 Hz, 1H), 8.93 (d, J=7.6 Hz, 1H).

2-Ethyl-N-(4-(4-(4-fluorophenyl)piperazin-1-yl)benzyl)imidazo[1,2-a]pyridine-3-carboxamide (303)

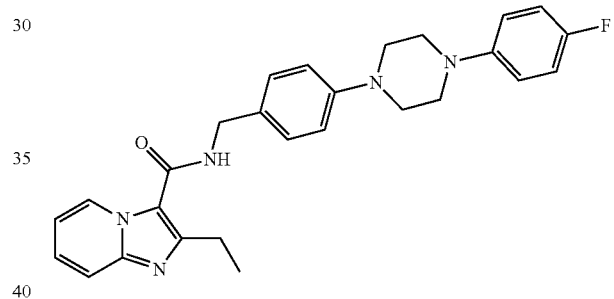

White solid; mp=189.2° C.; ¹H NMR (400 MHz, CDCl₃) δ 1.40 (t, J=7.8 Hz, 3H), 2.96 (q, J=7.6 Hz, 2H), 3.24-3.29 (m, 2H), 3.32-3.36 (m, 2H), 4.63 (d, J=5.6 Hz, 2H), 6.02-6.04 (m, 1H), 6.90-7.01 (m, 7H), 7.30-7.34 (m, 2H), 7.60 (d, J=9.2 Hz, 1H), 9.41 (d, J=7.2 Hz, 1H); LCMS (electrospray) m/z (M+H)⁺ 458.

8-(Difluoromethoxy)-2-ethyl-N-(4-(4-(4-fluorophenyl)piperazin-1-yl)benzyl)imidazo[1,2-a]pyridine-3-carboxamide (304)

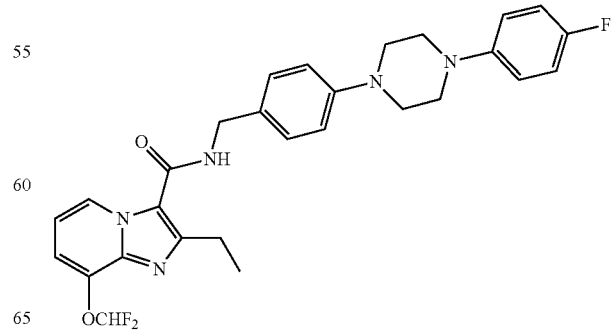

Pale yellow; mp=186.3° C.; ¹H NMR (400 MHz, CDCl₃) δ 1.38 (t, J=7.6 Hz, 3H), 2.98 (q, J=7.6 Hz, 2H), 3.24-3.27 (m, 4H), 3.34-3.36 (m, 4H), 4.63 (d, J=5.6 Hz, 2H), 6.05-6.07 (m, 1H), 6.85 (dd, J=7.2 Hz, 1H), 6.91-7.01 (m, 6H), 7.10 (d, J=7.6 Hz, 2H), 7.26 (t, J=74.2 Hz, 1H due to F₂), 9.24 (d, J=6.8 Hz, 1H); LCMS (electrospray) m/z (M+H)⁺ 524

8-Bromo-2-ethyl-N-(4-(4-(4-fluorophenyl)piperazin-1-yl)benzyl)imidazo[1,2-a]pyridine-3-carboxamide (305)

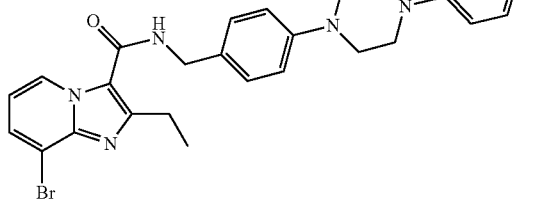

White solid; ¹H NMR (400 MHz, CDCl₃) δ 1.37 (t, J=7.6 Hz, 3H), 3.00 (q, J=7.6 Hz, 2H), 3.23-3.35 (m, 8H), 4.61 (d, J=5.6 Hz, 2H), 6.08 (brs, 1H), 6.77 (dd, J=6.8 Hz, 6.8 Hz, 1H), 6.90-7.00 (m, 6H), 7.29 (d, J=8.4 Hz, 2H), 7.56 (d, J=7.2 Hz, 1H), 9.38 (d, J=7.2 Hz, 1H); ¹³C NMR (100 MHz, CDCl₃) δ 14.1, 23.7, 43.4, 49.5, 50.6, 110.7, 113.3, 115.7, 115.9, 116.7, 118.4, 127.6, 129.0, 129.2, 129.4, 144.1, 148.0, 151.0, 151.5, 158.8, 161.3; LCMS (electrospray) m/z (M+H)⁺ 538.

2-Ethyl-6-fluoro-N-(4-(4-(4-fluorophenyl)piperazin-1-yl)benzyl)imidazo[1,2-a]pyridine-3-carboxamide (306)

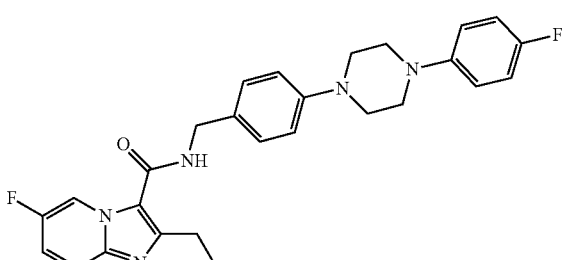

White solid; mp=200.9° C.; ¹H NMR (400 MHz, CDCl₃) δ 1.40 (t, J=7.8 Hz, 3H), 2.96 (q, J=7.6 Hz, 2H), 3.24-3.29 (m, 2H), 3.32-3.36 (m, 2H), 4.62 (d, J=5.6 Hz, 2H), 6.03-6.05 (m, 1H), 6.92-7.01 (m, 6H), 7.22-7.27 (m, 2H), 7.31 (d, J=8.4 Hz, 2H), 7.56 (dd, J=5.0, 9.8 Hz, 1H), 9.44-9.46 (m, 1H); LCMS (electrospray) m/z (M+H)⁺ 476.

6-Bromo-2-ethyl-N-(4-(4-(4-fluorophenyl)piperazin-1-yl)benzyl)imidazo[1,2-a]pyridine-3-carboxamide (307)

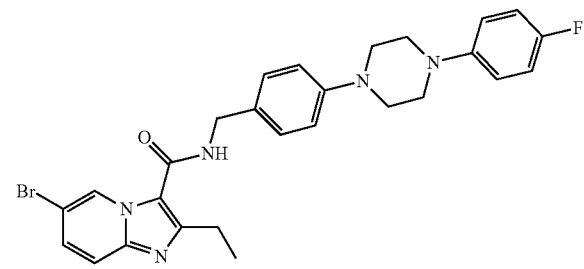 [SMILES: CCc1nc2ccc(Br)cn2c1C(=O)NCc1ccc(N2CCN(c3ccc(F)cc3)CC2)cc1]

White solid; mp=218.1° C.; ¹H NMR (400 MHz, CDCl₃) δ 1.40 (t, J=7.6 Hz, 3H), 2.95 (q, J=7.6 Hz, 2H), 3.24-3.29 (m, 2H), 3.31-3.36 (m, 2H), 4.62 (d, J=5.6 Hz, 2H), 6.04 (t, J=5.0 Hz, 1H), 6.92-7.01 (m, 6H), 7.31 (d, J=8.8 Hz, 2H), 7.39 (dd, J=2.0, 9.2 Hz, 1H), 7.49 (d, J=9.6 Hz, 1H), 9.63 (d, J=1.6 Hz, 1H); LCMS (electrospray) m/z (M+H)⁺ 536, 538 (Br⁻ isotope pattern).

2-Ethyl-N-(4-(4-(4-fluorophenyl)piperazin-1-yl)benzyl)-6-methylimidazo[1,2-a]pyridine-3-carboxamide (308)

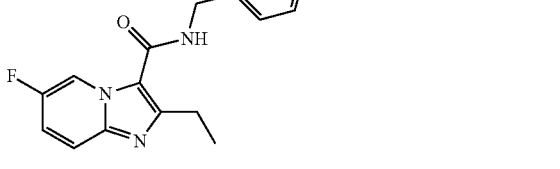

White solid; mp=187.6° C.; ¹H NMR (400 MHz, CDCl₃); δ 1.35 (t, J=7.6 Hz, 3H), 2.89 (s, 3H), 2.91 (q, J=7.6 Hz, 2H), 3.22-3.24 (m, 4H), 3.31-3.33 (m, 4H), 4.60 (d, J=5.2 Hz, 2H), 6.04 (brt, J=5.2 Hz, 1H), 6.89-6.99 (m, 6H), 7.13 (dd, J=1.6, 9.2 Hz, 1H), 7.28 (d, J=8.4 Hz, 2H), 7.46 (d, J=9.2 Hz, 1H), 9.18 (s, 1H); LCMS (electrospray) m/z 472 (M+H)⁺.

2-Ethyl-N-(4-(4-(4-fluorophenyl)piperazin-1-yl)benzyl)-7-methylimidazo[1,2-a]pyridine-3-carboxamide (309)

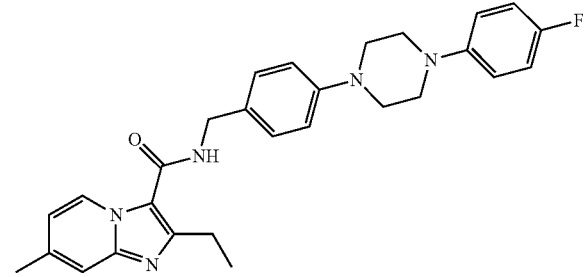 [SMILES: CCc1nc2cc(C)ccn2c1C(=O)NCc1ccc(N2CCN(c3ccc(F)cc3)CC2)cc1]

White solid; mp=203.7° C.; ¹H NMR (400 MHz, CDCl₃); δ 1.35 (t, J=7.6 Hz, 3H), 2.40 (s, 3H), 2.91 (q, J=7.6 Hz, 2H), 3.23-3.26 (m, 4H), 3.32-3.34 (m, 4H), 4.60 (d, J=5.6 Hz, 2H), 6.02 (brt, J=5.6 Hz, 1H), 6.72-6.74 (m, 1H), 6.91-7.00 (m, 6H), 7.29-7.33 (m, 3H), 9.25 (d, J=7.2 Hz, 1H); LCMS (electrospray) m/z 472 (M+H)⁺.

2-Ethyl-8-fluoro-N-(4-(4-(4-fluorophenyl)piperazin-1-yl)benzyl)imidazo[1,2-a]pyridine-3-carboxamide (310)

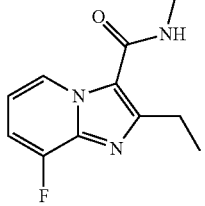

Pale yellow solid; mp=204.1° C.; ¹H NMR (400 MHz, CDCl₃+CD₃OD); δ 1.34 (t, J=7.6 Hz, 3H), 2.94 (q, J=7.6 Hz, 2H), 3.24-3.26 (m, 4H), 3.33-3.35 (m, 4H), 4.60 (d, J=5.6 Hz, 2H), 6.44 (brt, J=5.6 Hz, 1H), 6.81-6.86 (m, 1H), 6.92-7.06 (m, 7H), 7.29 (d, J=8.8 Hz, 2H), 9.08 (d, J=6.8 Hz, 1H); LCMS (electrospray) m/z 476 (M+H)⁺.

7-Bromo-2-ethyl-N-(4-(4-(4-fluorophenyl)piperazin-1-yl)benzyl)imidazo[1,2-a]pyridine-3-carboxamide (311)

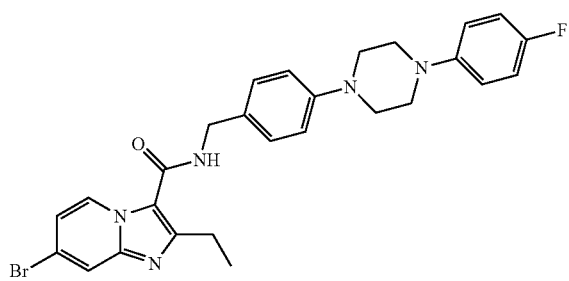

White solid; mp=214.6° C.; ¹H NMR (400 MHz, CDCl₃); δ 1.36 (t, J=7.6 Hz, 3H), 2.92 (q, J=7.6 Hz, 2H), 3.24-3.28 (m, 4H), 3.33-3.35 (m, 4H), 4.60 (d, J=5.2 Hz, 2H), 6.02 (brt, J=5.2 Hz, 1H), 6.91-7.02 (m, 7H), 7.28 (d, J=8.8 Hz, 2H), 7.76 (d, J=1.6 Hz, 1H), 9.28 (d, J=7.6 Hz, 1H); LCMS (electrospray) m/z 536, 538 (M+H)⁺ (Br⁻ isotope pattern).

2-Ethyl-N-(4-(4-(4-fluorophenyl)piperazin-1-yl)benzyl)-8-(pyridin-4-yl)imidazo[1,2-a]pyridine-3-carboxamide (312)

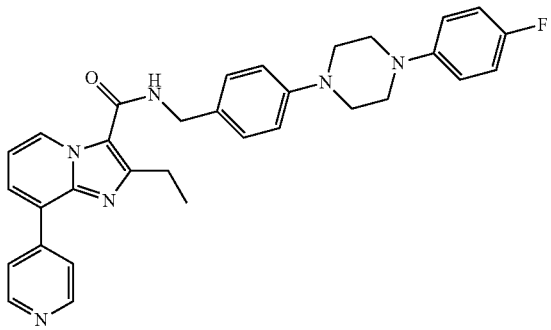 [SMILES: CCc1nc2c(-c3ccncc3)cccn2c1C(=O)NCc1ccc(N2CCN(c3ccc(F)cc3)CC2)cc1]

White solid; ¹H NMR (400 MHz, CDCl₃) δ 1.40 (t, J=7.6 Hz, 3H), 2.99 (q, J=7.6 Hz, 2H), 3.25 (t, J=5.2 Hz, 4H), 3.34 (t, J=5.2 Hz, 4H), 4.64 (d, J=5.6 Hz, 2H), 6.10 (brs, 1H), 6.91-7.04 (m, 7H), 7.32 (d, J=8.4 Hz, 2H), 7.53 (d, J=7.2 Hz, 1H), 7.99 (d, J=5.2 Hz, 2H), 8.72 (d, J=4.4 Hz, 2H), 9.47 (d, J=6.8 Hz, 1H); LCMS (electrospray) m/z (M+H)⁺ 535.

2-Ethyl-6-fluoro-N-(4-morpholinobenzyl)imidazo[1,2-a]pyridine-3-carboxamide (313)

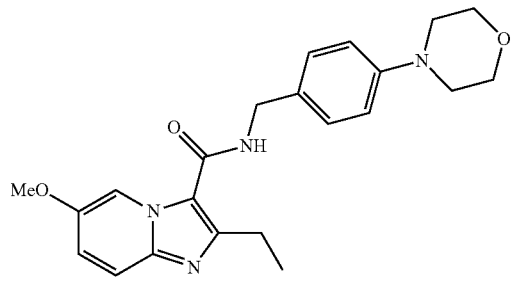 [SMILES: CCc1nc2ccc(OC)cn2c1C(=O)NCc1ccc(N2CCOCC2)cc1]

White solid; mp=193.4° C.; ¹H NMR (400 MHz, CDCl₃) δ 1.38 (t, J=7.4 Hz, 3H), 2.94 (q, J=7.6 Hz, 2H), 3.15-3.17 (m, 4H), 3.85-3.87 (m, 7H), 4.62 (d, J=52 Hz, 2H), 6.00-6.02 (m, 1H), 6.92 (d, J=9.6 Hz, 2H), 7.11 (dd, J=2.4, 9.6 Hz, 1H), 7.30 (d, J=8.8 Hz, 2H), 7.48 (d, J=9.6 Hz, 1H), 9.10 (d, J=2.4 Hz, 1H); LCMS (electrospray) m/z (M+H)⁺ 395

2-Ethyl-7-methoxy-N-(4-morpholinobenzyl)imidazo[1,2-a]pyridine-3-carboxamide (314)

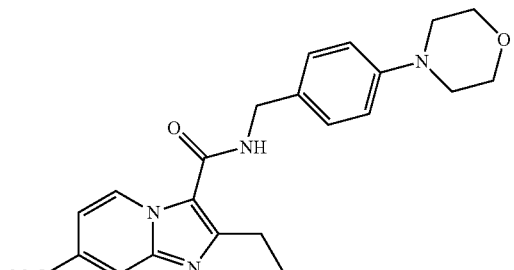

White solid; $^1$H NMR (400 MHz, CDCl$_3$); δ 1.33 (t, J=7.6 Hz, 3H), 2.86 (q, J=7.6 Hz, 2H), 3.12-3.14 (m, 4H), 3.80-3.88 (m, 4H), 3.83 (s, 3H), 4.56 (d, J=5.6 Hz, 2H), 5.98 (brt, J=5.6 Hz, 1H), 6.56 (dd, J=2.4, 7.6 Hz, 1H), 6.84 (d, J=2.4 Hz, 1H), 6.87 (d, J=8.8 Hz, 2H), 7.25 (d, J=8.8 Hz, 2H), 9.19 (d, J=7.6 Hz, 1H); $^{13}$C NMR (100 MHz, CDCl$_3$) δ 13.4, 23.5, 43.1, 49.4, 55.6, 67.0, 94.5, 107.4, 113.9, 116.0, 128.8, 128.9, 129.6, 148.1, 150.9, 151.0, 159.4, 161.5.

6-Bromo-2-ethyl-N-(4-morpholinobenzyl)imidazo[1,2-a]pyridine-3-carboxamide (315)

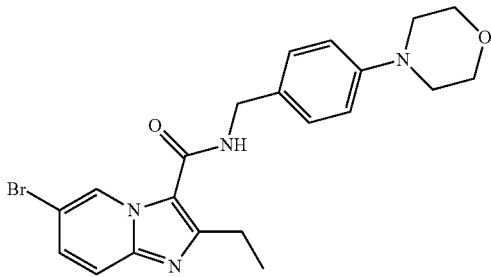 [SMILES: CCc1nc2ccc(Br)cn2c1C(=O)NCc1ccc(N2CCOCC2)cc1]

White solid; mp=228.2° C.; $^1$H NMR (400 MHz, CDCl$_3$); δ 1.38 (t, J=7.6 Hz, 3H), 2.95 (q, J=7.6 Hz, 2H), 3.16 (t, J=4.8 Hz, 4H), 3.86 (t, J=4.8 Hz, 4H), 4.61 (d, J=5.6 Hz, 2H), 6.02 (brs, 1H), 6.91 (d, J=8.8 Hz, 2H), 7.29 (d, J=8.8 Hz, 2H), 7.38 (dd, J=1.6 Hz, 9.6 Hz, 1H), 7.48 (d, J=9.6 Hz, 1H), 9.61 (d, J=0.8 Hz, 1H); LCMS (electrospray) m/z (M+H)$^+$ 443.

2-Ethyl-6-fluoro-N-(4-morpholinobenzyl)imidazo[1,2-a]pyridine-3-carboxamide (316)

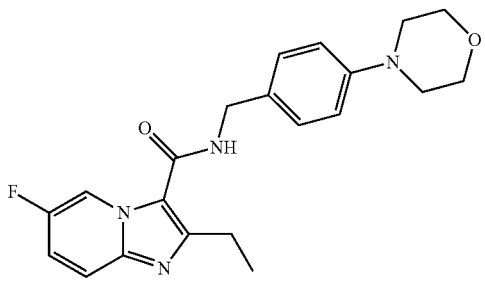 [SMILES: CCc1nc2ccc(F)cn2c1C(=O)NCc1ccc(N2CCOCC2)cc1]

White solid; mp=181.7° C.; $^1$H NMR (400 MHz, CDCl$_3$); δ 1.42 (t, J=7.6 Hz, 3H), 2.99 (q, J=7.6 Hz, 2H), 3.19 (t, J=4.8 Hz, 4H), 3.89 (t, J=4.8 Hz, 4H), 4.64 (d, J=5.2 Hz, 2H), 6.02 (brs, 1H), 6.91 (d, J=8.4 Hz, 2H), 7.26-7.33 (m, 3H), 7.60 (dd, J=5.2 Hz, 5.4 Hz, 1H), 9.48 (dd, J=2.4 Hz, 5.2 Hz, 1H); LCMS (electrospray) m/z (M+H)$^+$ 383.

2-Ethyl-8-fluoro-N-(4-morpholinobenzyl)imidazo[1,2-a]pyridine-3-carboxamide (317)

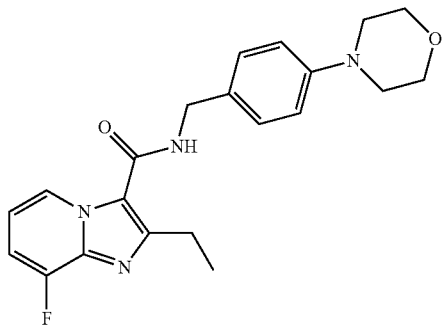

White solid; mp=197.3° C.; $^1$H NMR (400 MHz, CDCl$_3$); δ 1.39 (t, J=7.6 Hz, 3H), 2.98 (q, J=7.6 Hz, 2H), 3.15-3.17 (m, 4H), 3.85-3.87 (m, 4H), 4.61 (d, J=5.6 Hz, 2H), 6.05 (brs, 1H), 6.80-6.85 (m, 1H), 6.92 (d, J=8.8 Hz, 2H), 7.00-7.05 (m, 1H), 7.29 (d, J=8.8 Hz, 2H), 9.19 (dd, J=0.8 Hz, 7.2 Hz, 1H); LCMS (electrospray) m/z (M+H)$^+$ 383.

2-Ethyl-8-methoxy-N-(4-morpholinobenzyl)imidazo[1,2-a]pyridine-3-carboxamide (318)

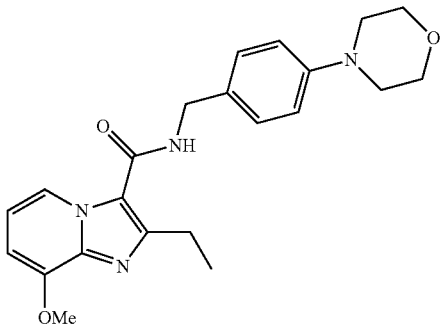 [SMILES: CCc1nc2c(OC)cccn2c1C(=O)NCc1ccc(N2CCOCC2)cc1]

Pale yellow solid; $^1$H NMR (400 MHz, CDCl$_3$); δ 1.33 (t, J=7.6 Hz, 3H), 2.92 (q, J=7.6 Hz, 2H), 3.12-3.14 (m, 4H), 3.82-3.84 (m, 4H), 3.98 (s, 3H), 4.58 (d, J=5.6 Hz, 1H), 6.08 (brs, 1H), 6.57 (d, J=7.2 Hz, 1H), 6.75 (dd, J=7.2, 7.2 Hz, 1H), 6.87 (d, J=8.8 Hz, 2H), 7.26 (d, J=8.8 Hz, 2H), 8.93 (d, J=7.2 Hz, 1H); $^{13}$C NMR (100 MHz, CDCl$_3$) δ 13.9, 23.6, 43.2, 49.3, 56.0, 67.0, 103.1, 113.0, 116.0, 120.9, 124.8, 128.9, 129.4, 140.4, 148.2, 149.9, 150.9, 161.5.

8-(Difluoromethoxy)-2-ethyl-N-(4-morpholinobenzyl)imidazo[1,2-a]pyridine-3-carboxamide (319)

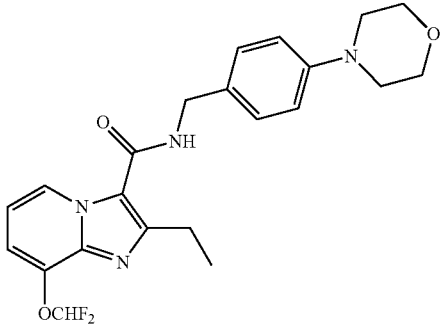 [SMILES: CCc1nc2c(OC(F)F)cccn2c1C(=O)NCc1ccc(N2CCOCC2)cc1]

Off-white solid; mp=163.0° C.; $^1$H NMR (400 MHz, CDCl$_3$) δ 1.38 (t, J=7.6 Hz, 3H), 2.97 (q, J=7.6 Hz, 2H), 3.16 (t, J=5.0 Hz, 4H), 3.86 (t, J=4.8 Hz, 4H), 4.62 (d, J=5.6 Hz, 2H), 6.03-6.05 (m, 1H), 6.85 (dd, J=7.6 Hz, 2H), 6.92 (d, J=6.8 Hz, 2H), 7.11 (d, J=7.6 Hz, 1H), 7.26 (t, J=74.2 Hz, 1H due to F$_2$), 7.29 (d, J=8.4 Hz, 2H), 9.25 (d, J=7.2 Hz, 1H); LCMS (electrospray) m/z (M+H)$^+$ 431

8-Bromo-2-ethyl-N-(4-morpholinobenzyl)imidazo[1,2-a]pyridine-3-carboxamide (320)

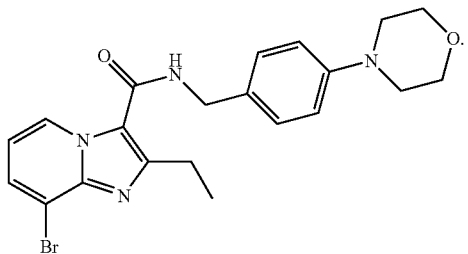 [SMILES: CCc1nc2c(Br)cccn2c1C(=O)NCc1ccc(N2CCOCC2)cc1]

White solid; ¹H NMR (400 MHz, CDCl₃) δ 1.36 (t, J=7.6 Hz, 3H), 2.99 (q, J=7.6 Hz, 2H), 3.15 (t, J=4.8 Hz, 4H), 3.85 (t, J=4.8 Hz, 4H), 4.60 (d, J=5.2 Hz, 2H), 6.06 (brs, 1H), 6.77 (dd, J=7.2 Hz, 1H), 6.90 (d, J=8.8 Hz, 2H), 7.28 (d, J=8.8 Hz, 2H), 7.56 (dd, J=0.8 Hz, 7.2 Hz, 1H), 9.37 (dd, J=0.8 Hz, 7.2 Hz, 1H); LCMS (electrospray) m/z (M+H)⁺ 445.

2-Ethyl-N-(4-morpholinobenzyl)-6-(trifluoromethyl)imidazo[1,2-a]pyridine-3-carboxamide (321)

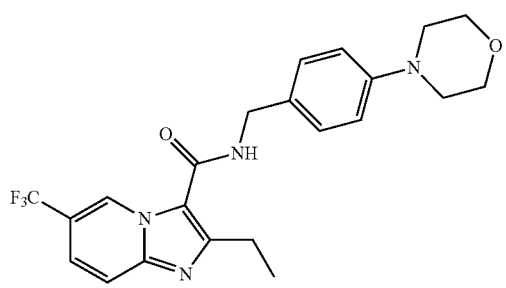 [SMILES: CCc1nc2ccc(C(F)(F)F)cn2c1C(=O)NCc1ccc(N2CCOCC2)cc1]

White solid; mp=207.6° C.; ¹H NMR (400 MHz, CDCl₃); δ 1.37 (t, J=7.2 Hz, 3H), 2.94 (q, J=7.2 Hz, 2H), 3.13-3.15 (m, 4H), 3.83-3.85 (m, 4H), 4.60 (d, J=5.2 Hz, 2H), 6.10 (brs, 1H), 6.89 (d, J=8.0 Hz, 2H), 7.27 (d, J=8.0 Hz, 2H), 7.44 (d, J=9.2 Hz, 1H), 7.65 (d, J=9.2 Hz, 1H), 9.82 (s, 1H).

2-Ethyl-N-(4-morpholinobenzyl)-7-(trifluoromethyl)imidazo[1,2-a]pyridine-3-carboxamide (322)

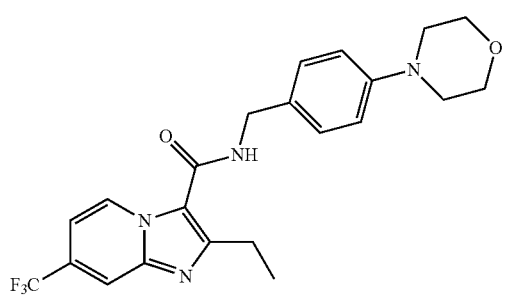

White solid; mp=174.1° C.; ¹H NMR (400 MHz, CDCl₃) δ 1.40 (t, J=7.6 Hz, 3H), 2.98 (q, J=7.6 Hz, 2H), 3.16 (t, J=4.8 Hz, 4H), 3.86 (t, J=4.8 Hz, 4H), 4.62 (d, J=5.6 Hz, 2H), 6.09-6.11 (m, 1H), 6.91 (d, J=8.8 Hz, 2H), 7.07 (dd, J=2.0, 7.6 Hz, 1H), 7.29 (d, J=8.4 Hz, 2H), 7.88-7.90 (m, 1H), 9.50 (d, J=7.2 Hz, 1H); LCMS (electrospray) m/z (M+H)⁺ 433

2-Ethyl-N-(4-morpholinobenzyl)-8-(trifluoromethyl)imidazo[1,2-a]pyridine-3-carboxamide (323)

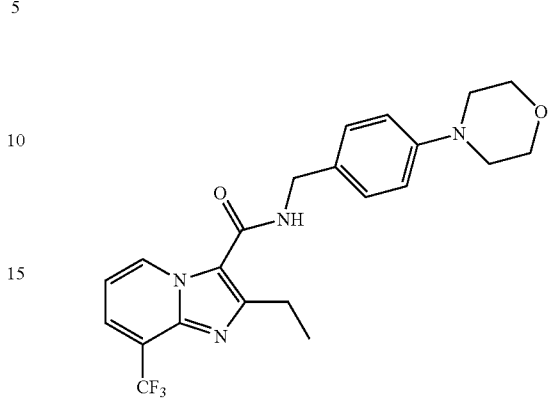

White solid; mp=200.6° C.; ¹H NMR (400 MHz, CDCl₃); δ 1.34 (t, J=7.6 Hz, 3H), 2.98 (q, J=7.6 Hz, 2H), 3.14-3.16 (m, 4H), 3.83-3.86 (m, 4H), 4.60 (d, J=5.6 Hz, 2H), 6.11 (brt, J=5.6 Hz, 1H), 6.89 (d, J=8.8 Hz, 2H), 6.93 (dd, J=6.8, 6.8 Hz, 1H), 7.26 (d, J=8.8 Hz, 2H), 7.62 (d, J=6.8 Hz, 1H), 9.54 (d, J=6.8 Hz, 1H).

7-Bromo-2-ethyl-N-(4-morpholinobenzyl)imidazo[1,2-a]pyridine-3-carboxamide (324)

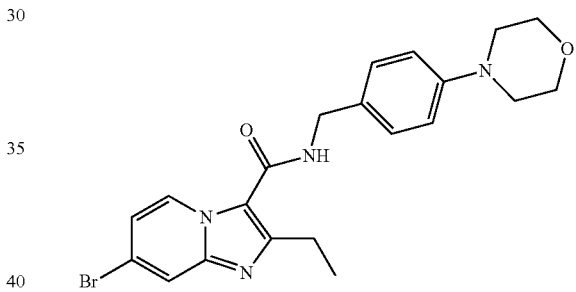

Pale gray solid; mp=202.6° C.; ¹H NMR (400 MHz, CDCl₃); δ 1.34 (t, J=7.6 Hz, 3H), 2.90 (q, J=7.6 Hz, 2H), 3.13-3.15 (m, 4H), 3.83-3.86 (m, 4H), 4.58 (d, J=5.6 Hz, 2H), 6.05 (brt, J=5.6 Hz, 1H), 6.88 (d, J=8.8 Hz, 2H), 6.97 (dd, J=2.0, 7.2 Hz, 1H), 7.26 (d, J=8.8 Hz, 2H), 7.74 (d, J=2.0 Hz, 1H), 9.25 (d, J=7.2 Hz, 1H); ¹³C NMR (100 MHz, CDCl₃) δ 13.4, 23.5, 43.2, 49.3, 67.0, 115.1, 116.0, 117.0, 119.1, 121.1, 128.5, 128.9, 129.2, 143.6, 151.0, 151.4, 161.2; LCMS (electrospray) m/z 443, 445 (M+H)⁺ (Br⁻ isotope pattern).

2-Ethyl-N-(4-morpholinobenzyl)-7-(pyridin-4-yl)imidazo[1,2-a]pyridine-3-carboxamide (325)

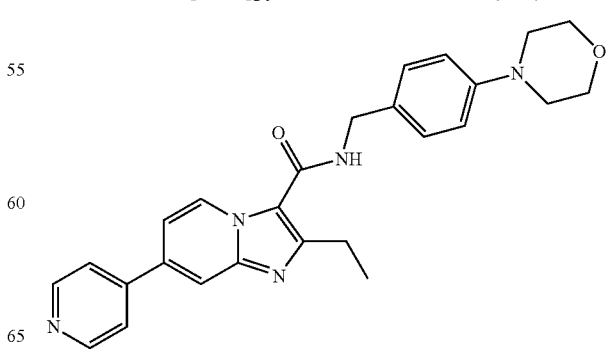

Yellow solid; mp=210.1° C.; ¹H NMR (400 MHz, CDCl₃); δ 1.37 (t, J=7.6 Hz, 3H), 2.94 (q, J=7.6 Hz, 2H), 3.12-3.15 (m, 4H), 3.82-3.85 (m, 4H), 4.60 (d, J=5.2 Hz, 2H), 6.16 (brt, J=5.2 Hz, 1H), 6.88 (d, J=8.8 Hz, 2H), 7.16 (dd, J=2.0, 7.2 Hz, 1H), 7.27 (d, J=8.8 Hz, 2H), 7.53 (d, J=6.0 Hz, 2H), 7.85 (d, J=2.0 Hz, 1H), 8.68 (d, J=6.0 Hz, 2H), 9.44 (d, J=7.2 Hz, 1H); ¹³C NMR (100 MHz, CDCl₃) δ 13.3, 23.6, 43.2, 49.3, 66.9, 111.8, 114.3, 115.3, 116.0, 121.2, 128.6, 128.9, 129.2, 136.3, 145.5, 146.1, 150.7, 151.0, 151.9, 161.2; LCMS (electrospray) m/z 442 (M+H)⁺.

2-Ethyl-N-(4-morpholinobenzyl)-7-(pyridin-3-yl)imidazo[1,2-a]pyridine-3-carboxamide (326)

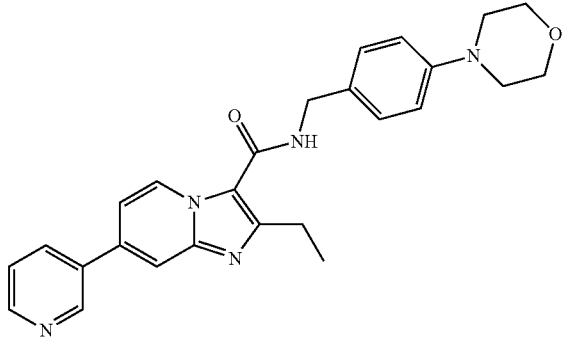 [SMILES: CCc1nc2cc(-c3cccnc3)ccn2c1C(=O)NCc1ccc(N2CCOCC2)cc1]

Yellow solid; mp=208.5° C.; ¹H NMR (400 MHz, CDCl₃); δ 1.36 (t, J=7.2 Hz, 3H), 2.93 (q, J=7.2 Hz, 2H), 3.12-3.15 (m, 4H), 3.82-3.85 (m, 4H), 4.59 (d, J=4.8 Hz, 2H), 6.21 (brs, 1H), 6.87 (d, J=8.4 Hz, 2H), 7.12 (d, J=6.0 Hz, 1H), 7.26 (d, J=8.4 Hz, 2H), 7.37 (dd, J=5.6, 6.0 Hz, 1H), 7.77 (brs, 1H), 7.90 (d, J=7.2 Hz, 1H), 8.60 (brs, 1H), 8.88 (brs, 1H), 9.41 (d, J=7.2 Hz, 1H); ¹³C NMR (100 MHz, CDCl₃) δ 13.3, 23.5, 43.2, 49.3, 66.9, 112.2, 113.8, 115.0, 116.0, 123.9, 128.5, 128.9, 129.3, 134.0, 134.2, 136.2, 146.3, 148.0, 149.6, 150.9, 151.7, 161.3; LCMS (electrospray) m/z 442 (M+H)⁺.

2-Ethyl-N-(4-morpholinobenzyl)-8-(pyridin-4-yl)imidazo[1,2-a]pyridine-3-carboxamide (327)

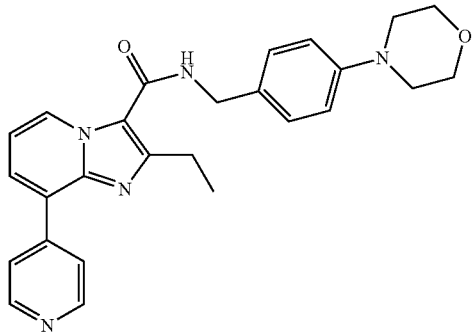 [SMILES: CCc1nc2c(-c3ccncc3)cccn2c1C(=O)NCc1ccc(N2CCOCC2)cc1]

White solid; ¹H NMR (400 MHz, CDCl₃) δ 1.40 (t, J=7.6 Hz, 3H), 2.99 (q, J=7.6 Hz, 2H), 3.16 (t, J=4.8 Hz, 4H), 3.86 (t, J=4.8 Hz, 4H), 4.63 (d, J=5.6 Hz, 2H), 6.07 (brs, 1H), 6.92 (d, J=8.8 Hz, 2H), 7.02 (dd, J=6.8, 6.8 Hz, 1H), 7.31 (d, J=8.8 Hz, 2H), 7.54 (dd, J=1.2, 7.2 Hz, 1H), 7.99 (d, J=6.0 Hz, 2H), 8.72 (d, J=5.2 Hz, 2H), 9.47 (dd, J=1.2 Hz, 5.6 Hz, 1H); LCMS (electrospray) m/z (M+H)⁺ 442.

2-Ethyl-7-(4-methylpiperazin-1-yl)-N-(4-morpholinobenzyl)imidazo[1,2-a]pyridine-3-carboxamide (328)

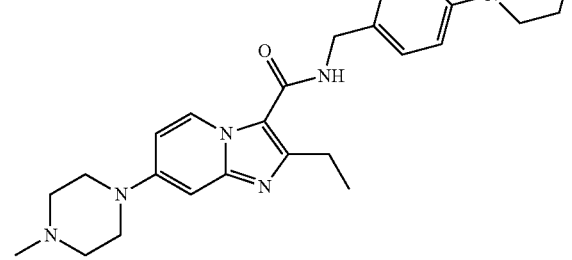

White solid; mp=204.8° C.; ¹H NMR (400 MHz, CDCl₃); δ 1.33 (t, J=7.6 Hz, 3H), 2.33 (s, 3H), 2.54-2.56 (m, 4H), 2.85 (q, J=7.6 Hz, 2H), 3.12-3.15 (m, 4H), 3.27-3.30 (m, 4H), 3.83-3.85 (m, 4H), 4.57 (d, J=5.6 Hz, 2H), 5.91 (brt, J=5.6 Hz, 1H), 6.62 (dd, J=2.4, 8.0 Hz, 1H), 6.5 (d, J=2.4 Hz, 1H), 6.88 (d, J=8.4 Hz, 2H), 7.26 (d, J=8.4 Hz, 2H), 9.16 (d, J=8.0 Hz, 1H); ¹³C NMR (100 MHz, CDCl₃) δ 13.4, 23.6, 43.1, 46.2, 47.8, 49.4, 54.7, 67.0, 96.4, 105.9, 113.2, 116.0, 128.3, 128.8, 129.8, 148.5, 150.0, 150.9, 151.2, 161.7; LCMS (electrospray) m/z 463 (M+H)⁺.

2-Ethyl-7-(4-(4-fluorophenyl)piperazin-1-yl)-N-(4-morpholinobenzyl)imidazo[1,2-a]pyridine-3-carboxamide (329)

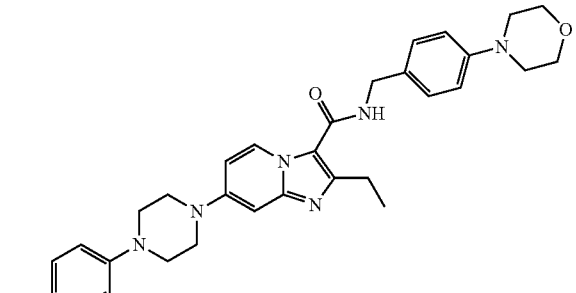

White solid; ¹H NMR (400 MHz, CDCl₃); δ 1.34 (t, J=7.6 Hz, 3H), 2.87 (q, J=7.6 Hz, 2H), 3.13-3.15 (m, 4H), 3.22-3.25 (m, 4H), 3.41-3.43 (m, 4H), 3.83-3.86 (m, 4H), 4.58 (d, J=5.2 Hz, 2H), 5.99 (brt, J=5.2 Hz, 1H), 6.67 (dd, J=2.4, 8.0 Hz, 1H), 6.81 (d, J=2.4 Hz, 1H), 6.88-6.93 (m, 4H), 6.96 (dd, J=8.4, 8.8 Hz, 2H), 7.27 (d, J=8.4 Hz, 2H), 9.19 (d, J=8.0 Hz, 1H); LCMS (electrospray) m/z 543 (M+H)⁺.

143

2-Ethyl-7-(4-phenylpiperazin-1-yl)-N-(4-(trifluoromethyl)benzyl)imidazo[1,2-a]pyridine-3-carboxamide (330)

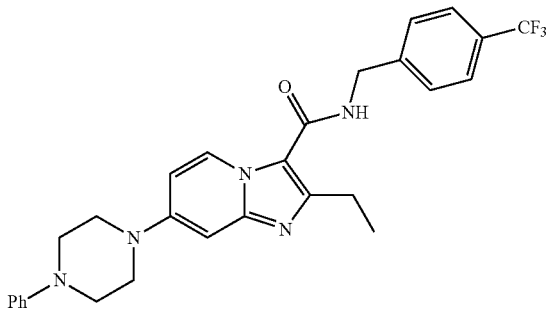 [SMILES: CCc1nc2cc(N3CCN(c4ccccc4)CC3)ccn2c1C(=O)NCc1ccc(C(F)(F)F)cc1]

Pale yellow solid; mp=235.2° C.; $^1$H NMR (400 MHz, CDCl$_3$); δ 1.40 (t, J=7.2 Hz, 3H), 2.93 (q, J=7.2 Hz, 2H), 3.34-3.36 (m, 4H), 3.44-3.48 (m, 4H), 4.74 (d, J=6.0 Hz, H), 6.07 (brt, J=6.0 Hz, 1H), 6.70 (dd, J=2.4, 7.6 Hz, 1H), 6.84 (d, J=2.4 Hz, 1H), 6.90 (dd, J=7.2, 7.6 Hz, 1H), 6.97 (d, J=8.4 Hz, 2H), 7.28-7.32 (m, 2H), 7.48 (d, J=8.0 Hz, 2H), 7.61 (d, J=8.4 Hz, 2H), 9.22 (d, J=7.6 Hz, 1H); LCMS (electrospray) m/z 508 (M+H)$^+$.

2-Ethyl-7-(4-(4-fluorobenzyl)piperazin-1-yl)-N-(4-morpholinobenzyl)imidazo[1,2-a]pyridine-3-carboxamide (331)

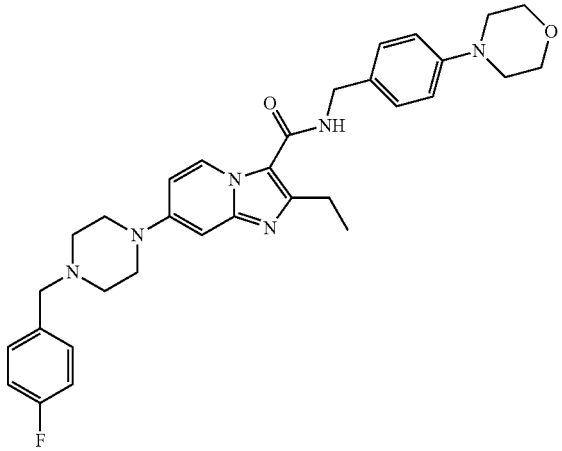 [SMILES: CCc1nc2cc(N3CCN(Cc4ccc(F)cc4)CC3)ccn2c1C(=O)NCc1ccc(N2CCOCC2)cc1]

White solid; mp=212.5° C.; $^1$H NMR (400 MHz, CDCl$_3$); δ 1.33 (t, J=7.6 Hz, 3H), 2.56-2.58 (m, 4H), 2.85 (q, J=7.6 Hz, 2H), 3.13-3.15 (m, 4H), 3.26-3.29 (m, 4H), 3.51 (s, 2H), 3.83-3.86 (m, 4H), 4.57 (d, J=5.6 Hz, 2H), 5.93 (brt, J=5.6 Hz, 1H), 6.62 (dd, J=2.4, 7.6 Hz, 1H), 6.75 (d, J=2.4 Hz, 1H), 6.88 (d, J=8.8 Hz, 2H), 6.98-7.03 (m, 2H), 7.26-7.31 (m, 4H), 9.15 (d, J=7.6 Hz, 1H).

144

6-Chloro-2-ethyl-N-(4-((4-(morpholine-4-carbonyl)benzyl)carbamoyl)benzyl) imidazo[1,2-a]pyridine-3-carboxamide (332)

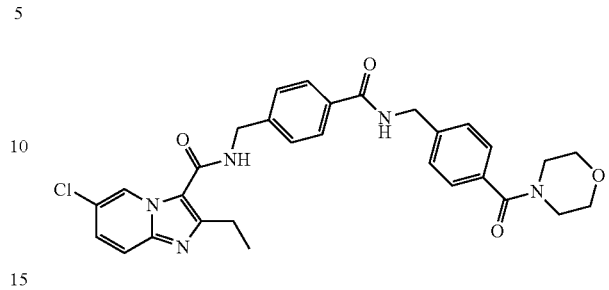

White-solid; $^1$H NMR (400 MHz, CDCl$_3$) δ 1.40 (t, J=7.6 Hz, 3H), 2.98 (q, J=7.6 Hz, 2H), 3.72 (m, 8H), 4.65 (d, J=6.0 Hz, 2H), 4.73 (d, J=6.0 Hz, 2H), 6.29 (brs, 1H), 6.62 (brs, 1H), 7.31 (dd, J=2.0 Hz, 9.6 Hz, 1H), 7.36 (s, 4H), 7.43 (d, J=8.0 Hz, 2H), 7.55 (d, J=9.6 Hz, 1H), 7.80 (d, J=8.0 Hz, 2H), 9.49 (s, 1H); LCMS (electrospray) m/z (M+H)$^+$ 560.

7-Chloro-2-ethyl-N-(4-(morpholine-4-carbonyl)benzyl)imidazo[1,2-a]pyridine-3-carboxamide (333)

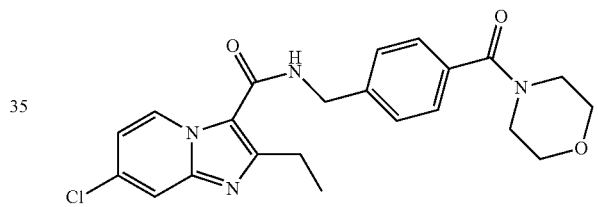

White solid; $^1$H NMR (400 MHz, CDCl$_3$) δ 1.42 (t, J=7.6 Hz, 3H), 2.99 (q, J=7.6 Hz, 2H), 3.70-3.71 (m, 8H), 4.72 (d, J=6.0 Hz, 2H), 6.17 (brs, 1H), 7.31 (dd, J=2.0 Hz, 9.2 Hz, 1H), 7.42 (s, 4H), 7.55 (dd, J=0.8 Hz, 9.6 Hz, 1H), 9.53 (dd, J=0.8 Hz, 2.0 Hz, 1H); LCMS (electrospray) m/z (M+H)$^+$ 427.

2-Ethyl-N-((2-(4-fluorophenyl)benzo[d]oxazol-5-yl)methyl)imidazo[1,2-a]pyridine-3-carboxamide (334)

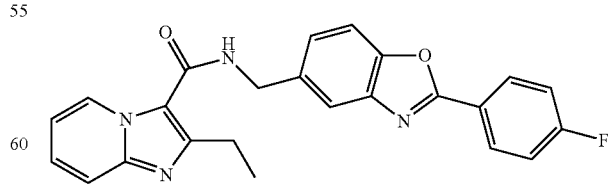

White solid; $^1$H NMR (400 MHz, DMSO-d$_6$) δ 1.25 (t, J=7.6 Hz, 3H), 2.99 (q, J=7.6 Hz, 2H), 4.65 (d, J=6.0 Hz, 2H), 6.99 (dd, J=7.2 Hz, 1H), 7.36 (dd, J=6.8 Hz, 1H), 7.42 (s, 1H), 7.45 (d, J=8.8 Hz, 2H), 7.58 (d, J=9.2 Hz, 1H), 7.74 (d, J=8.4

Hz, 1H), 7.77 (s, 1H), 8.23 (dd, J=5.2 Hz, 8.8 Hz, 2H), 8.47 (t, J=6.0 Hz, 1H), 8.97 (d, J=6.8 Hz, 1H); LCMS (electrospray) m/z (M+H)+ 415.

6-Chloro-2-ethyl-N-((2-(4-fluorophenyl)benzo[d]oxazol-5-yl)methyl)imidazo[1,2-a]pyridine-3-carboxamide (335)

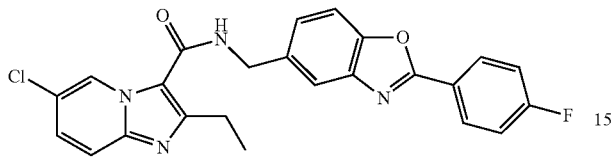

White solid; $^1$H NMR (400 MHz, DMSO-d$_6$) δ 1.25 (t, J=7.6 Hz, 3H), 2.99 (q, J=7.6 Hz, 2H), 4.65 (d, J=5.6 Hz, 2H), 7.41-7.46 (m, 4H), 7.64 (d, J=9.6 Hz, 1H), 7.74 (d, J=8.4 Hz, 1H), 7.78 (s, 1H), 8.21-8.25 (m, 2H), 8.54 (t, J=5.6 Hz, 1H), 9.08 (d, J=2.0 Hz, 1H); LCMS (electrospray) m/z (M+H)+ 449.

7-Chloro-2-ethyl-N-((2-(4-fluorophenyl)benzo[d]oxazol-5-yl)methyl)imidazo[1,2-a]pyridine-3-carboxamide (336)

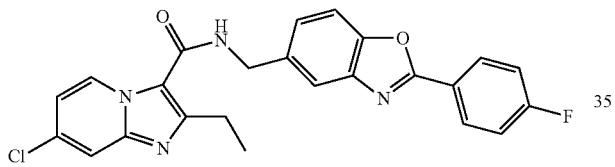

White solid; $^1$H NMR (400 MHz, DMSO-d$_6$) δ 1.25 (t, J=7.2 Hz, 3H), 2.98 (q, J=7.2 Hz, 2H), 4.64 (d, J=5.6 Hz, 2H), 7.07 (d, J=7.6 Hz, 1H), 7.42-7.46 (m, 3H), 7.75 (d, J=8.4 Hz, 2H), 7.77 (s, 1H), 8.23 (d, J=8.4 Hz, 2H), 8.55 (brs, 1H), 8.96 (d, J=7.2 Hz, 1H); LCMS (electrospray) m/z (M+H)+ 449.

6-Chloro-N-(4-(4-(4-chlorophenyl)piperidin-1-yl)benzyl)-2-ethylimidazo[1,2-a]pyridine-3-carboxamide (337)

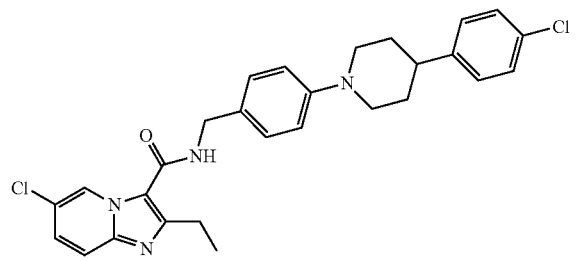 [SMILES: CCc1nc2ccc(Cl)cn2c1C(=O)NCc1ccc(N2CCC(c3ccc(Cl)cc3)CC2)cc1]

Pale yellow solid; $^1$H NMR (400 MHz, CDCl$_3$) δ 1.39 (t, J=7.6 Hz, 3H), 1.80-1.96 (m, 4H), 2.60-2.68 (m, 1H), 2.92-2.98 (m, 4H), 2.95 (q, J=7.6 Hz, 2H), 3.79-3.83 (m, 2H), 4.61 (q, J=5.2 Hz, 2H), 5.99-6.01 (m, 1H), 6.90 (dd, J=2.2, 7.4 Hz, 1H), 6.98 (d, J=8.4 Hz, 2H), 7.18 (d, J=8.4 Hz, 2H), 7.26-7.29 (m, 4H), 7.59 (d, J=2.0 Hz, 1H), 9.30 (d, J=7.6 Hz, 1H); LCMS (electrospray) m/z (M+H)+ 507

7-Chloro-N-(4-(4-(4-chlorophenyl)piperidin-1-yl)benzyl)-2-ethylimidazo[1,2-a]pyridine-3-carboxamide (338)

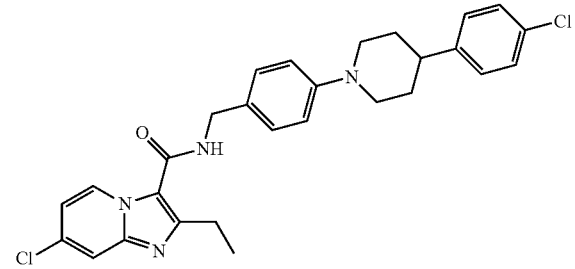 [SMILES: CCc1nc2cc(Cl)ccn2c1C(=O)NCc1ccc(N2CCC(c3ccc(Cl)cc3)CC2)cc1]

Pale yellow solid; mp=177.0° C.; $^1$H NMR (400 MHz, CDCl$_3$) δ 1.40 (t, J=7.4 Hz, 3H), 1.80-1.96 (m, 4H), 2.60-2.67 (m, 1H), 2.79-2.86 (m, 4H), 2.96 (q, J=7.4 Hz, 2H), 3.80-3.83 (m, 2H), 4.62 (q, J=5.2 Hz, 2H), 6.00-6.02 (m, 1H), 6.98 (dd, J=8.8 Hz, 2H), 7.18 (d, J=8.4 Hz, 2H), 7.26-7.31 (m, 4H), 7.54 (d, J=9.6 Hz, 2H), 9.30 (d, J=7.6 Hz, 1H).

6-Chloro-N-((2-cyclohexylbenzo[d]oxazol-5-yl)methyl)-2-ethylimidazo[1,2-a]pyridine-3-carboxamide (339)

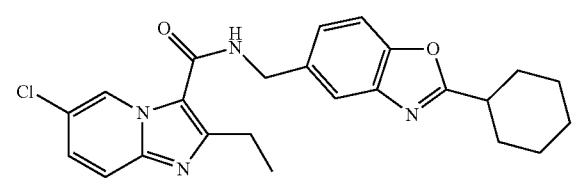 [SMILES: CCc1nc2ccc(Cl)cn2c1C(=O)NCc1ccc2oc(C3CCCCC3)nc2c1]

White solid; mp=169.7° C.; $^1$H NMR (400 MHz, CDCl$_3$) δ 1.30-1.44 (m, 4H), 1.59-1.88 (m, 8H), 2.16 (d, J=10.8 Hz, 2H), 2.96 (q, J=7.6 Hz, 2H), 4.78 (d, J=5.6 Hz, 2H), 6.19 (brs, 1H), 7.28 (d, J=1.6 Hz, 1H), 7.30-7.34 (m, 1H), 7.46 (d, J=8.0 Hz, 1H), 7.53 (d, J=9.2 Hz, 1H), 7.67 (s, 1H), 9.53 (d, J=2.4 Hz, 1H); LCMS (electrospray) m/z (M+H)+ 437.

7-Chloro-N-((2-cyclohexylbenzo[d]oxazol-5-yl)methyl)-2-ethylimidazo[1,2-a]pyridine-3-carboxamide (340)

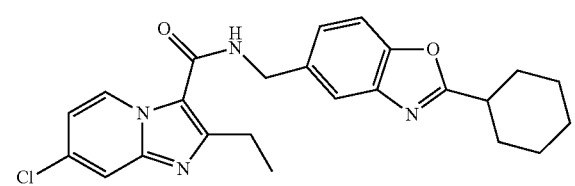 [SMILES: CCc1nc2cc(Cl)ccn2c1C(=O)NCc1ccc2oc(C3CCCCC3)nc2c1]

White solid; mp=163.0° C.; $^1$H NMR (400 MHz, CDCl$_3$) δ 1.30-1.46 (m, 6H), 1.60-1.73 (m, 4H), 1.86 (d, J=13.2 Hz, 2H), 2.15 (d, J=13.2 Hz, 2H), 2.95 (q, J=7.2 Hz, 2H), 4.77 (d, J=5.6 Hz, 2H), 6.12 (brs, 1H), 6.89 (d, J=7.2 Hz, 1H), 7.31 (d, J=8.0 Hz, 1H), 7.46 (d, J=8.0 Hz, 1H), 7.58 (s, 1H), 7.67 (s, 1H), 9.36 (d, J=7.2 Hz, 1H); LCMS (electrospray) m/z (M+H)+ 437.

6-Chloro-2-ethyl-N-(4-(4-(4-fluorophenyl)-4-hydroxypiperidin-1-yl)benzyl)imidazo[1,2-a]pyridine-3-carboxamide (341)

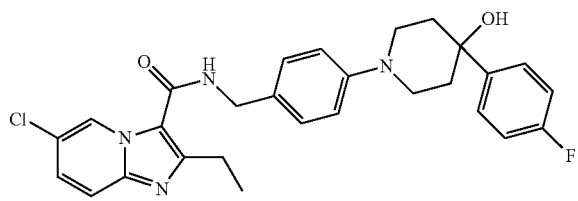 [SMILES: CCc1nc2ccc(Cl)cn2c1C(=O)NCc1ccc(N2CCC(O)(c3ccc(F)cc3)CC2)cc1]

White solid; mp=173.5° C.; ¹H NMR (400 MHz, CDCl₃) δ 1.35 (t, J=7.6 Hz, 3H), 1.66 (s, 1H), 1.85 (d, J=12.0 Hz, 2H), 2.18-2.26 (m, 2H), 2.91 (q, J=7.6 Hz, 2H), 3.21-3.26 (dd, J=10.4 Hz, 12.0 Hz, 2H), 3.58 (d, J=11.6 Hz, 2H), 4.60 (d, J=5.6 Hz, 2H), 6.00 (brs, 1H), 6.89 (dd, J=1.6 Hz, 7.6 Hz, 1H), 6.99 (d, J=8.4 Hz, 2H), 7.04 (dd, J=8.8 Hz, 2H), 7.26 (d, J=8.4 Hz, 2H), 7.48 (dd, J=5.2 Hz, 8.8 Hz, 2H), 7.56 (d, J=2.0 Hz, 1H), 9.35 (d, J=7.6 Hz, 1H); LCMS (electrospray) m/z (M+H)⁺ 507.

7-Chloro-2-ethyl-N-(4-(4-(4-fluorophenyl)-4-hydroxypiperidin-1-yl)benzyl)imidazo[1,2-a]pyridine-3-carboxamide (342)

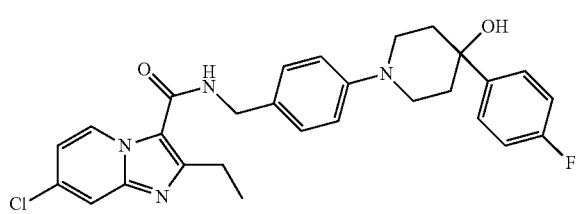 [SMILES: CCc1nc2cc(Cl)ccn2c1C(=O)NCc1ccc(N2CCC(O)(c3ccc(F)cc3)CC2)cc1]

White solid; mp=199.0° C.; ¹H NMR (400 MHz, CDCl₃) δ 1.38 (t, J=7.6 Hz, 3H), 1.6 (s, 1H), 1.86 (dd, J=2.8 Hz, 14.0 Hz, 2H), 2.19-2.26 (m, 2H), 2.95 (q, J=7.6 Hz, 2H), 3.20-3.27 (m, 2H), 3.59 (dd, J=2.4 Hz, 10.0 Hz, 2H), 4.61 (d, J=5.6 Hz, 2H), 6.02 (s, 1H), 6.98-7.06 (m, 4H), 7.27 (d, J=8.8 Hz, 2H), 7.29 (s, 1H), 7.46-7.51 (m, 2H), 7.53 (s, 1H), 9.52 (d, J=2.4 Hz, 1H); LCMS (electrospray) m/z (M+H)⁺ 507.

N-(4-(4-Carbamoylpiperidin-1-yl)benzyl)-6-chloro-2-ethylimidazo[1,2-a]pyridine-3-carboxamide (343)

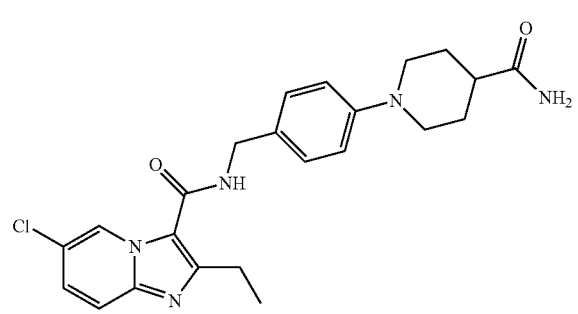 [SMILES: CCc1nc2ccc(Cl)cn2c1C(=O)NCc1ccc(N2CCC(C(N)=O)CC2)cc1]

White solid; mp=257.5° C.; ¹H NMR (400 MHz, DMSO-d⁶); δ 1.23 (t, J=7.2 Hz, 3H), 1.57-1.66 (m, 2H), 1.74-1.76 (m, 2H), 2.19-2.45 (m, 1H), 2.59-2.66 (m, 2H), 2.94 (q, J=7.2 Hz, 2H), 3.65-3.69 (m, 2H), 4.41 (d, J=6.0 Hz, 2H), 6.75 (brs, 1H), 6.90 (d, J=8.4 Hz, 2H), 7.20 (d, J=8.4 Hz, 2H), 7.26 (brs, 1H), 7.43 (dd, J=2.4, 9.6 Hz, 1H), 7.67 (d, J=9.6 Hz, 1H), 8.38 (brt, J=6.0 Hz, 1H), 9.06 (d, J=2.4 Hz, 1H); LCMS (electrospray) m/z 440 (M+H)⁺.

N-(4-(4-Carbamoylpiperidin-1-yl)benzyl)-7-chloro-2-ethylimidazo[1,2-a]pyridine-3-carboxamide (344)

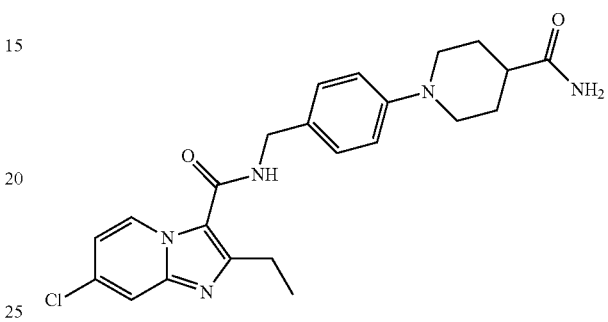

White solid; mp=244° C.; ¹H NMR (400 MHz, DMSO-d⁶); δ 1.23 (t, J=7.2 Hz, 3H), 1.56-1.66 (m, 2H), 1.74-1.76 (m, 2H), 2.18-2.24 (m, 1H), 2.59-2.66 (m, 2H), 2.92 (q, J=7.2 Hz, 2H), 3.65-3.68 (m, 2H), 4.40 (d, J=5.6 Hz, 2H), 6.75 (brs, 1H), 6.89 (d, J=8.8 Hz, 2H), 7.07 (dd, J=2.0, 7.6 Hz, 1H), 7.19 (d, J=8.8 Hz, 2H), 7.25 (brs, 1H), 7.77 (d, J=2.0 Hz, 1H), 8.36 (brt, J=5.6 Hz, 1H), 8.93 (d, J=7.6 Hz, 1H); LCMS (electrospray) m/z 440 (M+H)⁺.

6-Chloro-N-(4-(4-(dimethylcarbamoyl)piperidin-1-yl)benzyl)-2-ethylimidazo[1,2-a]pyridine-3-carboxamide (345)

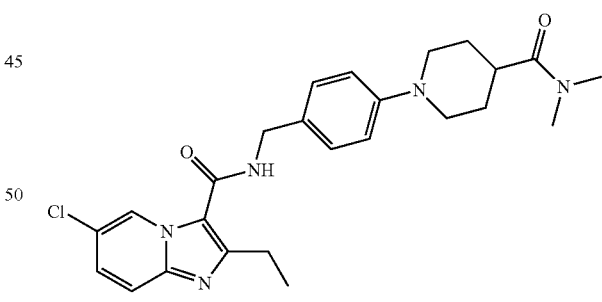

White solid; ¹H NMR (400 MHz, CDCl₃); δ 1.35 (t, J=7.6 Hz, 3H), 1.78-1.81 (m, 2H), 1.90-2.00 (m, 2H), 2.59-2.67 (m, 1H), 2.71-7.78 (m, 2H), 2.91-2.97 (m, 5H), 3.07 (s, 3H), 3.73-3.76 (m, 2H), 4.57 (d, J=5.2 Hz, 2H), 6.03 (brt, J=5.2 Hz, 1H), 6.90 (d, J=8.4 Hz, 2H), 7.23-7.28 (m, 3H), 7.50 (d, J=9.6 Hz, 1H), 9.50 (d, J=1.2 Hz, 1H); ¹³C NMR (100 MHz, CDCl₃) δ 13.3, 23.6, 28.4, 35.8, 37.2, 38.7, 43.3, 49.3, 115.4, 116.7, 117.0, 121.5, 126.3, 128.2, 128.5, 128.9, 144.5, 151.3, 151.4, 161.1, 174.7; LCMS (electrospray) m/z 468 (M+H)⁺.

7-Chloro-N-(4-(4-(dimethylcarbamoyl)piperidin-1-yl)benzyl)-2-ethylimidazo[1,2-a]pyridine-3-carboxamide (346)

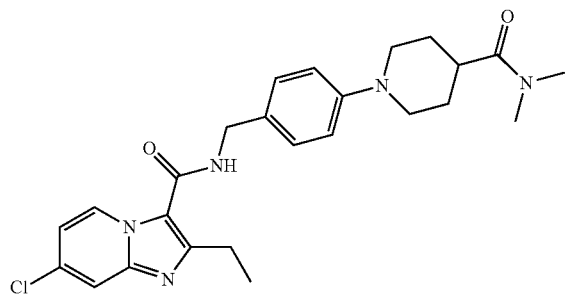 [SMILES: CCc1nc2cc(Cl)ccn2c1C(=O)NCc1ccc(N2CCC(C(=O)N(C)C)CC2)cc1]

Pale yellow solid; $^1$H NMR (400 MHz, CDCl$_3$); δ 1.33 (t, J=7.2 Hz, 3H), 1.77-1.80 (m, 2H), 1.88-1.99 (m, 2H), 2.58-2.66 (m, 1H), 2.70-2.77 (m, 2H), 2.89-2.95 (m, 5H), 3.06 (s, 3H), 3.71-3.74 (m, 2H), 4.56 (d, J=5.2 Hz, 2H), 6.07 (brs, 1H), 6.84 (dd, J=1.6, 7.2 Hz, 1H), 6.89 (d, J=8.4 Hz, 2H), 7.22 (d, J=8.4 Hz, 2H), 7.54 (d, J=1.6 Hz, 1H), 9.30 (d, J=7.2 Hz, 1H); $^{13}$C NMR (100 MHz, CDCl$_3$) δ 13.4, 23.5, 28.4, 35.8, 37.2, 38.7, 43.3, 49.3, 114.6, 115.1, 115.7, 116.7, 128.5, 128.6, 128.8, 133.5, 146.1, 151.2, 151.6, 161.2, 174.7; LCMS (electrospray) m/z 468 (M+H)$^+$.

6-Chloro-2-ethyl-N-(4-(4-(4-fluorobenzyloxy)piperidin-1-yl)benzyl)imidazo[1,2-a]pyridine-3-carboxamide (347)

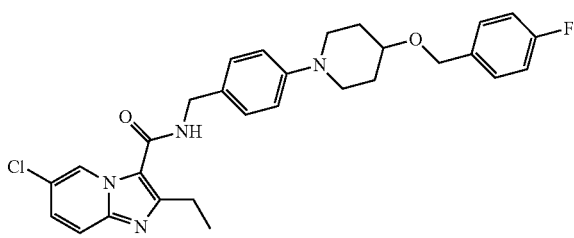 [SMILES: CCc1nc2ccc(Cl)cn2c1C(=O)NCc1ccc(N2CCC(OCc3ccc(F)cc3)CC2)cc1]

Pale pink solid; $^1$H NMR (400 MHz, CDCl$_3$); δ 1.35 (t, J=7.6 Hz, 3H), 1.73-1.82 (m, 2H), 2.00-2.04 (m, 2H), 2.91-2.98 (m, 4H), 3.50-3.59 (m, 3H), 4.53 (s, 2H), 4.58 (d, J=5.2 Hz, 2H), 6.00 (brt, J=5.2 Hz, 1H), 6.91 (d, J=8.8 Hz, 2H), 6.99-7.04 (m, 2H), 7.23-7.35 (m, 5H), 7.50 (d, J=9.6 Hz, 1H), 9.51 (d, J=2.0 Hz, 1H); LCMS (electrospray) m/z 521 (M+H)$^+$.

7-Chloro-2-ethyl-N-(4-(4-(4-fluorobenzyloxy)piperidin-1-yl)benzyl)imidazo[1,2-a]pyridine-3-carboxamide (348)

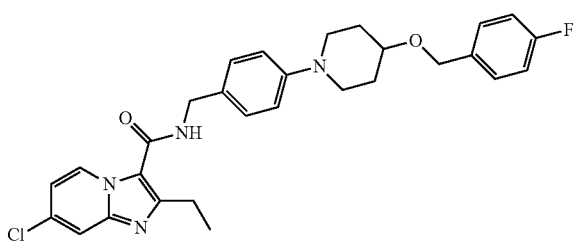 [SMILES: CCc1nc2cc(Cl)ccn2c1C(=O)NCc1ccc(N2CCC(OCc3ccc(F)cc3)CC2)cc1]

Pale pink solid; $^1$H NMR (400 MHz, CDCl$_3$); δ 1.34 (t, J=7.2 Hz, 3H), 1.73-1.82 (m, 2H), 1.96-2.07 (m, 2H), 2.91-2.95 (m, 4H), 3.49-3.59 (m, 3H), 4.52 (s, 2H), 4.56 (d, J=5.6 Hz, 2H), 5.99 (brt, J=5.6 Hz, 1H), 6.86-6.92 (m, 3H), 6.99-7.03 (m, 2H), 7.22-7.32 (m, 4H), 7.55 (d, J=1.6 Hz, 1H), 9.32 (d, J=7.2 Hz, 1H); LCMS (electrospray) m/z 521 (M+H)$^+$.

6-Chloro-N-(3-chloro-4-morpholinobenzyl)-2-ethylimidazo[1,2-a]pyridine-3-carboxamide (349)

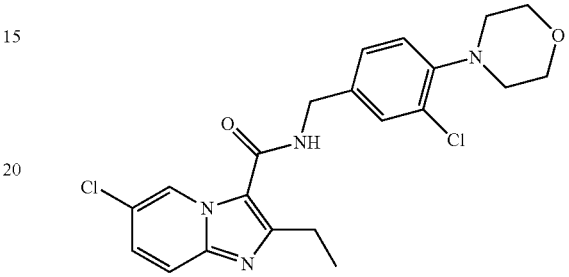

White solid; mp=175.5° C.; $^1$H NMR (400 MHz, CDCl$_3$); δ 1.37 (t, J=7.6 Hz, 3H), 2.94 (q, J=7.6 Hz, 2H), 2.99-3.03 (m, 4H), 3.83-3.85 (m, 4H), 4.58 (d, J=6.0 Hz, 2H), 6.15 (brt, J=6.0 Hz, 1H), 6.99 (d, J=8.0 Hz, 1H), 7.21 (dd, J=1.6, 8.0 Hz, 1H), 7.26-7.28 (m, 1H), 7.36 (d, J=1.6 Hz, 1H), 7.49 (d, J=9.2 Hz, 1H), 9.47 (d, J=0.8 Hz, 1H); $^{13}$C NMR (100 MHz, CDCl$_3$) δ 13.3, 23.7, 42.7, 51.8, 67.2, 115.1, 117.0, 120.7, 121.7, 126.3, 127.0, 128.4, 129.2, 130.1, 134.0, 144.6, 148.6, 151.6, 161.2; LCMS (electrospray) m/z 433 (M+H)$^+$.

7-Chloro-N-(3-chloro-4-morpholinobenzyl)-2-ethylimidazo[1,2-a]pyridine-3-carboxamide (350)

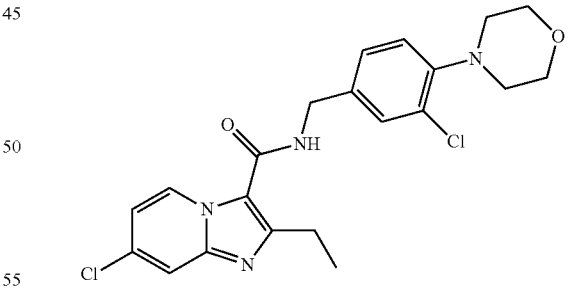

Pale yellow solid; $^1$H NMR (400 MHz, CDCl$_3$); δ 1.38 (t, J=7.6 Hz, 3H), 2.94 (q, J=7.6 Hz, 2H), 3.02-3.05 (m, 4H), 3.85-3.87 (m, 4H), 4.59 (d, J=5.6 Hz, 2H), 6.09 (brt, J=5.6 Hz, 1H), 6.88 (dd, J=2.0, 7.2 Hz, 1H), 7.00 (d, J=8.0 Hz, 1H), 7.22 (dd, J=1.6, 8.0 Hz, 1H), 7.37 (d, J=1.6 Hz, 1H), 7.57 (d, J=2.0 Hz, 1H), 9.32 (d, J=7.2 Hz, 1H); $^{13}$C NMR (100 MHz, CDCl$_3$) δ 13.4, 23.7, 42.7, 51.8, 67.3, 114.9, 115.8, 120.7, 127.1, 128.6, 129.2, 130.1, 133.8, 134.0, 146.3, 148.7, 151.9, 161.3 (hidden 1 carbon); LCMS (electrospray) m/z 433 (M+H)$^+$.

6-Chloro-2-ethyl-N-(4-(4-formylpiperidin-1-yl)benzyl)imidazo[1,2-a]pyridine-3-carboxamide (351)

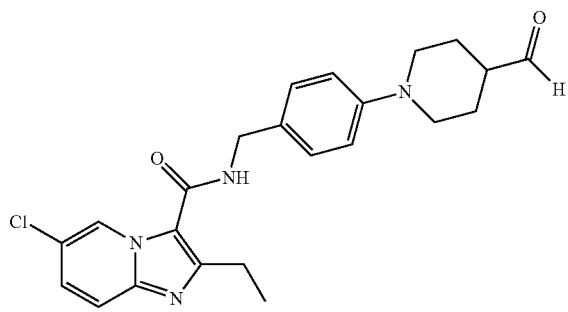 [SMILES: CCc1nc2ccc(Cl)cn2c1C(=O)NCc1ccc(N2CCC(C=O)CC2)cc1]

Pale yellow solid; $^1$H NMR (400 MHz, CDCl$_3$); δ 1.36 (t, J=7.6 Hz, 3H), 1.74-1.84 (m, 2H), 2.01-2.05 (m, 2H), 2.37-2.44 (m, 1H), 2.84-2.91 (m, 2H), 2.92 (q, J=7.6 Hz, 2H), 3.60-3.65 (m, 2H), 4.59 (d, J=5.6 Hz, 2H), 5.99 (brt, J=5.6 Hz, 1H), 6.92 (d, J=8.4 Hz, 2H), 7.25 (d, J=8.4 Hz, 2H), 7.27 (dd, J=2.4, 9.6 Hz, 1H), 7.52 (d, J=9.6 Hz, 1H), 9.52 (d, J=2.4 Hz, 1H), 9.70 (s, 1H); LCMS (electrospray) m/z 425 (M+H)$^+$.

7-Chloro-2-ethyl-N-(4-(4-formylpiperidin-1-yl)benzyl)imidazo[1,2-a]pyridine-3-carboxamide (352)

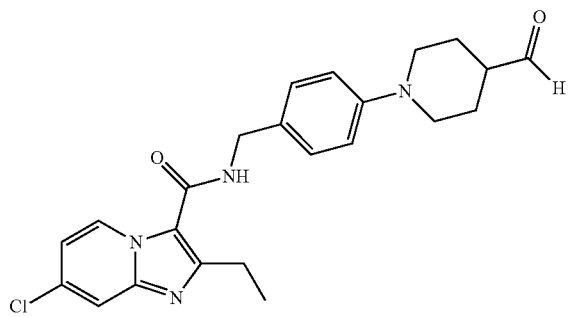 [SMILES: CCc1nc2cc(Cl)ccn2c1C(=O)NCc1ccc(N2CCC(C=O)CC2)cc1]

Pale yellow solid; $^1$H NMR (400 MHz, CDCl$_3$); δ 1.35 (t, J=7.6 Hz, 3H), 1.74-1.84 (m, 2H), 2.01-2.05 (m, 2H), 2.38-2.44 (m, 1H), 2.84-2.90 (m, 2H), 2.91 (q, J=7.6 Hz, 2H), 3.59-3.64 (m, 2H), 4.58 (d, J=5.2 Hz, 2H), 5.98 (brt, J=5.2 Hz, 1H), 6.88 (dd, J=2.0, 7.6 Hz, 1H), 6.91 (d, J=8.4 Hz, 2H), 7.52 (d, J=8.4 Hz, 2H), 7.57 (d, J=2.0 Hz, 1H), 9.34 (d, J=7.6 Hz, 1H), 9.70 (s, 1H); LCMS (electrospray) m/z 425 (M+H)$^+$.

Example 3

Additional Studies on Imidazopyridine Compounds

Kinetics of Inhibition and Bactericidal Activity

*Mycobacterium tuberculosis* H37Rv was incubated at an initial inoculum of 2×10$^6$ bacteria/ml in Middlebrook 7H9 media containing an increasing concentration of representative compound 47 or 54. Culture samples were collected over a 14 day period. Serial dilutions of the bacterial suspension were performed and plated on 7H 10 medium. Colonies were counted for the different dilutions after 3 weeks incubation at 37° C. under 5% CO$_2$ and compared to that obtained for the DMSO negative and PA-824 positive controls. PA-824 (Stover et al., 2000) is a TB Alliance small chemical compound currently in phase II clinical trials for the treatment of tuberculosis. PA-824 possibly acts via generation of radicals having non-specific toxic effects. However, the durg has been shown to inhibit mycolic acid and protein biosynthesis. In addition, PA-824 demonstrates anaerobic activity.

Figure 2:
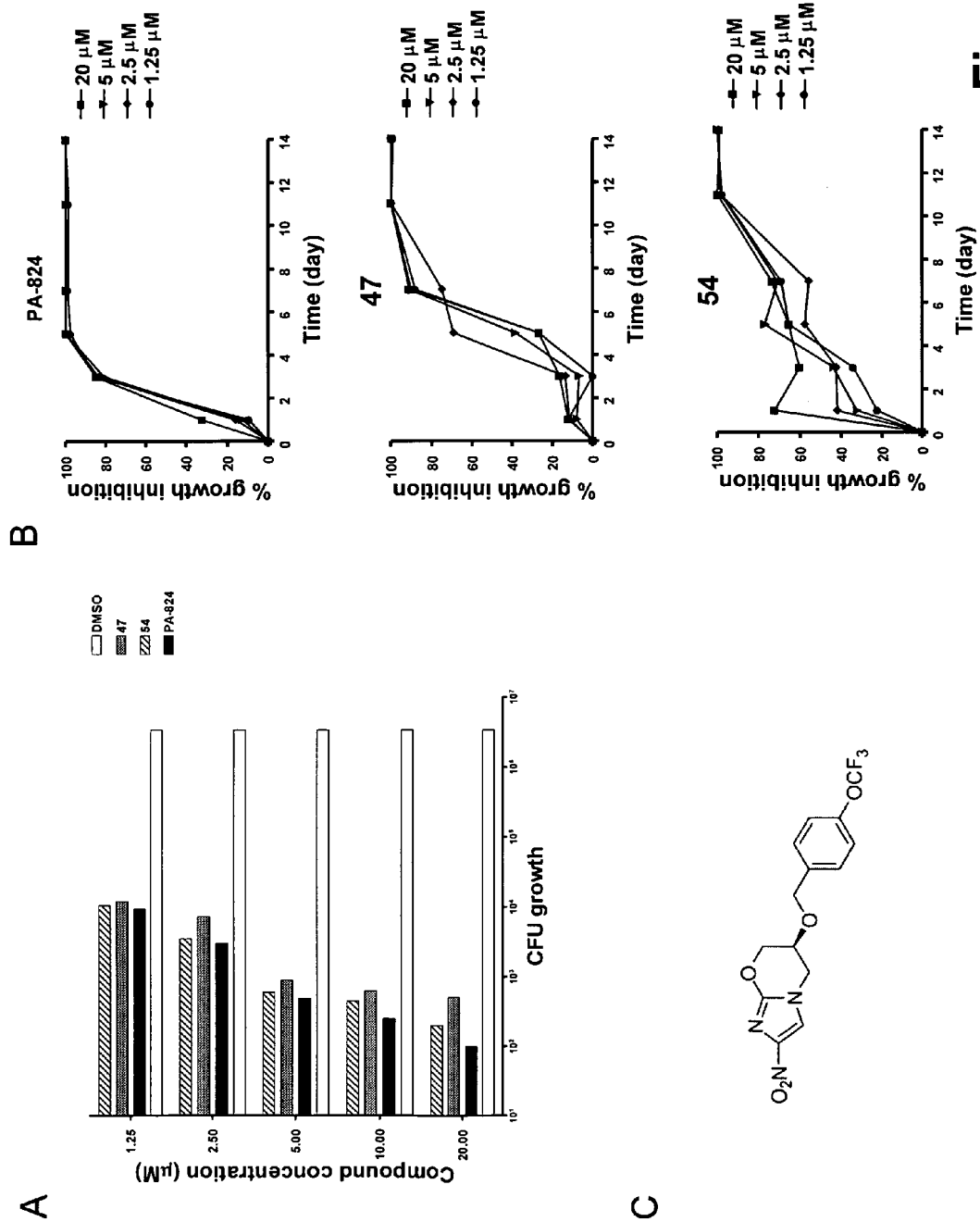
FIG. 2 illustrates the kinetics of inhibition and bactericidal activity of imidazopyridine compounds 47 and 54 compared to the reference compound PA-824 represented in terms of CFU reduction (A) and as a time course (B). Chemical structure of positive control PA-824 (C)

Bactericidal activity was demonstrated by the decrease in colony forming unit (CFU) number after incubation with various concentrations of either compound 47 or 54. DMSO control showed no decrease in CFU numbers (FIG. 2). The activity of both compounds was quite potent and reached 100% growth inhibition around the same time as the reference compound PA-824. These data demonstrate the therapeutic usefulness of this scaffold for the treatment of tuberculosis.

Activity Against MDR Strains

MIC of representative compounds 47 and 54, along with the reference compounds isioniazid (INH) and moxifloxacin (MFX), were determined by the Alamar blue method for 10 multi-drug resistant (MDR) clinical isolates that exhibit different antibiotic resistance profiles and 1 *M. tuberculosis* drug sensitive strain (lab strain H37Rv). Briefly, bacterial suspensions were incubated for 14 days in 7H9 medium containing increasing concentrations of compound. Resazurin was added to a 0.01% final concentration and fluorescence was measured to assess bacterial viability after a 24 h-incubation period. MIC was determined as the first concentration giving 80% bacterial growth inhibition compared to DMSO control.

All MDR tested strains showed an MIC lower than or equal to 1.25 μM for compound 47 and 0.625 for compound 54, while INH resistance was confirmed for all these strains (Table 2). These values are similar to that obtained for the *M. tuberculosis* drug sensitive strain (1.25 μM and 0.625 μM, respectively). Both compound 47 and compound 54 showed levels of activity comparable to or better than MFX. These data clearly show that this scaffold has therapeutic applicability for the treatment of tuberculosis and in particular multi-drug resistant strains of the disease.

In Vivo Activity in a Murine Model

The effect of compounds 177 and 185 on the bacterial load of TB-infected mice was compared to that of the reference compound Isoniazid (INH). 8-week old female BalbC mice were infected with 6×10$^5$ *M. tuberculosis* H37Rv via intra-nasal instillation. Mice were sacrificed at day 1 to control the number of CFU in the lungs. In the acute model of infection, mice were treated for 4 weeks, starting at day 1. Compounds were freshly dissolved in a 0.5% methylcellulose solution and administered by oral gavage 5 times/week. Bacterial load was assessed in lungs and spleen after homogenizing the organs in 1×PBS. Serial dilutions of organs homogenates were spread on Middlebrook 7H11 plates and CFU were determined after 3 weeks incubation at 37° C. under 5% CO2.

Figure 3:
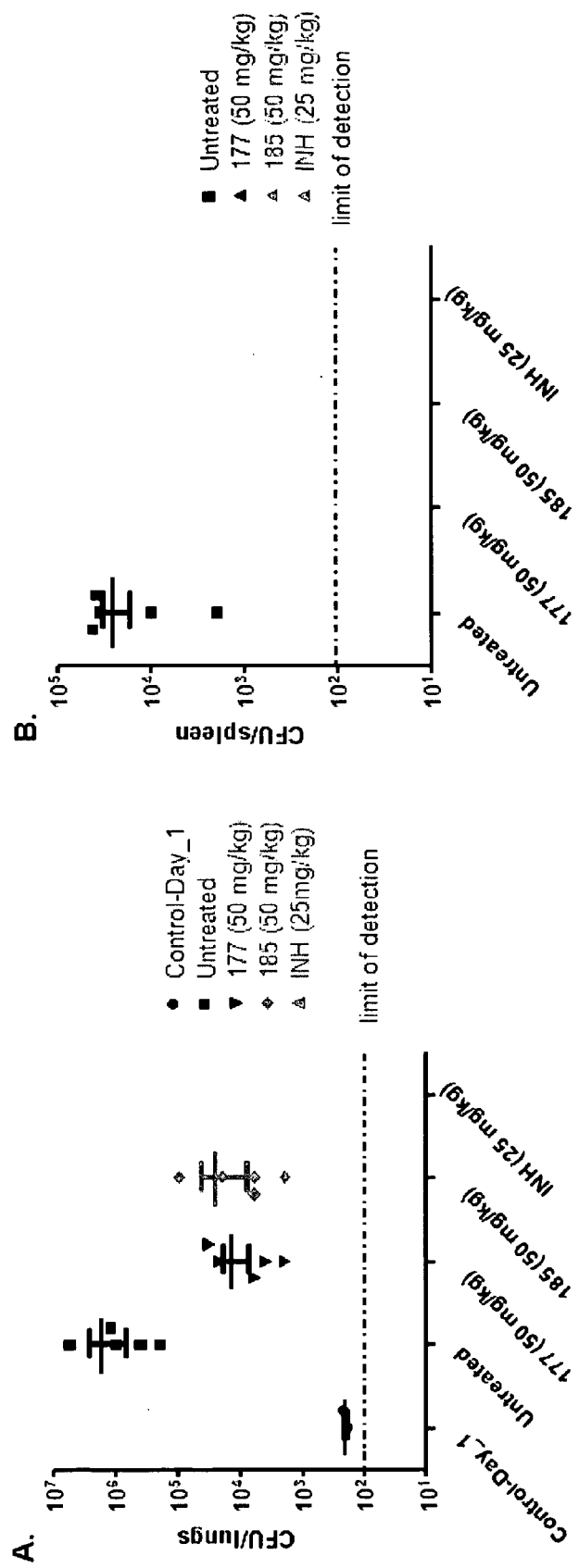
FIG. 3 shows the in vivo efficacy of compounds 177 and 185 in a murine model of acute tuberculosis infection.

In the acute model of infection (after 4 weeks of treatment; FIG. 3), a reduction of ~2 log CFU compared to untreated mice was observed in the lungs of mice treated with 50 mg/kg of either compound 177 or compound 185 administered orally (FIG. 3A). No CFU were detected in the spleen of those same mice, while the infection control mice presented an average of 2.5×10$^4$ CFU/spleen (FIG. 3B). No CFU were recovered from either lungs or spleen from mice treated with 25 mg/kg of INH. Overall both compound 177 and compound 185, demonstrated a significant effect in the acute mouse model of infection.

One of the current challenges for TB drug discovery is the identification of compounds that are active against persistent bacteria. Although the location and state of latent bacteria remains a matter of debate, one commonly shared, hypothesis for mycobacterial persistence is that *M. tuberculosis* bacilli are able to survive in macrophages for prolonged periods of time and, unlike other bacteria, are able to actively replicate. The intraphagosomal profile of *M. tuberculosis* is complex; a large variety of genes are over-expressed and timely regulated and are also dependent on environmental factors. Altogether, this makes the identification of one specific tubercle factor that could be selected as the ideal target difficult. Consequently, non-target cell-based assays are a critical tool in the search of intracellular *M. tuberculosis* inhibitors.

Investigation of *bacillus* growth inhibitors within macrophages has long been limited due to cumbersome CFU plating, slow *bacillus* growth, safety requirements and difficulties in setting-up appropriate infection conditions. As a consequence, this approach was always used as a secondary assay after the initial selection of compounds that are active on in vitro extracellular growth. With the advent of automated confocal microscopy, the above mentioned limitations could be readdressed and the methodology employed herein demonstrates the feasibility of large scale compound screening.

Obviously compounds found to be active against both intracellular and in vitro *M. tuberculosis* growth are the most promising. The best inhibitors isolated from this library have an inhibitory activity within the same range as INH and/or PA-824. Further structure activity relationship studies will contribute to determine if their activity can be additionally improved. Taken together, the above results show that monitoring *M. tuberculosis* growth with automated fluorescence microscopy is highly robust and reliable and that this method enables fast selection of potent anti-TB compounds.

TABLE 1

| Compound | QUM (μM) | QIM (μM) |
|---|---|---|
| 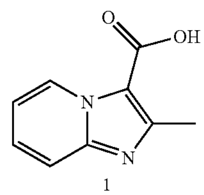  1 | + | + |
| 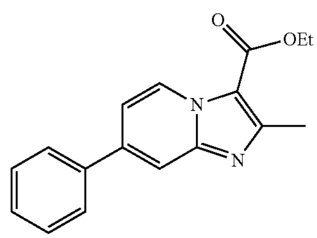 [SMILES: CCOC(=O)c1c(C)nc2cc(-c3ccccc3)ccn12]  2 | + | + |
| 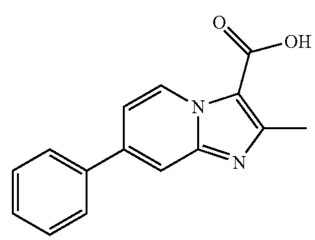 [SMILES: Cc1nc2cc(-c3ccccc3)ccn2c1C(=O)O]  3 | + | + |
| 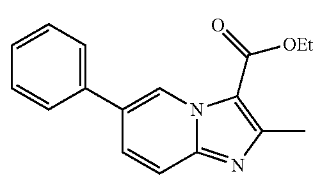 [SMILES: CCOC(=O)c1c(C)nc2ccc(-c3ccccc3)cn12]  4 | + | + |
| 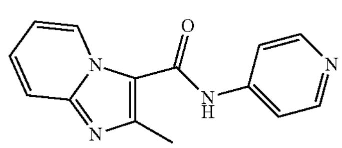 [SMILES: Cc1nc2ccccn2c1C(=O)Nc1ccncc1]  5 | + | + |

TABLE 1-continued
| Compound | QUM (μM) | QIM (μM) |
|---|---|---|
| 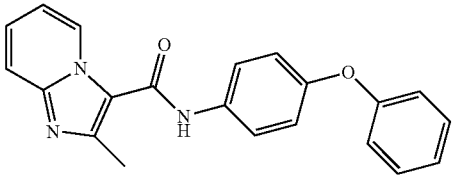 [SMILES: Cc1nc2ccccn2c1C(=O)Nc1ccc(Oc2ccccc2)cc1] 6 | + | + |
| 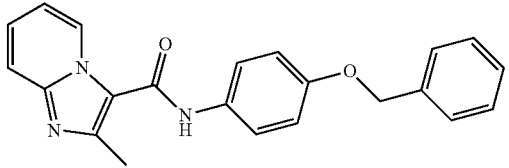 [SMILES: Cc1nc2ccccn2c1C(=O)Nc1ccc(OCc2ccccc2)cc1] 7 | + | + |
| 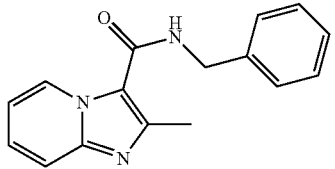 [SMILES: Cc1nc2ccccn2c1C(=O)NCc1ccccc1] 8 | + | ++ |
| 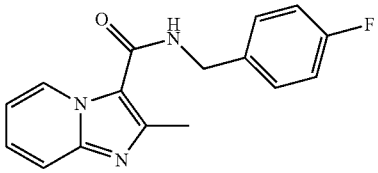 [SMILES: Cc1nc2ccccn2c1C(=O)NCc1ccc(F)cc1] 9 | + | + |
| 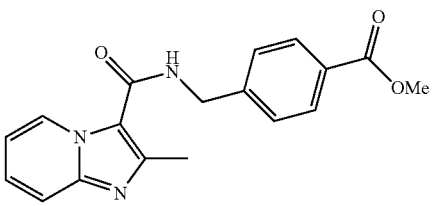 [SMILES: COC(=O)c1ccc(CNC(=O)c2c(C)nc3ccccn23)cc1] 10 | ++ | + |
| 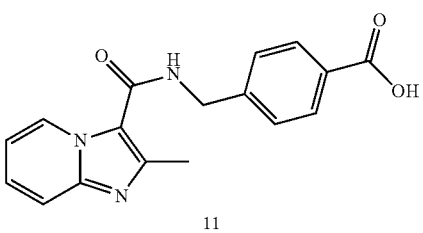 11 | + | + |
| 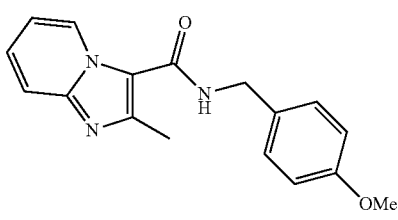 [SMILES: COc1ccc(CNC(=O)c2c(C)nc3ccccn23)cc1] 12 | ++ | ++ |

TABLE 1-continued
| Compound | QUM (μM) | QIM (μM) |
|---|---|---|
| 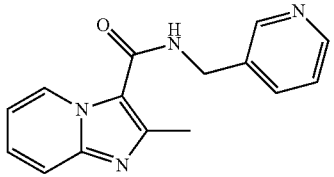 [SMILES: Cc1nc2ccccn2c1C(=O)NCc1cccnc1] 13 | + | + |
| 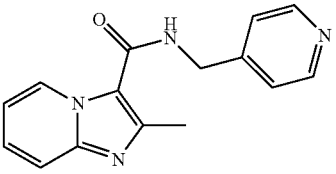 [SMILES: Cc1nc2ccccn2c1C(=O)NCc1ccncc1] 14 | + | + |
| 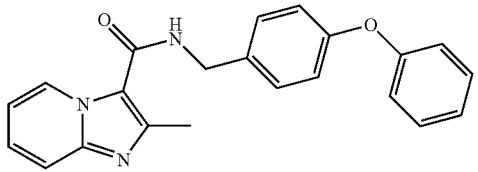 15 | ++ | +++ |
| 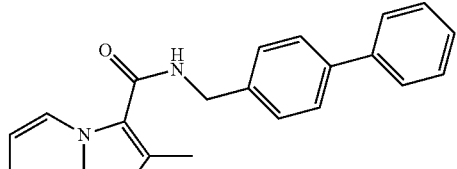 16 | +++ | +++ |
| 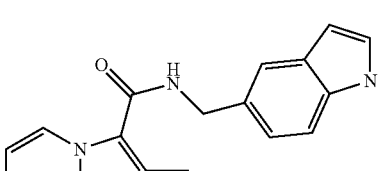 17 | ++ | ++ |
| 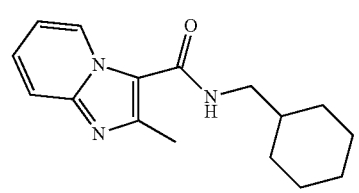 [SMILES: Cc1nc2ccccn2c1C(=O)NCC1CCCCC1] 18 | + | + |
| 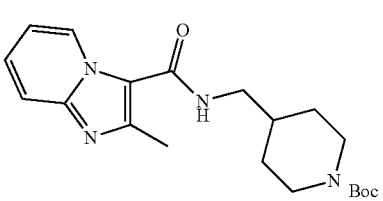 [SMILES: Cc1nc2ccccn2c1C(=O)NCC1CCNCC1] 19 | + | + |

TABLE 1-continued
| Compound | QUM (μM) | QIM (μM) |
|---|---|---|
| 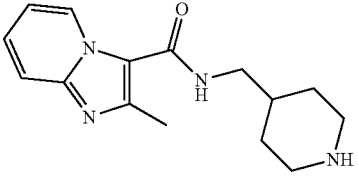 [SMILES: Cc1nc2ccccn2c1C(=O)NCC1CCNCC1] 20 | + | + |
| 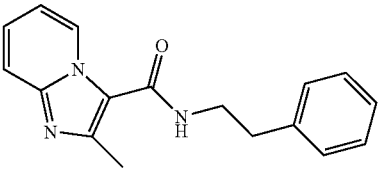 [SMILES: Cc1nc2ccccn2c1C(=O)NCCc1ccccc1] 21 | + | + |
| 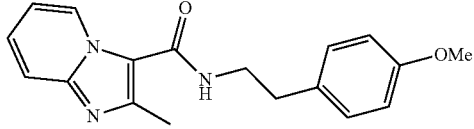 [SMILES: COc1ccc(CCNC(=O)c2c(C)nc3ccccn23)cc1] 22 | + | + |
| 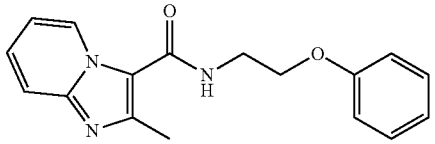 [SMILES: Cc1nc2ccccn2c1C(=O)NCCOc1ccccc1] 23 | ++ | ++ |
| 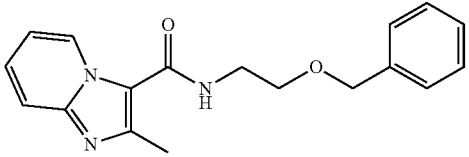 [SMILES: Cc1nc2ccccn2c1C(=O)NCCOCc1ccccc1] 24 | + | + |
| 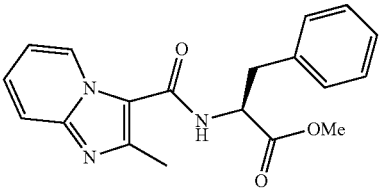 [SMILES: COC(=O)[C@H](Cc1ccccc1)NC(=O)c1c(C)nc2ccccn12] 25 | + | + |
| 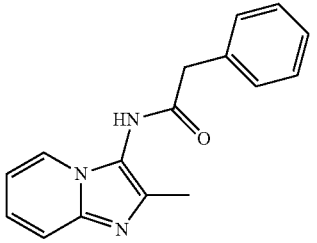 [SMILES: Cc1nc2ccccn2c1NC(=O)Cc1ccccc1] 26 | + | + |

TABLE 1-continued
| Compound | QUM (μM) | QIM (μM) |
|---|---|---|
| 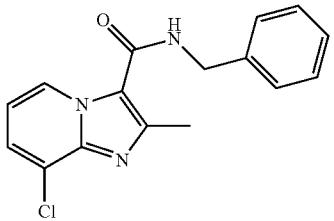 [SMILES: Cc1nc2c(Cl)cccn2c1C(=O)NCc1ccccc1] 27 | + | + |
| 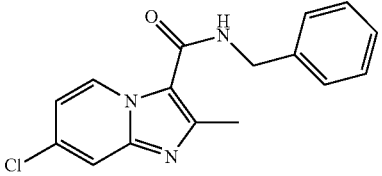 [SMILES: Cc1nc2cc(Cl)ccn2c1C(=O)NCc1ccccc1] 28 | + | ++ |
| 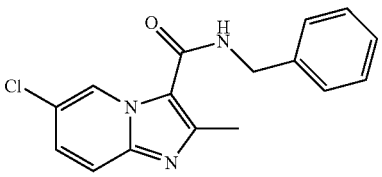 [SMILES: Cc1nc2ccc(Cl)cn2c1C(=O)NCc1ccccc1] 29 | ++ | ++ |
| 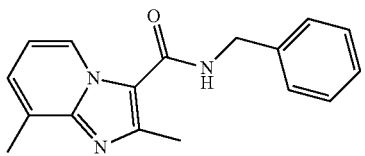 [SMILES: Cc1nc2c(C)cccn2c1C(=O)NCc1ccccc1] 30 | + | + |
| 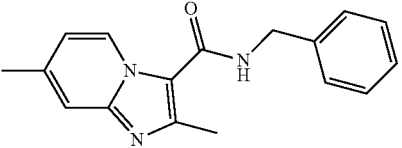 [SMILES: Cc1ccn2c(C(=O)NCc3ccccc3)c(C)nc2c1] 31 | ++ | +++ |
| 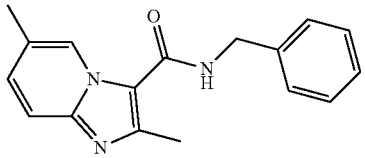 [SMILES: Cc1ccc2nc(C)c(C(=O)NCc3ccccc3)n2c1] 32 | +++ | +++ |
| 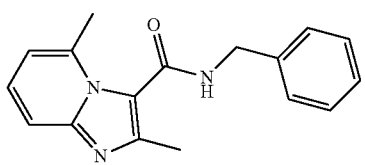 [SMILES: Cc1nc2cccc(C)n2c1C(=O)NCc1ccccc1] 33 | + | + |

TABLE 1-continued
| Compound | QUM (μM) | QIM (μM) |
|---|---|---|
| 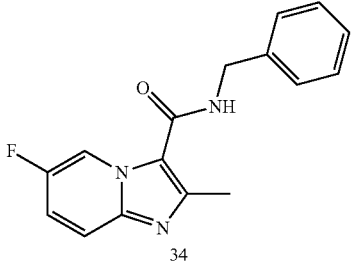 34 | ++ | ++ |
| 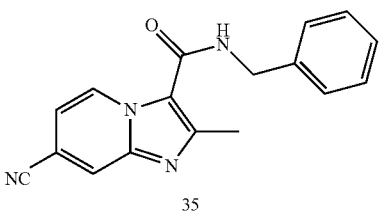 35 | + | + |
| 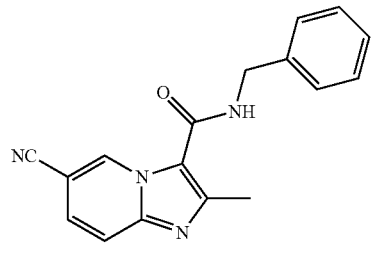 [SMILES: Cc1nc2ccc(C#N)cn2c1C(=O)NCc1ccccc1] 36 | + | + |
| 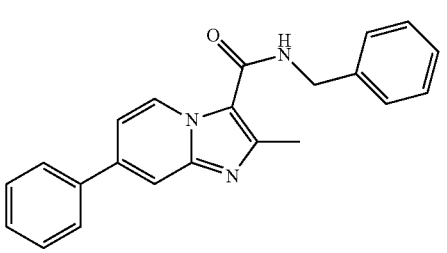 [SMILES: Cc1nc2cc(-c3ccccc3)ccn2c1C(=O)NCc1ccccc1] 37 | + | + |
| 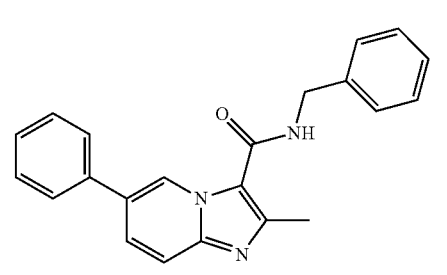 [SMILES: Cc1nc2ccc(-c3ccccc3)cn2c1C(=O)NCc1ccccc1] 38 | + | + |
| 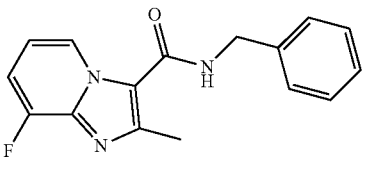 [SMILES: Cc1nc2c(F)cccn2c1C(=O)NCc1ccccc1] 39 | ++ | ++ |

TABLE 1-continued
| Compound | QUM (μM) | QIM (μM) |
|---|---|---|
| 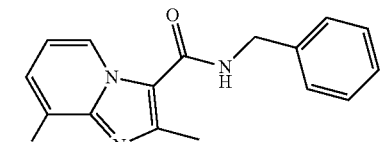 40 | + | + |
| 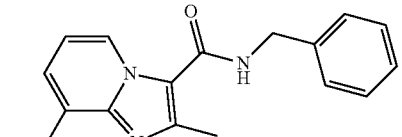 41 | + | + |
| 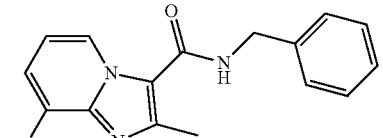 42 | + | + |
| 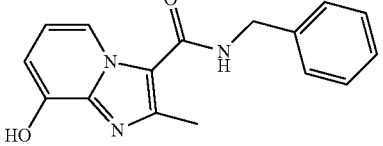 43 | + | + |
| 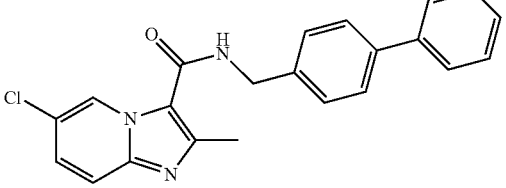 44 | +++ | +++ |
| 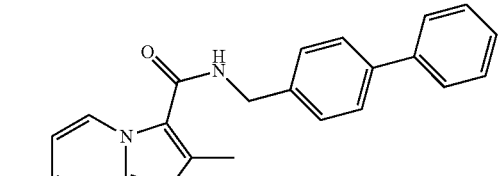 45 | +++ | +++ |
| 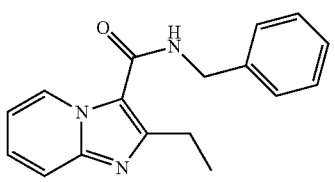 [SMILES: CCc1nc2ccccn2c1C(=O)NCc1ccccc1] 46 | ++ | ++ |

TABLE 1-continued
| Compound | QUM (μM) | QIM (μM) |
|---|---|---|
| 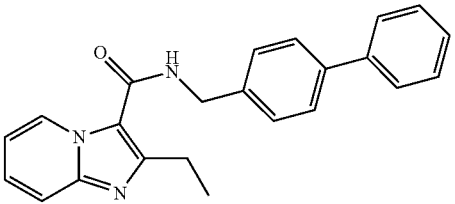 [SMILES: CCc1nc2ccccn2c1C(=O)NCc1ccc(-c2ccccc2)cc1] 47 | +++ | +++ |
| 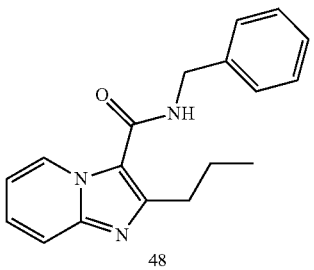 48 | ++ | + |
| 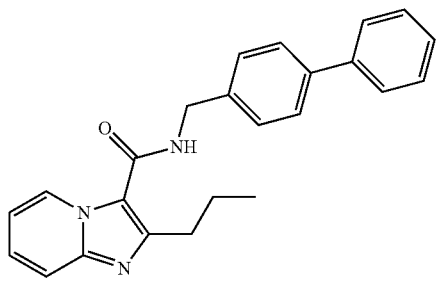 [SMILES: CCCc1nc2ccccn2c1C(=O)NCc1ccc(-c2ccccc2)cc1] 49 | +++ | +++ |
| 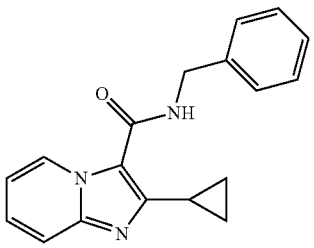 [SMILES: O=C(NCc1ccccc1)c1c(C2CC2)nc2ccccn12] 50 | ++ | ++ |
| 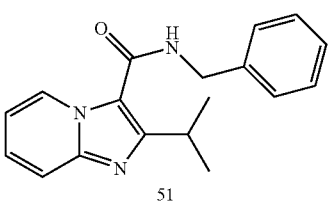 51 | + | + |
| 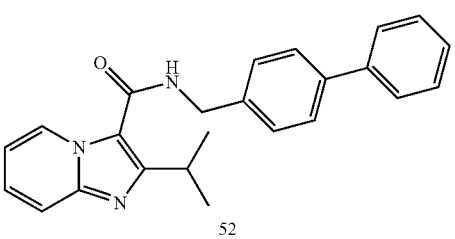 52 | ++ | ++ |

TABLE 1-continued
| Compound | QUM (μM) | QIM (μM) |
|---|---|---|
| 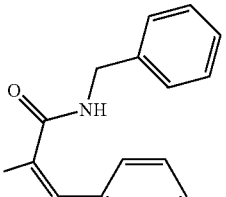 53 | + | + |
| 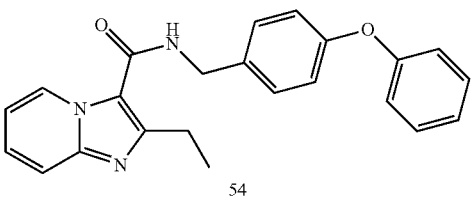 54 | +++ | +++ |
| 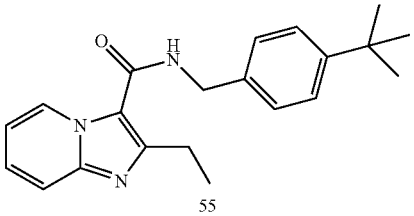 55 | +++ | +++ |
| 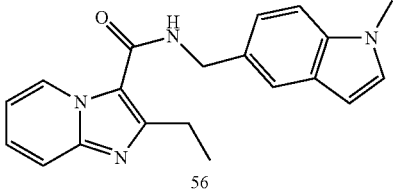 56 | +++ | +++ |
| 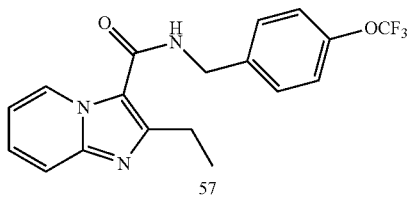 57 | +++ | +++ |
| 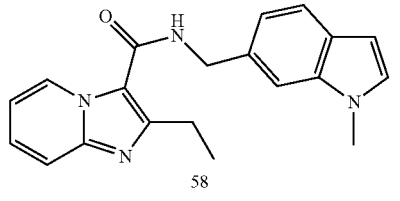 58 | ++ | ++ |
| 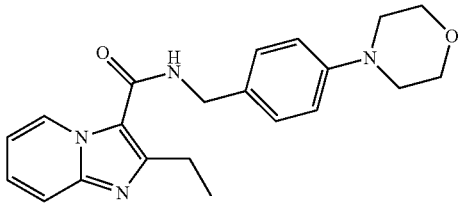 [SMILES: CCc1nc2ccccn2c1C(=O)NCc1ccc(N2CCOCC2)cc1] 59 | ++ | ++ |

TABLE 1-continued
| Compound | QUM (μM) | QIM (μM) |
|---|---|---|
| 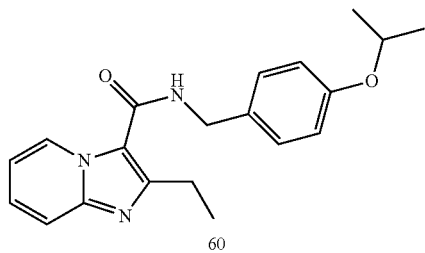 60 | +++ | +++ |
| 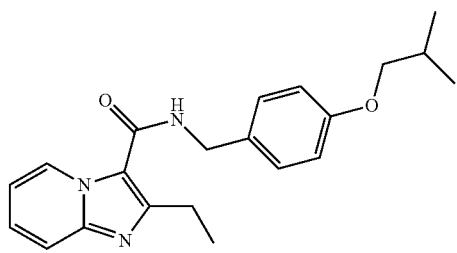 [SMILES: CCc1nc2ccccn2c1C(=O)NCc1ccc(OCC(C)C)cc1] 61 | +++ | +++ |
| 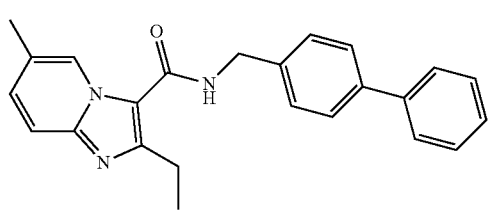 [SMILES: CCc1nc2ccc(C)cn2c1C(=O)NCc1ccc(-c2ccccc2)cc1] 62 | +++ | +++ |
| 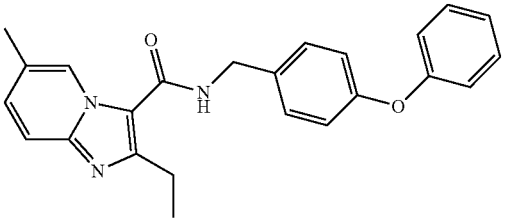 [SMILES: CCc1nc2ccc(C)cn2c1C(=O)NCc1ccc(Oc2ccccc2)cc1] 63 | +++ | +++ |
| 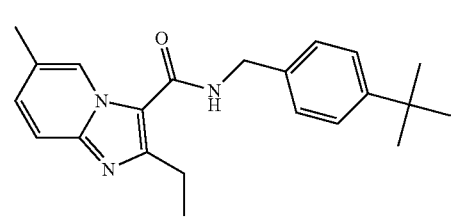 [SMILES: CCc1nc2ccc(C)cn2c1C(=O)NCc1ccc(C(C)(C)C)cc1] 64 | +++ | +++ |
| 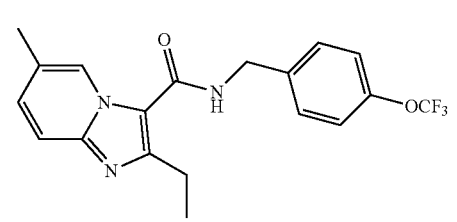 [SMILES: CCc1nc2ccc(C)cn2c1C(=O)NCc1ccc(OC(F)(F)F)cc1] 65 | +++ | +++ |

TABLE 1-continued
| Compound | QUM (μM) | QIM (μM) |
|---|---|---|
| 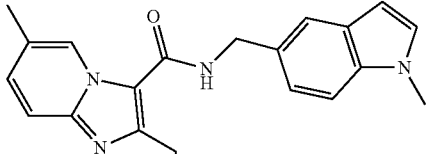 66 | +++ | +++ |
| 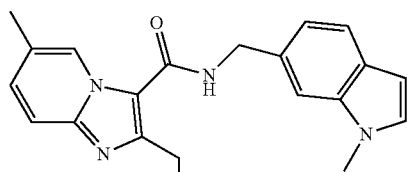 67 | +++ | +++ |
| 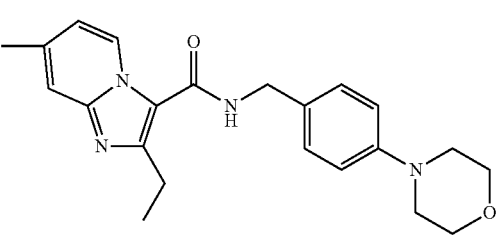 [SMILES: CCc1nc2cc(C)ccn2c1C(=O)NCc1ccc(N2CCOCC2)cc1] 68 | ++ | +++ |
| 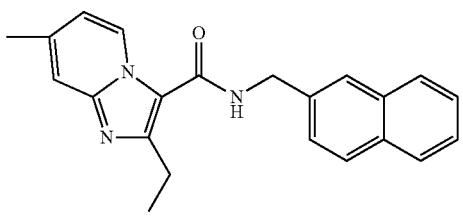 [SMILES: CCc1nc2cc(C)ccn2c1C(=O)NCc1ccc2ccccc2c1] 69 | ++ | +++ |
| 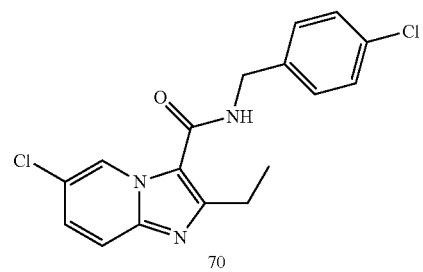 70 | +++ | +++ |
| 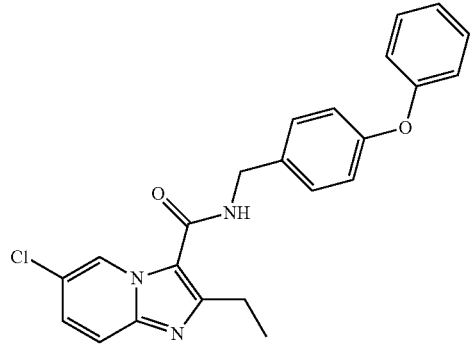 [SMILES: CCc1nc2ccc(Cl)cn2c1C(=O)NCc1ccc(Oc2ccccc2)cc1] 71 | +++ | +++ |

TABLE 1-continued
| Compound | QUM (μM) | QIM (μM) |
|---|---|---|
| 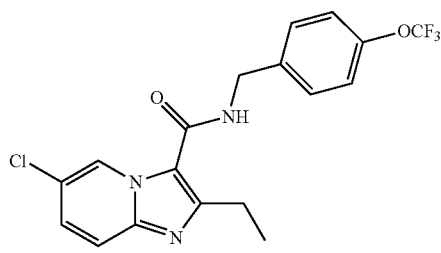 [SMILES: CCc1nc2ccc(Cl)cn2c1C(=O)NCc1ccc(OC(F)(F)F)cc1] 72 | +++ | +++ |
| 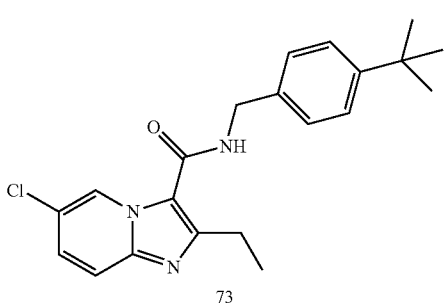 73 | +++ | +++ |
| 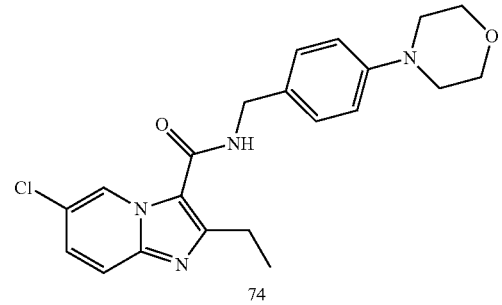 74 | +++ | +++ |
| 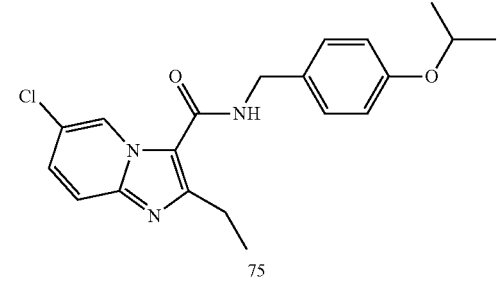 75 | +++ | +++ |
| 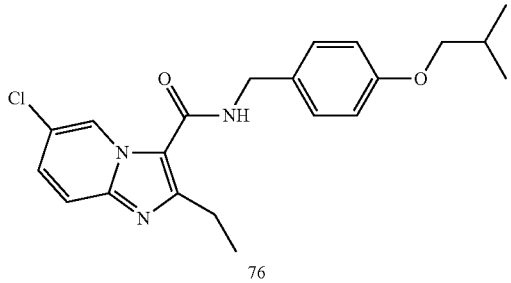 76 | +++ | +++ |

TABLE 1-continued
| Compound | QUM (μM) | QIM (μM) |
|---|---|---|
| 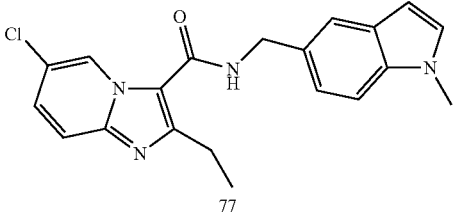 77 | +++ | +++ |
| 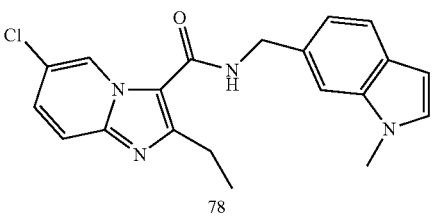 78 | +++ | +++ |
| 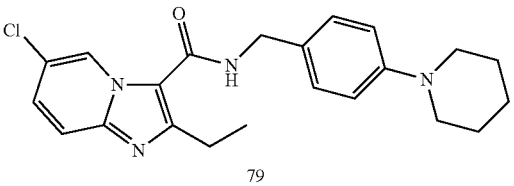 79 | +++ | +++ |
| 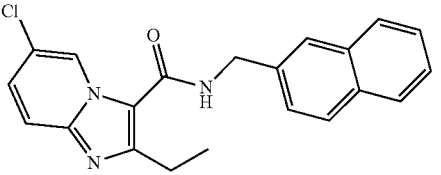 [SMILES: CCc1nc2ccc(Cl)cn2c1C(=O)NCc1ccc2ccccc2c1] 80 | +++ | +++ |
| 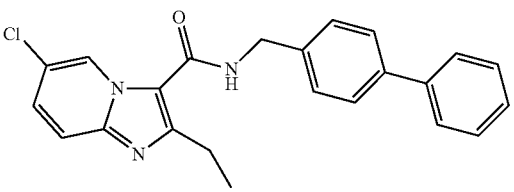 [SMILES: CCc1nc2ccc(Cl)cn2c1C(=O)NCc1ccc(-c2ccccc2)cc1] 81 | +++ | +++ |
| 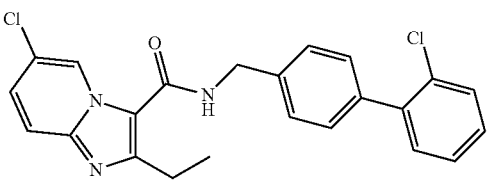 [SMILES: CCc1nc2ccc(Cl)cn2c1C(=O)NCc1ccc(-c2ccccc2Cl)cc1] 82 | +++ | +++ |
| 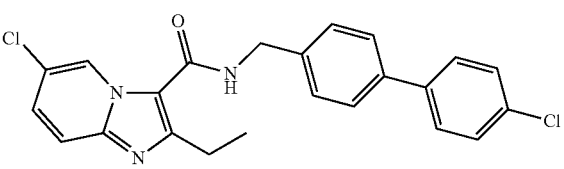 [SMILES: CCc1nc2ccc(Cl)cn2c1C(=O)NCc1ccc(-c2ccc(Cl)cc2)cc1] 83 | +++ | +++ |

TABLE 1-continued
| Compound | QUM (μM) | QIM (μM) |
|---|---|---|
| 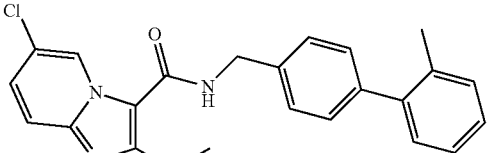 84 | +++ | +++ |
| 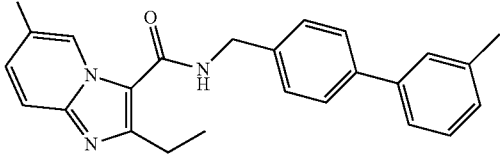 85 | +++ | +++ |
| 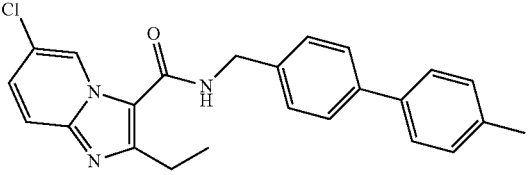 [SMILES: CCc1nc2ccc(Cl)cn2c1C(=O)NCc1ccc(-c2ccc(C)cc2)cc1] 86 | +++ | +++ |
| 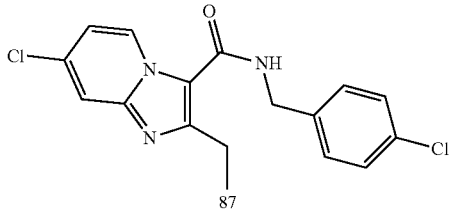 87 | +++ | +++ |
| 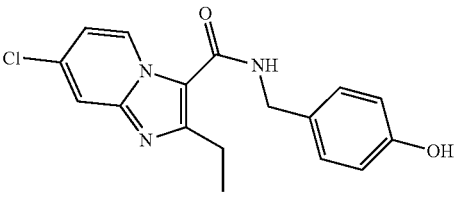 [SMILES: CCc1nc2cc(Cl)ccn2c1C(=O)NCc1ccc(O)cc1] 88 | ++ | ++ |
| 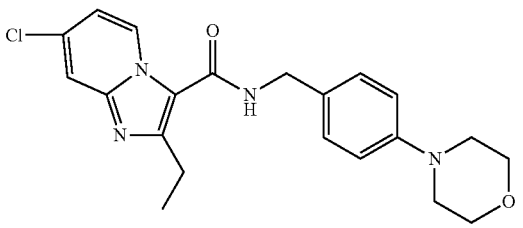 [SMILES: CCc1nc2cc(Cl)ccn2c1C(=O)NCc1ccc(N2CCOCC2)cc1] 89 | +++ | ++ |
| 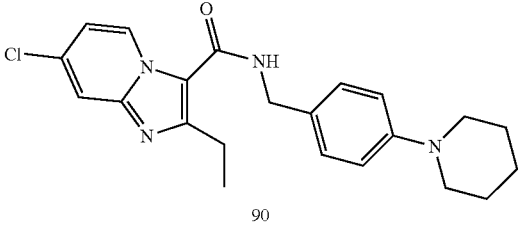 90 | +++ | +++ |

TABLE 1-continued
| Compound | QUM (μM) | QIM (μM) |
|---|---|---|
| 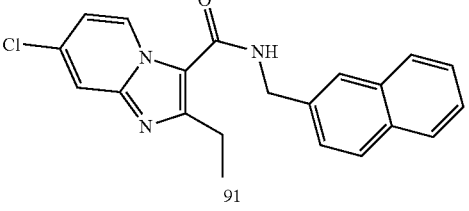 91 | +++ | ++ |
| 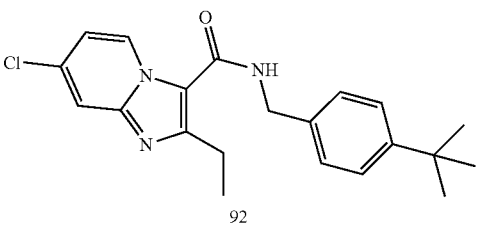 92 | +++ | +++ |
| 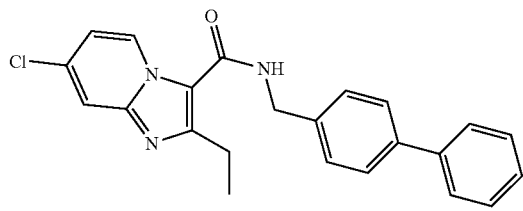 [SMILES: CCc1nc2cc(Cl)ccn2c1C(=O)NCc1ccc(-c2ccccc2)cc1] 93 | +++ | +++ |
| 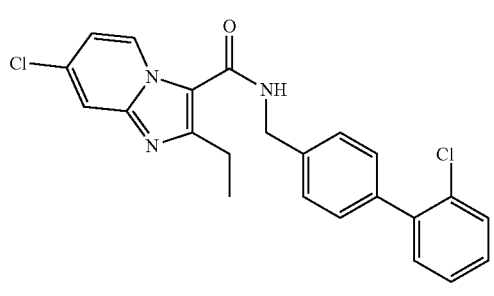 [SMILES: CCc1nc2cc(Cl)ccn2c1C(=O)NCc1ccc(-c2ccccc2Cl)cc1] 94 | +++ | +++ |
| 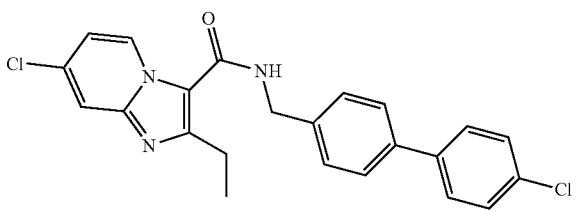 [SMILES: CCc1nc2cc(Cl)ccn2c1C(=O)NCc1ccc(-c2ccc(Cl)cc2)cc1] 95 | +++ | +++ |
| 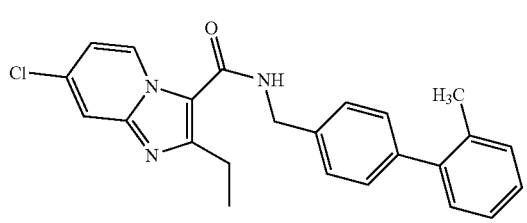 [SMILES: CCc1nc2cc(Cl)ccn2c1C(=O)NCc1ccc(-c2ccccc2C)cc1] 96 | +++ | +++ |

TABLE 1-continued
| Compound | QUM (μM) | QIM (μM) |
|---|---|---|
| 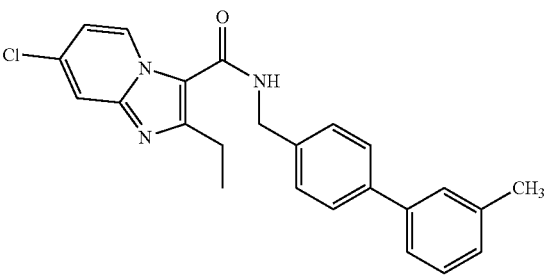 [SMILES: CCc1nc2cc(Cl)ccn2c1C(=O)NCc1ccc(-c2cccc(C)c2)cc1] 97 | +++ | +++ |
| 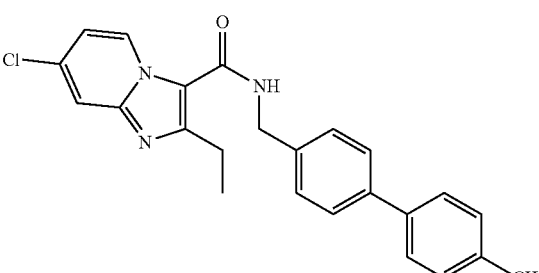 98 | +++ | +++ |
| 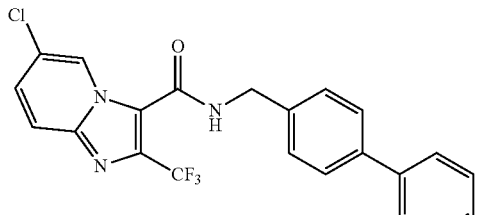 99 | +++ | +++ |
| 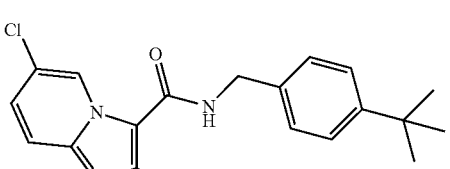 100 | +++ | +++ |
| 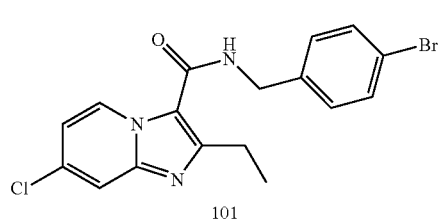 101 | ++ | +++ |
| 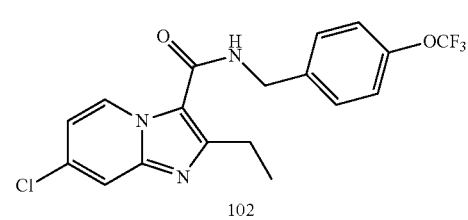 102 | +++ | ++ |

TABLE 1-continued
| Compound | QUM (μM) | QIM (μM) |
|---|---|---|
| 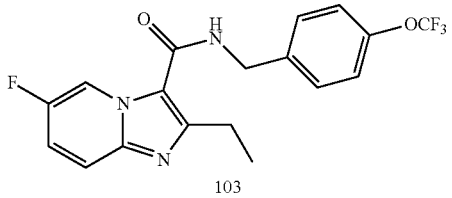103 | ++ | +++ |
| 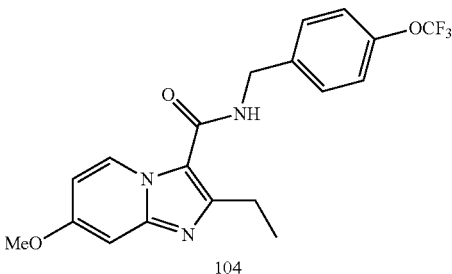104 | + | ++ |
| 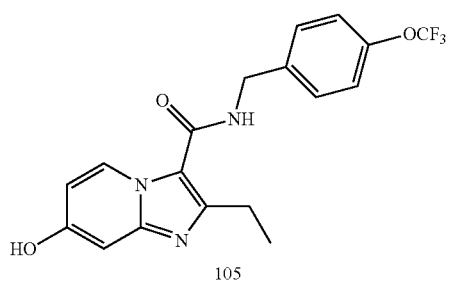105 | + | + |
| 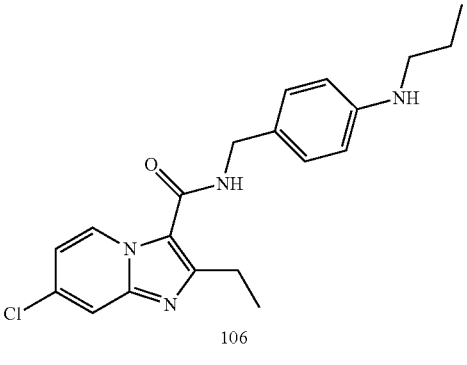106 | +++ | ++ |
| 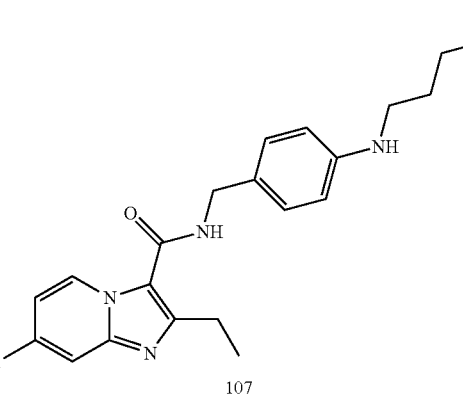107 | +++ | +++ |

TABLE 1-continued
| Compound | QUM (μM) | QIM (μM) |
|---|---|---|
| 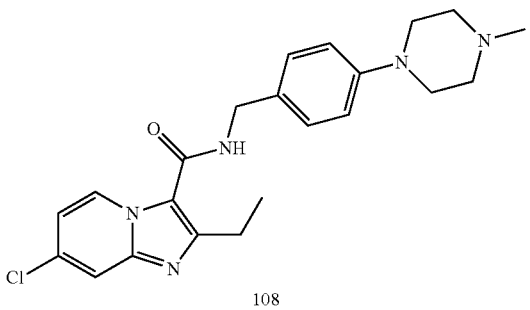 108 | ++ | ++ |
| 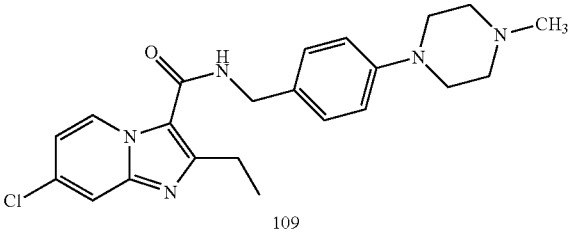 109 | ++ | ++ |
| 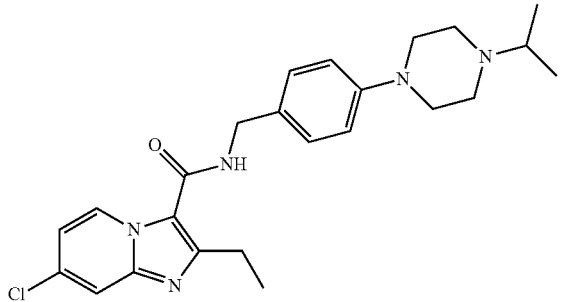 [SMILES: CCc1nc2cc(Cl)ccn2c1C(=O)NCc1ccc(N2CCN(C(C)C)CC2)cc1] 110 | ++ | +++ |
| 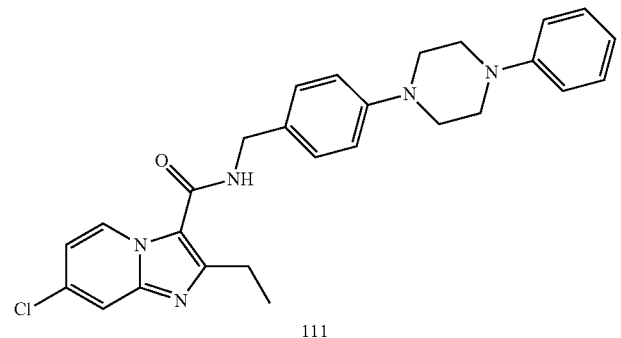 111 | +++ | +++ |
| 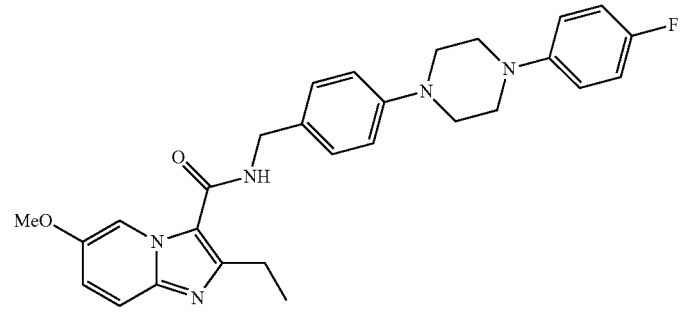 [SMILES: CCc1nc2ccc(OC)cn2c1C(=O)NCc1ccc(N2CCN(c3ccc(F)cc3)CC2)cc1] 112 | +++ | nd |

TABLE 1-continued
| Compound | QUM (μM) | QIM (μM) |
|---|---|---|
| 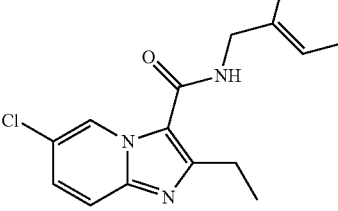 113 | +++ | +++ |
|  114 | +++ | nd |
| 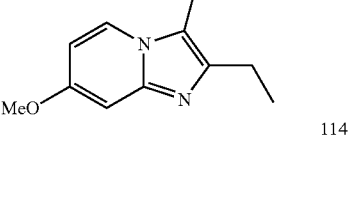 115 | +++ | nd |
| 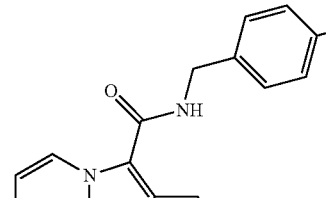 116 | +++ | +++ |
| 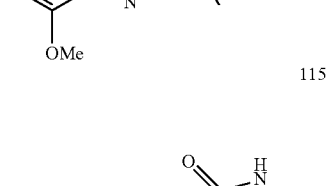 117 | +++ | +++ |

TABLE 1-continued
| Compound | QUM (μM) | QIM (μM) |
|---|---|---|
| 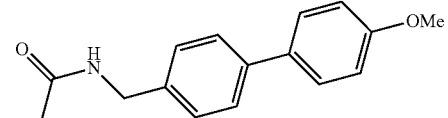 118 | +++ | +++ |
| 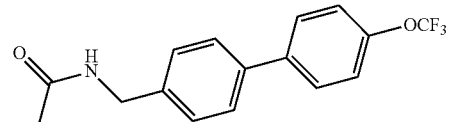 119 | +++ | +++ |
| 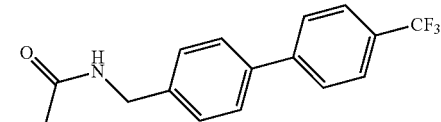 120 | +++ | +++ |
| 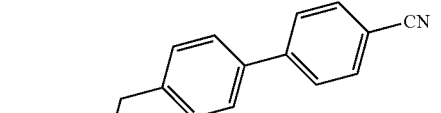 121 | +++ | +++ |
|  122 | +++ | +++ |
|  123 | ++ | +++ |

TABLE 1-continued
| Compound | QUM (μM) | QIM (μM) |
|---|---|---|
| 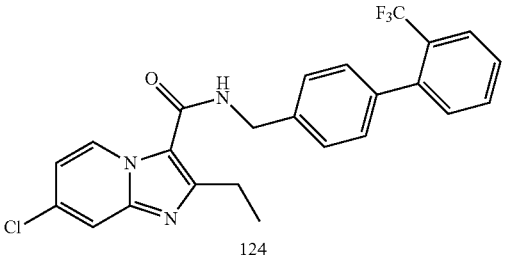 124 | ++ | +++ |
| 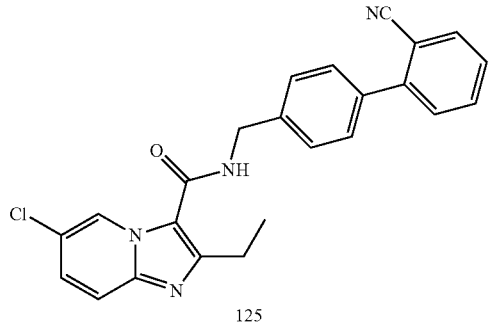 125 | +++ | ++ |
| 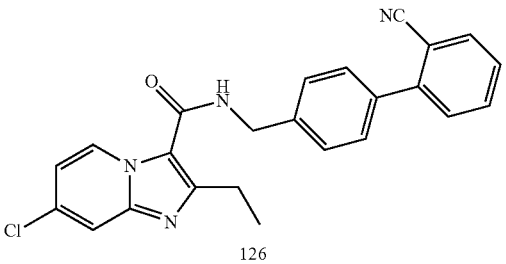 126 | +++ | ++ |
| 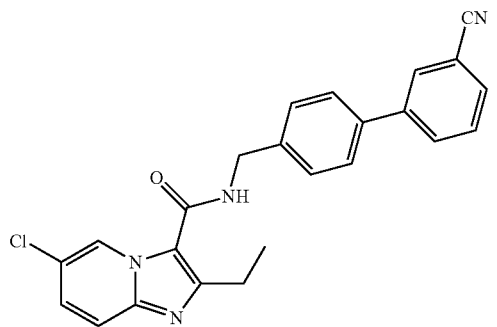 [SMILES: CCc1nc2ccc(Cl)cn2c1C(=O)NCc1ccc(-c2cccc(C#N)c2)cc1] 127 | + | +++ |
| 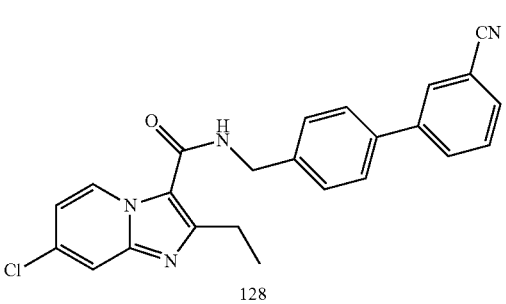 128 | + | +++ |

TABLE 1-continued
| Compound | QUM (μM) | QIM (μM) |
|---|---|---|
| 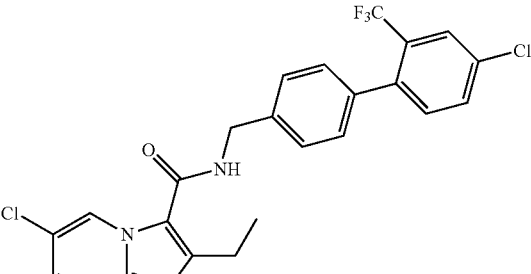 129 | +++ | +++ |
| 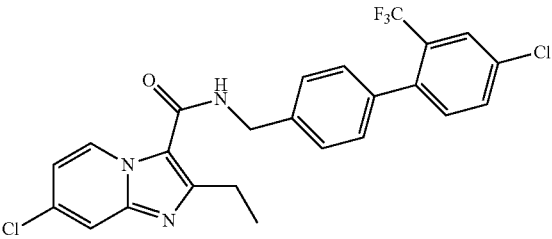 [SMILES: CCc1nc2cc(Cl)ccn2c1C(=O)NCc1ccc(-c2ccc(Cl)cc2C(F)(F)F)cc1] 130 | ++ | +++ |
| 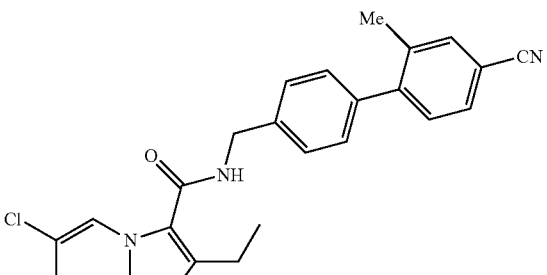 131 | +++ | +++ |
| 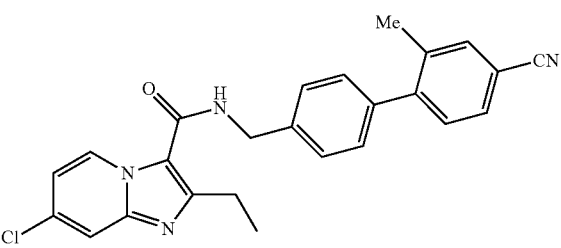 [SMILES: CCc1nc2cc(Cl)ccn2c1C(=O)NCc1ccc(-c2ccc(C#N)cc2C)cc1] 132 | +++ | +++ |
| 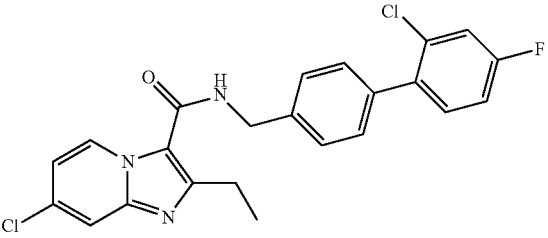 [SMILES: CCc1nc2cc(Cl)ccn2c1C(=O)NCc1ccc(-c2ccc(F)cc2Cl)cc1] 133 | +++ | +++ |

TABLE 1-continued
| Compound | QUM (μM) | QIM (μM) |
|---|---|---|
| 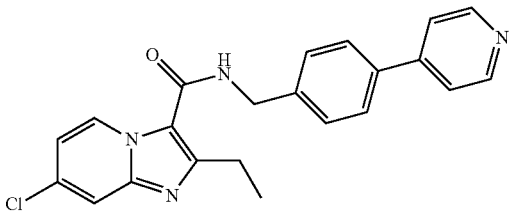 [SMILES: CCc1nc2cc(Cl)ccn2c1C(=O)NCc1ccc(-c2ccncc2)cc1] 134 | ++ | +++ |
| 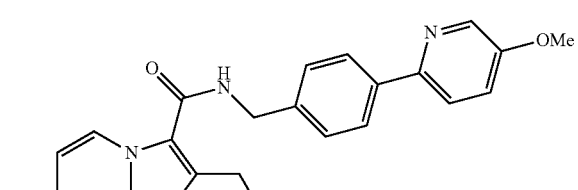 135 | ++ | +++ |
| 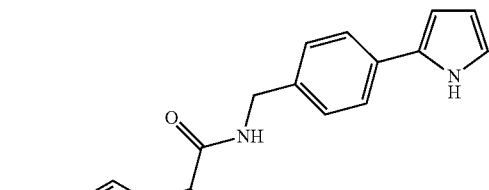 136 | ++ | ++ |
| 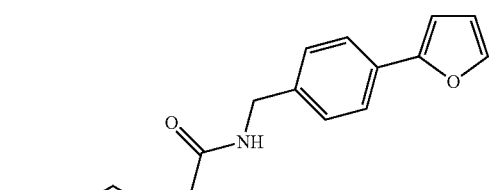 137 | ++ | +++ |
| 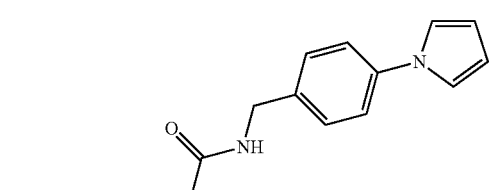 138 | +++ | +++ |

TABLE 1-continued
| Compound | QUM (μM) | QIM (μM) |
|---|---|---|
| 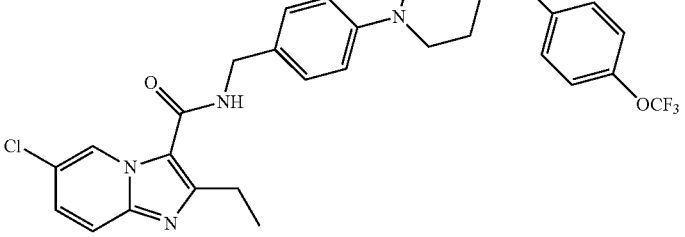 139 | +++ | +++ |
| 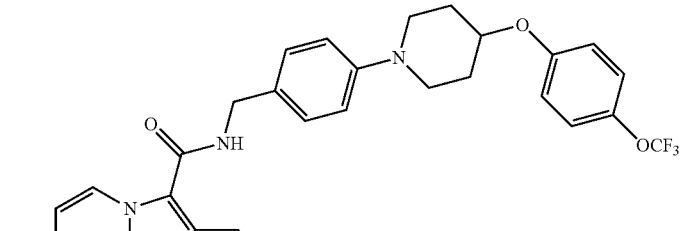 140 | +++ | +++ |
| 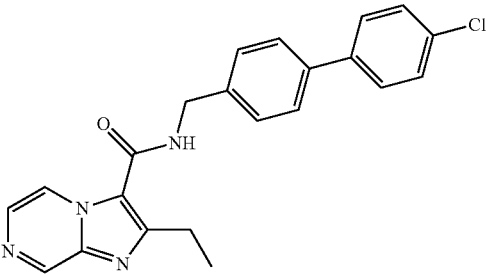 [SMILES: CCc1nc2cnccn2c1C(=O)NCc1ccc(-c2ccc(Cl)cc2)cc1] 141 | +++ | +++ |
| 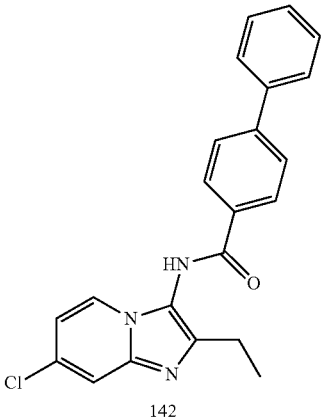 142 | + | + |

TABLE 1-continued
| Compound | QUM (μM) | QIM (μM) |
|---|---|---|
| 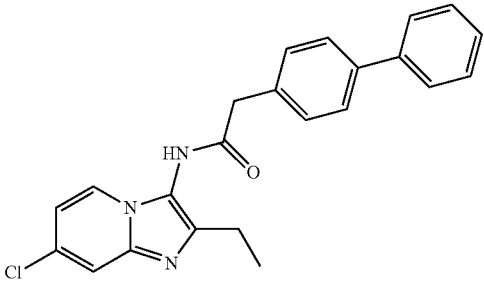 [SMILES: CCc1nc2cc(Cl)ccn2c1NC(=O)Cc1ccc(-c2ccccc2)cc1] 143 | ++ | +++ |
| 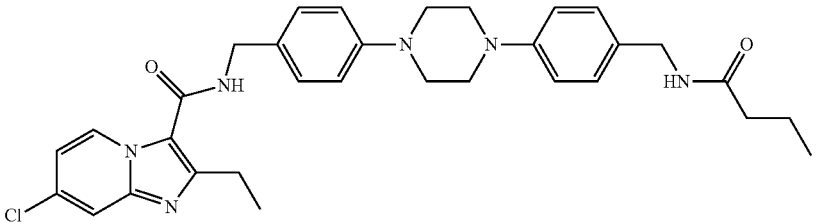 [SMILES: CCCC(=O)NCc1ccc(N2CCN(c3ccc(CNC(=O)c4c(CC)nc5cc(Cl)ccn45)cc3)CC2)cc1] 144 | +++ | +++ |
| 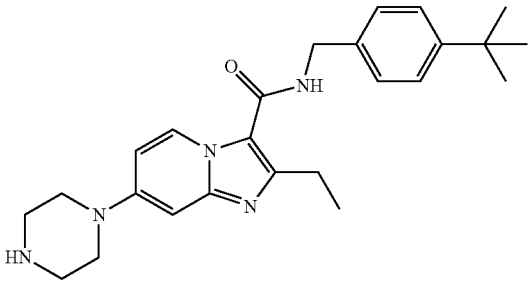 [SMILES: CCc1nc2cc(N3CCNCC3)ccn2c1C(=O)NCc1ccc(C(C)(C)C)cc1] 145 | + | + |
| 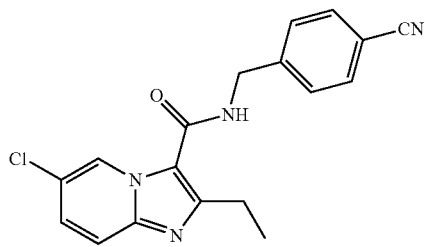 [SMILES: CCc1nc2ccc(Cl)cn2c1C(=O)NCc1ccc(C#N)cc1] 146 | + | ++ |
| 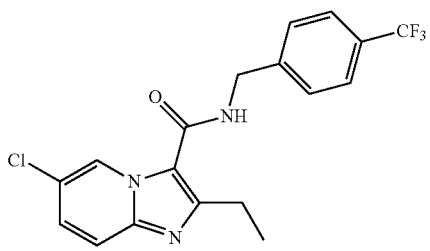 [SMILES: CCc1nc2ccc(Cl)cn2c1C(=O)NCc1ccc(C(F)(F)F)cc1] 147 | +++ | +++ |

TABLE 1-continued
| Compound | QUM (µM) | QIM (µM) |
|---|---|---|
| 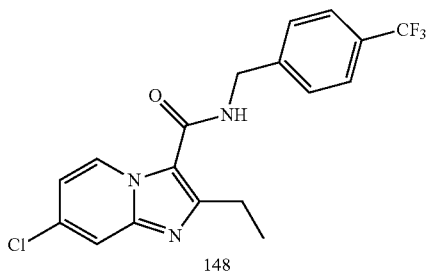 148 | +++ | +++ |
| 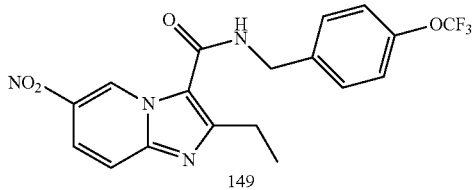 149 | + | + |
| 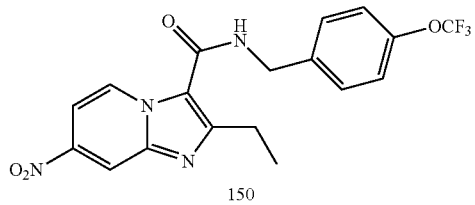 150 | + | + |
| 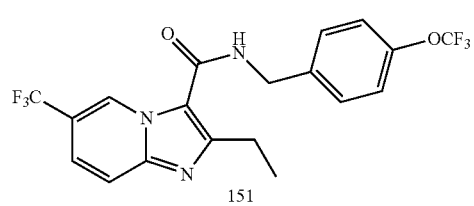 151 | ++ | + |
| 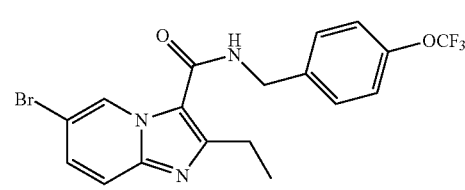 [SMILES: CCc1nc2ccc(Br)cn2c1C(=O)NCc1ccc(OC(F)(F)F)cc1] 152 | +++ | +++ |
| 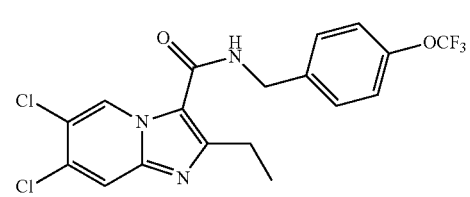 [SMILES: CCc1nc2cc(Cl)c(Cl)cn2c1C(=O)NCc1ccc(OC(F)(F)F)cc1] 153 | ++ | + |
| 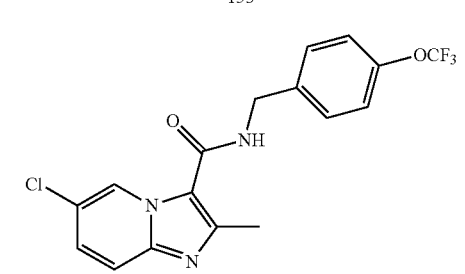 154 | +++ | ++ |

TABLE 1-continued
| Compound | QUM (μM) | QIM (μM) |
|---|---|---|
| 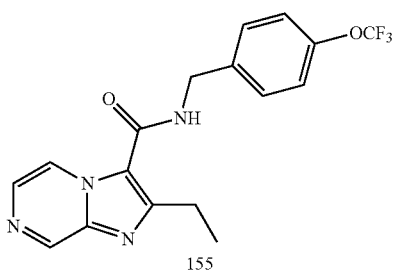 155 | + | + |
| 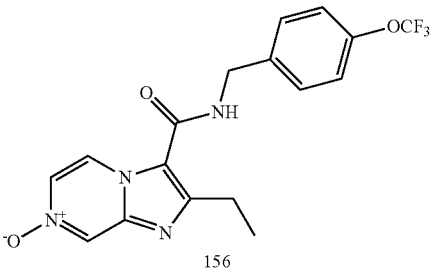 156 | + | + |
| 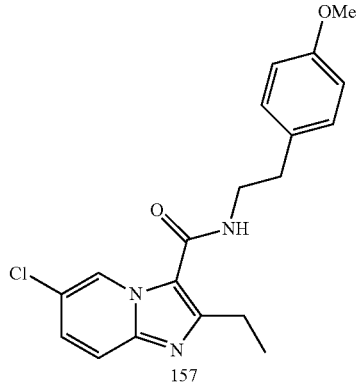 157 | +++ | +++ |
| 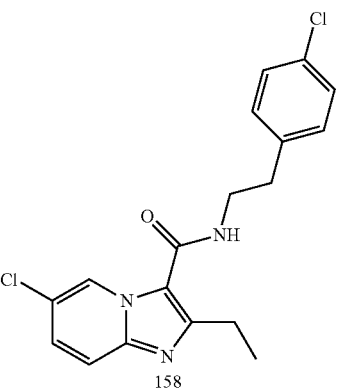 158 | +++ | +++ |
| 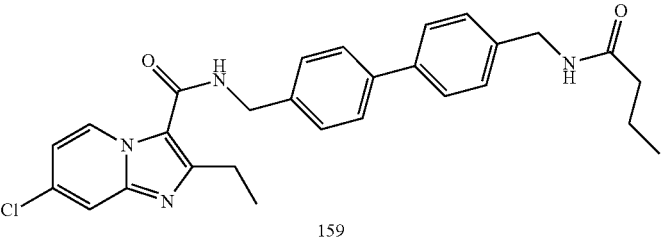 159 | +++ | +++ |

TABLE 1-continued
| Compound | QUM (μM) | QIM (μM) |
|---|---|---|
| 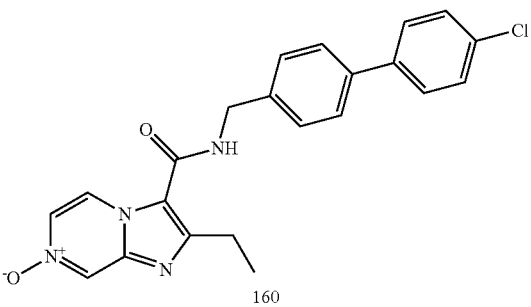 160 | + | + |
| 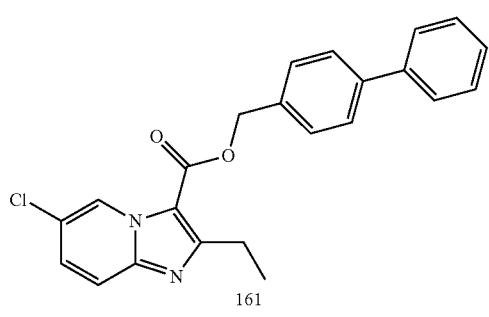 161 | +++ | +++ |
| 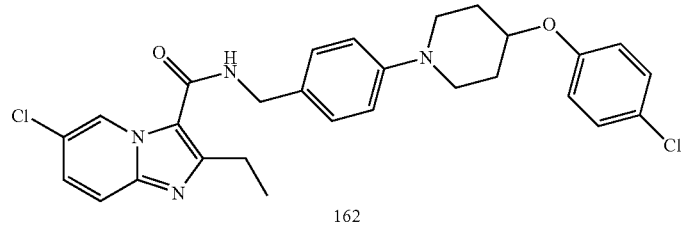 162 | +++ | +++ |
| 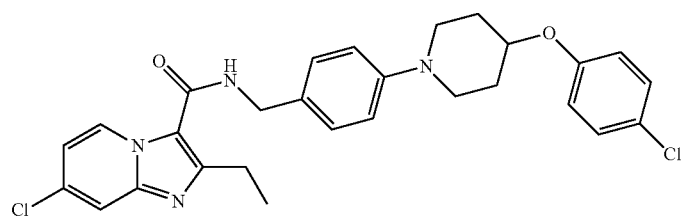 [SMILES: CCc1nc2cc(Cl)ccn2c1C(=O)NCc1ccc(N2CCC(Oc3ccc(Cl)cc3)CC2)cc1] 163 | +++ | +++ |
| 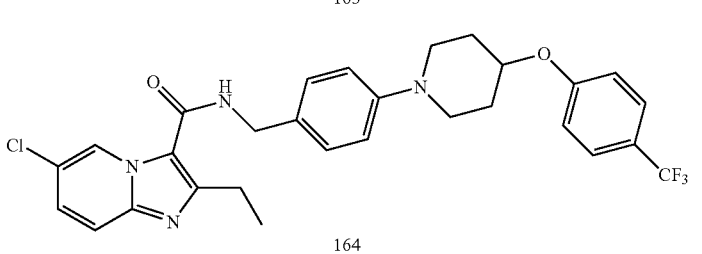 164 | +++ | +++ |
| 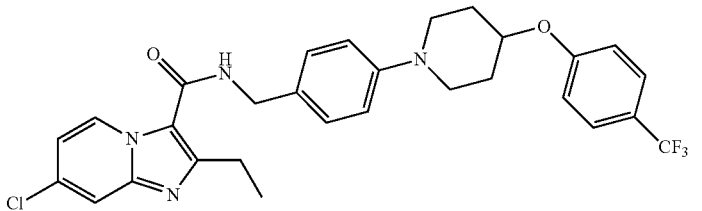 [SMILES: CCc1nc2cc(Cl)ccn2c1C(=O)NCc1ccc(N2CCC(Oc3ccc(C(F)(F)F)cc3)CC2)cc1] 165 | +++ | +++ |

TABLE 1-continued
| Compound | QUM (μM) | QIM (μM) |
|---|---|---|
| 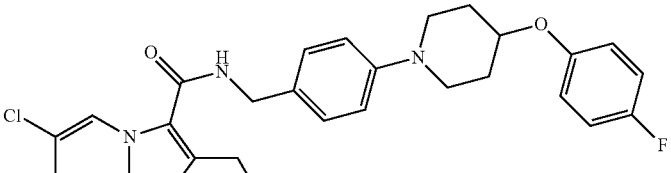 166 | +++ | +++ |
| 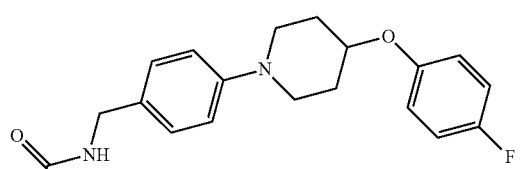 167 | +++ | +++ |
| 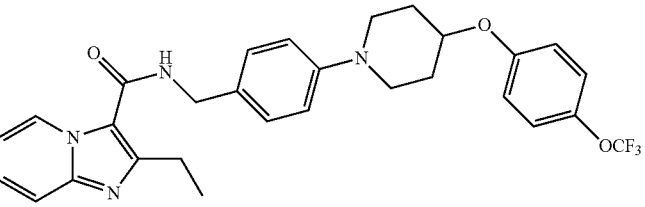 168 | ++ | ++ |
| 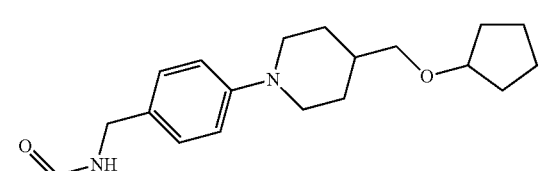 169 | +++ | nd |
| 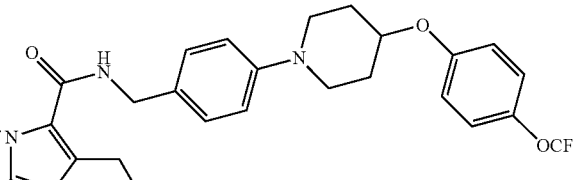 170 | ++ | ++ |
| 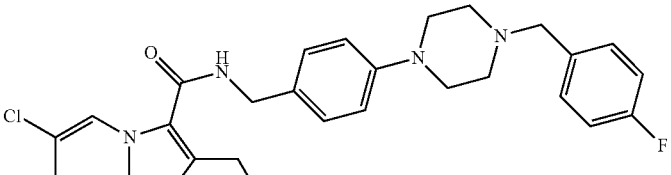 171 | +++ | +++ |

TABLE 1-continued

| Compound | QUM (μM) | QIM (μM) |
|---|---|---|
| 172 | +++ | +++ |
| 173 | +++ | +++ |
| 174 | +++ | +++ |
| 175 | + | +++ |
| 176 | +++ | +++ |

TABLE 1-continued

| Compound | QUM (μM) | QIM (μM) |
|---|---|---|
| 177 | +++ | +++ |
| 178 | +++ | +++ |
| 179 | +++ | +++ |
| 180 | +++ | +++ |

TABLE 1-continued
| Compound | QUM (μM) | QIM (μM) |
|---|---|---|
| 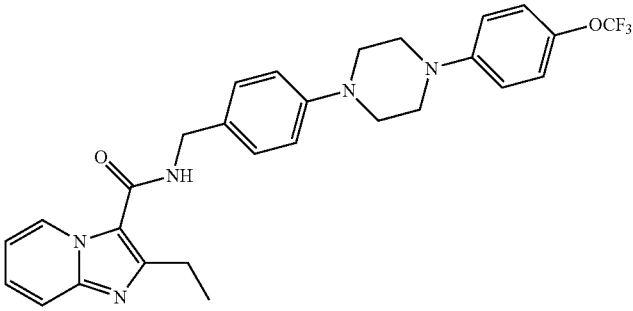 [SMILES: CCc1nc2ccccn2c1C(=O)NCc1ccc(N2CCN(c3ccc(OC(F)(F)F)cc3)CC2)cc1] 181 | +++ | +++ |
| 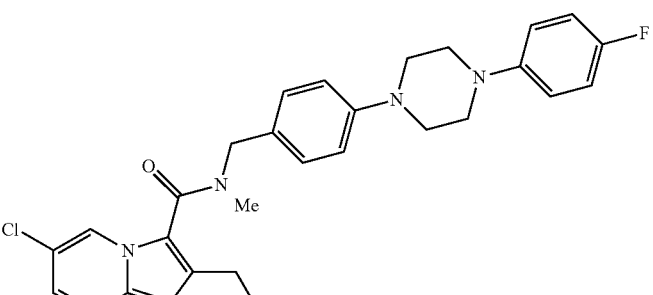 182 | +++ | ++ |
| 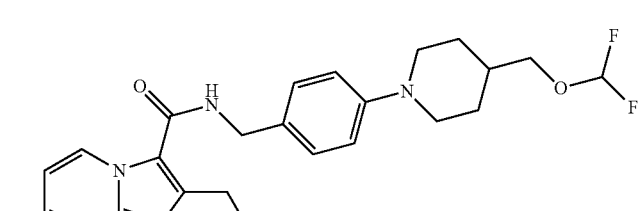 183 | +++ | nd |
| 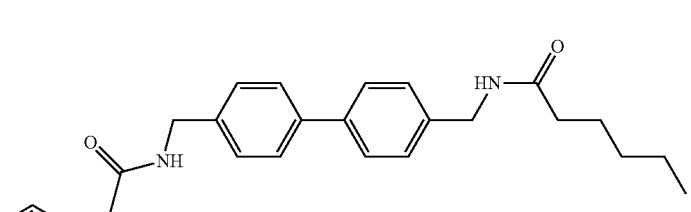 184 | +++ | +++ |
| 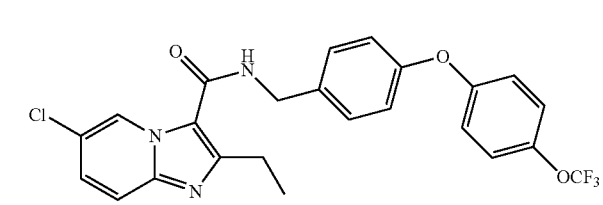 [SMILES: CCc1nc2ccc(Cl)cn2c1C(=O)NCc1ccc(Oc2ccc(OC(F)(F)F)cc2)cc1] 185 | +++ | +++ |

TABLE 1-continued
| Compound | QUM (μM) | QIM (μM) |
|---|---|---|
| 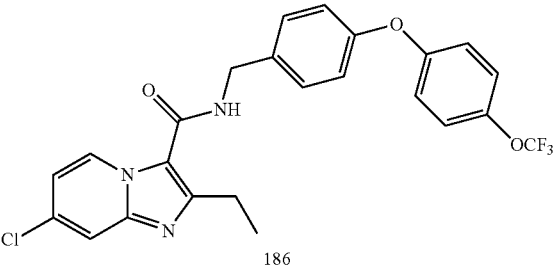 186 | +++ | +++ |
| 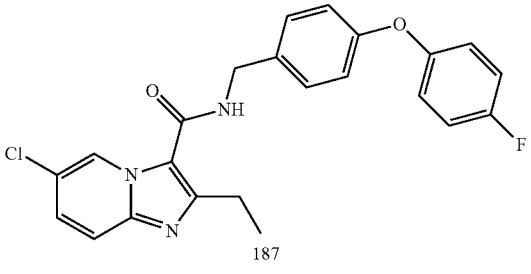 187 | +++ | +++ |
| 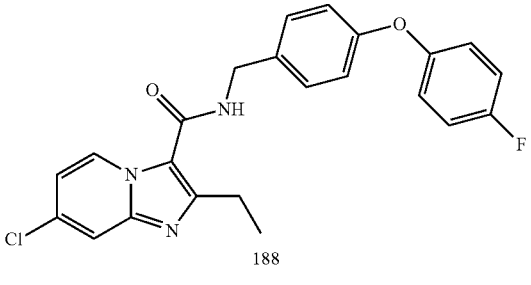 188 | +++ | +++ |
| 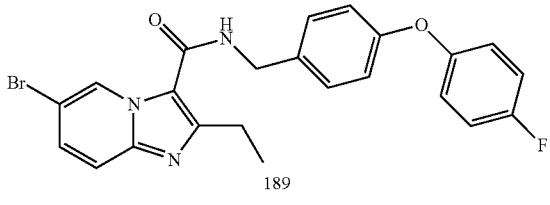 189 | +++ | +++ |
| 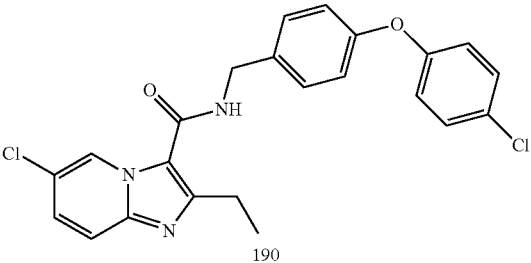 190 | +++ | +++ |
| 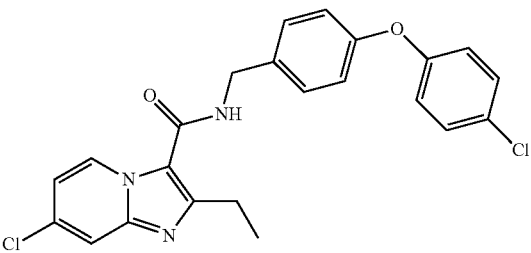 [SMILES: CCc1nc2cc(Cl)ccn2c1C(=O)NCc1ccc(Oc2ccc(Cl)cc2)cc1] 191 | +++ | +++ |

TABLE 1-continued
| Compound | QUM (μM) | QIM (μM) |
|---|---|---|
| 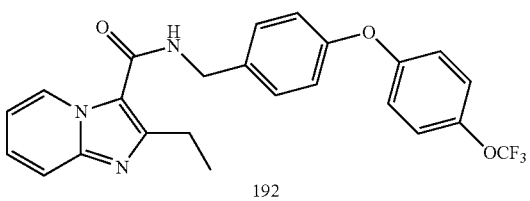 192 | +++ | +++ |
| 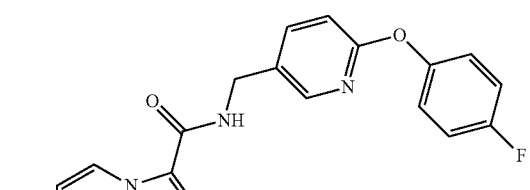 193 | +++ | +++ |
| 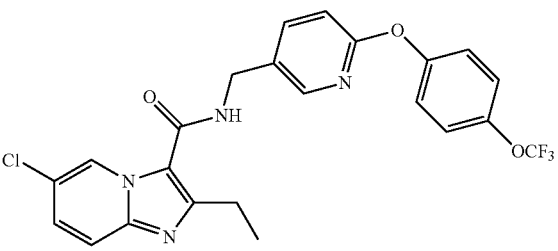 [SMILES: CCc1nc2ccc(Cl)cn2c1C(=O)NCc1ccc(Oc2ccc(OC(F)(F)F)cc2)nc1] 194 | ++ | +++ |
| 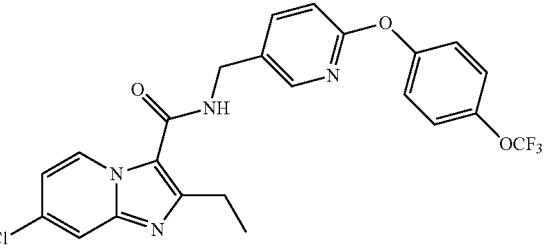 195 | ++ | ++ |
| 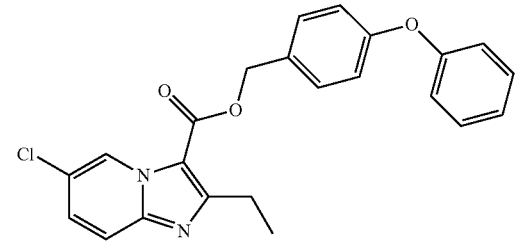 [SMILES: CCc1nc2ccc(Cl)cn2c1C(=O)OCc1ccc(Oc2ccccc2)cc1] 196 | ++ | +++ |
| 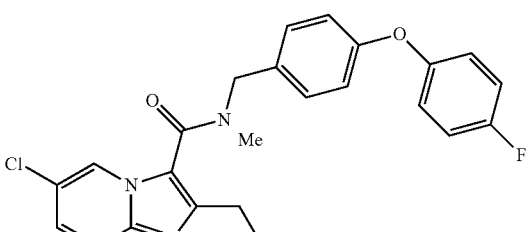 197 | ++ | ++ |

TABLE 1-continued
| Compound | QUM (μM) | QIM (μM) |
|---|---|---|
| 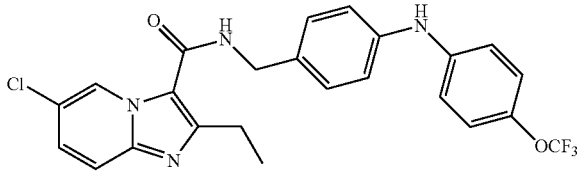 [SMILES: CCc1nc2ccc(Cl)cn2c1C(=O)NCc1ccc(Nc2ccc(OC(F)(F)F)cc2)cc1] 198 | ++ | +++ |
| 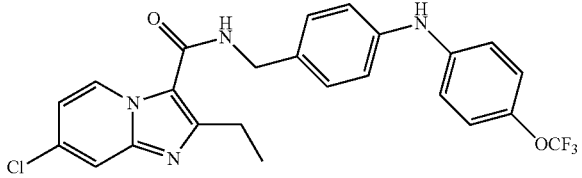 [SMILES: CCc1nc2cc(Cl)ccn2c1C(=O)NCc1ccc(Nc2ccc(OC(F)(F)F)cc2)cc1] 199 | +++ | +++ |
| 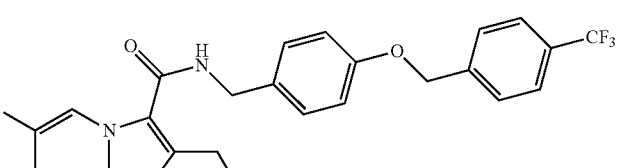 200 | +++ | +++ |
| 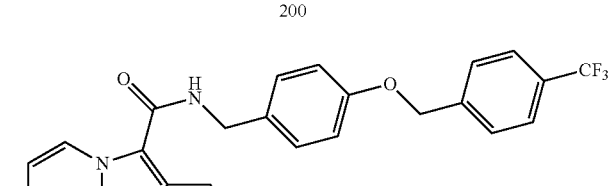 201 | +++ | +++ |
| 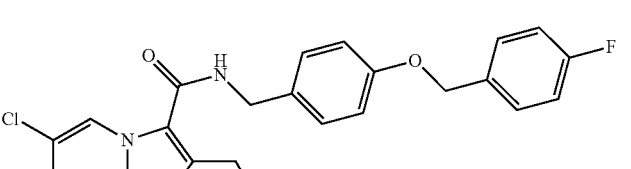 202 | +++ | +++ |
| 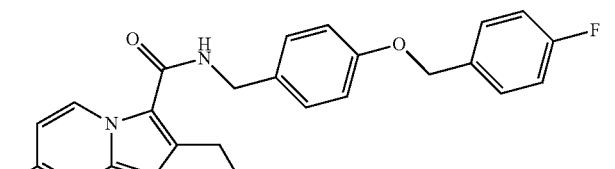 203 | ++ | ++ |
| 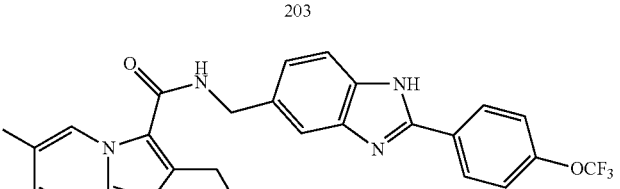 204 | + | + |

223
224
TABLE 1-continued
| Compound | QUM (μM) | QIM (μM) |
|---|---|---|
| 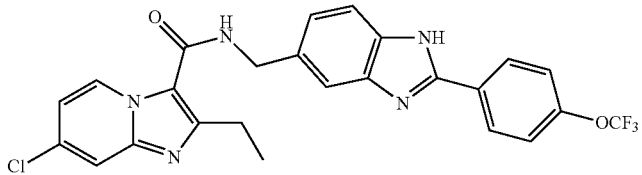 [SMILES: CCc1nc2cc(Cl)ccn2c1C(=O)NCc1ccc2[nH]c(-c3ccc(OC(F)(F)F)cc3)nc2c1] 205 | + | + |
| 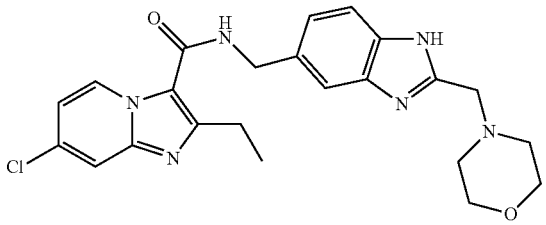 [SMILES: CCc1nc2cc(Cl)ccn2c1C(=O)NCc1ccc2[nH]c(CN3CCOCC3)nc2c1] 206 | + | + |
| 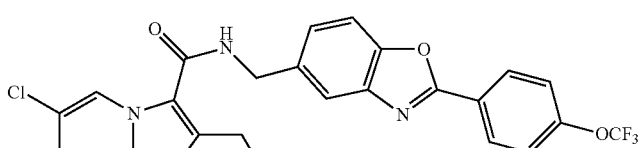 207 | +++ | +++ |
| 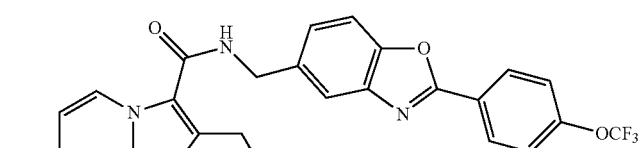 208 | +++ | +++ |
| 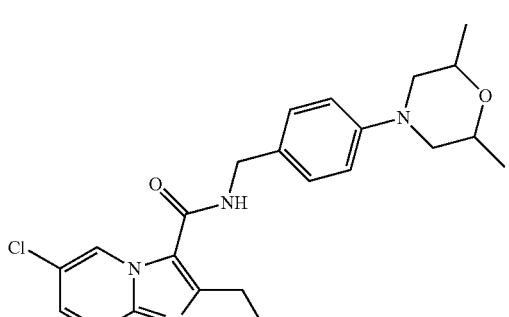 209 | +++ | +++ |
| 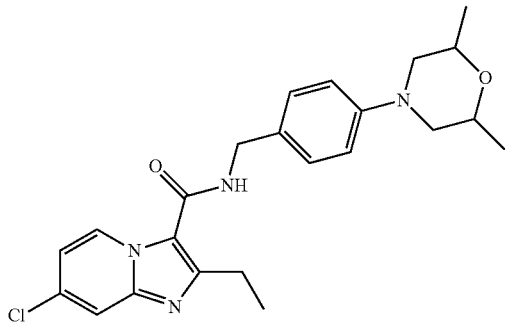 [SMILES: CCc1nc2cc(Cl)ccn2c1C(=O)NCc1ccc(N2CC(C)OC(C)C2)cc1] 210 | ++ | +++ |

TABLE 1-continued

| Compound | QUM (μM) | QIM (μM) |
|---|---|---|
| 211 | +++ | +++ |
| 212 | +++ | +++ |
| 213 | +++ | ++ |
| 214 | +++ | +++ |
| 215 | +++ | +++ |
| 216 | +++ | +++ |

TABLE 1-continued
| Compound | QUM (μM) | QIM (μM) |
|---|---|---|
| 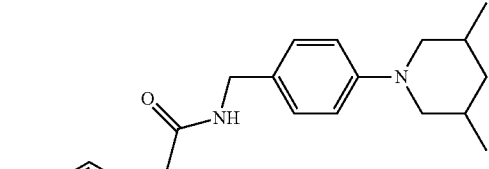 217 | +++ | +++ |
| 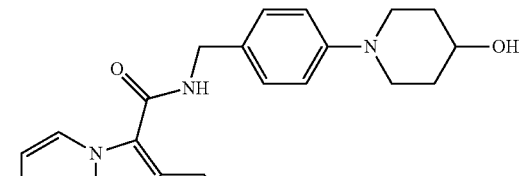 218 | +++ | + |
| 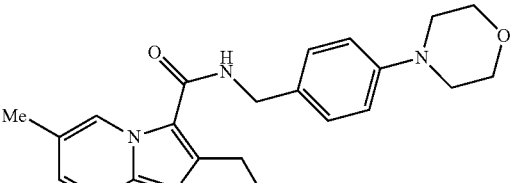 219 | +++ | nd |
| 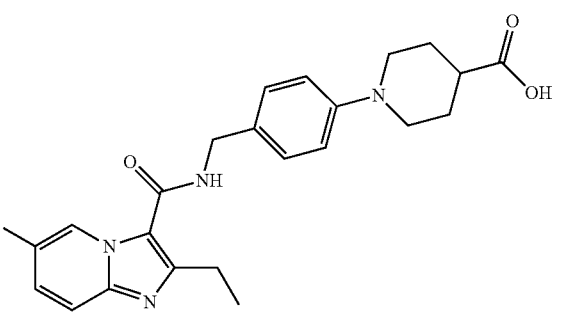 220 | +++ | nd |
| 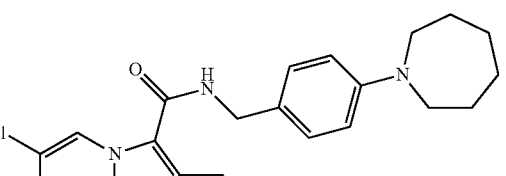 221 | +++ | +++ |

TABLE 1-continued
| Compound | QUM (µM) | QIM (µM) |
|---|---|---|
| 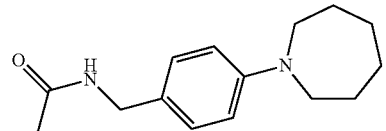 222 | +++ | +++ |
| 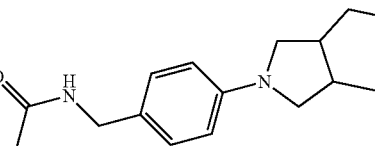 223 | +++ | nd |
| 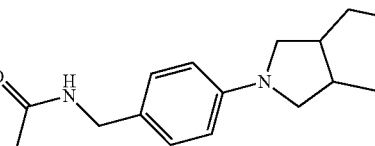 224 | +++ | nd |
| 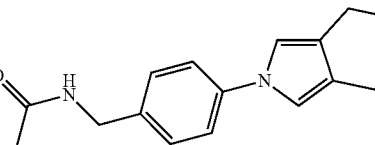 225 | +++ | nd |
| 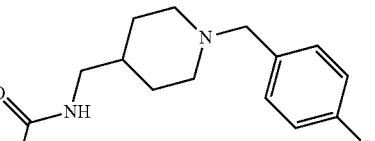 226 | +++ | +++ |
| 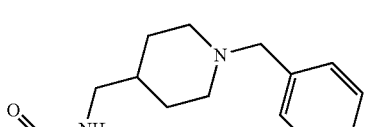 227 | ++ | +++ |

TABLE 1-continued

| Compound | QUM (μM) | QIM (μM) |
|---|---|---|
| 228 | + | + |
| 229 | + | + |
| 230 | + | + |
| 231 | +++ | +++ |
| 232 | ++ | ++ |

TABLE 1-continued
| Compound | QUM (μM) | QIM (μM) |
|---|---|---|
| 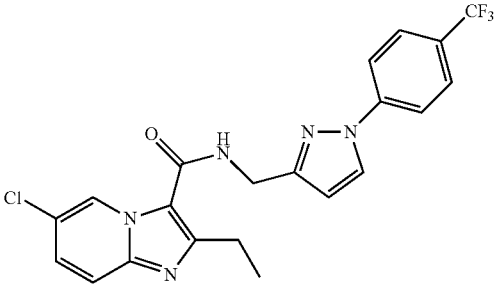 [SMILES: CCc1nc2ccc(Cl)cn2c1C(=O)NCc1ccn(-c2ccc(C(F)(F)F)cc2)n1] 233 | + | + |
| 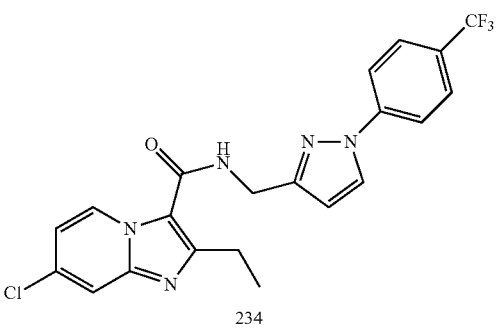 234 | ++ | ++ |
| 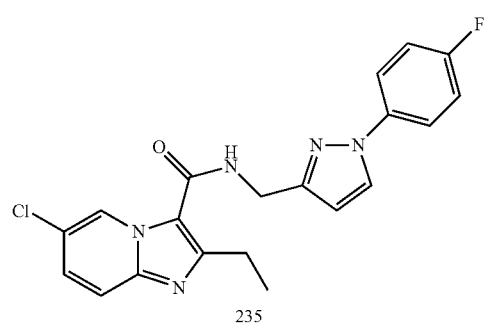 235 | ++ | ++ |
| 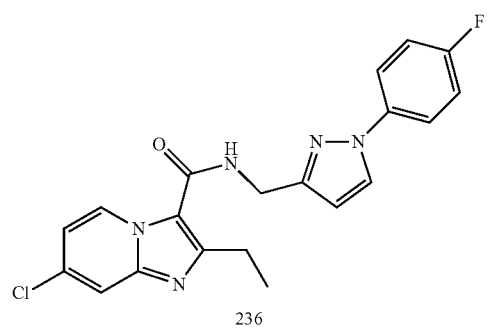 236 | ++ | + |
| 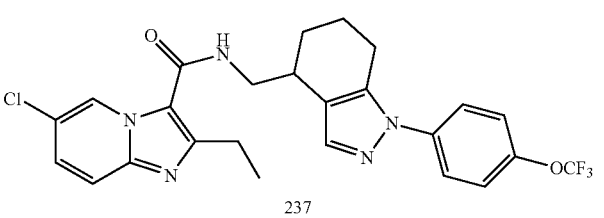 237 | + | + |

TABLE 1-continued
| Compound | QUM (µM) | QIM (µM) |
|---|---|---|
| 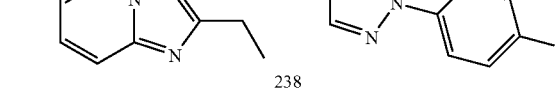 238 | + | + |
| 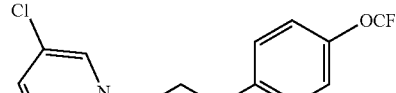 239 | + | + |
| 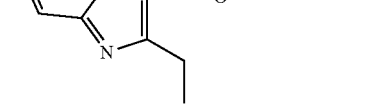 240 | + | + |
| 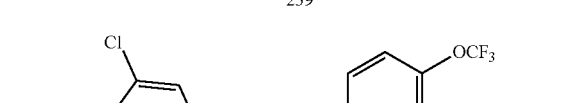 241 | + | + |
| 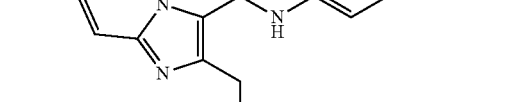 242 | + | + |
| 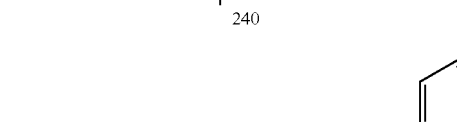 243 | + | + |

TABLE 1-continued
| Compound | QUM (μM) | QIM (μM) |
|---|---|---|
| 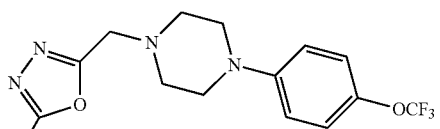 244 | ++ | ++ |
| 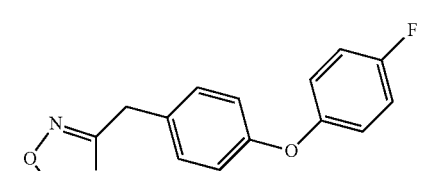 245 | ++ | nd |
| 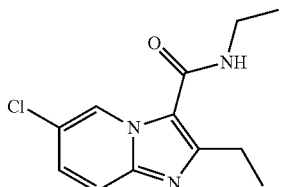 246 | + | nd |
| 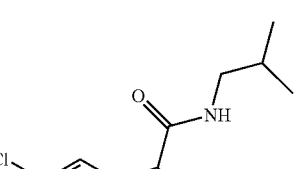 247 | + | nd |
| 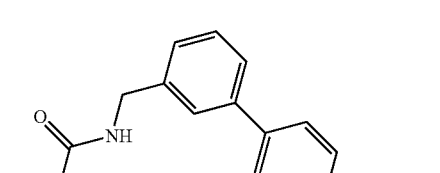 248 | +++ | nd |

TABLE 1-continued
| Compound | QUM (μM) | QIM (μM) |
|---|---|---|
| 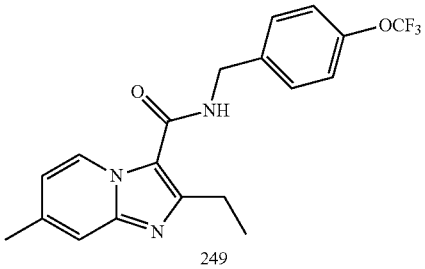 249 | +++ | nd |
| 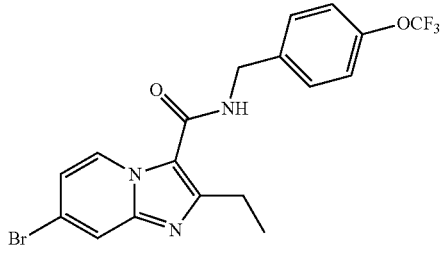 [SMILES: CCc1nc2cc(Br)ccn2c1C(=O)NCc1ccc(OC(F)(F)F)cc1] 250 | +++ | nd |
| 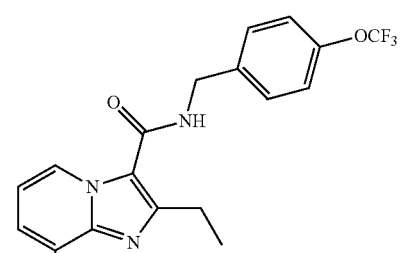 251 | +++ | nd |
| 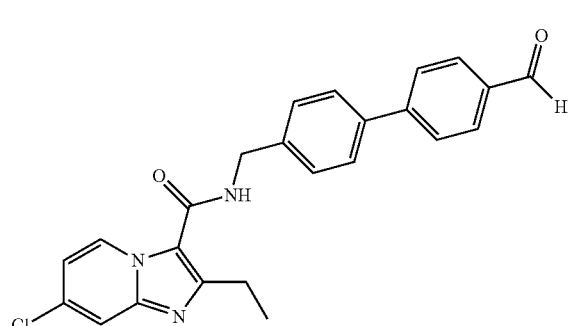 252 | +++ | nd |
| 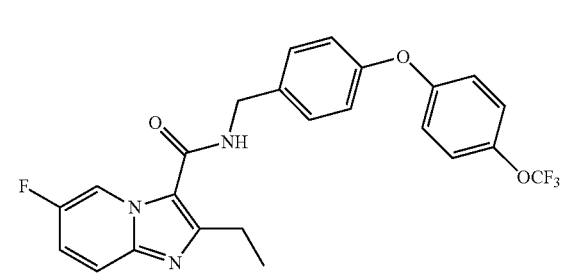 [SMILES: CCc1nc2ccc(F)cn2c1C(=O)NCc1ccc(Oc2ccc(OC(F)(F)F)cc2)cc1] 253 | +++ | nd |

TABLE 1-continued
| Compound | QUM (μM) | QIM (μM) |
|---|---|---|
| 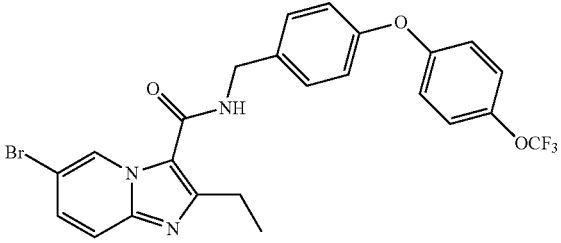 254 | +++ | nd |
| 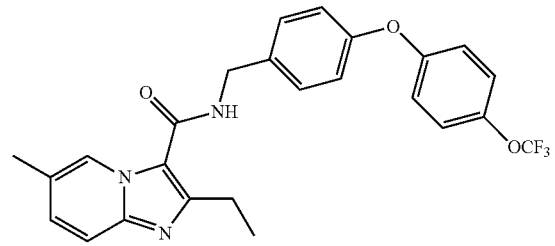 [SMILES: CCc1nc2ccc(C)cn2c1C(=O)NCc1ccc(Oc2ccc(OC(F)(F)F)cc2)cc1] 255 | +++ | nd |
| 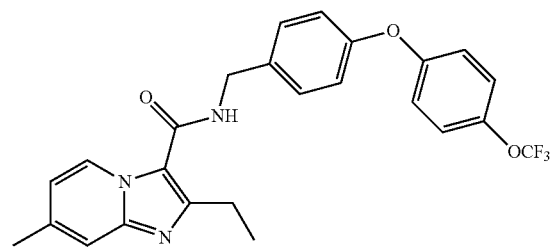 [SMILES: CCc1nc2cc(C)ccn2c1C(=O)NCc1ccc(Oc2ccc(OC(F)(F)F)cc2)cc1] 256 | +++ | nd |
| 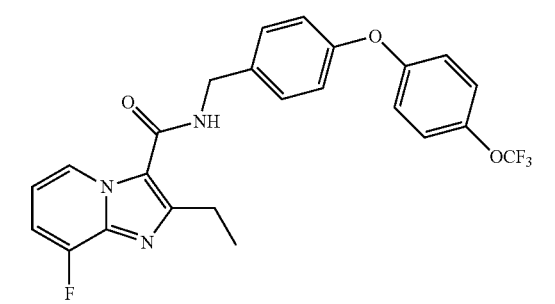 [SMILES: CCc1nc2c(F)cccn2c1C(=O)NCc1ccc(Oc2ccc(OC(F)(F)F)cc2)cc1] 257 | +++ | nd |
| 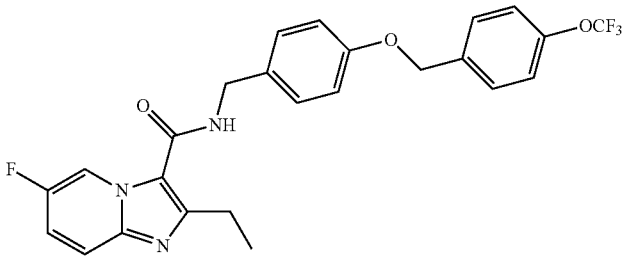 [SMILES: CCc1nc2ccc(F)cn2c1C(=O)NCc1ccc(OCc2ccc(OC(F)(F)F)cc2)cc1] 258 | +++ | +++ |

TABLE 1-continued
| Compound | QUM (μM) | QIM (μM) |
|---|---|---|
| 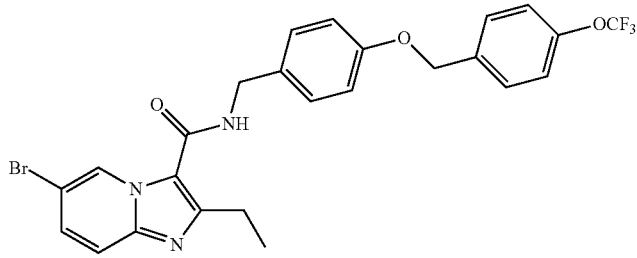 [SMILES: CCc1nc2ccc(Br)cn2c1C(=O)NCc1ccc(OCc2ccc(OC(F)(F)F)cc2)cc1] 259 | +++ | nd |
| 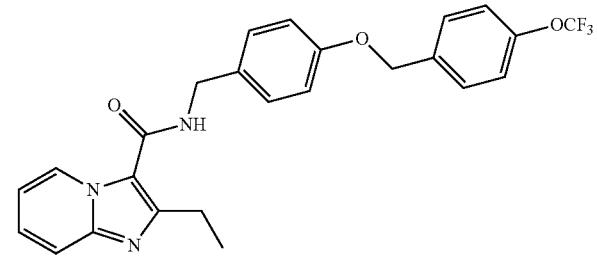 [SMILES: CCc1nc2ccccn2c1C(=O)NCc1ccc(OCc2ccc(OC(F)(F)F)cc2)cc1] 260 | +++ | nd |
| 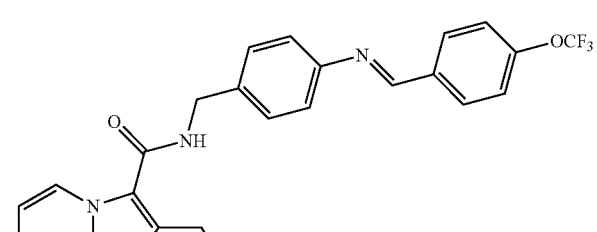 261 | + | + |
| 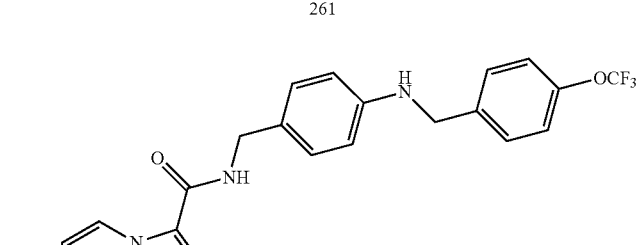 262 | +++ | +++ |
| 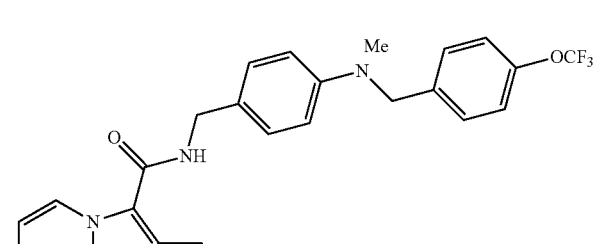 263 | +++ | +++ |

TABLE 1-continued
| Compound | QUM (μM) | QIM (μM) |
|---|---|---|
| 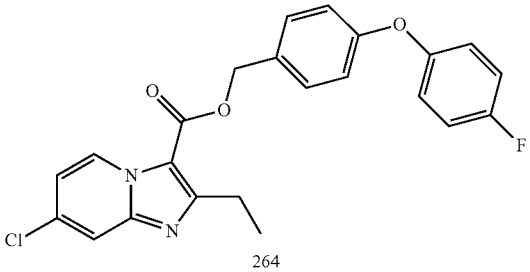 264 | +++ | nd |
| 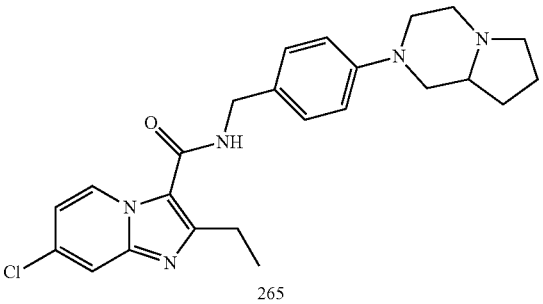 265 | + | nd |
| 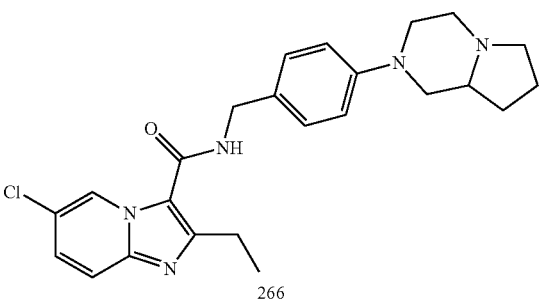 266 | + | nd |
| 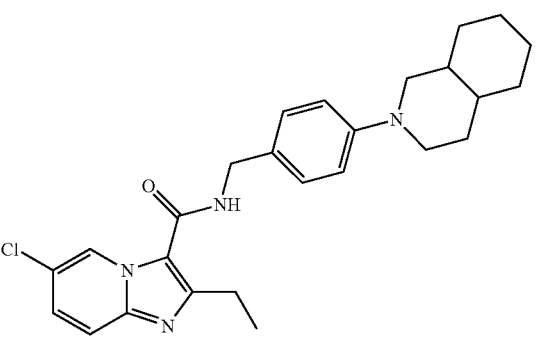 [SMILES: CCc1nc2ccc(Cl)cn2c1C(=O)NCc1ccc(N2CCC3CCCCC3C2)cc1] 267 | +++ | +++ |
| 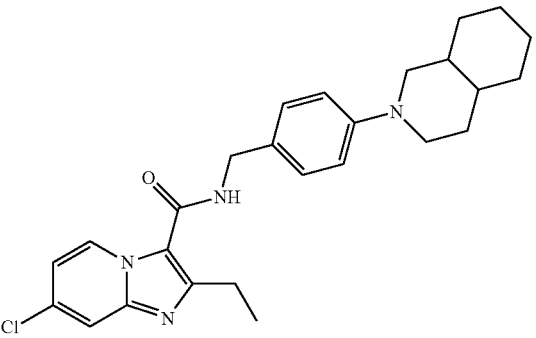 [SMILES: CCc1nc2cc(Cl)ccn2c1C(=O)NCc1ccc(N2CCC3CCCCC3C2)cc1] 268 | +++ | nd |

TABLE 1-continued
| Compound | QUM (μM) | QIM (μM) |
|---|---|---|
| 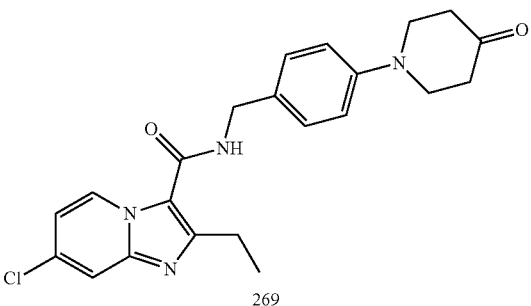 269 | +++ | ++ |
| 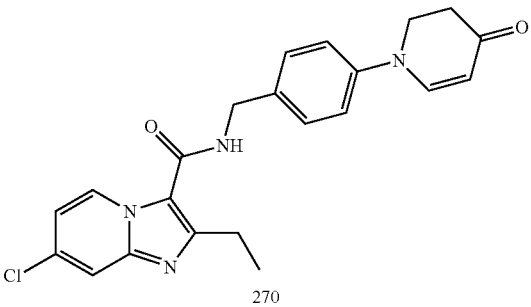 270 | + | + |
| 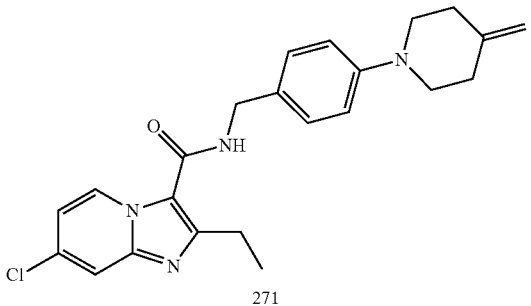 271 | +++ | nd |
| 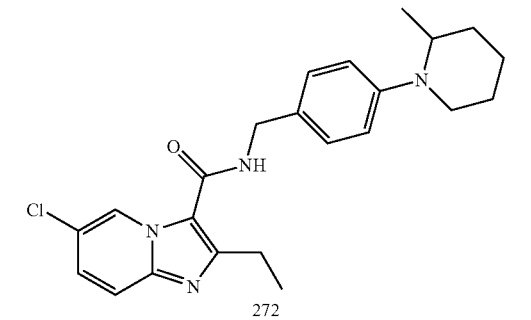 272 | +++ | +++ |
| 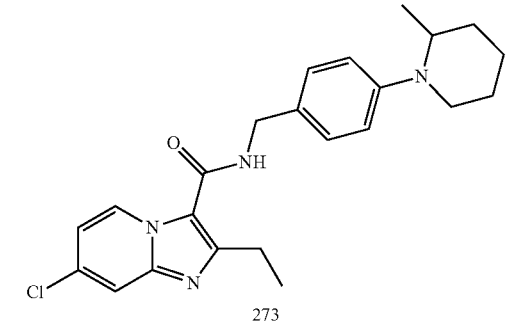 273 | +++ | +++ |

TABLE 1-continued

| Compound | QUM (μM) | QIM (μM) |
|---|---|---|
| 274 | +++ | nd |
| 275 | ++ | nd |
| 276 | + | nd |
| 277 | ++ | nd |
| 278 | ++ | nd |

TABLE 1-continued
| Compound | QUM (μM) | QIM (μM) |
|---|---|---|
| 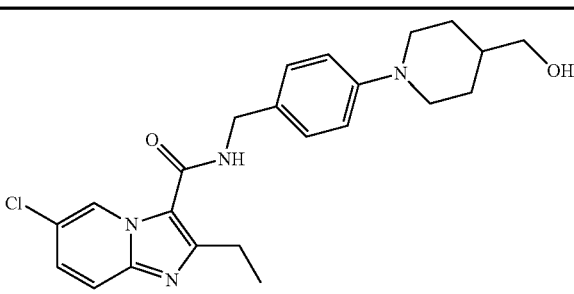 279 | + | nd |
| 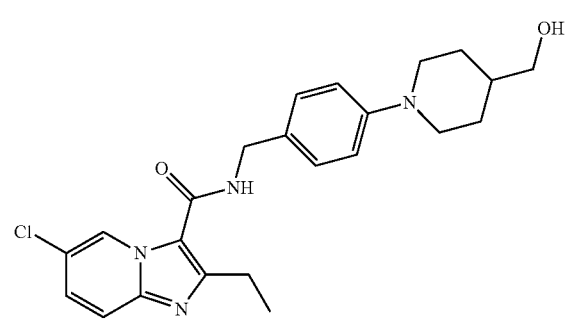 [SMILES: CCc1nc2ccc(Cl)cn2c1C(=O)NCc1ccc(N2CCC(CO)CC2)cc1] 280 | +++ | nd |
| 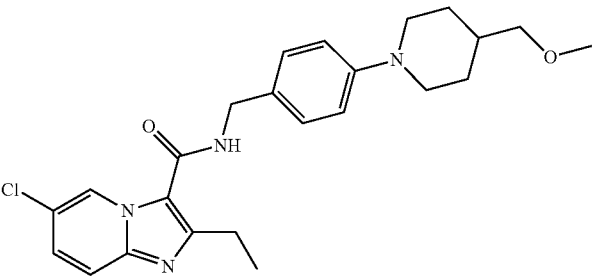 [SMILES: CCc1nc2ccc(Cl)cn2c1C(=O)NCc1ccc(N2CCC(COC)CC2)cc1] 281 | +++ | +++ |
| 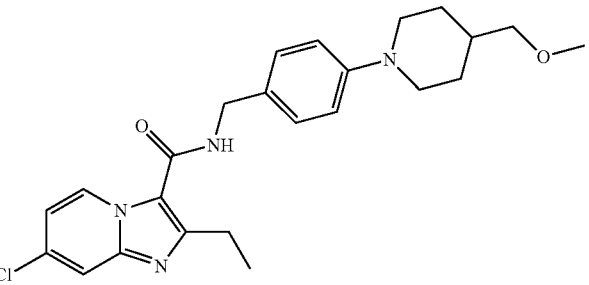 282 | +++ | +++ |
| 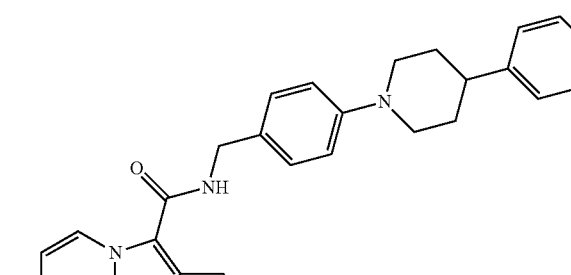 283 | +++ | nd |

TABLE 1-continued
| Compound | QUM (μM) | QIM (μM) |
|---|---|---|
| 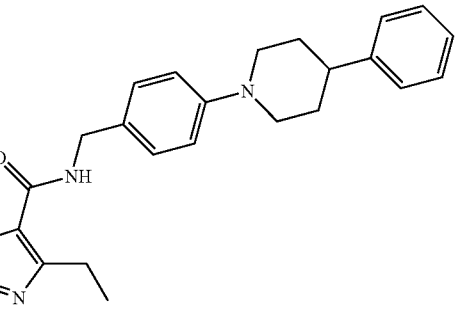 284 | +++ | nd |
| 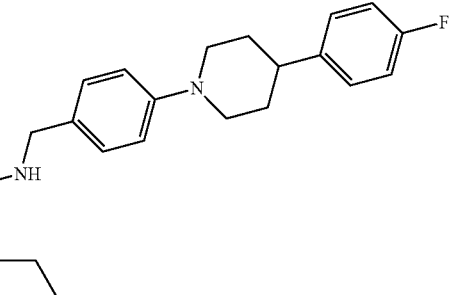 285 | +++ | nd |
| 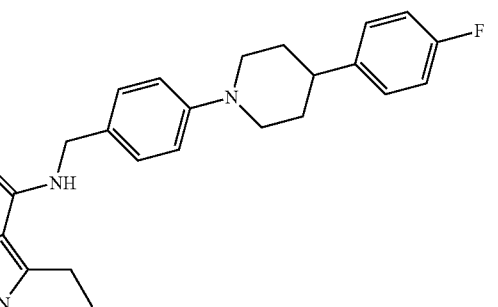 286 | +++ | +++ |
| 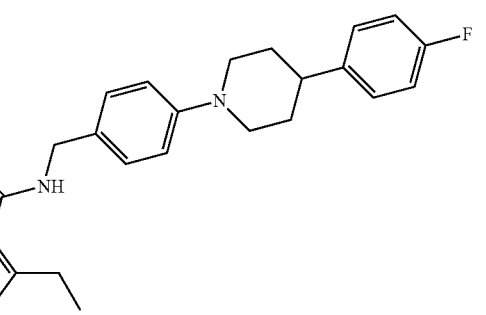 287 | +++ | +++ |

TABLE 1-continued
| Compound | QUM (μM) | QIM (μM) |
|---|---|---|
| 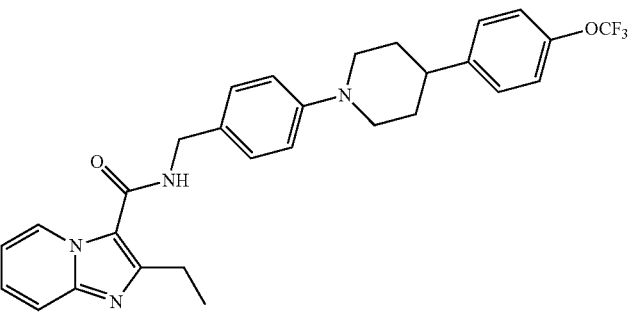 288 | +++ | nd |
| 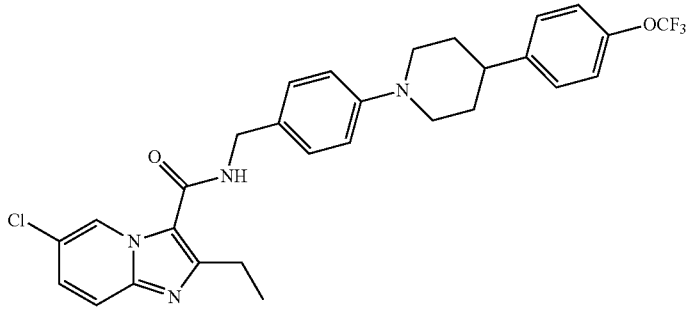 [SMILES: CCc1nc2ccc(Cl)cn2c1C(=O)NCc1ccc(N2CCC(c3ccc(OC(F)(F)F)cc3)CC2)cc1] 289 | +++ | nd |
| 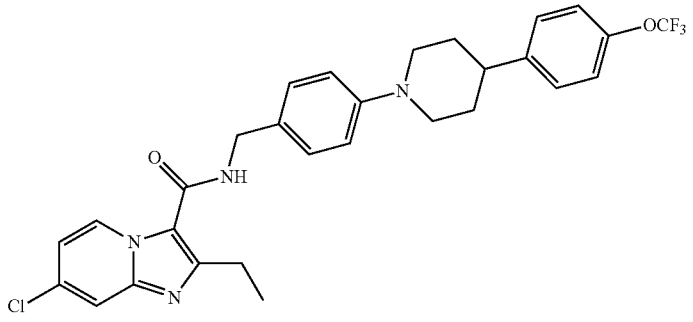 [SMILES: CCc1nc2cc(Cl)ccn2c1C(=O)NCc1ccc(N2CCC(c3ccc(OC(F)(F)F)cc3)CC2)cc1] 290 | +++ | nd |
| 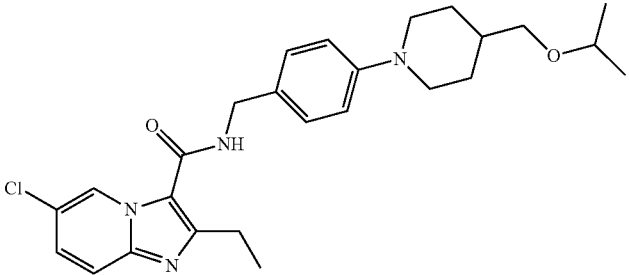 [SMILES: CCc1nc2ccc(Cl)cn2c1C(=O)NCc1ccc(N2CCC(COC(C)C)CC2)cc1] 291 | +++ | +++ |

TABLE 1-continued
| Compound | QUM (μM) | QIM (μM) |
|---|---|---|
| 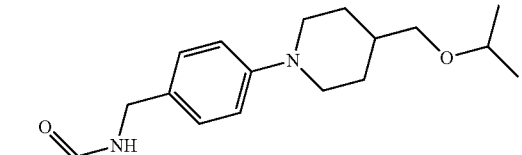 292 | +++ | +++ |
| 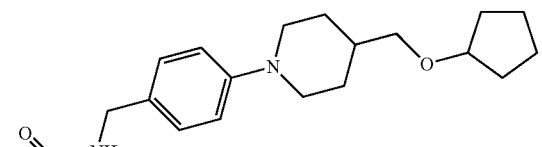 293 | +++ | nd |
| 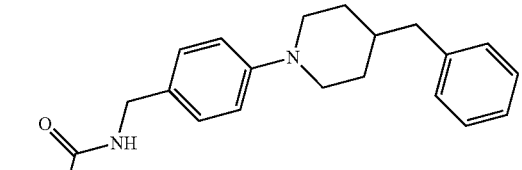 294 | ++ | nd |
| 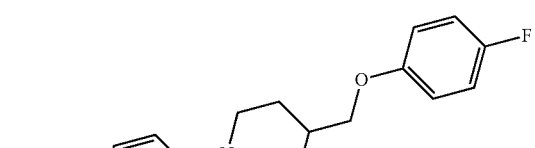 295 | +++ | +++ |

TABLE 1-continued
| Compound | QUM (μM) | QIM (μM) |
|---|---|---|
| 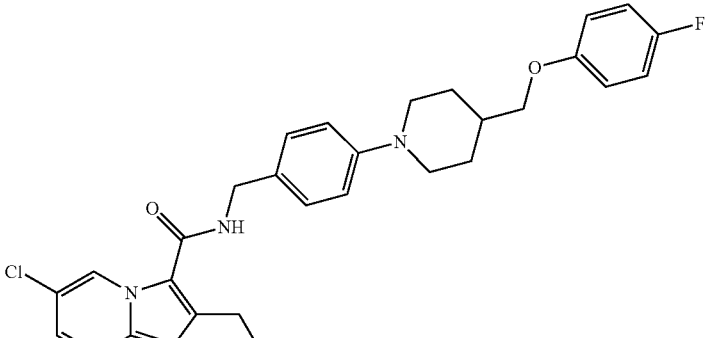 296 | +++ | +++ |
| 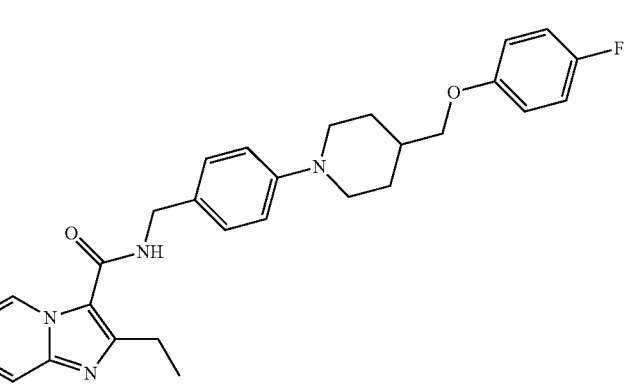 297 | +++ | +++ |
| 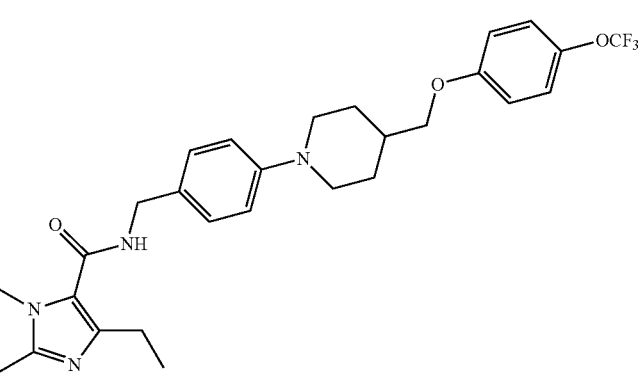 298 | +++ | nd |
| 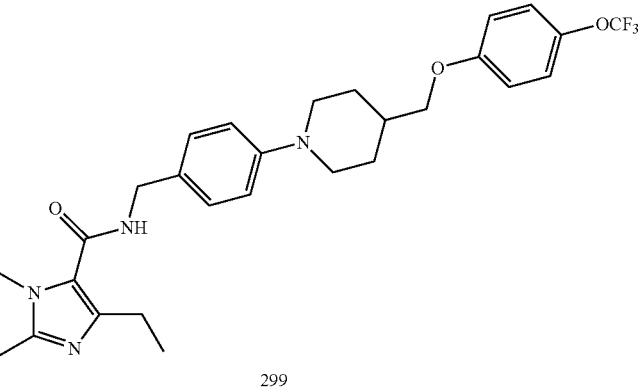 299 | +++ | nd |

TABLE 1-continued

| Compound | QUM (μM) | QIM (μM) |
|---|---|---|
| 300 | +++ | nd |
| 301 | +++ | nd |
| 302 | +++ | nd |
| 303 | +++ | +++ |

TABLE 1-continued
| Compound | QUM (μM) | QIM (μM) |
|---|---|---|
| 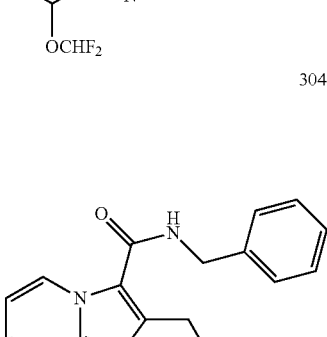 304 | +++ | nd |
| 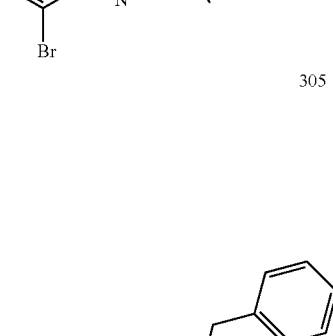 305 | +++ | nd |
| 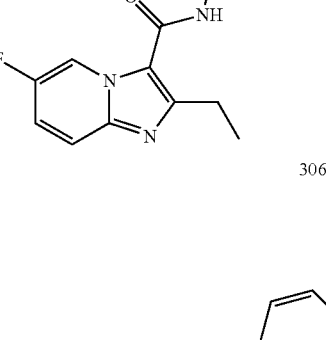 306 | +++ | +++ |
| 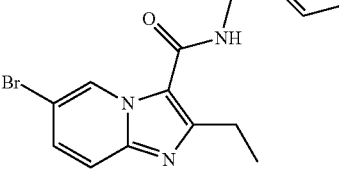 307 | +++ | +++ |

TABLE 1-continued

| Compound | QUM (μM) | QIM (μM) |
|---|---|---|
| 308 | +++ | nd |
| 309 | +++ | +++ |
| 310 | +++ | +++ |
| 311 | +++ | +++ |

TABLE 1-continued

| Compound | QUM (μM) | QIM (μM) |
|---|---|---|
| 312 | +++ | nd |
| 313 | +++ | nd |
| 314 | +++ | nd |
| 315 | +++ | +++ |

TABLE 1-continued

| Compound | QUM (μM) | QIM (μM) |
|---|---|---|
| 316 | ++ | ++ |
| 317 | +++ | +++ |
| 318 | +++ | nd |
| 319 | ++ | nd |

TABLE 1-continued
| Compound | QUM (μM) | QIM (μM) |
|---|---|---|
| 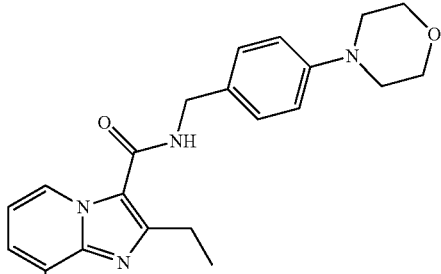 320 | +++ | nd |
| 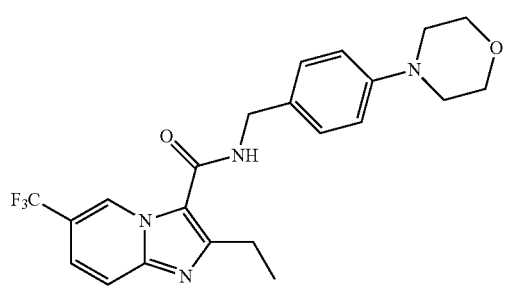 [SMILES: CCc1nc2ccc(C(F)(F)F)cn2c1C(=O)NCc1ccc(N2CCOCC2)cc1] 321 | +++ | nd |
| 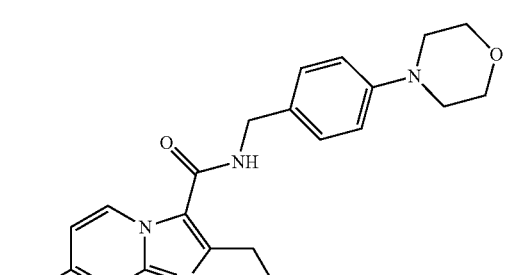 322 | ++ | nd |
| 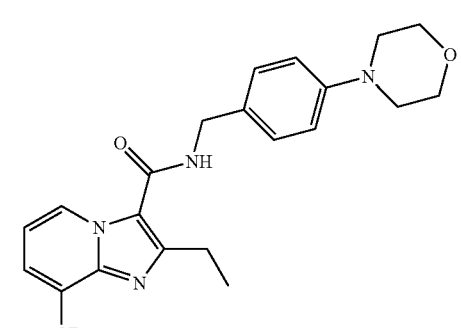 323 | ++ | nd |

TABLE 1-continued
| Compound | QUM (μM) | QIM (μM) |
|---|---|---|
| 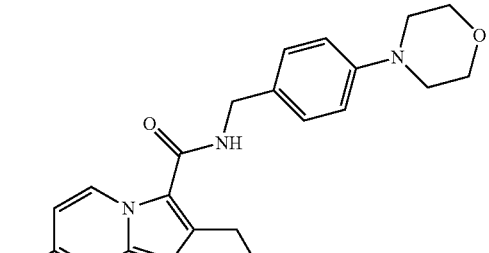  324 | +++ | +++ |
| 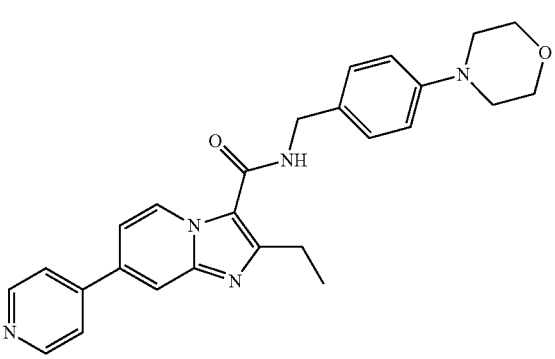 [SMILES: CCc1nc2cc(-c3ccncc3)ccn2c1C(=O)NCc1ccc(N2CCOCC2)cc1]  325 | + | + |
| 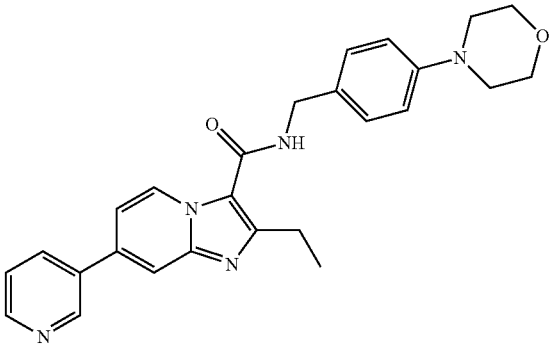 [SMILES: CCc1nc2cc(-c3cccnc3)ccn2c1C(=O)NCc1ccc(N2CCOCC2)cc1]  326 | + | + |
| 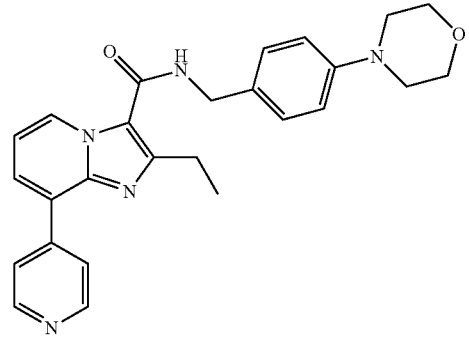 [SMILES: CCc1nc2c(-c3ccncc3)cccn2c1C(=O)NCc1ccc(N2CCOCC2)cc1]  327 | + | nd |

TABLE 1-continued

| Compound | QUM (μM) | QIM (μM) |
|---|---|---|
| 328 | + | + |
| 329 | + | + |
| 330 | + | +++ |

татdownTABLE 1-continued
| Compound | QUM (μM) | QIM (μM) |
|---|---|---|
| 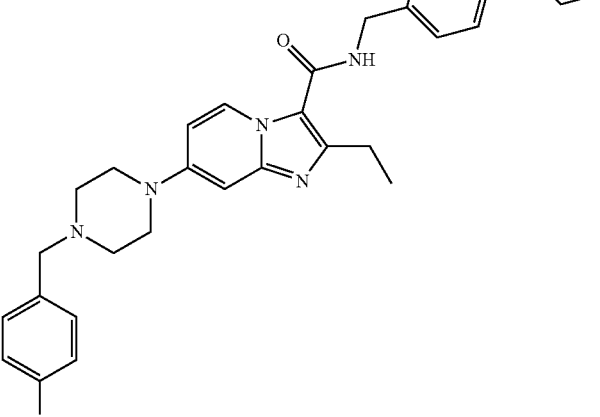 331 | + | + |
| 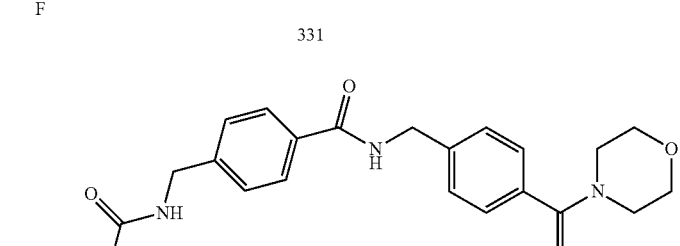 332 | + | nd |
| 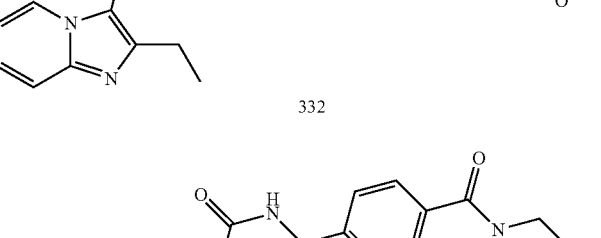 333 | + | nd |
| 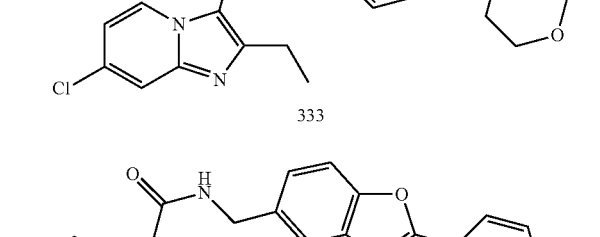 334 | +++ | nd |
| 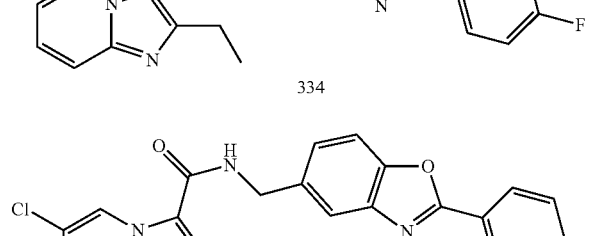 335 | +++ | nd |

TABLE 1-continued
| Compound | QUM (μM) | QIM (μM) |
|---|---|---|
| 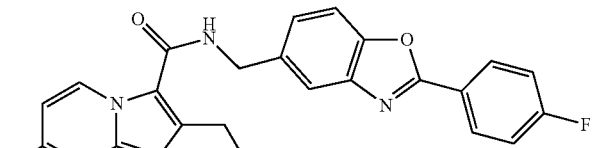 336 | +++ | nd |
| 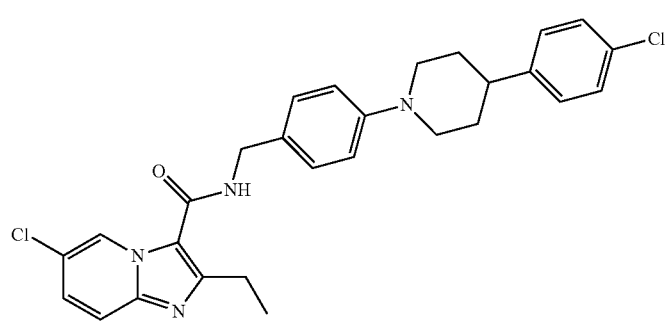 [SMILES: CCc1nc2ccc(Cl)cn2c1C(=O)NCc1ccc(N2CCC(c3ccc(Cl)cc3)CC2)cc1] 337 | +++ | nd |
| 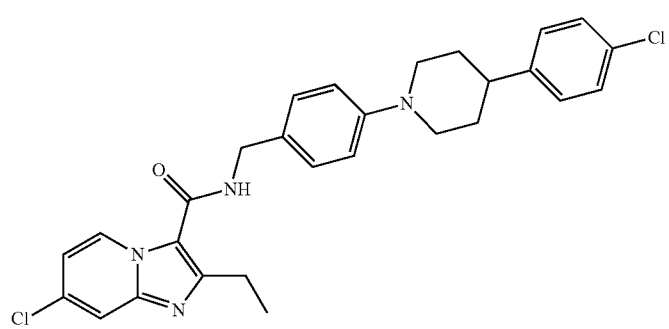 [SMILES: CCc1nc2cc(Cl)ccn2c1C(=O)NCc1ccc(N2CCC(c3ccc(Cl)cc3)CC2)cc1] 338 | +++ | nd |
| 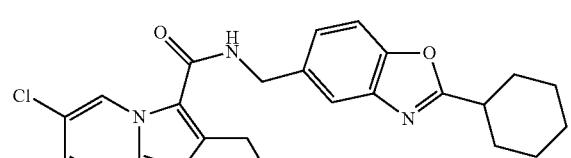 339 | +++ | nd |
| 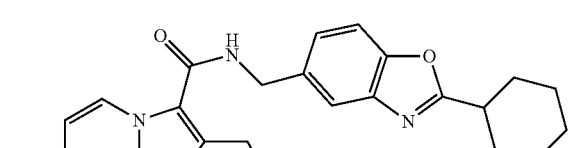 340 | +++ | nd |
| 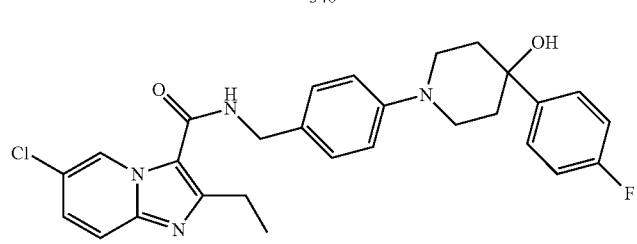 341 | +++ | nd |

TABLE 1-continued

| Compound | QUM (μM) | QIM (μM) |
|---|---|---|
| 342 | +++ | nd |
| 343 | +++ | nd |
| 344 | ++ | nd |
| 345 | +++ | nd |
| 346 | +++ | nd |

TABLE 1-continued
| Compound | QUM (μM) | QIM (μM) |
|---|---|---|
| 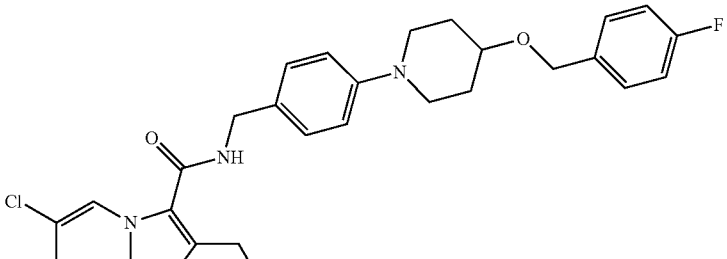 347 | +++ | nd |
| 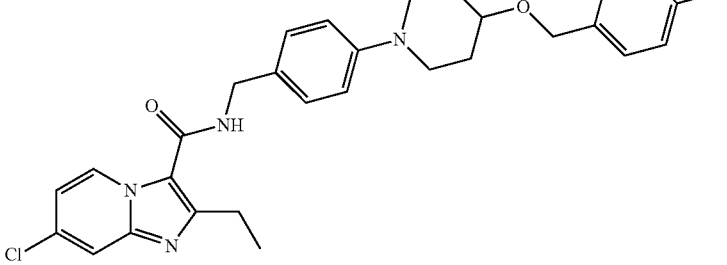 348 | ++ | nd |
| 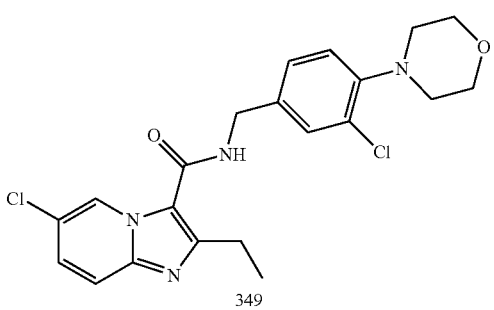 349 | +++ | nd |
| 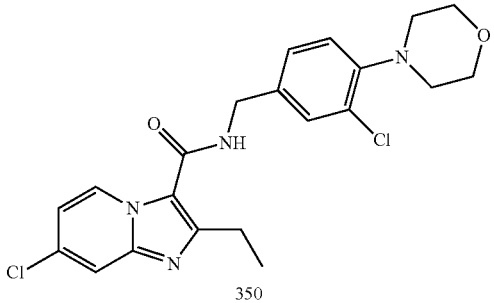 350 | +++ | nd |
| 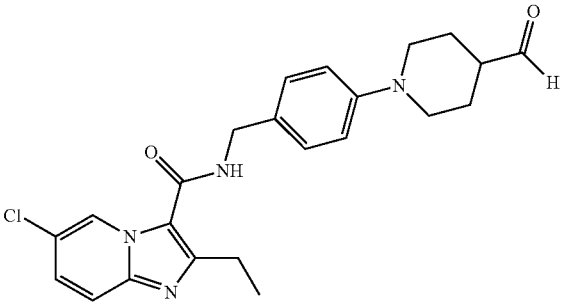 [SMILES: CCc1nc2ccc(Cl)cn2c1C(=O)NCc1ccc(N2CCC(C=O)CC2)cc1] 351 | +++ | nd |

TABLE 1-continued

| Compound | QUM (μM) | QIM (μM) |
|---|---|---|
| 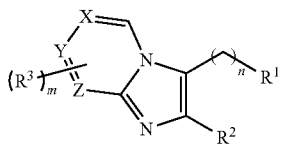 352 | +++ | nd |

Activity range:
+++ indicates <1 uM,
++ indicates between 1-20 uM,
+ indicates >20 uM
nd: not determined

TABLE 2

| | MIC$_{80}$ (μM) | | | | | | | | | | Sensitive Strain |
|---|---|---|---|---|---|---|---|---|---|---|---|
| | MDR isolates | | | | | | | | | | |
| Compound | #13 | #33 | #48 | #61 | #80 | #125 | #137 | #143 | #146 | #171 | H37Rv |
| 47 | 0.3125 | 0.3125 | 0.3125 | 0.3125 | 0.3125 | 0.625 | 1.25 | 1.25 | 0.15625 | 1.25 | 1.25 |
| 54 | 0.15625 | 0.15625 | 0.15625 | 0.15625 | 0.15625 | 0.3125 | 0.625 | 0.3125 | 0.3125 | 0.3125 | 0.625 |
| INH | 5 | 10 | 10 | 20 | 5 | 10 | 20 | 10 | 20 | 5 | 1.25 |
| MFX | 0.15625 | 0.3125 | 0.3125 | 0.3125 | 0.625 | 0.625 | 0.625 | 1.25 | 0.625 | 0.625 | 1.25 |

The invention claimed is:

1. A compound having the general formula Ia:

wherein
m is 0, 1, 2, 3 or 4;
n is 0, 1, 2, or 3;
X, Y and Z are CH;
$R^1$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, —$OR^4$, —C(O)$OR^4$, —C(O)$R^4$, —C(O)N($R^4$)$_2$, —CN, —NO$_2$, —NH$_2$, —N($R^4$)$_2$, —$OR^4$HetA, —$OR^4$N($R^4$)$_2$, —C(O)N($R^4$)$R^4$HetA, —C(O)N($R^4$)HetA, —C(O)HetA, —C(O)N($R^4$)$R^4$S(O)$_2$$R_4$; —S(O)$_2$N($R^4$)$_2$, —S(O)$_2$$R^4$, —N($R^4$)C(O)$R^4$S$R^4$, —N($R^4$)$R^4$S(O)$_2$$R^4$, —N($R^4$)S(O)$_2$$R^4$, —C(S)$R^4$, aryl, benzyl, and heterocyclyl, any of which is optionally substituted;
$R^2$ is, at each occurrence, independently selected from the group consisting of hydrogen, halogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —OH, —$OR^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, —CN, —NO$_2$, —NH$_2$, —N($R^5$)$_2$, —C(O)$R^5$, —C(O)$OR^5$, —C(O)N($R^5$)$_2$, —S$R^5$, —S(O)$R^5$, —S(O)$_2$$R^5$, —S(O)$_2$N($R^5$)$_2$, aryl, benzyl, heteroaryl, and heterocyclyl, any of which is optionally substituted;
$R^3$ is, at each occurrence, independently selected from the group consisting of hydrogen, halogen, $C_1$-$C_{10}$ alkyl, $C_3$-$C_{10}$ cycloalkyl, hydroxyl, —$OR^6$, —CN, —NO$_2$, —NH$_2$, —N($R^6$)C(O)$R^6$, —C(O)$R^6$, —C(O)$OR^6$, —C(O)N($R^6$)$_2$, —S(O)$R^6$, —S(O)$_2$$R^6$, —S(O)$_2$N($R^6$)$_2$, aryl, benzyl, heteroaryl, heterocyclyl, any of which is optionally substituted, or two groups of $R^3$ are connected to each other to make a five or six membered cyclic or heterocyclic ring, any of which is optionally substituted;
$R^4$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —C(O)$R^7$, —$R^7$($R^7$)C(O)$R^7$, —C(O)$OR^7$, —$R^7$($R^7$)C(O)$OR^7$, —C(O)N($R^7$)$_2$, —$R^7$($R^7$)C(O)N($R^7$)$_2$, —S(O)$R^7$, —S(O)$_2$$R^7$, —S(O)$_2$N($R^7$)$_2$, aryl, benzyl, heteroaryl, and heterocyclyl, any of which is optionally substituted; and
$R^5$, $R^6$ and $R^7$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted; and pharmaceutically acceptable salts thereof, and
wherein the compound has a formula selected from the
following formulae 5, 8, 13, 14, 17, 18, 20, 21, 23-43, 46,
48, 50, 51, 53, 59, 68, 69, 74, 79, 80, 89-91, 142, 143,
161, 196, 211-213, 219, 221, 222, 239-247, 264, 313-
329 and 331:

2-Methyl-N-(pyridin-4-yl)imidazo[1,2-a]pyridine-3-carboxamide (5)

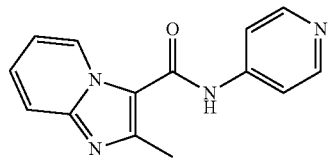 [SMILES: Cc1nc2ccccn2c1C(=O)Nc1ccncc1]

N-Benzyl-2-methylimidazo[1,2-a]pyridine-3-carboxamide (8)

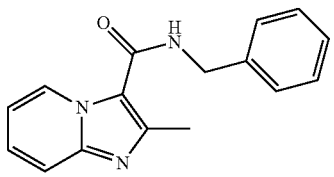 [SMILES: Cc1nc2ccccn2c1C(=O)NCc1ccccc1]

2-Methyl-N-(pyridin-3-ylmethyl)imidazo[1,2-a]pyridine-3-carboxamide (13)

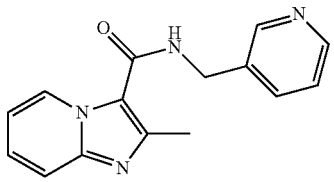 [SMILES: Cc1nc2ccccn2c1C(=O)NCc1cccnc1]

2-Methyl-N-(pyridin-4-ylmethyl)imidazo[1,2-a]pyridine-3-carboxamide (14)

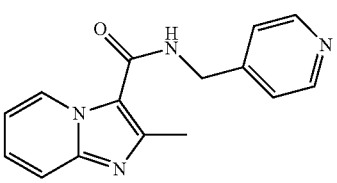 [SMILES: Cc1nc2ccccn2c1C(=O)NCc1ccncc1]

N-((1H-Indo)-5-yl)methyl)-2-methylimidazo[1,2-a]pyridine-3-carboxamide (17)

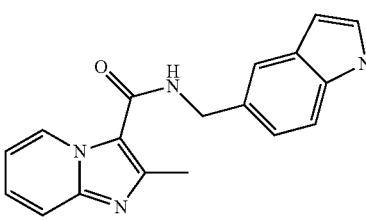

N—(Cyclohexylmethyl)-2-methylimidazo[1,2-a]pyridine-3-carboxamide (18)

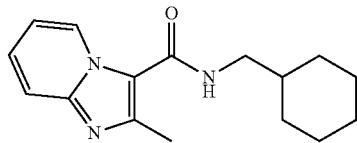 [SMILES: Cc1nc2ccccn2c1C(=O)NCC1CCCCC1]

2-Methyl-N-(piperidin-4-ylmethyl)imidazo[1,2-a]pyridine-3-carboxamide (20)

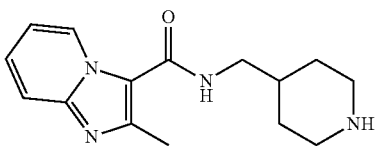 [SMILES: Cc1nc2ccccn2c1C(=O)NCC1CCNCC1]

2-Methyl-N-phenethylimidazo[1,2-a]pyridine-3-carboxamide (21)

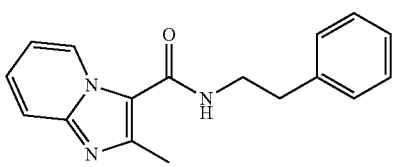 [SMILES: Cc1nc2ccccn2c1C(=O)NCCc1ccccc1]

2-Methyl-N-(2-phenoxyethyl)imidazo[1,2-a]pyridine-3-carboxamide (23)

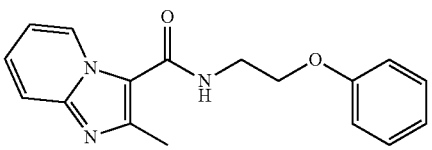 [SMILES: Cc1nc2ccccn2c1C(=O)NCCOc1ccccc1]

N-(2-(Benzyloxy)ethyl)-2-methylimidazo[1,2-a]pyridine-3-carboxamide (24)

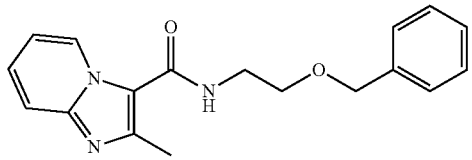 [SMILES: Cc1nc2ccccn2c1C(=O)NCCOCc1ccccc1]

(S)-Methyl 2-(2-methylimidazo[1,2-a]pyridine-3-carboxamido)-3-phenylpropanoate (25)

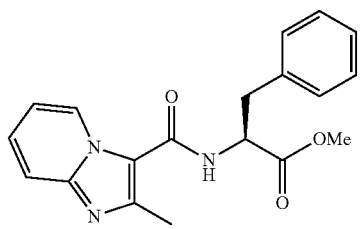 [SMILES: COC(=O)[C@H](Cc1ccccc1)NC(=O)c1c(C)nc2ccccn12]

N-(2-Methylimidazo[1,2-a]pyridin-3-yl)-2-phenylacetamide (26)

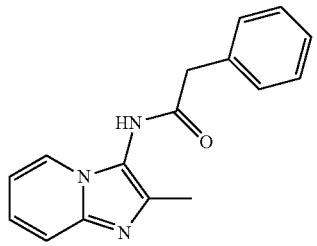 [SMILES: Cc1nc2ccccn2c1NC(=O)Cc1ccccc1]

N-Benzyl-8-chloro-2-methylimidazo[1,2-a]pyridine-3-carboxamide (27)

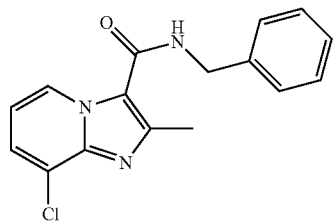 [SMILES: Cc1nc2c(Cl)cccn2c1C(=O)NCc1ccccc1]

N-Benzyl-7-chloro-2-methylimidazo[1,2-a]pyridine-3-carboxamide (28)

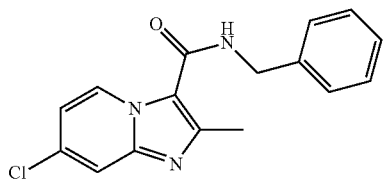 [SMILES: Cc1nc2cc(Cl)ccn2c1C(=O)NCc1ccccc1]

N-Benzyl-6-chloro-2-methylimidazo[1,2-a]pyridine-3-carboxamide (29)

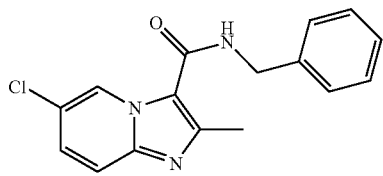 [SMILES: Cc1nc2ccc(Cl)cn2c1C(=O)NCc1ccccc1]

N-Benzyl-2,8-dimethylimidazo[1,2-a]pyridine-3-carboxamide (30)

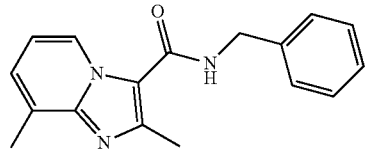 [SMILES: Cc1nc2c(C)cccn2c1C(=O)NCc1ccccc1]

N-Benzyl-2,7-dimethylimidazo[1,2-a]pyridine-3-carboxamide (31)

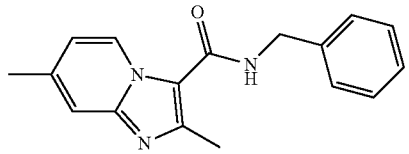

N-Benzyl-2,6-dimethylimidazo[1,2-a]pyridine-3-carboxamide (32)

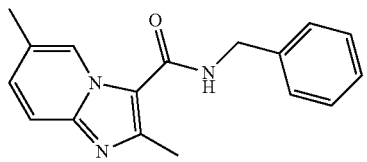 [SMILES: Cc1ccc2nc(C)c(C(=O)NCc3ccccc3)n2c1]

N-Benzyl-2,5-dimethylimidazo[1,2-a]pyridine-3-carboxamide (33)

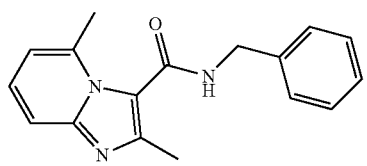 [SMILES: Cc1nc2cccc(C)n2c1C(=O)NCc1ccccc1]

N-Benzyl-6-fluoro-2-methylimidazo[1,2-a]pyridine-3-carboxamide (34)

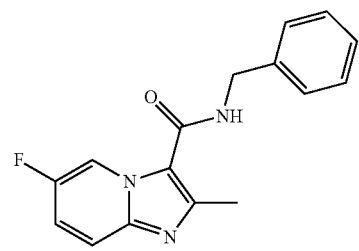 [SMILES: Cc1nc2ccc(F)cn2c1C(=O)NCc1ccccc1]

N-Benzyl-7-cyano-2-methylimidazo[1,2-a]pyridine-3-carboxamide (35)

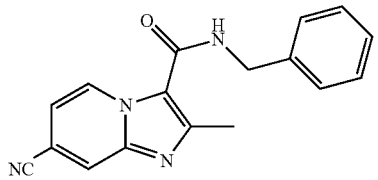

N-Benzyl-6-cyano-2-methylimidazo[1,2-a]pyridine-3-carboxamide (36)

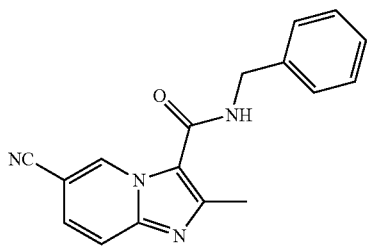 [SMILES: Cc1nc2ccc(C#N)cn2c1C(=O)NCc1ccccc1]

N-Benzyl-2-methyl-7-phenylimidazo[1,2-a]pyridine-3-carboxamide (37)

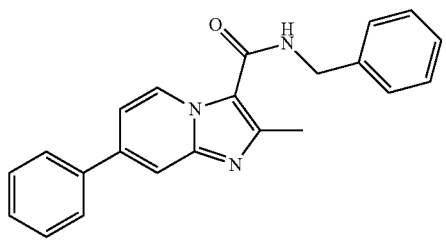 [SMILES: Cc1nc2cc(-c3ccccc3)ccn2c1C(=O)NCc1ccccc1]

N-Benzyl-2-methyl-6-phenylimidazo[1,2-a]pyridine-3-carboxamide (38)

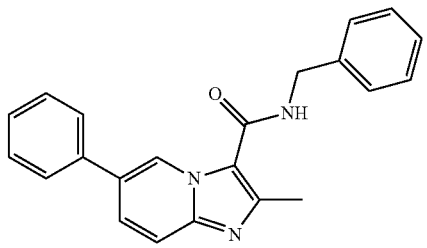 [SMILES: Cc1nc2ccc(-c3ccccc3)cn2c1C(=O)NCc1ccccc1]

N-Benzyl-8-fluoro-2-methylimidazo[1,2-a]pyridine-3-carboxamide (39)

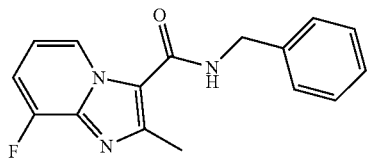

N-Benzyl-2-methyl-8-(trifluoromethyl)imidazo[1,2-a]pyridine-3-carboxamide (40)

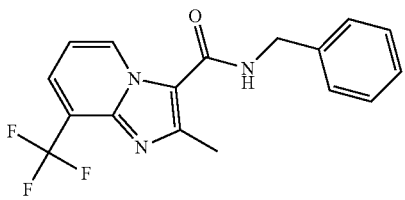

N-Benzyl-8-methoxy-2-methylimidazo[1,2-a]pyridine-3-carboxamide (41)

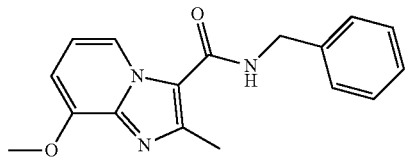 [SMILES: COc1cccn2c(C(=O)NCc3ccccc3)c(C)nc12]

N-Benzyl-8-cyano-2-methylimidazo[1,2-a]pyridine-3-carboxamide (42)

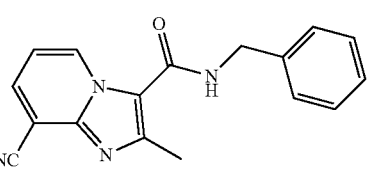

N-Benzyl-8-hydroxy-2-methylimidazo[1,2-a]pyridine-3-carboxamide (43)

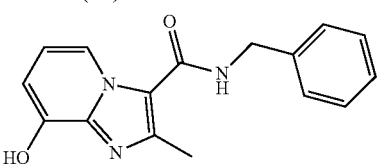

N-Benzyl-2-ethylimidazo[1,2-a]pyridine-3-carboxamide (46)

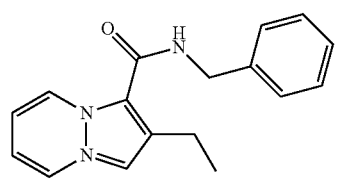

N-Benzyl-2-propylimidazo[1,2-a]pyridine-3-carboxamide (48)

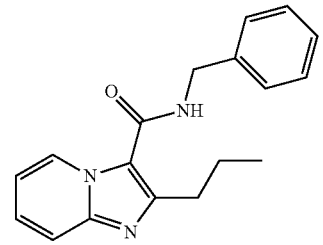 [SMILES: CCCc1nc2ccccn2c1C(=O)NCc1ccccc1]

N-Benzyl-2-cyclopropylimidazo[1,2-a]pyridine-3-carboxamide (50)

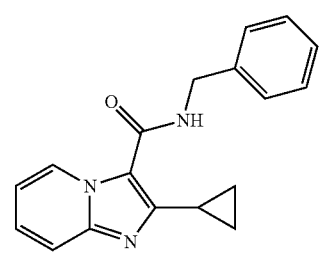 [SMILES: O=C(NCc1ccccc1)c1c(C2CC2)nc2ccccn12]

N-Benzyl-2-isopropylimidazo[1,2-a]pyridine-3-carboxamide (51)

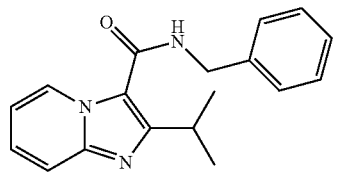 [SMILES: CC(C)c1nc2ccccn2c1C(=O)NCc1ccccc1]

N-Benzyl-2-phenylimidazo[1,2-a]pyridine-3-carboxamide (53)

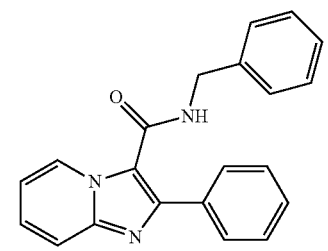 [SMILES: O=C(NCc1ccccc1)c1c(-c2ccccc2)nc2ccccn12]

2-Ethyl-N-(4-(trifluoromethoxy)benzyl)imidazo[1,2-a]pyridine-3-carboxamide (59)

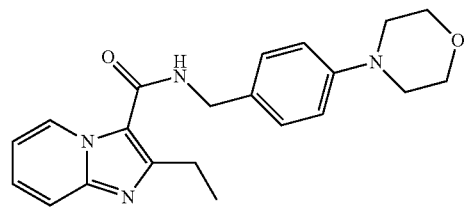 [SMILES: CCc1nc2ccccn2c1C(=O)NCc1ccc(N2CCOCC2)cc1]

2-Ethyl-7-methyl-N-(4-morpholinobenzyl)imidazo[1,2-a]pyridine-3-carboxamide (68)

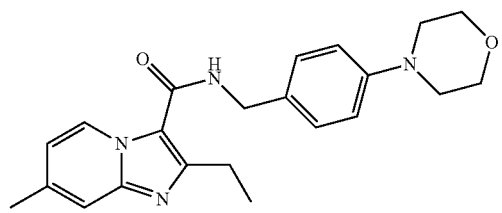 [SMILES: CCc1nc2cc(C)ccn2c1C(=O)NCc1ccc(N2CCOCC2)cc1]

2-Ethyl-7-methyl-N-(naphthalen-2-ylmethyl)imidazo[1,2-a]pyridine-3-carboxamide (69)

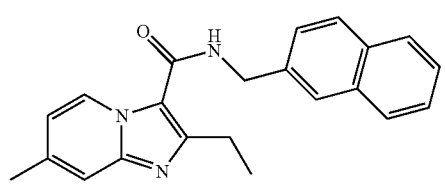 [SMILES: CCc1nc2cc(C)ccn2c1C(=O)NCc1ccc2ccccc2c1]

6-Chloro-2-methyl-N-(4-morpholinobenzyl)imidazo[1,2-a]pyridine-3-carboxamide (74)

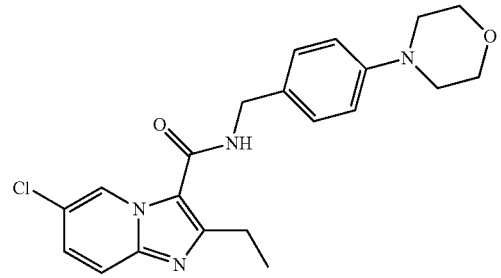 [SMILES: CCc1nc2ccc(Cl)cn2c1C(=O)NCc1ccc(N2CCOCC2)cc1]

6-Chloro-2-ethyl-N-(4-(piperidin-1-yl)benzyl)imidazo[1,2-a]pyridine-3-carboxamide (79)

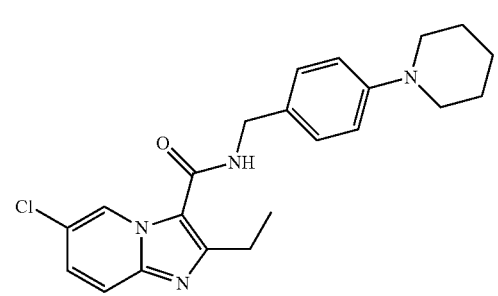 [SMILES: CCc1nc2ccc(Cl)cn2c1C(=O)NCc1ccc(N2CCCCC2)cc1]

6-Chloro-2-ethyl-N-(naphthalen-2-ylmethyl)imidazo[1,2-a]pyridine-3-carboxamide (80)

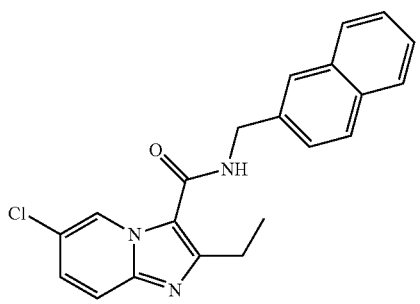 [SMILES: CCc1nc2ccc(Cl)cn2c1C(=O)NCc1ccc2ccccc2c1]

7-Chloro-2-ethyl-N-(4-morpholinobenzyl)imidazo[1,2-a]pyridine-3-carboxamide (89)

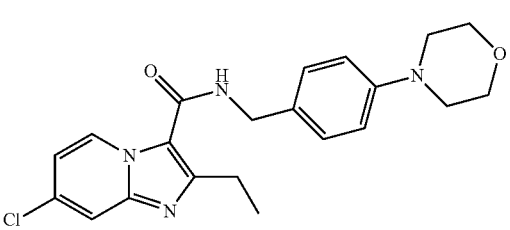 [SMILES: CCc1nc2cc(Cl)ccn2c1C(=O)NCc1ccc(N2CCOCC2)cc1]

7-Chloro-2-ethyl-N-(4-(piperidin-1-yl)benzyl)imidazo[1,2-a]pyridine-3-carboxamide (90)

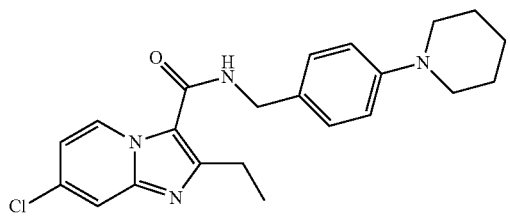 [SMILES: CCc1nc2cc(Cl)ccn2c1C(=O)NCc1ccc(N2CCCCC2)cc1]

7-Chloro-2-ethyl-N-(naphthalen-2-ylmethyl)imidazo[1,2-a]pyridine-3-carboxamide (91)

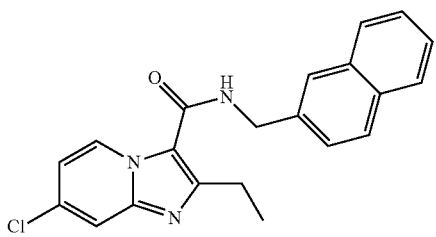 [SMILES: CCc1nc2cc(Cl)ccn2c1C(=O)NCc1ccc2ccccc2c1]

N-(7-Chloro-2-ethylimidazo[1,2-a]pyridin-3-yl)biphenyl-4-carboxamide (142)

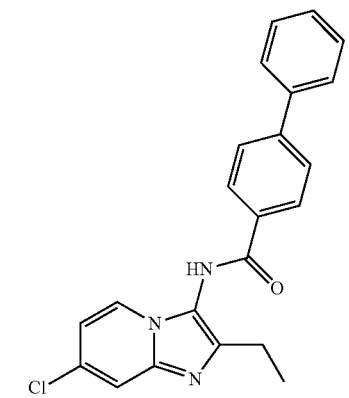 [SMILES: CCc1nc2cc(Cl)ccn2c1NC(=O)c1ccc(-c2ccccc2)cc1]

2-(Biphenyl-4-yl)-N-(7-chloro-2-ethylimidazo[1,2-a]pyridin-3-yl)acetamide (143)

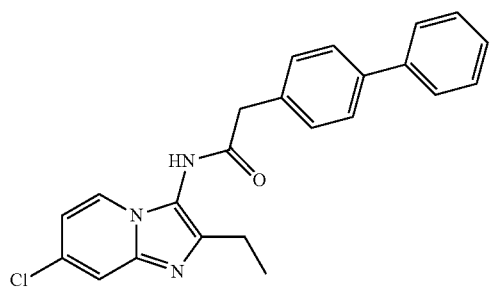 [SMILES: CCc1nc2cc(Cl)ccn2c1NC(=O)Cc1ccc(-c2ccccc2)cc1]

[1,1'-Biphenyl]-4-ylmethyl 6-chloro-2-ethylimidazo[1,2-a]pyridine-3-carboxylate (161)

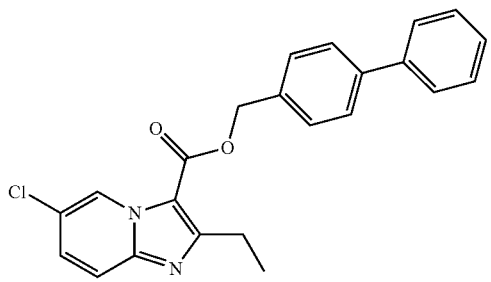 [SMILES: CCc1nc2ccc(Cl)cn2c1C(=O)OCc1ccc(-c2ccccc2)cc1]

4-Phenoxybenzyl 6-chloro-2-ethylimidazo[1,2-a]pyridine-3-carboxylate (196)

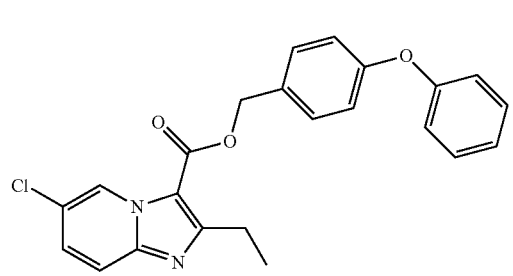 [SMILES: CCc1nc2ccc(Cl)cn2c1C(=O)OCc1ccc(Oc2ccccc2)cc1]

6-Chloro-2-ethyl-N-(4-(pyrrolidin-1-yl)benzyl)imidazo[1,2-a]pyridine-3-carboxamide (211)

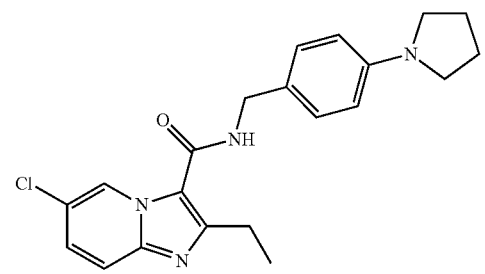 [SMILES: CCc1nc2ccc(Cl)cn2c1C(=O)NCc1ccc(N2CCCC2)cc1]

7-Chloro-2-ethyl-N-(4-(pyrrolidin-1-yl)benzyl)imidazo[1,2-a]pyridine-3-carboxamide (212)

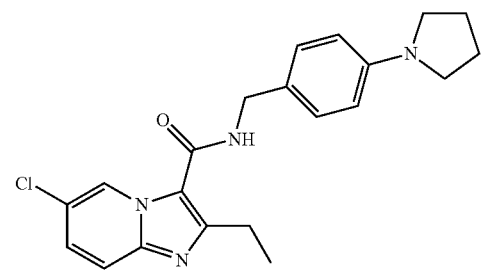 [SMILES: CCc1nc2ccc(Cl)cn2c1C(=O)NCc1ccc(N2CCCC2)cc1]

7-Chloro-N-(4-(5,6-dihydropyridin-1(2H)-yl)benzyl)-2-
ethylimidazo[1,2-a]pyridine-3-carboxamide (213)

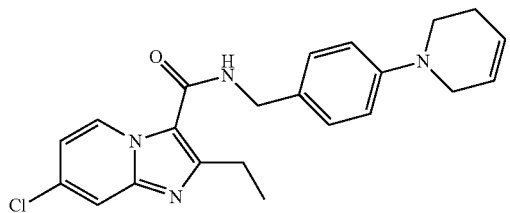

2-ethyl-6-methyl-N-(4-morpholinobenzyl)imidazo[1,2-a]
pyridine-3-carboxamide (219)

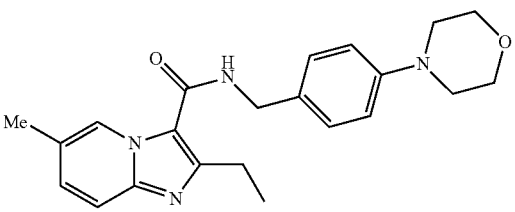 [SMILES: CCc1nc2ccc(C)cn2c1C(=O)NCc1ccc(N2CCOCC2)cc1]

N-(4-(Azepan-1-yl)benzyl)-6-chloro-2-ethylimidazo[1,2-
a]pyridine-3-carboxamide (221)

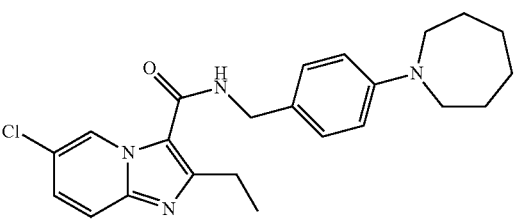 [SMILES: CCc1nc2ccc(Cl)cn2c1C(=O)NCc1ccc(N2CCCCCC2)cc1]

N-(4-(Azepan-1-yl)benzyl)-7-chloro-2-ethylimidazo[1,2-
a]pyridine-3-carboxamide (222)

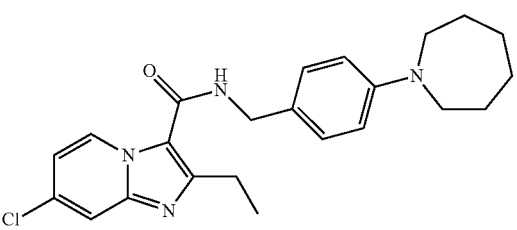 [SMILES: CCc1nc2cc(Cl)ccn2c1C(=O)NCc1ccc(N2CCCCCC2)cc1]

6-Chloro-2-ethyl-3-((4-(trifluoromethoxy)phenoxy)me-
thyl)imidazo[1,2-a]pyridine (239)

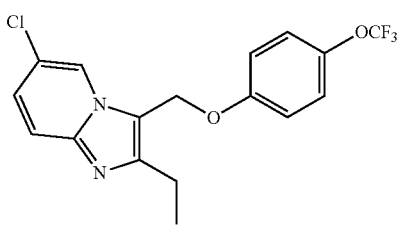 [SMILES: CCc1nc2ccc(Cl)cn2c1COc1ccc(OC(F)(F)F)cc1]

N-((6-Chloro-2-ethylimidazo[1,2-a]pyridin-3-yl)methyl)-
4-(trifluoromethoxy)aniline (240)

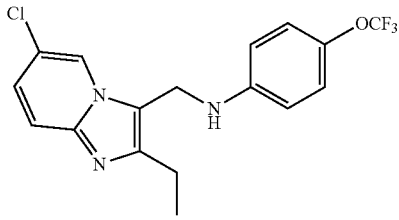 [SMILES: CCc1nc2ccc(Cl)cn2c1CNc1ccc(OC(F)(F)F)cc1]

N-((6-Chloro-2-ethylimidazo[1,2-a]pyridin-3-yl)methyl)-
4-(4-(4-fluorophenyl)piperazin-1-yl)aniline (241)

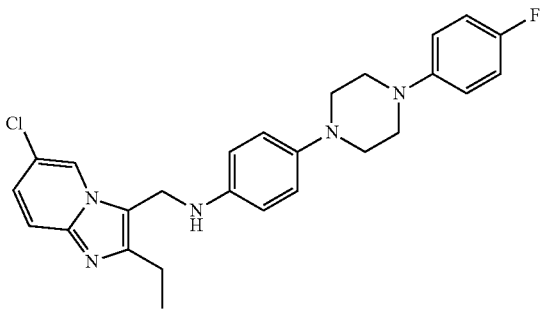 [SMILES: CCc1nc2ccc(Cl)cn2c1CNc1ccc(N2CCN(c3ccc(F)cc3)CC2)cc1]

N-((6-Chloro-2-ethylimidazo[1,2-a]pyridin-3-yl)methyl)-
4-(4-fluorophenoxy)aniline (242)

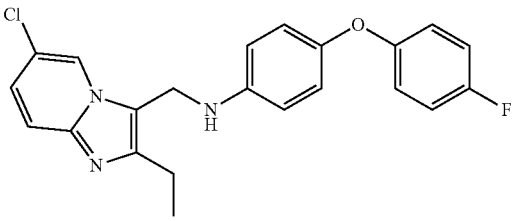 [SMILES: CCc1nc2ccc(Cl)cn2c1CNc1ccc(Oc2ccc(F)cc2)cc1]

5-(6-Chloro-2-ethylimidazo[1,2-a]pyridin-3-yl)-3-(4-(tri-
fluoromethoxy)benzyl)-1,2,4-oxadiazole (243)

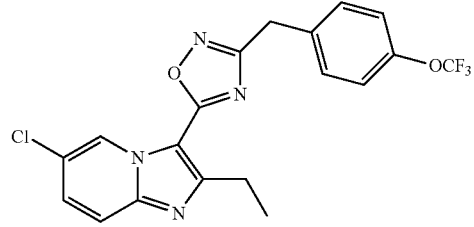 [SMILES: CCc1nc2ccc(Cl)cn2c1-c1nc(Cc2ccc(OC(F)(F)F)cc2)no1]

2-(7-Chloro-2-ethylimidazo[1,2-a]pyridin-3-yl)-5-((4-(4-
(trifluoromethoxy)phenyl)piperazin-1-yl)methyl)-1,3,
4-oxadiazole (244)

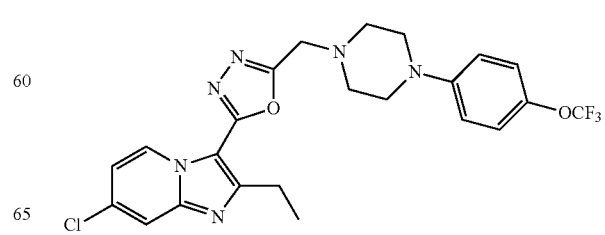

5-(6-Chloro-2-ethylimidazo[1,2-a]pyridin-3-yl)-3-(4-(4-fluorophenoxy)benzyl)-1,2,4-oxadiazole (245)

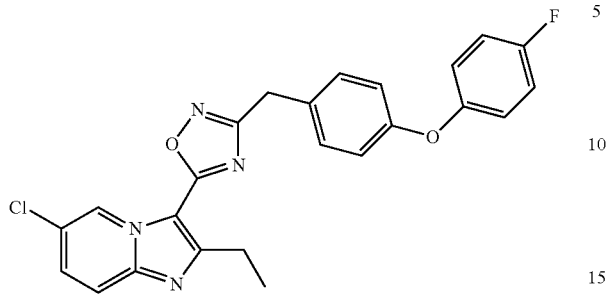

2-Ethyl-6-fluoro-N-(4-morpholinobenzyl)imidazo[1,2-a]pyridine-3-carboxamide (313)

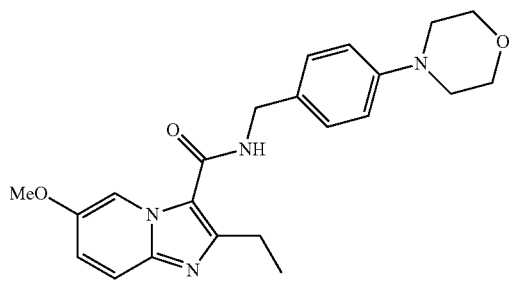

2-Ethyl-7-methoxy-N-(4-morpholinobenzyl)imidazo[1,2-a]pyridine-3-carboxamide (314)

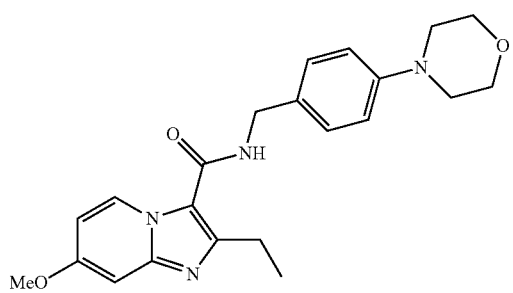

6-Chloro-N,2-diethylimidazo[1,2-a]pyridine-3-carboxamide (246)

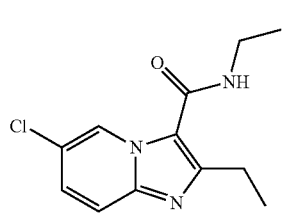 [SMILES: CCNC(=O)c1c(CC)nc2ccc(Cl)cn12]

6-Chloro-2-ethyl-N-isobutylimidazo[1,2-a]pyridine-3-carboxamide (247)

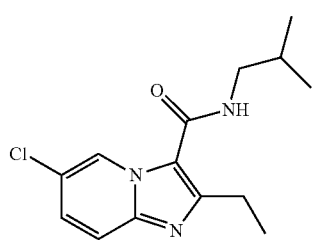 [SMILES: CCc1nc2ccc(Cl)cn2c1C(=O)NCC(C)C]

6-Bromo-2-ethyl-N-(4-morpholinobenzyl)imidazo[1,2-a]pyridine-3-carboxamide (315)

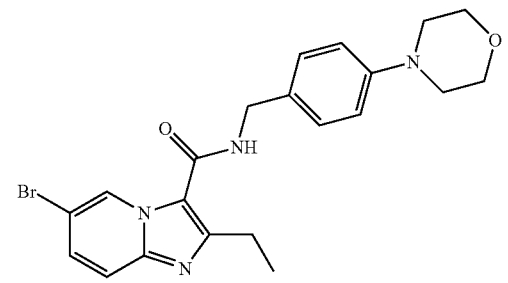

2-Ethyl-6-fluoro-N-(4-morpholinobenzyl)imidazo[1,2-a]pyridine-3-carboxamide (316)

7-Chloro-2-ethyl-N-(4-(4-fluorophenoxy)benzyl)imidazo[1,2-a]pyridine-3-carboxamide (264)

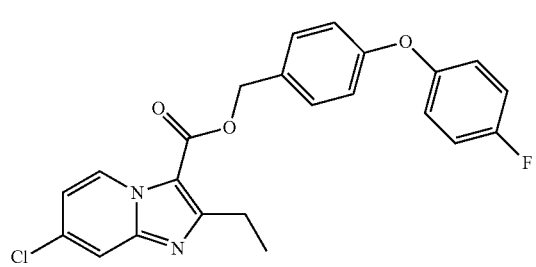 [SMILES: CCc1nc2cc(Cl)ccn2c1C(=O)OCc1ccc(Oc2ccc(F)cc2)cc1]

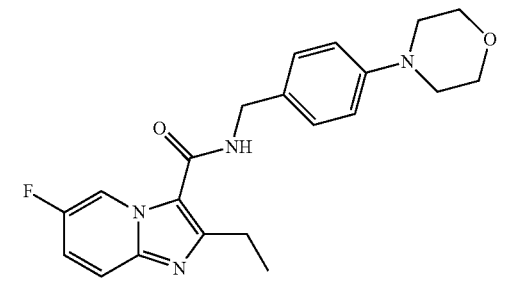 [SMILES: CCc1nc2ccc(F)cn2c1C(=O)NCc1ccc(N2CCOCC2)cc1]

2-Ethyl-8-fluoro-N-(4-morpholinobenzyl)imidazo[1,2-a]pyridine-3-carboxamide (317)

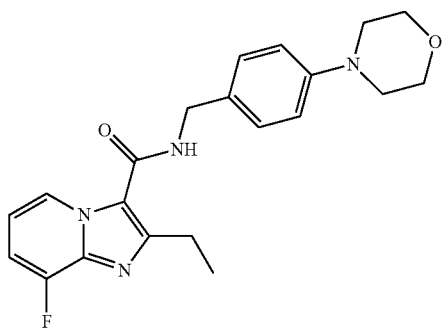 [SMILES: CCc1nc2c(F)cccn2c1C(=O)NCc1ccc(N2CCOCC2)cc1]

2-Ethyl-8-methoxy-N-(4-morpholinobenzyl)imidazo[1,2-a]pyridine-3-carboxamide (318)

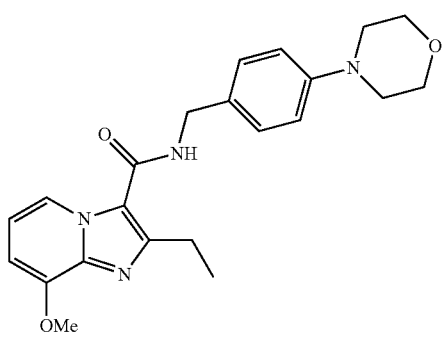 [SMILES: CCc1nc2c(OC)cccn2c1C(=O)NCc1ccc(N2CCOCC2)cc1]

8-(Difluoromethoxy)-2-ethyl-N-(4-morpholinobenzyl)imidazo[1,2-a]pyridine-3-carboxamide (319)

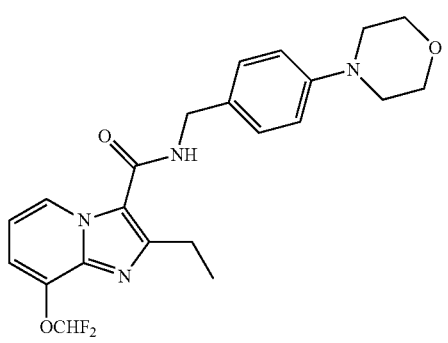 [SMILES: CCc1nc2c(OC(F)F)cccn2c1C(=O)NCc1ccc(N2CCOCC2)cc1]

8-Bromo-2-ethyl-N-(4-morpholinobenzyl)imidazo[1,2-a]pyridine-3-carboxamide (320)

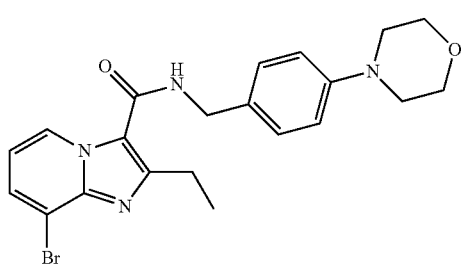 [SMILES: CCc1nc2c(Br)cccn2c1C(=O)NCc1ccc(N2CCOCC2)cc1]

2-Ethyl-N-(4-morpholinobenzyl)-6-(trifluoromethyl)imidazo[1,2-a]pyridine-3-carboxamide (321)

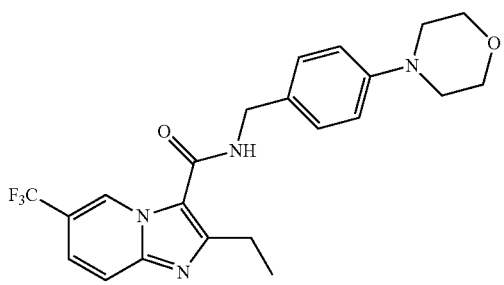 [SMILES: CCc1nc2ccc(C(F)(F)F)cn2c1C(=O)NCc1ccc(N2CCOCC2)cc1]

2-Ethyl-N-(4-morpholinobenzyl)-7-(trifluoromethyl)imidazo[1,2-a]pyridine-3-carboxamide (322)

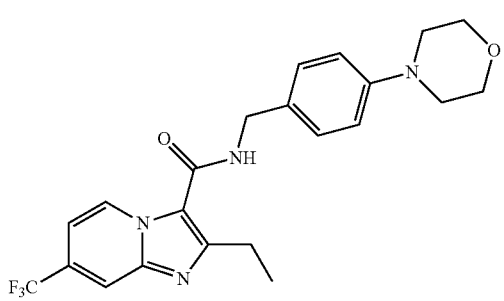 [SMILES: CCc1nc2cc(C(F)(F)F)ccn2c1C(=O)NCc1ccc(N2CCOCC2)cc1]

2-Ethyl-N-(4-morpholinobenzyl)-8-(trifluoromethyl)imidazo[1,2-a]pyridine-3-carboxamide (323)

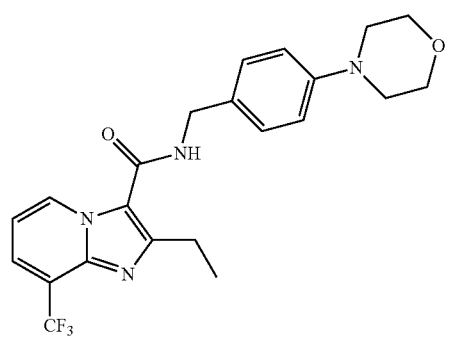 [SMILES: CCc1nc2c(C(F)(F)F)cccn2c1C(=O)NCc1ccc(N2CCOCC2)cc1]

7-Bromo-2-ethyl-N-(4-morpholinobenzyl)imidazo[1,2-a]pyridine-3-carboxamide (324)

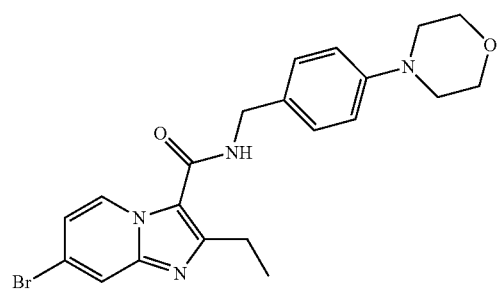 [SMILES: CCc1nc2cc(Br)ccn2c1C(=O)NCc1ccc(N2CCOCC2)cc1]

303

2-Ethyl-N-(4-morpholinobenzyl)-7-(pyridin-4-yl)imi-
dazo[1,2-a]pyridine-3-carboxamide (325)

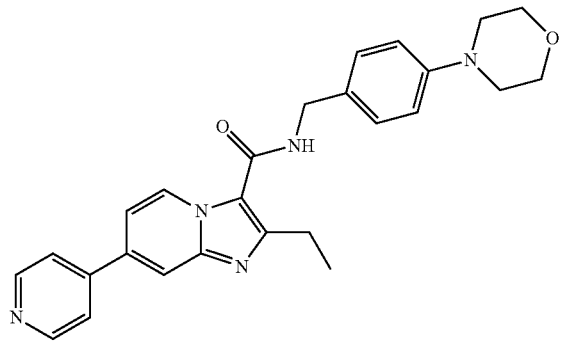 [SMILES: CCc1nc2cc(-c3ccncc3)ccn2c1C(=O)NCc1ccc(N2CCOCC2)cc1]

2-Ethyl-N-(4-morpholinobenzyl)-7-(pyridin-3-yl)imi-
dazo[1,2-a]pyridine-3-carboxamide (326)

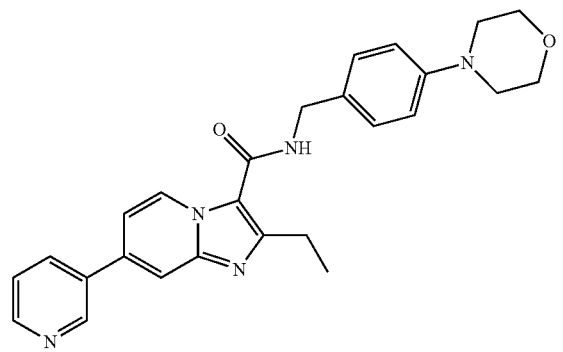 [SMILES: CCc1nc2cc(-c3cccnc3)ccn2c1C(=O)NCc1ccc(N2CCOCC2)cc1]

2-Ethyl-N-(4-morpholinobenzyl)-8-(pyridin-4-yl)imi-
dazo[1,2-a]pyridine-3-carboxamide (327)

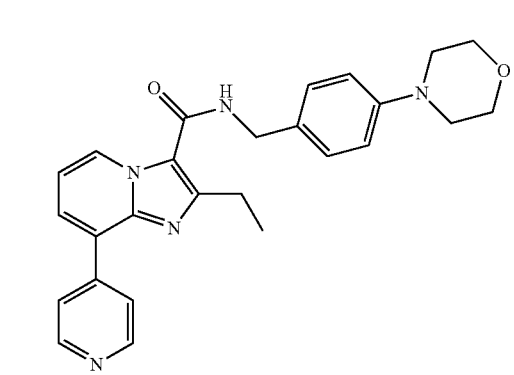 [SMILES: CCc1nc2c(-c3ccncc3)cccn2c1C(=O)NCc1ccc(N2CCOCC2)cc1]

2-Ethyl-7-(4-methylpiperazin-1-yl)-N-(4-morpholi-
nobenzyl)imidazo[1,2-a]pyridine-3-carboxamide (328)

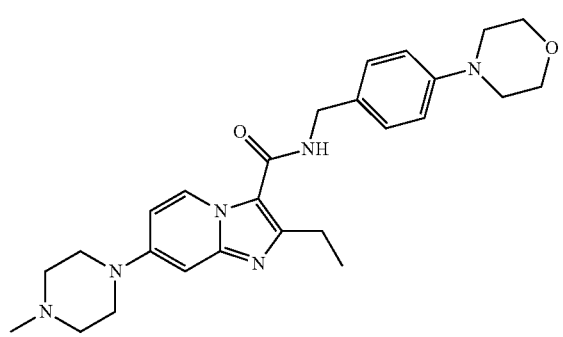 [SMILES: CCc1nc2cc(N3CCN(C)CC3)ccn2c1C(=O)NCc1ccc(N2CCOCC2)cc1]

304

2-Ethyl-7-(4-(4-fluorophenyl)piperazin-1-yl)-N-(4-mor-
pholinobenzyl)imidazo[1,2-a]pyridine-3-carboxamide
(329)

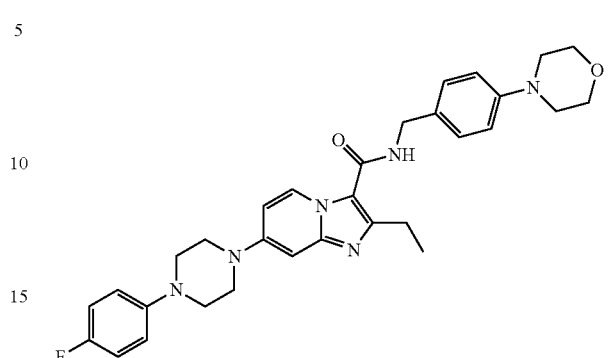

2-Ethyl-7-(4-(4-fluorobenzyl)piperazin-1-yl)-N-(4-mor-
pholinobenzyl)imidazo[1,2-a]pyridine-3-carboxamide
(331)

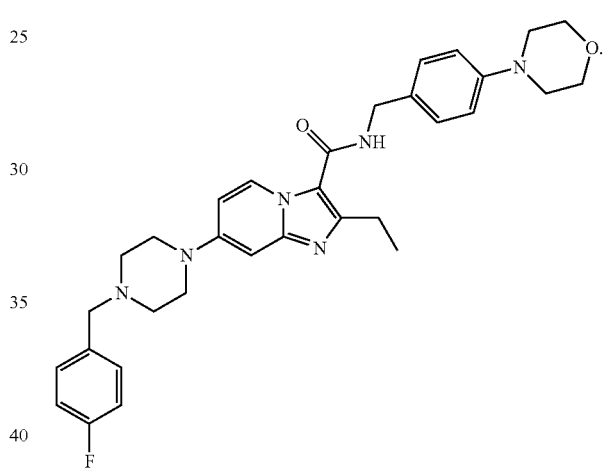

2. A compound having the general formula Ib:

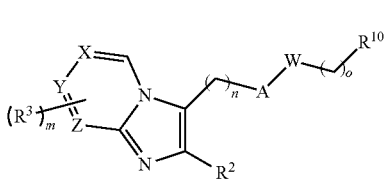

wherein
  o is 0, 1, 2, or 3;
  n is 0;
  m is 1, 2, 3 or 4;
  X, Y and Z are CH;
  A is C=O or C=S
  W is $NR^{11}$;
  $R^2$ is, at each occurrence, independently selected from the
    group consisting of hydrogen, halogen, $C_1$-$C_{10}$ alkyl,
    $C_3$-$C_{10}$ cycloalkyl, $C_2$-$C_{10}$ alkenyl, $C_3$-$C_{10}$ cycloalk-
    enyl, $C_2$-$C_{10}$ alkynyl, $C_1$-$C_{10}$ haloalkyl, —OH, —OR$^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, —CN, —NO$_2$, —NH$_2$, —N(R$^5$)$_2$, —C(O)R$^5$, —C(O)OR$^5$, —C(O)N(R$^5$)$_2$, —SR$^5$, —S(O)R$^5$, —S(O)$_2$R$^5$, —S(O)$_2$N(R$^5$)$_2$, aryl, benzyl, and heterocyclyl, any of which is optionally substituted;

R$^3$ is, at each occurrence, independently selected from the group consisting of hydrogen, halogen, $C_1$-$C_{10}$ alkyl, $C_3$-$C_{10}$ cycloalkyl, hydroxyl, —OR$^6$, —CN, —NO$_2$, —NH$_2$, —N(R$^6$)C(O)R$^6$, —C(O)R$^6$, —C(O)OR$^6$, —C(O)N(R$^6$)$_2$, —S(O)R$^6$, —S(O)$_2$R$^6$, —S(O)$_2$N(R$^6$)$_2$, aryl, benzyl, heteroaryl, heterocyclyl, any of which is optionally substituted, or two groups of R$^3$ are connected to each other to make a five or six membered cyclic or heterocyclic ring, any of which is optionally substituted;

R$^5$ and R$^6$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted;

R$^{10}$ is a moiety selected from the group consisting of

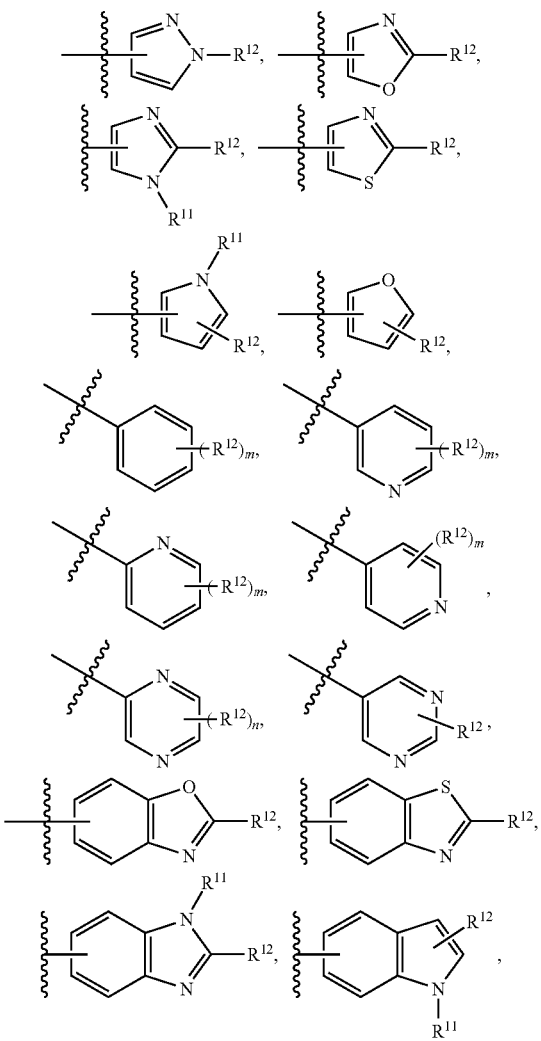

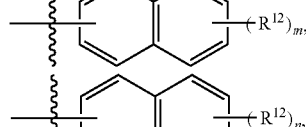

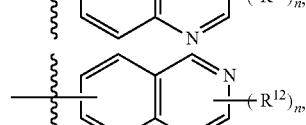

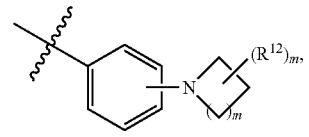

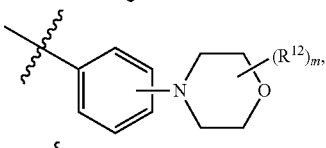

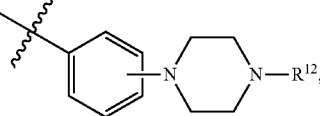

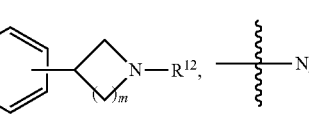

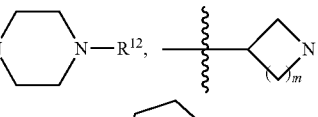

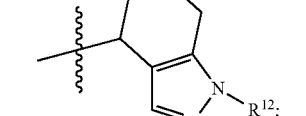

R$^{11}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, —OH, —OR$^{13}$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, —NH$_2$, —N(R$^{13}$)$_2$, —C(O)R$^{13}$, —C(O)OR$^{13}$, —C(O)N(R$^{13}$)$_2$, —S(O)R$^{13}$, —S(O)$_2$R$^{13}$, —S(O)$_2$N(R$^{13}$)$_2$, aryl, benzyl, heteroaryl, and heterocyclyl, any of which is optionally substituted;

R$^{12}$ is, at each occurrence, independently selected from the group consisting of $C_2$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, hydroxyl, —OR$^{14}$, —C(O)R$^{14}$, —C(O)OR$^{14}$, —CN, —NO$_2$, —NH$_2$, —N(R$^{14}$)$_2$, —C(O)N(R$^{14}$)$_2$, —S(O)R$^{14}$, —S(O)$_2$R$^{14}$, —S(O)$_2$N(R$^{14}$)$_2$, aryl, benzyl, heteroaryl, and heterocyclyl, any of which is optionally substituted;

R$^{13}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, C₂-C₁₀ alkynyl, C₁-C₁₀ haloalkyl, aryl, benzyl, heteroaryl, and heterocyclyl, any of which is optionally substituted; and R¹⁴ is, at each occurrence, independently selected from the group consisting of hydrogen, C₁-C₈ alkyl optionally substituted with at least one hydroxyl or halogen; C₃-C₇ cycloalkyl, C₂-C₁₀ alkenyl, C₃-C₁₀ cycloalkenyl, C₂-C₁₀ alkynyl, C₁-C₁₀ haloalkyl, aryl, benzyl, heteroaryl and heterocyclyl, any of which is optionally substituted, and pharmaceutically acceptable salts thereof.

3. The compound according to claim 2, having a formula selected from the following formulae 6, 7, 9-12, 15, 16, 19, 22, 44, 45, 47, 49, 52, 54-58, 60-67, 70-73, 75-78, 81-88, 92-141, 144-160, 162-195, 197-210, 214-218, 220, 223-238, 248-263, 265-312, 330 and 332-352:

2-Methyl-N-(4-phenoxyphenyl)imidazo[1,2-a]pyridine-3-carboxamide (6)

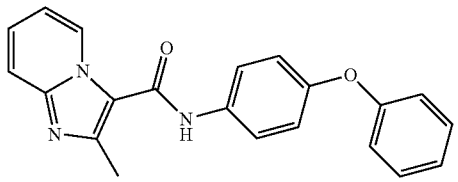 [SMILES: Cc1nc2ccccn2c1C(=O)Nc1ccc(Oc2ccccc2)cc1]

N-(4-(Benzyloxy)phenyl)-2-methylimidazo[1,2-a]pyridine-3-carboxamide (7)

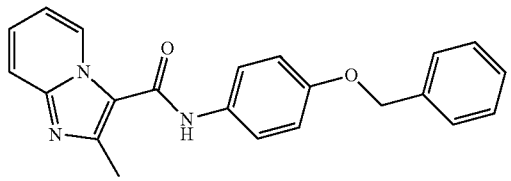 [SMILES: Cc1nc2ccccn2c1C(=O)Nc1ccc(OCc2ccccc2)cc1]

N-(4-Fluorobenzyl)-2-methylimidazo[1,2-a]pyridine-3-carboxamide (9)

Methyl 4-((2-me3thylimidazo[1,2-a]pyridine-3-carboxamido)methyl)benzoate (10)

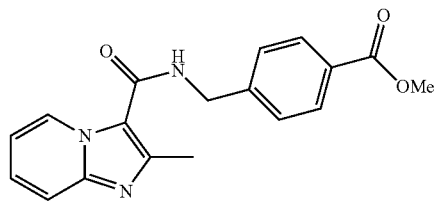 [SMILES: COC(=O)c1ccc(CNC(=O)c2c(C)nc3ccccn23)cc1]

4-((2-Methylimidazo[1,2-a]pyridine-3-carboxamido)methyl)benzoic acid (11)

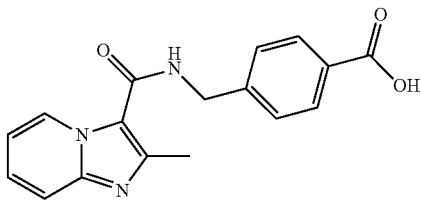 [SMILES: Cc1nc2ccccn2c1C(=O)NCc1ccc(C(=O)O)cc1]

N-(4-Methoxybenzyl)-2-methylimidazo[1,2-a]pyridine-3-carboxamide (12)

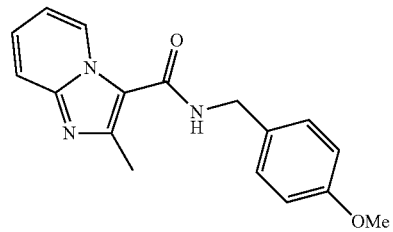 [SMILES: COc1ccc(CNC(=O)c2c(C)nc3ccccn23)cc1]

2-Methyl-N-(4-phenoxybenzyl)imidazo[1,2-a]pyridine-3-carboxamide (15)

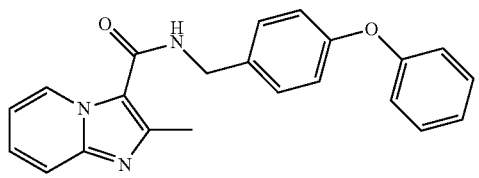 [SMILES: Cc1nc2ccccn2c1C(=O)NCc1ccc(Oc2ccccc2)cc1]

N-(Biphenyl-4-ylmethyl)-2-methylimidazo[1,2-a]pyridine-3-carboxamide (16)

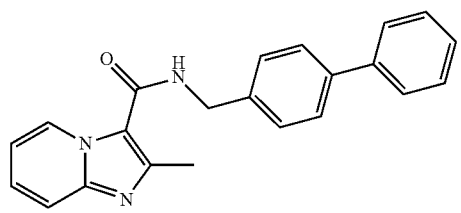 [SMILES: Cc1nc2ccccn2c1C(=O)NCc1ccc(-c2ccccc2)cc1]

tert-Butyl 4-((2-methylimidazo[1,2-a]pyridine-3-carboxamido)methyl)piperidine-1-carboxylate (19)

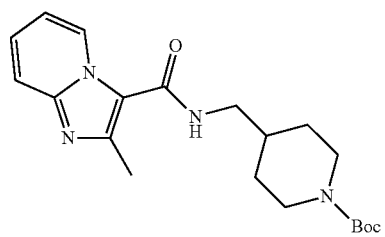 [SMILES: Cc1nc2ccccn2c1C(=O)NCC1CCN(C(=O)OC(C)(C)C)CC1]

N-(4-Methoxyphenethyl)-2-methylimidazo[1,2-a]pyridine-3-carboxamide (22)

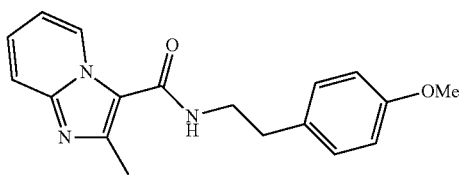 [SMILES: COc1ccc(CCNC(=O)c2c(C)nc3ccccn23)cc1]

N-(Biphenyl-4-ylmethyl)-6-chloro-2-methylimidazo[1,2-a]pyridine-3-carboxamide (44)

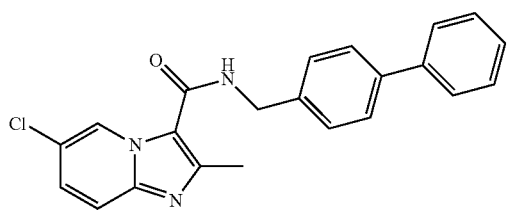 [SMILES: Cc1nc2ccc(Cl)cn2c1C(=O)NCc1ccc(-c2ccccc2)cc1]

N-(Biphenyl-4-ylmethyl)-7-chloro-2-methylimidazo[1,2-a]pyridine-3-carboxamide (45)

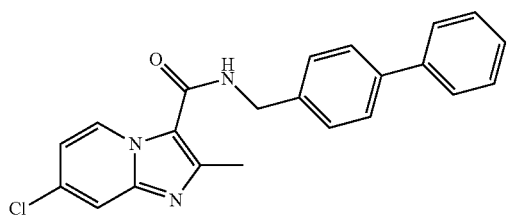

N-(Biphenyl-4-ylmethyl)-2-ethylimidazo[1,2-a]pyridine-3-carboxamide (47)

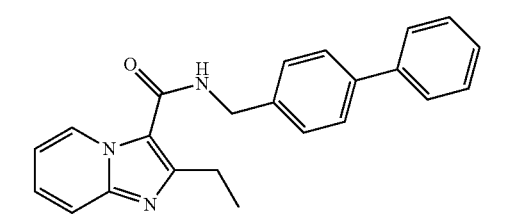

N-(Biphenyl-4-ylmethyl)-2-propylimidazo[1,2-a]pyridine-3-carboxamide (49)

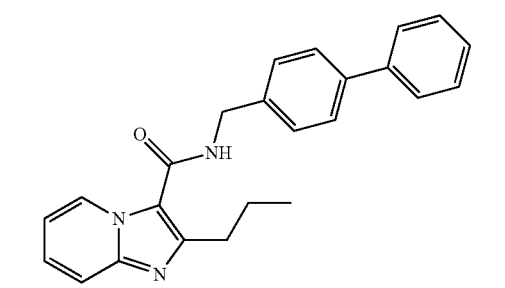 [SMILES: CCCc1nc2ccccn2c1C(=O)NCc1ccc(-c2ccccc2)cc1]

N-(Biphenyl-4-ylmethyl)-2-isopropylimidazo[1,2-a]pyridine-3-carboxamide (52)

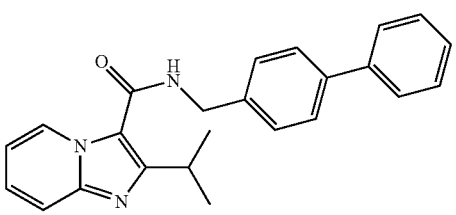 [SMILES: CC(C)c1nc2ccccn2c1C(=O)NCc1ccc(-c2ccccc2)cc1]

2-Ethyl-N-(4-phenoxybenzyl)imidazo[1,2-a]pyridine-3-carboxamide (54)

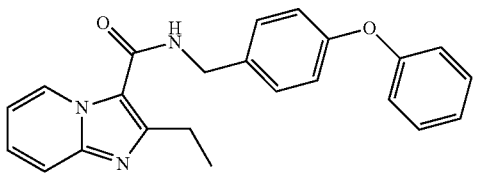 [SMILES: CCc1nc2ccccn2c1C(=O)NCc1ccc(Oc2ccccc2)cc1]

N-(4-tert-Butylbenzyl)-2-ethylimidazo[1,2-a]pyridine-3-carboxamide (55)

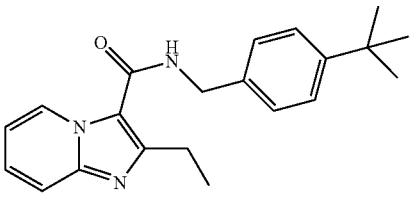 [SMILES: CCc1nc2ccccn2c1C(=O)NCc1ccc(C(C)(C)C)cc1]

2-Ethyl-N-((1-methyl-1H-indol-5-yl)methyl)imidazo[1,2-a]pyridine-3-carboxamide (56)

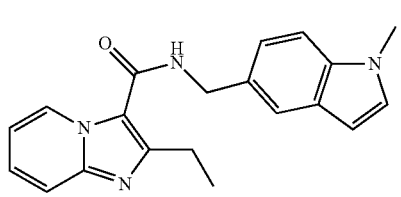 [SMILES: CCc1nc2ccccn2c1C(=O)NCc1ccc2c(ccn2C)c1]

2-Ethyl-N-(4-(trifluoromethoxy)benzyl)imidazo[1,2-a]pyridine-3-carboxamide (57)

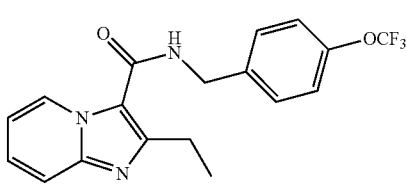 [SMILES: CCc1nc2ccccn2c1C(=O)NCc1ccc(OC(F)(F)F)cc1]

2-Ethyl-N-((1-methyl-1H-indol-6-yl)methyl)imidazo[1,2-a]pyridine-3-carboxamide (58)

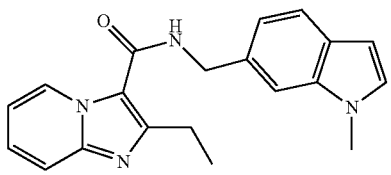 [SMILES: CCc1nc2ccccn2c1C(=O)NCc1ccc2ccn(C)c2c1]

2-Ethyl-N-(4-isopropoxybenzyl)imidazo[1,2-a]pyridine-3-carboxamide (60)

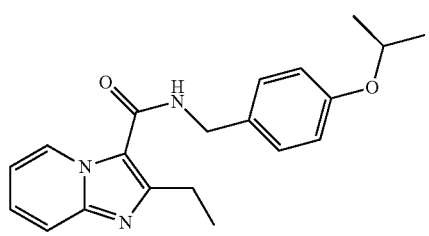 [SMILES: CCc1nc2ccccn2c1C(=O)NCc1ccc(OC(C)C)cc1]

2-Ethyl-N-(4-isobutoxybenzyl)imidazo[1,2-a]pyridine-3-carboxamide (61)

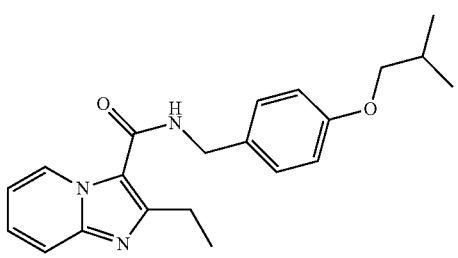 [SMILES: CCc1nc2ccccn2c1C(=O)NCc1ccc(OCC(C)C)cc1]

N-(Biphenyl-4-ylmethyl)-2-ethyl-6-methylimidazo[1,2-a]pyridine-3-carboxamide (62)

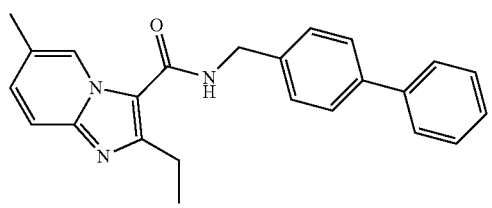 [SMILES: CCc1nc2ccc(C)cn2c1C(=O)NCc1ccc(-c2ccccc2)cc1]

2-Ethyl-6-methyl-N-(4-phenoxybenzyl)imidazo[1,2-a]pyridine-3-carboxamide (63)

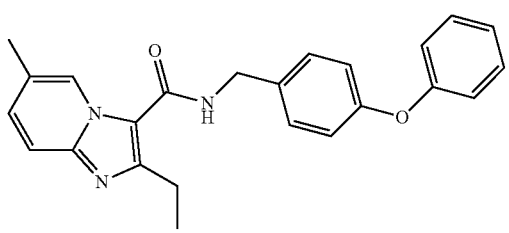 [SMILES: CCc1nc2ccc(C)cn2c1C(=O)NCc1ccc(Oc2ccccc2)cc1]

N-(4-tert-Butylbenzyl)-2-ethyl-6-methylimidazo[1,2-a]pyridine-3-carboxamide (64)

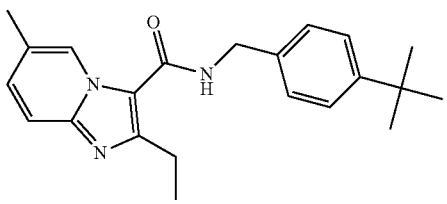 [SMILES: CCc1nc2ccc(C)cn2c1C(=O)NCc1ccc(C(C)(C)C)cc1]

2-Ethyl-6-methyl-N-(4-(trifluoromethoxy)benzyl)imidazo[1,2-a]pyridine-3-carboxamide (65)

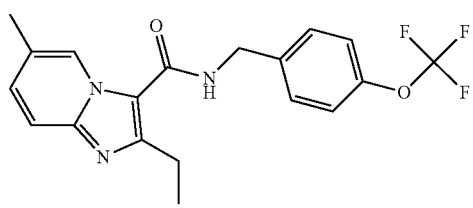 [SMILES: CCc1nc2ccc(C)cn2c1C(=O)NCc1ccc(OC(F)(F)F)cc1]

2-Ethyl-6-methyl-N-((1-methyl-1H-indol-5-yl)methyl)imidazo[1,2-a]pyridine-3-carboxamide (66)

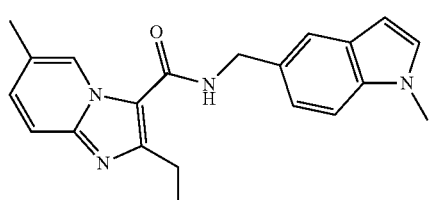

2-Ethyl-6-methyl-N-((1-methyl-1H-indol-6-yl)methyl)imidazo[1,2-a]pyridine-3-carboxamide (67)

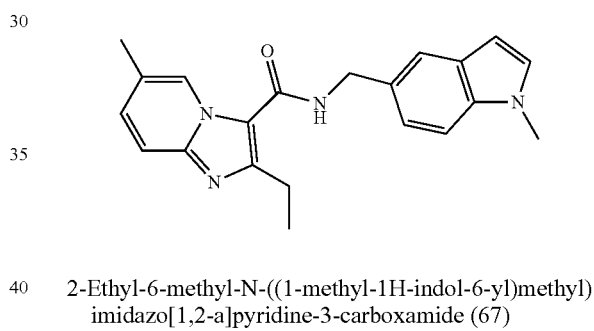

6-Chloro-N-(4-chlorobenzyl)-2-ethylimidazo[1,2-a]pyridine-3-carboxamide (70)

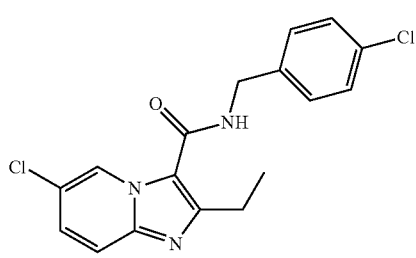 [SMILES: CCc1nc2ccc(Cl)cn2c1C(=O)NCc1ccc(Cl)cc1]

6-Chloro-2-methyl-N-(4-phenoxybenzyl)imidazo[1,2-a]
pyridine-3-carboxamide (71)

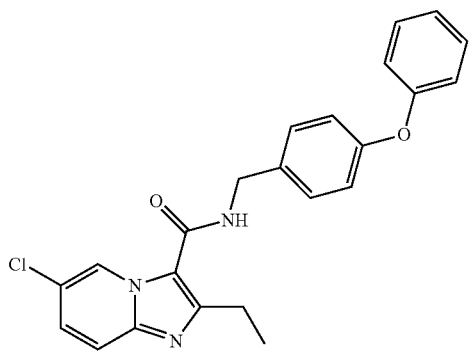 [SMILES: CCc1nc2ccc(Cl)cn2c1C(=O)NCc1ccc(Oc2ccccc2)cc1]

6-Chloro-2-methyl-N-(4-(trifluoromethoxy)benzyl)imi-
dazo[1,2-a]pyridine-3-carboxamide (72)

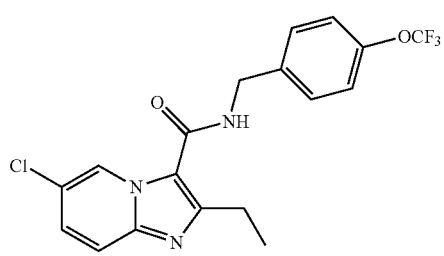 [SMILES: CCc1nc2ccc(Cl)cn2c1C(=O)NCc1ccc(OC(F)(F)F)cc1]

N-(4-tert-Butylbenzyl)-6-chloro-2-methylimidazo[1,2-a]
pyridine-3-carboxamide (73)

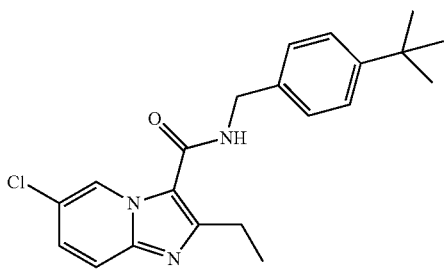 [SMILES: CCc1nc2ccc(Cl)cn2c1C(=O)NCc1ccc(C(C)(C)C)cc1]

6-Chloro-N-(4-isopropoxybenzyl)-2-methylimidazo[1,2-
a]pyridine-3-carboxamide (75)

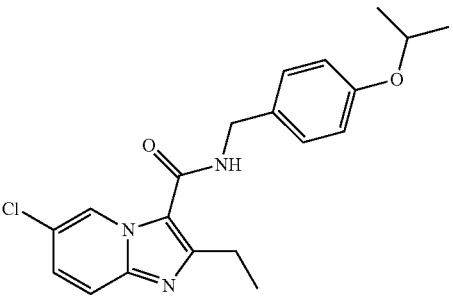 [SMILES: CCc1nc2ccc(Cl)cn2c1C(=O)NCc1ccc(OC(C)C)cc1]

6-Chloro-N-(4-isobutoxybenzyl)-2-methylimidazo[1,2-a]
pyridine-3-carboxamide (76)

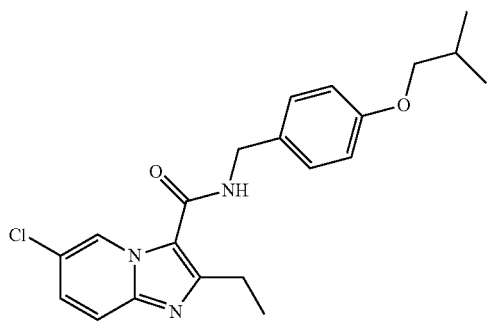 [SMILES: CCc1nc2ccc(Cl)cn2c1C(=O)NCc1ccc(OCC(C)C)cc1]

6-Chloro-2-methyl-N-((1-methyl-1H-indol-5-yl)methyl)
imidazo[1,2-a]pyridine-3-carboxamide (77)

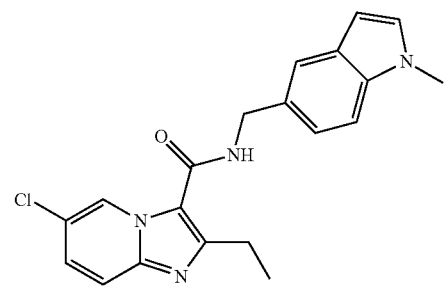 [SMILES: CCc1nc2ccc(Cl)cn2c1C(=O)NCc1ccc2c(ccn2C)c1]

6-Chloro-2-methyl-N-((1-methyl-1H-indol-6-yl)methyl)
imidazo[1,2-a]pyridine-3-carboxamide (78)

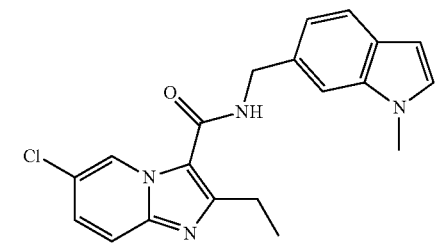 [SMILES: CCc1nc2ccc(Cl)cn2c1C(=O)NCc1ccc2ccn(C)c2c1]

N-(Biphenyl-4-ylmethyl)-6-chloro-2-methylimidazo[1,2-
a]pyridine-3-carboxamide (81)

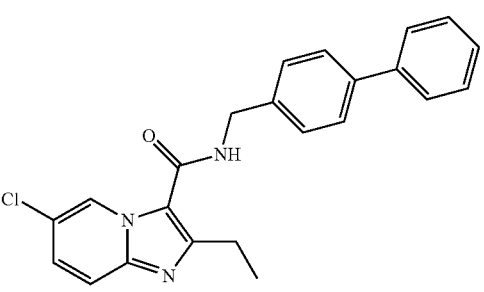 [SMILES: CCc1nc2ccc(Cl)cn2c1C(=O)NCc1ccc(-c2ccccc2)cc1]

315

6-Chloro-N-((2'-chlorobiphenyl-4-yl)methyl)-2-ethylimidazo[1,2-a]pyridine-3-carboxamide (82)

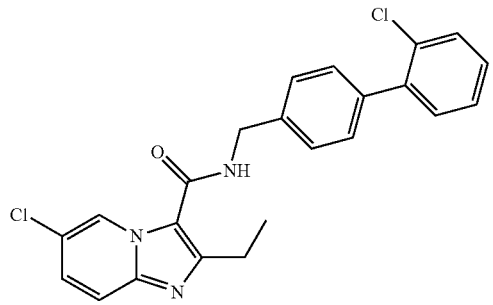

6-Chloro-N-((4'-chlorobiphenyl-4-yl)methyl)-2-ethylimidazo[1,2-a]pyridine-3-carboxamide (83)

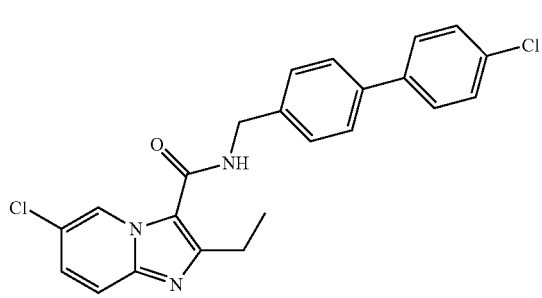 [SMILES: CCc1nc2ccc(Cl)cn2c1C(=O)NCc1ccc(-c2ccc(Cl)cc2)cc1]

6-Chloro-2-ethyl-N-((2'-methylbiphenyl-4-yl)methyl)imidazo[1,2-a]pyridine-3-carboxamide (84)

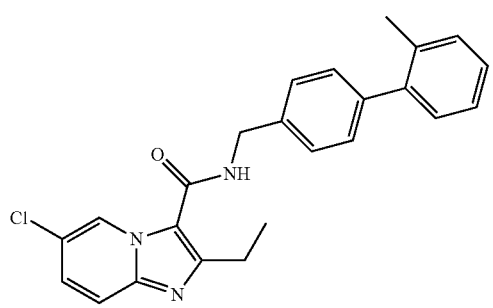 [SMILES: CCc1nc2ccc(Cl)cn2c1C(=O)NCc1ccc(-c2ccccc2C)cc1]

6-Chloro-2-ethyl-N-((3'-methylbiphenyl-4-yl)methyl)imidazo[1,2-a]pyridine-3-carboxamide (85)

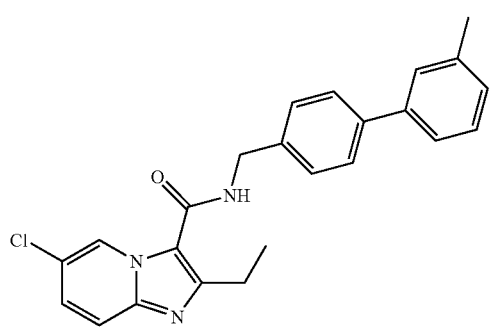 [SMILES: CCc1nc2ccc(Cl)cn2c1C(=O)NCc1ccc(-c2cccc(C)c2)cc1]

316

6-Chloro-2-ethyl-N-((4'-methylbiphenyl-4-yl)methyl)imidazo[1,2-a]pyridine-3-carboxamide (86)

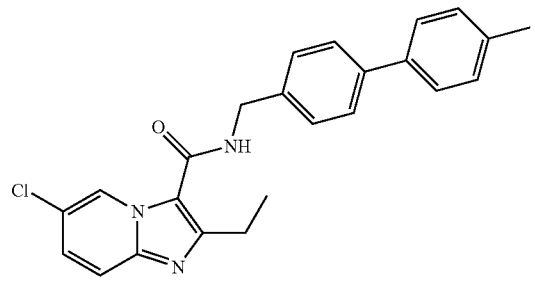 [SMILES: CCc1nc2ccc(Cl)cn2c1C(=O)NCc1ccc(-c2ccc(C)cc2)cc1]

7-Chloro-N-(4-chlorobenzyl)-2-ethylimidazo[1,2-a]pyridine-3-carboxamide (87)

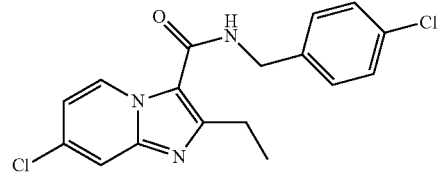

7-Chloro-2-ethyl-N-(4-hydroxybenzyl)imidazo[1,2-a]pyridine-3-carboxamide (88)

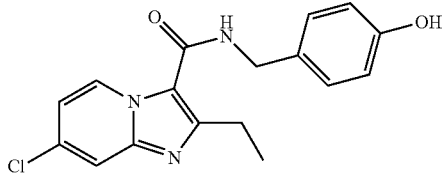 [SMILES: CCc1nc2cc(Cl)ccn2c1C(=O)NCc1ccc(O)cc1]

N-(4-tert-Butylbenzyl)-7-chloro-2-ethylimidazo[1,2-a]pyridine-3-carboxamide (92)

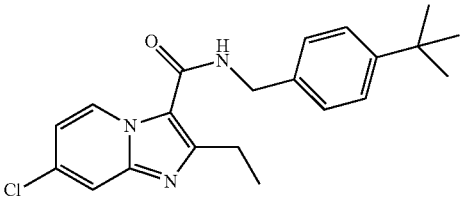 [SMILES: CCc1nc2cc(Cl)ccn2c1C(=O)NCc1ccc(C(C)(C)C)cc1]

N-(Biphenyl-4-ylmethyl)-7-chloro-2-ethylimidazo[1,2-a]pyridine-3-carboxamide (93)

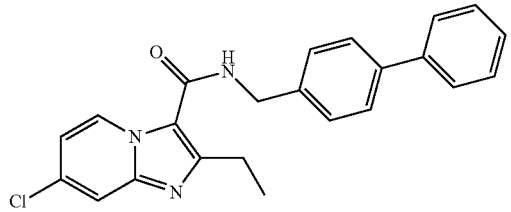 [SMILES: CCc1nc2cc(Cl)ccn2c1C(=O)NCc1ccc(-c2ccccc2)cc1]

7-Chloro-N-((2'-chlorobiphenyl-4-yl)methyl)-2-ethylimidazo[1,2-a]pyridine-3-carboxamide N-(Biphenyl-4-ylmethyl)-6-chloro-2-(trifluoromethyl)imidazo[1,2-a]pyridine-3-carboxamide (99)

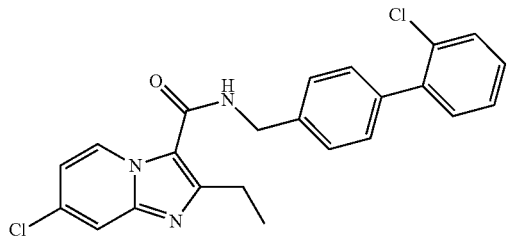

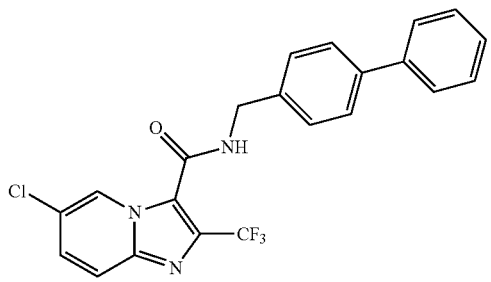

7-Chloro-N-((4'-chlorobiphenyl-4-yl)methyl)-2-ethylimidazo[1,2-a]pyridine-3-carboxamide (95)

N-(4-tert-Butylbenzyl)-6-chloro-2-(trifluoromethyl)imidazo[1,2-a]pyridine-3-carboxamide (100)

7-Chloro-2-ethyl-N-((2'-methylbiphenyl-4-yl)methyl)imidazo[1,2-a]pyridine-3-carboxamide (96)

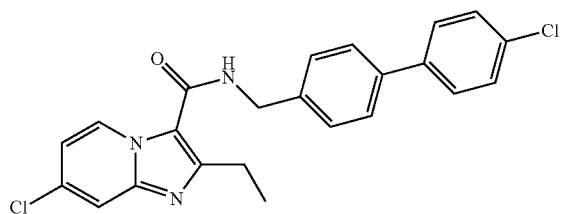 [SMILES: CCc1nc2cc(Cl)ccn2c1C(=O)NCc1ccc(-c2ccc(Cl)cc2)cc1]

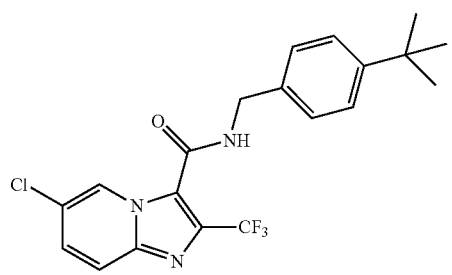 [SMILES: CC(C)(C)c1ccc(CNC(=O)c2c(C(F)(F)F)nc3ccc(Cl)cn23)cc1]

N-(4-Bromobenzyl)-7-chloro-2-ethylimidazo[1,2-a]pyridine-3-carboxamide (101)

7-Chloro-2-ethyl-N-((3'-methylbiphenyl-4-yl)methyl)imidazo[1,2-a]pyridine-3-carboxamide (97)

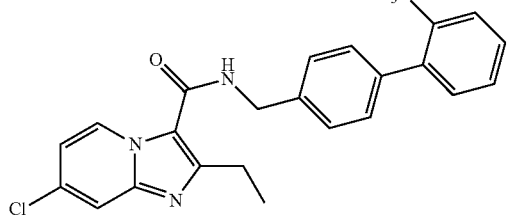

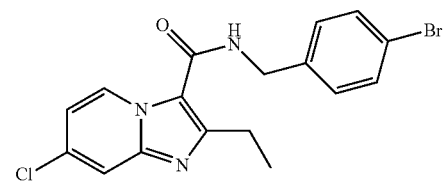 [SMILES: CCc1nc2cc(Cl)ccn2c1C(=O)NCc1ccc(Br)cc1]

7-Chloro-2-ethyl-N-(4-(trifluoromethoxy)benzyl)imidazo[1,2-a]pyridine-3-carboxamide (102)

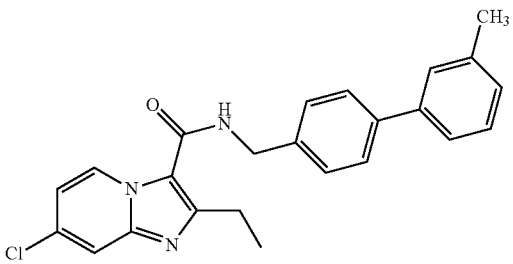

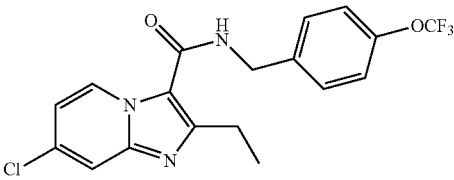 [SMILES: CCc1nc2cc(Cl)ccn2c1C(=O)NCc1ccc(OC(F)(F)F)cc1]

7-Chloro-2-ethyl-N-((4'-methylbiphenyl-4-yl)methyl)imidazo[1,2-a]pyridine-3-carboxamide (98)

2-Ethyl-6-fluoro-N-(4-(trifluoromethoxy)benzyl)imidazo[1,2-a]pyridine-3-carboxamide (103)

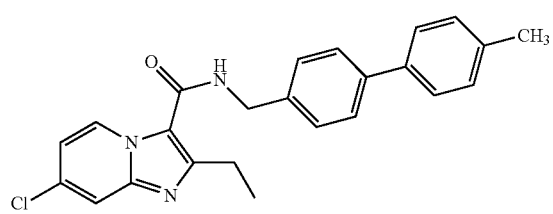

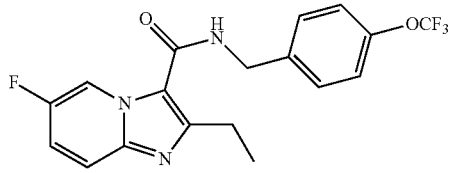 [SMILES: CCc1nc2ccc(F)cn2c1C(=O)NCc1ccc(OC(F)(F)F)cc1]

2-Ethyl-7-methoxy-N-(4-(trifluoromethoxy)benzyl)imi-
dazo[1,2-a]pyridine-3-carboxamide (104)

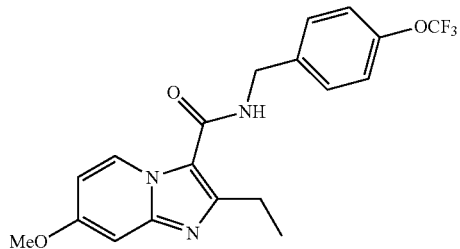 [SMILES: CCc1nc2cc(OC)ccn2c1C(=O)NCc1ccc(OC(F)(F)F)cc1]

2-Ethyl-7-hydroxy-N-(4-(trifluoromethoxy)benzyl)imi-
dazo[1,2-a]pyridine-3-carboxamide (105)

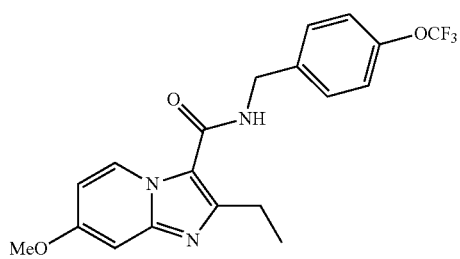 [SMILES: CCc1nc2cc(OC)ccn2c1C(=O)NCc1ccc(OC(F)(F)F)cc1]

7-Chloro-2-ethyl-N-(4-(propylamino)benzyl)imidazo[1,
2-a]pyridine-3-carboxamide (106)

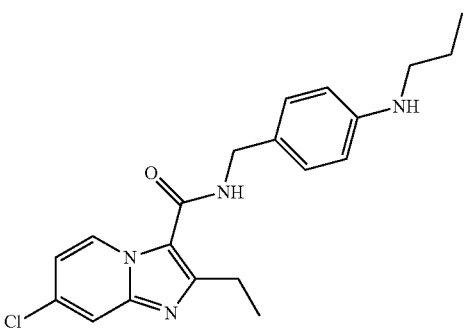 [SMILES: CCCNc1ccc(CNC(=O)c2c(CC)nc3cc(Cl)ccn23)cc1]

7-Chloro-2-ethyl-N-(4-(pentylamino)benzyl)imidazo[1,
2-a]pyridine-3-carboxamide (107)

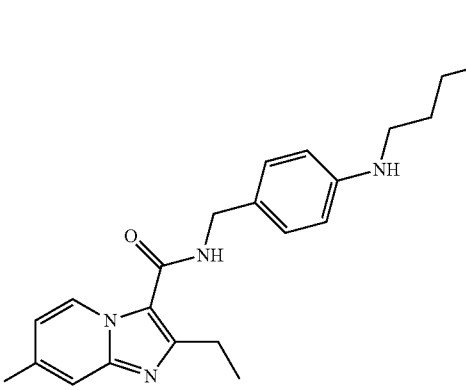

6-Chloro-2-ethyl-N-(4-(4-methylpiperazin-1-yl)benzyl)
imidazo[1,2-a]pyridine-3-carboxamide (108)

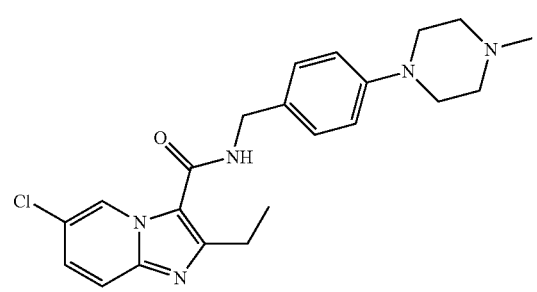 [SMILES: CCc1nc2ccc(Cl)cn2c1C(=O)NCc1ccc(N2CCN(C)CC2)cc1]

7-Chloro-2-ethyl-N-(4-(4-methylpiperazin-1-yl)benzyl)
imidazo[1,2-a]pyridine-3-carboxamide (109)

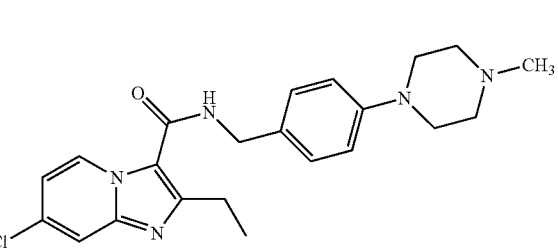

7-Chloro-2-ethyl-N-(4-(4-isopropylpiperazin-1-yl)ben-
zyl)imidazo[1,2-a]pyridine-3-carboxamide (110)

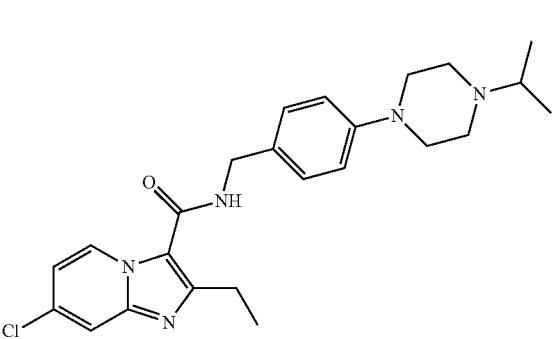 [SMILES: CCc1nc2cc(Cl)ccn2c1C(=O)NCc1ccc(N2CCN(C(C)C)CC2)cc1]

7-Chloro-2-ethyl-N-(4-(4-phenylpiperazin-1-yl)benzyl)
imidazo[1,2-a]pyridine-3-carboxamide (111)

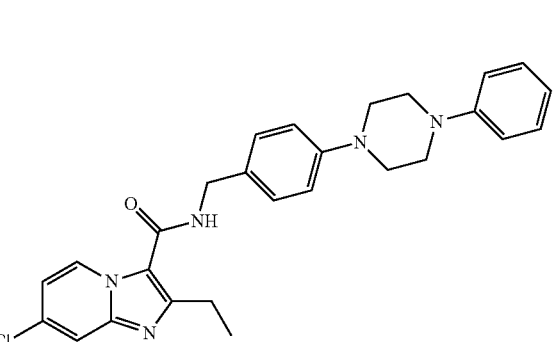

2-Ethyl-N-(4-(4-(4-fluorophenyl)piperazin-1-yl)benzyl)-6-methoxyimidazo[1,2-a]pyridine-3-carboxamide (112)

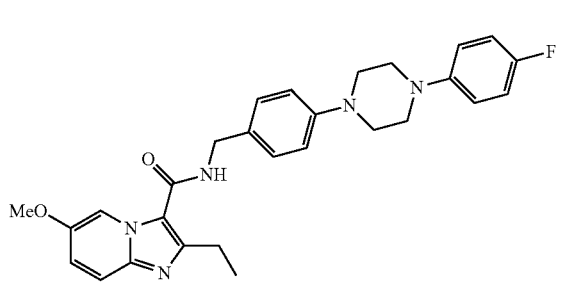 [SMILES: CCc1nc2ccc(OC)cn2c1C(=O)NCc1ccc(N2CCN(c3ccc(F)cc3)CC2)cc1]

6-Chloro-2-ethyl-N-(4-(4-(4-fluorophenyl)piperazin-1-yl)benzyl)imidazo[1,2-a]pyridine-3-carboxamide (113)

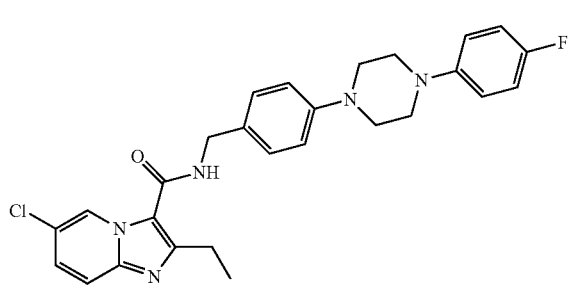

2-Ethyl-N-(4-(4-(4-fluorophenyl)piperazin-1-yl)benzyl)-7-methoxyimidazo[1,2-a]pyridine-3-carboxamide (114)

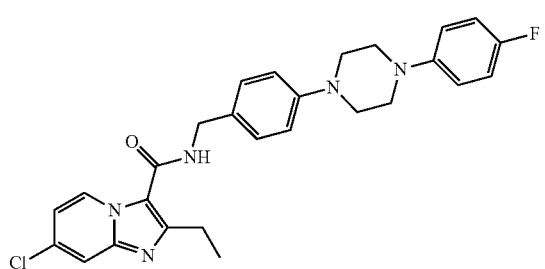 [SMILES: CCc1nc2cc(Cl)ccn2c1C(=O)NCc1ccc(N2CCN(c3ccc(F)cc3)CC2)cc1]

2-Ethyl-N-(4-(4-(4-fluorophenyl)piperazin-1-yl)benzyl)-8-methoxyimidazo[1,2-a]pyridine-3-carboxamide (115)

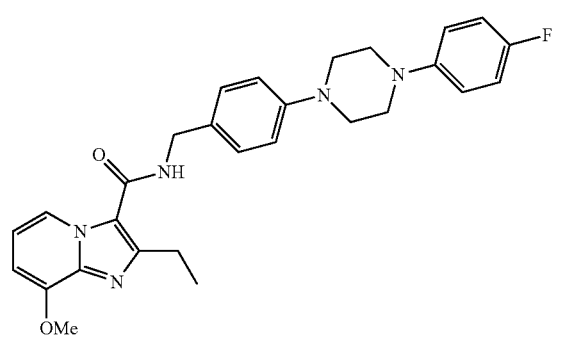 [SMILES: CCc1nc2c(OC)cccn2c1C(=O)NCc1ccc(N2CCN(c3ccc(F)cc3)CC2)cc1]

7-Chloro-2-ethyl-N-((4'-fluorobiphenyl-4-yl)methyl)imidazo[1,2-a]pyridine-3-carboxamide (116)

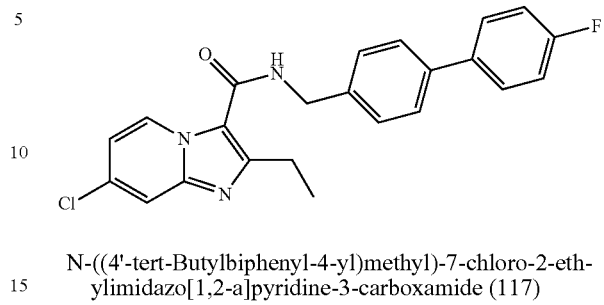

N-((4'-tert-Butylbiphenyl-4-yl)methyl)-7-chloro-2-ethylimidazo[1,2-a]pyridine-3-carboxamide (117)

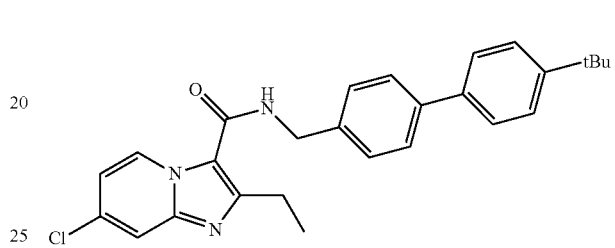

7-Chloro-2-ethyl-N-((4'-methoxybiphenyl-4-yl)methyl)imidazo[1,2-a]pyridine-3-carboxamide (118)

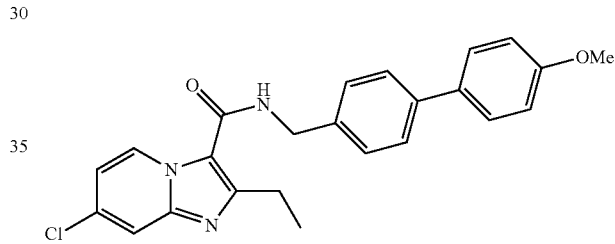

7-Chloro-2-ethyl-N-((4'-(trifluoromethoxy)biphenyl-4-yl)methyl)imidazo[1,2-a]pyridine-3-carboxamide (119)

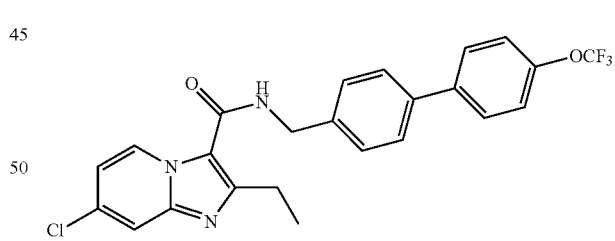

7-Chloro-2-ethyl-N-((4'-(trifluoromethyl)biphenyl-4-yl)methyl)imidazo[1,2-a]pyridine-3-carboxamide (120)

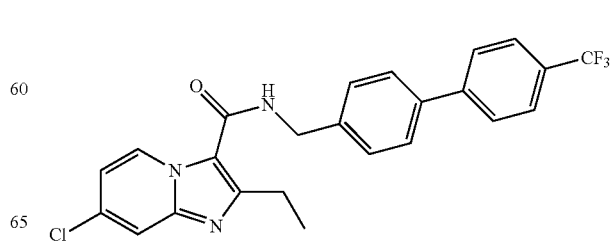

323

6-Chloro-N-((4'-cyanobiphenyl-4-yl)methyl)-2-ethylimidazo[1,2-a]pyridine-3-carboxamide (121)

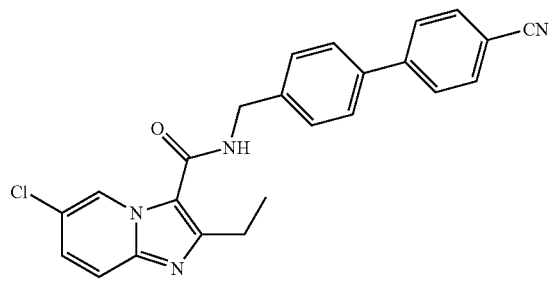 [SMILES: CCc1nc2ccc(Cl)cn2c1C(=O)NCc1ccc(-c2ccc(C#N)cc2)cc1]

7-Chloro-N-((4'-cyanobiphenyl-4-yl)methyl)-2-ethylimidazo[1,2-a]pyridine-3-carboxamide (122)

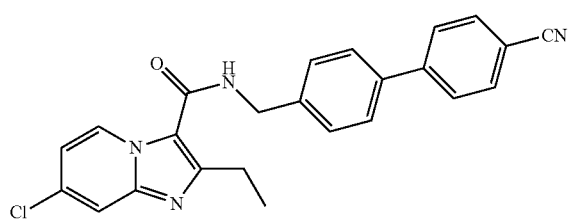 [SMILES: CCc1nc2cc(Cl)ccn2c1C(=O)NCc1ccc(-c2ccc(C#N)cc2)cc1]

6-Chloro-2-ethyl-N-((2'-(trifluoromethyl)biphenyl-4-yl)methyl)imidazo[1,2-a]pyridine-3-carboxamide (123)

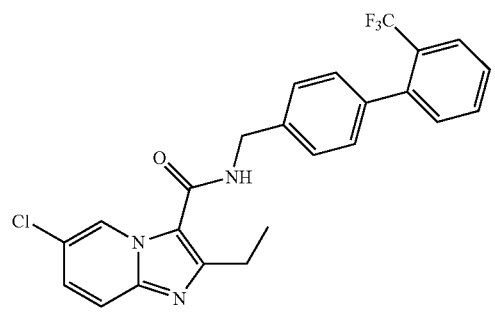

7-Chloro-2-ethyl-N-((2'-(trifluoromethyl)biphenyl-4-yl)methyl)imidazo[1,2-a]pyridine-3-carboxamide (124)

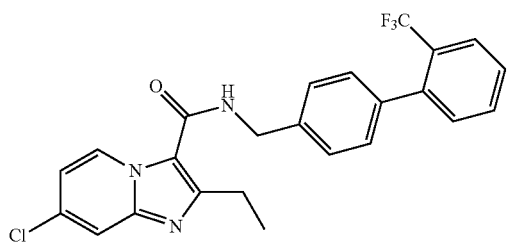

324

6-Chloro-N-((2'-cyanobiphenyl-4-yl)methyl)-2-ethylimidazo[1,2-a]pyridine-3-carboxamide (125)

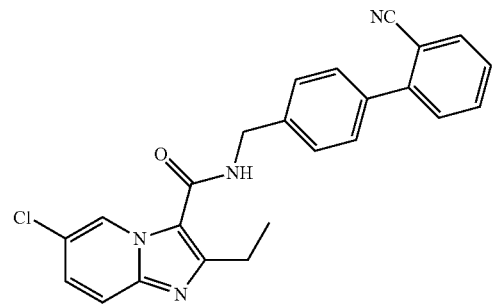

7-Chloro-N-((2'-cyanobiphenyl-4-yl)methyl)-2-ethylimidazo[1,2-a]pyridine-3-carboxamide (126)

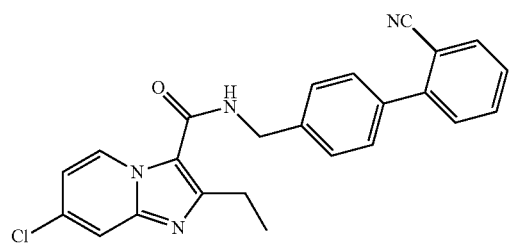 [SMILES: CCc1nc2cc(Cl)ccn2c1C(=O)NCc1ccc(-c2ccccc2C#N)cc1]

6-Chloro-N-((3'-cyanobiphenyl-4-yl)methyl)-2-ethylimidazo[1,2-a]pyridine-3-carboxamide (127)

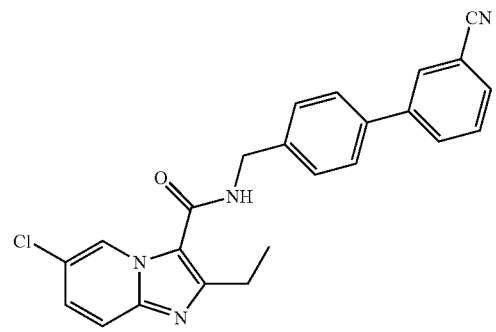 [SMILES: CCc1nc2ccc(Cl)cn2c1C(=O)NCc1ccc(-c2cccc(C#N)c2)cc1]

7-Chloro-N-((3'-cyanobiphenyl-4-yl)methyl)-2-ethylimidazo[1,2-a]pyridine-3-carboxamide (128)

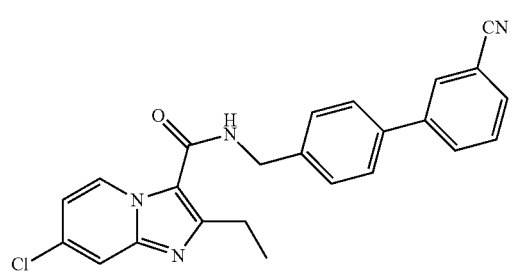 [SMILES: CCc1nc2cc(Cl)ccn2c1C(=O)NCc1ccc(-c2cccc(C#N)c2)cc1]

325

6-Chloro-N-((4'-chloro-2'-(trifluoromethyl)biphenyl-4-yl)methyl)-2-ethylimidazo[1,2-a]pyridine-3-carboxamide (129)

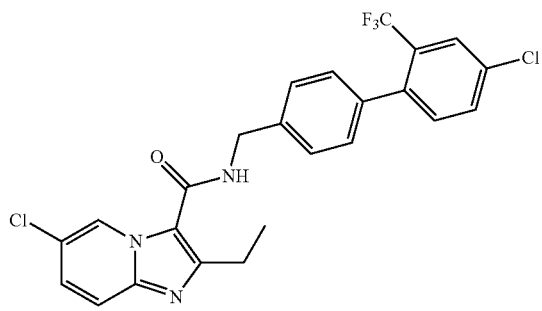 [SMILES: CCc1nc2ccc(Cl)cn2c1C(=O)NCc1ccc(-c2ccc(Cl)cc2C(F)(F)F)cc1]

7-Chloro-N-((4'-chloro-2'-(trifluoromethyl)biphenyl-4-yl)methyl)-2-ethylimidazo[1,2-a]pyridine-3-carboxamide (130)

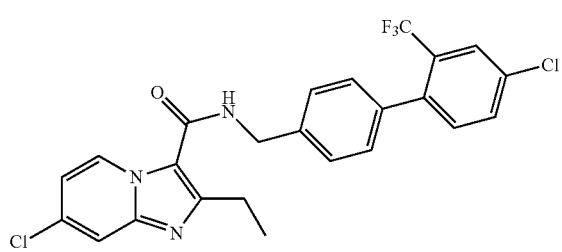 [SMILES: CCc1nc2cc(Cl)ccn2c1C(=O)NCc1ccc(-c2ccc(Cl)cc2C(F)(F)F)cc1]

6-Chloro-N-((4'-cyano-2'-methylbiphenyl-4-yl)methyl)-2-ethylimidazo[1,2-a]pyridine-3-carboxamide (131)

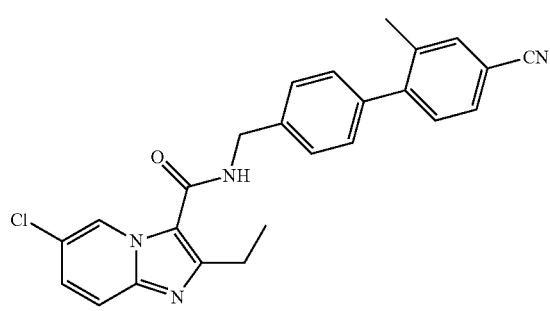 [SMILES: CCc1nc2ccc(Cl)cn2c1C(=O)NCc1ccc(-c2ccc(C#N)cc2C)cc1]

7-Chloro-N-((4'-cyano-2'-methylbiphenyl-4-yl)methyl)-2-ethylimidazo[1,2-a]pyridine-3-carboxamide (132)

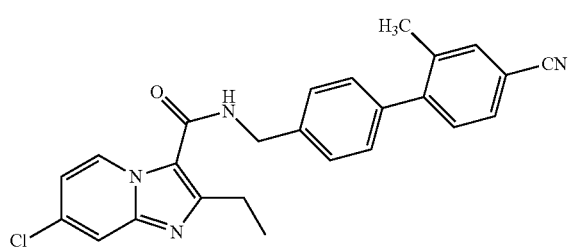 [SMILES: CCc1nc2cc(Cl)ccn2c1C(=O)NCc1ccc(-c2ccc(C#N)cc2C)cc1]

326

7-Chloro-N-((2'-chloro-4'-fluorobiphenyl-4-yl)methyl)-2-ethylimidazo[1,2-a]pyridine-3-carboxamide (133)

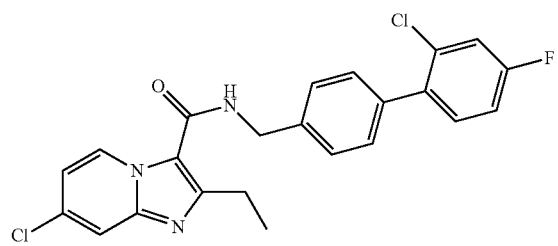

7-Chloro-2-ethyl-N-(4-(pyridin-4-yl)benzyl)imidazo[1,2-a]pyridine-3-carboxamide (134)

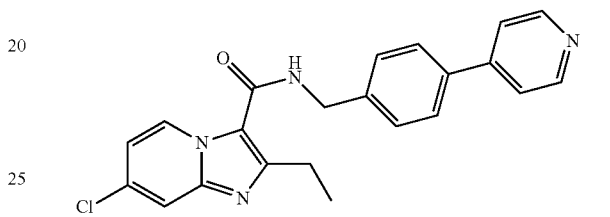

7-Chloro-2-ethyl-N-(4-(5-methoxypyridin-2-yl)benzyl)imidazo[1,2-a]pyridine-3-carboxamide (135)

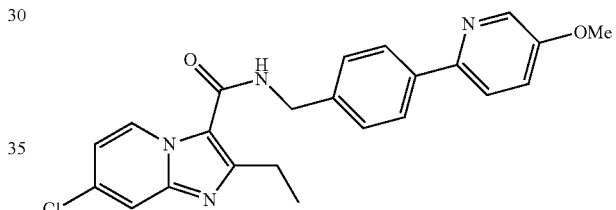

N-(4-(1H-Pyrrol-2-yl)benzyl)-7-chloro-2-ethylimidazo[1,2-a]pyridine-3-carboxamide (136)

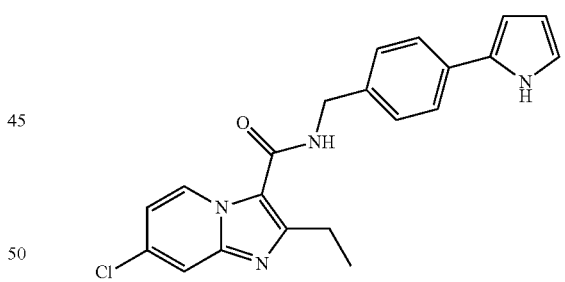

7-Chloro-2-ethyl-N-(4-(furan-2-yl)benzyl)imidazo[1,2-a]pyridine-3-carboxamide (137)

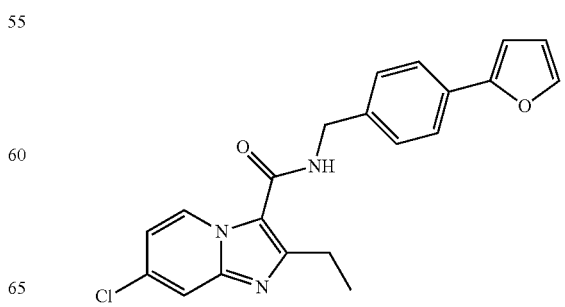

327

N-(4-(1H-Pyrrol-1-yl)benzyl)-7-chloro-2-ethylimidazo[1,2-a]pyridine-3-carboxamide (138)

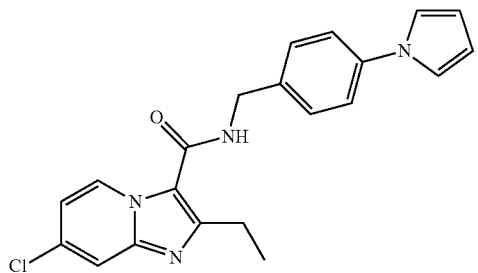 [SMILES: CCc1nc2cc(Cl)ccn2c1C(=O)NCc1ccc(-n2cccc2)cc1]

6-Chloro-2-ethyl-N-(4-(4-(4-(trifluoromethoxy)phenoxy)piperidin-1-yl)benzyl)imidazo-[1,2-a]pyridine-3-carboxamide (139)

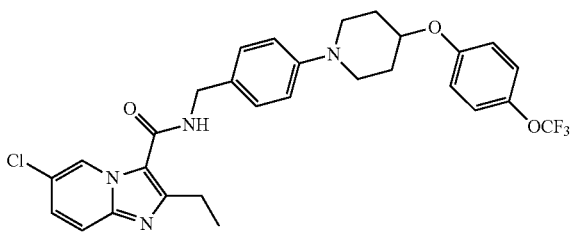

7-Chloro-2-ethyl-N-(4-(4-(4-(trifluoromethoxy)phenoxy)piperidin-1-yl)benzyl)imidazo-[1,2-a]pyridine-3-carboxamide (140)

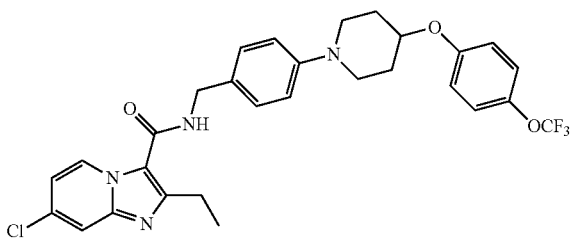

N-((4'-Chlorobiphenyl-4-yl)methyl)-2-ethylimidazo[1,2-a]pyrazine-3-carboxamide (141)

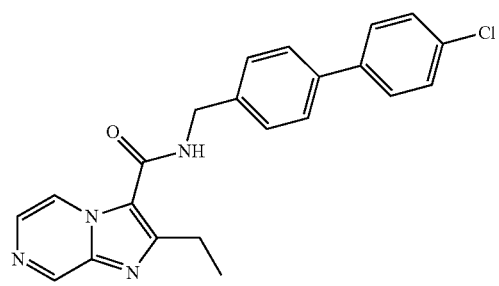 [SMILES: CCc1nc2cnccn2c1C(=O)NCc1ccc(-c2ccc(Cl)cc2)cc1]

N-(4-(4-(4-(Butyramidomethyl)phenyl)piperazin-1-yl)benzyl)-7-chloro-2-ethylimidazo-[1,2-a]pyridine-3-carboxamide (144)

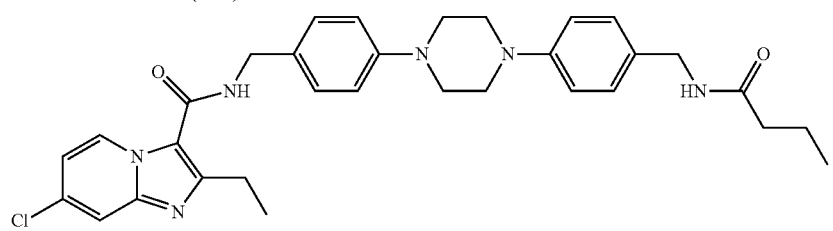

328

N-(4-tert-Butylbenzyl)-2-ethyl-7-(piperazin-1-yl)imidazo[1,2-a]pyridine-3-carboxamide (145)

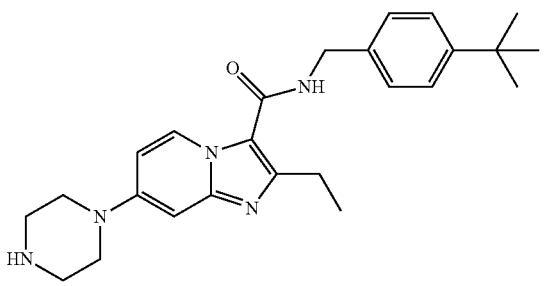 [SMILES: CCc1nc2cc(N3CCNCC3)ccn2c1C(=O)NCc1ccc(C(C)(C)C)cc1]

6-Chloro-N-(4-cyanobenzyl)-2-ethylimidazo[1,2-a]pyridine-3-carboxamide (146)

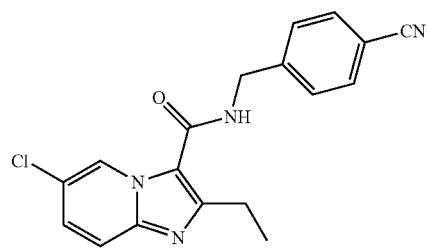 [SMILES: CCc1nc2ccc(Cl)cn2c1C(=O)NCc1ccc(C#N)cc1]

6-Chloro-2-ethyl-N-(4-(trifluoromethyl)benzyl)imidazo[1,2-a]pyridine-3-carboxamide (147)

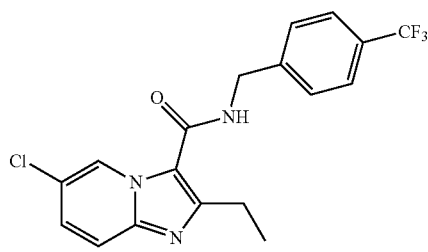 [SMILES: CCc1nc2ccc(Cl)cn2c1C(=O)NCc1ccc(C(F)(F)F)cc1]

7-Chloro-2-ethyl-N-(4-(trifluoromethyl)benzyl)imidazo[1,2-a]pyridine-3-carboxamide (148)

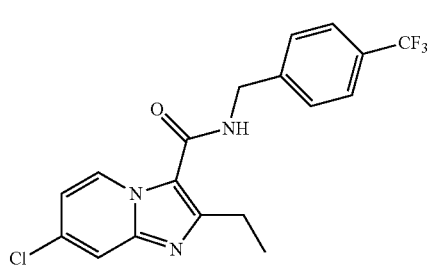 [SMILES: CCc1nc2cc(Cl)ccn2c1C(=O)NCc1ccc(C(F)(F)F)cc1]

2-Ethyl-6-nitro-N-(4-(trifluoromethoxy)benzyl)imidazo[1,2-a]pyridine-3-carboxamide (149)

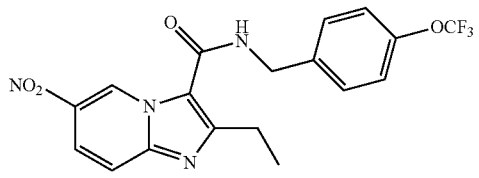 [SMILES: CCc1nc2ccc([N+](=O)[O-])cn2c1C(=O)NCc1ccc(OC(F)(F)F)cc1]

2-Ethyl-7-nitro-N-(4-(trifluoromethoxy)benzyl)imidazo[1,2-a]pyridine-3-carboxamide (150)

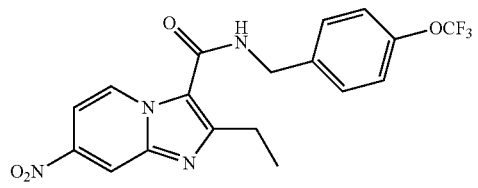 [SMILES: CCc1nc2cc([N+](=O)[O-])ccn2c1C(=O)NCc1ccc(OC(F)(F)F)cc1]

2-Ethyl-N-(4-(trifluoromethoxy)benzyl)-6-(trifluoromethyl)imidazo[1,2-a]pyridine-3-carboxamide (151)

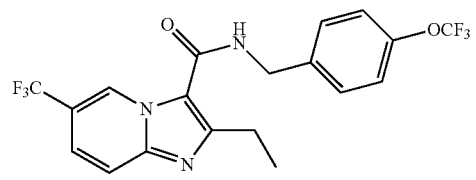 [SMILES: CCc1nc2ccc(C(F)(F)F)cn2c1C(=O)NCc1ccc(OC(F)(F)F)cc1]

6-Bromo-2-ethyl-N-(4-(trifluoromethoxy)benzyl)imidazo[1,2-a]pyridine-3-carboxamide (152)

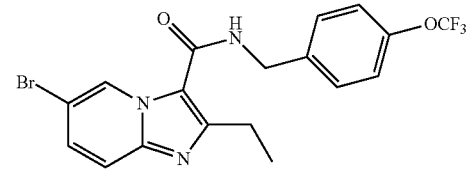 [SMILES: CCc1nc2ccc(Br)cn2c1C(=O)NCc1ccc(OC(F)(F)F)cc1]

6,7-Dichloro-2-ethyl-N-(4-(trifluoromethoxy)benzyl)imidazo[1,2-a]pyridine-3-carboxamide (153)

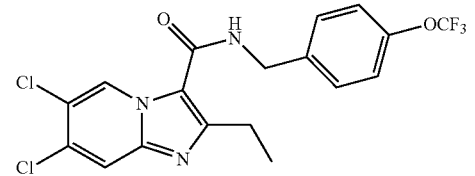 [SMILES: CCc1nc2cc(Cl)c(Cl)cn2c1C(=O)NCc1ccc(OC(F)(F)F)cc1]

6-Chloro-2-methyl-N-(4-(trifluoromethoxy)benzyl)imidazo[1,2-a]pyridine-3-carboxamide (154)

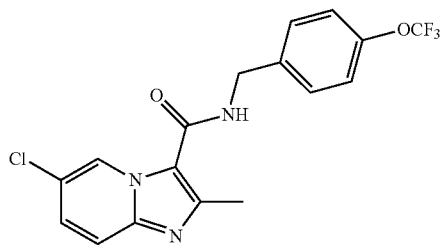 [SMILES: Cc1nc2ccc(Cl)cn2c1C(=O)NCc1ccc(OC(F)(F)F)cc1]

2-Ethyl-N-(4-(trifluoromethoxy)benzyl)imidazo[1,2-a]pyrazine-3-carboxamide (155)

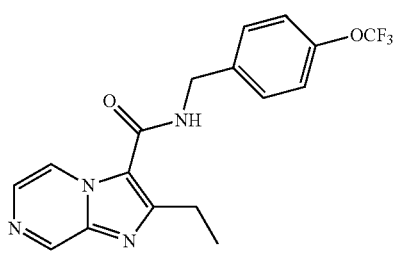 [SMILES: CCc1nc2cnccn2c1C(=O)NCc1ccc(OC(F)(F)F)cc1]

2-Ethyl-3-((4-(trifluoromethoxy)benzyl)carbamoyl)imidazo[1,2-a]pyrazine 7-oxide (156)

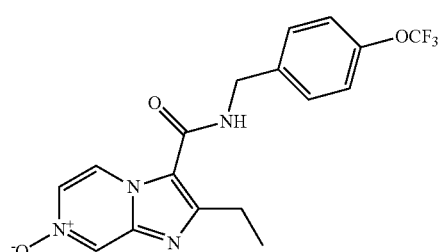

6-Chloro-2-ethyl-N-(4-methoxyphenethyl)imidazo[1,2-a]pyridine-3-carboxamide (157)

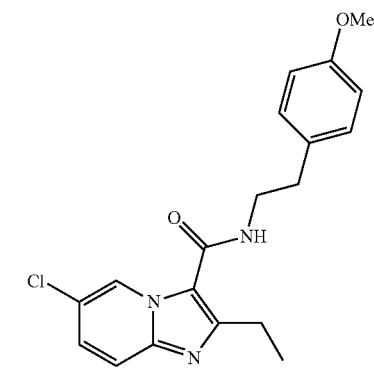 [SMILES: CCc1nc2ccc(Cl)cn2c1C(=O)NCCc1ccc(OC)cc1]

331

6-Chloro-N-(4-chlorophenethyl)-2-ethylimidazo[1,2-a]
pyridine-3-carboxamide (158)

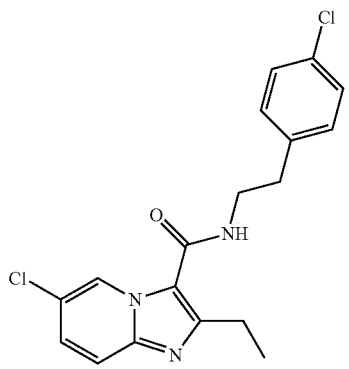 [SMILES: CCc1nc2ccc(Cl)cn2c1C(=O)NCCc1ccc(Cl)cc1]

N-((4'-(Butyramidomethyl)biphenyl-4-yl)methyl)-7-
chloro-2-ethylimidazo[1,2-a]pyridine-3-carboxamide
(159)

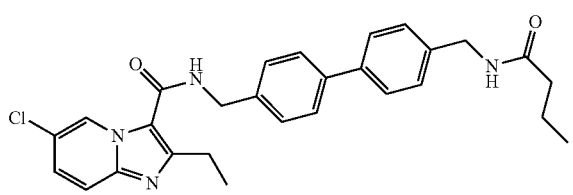 [SMILES: CCCC(=O)NCc1ccc(-c2ccc(CNC(=O)c3c(CC)nc4ccc(Cl)cn34)cc2)cc1]

3-(((4'-Chloro-[1,1'-biphenyl]-4-yl)methyl)carbamoyl)-2-
ethylimidazo[1,2-a]pyrazine 7-oxide (160)

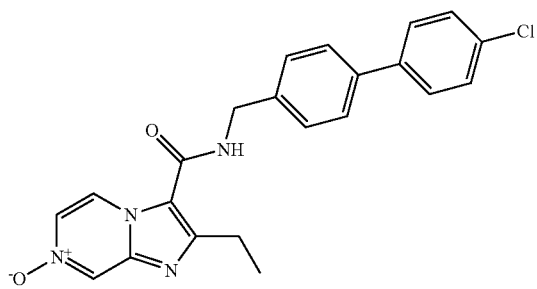

6-Chloro-N-(4-(4-(4-chlorophenoxy)piperidin-1-yl)ben-
zyl)-2-ethylimidazo[1,2-a]pyridine-3-carboxamide
(162)

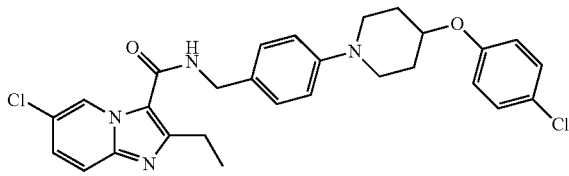 [SMILES: CCc1nc2ccc(Cl)cn2c1C(=O)NCc1ccc(N2CCC(Oc3ccc(Cl)cc3)CC2)cc1]

332

7-Chloro-N-(4-(4-(4-chlorophenoxy)piperidin-1-yl)ben-
zyl)-2-ethylimidazo[1,2-a]pyridine-3-carboxamide
(163)

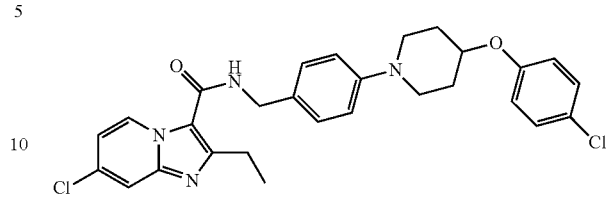

6-Chloro-2-ethyl-N-(4-(4-(4-(trifluoromethyl)phenoxy)
piperidin-1-yl)benzyl) imidazo[1,2-a]pyridine-3-car-
boxamide (164)

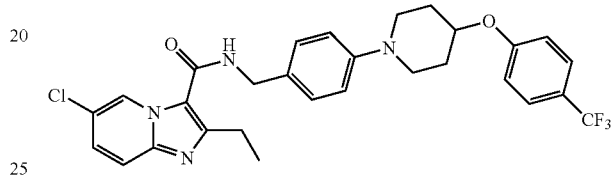

7-Chloro-2-ethyl-N-(4-(4-(4-(trifluoromethyl)phenoxy)
piperidin-1-yl)benzyl) imidazo[1,2-a]pyridine-3-car-
boxamide (165)

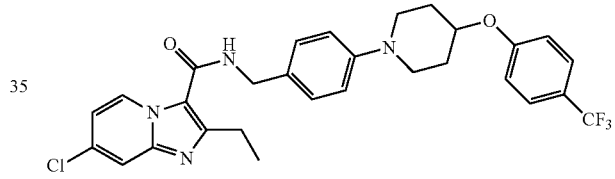

6-Chloro-2-ethyl-N-(4-(4-(4-fluorophenoxy)piperidin-1-
yl)benzyl)imidazo[1,2-a]pyridine-3-carboxamide (166)

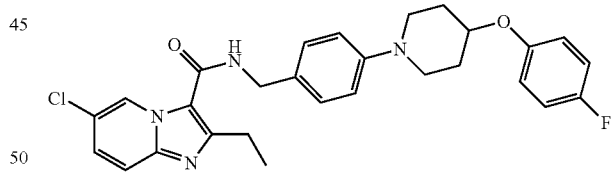

7-Chloro-2-ethyl-N-(4-(4-(4-fluorophenoxy)piperidin-1-
yl)benzyl)imidazo[1,2-a]pyridine-3-carboxamide (167)

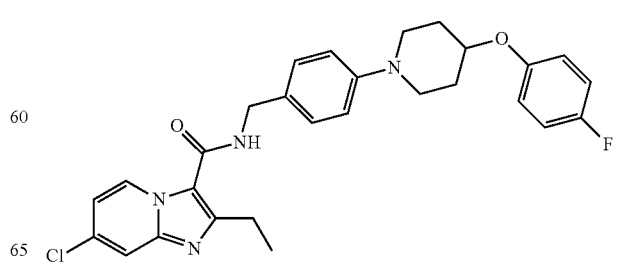

2-Ethyl-N-(4-(4-(4-(trifluoromethoxy)phenoxy)piperidin-1-yl)benzyl)-6-(trifluoromethyl)imidazo[1,2-a]pyridine-3-carboxamide (168)

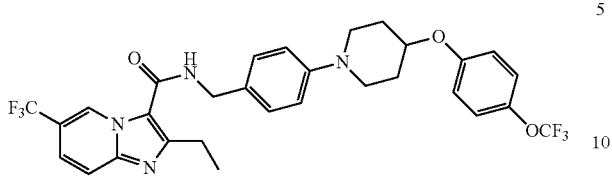

7-Chloro-N-(4-(4-(cyclopentyloxymethyl)piperidin-1-yl)benzyl)-2-ethylimidazo[1,2-a]pyridine-3-carboxamide (169)

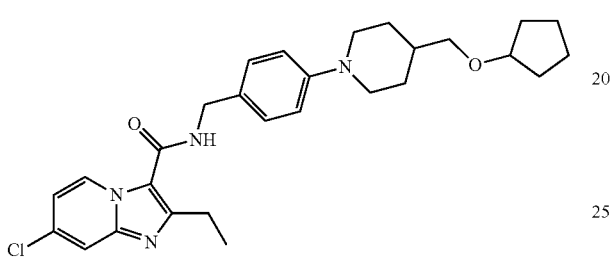

2-Ethyl-7-nitro-N-(4-(4-(4-(trifluoromethoxy)phenoxy)piperidin-1-yl)benzyl) imidazo[1,2-a]pyridine-3-carboxamide (170)


6-Chloro-2-ethyl-N-(4-(4-(4-fluorobenzyl)piperazin-1-yl)benzyl)imidazo[1,2-a]pyridine-3-carboxamide (171)


7-Chloro-2-ethyl-N-(4-(4-(4-fluorobenzyl)piperazin-1-yl)benzyl)imidazo[1,2-a]pyridine-3-carboxamide (172)

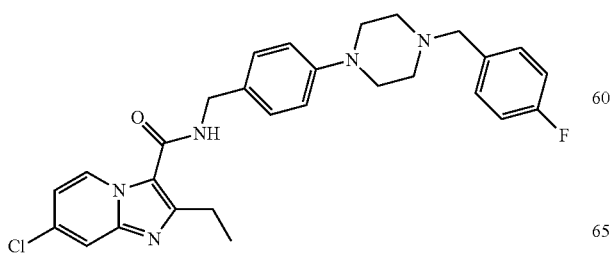

6-Chloro-2-ethyl-N-(4-(4-(4-(trifluoromethoxy)benzyl)piperazin-1-yl)benzyl)imidazo[1,2-a]pyridine-3-carboxamide (173)

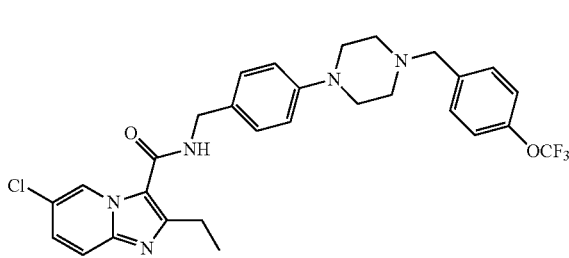 [SMILES: CCc1nc2ccc(Cl)cn2c1C(=O)NCc1ccc(N2CCN(Cc3ccc(OC(F)(F)F)cc3)CC2)cc1]

7-Chloro-2-ethyl-N-(4-(4-(4-(trifluoromethoxy)benzyl)piperazin-1-yl)benzyl)imidazo[1,2-a]pyridine-3-carboxamide (174)

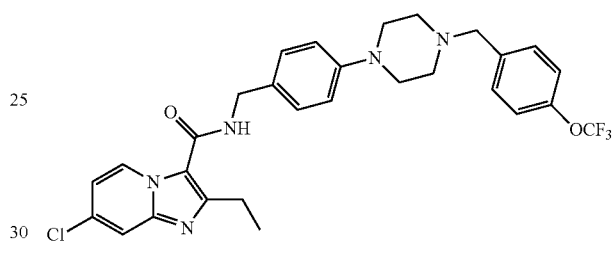

6,7-Dichloro-2-ethyl-N-(4-(4-(4-fluorobenzyl)piperazin-1-yl)benzyl)imidazo[1,2-a]pyridine-3-carboxamide (175)

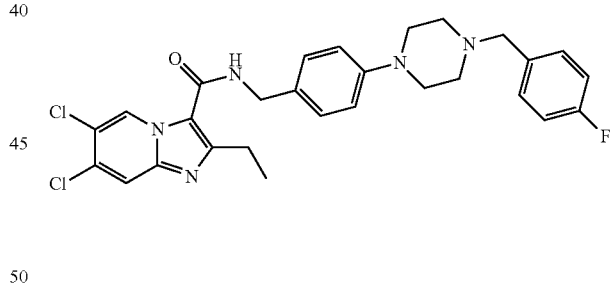

7-Chloro-2-ethyl-N-(4-(4-(4-fluorophenyl)piperazin-1-yl)benzyl)imidazo[1,2-a]pyridine-3-carboxamide (176)

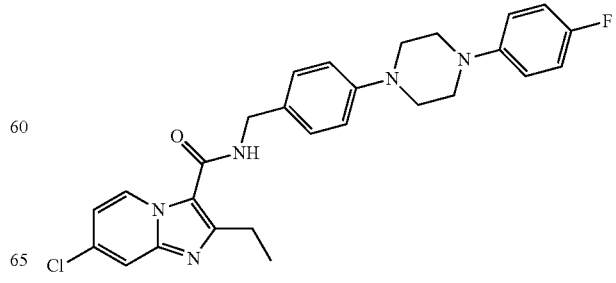

7-Chloro-2-ethyl-N-(4-(4-(4-fluorophenyl)piperazin-1-yl)benzyl)imidazo[1,2-a]pyridine-3-carboxamide trihydrochloride (177)

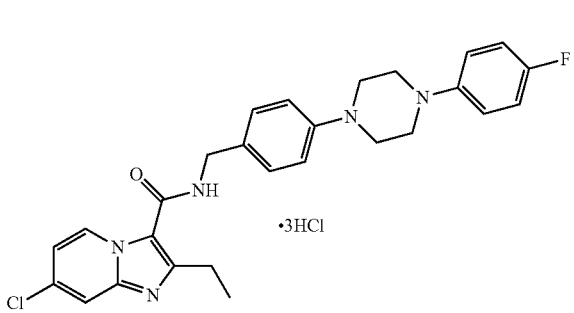

6-Chloro-2-ethyl-N-(4-(4-(4-(trifluoromethoxy)phenyl)piperazin-1-yl)benzyl)imidazo[1,2-a]pyridine-3-carboxamide (178)

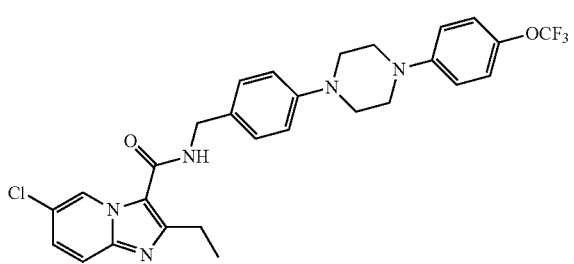

7-Chloro-2-ethyl-N-(4-(4-(4-(trifluoromethoxy)phenyl)piperazin-1-yl)benzyl)imidazo[1,2-a]pyridine-3-carboxamide (179)

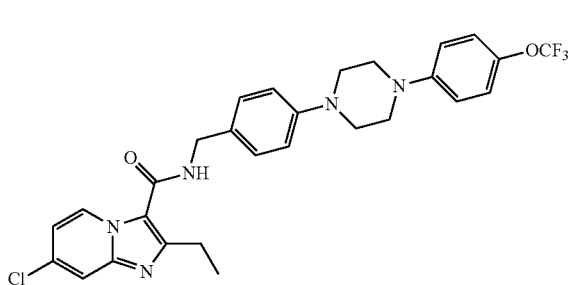 [SMILES: CCc1nc2cc(Cl)ccn2c1C(=O)NCc1ccc(N2CCN(c3ccc(OC(F)(F)F)cc3)CC2)cc1]

6,7-Dichloro-2-ethyl-N-(4-(4-(4-fluorophenyl)piperazin-1-yl)benzyl)imidazo[1,2-a]pyridine-3-carboxamide (180)

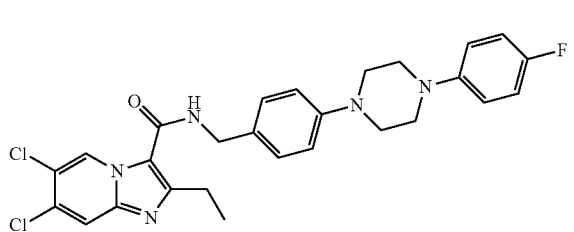 [SMILES: CCc1nc2cc(Cl)c(Cl)cn2c1C(=O)NCc1ccc(N2CCN(c3ccc(F)cc3)CC2)cc1]

2-Ethyl-N-(4-(4-(4-(trifluoromethoxy)phenyl)piperazin-1-yl)benzyl)imidazo[1,2-a]pyridine-3-carboxamide (181)

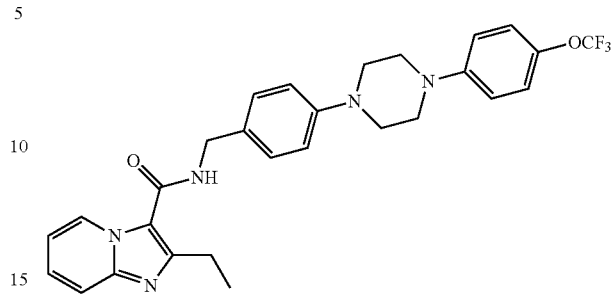

6-Chloro-2-ethyl-N-(4-(4-(4-fluorophenyl)piperazin-1-yl)benzyl)-N-methylimidazo[1,2-a]pyridine-3-carboxamide (182)

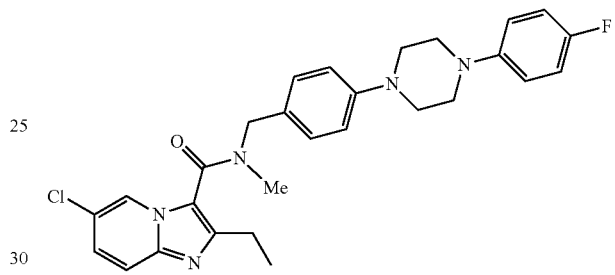

7-Chloro-N-(4-(4-((difluoromethoxy)methyl)piperidin-1-yl)benzyl)-2-ethylimidazo[1,2-a]pyridine-3-carboxamide (183)

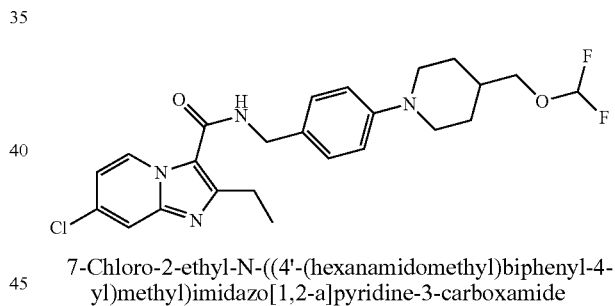

7-Chloro-2-ethyl-N-((4'-(hexanamidomethyl)biphenyl-4-yl)methyl)imidazo[1,2-a]pyridine-3-carboxamide (184)

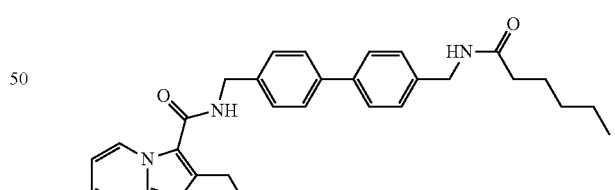

6-Chloro-2-ethyl-N-(4-(4-(trifluoromethoxy)phenoxy)benzyl)imidazo[1,2-a]pyridine-3-carboxamide (185)

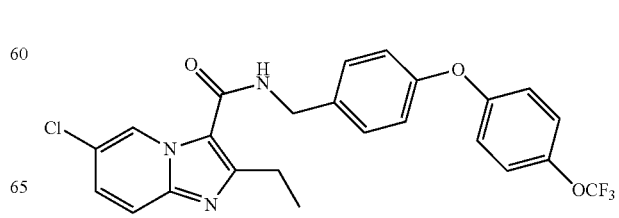

337

7-Chloro-2-ethyl-N-(4-(4-(trifluoromethoxy)phenoxy)benzyl)imidazo[1,2-a]pyridine-3-carboxamide (186)

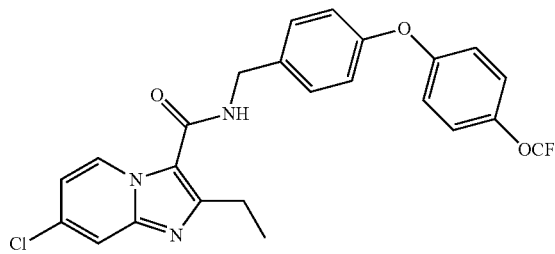

6-Chloro-2-ethyl-N-(4-(4-fluorophenoxy)benzyl)imidazo[1,2-a]pyridine-3-carboxamide (187)

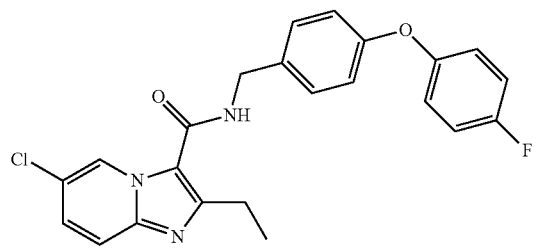 [SMILES: CCc1nc2ccc(Cl)cn2c1C(=O)NCc1ccc(Oc2ccc(F)cc2)cc1]

7-Chloro-2-ethyl-N-(4-(4-fluorophenoxy)benzyl)imidazo[1,2-a]pyridine-3-carboxamide (188)

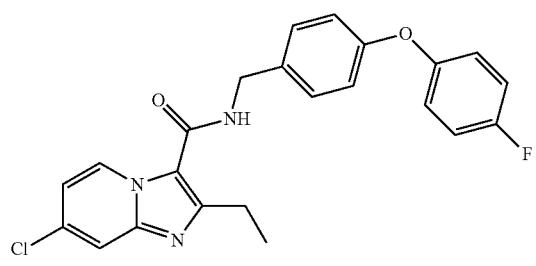 [SMILES: CCc1nc2cc(Cl)ccn2c1C(=O)NCc1ccc(Oc2ccc(F)cc2)cc1]

6-Bromo-2-ethyl-N-(4-(4-fluorophenoxy)benzyl)imidazo[1,2-a]pyridine-3-carboxamide (189)

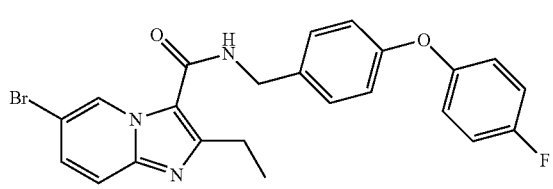 [SMILES: CCc1nc2ccc(Br)cn2c1C(=O)NCc1ccc(Oc2ccc(F)cc2)cc1]

6-Chloro-N-(4-(4-chlorophenoxy)benzyl)-2-ethylimidazo[1,2-a]pyridine-3-carboxamide (190)

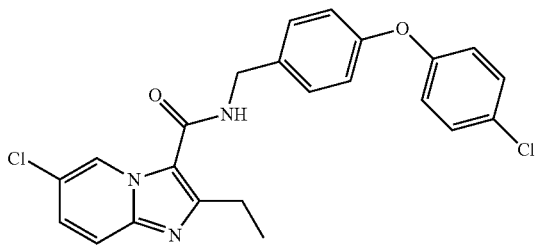 [SMILES: CCc1nc2ccc(Cl)cn2c1C(=O)NCc1ccc(Oc2ccc(Cl)cc2)cc1]

338

7-Chloro-N-(4-(4-chlorophenoxy)benzyl)-2-ethylimidazo[1,2-a]pyridine-3-carboxamide (191)

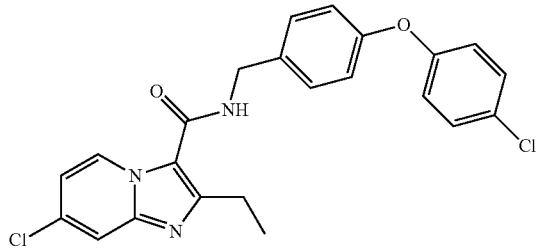 [SMILES: CCc1nc2cc(Cl)ccn2c1C(=O)NCc1ccc(Oc2ccc(Cl)cc2)cc1]

2-Ethyl-N-(4-(4-(trifluoromethoxy)phenoxy)benzyl)imidazo[1,2-a]pyridine-3-carboxamide (192)

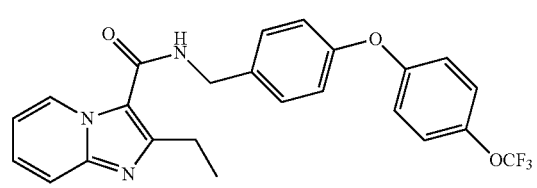 [SMILES: CCc1nc2ccccn2c1C(=O)NCc1ccc(Oc2ccc(OC(F)(F)F)cc2)cc1]

7-Chloro-2-ethyl-N-((6-(4-fluorophenoxy)pyridin-3-yl)methyl)imidazo[1,2-a]pyridine-3-carboxamide (193)

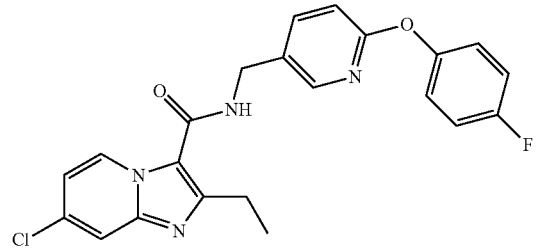

6-Chloro-2-ethyl-N-((6-(4-(trifluoromethoxy)phenoxy)pyridin-3-yl)methyl)imidazo[1,2-a]pyridine-3-carboxamide (194)

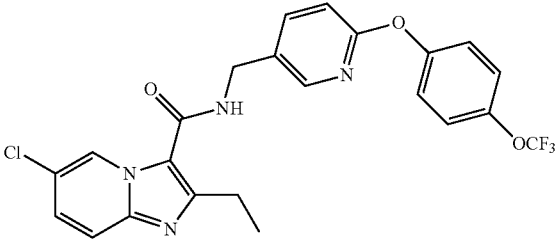 [SMILES: CCc1nc2ccc(Cl)cn2c1C(=O)NCc1ccc(Oc2ccc(OC(F)(F)F)cc2)nc1]

7-Chloro-2-ethyl-N-((6-(4-(trifluoromethoxy)phenoxy)pyridin-3-yl)methyl)imidazo[1,2-a]pyridine-3-carboxamide (195)

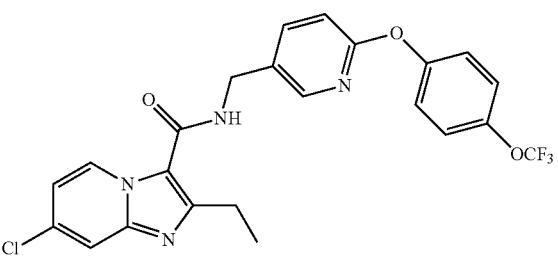

6-Chloro-2-ethyl-N-(4-(4-fluorophenoxy)benzyl)-N-methylimidazo[1,2-a]pyridine-3-carboxamide (197)

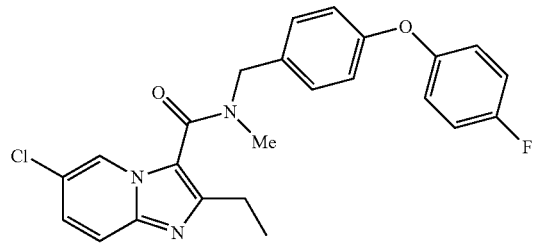 [SMILES: CCc1nc2ccc(Cl)cn2c1C(=O)N(C)Cc1ccc(Oc2ccc(F)cc2)cc1]

6-Chloro-2-ethyl-N-(4-(4-(trifluoromethoxy)phenylamino)benzyl)imidazo[1,2-a]pyridine-3-carboxamide (198)

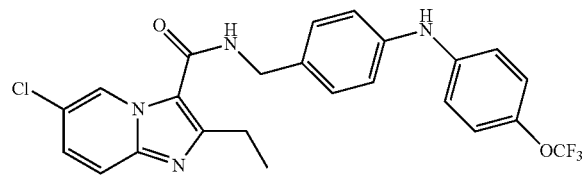

7-Chloro-2-ethyl-N-(4-(4-(trifluoromethoxy)phenylamino)benzyl)imidazo[1,2-a]pyridine-3-carboxamide (199)

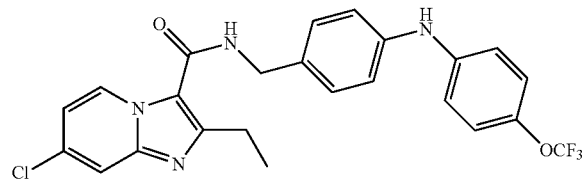 [SMILES: CCc1nc2cc(Cl)ccn2c1C(=O)NCc1ccc(Nc2ccc(OC(F)(F)F)cc2)cc1]

6-Chloro-2-ethyl-N-(4-(4-(trifluoromethyl)benzyloxy)benzyl)imidazo[1,2-a]pyridine-3-carboxamide (200)

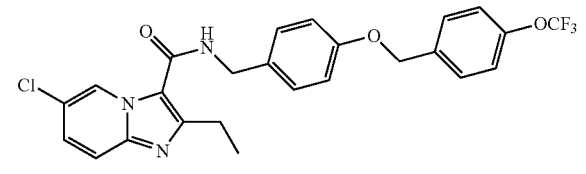 [SMILES: CCc1nc2ccc(Cl)cn2c1C(=O)NCc1ccc(OCc2ccc(OC(F)(F)F)cc2)cc1]

7-Chloro-2-ethyl-N-(4-(4-(trifluoromethyl)benzyloxy)benzyl)imidazo[1,2-a]pyridine-3-carboxamide (201)

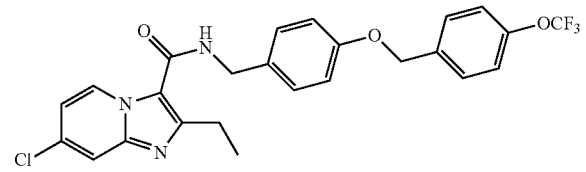 [SMILES: CCc1nc2cc(Cl)ccn2c1C(=O)NCc1ccc(OCc2ccc(OC(F)(F)F)cc2)cc1]

6-Chloro-2-ethyl-N-(4-(4-fluorobenzyloxy)benzyl)imidazo[1,2-a]pyridine-3-carboxamide (202)

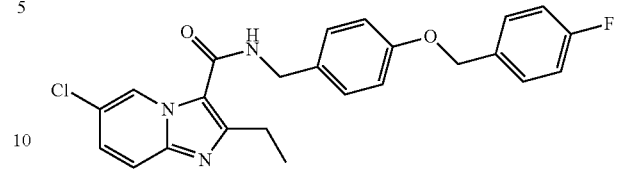

7-Chloro-2-ethyl-N-(4-(4-fluorobenzyloxy)benzyl)imidazo[1,2-a]pyridine-3-carboxamide (203)

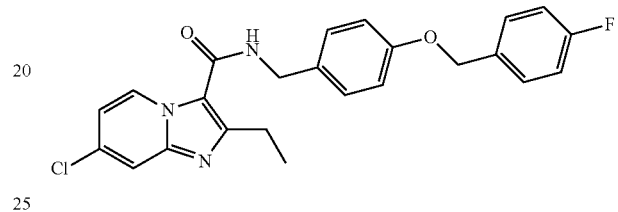

6-Chloro-2-ethyl-N-((2-(4-(trifluoromethoxy)phenyl)-1H-benzo[d]imidazol-5-yl)methyl) imidazo[1,2-a]pyridine-3-carboxamide (204)

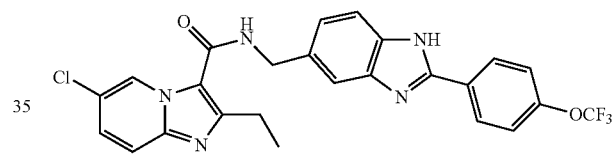

7-Chloro-2-ethyl-N-((2-(4-(trifluoromethoxy)phenyl)-1H-benzo[d]imidazol-5-yl)methyl) imidazo[1,2-a]pyridine-3-carboxamide (205)

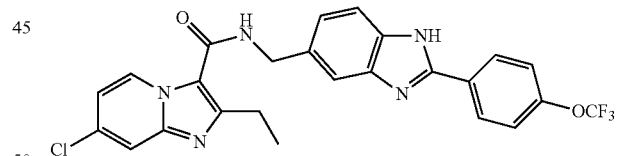

7-Chloro-2-ethyl-N-((2-(morpholinomethyl)-1H-benzo[d]imidazol-5-yl)methyl) imidazo[1,2-a]pyridine-3-carboxamide (206)

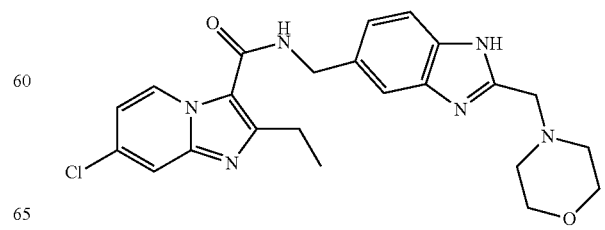

6-Chloro-2-ethyl-N-((2-(4-(trifluoromethoxy)phenyl)benzo[d]oxazol-5-yl)methyl)imidazo[1,2-a]pyridine-3-carboxamide (207)

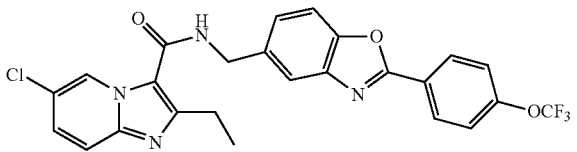 [SMILES: CCc1nc2ccc(Cl)cn2c1C(=O)NCc1ccc2oc(-c3ccc(OC(F)(F)F)cc3)nc2c1]

7-Chloro-2-ethyl-N-((2-(4-(trifluoromethoxy)phenyl)benzo[d]oxazol-5-yl)methyl)imidazo[1,2-a]pyridine-3-carboxamide (208)

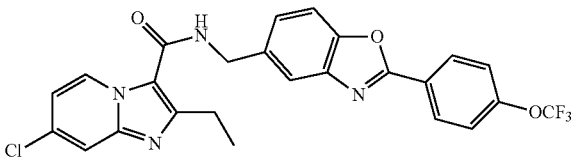 [SMILES: CCc1nc2cc(Cl)ccn2c1C(=O)NCc1ccc2oc(-c3ccc(OC(F)(F)F)cc3)nc2c1]

6-Chloro-N-(4-(2,6-dimethylmorpholino)benzyl)-2-ethylimidazo[1,2-a]pyridine-3-carboxamide (209)

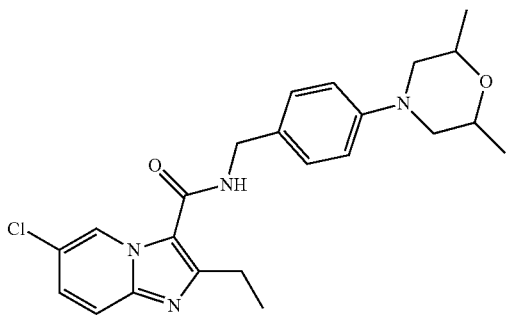 [SMILES: CCc1nc2ccc(Cl)cn2c1C(=O)NCc1ccc(N2CC(C)OC(C)C2)cc1]

7-Chloro-N-(4-(2,6-dimethylmorpholino)benzyl)-2-ethylimidazo[1,2-a]pyridine-3-carboxamide (210)

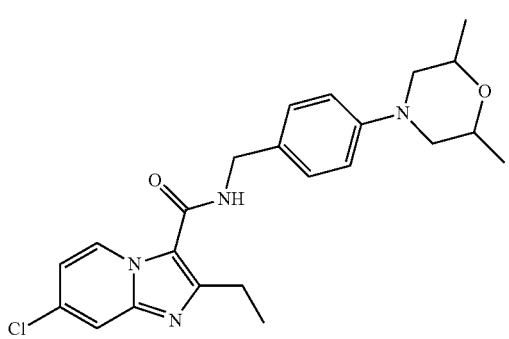 [SMILES: CCc1nc2cc(Cl)ccn2c1C(=O)NCc1ccc(N2CC(C)OC(C)C2)cc1]

6-Chloro-2-ethyl-N-(4-(4-methylpiperidin-1-yl)benzyl)imidazo[1,2-a]pyridine-3-carboxamide (214)

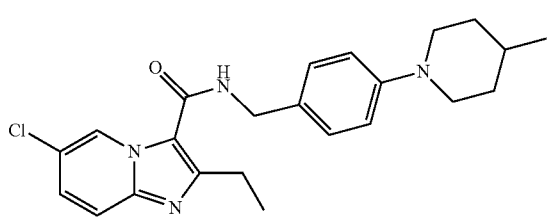 [SMILES: CCc1nc2ccc(Cl)cn2c1C(=O)NCc1ccc(N2CCC(C)CC2)cc1]

7-Chloro-2-ethyl-N-(4-(4-methylpiperidin-1-yl)benzyl)imidazo[1,2-a]pyridine-3-carboxamide (215)

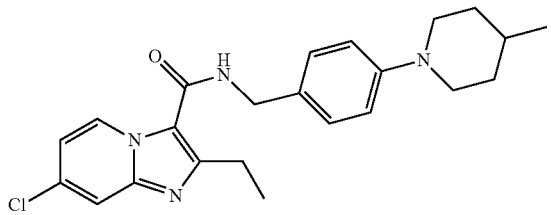 [SMILES: CCc1nc2cc(Cl)ccn2c1C(=O)NCc1ccc(N2CCC(C)CC2)cc1]

6-Chloro-N-(4-(3,5-dimethylpiperidin-1-yl)benzyl)-2-ethylimidazo[1,2-a]pyridine-3-carboxamide (216)

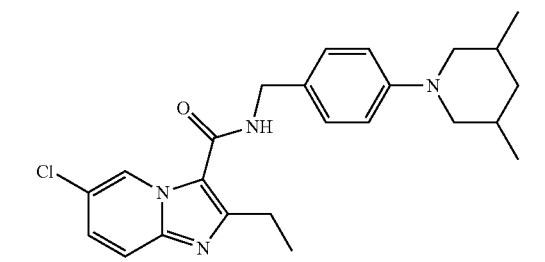 [SMILES: CCc1nc2ccc(Cl)cn2c1C(=O)NCc1ccc(N2CC(C)CC(C)C2)cc1]

7-Chloro-N-(4-(3,5-dimethylpiperidin-1-yl)benzyl)-2-ethylimidazo[1,2-a]pyridine-3-carboxamide (217)

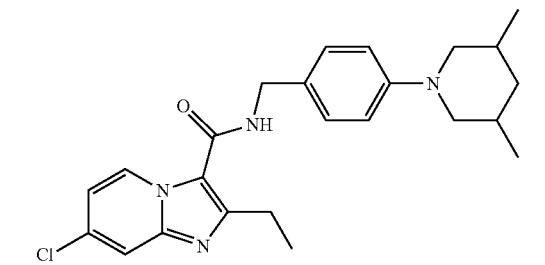 [SMILES: CCc1nc2cc(Cl)ccn2c1C(=O)NCc1ccc(N2CC(C)CC(C)C2)cc1]

7-Chloro-2-ethyl-N-(4-(4-hydroxypiperidin-1-yl)benzyl)imidazo[1,2-a]pyridine-3-carboxamide (218)

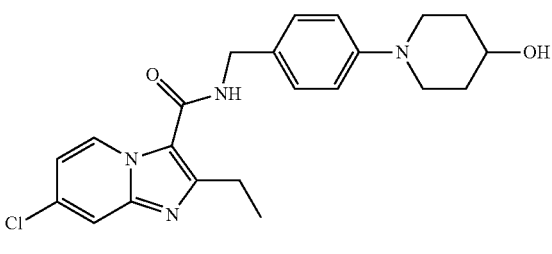 [SMILES: CCc1nc2cc(Cl)ccn2c1C(=O)NCc1ccc(N2CCC(O)CC2)cc1]

1-(4-((6-Chloro-2-ethylimidazo[1,2-a]pyridine-3-carboxamido)methyl)phenyl)piperidine-4-carboxylic acid (220)

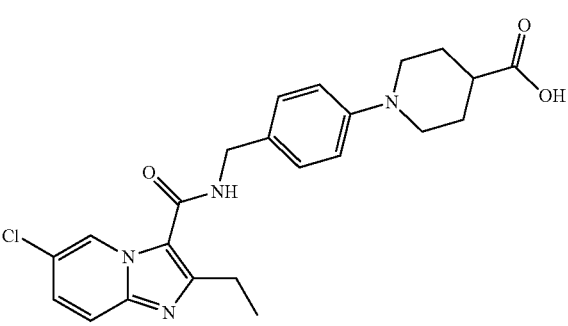 [SMILES: CCc1nc2ccc(Cl)cn2c1C(=O)NCc1ccc(N2CCC(C(=O)O)CC2)cc1]

7-Chloro-N-(4-(3a,4-dihydro-1H-isoindol-2(3H,7H,7aH)-yl)benzyl)-2-ethylimidazo[1,2-a]pyridine-3-carboxamide (223)

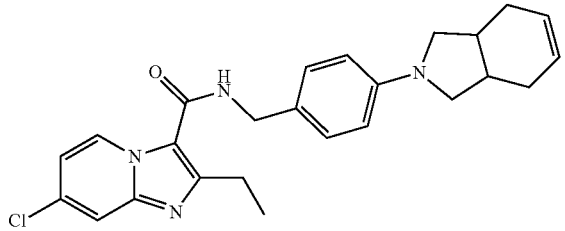 [SMILES: CCc1nc2cc(Cl)ccn2c1C(=O)NCc1ccc(N2CC3CC=CCC3C2)cc1]

N-(4-(1H-isoindol-2(3H,3aH,4H,5H,6H,7H,7aH)-yl)benzyl)-7-chloro-2-ethylimidazo[1,2-a]pyridine-3-carboxamide (224)

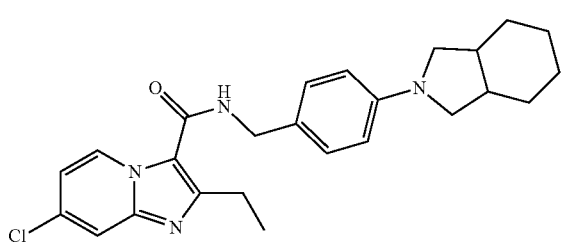 [SMILES: CCc1nc2cc(Cl)ccn2c1C(=O)NCc1ccc(N2CC3CCCCC3C2)cc1]

7-Chloro-2-ethyl-N-(4-(4,5,6,7-tetrahydro-2H-isoindol-2-yl)benzyl)imidazo[1,2-a]pyridine-3-carboxamide (225)

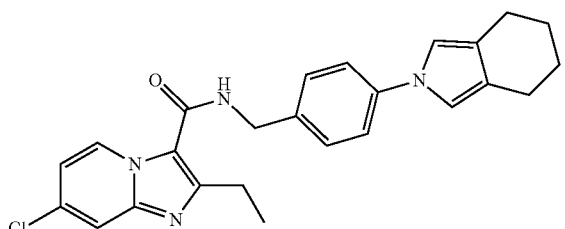

6-Chloro-2-ethyl-N-((1-(4-(trifluoromethoxy)benzyl)piperidin-4-yl)methyl)imidazo[1,2-a]pyridine-3-carboxamide (226)

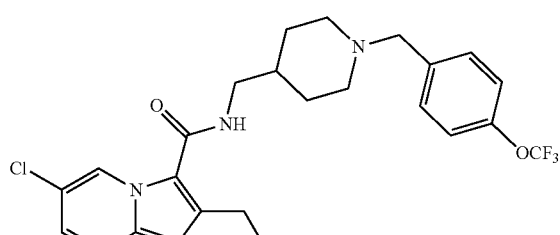

6-Chloro-2-ethyl-N-((1-(4-fluorobenzyl)piperidin-4-yl)methyl)imidazo[1,2-a]pyridine-3-carboxamide (227)

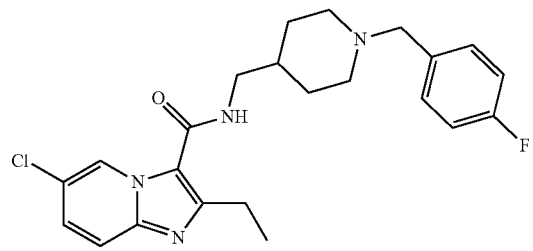 [SMILES: CCc1nc2ccc(Cl)cn2c1C(=O)NCC1CCN(Cc2ccc(F)cc2)CC1]

7-Chloro-2-ethyl-N-((1-(4-(trifluoromethoxy)benzyl)piperidin-4-yl)methyl)imidazo[1,2-a]pyridine-3-carboxamide (228)

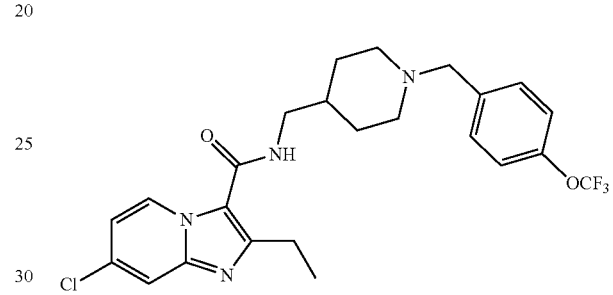

6-Chloro-2-ethyl-N-(1-(4-(trifluoromethoxy)benzyl)piperidin-4-yl)imidazo[1,2-a]pyridine-3-carboxamide (229)

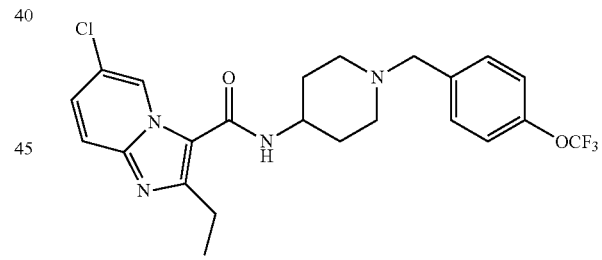

(6-Chloro-2-ethylimidazo[1,2-a]pyridin-3-yl)(4-(4-(trifluoromethoxy)benzyloxy)piperidin-1-yl)methanone (230)

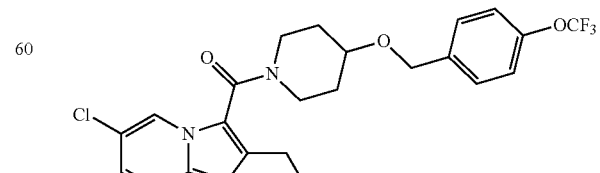

345

6-Chloro-2-ethyl-N-((1-(4-(trifluoromethoxy)phenyl)-1H-pyrazol-3-yl)methyl) imidazo[1,2-a]pyridine-3-carboxamide (231)

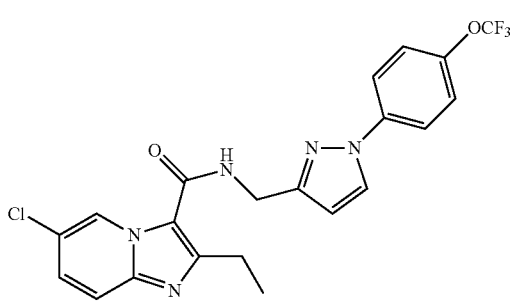 [SMILES: CCc1nc2ccc(Cl)cn2c1C(=O)NCc1ccn(-c2ccc(OC(F)(F)F)cc2)n1]

7-Chloro-2-ethyl-N-((1-(4-(trifluoromethoxy)phenyl)-1H-pyrazol-3-yl)methyl) imidazo[1,2-a]pyridine-3-carboxamide (232)

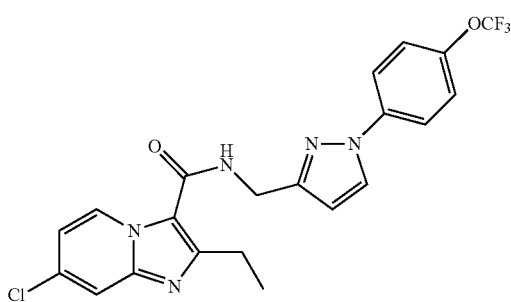 [SMILES: CCc1nc2cc(Cl)ccn2c1C(=O)NCc1ccn(-c2ccc(OC(F)(F)F)cc2)n1]

6-Chloro-2-ethyl-N-((1-(4-(trifluoromethyl)phenyl)-1H-pyrazol-3-yl)methyl)imidazo[1,2-a]pyridine-3-carboxamide (233)

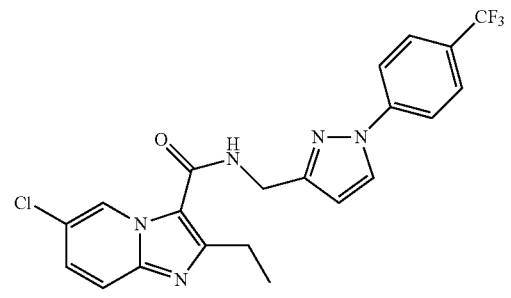 [SMILES: CCc1nc2ccc(Cl)cn2c1C(=O)NCc1ccn(-c2ccc(C(F)(F)F)cc2)n1]

7-Chloro-2-ethyl-N-((1-(4-(trifluoromethyl)phenyl)-1H-pyrazol-3-yl)methyl)imidazo[1,2-a]pyridine-3-carboxamide (234)

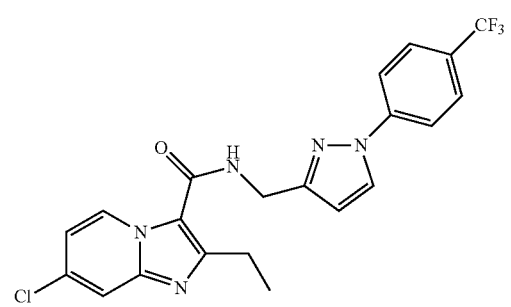 [SMILES: CCc1nc2cc(Cl)ccn2c1C(=O)NCc1ccn(-c2ccc(C(F)(F)F)cc2)n1]

346

6-Chloro-2-ethyl-N-((1-(4-fluorophenyl)-1H-pyrazol-3-yl)methyl)imidazo[1,2-a]pyridine-3-carboxamide (235)

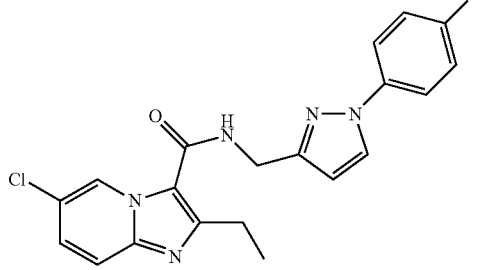

7-Chloro-2-ethyl-N-((1-(4-fluorophenyl)-1H-pyrazol-3-yl)methyl)imidazo[1,2-a]pyridine-3-carboxamide (236)

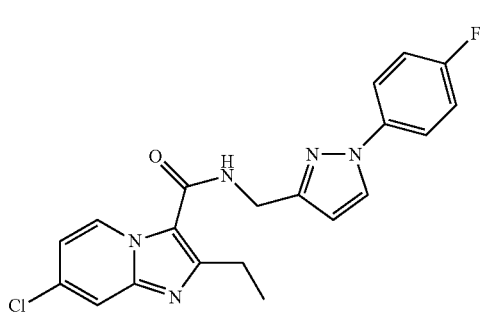 [SMILES: CCc1nc2cc(Cl)ccn2c1C(=O)NCc1ccn(-c2ccc(F)cc2)n1]

6-Chloro-2-ethyl-N-((1-(4-(trifluoromethoxy)phenyl)-4,5,6,7-tetrahydro-1H-indazol-4-yl)methyl)imidazo[1,2-a]pyridine-3-carboxamide (237)

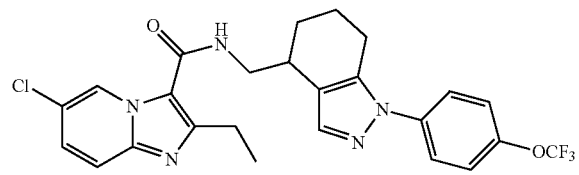 [SMILES: CCc1nc2ccc(Cl)cn2c1C(=O)NCC1CCCc2c1cnn2-c1ccc(OC(F)(F)F)cc1]

6-Chloro-2-ethyl-N-((1-(4-fluorophenyl)-4,5,6,7-tetrahydro-1H-indazol-4-yl)methyl) imidazo[1,2-a]pyridine-3-carboxamide (238)

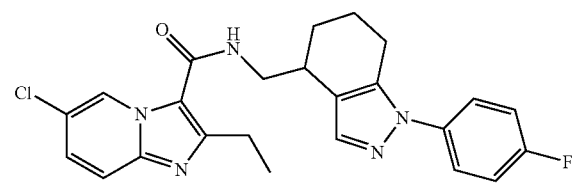 [SMILES: CCc1nc2ccc(Cl)cn2c1C(=O)NCC1CCCc2c1cnn2-c1ccc(F)cc1]

347

7-Chloro-2-ethyl-N-((4'-(trifluoromethoxy)biphenyl-3-yl)methyl)imidazo[1,2-a]pyridine-3-carboxamide (248)

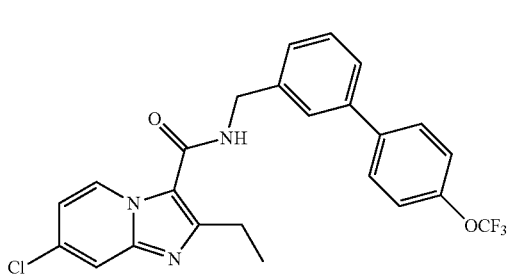 [SMILES: CCc1nc2cc(Cl)ccn2c1C(=O)NCc1cccc(-c2ccc(OC(F)(F)F)cc2)c1]

2-Ethyl-7-methyl-N-(4-(trifluoromethoxy)benzyl)imidazo[1,2-a]pyridine-3-carboxamide (249)

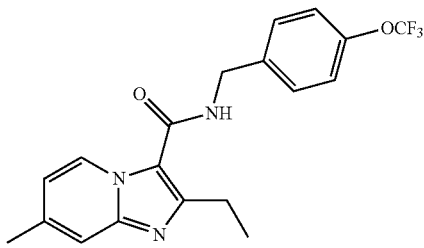 [SMILES: CCc1nc2cc(C)ccn2c1C(=O)NCc1ccc(OC(F)(F)F)cc1]

7-Bromo-2-ethyl-N-(4-(trifluoromethoxy)benzyl)imidazo[1,2-a]pyridine-3-carboxamide (250)

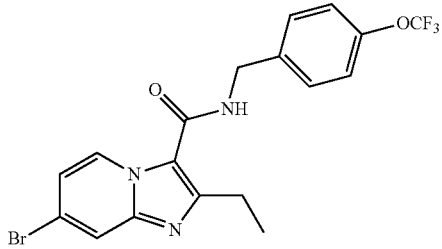

2-Ethyl-8-fluoro-N-(4-(trifluoromethoxy)benzyl)imidazo[1,2-a]pyridine-3-carboxamide (251)

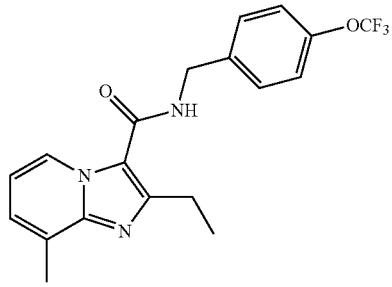 [SMILES: CCc1nc2c(C)cccn2c1C(=O)NCc1ccc(OC(F)(F)F)cc1]

348

7-Chloro-2-ethyl-N-((4'-formylbiphenyl-4-yl)methyl)imidazo[1,2-a]pyridine-3-carboxamide (252)

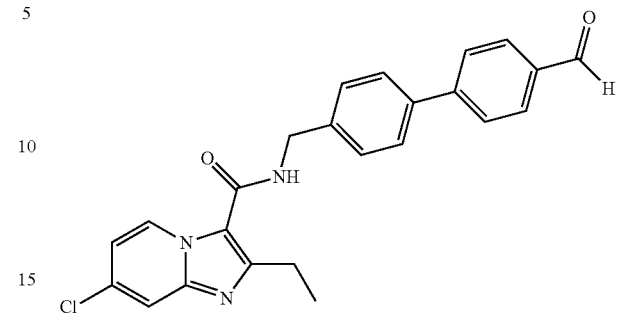

2-Ethyl-6-fluoro-N-(4-(4-(trifluoromethoxy)phenoxy)benzyl)imidazo[1,2-a]pyridine-3-carboxamide (253)

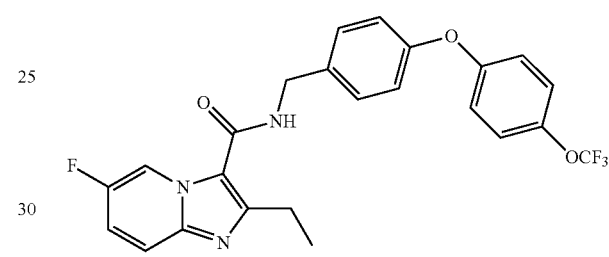

6-Bromo-2-ethyl-N-(4-(4-(trifluoromethoxy)phenoxy)benzyl)imidazo[1,2-a]pyridine-3-carboxamide (254)

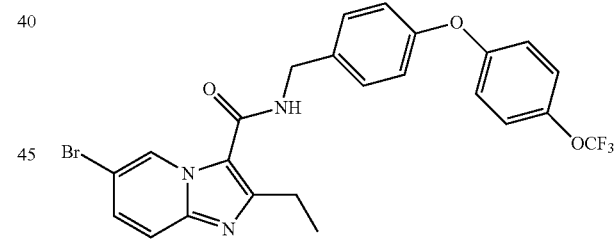

2-Ethyl-6-methyl-N-(4-(4-(trifluoromethoxy)phenoxy)benzyl)imidazo[1,2-a]pyridine-3-carboxamide (255)

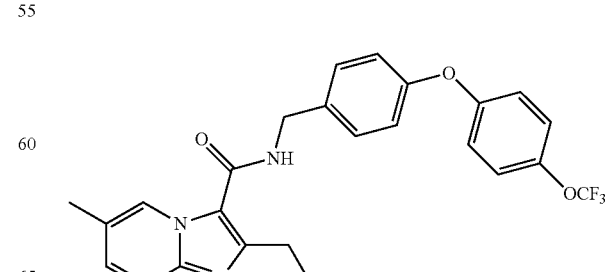

349

2-Ethyl-7-methyl-N-(4-(4-(trifluoromethoxy)phenoxy)benzyl)imidazo[1,2-a]pyridine-3-carboxamide (256)

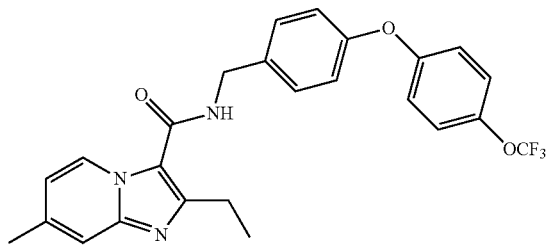 [SMILES: CCc1nc2cc(C)ccn2c1C(=O)NCc1ccc(Oc2ccc(OC(F)(F)F)cc2)cc1]

2-Ethyl-8-fluoro-N-(4-(4-(trifluoromethoxy)phenoxy)benzyl)imidazo[1,2-a]pyridine-3-carboxamide (257)

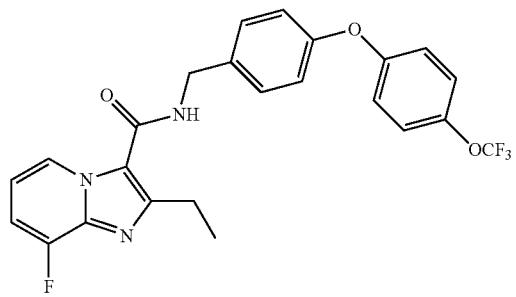 [SMILES: CCc1nc2c(F)cccn2c1C(=O)NCc1ccc(Oc2ccc(OC(F)(F)F)cc2)cc1]

2-Ethyl-6-fluoro-N-(4-(4-(trifluoromethoxy)benzyloxy)benzyl)imidazo[1,2-a]pyridine-3-carboxamide (258)

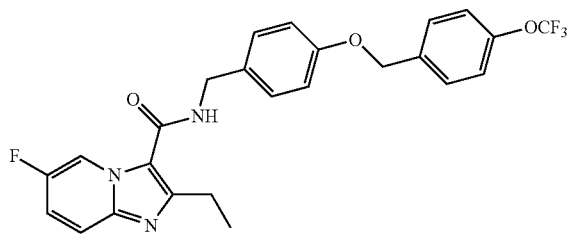 [SMILES: CCc1nc2ccc(F)cn2c1C(=O)NCc1ccc(OCc2ccc(OC(F)(F)F)cc2)cc1]

6-Bromo-2-ethyl-N-(4-(4-(trifluoromethoxy)benzyloxy)benzyl)imidazo[1,2-a]pyridine-3-carboxamide (259)

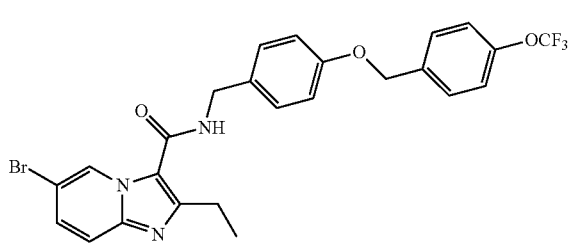 [SMILES: CCc1nc2ccc(Br)cn2c1C(=O)NCc1ccc(OCc2ccc(OC(F)(F)F)cc2)cc1]

2-Ethyl-N-(4-(4-(trifluoromethoxy)benzyloxy)benzyl)imidazo[1,2-a]pyridine-3-carboxamide (260)

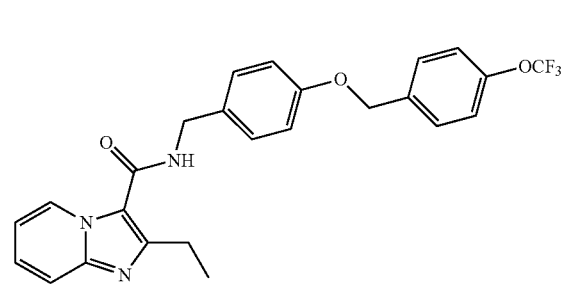 [SMILES: CCc1nc2ccccn2c1C(=O)NCc1ccc(/N=C/c2ccc(OC(F)(F)F)cc2)cc1]

350

(E)-7-Chloro-2-ethyl-N-(4-((4-(trifluoromethoxy)benzylidene)amino)benzyl)imidazo[1,2-a]pyridine-3-carboxamide (261)

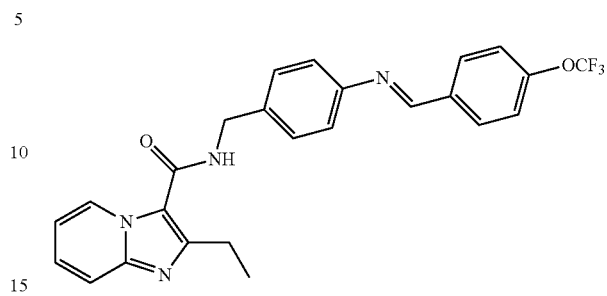

7-Chloro-2-ethyl-N-(4-((4-(trifluoromethoxy)benzyl)amino)benzyl)imidazo[1,2-a]pyridine-3-carboxamide (262)

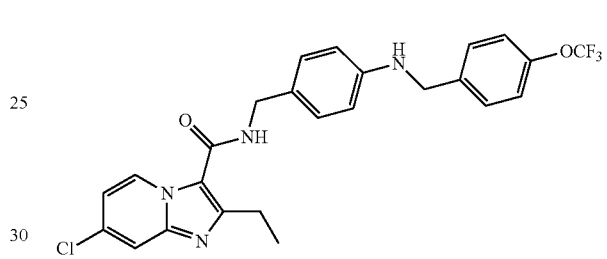

2-Ethyl-N-(4-(methyl(4-(trifluoromethoxy)benzyl)amino)benzyl)imidazo[1,2-a]pyridine-3-carboxamide (263)

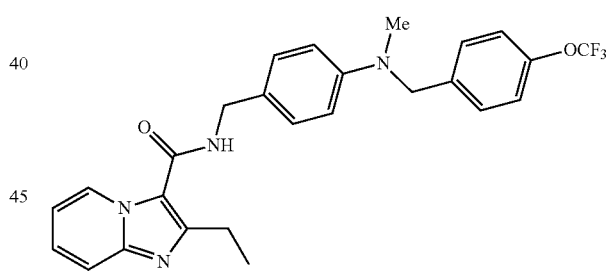

7-Chloro-2-ethyl-N-(4-(hexahydropyrrolo[1,2-a]pyrazin-2(1H)-yl)benzyl)imidazo[1,2-a]pyridine-3-carboxamide (265)

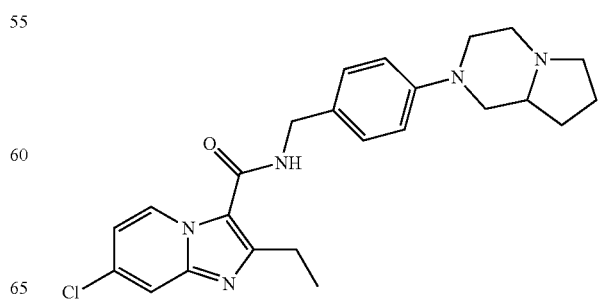

6-Chloro-2-ethyl-N-(4-(hexahydropyrrolo[1,2-a]pyrazin-2(1H)-yl)benzyl)imidazo[1,2-a]pyridine-3-carboxamide (266)

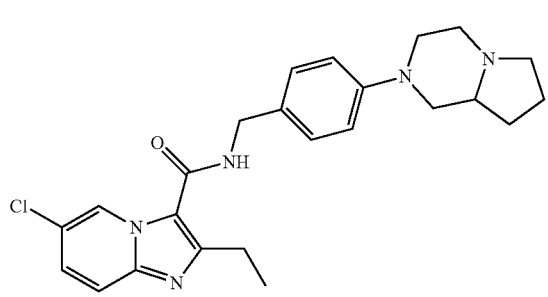 [SMILES: CCc1nc2ccc(Cl)cn2c1C(=O)NCc1ccc(N2CCN3CCCC3C2)cc1]

6-Chloro-2-ethyl-N-(4-(octahydroisoquinolin-2(1H)-yl)benzyl)imidazo[1,2-a]pyridine-3-carboxamide (267)

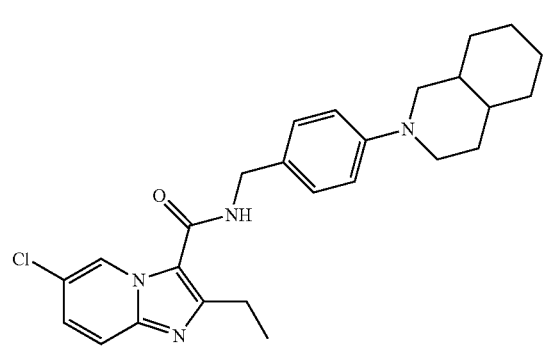 [SMILES: CCc1nc2ccc(Cl)cn2c1C(=O)NCc1ccc(N2CCC3CCCCC3C2)cc1]

7-Chloro-2-ethyl-N-(4-(octahydroisoquinolin-2(1H)-yl)benzyl)imidazo[1,2-a]pyridine-3-carboxamide (268)

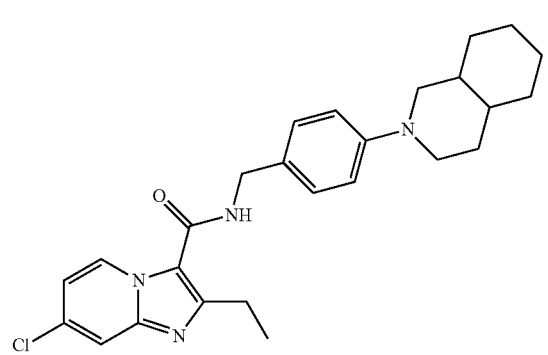 [SMILES: CCc1nc2cc(Cl)ccn2c1C(=O)NCc1ccc(N2CCC3CCCCC3C2)cc1]

7-Chloro-2-ethyl-N-(4-(4-oxopiperidin-1-yl)benzyl)imidazo[1,2-a]pyridine-3-carboxamide (269)

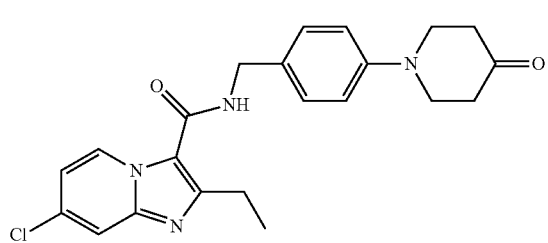 [SMILES: CCc1nc2cc(Cl)ccn2c1C(=O)NCc1ccc(N2CCC(=O)CC2)cc1]

7-Chloro-2-ethyl-N-(4-(4-oxo-3,4-dihydropyridin-1(2H)-yl)benzyl)imidazo[1,2-a]pyridine-3-carboxamide (270)

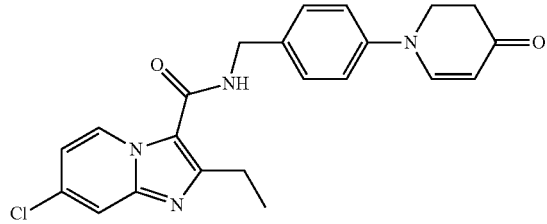 [SMILES: CCc1nc2cc(Cl)ccn2c1C(=O)NCc1ccc(N2C=CC(=O)CC2)cc1]

7-Chloro-2-ethyl-N-(4-(4-methylenepiperidin-1-yl)benzyl)imidazo[1,2-a]pyridine-3-carboxamide (271)

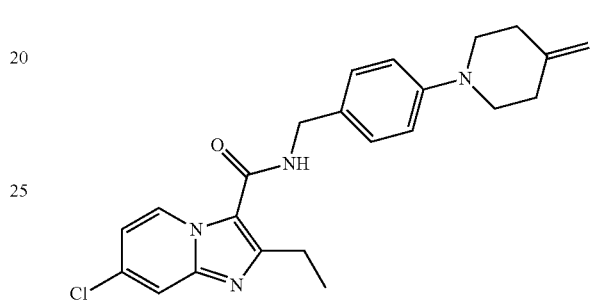

6-chloro-2-ethyl-N-(4-(2-methylpiperidin-1-yl)benzyl)imidazo[1,2-a]pyridine-3-carboxamide (272)

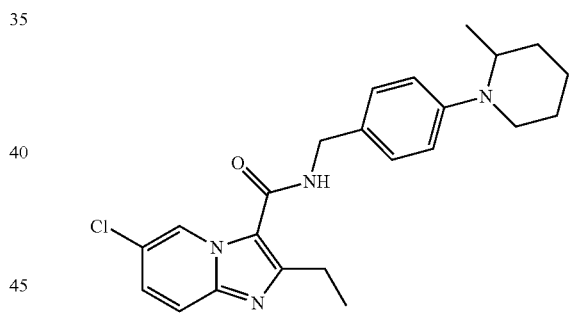

7-chloro-2-ethyl-N-(4-(2-methylpiperidin-1-yl)benzyl)imidazo[1,2-a]pyridine-3-carboxamide (273)

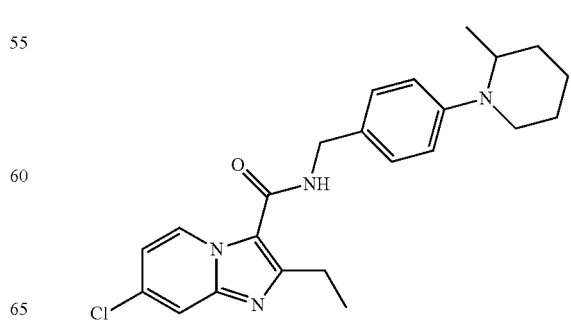

353

7-Chloro-N-(4-(4,4-dimethylpiperidin-1-yl)benzyl)-2-ethyl-1,8a-dihydroimidazo[1,2-a]pyridine-3-carboxamide (274)

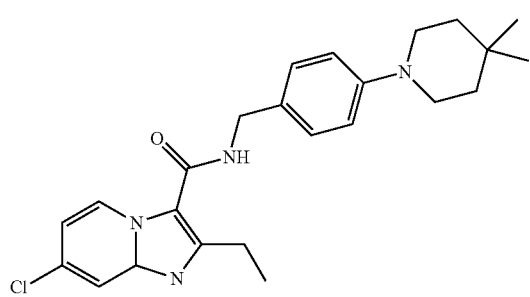 [SMILES: CCC1=C(C(=O)NCc2ccc(N3CCC(C)(C)CC3)cc2)N2C=CC(Cl)=CC2N1]

6-Chloro-2-ethyl-N-(4-(4-(trifluoromethyl)piperidin-1-yl)benzyl)imidazo[1,2-a]pyridine-3-carboxamide (275)

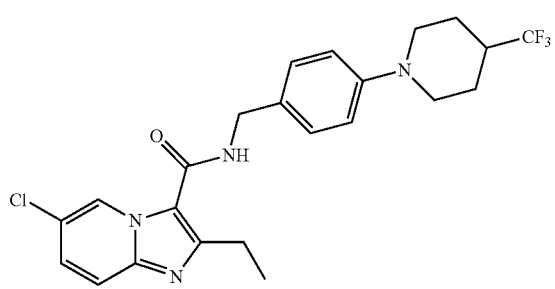 [SMILES: CCc1nc2ccc(Cl)cn2c1C(=O)NCc1ccc(N2CCC(C(F)(F)F)CC2)cc1]

7-Chloro-2-ethyl-N-(4-(4-(trifluoromethyl)piperidin-1-yl)benzyl)imidazo[1,2-a]pyridine-3-carboxamide (276)

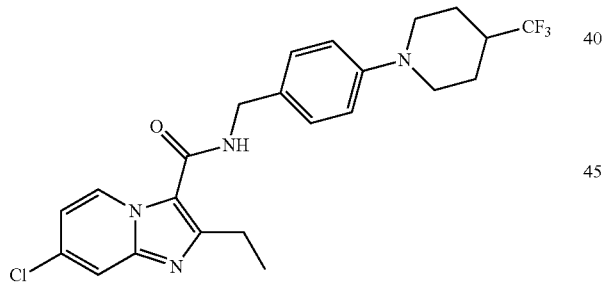

6-chloro-N-(4-(4,4-difluoropiperidin-1-yl)benzyl)-2-ethylimidazo[1,2-a]pyridine-3-carboxamide (277)

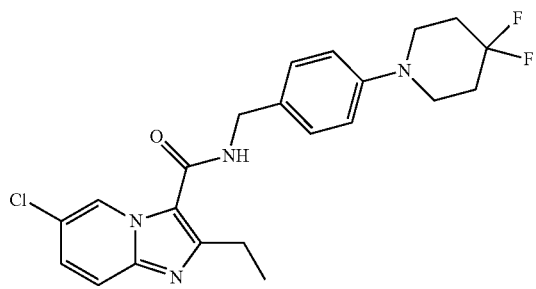 [SMILES: CCc1nc2ccc(Cl)cn2c1C(=O)NCc1ccc(N2CCC(F)(F)CC2)cc1]

354

7-Chloro-N-(4-(4,4-difluoropiperidin-1-yl)benzyl)-2-ethylimidazo[1,2-a]pyridine-3-carboxamide (278)

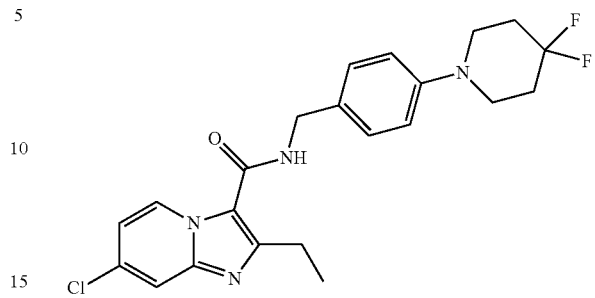

6-Chloro-2-ethyl-N-(4-(4-(hydroxymethyl)piperidin-1-yl)benzyl)imidazo[1,2-a]pyridine-3-carboxamide (279)

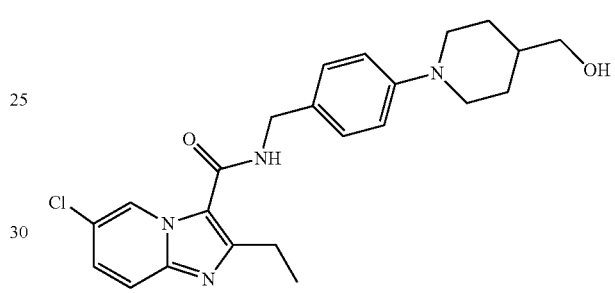

7-Chloro-2-ethyl-N-(4-(4-(hydroxymethyl)piperidin-1-yl)benzyl)imidazo[1,2-a]pyridine-3-carboxamide (280)

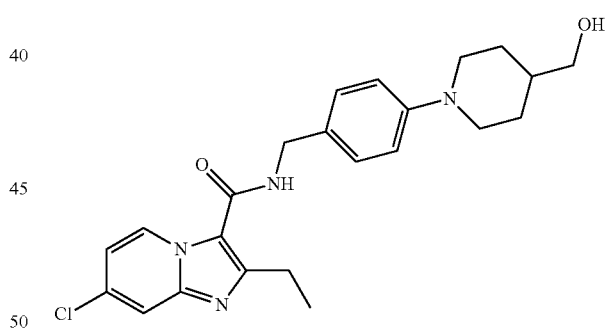

6-Chloro-2-ethyl-N-(4-(4-(methoxymethyl)piperidin-1-yl)benzyl)imidazo[1,2-a]pyridine-3-carboxamide (281)

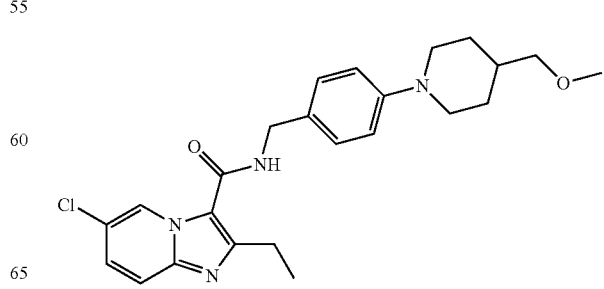

| 355 | 356 |

7-Chloro-2-ethyl-N-(4-(4-(methoxymethyl)piperidin-1-yl)benzyl)imidazo[1,2-a]pyridine-3-carboxamide (282)

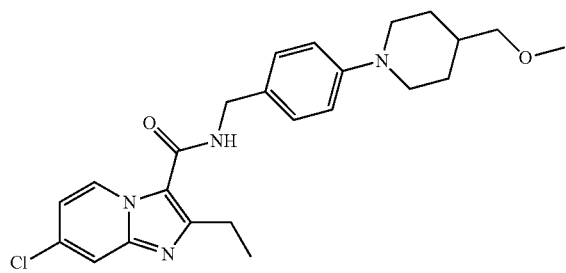 [SMILES: CCc1nc2cc(Cl)ccn2c1C(=O)NCc1ccc(N2CCC(COC)CC2)cc1]

6-Chloro-2-ethyl-N-(4-(4-(4-fluorophenyl)piperidin-1-yl)benzyl)imidazo[1,2-a]pyridine-3-carboxamide (286)

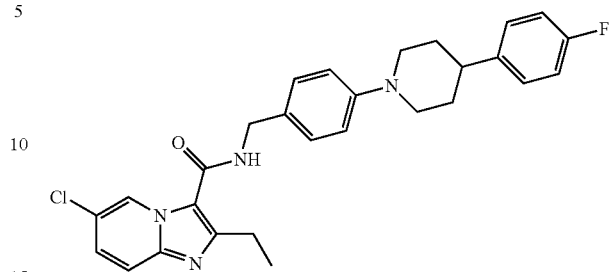

7-Chloro-2-ethyl-N-(4-(4-phenylpiperidin-1-yl)benzyl)imidazo[1,2-a]pyridine-3-carboxamide (283)

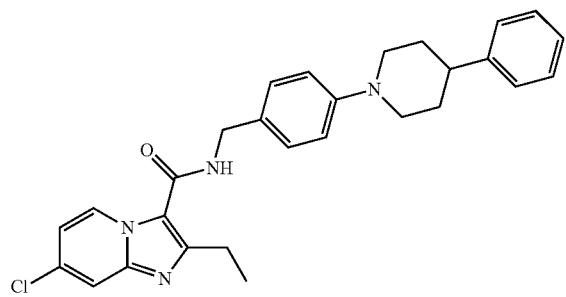

7-Chloro-2-ethyl-N-(4-(4-(4-fluorophenyl)piperidin-1-yl)benzyl)imidazo[1,2-a]pyridine-3-carboxamide (287)

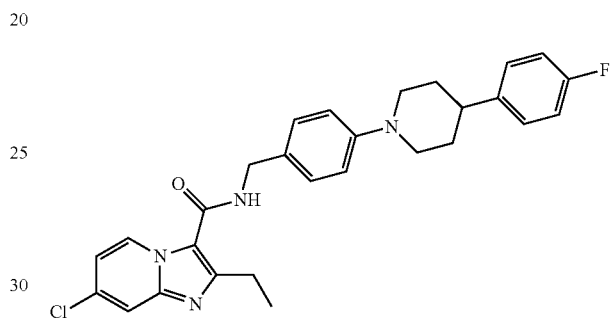

6-Chloro-2-ethyl-N-(4-(4-phenylpiperidin-1-yl)benzyl)imidazo[1,2-a]pyridine-3-carboxamide (284)

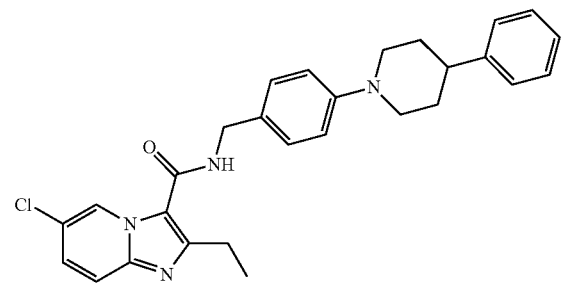 [SMILES: CCc1nc2ccc(Cl)cn2c1C(=O)NCc1ccc(N2CCC(c3ccccc3)CC2)cc1]

2-Ethyl-N-(4-(4-(4-(trifluoromethoxy)phenyl)piperidin-1-yl)benzyl)imidazo[1,2-a]pyridine-3-carboxamide (288)

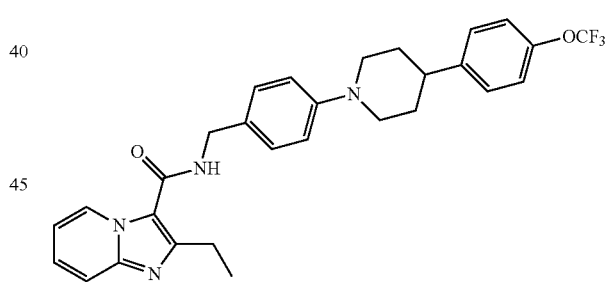

2-Ethyl-N-(4-(4-(4-fluorophenyl)piperidin-1-yl)benzyl)imidazo[1,2-a]pyridine-3-carboxamide (285)

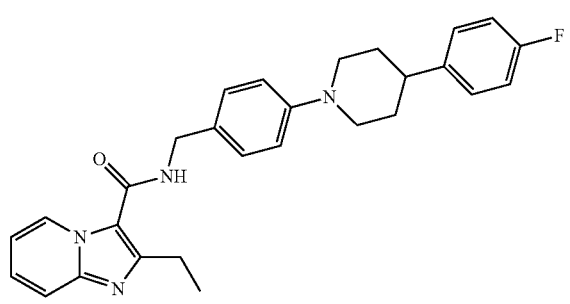

6-Chloro-2-ethyl-N-(4-(4-(4-(trifluoromethoxy)phenyl)piperidin-1-yl)benzyl)imidazo[1,2-a]pyridine-3-carboxamide (289)

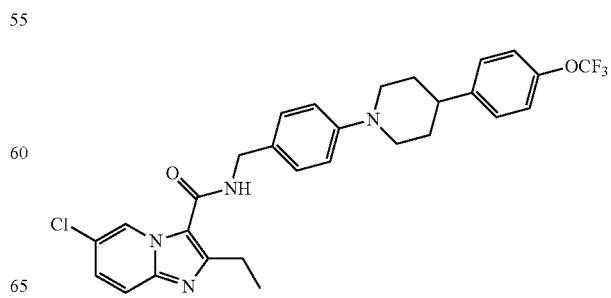

357

7-Chloro-2-ethyl-N-(4-(4-(4-(trifluoromethoxy)phenyl)piperidin-1-yl)benzyl)imidazo[1,2-a]pyridine-3-carboxamide (290)

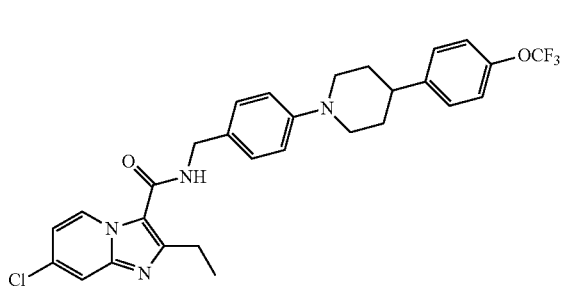 [SMILES: CCc1nc2cc(Cl)ccn2c1C(=O)NCc1ccc(N2CCC(c3ccc(OC(F)(F)F)cc3)CC2)cc1]

6-Chloro-2-ethyl-N-(4-(4-(isopropoxymethyl)piperidin-1-yl)benzyl)imidazo[1,2-a]pyridine-3-carboxamide (291)

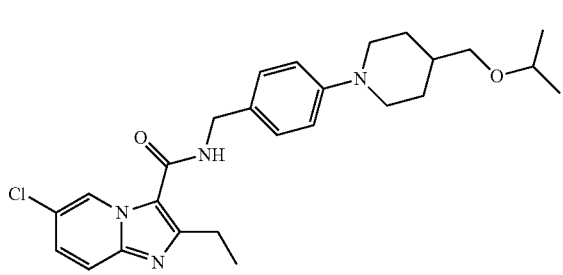 [SMILES: CCc1nc2ccc(Cl)cn2c1C(=O)NCc1ccc(N2CCC(COC(C)C)CC2)cc1]

7-Chloro-2-ethyl-N-(4-(4-(isopropoxymethyl)piperidin-1-yl)benzyl)imidazo[1,2-a]pyridine-3-carboxamide (292)

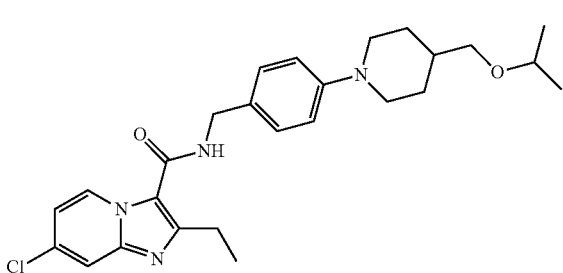 [SMILES: CCc1nc2cc(Cl)ccn2c1C(=O)NCc1ccc(N2CCC(COC(C)C)CC2)cc1]

6-Chloro-N-(4-(4-(cyclopentyloxymethyl)piperidin-1-yl)benzyl)-2-ethylimidazo[1,2-a]pyridine-3-carboxamide (293)

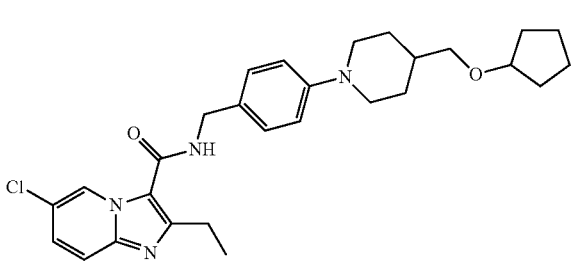 [SMILES: CCc1nc2ccc(Cl)cn2c1C(=O)NCc1ccc(N2CCC(COC3CCCC3)CC2)cc1]

358

N-(4-(4-Benzylpiperidin-1-yl)benzyl)-7-chloro-2-ethylimidazo[1,2-a]pyridine-3-carboxamide (294)

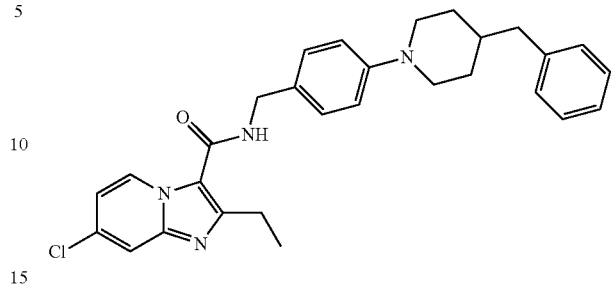

2-Ethyl-N-(4-(4-((4-fluorophenoxy)methyl)piperidin-1-yl)benzyl)imidazo[1,2-a]pyridine-3-carboxamide (295)

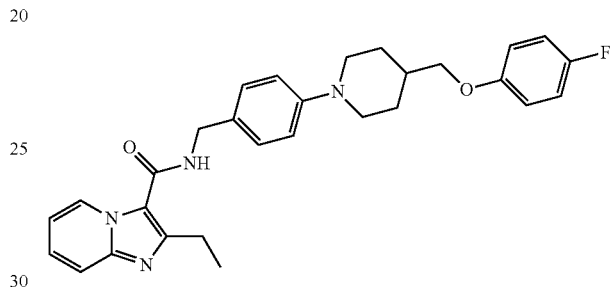

6-Chloro-2-ethyl-N-(4-(4-((4-fluorophenoxy)methyl)piperidin-1-yl)benzyl)imidazo[1,2-a]pyridine-3-carboxamide (296)

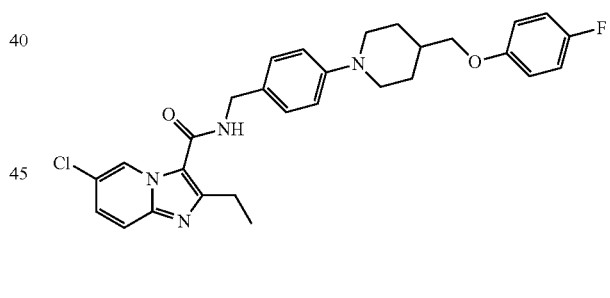

7-Chloro-2-ethyl-N-(4-(4-((4-fluorophenoxy)methyl)piperidin-1-yl)benzyl)imidazo[1,2-a]pyridine-3-carboxamide (297)

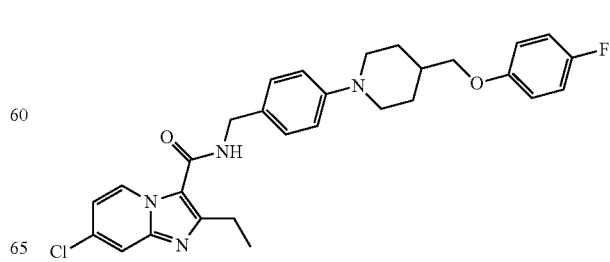

6-chloro-2-ethyl-N-(4-(4-((4-(trifluoromethoxy)phenoxy)methyl)piperidin-1-yl)benzyl)imidazo[1,2-a]pyridine-3-carboxamide (298)

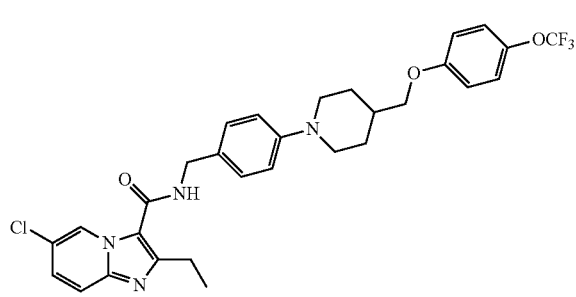 [SMILES: CCc1nc2ccc(Cl)cn2c1C(=O)NCc1ccc(N2CCC(COc3ccc(OC(F)(F)F)cc3)CC2)cc1]

7-Chloro-2-ethyl-N-(4-(4-((4-(trifluoromethoxy)phenoxy)methyl)piperidin-1-yl)benzyl)imidazo[1,2-a]pyridine-3-carboxamide (299)

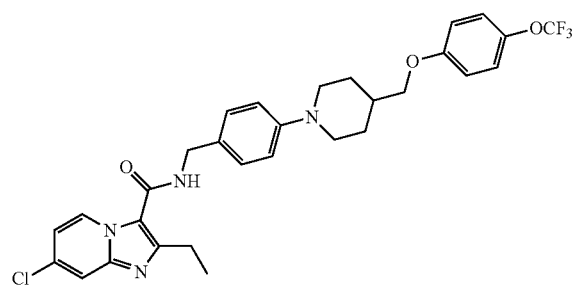 [SMILES: CCc1nc2cc(Cl)ccn2c1C(=O)NCc1ccc(N2CCC(COc3ccc(OC(F)(F)F)cc3)CC2)cc1]

Ethyl 1-(4-((6-chloro-2-ethylimidazo[1,2-a]pyridine-3-carboxamido)methyl)phenyl)piperidine-4-carboxylate (300)

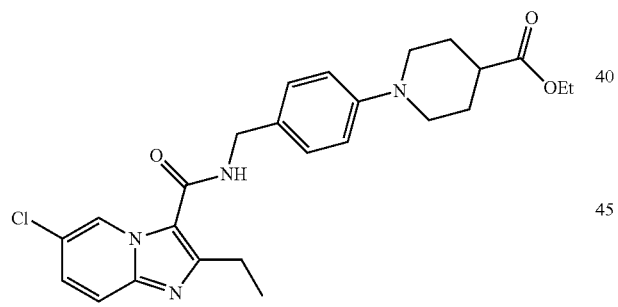

Ethyl 1-(4-((7-chloro-2-ethylimidazo[1,2-a]pyridine-3-carboxamido)methyl)phenyl)piperidine-4-carboxylate (301)

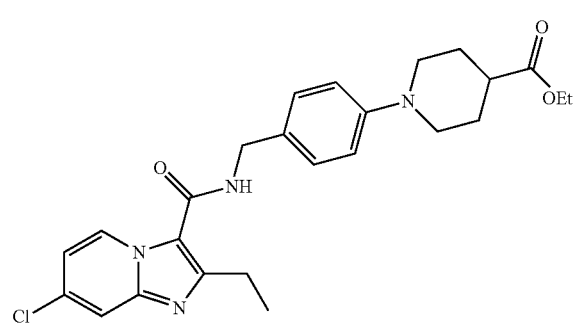 [SMILES: CCOC(=O)C1CCN(c2ccc(CNC(=O)c3c(CC)nc4cc(Cl)ccn34)cc2)CC1]

1-(4-((7-Chloro-2-ethyimidazo[1,2-a]pyridine-3-carboxamido)methyl)phenyl)piperidine-4-carboxylic acid (302)

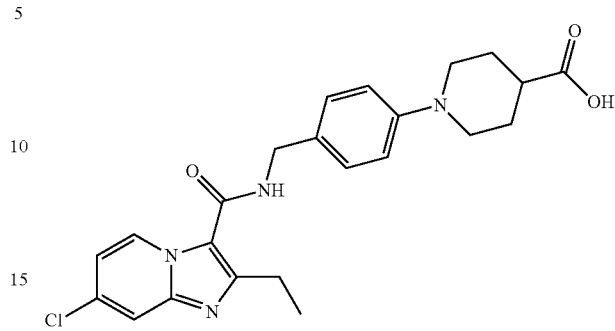

2-Ethyl-N-(4-(4-(4-fluorophenyl)piperazin-1-yl)benzyl)imidazo[1,2-a]pyridine-3-carboxamide (303)

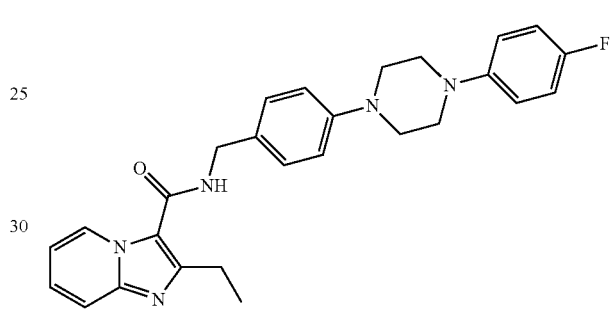

8-(Difluoromethoxy)-2-ethyl-N-(4-(4-(4-fluorophenyl)piperazin-1-yl)benzyl)imidazo[1,2-a]pyridine-3-carboxamide (304)

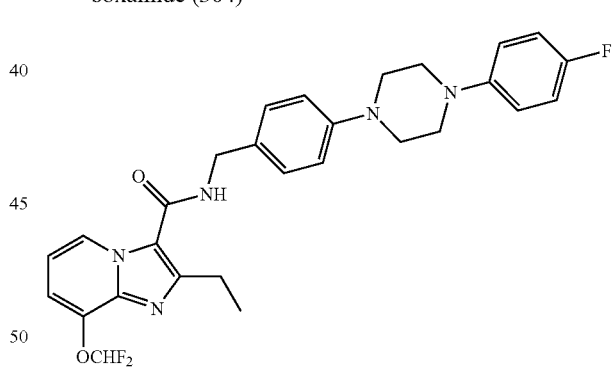

8-Bromo-2-ethyl-N-(4-(4-(4-fluorophenyl)piperazin-1-yl)benzyl)imidazo[1,2-a]pyridine-3-carboxamide (305)

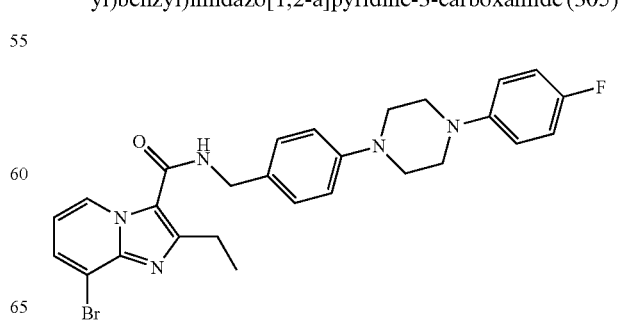

361

2-Ethyl-6-fluoro-N-(4-(4-(4-fluorophenyl)piperazin-1-yl)benzyl)imidazo[1,2-a]pyridine-3-carboxamide (306)

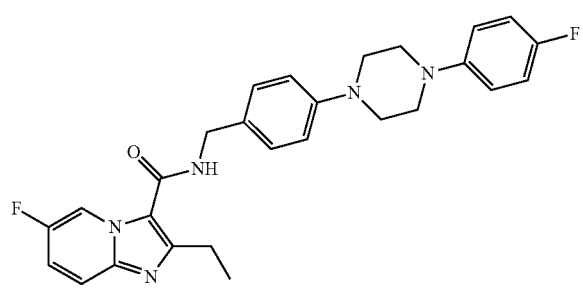 [SMILES: CCc1nc2ccc(F)cn2c1C(=O)NCc1ccc(N2CCN(c3ccc(F)cc3)CC2)cc1]

6-Bromo-2-ethyl-N-(4-(4-(4-fluorophenyl)piperazin-1-yl)benzyl)imidazo[1,2-a]pyridine-3-carboxamide (307)

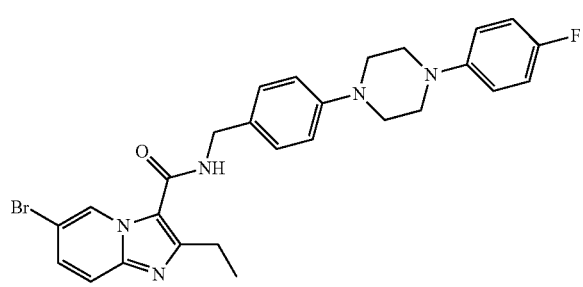

2-Ethyl-N-(4-(4-(4-fluorophenyl)piperazin-1-yl)benzyl)-6-methylimidazo[1,2-a]pyridine-3-carboxamide (308)

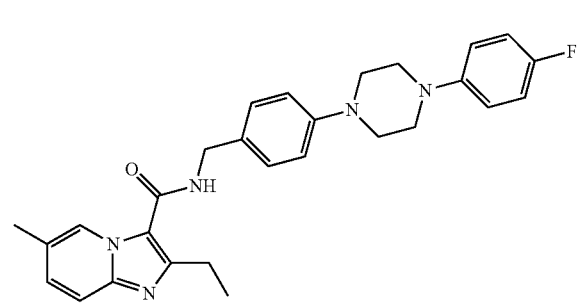 [SMILES: CCc1nc2ccc(C)cn2c1C(=O)NCc1ccc(N2CCN(c3ccc(F)cc3)CC2)cc1]

2-Ethyl-N-(4-(4-(4-fluorophenyl)piperazin-1-yl)benzyl)-7-methylimidazo[1,2-a]pyridine-3-carboxamide (309)

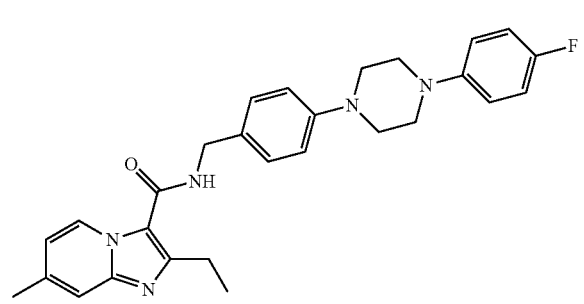 [SMILES: CCc1nc2cc(C)ccn2c1C(=O)NCc1ccc(N2CCN(c3ccc(F)cc3)CC2)cc1]

362

2-Ethyl-8-fluoro-N-(4-(4-(4-fluorophenyl)piperazin-1-yl)benzyl)imidazo[1,2-a]pyridine-3-carboxamide (310)

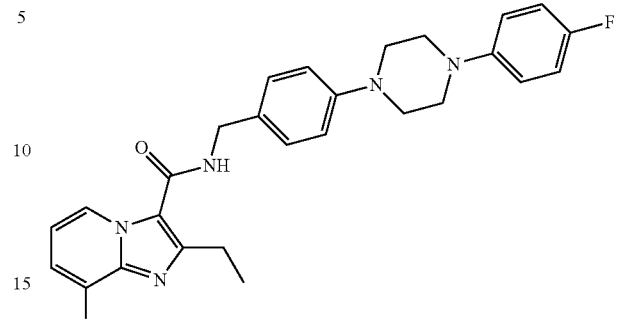

7-Bromo-2-ethyl-N-(4-(4-(4-fluorophenyl)piperazin-1-yl)benzyl)imidazo[1,2-a]pyridine-3-carboxamide (311)

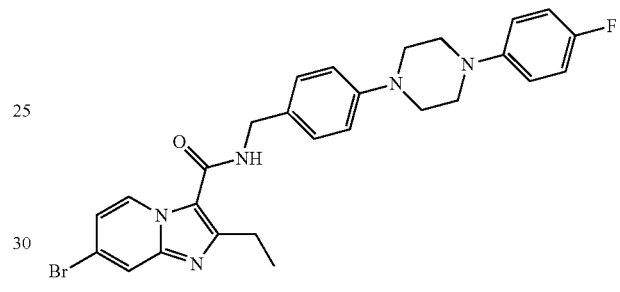

2-Ethyl-N-(4-(4-(4-fluorophenyl)piperazin-1-yl)benzyl)-8-(pyridin-4-yl)imidazo[1,2-a]pyridine-3-carboxamide (312)

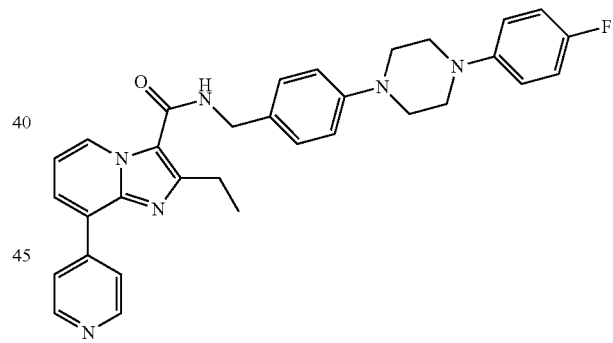

2-Ethyl-7-(4-phenylpiperazin-1-yl)-N-(4-(trifluoromethyl)benzyl)imidazo[1,2-a]pyridine-3-carboxamide (330)

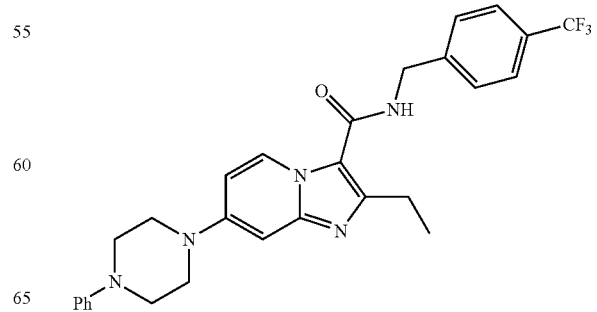

6-Chloro-2-ethyl-N-(4-((4-(morpholine-4-carbonyl)benzyl)carbamoyl)benzyl) imidazo[1,2-a]pyridine-3-carboxamide (332)

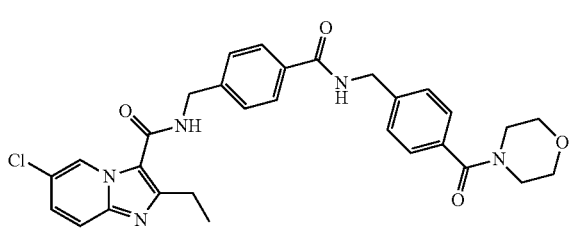 [SMILES: CCc1nc2ccc(Cl)cn2c1C(=O)NCc1ccc(C(=O)NCc2ccc(C(=O)N3CCOCC3)cc2)cc1]

7-Chloro-2-ethyl-N-(4-(morpholine-4-carbonyl)benzyl)imidazo[1,2-a]pyridine-3-carboxamide (333)

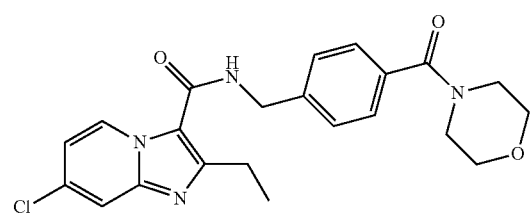 [SMILES: CCc1nc2cc(Cl)ccn2c1C(=O)NCc1ccc(C(=O)N2CCOCC2)cc1]

2-Ethyl-N-((2-(4-fluorophenyl)benzo[d]oxazol-5-yl)methyl)imidazo[1,2-a]pyridine-3-carboxamide (334)

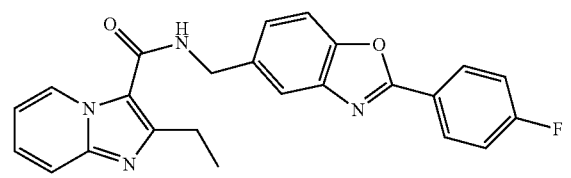 [SMILES: CCc1nc2ccccn2c1C(=O)NCc1ccc2oc(-c3ccc(F)cc3)nc2c1]

6-Chloro-2-ethyl-N-((2-(4-fluorophenyl)benzo[d]oxazol-5-yl)methyl)imidazo[1,2-a]pyridine-3-carboxamide (335)

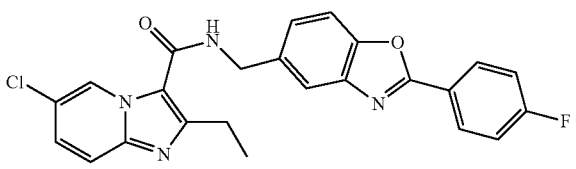 [SMILES: CCc1nc2ccc(Cl)cn2c1C(=O)NCc1ccc2oc(-c3ccc(F)cc3)nc2c1]

7-Chloro-2-ethyl-N-((2-(4-fluorophenyl)benzo[d]oxazol-5-yl)methyl)imidazo[1,2-a]pyridine-3-carboxamide (336)

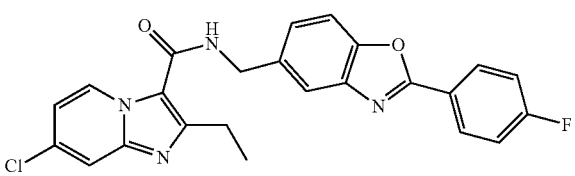 [SMILES: CCc1nc2cc(Cl)ccn2c1C(=O)NCc1ccc2oc(-c3ccc(F)cc3)nc2c1]

6-Chloro-N-(4-(4-(4-chlorophenyl)piperidin-1-yl)benzyl)-2-ethylimidazo[1,2-a]pyridine-3-carboxamide (337)

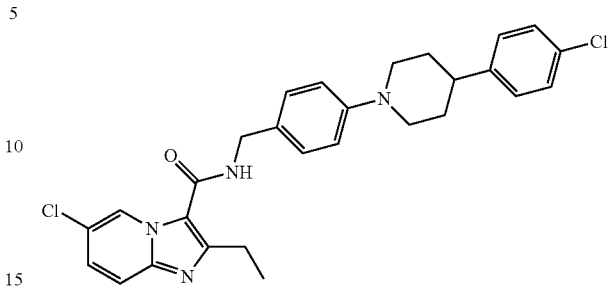

7-Chloro-N-(4-(4-(4-chlorophenyl)piperidin-1-yl)benzyl)-2-ethylimidazo[1,2-a]pyridine-3-carboxamide (338)

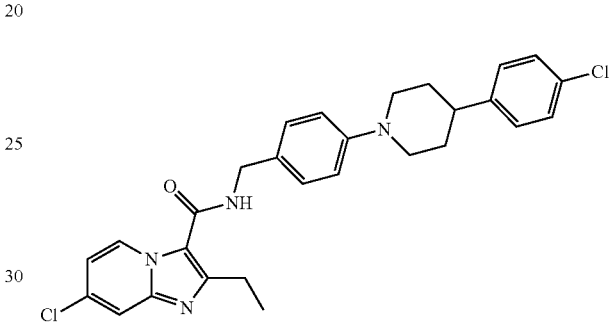

6-Chloro-N-((2-cyclohexylbenzo[d]oxazol-5-yl)methyl)-2-ethylimidazo[1,2-a]pyridine-3-carboxamide (339)

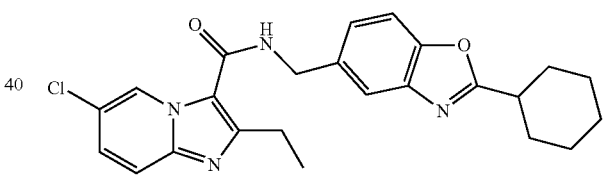

7-Chloro-N-((2-cyclohexylbenzo[d]oxazol-5-yl)methyl)-2-ethylimidazo[1,2-a]pyridine-3-carboxamide (340)

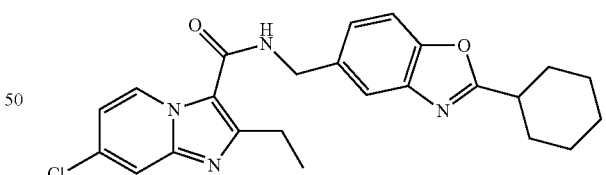

6-Chloro-2-ethyl-N-(4-(4-(4-fluorophenyl)-4-hydroxypiperidin-1-yl)benzyl)imidazo[1,2-a]pyridine-3-carboxamide (341)

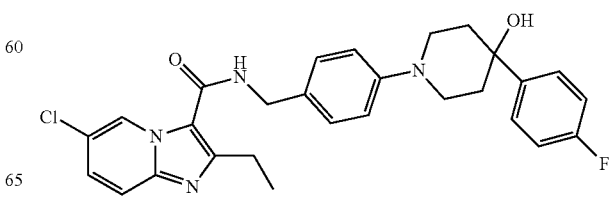

365

7-Chloro-2-ethyl-N-(4-(4-(4-fluorophenyl)-4-hydroxypiperidin-1-yl)benzyl)imidazo[1,2-a]pyridine-3-carboxamide (342)

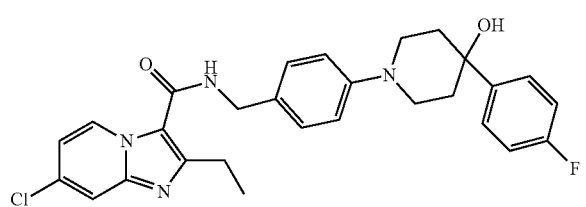 [SMILES: CCc1nc2cc(Cl)ccn2c1C(=O)NCc1ccc(N2CCC(O)(c3ccc(F)cc3)CC2)cc1]

N-(4-(4-Carbamoylpiperidin-1-yl)benzyl)-6-chloro-2-ethylimidazo[1,2-a]pyridine-3-carboxamide (343)

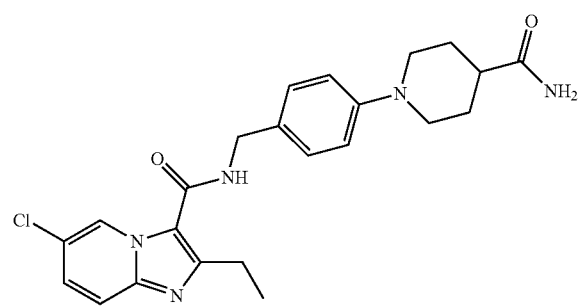 [SMILES: CCc1nc2ccc(Cl)cn2c1C(=O)NCc1ccc(N2CCC(C(N)=O)CC2)cc1]

N-(4-(4-Carbamoylpiperidin-1-yl)benzyl)-7-chloro-2-ethylimidazo[1,2-a]pyridine-3-carboxamide (344)

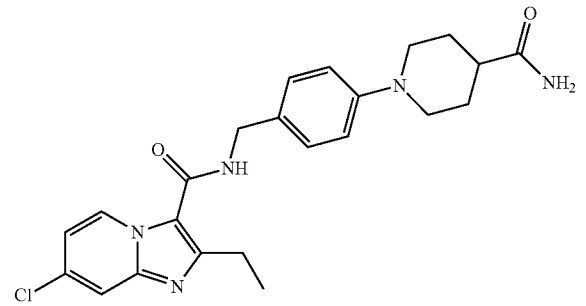 [SMILES: CCc1nc2cc(Cl)ccn2c1C(=O)NCc1ccc(N2CCC(C(N)=O)CC2)cc1]

6-Chloro-N-(4-(4-(dimethylcarbamoyl)piperidin-1-yl)benzyl)-2-ethylimidazo[1,2-a]pyridine-3-carboxamide (345)

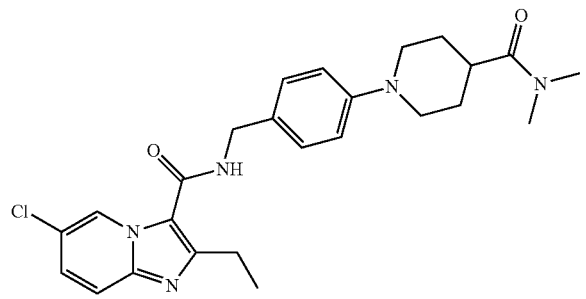 [SMILES: CCc1nc2ccc(Cl)cn2c1C(=O)NCc1ccc(N2CCC(C(=O)N(C)C)CC2)cc1]

366

7-Chloro-N-(4-(4-(dimethylcarbamoyl)piperidin-1-yl)benzyl)-2-ethylimidazo[1,2-a]pyridine-3-carboxamide (346)

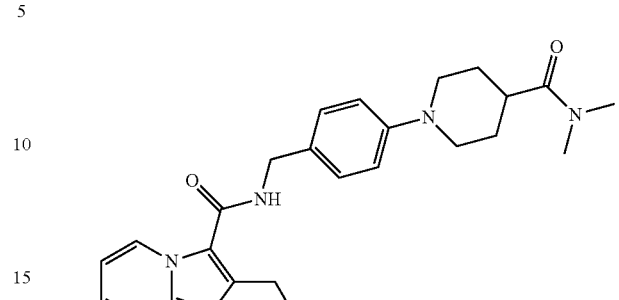

6-Chloro-2-ethyl-N-(4-(4-(4-fluorobenzyloxy)piperidin-1-yl)benzyl)imidazo[1,2-a]pyridine-3-carboxamide (347)

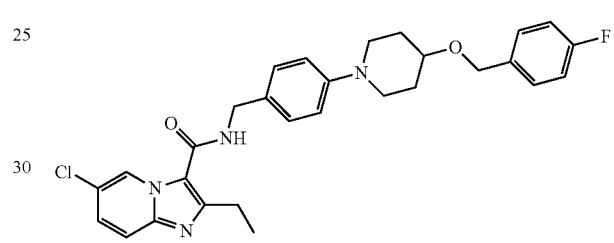

7-Chloro-2-ethyl-N-(4-(4-(4-fluorobenzyloxy)piperidin-1-yl)benzyl)imidazo[1,2-a]pyridine-3-carboxamide (348)

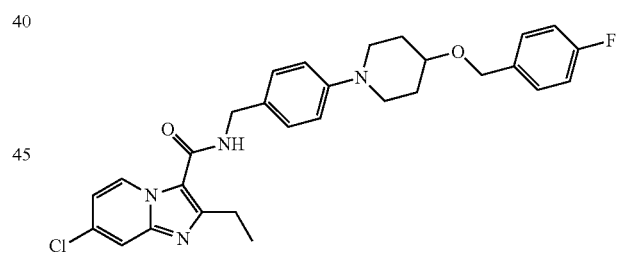

6-Chloro-N-(3-chloro-4-morpholinobenzyl)-2-ethylimidazo[1,2-a]pyridine-3-carboxamide (349)

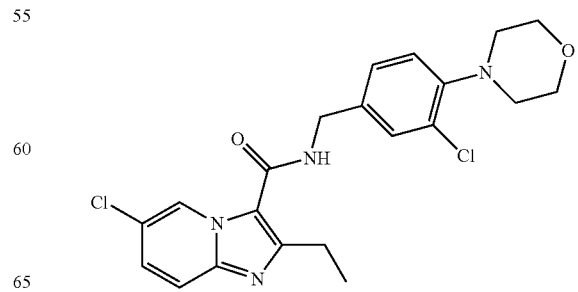

7-Chloro-N-(3-chloro-4-morpholinobenzyl)-2-ethylimidazo[1,2-a]pyridine-3-carboxamide (350)

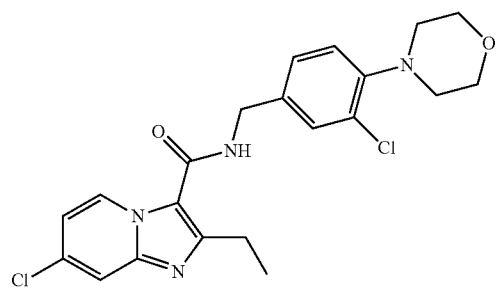 [SMILES: CCc1nc2cc(Cl)ccn2c1C(=O)NCc1ccc(N2CCOCC2)c(Cl)c1]

6-Chloro-2-ethyl-N-(4-(4-formylpiperidin-1-yl)benzyl)imidazo[1,2-a]pyridine-3-carboxamide (351)

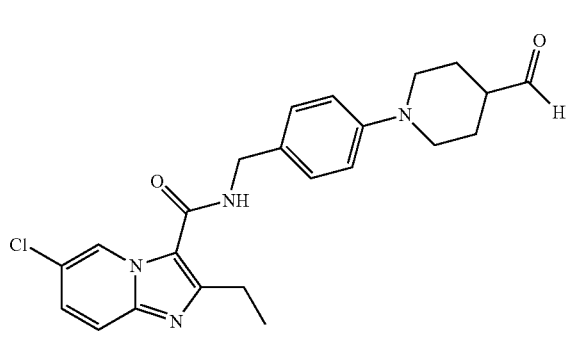 [SMILES: CCc1nc2ccc(Cl)cn2c1C(=O)NCc1ccc(N2CCC(C=O)CC2)cc1]

7-Chloro-2-ethyl-N-(4-(4-formylpiperidin-1-yl)benzyl)imidazo[1,2-a]pyridine-3-carboxamide (352)

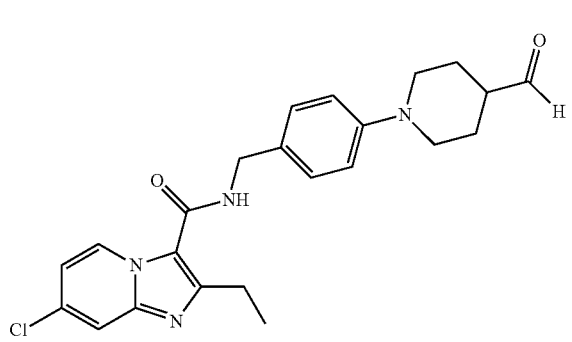 [SMILES: CCc1nc2cc(Cl)ccn2c1C(=O)NCc1ccc(N2CCC(C=O)CC2)cc1]

or a pharmaceutically acceptable salt thereof.

4. The compound according to claim 3, having one of the formulae 47, 54, 177 and 185, or a pharmaceutically acceptable salt thereof:

N-(Biphenyl-4-ylmethyl)-2-ethylimidazo[1,2-a]pyridine-3-carboxamide (47)

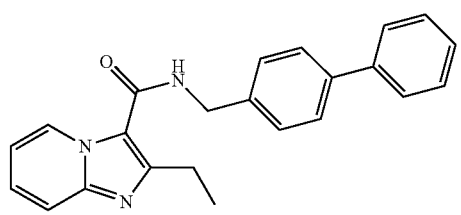 [SMILES: CCc1nc2ccccn2c1C(=O)NCc1ccc(-c2ccccc2)cc1]

2-Ethyl-N-(4-phenoxybenzyl)imidazo[1,2-a]pyridine-3-carboxamide (54)

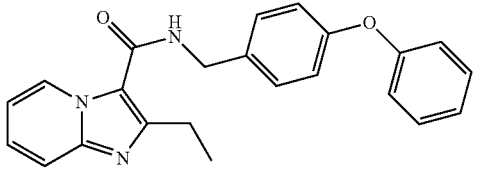 [SMILES: CCc1nc2ccccn2c1C(=O)NCc1ccc(Oc2ccccc2)cc1]

7-Chloro-2-ethyl-N-(4-(4-(4-fluorophenyl)piperazin-1-yl)benzyl)imidazo[1,2-a]pyridine-3-carboxamide trihydrochloride (177)

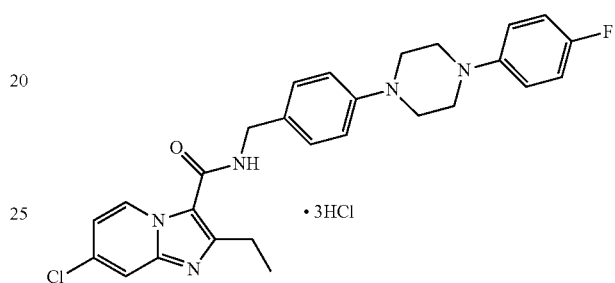

6-Chloro-2-ethyl-N-(4-(4-(trifluoromethoxy)phenoxy)benzyl)imidazo[1,2-a]pyridine-3-carboxamide (185)

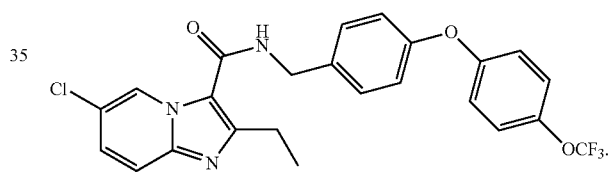

5. A pharmaceutical composition comprising a compound according to claim 2, and a pharmaceutically acceptable carrier.

6. A method of treatment of a bacterial infection, comprising the application of a suitable amount of a compound according to claim 1, to a person in need thereof.

7. A compound that competitively inhibits the specific binding of a compound according to claim 2.

8. A method of treatment of a bacterial infection, comprising the application, to a person in need of such treatment, of a suitable amount of a compound, which compound is characterized by an ability to competitively inhibit the specific binding of a compound according to claim 1 to a target protein.

9. The method, according to claim 6, used for the treatment of tuberculosis.

10. The method, according to claim 8, used for the treatment of tuberculosis.

11. The compound, according to claim 3, having a formula selected from formulae 15, 16, 44, 45, 47, 49, 54-57, 60-67, 70-73, 75-78, 81-87, 92-103, 106, 107, 110, 111, 113, 116-135, 137-141, 144, 147, 148, 152, 154, 157-159, 162-167, 171-182, 184-193, 198, 199-202, 209, 210, 214-218, 223-227, 231, 248-260, 262, 263, 267-269, 271-274, 280-293, 295-312 and 330:

2-Methyl-N-(4-phenoxybenzyl)imidazo[1,2-a]pyridine-3-carboxamide (15)

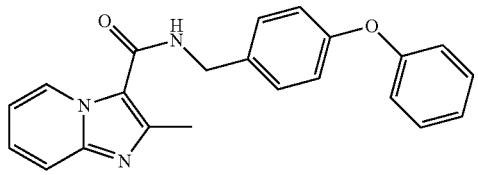 [SMILES: Cc1nc2ccccn2c1C(=O)NCc1ccc(Oc2ccccc2)cc1]

N-(Biphenyl-4-ylmethyl)-2-methylimidazo[1,2-a]pyridine-3-carboxamide (16)

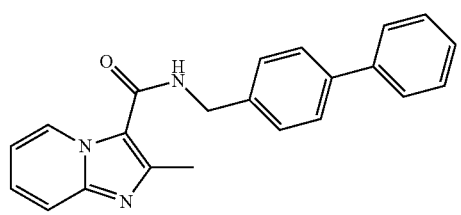 [SMILES: Cc1nc2ccccn2c1C(=O)NCc1ccc(-c2ccccc2)cc1]

N-(Biphenyl-4-ylmethyl)-6-chloro-2-methylimidazo[1,2-a]pyridine-3-carboxamide (44)

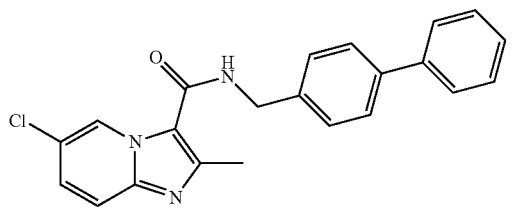 [SMILES: Cc1nc2ccc(Cl)cn2c1C(=O)NCc1ccc(-c2ccccc2)cc1]

N-(Biphenyl-4-ylmethyl)-7-chloro-2-methylimidazo[1,2-a]pyridine-3-carboxamide (45)

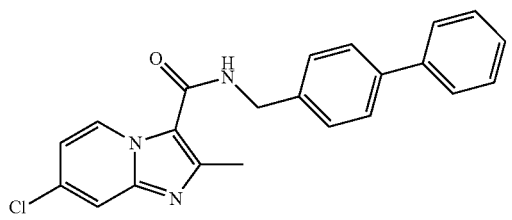 [SMILES: Cc1nc2cc(Cl)ccn2c1C(=O)NCc1ccc(-c2ccccc2)cc1]

N-(Biphenyl-4-ylmethyl)-2-ethylimidazo[1,2-a]pyridine-3-carboxamide (47)

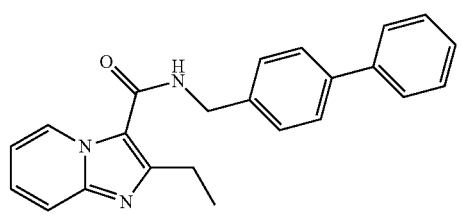 [SMILES: CCc1nc2ccccn2c1C(=O)NCc1ccc(-c2ccccc2)cc1]

N-(Biphenyl-4-ylmethyl)-2-propylimidazo[1,2-a]pyridine-3-carboxamide (49)

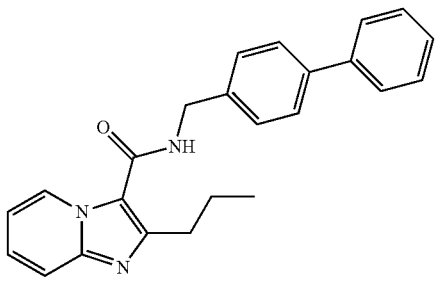 [SMILES: CCCc1nc2ccccn2c1C(=O)NCc1ccc(-c2ccccc2)cc1]

2-Ethyl-N-(4-phenoxybenzyl)imidazo[1,2-a]pyridine-3-carboxamide (54)

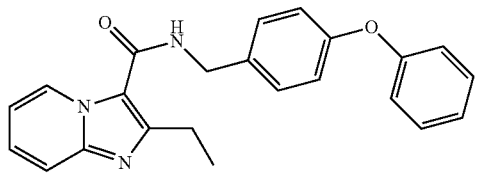 [SMILES: CCc1nc2ccccn2c1C(=O)NCc1ccc(Oc2ccccc2)cc1]

N-(4-tert-Butylbenzyl)-2-ethylimidazo[1,2-a]pyridine-3-carboxamide (55)

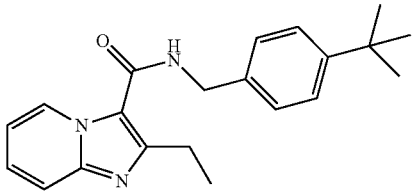 [SMILES: CCc1nc2ccccn2c1C(=O)NCc1ccc(C(C)(C)C)cc1]

2-Ethyl-N-((1-methyl-1H-indol-5-yl)methyl)imidazo[1,2-a]pyridine-3-carboxamide (56)

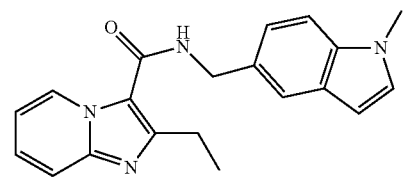 [SMILES: CCc1nc2ccccn2c1C(=O)NCc1ccc2c(ccn2C)c1]

2-Ethyl-N-(4-(trifluoromethoxy)benzyl)imidazo[1,2-a]pyridine-3-carboxamide (57)

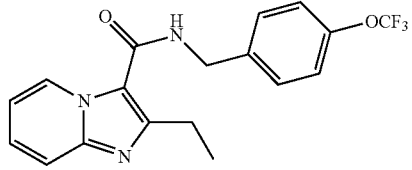 [SMILES: CCc1nc2ccccn2c1C(=O)NCc1ccc(OC(F)(F)F)cc1]

2-Ethyl-N-(4-isopropoxybenzyl)imidazo[1,2-a]pyridine-3-carboxamide (60)

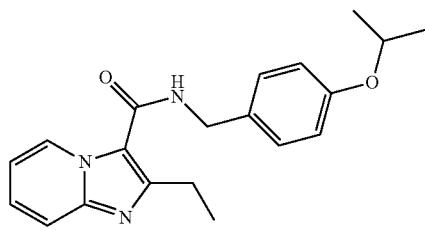 [SMILES: CCc1nc2ccccn2c1C(=O)NCc1ccc(OC(C)C)cc1]

2-Ethyl-N-(4-isobutoxybenzyl)imidazo[1,2-a]pyridine-3-carboxamide (61)

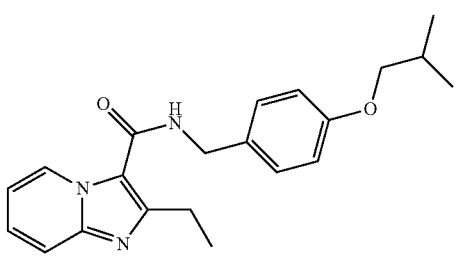 [SMILES: CCc1nc2ccccn2c1C(=O)NCc1ccc(OCC(C)C)cc1]

N-(Biphenyl-4-ylmethyl)-2-ethyl-6-methylimidazo[1,2-a]pyridine-3-carboxamide (62)

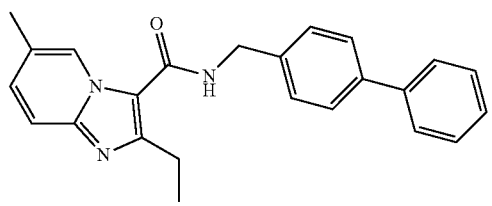 [SMILES: CCc1nc2ccc(C)cn2c1C(=O)NCc1ccc(-c2ccccc2)cc1]

2-Ethyl-6-methyl-N-(4-phenoxybenzyl)imidazo[1,2-a]pyridine-3-carboxamide (63)

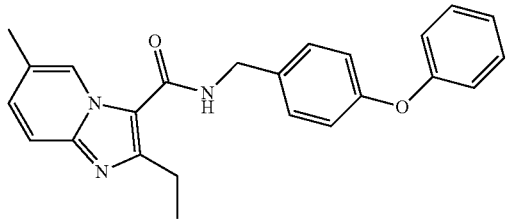 [SMILES: CCc1nc2ccc(C)cn2c1C(=O)NCc1ccc(Oc2ccccc2)cc1]

N-(4-tert-Butylbenzyl)-2-ethyl-6-methylimidazo[1,2-a]pyridine-3-carboxamide (64)

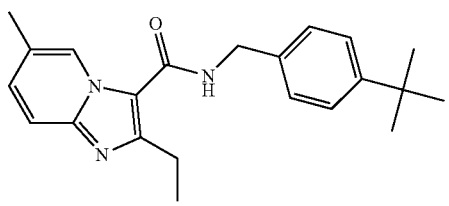

2-Ethyl-6-methyl-N-(4-(trifluoromethoxy)benzyl)imidazo[1,2-a]pyridine-3-carboxamide (65)

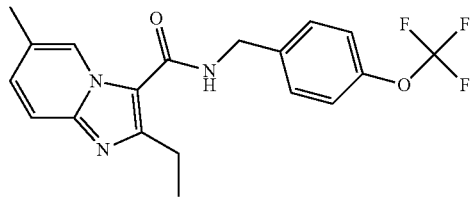 [SMILES: CCc1nc2ccc(C)cn2c1C(=O)NCc1ccc(OC(F)(F)F)cc1]

2-Ethyl-6-methyl-N-((1-methyl-1H-indol-5-yl)methyl)imidazo[1,2-a]pyridine-3-carboxamide (66)

2-Ethyl-6-methyl-N-((1-methyl-1H-indol-6-yl)methyl)imidazo[1,2-a]pyridine-3-carboxamide (67)

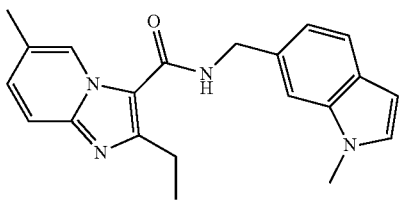 [SMILES: CCc1nc2ccc(C)cn2c1C(=O)NCc1ccc2ccn(C)c2c1]

6-Chloro-N-(4-chlorobenzyl)-2-ethylimidazo[1,2-a]pyridine-3-carboxamide (70)

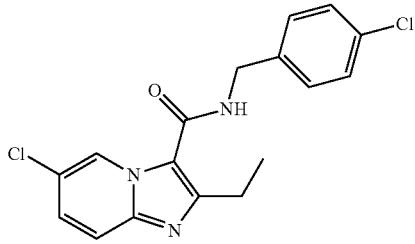 [SMILES: CCc1nc2ccc(Cl)cn2c1C(=O)NCc1ccc(Cl)cc1]

6-Chloro-2-methyl-N-(4-phenoxybenzyl)imidazo[1,2-a]pyridine-3-carboxamide (71)

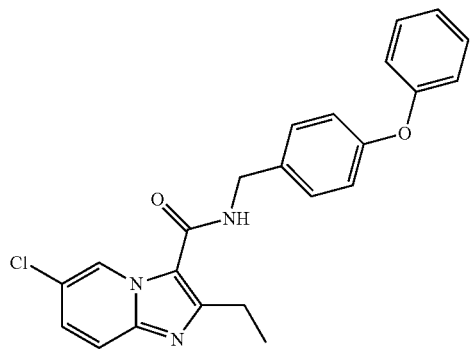 [SMILES: CCc1nc2ccc(Cl)cn2c1C(=O)NCc1ccc(Oc2ccccc2)cc1]

6-Chloro-2-methyl-N-(4-(trifluoromethoxy)benzyl)imidazo[1,2-a]pyridine-3-carboxamide (72)

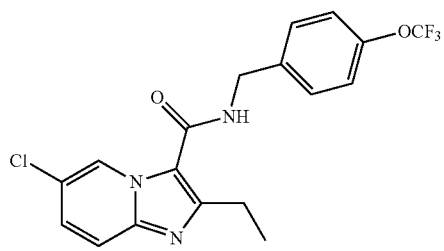 [SMILES: CCc1nc2ccc(Cl)cn2c1C(=O)NCc1ccc(OC(F)(F)F)cc1]

N-(4-tert-Butylbenzyl)-6-chloro-2-methylimidazo[1,2-a]pyridine-3-carboxamide (73)

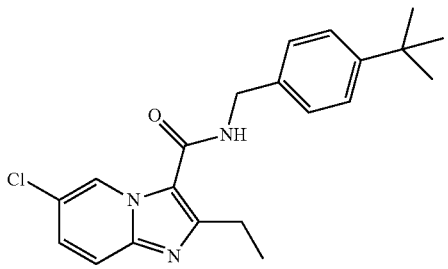 [SMILES: CCc1nc2ccc(Cl)cn2c1C(=O)NCc1ccc(C(C)(C)C)cc1]

6-Chloro-N-(4-isopropoxybenzyl)-2-methylimidazo[1,2-a]pyridine-3-carboxamide (75)

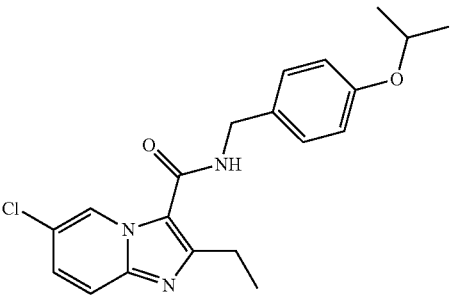 [SMILES: CCc1nc2ccc(Cl)cn2c1C(=O)NCc1ccc(OC(C)C)cc1]

6-Chloro-N-(4-isobutoxybenzyl)-2-methylimidazo[1,2-a]pyridine-3-carboxamide (76)

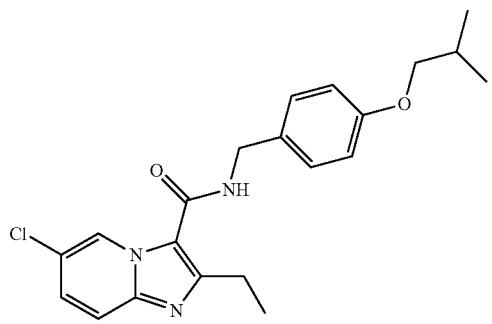 [SMILES: CCc1nc2ccc(Cl)cn2c1C(=O)NCc1ccc(OCC(C)C)cc1]

6-Chloro-2-methyl-N-((1-methyl-1H-indol-5-yl)methyl)imidazo[1,2-a]pyridine-3-carboxamide (77)

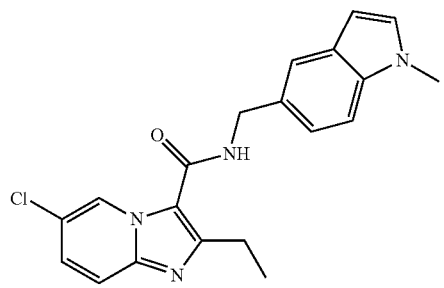 [SMILES: CCc1nc2ccc(Cl)cn2c1C(=O)NCc1ccc2c(ccn2C)c1]

6-Chloro-2-methyl-N-((1-methyl-1H-indol-6-yl)methyl)imidazo[1,2-a]pyridine-3-carboxamide (78)

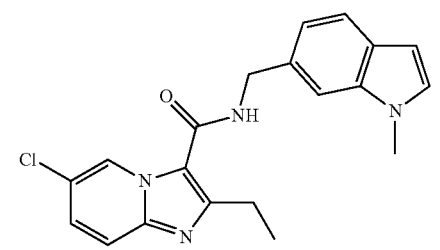 [SMILES: CCc1nc2ccc(Cl)cn2c1C(=O)NCc1ccc2ccn(C)c2c1]

N-(Biphenyl-4-ylmethyl)-6-chloro-2-methylimidazo[1,2-a]pyridine-3-carboxamide (81)

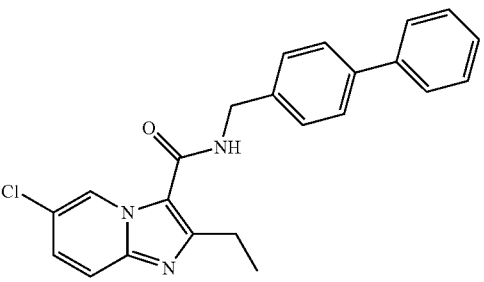

6-Chloro-N-((2'-chlorobiphenyl-4-yl)methyl)-2-ethylimidazo[1,2-a]pyridine-3-carboxamide (82)

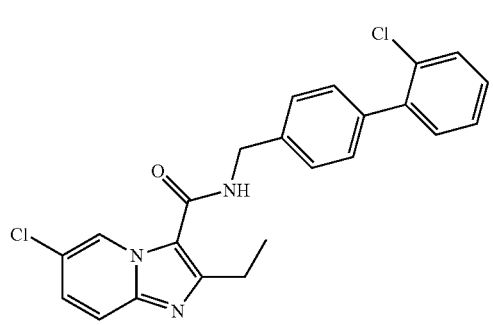

6-Chloro-N-((4'-chlorobiphenyl-4-yl)methyl)-2-ethylimidazo[1,2-a]pyridine-3-carboxamide (83)

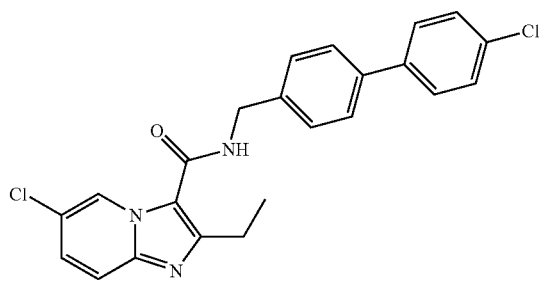 [SMILES: CCc1nc2ccc(Cl)cn2c1C(=O)NCc1ccc(-c2ccc(Cl)cc2)cc1]

6-Chloro-2-ethyl-N-((2'-methylbiphenyl-4-yl)methyl)imidazo[1,2-a]pyridine-3-carboxamide (84)

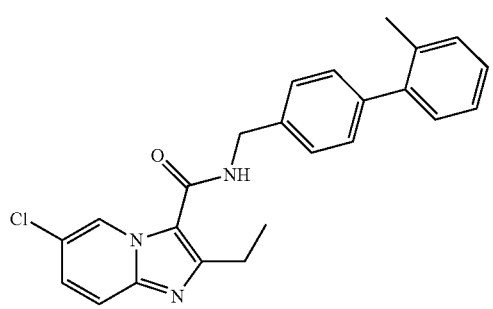 [SMILES: CCc1nc2ccc(Cl)cn2c1C(=O)NCc1ccc(-c2ccccc2C)cc1]

6-Chloro-2-ethyl-N-((3'-methylbiphenyl-4-yl)methyl)imidazo[1,2-a]pyridine-3-carboxamide (85)

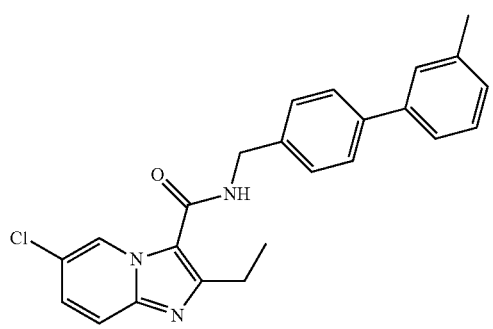 [SMILES: CCc1nc2ccc(Cl)cn2c1C(=O)NCc1ccc(-c2cccc(C)c2)cc1]

6-Chloro-2-ethyl-N-((4'-methylbiphenyl-4-yl)methyl)imidazo[1,2-a]pyridine-3-carboxamide (86)

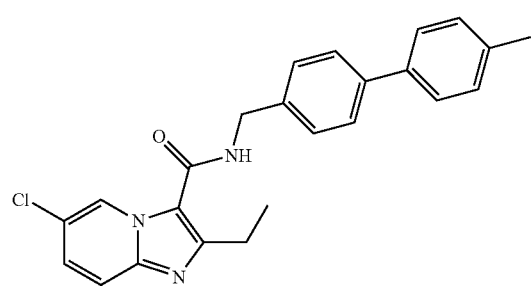 [SMILES: CCc1nc2ccc(Cl)cn2c1C(=O)NCc1ccc(-c2ccc(C)cc2)cc1]

7-Chloro-N-(4-chlorobenzyl)-2-ethylimidazo[1,2-a]pyridine-3-carboxamide (87)

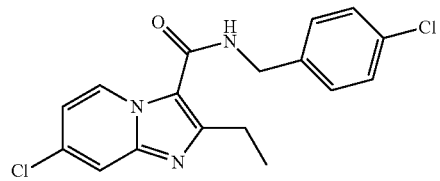 [SMILES: CCc1nc2cc(Cl)ccn2c1C(=O)NCc1ccc(Cl)cc1]

N-(4-tert-Butylbenzyl)-7-chloro-2-ethylimidazo[1,2-a]pyridine-3-carboxamide (92)

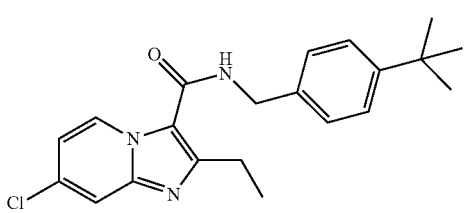 [SMILES: CCc1nc2cc(Cl)ccn2c1C(=O)NCc1ccc(C(C)(C)C)cc1]

N-(Biphenyl-4-ylmethyl)-7-chloro-2-ethylimidazo[1,2-a]pyridine-3-carboxamide (93)

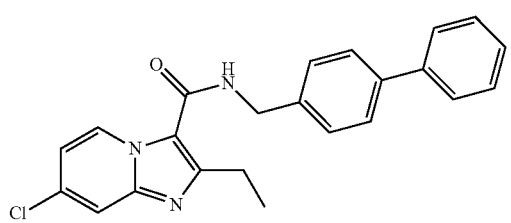 [SMILES: CCc1nc2cc(Cl)ccn2c1C(=O)NCc1ccc(-c2ccccc2)cc1]

7-Chloro-N-((2'-chlorobiphenyl-4-yl)methyl)-2-ethylimidazo[1,2-a]pyridine-3-carboxamide (94)

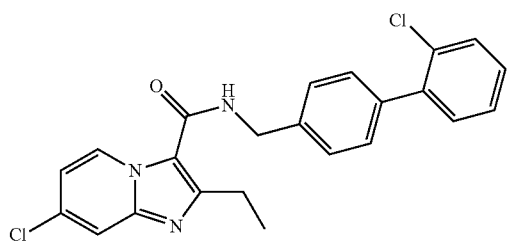

7-Chloro-N-((4'-chlorobiphenyl-4-yl)methyl)-2-ethylimidazo[1,2-a]pyridine-3-carboxamide (95)

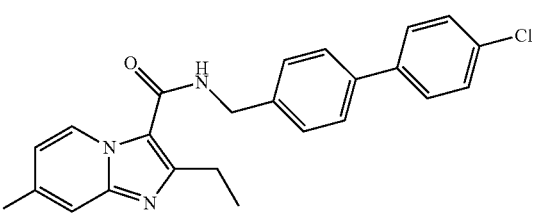

7-Chloro-2-ethyl-N-((2'-methylbiphenyl-4-yl)methyl)imidazo[1,2-a]pyridine-3-carboxamide (96)

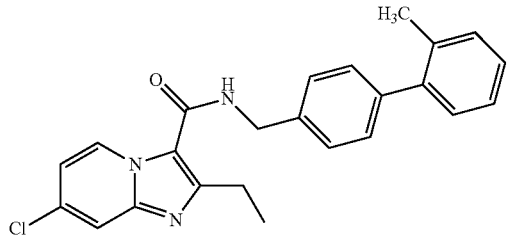

7-Chloro-2-ethyl-N-((3'-methylbiphenyl-4-yl)methyl)imidazo[1,2-a]pyridine-3-carboxamide (97)

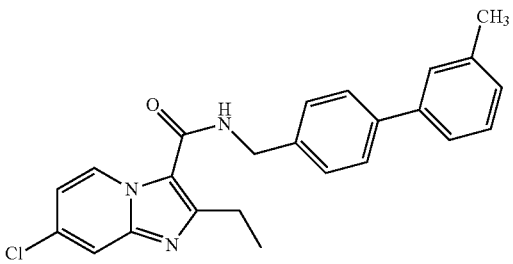 [SMILES: CCc1nc2cc(Cl)ccn2c1C(=O)NCc1ccc(-c2cccc(C)c2)cc1]

7-Chloro-2-ethyl-N-((4'-methylbiphenyl-4-yl)methyl)imidazo[1,2-a]pyridine-3-carboxamide (98)

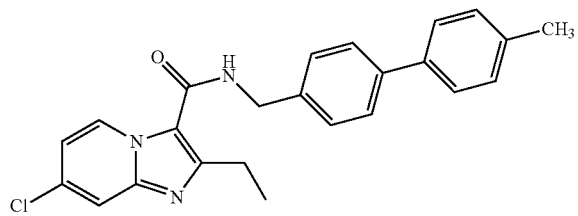 [SMILES: CCc1nc2cc(Cl)ccn2c1C(=O)NCc1ccc(-c2ccc(C)cc2)cc1]

N-(Biphenyl-4-ylmethyl)-6-chloro-2-(trifluoromethyl)imidazo[1,2-a]pyridine-3-carboxamide (99)

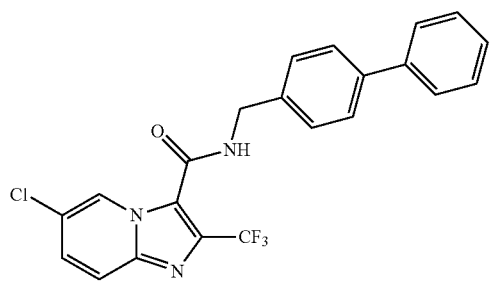 [SMILES: O=C(NCc1ccc(-c2ccccc2)cc1)c1c(C(F)(F)F)nc2ccc(Cl)cn12]

N-(4-tert-Butylbenzyl)-6-chloro-2-(trifluoromethyl)imidazo[1,2-a]pyridine-3-carboxamide (100)

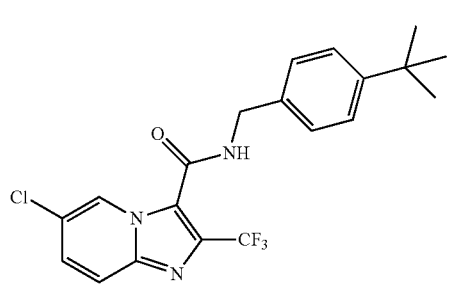 [SMILES: CC(C)(C)c1ccc(CNC(=O)c2c(C(F)(F)F)nc3ccc(Cl)cn23)cc1]

N-(4-Bromobenzyl)-7-chloro-2-ethylimidazo[1,2-a]pyridine-3-carboxamide (101)

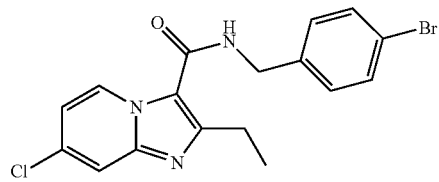 [SMILES: CCc1nc2cc(Cl)ccn2c1C(=O)NCc1ccc(Br)cc1]

7-Chloro-2-ethyl-N-(4-(trifluoromethoxy)benzyl)imidazo[1,2-a]pyridine-3-carboxamide (102)

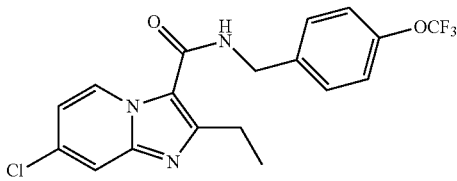 [SMILES: CCc1nc2cc(Cl)ccn2c1C(=O)NCc1ccc(OC(F)(F)F)cc1]

2-Ethyl-6-fluoro-N-(4-(trifluoromethoxy)benzyl)imidazo[1,2-a]pyridine-3-carboxamide (103)

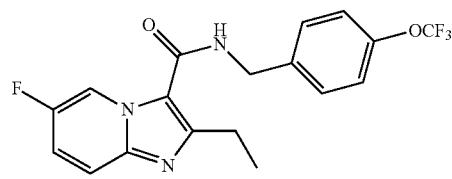 [SMILES: CCc1nc2ccc(F)cn2c1C(=O)NCc1ccc(OC(F)(F)F)cc1]

7-Chloro-2-ethyl-N-(4-(propylamino)benzyl)imidazo[1,2-a]pyridine-3-carboxamide (106)

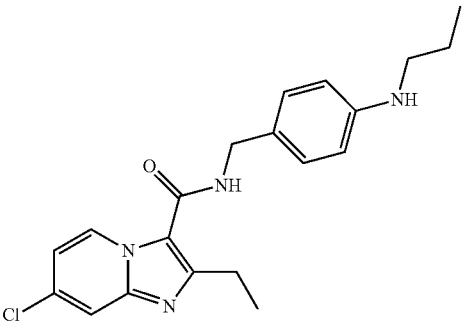 [SMILES: CCCNc1ccc(CNC(=O)c2c(CC)nc3cc(Cl)ccn23)cc1]

7-Chloro-2-ethyl-N-(4-(pentylamino)benzyl)imidazo[1,2-a]pyridine-3-carboxamide (107)

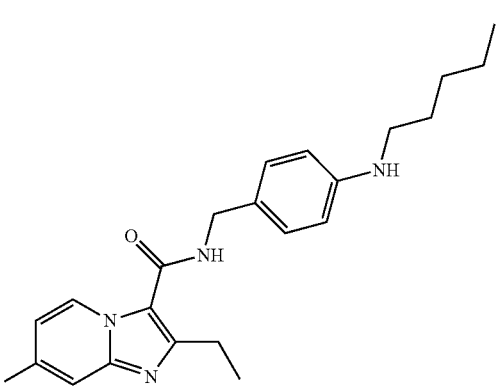

7-Chloro-2-ethyl-N-(4-(4-isopropylpiperazin-1-yl)benzyl)imidazo[1,2-a]pyridine-3-carboxamide (110)

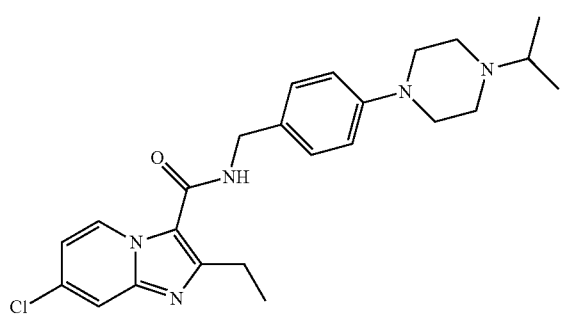 [SMILES: CCc1nc2cc(Cl)ccn2c1C(=O)NCc1ccc(N2CCN(C(C)C)CC2)cc1]

7-Chloro-2-ethyl-N-(4-(4-phenylpiperazin-1-yl)benzyl)imidazo[1,2-a]pyridine-3-carboxamide (111)

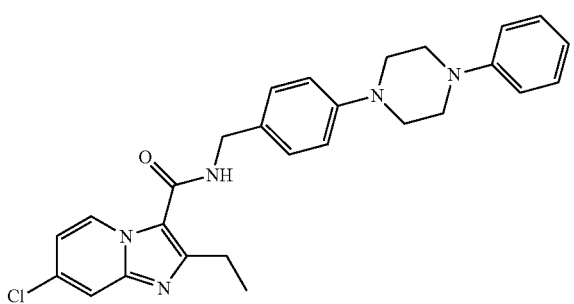

6-Chloro-2-ethyl-N-(4-(4-(4-fluorophenyl)piperazin-1-yl)benzyl)imidazo[1,2-a]pyridine-3-carboxamide (113)

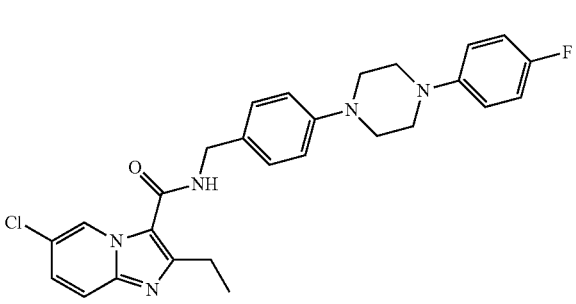 [SMILES: CCc1nc2ccc(Cl)cn2c1C(=O)NCc1ccc(N2CCN(c3ccc(F)cc3)CC2)cc1]

7-Chloro-2-ethyl-N-((4'-fluorobiphenyl-4-yl)methyl)imidazo[1,2-a]pyridine-3-carboxamide (116)

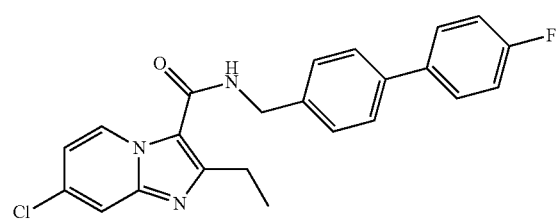 [SMILES: CCc1nc2cc(Cl)ccn2c1C(=O)NCc1ccc(-c2ccc(F)cc2)cc1]

N-((4'-tert-Butylbiphenyl-4-yl)methyl)-7-chloro-2-ethylimidazo[1,2-a]pyridine-3-carboxamide (117)

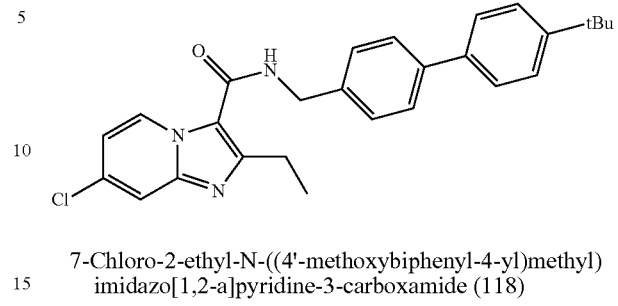

7-Chloro-2-ethyl-N-((4'-methoxybiphenyl-4-yl)methyl)imidazo[1,2-a]pyridine-3-carboxamide (118)

7-Chloro-2-ethyl-N-((4'-(trifluoromethoxy)biphenyl-4-yl)methyl)imidazo[1,2-a]pyridine-3-carboxamide (119)

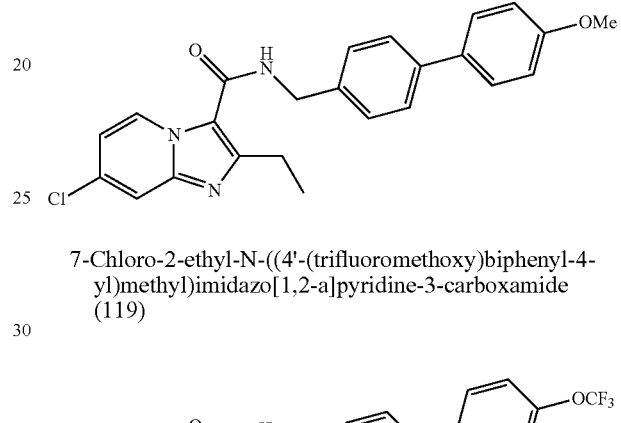

7-Chloro-2-ethyl-N-((4'-(trifluoromethyl)biphenyl-4-yl)methyl)imidazo[1,2-a]pyridine-3-carboxamide (120)

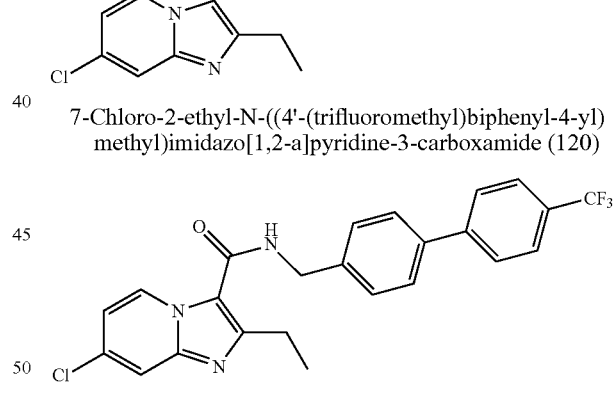

6-Chloro-N-((4'-cyanobiphenyl-4-yl)methyl)-2-ethylimidazo[1,2-a]pyridine-3-carboxamide (121)

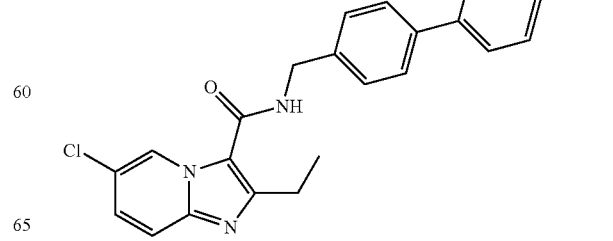

7-Chloro-N-((4'-cyanobiphenyl-4-yl)methyl)-2-ethylimidazo[1,2-a]pyridine-3-carboxamide (122)

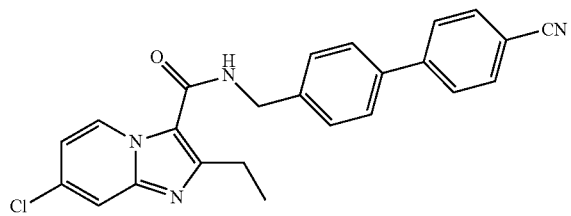 [SMILES: CCc1nc2cc(Cl)ccn2c1C(=O)NCc1ccc(-c2ccc(C#N)cc2)cc1]

6-Chloro-2-ethyl-N-((2'-(trifluoromethyl)biphenyl-4-yl)methyl)imidazo[1,2-a]pyridine-3-carboxamide (123)

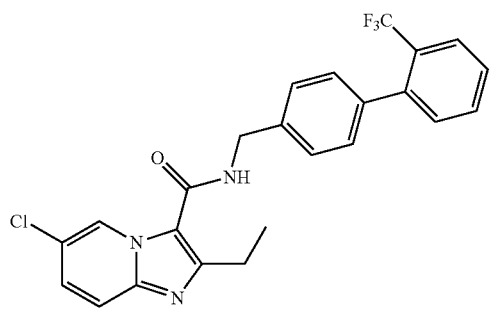 [SMILES: CCc1nc2ccc(Cl)cn2c1C(=O)NCc1ccc(-c2ccccc2C(F)(F)F)cc1]

7-Chloro-2-ethyl-N-((2'-(trifluoromethyl)biphenyl-4-yl)methyl)imidazo[1,2-a]pyridine-3-carboxamide (124)

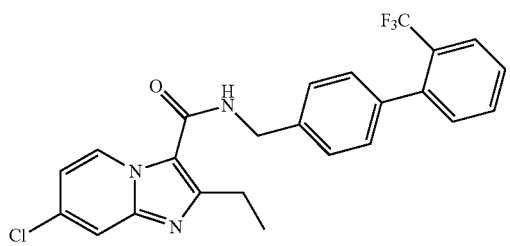

6-Chloro-N-((2'-cyanobiphenyl-4-yl)methyl)-2-ethylimidazo[1,2-a]pyridine-3-carboxamide (125)

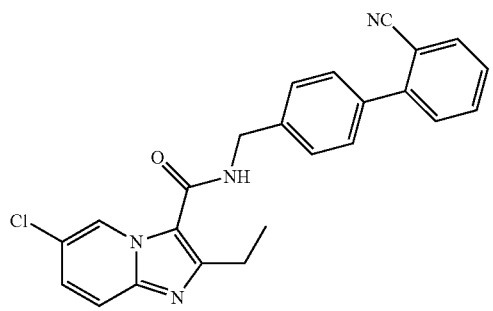

7-Chloro-N-((2'-cyanobiphenyl-4-yl)methyl)-2-ethylimidazo[1,2-a]pyridine-3-carboxamide (126)

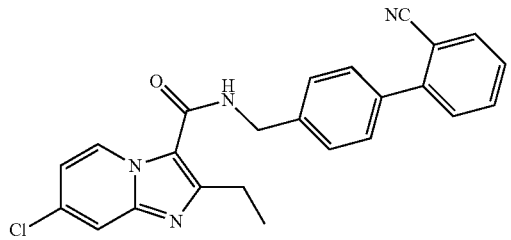 [SMILES: CCc1nc2cc(Cl)ccn2c1C(=O)NCc1ccc(-c2ccccc2C#N)cc1]

6-Chloro-N-((3'-cyanobiphenyl-4-yl)methyl)-2-ethylimidazo[1,2-a]pyridine-3-carboxamide (127)

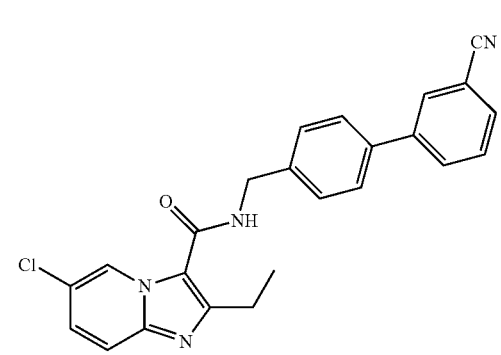 [SMILES: CCc1nc2ccc(Cl)cn2c1C(=O)NCc1ccc(-c2cccc(C#N)c2)cc1]

7-Chloro-N-((3'-cyanobiphenyl-4-yl)methyl)-2-ethylimidazo[1,2-a]pyridine-3-carboxamide (128)

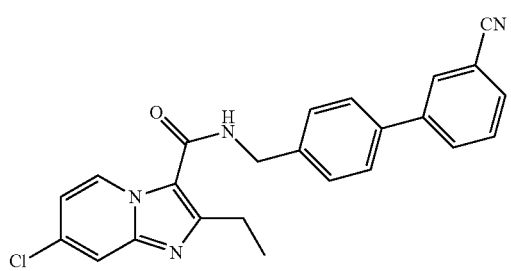 [SMILES: CCc1nc2cc(Cl)ccn2c1C(=O)NCc1ccc(-c2cccc(C#N)c2)cc1]

6-Chloro-N-((4'-chloro-2'-(trifluoromethyl)biphenyl-4-yl)methyl)-2-ethylimidazo[1,2-a]pyridine-3-carboxamide (129)

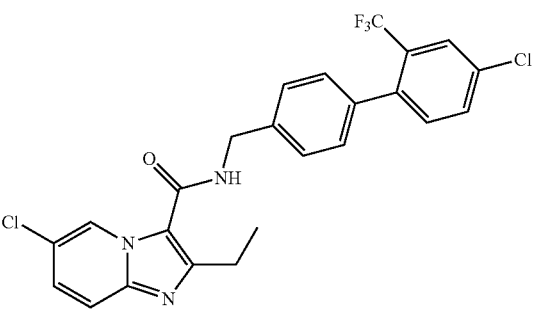 [SMILES: CCc1nc2ccc(Cl)cn2c1C(=O)NCc1ccc(-c2ccc(Cl)cc2C(F)(F)F)cc1]

7-Chloro-N-((4'-chloro-2'-(trifluoromethyl)biphenyl-4-yl)methyl)-2-ethylimidazo[1,2-a]pyridine-3-carboxamide (130)

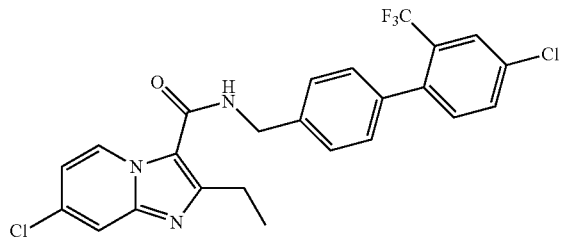 [SMILES: CCc1nc2cc(Cl)ccn2c1C(=O)NCc1ccc(-c2ccc(Cl)cc2C(F)(F)F)cc1]

6-Chloro-N-((4'-cyano-2'-methylbiphenyl-4-yl)methyl)-2-ethylimidazo[1,2-a]pyridine-3-carboxamide (131)

7-Chloro-N-((4'-cyano-2'-methylbiphenyl-4-yl)methyl)-2-ethylimidazo[1,2-a]pyridine-3-carboxamide (132)

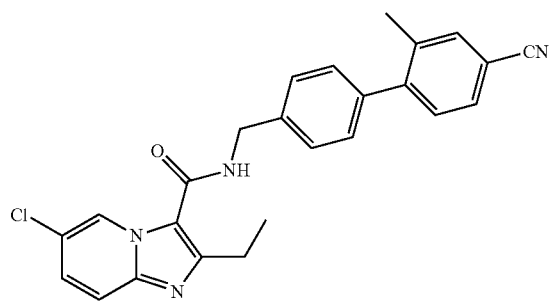 [SMILES: CCc1nc2ccc(Cl)cn2c1C(=O)NCc1ccc(-c2ccc(C#N)cc2C)cc1]

7-Chloro-N-((2'-chloro-4'-fluorobiphenyl-4-yl)methyl)-2-ethylimidazo[1,2-a]pyridine-3-carboxamide (133)

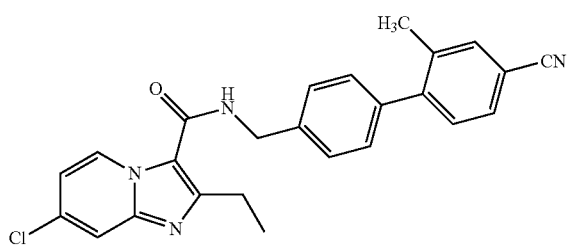 [SMILES: CCc1nc2cc(Cl)ccn2c1C(=O)NCc1ccc(-c2ccc(C#N)cc2C)cc1]

7-Chloro-2-ethyl-N-(4-(pyridin-4-yl)benzyl)imidazo[1,2-a]pyridine-3-carboxamide (134)

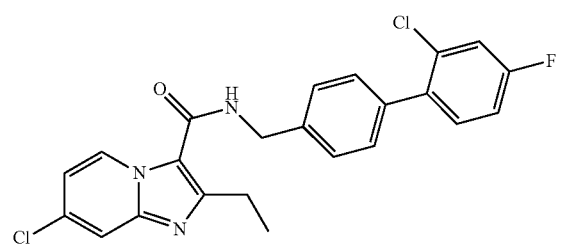 [SMILES: CCc1nc2cc(Cl)ccn2c1C(=O)NCc1ccc(-c2ccc(F)cc2Cl)cc1]

7-Chloro-2-ethyl-N-(4-(5-methoxypyridin-2-yl)benzyl)imidazo[1,2-a]pyridine-3-carboxamide (135)

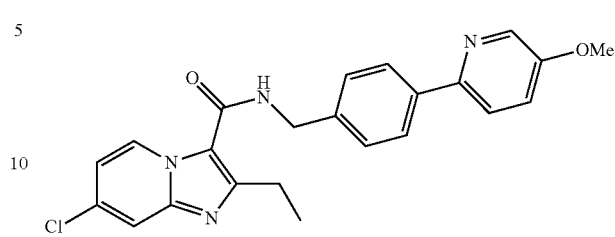

7-Chloro-2-ethyl-N-(4-(furan-2-yl)benzyl)imidazo[1,2-a]pyridine-3-carboxamide (137)

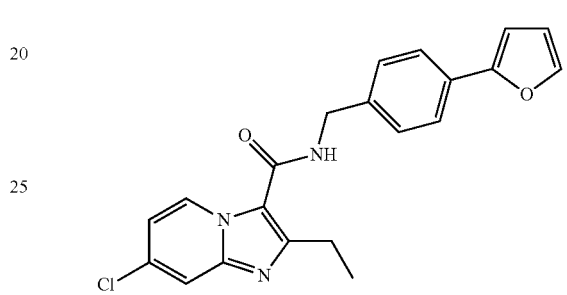

N-(4-(1H-Pyrrol-1-yl)benzyl)-7-chloro-2-ethylimidazo[1,2-a]pyridine-3-carboxamide (138)

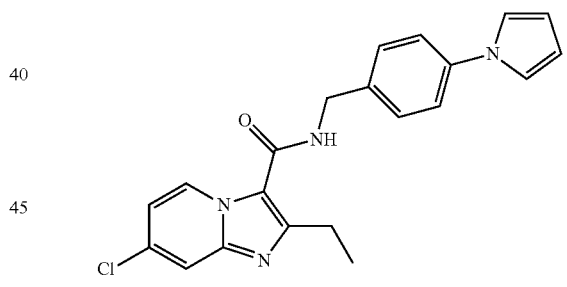

6-Chloro-2-ethyl-N-(4-(4-(4-(trifluoromethoxy)phenoxy)piperidin-1-yl)benzyl)imidazo-[1,2-a]pyridine-3-carboxamide (139)

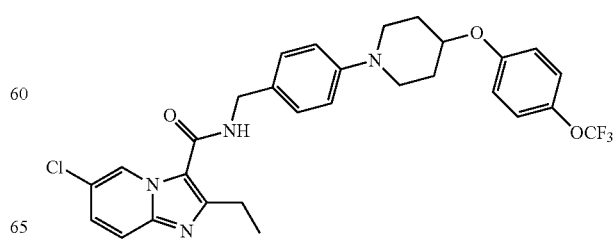

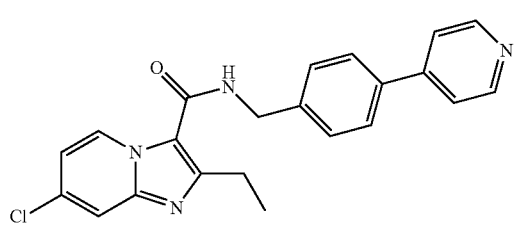 [SMILES: CCc1nc2cc(Cl)ccn2c1C(=O)NCc1ccc(-c2ccncc2)cc1]

7-Chloro-2-ethyl-N-(4-(4-(4-(trifluoromethoxy)phenoxy)piperidin-1-yl)benzyl)imidazo-[1,2-a]pyridine-3-carboxamide (140)

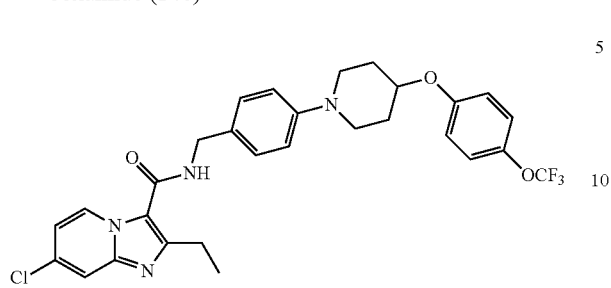

N-((4'-Chlorobiphenyl-4-yl)methyl)-2-ethylimidazo[1,2-a]pyrazine-3-carboxamide (141)

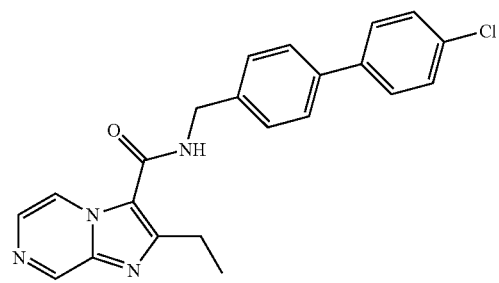 [SMILES: CCc1nc2cnccn2c1C(=O)NCc1ccc(-c2ccc(Cl)cc2)cc1]

N-(4-(4-(4-(Butyramidomethyl)phenyl)piperazin-1-yl)benzyl)-7-chloro-2-ethylimidazo-[1,2-a]pyridine-3-carboxamide (144)

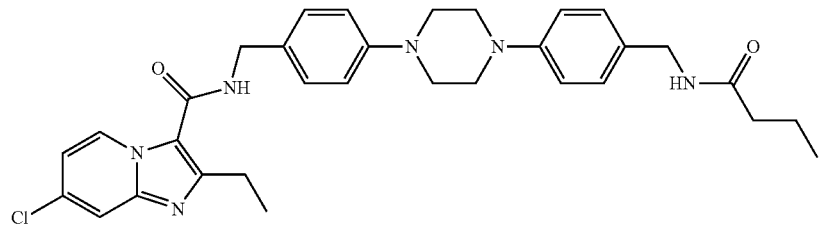 [SMILES: CCCC(=O)NCc1ccc(N2CCN(c3ccc(CNC(=O)c4c(CC)nc5cc(Cl)ccn45)cc3)CC2)cc1]

6-Chloro-2-ethyl-N-(4-(trifluoromethyl)benzyl)imidazo[1,2-a]pyridine-3-carboxamide (147)

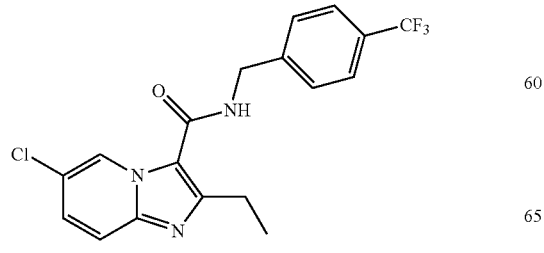

7-Chloro-2-ethyl-N-(4-(trifluoromethyl)benzyl)imidazo[1,2-a]pyridine-3-carboxamide (148)

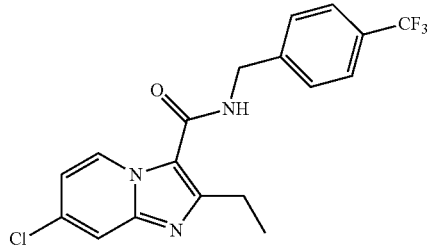 [SMILES: CCc1nc2cc(Cl)ccn2c1C(=O)NCc1ccc(C(F)(F)F)cc1]

6-Bromo-2-ethyl-N-(4-(trifluoromethoxy)benzyl)imidazo[1,2-a]pyridine-3-carboxamide (152)

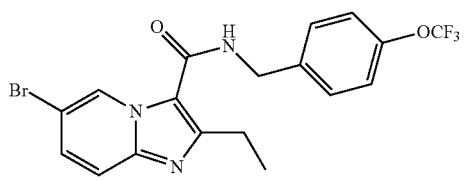 [SMILES: CCc1nc2ccc(Br)cn2c1C(=O)NCc1ccc(OC(F)(F)F)cc1]

6-Chloro-2-methyl-N-(4-(trifluoromethoxy)benzyl)imidazo[1,2-a]pyridine-3-carboxamide (154)

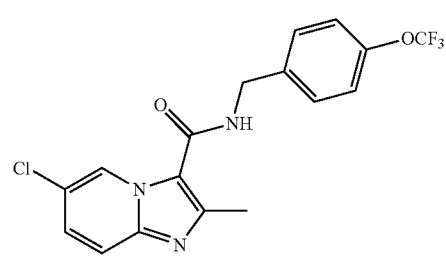 [SMILES: Cc1nc2ccc(Cl)cn2c1C(=O)NCc1ccc(OC(F)(F)F)cc1]

6-Chloro-2-ethyl-N-(4-methoxyphenethyl)imidazo[1,2-a]pyridine-3-carboxamide (157)

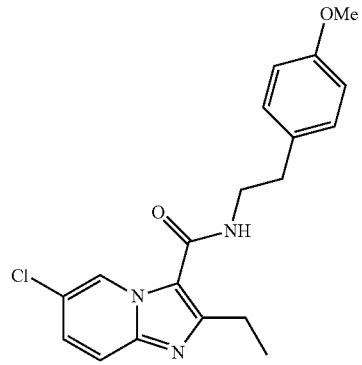 [SMILES: CCc1nc2ccc(Cl)cn2c1C(=O)NCCc1ccc(OC)cc1]

6-Chloro-N-(4-chlorophenethyl)-2-ethylimidazo[1,2-a]
pyridine-3-carboxamide (158)

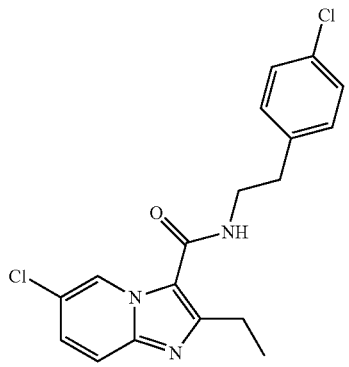 [SMILES: CCc1nc2ccc(Cl)cn2c1C(=O)NCCc1ccc(Cl)cc1]

N-((4'-(Butyramidomethyl)biphenyl-4-yl)methyl)-7-
chloro-2-ethylimidazo[1,2-a]pyridine-3-carboxamide
(159)

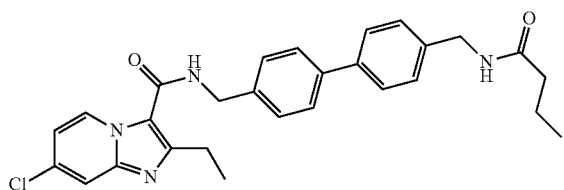 [SMILES: CCCC(=O)NCc1ccc(-c2ccc(CNC(=O)c3c(CC)nc4cc(Cl)ccn34)cc2)cc1]

6-Chloro-N-(4-(4-(4-chlorophenoxy)piperidin-1-yl)ben-
zyl)-2-ethylimidazo[1,2-a]pyridine-3-carboxamide
(162)

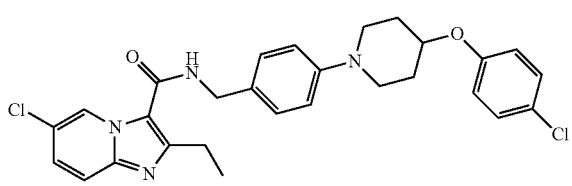 [SMILES: CCc1nc2ccc(Cl)cn2c1C(=O)NCc1ccc(N2CCC(Oc3ccc(Cl)cc3)CC2)cc1]

7-Chloro-N-(4-(4-(4-chlorophenoxy)piperidin-1-yl)ben-
zyl)-2-ethylimidazo[1,2-a]pyridine-3-carboxamide
(163)

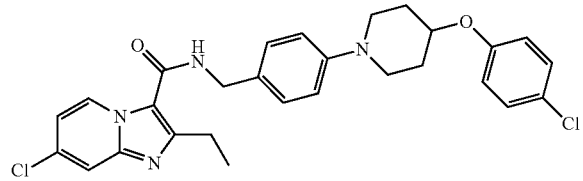 [SMILES: CCc1nc2cc(Cl)ccn2c1C(=O)NCc1ccc(N2CCC(Oc3ccc(Cl)cc3)CC2)cc1]

6-Chloro-2-ethyl-N-(4-(4-(4-(trifluoromethyl)phenoxy)
piperidin-1-yl)benzyl) imidazo[1,2-a]pyridine-3-car-
boxamide (164)

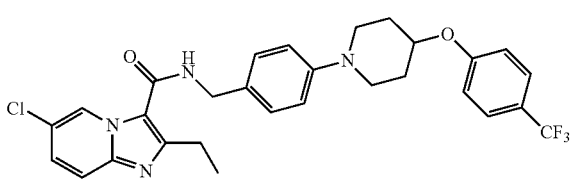 [SMILES: CCc1nc2ccc(Cl)cn2c1C(=O)NCc1ccc(N2CCC(Oc3ccc(C(F)(F)F)cc3)CC2)cc1]

7-Chloro-2-ethyl-N-(4-(4-(4-(trifluoromethyl)phenoxy)
piperidin-1-yl)benzyl) imidazo[1,2-a]pyridine-3-car-
boxamide (165)

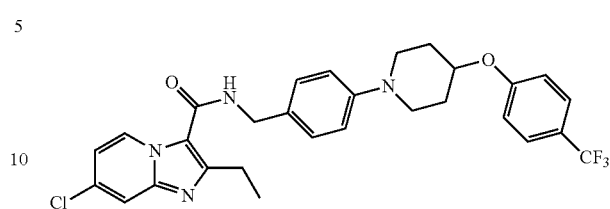

6-Chloro-2-ethyl-N-(4-(4-(4-fluorophenoxy)piperidin-1-
yl)benzyl)imidazo[1,2-a]pyridine-3-carboxamide (166)

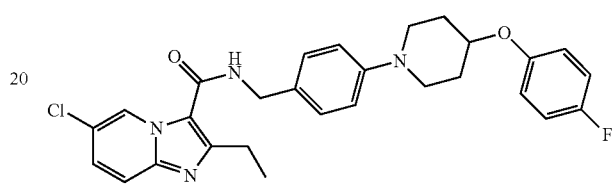

7-Chloro-2-ethyl-N-(4-(4-(4-fluorophenoxy)piperidin-1-
yl)benzyl)imidazo[1,2-a]pyridine-3-carboxamide (167)

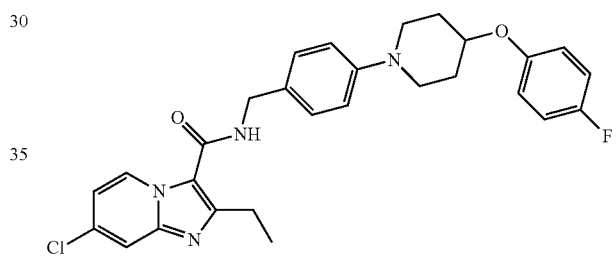

6-Chloro-2-ethyl-N-(4-(4-(4-fluorobenzyl)piperazin-1-
yl)benzyl)imidazo[1,2-a]pyridine-3-carboxamide (171)

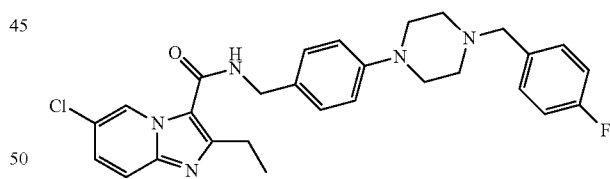

7-Chloro-2-ethyl-N-(4-(4-(4-fluorobenzyl)piperazin-1-
yl)benzyl)imidazo[1,2-a]pyridine-3-carboxamide (172)

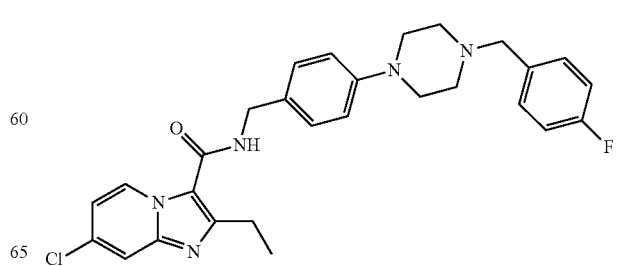

389

6-Chloro-2-ethyl-N-(4-(4-(4-(trifluoromethoxy)benzyl)piperazin-1-yl)benzyl)imidazo[1,2-a]pyridine-3-carboxamide (173)

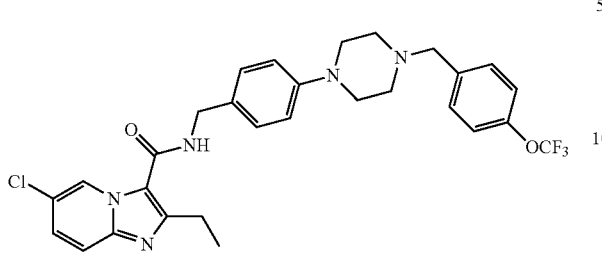

7-Chloro-2-ethyl-N-(4-(4-(4-(trifluoromethoxy)benzyl)piperazin-1-yl)benzyl)imidazo[1,2-a]pyridine-3-carboxamide (174)

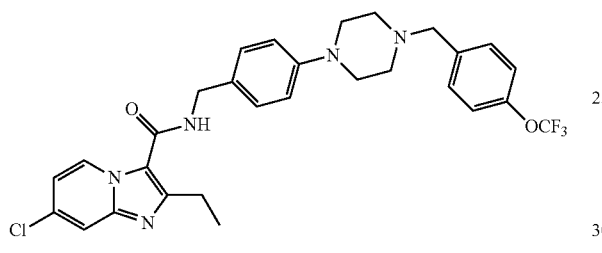

6,7-Dichloro-2-ethyl-N-(4-(4-(4-fluorobenzyl)piperazin-1-yl)benzyl)imidazo[1,2-a]pyridine-3-carboxamide (175)

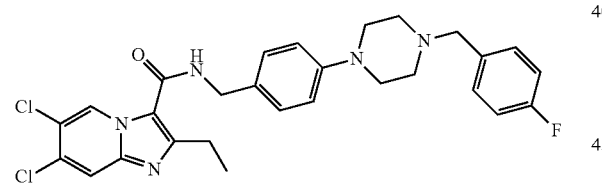

7-Chloro-2-ethyl-N-(4-(4-(4-fluorophenyl)piperazin-1-yl)benzyl)imidazo[1,2-a]pyridine-3-carboxamide (176)

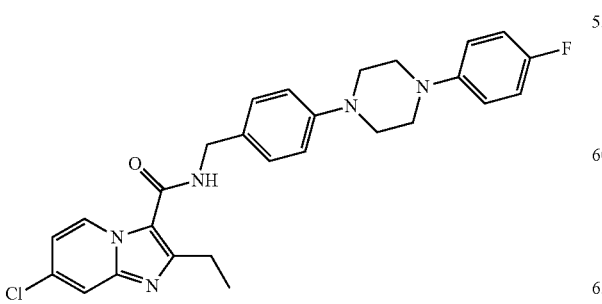

390

7-Chloro-2-ethyl-N-(4-(4-(4-fluorophenyl)piperazin-1-yl)benzyl)imidazo[1,2-a]pyridine-3-carboxamide trihydrochloride (177)

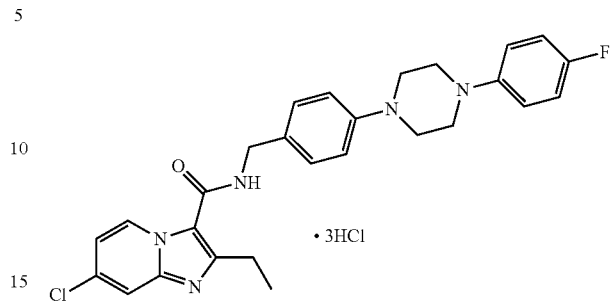

6-Chloro-2-ethyl-N-(4-(4-(4-(trifluoromethoxy)phenyl)piperazin-1-yl)benzyl)imidazo[1,2-a]pyridine-3-carboxamide (178)

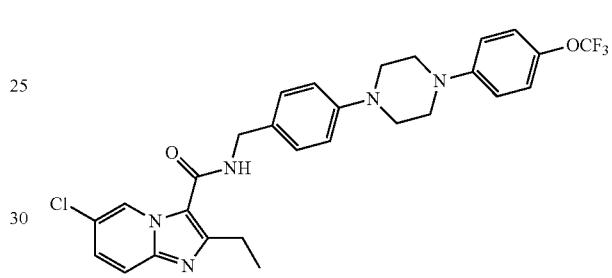

7-Chloro-2-ethyl-N-(4-(4-(4-(trifluoromethoxy)phenyl)piperazin-1-yl)benzyl)imidazo[1,2-a]pyridine-3-carboxamide (179)

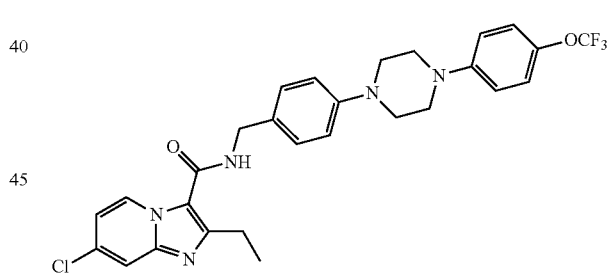

6,7-Dichloro-2-ethyl-N-(4-(4-(4-fluorophenyl)piperazin-1-yl)benzyl)imidazo[1,2-a]pyridine-3-carboxamide (180)

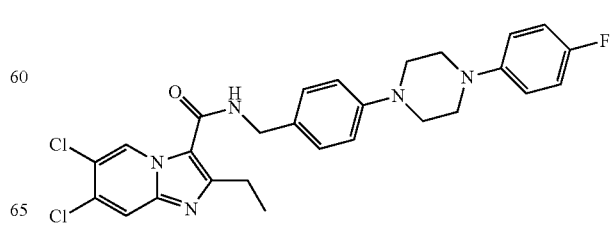

391

2-Ethyl-N-(4-(4-(4-(trifluoromethoxy)phenyl)piperazin-1-yl)benzyl)imidazo[1,2-a]pyridine-3-carboxamide (181)

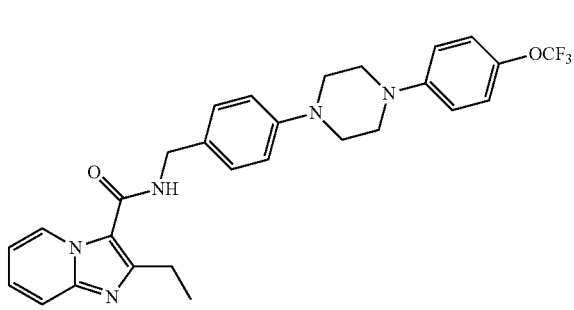

6-Chloro-2-ethyl-N-(4-(4-(4-fluorophenyl)piperazin-1-yl)benzyl)-N-methylimidazo[1,2-a]pyridine-3-carboxamide (182)

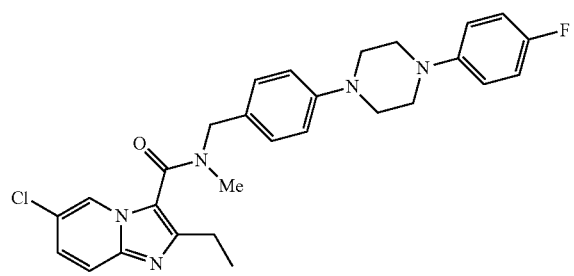 [SMILES: CCc1nc2ccc(Cl)cn2c1C(=O)N(C)Cc1ccc(N2CCN(c3ccc(F)cc3)CC2)cc1]

7-Chloro-2-ethyl-N-((4'-(hexanamidomethyl)biphenyl-4-yl)methyl)imidazo[1,2-a]pyridine-3-carboxamide (184)

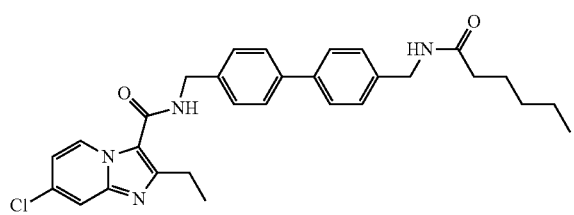 [SMILES: CCCCCC(=O)NCc1ccc(-c2ccc(CNC(=O)c3c(CC)nc4cc(Cl)ccn34)cc2)cc1]

6-Chloro-2-ethyl-N-(4-(4-(trifluoromethoxy)phenoxy)benzyl)imidazo[1,2-a]pyridine-3-carboxamide (185)

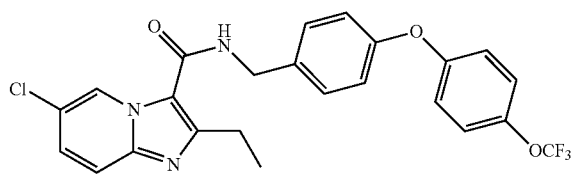 [SMILES: CCc1nc2ccc(Cl)cn2c1C(=O)NCc1ccc(Oc2ccc(OC(F)(F)F)cc2)cc1]

392

7-Chloro-2-ethyl-N-(4-(4-(trifluoromethoxy)phenoxy)benzyl)imidazo[1,2-a]pyridine-3-carboxamide (186)

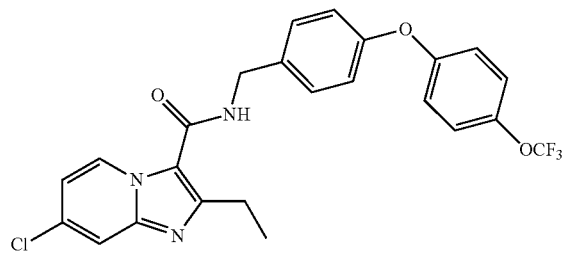

6-Chloro-2-ethyl-N-(4-(4-fluorophenoxy)benzyl)imidazo[1,2-a]pyridine-3-carboxamide (187)

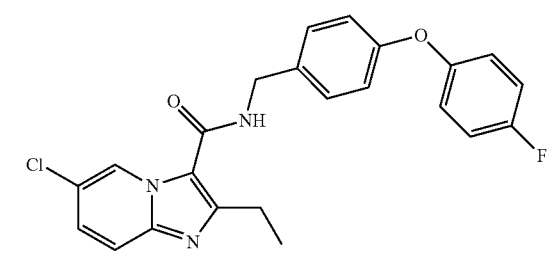 [SMILES: CCc1nc2ccc(Cl)cn2c1C(=O)NCc1ccc(Oc2ccc(F)cc2)cc1]

7-Chloro-2-ethyl-N-(4-(4-fluorophenoxy)benzyl)imidazo[1,2-a]pyridine-3-carboxamide (188)

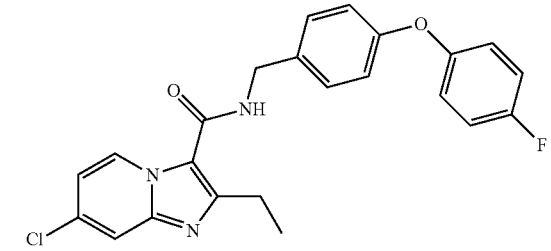

6-Bromo-2-ethyl-N-(4-(4-fluorophenoxy)benzyl)imidazo[1,2-a]pyridine-3-carboxamide (189)

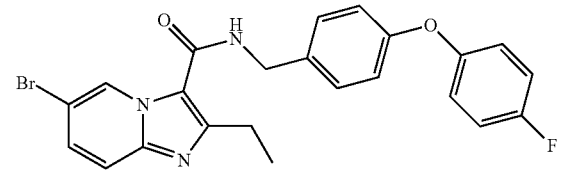 [SMILES: CCc1nc2ccc(Br)cn2c1C(=O)NCc1ccc(Oc2ccc(F)cc2)cc1]

6-Chloro-N-(4-(4-chlorophenoxy)benzyl)-2-ethylimidazo[1,2-a]pyridine-3-carboxamide (190)

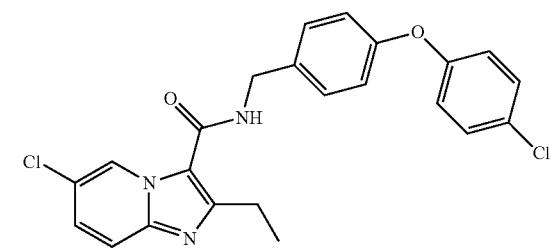 [SMILES: CCc1nc2ccc(Cl)cn2c1C(=O)NCc1ccc(Oc2ccc(Cl)cc2)cc1]

393

7-Chloro-N-(4-(4-chlorophenoxy)benzyl)-2-ethylimidazo[1,2-a]pyridine-3-carboxamide (191)

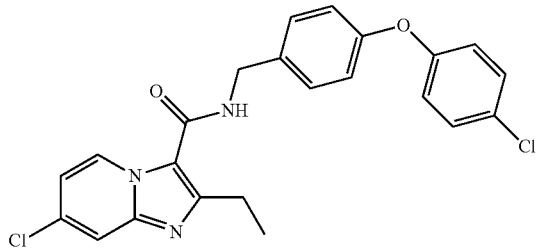 [SMILES: CCc1nc2cc(Cl)ccn2c1C(=O)NCc1ccc(Oc2ccc(Cl)cc2)cc1]

2-Ethyl-N-(4-(4-(trifluoromethoxy)phenoxy)benzyl)imidazo[1,2-a]pyridine-3-carboxamide (192)

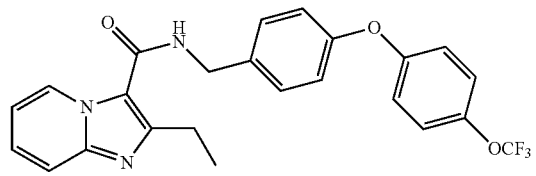 [SMILES: CCc1nc2ccccn2c1C(=O)NCc1ccc(Oc2ccc(OC(F)(F)F)cc2)cc1]

7-Chloro-2-ethyl-N-((6-(4-fluorophenoxy)pyridin-3-yl)methyl)imidazo[1,2-a]pyridine-3-carboxamide (193)

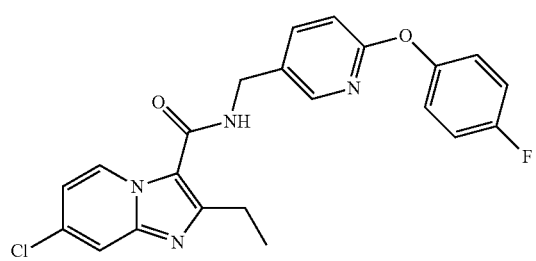 [SMILES: CCc1nc2cc(Cl)ccn2c1C(=O)NCc1ccc(Oc2ccc(F)cc2)nc1]

6-Chloro-2-ethyl-N-(4-(4-(trifluoromethoxy)phenylamino)benzyl)imidazo[1,2-a]pyridine-3-carboxamide (198)

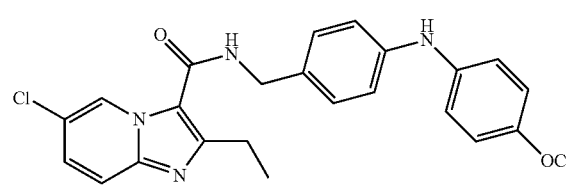

7-Chloro-2-ethyl-N-(4-(4-(trifluoromethoxy)phenylamino)benzyl)imidazo[1,2-a]pyridine-3-carboxamide (199)

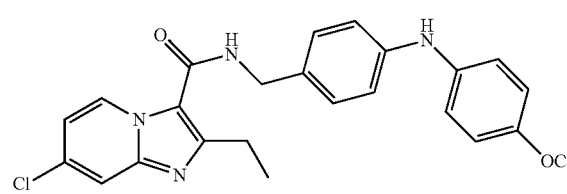

394

6-Chloro-2-ethyl-N-(4-(4-(trifluoromethyl)benzyloxy)benzyl)imidazo[1,2-a]pyridine-3-carboxamide (200)

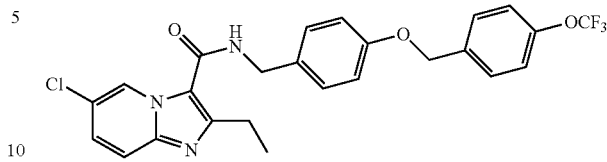

7-Chloro-2-ethyl-N-(4-(4-(trifluoromethyl)benzyloxy)benzyl)imidazo[1,2-a]pyridine-3-carboxamide (201)

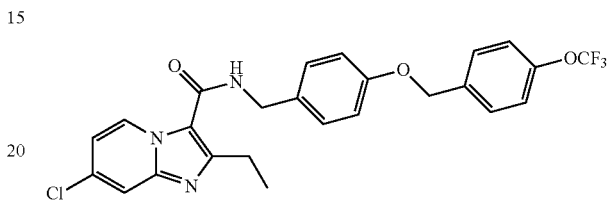

6-Chloro-2-ethyl-N-(4-(4-fluorobenzyloxy)benzyl)imidazo[1,2-a]pyridine-3-carboxamide (202)

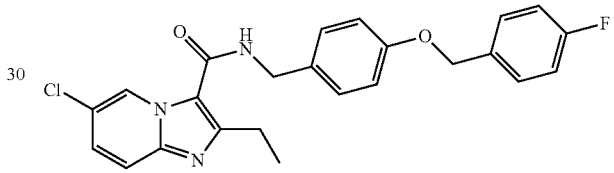

6-Chloro-N-(4-(2,6-dimethylmorpholino)benzyl)-2-ethylimidazo[1,2-a]pyridine-3-carboxamide (209)

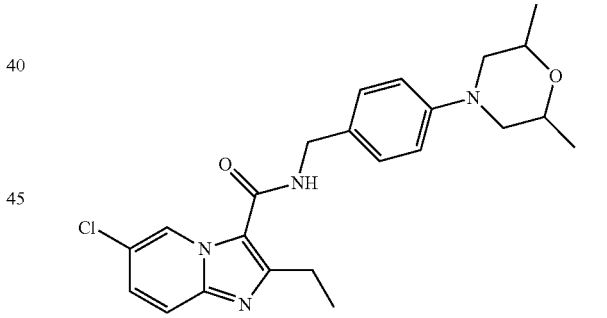

7-Chloro-N-(4-(2,6-dimethylmorpholino)benzyl)-2-ethylimidazo[1,2-a]pyridine-3-carboxamide (210)

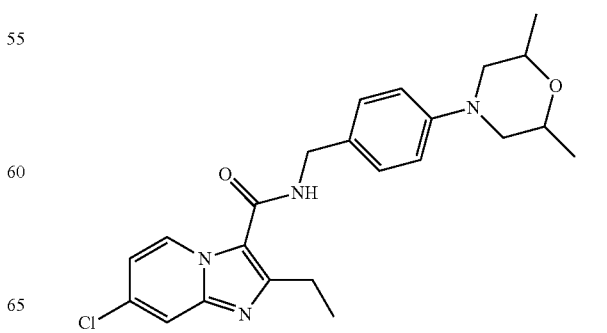

6-Chloro-2-ethyl-N-(4-(4-methylpiperidin-1-yl)benzyl)imidazo[1,2-a]pyridine-3-carboxamide (214)

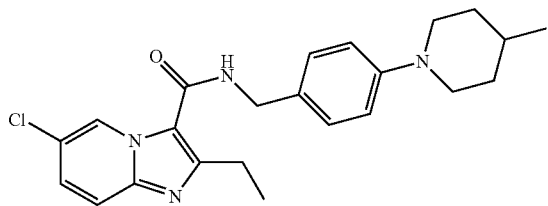 [SMILES: CCc1nc2ccc(Cl)cn2c1C(=O)NCc1ccc(N2CCC(C)CC2)cc1]

7-Chloro-2-ethyl-N-(4-(4-methylpiperidin-1-yl)benzyl)imidazo[1,2-a]pyridine-3-carboxamide (215)

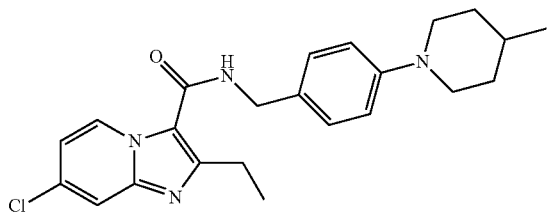 [SMILES: CCc1nc2cc(Cl)ccn2c1C(=O)NCc1ccc(N2CCC(C)CC2)cc1]

6-Chloro-N-(4-(3,5-dimethylpiperidin-1-yl)benzyl)-2-ethylimidazo[1,2-a]pyridine-3-carboxamide (216)

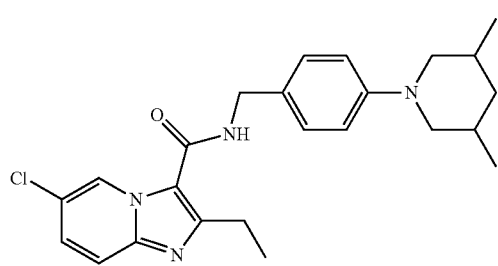 [SMILES: CCc1nc2ccc(Cl)cn2c1C(=O)NCc1ccc(N2CC(C)CC(C)C2)cc1]

7-Chloro-N-(4-(3,5-dimethylpiperidin-1-yl)benzyl)-2-ethylimidazo[1,2-a]pyridine-3-carboxamide (217)

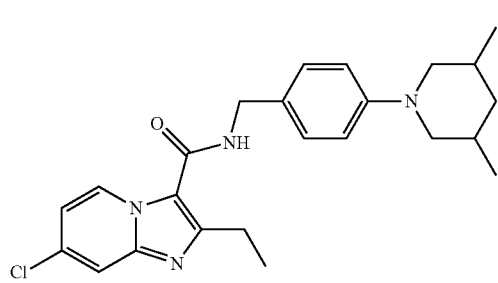 [SMILES: CCc1nc2cc(Cl)ccn2c1C(=O)NCc1ccc(N2CC(C)CC(C)C2)cc1]

7-Chloro-2-ethyl-N-(4-(4-hydroxypiperidin-1-yl)benzyl)imidazo[1,2-a]pyridine-3-carboxamide (218)

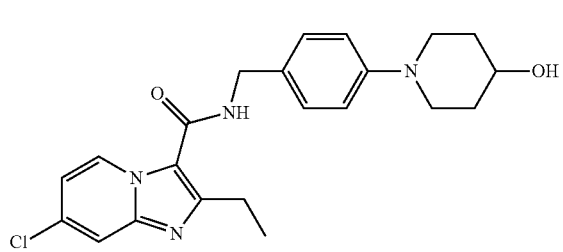 [SMILES: CCc1nc2cc(Cl)ccn2c1C(=O)NCc1ccc(N2CCC(O)CC2)cc1]

7-Chloro-N-(4-(3a,4-dihydro-1H-isoindol-2(3H,7H,7aH)-yl)benzyl)-2-ethylimidazo[1,2-a]pyridine-3-carboxamide (223)

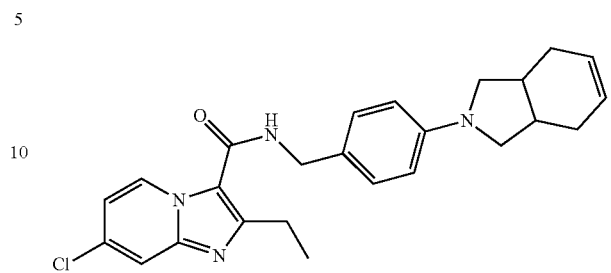

N-(4-(1H-isoindol-2(3H,3aH,4H,5H,6H,7H,7aH)-yl)benzyl)-7-chloro-2-ethylimidazo[1,2-a]pyridine-3-carboxamide (224)

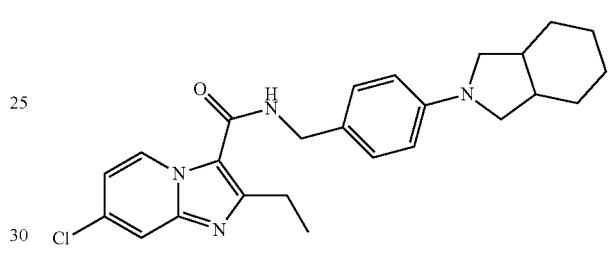

7-Chloro-2-ethyl-N-(4-(4,5,6,7-tetrahydro-2H-isoindol-2-yl)benzyl)imidazo[1,2-a]pyridine-3-carboxamide (225)

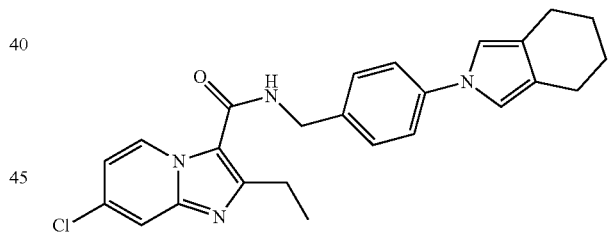

6-Chloro-2-ethyl-N-((1-(4-(trifluoromethoxy)benzyl)piperidin-4-yl)methyl)imidazo[1,2-a]pyridine-3-carboxamide (226)

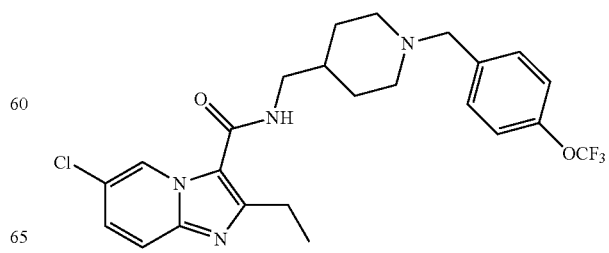

6-Chloro-2-ethyl-N-((1-(4-fluorobenzyl)piperidin-4-yl)methyl)imidazo[1,2-a]pyridine-3-carboxamide (227)

7-Bromo-2-ethyl-N-(4-(trifluoromethoxy)benzyl)imidazo[1,2-a]pyridine-3-carboxamide (250)

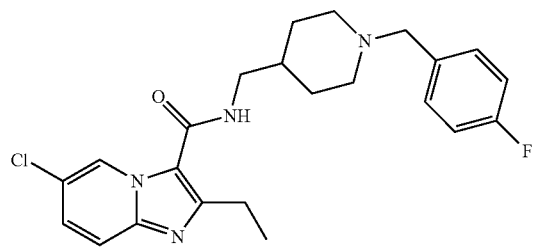 [SMILES: CCc1nc2ccc(Cl)cn2c1C(=O)NCC1CCN(Cc2ccc(F)cc2)CC1]
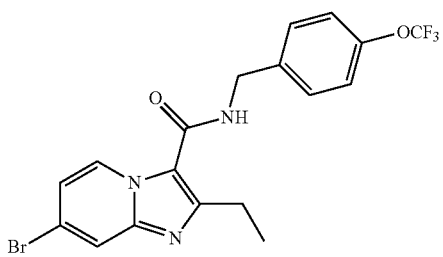

6-Chloro-2-ethyl-N-((1-(4-(trifluoromethoxy)phenyl)-1H-pyrazol-3-yl)methyl) imidazo[1,2-a]pyridine-3-carboxamide (231)

2-Ethyl-8-fluoro-N-(4-(trifluoromethoxy)benzyl)imidazo[1,2-a]pyridine-3-carboxamide (251)

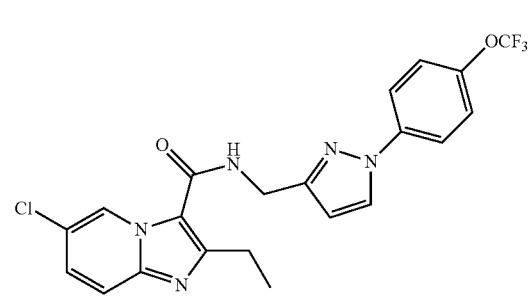 [SMILES: CCc1nc2ccc(Cl)cn2c1C(=O)NCc1ccn(-c2ccc(OC(F)(F)F)cc2)n1]
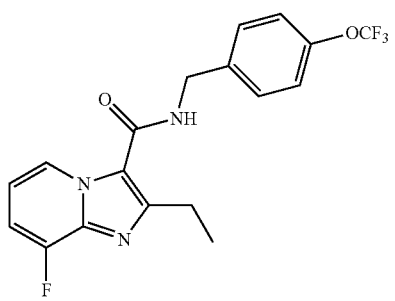

7-Chloro-2-ethyl-N-((4'-(trifluoromethoxy)biphenyl-3-yl)methyl)imidazo[1,2-a]pyridine-3-carboxamide (248)

7-Chloro-2-ethyl-N-((4'-formylbiphenyl-4-yl)methyl)imidazo[1,2-a]pyridine-3-carboxamide (252)

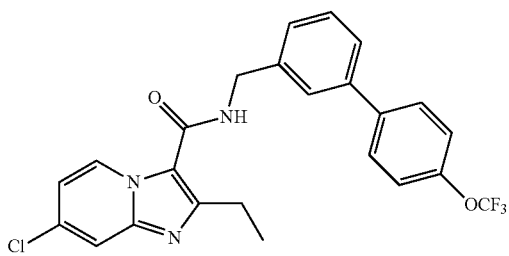 [SMILES: CCc1nc2cc(Cl)ccn2c1C(=O)NCc1cccc(-c2ccc(OC(F)(F)F)cc2)c1]
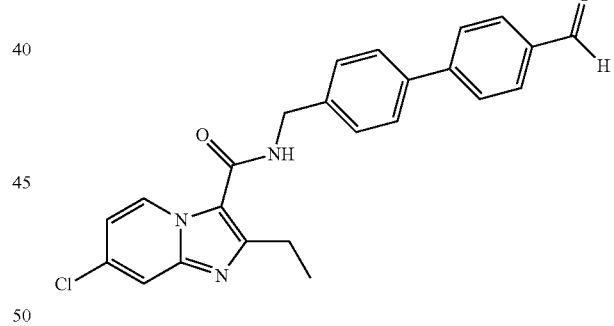

2-Ethyl-7-methyl-N-(4-(trifluoromethoxy)benzyl)imidazo[1,2-a]pyridine-3-carboxamide (249)

2-Ethyl-6-fluoro-N-(4-(4-(trifluoromethoxy)phenoxy)benzyl)imidazo[1,2-a]pyridine-3-carboxamide (253)

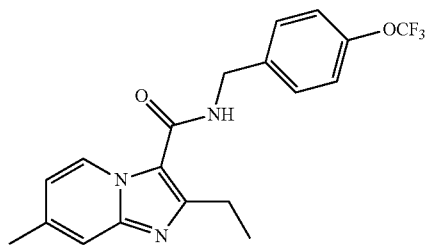 [SMILES: CCc1nc2cc(C)ccn2c1C(=O)NCc1ccc(OC(F)(F)F)cc1]
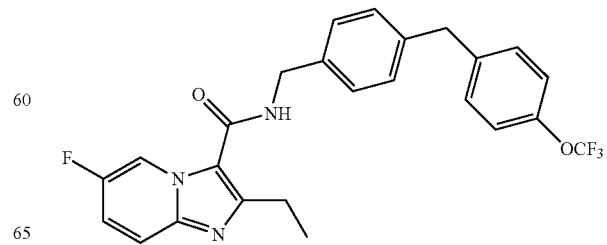

399

6-Bromo-2-ethyl-N-(4-(4-(trifluoromethoxy)phenoxy)
benzyl)imidazo[1,2-a]pyridine-3-carboxamide (254)

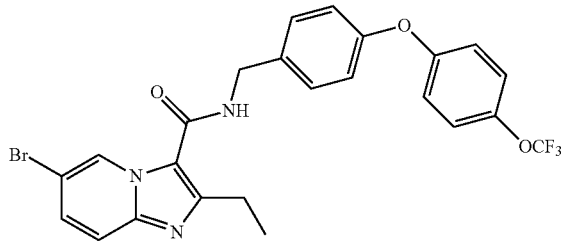

2-Ethyl-6-methyl-N-(4-(4-(trifluoromethoxy)phenoxy)
benzyl)imidazo[1,2-a]pyridine-3-carboxamide (255)

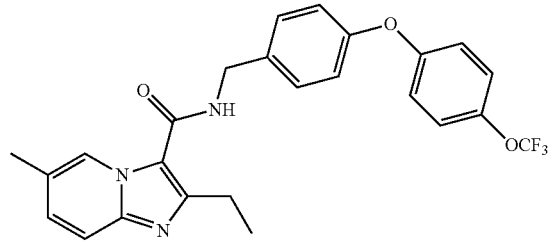 [SMILES: CCc1nc2ccc(C)cn2c1C(=O)NCc1ccc(Oc2ccc(OC(F)(F)F)cc2)cc1]

2-Ethyl-7-methyl-N-(4-(4-(trifluoromethoxy)phenoxy)
benzyl)imidazo[1,2-a]pyridine-3-carboxamide (256)

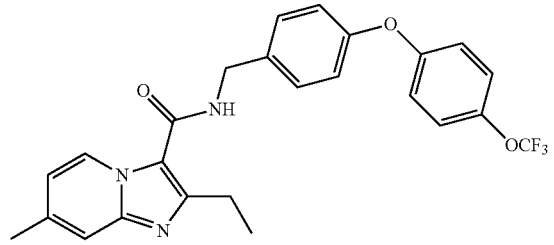 [SMILES: CCc1nc2cc(C)ccn2c1C(=O)NCc1ccc(Oc2ccc(OC(F)(F)F)cc2)cc1]

2-Ethyl-8-fluoro-N-(4-(4-(trifluoromethoxy)phenoxy)
benzyl)imidazo[1,2-a]pyridine-3-carboxamide (257)

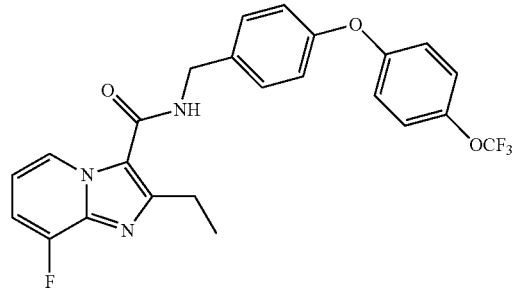 [SMILES: CCc1nc2c(F)cccn2c1C(=O)NCc1ccc(Oc2ccc(OC(F)(F)F)cc2)cc1]

400

2-Ethyl-6-fluoro-N-(4-(4-(trifluoromethoxy)benzyloxy)
benzyl)imidazo[1,2-a]pyridine-3-carboxamide (258)

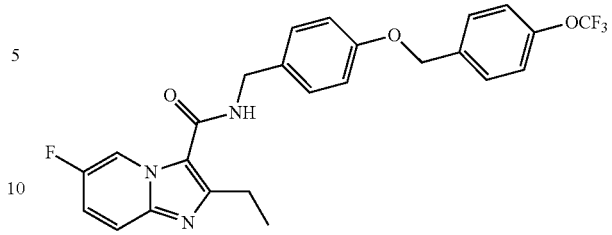

6-Bromo-2-ethyl-N-(4-(4-(trifluoromethoxy)benzyloxy)
benzyl)imidazo[1,2-a]pyridine-3-carboxamide (259)

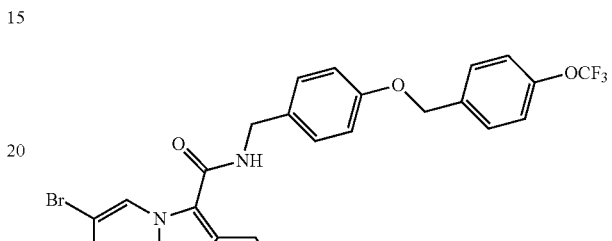

2-Ethyl-N-(4-(4-(trifluoromethoxy)benzyloxy)benzyl)
imidazo[1,2-a]pyridine-3-carboxamide (260)

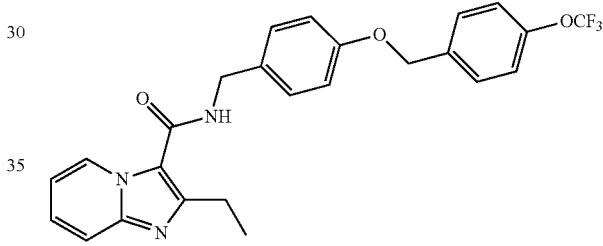

7-Chloro-2-ethyl-N-(4-((4-(trifluoromethoxy)benzyl)
amino)benzyl)imidazo[1,2-a]pyridine-3-carboxamide
(262)

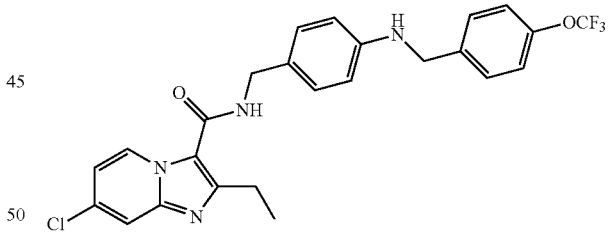

2-Ethyl-N-(4-(methyl(4-(trifluoromethoxy)benzyl)
amino)benzyl)imidazo[1,2-a]pyridine-3-carboxamide
(263)

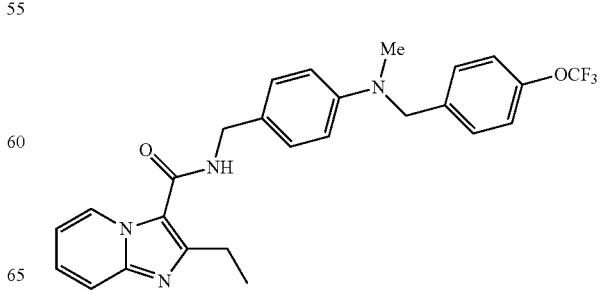

| 401 | 402 |
|---|---|
| 6-Chloro-2-ethyl-N-(4-(octahydroisoquinolin-2(1H)-yl) benzyl)imidazo[1,2-a]pyridine-3-carboxamide (267) | 6-chloro-2-ethyl-N-(4-(2-methylpiperidin-1-yl)benzyl) imidazo[1,2-a]pyridine-3-carboxamide (272) |

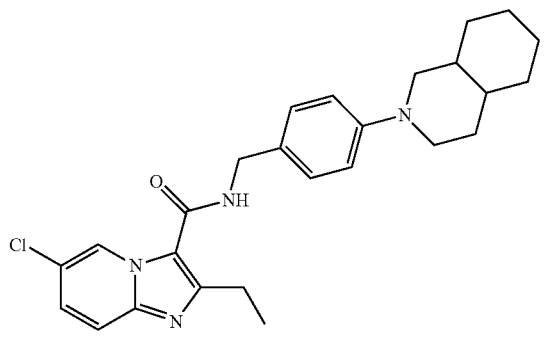 [SMILES: CCc1nc2ccc(Cl)cn2c1C(=O)NCc1ccc(N2CCC3CCCCC3C2)cc1]

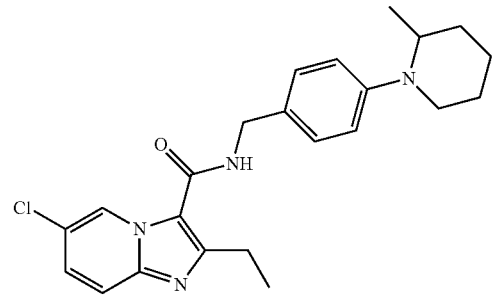

7-Chloro-2-ethyl-N-(4-(octahydroisoquinolin-2(1H)-yl) benzyl)imidazo[1,2-a]pyridine-3-carboxamide (268)

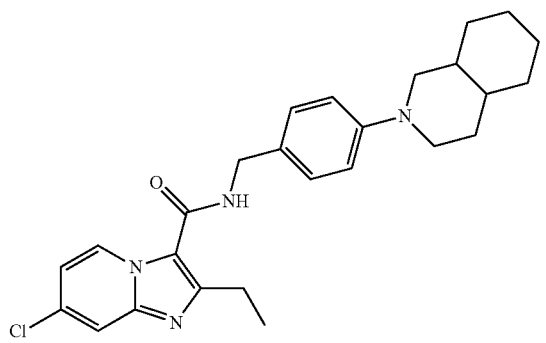 [SMILES: CCc1nc2cc(Cl)ccn2c1C(=O)NCc1ccc(N2CCC3CCCCC3C2)cc1]

7-chloro-2-ethyl-N-(4-(2-methylpiperidin-1-yl)benzyl) imidazo[1,2-a]pyridine-3-carboxamide (273)

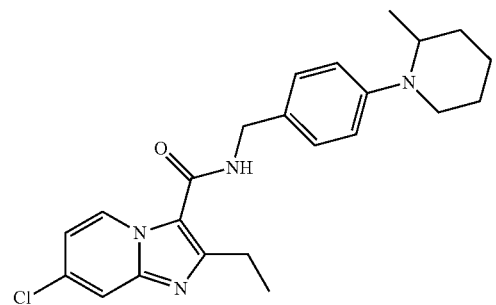

7-Chloro-2-ethyl-N-(4-(4-oxopiperidin-1-yl)benzyl)imidazo[1,2-a]pyridine-3-carboxamide (269)

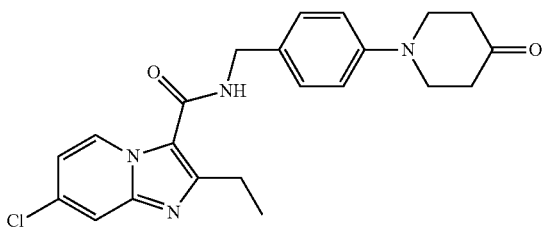 [SMILES: CCc1nc2cc(Cl)ccn2c1C(=O)NCc1ccc(N2CCC(=O)CC2)cc1]

7-Chloro-N-(4-(4,4-dimethylpiperidin-1-yl)benzyl)-2-ethyl-1,8a-dihydroimidazo[1,2-a]pyridine-3-carboxamide (274)

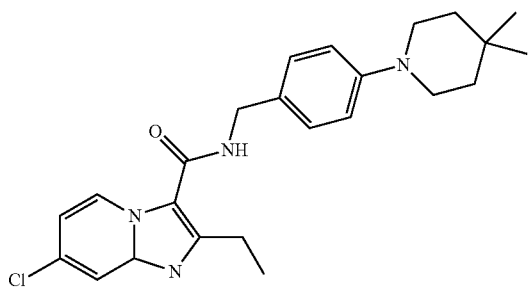

7-Chloro-2-ethyl-N-(4-(4-methylenepiperidin-1-yl)benzyl)imidazo[1,2-a]pyridine-3-carboxamide (271)

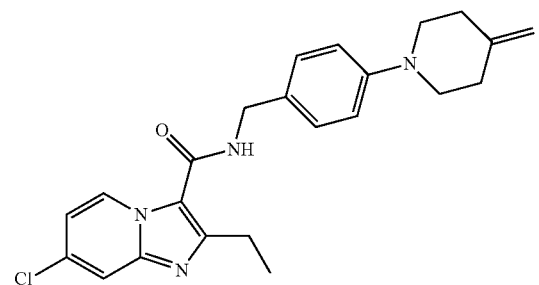 [SMILES: C=C1CCN(c2ccc(CNC(=O)c3c(CC)nc4cc(Cl)ccn34)cc2)CC1]

7-Chloro-2-ethyl-N-(4-(4-(hydroxymethyl)piperidin-1-yl)benzyl)imidazo[1,2-a]pyridine-3-carboxamide (280)

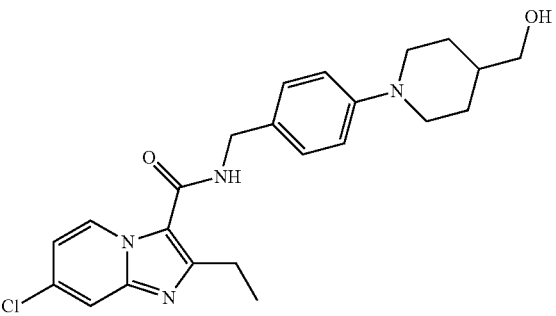 [SMILES: CCc1nc2cc(Cl)ccn2c1C(=O)NCc1ccc(N2CCC(CO)CC2)cc1]

403

6-Chloro-2-ethyl-N-(4-(4-(methoxymethyl)piperidin-1-yl)benzyl)imidazo[1,2-a]pyridine-3-carboxamide (281)

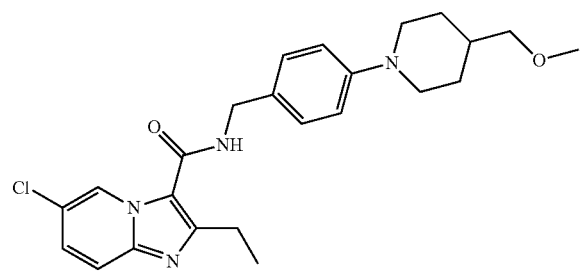 [SMILES: CCc1nc2ccc(Cl)cn2c1C(=O)NCc1ccc(N2CCC(COC)CC2)cc1]

7-Chloro-2-ethyl-N-(4-(4-(methoxymethyl)piperidin-1-yl)benzyl)imidazo[1,2-a]pyridine-3-carboxamide (282)

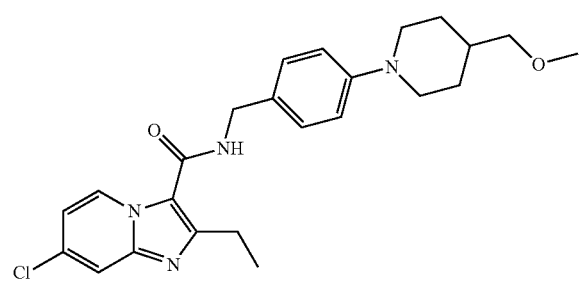 [SMILES: CCc1nc2cc(Cl)ccn2c1C(=O)NCc1ccc(N2CCC(COC)CC2)cc1]

7-Chloro-2-ethyl-N-(4-(4-phenylpiperidin-1-yl)benzyl)imidazo[1,2-a]pyridine-3-carboxamide (283)

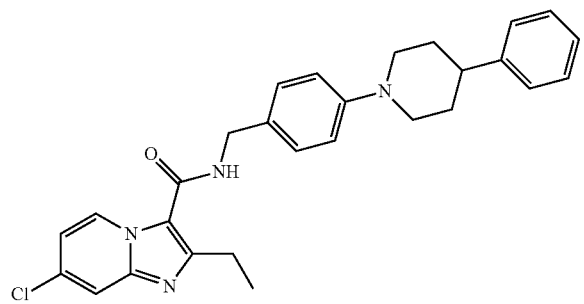 [SMILES: CCc1nc2cc(Cl)ccn2c1C(=O)NCc1ccc(N2CCC(c3ccccc3)CC2)cc1]

6-Chloro-2-ethyl-N-(4-(4-phenylpiperidin-1-yl)benzyl)imidazo[1,2-a]pyridine-3-carboxamide (284)

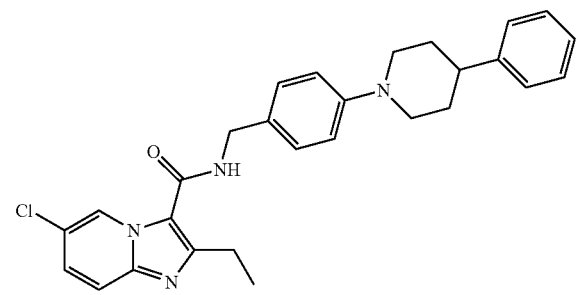 [SMILES: CCc1nc2ccc(Cl)cn2c1C(=O)NCc1ccc(N2CCC(c3ccccc3)CC2)cc1]

404

2-Ethyl-N-(4-(4-(4-fluorophenyl)piperidin-1-yl)benzyl)imidazo[1,2-a]pyridine-3-carboxamide (285)

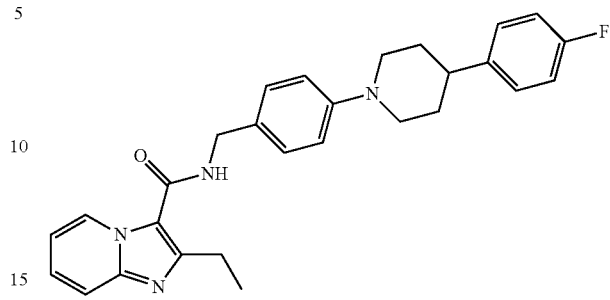

6-Chloro-2-ethyl-N-(4-(4-(4-fluorophenyl)piperidin-1-yl)benzyl)imidazo[1,2-a]pyridine-3-carboxamide (286)

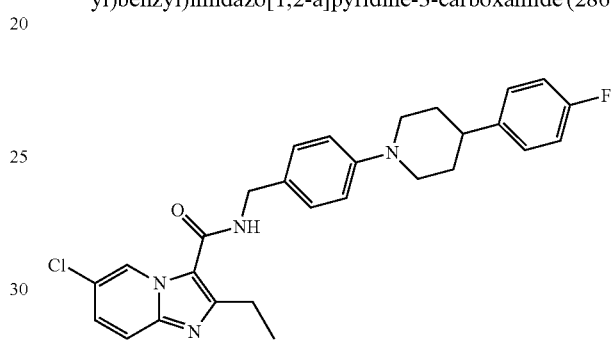

7-Chloro-2-ethyl-N-(4-(4-(4-fluorophenyl)piperidin-1-yl)benzyl)imidazo[1,2-a]pyridine-3-carboxamide (287)

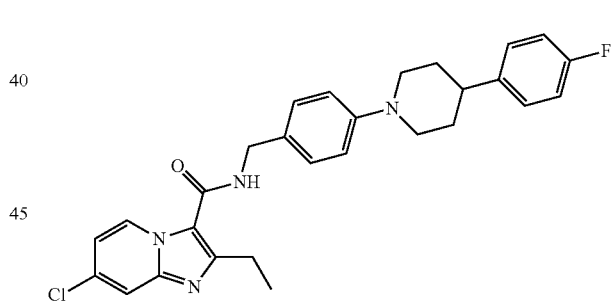

2-Ethyl-N-(4-(4-(4-(trifluoromethoxy)phenyl)piperidin-1-yl)benzyl)imidazo[1,2-a]pyridine-3-carboxamide (288)

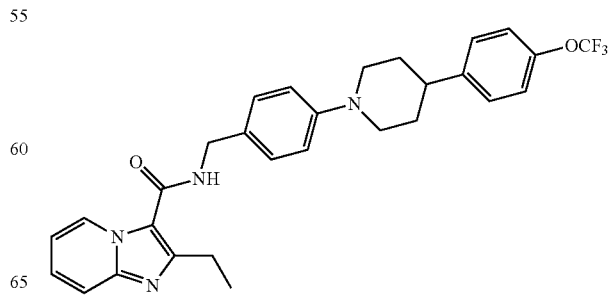

405

6-Chloro-2-ethyl-N-(4-(4-(4-(trifluoromethoxy)phenyl)piperidin-1-yl)benzyl)imidazo[1,2-a]pyridine-3-carboxamide (289)

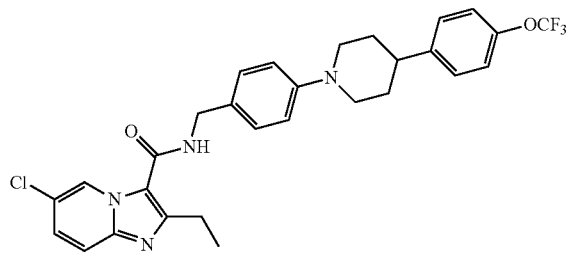 [SMILES: CCc1nc2ccc(Cl)cn2c1C(=O)NCc1ccc(N2CCC(c3ccc(OC(F)(F)F)cc3)CC2)cc1]

7-Chloro-2-ethyl-N-(4-(4-(4-(trifluoromethoxy)phenyl)piperidin-1-yl)benzyl)imidazo[1,2-a]pyridine-3-carboxamide (290)

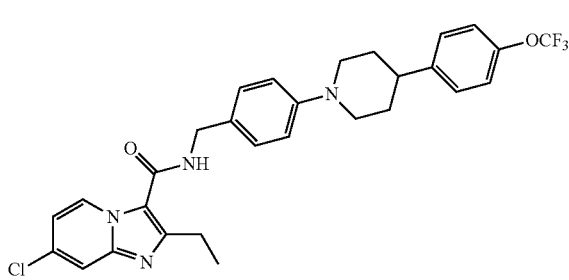 [SMILES: CCc1nc2cc(Cl)ccn2c1C(=O)NCc1ccc(N2CCC(c3ccc(OC(F)(F)F)cc3)CC2)cc1]

6-Chloro-2-ethyl-N-(4-(4-(isopropoxymethyl)piperidin-1-yl)benzyl)imidazo[1,2-a]pyridine-3-carboxamide (291)

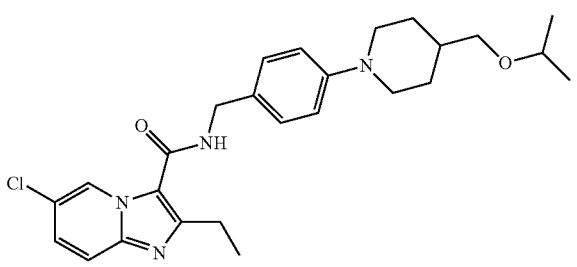 [SMILES: CCc1nc2ccc(Cl)cn2c1C(=O)NCc1ccc(N2CCC(COC(C)C)CC2)cc1]

7-Chloro-2-ethyl-N-(4-(4-(isopropoxymethyl)piperidin-1-yl)benzyl)imidazo[1,2-a]pyridine-3-carboxamide (292)

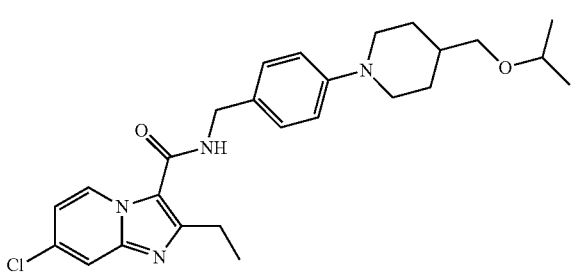 [SMILES: CCc1nc2cc(Cl)ccn2c1C(=O)NCc1ccc(N2CCC(COC(C)C)CC2)cc1]

406

6-Chloro-N-(4-(4-(cyclopentyloxymethyl)piperidin-1-yl)benzyl)-2-ethylimidazo[1,2-a]pyridine-3-carboxamide (293)

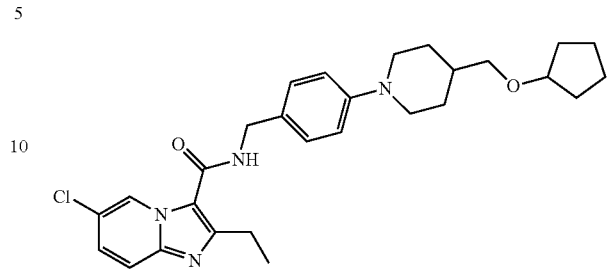

2-Ethyl-N-(4-(4-((4-fluorophenoxy)methyl)piperidin-1-yl)benzyl)imidazo[1,2-a]pyridine-3-carboxamide (295)

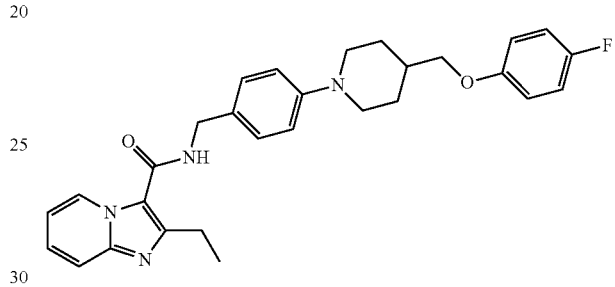

6-Chloro-2-ethyl-N-(4-(4-((4-fluorophenoxy)methyl)piperidin-1-yl)benzyl)imidazo[1,2-a]pyridine-3-carboxamide (296)

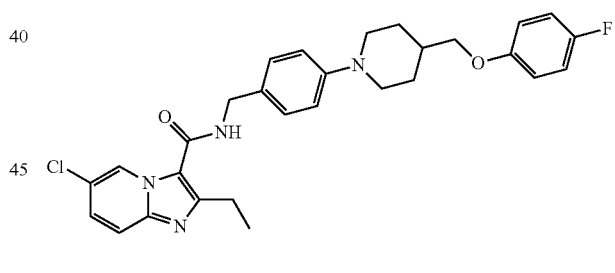

7-Chloro-2-ethyl-N-(4-(4-((4-fluorophenoxy)methyl)piperidin-1-yl)benzyl)imidazo[1,2-a]pyridine-3-carboxamide (297)

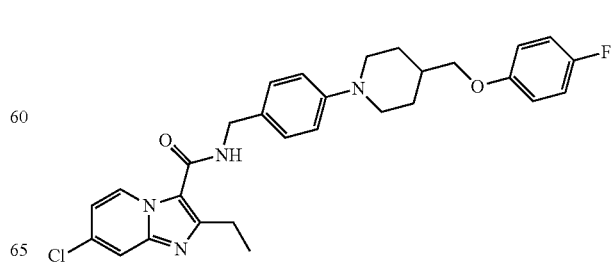

407

6-chloro-2-ethyl-N-(4-(4-((4-(trifluoromethoxy)phenoxy)methyl)piperidin-1-yl)benzyl)imidazo[1,2-a]pyridine-3-carboxamide (298)

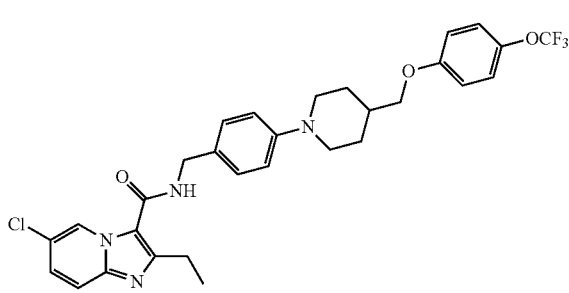 [SMILES: CCc1nc2ccc(Cl)cn2c1C(=O)NCc1ccc(N2CCC(COc3ccc(OC(F)(F)F)cc3)CC2)cc1]

7-Chloro-2-ethyl-N-(4-(4-((4-(trifluoromethoxy)phenoxy)methyl)piperidin-1-yl)benzyl)imidazo[1,2-a]pyridine-3-carboxamide (299)

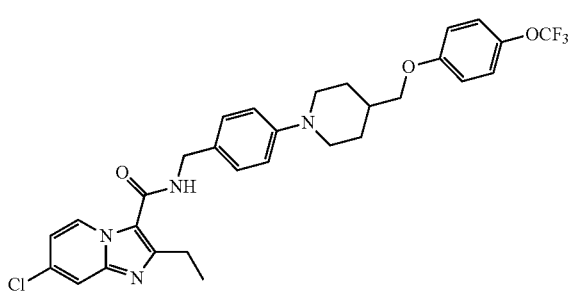 [SMILES: CCc1nc2cc(Cl)ccn2c1C(=O)NCc1ccc(N2CCC(COc3ccc(OC(F)(F)F)cc3)CC2)cc1]

Ethyl 1-(4-((6-chloro-2-ethylimidazo[1,2-a]pyridine-3-carboxamido)methyl)phenyl)piperidine-4-carboxylate (300)

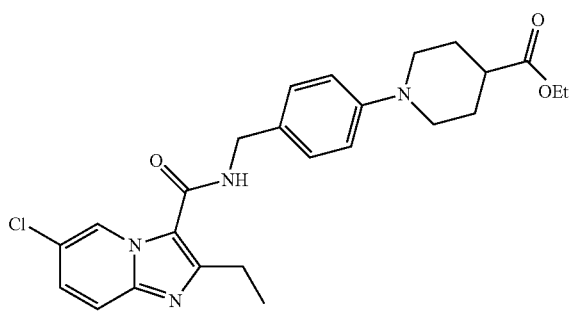 [SMILES: CCOC(=O)C1CCN(c2ccc(CNC(=O)c3c(CC)nc4ccc(Cl)cn34)cc2)CC1]

Ethyl 1-(4-((7-chloro-2-ethylimidazo[1,2-a]pyridine-3-carboxamido)methyl)phenyl)piperidine-4-carboxylate (301)

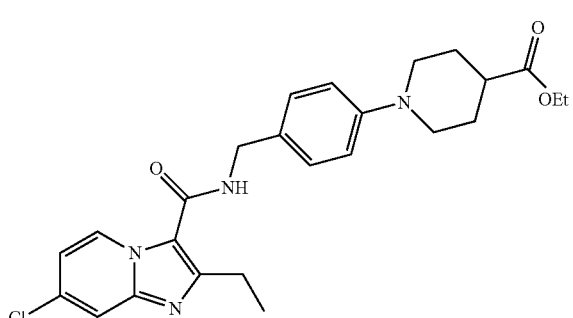

408

1-(4-((7-Chloro-2-ethylimidazo[1,2-a]pyridine-3-carboxamido)methyl)phenyl)piperidine-4-carboxylic acid (302)

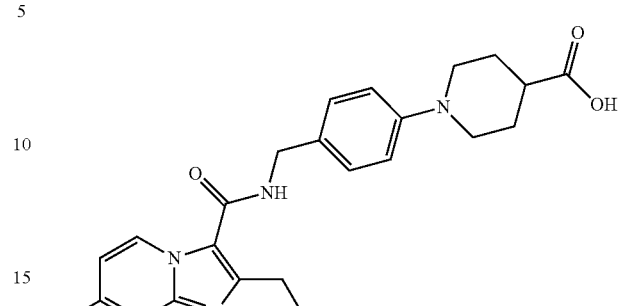

2-Ethyl-N-(4-(4-(4-fluorophenyl)piperazin-1-yl)benzyl)imidazo[1,2-a]pyridine-3-carboxamide (303)

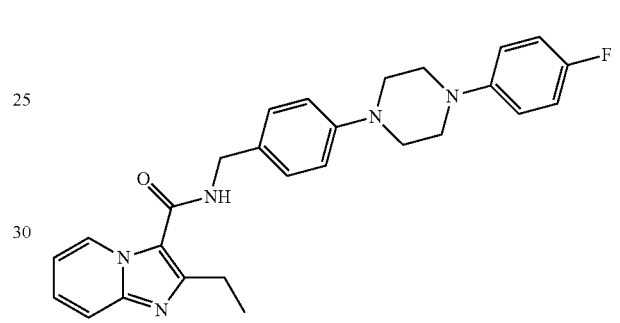

8-(Difluoromethoxy)-2-ethyl-N-(4-(4-(4-fluorophenyl)piperazin-1-yl)benzyl)imidazo[1,2-a]pyridine-3-carboxamide (304)

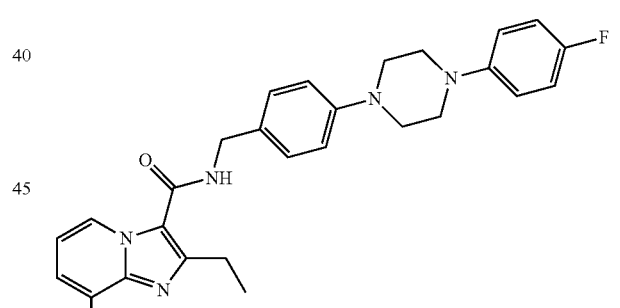

8-Bromo-2-ethyl-N-(4-(4-(4-fluorophenyl)piperazin-1-yl)benzyl)imidazo[1,2-a]pyridine-3-carboxamide (305)

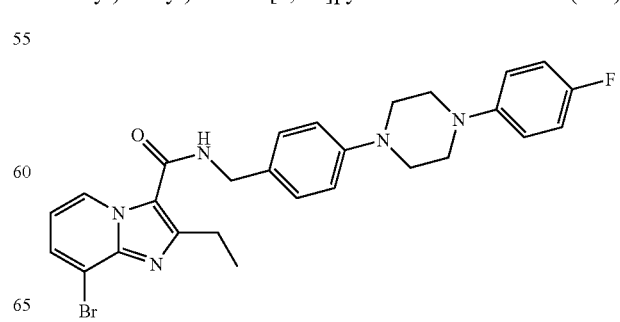

409

2-Ethyl-6-fluoro-N-(4-(4-(4-fluorophenyl)piperazin-1-yl)benzyl)imidazo[1,2-a]pyridine-3-carboxamide (306)

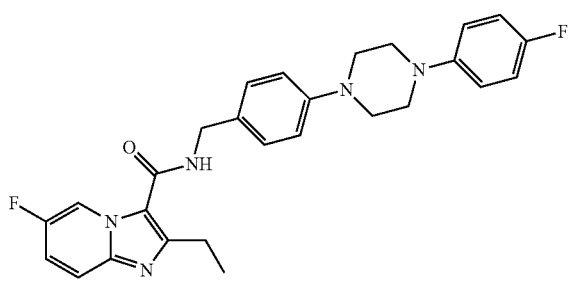 [SMILES: CCc1nc2ccc(F)cn2c1C(=O)NCc1ccc(N2CCN(c3ccc(F)cc3)CC2)cc1]

6-Bromo-2-ethyl-N-(4-(4-(4-fluorophenyl)piperazin-1-yl)benzyl)imidazo[1,2-a]pyridine-3-carboxamide (307)

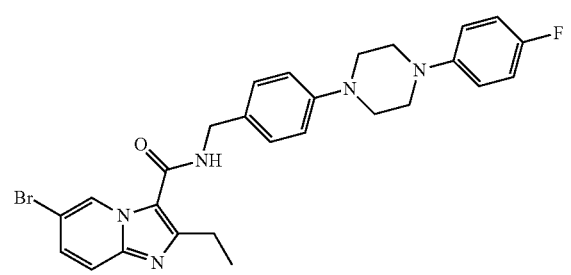 [SMILES: CCc1nc2ccc(Br)cn2c1C(=O)NCc1ccc(N2CCN(c3ccc(F)cc3)CC2)cc1]

2-Ethyl-N-(4-(4-(4-fluorophenyl)piperazin-1-yl)benzyl)-6-methylimidazo[1,2-a]pyridine-3-carboxamide (308)

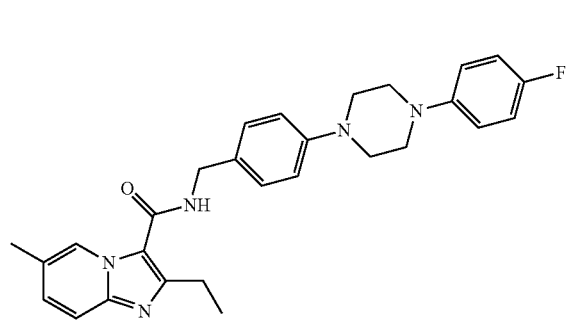 [SMILES: CCc1nc2ccc(C)cn2c1C(=O)NCc1ccc(N2CCN(c3ccc(F)cc3)CC2)cc1]

2-Ethyl-N-(4-(4-(4-fluorophenyl)piperazin-1-yl)benzyl)-7-methylimidazo[1,2-a]pyridine-3-carboxamide (309)

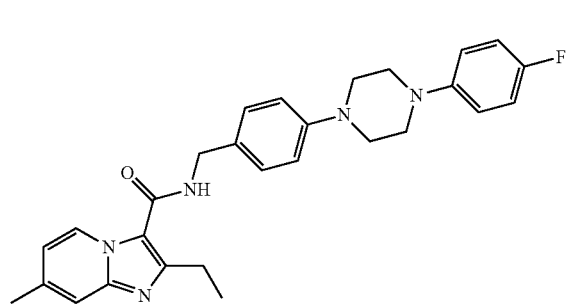 [SMILES: CCc1nc2cc(C)ccn2c1C(=O)NCc1ccc(N2CCN(c3ccc(F)cc3)CC2)cc1]

410

2-Ethyl-8-fluoro-N-(4-(4-(4-fluorophenyl)piperazin-1-yl)benzyl)imidazo[1,2-a]pyridine-3-carboxamide (310)

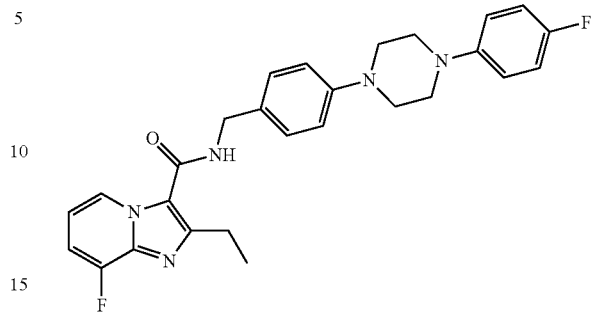

7-Bromo-2-ethyl-N-(4-(4-(4-fluorophenyl)piperazin-1-yl)benzyl)imidazo[1,2-a]pyridine-3-carboxamide (311)

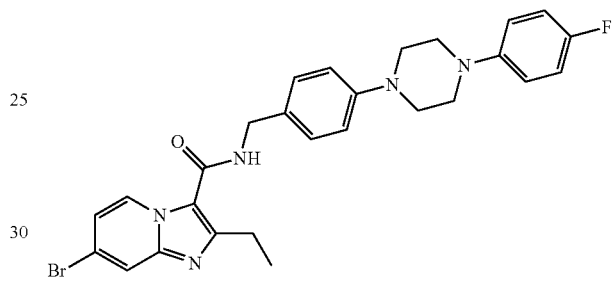

2-Ethyl-N-(4-(4-(4-fluorophenyl)piperazin-1-yl)benzyl)-8-(pyridin-4-yl)imidazo[1,2-a]pyridine-3-carboxamide (312)

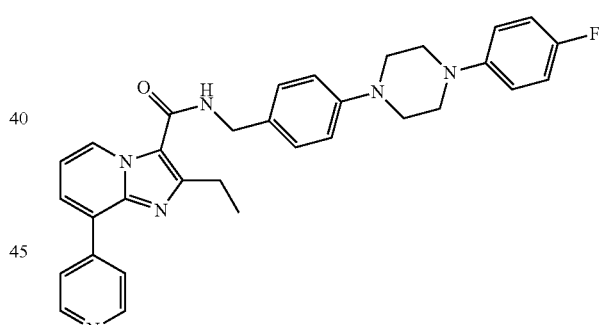

2-Ethyl-7-(4-phenylpiperazin-1-yl)-N-(4-(trifluoromethyl)benzyl)imidazo[1,2-a]pyridine-3-carboxamide (330)

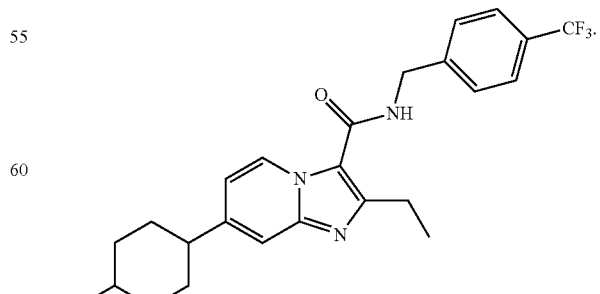

12. The compound according to claim 1, having a formula selected from formulae 5, 8, 13, 14, 17, 18, 20, 21, 23-43, 46, 48, 50, 51, 53, 59, 68, 69, 74, 79, 80, 89-91, 142, 143, 196, 211-213, 219, 221, 222, 243, 247, 313-329 and 331:

2-Methyl-N-(pyridin-4-yl)imidazo[1,2-a]pyridine-3-carboxamide (5)

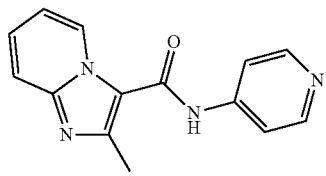 [SMILES: Cc1nc2ccccn2c1C(=O)Nc1ccncc1]

N-Benzyl-2-methylimidazo[1,2-a]pyridine-3-carboxamide (8)

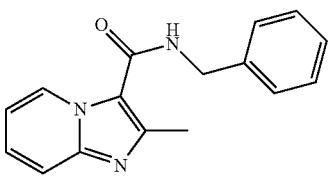 [SMILES: Cc1nc2ccccn2c1C(=O)NCc1ccccc1]

2-Methyl-N-(pyridin-3-ylmethyl)imidazo[1,2-a]pyridine-3-carboxamide (13)

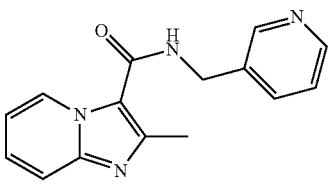 [SMILES: Cc1nc2ccccn2c1C(=O)NCc1cccnc1]

2-Methyl-N-(pyridin-4-ylmethyl)imidazo[1,2-a]pyridine-3-carboxamide (14)

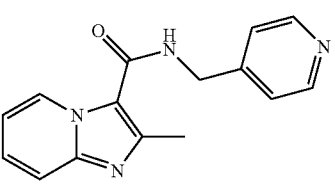 [SMILES: Cc1nc2ccccn2c1C(=O)NCc1ccncc1]

N-((1H-Indol-5-yl)methyl)-2-methylimidazo[1,2-a]pyridine-3-carboxamide (17)

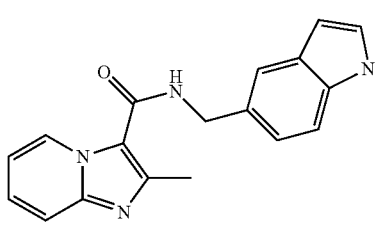 [SMILES: Cc1nc2ccccn2c1C(=O)NCc1ccc2[nH]ccc2c1]

N—(Cyclohexylmethyl)-2-methylimidazo[1,2-a]pyridine-3-carboxamide (18)

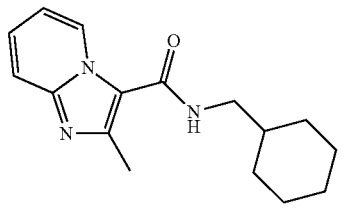 [SMILES: Cc1nc2ccccn2c1C(=O)NCC1CCCCC1]

2-Methyl-N-(piperidin-4-ylmethyl)imidazo[1,2-a]pyridine-3-carboxamide (20)

2-Methyl-N-phenethylimidazo[1,2-a]pyridine-3-carboxamide (21)

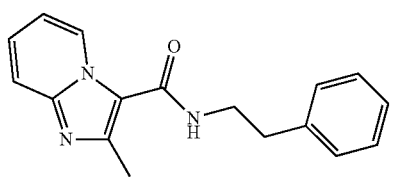 [SMILES: Cc1nc2ccccn2c1C(=O)NCCc1ccccc1]

2-Methyl-N-(2-phenoxyethyl)imidazo[1,2-a]pyridine-3-carboxamide (23)

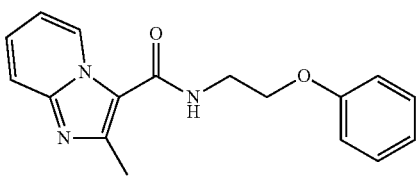 [SMILES: Cc1nc2ccccn2c1C(=O)NCCOc1ccccc1]

N-(2-(Benzyloxy)ethyl)-2-methylimidazo[1,2-a]pyridine-3-carboxamide (24)

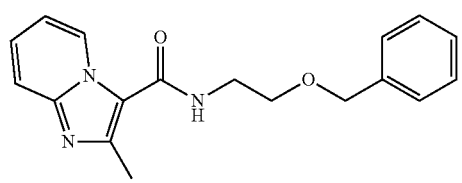 [SMILES: Cc1nc2ccccn2c1C(=O)NCCOCc1ccccc1]

(S)-Methyl 2-(2-methylimidazo[1,2-a]pyridine-3-carboxamido)-3-phenylpropanoate (25)

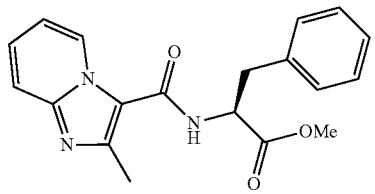 [SMILES: COC(=O)[C@H](Cc1ccccc1)NC(=O)c1c(C)nc2ccccn12]

N-(2-Methylimidazo[1,2-a]pyridin-3-yl)-2-phenylacetamide (26)

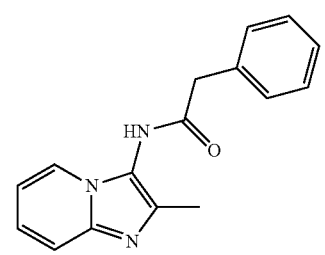 [SMILES: Cc1nc2ccccn2c1NC(=O)Cc1ccccc1]

N-Benzyl-8-chloro-2-methylimidazo[1,2-a]pyridine-3-carboxamide (27)

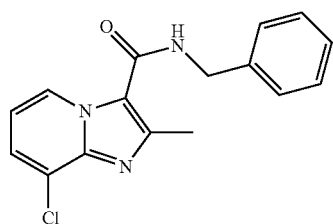 [SMILES: Cc1nc2c(Cl)cccn2c1C(=O)NCc1ccccc1]

N-Benzyl-7-chloro-2-methylimidazo[1,2-a]pyridine-3-carboxamide (28)

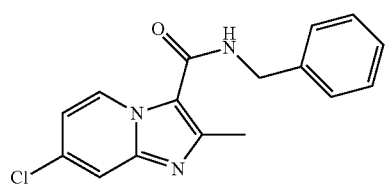 [SMILES: Cc1nc2cc(Cl)ccn2c1C(=O)NCc1ccccc1]

N-Benzyl-6-chloro-2-methylimidazo[1,2-a]pyridine-3-carboxamide (29)

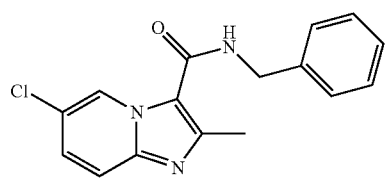 [SMILES: Cc1nc2ccc(Cl)cn2c1C(=O)NCc1ccccc1]

N-Benzyl-2,8-dimethylimidazo[1,2-a]pyridine-3-carboxamide (30)

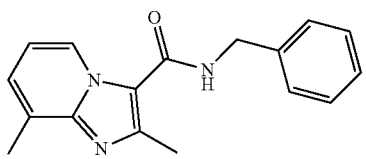 [SMILES: Cc1nc2c(C)cccn2c1C(=O)NCc1ccccc1]

N-Benzyl-2,7-dimethylimidazo[1,2-a]pyridine-3-carboxamide (31)

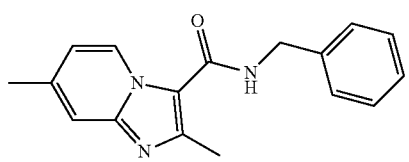 [SMILES: Cc1ccn2c(C(=O)NCc3ccccc3)c(C)nc2c1]

N-Benzyl-2,6-dimethylimidazo[1,2-a]pyridine-3-carboxamide (32)

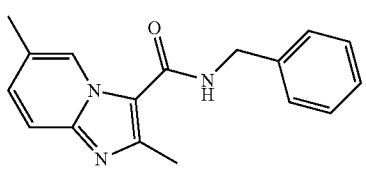 [SMILES: Cc1ccc2nc(C)c(C(=O)NCc3ccccc3)n2c1]

N-Benzyl-2,5-dimethylimidazo[1,2-a]pyridine-3-carboxamide (33)

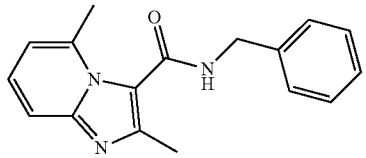 [SMILES: Cc1nc2cccc(C)n2c1C(=O)NCc1ccccc1]

N-Benzyl-6-fluoro-2-methylimidazo[1,2-a]pyridine-3-carboxamide (34)

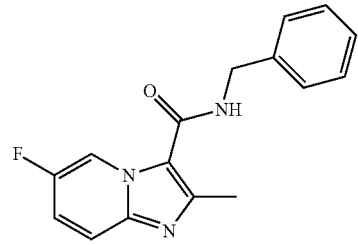 [SMILES: Cc1nc2ccc(F)cn2c1C(=O)NCc1ccccc1]

N-Benzyl-7-cyano-2-methylimidazo[1,2-a]pyridine-3-carboxamide (35)

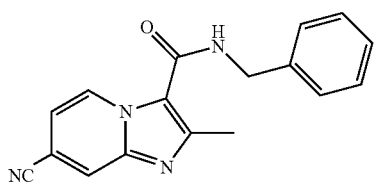

N-Benzyl-6-cyano-2-methylimidazo[1,2-a]pyridine-3-carboxamide (36)

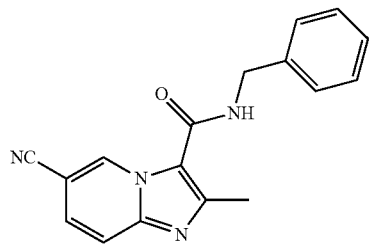 [SMILES: Cc1nc2ccc(C#N)cn2c1C(=O)NCc1ccccc1]

N-Benzyl-2-methyl-7-phenylimidazo[1,2-a]pyridine-3-carboxamide (37)

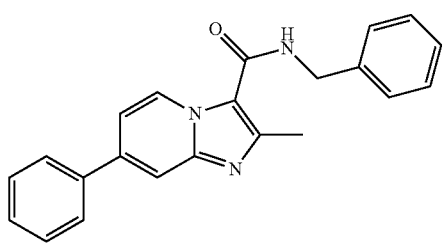 [SMILES: Cc1nc2cc(-c3ccccc3)ccn2c1C(=O)NCc1ccccc1]

N-Benzyl-2-methyl-6-phenylimidazo[1,2-a]pyridine-3-carboxamide (38)

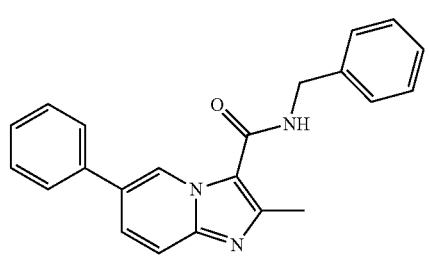 [SMILES: Cc1nc2ccc(-c3ccccc3)cn2c1C(=O)NCc1ccccc1]

N-Benzyl-8-fluoro-2-methylimidazo[1,2-a]pyridine-3-carboxamide (39)

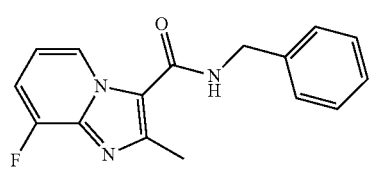

N-Benzyl-2-methyl-8-(trifluoromethyl)imidazo[1,2-a]pyridine-3-carboxamide (40)

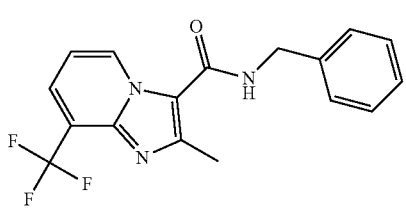 [SMILES: Cc1nc2c(C(F)(F)F)cccn2c1C(=O)NCc1ccccc1]

N-Benzyl-8-methoxy-2-methylimidazo[1,2-a]pyridine-3-carboxamide (41)

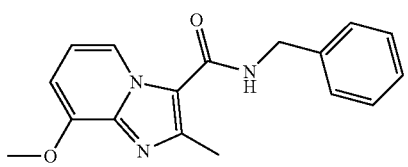 [SMILES: COc1cccn2c(C(=O)NCc3ccccc3)c(C)nc12]

N-Benzyl-8-cyano-2-methylimidazo[1,2-a]pyridine-3-carboxamide (42)

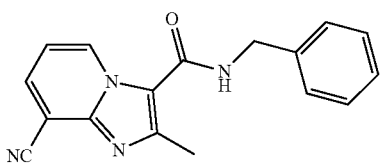

N-Benzyl-8-hydroxy-2-methylimidazo[1,2-a]pyridine-3-carboxamide (43)

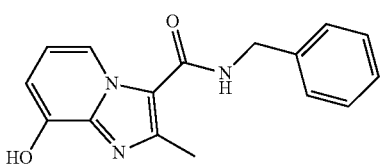 [SMILES: Cc1nc2c(C#N)cccn2c1C(=O)NCc1ccccc1]

N-Benzyl-2-ethylimidazo[1,2-a]pyridine-3-carboxamide (46)

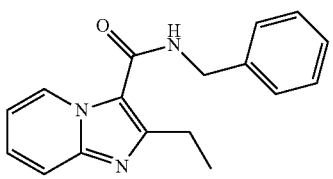 [SMILES: CCc1nc2ccccn2c1C(=O)NCc1ccccc1]

N-Benzyl-2-propylimidazo[1,2-a]pyridine-3-carboxamide (48)

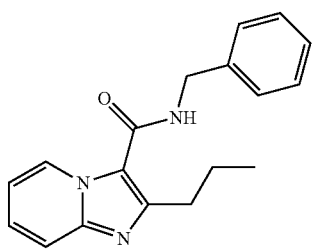 [SMILES: CCCc1nc2ccccn2c1C(=O)NCc1ccccc1]

N-Benzyl-2-cyclopropylimidazo[1,2-a]pyridine-3-carboxamide (50)

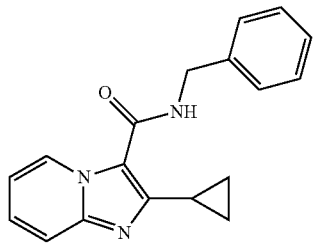 [SMILES: O=C(NCc1ccccc1)c1c(C2CC2)nc2ccccn12]

N-Benzyl-2-isopropylimidazo[1,2-a]pyridine-3-carboxamide (51)

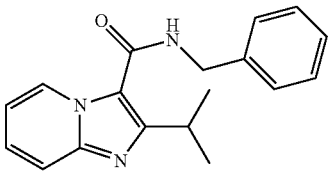 [SMILES: CC(C)c1nc2ccccn2c1C(=O)NCc1ccccc1]

N-Benzyl-2-phenylimidazo[1,2-a]pyridine-3-carboxamide (53)

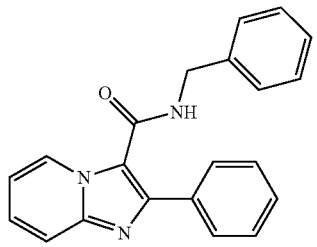 [SMILES: O=C(NCc1ccccc1)c1c(-c2ccccc2)nc2ccccn12]

2-Ethyl-N-(4-(trifluoromethoxy)benzyl)imidazo[1,2-a]pyridine-3-carboxamide (59)

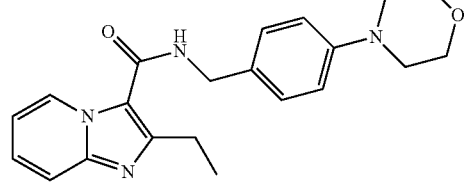

2-Ethyl-7-methyl-N-(4-morpholinobenzyl)imidazo[1,2-a]pyridine-3-carboxamide (68)

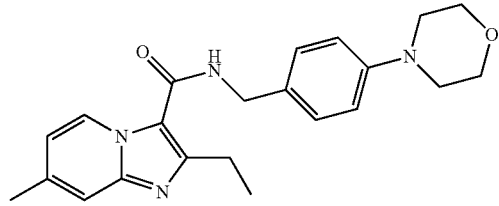 [SMILES: CCc1nc2cc(C)ccn2c1C(=O)NCc1ccc(N2CCOCC2)cc1]

2-Ethyl-7-methyl-N-(naphthalen-2-ylmethyl)imidazo[1,2-a]pyridine-3-carboxamide (69)

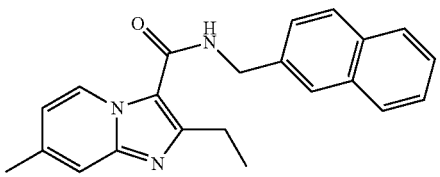 [SMILES: CCc1nc2cc(C)ccn2c1C(=O)NCc1ccc2ccccc2c1]

6-Chloro-2-methyl-N-(4-morpholinobenzyl)imidazo[1,2-a]pyridine-3-carboxamide (74)

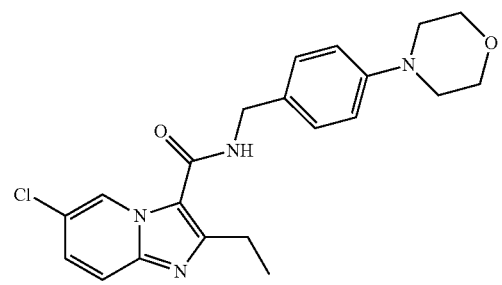 [SMILES: CCc1nc2ccc(Cl)cn2c1C(=O)NCc1ccc(N2CCOCC2)cc1]

6-Chloro-2-ethyl-N-(4-(piperidin-1-yl)benzyl)imidazo[1,2-a]pyridine-3-carboxamide (79)

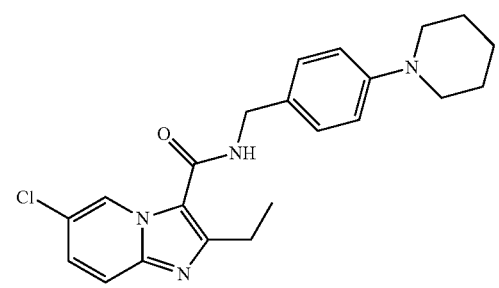 [SMILES: CCc1nc2ccc(Cl)cn2c1C(=O)NCc1ccc(N2CCCCC2)cc1]

6-Chloro-2-ethyl-N-(naphthalen-2-ylmethyl)imidazo[1,2-a]pyridine-3-carboxamide (80)

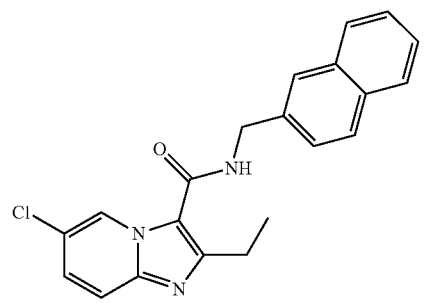 [SMILES: CCc1nc2ccc(Cl)cn2c1C(=O)NCc1ccc2ccccc2c1]

419

7-Chloro-2-ethyl-N-(4-morpholinobenzyl)imidazo[1,2-a]pyridine-3-carboxamide (89)

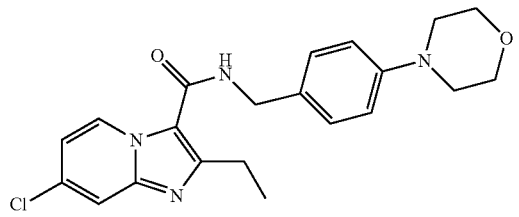 [SMILES: CCc1nc2cc(Cl)ccn2c1C(=O)NCc1ccc(N2CCOCC2)cc1]

7-Chloro-2-ethyl-N-(4-(piperidin-1-yl)benzyl)imidazo[1,2-a]pyridine-3-carboxamide (90)

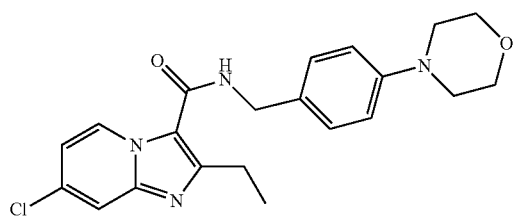 [SMILES: CCc1nc2cc(Cl)ccn2c1C(=O)NCc1ccc(N2CCOCC2)cc1]

7-Chloro-2-ethyl-N-(naphthalen-2-ylmethyl)imidazo[1,2-a]pyridine-3-carboxamide (91)

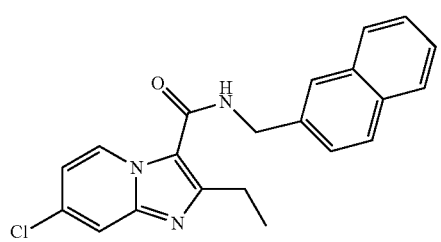 [SMILES: CCc1nc2cc(Cl)ccn2c1C(=O)NCc1ccc2ccccc2c1]

N-(7-Chloro-2-ethylimidazo[1,2-a]pyridin-3-yl)biphenyl-4-carboxamide (142)

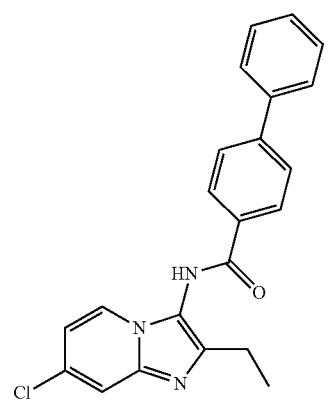 [SMILES: CCc1nc2cc(Cl)ccn2c1NC(=O)c1ccc(-c2ccccc2)cc1]

420

2-(Biphenyl-4-yl)-N-(7-chloro-2-ethylimidazo[1,2-a]pyridin-3-yl)acetamide (143)

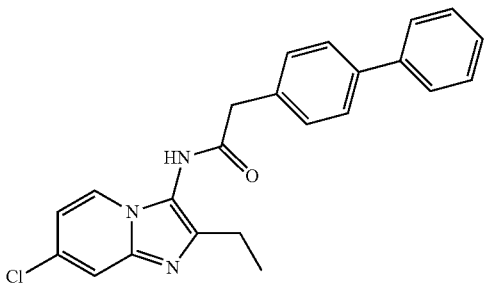 [SMILES: CCc1nc2cc(Cl)ccn2c1NC(=O)Cc1ccc(-c2ccccc2)cc1]

4-Phenoxybenzyl 6-chloro-2-ethylimidazo[1,2-a]pyridine-3-carboxylate (196)

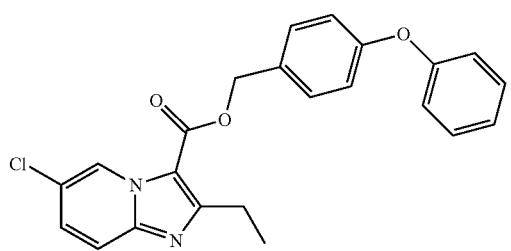 [SMILES: CCc1nc2ccc(Cl)cn2c1C(=O)OCc1ccc(Oc2ccccc2)cc1]

6-Chloro-2-ethyl-N-(4-(pyrrolidin-1-yl)benzyl)imidazo[1,2-a]pyridine-3-carboxamide (211)

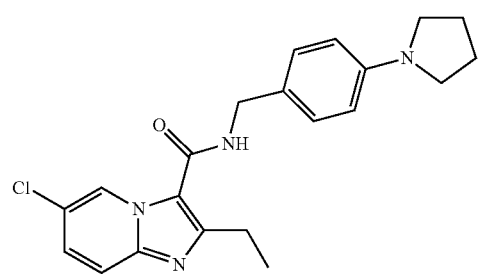 [SMILES: CCc1nc2ccc(Cl)cn2c1C(=O)NCc1ccc(N2CCCC2)cc1]

7-Chloro-2-ethyl-N-(4-(pyrrolidin-1-yl)benzyl)imidazo[1,2-a]pyridine-3-carboxamide (212)

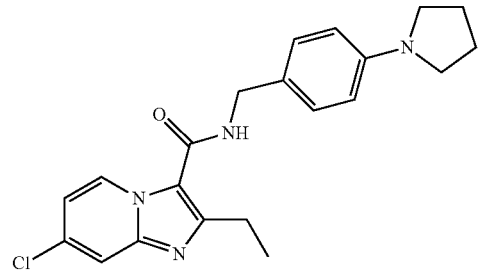 [SMILES: CCc1nc2cc(Cl)ccn2c1C(=O)NCc1ccc(N2CCCC2)cc1]

7-Chloro-N-(4-(5,6-dihydropyridin-1(2H)-yl)benzyl)-2-ethylimidazo[1,2-a]pyridine-3-carboxamide (213)

6-Chloro-2-ethyl-N-isobutylimidazo[1,2-a]pyridine-3-carboxamide (247)

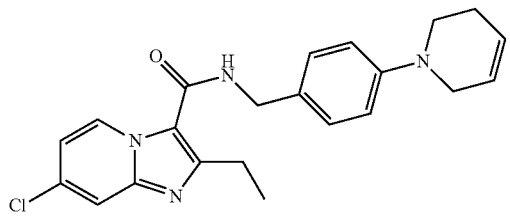 [SMILES: CCc1nc2cc(Cl)ccn2c1C(=O)NCc1ccc(N2CC=CCC2)cc1]

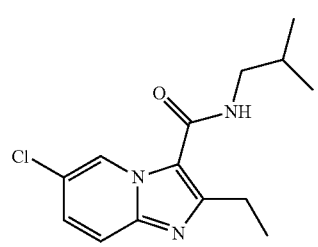

2-ethyl-6-methyl-N-(4-morpholinobenzyl)imidazo[1,2-a]pyridine-3-carboxamide (219)

2-Ethyl-6-fluoro-N-(4-morpholinobenzyl)imidazo[1,2-a]pyridine-3-carboxamide (313)

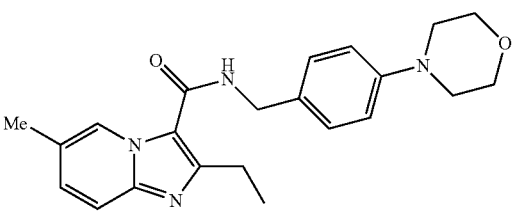 [SMILES: CCc1nc2ccc(C)cn2c1C(=O)NCc1ccc(N2CCOCC2)cc1]

N-(4-(Azepan-1-yl)benzyl)-6-chloro-2-ethylimidazo[1,2-a]pyridine-3-carboxamide (221)

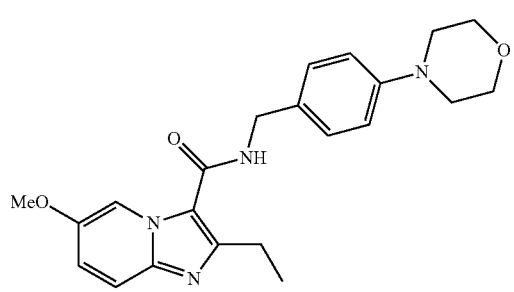

2-Ethyl-7-methoxy-N-(4-morpholinobenzyl)imidazo[1,2-a]pyridine-3-carboxamide (314)

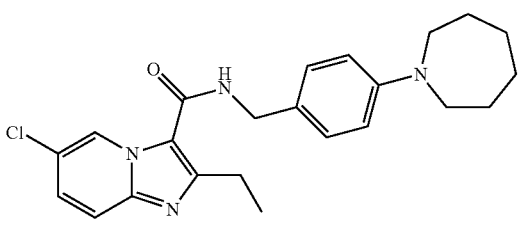 [SMILES: CCc1nc2ccc(Cl)cn2c1C(=O)NCc1ccc(N2CCCCCC2)cc1]

N-(4-(Azepan-1-yl)benzyl)-7-chloro-2-ethylimidazo[1,2-a]pyridine-3-carboxamide (222)

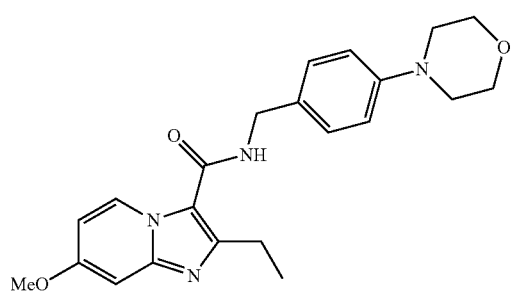

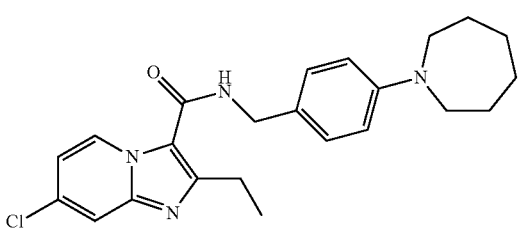 [SMILES: CCc1nc2cc(Cl)ccn2c1C(=O)NCc1ccc(N2CCCCCC2)cc1]

6-Bromo-2-ethyl-N-(4-morpholinobenzyl)imidazo[1,2-a]pyridine-3-carboxamide (315)

5-(6-Chloro-2-ethylimidazo[1,2-a]pyridin-3-yl)-3-(4-(trifluoromethoxy)benzyl)-1,2,4-oxadiazole (243)

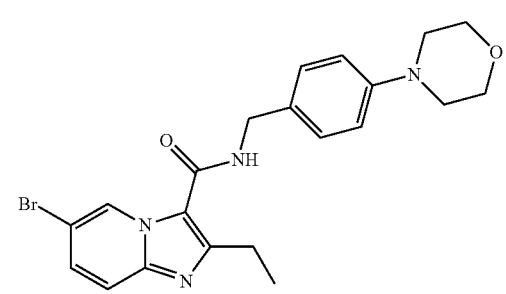

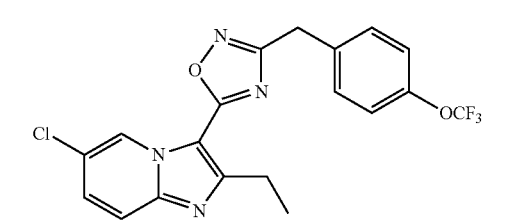 [SMILES: CCc1nc2ccc(Cl)cn2c1-c1nc(Cc2ccc(OC(F)(F)F)cc2)no1]

423

2-Ethyl-6-fluoro-N-(4-morpholinobenzyl)imidazo[1,2-a]pyridine-3-carboxamide (316)

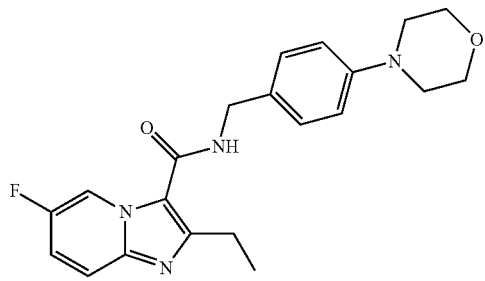 [SMILES: CCc1nc2ccc(F)cn2c1C(=O)NCc1ccc(N2CCOCC2)cc1]

2-Ethyl-8-fluoro-N-(4-morpholinobenzyl)imidazo[1,2-a]pyridine-3-carboxamide (317)

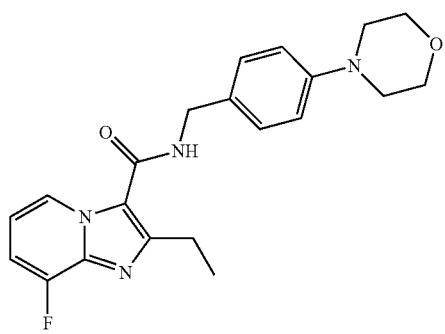 [SMILES: CCc1nc2c(F)cccn2c1C(=O)NCc1ccc(N2CCOCC2)cc1]

2-Ethyl-8-methoxy-N-(4-morpholinobenzyl)imidazo[1,2-a]pyridine-3-carboxamide (318)

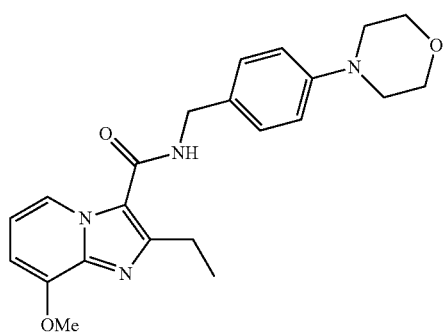 [SMILES: CCc1nc2c(OC)cccn2c1C(=O)NCc1ccc(N2CCOCC2)cc1]

8-(Difluoromethoxy)-2-ethyl-N-(4-morpholinobenzyl)imidazo[1,2-a]pyridine-3-carboxamide (319)

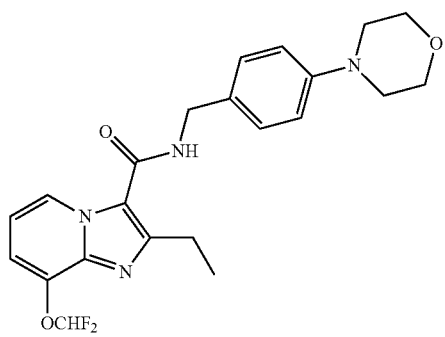 [SMILES: CCc1nc2c(OC(F)F)cccn2c1C(=O)NCc1ccc(N2CCOCC2)cc1]

424

8-Bromo-2-ethyl-N-(4-morpholinobenzyl)imidazo[1,2-a]pyridine-3-carboxamide (320)

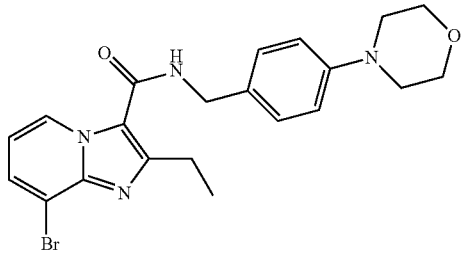 [SMILES: CCc1nc2c(Br)cccn2c1C(=O)NCc1ccc(N2CCOCC2)cc1]

2-Ethyl-N-(4-morpholinobenzyl)-6-(trifluoromethyl)imidazo[1,2-a]pyridine-3-carboxamide (321)

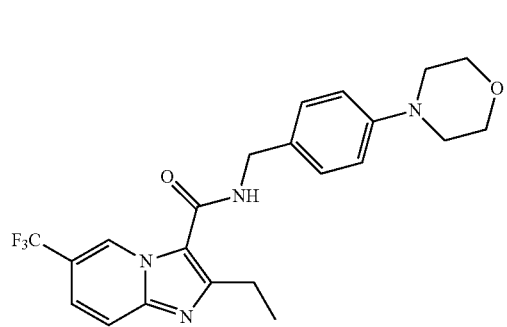 [SMILES: CCc1nc2ccc(C(F)(F)F)cn2c1C(=O)NCc1ccc(N2CCOCC2)cc1]

2-Ethyl-N-(4-morpholinobenzyl)-7-(trifluoromethyl)imidazo[1,2-a]pyridine-3-carboxamide (322)

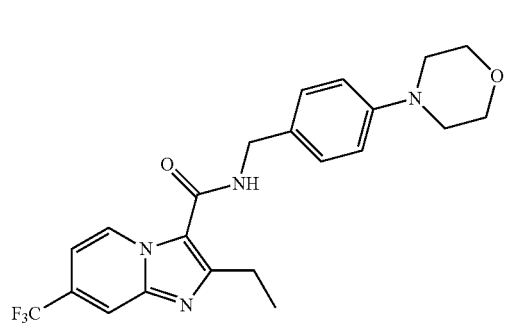 [SMILES: CCc1nc2cc(C(F)(F)F)ccn2c1C(=O)NCc1ccc(N2CCOCC2)cc1]

2-Ethyl-N-(4-morpholinobenzyl)-8-(trifluoromethyl)imidazo[1,2-a]pyridine-3-carboxamide (323)

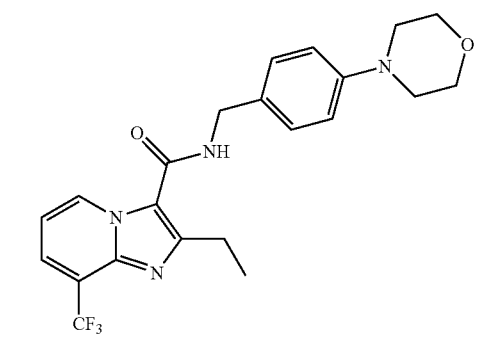 [SMILES: CCc1nc2c(C(F)(F)F)cccn2c1C(=O)NCc1ccc(N2CCOCC2)cc1]

425

7-Bromo-2-ethyl-N-(4-morpholinobenzyl)imidazo[1,2-a]pyridine-3-carboxamide (324)

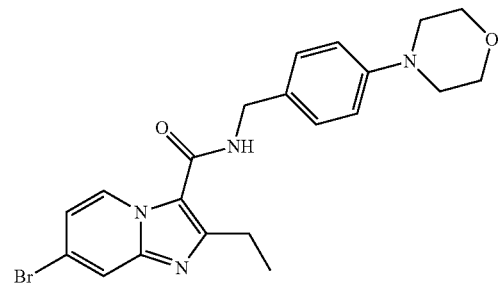

2-Ethyl-N-(4-morpholinobenzyl)-7-(pyridin-4-yl)imidazo[1,2-a]pyridine-3-carboxamide (325)

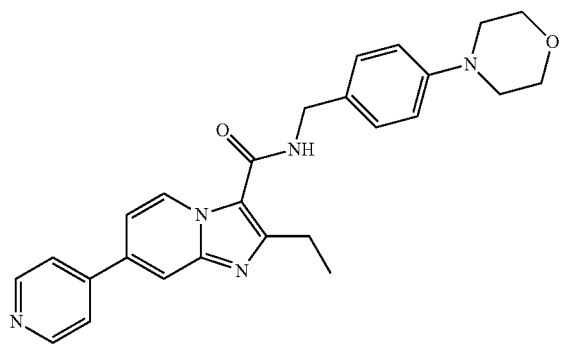 [SMILES: CCc1nc2cc(-c3ccncc3)ccn2c1C(=O)NCc1ccc(N2CCOCC2)cc1]

2-Ethyl-N-(4-morpholinobenzyl)-7-(pyridin-3-yl)imidazo[1,2-a]pyridine-3-carboxamide (326)

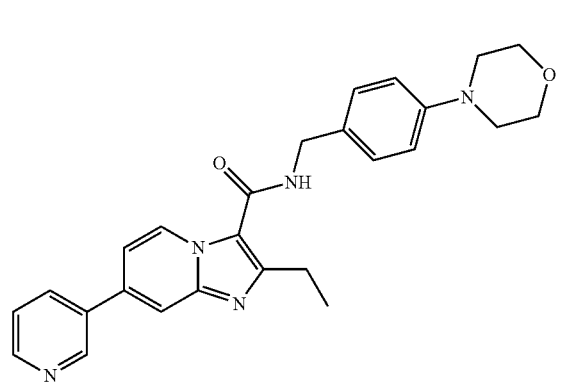 [SMILES: CCc1nc2cc(-c3cccnc3)ccn2c1C(=O)NCc1ccc(N2CCOCC2)cc1]

2-Ethyl-N-(4-morpholinobenzyl)-8-(pyridin-4-yl)imidazo[1,2-a]pyridine-3-carboxamide (327)

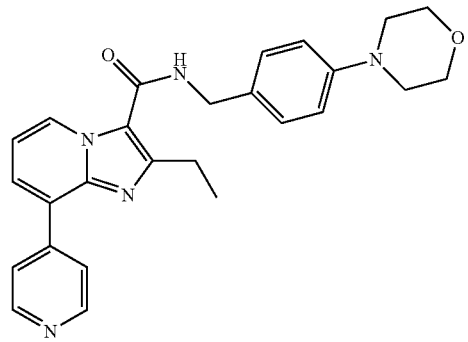 [SMILES: CCc1nc2c(-c3ccncc3)cccn2c1C(=O)NCc1ccc(N2CCOCC2)cc1]

426

2-Ethyl-7-(4-methylpiperazin-1-yl)-N-(4-morpholinobenzyl)imidazo[1,2-a]pyridine-3-carboxamide (328)

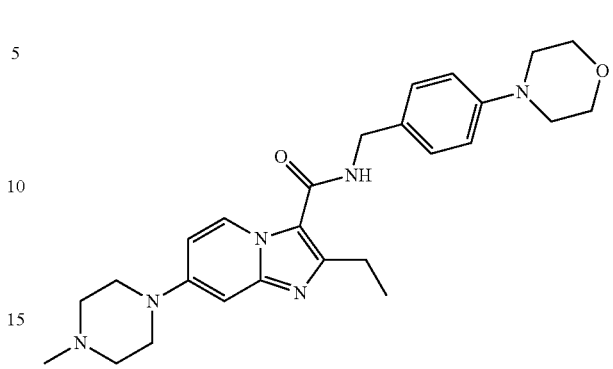

2-Ethyl-7-(4-(4-fluorophenyl)piperazin-1-yl)-N-(4-morpholinobenzyl)imidazo[1,2-a]pyridine-3-carboxamide (329)

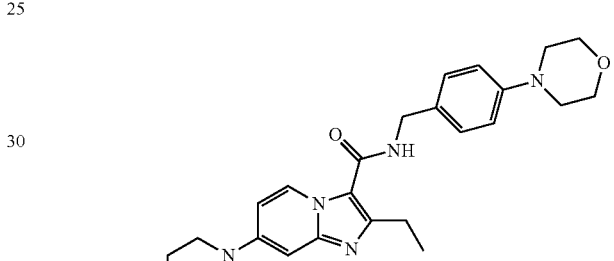

2-Ethyl-7-(4-(4-fluorobenzyl)piperazin-1-yl)-N-(4-morpholinobenzyl)imidazo[1,2-a]pyridine-3-carboxamide (331)

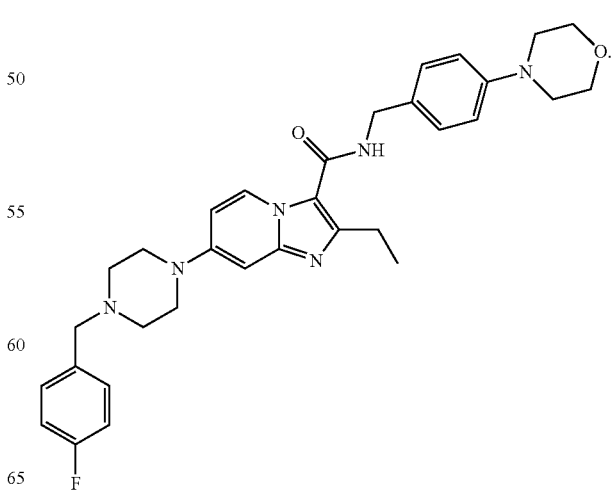

13. The compound according to claim 1, having a formula selected from formulae 161, 239-242 and 264:

[1,1'-Biphenyl]-4-ylmethyl 6-chloro-2-ethylimidazo[1,2-a]pyridine-3-carboxylate (161)

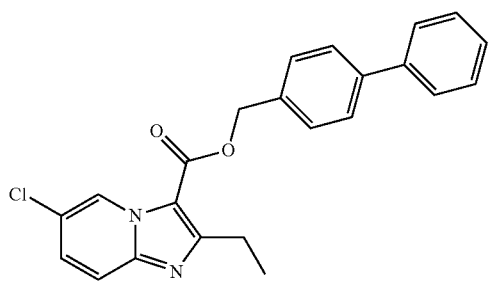 [SMILES: CCc1nc2ccc(Cl)cn2c1C(=O)OCc1ccc(-c2ccccc2)cc1]

6-Chloro-2-ethyl-3-((4-(trifluoromethoxy)phenoxy)methyl)imidazo[1,2-a]pyridine (239)

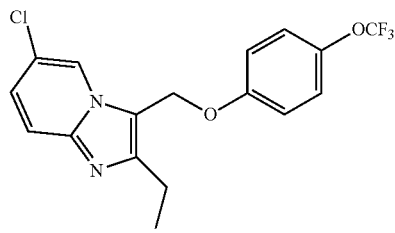 [SMILES: CCc1nc2ccc(Cl)cn2c1COc1ccc(OC(F)(F)F)cc1]

N-((6-Chloro-2-ethylimidazo[1,2-a]pyridin-3-yl)methyl)-4-(trifluoromethoxy)aniline (240)

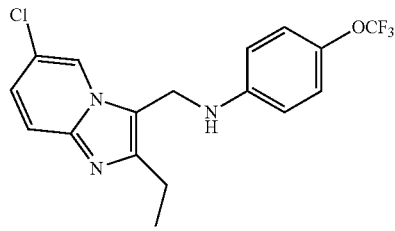 [SMILES: CCc1nc2ccc(Cl)cn2c1CNc1ccc(OC(F)(F)F)cc1]

N-((6-Chloro-2-ethylimidazo[1,2-a]pyridin-3-yl)methyl)-4-(4-(4-fluorophenyl)piperazin-1-yl)aniline (241)

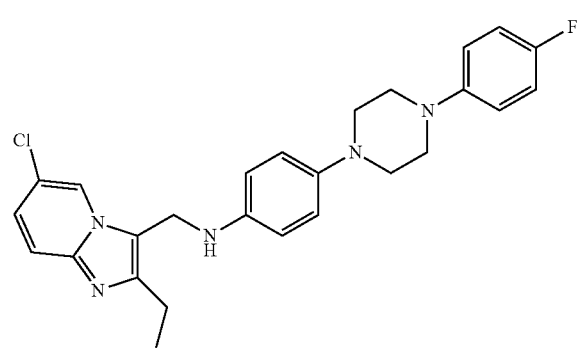 [SMILES: CCc1nc2ccc(Cl)cn2c1CNc1ccc(N2CCN(c3ccc(F)cc3)CC2)cc1]

N-((6-Chloro-2-ethylimidazo[1,2-a]pyridin-3-yl)methyl)-4-(4-fluorophenoxy)aniline (242)

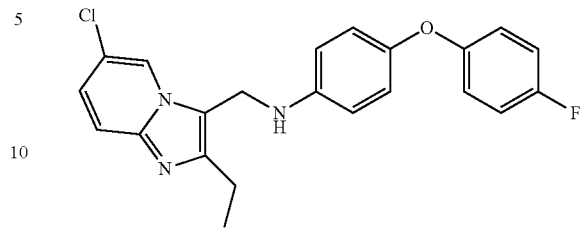

7-Chloro-2-ethyl-N-(4-(4-fluorophenoxy)benzyl)imidazo[1,2-a]pyridine-3-carboxamide (264)

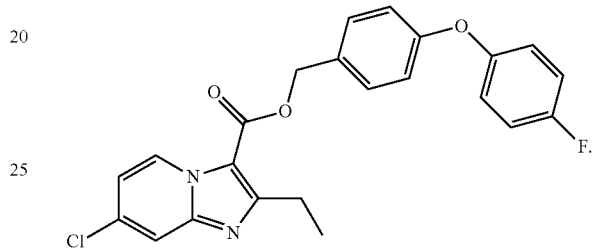

14. A pharmaceutical composition comprising a compound according to claim 12, and a pharmaceutically acceptable carrier.

15. A pharmaceutical composition comprising a compound according to claim 13, and a pharmaceutically acceptable carrier.

16. A compound that competitively inhibits the specific binding of a compound according to claim 12.

17. A compound that competitively inhibits the specific binding of a compound according to claim 13.

18. A method of treatment of a bacterial infection, comprising the application of a suitable amount of a compound according to claim 2, to a person in need thereof.

19. The method, according to claim 18, used for the treatment of tuberculosis.

20. A method of treatment of a bacterial infection, comprising the application, to a person in need of such treatment, of a suitable amount of a compound, which compound is characterized by an ability to competitively inhibit the specific binding of a compound according to claim 2 to a target protein.

21. The method, according to claim 20, used for the treatment of tuberculosis.

* * * * *

UNITED STATES PATENT AND TRADEMARK OFFICE
CERTIFICATE OF CORRECTION

PATENT NO. : D616,155 S
APPLICATION NO. : 29/335398
DATED : October 21, 2014
INVENTOR(S) : Zaesung No et al.

It is certified that error appears in the above-identified patent and that said Letters Patent is hereby corrected as shown below:

Delete title page and substitute therefore with the attached title page consisting of the corrected number of claims in patent.

In the Claims:

Delete Claims 1-21, Column 285, line 39-Column 428, line 57 and substitute therefore with the following Claims 1-14, Claims 7-8,10, 16-17 and 20-21 have been cancelled.

Claims 1-14 should read as follows:

1. A compound having the general formula Ia:

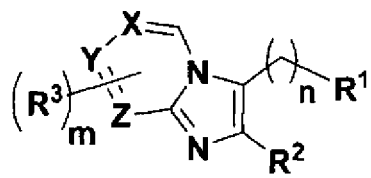

Ia wherein m is 0, 1, 2, 3 or 4;

n is 0, 1, 2, or 3;

X, Y and Z are CH;

$R^1$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, -$OR^4$, -$C(O)OR^4$, -$C(O)R^4$, Signed and Sealed this
Twenty-third Day of June, 2015

Michelle K. Lee
*Director of the United States Patent and Trademark Office*

-C(O)N(R$^4$)$_2$, -CN, -NO$_2$, -NH$_2$, -N(R$^4$)$_2$, -OR$^4$HetA, -OR$^4$N(R$^4$)$_2$, -C(O)N(R$^4$)R$^4$HetA, -C(O)N(R$^4$)HetA, -C(O)HetA, -C(O)N(R$^4$)R$^4$S(O)$_2$R$_4$; -S(O)$_2$N(R$^4$)$_2$, -S(O)$_2$R$^4$, -N(R$^4$)C(O)R$^4$SR$^4$, -N(R$^4$)R$^4$S(O)$_2$R$^4$, -N(R$^4$)S(O)$_2$R$^4$, -C(S)R$^4$, aryl, benzyl, and heterocyclyl, any of which is optionally substituted;

R$^2$ is, at each occurrence, independently selected from the group consisting of hydrogen, halogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, -OH, -OR$^5$, C$_1$-C$_{10}$ alkoxy, C$_3$-C$_{10}$ cycloalkoxy, C$_3$-C$_{15}$ cycloalkylalkoxy, C$_3$-C$_{15}$ cycloalkylalkyl, -CN, -NO$_2$, -NH$_2$, -N(R$^5$)$_2$, -C(O)R$^5$, -C(O)OR$^5$, -C(O)N(R$^5$)$_2$, -SR$^5$, -S(O)R$^5$, -S(O)$_2$R$^5$, -S(O)$_2$N(R$^5$)$_2$, aryl, benzyl, heteroaryl, and heterocyclyl, any of which is optionally substituted;

R$^3$ is, at each occurrence, independently selected from the group consisting of hydrogen, halogen, C$_1$-C$_{10}$ alkyl, C$_3$-C$_{10}$ cycloalkyl, hydroxyl, -OR$^6$, -CN, -NO$_2$, -NH$_2$, -N(R$^6$)C(O)R$^6$, -C(O)R$^6$, -C(O)OR$^6$, -C(O)N(R$^6$)$_2$, -S(O)R$^6$, -S(O)$_2$R$^6$, -S(O)$_2$N(R$^6$)$_2$, aryl, benzyl, heteroaryl, heterocyclyl, any of which is optionally substituted, or two groups of R$^3$ are connected to each other to make a five or six membered cyclic or heterocyclic ring, any of which is optionally substituted;

R$^4$ is, at each occurrence, independently selected from the group consisting of hydrogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, -C(O)R$^7$, -R$^7$(R$^7$)C(O)R$^7$, -C(O)OR$^7$, -R$^7$(R$^7$)C(O)OR$^7$, -C(O)N(R$^7$)$_2$, -R$^7$(R$^7$)C(O)N(R$^7$)$_2$, -S(O)R$^7$, -S(O)$_2$R$^7$, -S(O)$_2$N(R$^7$)$_2$, aryl, benzyl, heteroaryl, and heterocyclyl, any of which is optionally substituted; and R$^5$, R$^6$ and R$^7$ are, at each occurrence, independently selected from the group consisting of hydrogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, aryl, benzyl, heteroaryl, and heterocyclyl, any of which is optionally substituted; and pharmaceutically acceptable salts thereof, and wherein the compound has a formula selected from the following formulae 5, 8, 13, 14, 17, 18, 20, 21, 23-43, 46, 48, 50, 51, 53, 59, 68, 69, 74, 79, 80, 89-91, 142, 143, 161, 196, 211-213, 219, 221, 222, 239-247, 264, 313-329 and 331:

2-Methyl-N-(pyridin-4-yl)imidazo[1,2-a]pyridine-3-carboxamide (5)
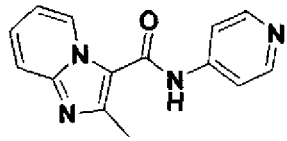
N-Benzyl-2-methylimidazo[1,2-a]pyridine-3-carboxamide (8)
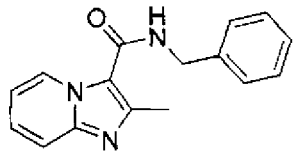
2-Methyl-N-(pyridin-3-ylmethyl)imidazo[1,2-pyridina]pyridine-3-carboxamide (13)
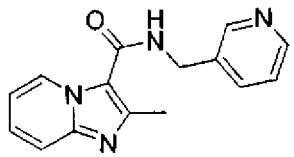
2-Methyl-N-(pyridin-4-ylmethyl)imidazo[1,2-a]pyridine-3-carboxamide (14)
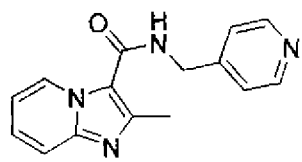
N-((1H-Indol-5-yl)methyl)-2-methylimidazo[1,2-a]pyridine-3-carboxamide (17)
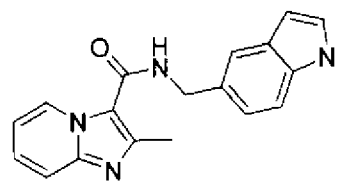
N-(Cyclohexylmethyl)-2-methylimidazo[1,2-a]pyridine-3-carboxamide (18)
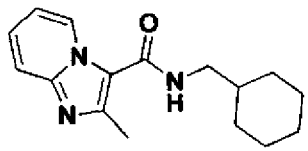

2-Methyl-N-(piperidin-4-ylmethyl)imidazo[1,2-a]pyridine-3-carboxamide (20)
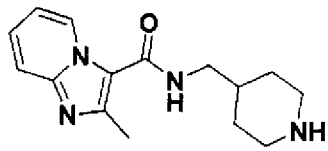
2-Methyl-N-phenethylimidazo[1,2-a]pyridine-3-carboxamide (21)
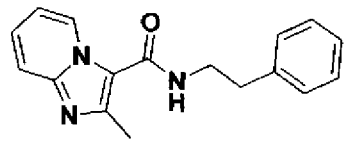
2-Methyl-N-(2-phenoxyethyl)imidazo[1,2-a]pyridine-3-carboxamide (23)
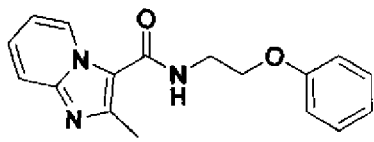
N-(2-(Benzyloxy)ethyl)-2-methylimidazo[1,2-a]pyridine-3-carboxamide (24)
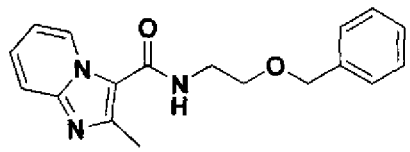
(S)-Methyl 2-(2-methylimidazo[1,2-a]pyridine-3-carboxamido)-3-phenylpropanoate (25)
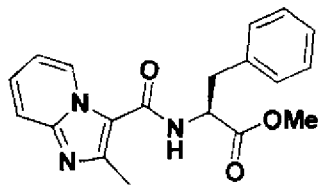
N-(2-Methylimidazo[1,2-a]pyridin-3-yl)-2-phenylacetamide (26)
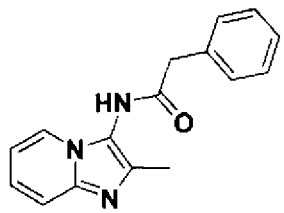

N-Benzyl-8-chloro-2-methylimidazo[1,2-a]pyridine-3-carboxamide (27)
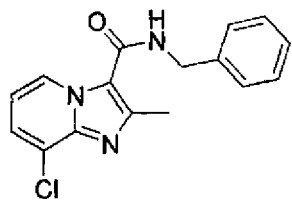
N-Benzyl-7-chltoro-2-methylimidazo[1,2-a]lpyridine-3-carboxamide (28)
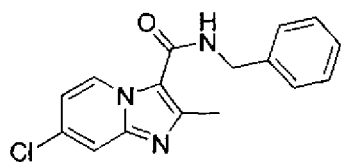
N-Benzyl-6-chloro-2-methylimidazo[1,2-a]pyridine-3-carboxamide (29)
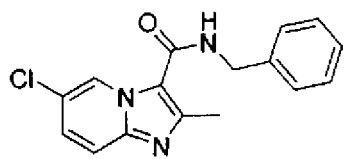
N-Benzyl-2,8-dimethylimidazo[1,2-a]pyridine-3-carboxamide (30)
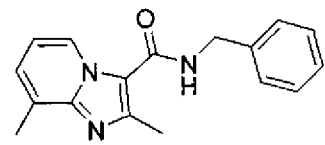
N-Benzyl-2,7-dimethylimidazo[1,2-a]pyridine-3-carboxamide (31)
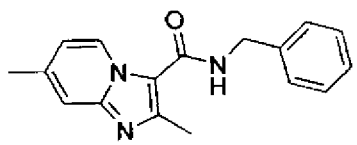
N-Benzyl-2,6-dimethylimidazo[1,2-a]pyridine-3-carboxamide (32)
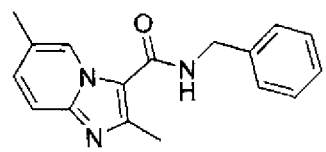

N-Benzyl-2,5-dimethylimidazo[1,2-a]pyridine-3-carboxamide (33)
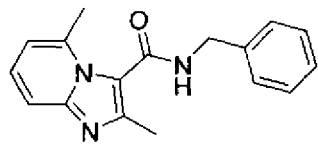
N-Benzyl-6-fluoro-2-methylimidazo[1,2-a]pyridine-3-carboxamide (34)
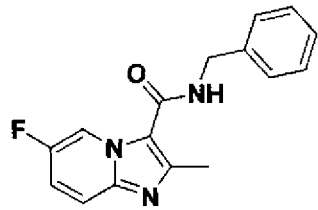
N-Benzyl-7-cyano-2-methylimidazo[1,2-a]pyridine-3-carboxamide (35)
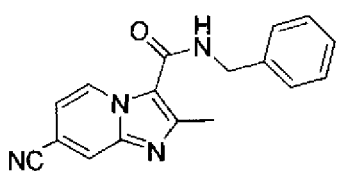
N-Benzyl-6-cyano-2-methylimidazo[1,2-a]pyridine-3-carboxamide (36)
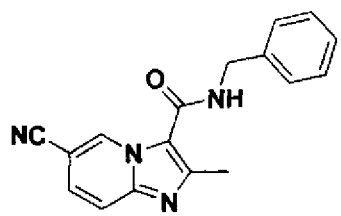
N-Benzyl-2-methyl-7-phenylimidazo[1,2-a]pyridine-3-carboxamide (37)
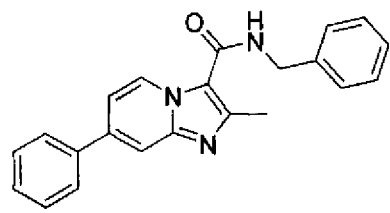

N-Benzyl-2-methyl-6-phenylimidazo[1,2-a]pyridine-3-carboxamide (38)
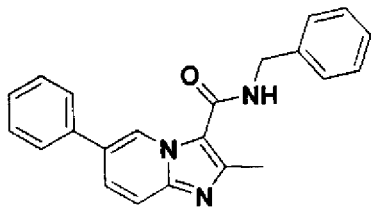
N-Benzyl-8-fluoro-2-methylimidazo[1,2-a]pyridine-3-carboxamide (39)
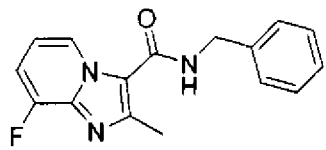
N-Benzyl-2-methyl-8-(trifluoromethyl)imidazo[1,2-a]pyridine-3-carboxamide (40)
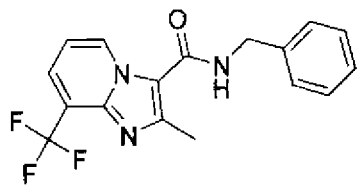
N-Benzyl-8-methoxy-2-methylimidazo[1,2-a]pyridine-3-carboxamide (41)
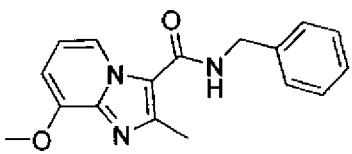
N-Benzyl-8-cyano-2-methylimidazo[1,2-a]pyridine-3-carboxamide (42)
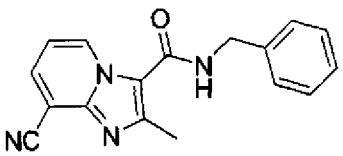
N-Benzyl-8-hydroxy-2-methylimidazo[1,2-a]pyridine-3-carboxamide (43)
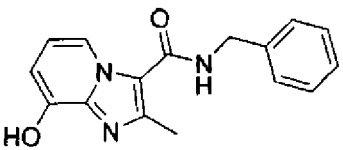

N-Benzyl-2-ethylimidazo[1,2-a]pyridine-3-carboxamide (46)
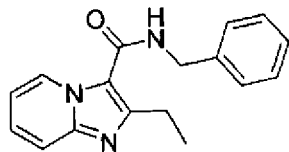
N-Benzyl-2-propylimidazo[1,2-a]pyridine-3-carboxamide (48)
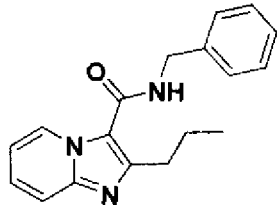
N-Benzyl-2-cyclopropylimidazo[1,2-a]pyridine-3-carboxamide (50)
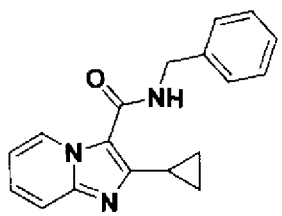
N-Benzyl-2-isopropylimidazo[1,2-a]pyridine-3-carboxamide (51)
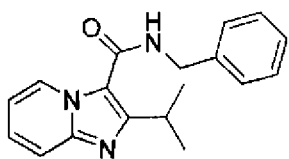
N-Benzyl-2-phenylimidazo[1,2-a]pyridine-3-carboxamide (53)
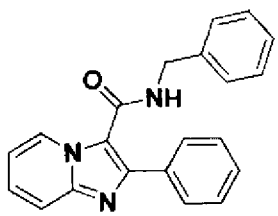

2-Ethyl-N-(4-(trifluoromethoxy)benzyl)imidazo[1,2-a]pyridine-3-carboxamide (59)
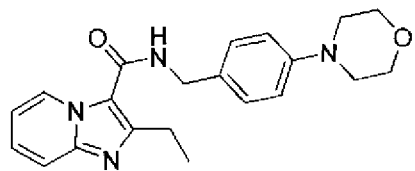
2-Ethyl-7-methyl-N-(4-morpholinobenzyl)imidazo[1,2-a]pyridine-3-carboxamide (68)
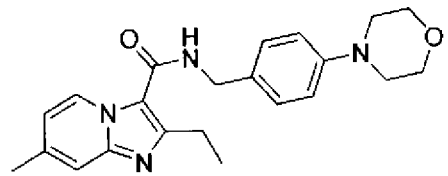
2-Ethyl-7-methyl-N-(naphthalen-2-ylmethyl)imidazo[1,2-a]pyridine-3-carboxamide (69)
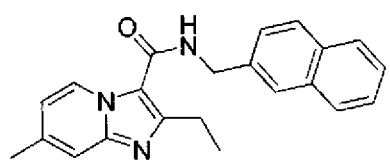
6-Chloro-2-methyl-N-(4-morpholinobenzyl)imidazo[1,2-a]pyridine-3-carboxamide (74)
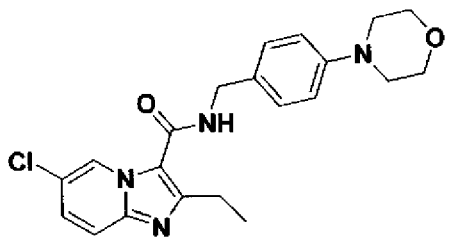
6-Chloro-2-ethyl-N-(4-(piperidin-1-yl)benzyl)imidazo[1,2-a]pyridine-3-carboxamide (79)
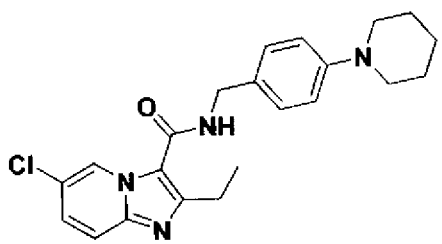

6-Chloro-2-ethyl-N-(naphthalen-2-ylmethyl)imidazo[1,2-a]pyridine-3-carboxamide (80)
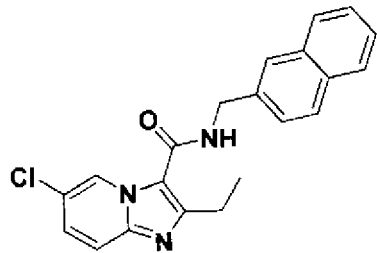
7-Chloro-2-ethyl-N-(4-morpholinobenzyl)imidazo[1,2-a]pyridine-3-carboxamide (89)
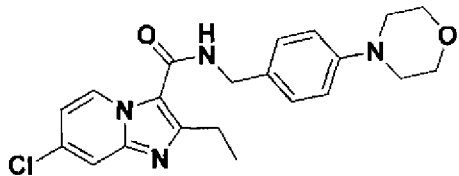
7-Chloro-2-ethyl-N-(4-(piperidin-1-yl)benzyl)imidazo[1,2-a]pyridine-3-carboxamide (90)
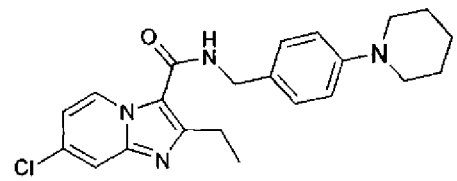
7-Chloro-2-ethyl-N-(naphthalen-2-ylmethyl)imidazo[1,2-a]pyridine-3-carboxamide (91)
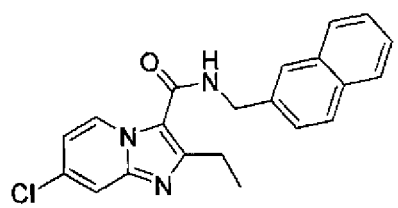
N-(7-Chloro-2-ethylimidazo[1,2-a]pyridin-3-yl)biphenyl-4-carboxamide (142)
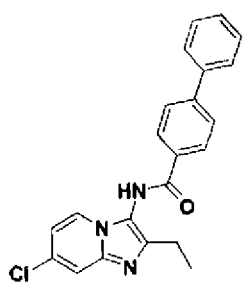

2-(Biphenyl-4-yl)-N-(7-chloro-2-ethylimidazo[1,2-a]pyridin-3-yl)acetamide (143)
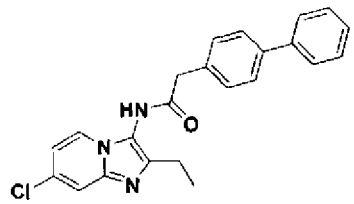
[1,1'-Biphenyl]-4-ylmethyl 6-chloro-2-ethylimidazo[1,2-a]pyridine-3-carboxylate (161)
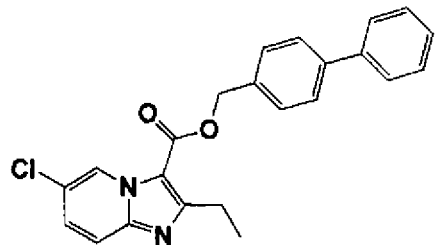
4-Phenoxybenzyl 6-chloro-2-ethylimidazo[1,2-a]pyridine-3-carboxylate (196)
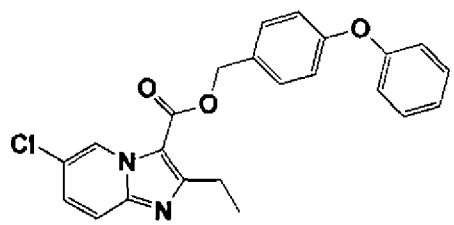
6-Chloro-2-ethyl-N-(4-(pyrrolidin-1-yl)benzyl)imidazo[1,2-a]pyridine-3-carboxamide (211)
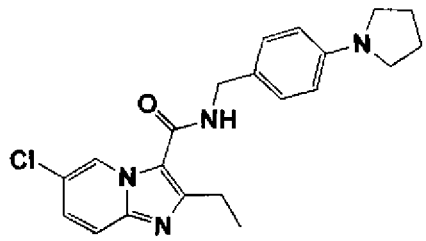
7-Chloro-2-ethyl-N-(4-(pyrrolidin-1-yl)benzyl)imidazo[1,2-a]pyridine-3-carboxamide (212)
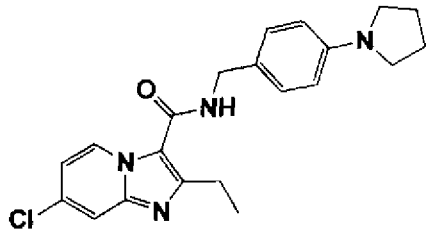

7-Chloro-N-(4-(5,6-dihydropyridin-1(2H)-yl)benzyl)-2-ethylimidazo[1,2-a]pyridine-3-carboxamide (213)
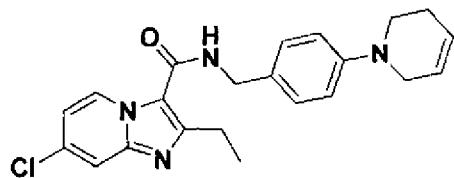
2-ethyl-6-methyl-N-(4-morpholinobenzyl)imidazo[1,2-a]pyridine-3-carboxamide (219)
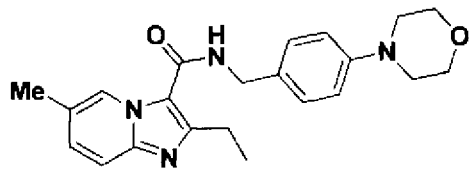
N-(4-(Azepan-1-yl)benzyl)-6-chloro-2-ethylimidazo[1,2-a]pyridine-3-carboxamide (221)
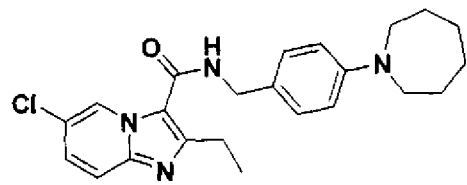
N-(4-(Azepan-1-yl)benzyl)-7-chloro-2-ethylimidazo[1,2-a]pyridine-3-carboxamide (222)
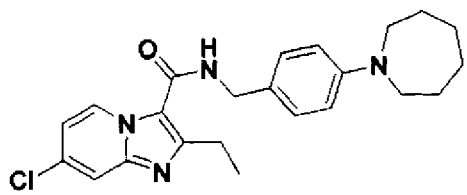
6-Chloro-2-ethyl-3-((4-(trifluoromethoxy)phenoxy)methyl)imidazo[1,2-a]pyridine (239)
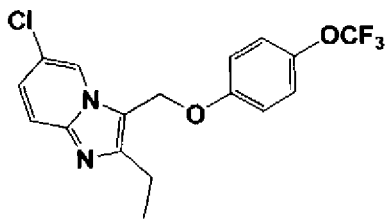

N-((6-Chloro-2-ethylimidazo[1,2-a]pyridin-3-yl)methyl)-4-(trifluoromethoxy)aniline (240)
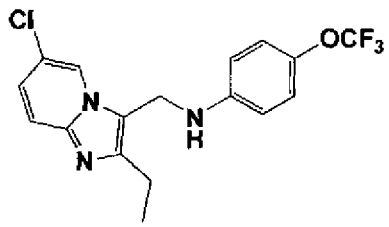
N-((6-Chloro-2-ethylimidazo[1,2-a]pyridin-3-yl)methyl)-4-(4-(4-fluorophenyl)piperazin-1-yl)aniline (241)
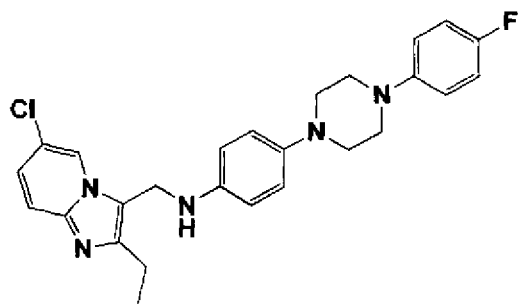
N-((6-Chloro-2-ethylimidazo[1,2-a]pyridin-3-yl)methyl)-4-(4-fluorophenoxy)aniline (242)
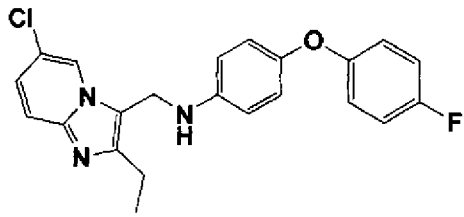
5-(6-Chloro-2-ethylimidazo[1,2-a]pyridin-3-yl)-3-(4-(trifluoromethoxy)benzyl)-1,2,4-oxadiazole (243)
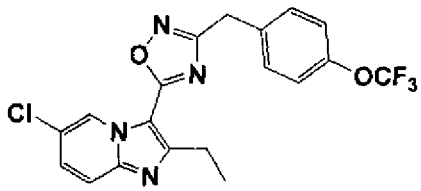

2-(7-Chloro-2-ethylimidazo[1,2-a]pyridin-3-yl)-5-((4-(4-(trifluoromethoxy)phenyl)piperazin-1-yl)methyl)-1,3,4-oxadiazole (244)
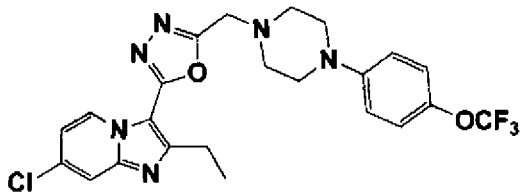
5-(6-Chloro-2-ethylimidazo[1,2-a]pyridin-3-yl)-3-(4-(4-fluorophenoxy)benzyl)-1,2,4-oxadiazole (245)
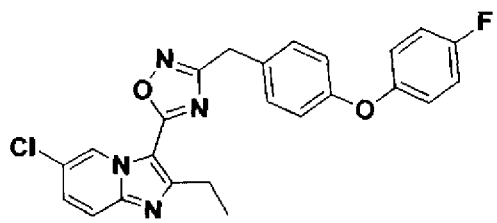
6-Chloro-N,2-diethylimidazo[1,2-a]pyridine-3-carboxamide (246)
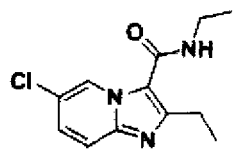
6-Chloro-2-ethyl-N-isobutylimidazo[1,2-a]pyridine-3-carboxamide (247)
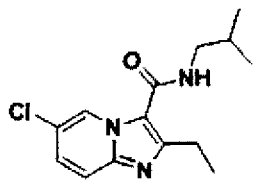
7-Chloro-2-ethyl-N-(4-(4-fluorophenoxy)benzyl)imidazo[1,2-a]pyridine-3-carboxamide (264)
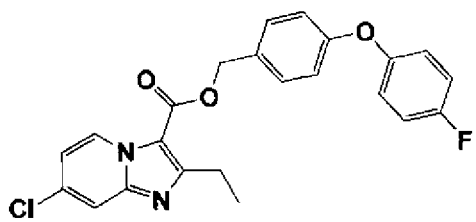

2-Ethyl-6-fluoro-N-(4-morpholinobenzyl)imidazo[1,2-a]pyridine-3-carboxamide (313)
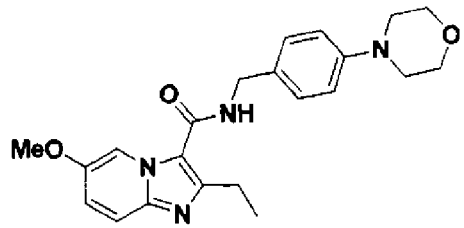
2-Ethyl-7-methoxy-*N*-(4-morpholinobenzyl)imidazo[1,2-a]pyridine-3-carboxamide (314)
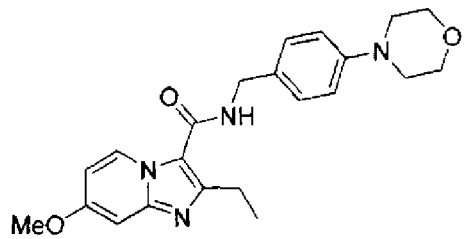
6-Bromo-2-ethyl-N-(4-morpholinobenzyl)imidazo[1,2-a]pyridine-3-carboxamide (315)
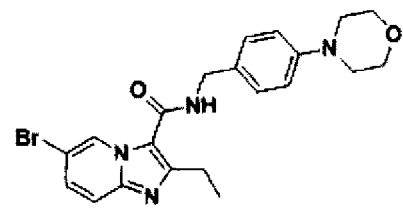
2-Ethyl-6-fluoro-N-(4-morpholinobenzyl)imidazo[1,2-a]pyridine-3-carboxamide (316)
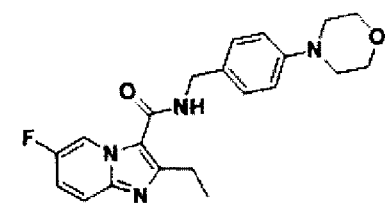
2-Ethyl-8-fluoro-N-(4-morpholinobenzyl)imidazo[1,2-a]pyridine-3-carboxamide (317)
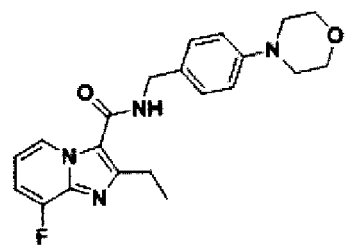

2-Ethyl-8-methoxy-*N*-(4-morpholinobenzyl)imidazo[1,2-a]pyridine-3-carboxamide (318)
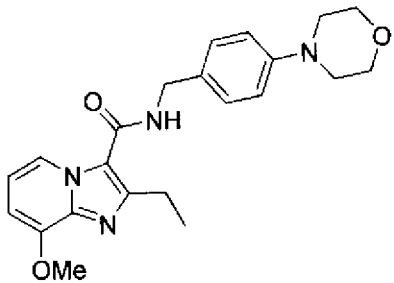
8-(Difluoromethoxy)-2-ethyl-N-(4-morpholinobenzyl)imidazo[1,2-a]pyridine-3-carboxamide (319)
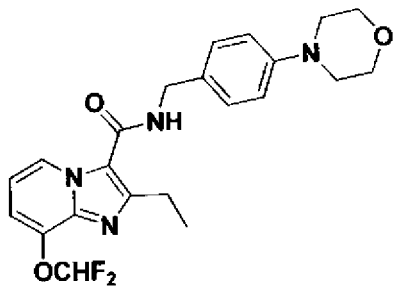
8-Bromo-2-ethyl-*N*-(4-morpholinobenzyl)imidazo[1,2-a]pyridine-3-carboxamide (320)
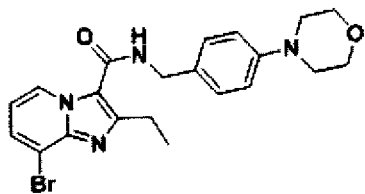
2-Ethyl-*N*-(4-morpholinobenzyl)-6-(trifluoromethyl)imidazo[1,2-a]pyridine-3-carboxamide (321)
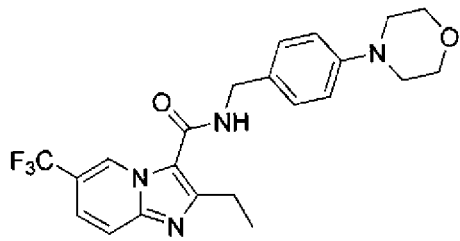

2-Ethyl-N-(4-morpholinobenzyl)-7-(trifluoromethyl)imidazo[1,2-a]pyridine-3-carboxamide (322)
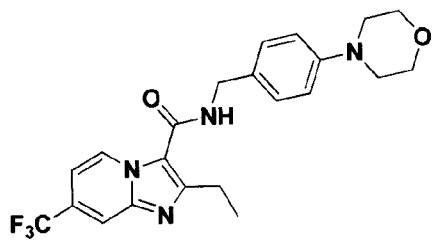
2-Ethyl-*N*-(4-morpholinobenzyl)-8-(trifluoromethyl)imidazo[1,2-a]pyridine-3-carboxamide (323)
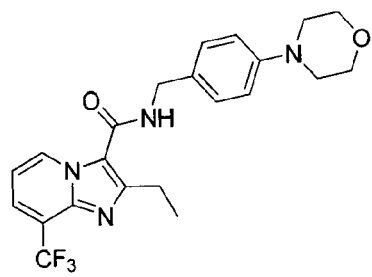
7-Bromo-2-ethyl-*N*-(4-morpholinobenzyl)imidazo[1,2-a]pyridine-3-carboxamide (324)
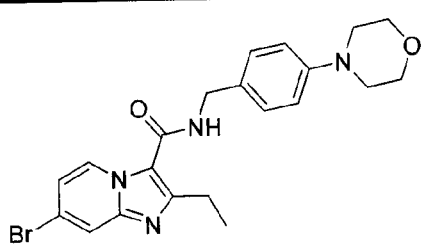
2-Ethyl-*N*-(4-morpholinobenzyl)-7-(pyridin-4-yl)imidazo[1,2-a]pyridine-3-carboxamide (325)
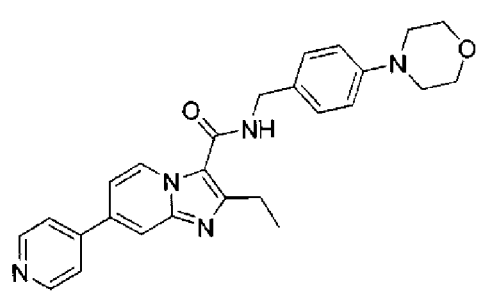

2-Ethyl-*N*-(4-morpholinobenzyl)-7-(pyridin-3-yl)imidazo[1,2-a]pyridine-3-carboxamide (326)
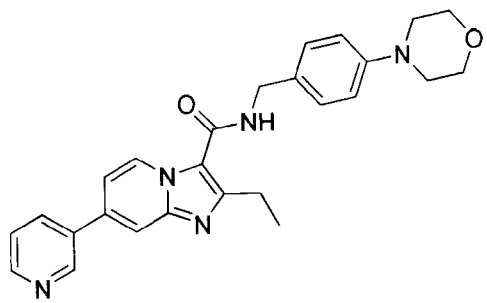
2-Ethyl-*N*-(4-morpholinobenzyl)-8-(pyridin-4-yl)imidazo[1,2-a]pyridine-3-carboxamide (327)
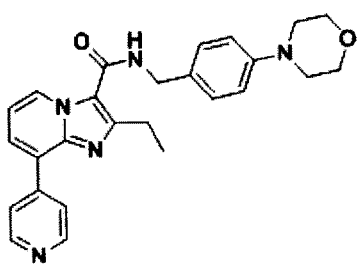
2-Ethyl-7-(4-methylpiperazin-1-yl)-*N*-(4-morpholinobenzyl)imidazo[1,2-a]pyridine-3-carboxamide (328)
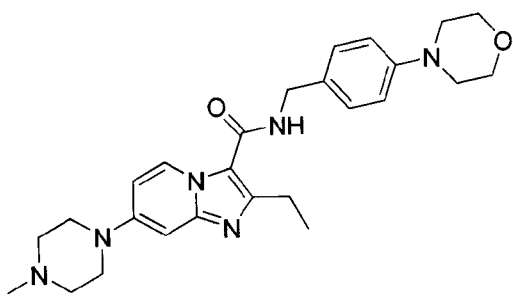

2-Ethyl-7-(4-(4-fluorophenyl)piperazin-1-yl)-*N*-(4-morpholinobenzyl)imidazo[1,2-a]pyridine-3-carboxamide(329)
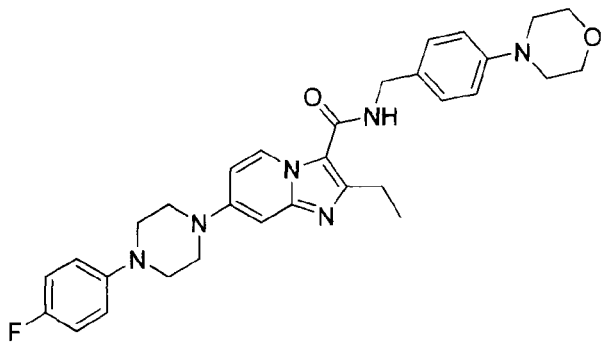
2-Ethyl-7-(4-(4-fluorobenzyl)piperazin-1-yl)-*N*-(4-morpholinobenzyl)imidazo[1,2-a]pyridine-3-carboxamide (331)
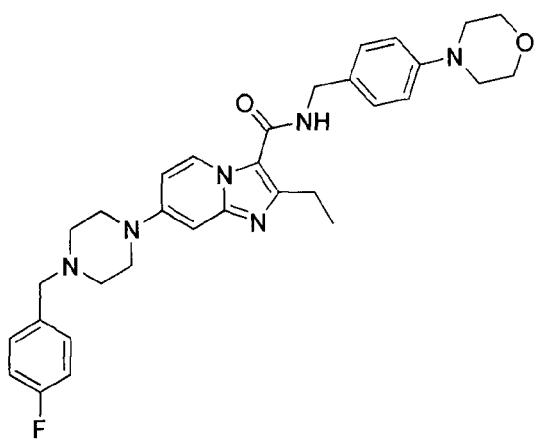
2. A compound having the general formula Ib:
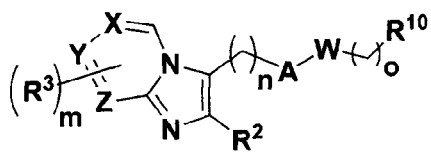
Ib
wherein o is 0, 1, 2, or 3;

n is 0;

m is 1, 2, 3 or 4;

X, Y and Z are CH;

A is C=O or C=S

W is $NR^{11}$;

$R^2$ is, at each occurrence, independently selected from the group consisting of hydrogen, halogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -OH, -$OR^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, -CN, -$NO_2$, -$NH_2$, -$N(R^5)_2$, -$C(O)R^5$, -$C(O)OR^5$, -$C(O)N(R^5)_2$, -$SR^5$, -$S(O)R^5$, -$S(O)_2R^5$, -$S(O)_2N(R^5)_2$, aryl, benzyl, and heterocyclyl, any of which is optionally substituted;

$R^3$ is, at each occurrence, independently selected from the group consisting of hydrogen, halogen, $C_1$-$C_{10}$ alkyl, $C_3$-$C_{10}$ cycloalkyl, hydroxyl, -$OR^6$, -CN, -$NO_2$, -$NH_2$, -$N(R^6)C(O)R^6$, -$C(O)R^6$, -$C(O)OR^6$, -$C(O)N(R^6)_2$, -$S(O)R^6$, -$S(O)_2R^6$, -$S(O)_2N(R^6)_2$, aryl, benzyl, heteroaryl, heterocyclyl, any of which is optionally substituted, or two groups of $R^3$ are connected to each other to make a five or six membered cyclic or heterocyclic ring, any of which is optionally substituted;

$R^5$ and $R^6$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted;

$R^{10}$ is a moiety selected from the group consisting of

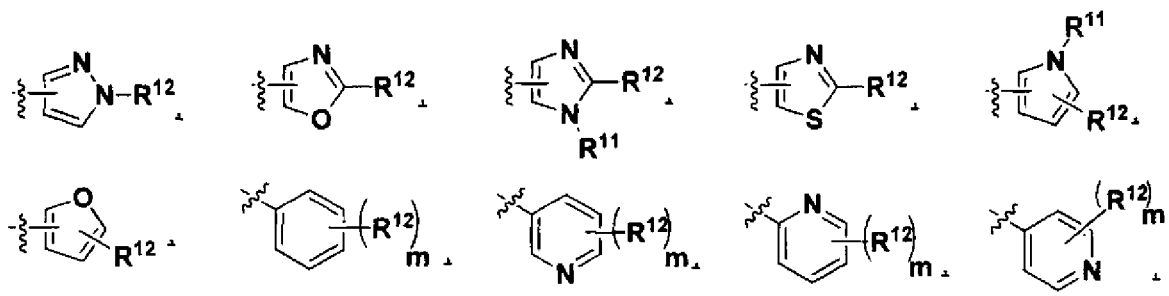

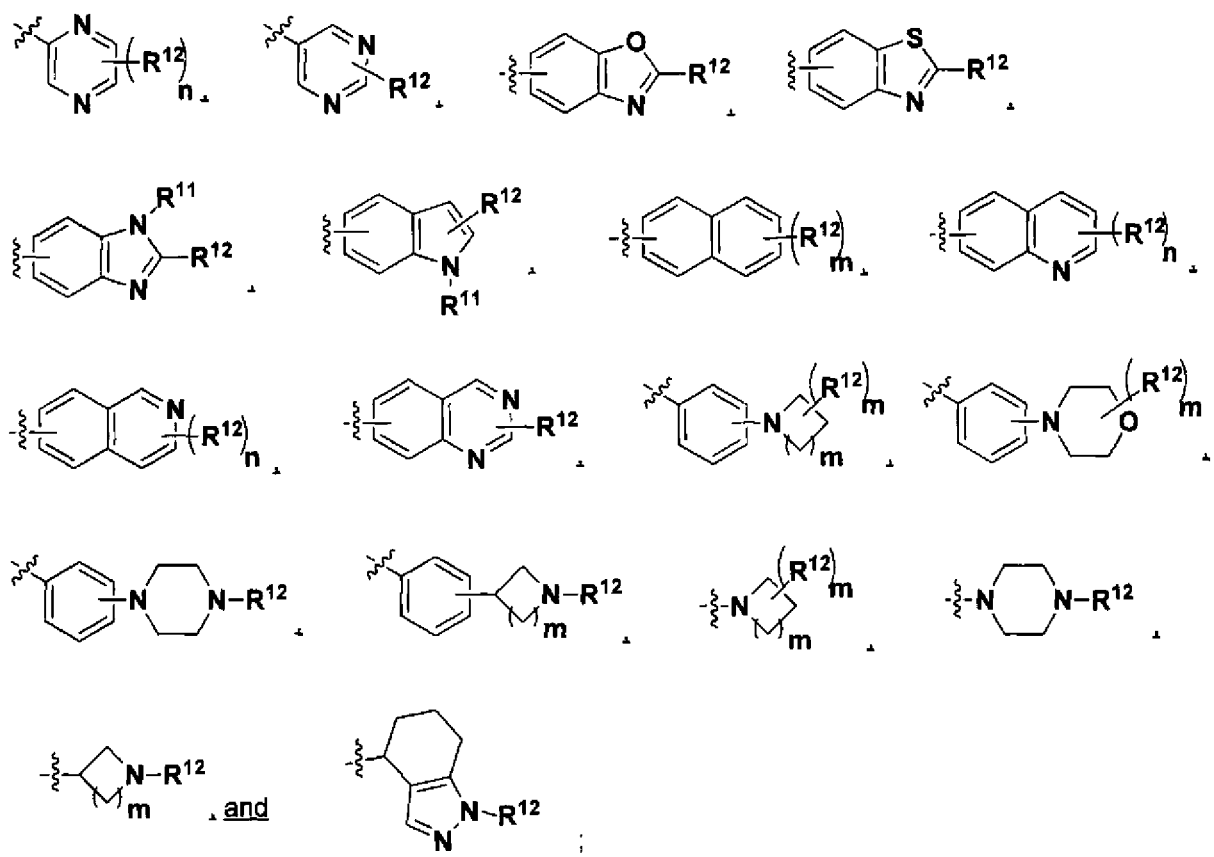

$R^{11}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -OH, -$OR^{13}$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, -$NH_2$, -$N(R^{13})_2$, -$C(O)R^{13}$, -$C(O)OR^{13}$, -$C(O)N(R^{13})_2$, -$S(O)R^{13}$, -$S(O)_2R^{13}$, -$S(O)_2N(R^{13})_2$, aryl, benzyl, heteroaryl, and heterocyclyl, any of which is optionally substituted;

$R^{12}$ is, at each occurrence, independently selected from the group consisting of $C_2$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, hydroxyl, -$OR^{14}$, -$C(O)R^{14}$, -$C(O)OR^{14}$, -CN, -$NO_2$, -$NH_2$, -$N(R^{14})_2$, -$C(O)N(R^{14})_2$, -$S(O)R^{14}$, -$S(O)_2R^{14}$, -$S(O)_2N(R^{14})_2$, aryl, benzyl, heteroaryl, and heterocyclyl, any of which is optionally substituted;

$R^{13}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted; and $R^{14}$ is, at each occurrence, independently selected from the group consisting of hydrogen, $C_1$-$C_8$ alkyl optionally substituted with at least one hydroxyl or halogen; $C_3$-$C_7$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl and heterocyclyl, any of which is optionally substituted, and pharmaceutically acceptable salts thereof.

3. The compound according to claim 2, having a formula selected from the following formulae 6, 7, 9-12, 15, 16, 19, 22, 44, 45, 47, 49, 52, 54-58, 60-67, 70-73, 75-78, 81-88, 92-141, 144-160, 162-195, 197-210, 214-218, 220, 223-238, 248-263, 265-312, 330 and 332-352:

2-Methyl-N-(4-phenoxyphenyl)imidazo[1,2-a]pyridine-3-carboxamide (6)

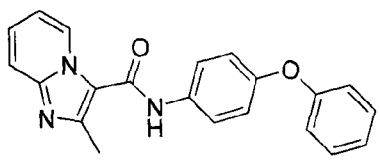

N-(4-(Benzyloxy)phenyl)-2-methylimidazo[1,2-a]pyridine-3-carboxamide (7)

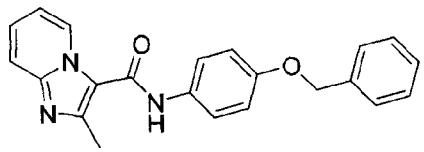

N-(4-Fluorobenzyl)-2-methylimidazo[1,2-a]pyridine-3-carboxamide (9)

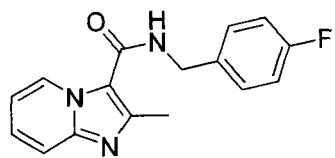

Methyl 4-((2-me3thylimidazo[1,2-a]pyridine-3-carboxamido)methyl)benzoate (10)
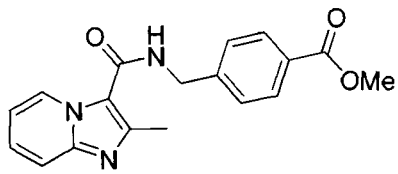
4-((2-Methylimidazo[1,2-a]pyridine-3-carboxamido)methyl)benzoic acid (11)
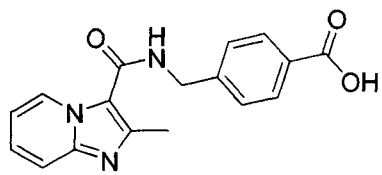
N-(4-Methoxybenzyl)-2-methylimidazo[1,2-a]pyridine-3-carboxamide (12)
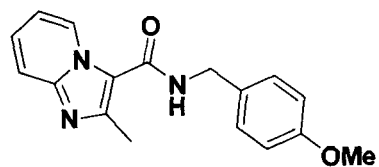
2-Methyl-N-(4-phenoxybenzyl)imidazo[1,2-a]pyridine-3-carboxamide (15)
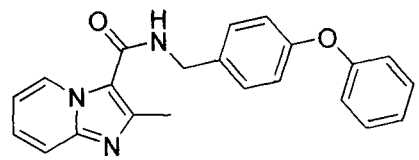
N-(Biphenyl-4-ylmethyl)-2-methylimidazo[1,2-a]pyridine-3-carboxamide (16)
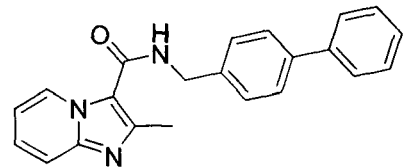

tert-Butyl 4-((2-methylimidazo[1,2-a]pyridine-3-carboxamido)methyl)piperidine-1-carboxylate (19)
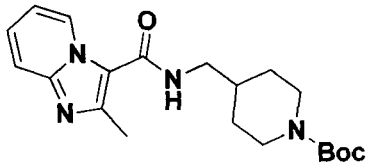
N-(4-Methoxyphenethyl)-2-methylimidazo[1,2-a]pyridine-3-carboxamide (22)
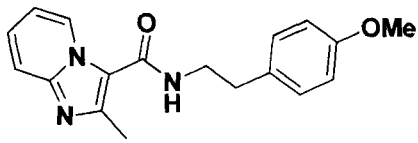
N-(Biphenyl-4-ylmethyl)-6-chloro-2-methylimidazo[1,2-a]pyridine-3-carboxamide (44)
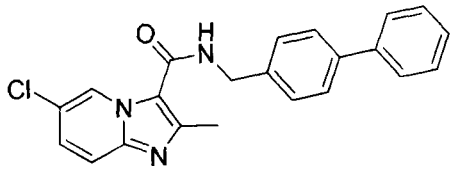
N-(Biphenyl-4-ylmethyl)-7-chloro-2-methylimidazo[1,2-a]pyridine-3-carboxamide (45)
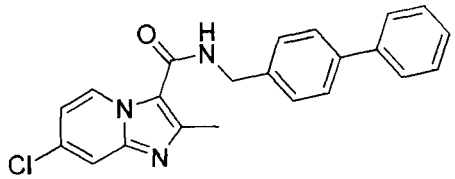
N-(Biphenyl-4-ylmethyl)-2-ethylimidazo[1,2-a]pyridine-3-carboxamide (47)
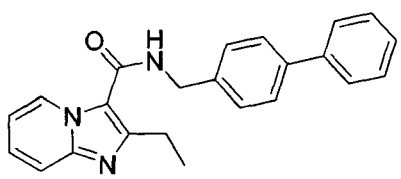

N-(Biphenyl-4-ylmethyl)-2-propylimidazo[1,2-a]pyridine-3-carboxamide (49)

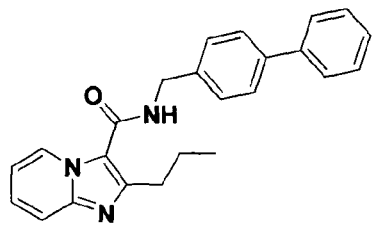

N-(Biphenyl-4-ylmethyl)-2-isopropylimidazo[1,2-a]pyridine-3-carboxamide (52)

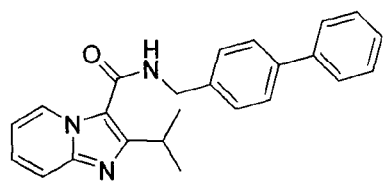

2-Ethyl-N-(4-phenoxybenzyl)imidazo[1,2-a]pyridine-3-carboxamide (54)

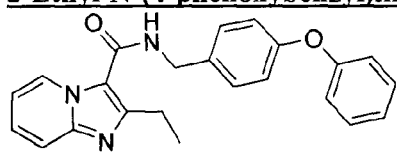

N-(4-tert-Butylbenzyl)-2-ethylimidazo[1,2-a]pyridine-3-carboxamide (55)

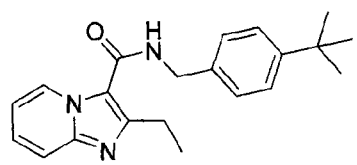

2-Ethyl-N-((1-methyl-1H-indol-5-yl)methyl)imidazo[1,2-a]pyridine-3-carboxamide (56)

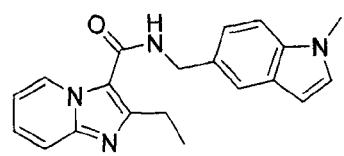

2-Ethyl-N-(4-(trifluoromethoxy)benzyl)imidazo[1,2-a]pyridine-3-carboxamide (57)

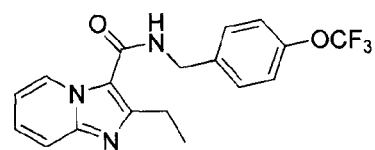

2-Ethyl-N-((1-methyl-1H-indol-6-yl)methyl)imidazo[1,2-a]pyridine-3-carboxamide (58)
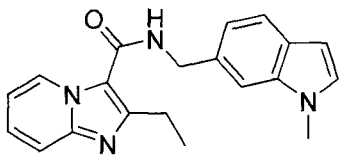
2-Ethyl-N-(4-isopropoxybenzyl)imidazo[1,2-a]pyridine-3-carboxamide (60)
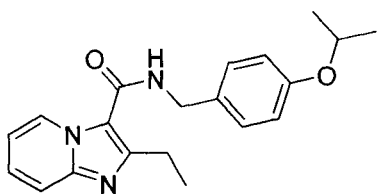
2-Ethyl-N-(4-isobutoxybenzyl)imidazo[1,2-a]pyridine-3-carboxamide (61)
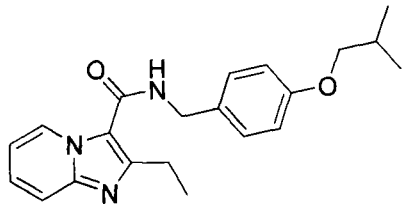
N-(Biphenyl-4-ylmethyl)-2-ethyl-6-methylimidazo[1,2-a]pyridine-3-carboxamide (62)
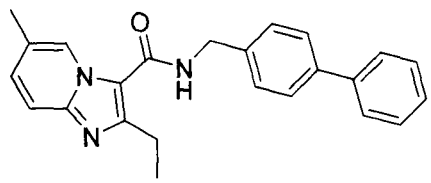
2-Ethyl-6-methyl-N-(4-phenoxybenzyl)imidazo[1,2-a]pyridine-3-carboxamide (63)
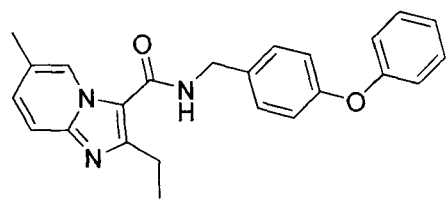

N-(4-tert-Butylbenzyl)-2-ethyl-6-methylimidazo[1,2-a]pyridine-3-carboxamide (64)
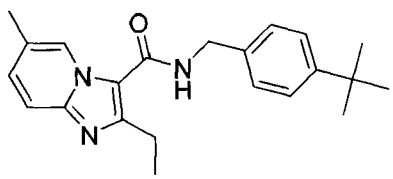
2-Ethyl-6-methyl-N-(4-(trifluoromethoxy)benzyl)imidazo[1,2-a]pyridine-3-carboxamide (65)
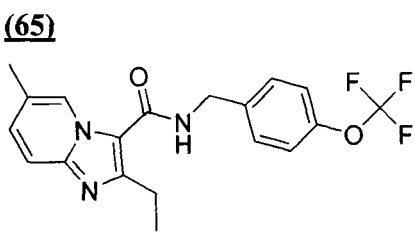
2-Ethyl-6-methyl-N-((1-methyl-1H-indol-5-yl)methyl)imidazo[1,2-a]pyridine-3-carboxamide (66)
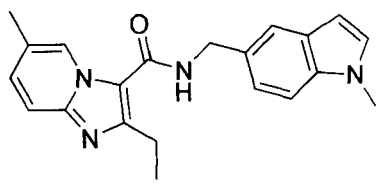
2-Ethyl-6-methyl-N-((1-methyl-1H-indol-6-yl)methyl)imidazo[1,2-a]pyridine-3-carboxamide (67)
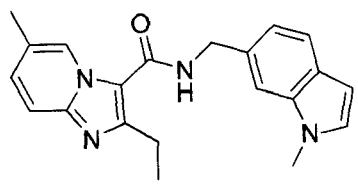

6-Chloro-N-(4-chlorobenzyl)-2-ethylimidazo[1,2-a]pyridine-3-carboxamide (70)
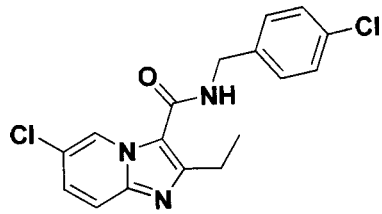
6-Chloro-2-methyl-N-(4-phenoxybenzyl)imidazo[1,2-a]pyridine-3-carboxamide (71)
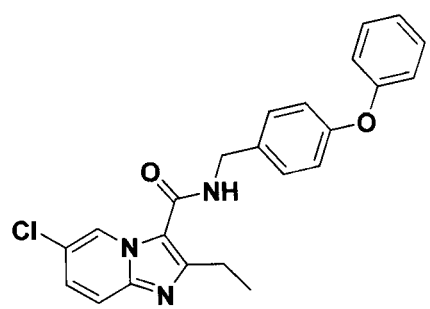
6-Chloro-2-methyl-N-(4-(trifluoromethoxy)benzyl)imidazo[1,2-a]pyridine-3-carboxamide (72)
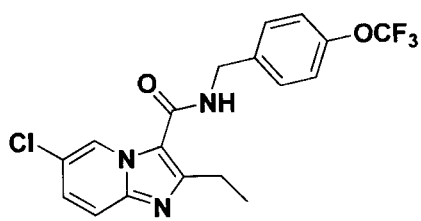
N-(4-tert-Butylbenzyl)-6-chloro-2-methylimidazo[1,2-a]pyridine-3-carboxamide (73)
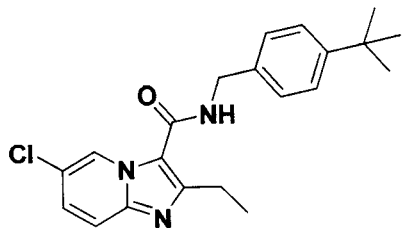

6-Chloro-N-(4-isopropoxybenzyl)-2-methylimidazo[1,2-a]pyridine-3-carboxamide (75)
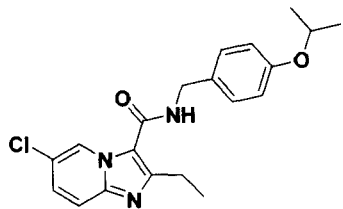
6-Chloro-N-(4-isobutoxybenzyl)-2-methylimidazo[1,2-a]pyridine-3-carboxamide (76)
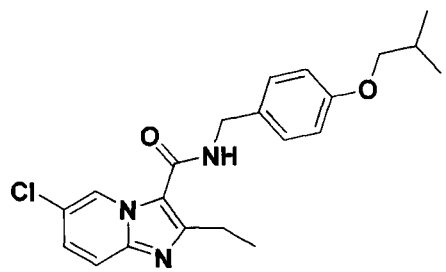
6-Chloro-2-methyl-N-((1-methyl-1H-indol-5-yl)methyl)imidazo[1,2-a]pyridine-3-carboxamide (77)
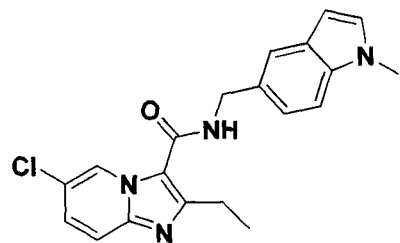
6-Chloro-2-methyl-N-((1-methyl-1H-indol-6-yl)methyl)imidazo[1,2-a]pyridine-3-carboxamide (78)
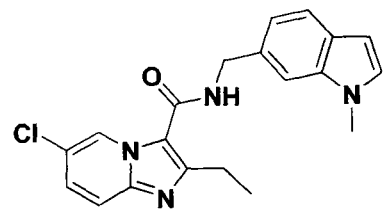

N-(Biphenyl-4-ylmethyl)-6-chloro-2-methylimidazo[1,2-a]pyridine-3-carboxamide (81)
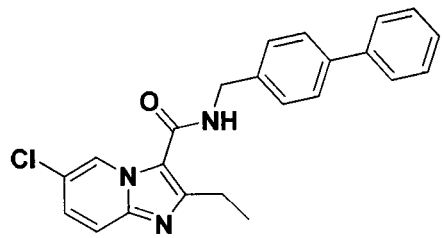
6-Chloro-N-((2'-chlorobiphenyl-4-yl)methyl)-2-ethylimidazo[1,2-a]pyridine-3-carboxamide (82)
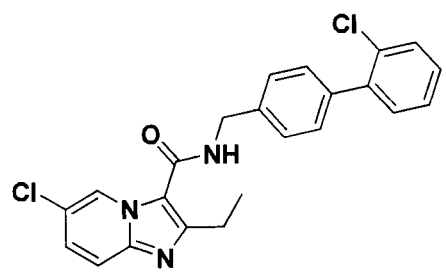
6-Chloro-N-((4'-chlorobiphenyl-4-yl)methyl)-2-ethylimidazo[1,2-a]pyridine-3-carboxamide (83)
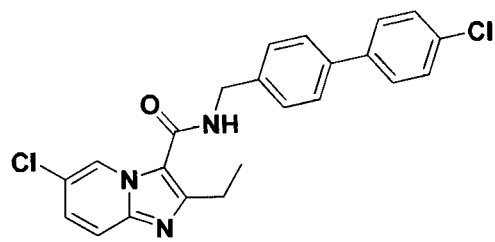
6-Chloro-2-ethyl-N-((2'-methylbiphenyl-4-yl)methyl)imidazo[1,2-a]pyridine-3-carboxamide (84)
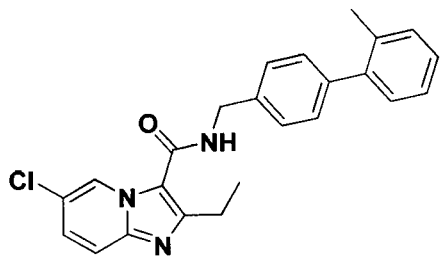

6-Chloro-2-ethyl-N-((3'-methylbiphenyl-4-yl)methyl)imidazo[1,2-a]pyridine-3-carboxamide (85)
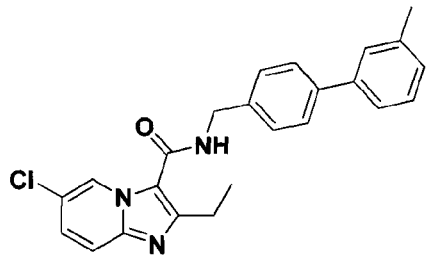
6-Chloro-2-ethyl-N-((4'-methylbiphenyl-4-yl)methyl)imidazo[1,2-a]pyridine-3-carboxamide (86)
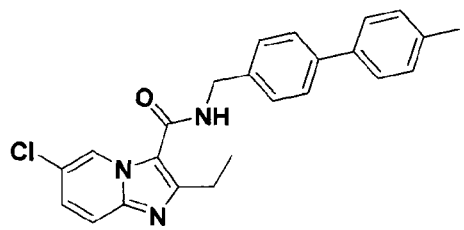
7-Chloro-N-(4-chlorobenzyl)-2-ethylimidazo[1,2-a]pyridine-3-carboxamide (87)
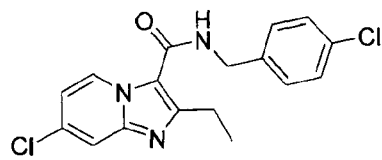
7-Chloro-2-ethyl-N-(4-hydroxybenzyl)imidazo[1,2-a]pyridine-3-carboxamide (88)
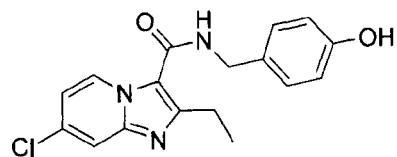
N-(4-tert-Butylbenzyl)-7-chloro-2-ethylimidazo[1,2-a]pyridine-3-carboxamide (92)
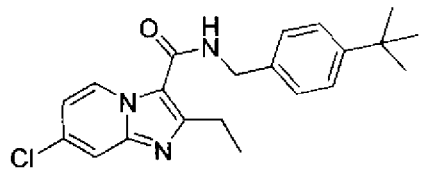

N-(Biphenyl-4-ylmethyl)-7-chloro-2-ethylimidazo[1,2-a]pyridine-3-carboxamide (93)
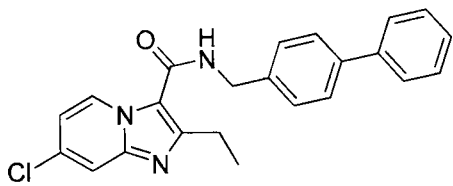
7-Chloro-N-((2'-chlorobiphenyl-4-yl)methyl)-2-ethylimidazo[1,2-a]pyridine-3-carboxamide (94)
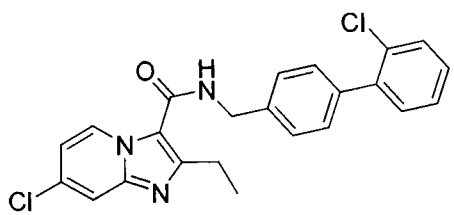
7-Chloro-N-((4'-chlorobiphenyl-4-yl)methyl)-2-ethylimidazo[1,2-a]pyridine-3-carboxamide (95)
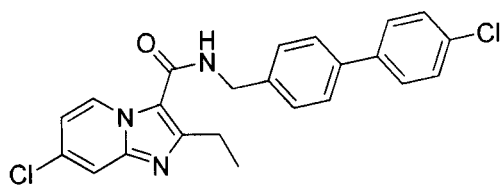
7-Chloro-2-ethyl-N-((2'-methylbiphenyl-4-yl)methyl)imidazo[1,2-a]pyridine-3-carboxamide (96)
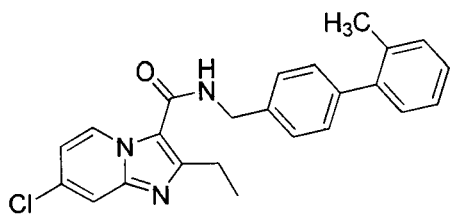

7-Chloro-2-ethyl-N-((3'-methylbiphenyl-4-yl)methyl)imidazo[1,2-a]pyridine-3-carboxamide (97)

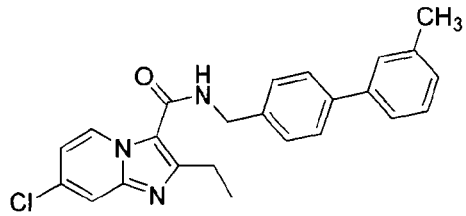

7-Chloro-2-ethyl-N-((4'-methylbiphenyl-4-yl)methyl)imidazo[1,2-a]pyridine-3-carboxamide (98)

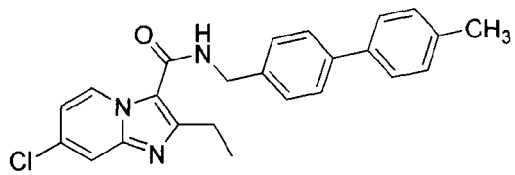

N-(Biphenyl-4-ylmethyl)-6-chloro-2-(trifluoromethyl)imidazo[1,2-a]pyridine-3-carboxamide (99)

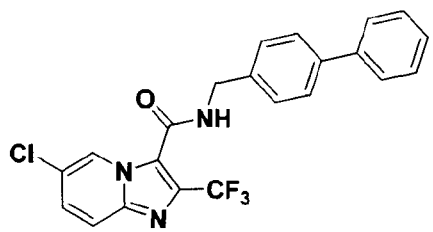

N-(4-tert-Butylbenzyl)-6-chloro-2-(trifluoromethyl)imidazo[1,2-a]pyridine-3-carboxamide (100)

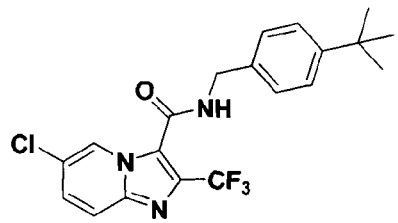

N-(4-Bromobenzyl)-7-chloro-2-ethylimidazo[1,2-a]pyridine-3-carboxamide (101)

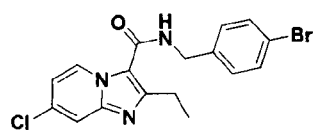

7-Chloro-2-ethyl-N-(4-(trifluoromethoxy)benzyl)imidazo[1,2-a]pyridine-3-carboxamide (102)

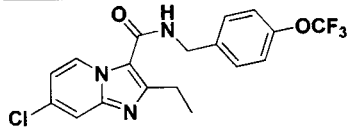

2-Ethyl-6-fluoro-N-(4-(trifluoromethoxy)benzyl)imidazo[1,2-a]pyridine-3-carboxamide (103)

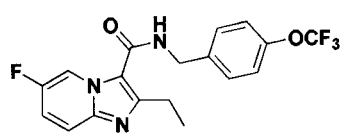

2-Ethyl-7-methoxy-N-(4-(trifluoromethoxy)benzyl)imidazo[1,2-a]pyridine-3-carboxamide (104)

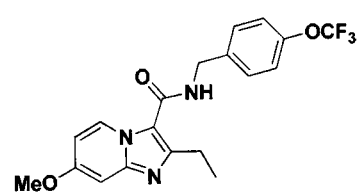

2-Ethyl-7-hydroxy-N-(4-(trifluoromethoxy)benzyl)imidazo[1,2-a]pyridine-3-carboxamide (105)

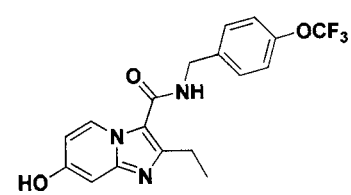

7-Chloro-2-ethyl-N-(4-(propylamino)benzyl)imidazo[1,2-a]pyridine-3-carboxamide (106)

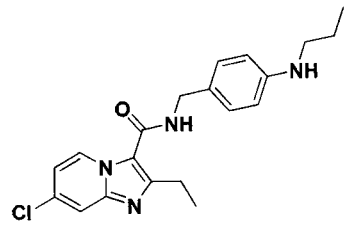

7-Chloro-2-ethyl-N-(4-(pentylamino)benzyl)imidazo[1,2-a]pyridine-3-carboxamide (107)

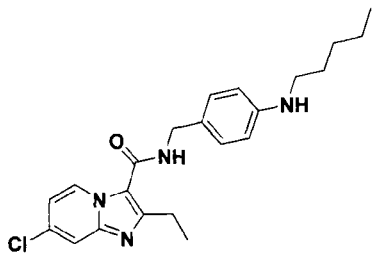

6-Chloro-2-ethyl-N-(4-(4-methylpiperazin-1-yl)benzyl)imidazo[1,2-a]pyridine-3-carboxamide (108)

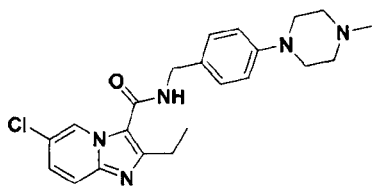

7-Chloro-2-ethyl-N-(4-(4-methylpiperazin-1-yl)benzyl)imidazo[1,2-a]pyridine-3-carboxamide (109)

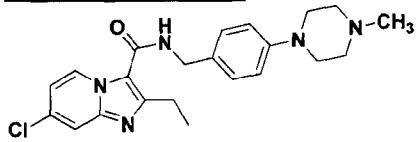

7-Chloro-2-ethyl-N-(4-(4-isopropylpiperazin-1-yl)benzyl)imidazo[1,2-a]pyridine-3-carboxamide (110)

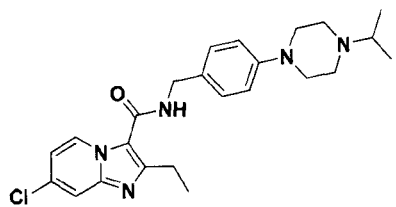

7-Chloro-2-ethyl-N-(4-(4-phenylpiperazin-1-yl)benzyl)imidazo[1,2-a]pyridine-3-carboxamide (111)

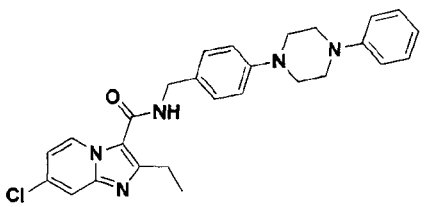

2-Ethyl-N-(4-(4-(4-fluorophenyl)piperazin-1-yl)benzyl)-6-methoxyimidazo[1,2-a]pyridine-3-carboxamide (112)
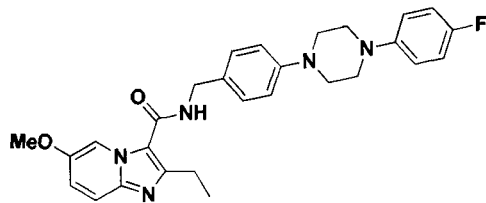
6-Chloro-2-ethyl-N-(4-(4-(4-fluorophenyl)piperazin-1-yl)benzyl)imidazo[1,2-a]pyridine-3-carboxamide (113)
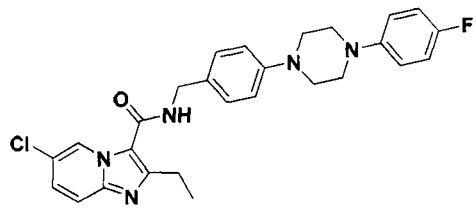
2-Ethyl-*N*-(4-(4-(4-fluorophenyl)piperazin-1-yl)benzyl)-7-methoxyimidazo[1,2-a]pyridine-3-carboxamide(114)
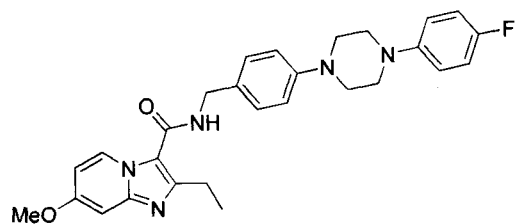
2-Ethyl-*N*-(4-(4-(4-fluorophenyl)piperazin-1-yl)benzyl)-8-methoxyimidazo[1,2-a]pyridine-3-carboxamide(115)
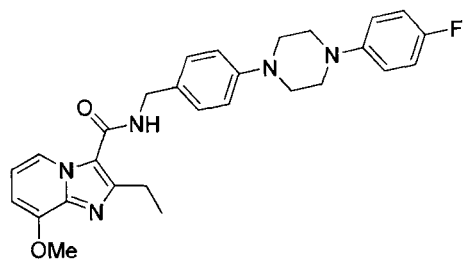

7-Chloro-2-ethyl-N-((4'-fluorobiphenyl-4-yl)methyl)imidazo[1,2-a]pyridine-3-carboxamide (116)

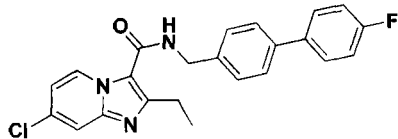

N-((4'-tert-Butylbiphenyl-4-yl)methyl)-7-chloro-2-ethylimidazo[1,2-a]pyridine-3-carboxamide (117)

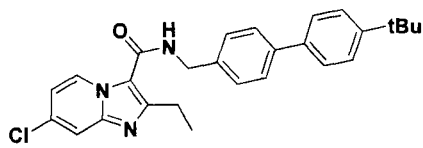

7-Chloro-2-ethyl-N-((4'-methoxybiphenyl-4-yl)methyl)imidazo[1,2-a]pyridine-3-carboxamide (118)

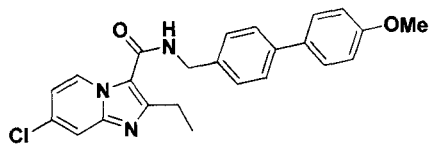

7-Chloro-2-ethyl-N-((4'-(trifluoromethoxy)biphenyl-4-yl)methyl)imidazo[1,2-a]pyridine-3-carboxamide (119)

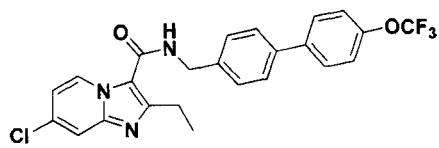

7-Chloro-2-ethyl-N-((4'-(trifluoromethyl)biphenyl-4-yl)methyl)imidazo[1,2-a]pyridine-3-carboxamide (120)

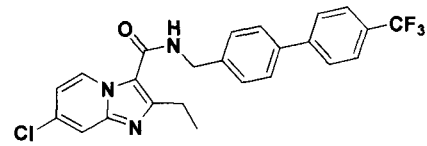

6-Chloro-N-((4'-cyanobiphenyl-4-yl)methyl)-2-ethylimidazo[1,2-a]pyridine-3-carboxamide (121)
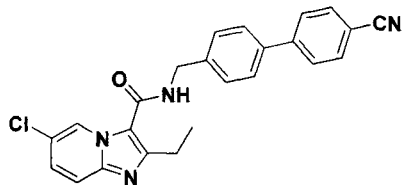
7-Chloro-N-((4'-cyanobiphenyl-4-yl)methyl)-2-ethylimidazo[1,2-a]pyridine-3-carboxamide (122)
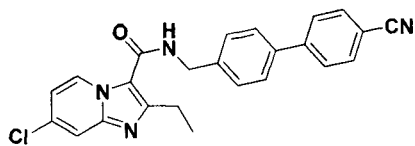
6-Chloro-2-ethyl-N-((2'-(trifluoromethyl)biphenyl-4-yl)methyl)imidazo[1,2-a]pyridine-3-carboxamide (123)
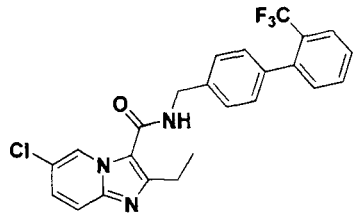
7-Chloro-2-ethyl-N-((2'-(trifluoromethyl)biphenyl-4-yl)methyl)imidazo[1,2-a]pyridine-3-carboxamide (124)
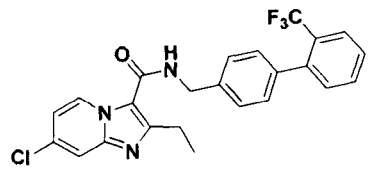

6-Chloro-N-((2'-cyanobiphenyl-4-yl)methyl)-2-ethylimidazo[1,2-a]pyridine-3-carboxamide (125)
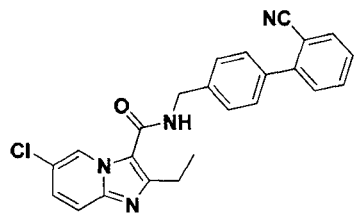
7-Chloro-N-((2'-cyanobiphenyl-4-yl)methyl)-2-ethylimidazo[1,2-a]pyridine-3-carboxamide (126)
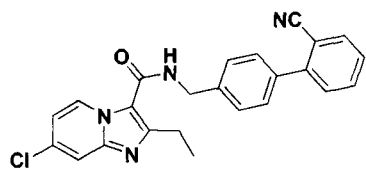
6-Chloro-N-((3'-cyanobiphenyl-4-yl)methyl)-2-ethylimidazo[1,2-a]pyridine-3-carboxamide (127)
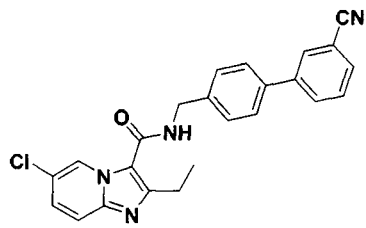
7-Chloro-N-((3'-cyanobiphenyl-4-yl)methyl)-2-ethylimidazo[1,2-a]pyridine-3-carboxamide (128)
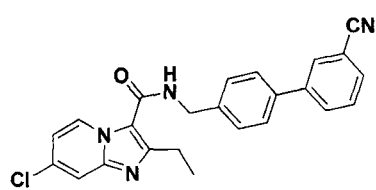

6-Chloro-N-((4'-chloro-2'-(trifluoromethyl)biphenyl-4-yl)methyl)-2-ethylimidazo[1,2-a]pyridine-3-carboxamide (129)

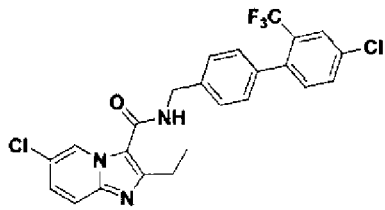

7-Chloro-N-((4'-chloro-2'-(trifluoromethyl)biphenyl-4-yl)methyl)-2-ethylimidazo[1,2-a]pyridine-3-carboxamide (130)

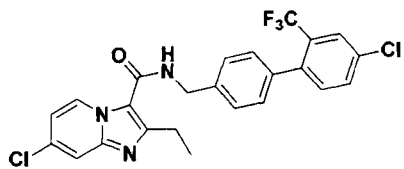

6-Chloro-N-((4'-cyano-2'-methylbiphenyl-4-yl)methyl)-2-ethylimidazo[1,2-a]pyridine-3-carboxamide (131)

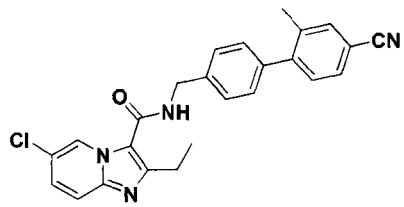

7-Chloro-N-((4'-cyano-2'-methylbiphenyl-4-yl)methyl)-2-ethylimidazo[1,2-a]pyridine-3-carboxamide (132)

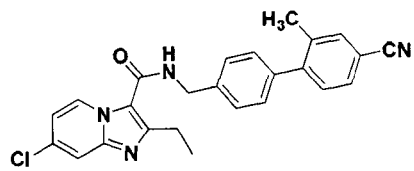

7-Chloro-N-((2'-chloro-4'-fluorobiphenyl-4-yl)methyl)-2-ethylimidazo[1,2-a]pyridine-3-carboxamide (133)

7-Chloro-2-ethyl-N-(4-(pyridin-4-yl)benzyl)imidazo[1,2-a]pyridine-3-carboxamide (134)
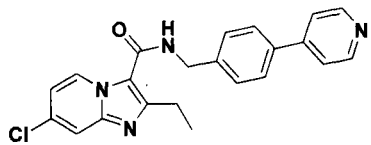
7-Chloro-2-ethyl-N-(4-(5-methoxypyridin-2-yl)benzyl)imidazo[1,2-a]pyridine-3-carboxamide (135)
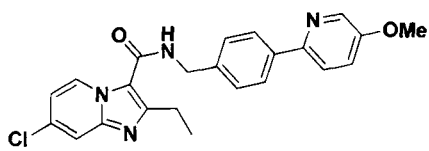
N-(4-(1H-Pyrrol-2-yl)benzyl)-7-chloro-2-ethylimidazo[1,2-a]pyridine-3-carboxamide (136)
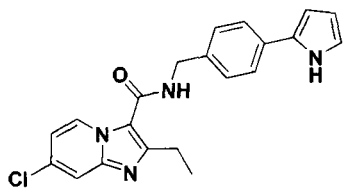
7-Chloro-2-ethyl-N-(4-(furan-2-yl)benzyl)imidazo[1,2-a]pyridine-3-carboxamide (137)
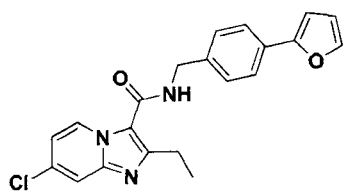
N-(4-(1H-Pyrrol-1-yl)benzyl)-7-chloro-2-ethylimidazo[1,2-a]pyridine-3-carboxamide (138)
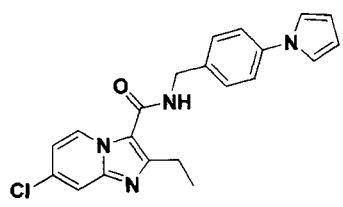

6-Chloro-2-ethyl-N-(4-(4-(4-(trifluoromethoxy)phenoxy)piperidin-1-yl)benzyl)imidazo-[1,2-a]pyridine-3-carboxamide (139)

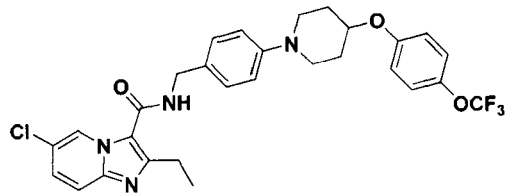

7-Chloro-2-ethyl-N-(4-(4-(4-(trifluoromethoxy)phenoxy)piperidin-1-yl)benzyl)imidazo-[1,2-a]pyridine-3-carboxamide (140)

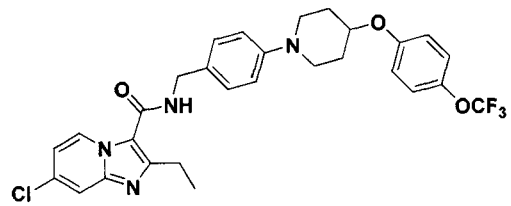

N-((4'-Chlorobiphenyl-4-yl)methyl)-2-ethylimidazo[1,2-a]pyrazine-3-carboxamide (141)

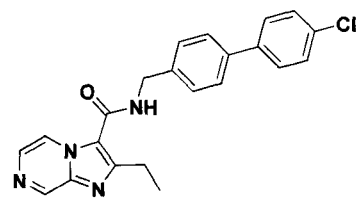

N-(4-(4-(4-(Butyramidomethyl)phenyl)piperazin-1-yl)benzyl)-7-chloro-2-ethylimidazo-[1,2-a]pyridine-3-carboxamide (144)

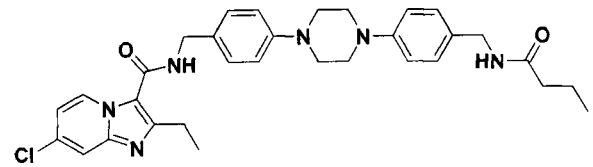

N-(4-tert-Butylbenzyl)-2-ethyl-7-(piperazin-1-yl)imidazo[1,2-a]pyridine-3-carboxamide (145)

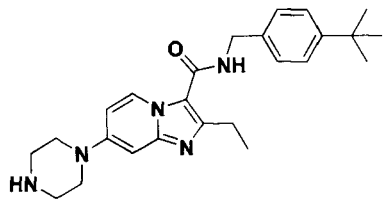

6-Chloro-N-(4-cyanobenzyl)-2-ethylimidazo[1,2-a]pyridine-3-carboxamide (146)
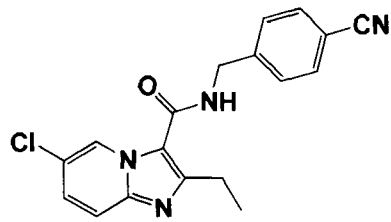
6-Chloro-2-ethyl-N-(4-(trifluoromethyl)benzyl)imidazo[1,2-a]pyridine-3-carboxamide (147)
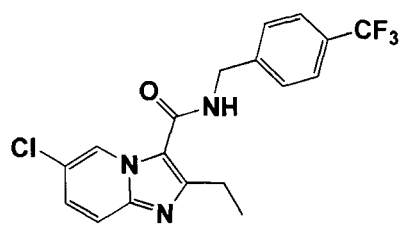
7-Chloro-2-ethyl-N-(4-(trifluoromethyl)benzyl)imidazo[1,2-a]pyridine-3-carboxamide (148)
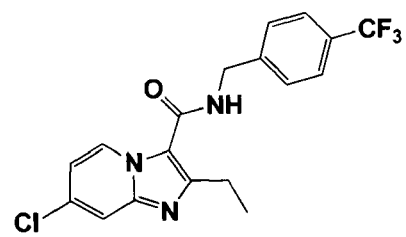
2-Ethyl-6-nitro-N-(4-(trifluoromethoxy)benzyl)imidazo[1,2-a]pyridine-3-carboxamide (149)
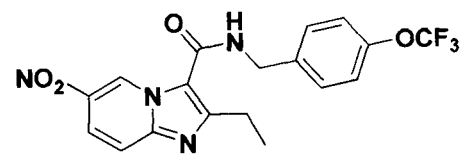
2-Ethyl-7-nitro-N-(4-(trifluoromethoxy)benzyl)imidazo[1,2-a]pyridine-3-carboxamide (150)
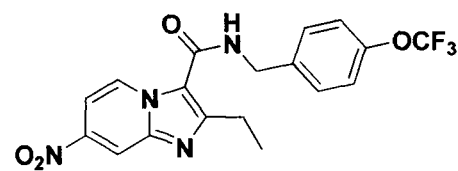

2-Ethyl-N-(4-(trifluoromethoxy)benzyl)-6-(trifluoromethyl)imidazo[1,2-a]pyridine-3-carboxamide (151)
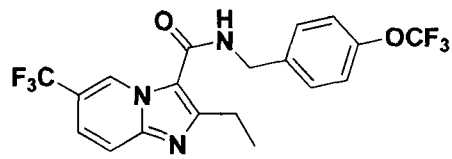
6-Bromo-2-ethyl-N-(4-(trifluoromethoxy)benzyl)imidazo[1,2-a]pyridine-3-carboxamide (152)
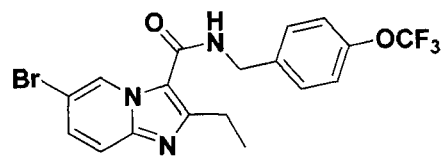
6,7-Dichloro-2-ethyl-N-(4-(trifluoromethoxy)benzyl)imidazo[1,2-a]pyridine-3-carboxamide (153)
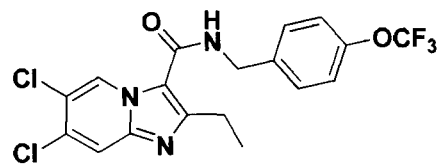
6-Chloro-2-methyl-N-(4-(trifluoromethoxy)benzyl)imidazo[1,2-a]pyridine-3-carboxamide (154)
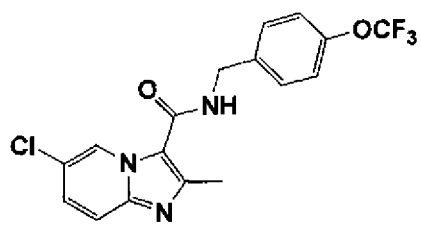

2-Ethyl-N-(4-(trifluoromethoxy)benzyl)imidazo[1,2-a]pyrazine-3-carboxamide (155)
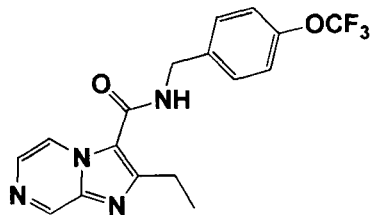
2-Ethyl-3-((4-(trifluoromethoxy)benzyl)carbamoyl)imidazo[1,2-a]pyrazine 7-oxide (156)
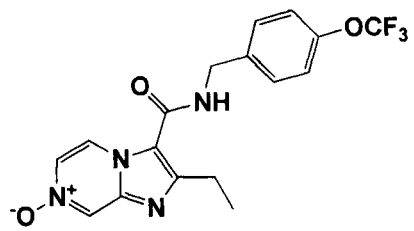
6-Chloro-2-ethyl-N-(4-methoxyphenethyl)imidazo[1,2-a]pyridine-3-carboxamide (157)
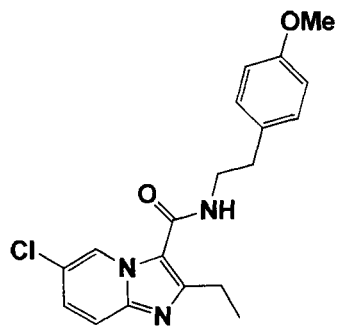
6-Chloro-N-(4-chlorophenethyl)-2-ethylimidazo[1,2-a]pyridine-3-carboxamide (158)
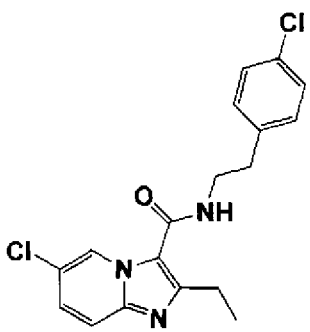

N-((4'-(Butyramidomethyl)biphenyl-4-yl)methyl)-7-chloro-2-ethylimidazo[1,2-a]pyridine-3-carboxamide (159)
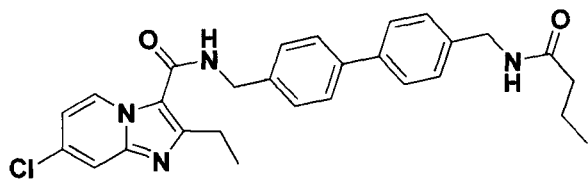
3-(((4'-Chloro-[1,1'-biphenyl]-4-yl)methyl)carbamoyl)-2-ethylimidazo[1,2-a]pyrazine 7-oxide (160)
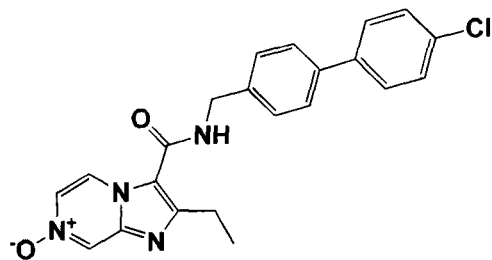
6-Chloro-N-(4-(4-(4-chlorophenoxy)piperidin-1-yl)benzyl)-2-ethylimidazo[1,2-a] pyridine-3-carboxamide (162)
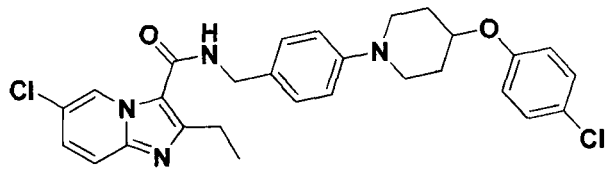
7-Chloro-N-(4-(4-(4-chlorophenoxy)piperidin-1-yl)benzyl)-2-ethylimidazo[1,2-a] pyridine-3-carboxamide (163)
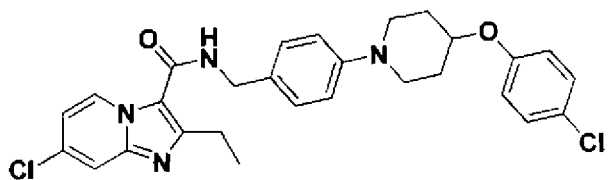

6-Chloro-2-ethyl-N-(4-(4-(4-(trifluoromethyl)phenoxy)piperidin-1-yl)benzyl) imidazo[1,2-a]pyridine-3-carboxamide (164)
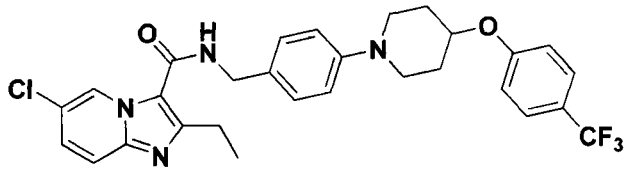
7-Chloro-2-ethyl-N-(4-(4-(4-(trifluoromethyl)phenoxy)piperidin-1-yl)benzyl) imidazo[1,2-a]pyridine-3-carboxamide (165)
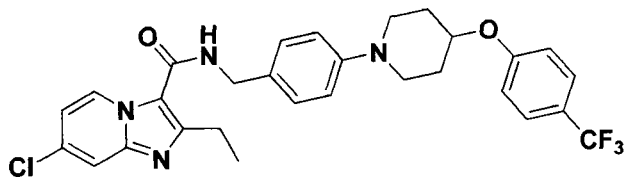
6-Chloro-2-ethyl-N-(4-(4-(4-fluorophenoxy)piperidin-1-yl)benzyl)imidazo[1,2-a] pyridine-3-carboxamide (166)
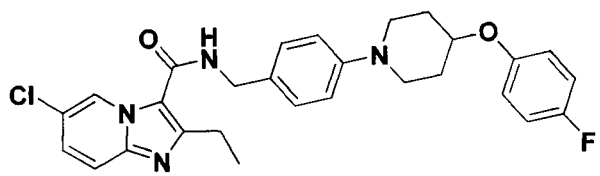
7-Chloro-2-ethyl-N-(4-(4-(4-fluorophenoxy)piperidin-1-yl)benzyl)imidazo[1,2-a]pyridine-3-carboxamide (167)
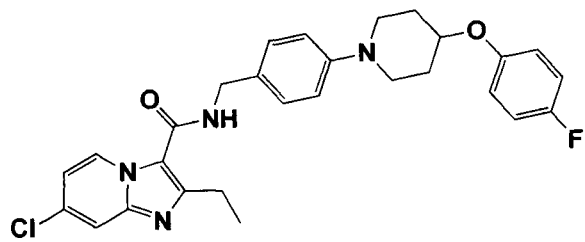

2-Ethyl-N-(4-(4-(4-(trifluoromethoxy)phenoxy)piperidin-1-yl)benzyl)-6-(trifluoromethyl)imidazo[1,2-a]pyridine-3-carboxamide (168)

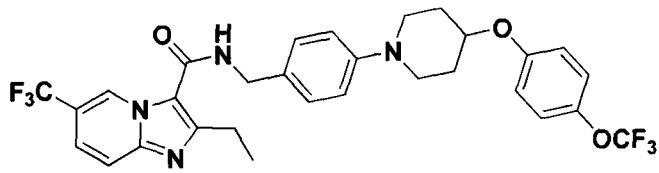

7-Chloro-*N*-(4-(4-(cyclopentyloxymethyl)piperidin-1-yl)benzyl)-2-ethylimidazo[1,2-a]pyridine-3-carboxamide(169)

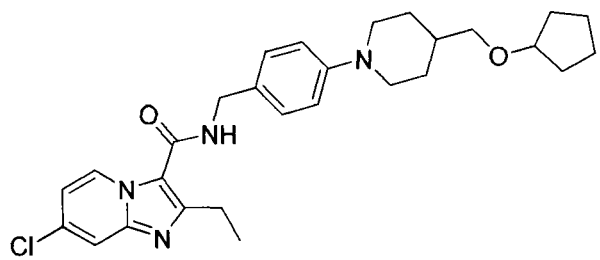

2-Ethyl-7-nitro-N-(4-(4-(4-(trifluoromethoxy)phenoxy)piperidin-1-yl)benzyl) imidazo[1,2-a]pyridine-3-carboxamide (170)

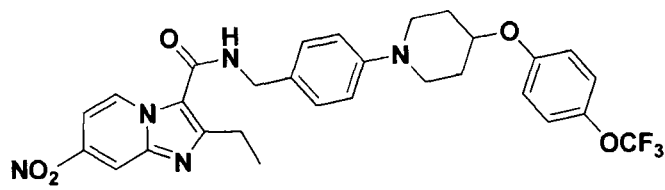

6-Chloro-2-ethyl-N-(4-(4-(4-fluorobenzyl)piperazin-1-yl)benzyl)imidazo[1,2-a]pyridine-3-carboxamide (171)

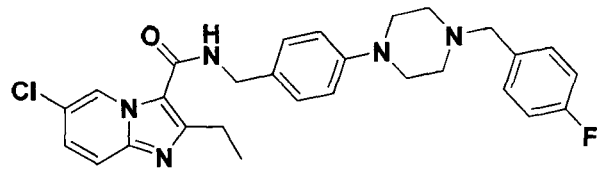

7-Chloro-2-ethyl-N-(4-(4-(4-fluorobenzyl)piperazin-1-yl)benzyl)imidazo[1,2-a]pyridine-3-carboxamide (172)
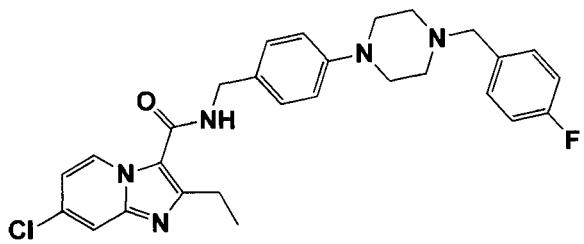
6-Chloro-2-ethyl-N-(4-(4-(4-(trifluoromethoxy)benzyl)piperazin-1-yl)benzyl)imidazo[1,2-a]pyridine-3-carboxamide (173)
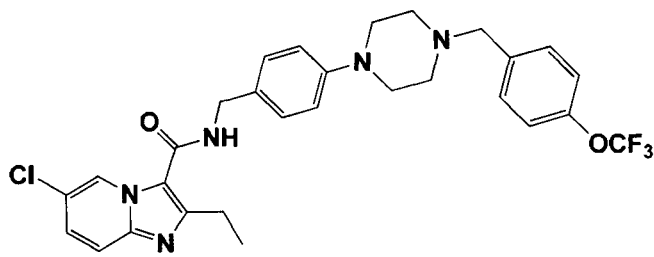
7-Chloro-2-ethyl-N-(4-(4-(4-(trifluoromethoxy)benzyl)piperazin-1-yl)benzyl)imidazo[1,2-a]pyridine-3-carboxamide (174)
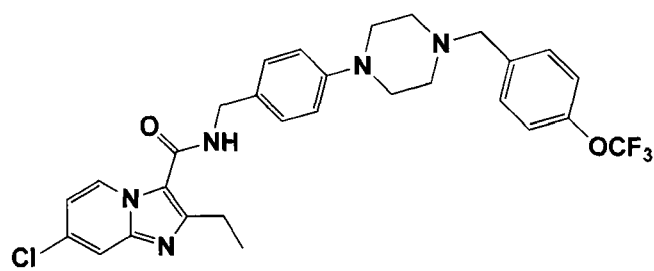
6,7-Dichloro-2-ethyl-N-(4-(4-(4-fluorobenzyl)piperazin-1-yl)benzyl)imidazo[1,2-a] pyridine-3-carboxamide (175)
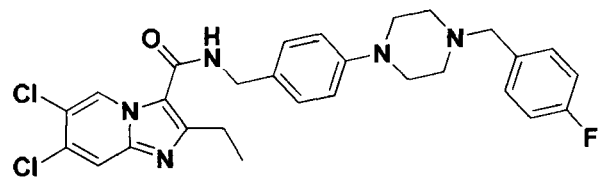

7-Chloro-2-ethyl-N-(4-(4-(4-fluorophenyl)piperazin-1-yl)benzyl)imidazo[1,2-a]pyridine-3-carboxamide (176)
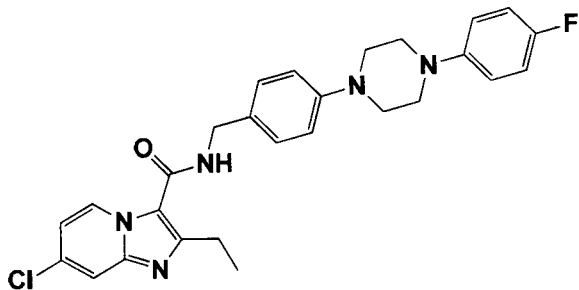
7-Chloro-2-ethyl-N-(4-(4-(4-fluorophenyl)piperazin-1-yl)benzyl)imidazo[1,2-a]pyridine-3-carboxamide trihydrochloride (177)
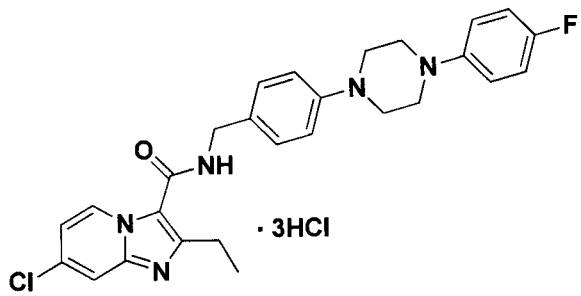
6-Chloro-2-ethyl-N-(4-(4-(4-(trifluoromethoxy)phenyl)piperazin-1-yl)benzyl)imidazo[1,2-a]pyridine-3-carboxamide (178)
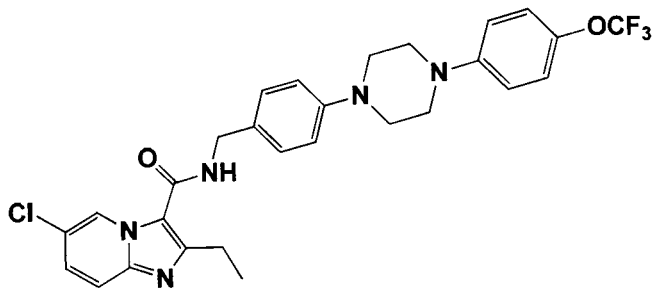

7-Chloro-2-ethyl-N-(4-(4-(4-(trifluoromethoxy)phenyl)piperazin-1-yl)benzyl)imidazo[1,2-a]pyridine-3-carboxamide (179)
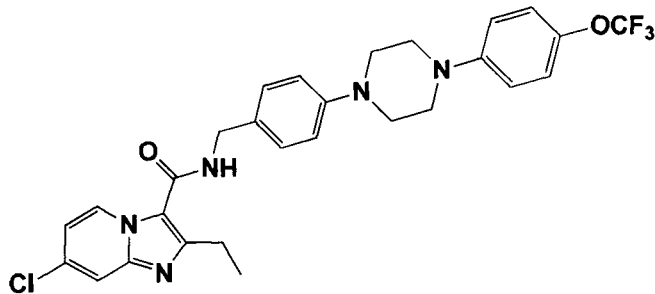
6,7-Dichloro-2-ethyl-N-(4-(4-(4-fluorophenyl)piperazin-1-yl)benzyl)imidazo[1,2-a]pyridine-3-carboxamide (180)
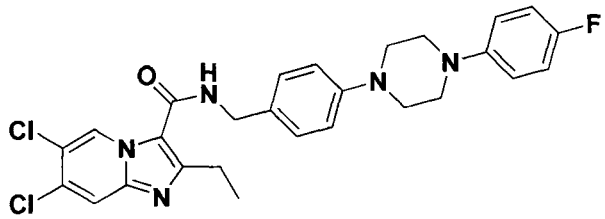
2-Ethyl-N-(4-(4-(4-(trifluoromethoxy)phenyl)piperazin-1-yl)benzyl)imidazo[1,2-a]pyridine-3-carboxamide (181)
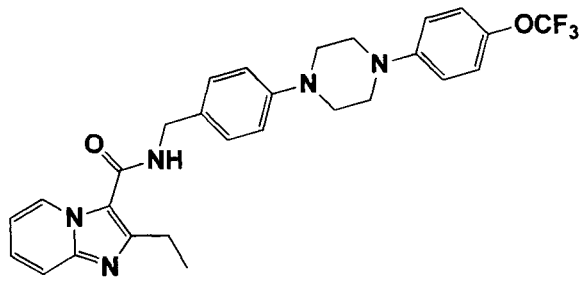
6-Chloro-2-ethyl-N-(4-(4-(4-fluorophenyl)piperazin-1-yl)benzyl)-N-methylimidazo[1,2-a]pyridine-3-carboxamide (182)
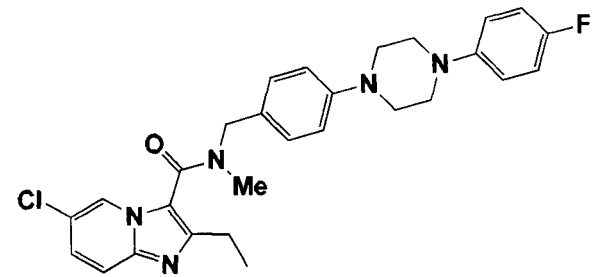

7-Chloro-*N*-(4-(4-((difluoromethoxy)methyl)piperidin-1-yl)benzyl)-2-ethylimidazo[1,2-a]pyridine-3-carboxamide (183)
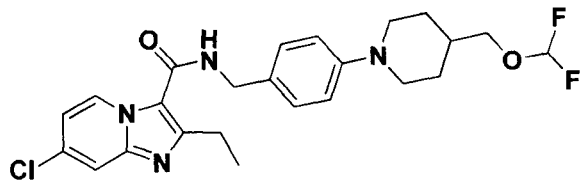
7-Chloro-2-ethyl-*N*-((4'-(hexanamidomethyl)biphenyl-4-yl)methyl)imidazo[1,2-a]pyridine-3-carboxamide (184)
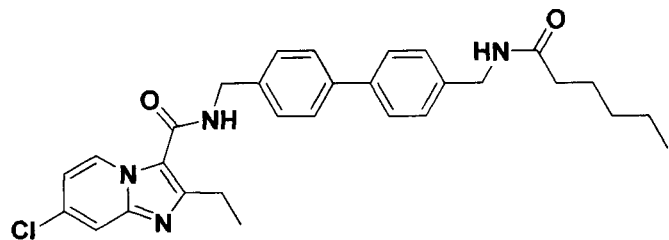
6-Chloro-2-ethyl-N-(4-(4-(trifluoromethoxy)phenoxy)benzyl)imidazo[1,2-a]pyridine-3-carboxamide (185)
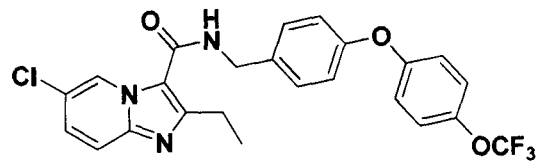
7-Chloro-2-ethyl-N-(4-(4-(trifluoromethoxy)phenoxy)benzyl)imidazo[1,2-a]pyridine-3-carboxamide (186)
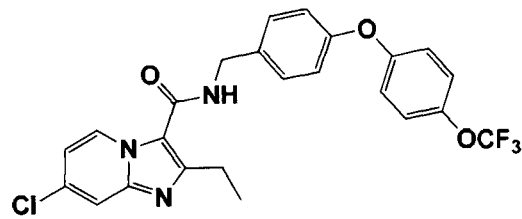

6-Chloro-2-ethyl-N-(4-(4-fluorophenoxy)benzyl)imidazo[1,2-a]pyridine-3-carboxamide (187)
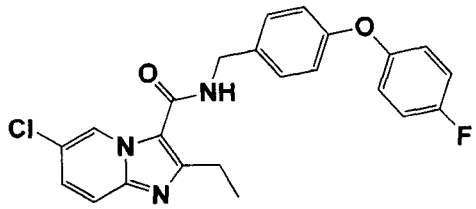
7-Chloro-2-ethyl-N-(4-(4-fluorophenoxy)benzyl)imidazo[1,2-a]pyridine-3-carboxamide (188)
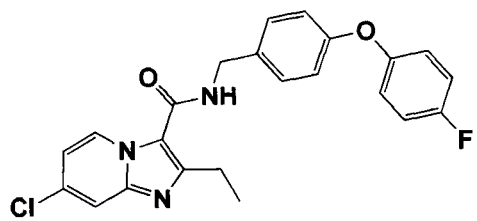
6-Bromo-2-ethyl-N-(4-(4-fluorophenoxy)benzyl)imidazo[1,2-a]pyridine-3-carboxamide (189)
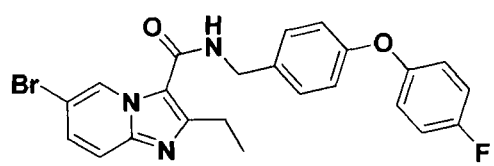
6-Chloro-N-(4-(4-chlorophenoxy)benzyl)-2-ethylimidazo[1,2-a]pyridine-3-carboxamide (190)
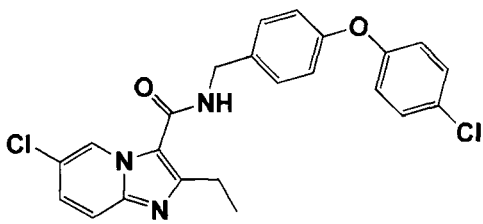

7-Chloro-N-(4-(4-chlorophenoxy)benzyl)-2-ethylimidazo[1,2-a]pyridine-3-carboxamide (191)
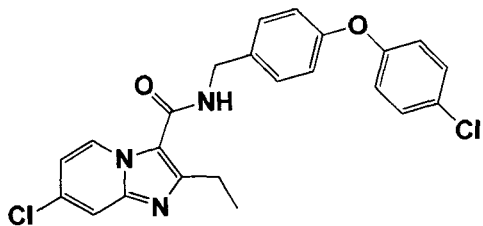
2-Ethyl-N-(4-(4-(trifluoromethoxy)phenoxy)benzyl)imidazo[1,2-a]pyridine-3-carboxamide (192)
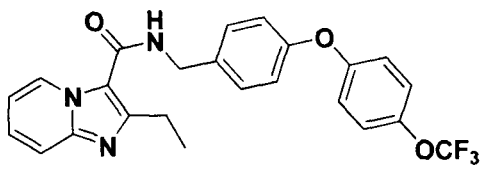
7-Chloro-2-ethyl-N-((6-(4-fluorophenoxy)pyridin-3-yl)methyl)imidazo[1,2-a]pyridine-3-carboxamide (193)
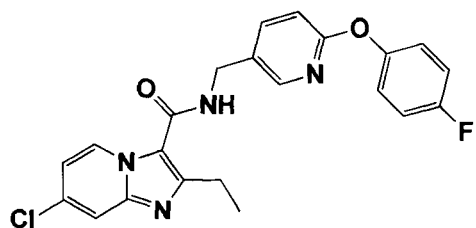
6-Chloro-2-ethyl-N-((6-(4-(trifluoromethoxy)phenoxy)pyridin-3-yl)methyl)imidazo[1,2-a]pyridine-3-carboxamide (194)
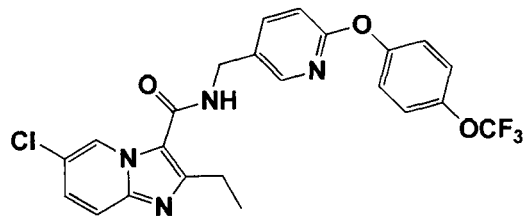

7-Chloro-2-ethyl-N-((6-(4-(trifluoromethoxy)phenoxy)pyridin-3-yl)methyl)imidazo[1,2-a]pyridine-3-carboxamide (195)
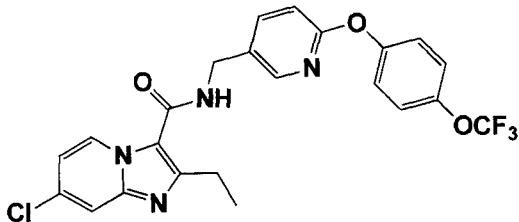
6-Chloro-2-ethyl-N-(4-(4-fluorophenoxy)benzyl)-N-methylimidazo[1,2-a]pyridine-3-carboxamide (197)
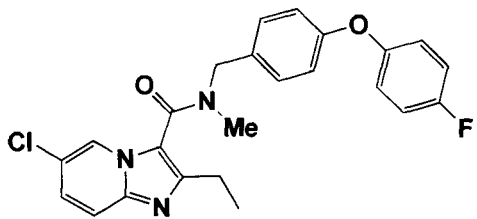
6-Chloro-2-ethyl-N-(4-(4-(trifluoromethoxy)phenylamino)benzyl)imidazo[1,2-a] pyridine-3-carboxamide (198)
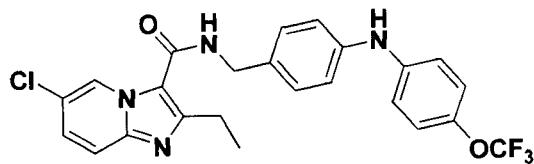
7-Chloro-2-ethyl-N-(4-(4-(trifluoromethoxy)phenylamino)benzyl)imidazo[1,2-a] pyridine-3-carboxamide (199)
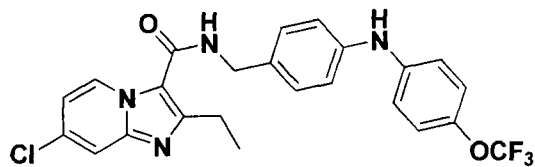

6-Chloro-2-ethyl-N-(4-(4-(trifluoromethyl)benzyloxy)benzyl)imidazo[1,2-a]pyridine-3-carboxamide (200)

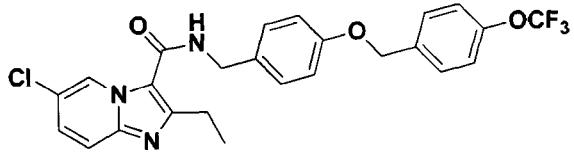

7-Chloro-2-ethyl-N-(4-(4-(trifluoromethyl)benzyloxy)benzyl)imidazo[1,2-a]pyridine-3-carboxamide (201)

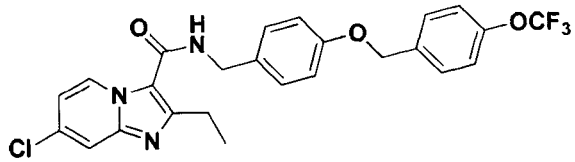

6-Chloro-2-ethyl-N-(4-(4-fluorobenzyloxy)benzyl)imidazo[1,2-a]pyridine-3-carboxamide (202)

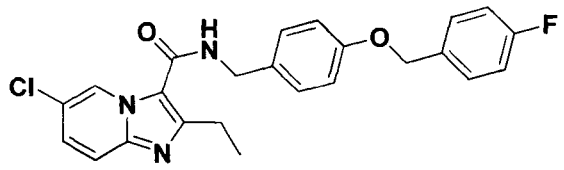

7-Chloro-2-ethyl-N-(4-(4-fluorobenzyloxy)benzyl)imidazo[1,2-a]pyridine-3-carboxamide (203)

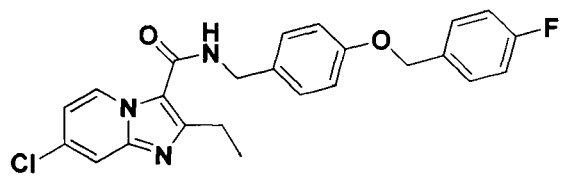

6-Chloro-2-ethyl-N-((2-(4-(trifluoromethoxy)phenyl)-1H-benzo[d]imidazol-5-yl)methyl)imidazo[1,2-a]pyridine-3-carboxamide (204)

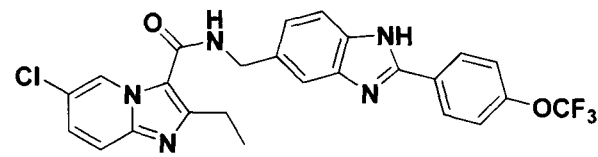

7-Chloro-2-ethyl-N-((2-(4-(trifluoromethoxy)phenyl)-1H-benzo[d]imidazol-5-yl)methyl)imidazo[1,2-a]pyridine-3-carboxamide (205)

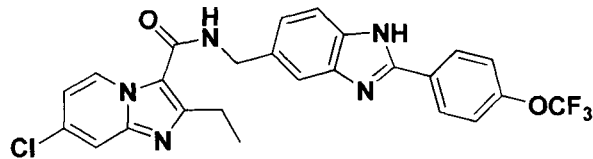

7-Chloro-2-ethyl-N-((2-(morpholinomethyl)-1H-benzo[d]imidazol-5-yl)methyl)imidazo[1,2-a]pyridine-3-carboxamide (206)

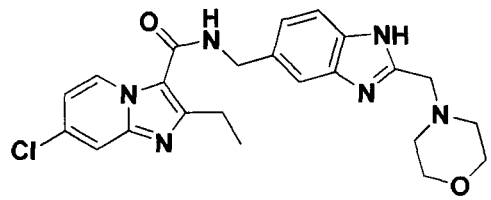

6-Chloro-2-ethyl-N-((2-(4-(trifluoromethoxy)phenyl)benzo[d]oxazol-5-yl)methyl)imidazo[1,2-a]pyridine-3-carboxamide (207)

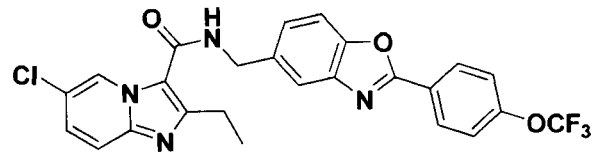

7-Chloro-2-ethyl-N-((2-(4-(trifluoromethoxy)phenyl)benzo[d]oxazol-5-yl)methyl)imidazo[1,2-a]pyridine-3-carboxamide (208)

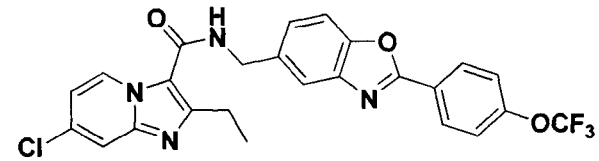

6-Chloro-N-(4-(2,6-dimethylmorpholino)benzyl)-2-ethylimidazo[1,2-a]pyridine-3-carboxamide (209)
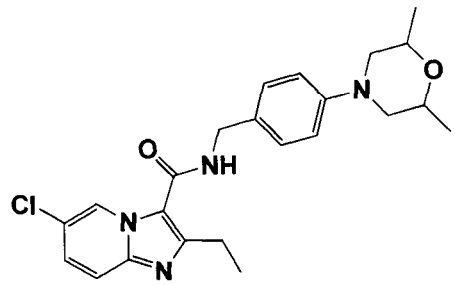
7-Chloro-N-(4-(2,6-dimethylmorpholino)benzyl)-2-ethylimidazo[1,2-a]pyridine-3-carboxamide (210)
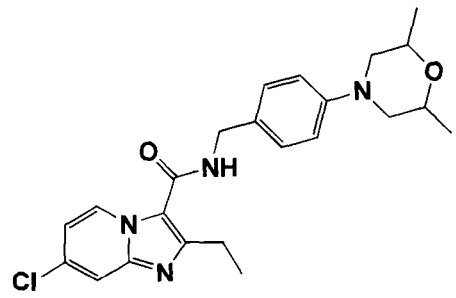
6-Chloro-2-ethyl-N-(4-(4-methylpiperidin-1-yl)benzyl)imidazo[1,2-a]pyridine-3-carboxamide (214)
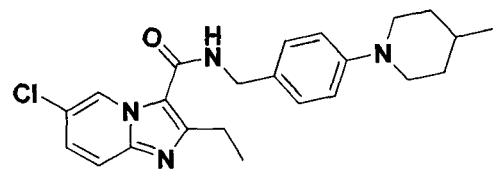
7-Chloro-2-ethyl-N-(4-(4-methylpiperidin-1-yl)benzyl)imidazo[1,2-a]pyridine-3-carboxamide (215)
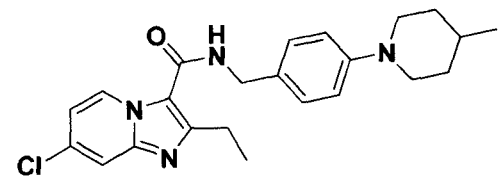

6-Chloro-*N*-(4-(3,5-dimethylpiperidin-1-yl)benzyl)-2-ethylimidazo[1,2-a]pyridine-3-carboxamide (216)
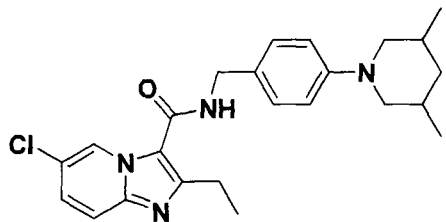
7-Chloro-*N*-(4-(3,5-dimethylpiperidin-1-yl)benzyl)-2-ethylimidazo[1,2-a]pyridine-3-carboxamide (217)
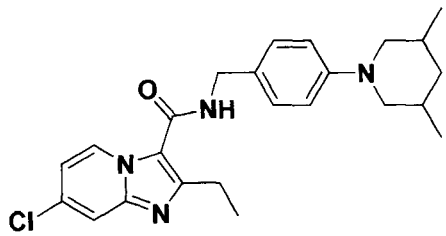
7-Chloro-2-ethyl-*N*-(4-(4-hydroxypiperidin-1-yl)benzyl)imidazo[1,2-a]pyridine-3-carboxamide (218)
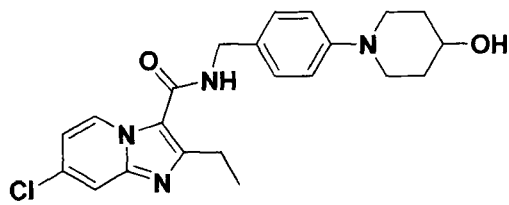
1-(4-((6-Chloro-2-ethylimidazo[1,2-a]pyridine-3-carboxamido)methyl)phenyl)piperidine-4-carboxylic acid (220)
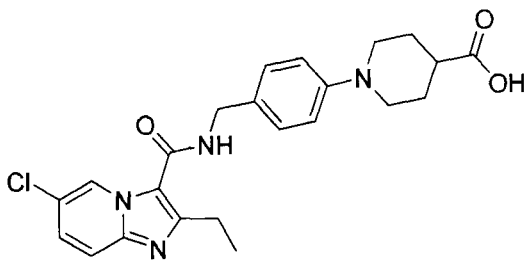

7-Chloro-N-(4-(3a,4-dihydro-1H-isoindol-2(3H,7H,7aH)-yl)benzyl)-2-ethylimidazo[1,2-a]pyridine-3-carboxamide (223)
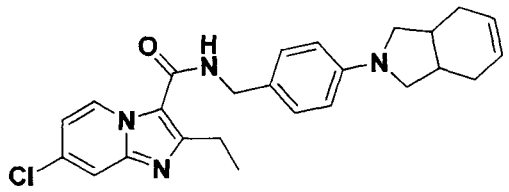
N-(4-(1H-isoindol-2(3H,3aH,4H,5H,6H,7H,7aH)-yl)benzyl)-7-chloro-2-ethylimidazo[1,2-a]pyridine-3-carboxamide (224)
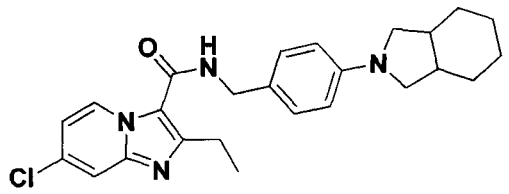
7-Chloro-2-ethyl-N-(4-(4,5,6,7-tetrahydro-2H-isoindol-2-yl)benzyl)imidazo[1,2-a]pyridine-3-carboxamide (225)
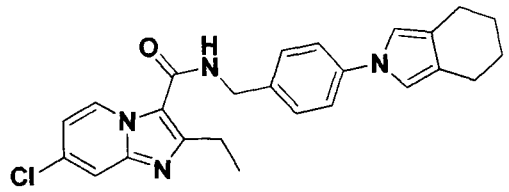
6-Chloro-2-ethyl-N-((1-(4-(trifluoromethoxy)benzyl)piperidin-4-yl)methyl)imidazo[1,2-a]pyridine-3-carboxamide (226)
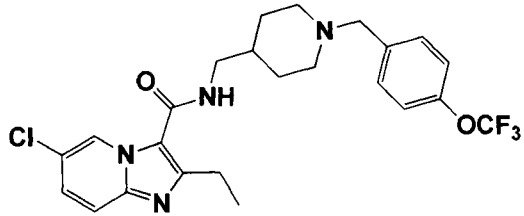

6-Chloro-2-ethyl-N-((1-(4-fluorobenzyl)piperidin-4-yl)methyl)imidazo[1,2-a]pyridine-3-carboxamide (227)
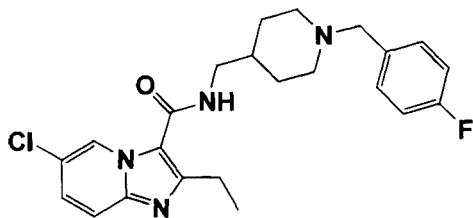
7-Chloro-2-ethyl-N-((1-(4-(trifluoromethoxy)benzyl)piperidin-4-yl)methyl)imidazo[1,2-a]pyridine-3-carboxamide (228)
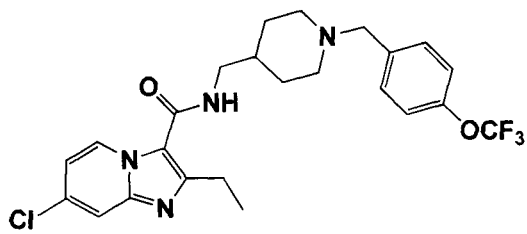
6-Chloro-2-ethyl-N-(1-(4-(trifluoromethoxy)benzyl)piperidin-4-yl)imidazo[1,2-a]pyridine-3-carboxamide (229)
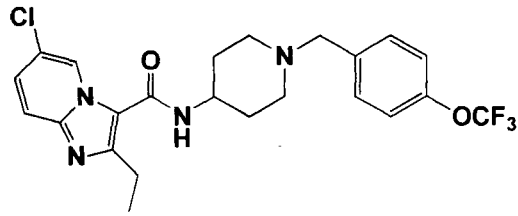
(6-Chloro-2-ethylimidazo[1,2-a]pyridin-3-yl)(4-(4-(trifluoromethoxy)benzyloxy) piperidin-1-yl)methanone (230)
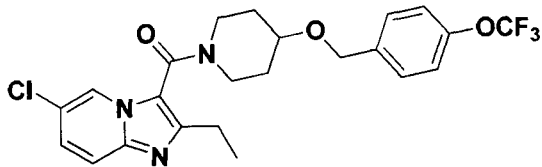

6-Chloro-2-ethyl-N-((1-(4-(trifluoromethoxy)phenyl)-1H-pyrazol-3-yl)methyl) imidazo[1,2-a]pyridine-3-carboxamide (231)

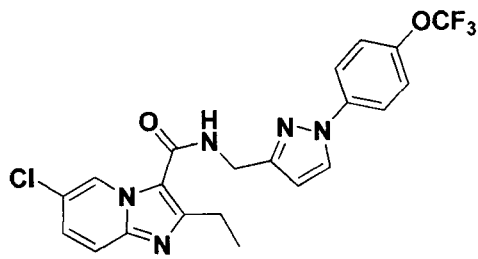

7-Chloro-2-ethyl-N-((1-(4-(trifluoromethoxy)phenyl)-1H-pyrazol-3-yl)methyl) imidazo[1,2-a]pyridine-3-carboxamide (232)

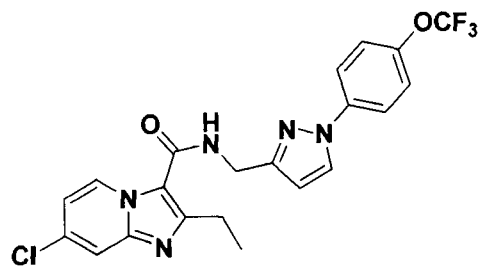

6-Chloro-2-ethyl-N-((1-(4-(trifluoromethyl)phenyl)-1H-pyrazol-3-yl)methyl)imidazo [1,2-a]pyridine-3-carboxamide (233)

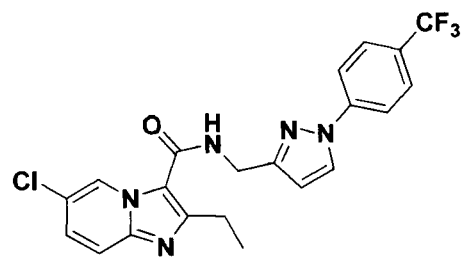

7-Chloro-2-ethyl-N-((1-(4-(trifluoromethyl)phenyl)-1H-pyrazol-3-yl)methyl)imidazo [1,2-a]pyridine-3-carboxamide (234)

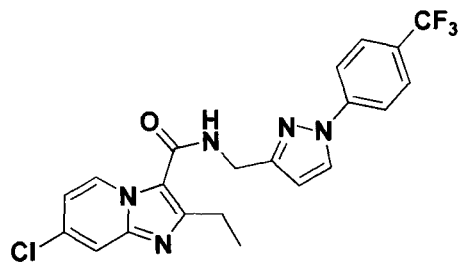

6-Chloro-2-ethyl-N-((1-(4-fluorophenyl)-1H-pyrazol-3-yl)methyl)imidazo[1,2-a] pyridine-3-carboxamide (235)
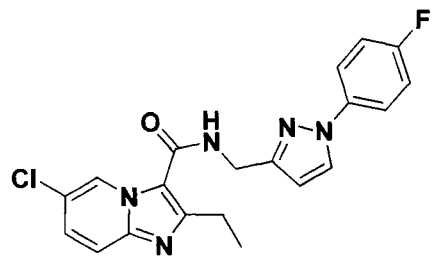
7-Chloro-2-ethyl-N-((1-(4-fluorophenyl)-1H-pyrazol-3-yl)methyl)imidazo[1,2-a] pyridine-3-carboxamide (236)
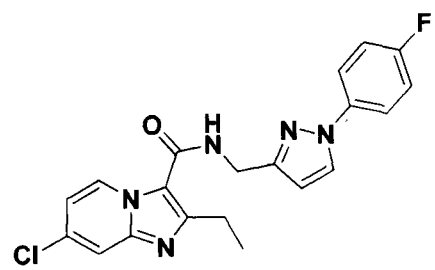
6-Chloro-2-ethyl-N-((1-(4-(trifluoromethoxy)phenyl)-4,5,6,7-tetrahydro-1H-indazol-4-yl)methyl)imidazo[1,2-a]pyridine-3-carboxamide (237)
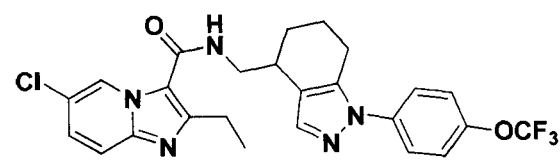
6-Chloro-2-ethyl-N-((1-(4-fluorophenyl)-4,5,6,7-tetrahydro-1H-indazol-4-yl)methyl) imidazo[1,2-a]pyridine-3-carboxamide (238)
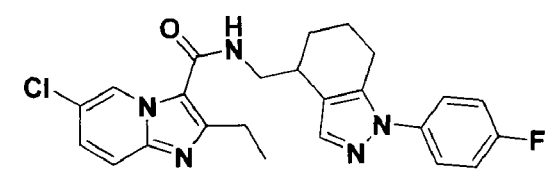

7-Chloro-2-ethyl-*N*-((4'-(trifluoromethoxy)biphenyl-3-yl)methyl)imidazo[1,2-a]pyridine-3-carboxamide (248)
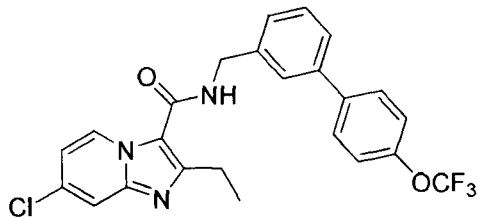
2-Ethyl-7-methyl-*N*-(4-(trifluoromethoxy)benzyl)imidazo[1,2-a]pyridine-3-carboxamide (249)
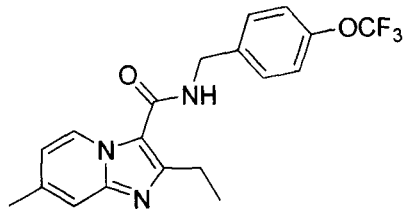
7-Bromo-2-ethyl-*N*-(4-(trifluoromethoxy)benzyl)imidazo[1,2-a]pyridine-3-carboxamide (250)
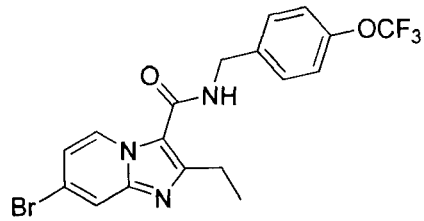
2-Ethyl-8-fluoro-*N*-(4-(trifluoromethoxy)benzyl)imidazo[1,2-a]pyridine-3-carboxamide(251)
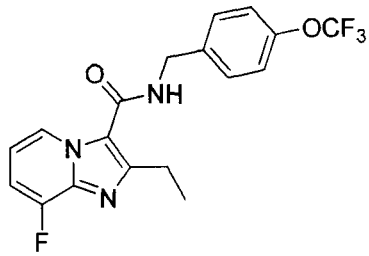

7-Chloro-2-ethyl-*N*-((4'-formylbiphenyl-4-yl)methyl)imidazo[1,2-a]pyridine-3-carboxamide(252)
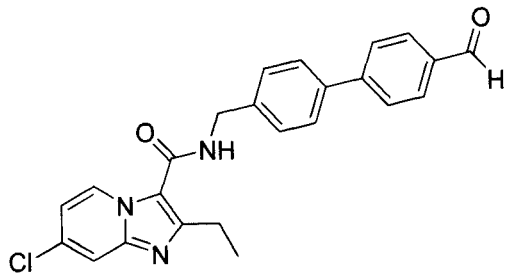
2-Ethyl-6-fluoro-N-(4-(4-(trifluoromethoxy)phenoxy)benzyl)imidazo[1,2-a]pyridine-3-carboxamide (253)
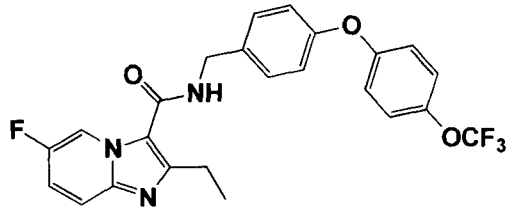
6-Bromo-2-ethyl-N-(4-(4-(trifluoromethoxy)phenoxy)benzyl)imidazo[1,2-a]pyridine-3-carboxamide (254)
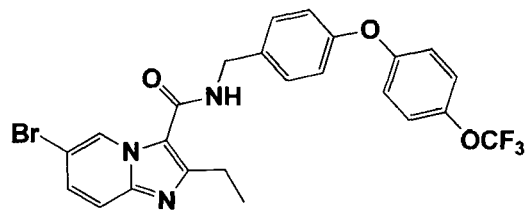
2-Ethyl-6-methyl-*N*-(4-(4-(trifluoromethoxy)phenoxy)benzyl)imidazo[1,2-a]pyridine-3-carboxamide (255)
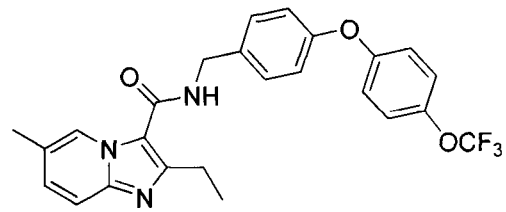

2-Ethyl-7-methyl-*N*-(4-(4-(trifluoromethoxy)phenoxy)benzyl)imidazo[1,2-a]pyridine-3-carboxamide (256)
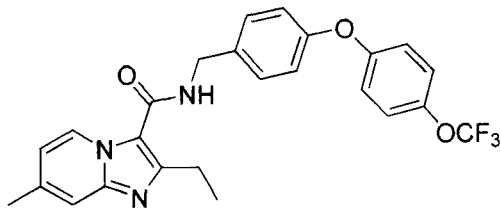
2-Ethyl-8-fluoro-*N*-(4-(4-(trifluoromethoxy)phenoxy)benzyl)imidazo[1,2-a]pyridine-3-carboxamide (257)
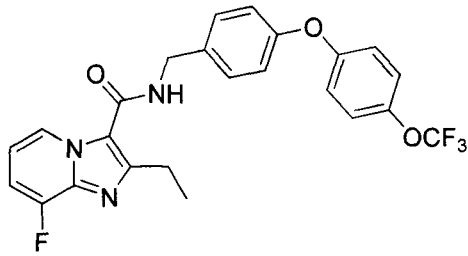
2-Ethyl-6-fluoro-*N*-(4-(4-(trifluoromethoxy)benzyloxy)benzyl)imidazo[1,2-a]pyridine-3-carboxamide (258)
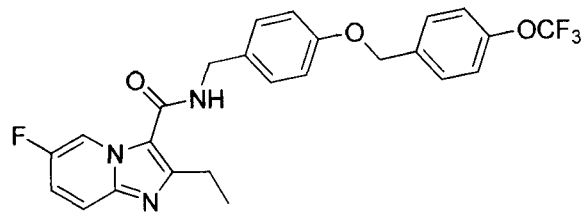
6-Bromo-2-ethyl-*N*-(4-(4-(trifluoromethoxy)benzyloxy)benzyl)imidazo[1,2-a]pyridine-3-carboxamide (259)
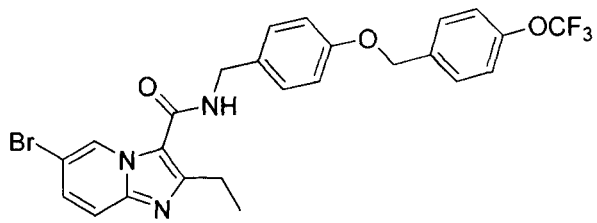

2-Ethyl-*N*-(4-(4-(trifluoromethoxy)benzyloxy)benzyl)imidazo[1,2-a]pyridine-3-carboxamide (260)
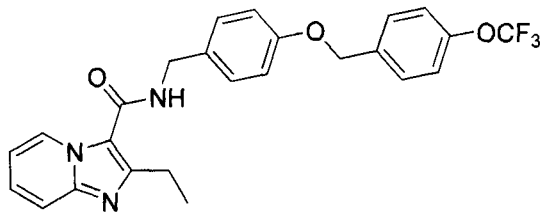
(E)-7-Chloro-2-ethyl-N-(4-((4-(trifluoromethoxy)benzylidene)amino)benzyl)imidazo[1,2-a]pyridine-3-carboxamide (261)
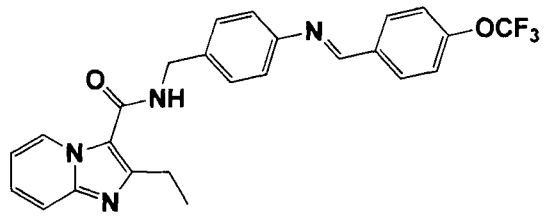
7-Chloro-2-ethyl-N-(4-((4-(trifluoromethoxy)benzyl)amino)benzyl)imidazo[1,2-a]pyridine-3-carboxamide (262)
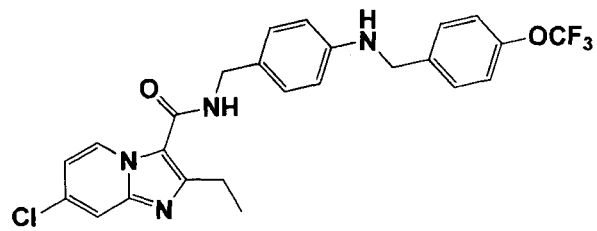
2-Ethyl-N-(4-(methyl(4-(trifluoromethoxy)benzyl)amino)benzyl)imidazo[1,2-a]pyridine-3-carboxamide (263)
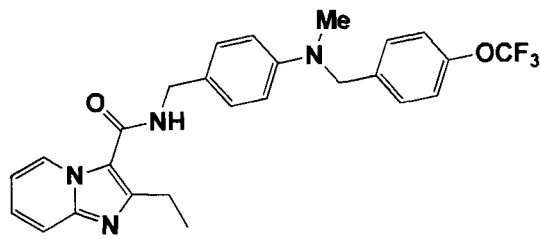

7-Chloro-2-ethyl-N-(4-(hexahydropyrrolo[1,2-a]pyrazin-2(1H)-yl)benzyl)imidazo[1,2-a]pyridine-3-carboxamide (265)
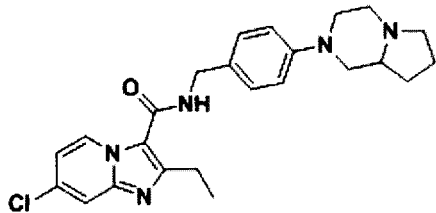
6-Chloro-2-ethyl-N-(4-(hexahydropyrrolo[1,2-a]pyrazin-2(1H)-yl)benzyl)imidazo[1,2-a]pyridine-3-carboxamide (266)
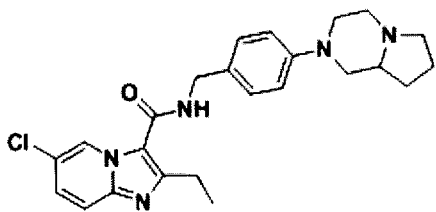
6-Chloro-2-ethyl-*N*-(4-(octahydroisoquinolin-2(1H)-yl)benzyl)imidazo[1,2-a]pyridine-3-carboxamide (267)
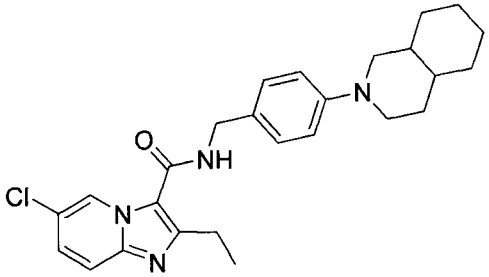
7-Chloro-2-ethyl-*N*-(4-(octahydroisoquinolin-2(1H)-yl)benzyl)imidazo[1,2-a]pyridine-3-carboxamide (268)
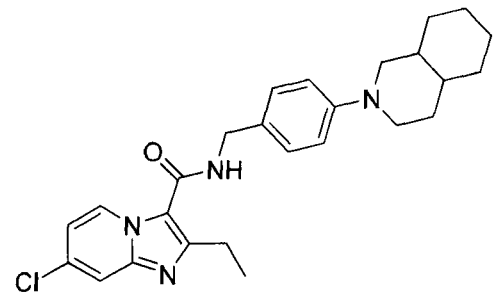

7-Chloro-2-ethyl-*N*-(4-(4-oxopiperidin-1-yl)benzyl)imidazo[1,2-a]pyridine-3-carboxamide (269)
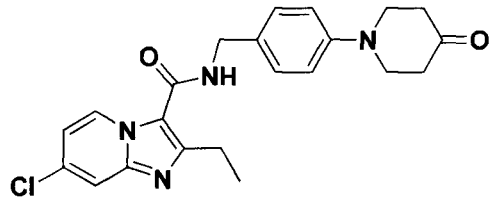
7-Chloro-2-ethyl-*N*-(4-(4-oxo-3,4-dihydropyridin-1(2H)-yl)benzyl)imidazo[1,2-a]pyridine-3-carboxamide (270)
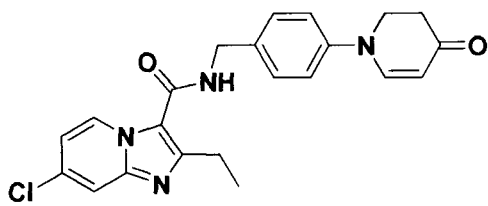
7-Chloro-2-ethyl-*N*-(4-(4-methylenepiperidin-1-yl)benzyl)imidazo[1,2-a]pyridine-3-carboxamide (271)
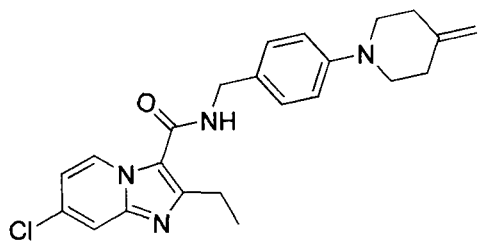
6-chloro-2-ethyl-*N*-(4-(2-methylpiperidin-1-yl)benzyl)imidazo[1,2-a]pyridine-3-carboxamide (272)
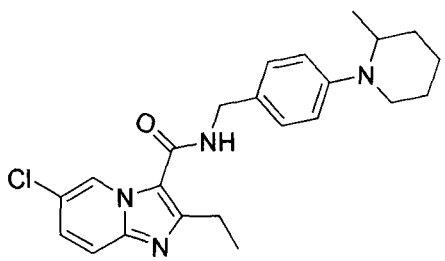

7-chloro-2-ethyl-*N*-(4-(2-methylpiperidin-1-yl)benzyl)imidazo[1,2-a]pyridine-3-carboxamide (273)
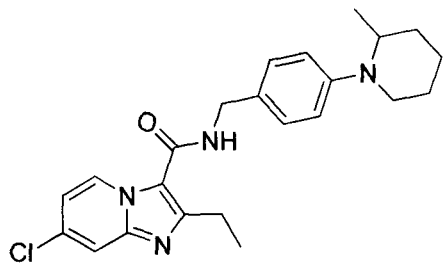
7-Chloro-*N*-(4-(4,4-dimethylpiperidin-1-yl)benzyl)-2-ethyl-1,8a-dihydroimidazo[1,2-a]pyridine-3-carboxamide (274)
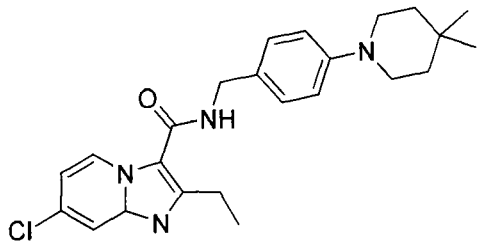
6-Chloro-2-ethyl-*N*-(4-(4-(trifluoromethyl)piperidin-1-yl)benzyl)imidazo[1,2-a]pyridine-3-carboxamide (275)
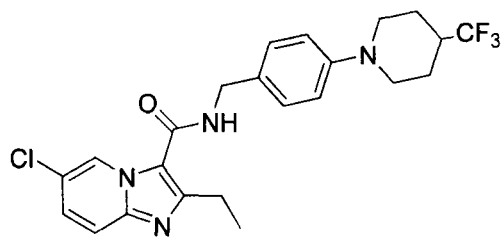
7-Chloro-2-ethyl-*N*-(4-(4-(trifluoromethyl)piperidin-1-yl)benzyl)imidazo[1,2-a]pyridine-3-carboxamide (276)
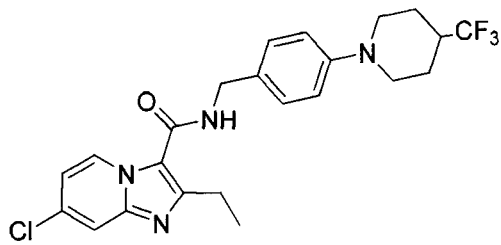

6-chloro-N-(4-(4,4-difluoropiperidin-1-yl)benzyl)-2-ethylimidazo[1,2-a]pyridine-3-carboxamide (277)
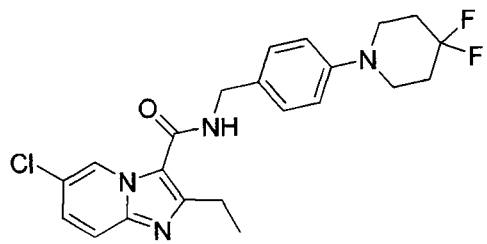
7-Chloro-*N*-(4-(4,4-difluoropiperidin-1-yl)benzyl)-2-ethylimidazo[1,2-a]pyridine-3-carboxamide (278)
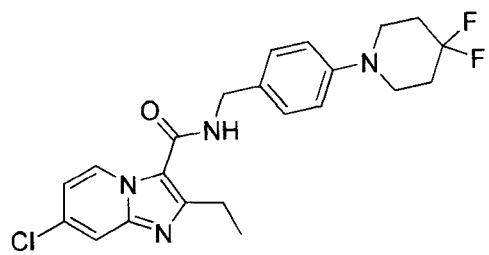
6-Chloro-2-ethyl-*N*-(4-(4-(hydroxymethyl)piperidin-1-yl)benzyl)imidazo[1,2-a]pyridine-3-carboxamide (279)
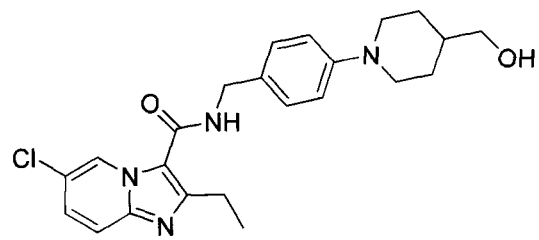
7-Chloro-2-ethyl-*N*-(4-(4-(hydroxymethyl)piperidin-1-yl)benzyl)imidazo[1,2-a]pyridine-3-carboxamide (280)
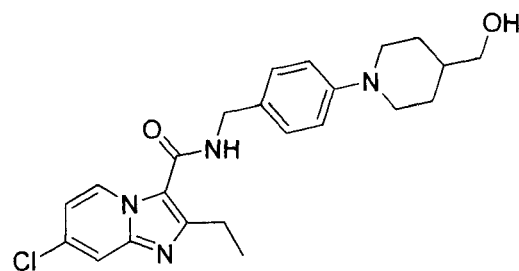

6-Chloro-2-ethyl-*N*-(4-(4-(methoxymethyl)piperidin-1-yl)benzyl)imidazo[1,2-a]pyridine-3-carboxamide (281)
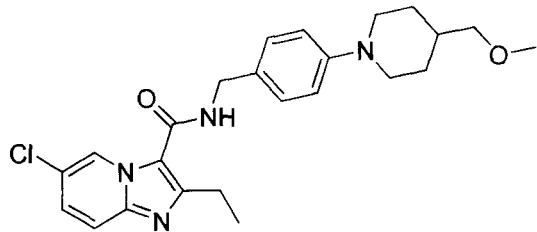
7-Chloro-2-ethyl-*N*-(4-(4-(methoxymethyl)piperidin-1-yl)benzyl)imidazo[1,2-a]pyridine-3-carboxamide (282)
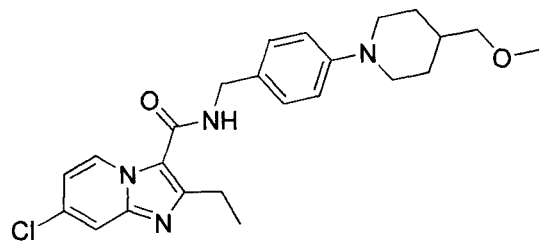
7-Chloro-2-ethyl-*N*-(4-(4-phenylpiperidin-1-yl)benzyl)imidazo[1,2-a]pyridine-3-carboxamide (283)
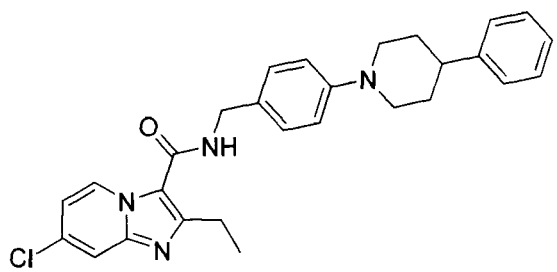
6-Chloro-2-ethyl-*N*-(4-(4-phenylpiperidin-1-yl)benzyl)imidazo[1,2-a]pyridine-3-carboxamide (284)
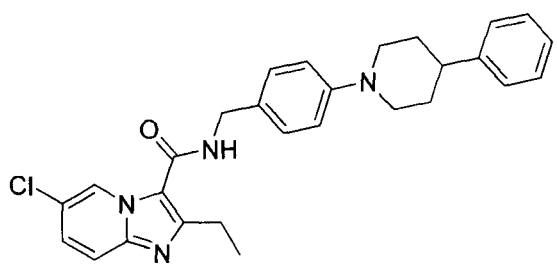

2-Ethyl-*N*-(4-(4-(4-fluorophenyl)piperidin-1-yl)benzyl)imidazo[1,2-a]pyridine-3-carboxamide(285)
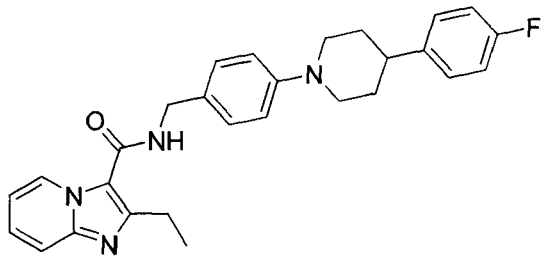
6-Chloro-2-ethyl-*N*-(4-(4-(4-fluorophenyl)piperidin-1-yl)benzyl)imidazo[1,2-a]pyridine-3-carboxamide (286)
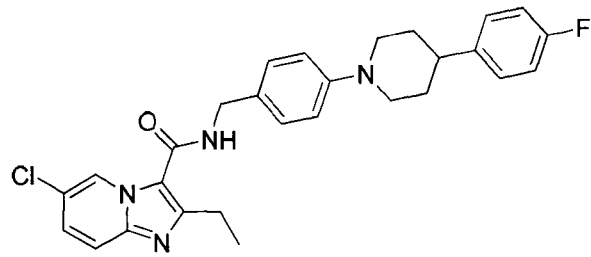
7-Chloro-2-ethyl-*N*-(4-(4-(4-fluorophenyl)piperidin-1-yl)benzyl)imidazo[1,2-a]pyridine-3-carboxamide (287)
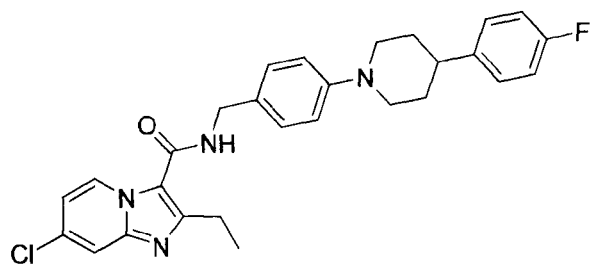
2-Ethyl-*N*-(4-(4-(4-(trifluoromethoxy)phenyl)piperidin-1-yl)benzyl)imidazo[1,2-a]pyridine-3-carboxamide(288)
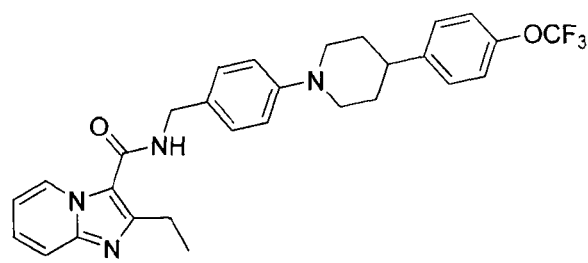

6-Chloro-2-ethyl-*N*-(4-(4-(4-(trifluoromethoxy)phenyl)piperidin-1-yl)benzyl)imidazo[1,2-a]pyridine-3-carboxamide (289)

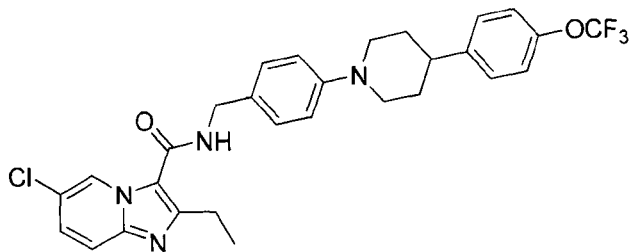

7-Chloro-2-ethyl-*N*-(4-(4-(4-(trifluoromethoxy)phenyl)piperidin-1-yl)benzyl)imidazo[1,2-a]pyridine-3-carboxamide(290)

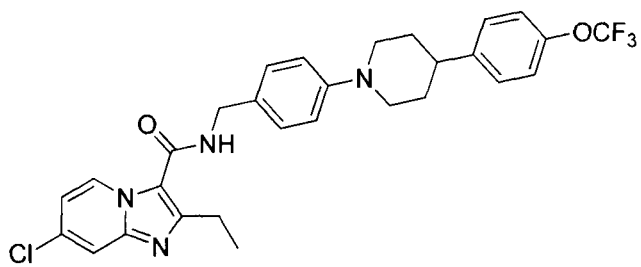

6-Chloro-2-ethyl-*N*-(4-(4-(isopropoxymethyl)piperidin-1-yl)benzyl)imidazo[1,2-a]pyridine-3-carboxamide(291)

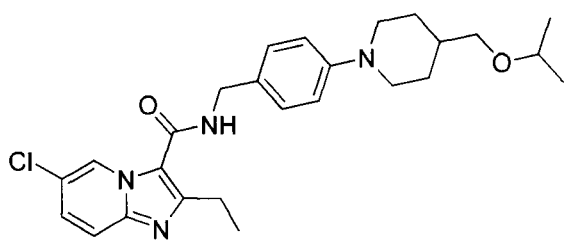

7-Chloro-2-ethyl-*N*-(4-(4-(isopropoxymethyl)piperidin-1-yl)benzyl)imidazo[1,2-a]pyridine-3-carboxamide(292)

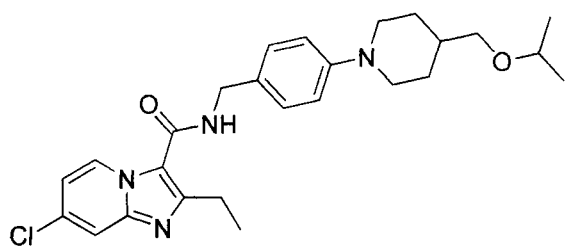

6-Chloro-*N*-(4-(4-(cyclopentyloxymethyl)piperidin-1-yl)benzyl)-2-ethylimidazo[1,2-a]pyridine-3-carboxamide(293)
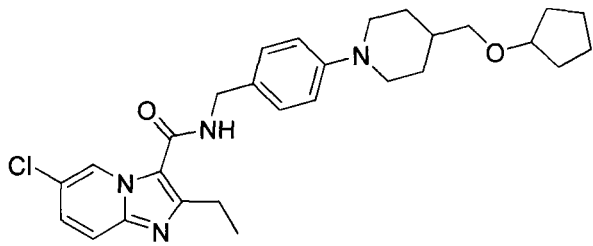
*N*-(4-(4-Benzylpiperidin-1-yl)benzyl)-7-chloro-2-ethylimidazo[1,2-a]pyridine-3-carboxamide (294)
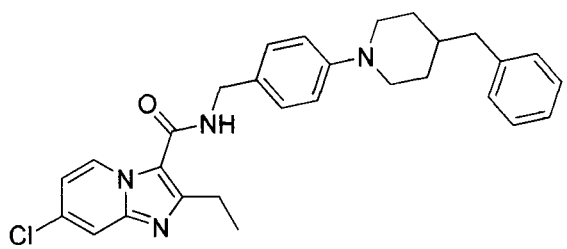
2-Ethyl-N-(4-(4-((4-fluorophenoxy)methyl)piperidin-1-yl)benzyl)imidazo[1,2-a]pyridine-3-carboxamide (295)
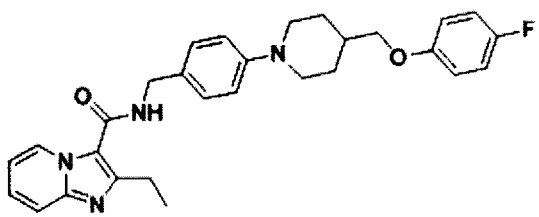
6-Chloro-2-ethyl-N-(4-(4-((4-fluorophenoxy)methyl)piperidin-1-yl)benzyl)imidazo[1,2-a]pyridine-3-carboxamide (296)
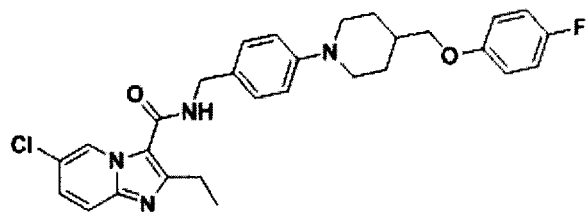

7-Chloro-2-ethyl-N-(4-(4-((4-fluorophenoxy)methyl)piperidin-1-yl)benzyl)imidazo[1,2-a]pyridine-3-carboxamide (297)

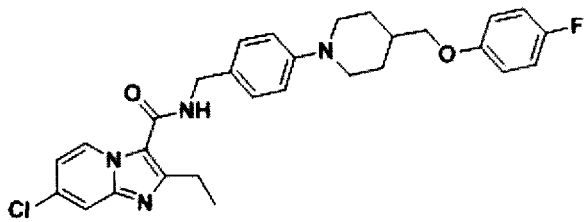

6-chloro-2-ethyl-*N*-(4-(4-((4-(trifluoromethoxy)phenoxy)methyl)piperidin-1-yl)benzyl)imidazo[1,2-a]pyridine-3-carboxamide (298)

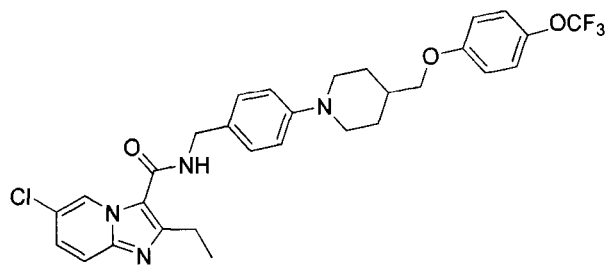

7-Chloro-2-ethyl-*N*-(4-(4-((4-(trifluoromethoxy)phenoxy)methyl)piperidin-1-yl)benzyl)imidazo[1,2-a]pyridine-3-carboxamide (299)

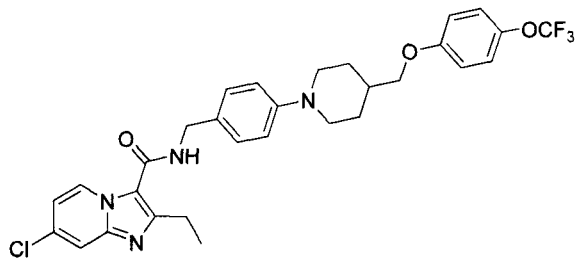

Ethyl 1-(4-((6-chloro-2-ethylimidazo[1,2-a]pyridine-3-carboxamido)methyl)phenyl)piperidine-4-carboxylate (300)

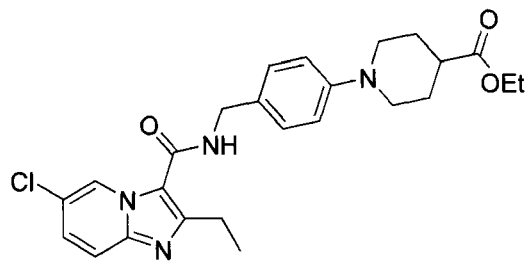

Ethyl 1-(4-((7-chloro-2-ethylimidazo[1,2-a]pyridine-3-carboxamido)methyl)phenyl) piperidine-4-carboxylate (301)
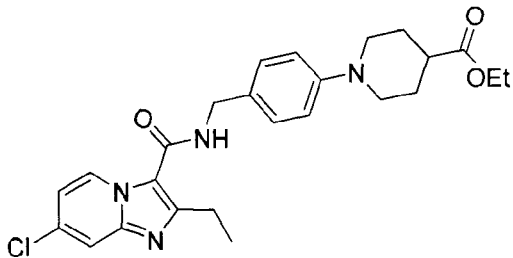
1-(4-((7-Chloro-2-ethylimidazo[1,2-a]pyridine-3-carboxamido)methyl)phenyl) piperidine-4-carboxylic acid (302)
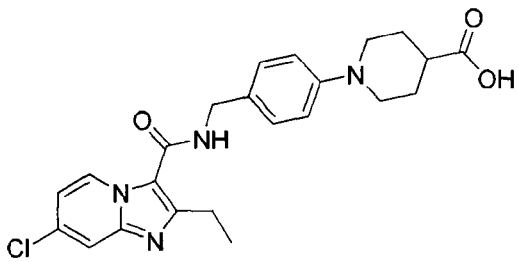
2-Ethyl-N-(4-(4-(4-fluorophenyl)piperazin-1-yl)benzyl)imidazo[1,2-a]pyridine-3-carboxamide (303)
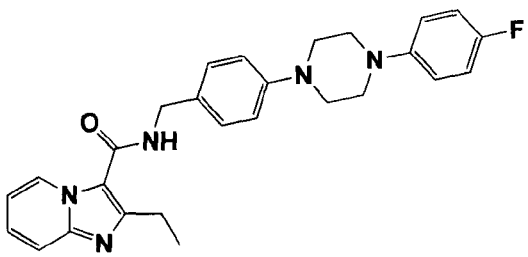
8-(Difluoromethoxy)-2-ethyl-N-(4-(4-(4-fluorophenyl)piperazin-1-yl)benzyl)imidazo[1,2-a]pyridine-3-carboxamide (304)
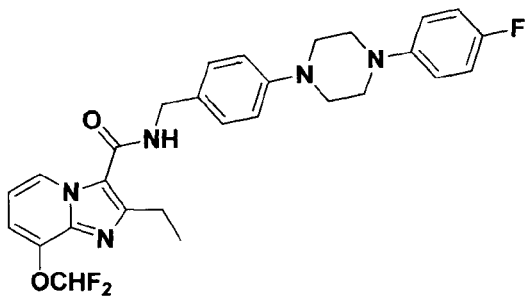

8-Bromo-2-ethyl-*N*-(4-(4-(4-fluorophenyl)piperazin-1-yl)benzyl)imidazo[1,2-a]pyridine-3-carboxamide (305)
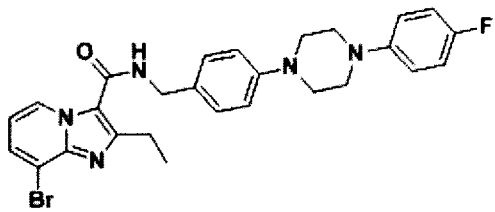
2-Ethyl-6-fluoro-N-(4-(4-(4-fluorophenyl)piperazin-1-yl)benzyl)imidazo[1,2-a]pyridine-3-carboxamide (306)
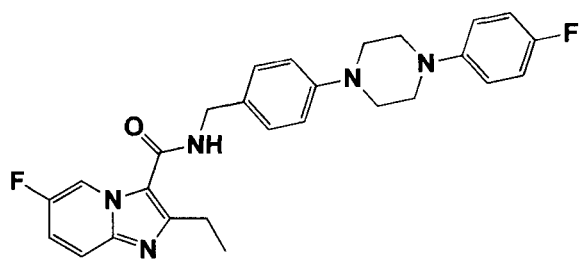
6-Bromo-2-ethyl-N-(4-(4-(4-fluorophenyl)piperazin-1-yl)benzyl)imidazo[1,2-a]pyridine-3-carboxamide (307)
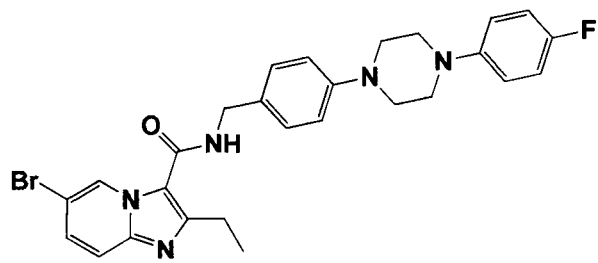
2-Ethyl-*N*-(4-(4-(4-fluorophenyl)piperazin-1-yl)benzyl)-6-methylimidazo[1,2-a]pyridine-3-carboxamide (308)
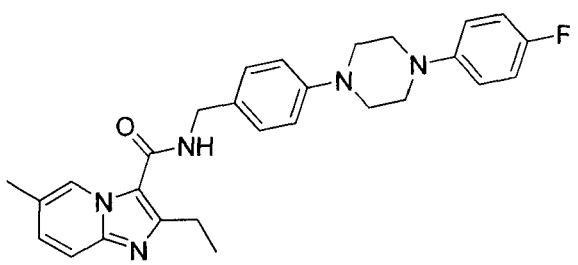

2-Ethyl-*N*-(4-(4-(4-fluorophenyl)piperazin-1-yl)benzyl)-7-methylimidazo[1,2-a]pyridine-3-carboxamide (309)
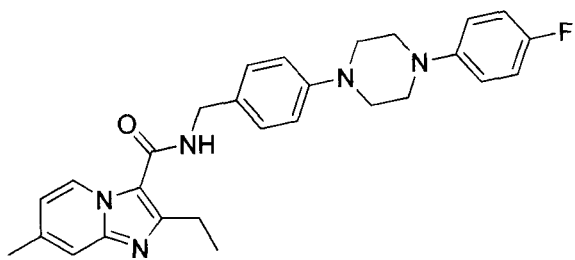
2-Ethyl-8-fluoro-*N*-(4-(4-(4-fluorophenyl)piperazin-1-yl)benzyl)imidazo[1,2-a]pyridine-3-carboxamide (310)
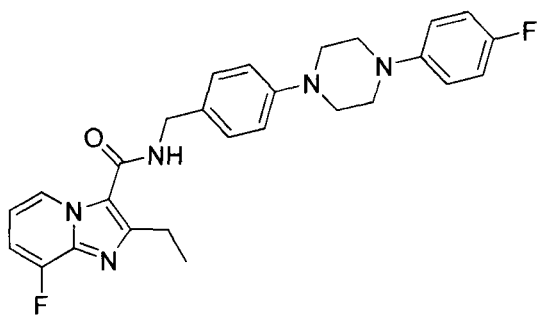
7-Bromo-2-ethyl-*N*-(4-(4-(4-fluorophenyl)piperazin-1-yl)benzyl)imidazo[1,2-a]pyridine-3-carboxamide (311)
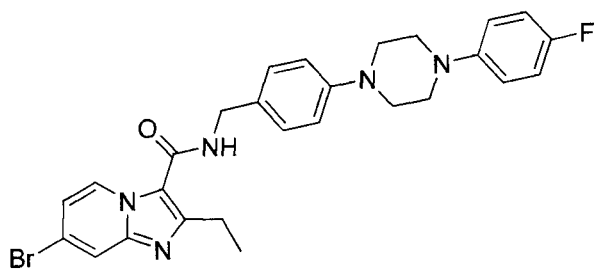

2-Ethyl-*N*-(4-(4-(4-fluorophenyl)piperazin-1-yl)benzyl)-8-(pyridin-4-yl)imidazo[1,2-a]pyridine-3-carboxamide (312)
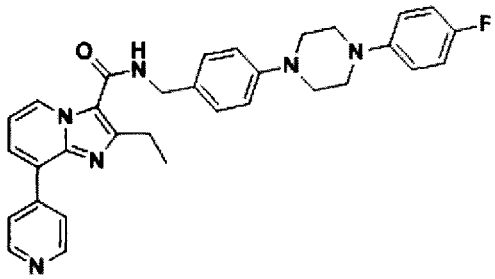
2-Ethyl-7-(4-phenylpiperazin-1-yl)-*N*-(4-(trifluoromethyl)benzyl)imidazo[1,2-a]pyridine-3-carboxamide (330)
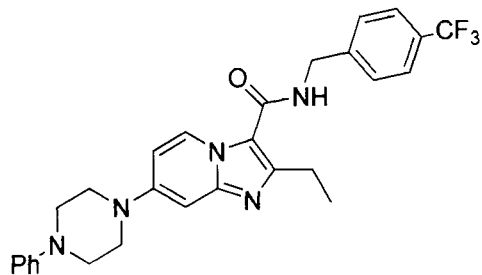
6-Chloro-2-ethyl-*N*-(4-((4-(morpholine-4-carbonyl)benzyl)carbamoyl)benzyl) imidazo[1,2-a]pyridine-3-carboxamide (332)
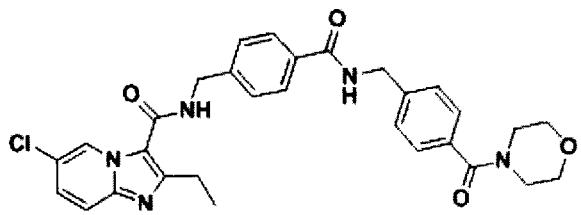
7-Chloro-2-ethyl-*N*-(4-(morpholine-4-carbonyl)benzyl)imidazo[1,2-a]pyridine-3-carboxamide (333)
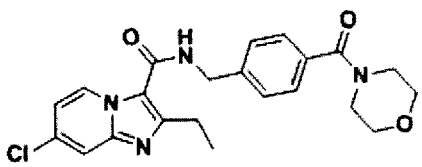

2-Ethyl-*N*-((2-(4-fluorophenyl)benzo[d]oxazol-5-yl)methyl)imidazo[1,2-a]pyridine-3-carboxamide (334)

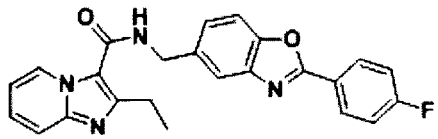

6-Chloro-2-ethyl-*N*-((2-(4-fluorophenyl)benzo[d]oxazol-5-yl)methyl)imidazo[1,2-a]pyridine-3-carboxamide (335)

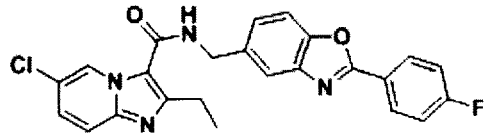

7-Chloro-2-ethyl-*N*-((2-(4-fluorophenyl)benzo[d]oxazol-5-yl)methyl)imidazo[1,2-a]pyridine-3-carboxamide (336)

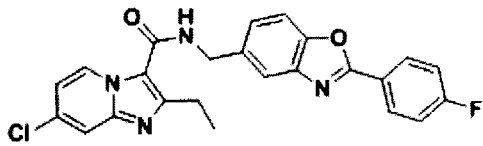

6-Chloro-N-(4-(4-(4-chlorophenyl)piperidin-1-yl)benzyl)-2-ethylimidazo[1,2-a]pyridine-3-carboxamide (337)

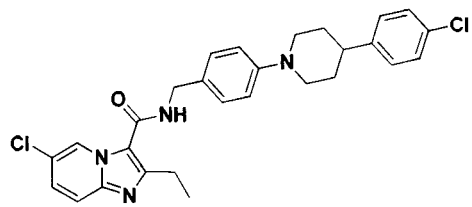

7-Chloro-N-(4-(4-(4-chlorophenyl)piperidin-1-yl)benzyl)-2-ethylimidazo[1,2-a]pyridine-3-carboxamide (338)

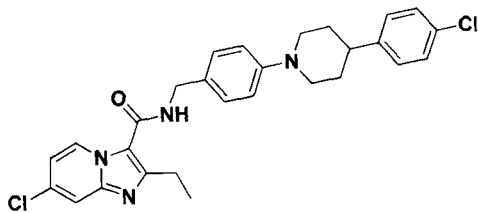

6-Chloro-*N*-((2-cyclohexylbenzo[d]oxazol-5-yl)methyl)-2-ethylimidazo[1,2-a]pyridine-3-carboxamide (339)
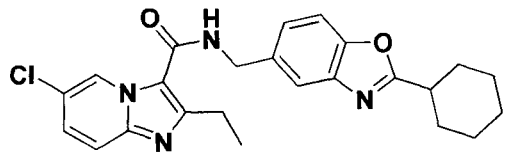
7-Chloro-*N*-((2-cyclohexylbenzo[d]oxazol-5-yl)methyl)-2-ethylimidazo[1,2-a]pyridine-3-carboxamide (340)
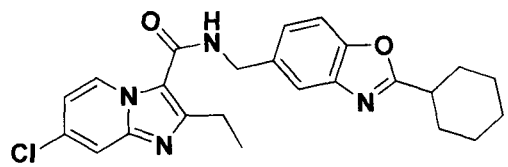
6-Chloro-2-ethyl-*N*-(4-(4-(4-fluorophenyl)-4-hydroxypiperidin-1-yl)benzyl)imidazo[1,2-a]pyridine-3-carboxamide (341)
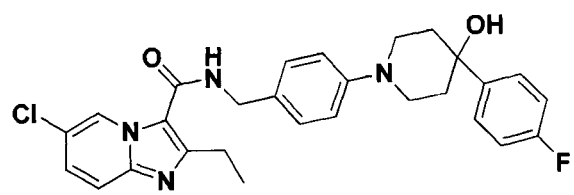
7-Chloro-2-ethyl-*N*-(4-(4-(4-fluorophenyl)-4-hydroxypiperidin-1-yl)benzyl)imidazo[1,2-a]pyridine-3-carboxamide (342)
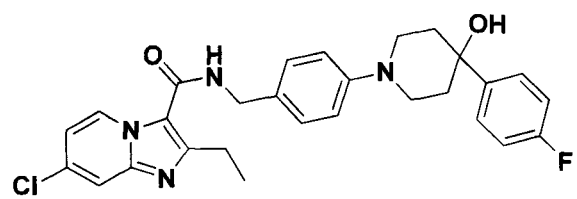

*N*-(4-(4-Carbamoylpiperidin-1-yl)benzyl)-6-chloro-2-ethylimidazo[1,2-a]pyridine-3-carboxamide (343)
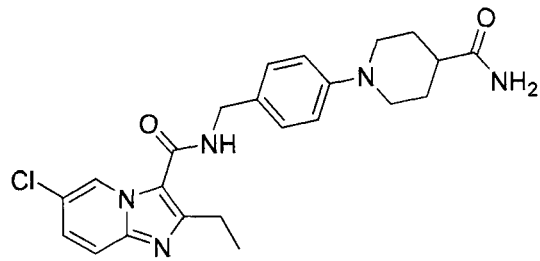
*N*-(4-(4-Carbamoylpiperidin-1-yl)benzyl)-7-chloro-2-ethylimidazo[1,2-a]pyridine-3-carboxamide (344)
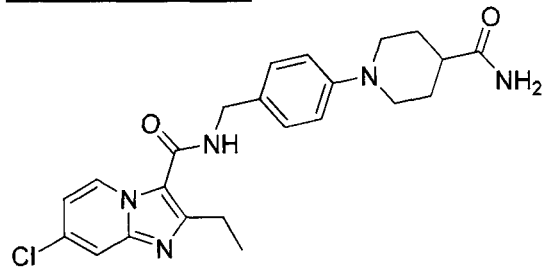
6-Chloro-*N*-(4-(4-(dimethylcarbamoyl)piperidin-1-yl)benzyl)-2-ethylimidazo[1,2-a]pyridine-3-carboxamide (345)
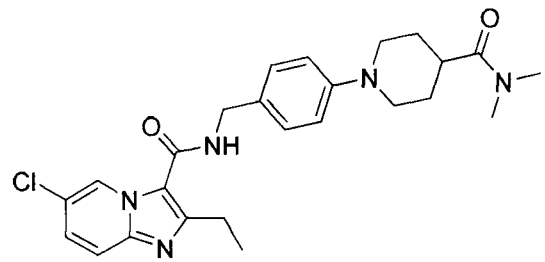
7-Chloro-*N*-(4-(4-(dimethylcarbamoyl)piperidin-1-yl)benzyl)-2-ethylimidazo[1,2-a]pyridine-3-carboxamide (346)
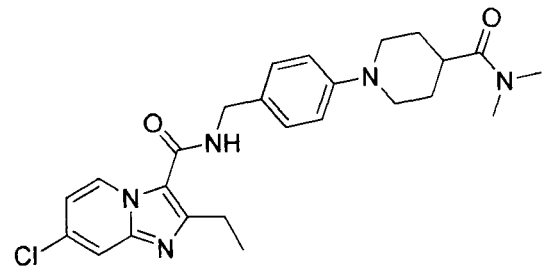

6-Chloro-2-ethyl-*N*-(4-(4-(4-fluorobenzyloxy)piperidin-1-yl)benzyl)imidazo[1,2-a]pyridine-3-carboxamide (347)
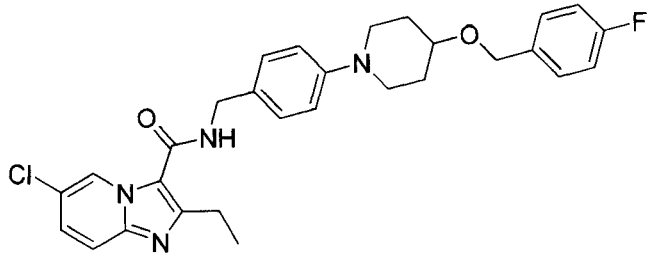
7-Chloro-2-ethyl-*N*-(4-(4-(4-fluorobenzyloxy)piperidin-1-yl)benzyl)imidazo[1,2-a]pyridine-3-carboxamide (348)
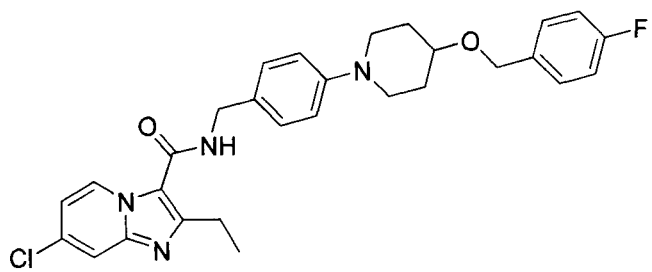
6-Chloro-*N*-(3-chloro-4-morpholinobenzyl)-2-ethylimidazo[1,2-a]pyridine-3-carboxamide (349)
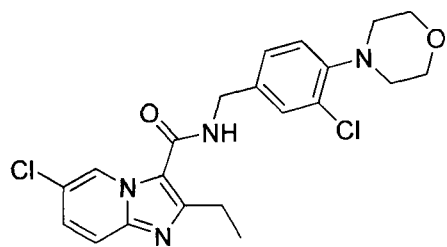
7-Chloro-*N*-(3-chloro-4-morpholinobenzyl)-2-ethylimidazo[1,2-a]pyridine-3-carboxamide (350)
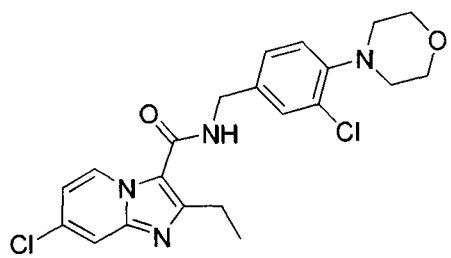

6-Chloro-2-ethyl-*N*-(4-(4-formylpiperidin-1-yl)benzyl)imidazo[1,2-a]pyridine-3-carboxamide (351)

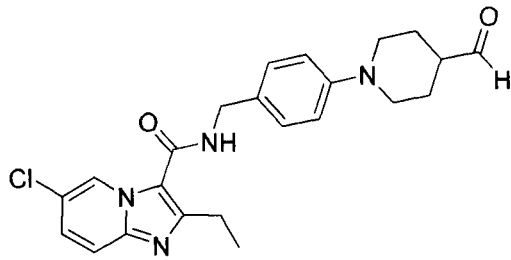

7-Chloro-2-ethyl-N-(4-(4-formylpiperidin-1-yl)benzyl)imidazo[1,2-a]pyridine-3-carboxamide (352)

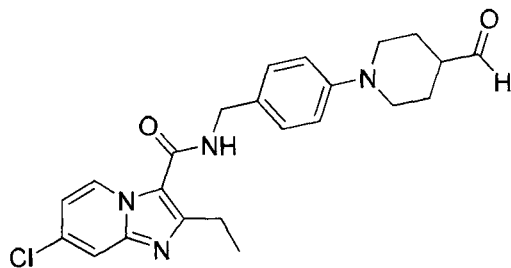

or a pharmaceutically acceptable salt thereof.

4. The compound according to claim 3, having one of the formulae 47, 54, 177 and 185, or a pharmaceutically acceptable salt thereof:

N-(Biphenyl-4-ylmethyl)-2-ethylimidazo[1,2-a]pyridine-3-carboxamide (47)

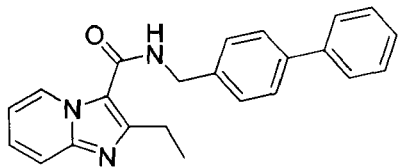

2-Ethyl-N-(4-phenoxybenzyl)imidazo[1,2-a]pyridine-3-carboxamide (54)

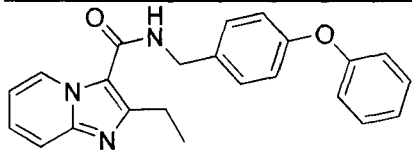

7-Chloro-2-ethyl-N-(4-(4-(4-fluorophenyl)piperazin-1-yl)benzyl)imidazo[1,2-a]pyridine-3-carboxamide trihydrochloride (177)

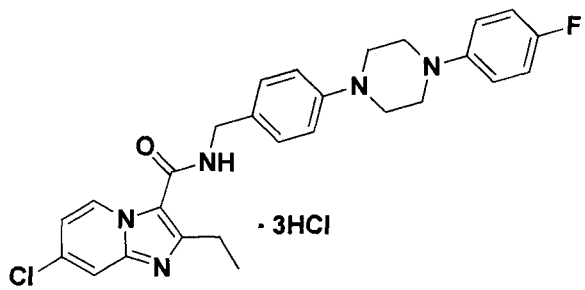

6-Chloro-2-ethyl-N-(4-(4-(trifluoromethoxy)phenoxy)benzyl)imidazo[1,2-a]pyridine-3-carboxamide (185)

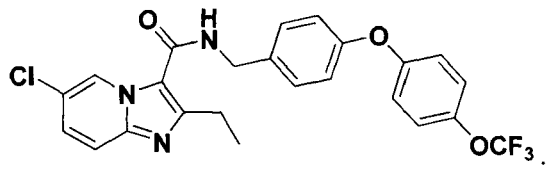

5. A pharmaceutical composition comprising a compound according to claim 2, and a pharmaceutically acceptable carrier.

6. A method of treatment of a bacterial infection, comprising the application of a suitable amount of a compound according to claim 1, to a person in need thereof.

7. The method, according to claim 6, used for the treatment of tuberculosis.

8. The compound, according to claim 3, having a formula selected from formulae 15, 16, 44, 45, 47, 49, 54-57, 60-67, 70-73, 75-78, 81-87, 92-103, 106, 107, 110, 111, 113, 116-135, 137-141, 144, 147, 148, 152, 154, 157-159, 162-167, 171-182, 184-193, 198, 199-202, 209, 210, 214-218, 223-227, 231, 248-260, 262, 263, 267-269, 271-274, 280-293, 295-312 and 330:

2-Methyl-N-(4-phenoxybenzyl)imidazo[1,2-a]pyridine-3-carboxamide (15)
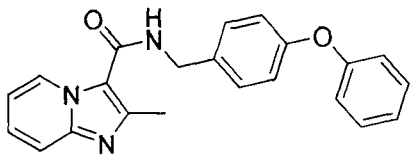
N-(Biphenyl-4-ylmethyl)-2-methylimidazo[1,2-a]pyridine-3-carboxamide (16)
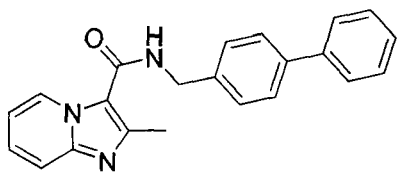
N-(Biphenyl-4-ylmethyl)-6-chloro-2-methylimidazo[1,2-a]pyridine-3-carboxamide (44)
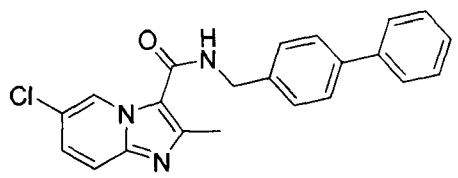
N-(Biphenyl-4-ylmethyl)-7-chloro-2-methylimidazo[1,2-a]pyridine-3-carboxamide (45)
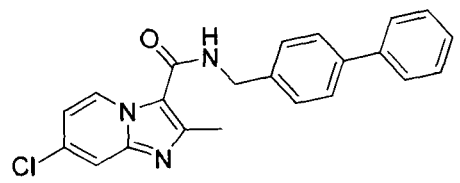
N-(Biphenyl-4-ylmethyl)-2-ethylimidazo[1,2-a]pyridine-3-carboxamide (47)
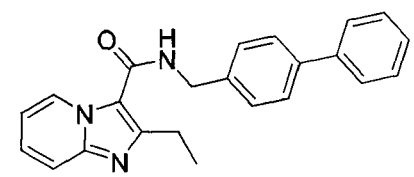

N-(Biphenyl-4-ylmethyl)-2-propylimidazo[1,2-a]pyridine-3-carboxamide (49)
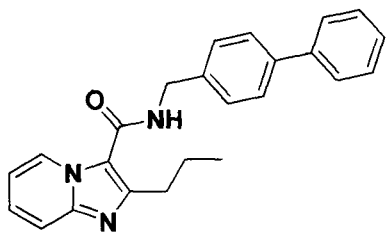
2-Ethyl-N-(4-phenoxybenzyl)imidazo[1,2-a]pyridine-3-carboxamide (54)
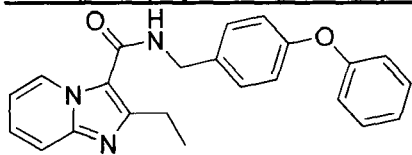
N-(4-tert-Butylbenzyl)-2-ethylimidazo[1,2-a]pyridine-3-carboxamide (55)
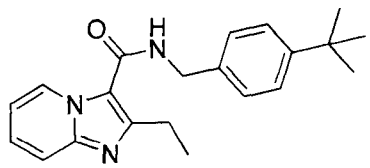
2-Ethyl-N-((1-methyl-1H-indol-5-yl)methyl)imidazo[1,2-a]pyridine-3-carboxamide (56)
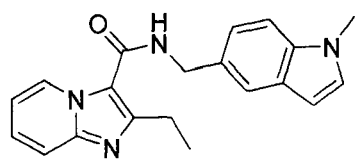
2-Ethyl-N-(4-(trifluoromethoxy)benzyl)imidazo[1,2-a]pyridine-3-carboxamide (57)
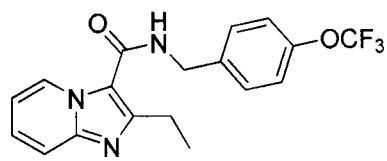

2-Ethyl-N-(4-isopropoxybenzyl)imidazo[1,2-a]pyridine-3-carboxamide (60)
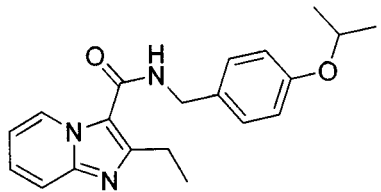
2-Ethyl-N-(4-isobutoxybenzyl)imidazo[1,2-a]pyridine-3-carboxamide (61)
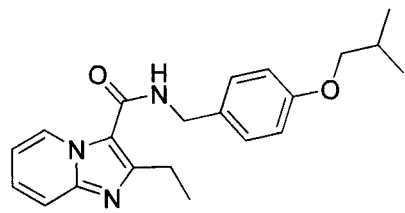
N-(Biphenyl-4-ylmethyl)-2-ethyl-6-methylimidazo[1,2-a]pyridine-3-carboxamide (62)
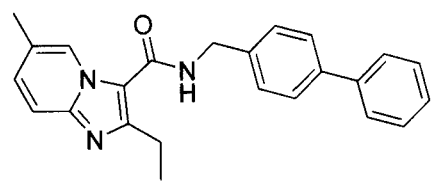
2-Ethyl-6-methyl-N-(4-phenoxybenzyl)imidazo[1,2-a]pyridine-3-carboxamide (63)
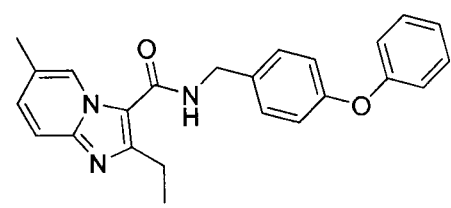
N-(4-tert-Butylbenzyl)-2-ethyl-6-methylimidazo[1,2-a]pyridine-3-carboxamide (64)
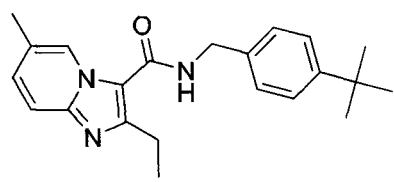

2-Ethyl-6-methyl-N-(4-(trifluoromethoxy)benzyl)imidazo[1,2-a]pyridine-3-carboxamide (65)
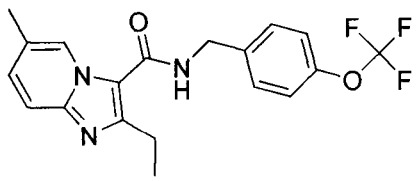
2-Ethyl-6-methyl-N-((1-methyl-1H-indol-5-yl)methyl)imidazo[1,2-a]pyridine-3-carboxamide (66)
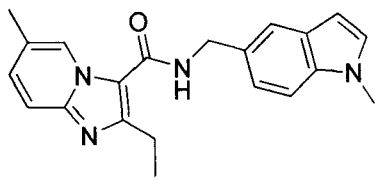
2-Ethyl-6-methyl-N-((1-methyl-1H-indol-6-yl)methyl)imidazo[1,2-a]pyridine-3-carboxamide (67)
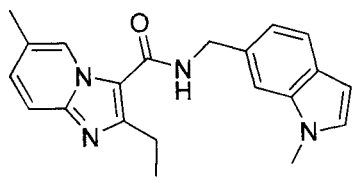
6-Chloro-N-(4-chlorobenzyl)-2-ethylimidazo[1,2-a]pyridine-3-carboxamide (70)
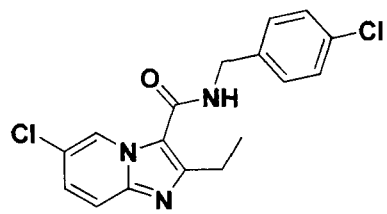

6-Chloro-2-methyl-N-(4-phenoxybenzyl)imidazo[1,2-a]pyridine-3-carboxamide (71)
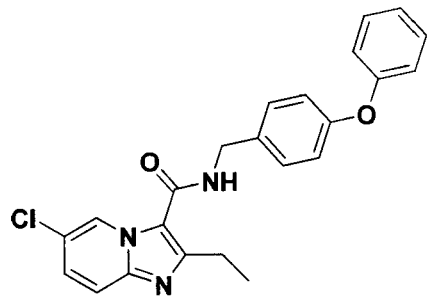
6-Chloro-2-methyl-N-(4-(trifluoromethoxy)benzyl)imidazo[1,2-a]pyridine-3-carboxamide (72)
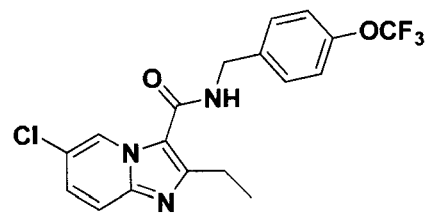
N-(4-tert-Butylbenzyl)-6-chloro-2-methylimidazo[1,2-a]pyridine-3-carboxamide (73)
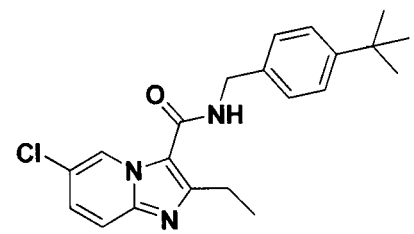
6-Chloro-N-(4-isopropoxybenzyl)-2-methylimidazo[1,2-a]pyridine-3-carboxamide (75)
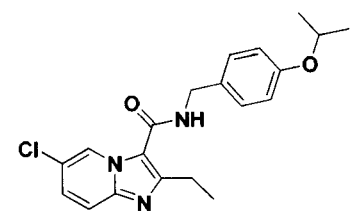

6-Chloro-N-(4-isobutoxybenzyl)-2-methylimidazo[1,2-a]pyridine-3-carboxamide (76)
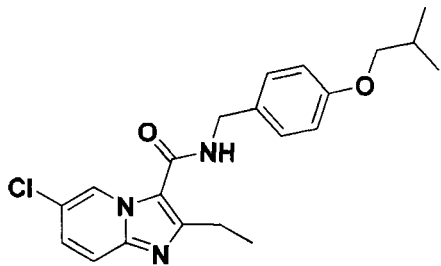
6-Chloro-2-methyl-N-((1-methyl-1H-indol-5-yl)methyl)imidazo[1,2-a]pyridine-3-carboxamide (77)
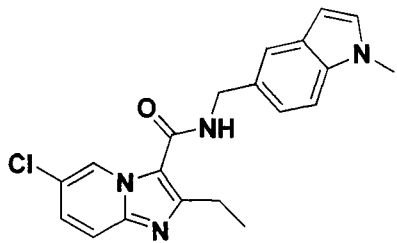
6-Chloro-2-methyl-N-((1-methyl-1H-indol-6-yl)methyl)imidazo[1,2-a]pyridine-3-carboxamide (78)
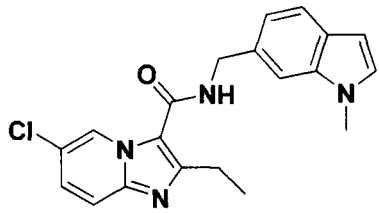
N-(Biphenyl-4-ylmethyl)-6-chloro-2-methylimidazo[1,2-a]pyridine-3-carboxamide (81)
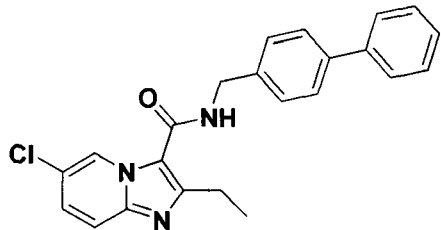

6-Chloro-N-((2'-chlorobiphenyl-4-yl)methyl)-2-ethylimidazo[1,2-a]pyridine-3-carboxamide (82)
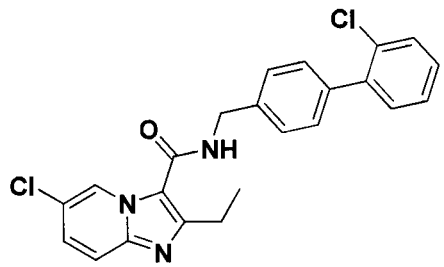
6-Chloro-N-((4'-chlorobiphenyl-4-yl)methyl)-2-ethylimidazo[1,2-a]pyridine-3-carboxamide (83)
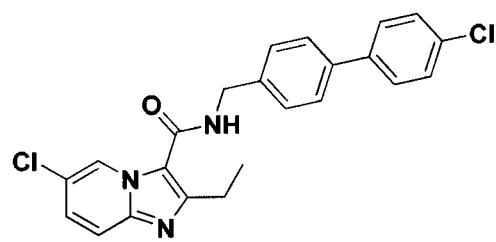
6-Chloro-2-ethyl-N-((2'-methylbiphenyl-4-yl)methyl)imidazo[1,2-a]pyridine-3-carboxamide (84)
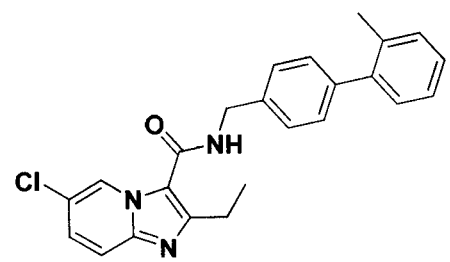
6-Chloro-2-ethyl-N-((3'-methylbiphenyl-4-yl)methyl)imidazo[1,2-a]pyridine-3-carboxamide (85)
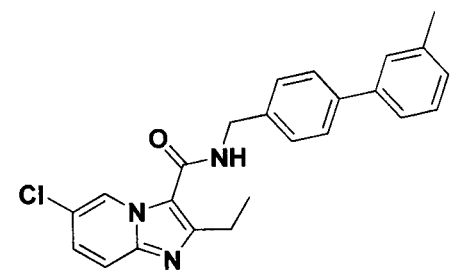

6-Chloro-2-ethyl-N-((4'-methylbiphenyl-4-yl)methyl)imidazo[1,2-a]pyridine-3-carboxamide (86)
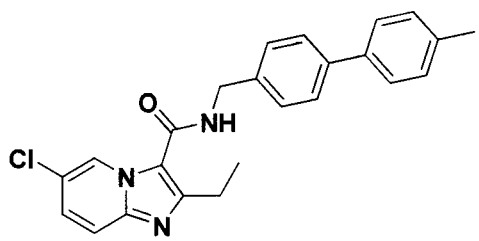
7-Chloro-N-(4-chlorobenzyl)-2-ethylimidazo[1,2-a]pyridine-3-carboxamide (87)
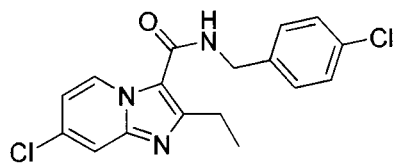
N-(4-tert-Butylbenzyl)-7-chloro-2-ethylimidazo[1,2-a]pyridine-3-carboxamide (92)
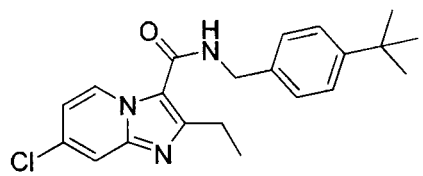
N-(Biphenyl-4-ylmethyl)-7-chloro-2-ethylimidazo[1,2-a]pyridine-3-carboxamide (93)
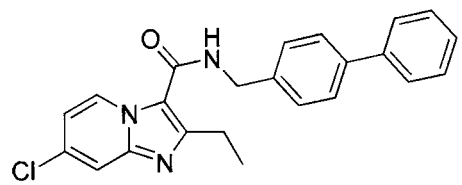
7-Chloro-N-((2'-chlorobiphenyl-4-yl)methyl)-2-ethylimidazo[1,2-a]pyridine-3-carboxamide (94)
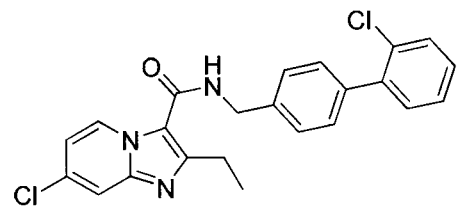

7-Chloro-N-((4'-chlorobiphenyl-4-yl)methyl)-2-ethylimidazo[1,2-a]pyridine-3-carboxamide (95)
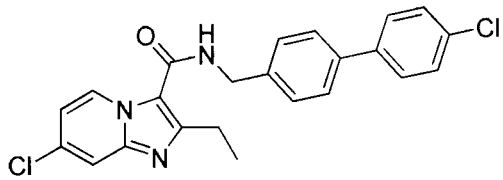
7-Chloro-2-ethyl-N-((2'-methylbiphenyl-4-yl)methyl)imidazo[1,2-a]pyridine-3-carboxamide (96)
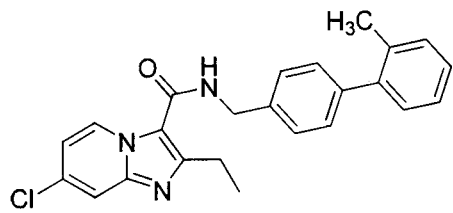
7-Chloro-2-ethyl-N-((3'-methylbiphenyl-4-yl)methyl)imidazo[1,2-a]pyridine-3-carboxamide (97)
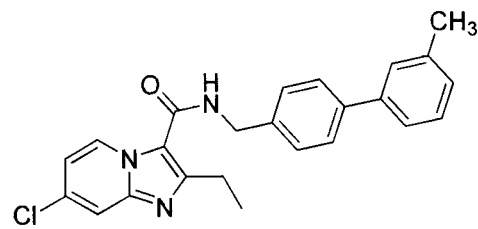
7-Chloro-2-ethyl-N-((4'-methylbiphenyl-4-yl)methyl)imidazo[1,2-a]pyridine-3-carboxamide (98)
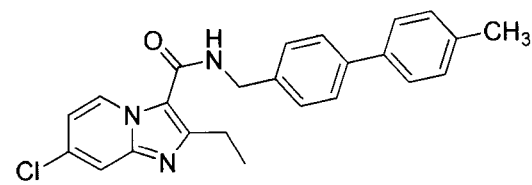

N-(Biphenyl-4-ylmethyl)-6-chloro-2-(trifluoromethyl)imidazo[1,2-a]pyridine-3-carboxamide (99)

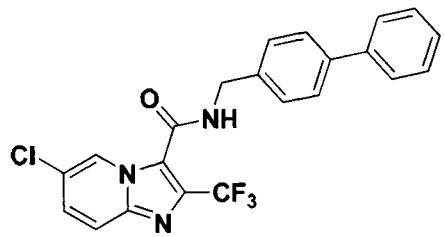

N-(4-tert-Butylbenzyl)-6-chloro-2-(trifluoromethyl)imidazo[1,2-a]pyridine-3-carboxamide (100)

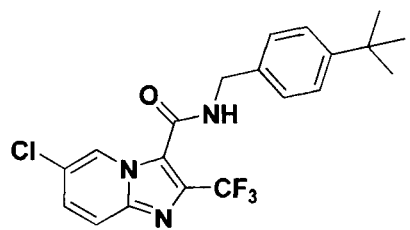

N-(4-Bromobenzyl)-7-chloro-2-ethylimidazo[1,2-a]pyridine-3-carboxamide (101)

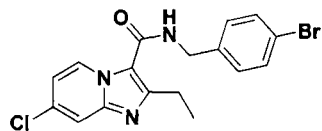

7-Chloro-2-ethyl-N-(4-(trifluoromethoxy)benzyl)imidazo[1,2-a]pyridine-3-carboxamide (102)

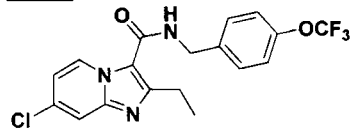

2-Ethyl-6-fluoro-N-(4-(trifluoromethoxy)benzyl)imidazo[1,2-a]pyridine-3-carboxamide (103)

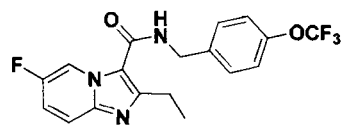

7-Chloro-2-ethyl-N-(4-(propylamino)benzyl)imidazo[1,2-a]pyridine-3-carboxamide (106)
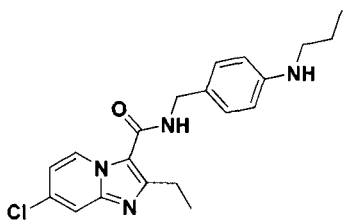
7-Chloro-2-ethyl-N-(4-(pentylamino)benzyl)imidazo[1,2-a]pyridine-3-carboxamide (107)
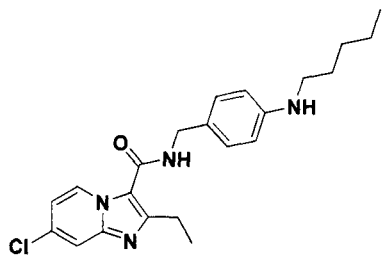
7-Chloro-2-ethyl-N-(4-(4-isopropylpiperazin-1-yl)benzyl)imidazo[1,2-a]pyridine-3-carboxamide (110)
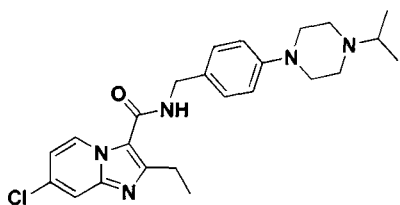
7-Chloro-2-ethyl-N-(4-(4-phenylpiperazin-1-yl)benzyl)imidazo[1,2-a]pyridine-3-carboxamide (111)
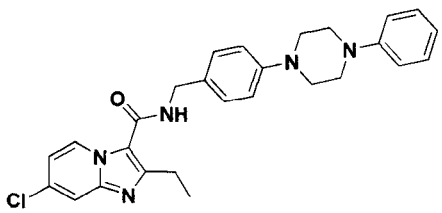

6-Chloro-2-ethyl-N-(4-(4-(4-fluorophenyl)piperazin-1-yl)benzyl)imidazo[1,2-a]pyridine-3-carboxamide (113)

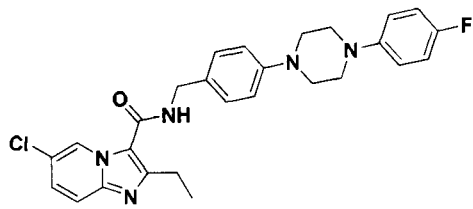

7-Chloro-2-ethyl-N-((4'-fluorobiphenyl-4-yl)methyl)imidazo[1,2-a]pyridine-3-carboxamide (116)

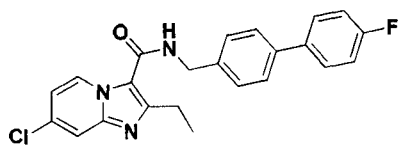

N-((4'-tert-Butylbiphenyl-4-yl)methyl)-7-chloro-2-ethylimidazo[1,2-a]pyridine-3-carboxamide (117)

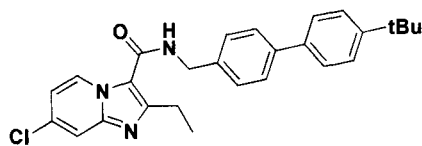

7-Chloro-2-ethyl-N-((4'-methoxybiphenyl-4-yl)methyl)imidazo[1,2-a]pyridine-3-carboxamide (118)

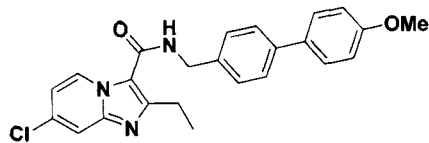

7-Chloro-2-ethyl-N-((4'-(trifluoromethoxy)biphenyl-4-yl)methyl)imidazo[1,2-a]pyridine-3-carboxamide (119)

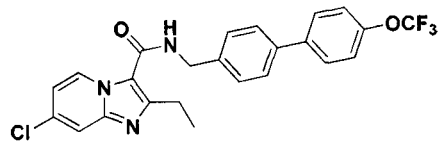

7-Chloro-2-ethyl-N-((4'-(trifluoromethyl)biphenyl-4-yl)methyl)imidazo[1,2-a]pyridine-3-carboxamide (120)

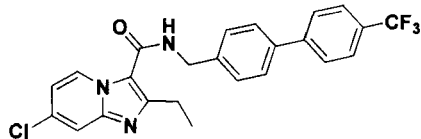

6-Chloro-N-((4'-cyanobiphenyl-4-yl)methyl)-2-ethylimidazo[1,2-a]pyridine-3-carboxamide (121)

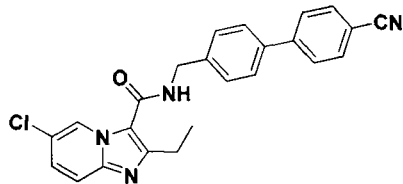

7-Chloro-N-((4'-cyanobiphenyl-4-yl)methyl)-2-ethylimidazo[1,2-a]pyridine-3-carboxamide (122)

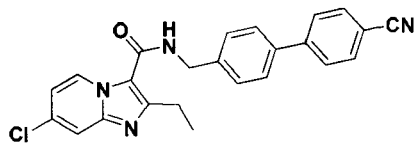

6-Chloro-2-ethyl-N-((2'-(trifluoromethyl)biphenyl-4-yl)methyl)imidazo[1,2-a]pyridine-3-carboxamide (123)

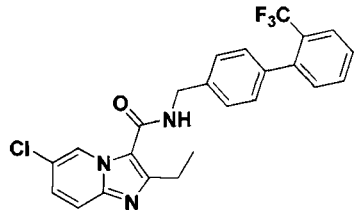

7-Chloro-2-ethyl-N-((2'-(trifluoromethyl)biphenyl-4-yl)methyl)imidazo[1,2-a]pyridine-3-carboxamide (124)

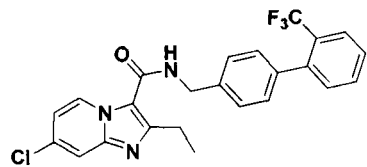

6-Chloro-N-((2'-cyanobiphenyl-4-yl)methyl)-2-ethylimidazo[1,2-a]pyridine-3-carboxamide (125)
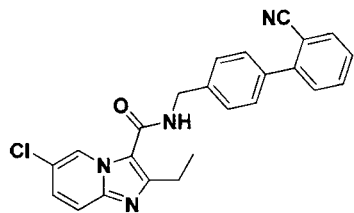
7-Chloro-N-((2'-cyanobiphenyl-4-yl)methyl)-2-ethylimidazo[1,2-a]pyridine-3-carboxamide (126)
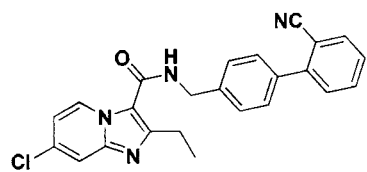
6-Chloro-N-((3'-cyanobiphenyl-4-yl)methyl)-2-ethylimidazo[1,2-a]pyridine-3-carboxamide (127)
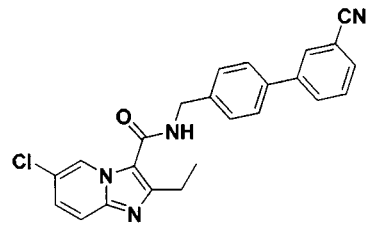
7-Chloro-N-((3'-cyanobiphenyl-4-yl)methyl)-2-ethylimidazo[1,2-a]pyridine-3-carboxamide (128)
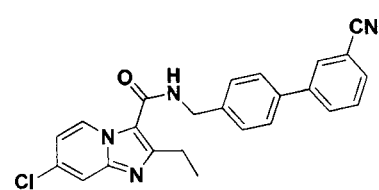

6-Chloro-N-((4'-chloro-2'-(trifluoromethyl)biphenyl-4-yl)methyl)-2-ethylimidazo[1,2-a]pyridine-3-carboxamide (129)

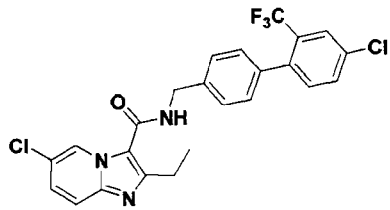

7-Chloro-N-((4'-chloro-2'-(trifluoromethyl)biphenyl-4-yl)methyl)-2-ethylimidazo[1,2-a]pyridine-3-carboxamide (130)

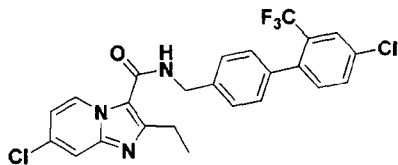

6-Chloro-N-((4'-cyano-2'-methylbiphenyl-4-yl)methyl)-2-ethylimidazo[1,2-a]pyridine-3-carboxamide (131)

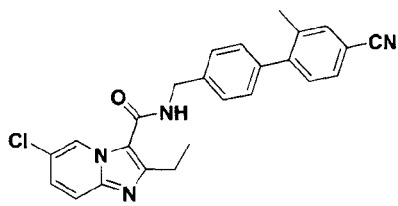

7-Chloro-N-((4'-cyano-2'-methylbiphenyl-4-yl)methyl)-2-ethylimidazo[1,2-a]pyridine-3-carboxamide (132)

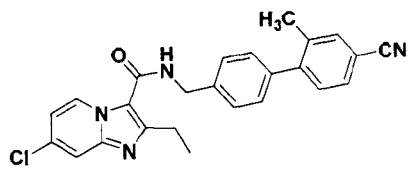

7-Chloro-N-((2'-chloro-4'-fluorobiphenyl-4-yl)methyl)-2-ethylimidazo[1,2-a]pyridine-3-carboxamide (133)

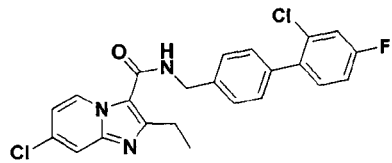

7-Chloro-2-ethyl-N-(4-(pyridin-4-yl)benzyl)imidazo[1,2-a]pyridine-3-carboxamide (134)

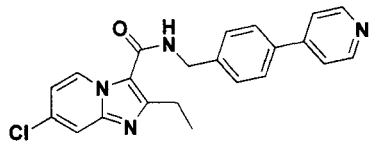

7-Chloro-2-ethyl-N-(4-(5-methoxypyridin-2-yl)benzyl)imidazo[1,2-a]pyridine-3-carboxamide (135)

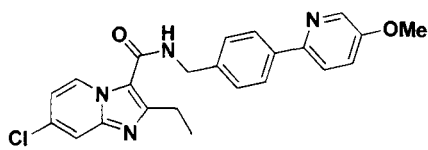

7-Chloro-2-ethyl-N-(4-(furan-2-yl)benzyl)imidazo[1,2-a]pyridine-3-carboxamide (137)

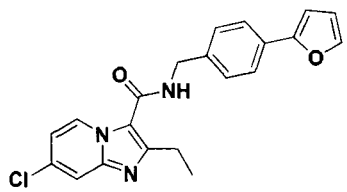

N-(4-(1H-Pyrrol-1-yl)benzyl)-7-chloro-2-ethylimidazo[1,2-a]pyridine-3-carboxamide (138)

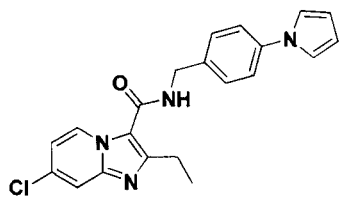

6-Chloro-2-ethyl-N-(4-(4-(4-(trifluoromethoxy)phenoxy)piperidin-1-yl)benzyl)imidazo-[1,2-a]pyridine-3-carboxamide (139)

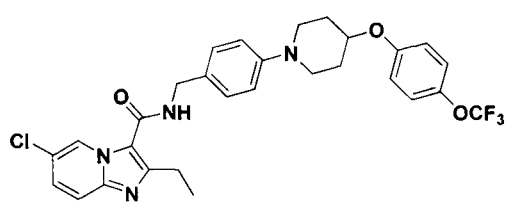

7-Chloro-2-ethyl-N-(4-(4-(4-(trifluoromethoxy)phenoxy)piperidin-1-yl)benzyl)imidazo-[1,2-a]pyridine-3-carboxamide (140)

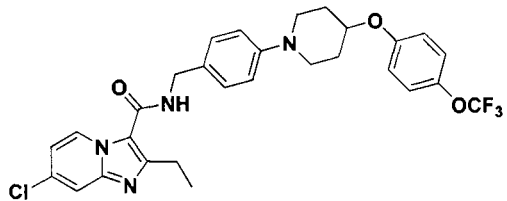

N-((4'-Chlorobiphenyl-4-yl)methyl)-2-ethylimidazo[1,2-a]pyrazine-3-carboxamide (141)

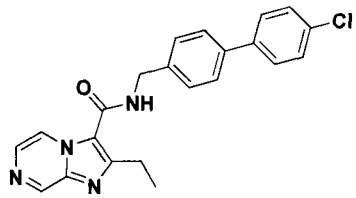

N-(4-(4-(4-(Butyramidomethyl)phenyl)piperazin-1-yl)benzyl)-7-chloro-2-ethylimidazo-[1,2-a]pyridine-3-carboxamide (144)

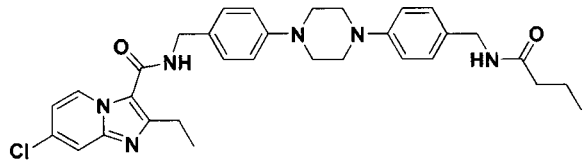

6-Chloro-2-ethyl-N-(4-(trifluoromethyl)benzyl)imidazo[1,2-a]pyridine-3-carboxamide (147)

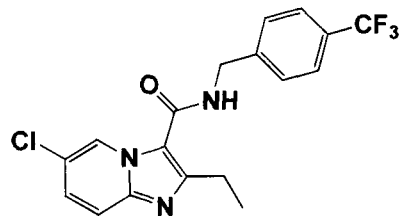

7-Chloro-2-ethyl-N-(4-(trifluoromethyl)benzyl)imidazo[1,2-a]pyridine-3-carboxamide (148)

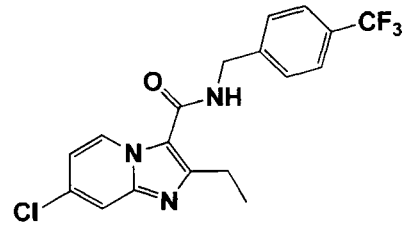

6-Bromo-2-ethyl-N-(4-(trifluoromethoxy)benzyl)imidazo[1,2-a]pyridine-3-carboxamide (152)
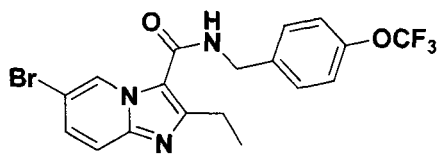
6-Chloro-2-methyl-N-(4-(trifluoromethoxy)benzyl)imidazo[1,2-a]pyridine-3-carboxamide (154)
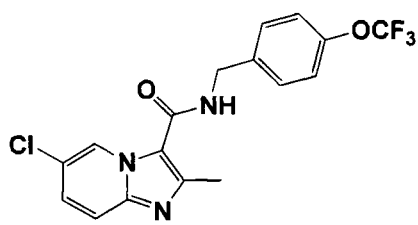
6-Chloro-2-ethyl-N-(4-methoxyphenethyl)imidazo[1,2-a]pyridine-3-carboxamide (157)
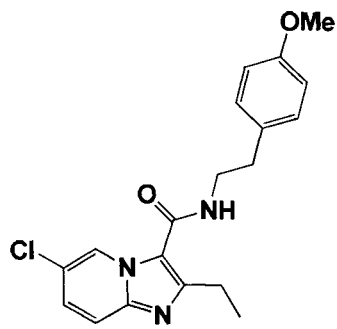
6-Chloro-N-(4-chlorophenethyl)-2-ethylimidazo[1,2-a]pyridine-3-carboxamide (158)
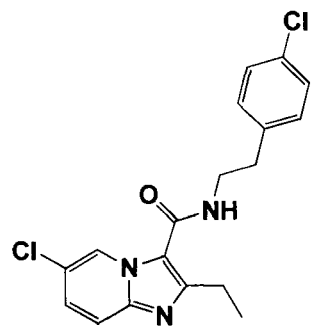

N-((4'-(Butyramidomethyl)biphenyl-4-yl)methyl)-7-chloro-2-ethylimidazo[1,2-a]pyridine-3-carboxamide (159)
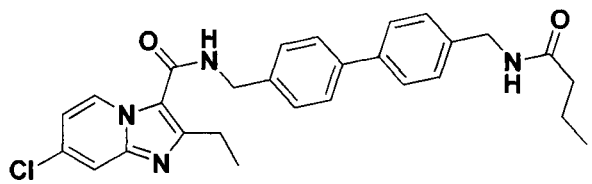
6-Chloro-N-(4-(4-(4-chlorophenoxy)piperidin-1-yl)benzyl)-2-ethylimidazo[1,2-a] pyridine-3-carboxamide (162)
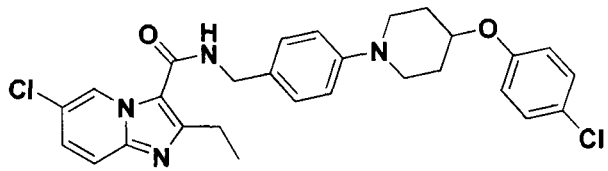
7-Chloro-N-(4-(4-(4-chlorophenoxy)piperidin-1-yl)benzyl)-2-ethylimidazo[1,2-a] pyridine-3-carboxamide (163)
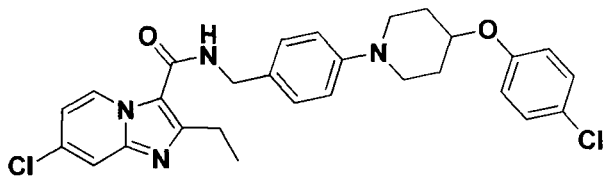
6-Chloro-2-ethyl-N-(4-(4-(4-(trifluoromethyl)phenoxy)piperidin-1-yl)benzyl) imidazo[1,2-a]pyridine-3-carboxamide (164)
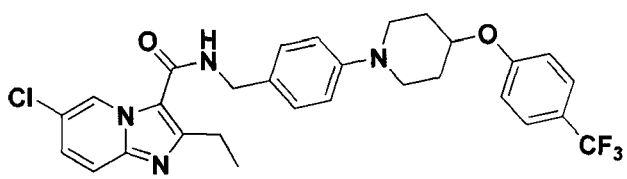

7-Chloro-2-ethyl-N-(4-(4-(4-(trifluoromethyl)phenoxy)piperidin-1-yl)benzyl) imidazo[1,2-a]pyridine-3-carboxamide (165)
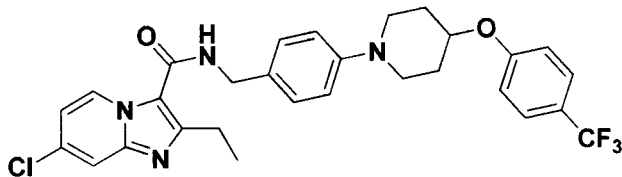
6-Chloro-2-ethyl-N-(4-(4-(4-fluorophenoxy)piperidin-1-yl)benzyl)imidazo[1,2-a] pyridine-3-carboxamide (166)
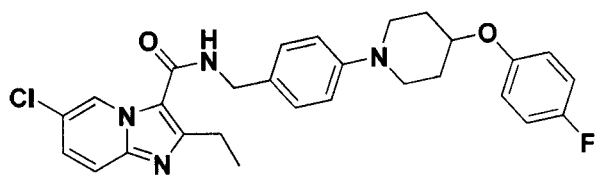
7-Chloro-2-ethyl-N-(4-(4-(4-fluorophenoxy)piperidin-1-yl)benzyl)imidazo[1,2-a]pyridine-3-carboxamide (167)
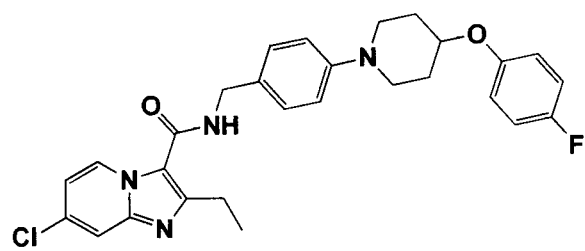
6-Chloro-2-ethyl-N-(4-(4-(4-fluorobenzyl)piperazin-1-yl)benzyl)imidazo[1,2-a]pyridine-3-carboxamide (171)
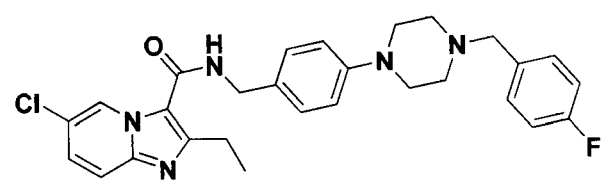

7-Chloro-2-ethyl-N-(4-(4-(4-fluorobenzyl)piperazin-1-yl)benzyl)imidazo[1,2-a]pyridine-3-carboxamide (172)
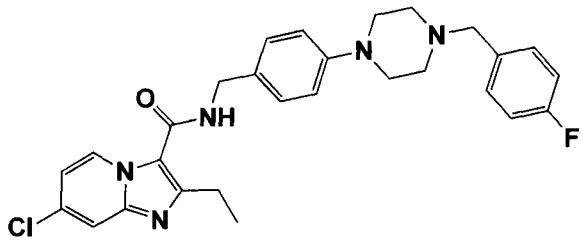
6-Chloro-2-ethyl-N-(4-(4-(4-(trifluoromethoxy)benzyl)piperazin-1-yl)benzyl)imidazo[1,2-a]pyridine-3-carboxamide (173)
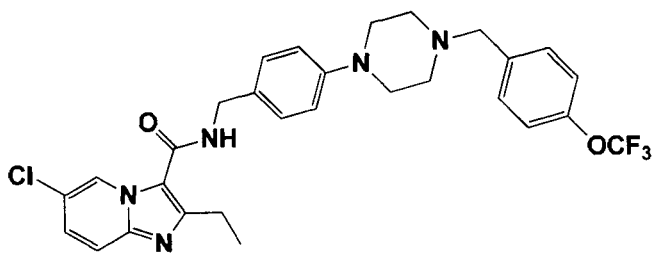
7-Chloro-2-ethyl-N-(4-(4-(4-(trifluoromethoxy)benzyl)piperazin-1-yl)benzyl)imidazo[1,2-a]pyridine-3-carboxamide (174)
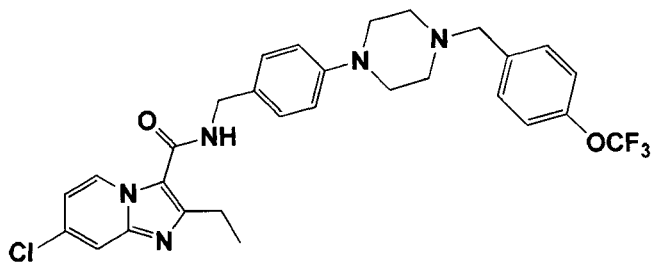
6,7-Dichloro-2-ethyl-N-(4-(4-(4-fluorobenzyl)piperazin-1-yl)benzyl)imidazo[1,2-a] pyridine-3-carboxamide (175)
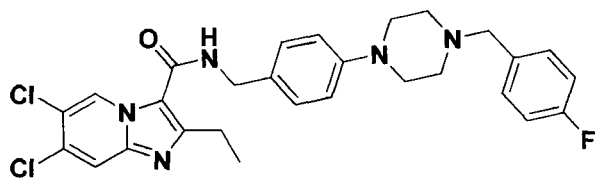

7-Chloro-2-ethyl-N-(4-(4-(4-fluorophenyl)piperazin-1-yl)benzyl)imidazo[1,2-a]pyridine-3-carboxamide (176)
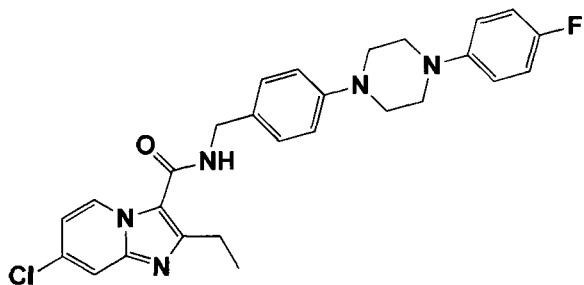
7-Chloro-2-ethyl-N-(4-(4-(4-fluorophenyl)piperazin-1-yl)benzyl)imidazo[1,2-a]pyridine-3-carboxamide trihydrochloride (177)
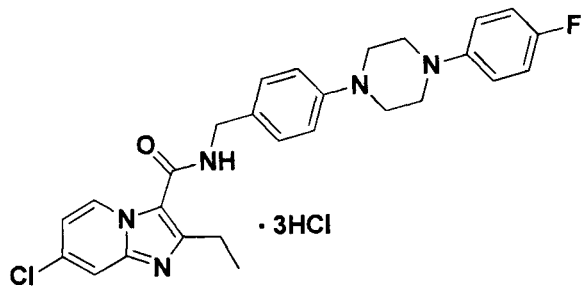
6-Chloro-2-ethyl-N-(4-(4-(4-(trifluoromethoxy)phenyl)piperazin-1-yl)benzyl)imidazo[1,2-a]pyridine-3-carboxamide (178)
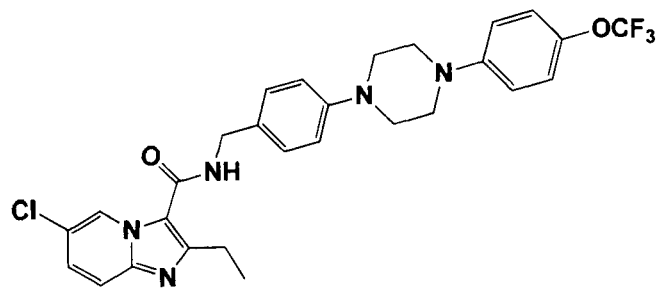

7-Chloro-2-ethyl-N-(4-(4-(4-(trifluoromethoxy)phenyl)piperazin-1-yl)benzyl)imidazo[1,2-a]pyridine-3-carboxamide (179)
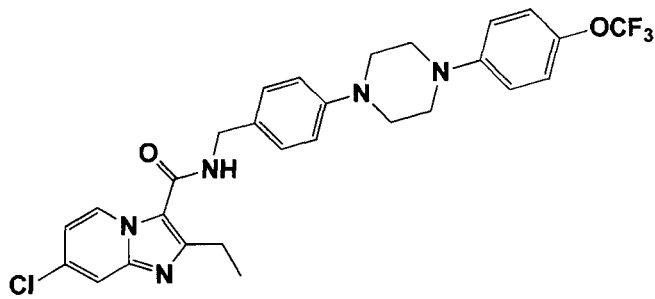
6,7-Dichloro-2-ethyl-N-(4-(4-(4-fluorophenyl)piperazin-1-yl)benzyl)imidazo[1,2-a]pyridine-3-carboxamide (180)
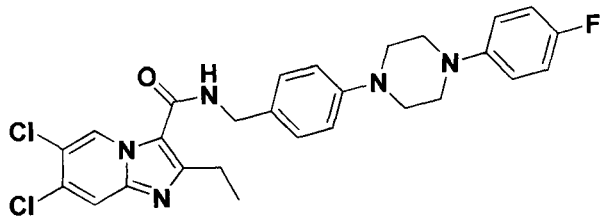
2-Ethyl-N-(4-(4-(4-(trifluoromethoxy)phenyl)piperazin-1-yl)benzyl)imidazo[1,2-a]pyridine-3-carboxamide (181)
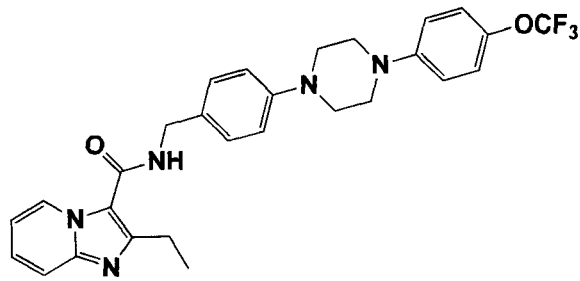
6-Chloro-2-ethyl-N-(4-(4-(4-fluorophenyl)piperazin-1-yl)benzyl)-N-methylimidazo[1,2-a]pyridine-3-carboxamide (182)
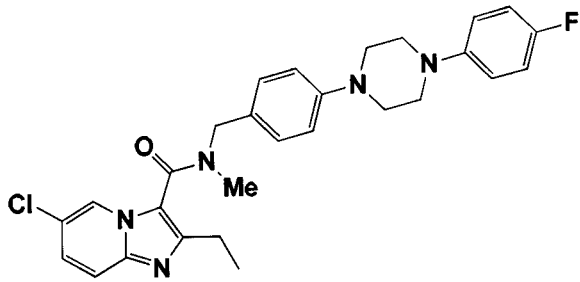

7-Chloro-2-ethyl-*N*-((4'-(hexanamidomethyl)biphenyl-4-yl)methyl)imidazo[1,2-a]pyridine-3-carboxamide (184)
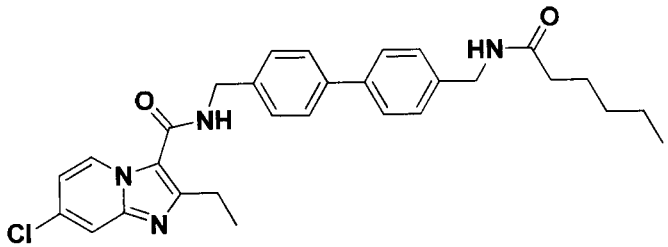
6-Chloro-2-ethyl-N-(4-(4-(trifluoromethoxy)phenoxy)benzyl)imidazo[1,2-a]pyridine-3-carboxamide (185)
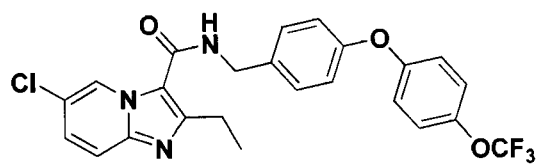
7-Chloro-2-ethyl-N-(4-(4-(trifluoromethoxy)phenoxy)benzyl)imidazo[1,2-a]pyridine-3-carboxamide (186)
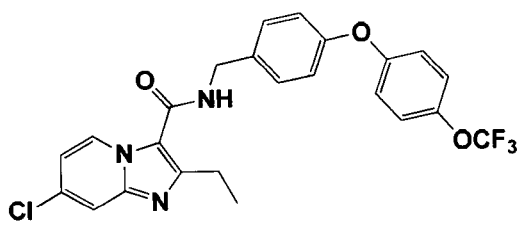
6-Chloro-2-ethyl-N-(4-(4-fluorophenoxy)benzyl)imidazo[1,2-a]pyridine-3-carboxamide (187)
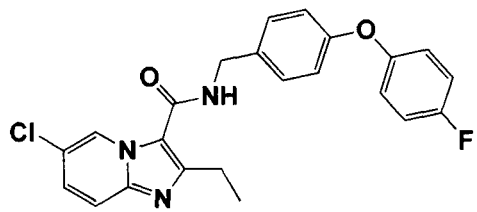

7-Chloro-2-ethyl-N-(4-(4-fluorophenoxy)benzyl)imidazo[1,2-a]pyridine-3-carboxamide (188)
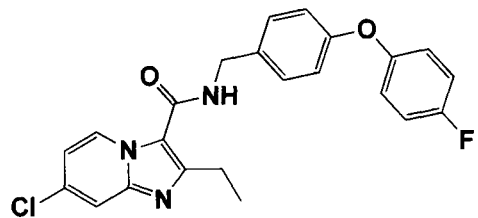
6-Bromo-2-ethyl-N-(4-(4-fluorophenoxy)benzyl)imidazo[1,2-a]pyridine-3-carboxamide (189)
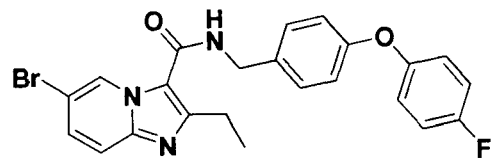
6-Chloro-N-(4-(4-chlorophenoxy)benzyl)-2-ethylimidazo[1,2-a]pyridine-3-carboxamide (190)
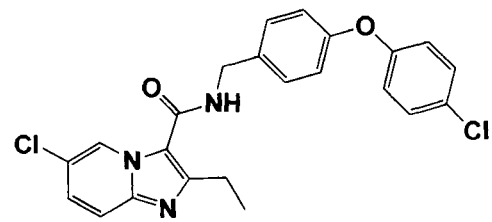
7-Chloro-N-(4-(4-chlorophenoxy)benzyl)-2-ethylimidazo[1,2-a]pyridine-3-carboxamide (191)
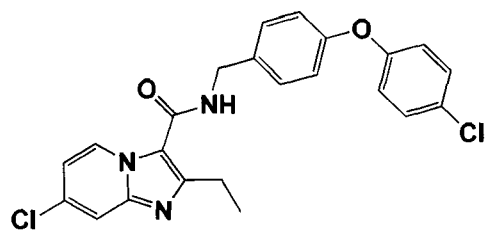

2-Ethyl-N-(4-(4-(trifluoromethoxy)phenoxy)benzyl)imidazo[1,2-a]pyridine-3-carboxamide (192)
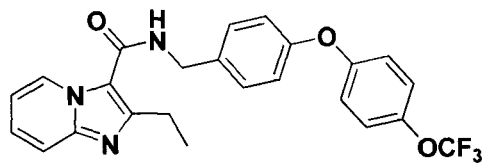
7-Chloro-2-ethyl-N-((6-(4-fluorophenoxy)pyridin-3-yl)methyl)imidazo[1,2-a]pyridine-3-carboxamide (193)
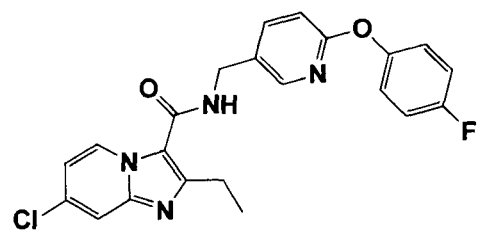
6-Chloro-2-ethyl-N-(4-(4-(trifluoromethoxy)phenylamino)benzyl)imidazo[1,2-a] pyridine-3-carboxamide (198)
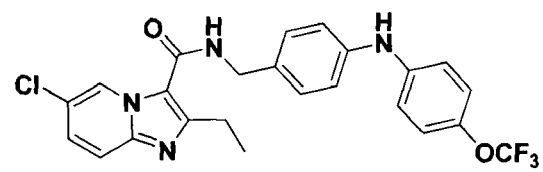
7-Chloro-2-ethyl-N-(4-(4-(trifluoromethoxy)phenylamino)benzyl)imidazo[1,2-a] pyridine-3-carboxamide (199)
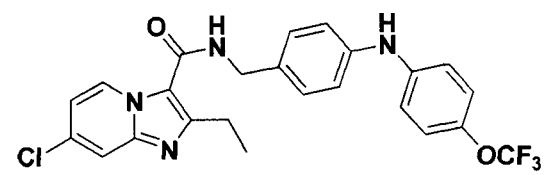

6-Chloro-2-ethyl-N-(4-(4-(trifluoromethyl)benzyloxy)benzyl)imidazo[1,2-a]pyridine-3-carboxamide (200)
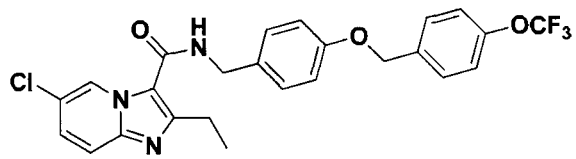
7-Chloro-2-ethyl-N-(4-(4-(trifluoromethyl)benzyloxy)benzyl)imidazo[1,2-a]pyridine-3-carboxamide (201)
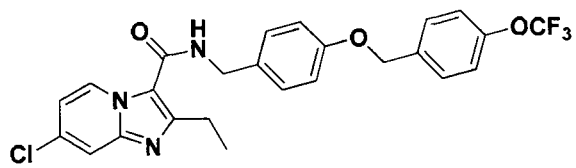
6-Chloro-2-ethyl-N-(4-(4-fluorobenzyloxy)benzyl)imidazo[1,2-a]pyridine-3-carboxamide (202)
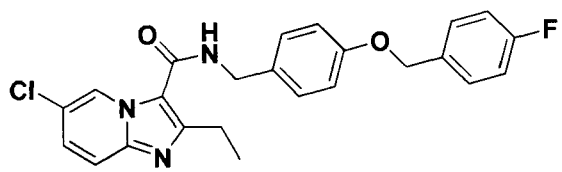
6-Chloro-N-(4-(2,6-dimethylmorpholino)benzyl)-2-ethylimidazo[1,2-a]pyridine-3-carboxamide (209)
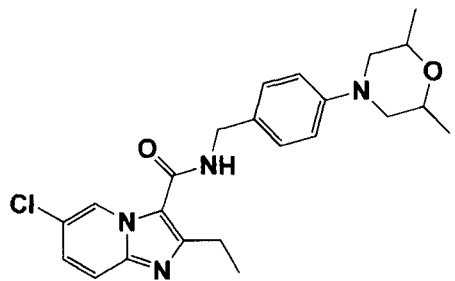

7-Chloro-N-(4-(2,6-dimethylmorpholino)benzyl)-2-ethylimidazo[1,2-a]pyridine-3-carboxamide (210)
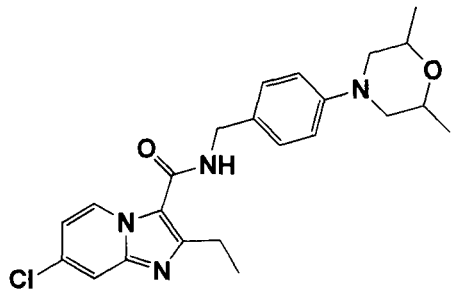
6-Chloro-2-ethyl-N-(4-(4-methylpiperidin-1-yl)benzyl)imidazo[1,2-a]pyridine-3-carboxamide (214)
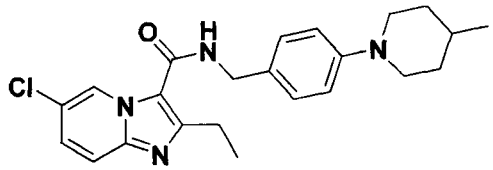
7-Chloro-2-ethyl-N-(4-(4-methylpiperidin-1-yl)benzyl)imidazo[1,2-a]pyridine-3-carboxamide (215)
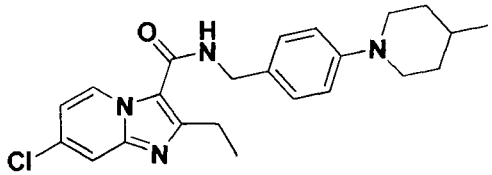
6-Chloro-*N*-(4-(3,5-dimethylpiperidin-1-yl)benzyl)-2-ethylimidazo[1,2-a]pyridine-3-carboxamide (216)
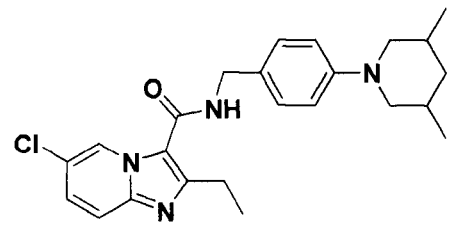

7-Chloro-*N*-(4-(3,5-dimethylpiperidin-1-yl)benzyl)-2-ethylimidazo[1,2-a]pyridine-3-carboxamide (217)
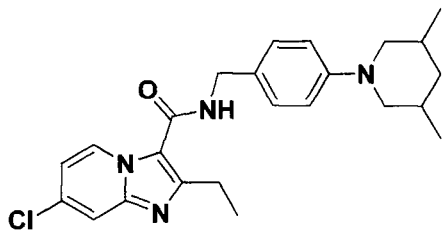
7-Chloro-2-ethyl-*N*-(4-(4-hydroxypiperidin-1-yl)benzyl)imidazo[1,2-a]pyridine-3-carboxamide (218)
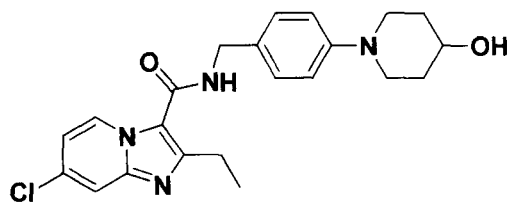
7-Chloro-N-(4-(3a,4-dihydro-1H-isoindol-2(3H,7H,7aH)-yl)benzyl)-2-ethylimidazo[1,2-a]pyridine-3-carboxamide (223)
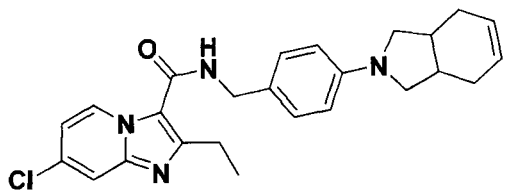
N-(4-(1H-isoindol-2(3H,3aH,4H,5H,6H,7H,7aH)-yl)benzyl)-7-chloro-2-ethylimidazo[1,2-a]pyridine-3-carboxamide (224)
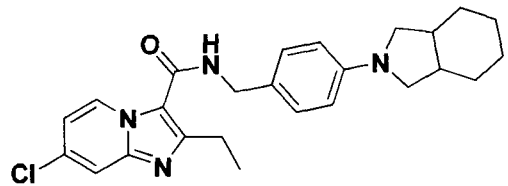

7-Chloro-2-ethyl-N-(4-(4,5,6,7-tetrahydro-2H-isoindol-2-yl)benzyl)imidazo[1,2-a]pyridine-3-carboxamide (225)
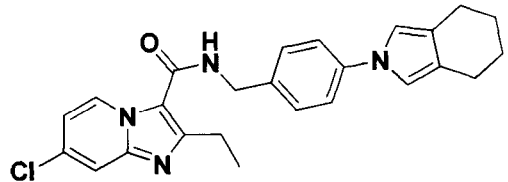
6-Chloro-2-ethyl-N-((1-(4-(trifluoromethoxy)benzyl)piperidin-4-yl)methyl)imidazo[1,2-a]pyridine-3-carboxamide (226)
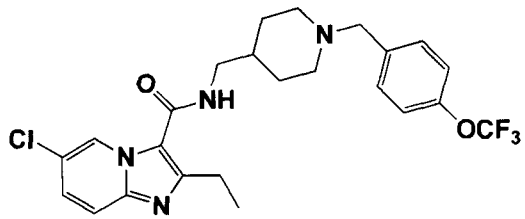
6-Chloro-2-ethyl-N-((1-(4-fluorobenzyl)piperidin-4-yl)methyl)imidazo[1,2-a]pyridine-3-carboxamide (227)
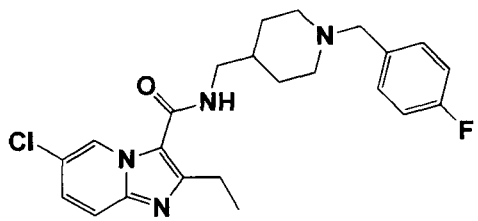
6-Chloro-2-ethyl-N-((1-(4-(trifluoromethoxy)phenyl)-1H-pyrazol-3-yl)methyl) imidazo[1,2-a]pyridine-3-carboxamide (231)
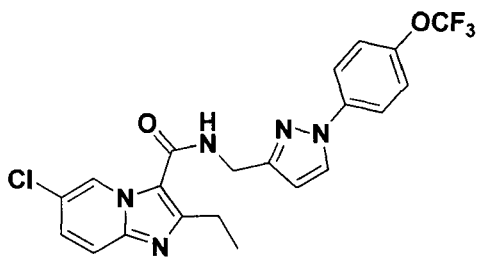

7-Chloro-2-ethyl-*N*-((4'-(trifluoromethoxy)biphenyl-3-yl)methyl)imidazo[1,2-a]pyridine-3-carboxamide (248)
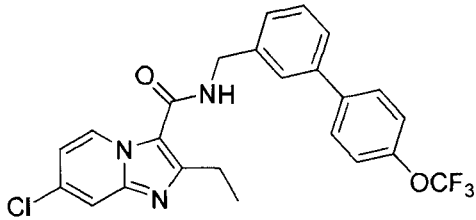
2-Ethyl-7-methyl-*N*-(4-(trifluoromethoxy)benzyl)imidazo[1,2-a]pyridine-3-carboxamide (249)
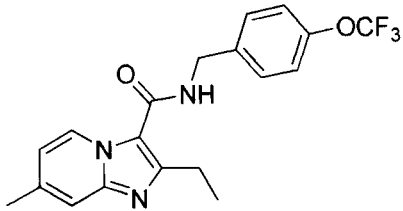
7-Bromo-2-ethyl-*N*-(4-(trifluoromethoxy)benzyl)imidazo[1,2-a]pyridine-3-carboxamide (250)
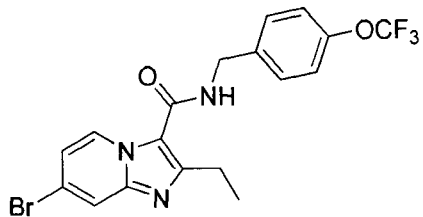
2-Ethyl-8-fluoro-*N*-(4-(trifluoromethoxy)benzyl)imidazo[1,2-a]pyridine-3-carboxamide(251)
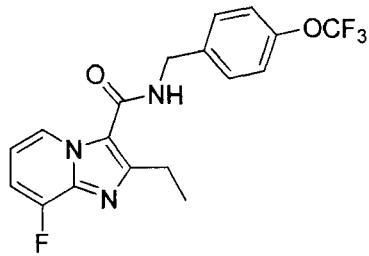

7-Chloro-2-ethyl-*N*-((4'-formylbiphenyl-4-yl)methyl)imidazo[1,2-a]pyridine-3-carboxamide(252)
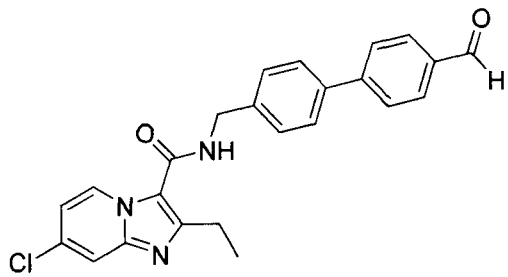
2-Ethyl-6-fluoro-N-(4-(4-(trifluoromethoxy)phenoxy)benzyl)imidazo[1,2-a]pyridine-3-carboxamide (253)
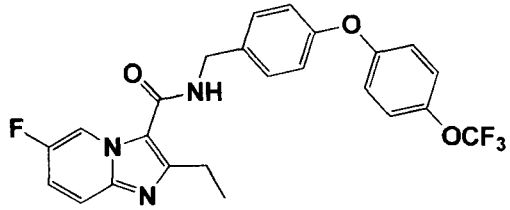
6-Bromo-2-ethyl-N-(4-(4-(trifluoromethoxy)phenoxy)benzyl)imidazo[1,2-a]pyridine-3-carboxamide (254)
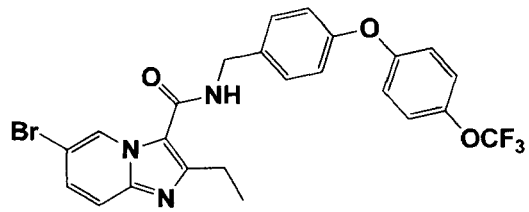
2-Ethyl-6-methyl-*N*-(4-(4-(trifluoromethoxy)phenoxy)benzyl)imidazo[1,2-a]pyridine-3-carboxamide (255)
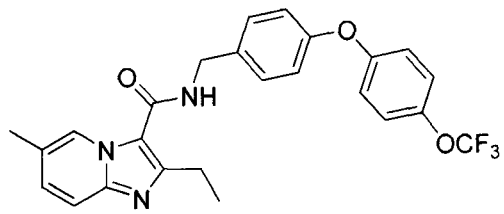

2-Ethyl-7-methyl-*N*-(4-(4-(trifluoromethoxy)phenoxy)benzyl)imidazo[1,2-a]pyridine-3-carboxamide (256)
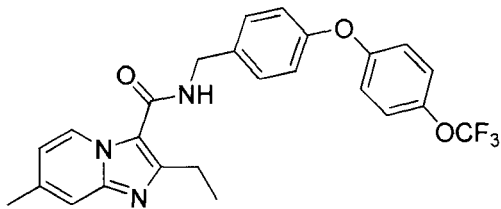
2-Ethyl-8-fluoro-*N*-(4-(4-(trifluoromethoxy)phenoxy)benzyl)imidazo[1,2-a]pyridine-3-carboxamide (257)
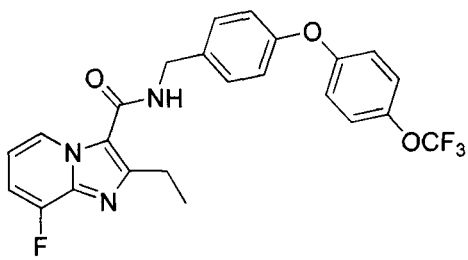
2-Ethyl-6-fluoro-*N*-(4-(4-(trifluoromethoxy)benzyloxy)benzyl)imidazo[1,2-a]pyridine-3-carboxamide (258)
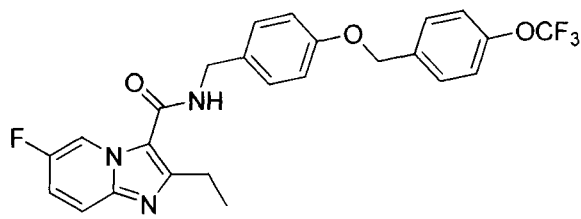
6-Bromo-2-ethyl-*N*-(4-(4-(trifluoromethoxy)benzyloxy)benzyl)imidazo[1,2-a]pyridine-3-carboxamide (259)
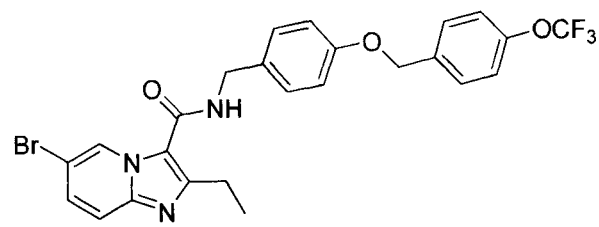

2-Ethyl-*N*-(4-(4-(trifluoromethoxy)benzyloxy)benzyl)imidazo[1,2-a]pyridine-3-carboxamide (260)
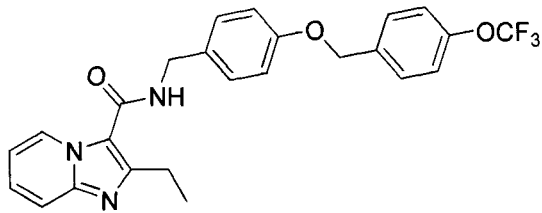
7-Chloro-2-ethyl-N-(4-((4-(trifluoromethoxy)benzyl)amino)benzyl)imidazo[1,2-a]pyridine-3-carboxamide (262)
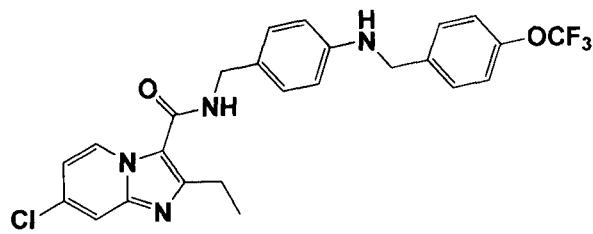
2-Ethyl-N-(4-(methyl(4-(trifluoromethoxy)benzyl)amino)benzyl)imidazo[1,2-a]pyridine-3-carboxamide (263)
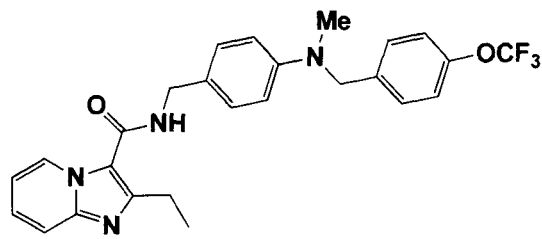
6-Chloro-2-ethyl-*N*-(4-(octahydroisoquinolin-2(1H)-yl)benzyl)imidazo[1,2-a]pyridine-3-carboxamide (267)
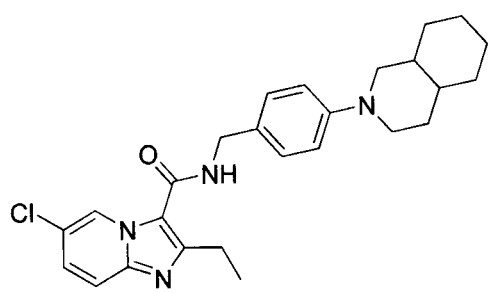

7-Chloro-2-ethyl-*N*-(4-(octahydroisoquinolin-2(1H)-yl)benzyl)imidazo[1,2-a]pyridine-3-carboxamide (268)
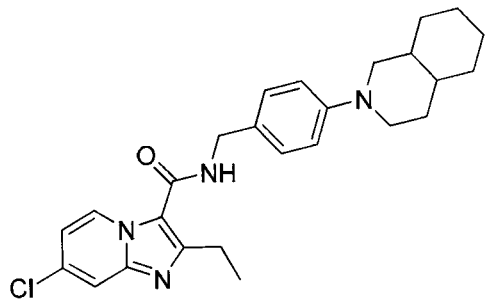
7-Chloro-2-ethyl-*N*-(4-(4-oxopiperidin-1-yl)benzyl)imidazo[1,2-a]pyridine-3-carboxamide (269)
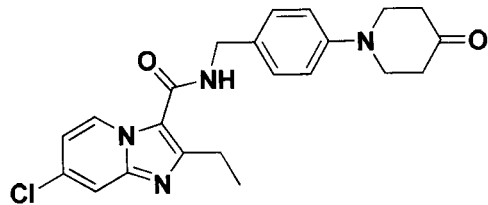
7-Chloro-2-ethyl-*N*-(4-(4-methylenepiperidin-1-yl)benzyl)imidazo[1,2-a]pyridine-3-carboxamide (271)
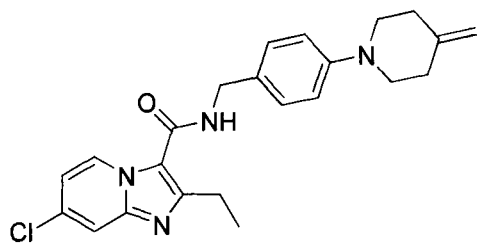
6-chloro-2-ethyl-*N*-(4-(2-methylpiperidin-1-yl)benzyl)imidazo[1,2-a]pyridine-3-carboxamide (272)
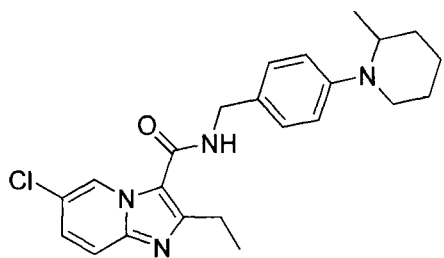

7-chloro-2-ethyl-*N*-(4-(2-methylpiperidin-1-yl)benzyl)imidazo[1,2-a]pyridine-3-carboxamide (273)
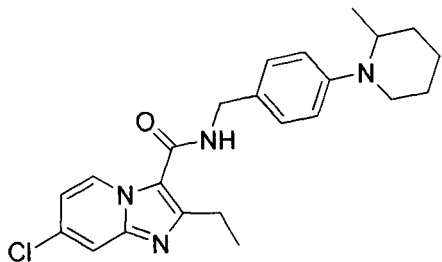
7-Chloro-*N*-(4-(4,4-dimethylpiperidin-1-yl)benzyl)-2-ethyl-1,8a-dihydroimidazo[1,2-a]pyridine-3-carboxamide (274)
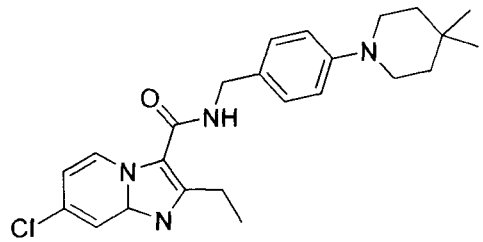
7-Chloro-2-ethyl-*N*-(4-(4-(hydroxymethyl)piperidin-1-yl)benzyl)imidazo[1,2-a]pyridine-3-carboxamide (280)
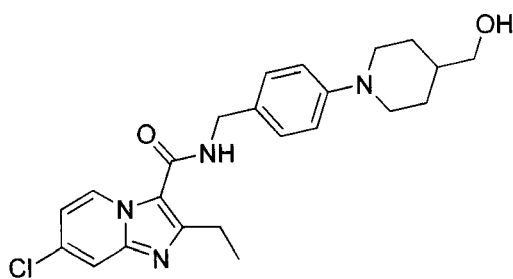
6-Chloro-2-ethyl-*N*-(4-(4-(methoxymethyl)piperidin-1-yl)benzyl)imidazo[1,2-a]pyridine-3-carboxamide (281)
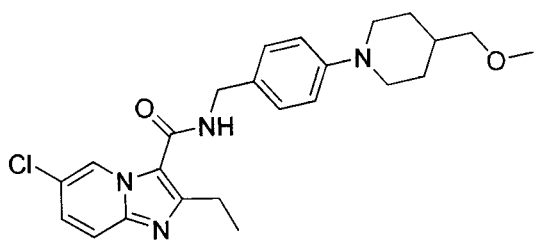

7-Chloro-2-ethyl-*N*-(4-(4-(methoxymethyl)piperidin-1-yl)benzyl)imidazo[1,2-a]pyridine-3-carboxamide (282)
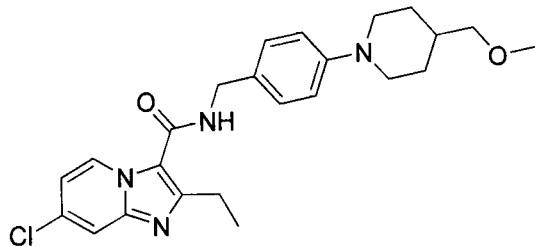
7-Chloro-2-ethyl-*N*-(4-(4-phenylpiperidin-1-yl)benzyl)imidazo[1,2-a]pyridine-3-carboxamide (283)
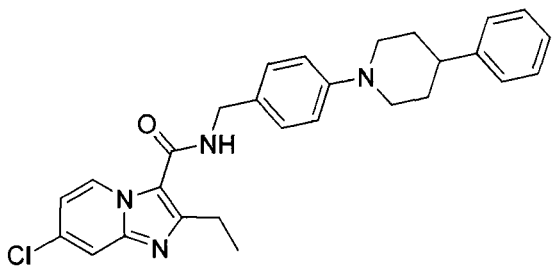
6-Chloro-2-ethyl-*N*-(4-(4-phenylpiperidin-1-yl)benzyl)imidazo[1,2-a]pyridine-3-carboxamide (284)
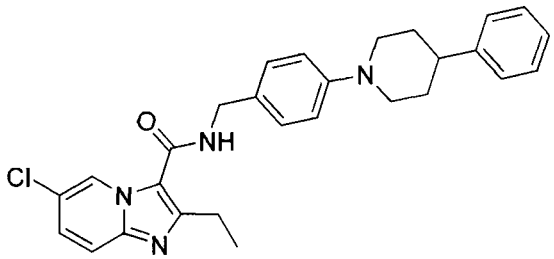
2-Ethyl-*N*-(4-(4-(4-fluorophenyl)piperidin-1-yl)benzyl)imidazo[1,2-a]pyridine-3-carboxamide(285)
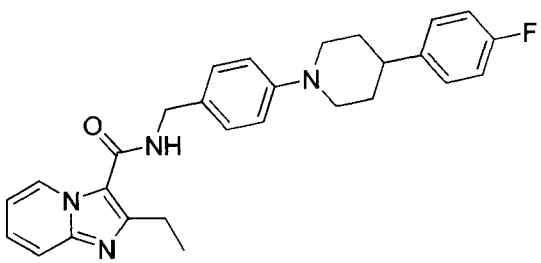

6-Chloro-2-ethyl-*N*-(4-(4-(4-fluorophenyl)piperidin-1-yl)benzyl)imidazo[1,2-a]pyridine-3-carboxamide (286)
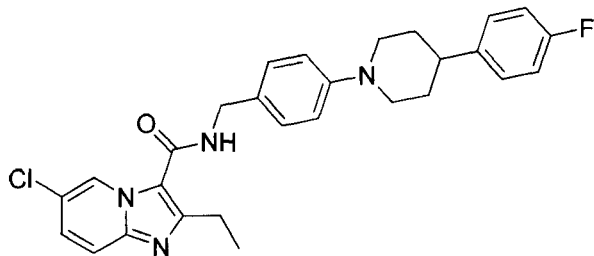
7-Chloro-2-ethyl-*N*-(4-(4-(4-fluorophenyl)piperidin-1-yl)benzyl)imidazo[1,2-a]pyridine-3-carboxamide (287)
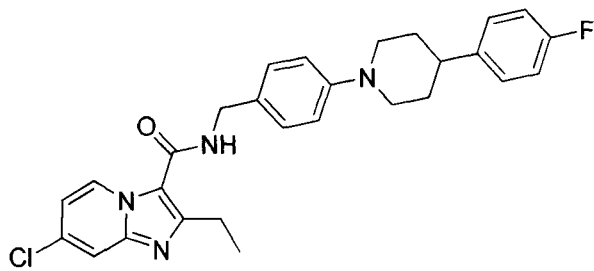
2-Ethyl-*N*-(4-(4-(4-(trifluoromethoxy)phenyl)piperidin-1-yl)benzyl)imidazo[1,2-a]pyridine-3-carboxamide(288)
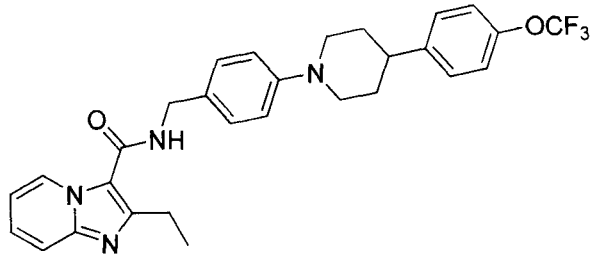

6-Chloro-2-ethyl-*N*-(4-(4-(4-(trifluoromethoxy)phenyl)piperidin-1-yl)benzyl)imidazo[1,2-a]pyridine-3-carboxamide (289)

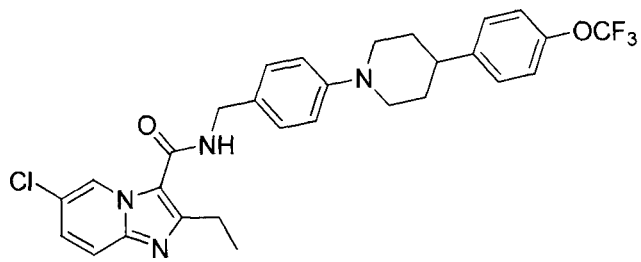

7-Chloro-2-ethyl-*N*-(4-(4-(4-(trifluoromethoxy)phenyl)piperidin-1-yl)benzyl)imidazo[1,2-a]pyridine-3-carboxamide(290)

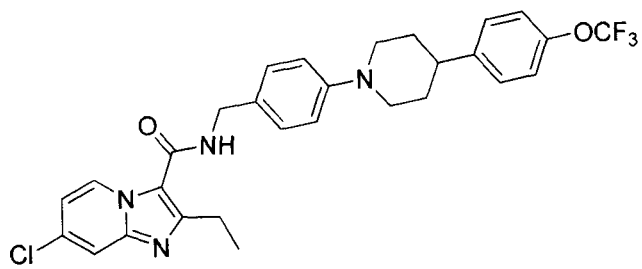

6-Chloro-2-ethyl-*N*-(4-(4-(isopropoxymethyl)piperidin-1-yl)benzyl)imidazo[1,2-a]pyridine-3-carboxamide(291)

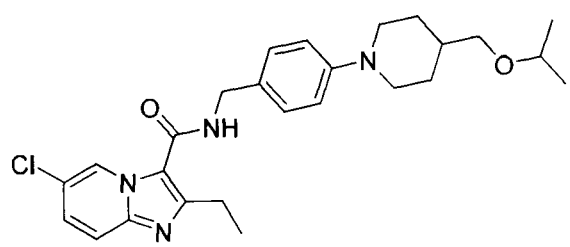

7-Chloro-2-ethyl-*N*-(4-(4-(isopropoxymethyl)piperidin-1-yl)benzyl)imidazo[1,2-a]pyridine-3-carboxamide(292)

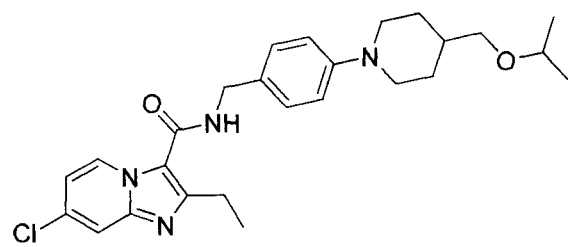

6-Chloro-*N*-(4-(4-(cyclopentyloxymethyl)piperidin-1-yl)benzyl)-2-ethylimidazo[1,2-a]pyridine-3-carboxamide(293)
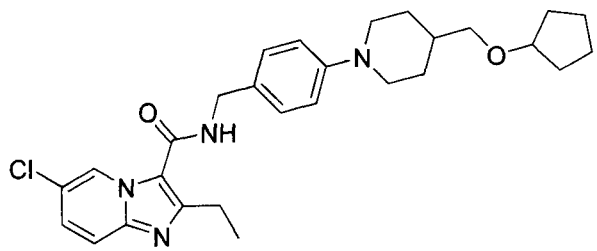
2-Ethyl-N-(4-(4-((4-fluorophenoxy)methyl)piperidin-1-yl)benzyl)imidazo[1,2-a]pyridine-3-carboxamide (295)
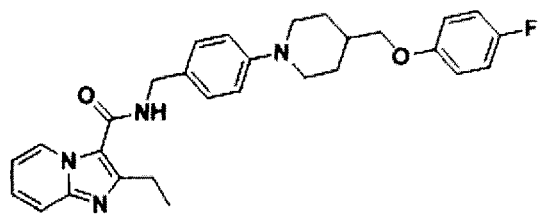
6-Chloro-2-ethyl-N-(4-(4-((4-fluorophenoxy)methyl)piperidin-1-yl)benzyl)imidazo[1,2-a]pyridine-3-carboxamide (296)
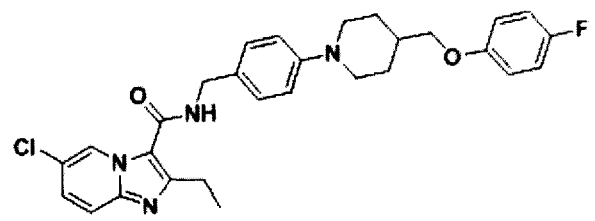
7-Chloro-2-ethyl-N-(4-(4-((4-fluorophenoxy)methyl)piperidin-1-yl)benzyl)imidazo[1,2-a]pyridine-3-carboxamide (297)
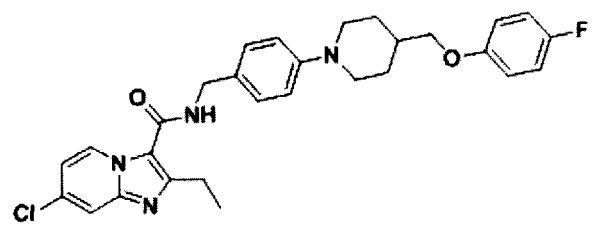

6-chloro-2-ethyl-*N*-(4-(4-((4-(trifluoromethoxy)phenoxy)methyl)piperidin-1-yl)benzyl)imidazo[1,2-a]pyridine-3-carboxamide (298)

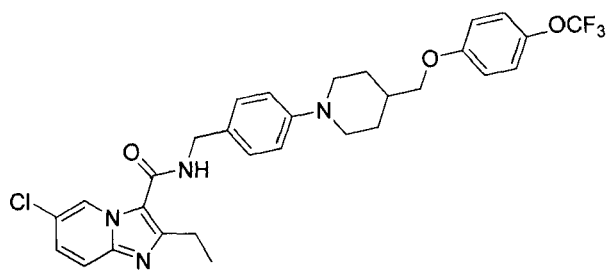

7-Chloro-2-ethyl-*N*-(4-(4-((4-(trifluoromethoxy)phenoxy)methyl)piperidin-1-yl)benzyl)imidazo[1,2-a]pyridine-3-carboxamide (299)

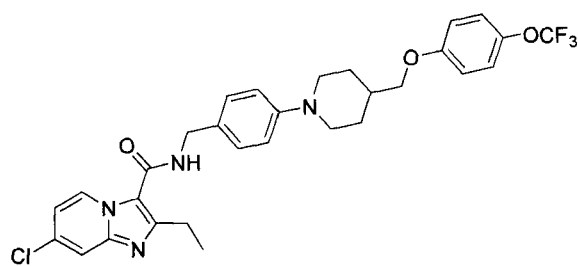

Ethyl 1-(4-((6-chloro-2-ethylimidazo[1,2-a]pyridine-3-carboxamido)methyl)phenyl)piperidine-4-carboxylate (300)

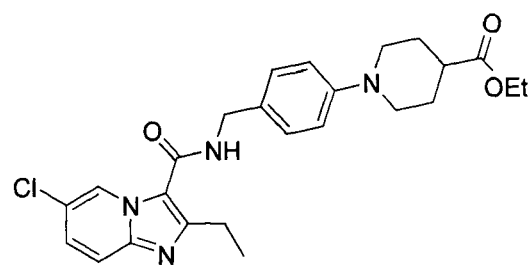

Ethyl 1-(4-((7-chloro-2-ethylimidazo[1,2-a]pyridine-3-carboxamido)methyl)phenyl)piperidine-4-carboxylate (301)

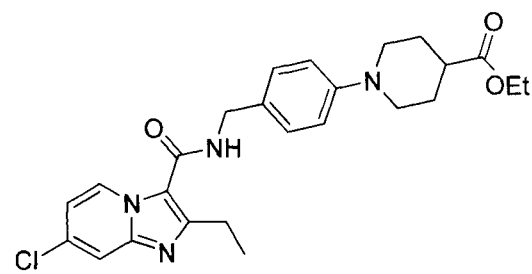

1-(4-((7-Chloro-2-ethylimidazo[1,2-a]pyridine-3-carboxamido)methyl)phenyl) piperidine-4-carboxylic acid (302)
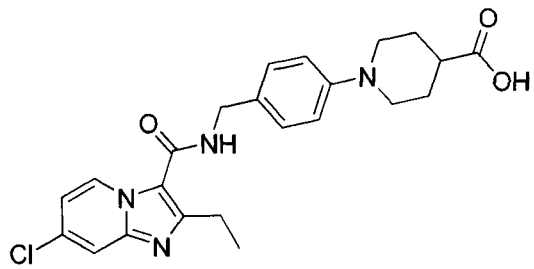
2-Ethyl-N-(4-(4-(4-fluorophenyl)piperazin-1-yl)benzyl)imidazo[1,2-a]pyridine-3-carboxamide (303)
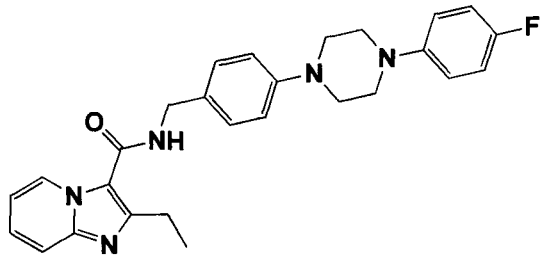
8-(Difluoromethoxy)-2-ethyl-N-(4-(4-(4-fluorophenyl)piperazin-1-yl)benzyl)imidazo[1,2-a]pyridine-3-carboxamide (304)
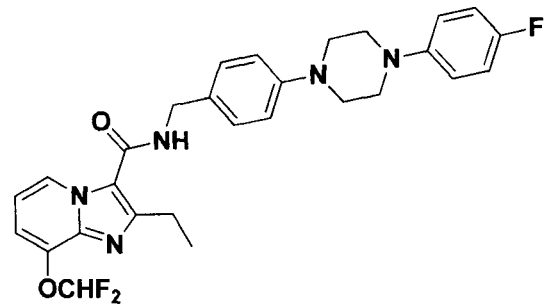
**8-Bromo-2-ethyl-*N*-(4-(4-(4-fluorophenyl)piperazin-1-yl)benzyl)imidazo[1,2-a]pyridine-3-carboxamide (305)**
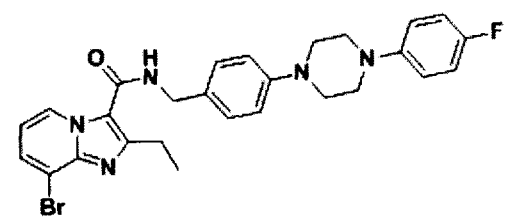

2-Ethyl-6-fluoro-N-(4-(4-(4-fluorophenyl)piperazin-1-yl)benzyl)imidazo[1,2-a]pyridine-3-carboxamide (306)
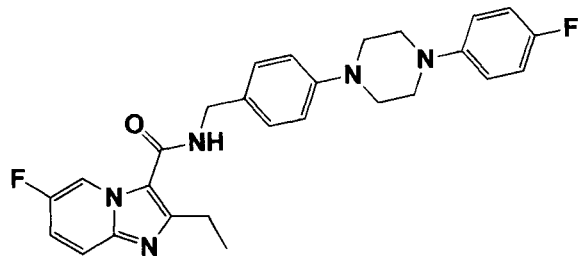
6-Bromo-2-ethyl-N-(4-(4-(4-fluorophenyl)piperazin-1-yl)benzyl)imidazo[1,2-a]pyridine-3-carboxamide (307)
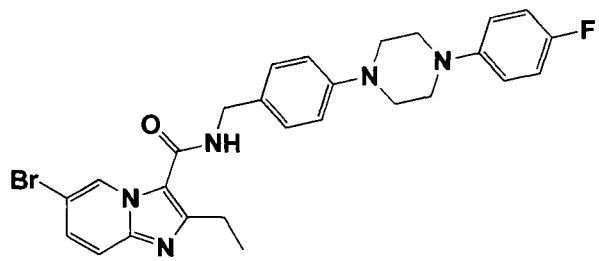
2-Ethyl-*N*-(4-(4-(4-fluorophenyl)piperazin-1-yl)benzyl)-6-methylimidazo[1,2-a]pyridine-3-carboxamide (308)
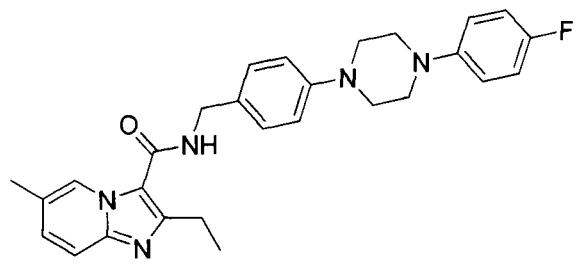
2-Ethyl-*N*-(4-(4-(4-fluorophenyl)piperazin-1-yl)benzyl)-7-methylimidazo[1,2-a]pyridine-3-carboxamide (309)
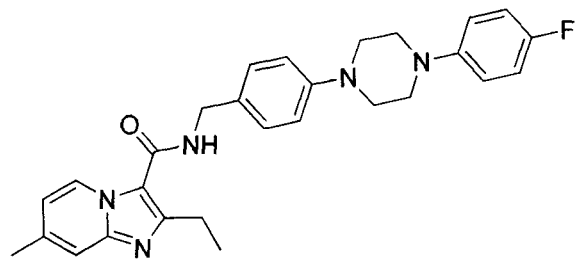

2-Ethyl-8-fluoro-*N*-(4-(4-(4-fluorophenyl)piperazin-1-yl)benzyl)imidazo[1,2-a]pyridine-3-carboxamide (310)
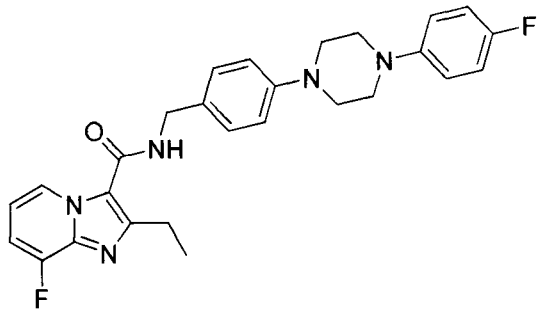
7-Bromo-2-ethyl-*N*-(4-(4-(4-fluorophenyl)piperazin-1-yl)benzyl)imidazo[1,2-a]pyridine-3-carboxamide (311)
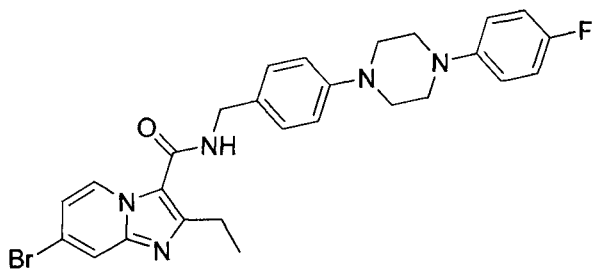
2-Ethyl-*N*-(4-(4-(4-fluorophenyl)piperazin-1-yl)benzyl)-8-(pyridin-4-yl)imidazo[1,2-a]pyridine-3-carboxamide (312)
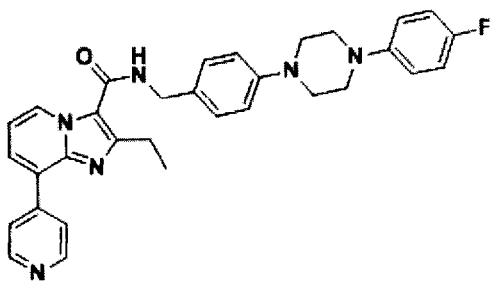

2-Ethyl-7-(4-phenylpiperazin-1-yl)-*N*-(4-(trifluoromethyl)benzyl)imidazo[1,2-a]pyridine-3-carboxamide (330)
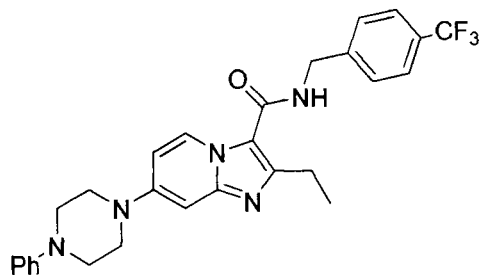
9. The compound according to claim 1, having a formula selected from formulae 5, 8, 13, 14, 17, 18, 20, 21, 23-43, 46, 48, 50, 51, 53, 59, 68, 69, 74, 79, 80, 89-91, 142, 143, 196, 211-213, 219, 221, 222, 243, 247, 313-329 and 331:
2-Methyl-N-(pyridin-4-yl)imidazo[1,2-a]pyridine-3-carboxamide (5)
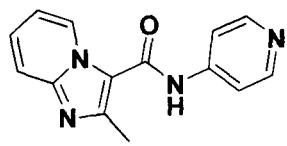
N-Benzyl-2-methylimidazo[1,2-a]pyridine-3-carboxamide (8)
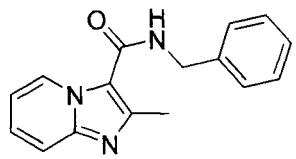
2-Methyl-N-(pyridin-3-ylmethyl)imidazo[1,2-a]pyridine-3-carboxamide (13)
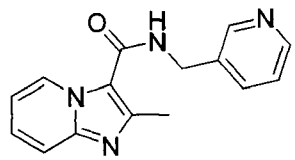

2-Methyl-N-(pyridin-4-ylmethyl)imidazo[1,2-a]pyridine-3-carboxamide (14)
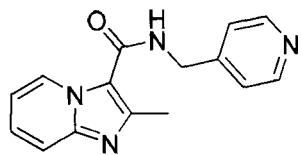
N-((1H-Indol-5-yl)methyl)-2-methylimidazo[1,2-a]pyridine-3-carboxamide (17)
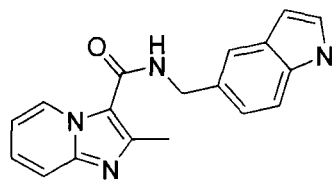
N-(Cyclohexylmethyl)-2-methylimidazo[1,2-a]pyridine-3-carboxamide (18)
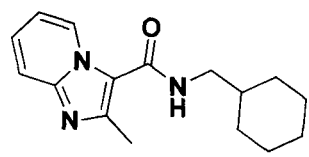
2-Methyl-N-(piperidin-4-ylmethyl)imidazo[1,2-a]pyridine-3-carboxamide (20)
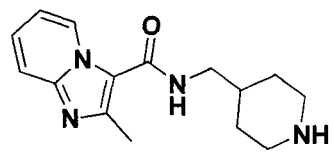
2-Methyl-N-phenethylimidazo[1,2-a]pyridine-3-carboxamide (21)
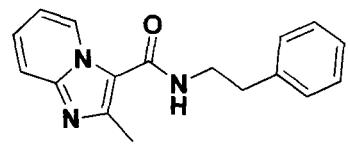
2-Methyl-N-(2-phenoxyethyl)imidazo[1,2-a]pyridine-3-carboxamide (23)
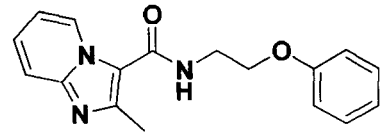

N-(2-(Benzyloxy)ethyl)-2-methylimidazo[1,2-a]pyridine-3-carboxamide (24)
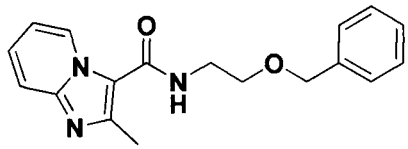
(S)-Methyl 2-(2-methylimidazo[1,2-a]pyridine-3-carboxamido)-3-phenylpropanoate (25)
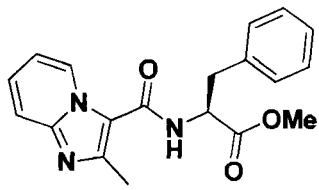
N-(2-Methylimidazo[1,2-a]pyridin-3-yl)-2-phenylacetamide (26)
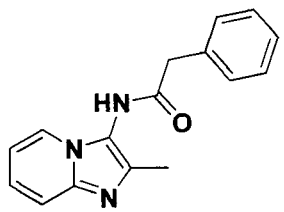
N-Benzyl-8-chloro-2-methylimidazo[1,2-a]pyridine-3-carboxamide (27)
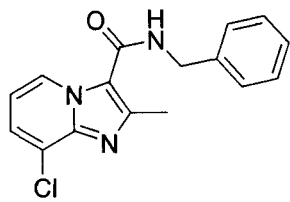
N-Benzyl-7-chloro-2-methylimidazo[1,2-a]pyridine-3-carboxamide (28)
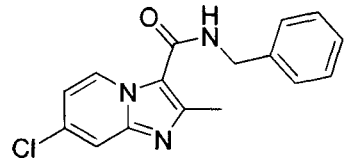

N-Benzyl-6-chloro-2-methylimidazo[1,2-a]pyridine-3-carboxamide (29)
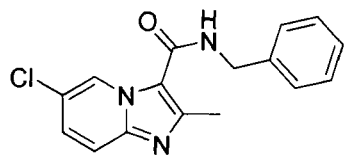
N-Benzyl-2,8-dimethylimidazo[1,2-a]pyridine-3-carboxamide (30)
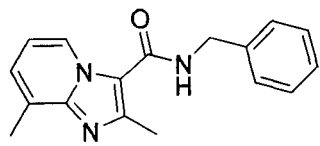
N-Benzyl-2,7-dimethylimidazo[1,2-a]pyridine-3-carboxamide (31)
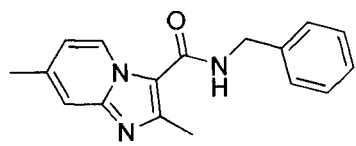
N-Benzyl-2,6-dimethylimidazo[1,2-a]pyridine-3-carboxamide (32)
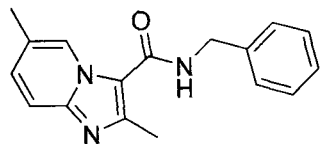
N-Benzyl-2,5-dimethylimidazo[1,2-a]pyridine-3-carboxamide (33)
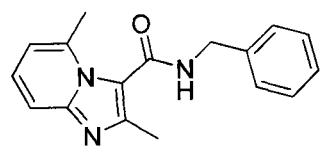
N-Benzyl-6-fluoro-2-methylimidazo[1,2-a]pyridine-3-carboxamide (34)
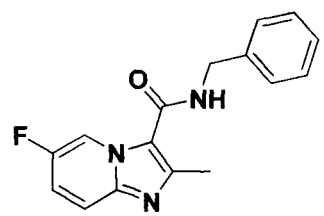

N-Benzyl-7-cyano-2-methylimidazo[1,2-a]pyridine-3-carboxamide (35)
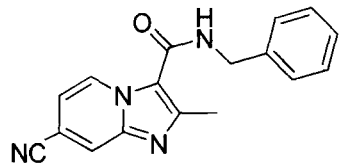
N-Benzyl-6-cyano-2-methylimidazo[1,2-a]pyridine-3-carboxamide (36)
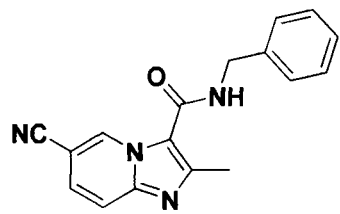
N-Benzyl-2-methyl-7-phenylimidazo[1,2-a]pyridine-3-carboxamide (37)
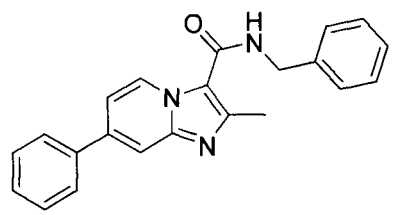
N-Benzyl-2-methyl-6-phenylimidazo[1,2-a]pyridine-3-carboxamide (38)
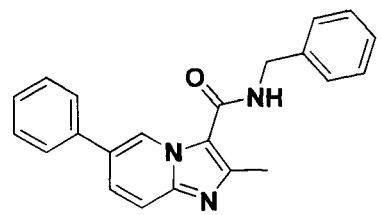
N-Benzyl-8-fluoro-2-methylimidazo[1,2-a]pyridine-3-carboxamide (39)
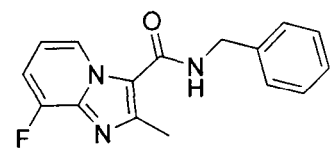

N-Benzyl-2-methyl-8-(trifluoromethyl)imidazo[1,2-a]pyridine-3-carboxamide (40)
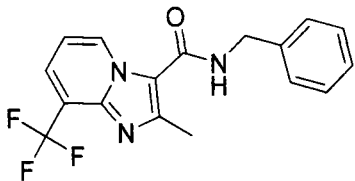
N-Benzyl-8-methoxy-2-methylimidazo[1,2-a]pyridine-3-carboxamide (41)
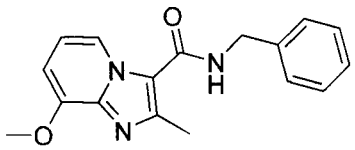
N-Benzyl-8-cyano-2-methylimidazo[1,2-a]pyridine-3-carboxamide (42)
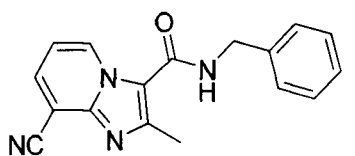
N-Benzyl-8-hydroxy-2-methylimidazo[1,2-a]pyridine-3-carboxamide (43)
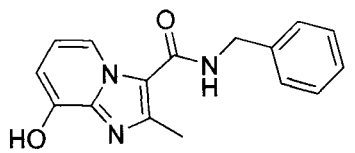
N-Benzyl-2-ethylimidazo[1,2-a]pyridine-3-carboxamide (46)
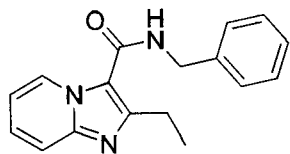

N-Benzyl-2-propylimidazo[1,2-a]pyridine-3-carboxamide (48)
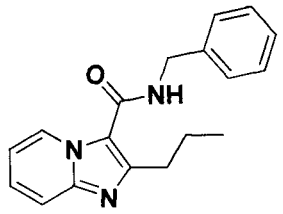
N-Benzyl-2-cyclopropylimidazo[1,2-a]pyridine-3-carboxamide (50)
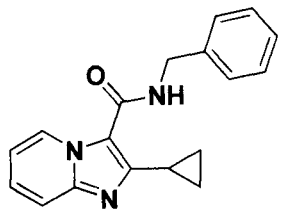
N-Benzyl-2-isopropylimidazo[1,2-a]pyridine-3-carboxamide (51)
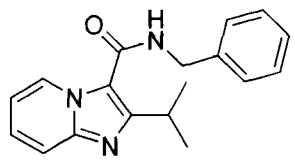
N-Benzyl-2-phenylimidazo[1,2-a]pyridine-3-carboxamide (53)
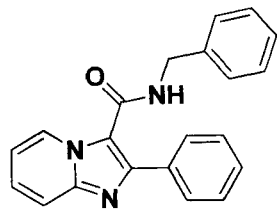
2-Ethyl-N-(4-(trifluoromethoxy)benzyl)imidazo[1,2-a]pyridine-3-carboxamide (59)
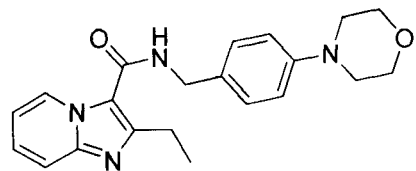

2-Ethyl-7-methyl-N-(4-morpholinobenzyl)imidazo[1,2-a]pyridine-3-carboxamide (68)
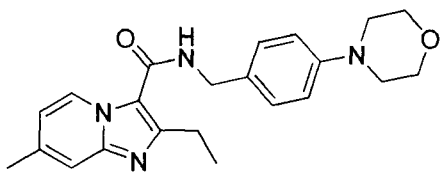
2-Ethyl-7-methyl-N-(naphthalen-2-ylmethyl)imidazo[1,2-a]pyridine-3-carboxamide (69)
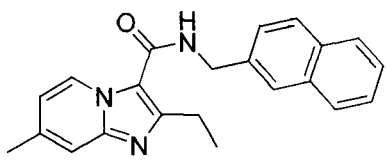
6-Chloro-2-methyl-N-(4-morpholinobenzyl)imidazo[1,2-a]pyridine-3-carboxamide (74)
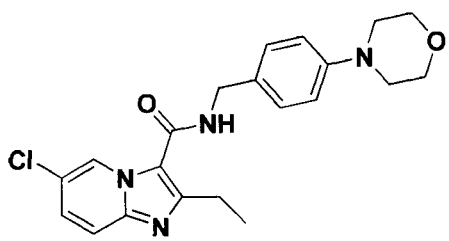
6-Chloro-2-ethyl-N-(4-(piperidin-1-yl)benzyl)imidazo[1,2-a]pyridine-3-carboxamide (79)
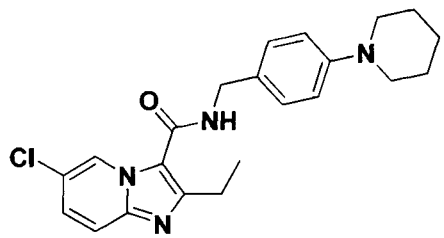
6-Chloro-2-ethyl-N-(naphthalen-2-ylmethyl)imidazo[1,2-a]pyridine-3-carboxamide (80)
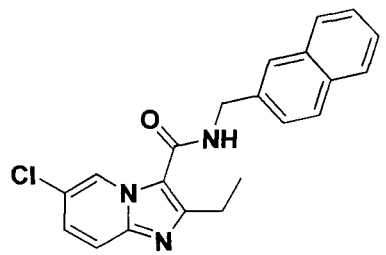

7-Chloro-2-ethyl-N-(4-morpholinobenzyl)imidazo[1,2-a]pyridine-3-carboxamide (89)
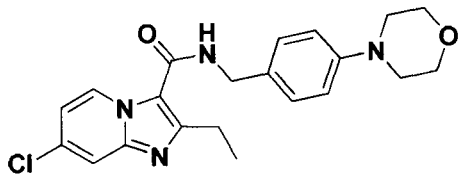
7-Chloro-2-ethyl-N-(4-(piperidin-1-yl)benzyl)imidazo[1,2-a]pyridine-3-carboxamide (90)
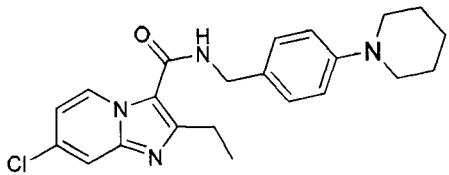
7-Chloro-2-ethyl-N-(naphthalen-2-ylmethyl)imidazo[1,2-a]pyridine-3-carboxamide (91)
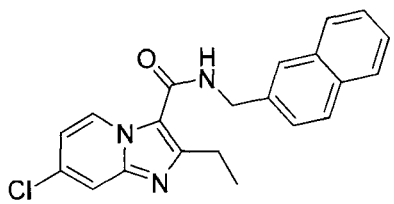
N-(7-Chloro-2-ethylimidazo[1,2-a]pyridin-3-yl)biphenyl-4-carboxamide (142)
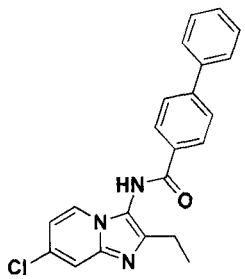
2-(Biphenyl-4-yl)-N-(7-chloro-2-ethylimidazo[1,2-a]pyridin-3-yl)acetamide (143)
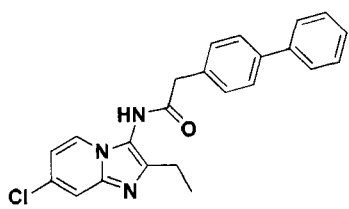

4-Phenoxybenzyl 6-chloro-2-ethylimidazo[1,2-a]pyridine-3-carboxylate (196)
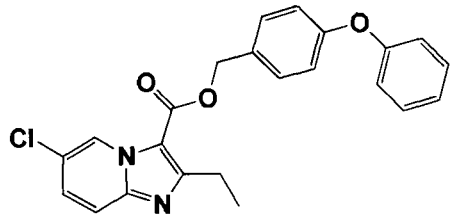
6-Chloro-2-ethyl-N-(4-(pyrrolidin-1-yl)benzyl)imidazo[1,2-a]pyridine-3-carboxamide (211)
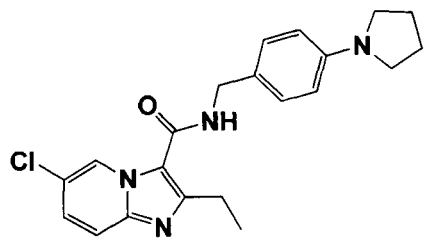
7-Chloro-2-ethyl-N-(4-(pyrrolidin-1-yl)benzyl)imidazo[1,2-a]pyridine-3-carboxamide (212)
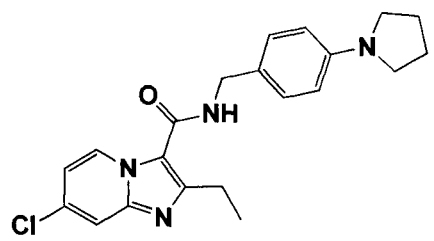
7-Chloro-N-(4-(5,6-dihydropyridin-1(2H)-yl)benzyl)-2-ethylimidazo[1,2-a]pyridine-3-carboxamide (213)
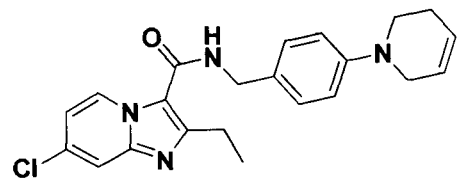
2-ethyl-6-methyl-N-(4-morpholinobenzyl)imidazo[1,2-a]pyridine-3-carboxamide (219)

N-(4-(Azepan-1-yl)benzyl)-6-chloro-2-ethylimidazo[1,2-a]pyridine-3-carboxamide (221)
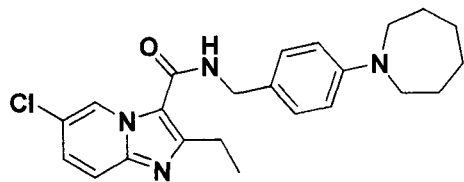
N-(4-(Azepan-1-yl)benzyl)-7-chloro-2-ethylimidazo[1,2-a]pyridine-3-carboxamide (222)
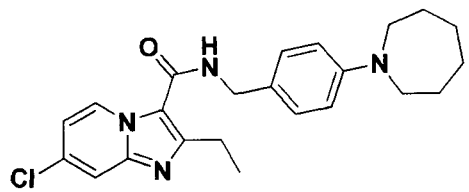
5-(6-Chloro-2-ethylimidazo[1,2-a]pyridin-3-yl)-3-(4-(trifluoromethoxy)benzyl)-1,2,4-oxadiazole (243)
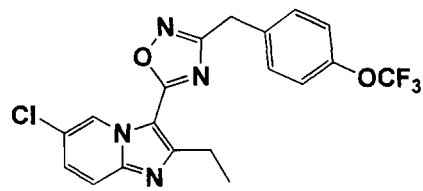
6-Chloro-2-ethyl-N-isobutylimidazo[1,2-a]pyridine-3-carboxamide (247)
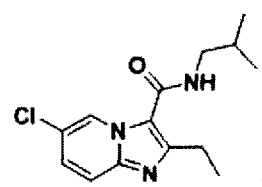
2-Ethyl-6-fluoro-N-(4-morpholinobenzyl)imidazo[1,2-a]pyridine-3-carboxamide (313)
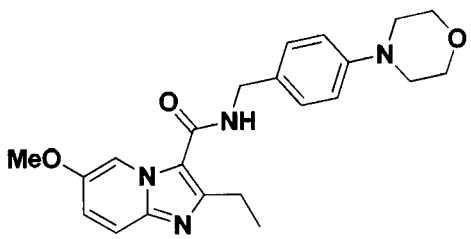

2-Ethyl-7-methoxy-*N*-(4-morpholinobenzyl)imidazo[1,2-a]pyridine-3-carboxamide (314)
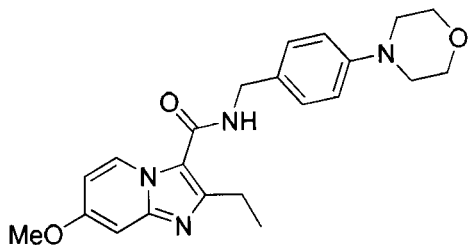
6-Bromo-2-ethyl-N-(4-morpholinobenzyl)imidazo[1,2-a]pyridine-3-carboxamide (315)
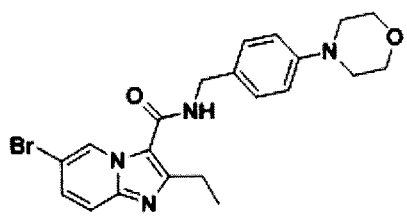
2-Ethyl-6-fluoro-N-(4-morpholinobenzyl)imidazo[1,2-a]pyridine-3-carboxamide (316)
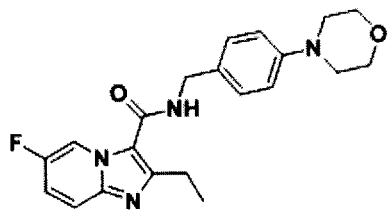
2-Ethyl-8-fluoro-N-(4-morpholinobenzyl)imidazo[1,2-a]pyridine-3-carboxamide (317)
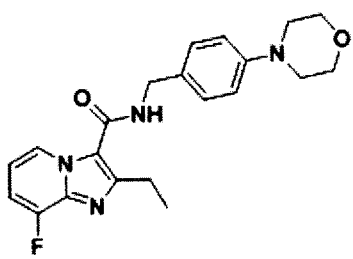
2-Ethyl-8-methoxy-*N*-(4-morpholinobenzyl)imidazo[1,2-a]pyridine-3-carboxamide (318)
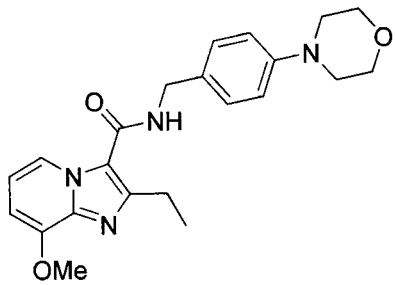

8-(Difluoromethoxy)-2-ethyl-N-(4-morpholinobenzyl)imidazo[1,2-a]pyridine-3-carboxamide (319)
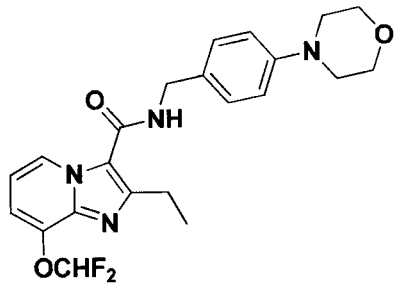
8-Bromo-2-ethyl-*N*-(4-morpholinobenzyl)imidazo[1,2-a]pyridine-3-carboxamide (320)
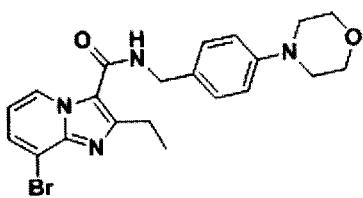
2-Ethyl-*N*-(4-morpholinobenzyl)-6-(trifluoromethyl)imidazo[1,2-a]pyridine-3-carboxamide (321)
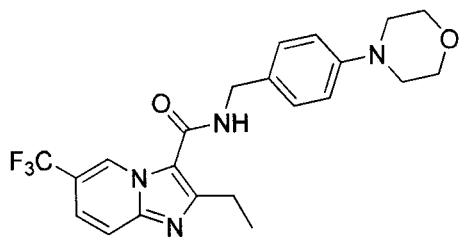
2-Ethyl-N-(4-morpholinobenzyl)-7-(trifluoromethyl)imidazo[1,2-a]pyridine-3-carboxamide (322)
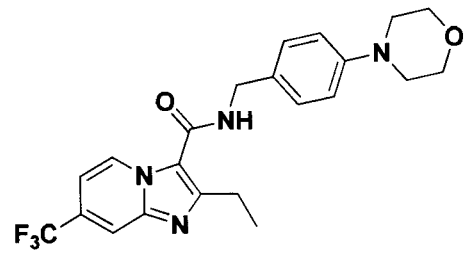

2-Ethyl-*N*-(4-morpholinobenzyl)-8-(trifluoromethyl)imidazo[1,2-a]pyridine-3-carboxamide (323)
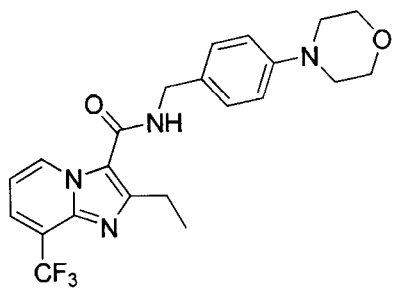
7-Bromo-2-ethyl-*N*-(4-morpholinobenzyl)imidazo[1,2-a]pyridine-3-carboxamide (324)
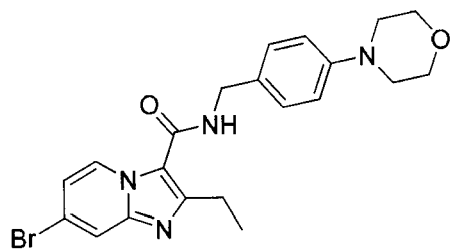
2-Ethyl-*N*-(4-morpholinobenzyl)-7-(pyridin-4-yl)imidazo[1,2-a]pyridine-3-carboxamide (325)
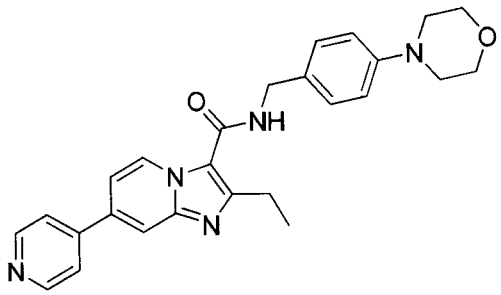
2-Ethyl-*N*-(4-morpholinobenzyl)-7-(pyridin-3-yl)imidazo[1,2-a]pyridine-3-carboxamide (326)
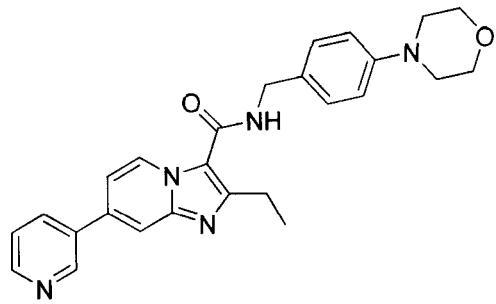

2-Ethyl-N-(4-morpholinobenzyl)-8-(pyridin-4-yl)imidazo[1,2-a]pyridine-3-carboxamide (327)
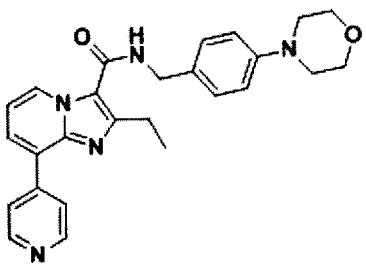
2-Ethyl-7-(4-methylpiperazin-1-yl)-N-(4-morpholinobenzyl)imidazo[1,2-a]pyridine-3-carboxamide (328)
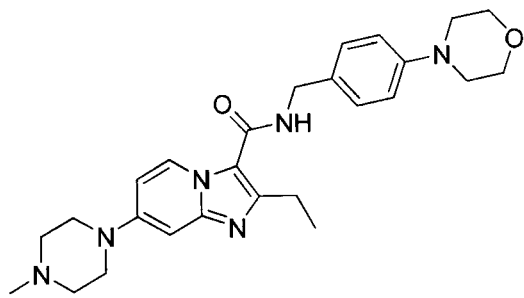
2-Ethyl-7-(4-(4-fluorophenyl)piperazin-1-yl)-N-(4-morpholinobenzyl)imidazo[1,2-a]pyridine-3-carboxamide (329)
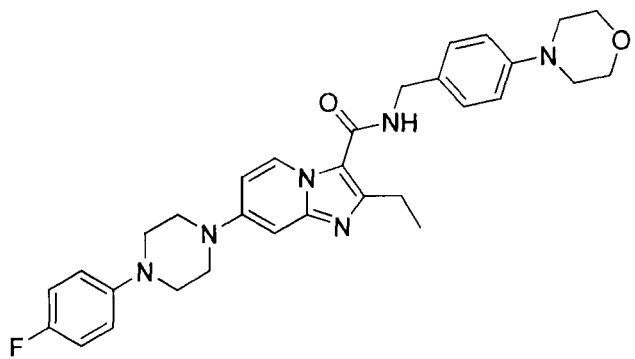

2-Ethyl-7-(4-(4-fluorobenzyl)piperazin-1-yl)-*N*-(4-morpholinobenzyl)imidazo[1,2-a]pyridine-3-carboxamide (331)
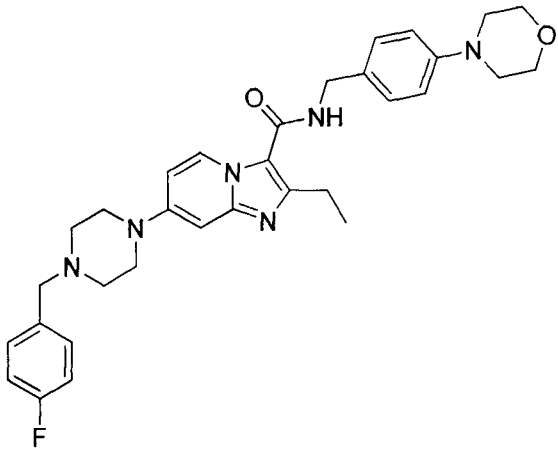
10. The compound according to claim 1, having a formula selected from formulae 161, 239-242 and 264:
[1,1'-Biphenyl]-4-ylmethyl 6-chloro-2-ethylimidazo[1,2-a]pyridine-3-carboxylate (161)
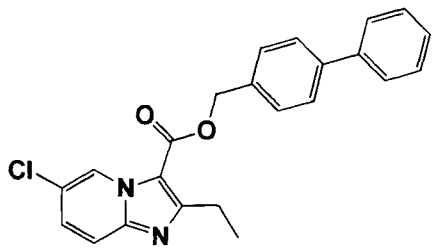
6-Chloro-2-ethyl-3-((4-(trifluoromethoxy)phenoxy)methyl)imidazo[1,2-a]pyridine (239)
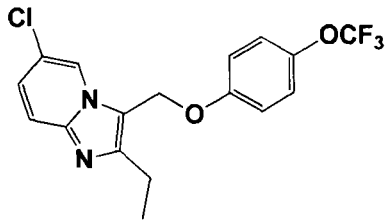

N-((6-Chloro-2-ethylimidazo[1,2-a]pyridin-3-yl)methyl)-4-(trifluoromethoxy)aniline (240)

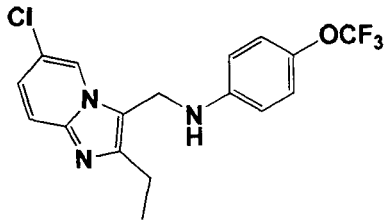

N-((6-Chloro-2-ethylimidazo[1,2-a]pyridin-3-yl)methyl)-4-(4-(4-fluorophenyl)piperazin-1-yl)aniline (241)

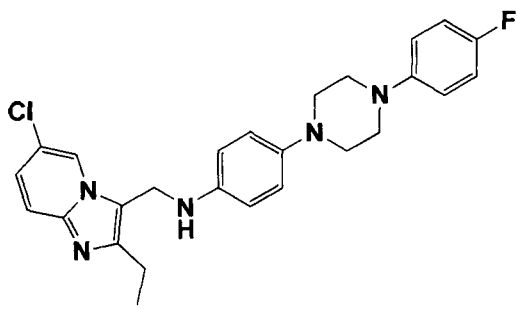

N-((6-Chloro-2-ethylimidazo[1,2-a]pyridin-3-yl)methyl)-4-(4-fluorophenoxy)aniline (242)

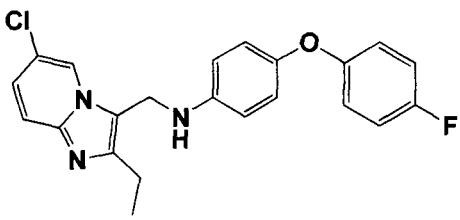

7-Chloro-2-ethyl-N-(4-(4-fluorophenoxy)benzyl)imidazo[1,2-a]pyridine-3-carboxamide (264)

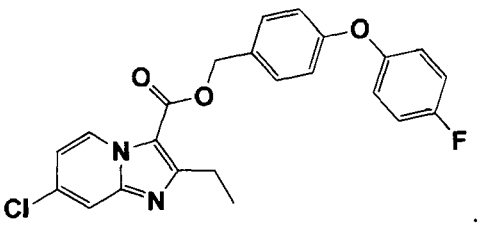

11. A pharmaceutical composition comprising a compound according to claim 9, and a pharmaceutically acceptable carrier.

12. A pharmaceutical composition comprising a compound according to claim 10, and a pharmaceutically acceptable carrier.

13 A method of treatment of a bacterial infection, comprising the application of a suitable amount of a compound according to claim 2, to a person in need thereof.

14. The method, according to claim 13, used for the treatment of tuberculosis.

(12) United States Patent
No et al.

(10) Patent No.: US 8,865,734 B2
(45) Date of Patent: Oct. 21, 2014

(54) ANTI-INFECTIVE COMPOUNDS

(75) Inventors: Zaesung No, Gyeonggido (KR); Jaeseung Kim, Seoul (KR); Priscille Brodin, Paris (FR); Min Jung Seo, Gyeonggi-do (KR); Young Mi Kim, Gyeonggi-do (KR); Jonathan Cechetto, Seoul (KR); Heekyoung Jeon, Gyeonggi-do (KR); Auguste Genovesio, Paris (FR); Saeyeon Lee, Gyeonggi-do (KR); Sunhee Kang, Gyeonggi-do (KR); Fanny Anne Ewann, Haramont (FR); Ji Youn Nam, CheongJu (KR); Thierry Christophe, Pontarlier (FR); Denis Philippe Cedric Fenistein, Amsterdam (NL); Jamung Heo, Chungcheongnam-do (KR); Jang Jiyeon, Seoul (KR)

(73) Assignees: Institut Pasteur Korea, Gyeonggi-Do (KR); Institut National de la Sante et de la Rech, Paris (FR)

( * ) Notice: Subject to any disclaimer, the term of this patent is extended or adjusted under 35 U.S.C. 154(b) by 0 days.

(21) Appl. No.: 13/634,165

(22) PCT Filed: Mar. 18, 2011

(86) PCT No.: PCT/EP2011/001345
§ 371 (c)(1),
(2), (4) Date: Nov. 26, 2012

(87) PCT Pub. No.: WO2011/113606
PCT Pub. Date: Sep. 22, 2011

(65) Prior Publication Data
US 2013/0065884 A1 Mar. 14, 2013

Related U.S. Application Data

(60) Provisional application No. 61/315,113, filed on Mar. 18, 2010, provisional application No. 61/440,937, filed on Feb. 9, 2011.

(51) Int. Cl.
*C07D 401/04* (2006.01)
*A61K 31/437* (2006.01)

(52) U.S. Cl.
CPC ............ *C07D 401/04* (2013.01); *A61K 31/437* (2013.01)
USPC .......................................... 514/300; 546/121

(58) Field of Classification Search
CPC ...................... C07D 401/04; A61K 31/437
USPC .................... 514/300; 546/121; 544/106, 362
See application file for complete search history.

(56) References Cited

U.S. PATENT DOCUMENTS

| | | | |
|---|---|---|---|
| 3,105,834 A * | 10/1963 | Wei | 544/281 |
| 3,133,076 A * | 5/1964 | Ferrari | 430/570 |
| 3,234,218 A * | 2/1966 | Eichenberger et al. | 548/193 |
| 6,080,767 A * | 6/2000 | Klein et al. | 514/357 |

FOREIGN PATENT DOCUMENTS

| | | | |
|---|---|---|---|
| WO | WO 01/92257 A1 | | 12/2001 |
| WO | 2007034278 | * | 3/2007 |
| WO | 2007034282 | * | 3/2007 |
| WO | WO 2007/027999 A2 | | 3/2007 |
| WO | WO 2008/082490 A2 | | 7/2008 |
| WO | WO 2008/154271 A1 | | 12/2008 |
| WO | WO 2009/015208 A1 | | 1/2009 |
| WO | WO 2011/050245 A1 | | 4/2011 |
| WO | WO 2011/057145 A2 | | 5/2011 |

OTHER PUBLICATIONS

Bristow et al., J. Ckem. Soc. (1954) 616-29.*
Paudler et al., Journal of Organic Chemistry (1968), 33(4), 1638-9.*
Boehme et al., Archiv der Pharmazie (Weinheim, Germany) (1976), 309(12), 959-65.*
Saldabols et al., Khimiko-Farmatsevticheskii Zhurnal (1977), 11(6), 64-70.*
Gueiffier et al., Journal of Medicinal Chemistry (1996), 39(14), 2856-2859.*
Chavignon et al., Heterocycles (1995), 41(9), 2019-26.*
Royer et al., Bulletin de la Societe Chimique de France (1961) 933-8.*
Takizawa et al., Inorganic Chemistry (2007), 46(10), 4308-4319.*
Kawamoto et al., "Efficient syntheses of a novel 5-thia-1-azacycl[3.3.2]azine ring system and 3H-1, 4-diazacycl[3.3.2]azine derivatives," 2000. *Tetrahedron Letters*, vol. 41, No. 18, p. 3447-3451.
Database Reaxys [Online], Database accession No. 8503486.
Database Reaxys [Online], Database accession No. 84996050.
Database Registry [Online], Chemical Abstracts 2010, retrieved from STN; Database accession No. 1235377-77-1.
Database Caplus [Online] Chemical Abstract Service, "Interaction of bromomalonic acid N,N'dibenzylamide with bifunctional amines A pathway to the new pharmacologically active substances," STN Accession No. 2004:36264, 2003, XP002638964, *Medichna Khimiya*, vol. 5, No. 3, 2003, pp. 95-99.
Database Registry [Online] Chemical Abstract Service, STN Database Accession No. 1181391-06-9, Sep. 9, 2009, XP002638965.
Database Registry [Online] Chemical Abstract Service, STN Database Accession No. 1181334-07-5, Sep. 8, 2009, XP002638966.
Database Registry [Online] Chemical Abstract Service, STN Database Accession No. 1181286-95-2, Sep. 8, 2009, XP002638967.
Database Registry [Online] Chemical Abstract Service, STN Database Accession No. 1181266-00-1, Sep. 8, 2009, XP002638968.
Database Registry [Online] Chemical Abstract Service, STN Database Accession No. 1147732-93-1, May 20, 2009, XP002638969.
Database Registry [Online] Chemical Abstract Service, STN Database Accession No. 570361-25-0, Aug. 21, 2003, XP002638970.

(Continued)

*Primary Examiner* — Niloofar Rahmani
(74) *Attorney, Agent, or Firm* — Saliwanchik, Lloyd & Eisenschenk

(57) ABSTRACT

The present invention relates to small molecule compounds and their use in the treatment of bacterial infections, in particular Tuberculosis.

14 Claims, 3 Drawing Sheets

UNITED STATES PATENT AND TRADEMARK OFFICE
CERTIFICATE OF CORRECTION

| | | |
|---|---|---|
| PATENT NO. | : 8,865,734 B2 | Page 1 of 149 |
| APPLICATION NO. | : 13/634165 | |
| DATED | : October 21, 2014 | |
| INVENTOR(S) | : Zaesung No et al. | |

It is certified that error appears in the above-identified patent and that said Letters Patent is hereby corrected as shown below:

Delete title page and substitute therefore with the attached title page consisting of the corrected number of claims in patent.

In the Claims

Delete Claims 1-21, Column 285, line 39-Column 428, line 57 and substitute therefore with the following Claims 1-14. Claims 7-8, 10, 16-17 and 20-21 have been cancelled.

Claims 1-14 should read as follows:

1. A compound having the general formula Ia:

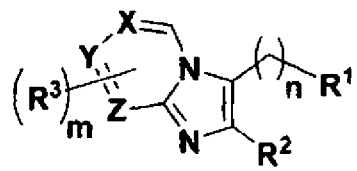

Ia wherein m is 0, 1, 2, 3 or 4;

n is 0, 1, 2, or 3;

X, Y and Z are CH;

Signed and Sealed this
Fourteenth Day of July, 2015

Michelle K. Lee
*Director of the United States Patent and Trademark Office*

CERTIFICATE OF CORRECTION (continued)
U.S. Pat. No. 8,865,734 B2

$R^1$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, -$OR^4$, -$C(O)OR^4$, -$C(O)R^4$, -$C(O)N(R^4)_2$, -CN, -$NO_2$, -$NH_2$, -$N(R^4)_2$, -$OR^4$HetA, -$OR^4N(R^4)_2$, -$C(O)N(R^4)R^4$HetA, -$C(O)N(R^4)$HetA, -$C(O)$HetA, -$C(O)N(R^4)R^4S(O)_2R_4$; -$S(O)_2N(R^4)_2$, -$S(O)_2R^4$, -$N(R^4)C(O)R^4SR^4$, -$N(R^4)R^4S(O)_2R^4$, -$N(R^4)S(O)_2R^4$, -$C(S)R^4$, aryl, benzyl, and heterocyclyl, any of which is optionally substituted;

$R^2$ is, at each occurrence, independently selected from the group consisting of hydrogen, halogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -OH, -$OR^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, -CN, -$NO_2$, -$NH_2$, -$N(R^5)_2$, -$C(O)R^5$, -$C(O)OR^5$, -$C(O)N(R^5)_2$, -$SR^5$, -$S(O)R^5$, -$S(O)_2R^5$, -$S(O)_2N(R^5)_2$, aryl, benzyl, heteroaryl, and heterocyclyl, any of which is optionally substituted;

$R^3$ is, at each occurrence, independently selected from the group consisting of hydrogen, halogen, $C_1$-$C_{10}$ alkyl, $C_3$-$C_{10}$ cycloalkyl, hydroxyl, -$OR^6$, -CN, -$NO_2$, -$NH_2$, -$N(R^6)C(O)R^6$, -$C(O)R^6$, -$C(O)OR^6$, -$C(O)N(R^6)_2$, -$S(O)R^6$, -$S(O)_2R^6$, -$S(O)_2N(R^6)_2$, aryl, benzyl, heteroaryl, heterocyclyl, any of which is optionally substituted, or two groups of $R^3$ are connected to each other to make a five or six membered cyclic or heterocyclic ring, any of which is optionally substituted;

$R^4$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -$C(O)R^7$, -$R^7(R^7)C(O)R^7$, -$C(O)OR^7$, -$R^7(R^7)C(O)OR^7$, -$C(O)N(R^7)_2$, -$R^7(R^7)C(O)N(R^7)_2$, -$S(O)R^7$, -$S(O)_2R^7$, -$S(O)_2N(R^7)_2$, aryl, benzyl, heteroaryl, and heterocyclyl, any of which is optionally substituted; and $R^5$, $R^6$ and $R^7$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted; and pharmaceutically acceptable salts thereof, and wherein the compound has a formula selected from the following formulae 5, 8, 13, 14, 17, 18, 20, 21, 23-43, 46, 48, 50, 51, 53, 59, 68, 69, 74, 79, 80, 89-91, 142, 143, 161, 196, 211-213, 219, 221, 222, 239-247, 264, 313-329 and 331:
2-Methyl-N-(pyridin-4-yl)imidazo[1,2-a]pyridine-3-carboxamide (5)
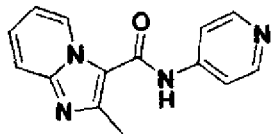
N-Benzyl-2-methylimidazo[1,2-a]pyridine-3-carboxamide (8)
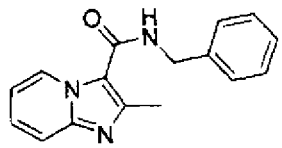
2-Methyl-N-(pyridin-3-ylmethyl)imidazo[1,2-a]pyridine-3-carboxamide (13)
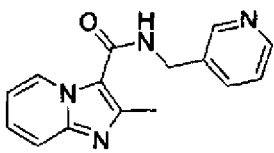
2-Methyl-N-(pyridin-4-ylmethyl)imidazo[1,2-a]pyridine-3-carboxamide (14)
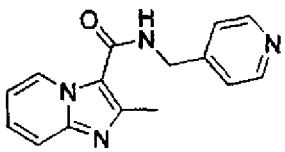
N-((1H-Indol-5-yl)methyl)-2-methylimidazo[1,2-a]pyridine-3-carboxamide (17)
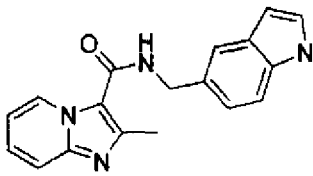

N-(Cyclohexylmethyl)-2-methylimidazo[1,2-a]pyridine-3-carboxamide (18)
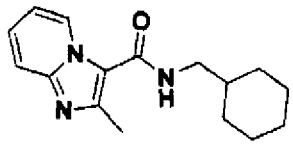
2-Methyl-N-(piperidin-4-ylmethyl)imidazo[1,2-a]pyridine-3-carboxamide (20)
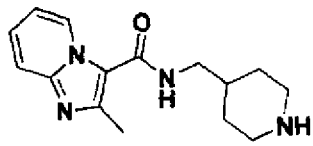
2-Methyl-N-phenethylimidazo[1,2-a]pyridine-3-carboxamide (21)
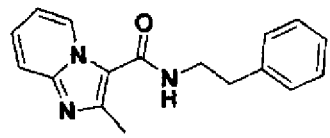
2-Methyl-N-(2-phenoxyethyl)imidazo[1,2-a]pyridine-3-carboxamide (23)
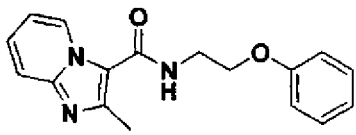
N-(2-(Benzyloxy)ethyl)-2-methylimidazo[1,2-a]pyridine-3-carboxamide (24)
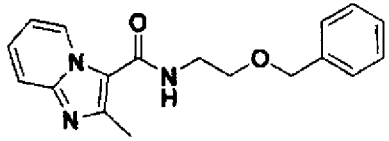
(S)-Methyl 2-(2-methylimidazo[1,2-a]pyridine-3-carboxamido)-3-phenylpropanoate (25)
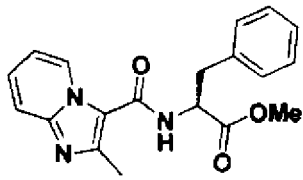

N-(2-Methylimidazo[1,2-a]pyridin-3-yl)-2-phenylacetamide (26)
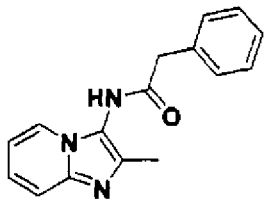
N-Benzyl-8-chloro-2-methylimidazo[1,2-a]pyridine-3-carboxamide (27)
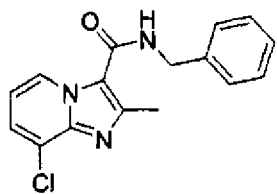
N-Benzyl-7-chloro-2-methylimidazo[1,2-a]pyridine-3-carboxamide (28)
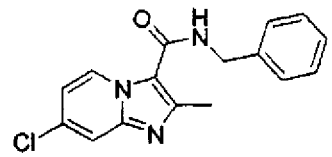
N-Benzyl-6-chloro-2-methylimidazo[1,2-a]pyridine-3-carboxamide (29)
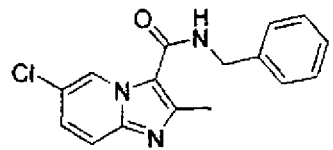
N-Benzyl-2,8-dimethylimidazo[1,2-a]pyridine-3-carboxamide (30)
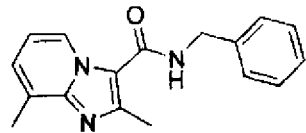
N-Benzyl-2,7-dimethylimidazo[1,2-a]pyridine-3-carboxamide (31)
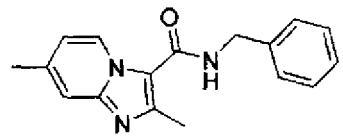

N-Benzyl-2,6-dimethylimidazo[1,2-a]pyridine-3-carboxamide (32)
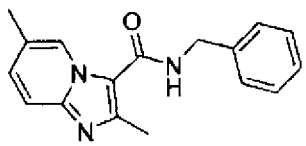
N-Benzyl-2,5-dimethylimidazo[1,2-a]pyridine-3-carboxamide (33)
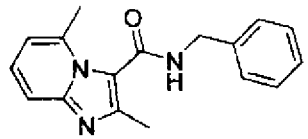
N-Benzyl-6-fluoro-2-methylimidazo[1,2-a]pyridine-3-carboxamide (34)
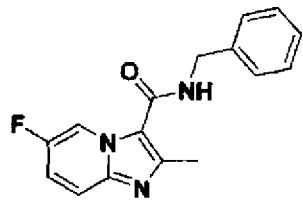
N-Benzyl-7-cyano-2-methylimidazo[1,2-a]pyridine-3-carboxamide (35)
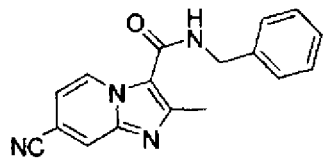
N-Benzyl-6-cyano-2-methylimidazo[1,2-a]pyridine-3-carboxamide (36)
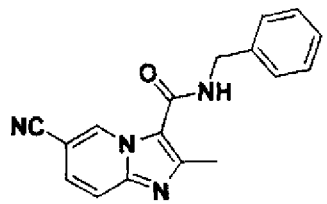
N-Benzyl-2-methyl-7-phenylimidazo[1,2-a]pyridine-3-carboxamide (37)
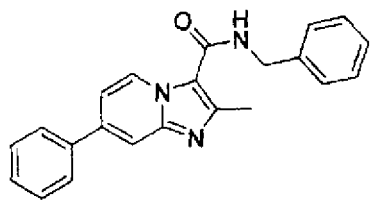

N-Benzyl-2-methyl-6-phenylimidazo[1,2-a]pyridine-3-carboxamide (38)
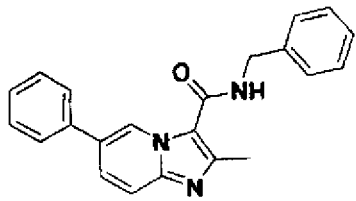
N-Benzyl-8-fluoro-2-methylimidazo[1,2-a]pyridine-3-carboxamide (39)
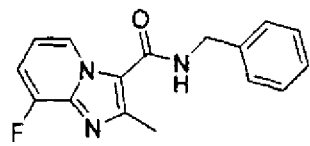
N-Benzyl-2-methyl-8-(trifluoromethyl)imidazo[1,2-a]pyridine-3-carboxamide (40)
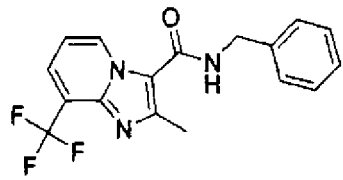
N-Benzyl-8-methoxy-2-methylimidazo[1,2-a]pyridine-3-carboxamide (41)
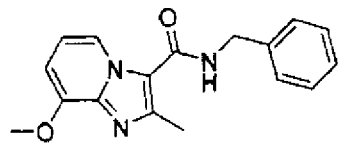
N-Benzyl-8-cyano-2-methylimidazo[1,2-a]pyridine-3-carboxamide (42)
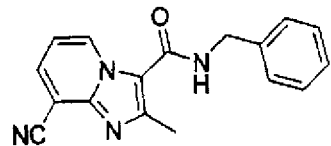
N-Benzyl-8-hydroxy-2-methylimidazo[1,2-a]pyridine-3-carboxamide (43)
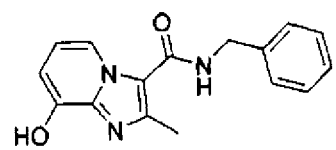

N-Benzyl-2-ethylimidazo[1,2-a]pyridine-3-carboxamide (46)
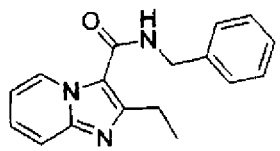
N-Benzyl-2-propylimidazo[1,2-a]pyridine-3-carboxamide (48)
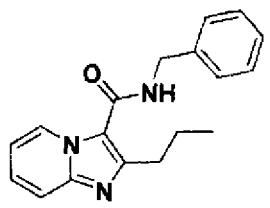
N-Benzyl-2-cyclopropylimidazo[1,2-a]pyridine-3-carboxamide (50)
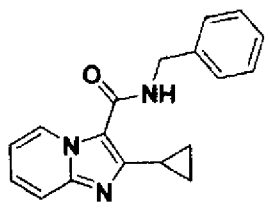
N-Benzyl-2-isopropylimidazo[1,2-a]pyridine-3-carboxamide (51)
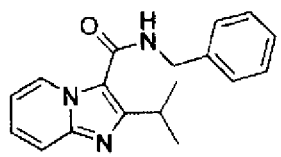
N-Benzyl-2-phenylimidazo[1,2-a]pyridine-3-carboxamide (53)
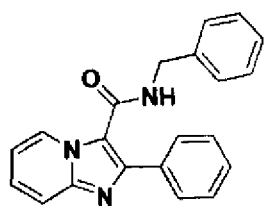
2-Ethyl-N-(4-(trifluoromethoxy)benzyl)imidazo[1,2-a]pyridine-3-carboxamide (59)
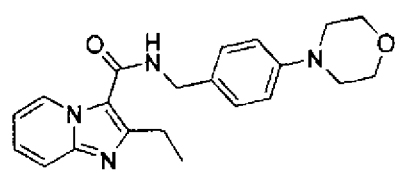

2-Ethyl-7-methyl-N-(4-morpholinobenzyl)imidazo[1,2-a]pyridine-3-carboxamide (68)
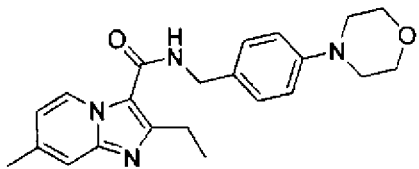
2-Ethyl-7-methyl-N-(naphthalen-2-ylmethyl)imidazo[1,2-a]pyridine-3-carboxamide (69)
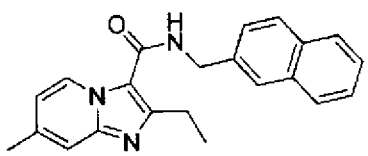
6-Chloro-2-methyl-N-(4-morpholinobenzyl)imidazo[1,2-a]pyridine-3-carboxamide (74)
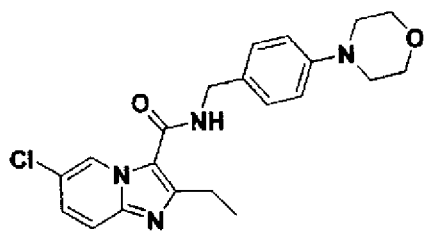
6-Chloro-2-ethyl-N-(4-(piperidin-1-yl)benzyl)imidazo[1,2-a]pyridine-3-carboxamide (79)
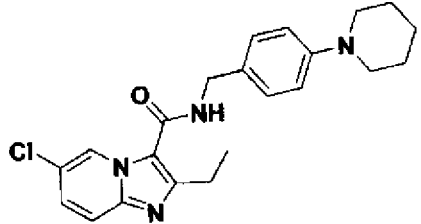
6-Chloro-2-ethyl-N-(naphthalen-2-ylmethyl)imidazo[1,2-a]pyridine-3-carboxamide (80)
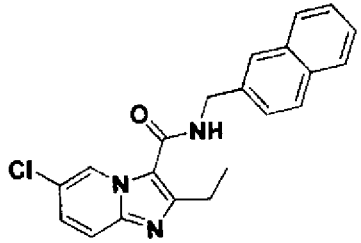

7-Chloro-2-ethyl-N-(4-morpholinobenzyl)imidazo[1,2-a]pyridine-3-carboxamide (89)
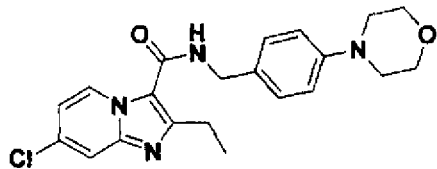
7-Chloro-2-ethyl-N-(4-(piperidin-1-yl)benzyl)imidazo[1,2-a]pyridine-3-carboxamide (90)
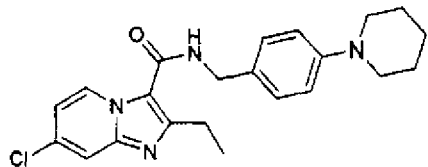
7-Chloro-2-ethyl-N-(naphthalen-2-ylmethyl)imidazo[1,2-a]pyridine-3-carboxamide (91)
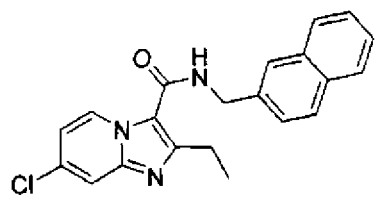
N-(7-Chloro-2-ethylimidazo[1,2-a]pyridin-3-yl)biphenyl-4-carboxamide (142)
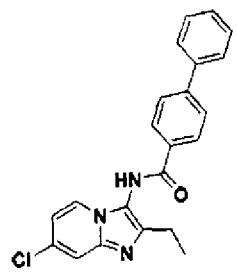
2-(Biphenyl-4-yl)-N-(7-chloro-2-ethylimidazo[1,2-a]pyridin-3-yl)acetamide (143)
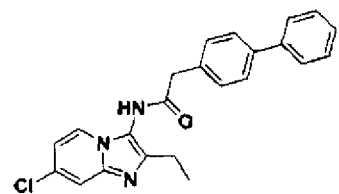

[1,1'-Biphenyl]-4-ylmethyl 6-chloro-2-ethylimidazo[1,2-a]pyridine-3-carboxylate (161)
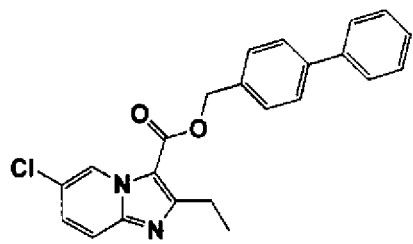
4-Phenoxybenzyl 6-chloro-2-ethylimidazo[1,2-a]pyridine-3-carboxylate (196)
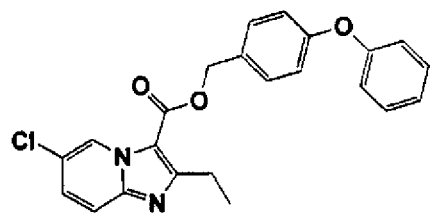
6-Chloro-2-ethyl-N-(4-(pyrrolidin-1-yl)benzyl)imidazo[1,2-a]pyridine-3-carboxamide (211)
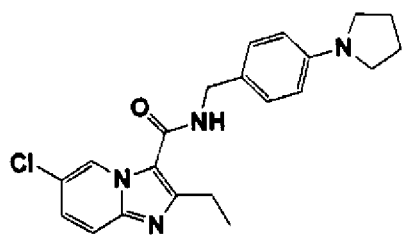
7-Chloro-2-ethyl-N-(4-(pyrrolidin-1-yl)benzyl)imidazo[1,2-a]pyridine-3-carboxamide (212)
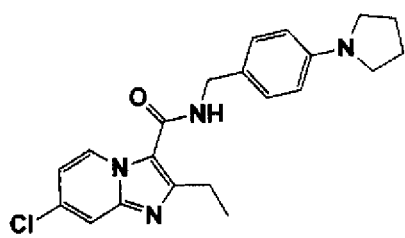
7-Chloro-N-(4-(5,6-dihydropyridin-1(2H)-yl)benzyl)-2-ethylimidazo[1,2-a]pyridine-3-carboxamide (213)
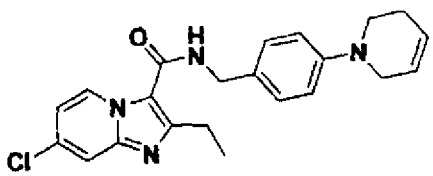

2-ethyl-6-methyl-N-(4-morpholinobenzyl)imidazo[1,2-a]pyridine-3-carboxamide (219)
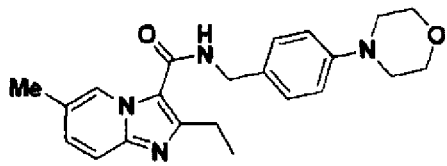
N-(4-(Azepan-1-yl)benzyl)-6-chloro-2-ethylimidazo[1,2-a]pyridine-3-carboxamide (221)
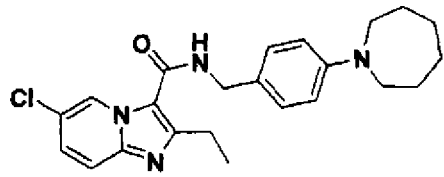
N-(4-(Azepan-1-yl)benzyl)-7-chloro-2-ethylimidazo[1,2-a]pyridine-3-carboxamide (222)
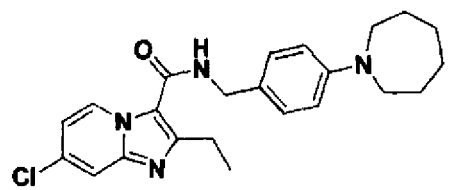
6-Chloro-2-ethyl-3-((4-(trifluoromethoxy)phenoxy)methyl)imidazo[1,2-a]pyridine (239)
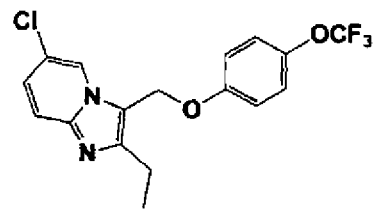
N-((6-Chloro-2-ethylimidazo[1,2-a]pyridin-3-yl)methyl)-4-(trifluoromethoxy)aniline (240)
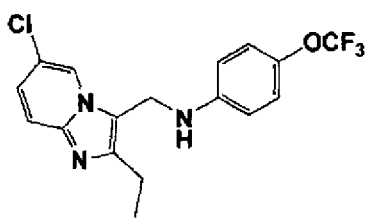

N-((6-Chloro-2-ethylimidazo[1,2-a]pyridin-3-yl)methyl)-4-(4-(4-fluorophenyl)piperazin-1-yl)aniline (241)
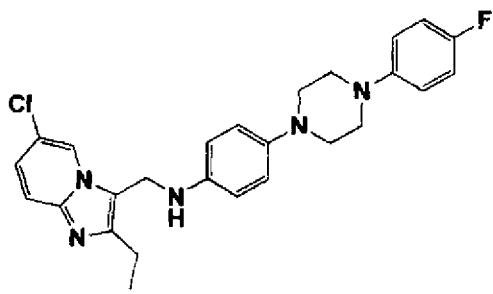
N-((6-Chloro-2-ethylimidazo[1,2-a]pyridin-3-yl)methyl)-4-(4-fluorophenoxy)aniline (242)
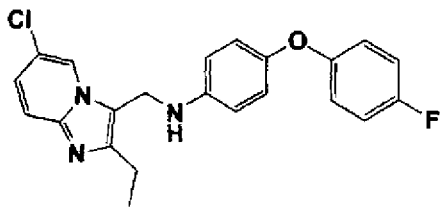
5-(6-Chloro-2-ethylimidazo[1,2-a]pyridin-3-yl)-3-(4-(trifluoromethoxy)benzyl)-1,2,4-oxadiazole (243)
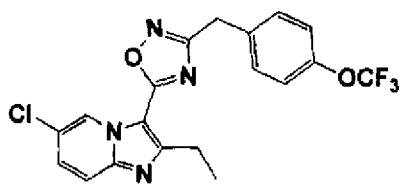
2-(7-Chloro-2-ethylimidazo[1,2-a]pyridin-3-yl)-5-((4-(4-(trifluoromethoxy)phenyl)piperazin-1-yl)methyl)-1,3,4-oxadiazole (244)
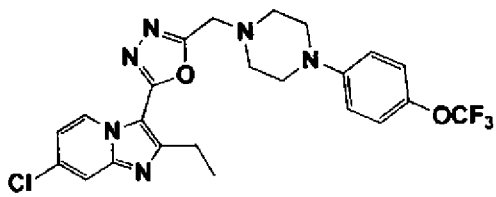

5-(6-Chloro-2-ethylimidazo[1,2-a]pyridin-3-yl)-3-(4-(4-fluorophenoxy)benzyl)-1,2,4-oxadiazole (245)
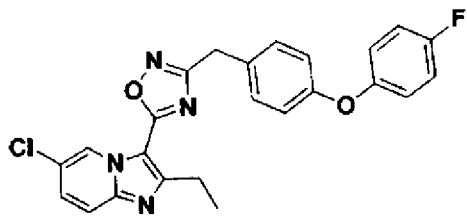
6-Chloro-N,2-diethylimidazo[1,2-a]pyridine-3-carboxamide (246)
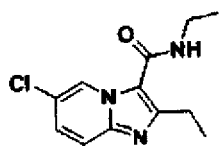
6-Chloro-2-ethyl-N-isobutylimidazo[1,2-a]pyridine-3-carboxamide (247)
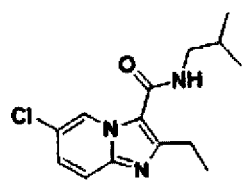
7-Chloro-2-ethyl-N-(4-(4-fluorophenoxy)benzyl)imidazo[1,2-a]pyridine-3-carboxamide (264)
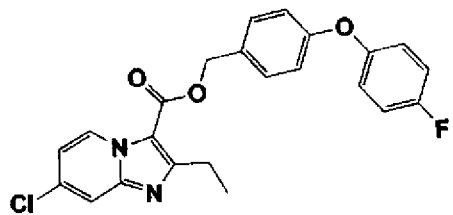

2-Ethyl-6-fluoro-N-(4-morpholinobenzyl)imidazo[1,2-a]pyridine-3-carboxamide (313)
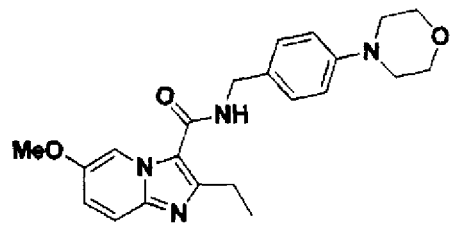
2-Ethyl-7-methoxy-*N*-(4-morpholinobenzyl)imidazo[1,2-a]pyridine-3-carboxamide (314)
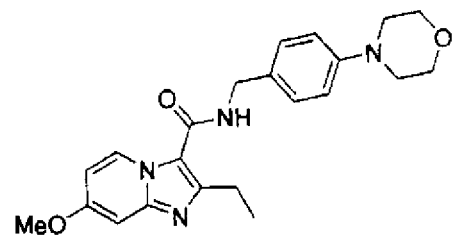
6-Bromo-2-ethyl-N-(4-morpholinobenzyl)imidazo[1,2-a]pyridine-3-carboxamide (315)
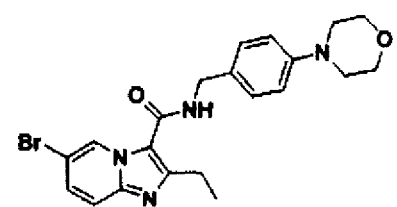
2-Ethyl-6-fluoro-N-(4-morpholinobenzyl)imidazo[1,2-a]pyridine-3-carboxamide (316)
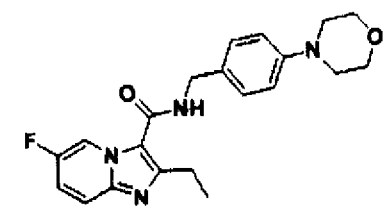

2-Ethyl-8-fluoro-N-(4-morpholinobenzyl)imidazo[1,2-a]pyridine-3-carboxamide (317)
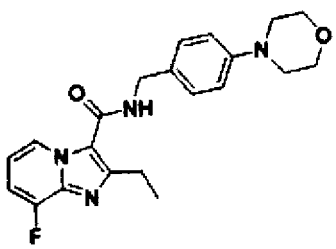
2-Ethyl-8-methoxy-N-(4-morpholinobenzyl)imidazo[1,2-a]pyridine-3-carboxamide (318)
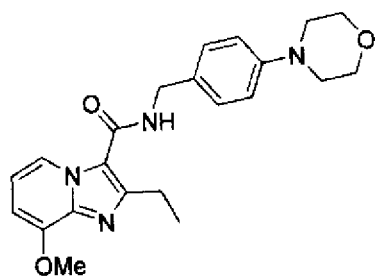
8-(Difluoromethoxy)-2-ethyl-N-(4-morpholinobenzyl)imidazo[1,2-a]pyridine-3-carboxamide (319)
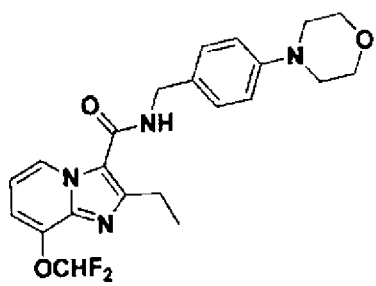
8-Bromo-2-ethyl-N-(4-morpholinobenzyl)imidazo[1,2-a]pyridine-3-carboxamide (320)
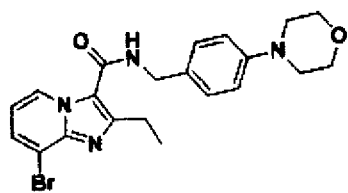

2-Ethyl-*N*-(4-morpholinobenzyl)-6-(trifluoromethyl)imidazo[1,2-a]pyridine-3-carboxamide (321)
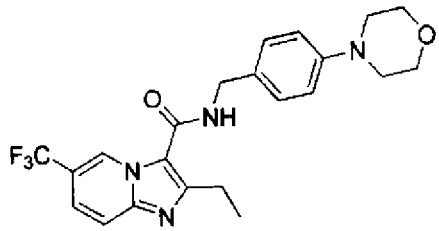
2-Ethyl-N-(4-morpholinobenzyl)-7-(trifluoromethyl)imidazo[1,2-a]pyridine-3-carboxamide (322)
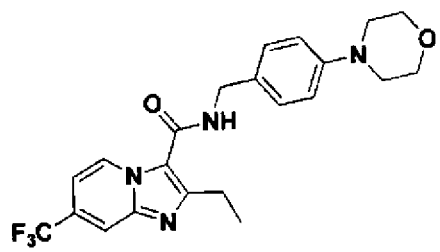
2-Ethyl-*N*-(4-morpholinobenzyl)-8-(trifluoromethyl)imidazo[1,2-a]pyridine-3-carboxamide (323)
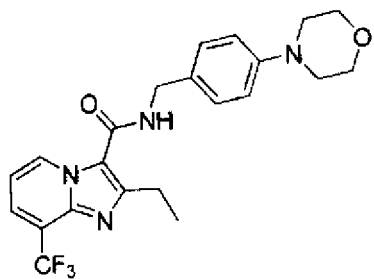
7-Bromo-2-ethyl-*N*-(4-morpholinobenzyl)imidazo[1,2-a]pyridine-3-carboxamide (324)
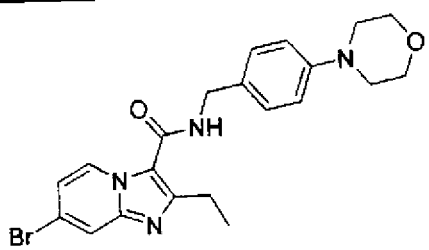

2-Ethyl-*N*-(4-morpholinobenzyl)-7-(pyridin-4-yl)imidazo[1,2-a]pyridine-3-carboxamide (325)
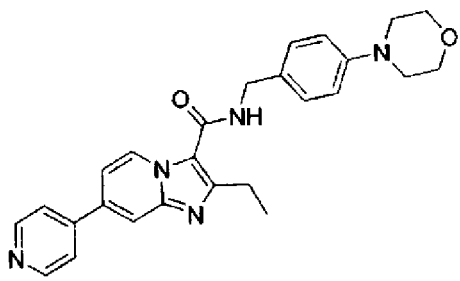
2-Ethyl-*N*-(4-morpholinobenzyl)-7-(pyridin-3-yl)imidazo[1,2-a]pyridine-3-carboxamide (326)
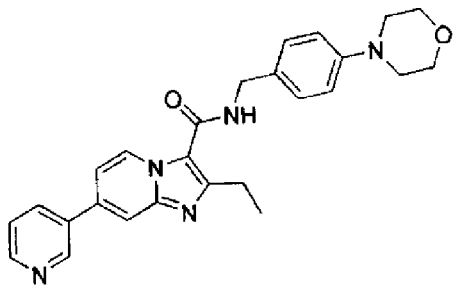
2-Ethyl-*N*-(4-morpholinobenzyl)-8-(pyridin-4-yl)imidazo[1,2-a]pyridine-3-carboxamide (327)
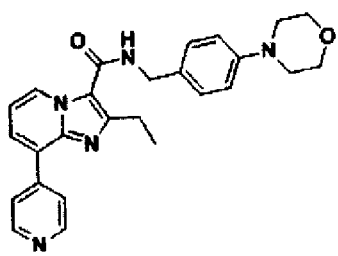
2-Ethyl-7-(4-methylpiperazin-1-yl)-*N*-(4-morpholinobenzyl)imidazo[1,2-a]pyridine-3-carboxamide (328)
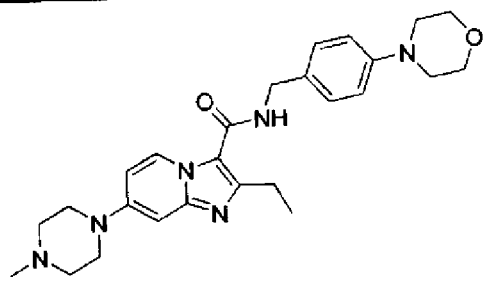

**2-Ethyl-7-(4-(4-fluorophenyl)piperazin-1-yl)-*N*-(4-morpholinobenzyl)imidazo[1,2-a]pyridine-3-carboxamide(329)**
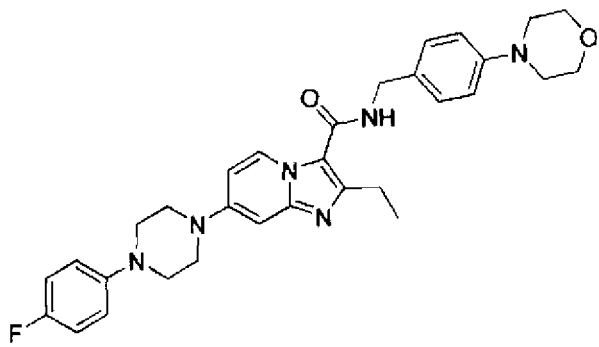
**2-Ethyl-7-(4-(4-fluorobenzyl)piperazin-1-yl)-*N*-(4-morpholinobenzyl)imidazo[1,2-a]pyridine-3-carboxamide (331)**
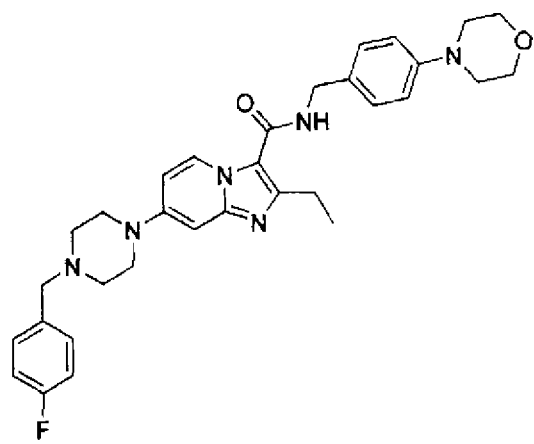
2. A compound having the general formula Ib:
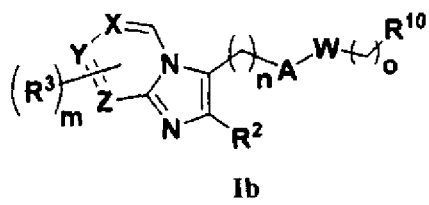
Ib
wherein o is 0, 1, 2, or 3;

n is 0;

m is 1, 2, 3 or 4;

X, Y and Z are CH;

A is C=O or C=S

W is $NR^{11}$;

$R^2$ is, at each occurrence, independently selected from the group consisting of hydrogen, halogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -OH, -$OR^5$, $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, -CN, -$NO_2$, -$NH_2$, -$N(R^5)_2$, -$C(O)R^5$, -$C(O)OR^5$, -$C(O)N(R^5)_2$, -$SR^5$, -$S(O)R^5$, -$S(O)_2R^5$, -$S(O)_2N(R^5)_2$, aryl, benzyl, and heterocyclyl, any of which is optionally substituted;

$R^3$ is, at each occurrence, independently selected from the group consisting of hydrogen, halogen, $C_1$-$C_{10}$ alkyl, $C_3$-$C_{10}$ cycloalkyl, hydroxyl, -$OR^6$, -CN, -$NO_2$, -$NH_2$, -$N(R^6)C(O)R^6$, -$C(O)R^6$, -$C(O)OR^6$, -$C(O)N(R^6)_2$, -$S(O)R^6$, -$S(O)_2R^6$, -$S(O)_2N(R^6)_2$, aryl, benzyl, heteroaryl, heterocyclyl, any of which is optionally substituted, or two groups of $R^3$ are connected to each other to make a five or six membered cyclic or heterocyclic ring, any of which is optionally substituted;

$R^5$ and $R^6$ are, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted;

$R^{10}$ is a moiety selected from the group consisting of

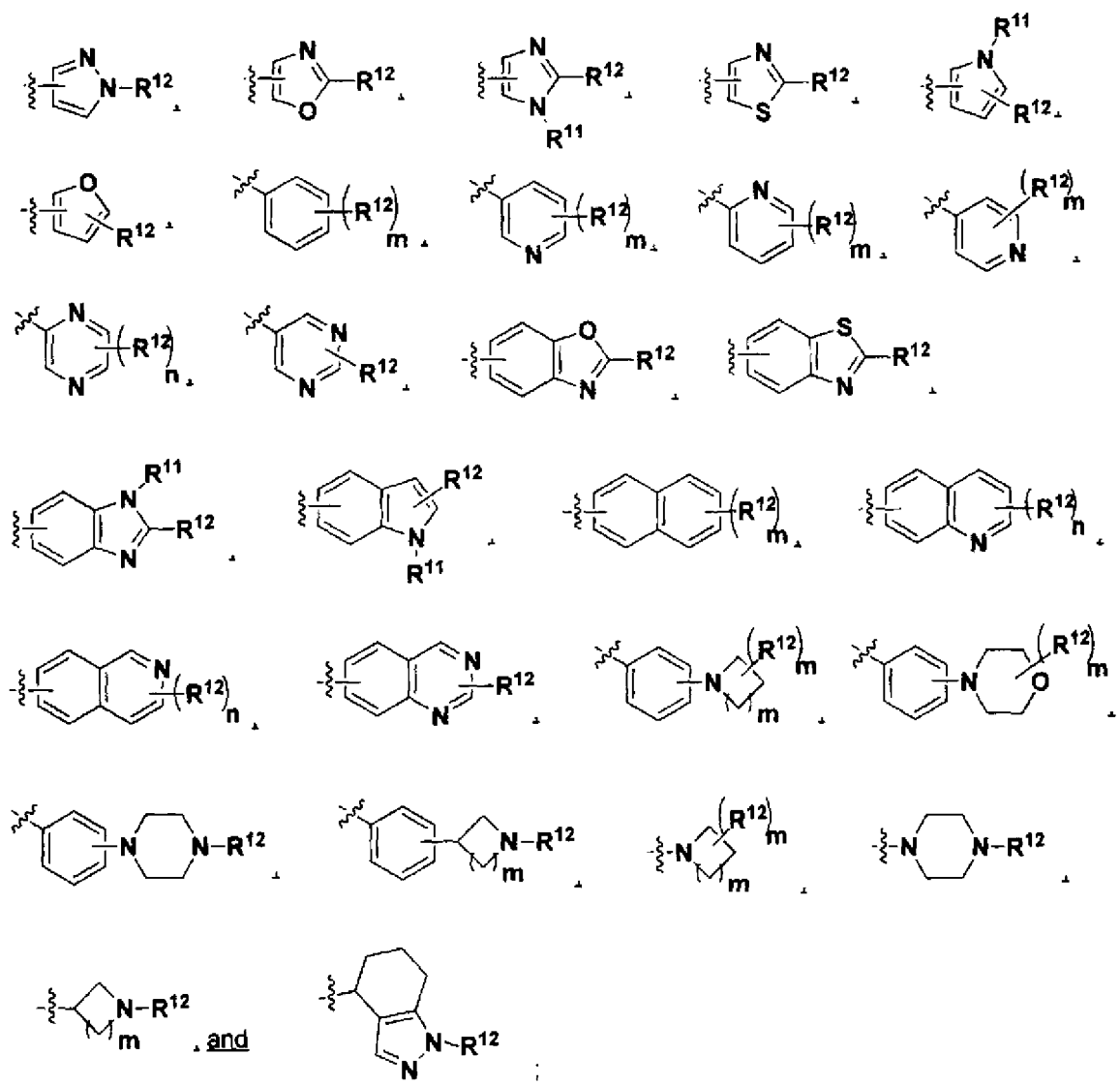

R[11] is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, -OH, -OR[13], $C_1$-$C_{10}$ alkoxy, $C_3$-$C_{10}$ cycloalkoxy, $C_3$-$C_{15}$ cycloalkylalkoxy, $C_3$-$C_{15}$ cycloalkylalkyl, -NH$_2$, -N(R[13])$_2$, -C(O)R[13], -C(O)OR[13], -C(O)N(R[13])$_2$, -S(O)R[13], -S(O)$_2$R[13], -S(O)$_2$N(R[13])$_2$, aryl, benzyl, heteroaryl, and heterocyclyl, any of which is optionally substituted;

R[12] is, at each occurrence, independently selected from the group consisting of $C_2$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, hydroxyl, -

$OR^{14}$, $-C(O)R^{14}$, $-C(O)OR^{14}$, $-CN$, $-NO_2$, $-NH_2$, $-N(R^{14})_2$, $-C(O)N(R^{14})_2$, $-S(O)R^{14}$, $-S(O)_2R^{14}$, $-S(O)_2N(R^{14})_2$, aryl, benzyl, heteroaryl, and heterocyclyl, any of which is optionally substituted;

$R^{13}$ is, at each occurrence, independently selected from the group consisting of hydrogen, $C_1$-$C_{10}$ alkyl, $C_3$-$C_{10}$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl, and heterocyclyl, any of which is optionally substituted; and $R^{14}$ is, at each occurrence, independently selected from the group consisting of hydrogen, $C_1$-$C_8$ alkyl optionally substituted with at least one hydroxyl or halogen; $C_3$-$C_7$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, benzyl, heteroaryl and heterocyclyl, any of which is optionally substituted, and pharmaceutically acceptable salts thereof.

3. The compound according to claim 2, having a formula selected from the following formulae 6, 7, 9-12, 15, 16, 19, 22, 44, 45, 47, 49, 52, 54-58, 60-67, 70-73, 75-78, 81-88, 92-141, 144-160, 162-195, 197-210, 214-218, 220, 223-238, 248-263, 265-312, 330 and 332-352:

2-Methyl-N-(4-phenoxyphenyl)imidazo[1,2-a]pyridine-3-carboxamide (6)

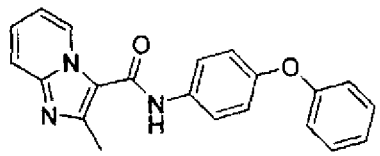

N-(4-(Benzyloxy)phenyl)-2-methylimidazo[1,2-a]pyridine-3-carboxamide (7)

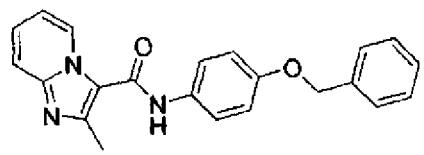

N-(4-Fluorobenzyl)-2-methylimidazo[1,2-a]pyridine-3-carboxamide (9)
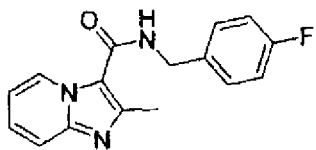
Methyl 4-((2-me3thylimidazo[1,2-a]pyridine-3-carboxamido)methyl)benzoate (10)
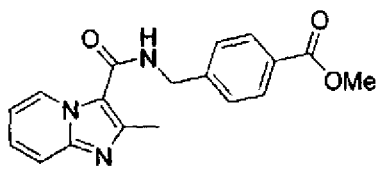
4-((2-Methylimidazo[1,2-a]pyridine-3-carboxamido)methyl)benzoic acid (11)
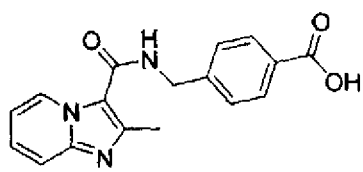
N-(4-Methoxybenzyl)-2-methylimidazo[1,2-a]pyridine-3-carboxamide (12)
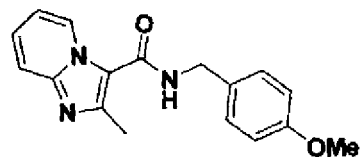
2-Methyl-N-(4-phenoxybenzyl)imidazo[1,2-a]pyridine-3-carboxamide (15)
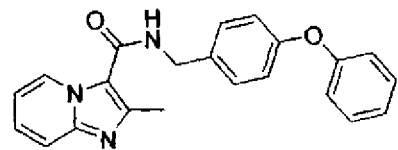
N-(Biphenyl-4-ylmethyl)-2-methylimidazo[1,2-a]pyridine-3-carboxamide (16)
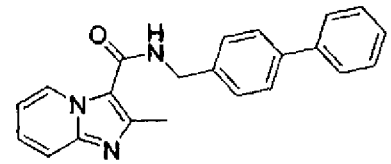

tert-Butyl 4-((2-methylimidazo[1,2-a]pyridine-3-carboxamido)methyl)piperidine-1-carboxylate (19)
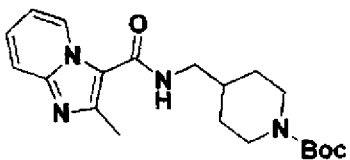
N-(4-Methoxyphenethyl)-2-methylimidazo[1,2-a]pyridine-3-carboxamide (22)
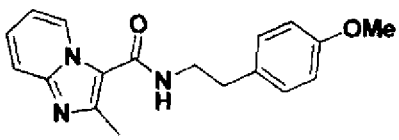
N-(Biphenyl-4-ylmethyl)-6-chloro-2-methylimidazo[1,2-a]pyridine-3-carboxamide (44)
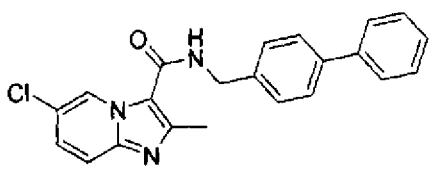
N-(Biphenyl-4-ylmethyl)-7-chloro-2-methylimidazo[1,2-a]pyridine-3-carboxamide (45)
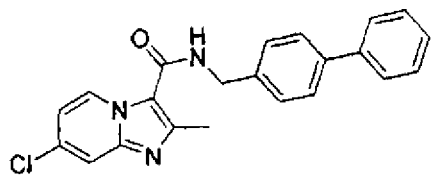
N-(Biphenyl-4-ylmethyl)-2-ethylimidazo[1,2-a]pyridine-3-carboxamide (47)
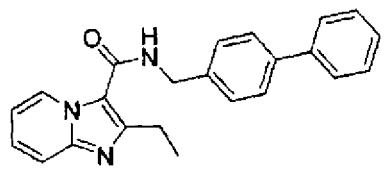

N-(Biphenyl-4-ylmethyl)-2-propylimidazo[1,2-a]pyridine-3-carboxamide (49)

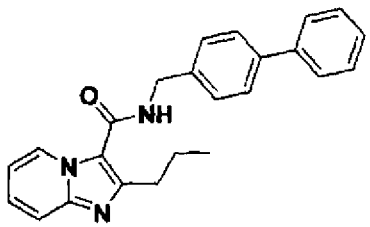

N-(Biphenyl-4-ylmethyl)-2-isopropylimidazo[1,2-a]pyridine-3-carboxamide (52)

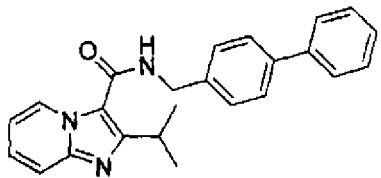

2-Ethyl-N-(4-phenoxybenzyl)imidazo[1,2-a]pyridine-3-carboxamide (54)

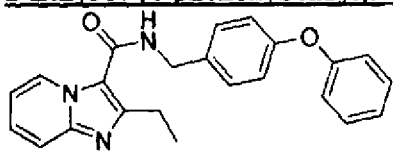

N-(4-tert-Butylbenzyl)-2-ethylimidazo[1,2-a]pyridine-3-carboxamide (55)

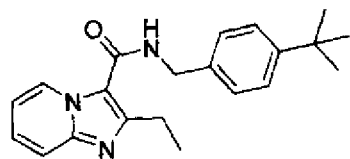

2-Ethyl-N-((1-methyl-1H-indol-5-yl)methyl)imidazo[1,2-a]pyridine-3-carboxamide (56)

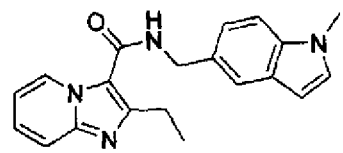

2-Ethyl-N-(4-(trifluoromethoxy)benzyl)imidazo[1,2-a]pyridine-3-carboxamide (57)

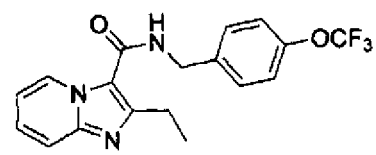

2-Ethyl-N-((1-methyl-1H-indol-6-yl)methyl)imidazo[1,2-a]pyridine-3-carboxamide (58)
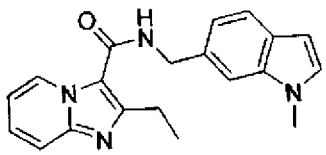
2-Ethyl-N-(4-isopropoxybenzyl)imidazo[1,2-a]pyridine-3-carboxamide (60)
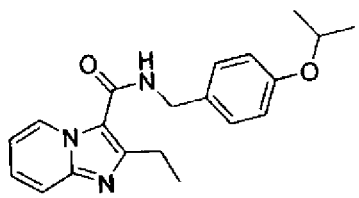
2-Ethyl-N-(4-isobutoxybenzyl)imidazo[1,2-a]pyridine-3-carboxamide (61)
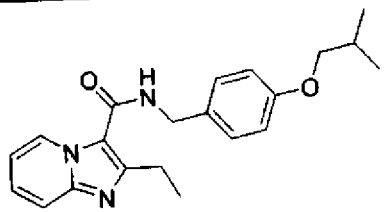
N-(Biphenyl-4-ylmethyl)-2-ethyl-6-methylimidazo[1,2-a]pyridine-3-carboxamide (62)
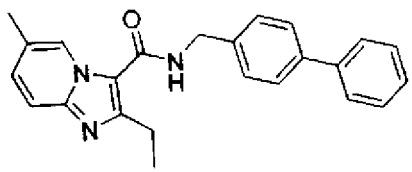
2-Ethyl-6-methyl-N-(4-phenoxybenzyl)imidazo[1,2-a]pyridine-3-carboxamide (63)
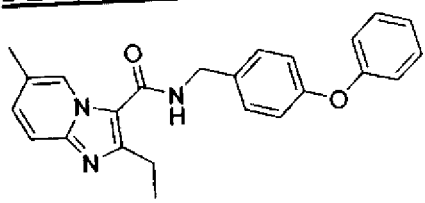

N-(4-tert-Butylbenzyl)-2-ethyl-6-methylimidazo[1,2-a]pyridine-3-carboxamide (64)
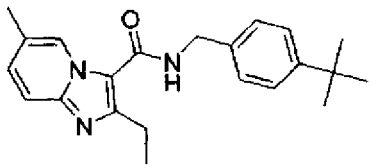
2-Ethyl-6-methyl-N-(4-(trifluoromethoxy)benzyl)imidazo[1,2-a]pyridine-3-carboxamide (65)
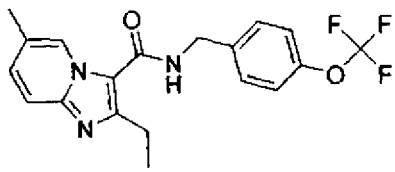
2-Ethyl-6-methyl-N-((1-methyl-1H-indol-5-yl)methyl)imidazo[1,2-a]pyridine-3-carboxamide (66)
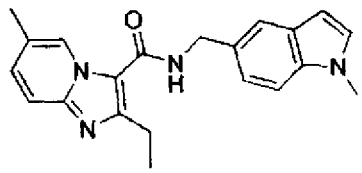
2-Ethyl-6-methyl-N-((1-methyl-1H-indol-6-yl)methyl)imidazo[1,2-a]pyridine-3-carboxamide (67)
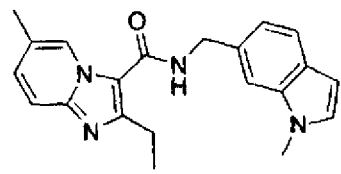
6-Chloro-N-(4-chlorobenzyl)-2-ethylimidazo[1,2-a]pyridine-3-carboxamide (70)
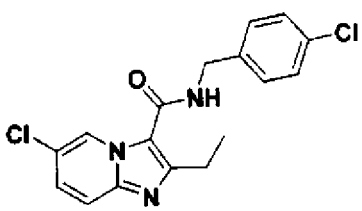

6-Chloro-2-methyl-N-(4-phenoxybenzyl)imidazo[1,2-a]pyridine-3-carboxamide (71)
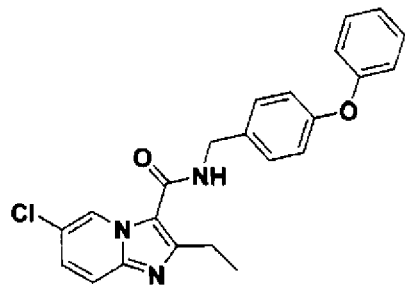
6-Chloro-2-methyl-N-(4-(trifluoromethoxy)benzyl)imidazo[1,2-a]pyridine-3-carboxamide (72)
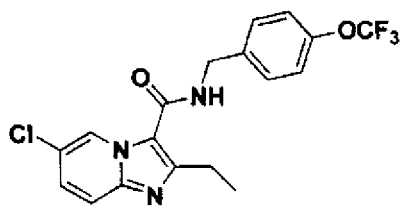
N-(4-tert-Butylbenzyl)-6-chloro-2-methylimidazo[1,2-a]pyridine-3-carboxamide (73)
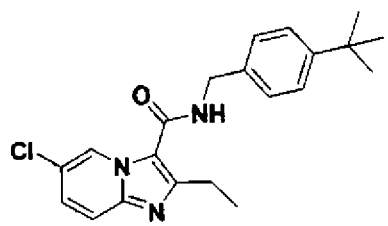
6-Chloro-N-(4-isopropoxybenzyl)-2-methylimidazo[1,2-a]pyridine-3-carboxamide (75)
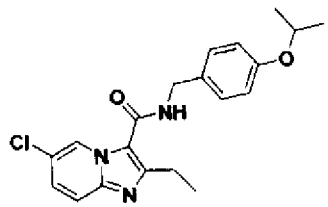

6-Chloro-N-(4-isobutoxybenzyl)-2-methylimidazo[1,2-a]pyridine-3-carboxamide (76)
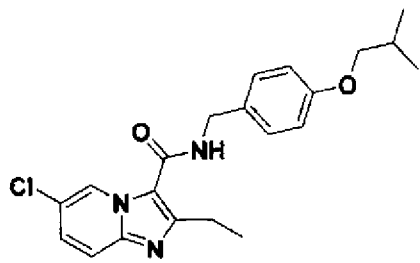
6-Chloro-2-methyl-N-((1-methyl-1H-indol-5-yl)methyl)imidazo[1,2-a]pyridine-3-carboxamide (77)
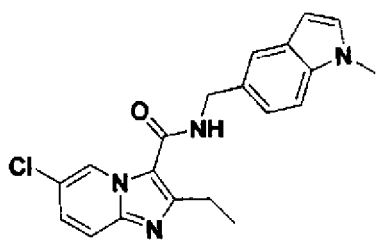
6-Chloro-2-methyl-N-((1-methyl-1H-indol-6-yl)methyl)imidazo[1,2-a]pyridine-3-carboxamide (78)
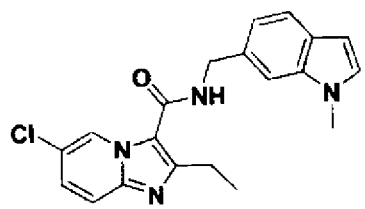
N-(Biphenyl-4-ylmethyl)-6-chloro-2-methylimidazo[1,2-a]pyridine-3-carboxamide (81)
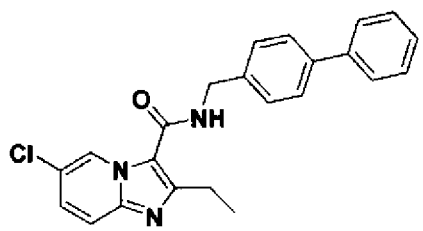

6-Chloro-N-((2'-chlorobiphenyl-4-yl)methyl)-2-ethylimidazo[1,2-a]pyridine-3-carboxamide (82)
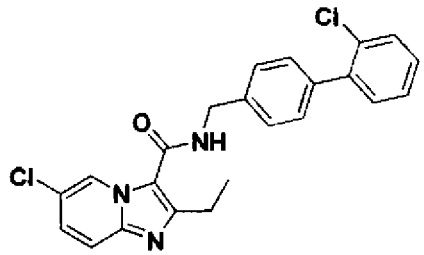
6-Chloro-N-((4'-chlorobiphenyl-4-yl)methyl)-2-ethylimidazo[1,2-a]pyridine-3-carboxamide (83)
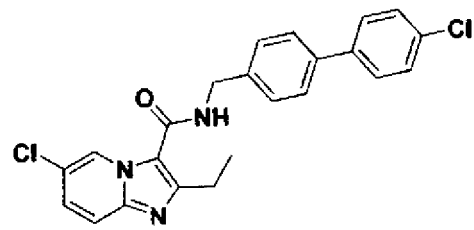
6-Chloro-2-ethyl-N-((2'-methylbiphenyl-4-yl)methyl)imidazo[1,2-a]pyridine-3-carboxamide (84)
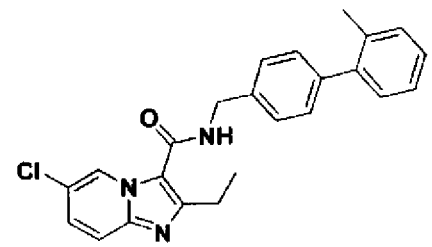
6-Chloro-2-ethyl-N-((3'-methylbiphenyl-4-yl)methyl)imidazo[1,2-a]pyridine-3-carboxamide (85)
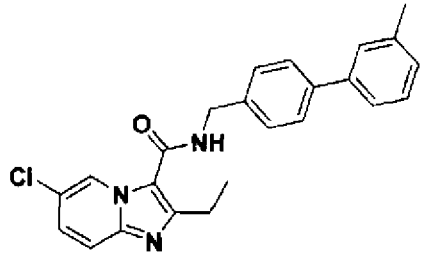

6-Chloro-2-ethyl-N-((4'-methylbiphenyl-4-yl)methyl)imidazo[1,2-a]pyridine-3-carboxamide (86)
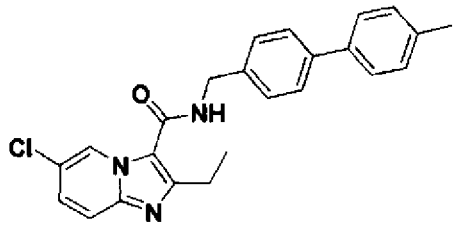
7-Chloro-N-(4-chlorobenzyl)-2-ethylimidazo[1,2-a]pyridine-3-carboxamide (87)
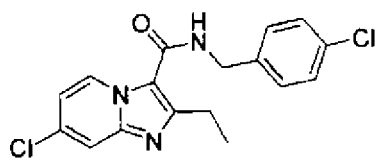
7-Chloro-2-ethyl-N-(4-hydroxybenzyl)imidazo[1,2-a]pyridine-3-carboxamide (88)
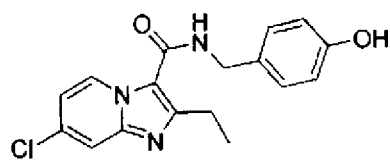
N-(4-tert-Butylbenzyl)-7-chloro-2-ethylimidazo[1,2-a]pyridine-3-carboxamide (92)
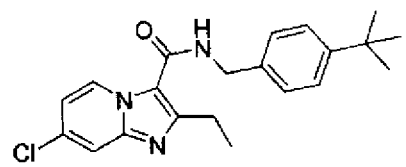
N-(Biphenyl-4-ylmethyl)-7-chloro-2-ethylimidazo[1,2-a]pyridine-3-carboxamide (93)
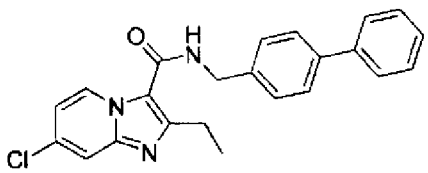

7-Chloro-N-((2'-chlorobiphenyl-4-yl)methyl)-2-ethylimidazo[1,2-a]pyridine-3-carboxamide (94)

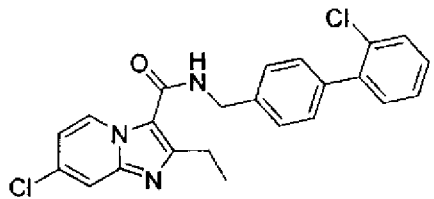

7-Chloro-N-((4'-chlorobiphenyl-4-yl)methyl)-2-ethylimidazo[1,2-a]pyridine-3-carboxamide (95)

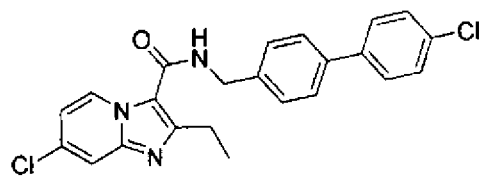

7-Chloro-2-ethyl-N-((2'-methylbiphenyl-4-yl)methyl)imidazo[1,2-a]pyridine-3-carboxamide (96)

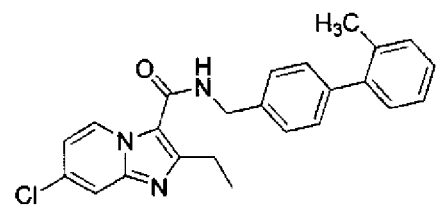

7-Chloro-2-ethyl-N-((3'-methylbiphenyl-4-yl)methyl)imidazo[1,2-a]pyridine-3-carboxamide (97)

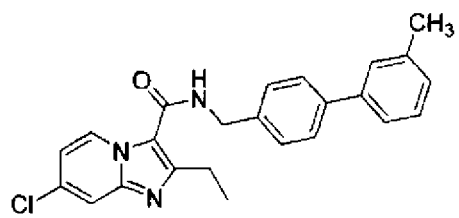

7-Chloro-2-ethyl-N-((4'-methylbiphenyl-4-yl)methyl)imidazo[1,2-a]pyridine-3-carboxamide (98)

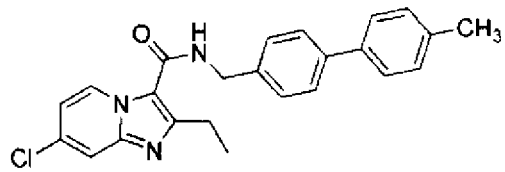

N-(Biphenyl-4-ylmethyl)-6-chloro-2-(trifluoromethyl)imidazo[1,2-a]pyridine-3-carboxamide (99)

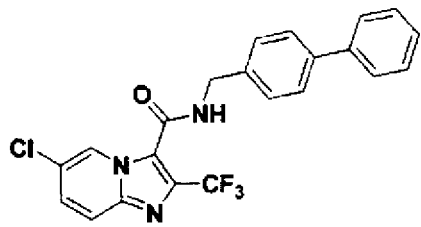

N-(4-tert-Butylbenzyl)-6-chloro-2-(trifluoromethyl)imidazo[1,2-a]pyridine-3-carboxamide (100)

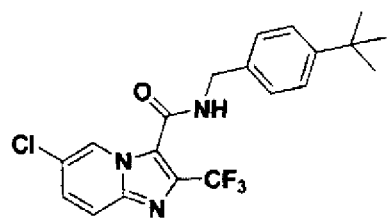

N-(4-Bromobenzyl)-7-chloro-2-ethylimidazo[1,2-a]pyridine-3-carboxamide (101)

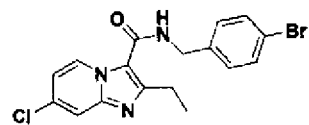

7-Chloro-2-ethyl-N-(4-(trifluoromethoxy)benzyl)imidazo[1,2-a]pyridine-3-carboxamide (102)

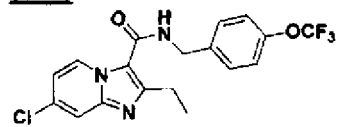

2-Ethyl-6-fluoro-N-(4-(trifluoromethoxy)benzyl)imidazo[1,2-a]pyridine-3-carboxamide (103)

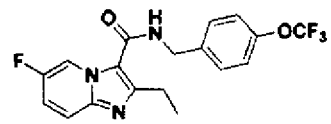

2-Ethyl-7-methoxy-N-(4-(trifluoromethoxy)benzyl)imidazo[1,2-a]pyridine-3-carboxamide (104)
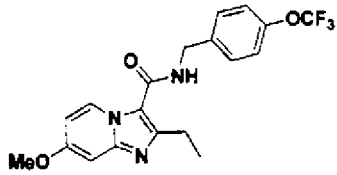
2-Ethyl-7-hydroxy-N-(4-(trifluoromethoxy)benzyl)imidazo[1,2-a]pyridine-3-carboxamide (105)
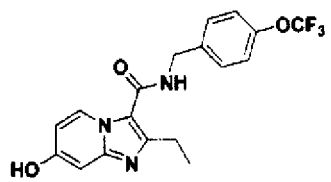
7-Chloro-2-ethyl-N-(4-(propylamino)benzyl)imidazo[1,2-a]pyridine-3-carboxamide (106)
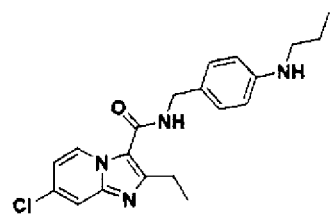
7-Chloro-2-ethyl-N-(4-(pentylamino)benzyl)imidazo[1,2-a]pyridine-3-carboxamide (107)
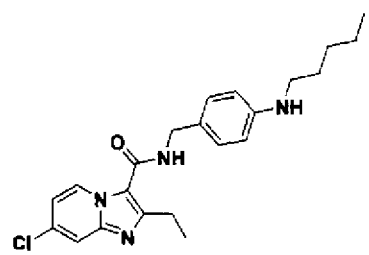
6-Chloro-2-ethyl-N-(4-(4-methylpiperazin-1-yl)benzyl)imidazo[1,2-a]pyridine-3-carboxamide (108)
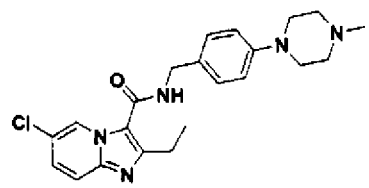

7-Chloro-2-ethyl-N-(4-(4-methylpiperazin-1-yl)benzyl)imidazo[1,2-a]pyridine-3-carboxamide (109)

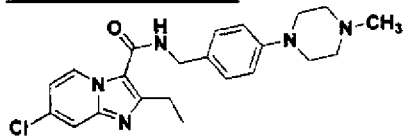

7-Chloro-2-ethyl-N-(4-(4-isopropylpiperazin-1-yl)benzyl)imidazo[1,2-a]pyridine-3-carboxamide (110)

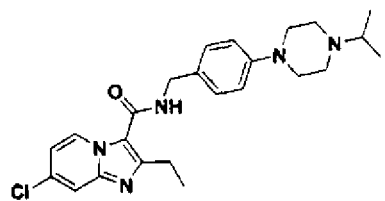

7-Chloro-2-ethyl-N-(4-(4-phenylpiperazin-1-yl)benzyl)imidazo[1,2-a]pyridine-3-carboxamide (111)

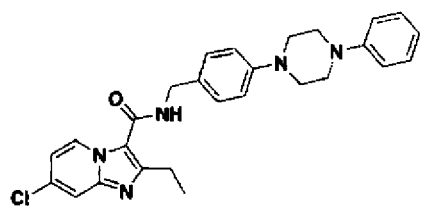

2-Ethyl-N-(4-(4-(4-fluorophenyl)piperazin-1-yl)benzyl)-6-methoxyimidazo[1,2-a]pyridine-3-carboxamide (112)

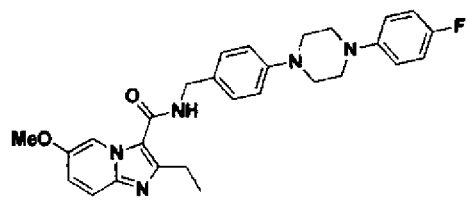

6-Chloro-2-ethyl-N-(4-(4-(4-fluorophenyl)piperazin-1-yl)benzyl)imidazo[1,2-a]pyridine-3-carboxamide (113)

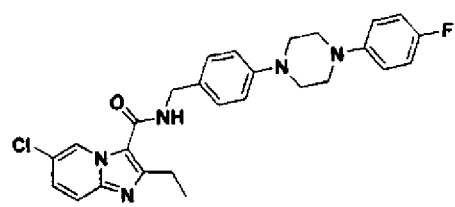

2-Ethyl-*N*-(4-(4-(4-fluorophenyl)piperazin-1-yl)benzyl)-7-methoxyimidazo[1,2-a]pyridine-3-carboxamide(114)

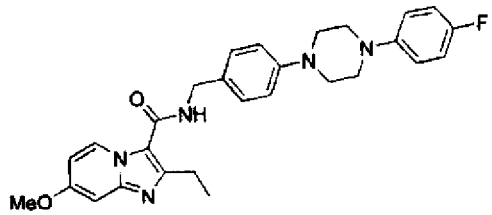

2-Ethyl-*N*-(4-(4-(4-fluorophenyl)piperazin-1-yl)benzyl)-8-methoxyimidazo[1,2-a]pyridine-3-carboxamide(115)

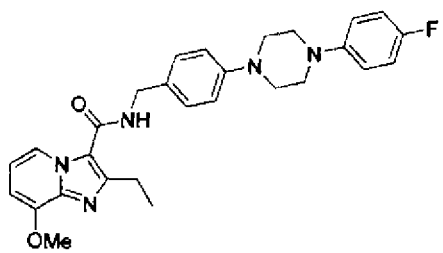

7-Chloro-2-ethyl-N-((4'-fluorobiphenyl-4-yl)methyl)imidazo[1,2-a]pyridine-3-carboxamide (116)

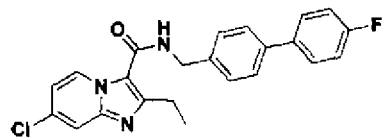

N-((4'-tert-Butylbiphenyl-4-yl)methyl)-7-chloro-2-ethylimidazo[1,2-a]pyridine-3-carboxamide (117)

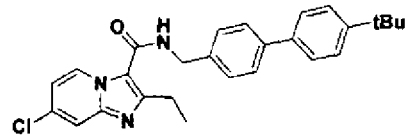

7-Chloro-2-ethyl-N-((4'-methoxybiphenyl-4-yl)methyl)imidazo[1,2-a]pyridine-3-carboxamide (118)

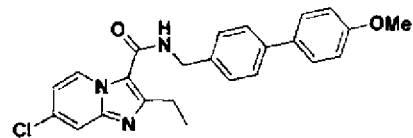

7-Chloro-2-ethyl-N-((4'-(trifluoromethoxy)biphenyl-4-yl)methyl)imidazo[1,2-a]pyridine-3-carboxamide (119)

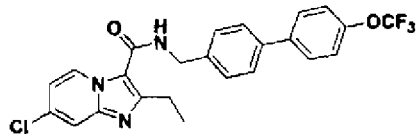

7-Chloro-2-ethyl-N-((4'-(trifluoromethyl)biphenyl-4-yl)methyl)imidazo[1,2-a]pyridine-3-carboxamide (120)

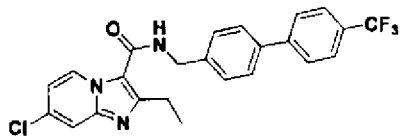

6-Chloro-N-((4'-cyanobiphenyl-4-yl)methyl)-2-ethylimidazo[1,2-a]pyridine-3-carboxamide (121)

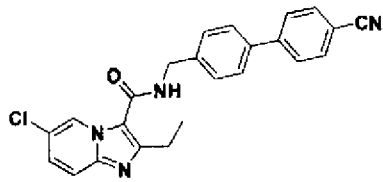

7-Chloro-N-((4'-cyanobiphenyl-4-yl)methyl)-2-ethylimidazo[1,2-a]pyridine-3-carboxamide (122)

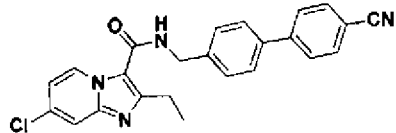

6-Chloro-2-ethyl-N-((2'-(trifluoromethyl)biphenyl-4-yl)methyl)imidazo[1,2-a]pyridine-3-carboxamide (123)

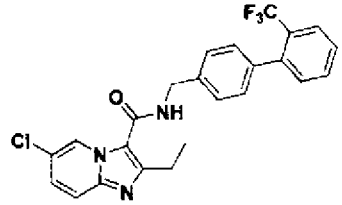

7-Chloro-2-ethyl-N-((2'-(trifluoromethyl)biphenyl-4-yl)methyl)imidazo[1,2-a]pyridine-3-carboxamide (124)

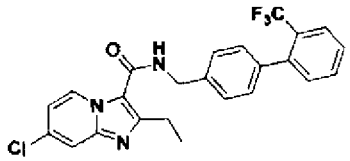

6-Chloro-N-((2'-cyanobiphenyl-4-yl)methyl)-2-ethylimidazo[1,2-a]pyridine-3-carboxamide (125)

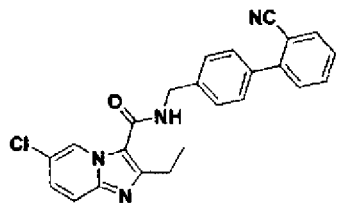

7-Chloro-N-((2'-cyanobiphenyl-4-yl)methyl)-2-ethylimidazo[1,2-a]pyridine-3-carboxamide (126)

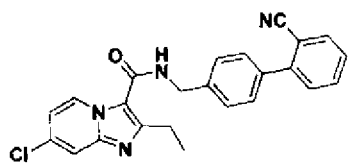

6-Chloro-N-((3'-cyanobiphenyl-4-yl)methyl)-2-ethylimidazo[1,2-a]pyridine-3-carboxamide (127)

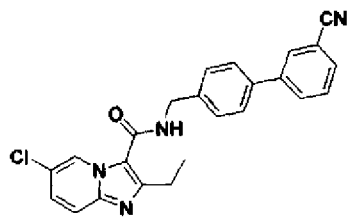

7-Chloro-N-((3'-cyanobiphenyl-4-yl)methyl)-2-ethylimidazo[1,2-a]pyridine-3-carboxamide (128)

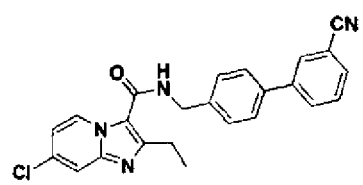

6-Chloro-N-((4'-chloro-2'-(trifluoromethyl)biphenyl-4-yl)methyl)-2-ethylimidazo[1,2-a]pyridine-3-carboxamide (129)

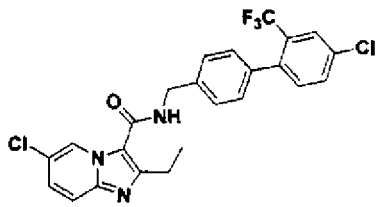

7-Chloro-N-((4'-chloro-2'-(trifluoromethyl)biphenyl-4-yl)methyl)-2-ethylimidazo[1,2-a]pyridine-3-carboxamide (130)

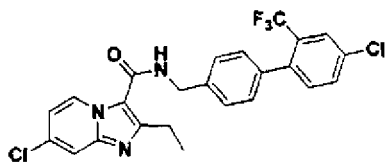

6-Chloro-N-((4'-cyano-2'-methylbiphenyl-4-yl)methyl)-2-ethylimidazo[1,2-a]pyridine-3-carboxamide (131)

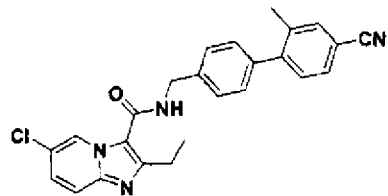

7-Chloro-N-((4'-cyano-2'-methylbiphenyl-4-yl)methyl)-2-ethylimidazo[1,2-a]pyridine-3-carboxamide (132)

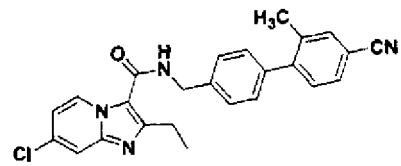

7-Chloro-N-((2'-chloro-4'-fluorobiphenyl-4-yl)methyl)-2-ethylimidazo[1,2-a]pyridine-3-carboxamide (133)

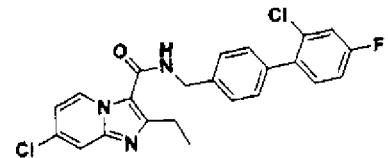

7-Chloro-2-ethyl-N-(4-(pyridin-4-yl)benzyl)imidazo[1,2-a]pyridine-3-carboxamide (134)
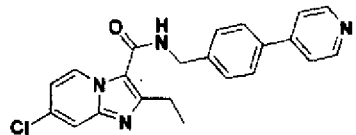
7-Chloro-2-ethyl-N-(4-(5-methoxypyridin-2-yl)benzyl)imidazo[1,2-a]pyridine-3-carboxamide (135)
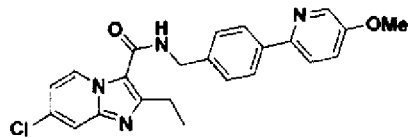
N-(4-(1H-Pyrrol-2-yl)benzyl)-7-chloro-2-ethylimidazo[1,2-a]pyridine-3-carboxamide (136)
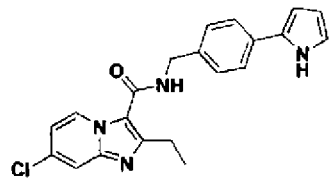
7-Chloro-2-ethyl-N-(4-(furan-2-yl)benzyl)imidazo[1,2-a]pyridine-3-carboxamide (137)
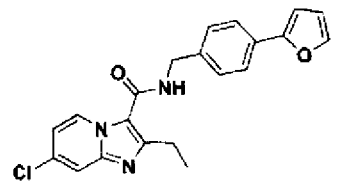
N-(4-(1H-Pyrrol-1-yl)benzyl)-7-chloro-2-ethylimidazo[1,2-a]pyridine-3-carboxamide (138)
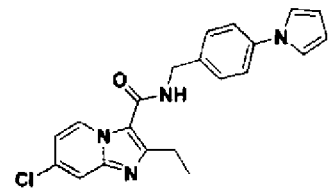

6-Chloro-2-ethyl-N-(4-(4-(4-(trifluoromethoxy)phenoxy)piperidin-1-yl)benzyl)imidazo-[1,2-a]pyridine-3-carboxamide (139)
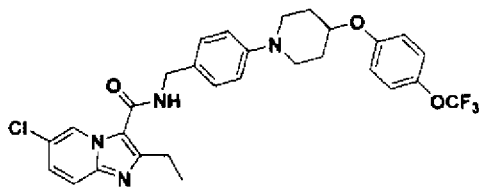
7-Chloro-2-ethyl-N-(4-(4-(4-(trifluoromethoxy)phenoxy)piperidin-1-yl)benzyl)imidazo-[1,2-a]pyridine-3-carboxamide (140)
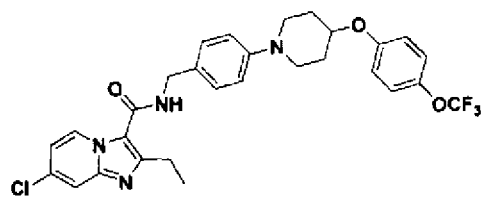
N-((4'-Chlorobiphenyl-4-yl)methyl)-2-ethylimidazo[1,2-a]pyrazine-3-carboxamide (141)
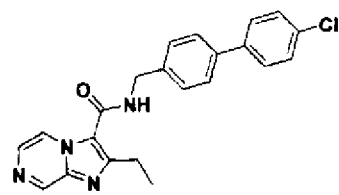
N-(4-(4-(4-(Butyramidomethyl)phenyl)piperazin-1-yl)benzyl)-7-chloro-2-ethylimidazo-[1,2-a]pyridine-3-carboxamide (144)
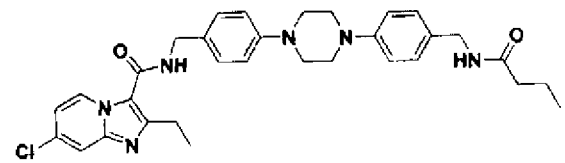

N-(4-tert-Butylbenzyl)-2-ethyl-7-(piperazin-1-yl)imidazo[1,2-a]pyridine-3-carboxamide (145)
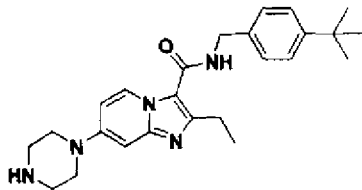
6-Chloro-N-(4-cyanobenzyl)-2-ethylimidazo[1,2-a]pyridine-3-carboxamide (146)
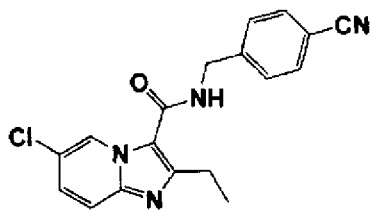
6-Chloro-2-ethyl-N-(4-(trifluoromethyl)benzyl)imidazo[1,2-a]pyridine-3-carboxamide (147)
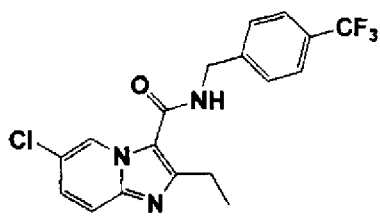
7-Chloro-2-ethyl-N-(4-(trifluoromethyl)benzyl)imidazo[1,2-a]pyridine-3-carboxamide (148)
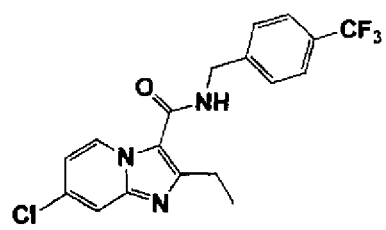
2-Ethyl-6-nitro-N-(4-(trifluoromethoxy)benzyl)imidazo[1,2-a]pyridine-3-carboxamide (149)
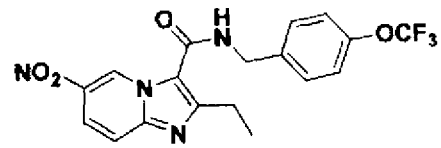

2-Ethyl-7-nitro-N-(4-(trifluoromethoxy)benzyl)imidazo[1,2-a]pyridine-3-carboxamide (150)

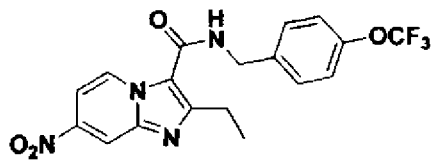

2-Ethyl-N-(4-(trifluoromethoxy)benzyl)-6-(trifluoromethyl)imidazo[1,2-a]pyridine-3-carboxamide (151)

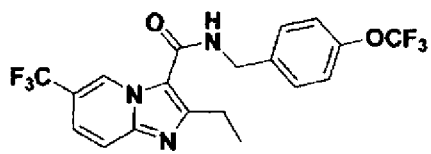

6-Bromo-2-ethyl-N-(4-(trifluoromethoxy)benzyl)imidazo[1,2-a]pyridine-3-carboxamide (152)

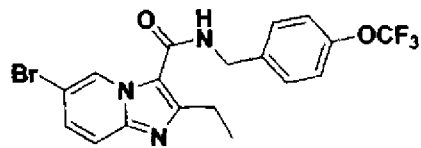

6,7-Dichloro-2-ethyl-N-(4-(trifluoromethoxy)benzyl)imidazo[1,2-a]pyridine-3-carboxamide (153)

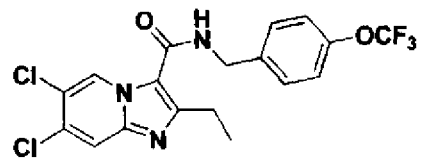

6-Chloro-2-methyl-N-(4-(trifluoromethoxy)benzyl)imidazo[1,2-a]pyridine-3-carboxamide (154)

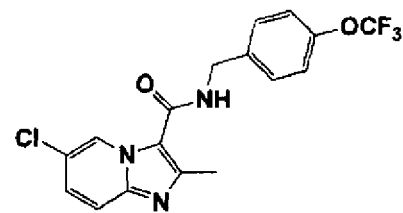

2-Ethyl-N-(4-(trifluoromethoxy)benzyl)imidazo[1,2-a]pyrazine-3-carboxamide (155)
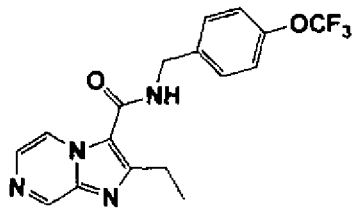
2-Ethyl-3-((4-(trifluoromethoxy)benzyl)carbamoyl)imidazo[1,2-a]pyrazine 7-oxide (156)
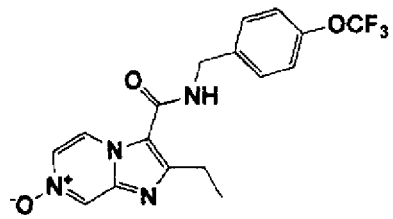
6-Chloro-2-ethyl-N-(4-methoxyphenethyl)imidazo[1,2-a]pyridine-3-carboxamide (157)
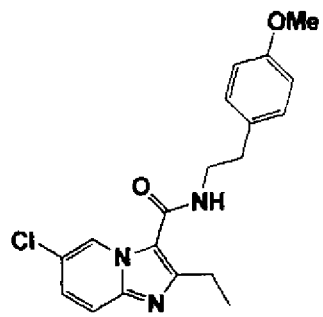
6-Chloro-N-(4-chlorophenethyl)-2-ethylimidazo[1,2-a]pyridine-3-carboxamide (158)
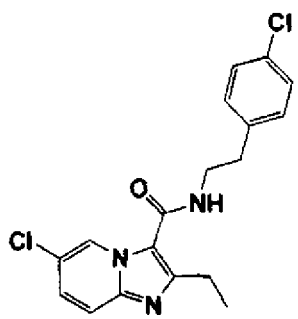

*N*-((4'-(Butyramidomethyl)biphenyl-4-yl)methyl)-7-chloro-2-ethylimidazo[1,2-a]pyridine-3-carboxamide (159)
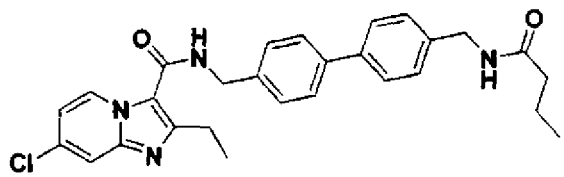
3-(((4'-Chloro-[1,1'-biphenyl]-4-yl)methyl)carbamoyl)-2-ethylimidazo[1,2-a]pyrazine 7-oxide (160)
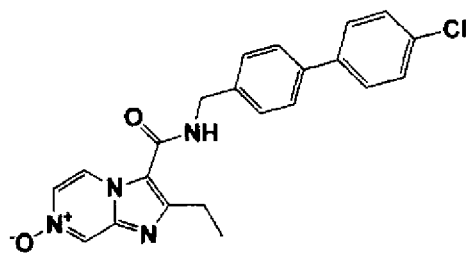
6-Chloro-N-(4-(4-(4-chlorophenoxy)piperidin-1-yl)benzyl)-2-ethylimidazo[1,2-a] pyridine-3-carboxamide (162)
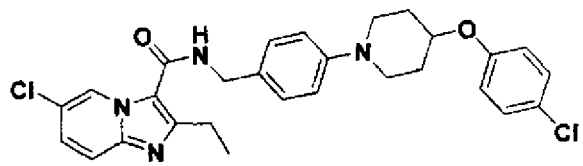
7-Chloro-N-(4-(4-(4-chlorophenoxy)piperidin-1-yl)benzyl)-2-ethylimidazo[1,2-a] pyridine-3-carboxamide (163)
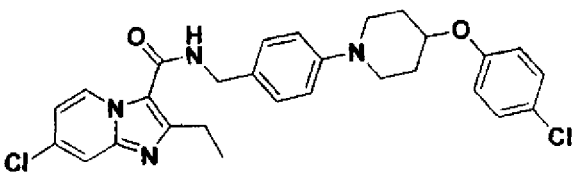

6-Chloro-2-ethyl-N-(4-(4-(4-(trifluoromethyl)phenoxy)piperidin-1-yl)benzyl) imidazo[1,2-a]pyridine-3-carboxamide (164)
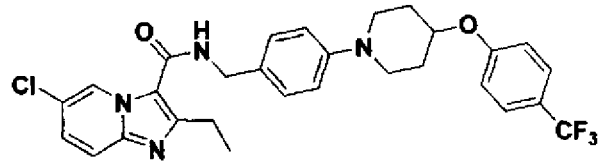
7-Chloro-2-ethyl-N-(4-(4-(4-(trifluoromethyl)phenoxy)piperidin-1-yl)benzyl) imidazo[1,2-a]pyridine-3-carboxamide (165)
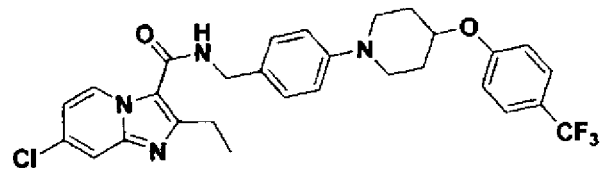
6-Chloro-2-ethyl-N-(4-(4-(4-fluorophenoxy)piperidin-1-yl)benzyl)imidazo[1,2-a] pyridine-3-carboxamide (166)
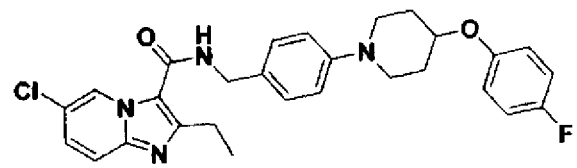
7-Chloro-2-ethyl-N-(4-(4-(4-fluorophenoxy)piperidin-1-yl)benzyl)imidazo[1,2-a]pyridine-3-carboxamide (167)
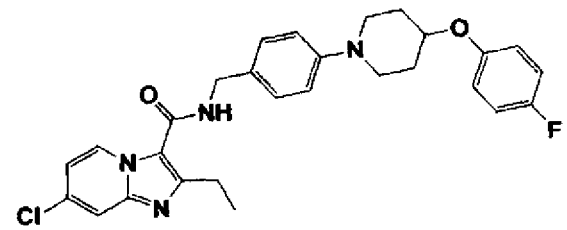

2-Ethyl-N-(4-(4-(4-(trifluoromethoxy)phenoxy)piperidin-1-yl)benzyl)-6-(trifluoromethyl)imidazo[1,2-a]pyridine-3-carboxamide (168)

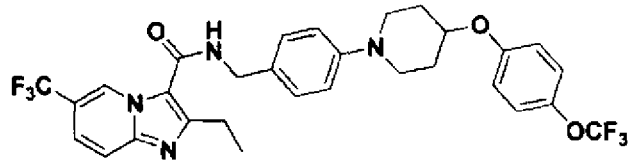

7-Chloro-N-(4-(4-(cyclopentyloxymethyl)piperidin-1-yl)benzyl)-2-ethylimidazo[1,2-a]pyridine-3-carboxamide(169)

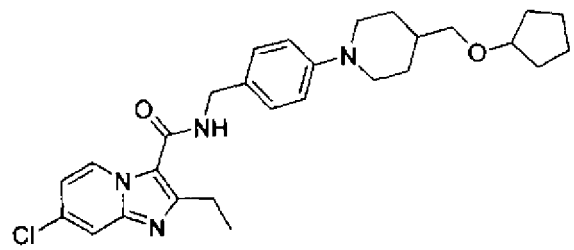

2-Ethyl-7-nitro-N-(4-(4-(4-(trifluoromethoxy)phenoxy)piperidin-1-yl)benzyl) imidazo[1,2-a]pyridine-3-carboxamide (170)

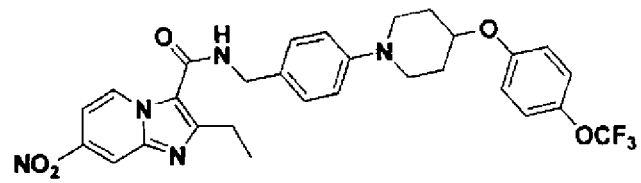

6-Chloro-2-ethyl-N-(4-(4-(4-fluorobenzyl)piperazin-1-yl)benzyl)imidazo[1,2-a]pyridine-3-carboxamide (171)

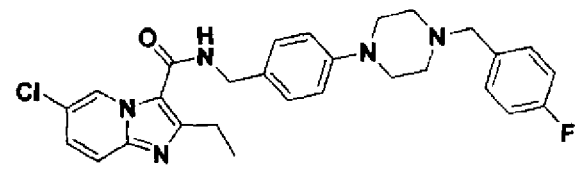

7-Chloro-2-ethyl-N-(4-(4-(4-fluorobenzyl)piperazin-1-yl)benzyl)imidazo[1,2-a]pyridine-3-carboxamide (172)
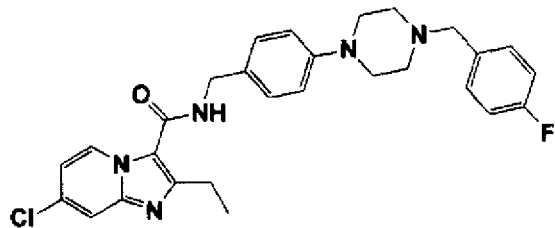
6-Chloro-2-ethyl-N-(4-(4-(4-(trifluoromethoxy)benzyl)piperazin-1-yl)benzyl)imidazo[1,2-a]pyridine-3-carboxamide (173)
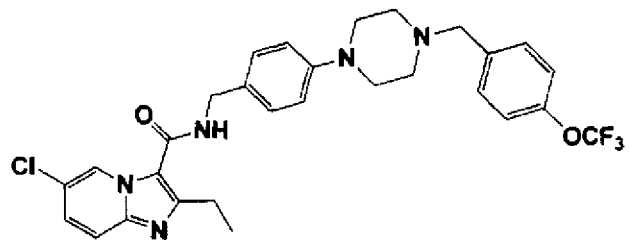
7-Chloro-2-ethyl-N-(4-(4-(4-(trifluoromethoxy)benzyl)piperazin-1-yl)benzyl)imidazo[1,2-a]pyridine-3-carboxamide (174)
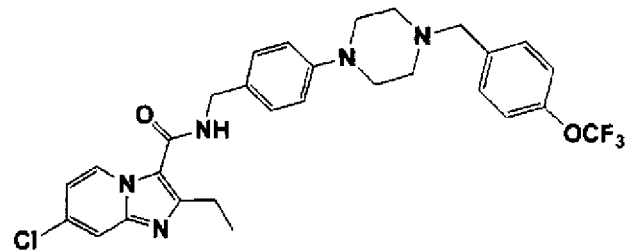
6,7-Dichloro-2-ethyl-N-(4-(4-(4-fluorobenzyl)piperazin-1-yl)benzyl)imidazo[1,2-a]pyridine-3-carboxamide (175)
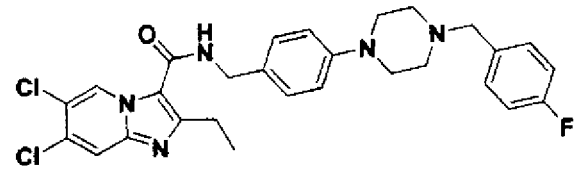

7-Chloro-2-ethyl-N-(4-(4-(4-fluorophenyl)piperazin-1-yl)benzyl)imidazo[1,2-a]pyridine-3-carboxamide (176)
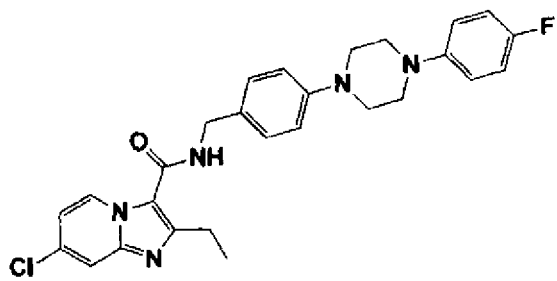
7-Chloro-2-ethyl-N-(4-(4-(4-fluorophenyl)piperazin-1-yl)benzyl)imidazo[1,2-a]pyridine-3-carboxamide trihydrochloride (177)
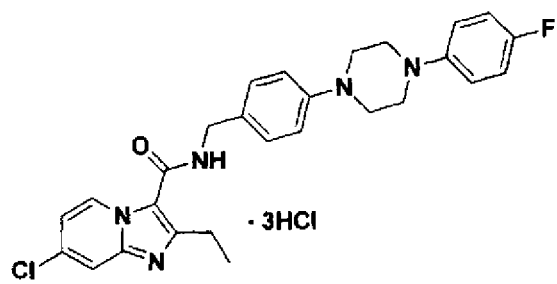
6-Chloro-2-ethyl-N-(4-(4-(4-(trifluoromethoxy)phenyl)piperazin-1-yl)benzyl)imidazo[1,2-a]pyridine-3-carboxamide (178)
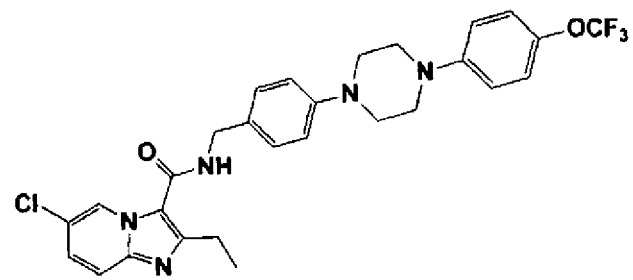

7-Chloro-2-ethyl-N-(4-(4-(4-(trifluoromethoxy)phenyl)piperazin-1-yl)benzyl)imidazo[1,2-a]pyridine-3-carboxamide (179)
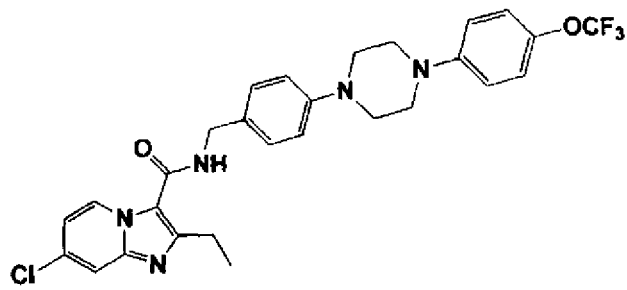
6,7-Dichloro-2-ethyl-N-(4-(4-(4-fluorophenyl)piperazin-1-yl)benzyl)imidazo[1,2-a]pyridine-3-carboxamide (180)
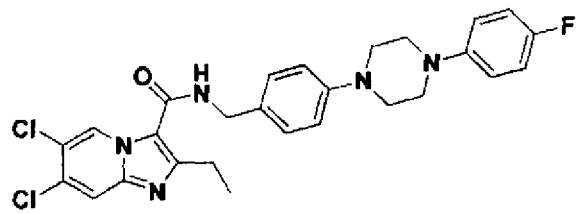
2-Ethyl-N-(4-(4-(4-(trifluoromethoxy)phenyl)piperazin-1-yl)benzyl)imidazo[1,2-a]pyridine-3-carboxamide (181)
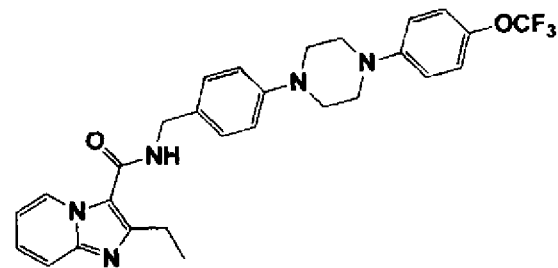

6-Chloro-2-ethyl-N-(4-(4-(4-fluorophenyl)piperazin-1-yl)benzyl)-N-methylimidazo[1,2-a]pyridine-3-carboxamide (182)
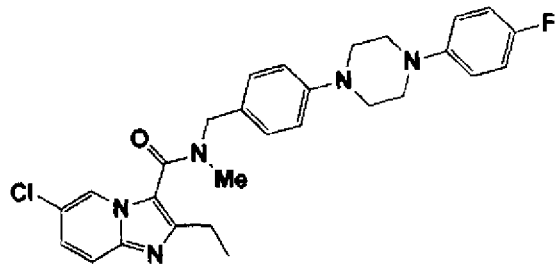
7-Chloro-N-(4-(4-((difluoromethoxy)methyl)piperidin-1-yl)benzyl)-2-ethylimidazo[1,2-a]pyridine-3-carboxamide (183)
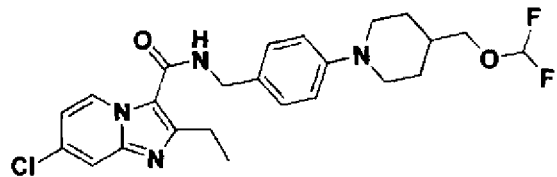
7-Chloro-2-ethyl-N-((4'-(hexanamidomethyl)biphenyl-4-yl)methyl)imidazo[1,2-a]pyridine-3-carboxamide (184)
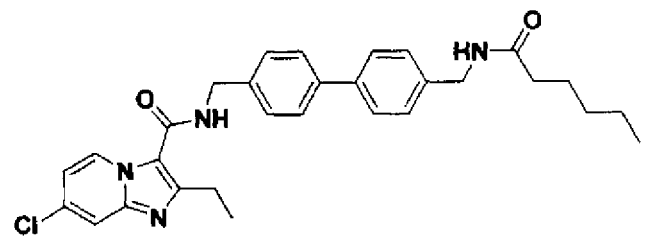
6-Chloro-2-ethyl-N-(4-(4-(trifluoromethoxy)phenoxy)benzyl)imidazo[1,2-a]pyridine-3-carboxamide (185)
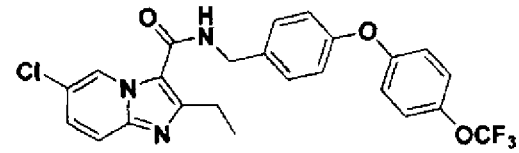

7-Chloro-2-ethyl-N-(4-(4-(trifluoromethoxy)phenoxy)benzyl)imidazo[1,2-a]pyridine-3-carboxamide (186)
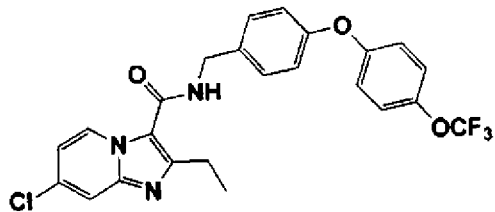
6-Chloro-2-ethyl-N-(4-(4-fluorophenoxy)benzyl)imidazo[1,2-a]pyridine-3-carboxamide (187)
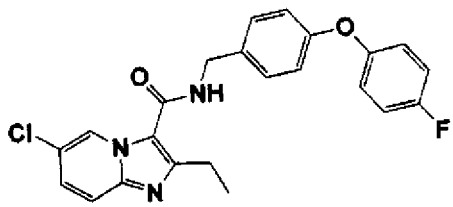
7-Chloro-2-ethyl-N-(4-(4-fluorophenoxy)benzyl)imidazo[1,2-a]pyridine-3-carboxamide (188)
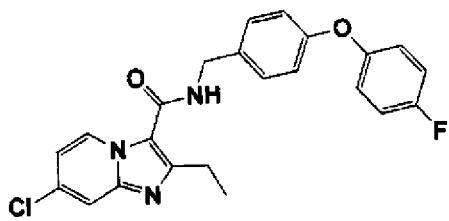
6-Bromo-2-ethyl-N-(4-(4-fluorophenoxy)benzyl)imidazo[1,2-a]pyridine-3-carboxamide (189)
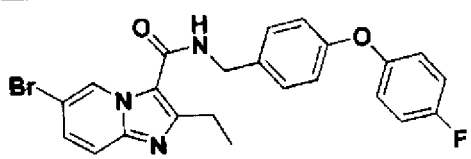

6-Chloro-N-(4-(4-chlorophenoxy)benzyl)-2-ethylimidazo[1,2-a]pyridine-3-carboxamide (190)
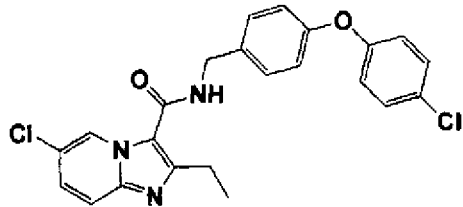
7-Chloro-N-(4-(4-chlorophenoxy)benzyl)-2-ethylimidazo[1,2-a]pyridine-3-carboxamide (191)
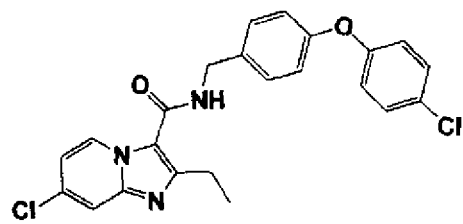
2-Ethyl-N-(4-(4-(trifluoromethoxy)phenoxy)benzyl)imidazo[1,2-a]pyridine-3-carboxamide (192)
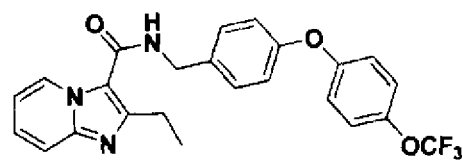
7-Chloro-2-ethyl-N-((6-(4-fluorophenoxy)pyridin-3-yl)methyl)imidazo[1,2-a]pyridine-3-carboxamide (193)
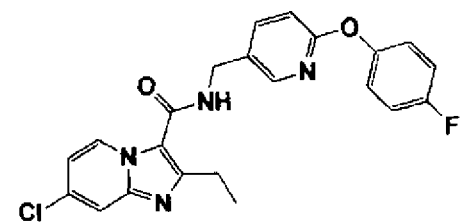

6-Chloro-2-ethyl-N-((6-(4-(trifluoromethoxy)phenoxy)pyridin-3-yl)methyl)imidazo[1,2-a]pyridine-3-carboxamide (194)
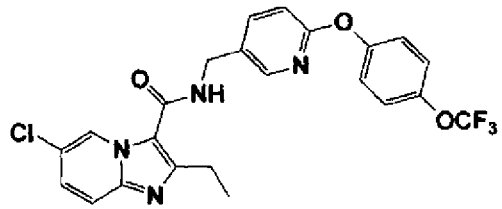
7-Chloro-2-ethyl-N-((6-(4-(trifluoromethoxy)phenoxy)pyridin-3-yl)methyl)imidazo[1,2-a]pyridine-3-carboxamide (195)
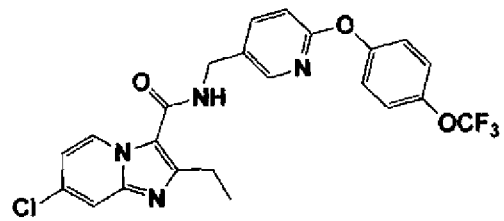
6-Chloro-2-ethyl-N-(4-(4-fluorophenoxy)benzyl)-N-methylimidazo[1,2-a]pyridine-3-carboxamide (197)
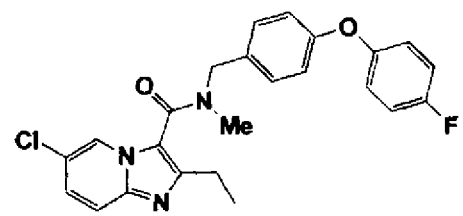
6-Chloro-2-ethyl-N-(4-(4-(trifluoromethoxy)phenylamino)benzyl)imidazo[1,2-a]pyridine-3-carboxamide (198)
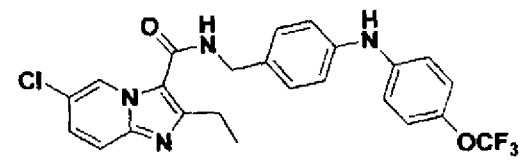

7-Chloro-2-ethyl-N-(4-(4-(trifluoromethoxy)phenylamino)benzyl)imidazo[1,2-a]pyridine-3-carboxamide (199)

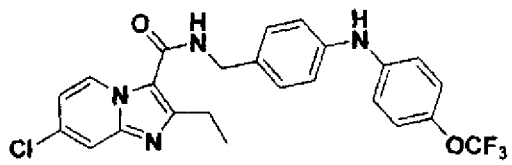

6-Chloro-2-ethyl-N-(4-(4-(trifluoromethyl)benzyloxy)benzyl)imidazo[1,2-a]pyridine-3-carboxamide (200)

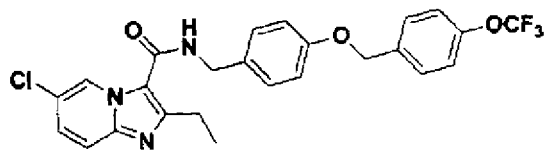

7-Chloro-2-ethyl-N-(4-(4-(trifluoromethyl)benzyloxy)benzyl)imidazo[1,2-a]pyridine-3-carboxamide (201)

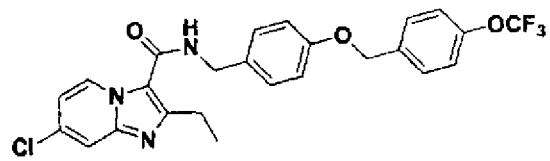

6-Chloro-2-ethyl-N-(4-(4-fluorobenzyloxy)benzyl)imidazo[1,2-a]pyridine-3-carboxamide (202)

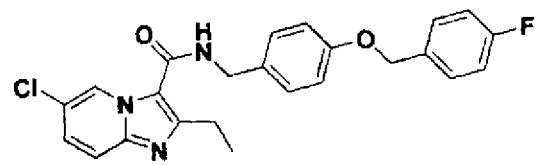

7-Chloro-2-ethyl-N-(4-(4-fluorobenzyloxy)benzyl)imidazo[1,2-a]pyridine-3-carboxamide (203)

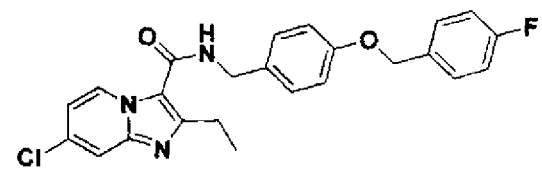

6-Chloro-2-ethyl-N-((2-(4-(trifluoromethoxy)phenyl)-1H-benzo[d]imidazol-5-yl)methyl)imidazo[1,2-a]pyridine-3-carboxamide (204)

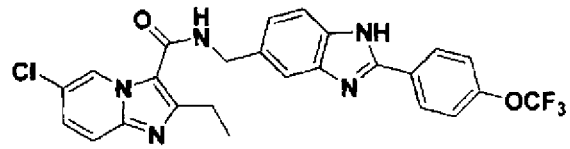

7-Chloro-2-ethyl-N-((2-(4-(trifluoromethoxy)phenyl)-1H-benzo[d]imidazol-5-yl)methyl)imidazo[1,2-a]pyridine-3-carboxamide (205)

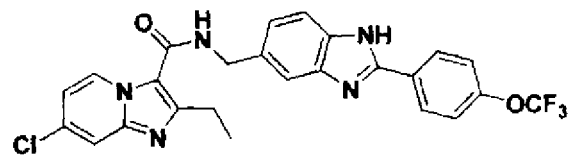

7-Chloro-2-ethyl-N-((2-(morpholinomethyl)-1H-benzo[d]imidazol-5-yl)methyl)imidazo[1,2-a]pyridine-3-carboxamide (206)

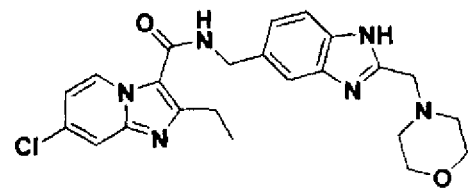

6-Chloro-2-ethyl-N-((2-(4-(trifluoromethoxy)phenyl)benzo[d]oxazol-5-yl)methyl)imidazo[1,2-a]pyridine-3-carboxamide (207)

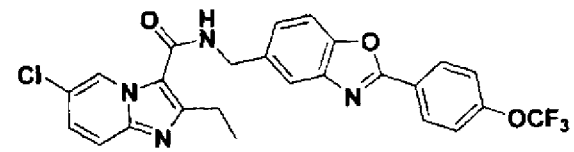

7-Chloro-2-ethyl-N-((2-(4-(trifluoromethoxy)phenyl)benzo[d]oxazol-5-yl)methyl)imidazo[1,2-a]pyridine-3-carboxamide (208)
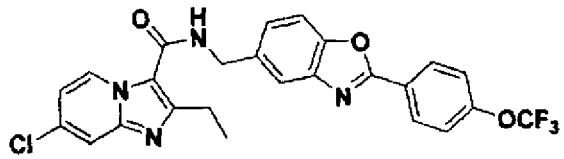
6-Chloro-N-(4-(2,6-dimethylmorpholino)benzyl)-2-ethylimidazo[1,2-a]pyridine-3-carboxamide (209)
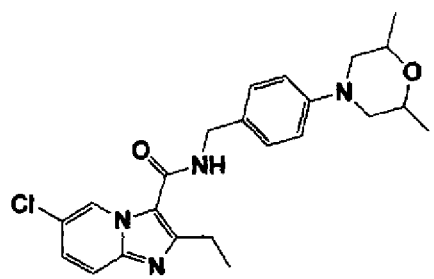
7-Chloro-N-(4-(2,6-dimethylmorpholino)benzyl)-2-ethylimidazo[1,2-a]pyridine-3-carboxamide (210)
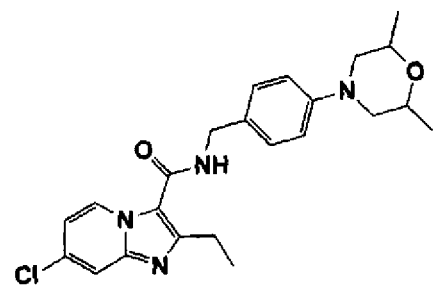
6-Chloro-2-ethyl-N-(4-(4-methylpiperidin-1-yl)benzyl)imidazo[1,2-a]pyridine-3-carboxamide (214)
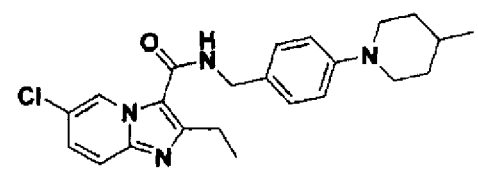

7-Chloro-2-ethyl-N-(4-(4-methylpiperidin-1-yl)benzyl)imidazo[1,2-a]pyridine-3-carboxamide (215)
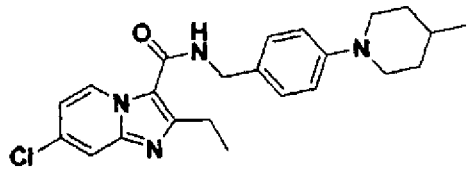
6-Chloro-N-(4-(3,5-dimethylpiperidin-1-yl)benzyl)-2-ethylimidazo[1,2-a]pyridine-3-carboxamide (216)
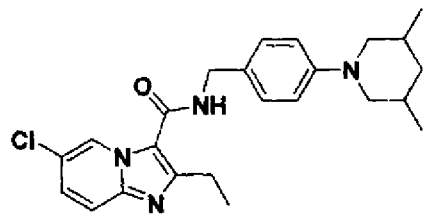
7-Chloro-N-(4-(3,5-dimethylpiperidin-1-yl)benzyl)-2-ethylimidazo[1,2-a]pyridine-3-carboxamide (217)
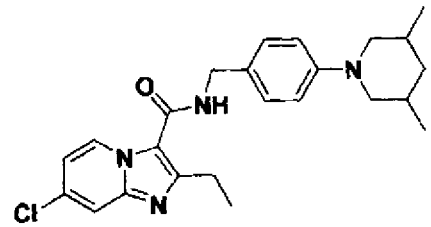
7-Chloro-2-ethyl-N-(4-(4-hydroxypiperidin-1-yl)benzyl)imidazo[1,2-a]pyridine-3-carboxamide (218)
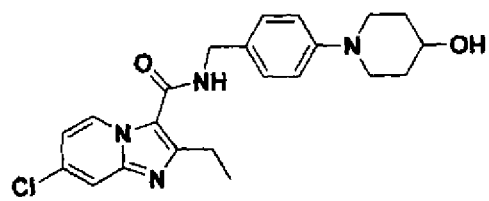

1-(4-((6-Chloro-2-ethylimidazo[1,2-a]pyridine-3-carboxamido)methyl)phenyl)piperidine-4-carboxylic acid (220)
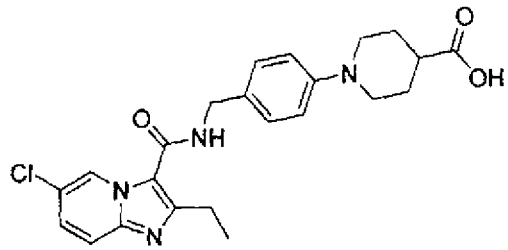
7-Chloro-N-(4-(3a,4-dihydro-1H-isoindol-2(3H,7H,7aH)-yl)benzyl)-2-ethylimidazo[1,2-a]pyridine-3-carboxamide (223)
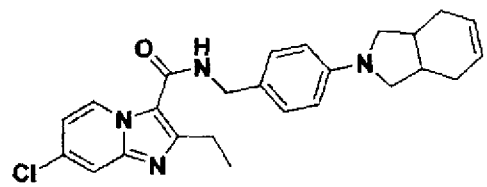
N-(4-(1H-isoindol-2(3H,3aH,4H,5H,6H,7H,7aH)-yl)benzyl)-7-chloro-2-ethylimidazo[1,2-a]pyridine-3-carboxamide (224)
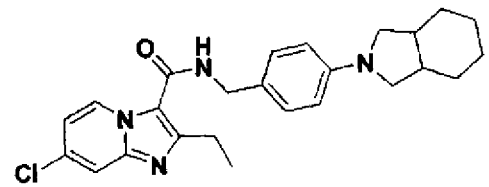
7-Chloro-2-ethyl-N-(4-(4,5,6,7-tetrahydro-2H-isoindol-2-yl)benzyl)imidazo[1,2-a]pyridine-3-carboxamide (225)
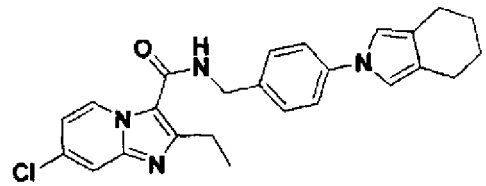

6-Chloro-2-ethyl-N-((1-(4-(trifluoromethoxy)benzyl)piperidin-4-yl)methyl)imidazo[1,2-a]pyridine-3-carboxamide (226)
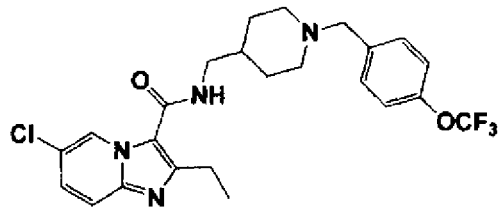
6-Chloro-2-ethyl-N-((1-(4-fluorobenzyl)piperidin-4-yl)methyl)imidazo[1,2-a]pyridine-3-carboxamide (227)
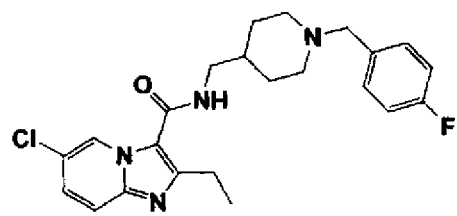
7-Chloro-2-ethyl-N-((1-(4-(trifluoromethoxy)benzyl)piperidin-4-yl)methyl)imidazo[1,2-a]pyridine-3-carboxamide (228)
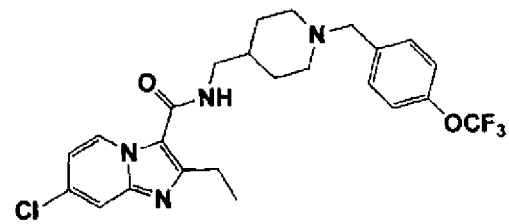
6-Chloro-2-ethyl-N-(1-(4-(trifluoromethoxy)benzyl)piperidin-4-yl)imidazo[1,2-a]pyridine-3-carboxamide (229)
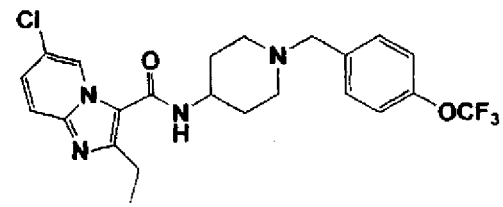

(6-Chloro-2-ethylimidazo[1,2-a]pyridin-3-yl)(4-(4-(trifluoromethoxy)benzyloxy) piperidin-1-yl)methanone (230)

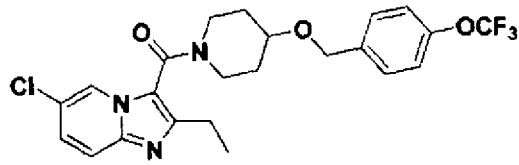

6-Chloro-2-ethyl-N-((1-(4-(trifluoromethoxy)phenyl)-1H-pyrazol-3-yl)methyl) imidazo[1,2-a]pyridine-3-carboxamide (231)

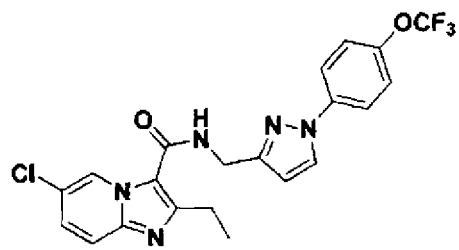

7-Chloro-2-ethyl-N-((1-(4-(trifluoromethoxy)phenyl)-1H-pyrazol-3-yl)methyl) imidazo[1,2-a]pyridine-3-carboxamide (232)

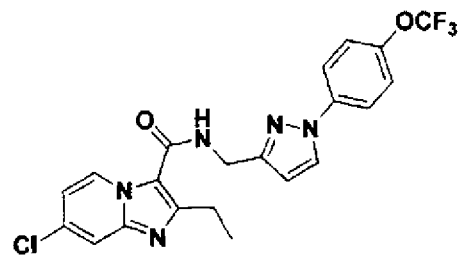

6-Chloro-2-ethyl-N-((1-(4-(trifluoromethyl)phenyl)-1H-pyrazol-3-yl)methyl)imidazo [1,2-a]pyridine-3-carboxamide (233)

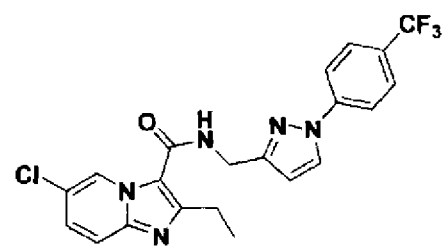

7-Chloro-2-ethyl-N-((1-(4-(trifluoromethyl)phenyl)-1H-pyrazol-3-yl)methyl)imidazo [1,2-a]pyridine-3-carboxamide (234)
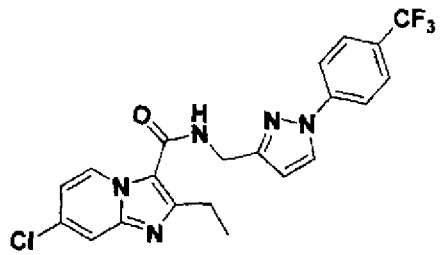
6-Chloro-2-ethyl-N-((1-(4-fluorophenyl)-1H-pyrazol-3-yl)methyl)imidazo[1,2-a] pyridine-3-carboxamide (235)
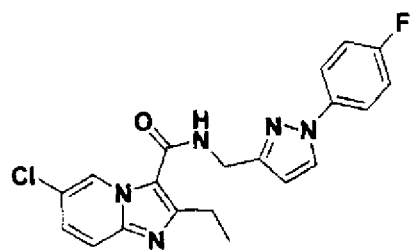
7-Chloro-2-ethyl-N-((1-(4-fluorophenyl)-1H-pyrazol-3-yl)methyl)imidazo[1,2-a] pyridine-3-carboxamide (236)
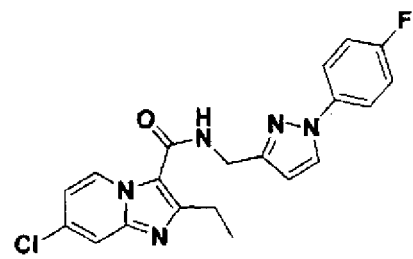
6-Chloro-2-ethyl-N-((1-(4-(trifluoromethoxy)phenyl)-4,5,6,7-tetrahydro-1H-indazol-4-yl)methyl)imidazo[1,2-a]pyridine-3-carboxamide (237)
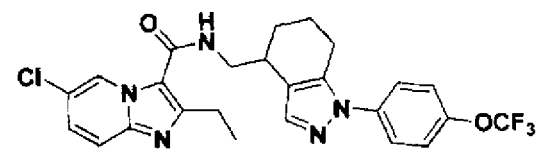

6-Chloro-2-ethyl-N-((1-(4-fluorophenyl)-4,5,6,7-tetrahydro-1H-indazol-4-yl)methyl)imidazo[1,2-a]pyridine-3-carboxamide (238)
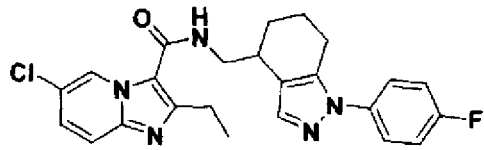
7-Chloro-2-ethyl-*N*-((4'-(trifluoromethoxy)biphenyl-3-yl)methyl)imidazo[1,2-a]pyridine-3-carboxamide (248)
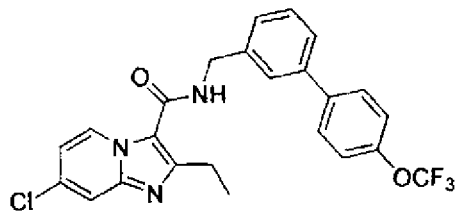
2-Ethyl-7-methyl-*N*-(4-(trifluoromethoxy)benzyl)imidazo[1,2-a]pyridine-3-carboxamide (249)
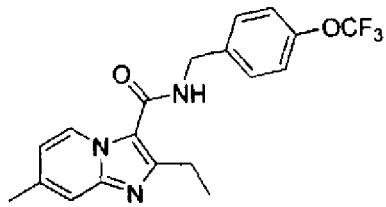
7-Bromo-2-ethyl-*N*-(4-(trifluoromethoxy)benzyl)imidazo[1,2-a]pyridine-3-carboxamide (250)
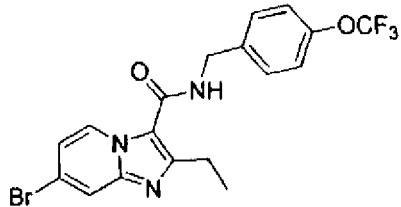

2-Ethyl-8-fluoro-*N*-(4-(trifluoromethoxy)benzyl)imidazo[1,2-a]pyridine-3-carboxamide(251)
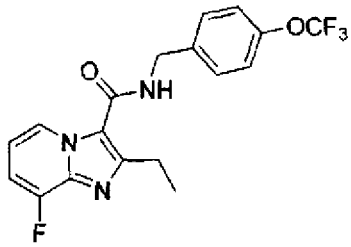
7-Chloro-2-ethyl-*N*-((4'-formylbiphenyl-4-yl)methyl)imidazo[1,2-a]pyridine-3-carboxamide(252)
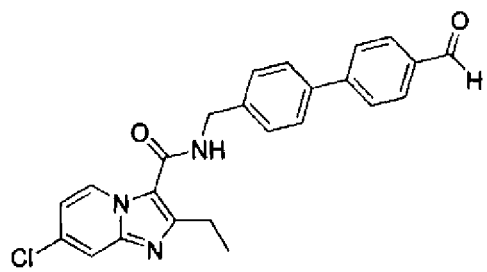
2-Ethyl-6-fluoro-N-(4-(4-(trifluoromethoxy)phenoxy)benzyl)imidazo[1,2-a]pyridine-3-carboxamide (253)
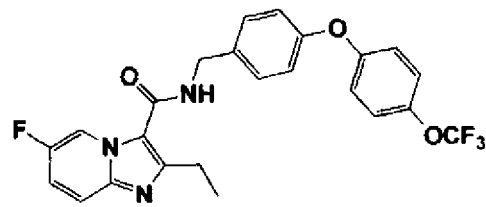
6-Bromo-2-ethyl-N-(4-(4-(trifluoromethoxy)phenoxy)benzyl)imidazo[1,2-a]pyridine-3-carboxamide (254)
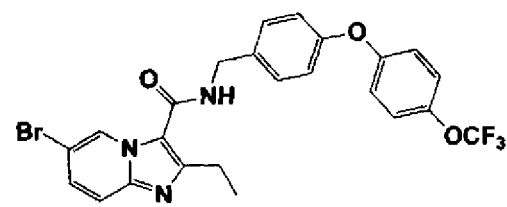

2-Ethyl-6-methyl-N-(4-(4-(trifluoromethoxy)phenoxy)benzyl)imidazo[1,2-a]pyridine-3-carboxamide (255)
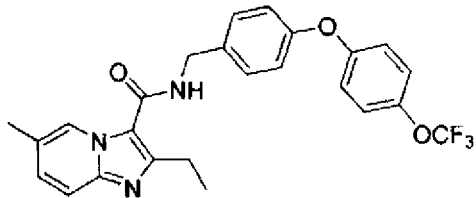
2-Ethyl-7-methyl-N-(4-(4-(trifluoromethoxy)phenoxy)benzyl)imidazo[1,2-a]pyridine-3-carboxamide (256)
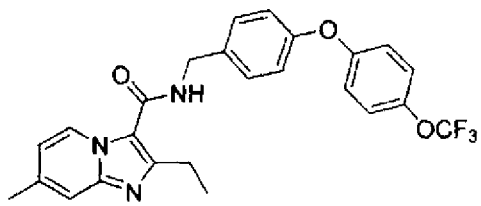
2-Ethyl-8-fluoro-N-(4-(4-(trifluoromethoxy)phenoxy)benzyl)imidazo[1,2-a]pyridine-3-carboxamide (257)
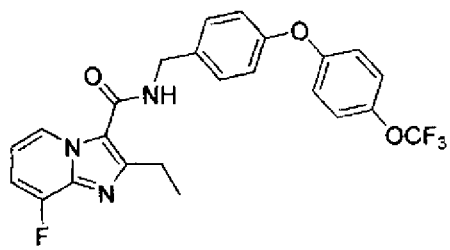
2-Ethyl-6-fluoro-N-(4-(4-(trifluoromethoxy)benzyloxy)benzyl)imidazo[1,2-a]pyridine-3-carboxamide (258)
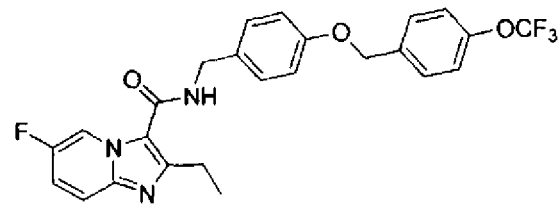

6-Bromo-2-ethyl-*N*-(4-(4-(trifluoromethoxy)benzyloxy)benzyl)imidazo[1,2-a]pyridine-3-carboxamide (259)
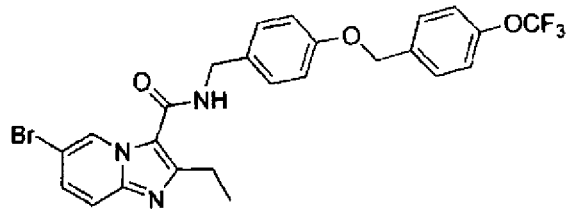
2-Ethyl-*N*-(4-(4-(trifluoromethoxy)benzyloxy)benzyl)imidazo[1,2-a]pyridine-3-carboxamide (260)
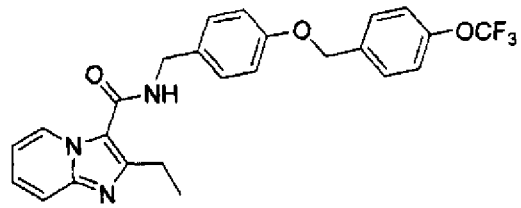
(E)-7-Chloro-2-ethyl-N-(4-((4-(trifluoromethoxy)benzylidene)amino)benzyl)imidazo[1,2-a]pyridine-3-carboxamide (261)
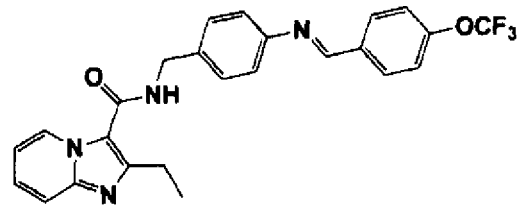
7-Chloro-2-ethyl-N-(4-((4-(trifluoromethoxy)benzyl)amino)benzyl)imidazo[1,2-a]pyridine-3-carboxamide (262)
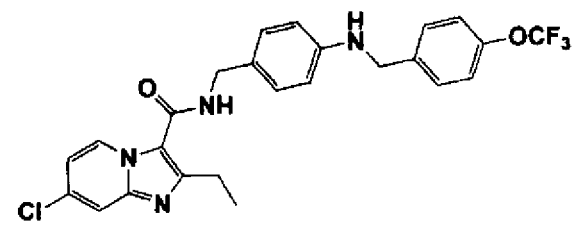

2-Ethyl-N-(4-(methyl(4-(trifluoromethoxy)benzyl)amino)benzyl)imidazo[1,2-a]pyridine-3-carboxamide (263)
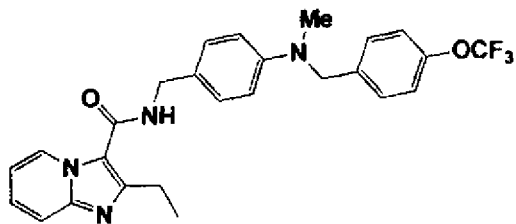
7-Chloro-2-ethyl-N-(4-(hexahydropyrrolo[1,2-a]pyrazin-2(1H)-yl)benzyl)imidazo[1,2-a]pyridine-3-carboxamide (265)
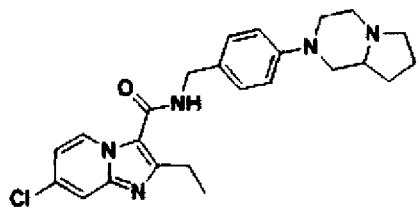
6-Chloro-2-ethyl-N-(4-(hexahydropyrrolo[1,2-a]pyrazin-2(1H)-yl)benzyl)imidazo[1,2-a]pyridine-3-carboxamide (266)
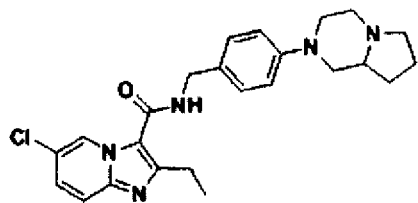
6-Chloro-2-ethyl-*N*-(4-(octahydroisoquinolin-2(1H)-yl)benzyl)imidazo[1,2-a]pyridine-3-carboxamide (267)
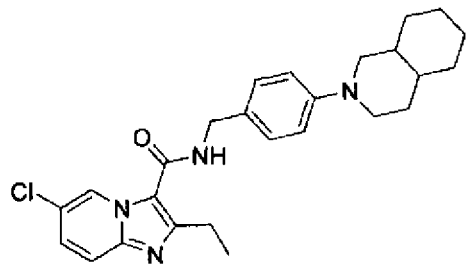

7-Chloro-2-ethyl-*N*-(4-(octahydroisoquinolin-2(1H)-yl)benzyl)imidazo[1,2-a]pyridine-3-carboxamide (268)
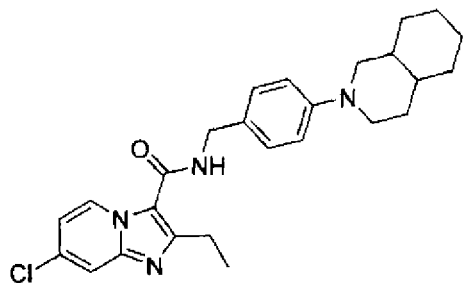
7-Chloro-2-ethyl-*N*-(4-(4-oxopiperidin-1-yl)benzyl)imidazo[1,2-a]pyridine-3-carboxamide (269)
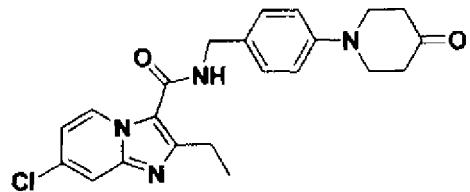
7-Chloro-2-ethyl-*N*-(4-(4-oxo-3,4-dihydropyridin-1(2H)-yl)benzyl)imidazo[1,2-a]pyridine-3-carboxamide (270)
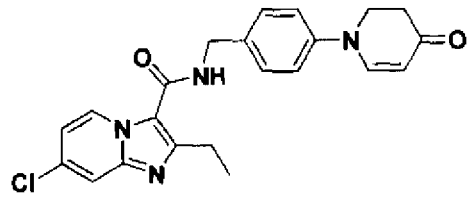
7-Chloro-2-ethyl-*N*-(4-(4-methylenepiperidin-1-yl)benzyl)imidazo[1,2-a]pyridine-3-carboxamide (271)
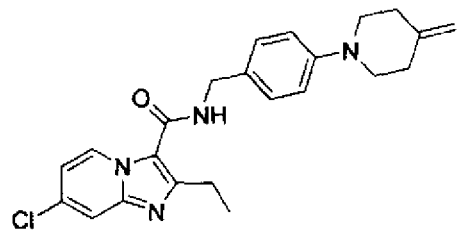

6-chloro-2-ethyl-*N*-(4-(2-methylpiperidin-1-yl)benzyl)imidazo[1,2-a]pyridine-3-carboxamide (272)
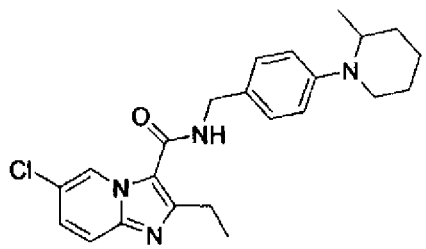
7-chloro-2-ethyl-*N*-(4-(2-methylpiperidin-1-yl)benzyl)imidazo[1,2-a]pyridine-3-carboxamide (273)
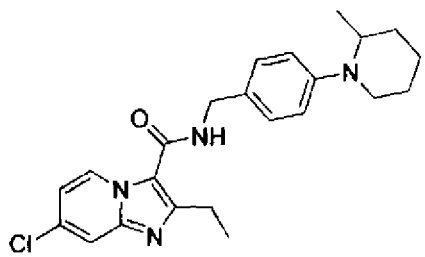
7-Chloro-*N*-(4-(4,4-dimethylpiperidin-1-yl)benzyl)-2-ethyl-1,8a-dihydroimidazo[1,2-a]pyridine-3-carboxamide (274)
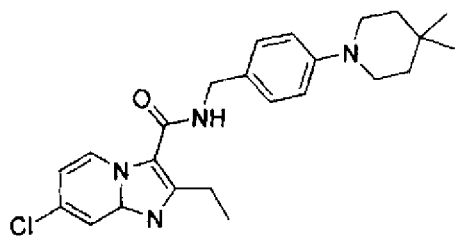
6-Chloro-2-ethyl-*N*-(4-(4-(trifluoromethyl)piperidin-1-yl)benzyl)imidazo[1,2-a]pyridine-3-carboxamide (275)
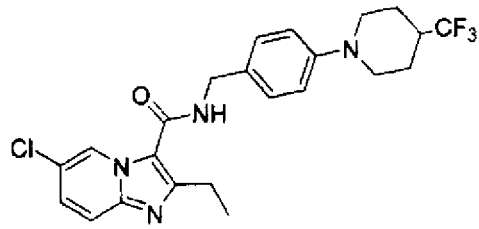

7-Chloro-2-ethyl-*N*-(4-(4-(trifluoromethyl)piperidin-1-yl)benzyl)imidazo[1,2-a]pyridine-3-carboxamide (276)
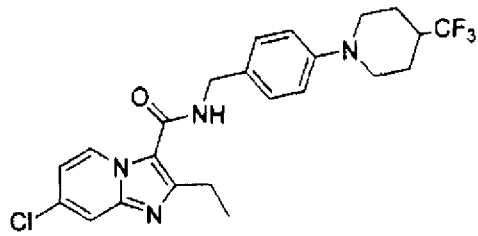
6-chloro-N-(4-(4,4-difluoropiperidin-1-yl)benzyl)-2-ethylimidazo[1,2-a]pyridine-3-carboxamide (277)
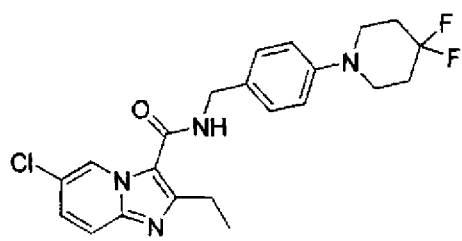
7-Chloro-*N*-(4-(4,4-difluoropiperidin-1-yl)benzyl)-2-ethylimidazo[1,2-a]pyridine-3-carboxamide (278)
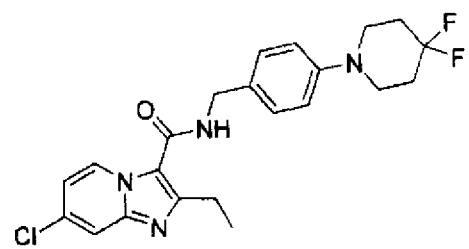
6-Chloro-2-ethyl-*N*-(4-(4-(hydroxymethyl)piperidin-1-yl)benzyl)imidazo[1,2-a]pyridine-3-carboxamide (279)
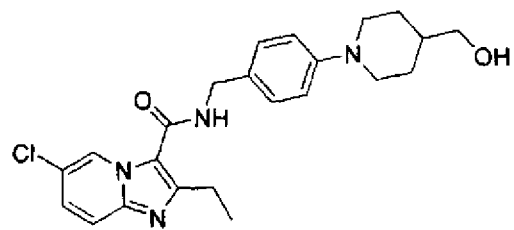

7-Chloro-2-ethyl-*N*-(4-(4-(hydroxymethyl)piperidin-1-yl)benzyl)imidazo[1,2-a]pyridine-3-carboxamide (280)
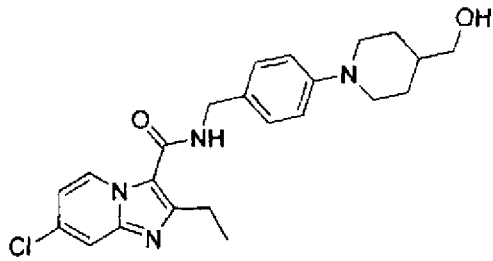
6-Chloro-2-ethyl-*N*-(4-(4-(methoxymethyl)piperidin-1-yl)benzyl)imidazo[1,2-a]pyridine-3-carboxamide (281)
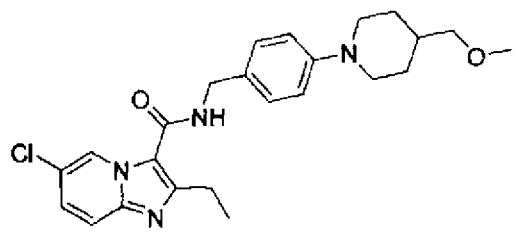
7-Chloro-2-ethyl-*N*-(4-(4-(methoxymethyl)piperidin-1-yl)benzyl)imidazo[1,2-a]pyridine-3-carboxamide (282)
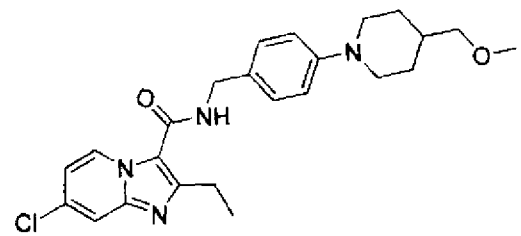
7-Chloro-2-ethyl-*N*-(4-(4-phenylpiperidin-1-yl)benzyl)imidazo[1,2-a]pyridine-3-carboxamide (283)
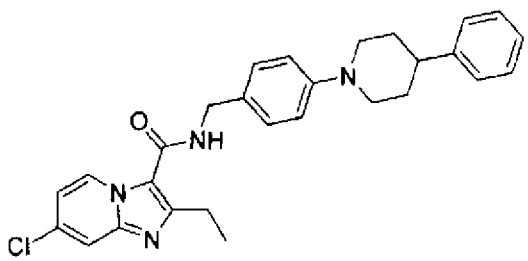

6-Chloro-2-ethyl-*N*-(4-(4-phenylpiperidin-1-yl)benzyl)imidazo[1,2-a]pyridine-3-carboxamide (284)
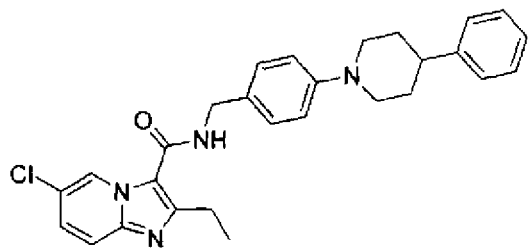
2-Ethyl-*N*-(4-(4-(4-fluorophenyl)piperidin-1-yl)benzyl)imidazo[1,2-a]pyridine-3-carboxamide (285)
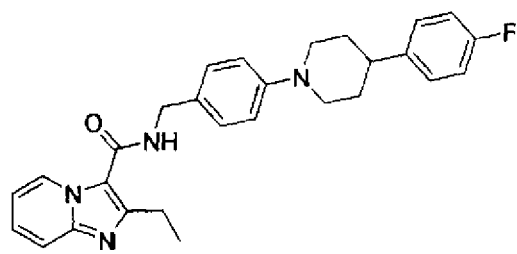
6-Chloro-2-ethyl-*N*-(4-(4-(4-fluorophenyl)piperidin-1-yl)benzyl)imidazo[1,2-a]pyridine-3-carboxamide (286)
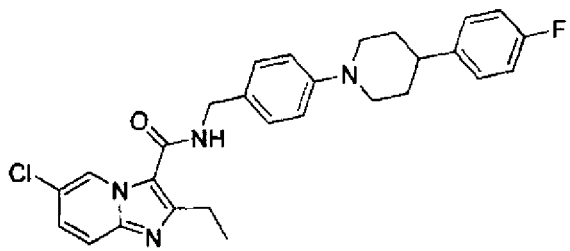
7-Chloro-2-ethyl-*N*-(4-(4-(4-fluorophenyl)piperidin-1-yl)benzyl)imidazo[1,2-a]pyridine-3-carboxamide (287)
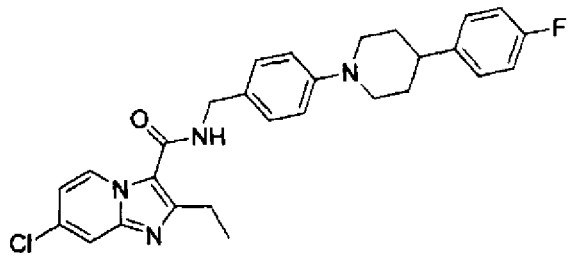

2-Ethyl-*N*-(4-(4-(4-(trifluoromethoxy)phenyl)piperidin-1-yl)benzyl)imidazo[1,2-a]pyridine-3-carboxamide(288)

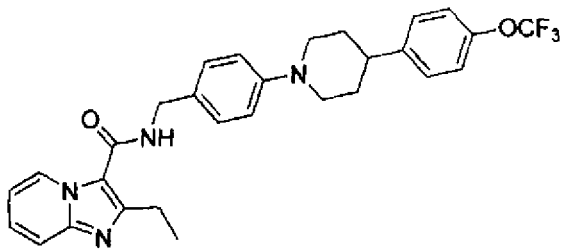

6-Chloro-2-ethyl-*N*-(4-(4-(4-(trifluoromethoxy)phenyl)piperidin-1-yl)benzyl)imidazo[1,2-a]pyridine-3-carboxamide (289)

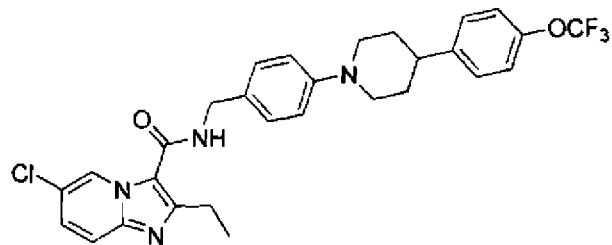

7-Chloro-2-ethyl-*N*-(4-(4-(4-(trifluoromethoxy)phenyl)piperidin-1-yl)benzyl)imidazo[1,2-a]pyridine-3-carboxamide(290)

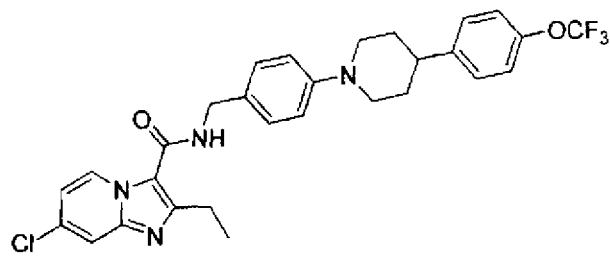

6-Chloro-2-ethyl-*N*-(4-(4-(isopropoxymethyl)piperidin-1-yl)benzyl)imidazo[1,2-a]pyridine-3-carboxamide(291)

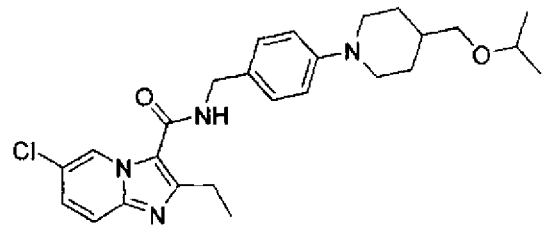

7-Chloro-2-ethyl-*N*-(4-(4-(isopropoxymethyl)piperidin-1-yl)benzyl)imidazo[1,2-a]pyridine-3-carboxamide(292)
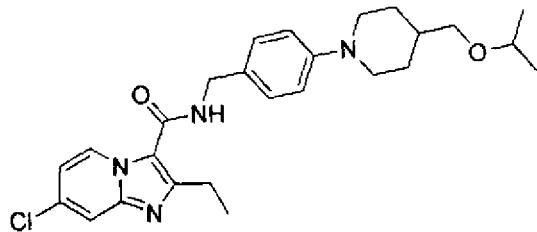
6-Chloro-*N*-(4-(4-(cyclopentyloxymethyl)piperidin-1-yl)benzyl)-2-ethylimidazo[1,2-a]pyridine-3-carboxamide(293)
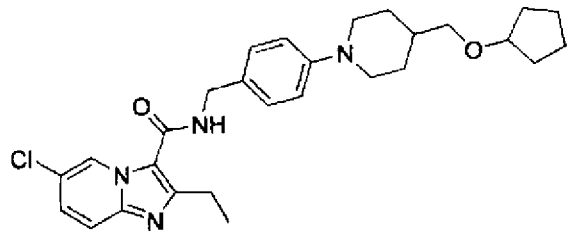
*N*-(4-(4-Benzylpiperidin-1-yl)benzyl)-7-chloro-2-ethylimidazo[1,2-a]pyridine-3-carboxamide (294)
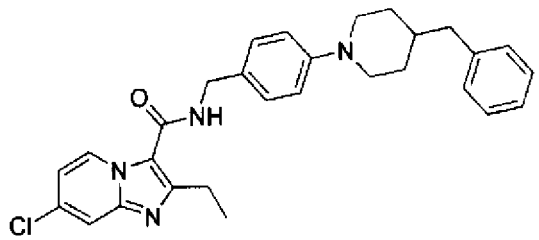
2-Ethyl-N-(4-(4-((4-fluorophenoxy)methyl)piperidin-1-yl)benzyl)imidazo[1,2-a]pyridine-3-carboxamide (295)
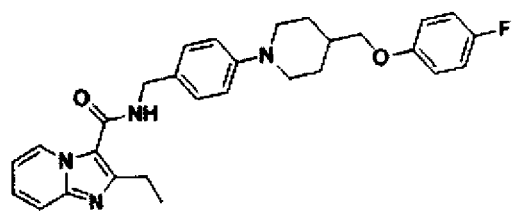

6-Chloro-2-ethyl-N-(4-(4-((4-fluorophenoxy)methyl)piperidin-1-yl)benzyl)imidazo[1,2-a]pyridine-3-carboxamide (296)

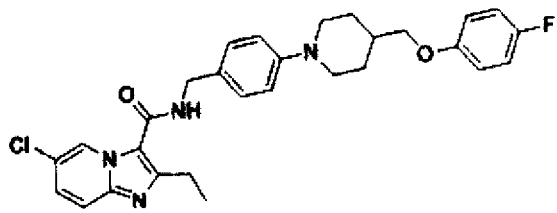

7-Chloro-2-ethyl-N-(4-(4-((4-fluorophenoxy)methyl)piperidin-1-yl)benzyl)imidazo[1,2-a]pyridine-3-carboxamide (297)

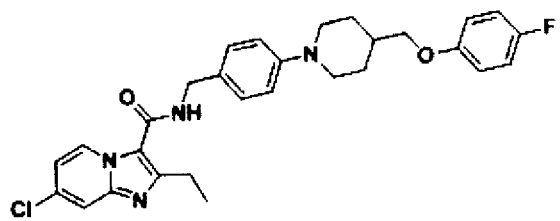

6-chloro-2-ethyl-*N*-(4-(4-((4-(trifluoromethoxy)phenoxy)methyl)piperidin-1-yl)benzyl)imidazo[1,2-a]pyridine-3-carboxamide (298)

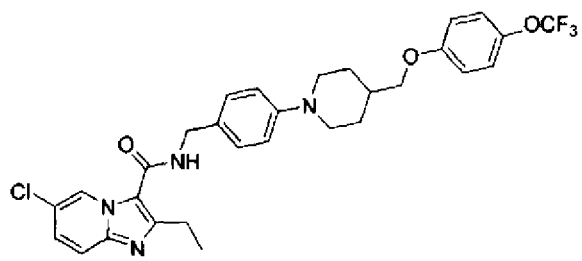

7-Chloro-2-ethyl-*N*-(4-(4-((4-(trifluoromethoxy)phenoxy)methyl)piperidin-1-yl)benzyl)imidazo[1,2-a]pyridine-3-carboxamide (299)

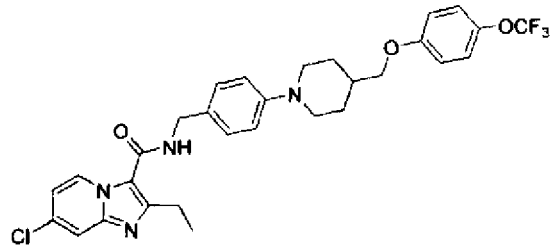

Ethyl 1-(4-((6-chloro-2-ethylimidazo[1,2-a]pyridine-3-carboxamido)methyl)phenyl) piperidine-4-carboxylate (300)
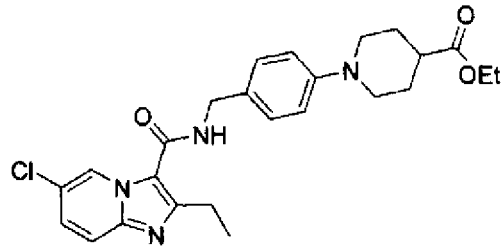
Ethyl 1-(4-((7-chloro-2-ethylimidazo[1,2-a]pyridine-3-carboxamido)methyl)phenyl) piperidine-4-carboxylate (301)
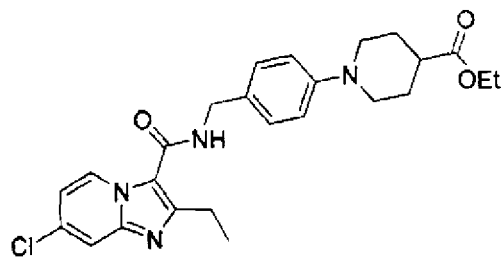
1-(4-((7-Chloro-2-ethylimidazo[1,2-a]pyridine-3-carboxamido)methyl)phenyl) piperidine-4-carboxylic acid (302)
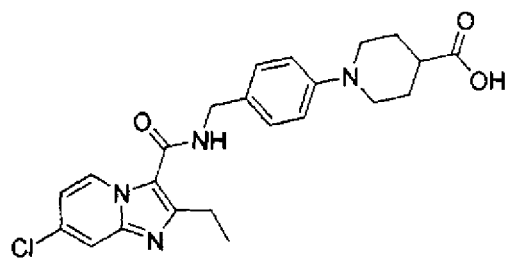
2-Ethyl-N-(4-(4-(4-fluorophenyl)piperazin-1-yl)benzyl)imidazo[1,2-a]pyridine-3-carboxamide (303)
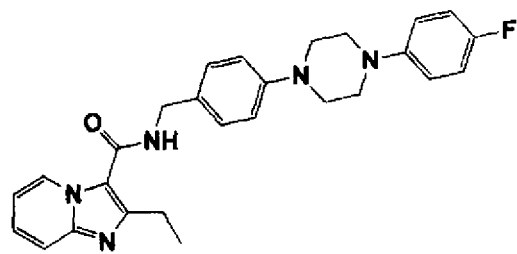

8-(Difluoromethoxy)-2-ethyl-N-(4-(4-(4-fluorophenyl)piperazin-1-yl)benzyl)imidazo[1,2-a]pyridine-3-carboxamide (304)
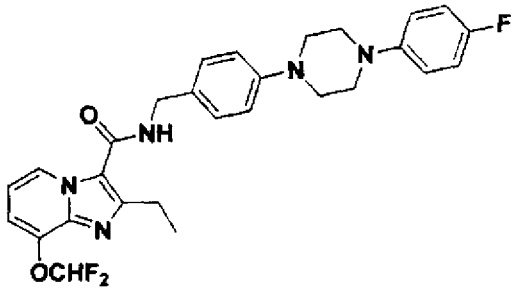
8-Bromo-2-ethyl-N-(4-(4-(4-fluorophenyl)piperazin-1-yl)benzyl)imidazo[1,2-a]pyridine-3-carboxamide (305)
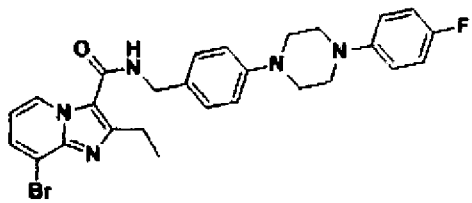
2-Ethyl-6-fluoro-N-(4-(4-(4-fluorophenyl)piperazin-1-yl)benzyl)imidazo[1,2-a]pyridine-3-carboxamide (306)
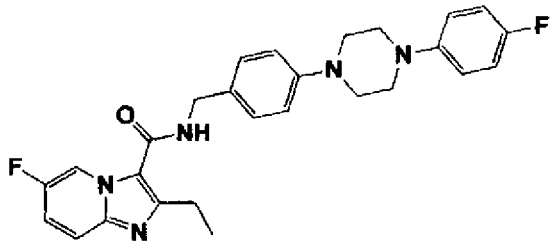
6-Bromo-2-ethyl-N-(4-(4-(4-fluorophenyl)piperazin-1-yl)benzyl)imidazo[1,2-a]pyridine-3-carboxamide (307)
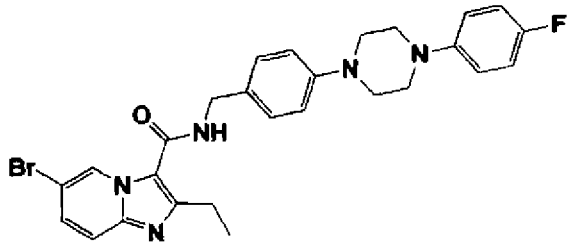

2-Ethyl-*N*-(4-(4-(4-fluorophenyl)piperazin-1-yl)benzyl)-6-methylimidazo[1,2-a]pyridine-3-carboxamide (308)
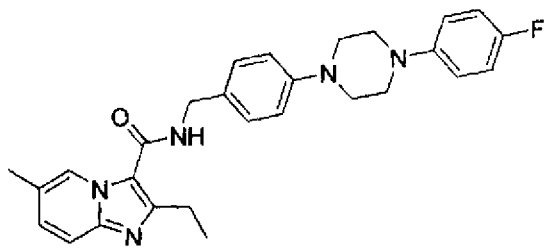
2-Ethyl-*N*-(4-(4-(4-fluorophenyl)piperazin-1-yl)benzyl)-7-methylimidazo[1,2-a]pyridine-3-carboxamide (309)
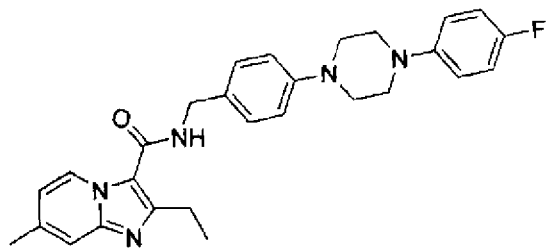
2-Ethyl-8-fluoro-*N*-(4-(4-(4-fluorophenyl)piperazin-1-yl)benzyl)imidazo[1,2-a]pyridine-3-carboxamide (310)
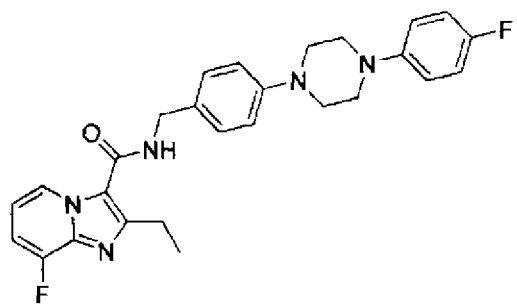
7-Bromo-2-ethyl-*N*-(4-(4-(4-fluorophenyl)piperazin-1-yl)benzyl)imidazo[1,2-a]pyridine-3-carboxamide (311)
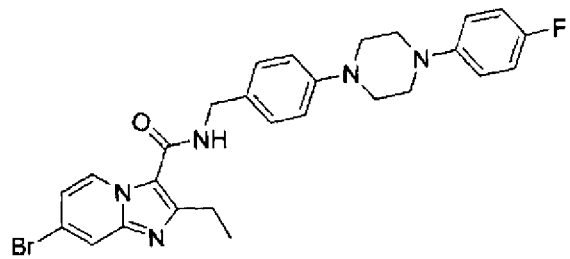

2-Ethyl-*N*-(4-(4-(4-fluorophenyl)piperazin-1-yl)benzyl)-8-(pyridin-4-yl)imidazo[1,2-a]pyridine-3-carboxamide (312)
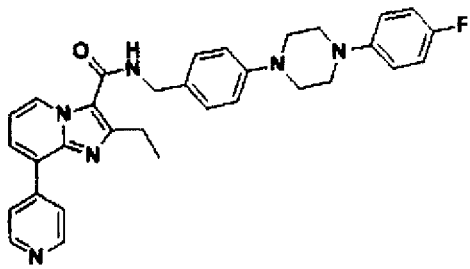
2-Ethyl-7-(4-phenylpiperazin-1-yl)-*N*-(4-(trifluoromethyl)benzyl)imidazo[1,2-a]pyridine-3-carboxamide (330)
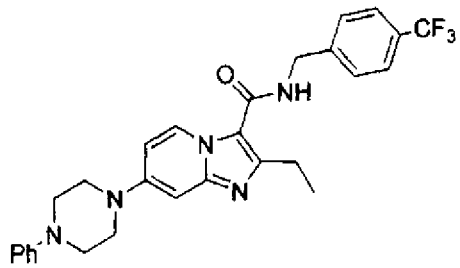
6-Chloro-2-ethyl-*N*-(4-((4-(morpholine-4-carbonyl)benzyl)carbamoyl)benzyl) imidazo[1,2-a]pyridine-3-carboxamide (332)
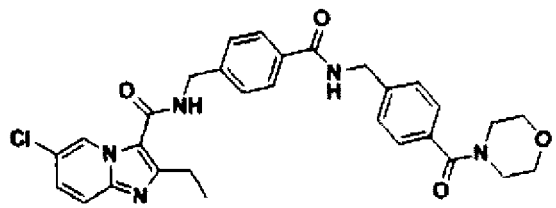
7-Chloro-2-ethyl-*N*-(4-(morpholine-4-carbonyl)benzyl)imidazo[1,2-a]pyridine-3-carboxamide (333)
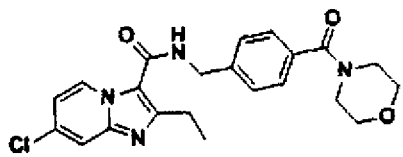

2-Ethyl-*N*-((2-(4-fluorophenyl)benzo[d]oxazol-5-yl)methyl)imidazo[1,2-a]pyridine-3-carboxamide (334)
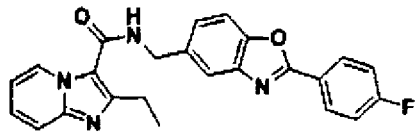
6-Chloro-2-ethyl-*N*-((2-(4-fluorophenyl)benzo[d]oxazol-5-yl)methyl)imidazo[1,2-a]pyridine-3-carboxamide (335)
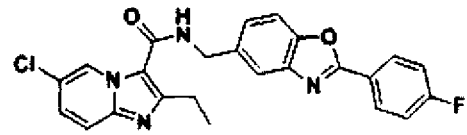
7-Chloro-2-ethyl-*N*-((2-(4-fluorophenyl)benzo[d]oxazol-5-yl)methyl)imidazo[1,2-a]pyridine-3-carboxamide (336)
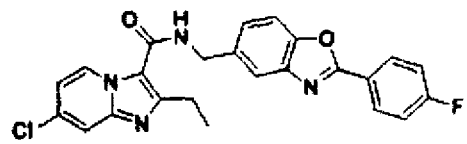
6-Chloro-N-(4-(4-(4-chlorophenyl)piperidin-1-yl)benzyl)-2-ethylimidazo[1,2-a]pyridine-3-carboxamide (337)
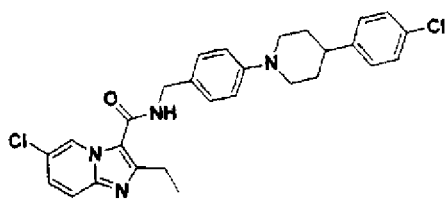

7-Chloro-N-(4-(4-(4-chlorophenyl)piperidin-1-yl)benzyl)-2-ethylimidazo[1,2-a]pyridine-3-carboxamide (338)
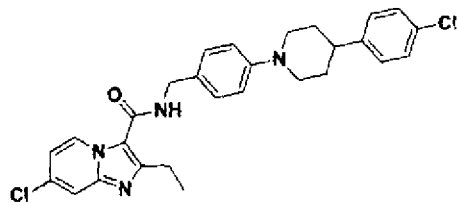
6-Chloro-N-((2-cyclohexylbenzo[d]oxazol-5-yl)methyl)-2-ethylimidazo[1,2-a]pyridine-3-carboxamide (339)
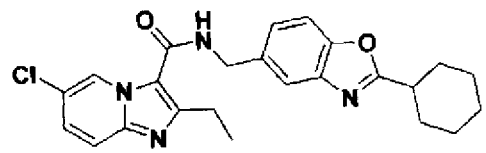
7-Chloro-N-((2-cyclohexylbenzo[d]oxazol-5-yl)methyl)-2-ethylimidazo[1,2-a]pyridine-3-carboxamide (340)
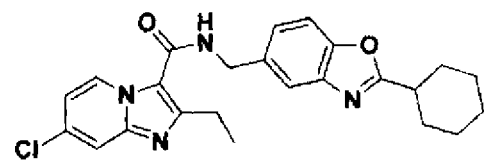
6-Chloro-2-ethyl-N-(4-(4-(4-fluorophenyl)-4-hydroxypiperidin-1-yl)benzyl)imidazo[1,2-a]pyridine-3-carboxamide (341)
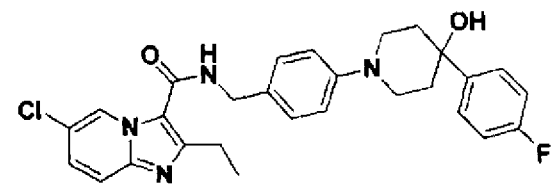

7-Chloro-2-ethyl-*N*-(4-(4-(4-fluorophenyl)-4-hydroxypiperidin-1-yl)benzyl)imidazo[1,2-a]pyridine-3-carboxamide (342)
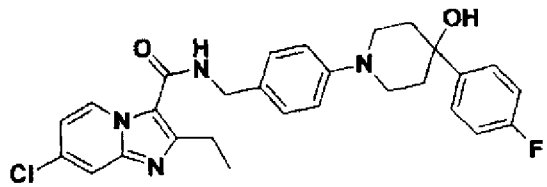
*N*-(4-(4-Carbamoylpiperidin-1-yl)benzyl)-6-chloro-2-ethylimidazo[1,2-a]pyridine-3-carboxamide (343)
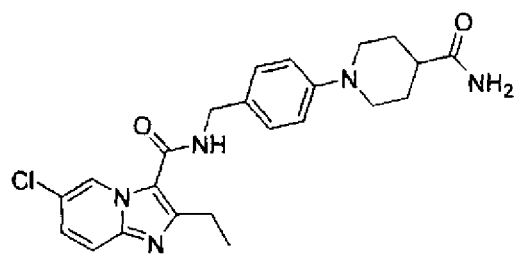
*N*-(4-(4-Carbamoylpiperidin-1-yl)benzyl)-7-chloro-2-ethylimidazo[1,2-a]pyridine-3-carboxamide (344)
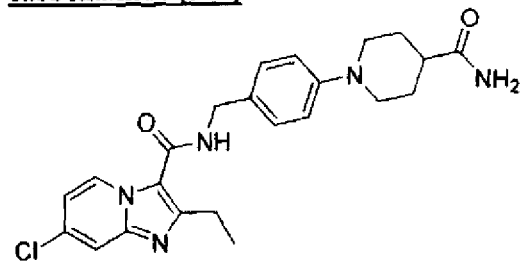
6-Chloro-*N*-(4-(4-(dimethylcarbamoyl)piperidin-1-yl)benzyl)-2-ethylimidazo[1,2-a]pyridine-3-carboxamide (345)
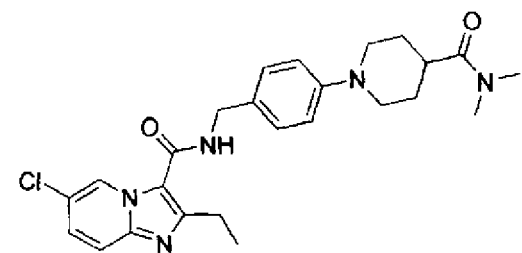

7-Chloro-*N*-(4-(4-(dimethylcarbamoyl)piperidin-1-yl)benzyl)-2-ethylimidazo[1,2-a]pyridine-3-carboxamide (346)
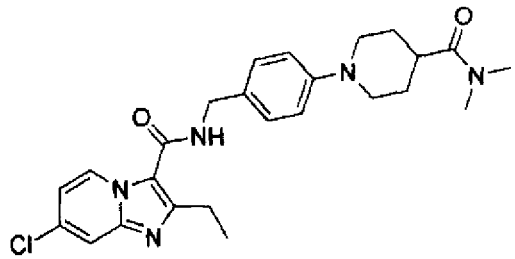
6-Chloro-2-ethyl-*N*-(4-(4-(4-fluorobenzyloxy)piperidin-1-yl)benzyl)imidazo[1,2-a]pyridine-3-carboxamide (347)
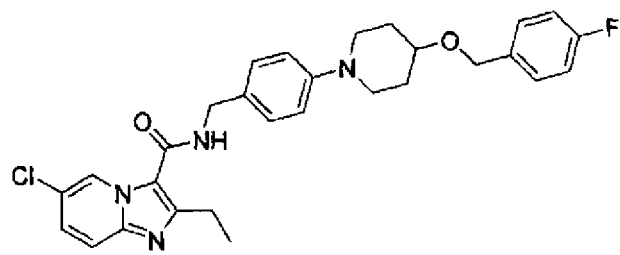
7-Chloro-2-ethyl-*N*-(4-(4-(4-fluorobenzyloxy)piperidin-1-yl)benzyl)imidazo[1,2-a]pyridine-3-carboxamide (348)
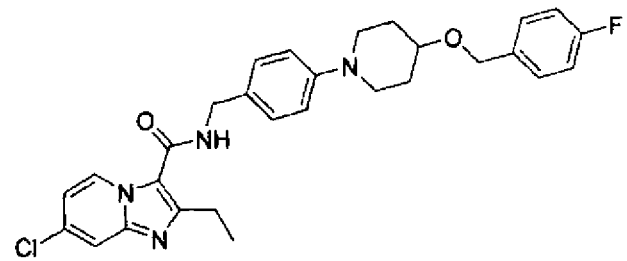
6-Chloro-*N*-(3-chloro-4-morpholinobenzyl)-2-ethylimidazo[1,2-a]pyridine-3-carboxamide (349)
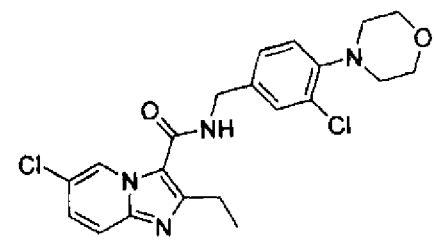

7-Chloro-*N*-(3-chloro-4-morpholinobenzyl)-2-ethylimidazo[1,2-a]pyridine-3-carboxamide (350)

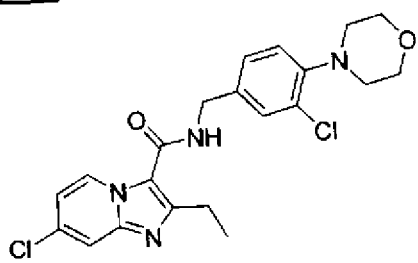

6-Chloro-2-ethyl-*N*-(4-(4-formylpiperidin-1-yl)benzyl)imidazo[1,2-a]pyridine-3-carboxamide (351)

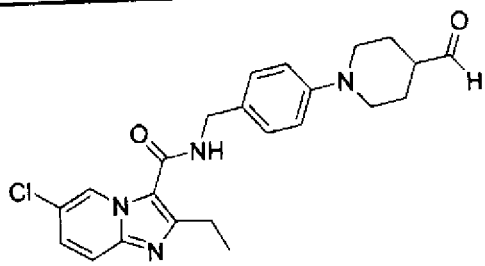

7-Chloro-2-ethyl-N-(4-(4-formylpiperidin-1-yl)benzyl)imidazo[1,2-a]pyridine-3-carboxamide (352)

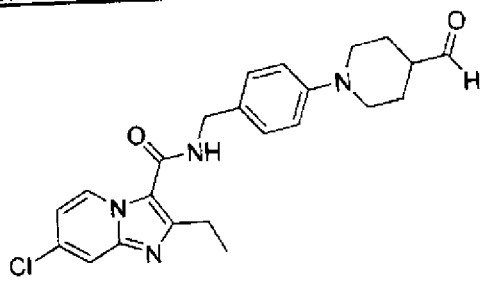

or a pharmaceutically acceptable salt thereof.

4. The compound according to claim 3, having one of the formulae 47, 54, 177 and 185, or a pharmaceutically acceptable salt thereof:

N-(Biphenyl-4-ylmethyl)-2-ethylimidazo[1,2-a]pyridine-3-carboxamide (47)

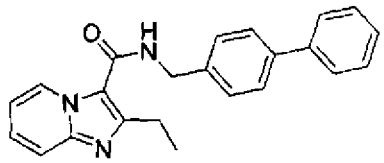

2-Ethyl-N-(4-phenoxybenzyl)imidazo[1,2-a]pyridine-3-carboxamide (54)

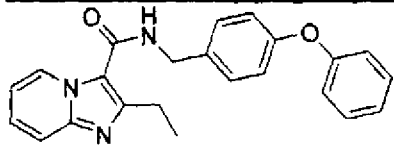

7-Chloro-2-ethyl-N-(4-(4-(4-fluorophenyl)piperazin-1-yl)benzyl)imidazo[1,2-a]pyridine-3-carboxamide trihydrochloride (177)

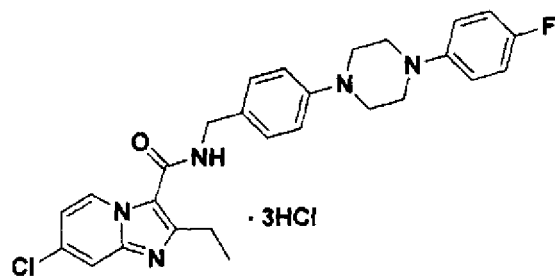

6-Chloro-2-ethyl-N-(4-(4-(trifluoromethoxy)phenoxy)benzyl)imidazo[1,2-a]pyridine-3-carboxamide (185)

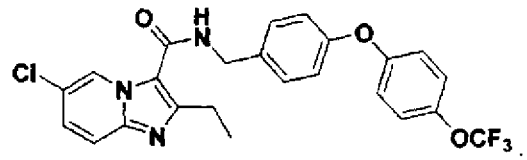

5. A pharmaceutical composition comprising a compound according to claim 2, and a pharmaceutically acceptable carrier.

6. A method of treatment of a bacterial infection, comprising the application of a suitable amount of a compound according to claim 1, to a person in need thereof.

7. The method, according to claim 6, used for the treatment of tuberculosis.

8. The compound, according to claim 3, having a formula selected from formulae 15, 16, 44, 45, 47, 49, 54-57, 60-67, 70-73, 75-78, 81-87, 92-103, 106, 107, 110, 111, 113, 116-135, 137-141, 144, 147, 148, 152, 154, 157-159, 162-167, 171-182, 184-193, 198, 199-202, 209, 210, 214-218, 223-227, 231, 248-260, 262, 263, 267-269, 271-274, 280-293, 295-312 and 330:

2-Methyl-N-(4-phenoxybenzyl)imidazo[1,2-a]pyridine-3-carboxamide (15)

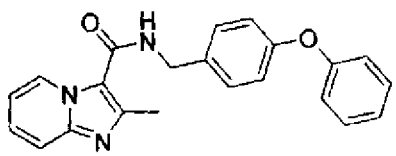

N-(Biphenyl-4-ylmethyl)-2-methylimidazo[1,2-a]pyridine-3-carboxamide (16)

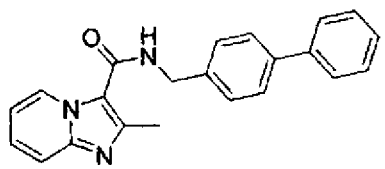

N-(Biphenyl-4-ylmethyl)-6-chloro-2-methylimidazo[1,2-a]pyridine-3-carboxamide (44)

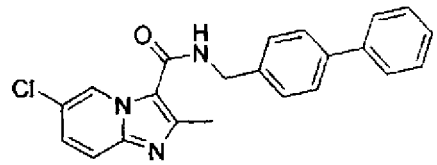

N-(Biphenyl-4-ylmethyl)-7-chloro-2-methylimidazo[1,2-a]pyridine-3-carboxamide (45)

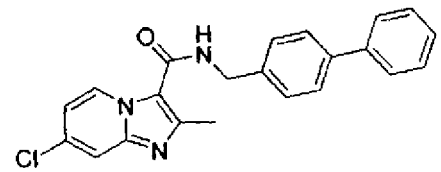

N-(Biphenyl-4-ylmethyl)-2-ethylimidazo[1,2-a]pyridine-3-carboxamide (47)
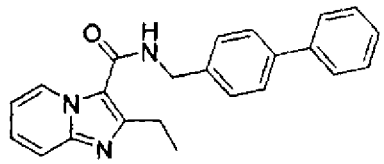
N-(Biphenyl-4-ylmethyl)-2-propylimidazo[1,2-a]pyridine-3-carboxamide (49)
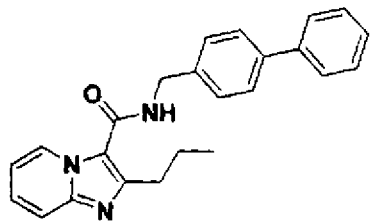
2-Ethyl-N-(4-phenoxybenzyl)imidazo[1,2-a]pyridine-3-carboxamide (54)
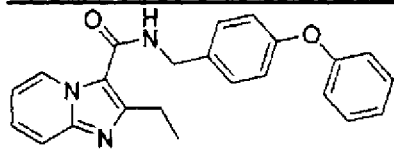
N-(4-tert-Butylbenzyl)-2-ethylimidazo[1,2-a]pyridine-3-carboxamide (55)
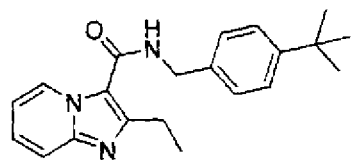
2-Ethyl-N-((1-methyl-1H-indol-5-yl)methyl)imidazo[1,2-a]pyridine-3-carboxamide (56)
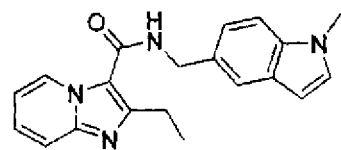

2-Ethyl-N-(4-(trifluoromethoxy)benzyl)imidazo[1,2-a]pyridine-3-carboxamide (57)

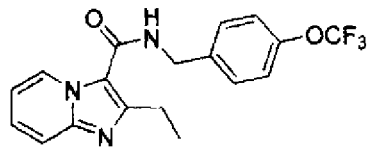

2-Ethyl-N-(4-isopropoxybenzyl)imidazo[1,2-a]pyridine-3-carboxamide (60)

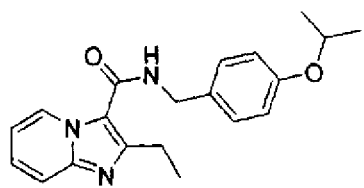

2-Ethyl-N-(4-isobutoxybenzyl)imidazo[1,2-a]pyridine-3-carboxamide (61)

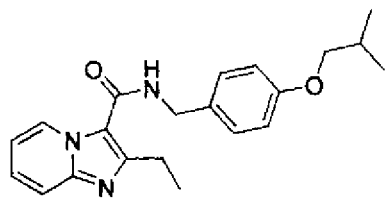

N-(Biphenyl-4-ylmethyl)-2-ethyl-6-methylimidazo[1,2-a]pyridine-3-carboxamide (62)

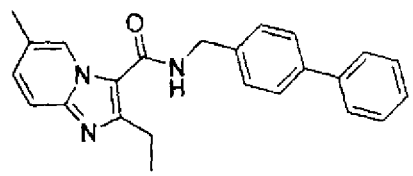

2-Ethyl-6-methyl-N-(4-phenoxybenzyl)imidazo[1,2-a]pyridine-3-carboxamide (63)

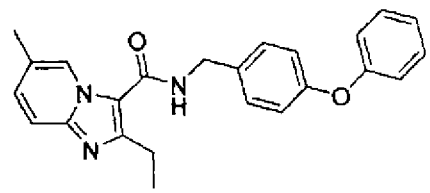

N-(4-tert-Butylbenzyl)-2-ethyl-6-methylimidazo[1,2-a]pyridine-3-carboxamide (64)

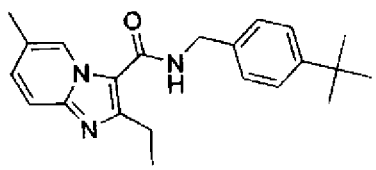
2-Ethyl-6-methyl-N-(4-(trifluoromethoxy)benzyl)imidazo[1,2-a]pyridine-3-carboxamide (65)
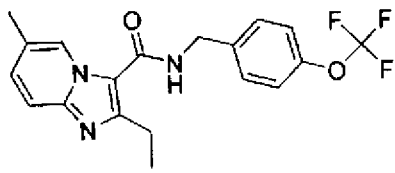
2-Ethyl-6-methyl-N-((1-methyl-1H-indol-5-yl)methyl)imidazo[1,2-a]pyridine-3-carboxamide (66)
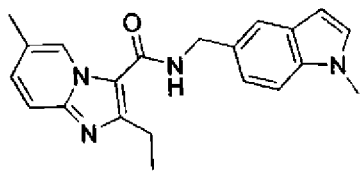
2-Ethyl-6-methyl-N-((1-methyl-1H-indol-6-yl)methyl)imidazo[1,2-a]pyridine-3-carboxamide (67)
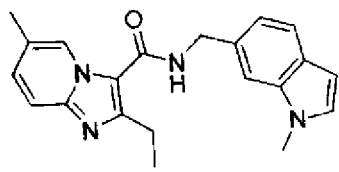
6-Chloro-N-(4-chlorobenzyl)-2-ethylimidazo[1,2-a]pyridine-3-carboxamide (70)
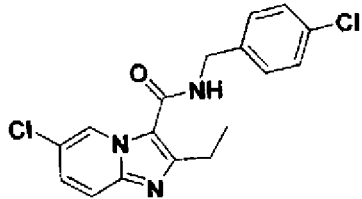

6-Chloro-2-methyl-N-(4-phenoxybenzyl)imidazo[1,2-a]pyridine-3-carboxamide (71)
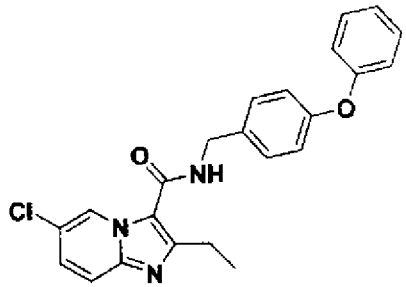
6-Chloro-2-methyl-N-(4-(trifluoromethoxy)benzyl)imidazo[1,2-a]pyridine-3-carboxamide (72)
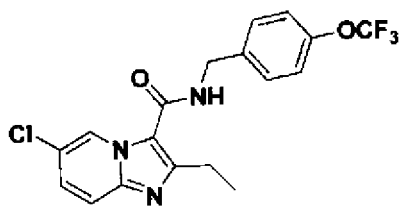
N-(4-tert-Butylbenzyl)-6-chloro-2-methylimidazo[1,2-a]pyridine-3-carboxamide (73)
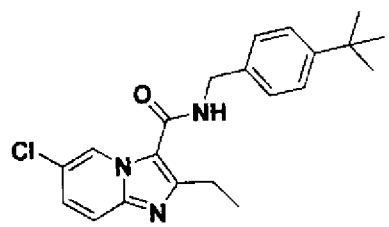
6-Chloro-N-(4-isopropoxybenzyl)-2-methylimidazo[1,2-a]pyridine-3-carboxamide (75)
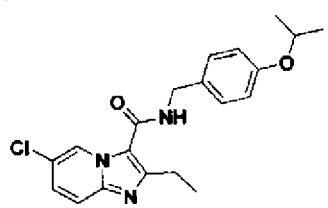

6-Chloro-N-(4-isobutoxybenzyl)-2-methylimidazo[1,2-a]pyridine-3-carboxamide (76)
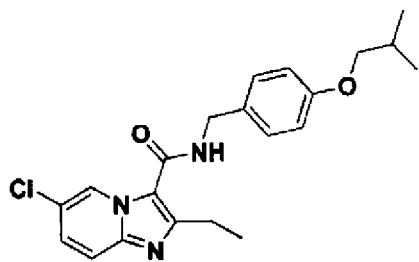
6-Chloro-2-methyl-N-((1-methyl-1H-indol-5-yl)methyl)imidazo[1,2-a]pyridine-3-carboxamide (77)
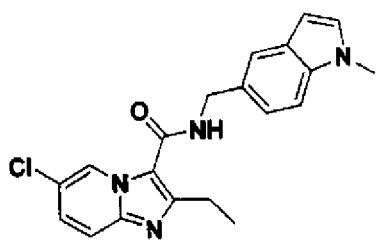
6-Chloro-2-methyl-N-((1-methyl-1H-indol-6-yl)methyl)imidazo[1,2-a]pyridine-3-carboxamide (78)
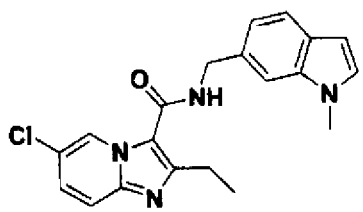
N-(Biphenyl-4-ylmethyl)-6-chloro-2-methylimidazo[1,2-a]pyridine-3-carboxamide (81)
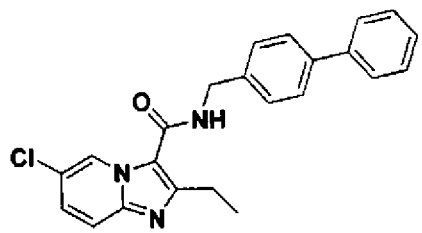

6-Chloro-N-((2'-chlorobiphenyl-4-yl)methyl)-2-ethylimidazo[1,2-a]pyridine-3-carboxamide (82)
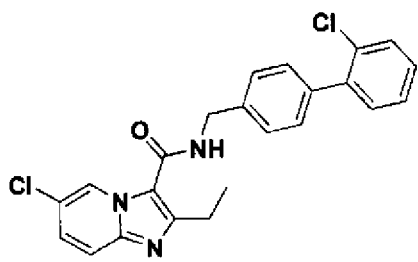
6-Chloro-N-((4'-chlorobiphenyl-4-yl)methyl)-2-ethylimidazo[1,2-a]pyridine-3-carboxamide (83)
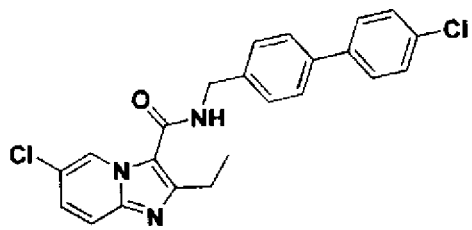
6-Chloro-2-ethyl-N-((2'-methylbiphenyl-4-yl)methyl)imidazo[1,2-a]pyridine-3-carboxamide (84)
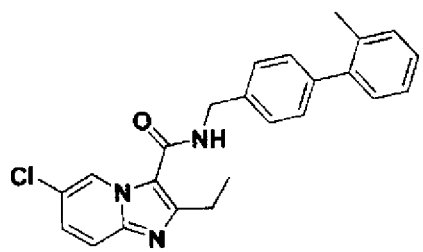
6-Chloro-2-ethyl-N-((3'-methylbiphenyl-4-yl)methyl)imidazo[1,2-a]pyridine-3-carboxamide (85)
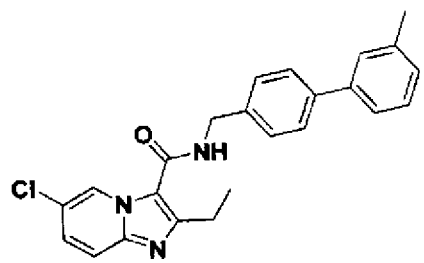

6-Chloro-2-ethyl-N-((4'-methylbiphenyl-4-yl)methyl)imidazo[1,2-a]pyridine-3-carboxamide (86)
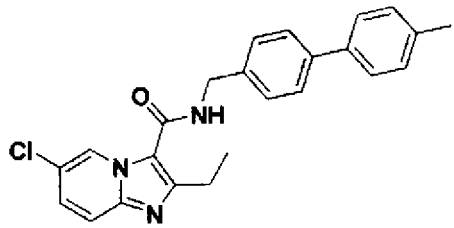
7-Chloro-N-(4-chlorobenzyl)-2-ethylimidazo[1,2-a]pyridine-3-carboxamide (87)
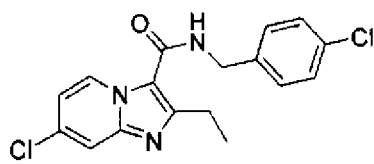
N-(4-tert-Butylbenzyl)-7-chloro-2-ethylimidazo[1,2-a]pyridine-3-carboxamide (92)
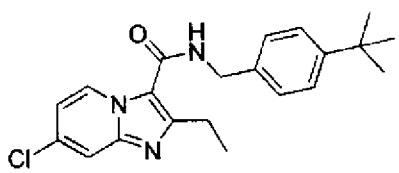
N-(Biphenyl-4-ylmethyl)-7-chloro-2-ethylimidazo[1,2-a]pyridine-3-carboxamide (93)
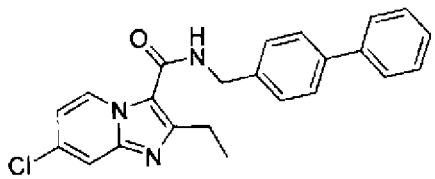
7-Chloro-N-((2'-chlorobiphenyl-4-yl)methyl)-2-ethylimidazo[1,2-a]pyridine-3-carboxamide (94)
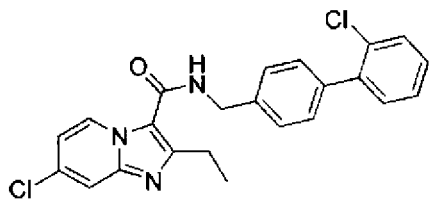

7-Chloro-N-((4'-chlorobiphenyl-4-yl)methyl)-2-ethylimidazo[1,2-a]pyridine-3-carboxamide (95)
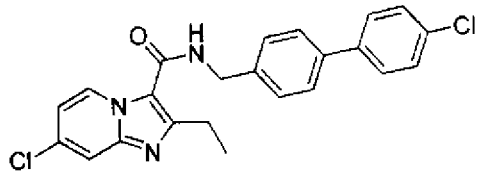
7-Chloro-2-ethyl-N-((2'-methylbiphenyl-4-yl)methyl)imidazo[1,2-a]pyridine-3-carboxamide (96)
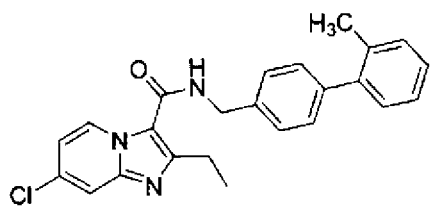
7-Chloro-2-ethyl-N-((3'-methylbiphenyl-4-yl)methyl)imidazo[1,2-a]pyridine-3-carboxamide (97)
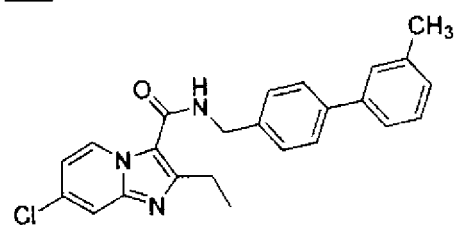
7-Chloro-2-ethyl-N-((4'-methylbiphenyl-4-yl)methyl)imidazo[1,2-a]pyridine-3-carboxamide (98)
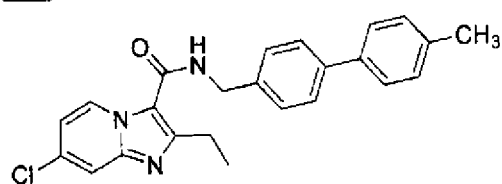

N-(Biphenyl-4-ylmethyl)-6-chloro-2-(trifluoromethyl)imidazo[1,2-a]pyridine-3-carboxamide (99)

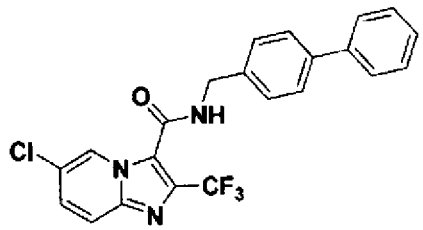

N-(4-tert-Butylbenzyl)-6-chloro-2-(trifluoromethyl)imidazo[1,2-a]pyridine-3-carboxamide (100)

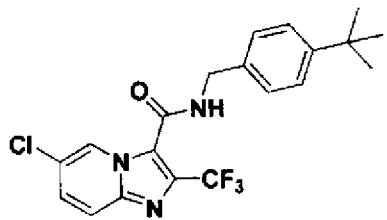

N-(4-Bromobenzyl)-7-chloro-2-ethylimidazo[1,2-a]pyridine-3-carboxamide (101)

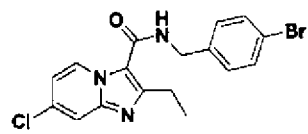

7-Chloro-2-ethyl-N-(4-(trifluoromethoxy)benzyl)imidazo[1,2-a]pyridine-3-carboxamide (102)

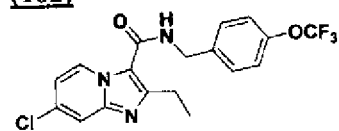

2-Ethyl-6-fluoro-N-(4-(trifluoromethoxy)benzyl)imidazo[1,2-a]pyridine-3-carboxamide (103)

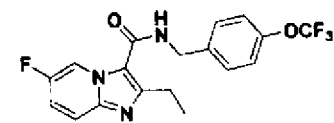

7-Chloro-2-ethyl-N-(4-(propylamino)benzyl)imidazo[1,2-a]pyridine-3-carboxamide (106)
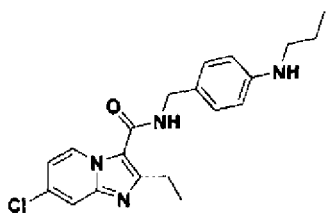
7-Chloro-2-ethyl-N-(4-(pentylamino)benzyl)imidazo[1,2-a]pyridine-3-carboxamide (107)
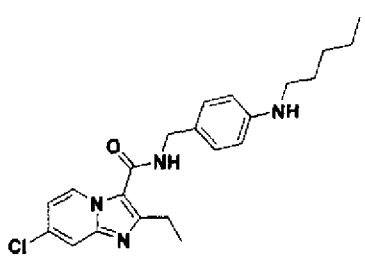
7-Chloro-2-ethyl-N-(4-(4-isopropylpiperazin-1-yl)benzyl)imidazo[1,2-a]pyridine-3-carboxamide (110)
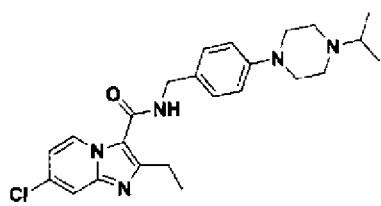
7-Chloro-2-ethyl-N-(4-(4-phenylpiperazin-1-yl)benzyl)imidazo[1,2-a]pyridine-3-carboxamide (111)
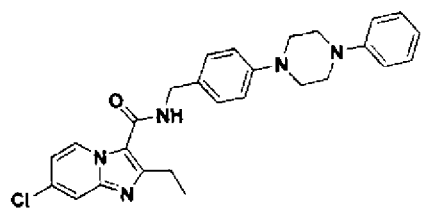

6-Chloro-2-ethyl-N-(4-(4-(4-fluorophenyl)piperazin-1-yl)benzyl)imidazo[1,2-a]pyridine-3-carboxamide (113)

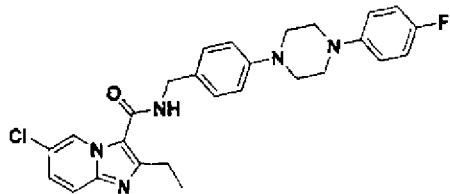

7-Chloro-2-ethyl-N-((4'-fluorobiphenyl-4-yl)methyl)imidazo[1,2-a]pyridine-3-carboxamide (116)

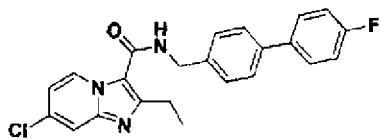

N-((4'-tert-Butylbiphenyl-4-yl)methyl)-7-chloro-2-ethylimidazo[1,2-a]pyridine-3-carboxamide (117)

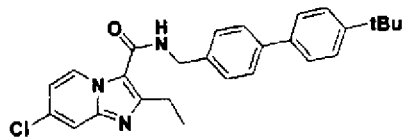

7-Chloro-2-ethyl-N-((4'-methoxybiphenyl-4-yl)methyl)imidazo[1,2-a]pyridine-3-carboxamide (118)

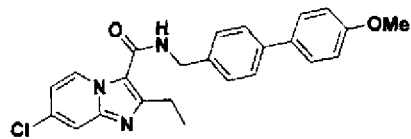

7-Chloro-2-ethyl-N-((4'-(trifluoromethoxy)biphenyl-4-yl)methyl)imidazo[1,2-a]pyridine-3-carboxamide (119)

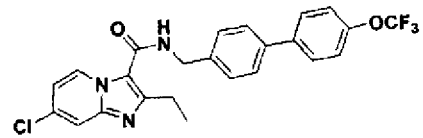

7-Chloro-2-ethyl-N-((4'-(trifluoromethyl)biphenyl-4-yl)methyl)imidazo[1,2-a]pyridine-3-carboxamide (120)

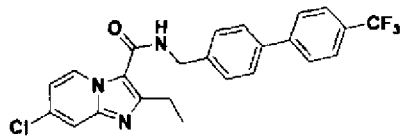

6-Chloro-N-((4'-cyanobiphenyl-4-yl)methyl)-2-ethylimidazo[1,2-a]pyridine-3-carboxamide (121)

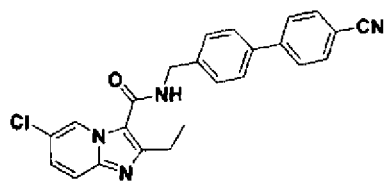

7-Chloro-N-((4'-cyanobiphenyl-4-yl)methyl)-2-ethylimidazo[1,2-a]pyridine-3-carboxamide (122)

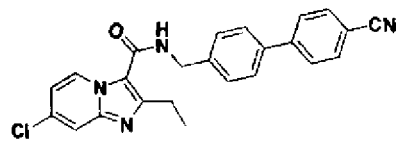

6-Chloro-2-ethyl-N-((2'-(trifluoromethyl)biphenyl-4-yl)methyl)imidazo[1,2-a]pyridine-3-carboxamide (123)

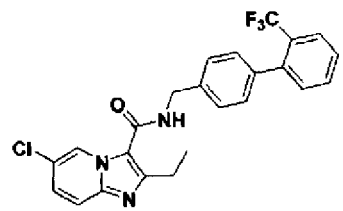

7-Chloro-2-ethyl-N-((2'-(trifluoromethyl)biphenyl-4-yl)methyl)imidazo[1,2-a]pyridine-3-carboxamide (124)

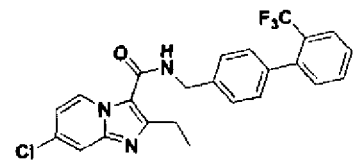

6-Chloro-N-((2'-cyanobiphenyl-4-yl)methyl)-2-ethylimidazo[1,2-a]pyridine-3-carboxamide (125)
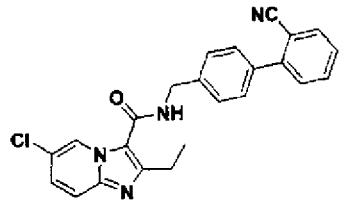
7-Chloro-N-((2'-cyanobiphenyl-4-yl)methyl)-2-ethylimidazo[1,2-a]pyridine-3-carboxamide (126)
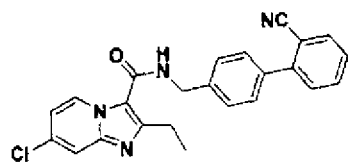
6-Chloro-N-((3'-cyanobiphenyl-4-yl)methyl)-2-ethylimidazo[1,2-a]pyridine-3-carboxamide (127)
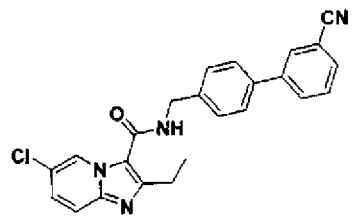
7-Chloro-N-((3'-cyanobiphenyl-4-yl)methyl)-2-ethylimidazo[1,2-a]pyridine-3-carboxamide (128)
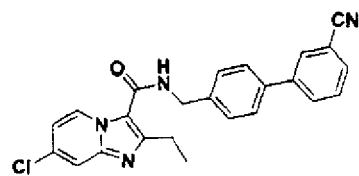

6-Chloro-N-((4'-chloro-2'-(trifluoromethyl)biphenyl-4-yl)methyl)-2-ethylimidazo[1,2-a]pyridine-3-carboxamide (129)

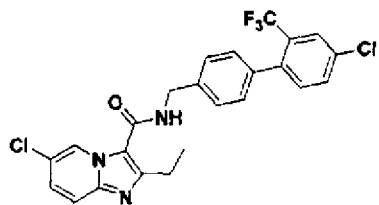

7-Chloro-N-((4'-chloro-2'-(trifluoromethyl)biphenyl-4-yl)methyl)-2-ethylimidazo[1,2-a]pyridine-3-carboxamide (130)

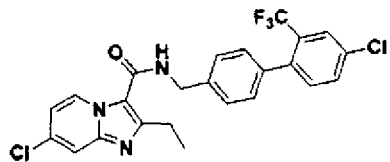

6-Chloro-N-((4'-cyano-2'-methylbiphenyl-4-yl)methyl)-2-ethylimidazo[1,2-a]pyridine-3-carboxamide (131)

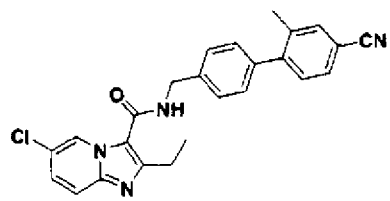

7-Chloro-N-((4'-cyano-2'-methylbiphenyl-4-yl)methyl)-2-ethylimidazo[1,2-a]pyridine-3-carboxamide (132)

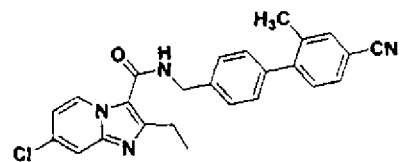

7-Chloro-N-((2'-chloro-4'-fluorobiphenyl-4-yl)methyl)-2-ethylimidazo[1,2-a]pyridine-3-carboxamide (133)

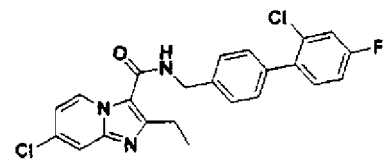

7-Chloro-2-ethyl-N-(4-(pyridin-4-yl)benzyl)imidazo[1,2-a]pyridine-3-carboxamide (134)

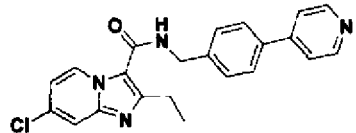

7-Chloro-2-ethyl-N-(4-(5-methoxypyridin-2-yl)benzyl)imidazo[1,2-a]pyridine-3-carboxamide (135)

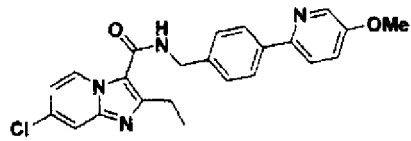

7-Chloro-2-ethyl-N-(4-(furan-2-yl)benzyl)imidazo[1,2-a]pyridine-3-carboxamide (137)

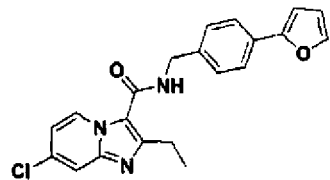

N-(4-(1H-Pyrrol-1-yl)benzyl)-7-chloro-2-ethylimidazo[1,2-a]pyridine-3-carboxamide (138)

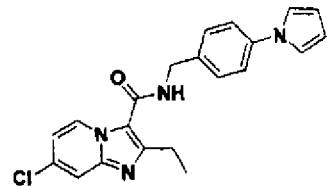

6-Chloro-2-ethyl-N-(4-(4-(4-(trifluoromethoxy)phenoxy)piperidin-1-yl)benzyl)imidazo-[1,2-a]pyridine-3-carboxamide (139)

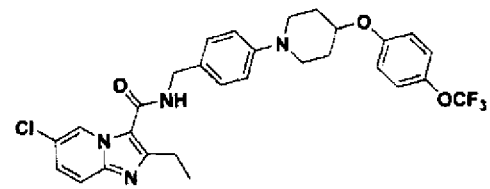

7-Chloro-2-ethyl-N-(4-(4-(4-(trifluoromethoxy)phenoxy)piperidin-1-yl)benzyl)imidazo-[1,2-a]pyridine-3-carboxamide (140)

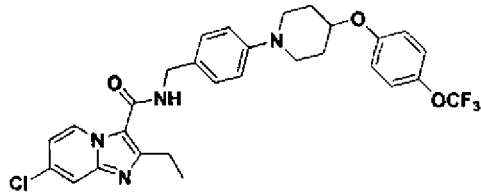

N-((4'-Chlorobiphenyl-4-yl)methyl)-2-ethylimidazo[1,2-a]pyrazine-3-carboxamide (141)

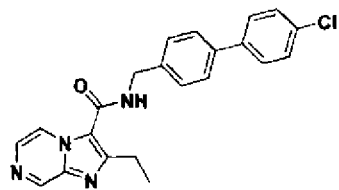

N-(4-(4-(4-(Butyramidomethyl)phenyl)piperazin-1-yl)benzyl)-7-chloro-2-ethylimidazo-[1,2-a]pyridine-3-carboxamide (144)

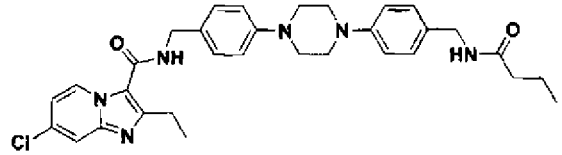

6-Chloro-2-ethyl-N-(4-(trifluoromethyl)benzyl)imidazo[1,2-a]pyridine-3-carboxamide (147)

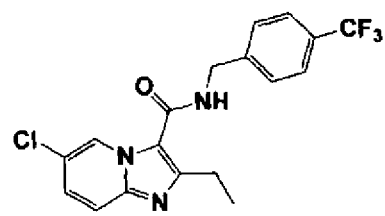

7-Chloro-2-ethyl-N-(4-(trifluoromethyl)benzyl)imidazo[1,2-a]pyridine-3-carboxamide (148)

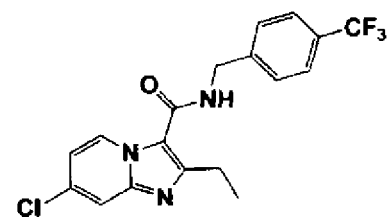

6-Bromo-2-ethyl-N-(4-(trifluoromethoxy)benzyl)imidazo[1,2-a]pyridine-3-carboxamide (152)
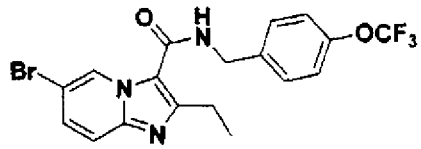
6-Chloro-2-methyl-N-(4-(trifluoromethoxy)benzyl)imidazo[1,2-a]pyridine-3-carboxamide (154)
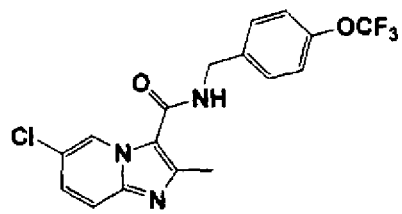
6-Chloro-2-ethyl-N-(4-methoxyphenethyl)imidazo[1,2-a]pyridine-3-carboxamide (157)
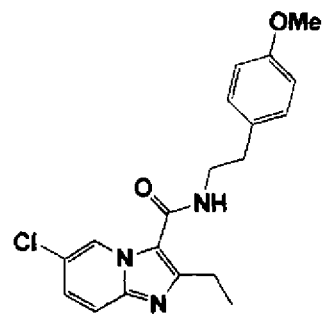
6-Chloro-N-(4-chlorophenethyl)-2-ethylimidazo[1,2-a]pyridine-3-carboxamide (158)
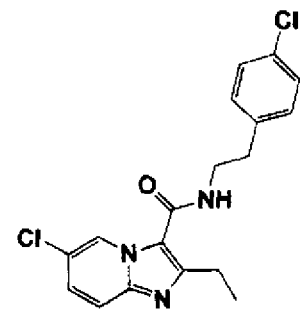

N-((4'-(Butyramidomethyl)biphenyl-4-yl)methyl)-7-chloro-2-ethylimidazo[1,2-a]pyridine-3-carboxamide (159)

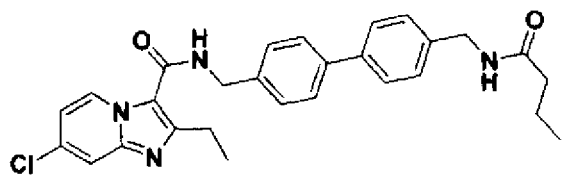

6-Chloro-N-(4-(4-(4-chlorophenoxy)piperidin-1-yl)benzyl)-2-ethylimidazo[1,2-a] pyridine-3-carboxamide (162)

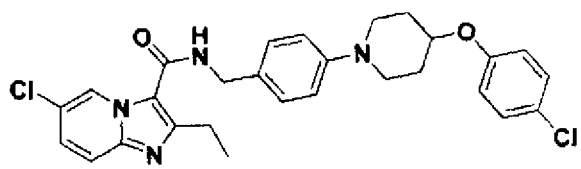

7-Chloro-N-(4-(4-(4-chlorophenoxy)piperidin-1-yl)benzyl)-2-ethylimidazo[1,2-a] pyridine-3-carboxamide (163)

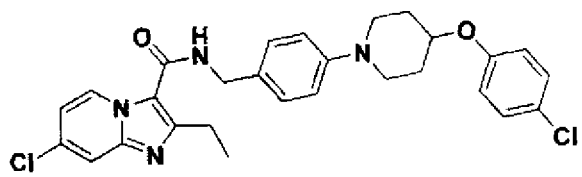

6-Chloro-2-ethyl-N-(4-(4-(4-(trifluoromethyl)phenoxy)piperidin-1-yl)benzyl) imidazo[1,2-a]pyridine-3-carboxamide (164)

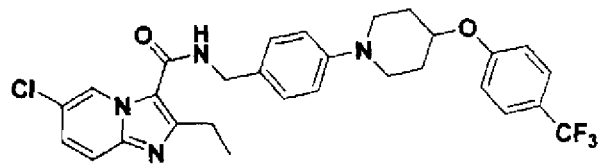

7-Chloro-2-ethyl-N-(4-(4-(4-(trifluoromethyl)phenoxy)piperidin-1-yl)benzyl) imidazo[1,2-a]pyridine-3-carboxamide (165)

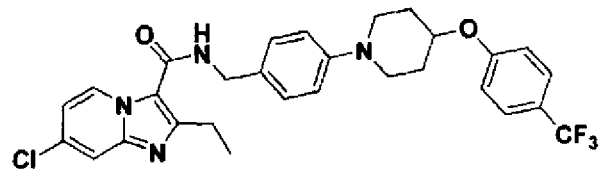

6-Chloro-2-ethyl-N-(4-(4-(4-fluorophenoxy)piperidin-1-yl)benzyl)imidazo[1,2-a] pyridine-3-carboxamide (166)
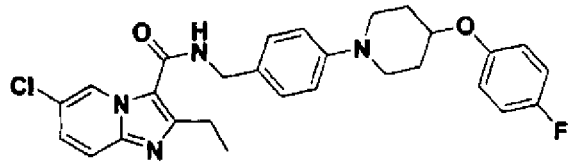
7-Chloro-2-ethyl-N-(4-(4-(4-fluorophenoxy)piperidin-1-yl)benzyl)imidazo[1,2-a]pyridine-3-carboxamide (167)
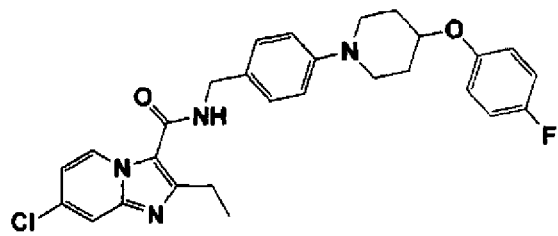
6-Chloro-2-ethyl-N-(4-(4-(4-fluorobenzyl)piperazin-1-yl)benzyl)imidazo[1,2-a]pyridine-3-carboxamide (171)
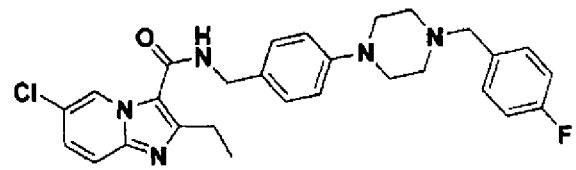
7-Chloro-2-ethyl-N-(4-(4-(4-fluorobenzyl)piperazin-1-yl)benzyl)imidazo[1,2-a]pyridine-3-carboxamide (172)
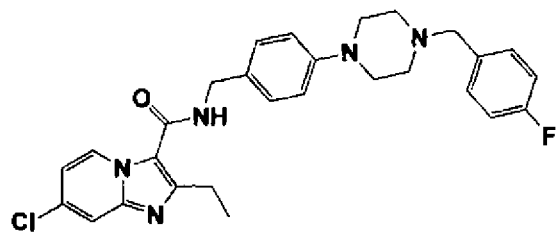

6-Chloro-2-ethyl-N-(4-(4-(4-(trifluoromethoxy)benzyl)piperazin-1-yl)benzyl)imidazo[1,2-a]pyridine-3-carboxamide (173)
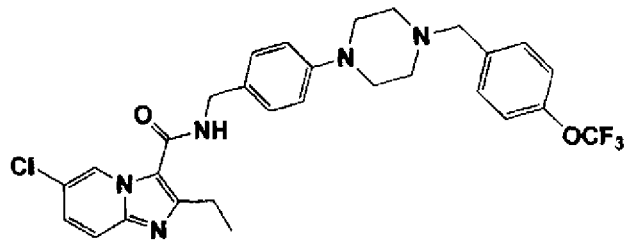
7-Chloro-2-ethyl-N-(4-(4-(4-(trifluoromethoxy)benzyl)piperazin-1-yl)benzyl)imidazo[1,2-a]pyridine-3-carboxamide (174)
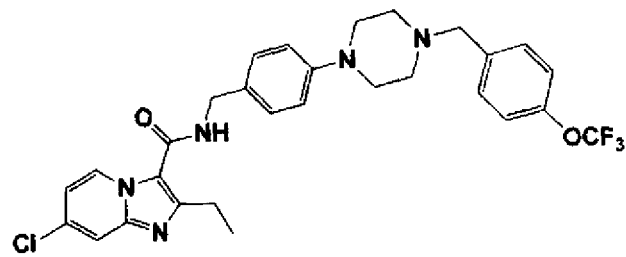
6,7-Dichloro-2-ethyl-N-(4-(4-(4-fluorobenzyl)piperazin-1-yl)benzyl)imidazo[1,2-a]pyridine-3-carboxamide (175)
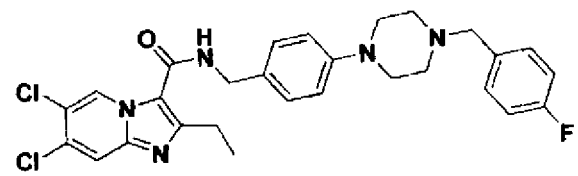
7-Chloro-2-ethyl-N-(4-(4-(4-fluorophenyl)piperazin-1-yl)benzyl)imidazo[1,2-a]pyridine-3-carboxamide (176)
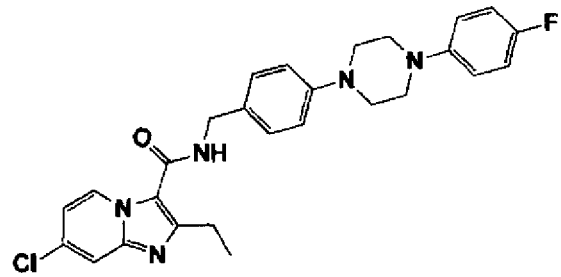

7-Chloro-2-ethyl-N-(4-(4-(4-fluorophenyl)piperazin-1-yl)benzyl)imidazo[1,2-a]pyridine-3-carboxamide trihydrochloride (177)

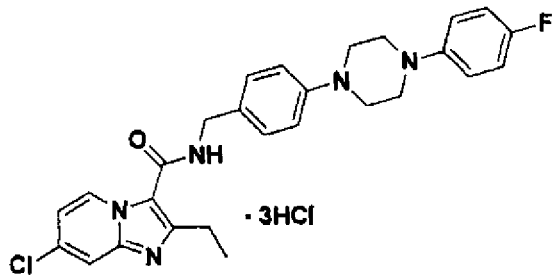

6-Chloro-2-ethyl-N-(4-(4-(4-(trifluoromethoxy)phenyl)piperazin-1-yl)benzyl)imidazo[1,2-a]pyridine-3-carboxamide (178)

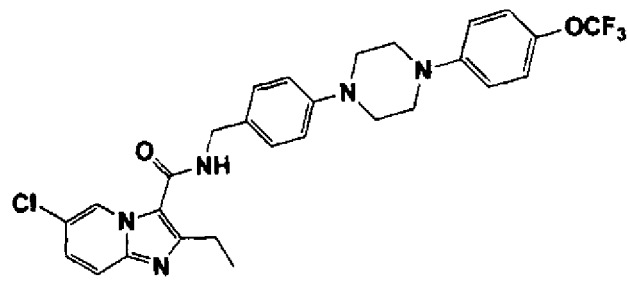

7-Chloro-2-ethyl-N-(4-(4-(4-(trifluoromethoxy)phenyl)piperazin-1-yl)benzyl)imidazo[1,2-a]pyridine-3-carboxamide (179)

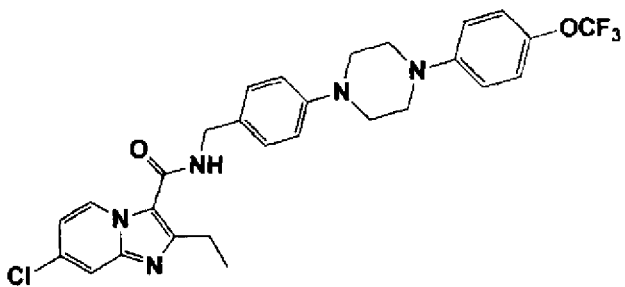

6,7-Dichloro-2-ethyl-N-(4-(4-(4-fluorophenyl)piperazin-1-yl)benzyl)imidazo[1,2-a]pyridine-3-carboxamide (180)

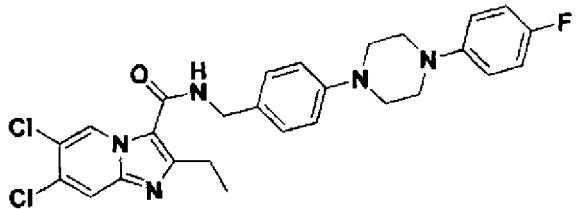

2-Ethyl-N-(4-(4-(4-(trifluoromethoxy)phenyl)piperazin-1-yl)benzyl)imidazo[1,2-a]pyridine-3-carboxamide (181)
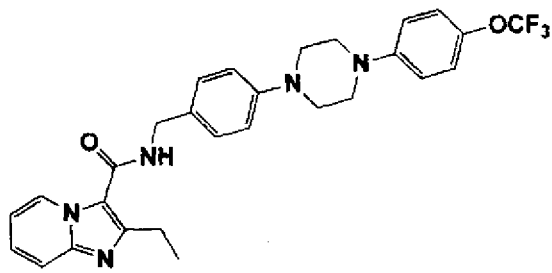
6-Chloro-2-ethyl-N-(4-(4-(4-fluorophenyl)piperazin-1-yl)benzyl)-N-methylimidazo[1,2-a]pyridine-3-carboxamide (182)
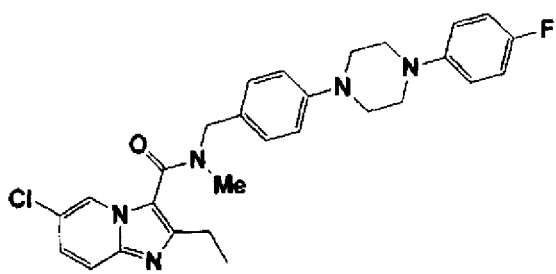
7-Chloro-2-ethyl-*N*-((4'-(hexanamidomethyl)biphenyl-4-yl)methyl)imidazo[1,2-a]pyridine-3-carboxamide (184)
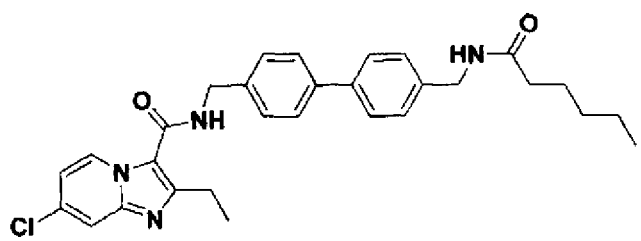
6-Chloro-2-ethyl-N-(4-(4-(trifluoromethoxy)phenoxy)benzyl)imidazo[1,2-a]pyridine-3-carboxamide (185)
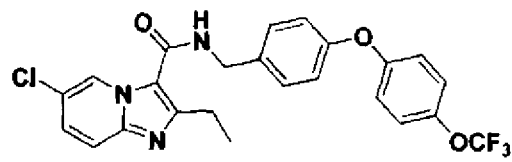

7-Chloro-2-ethyl-N-(4-(4-(trifluoromethoxy)phenoxy)benzyl)imidazo[1,2-a]pyridine-3-carboxamide (186)
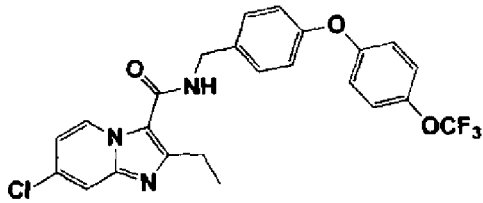
6-Chloro-2-ethyl-N-(4-(4-fluorophenoxy)benzyl)imidazo[1,2-a]pyridine-3-carboxamide (187)
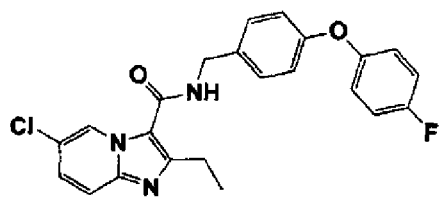
7-Chloro-2-ethyl-N-(4-(4-fluorophenoxy)benzyl)imidazo[1,2-a]pyridine-3-carboxamide (188)
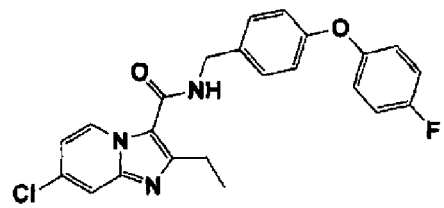
6-Bromo-2-ethyl-N-(4-(4-fluorophenoxy)benzyl)imidazo[1,2-a]pyridine-3-carboxamide (189)
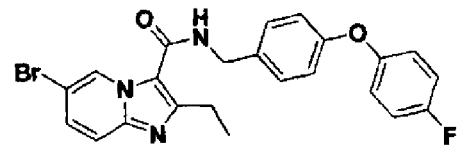
6-Chloro-N-(4-(4-chlorophenoxy)benzyl)-2-ethylimidazo[1,2-a]pyridine-3-carboxamide (190)
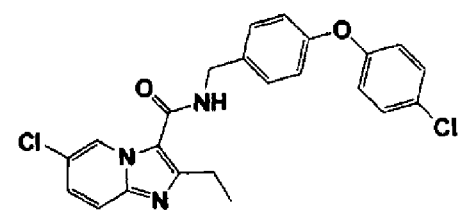

7-Chloro-N-(4-(4-chlorophenoxy)benzyl)-2-ethylimidazo[1,2-a]pyridine-3-carboxamide (191)
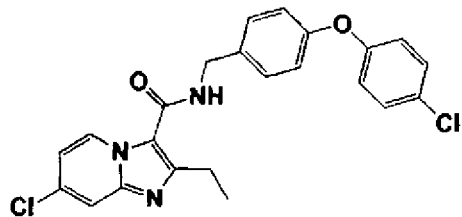
2-Ethyl-N-(4-(4-(trifluoromethoxy)phenoxy)benzyl)imidazo[1,2-a]pyridine-3-carboxamide (192)
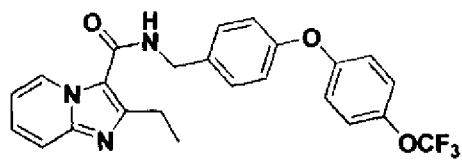
7-Chloro-2-ethyl-N-((6-(4-fluorophenoxy)pyridin-3-yl)methyl)imidazo[1,2-a]pyridine-3-carboxamide (193)
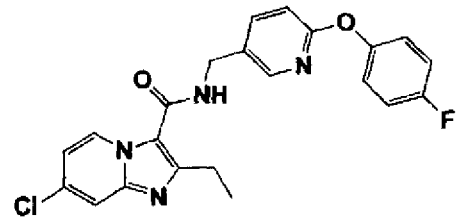
6-Chloro-2-ethyl-N-(4-(4-(trifluoromethoxy)phenylamino)benzyl)imidazo[1,2-a] pyridine-3-carboxamide (198)
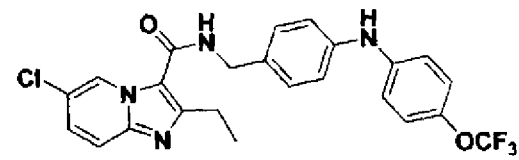

7-Chloro-2-ethyl-N-(4-(4-(trifluoromethoxy)phenylamino)benzyl)imidazo[1,2-a]pyridine-3-carboxamide (199)

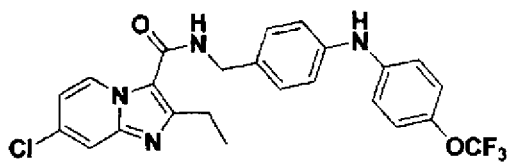

6-Chloro-2-ethyl-N-(4-(4-(trifluoromethyl)benzyloxy)benzyl)imidazo[1,2-a]pyridine-3-carboxamide (200)

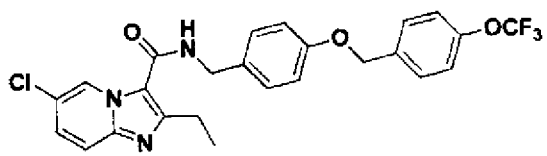

7-Chloro-2-ethyl-N-(4-(4-(trifluoromethyl)benzyloxy)benzyl)imidazo[1,2-a]pyridine-3-carboxamide (201)

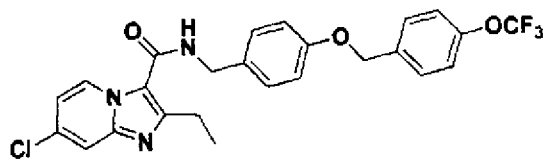

6-Chloro-2-ethyl-N-(4-(4-fluorobenzyloxy)benzyl)imidazo[1,2-a]pyridine-3-carboxamide (202)

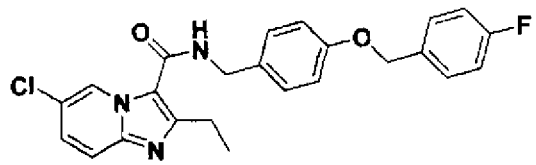

6-Chloro-N-(4-(2,6-dimethylmorpholino)benzyl)-2-ethylimidazo[1,2-a]pyridine-3-carboxamide (209)

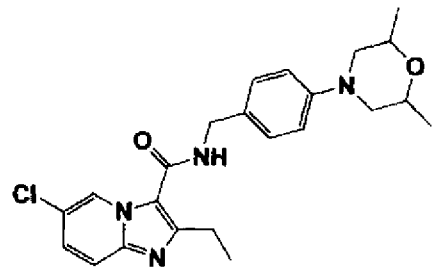

7-Chloro-N-(4-(2,6-dimethylmorpholino)benzyl)-2-ethylimidazo[1,2-a]pyridine-3-carboxamide (210)
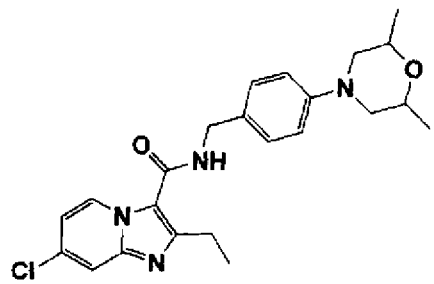
6-Chloro-2-ethyl-N-(4-(4-methylpiperidin-1-yl)benzyl)imidazo[1,2-a]pyridine-3-carboxamide (214)
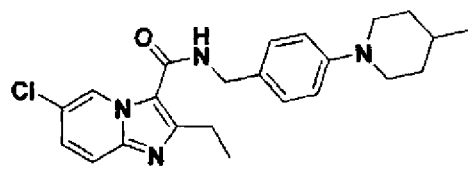
7-Chloro-2-ethyl-N-(4-(4-methylpiperidin-1-yl)benzyl)imidazo[1,2-a]pyridine-3-carboxamide (215)
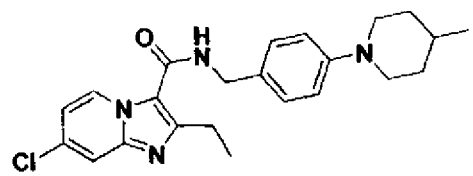
6-Chloro-N-(4-(3,5-dimethylpiperidin-1-yl)benzyl)-2-ethylimidazo[1,2-a]pyridine-3-carboxamide (216)
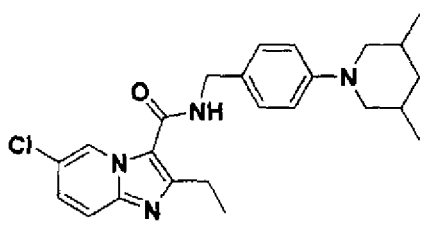

7-Chloro-*N*-(4-(3,5-dimethylpiperidin-1-yl)benzyl)-2-ethylimidazo[1,2-a]pyridine-3-carboxamide (217)
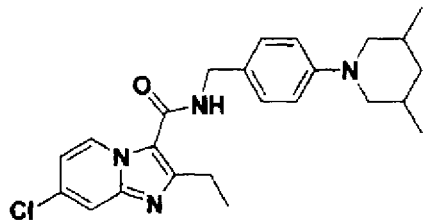
7-Chloro-2-ethyl-*N*-(4-(4-hydroxypiperidin-1-yl)benzyl)imidazo[1,2-a]pyridine-3-carboxamide (218)
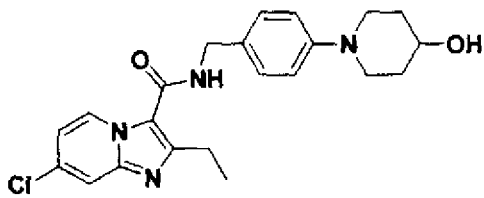
7-Chloro-N-(4-(3a,4-dihydro-1H-isoindol-2(3H,7H,7aH)-yl)benzyl)-2-ethylimidazo[1,2-a]pyridine-3-carboxamide (223)
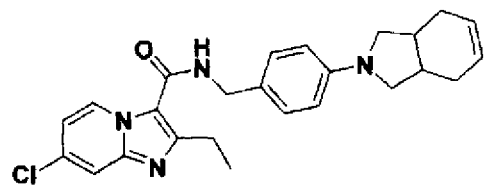
N-(4-(1H-isoindol-2(3H,3aH,4H,5H,6H,7H,7aH)-yl)benzyl)-7-chloro-2-ethylimidazo[1,2-a]pyridine-3-carboxamide (224)
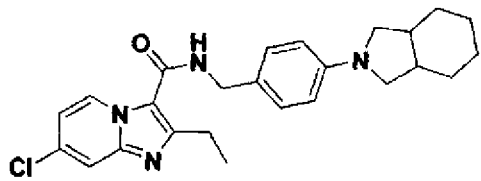

7-Chloro-2-ethyl-N-(4-(4,5,6,7-tetrahydro-2H-isoindol-2-yl)benzyl)imidazo[1,2-a]pyridine-3-carboxamide (225)
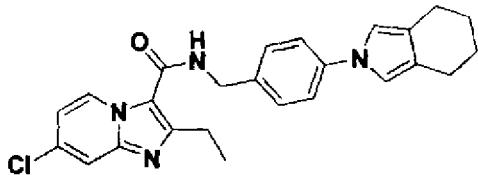
6-Chloro-2-ethyl-N-((1-(4-(trifluoromethoxy)benzyl)piperidin-4-yl)methyl)imidazo[1,2-a]pyridine-3-carboxamide (226)
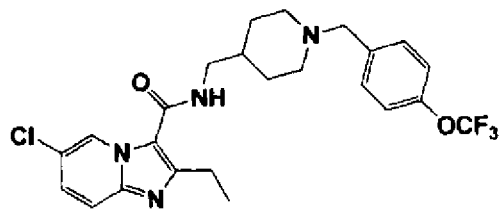
6-Chloro-2-ethyl-N-((1-(4-fluorobenzyl)piperidin-4-yl)methyl)imidazo[1,2-a]pyridine-3-carboxamide (227)
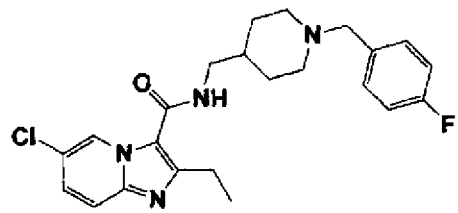
6-Chloro-2-ethyl-N-((1-(4-(trifluoromethoxy)phenyl)-1H-pyrazol-3-yl)methyl) imidazo[1,2-a]pyridine-3-carboxamide (231)
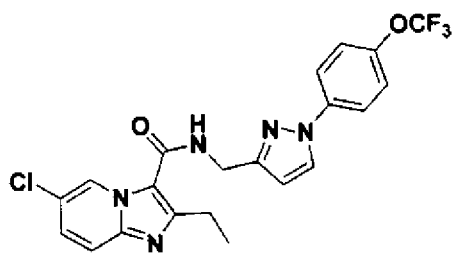

7-Chloro-2-ethyl-*N*-((4'-(trifluoromethoxy)biphenyl-3-yl)methyl)imidazo[1,2-a]pyridine-3-carboxamide (248)
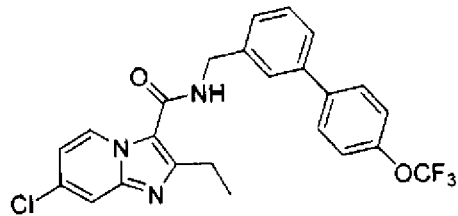
2-Ethyl-7-methyl-*N*-(4-(trifluoromethoxy)benzyl)imidazo[1,2-a]pyridine-3-carboxamide (249)
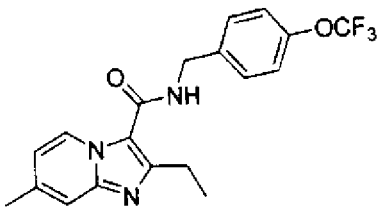
7-Bromo-2-ethyl-*N*-(4-(trifluoromethoxy)benzyl)imidazo[1,2-a]pyridine-3-carboxamide (250)
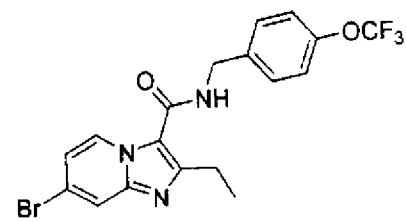
2-Ethyl-8-fluoro-*N*-(4-(trifluoromethoxy)benzyl)imidazo[1,2-a]pyridine-3-carboxamide (251)
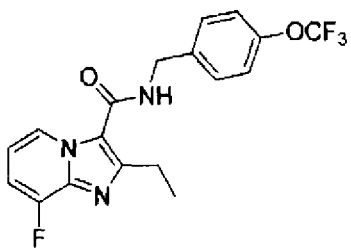

7-Chloro-2-ethyl-*N*-((4'-formylbiphenyl-4-yl)methyl)imidazo[1,2-a]pyridine-3-carboxamide(252)
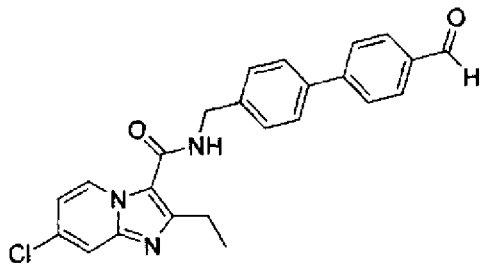
2-Ethyl-6-fluoro-N-(4-(4-(trifluoromethoxy)phenoxy)benzyl)imidazo[1,2-a]pyridine-3-carboxamide (253)
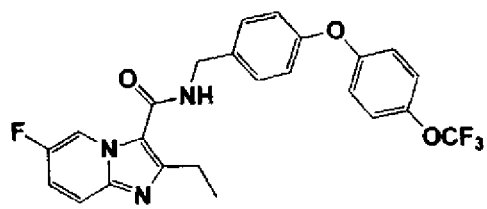
6-Bromo-2-ethyl-N-(4-(4-(trifluoromethoxy)phenoxy)benzyl)imidazo[1,2-a]pyridine-3-carboxamide (254)
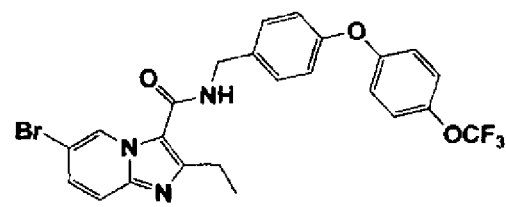
2-Ethyl-6-methyl-*N*-(4-(4-(trifluoromethoxy)phenoxy)benzyl)imidazo[1,2-a]pyridine-3-carboxamide (255)
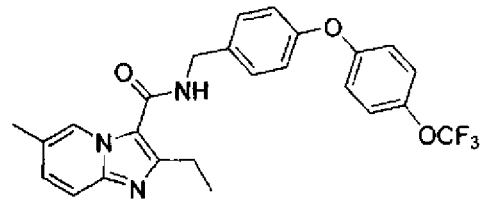

2-Ethyl-7-methyl-N-(4-(4-(trifluoromethoxy)phenoxy)benzyl)imidazo[1,2-a]pyridine-3-carboxamide (256)
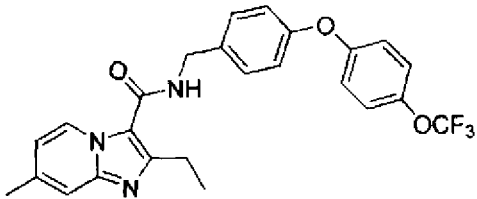
2-Ethyl-8-fluoro-N-(4-(4-(trifluoromethoxy)phenoxy)benzyl)imidazo[1,2-a]pyridine-3-carboxamide (257)
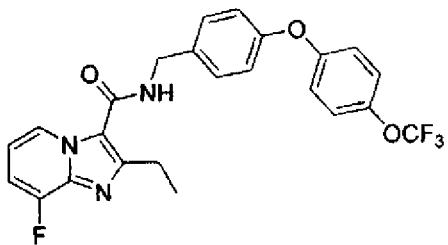
2-Ethyl-6-fluoro-N-(4-(4-(trifluoromethoxy)benzyloxy)benzyl)imidazo[1,2-a]pyridine-3-carboxamide (258)
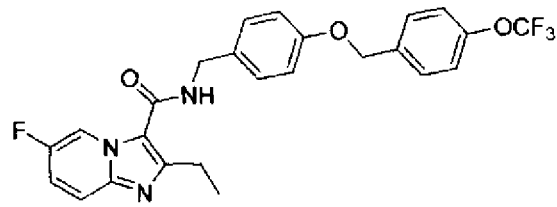

6-Bromo-2-ethyl-*N*-(4-(4-(trifluoromethoxy)benzyloxy)benzyl)imidazo[1,2-a]pyridine-3-carboxamide (259)
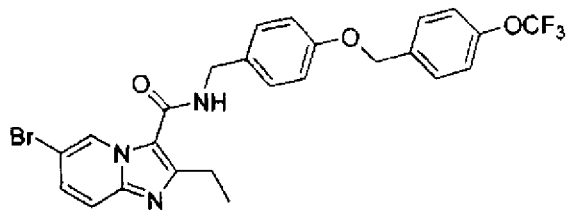
2-Ethyl-*N*-(4-(4-(trifluoromethoxy)benzyloxy)benzyl)imidazo[1,2-a]pyridine-3-carboxamide (260)
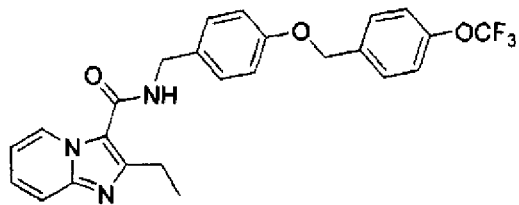
7-Chloro-2-ethyl-N-(4-((4-(trifluoromethoxy)benzyl)amino)benzyl)imidazo[1,2-a]pyridine-3-carboxamide (262)
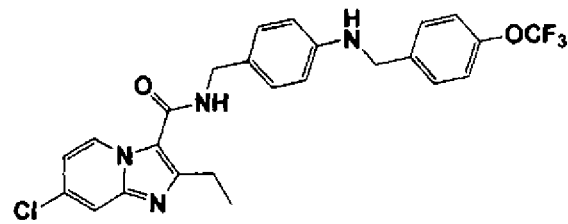
2-Ethyl-N-(4-(methyl(4-(trifluoromethoxy)benzyl)amino)benzyl)imidazo[1,2-a]pyridine-3-carboxamide (263)
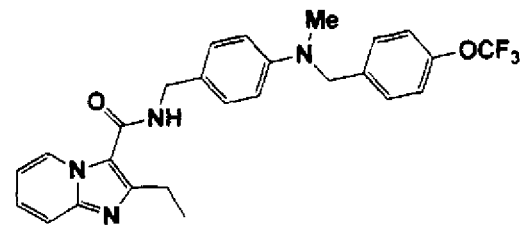

6-Chloro-2-ethyl-*N*-(4-(octahydroisoquinolin-2(1H)-yl)benzyl)imidazo[1,2-a]pyridine-3-carboxamide (267)
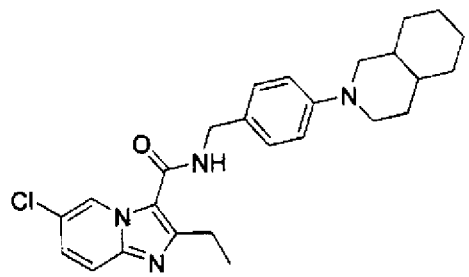
7-Chloro-2-ethyl-*N*-(4-(octahydroisoquinolin-2(1H)-yl)benzyl)imidazo[1,2-a]pyridine-3-carboxamide (268)
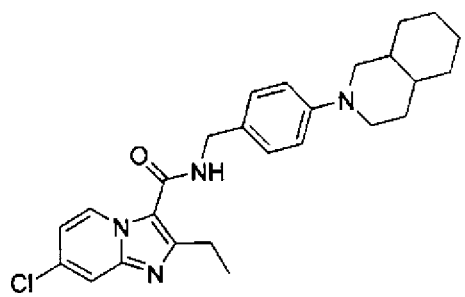
7-Chloro-2-ethyl-*N*-(4-(4-oxopiperidin-1-yl)benzyl)imidazo[1,2-a]pyridine-3-carboxamide (269)
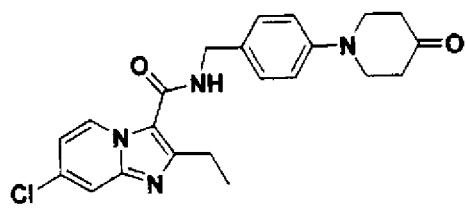

7-Chloro-2-ethyl-*N*-(4-(4-methylenepiperidin-1-yl)benzyl)imidazo[1,2-a]pyridine-3-carboxamide (271)
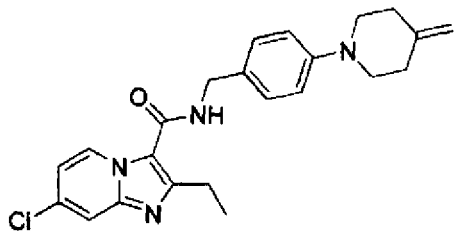
6-chloro-2-ethyl-*N*-(4-(2-methylpiperidin-1-yl)benzyl)imidazo[1,2-a]pyridine-3-carboxamide (272)
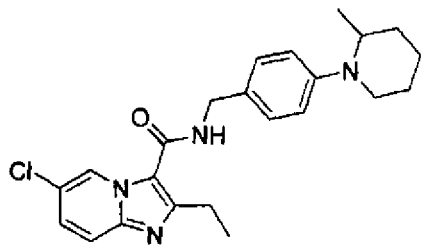
7-chloro-2-ethyl-*N*-(4-(2-methylpiperidin-1-yl)benzyl)imidazo[1,2-a]pyridine-3-carboxamide (273)
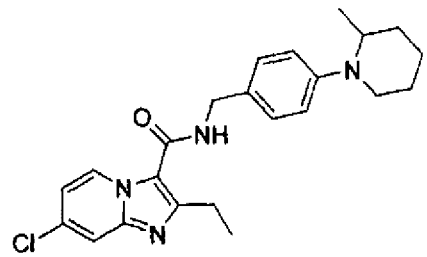
7-Chloro-*N*-(4-(4,4-dimethylpiperidin-1-yl)benzyl)-2-ethyl-1,8a-dihydroimidazo[1,2-a]pyridine-3-carboxamide (274)
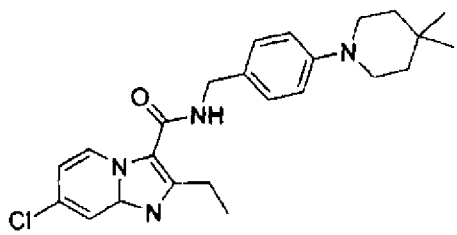

7-Chloro-2-ethyl-N-(4-(4-(hydroxymethyl)piperidin-1-yl)benzyl)imidazo[1,2-a]pyridine-3-carboxamide (280)
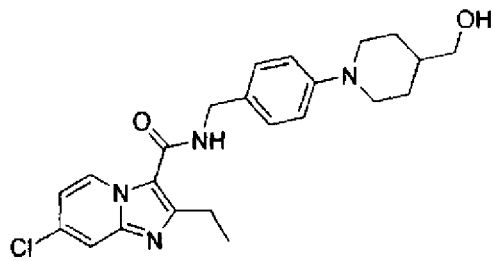
6-Chloro-2-ethyl-N-(4-(4-(methoxymethyl)piperidin-1-yl)benzyl)imidazo[1,2-a]pyridine-3-carboxamide (281)
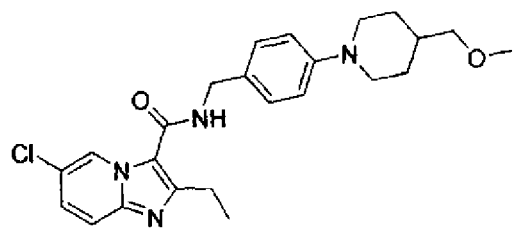
7-Chloro-2-ethyl-N-(4-(4-(methoxymethyl)piperidin-1-yl)benzyl)imidazo[1,2-a]pyridine-3-carboxamide (282)
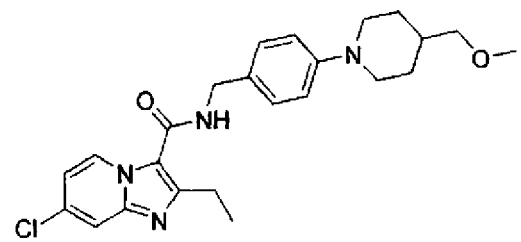

7-Chloro-2-ethyl-*N*-(4-(4-phenylpiperidin-1-yl)benzyl)imidazo[1,2-a]pyridine-3-carboxamide (283)
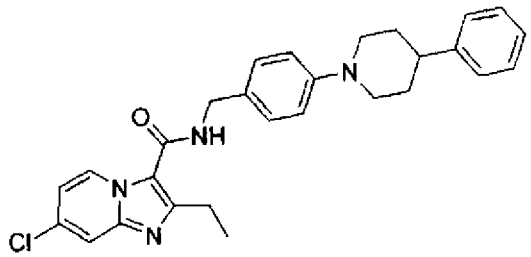
6-Chloro-2-ethyl-*N*-(4-(4-phenylpiperidin-1-yl)benzyl)imidazo[1,2-a]pyridine-3-carboxamide (284)
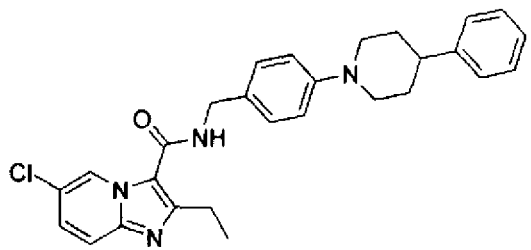
2-Ethyl-*N*-(4-(4-(4-fluorophenyl)piperidin-1-yl)benzyl)imidazo[1,2-a]pyridine-3-carboxamide(285)
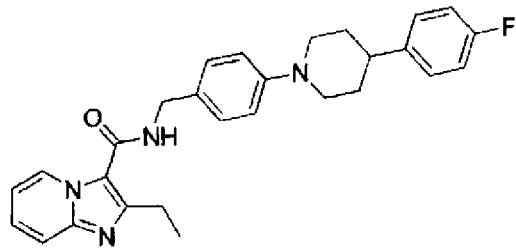

6-Chloro-2-ethyl-*N*-(4-(4-(4-fluorophenyl)piperidin-1-yl)benzyl)imidazo[1,2-a]pyridine-3-carboxamide (286)
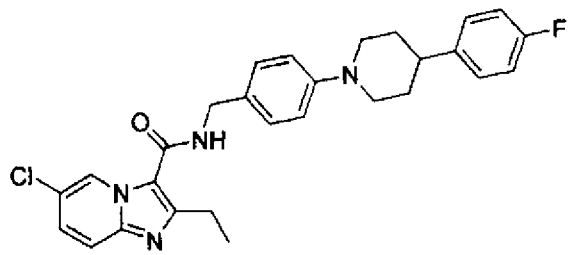
7-Chloro-2-ethyl-*N*-(4-(4-(4-fluorophenyl)piperidin-1-yl)benzyl)imidazo[1,2-a]pyridine-3-carboxamide (287)
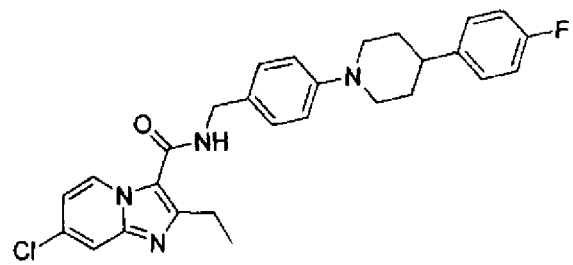
2-Ethyl-*N*-(4-(4-(4-(trifluoromethoxy)phenyl)piperidin-1-yl)benzyl)imidazo[1,2-a]pyridine-3-carboxamide (288)
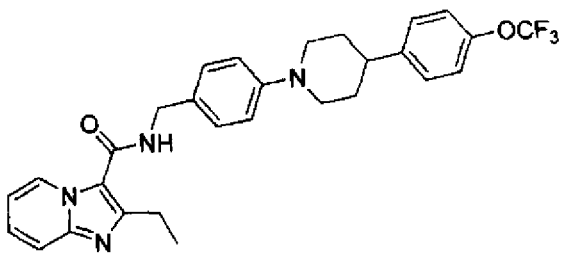

6-Chloro-2-ethyl-*N*-(4-(4-(4-(trifluoromethoxy)phenyl)piperidin-1-yl)benzyl)imidazo[1,2-a]pyridine-3-carboxamide (289)

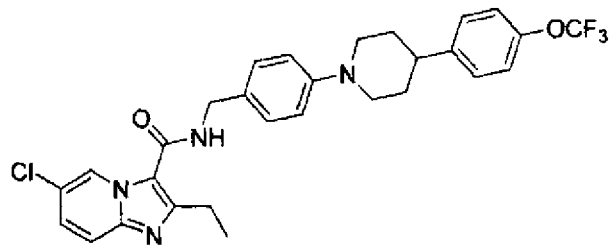

7-Chloro-2-ethyl-*N*-(4-(4-(4-(trifluoromethoxy)phenyl)piperidin-1-yl)benzyl)imidazo[1,2-a]pyridine-3-carboxamide(290)

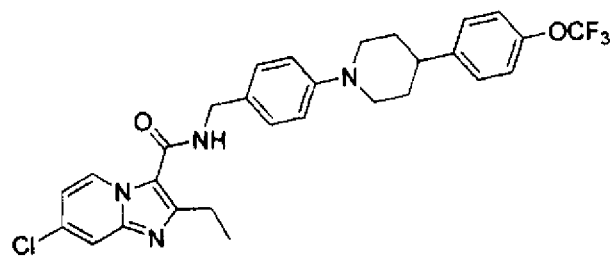

6-Chloro-2-ethyl-*N*-(4-(4-(isopropoxymethyl)piperidin-1-yl)benzyl)imidazo[1,2-a]pyridine-3-carboxamide(291)

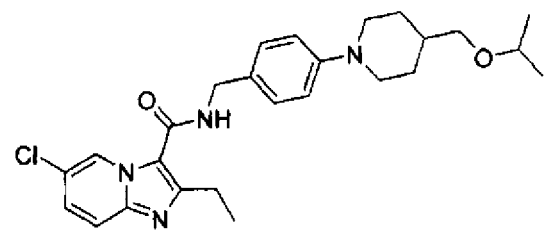

7-Chloro-2-ethyl-*N*-(4-(4-(isopropoxymethyl)piperidin-1-yl)benzyl)imidazo[1,2-a]pyridine-3-carboxamide(292)

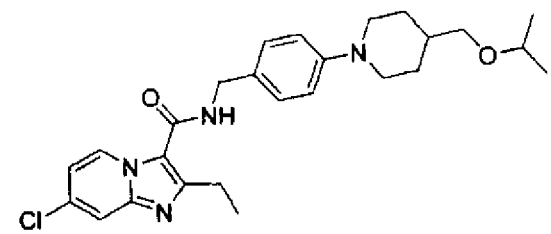

6-Chloro-*N*-(4-(4-(cyclopentyloxymethyl)piperidin-1-yl)benzyl)-2-ethylimidazo[1,2-a]pyridine-3-carboxamide(293)
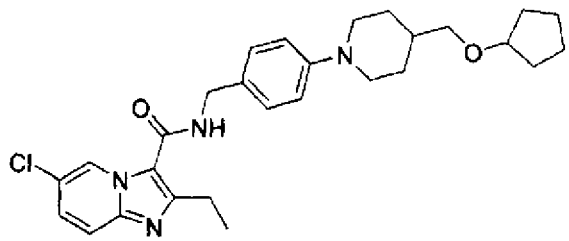
2-Ethyl-N-(4-(4-((4-fluorophenoxy)methyl)piperidin-1-yl)benzyl)imidazo[1,2-a]pyridine-3-carboxamide (295)
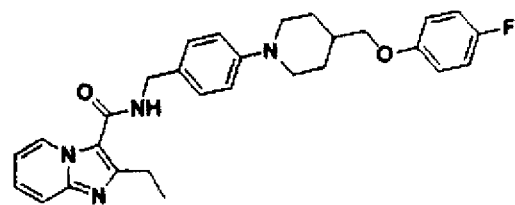
6-Chloro-2-ethyl-N-(4-(4-((4-fluorophenoxy)methyl)piperidin-1-yl)benzyl)imidazo[1,2-a]pyridine-3-carboxamide (296)
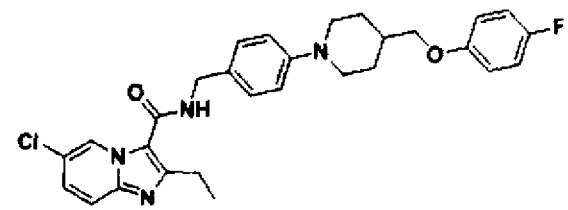
7-Chloro-2-ethyl-N-(4-(4-((4-fluorophenoxy)methyl)piperidin-1-yl)benzyl)imidazo[1,2-a]pyridine-3-carboxamide (297)
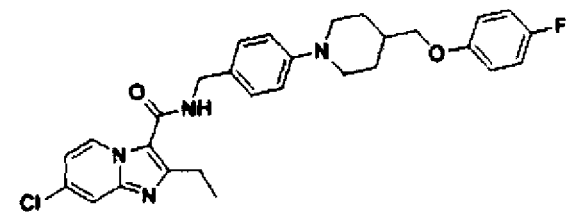

6-chloro-2-ethyl-*N*-(4-(4-((4-(trifluoromethoxy)phenoxy)methyl)piperidin-1-yl)benzyl)imidazo[1,2-a]pyridine-3-carboxamide (298)
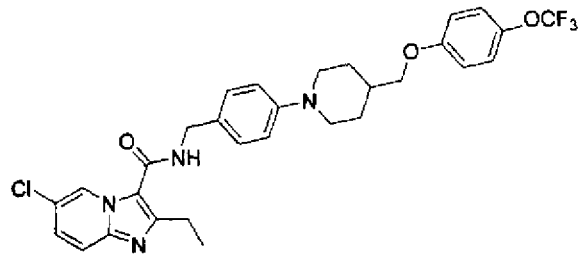
7-Chloro-2-ethyl-*N*-(4-(4-((4-(trifluoromethoxy)phenoxy)methyl)piperidin-1-yl)benzyl)imidazo[1,2-a]pyridine-3-carboxamide (299)
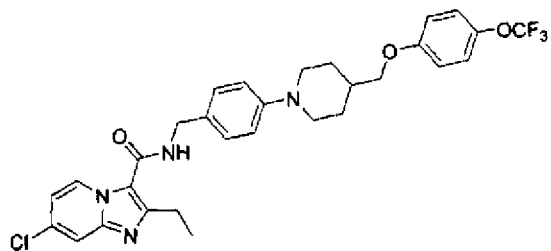
Ethyl 1-(4-((6-chloro-2-ethylimidazo[1,2-a]pyridine-3-carboxamido)methyl)phenyl)piperidine-4-carboxylate (300)
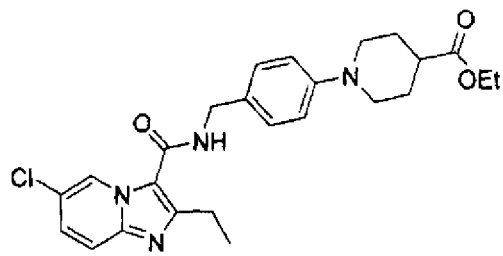

Ethyl 1-(4-((7-chloro-2-ethylimidazo[1,2-a]pyridine-3-carboxamido)methyl)phenyl) piperidine-4-carboxylate (301)
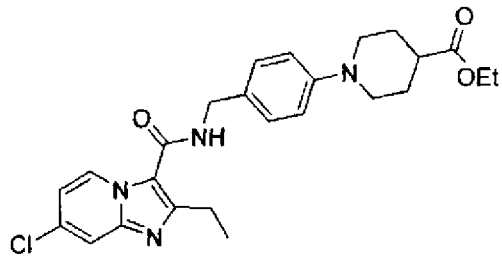
1-(4-((7-Chloro-2-ethylimidazo[1,2-a]pyridine-3-carboxamido)methyl)phenyl) piperidine-4-carboxylic acid (302)
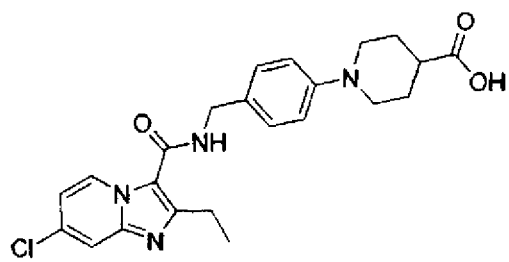
2-Ethyl-N-(4-(4-(4-fluorophenyl)piperazin-1-yl)benzyl)imidazo[1,2-a]pyridine-3-carboxamide (303)
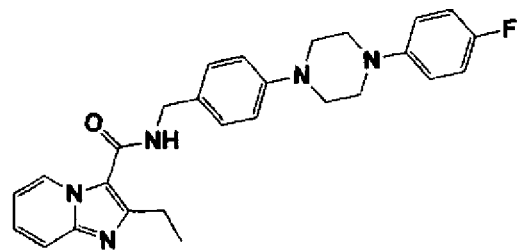

8-(Difluoromethoxy)-2-ethyl-N-(4-(4-(4-fluorophenyl)piperazin-1-yl)benzyl)imidazo[1,2-a]pyridine-3-carboxamide (304)
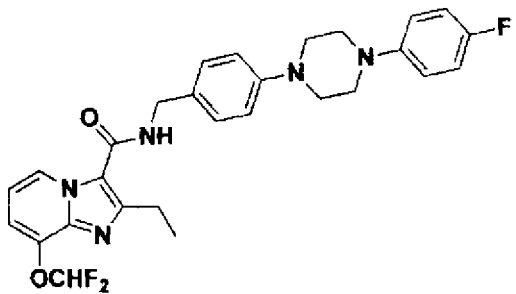
**8-Bromo-2-ethyl-*N*-(4-(4-(4-fluorophenyl)piperazin-1-yl)benzyl)imidazo[1,2-a]pyridine-3-carboxamide (305)**
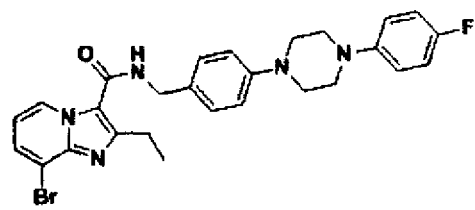
2-Ethyl-6-fluoro-N-(4-(4-(4-fluorophenyl)piperazin-1-yl)benzyl)imidazo[1,2-a]pyridine-3-carboxamide (306)
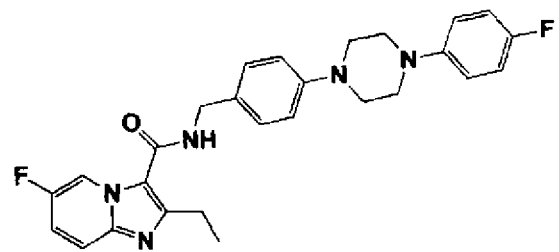

6-Bromo-2-ethyl-N-(4-(4-(4-fluorophenyl)piperazin-1-yl)benzyl)imidazo[1,2-a]pyridine-3-carboxamide (307)
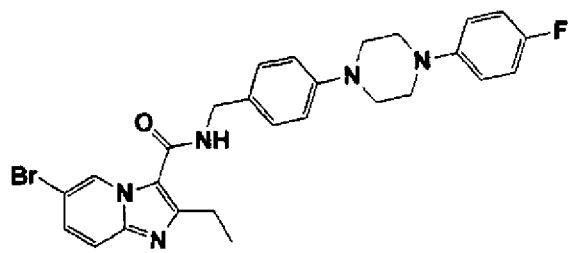
2-Ethyl-N-(4-(4-(4-fluorophenyl)piperazin-1-yl)benzyl)-6-methylimidazo[1,2-a]pyridine-3-carboxamide (308)
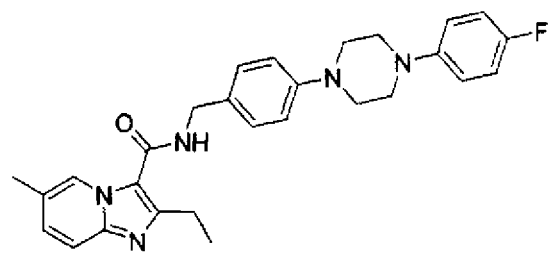
2-Ethyl-N-(4-(4-(4-fluorophenyl)piperazin-1-yl)benzyl)-7-methylimidazo[1,2-a]pyridine-3-carboxamide (309)
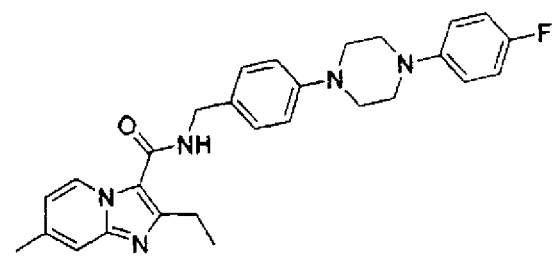

2-Ethyl-8-fluoro-*N*-(4-(4-(4-fluorophenyl)piperazin-1-yl)benzyl)imidazo[1,2-a]pyridine-3-carboxamide (310)
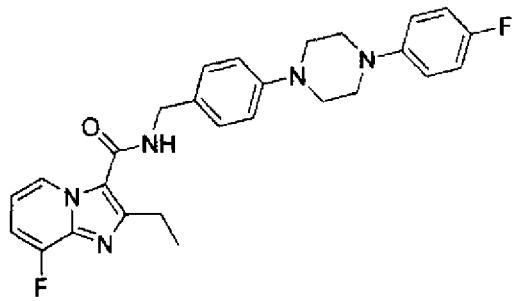
7-Bromo-2-ethyl-*N*-(4-(4-(4-fluorophenyl)piperazin-1-yl)benzyl)imidazo[1,2-a]pyridine-3-carboxamide (311)
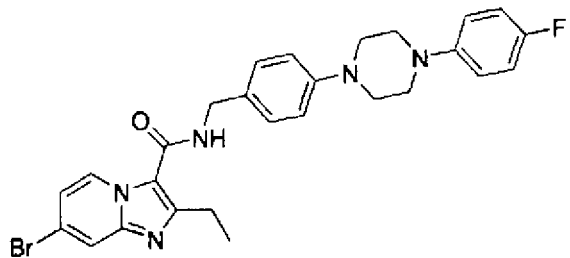
2-Ethyl-*N*-(4-(4-(4-fluorophenyl)piperazin-1-yl)benzyl)-8-(pyridin-4-yl)imidazo[1,2-a]pyridine-3-carboxamide (312)
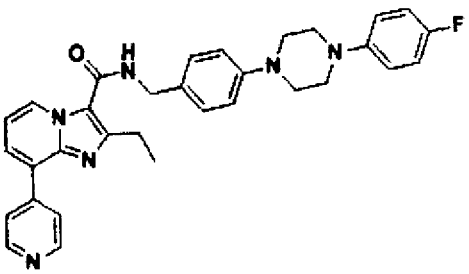

2-Ethyl-7-(4-phenylpiperazin-1-yl)-*N*-(4-(trifluoromethyl)benzyl)imidazo[1,2-a]pyridine-3-carboxamide (330)
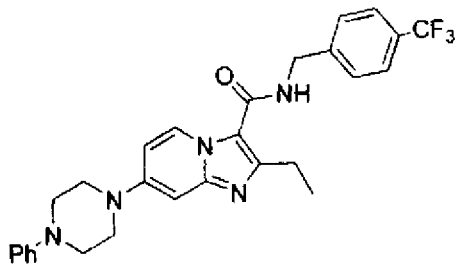
9. The compound according to claim 1, having a formula selected from formulae 5, 8, 13, 14, 17, 18, 20, 21, 23-43, 46, 48, 50, 51, 53, 59, 68, 69, 74, 79, 80, 89-91, 142, 143, 196, 211-213, 219, 221, 222, 243, 247, 313-329 and 331:
2-Methyl-*N*-(pyridin-4-yl)imidazo[1,2-a]pyridine-3-carboxamide (5)
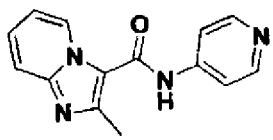
N-Benzyl-2-methylimidazo[1,2-a]pyridine-3-carboxamide (8)
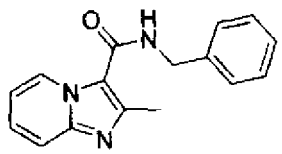
2-Methyl-*N*-(pyridin-3-ylmethyl)imidazo[1,2-a]pyridine-3-carboxamide (13)
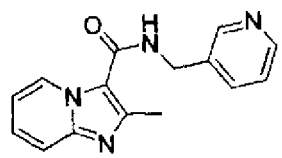

2-Methyl-N-(pyridin-4-ylmethyl)imidazo[1,2-a]pyridine-3-carboxamide (14)
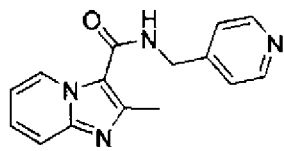
N-((1H-Indol-5-yl)methyl)-2-methylimidazo[1,2-a]pyridine-3-carboxamide (17)
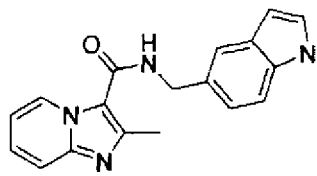
N-(Cyclohexylmethyl)-2-methylimidazo[1,2-a]pyridine-3-carboxamide (18)
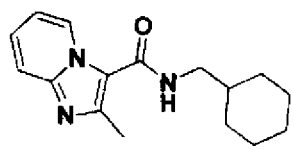
2-Methyl-N-(piperidin-4-ylmethyl)imidazo[1,2-a]pyridine-3-carboxamide (20)
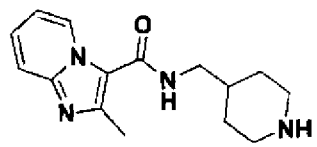
2-Methyl-N-phenethylimidazo[1,2-a]pyridine-3-carboxamide (21)
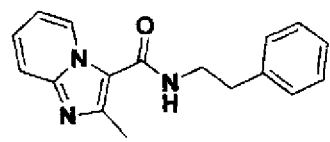
2-Methyl-N-(2-phenoxyethyl)imidazo[1,2-a]pyridine-3-carboxamide (23)
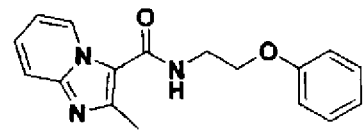

N-(2-(Benzyloxy)ethyl)-2-methylimidazo[1,2-a]pyridine-3-carboxamide (24)
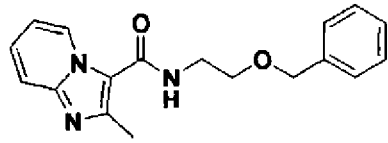
(S)-Methyl 2-(2-methylimidazo[1,2-a]pyridine-3-carboxamido)-3-phenylpropanoate (25)
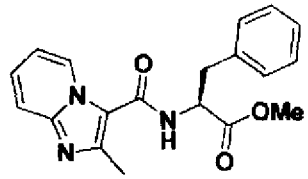
N-(2-Methylimidazo[1,2-a]pyridin-3-yl)-2-phenylacetamide (26)
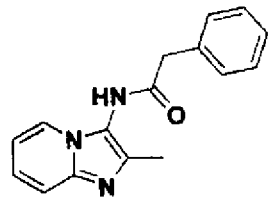
N-Benzyl-8-chloro-2-methylimidazo[1,2-a]pyridine-3-carboxamide (27)
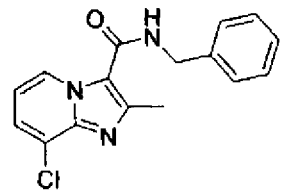
N-Benzyl-7-chloro-2-methylimidazo[1,2-a]pyridine-3-carboxamide (28)
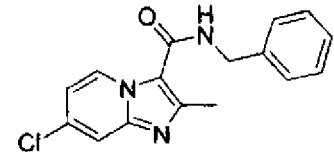

N-Benzyl-6-chloro-2-methylimidazo[1,2-a]pyridine-3-carboxamide (29)
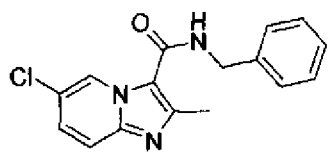
N-Benzyl-2,8-dimethylimidazo[1,2-a]pyridine-3-carboxamide (30)
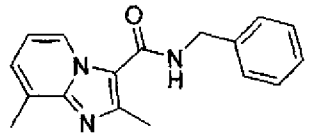
N-Benzyl-2,7-dimethylimidazo[1,2-a]pyridine-3-carboxamide (31)
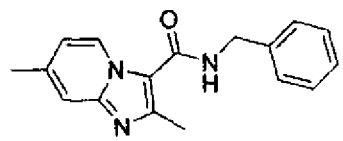
N-Benzyl-2,6-dimethylimidazo[1,2-a]pyridine-3-carboxamide (32)
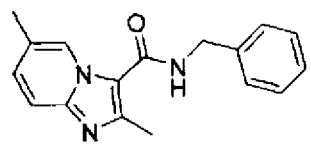
N-Benzyl-2,5-dimethylimidazo[1,2-a]pyridine-3-carboxamide (33)
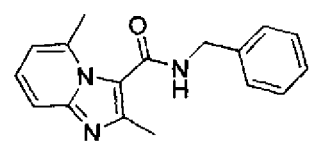
N-Benzyl-6-fluoro-2-methylimidazo[1,2-a]pyridine-3-carboxamide (34)
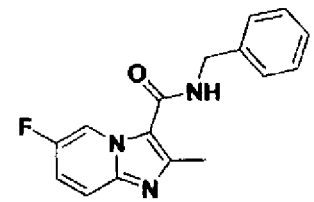

N-Benzyl-7-cyano-2-methylimidazo[1,2-a]pyridine-3-carboxamide (35)
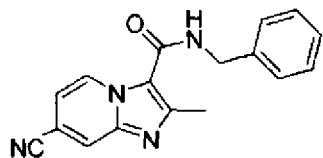
N-Benzyl-6-cyano-2-methylimidazo[1,2-a]pyridine-3-carboxamide (36)
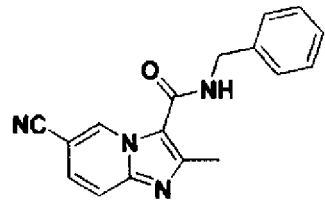
N-Benzyl-2-methyl-7-phenylimidazo[1,2-a]pyridine-3-carboxamide (37)
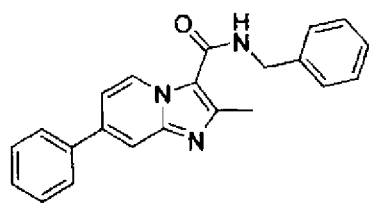
N-Benzyl-2-methyl-6-phenylimidazo[1,2-a]pyridine-3-carboxamide (38)
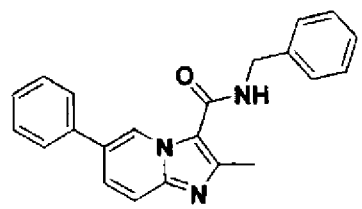
N-Benzyl-8-fluoro-2-methylimidazo[1,2-a]pyridine-3-carboxamide (39)
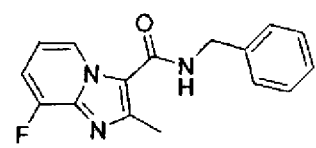

N-Benzyl-2-methyl-8-(trifluoromethyl)imidazo[1,2-a]pyridine-3-carboxamide (40)
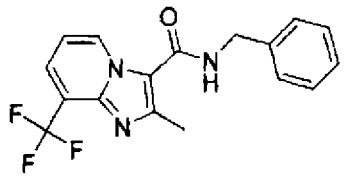
N-Benzyl-8-methoxy-2-methylimidazo[1,2-a]pyridine-3-carboxamide (41)
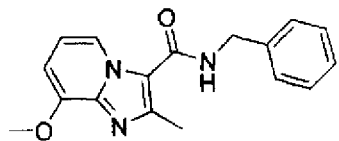
N-Benzyl-8-cyano-2-methylimidazo[1,2-a]pyridine-3-carboxamide (42)
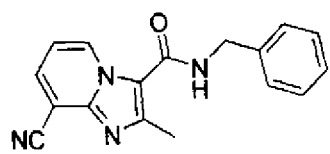
N-Benzyl-8-hydroxy-2-methylimidazo[1,2-a]pyridine-3-carboxamide (43)
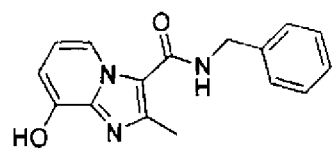
N-Benzyl-2-ethylimidazo[1,2-a]pyridine-3-carboxamide (46)
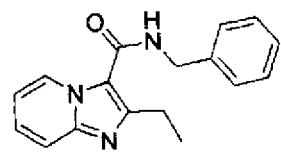

N-Benzyl-2-propylimidazo[1,2-a]pyridine-3-carboxamide (48)
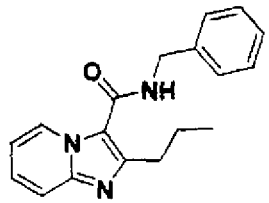
N-Benzyl-2-cyclopropylimidazo[1,2-a]pyridine-3-carboxamide (50)
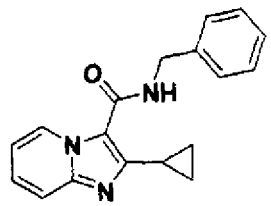
N-Benzyl-2-isopropylimidazo[1,2-a]pyridine-3-carboxamide (51)
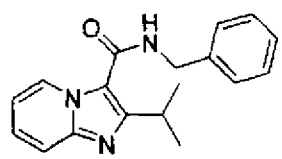
N-Benzyl-2-phenylimidazo[1,2-a]pyridine-3-carboxamide (53)
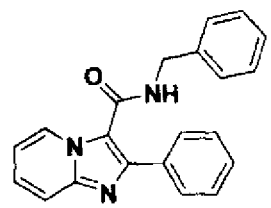
2-Ethyl-N-(4-(trifluoromethoxy)benzyl)imidazo[1,2-a]pyridine-3-carboxamide (59)
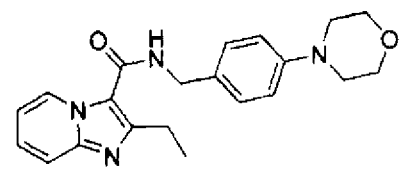

2-Ethyl-7-methyl-N-(4-morpholinobenzyl)imidazo[1,2-a]pyridine-3-carboxamide (68)
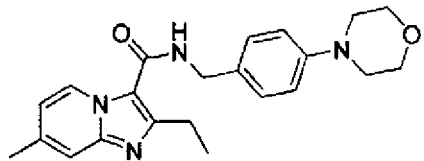
2-Ethyl-7-methyl-N-(naphthalen-2-ylmethyl)imidazo[1,2-a]pyridine-3-carboxamide (69)
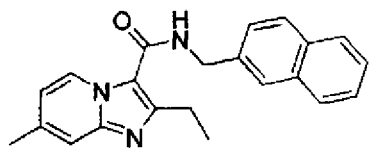
6-Chloro-2-methyl-N-(4-morpholinobenzyl)imidazo[1,2-a]pyridine-3-carboxamide (74)
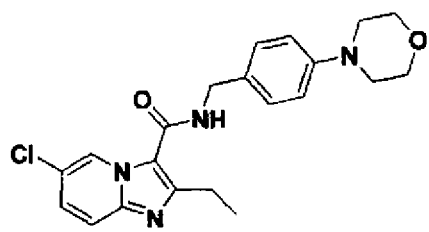
6-Chloro-2-ethyl-N-(4-(piperidin-1-yl)benzyl)imidazo[1,2-a]pyridine-3-carboxamide (79)
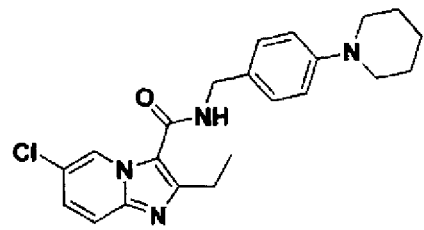
6-Chloro-2-ethyl-N-(naphthalen-2-ylmethyl)imidazo[1,2-a]pyridine-3-carboxamide (80)
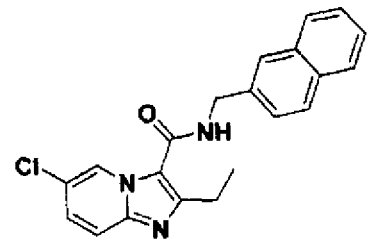

7-Chloro-2-ethyl-N-(4-morpholinobenzyl)imidazo[1,2-a]pyridine-3-carboxamide (89)
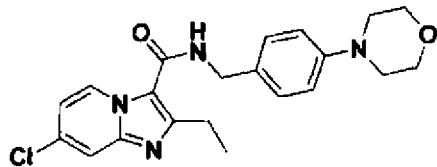
7-Chloro-2-ethyl-N-(4-(piperidin-1-yl)benzyl)imidazo[1,2-a]pyridine-3-carboxamide (90)
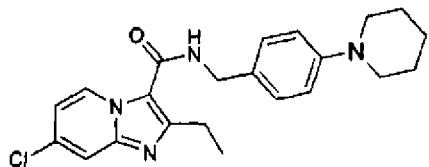
7-Chloro-2-ethyl-N-(naphthalen-2-ylmethyl)imidazo[1,2-a]pyridine-3-carboxamide (91)
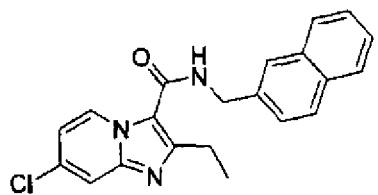
N-(7-Chloro-2-ethylimidazo[1,2-a]pyridin-3-yl)biphenyl-4-carboxamide (142)
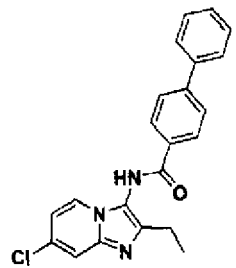
2-(Biphenyl-4-yl)-N-(7-chloro-2-ethylimidazo[1,2-a]pyridin-3-yl)acetamide (143)
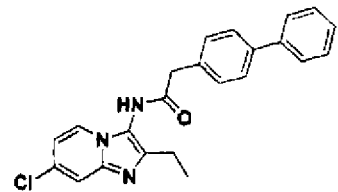

4-Phenoxybenzyl 6-chloro-2-ethylimidazo[1,2-a]pyridine-3-carboxylate (196)
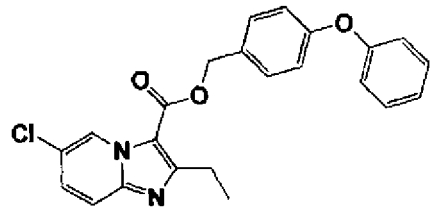
6-Chloro-2-ethyl-N-(4-(pyrrolidin-1-yl)benzyl)imidazo[1,2-a]pyridine-3-carboxamide (211)
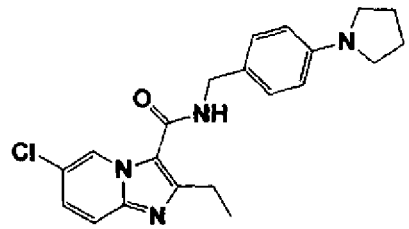
7-Chloro-2-ethyl-N-(4-(pyrrolidin-1-yl)benzyl)imidazo[1,2-a]pyridine-3-carboxamide (212)
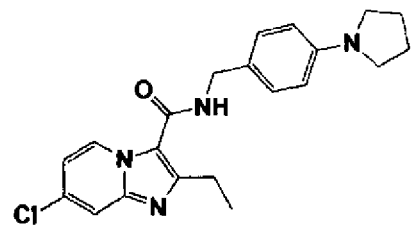
7-Chloro-N-(4-(5,6-dihydropyridin-1(2H)-yl)benzyl)-2-ethylimidazo[1,2-a]pyridine-3-carboxamide (213)
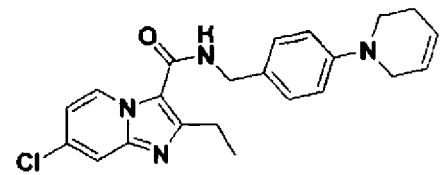
2-ethyl-6-methyl-N-(4-morpholinobenzyl)imidazo[1,2-a]pyridine-3-carboxamide (219)
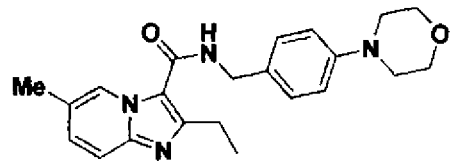

N-(4-(Azepan-1-yl)benzyl)-6-chloro-2-ethylimidazo[1,2-a]pyridine-3-carboxamide (221)
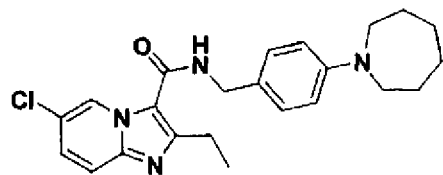
N-(4-(Azepan-1-yl)benzyl)-7-chloro-2-ethylimidazo[1,2-a]pyridine-3-carboxamide (222)
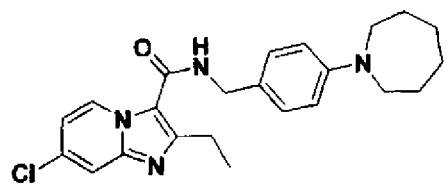
5-(6-Chloro-2-ethylimidazo[1,2-a]pyridin-3-yl)-3-(4-(trifluoromethoxy)benzyl)-1,2,4-oxadiazole (243)
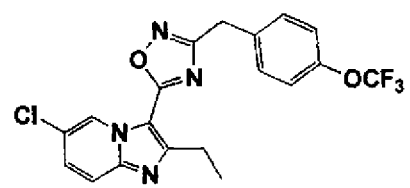
6-Chloro-2-ethyl-N-isobutylimidazo[1,2-a]pyridine-3-carboxamide (247)
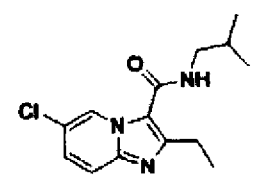

2-Ethyl-6-fluoro-N-(4-morpholinobenzyl)imidazo[1,2-a]pyridine-3-carboxamide (313)
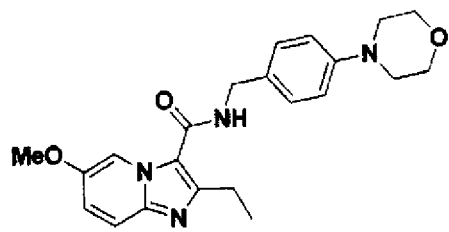
2-Ethyl-7-methoxy-*N*-(4-morpholinobenzyl)imidazo[1,2-a]pyridine-3-carboxamide(314)
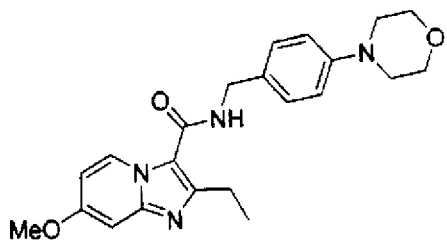
6-Bromo-2-ethyl-N-(4-morpholinobenzyl)imidazo[1,2-a]pyridine-3-carboxamide (315)
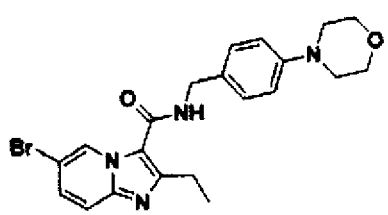
2-Ethyl-6-fluoro-N-(4-morpholinobenzyl)imidazo[1,2-a]pyridine-3-carboxamide (316)
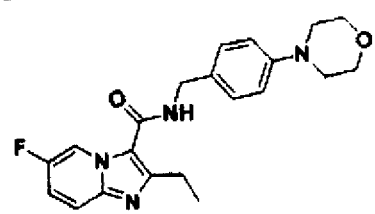

2-Ethyl-8-fluoro-N-(4-morpholinobenzyl)imidazo[1,2-a]pyridine-3-carboxamide (317)
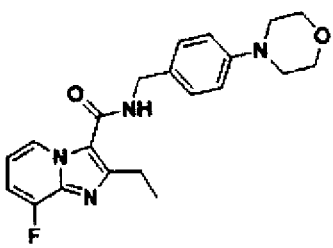
2-Ethyl-8-methoxy-N-(4-morpholinobenzyl)imidazo[1,2-a]pyridine-3-carboxamide (318)
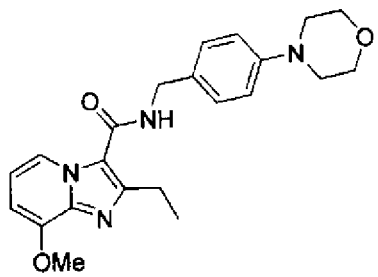
8-(Difluoromethoxy)-2-ethyl-N-(4-morpholinobenzyl)imidazo[1,2-a]pyridine-3-carboxamide (319)
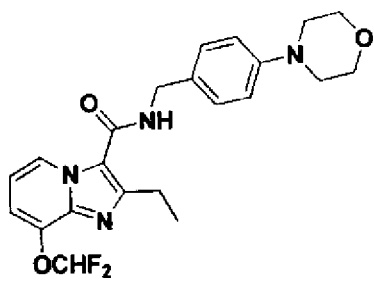
8-Bromo-2-ethyl-N-(4-morpholinobenzyl)imidazo[1,2-a]pyridine-3-carboxamide (320)
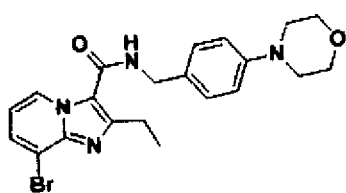

2-Ethyl-*N*-(4-morpholinobenzyl)-6-(trifluoromethyl)imidazo[1,2-a]pyridine-3-carboxamide (321)
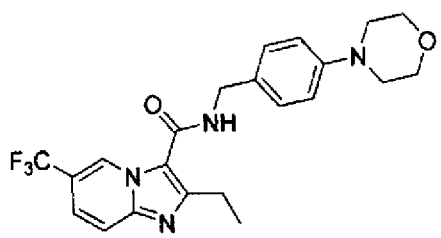
2-Ethyl-N-(4-morpholinobenzyl)-7-(trifluoromethyl)imidazo[1,2-a]pyridine-3-carboxamide (322)
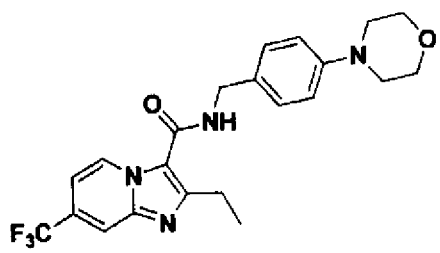
2-Ethyl-*N*-(4-morpholinobenzyl)-8-(trifluoromethyl)imidazo[1,2-a]pyridine-3-carboxamide (323)
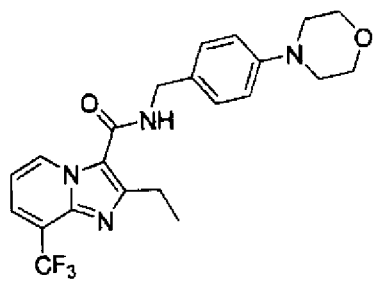
7-Bromo-2-ethyl-*N*-(4-morpholinobenzyl)imidazo[1,2-a]pyridine-3-carboxamide (324)
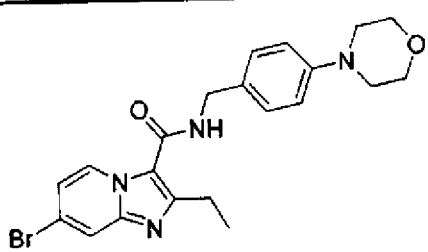

2-Ethyl-*N*-(4-morpholinobenzyl)-7-(pyridin-4-yl)imidazo[1,2-a]pyridine-3-carboxamide (325)
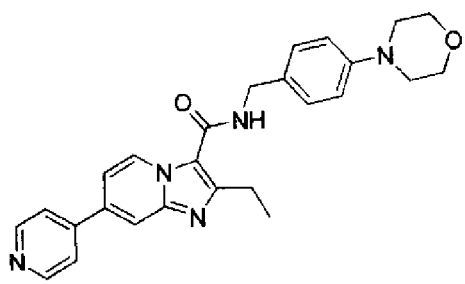
2-Ethyl-*N*-(4-morpholinobenzyl)-7-(pyridin-3-yl)imidazo[1,2-a]pyridine-3-carboxamide (326)
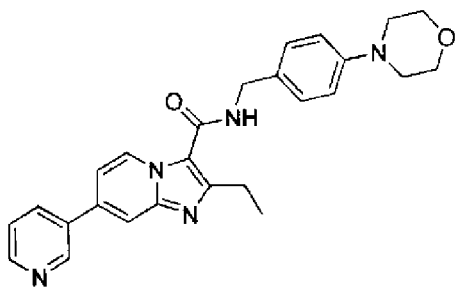
2-Ethyl-*N*-(4-morpholinobenzyl)-8-(pyridin-4-yl)imidazo[1,2-a]pyridine-3-carboxamide (327)
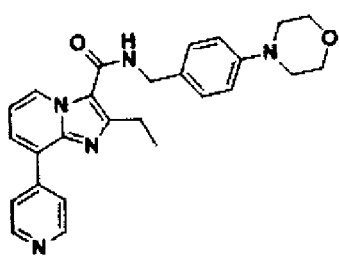
2-Ethyl-7-(4-methylpiperazin-1-yl)-*N*-(4-morpholinobenzyl)imidazo[1,2-a]pyridine-3-carboxamide (328)
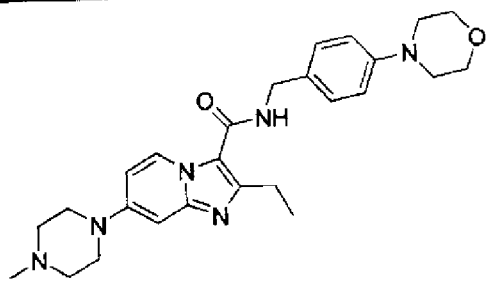

2-Ethyl-7-(4-(4-fluorophenyl)piperazin-1-yl)-*N*-(4-morpholinobenzyl)imidazo[1,2-a]pyridine-3-carboxamide(329)
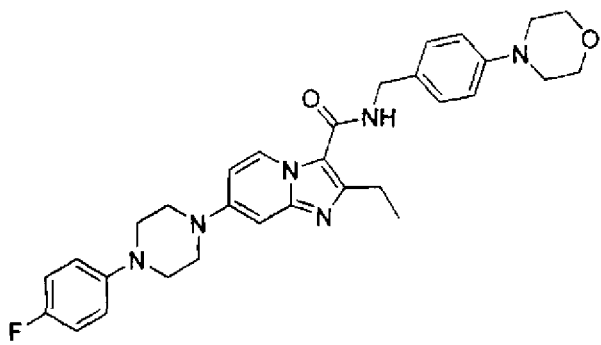
2-Ethyl-7-(4-(4-fluorobenzyl)piperazin-1-yl)-*N*-(4-morpholinobenzyl)imidazo[1,2-a]pyridine-3-carboxamide (331)
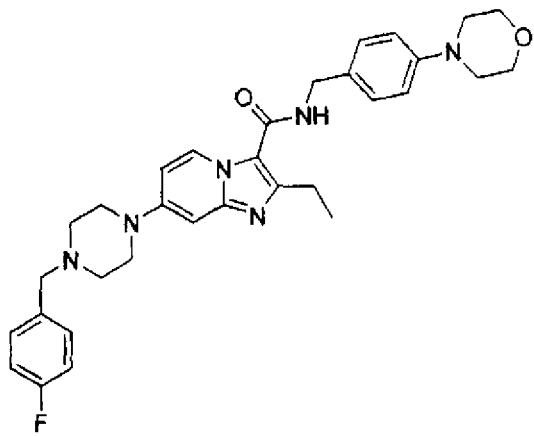
10. The compound according to claim 1, having a formula selected from formulae 161, 239-242 and 264:
[1,1'-Biphenyl]-4-ylmethyl 6-chloro-2-ethylimidazo[1,2-a]pyridine-3-carboxylate (161)
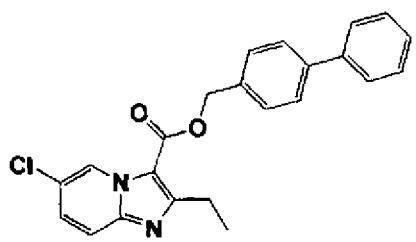

6-Chloro-2-ethyl-3-((4-(trifluoromethoxy)phenoxy)methyl)imidazo[1,2-a]pyridine (239)
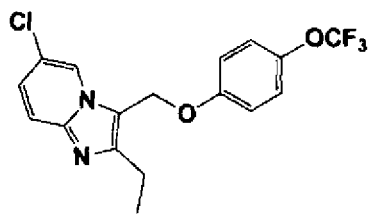
N-((6-Chloro-2-ethylimidazo[1,2-a]pyridin-3-yl)methyl)-4-(trifluoromethoxy)aniline (240)
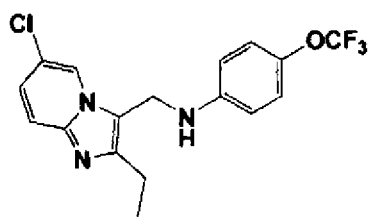
N-((6-Chloro-2-ethylimidazo[1,2-a]pyridin-3-yl)methyl)-4-(4-(4-fluorophenyl)piperazin-1-yl)aniline (241)
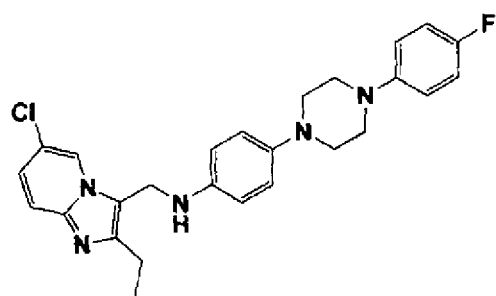
N-((6-Chloro-2-ethylimidazo[1,2-a]pyridin-3-yl)methyl)-4-(4-fluorophenoxy)aniline (242)
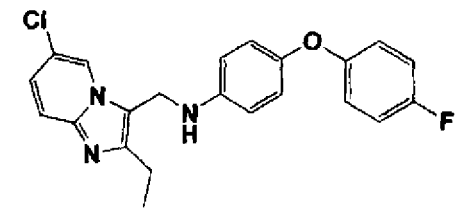

7-Chloro-2-ethyl-N-(4-(4-fluorophenoxy)benzyl)imidazo[1,2-a]pyridine-3-carboxamide (264)

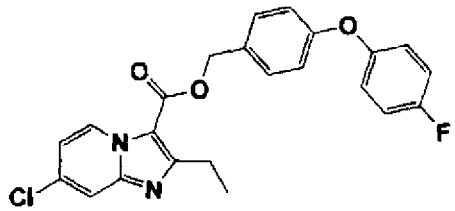

11. A pharmaceutical composition comprising a compound according to claim 9, and a pharmaceutically acceptable carrier.

12. A pharmaceutical composition comprising a compound according to claim 10, and a pharmaceutically acceptable carrier.

13. A method of treatment of a bacterial infection, comprising the application of a suitable amount of a compound according to claim 2, to a person in need thereof.

14. The method, according to claim 13, used for the treatment of tuberculosis.

(12) United States Patent
No et al.

(10) Patent No.: US 8,865,734 B2
(45) Date of Patent: Oct. 21, 2014

(54) ANTI-INFECTIVE COMPOUNDS

(75) Inventors: Zaesung No, Gyeonggido (KR); Jaeseung Kim, Seoul (KR); Priscille Brodin, Paris (FR); Min Jung Seo, Gyeonggi-do (KR); Young Mi Kim, Gyeonggi-do (KR); Jonathan Cechetto, Seoul (KR); Heekyoung Jeon, Gyeonggi-do (KR); Auguste Genovesio, Paris (FR); Saeyeon Lee, Gyeonggi-do (KR); Sunhee Kang, Gyeonggi-do (KR); Fanny Anne Ewann, Haramont (FR); Ji Youn Nam, Cheongju (KR); Thierry Christophe, Pontarlier (FR); Denis Philippe Cedric Fenistein, Amsterdam (NL); Jamung Heo, Chungcheongnam-do (KR); Jang Jiyeon, Seoul (KR)

(73) Assignees: Institut Pasteur Korea, Gyeonggi-Do (KR); Institut National de la Sante et de la Rech, Paris (FR)

(*) Notice: Subject to any disclaimer, the term of this patent is extended or adjusted under 35 U.S.C. 154(b) by 0 days.

(21) Appl. No.: 13/634,165

(22) PCT Filed: Mar. 18, 2011

(86) PCT No.: PCT/EP2011/001345
§ 371 (c)(1),
(2), (4) Date: Nov. 26, 2012

(87) PCT Pub. No.: WO2011/113606
PCT Pub. Date: Sep. 22, 2011

(65) Prior Publication Data
US 2013/0065884 A1 Mar. 14, 2013

Related U.S. Application Data

(60) Provisional application No. 61/315,113, filed on Mar. 18, 2010, provisional application No. 61/440,937, filed on Feb. 9, 2011.

(51) Int. Cl.
*C07D 401/04* (2006.01)
*A61K 31/437* (2006.01)

(52) U.S. Cl.
CPC .......... *C07D 401/04* (2013.01); *A61K 31/437* (2013.01)
USPC .................................. 514/300; 546/121

(58) Field of Classification Search
CPC ................... C07D 401/04; A61K 31/437
USPC ............. 514/300; 546/121; 544/106, 362
See application file for complete search history.

(56) References Cited

U.S. PATENT DOCUMENTS

| 3,105,834 A | * | 10/1963 | Wei | 544/281 |
| 3,133,076 A | * | 5/1964 | Ferrari | 430/570 |
| 3,234,218 A | * | 2/1966 | Eichenberger et al. | 548/193 |
| 6,080,767 A | * | 6/2000 | Klein et al. | 514/357 |

FOREIGN PATENT DOCUMENTS

| WO | WO 01/92257 A1 | 12/2001 |
| WO | 2007034278 | * 3/2007 |
| WO | 2007034282 | * 3/2007 |
| WO | WO 2007/027999 A2 | 3/2007 |
| WO | WO 2008/082490 A2 | 7/2008 |
| WO | WO 2008/154271 A1 | 12/2008 |
| WO | WO 2009/015208 A1 | 1/2009 |
| WO | WO 2011/050245 A1 | 4/2011 |
| WO | WO 2011/057145 A2 | 5/2011 |

OTHER PUBLICATIONS

Bristow et al., J. Chem. Soc. (1954) 616-29.*
Paudler et al., Journal of Organic Chemistry (1968), 33(4), 1638-9.*
Boehme et al., Archiv der Pharmazie (Weinheim, Germany) (1976), 309(12), 959-65.*
Saldabols et al., Khimiko-Farmatsevticheskii Zhurnal (1977), 11(6), 64-70.*
Inciffier et al., Journal of Medicinal Chemistry (1996), 39(14), 2856-2859.*
Chavignon et al., Heterocycles (1995), 41(9), 2019-26.*
Royer et al., Bulletin de la Societe Chimique de France (1961) 933-8.*
Takizawa et al., Inorganic Chemistry (2007), 46(10), 4308-4319.*
Kawamoto et al., "Efficient syntheses of a novel 5-thia-1-azacycl[3.3.2]azine ring system and 3H-1, 4-diazacycl[3.3.2]azine derivatives," 2000, *Tetrahedron Letters*, vol. 41, No. 18, p. 3447-3451.
Database Reaxys [Online], Database accession No. 8503486.
Database Reaxys [Online], Database accession No. 84996050.
Database Registry [Online], Chemical Abstracts 2010, retrieved from STN; Database accession No. 1235377-77-1.
Database Caplus [Online] Chemical Abstract Service, "Interaction of bromomalonic acid N,N'dibenzylamide with bifunctional amines A pathway to the new pharmacologically active substances," STN Accession No. 2004:36264, 2003, XP002638964, *Medichna Khimiya*, vol. 5, No. 3, 2003, pp. 95-99.
Database Registry [Online] Chemical Abstract Service, STN Database Accession No. 1181391-06-9, Sep. 9, 2009, XP002638965.
Database Registry [Online] Chemical Abstract Service, STN Database Accession No. 1181334-07-5, Sep. 8, 2009, XP002638966.
Database Registry [Online] Chemical Abstract Service, STN Database Accession No. 1181286-95-2, Sep. 8, 2009, XP002638967.
Database Registry [Online] Chemical Abstract Service, STN Database Accession No. 1181266-00-1, Sep. 8, 2009, XP002638968.
Database Registry [Online] Chemical Abstract Service, STN Database Accession No. 1147732-93-1, May 20, 2009, XP002638969.
Database Registry [Online] Chemical Abstract Service, STN Database Accession No. 570361-25-0, Aug. 21, 2003, XP002638970.

(Continued)

*Primary Examiner* — Niloofar Rahmani
(74) *Attorney, Agent, or Firm* — Saliwanchik, Lloyd & Eisenschenk

(57) ABSTRACT

The present invention relates to small molecule compounds and their use in the treatment of bacterial infections, in particular Tuberculosis.

14 Claims, 3 Drawing Sheets